US011691963B2

(12) United States Patent
Masse et al.

(10) Patent No.: US 11,691,963 B2
(45) Date of Patent: Jul. 4, 2023

(54) 6-HETEROARYLOXY BENZIMIDAZOLES AND AZABENZIMIDAZOLES AS JAK2 INHIBITORS

(71) Applicant: Ajax Therapeutics, Inc., New York, NY (US)

(72) Inventors: Craig E. Masse, Cambridge, MA (US); Jeremy R. Greenwood, Brooklyn, NY (US); Sayan Mondal, Newark, NJ (US); Jiayi Xu, Marlboro, NJ (US); Phani Ghanakota, Edison, NJ (US); Fiona Michelle McRobb, New York, NY (US); Nicholas Boyles, Hillsboro, OR (US)

(73) Assignee: Ajax Therapeutics, Inc., New York, NY (US)

( * ) Notice: Subject to any disclaimer, the term of this patent is extended or adjusted under 35 U.S.C. 154(b) by 108 days.

(21) Appl. No.: 17/308,740

(22) Filed: May 5, 2021

(65) Prior Publication Data
US 2022/0411403 A1  Dec. 29, 2022

Related U.S. Application Data

(60) Provisional application No. 63/130,254, filed on Dec. 23, 2020, provisional application No. 63/087,717, filed on Oct. 5, 2020, provisional application No. 63/020,645, filed on May 6, 2020.

(51) Int. Cl.
*C07D 401/14* (2006.01)
*C07D 401/12* (2006.01)
*C07D 405/14* (2006.01)
*C07D 413/14* (2006.01)
*C07D 417/14* (2006.01)
*C07D 471/04* (2006.01)

(52) U.S. Cl.
CPC ......... *C07D 401/14* (2013.01); *C07D 401/12* (2013.01); *C07D 405/14* (2013.01); *C07D 413/14* (2013.01); *C07D 417/14* (2013.01); *C07D 471/04* (2013.01)

(58) Field of Classification Search
CPC .. C07D 401/14; C07D 401/12; C07D 405/14; C07D 413/14; C07D 417/14; C07D 417/04
USPC ................................................... 514/210.21
See application file for complete search history.

(56) References Cited

U.S. PATENT DOCUMENTS

| 5,270,148 | A  | 12/1993 | Morigaki et al. |
| 5,512,590 | A  | 4/1996  | George et al. |
| 5,616,537 | A  | 4/1997  | Yokota et al. |
| 5,702,877 | A  | 12/1997 | Odenwalder et al. |
| 5,814,633 | A  | 9/1998  | Muller et al. |
| 5,852,046 | A  | 12/1998 | Lang et al. |
| 5,994,629 | A  | 11/1999 | Bojsen et al. |
| 6,329,383 | B1 | 12/2001 | Hedgecock et al. |
| 6,346,531 | B1 | 2/2002  | Luengo et al. |
| 6,444,816 | B1 | 9/2002  | Das et al. |
| 6,552,192 | B1 | 4/2003  | Hanus et al. |
| 6,566,372 | B1 | 5/2003  | Zhi et al. |
| 6,630,470 | B1 | 10/2003 | Luengo et al. |
| 6,743,800 | B1 | 6/2004  | Peyman et al. |
| 6,747,016 | B1 | 6/2004  | Peyman et al. |
| 7,256,196 | B1 | 8/2007  | Sabat et al. |
| 7,531,553 | B2 | 5/2009  | Di Pietro et al. |
| 8,114,874 | B2 | 2/2012  | Zou et al. |
| 8,293,923 | B2 | 10/2012 | Guckian et al. |
| 8,614,330 | B2 | 12/2013 | Amiri et al. |
| 8,846,697 | B2 | 9/2014  | Carson et al. |
| 9,145,438 | B2 | 9/2015  | Chesworth et al. |
| 9,200,020 | B2 | 12/2015 | De Jersey et al. |
| 9,284,299 | B2 | 3/2016  | Ji et al. |
| 10,766,888 | B1 | 9/2020 | Biddle et al. |
| 2001/0056090 | A1 | 12/2001 | Aquila et al. |
| 2002/0010159 | A1 | 1/2002  | Weigele et al. |
| 2002/0052368 | A1 | 5/2002  | Marlowe et al. |
| 2002/0058677 | A1 | 5/2002  | Marlowe et al. |
| 2002/0068721 | A1 | 6/2002  | Weigele et al. |
| 2002/0094994 | A1 | 7/2002  | Bourzat et al. |
| 2002/0120144 | A1 | 8/2002  | Akama et al. |
| 2002/0165261 | A1 | 11/2002 | Borisy et al. |
| 2002/0173506 | A1 | 11/2002 | Clark et al. |
| 2003/0109714 | A1 | 6/2003  | Wishart et al. |
| 2003/0187261 | A1 | 10/2003 | Havlicek et al. |
| 2003/0199564 | A1 | 10/2003 | Fenton et al. |
| 2004/0006117 | A1 | 1/2004  | Blume et al. |
| 2004/0034224 | A1 | 2/2004  | Hammarstrom et al. |
| 2004/0077633 | A1 | 4/2004  | Watson et al. |
| 2004/0082583 | A1 | 4/2004  | Cheung et al. |
| 2004/0122237 | A1 | 6/2004  | Amiri et al. |

(Continued)

FOREIGN PATENT DOCUMENTS

CN       1148043 A      4/1997
CN     101239980 A      8/2008
(Continued)

OTHER PUBLICATIONS

Akhtar, W. et al., Therapeutic evolution of benzimidazole derivatives in the last quinquennial period, European Journal of Medicinal Chemistry, 126:705-753 (2017).
Choi, H.G. et al., Development of 'DFG-out' inhibitors of gatekeeper mutant kinases, Bioorganic & Medicinal Chemistry Letters, 22:5297-5302 (2012).
Clark, J. et al., Discovery and Development of Janus Kinase (JAK) Inhibitors for Inflammatory Diseases, Journal of Medicinal Chemistry, J. Med. Chem., 57:5023-5038 (2014).
Jaffer, T. and MA, D., The emerging role of chemokine receptor CXCR2 in cancer progression, Transl. Cancer Res., 5(Suppl 4):S616-S628 (2016).

(Continued)

*Primary Examiner* — Kahsay Habte
(74) *Attorney, Agent, or Firm* — Choate, Hall & Stewart LLP; John P. Rearick; Erica M. D'Amato

(57) ABSTRACT

The present disclosure provides 6-heteroaryloxy benzimidazole and azabenzimidazole compounds and compositions thereof useful for inhibiting JAK2.

30 Claims, No Drawings

(56) References Cited

U.S. PATENT DOCUMENTS

| | | |
|---|---|---|
| 2004/0171630 A1 | 9/2004 | Kim et al. |
| 2004/0198725 A1 | 10/2004 | Sun et al. |
| 2005/0049263 A1 | 3/2005 | Kasibhatla et al. |
| 2005/0101647 A1 | 5/2005 | Oda et al. |
| 2005/0137234 A1 | 6/2005 | Bressi et al. |
| 2005/0192287 A1 | 9/2005 | Costales et al. |
| 2005/0209176 A1 | 9/2005 | Meutermans et al. |
| 2005/0239821 A1 | 10/2005 | Neyts et al. |
| 2005/0272765 A1 | 12/2005 | Feng et al. |
| 2005/0282802 A1 | 12/2005 | Kostik et al. |
| 2006/0042026 A1 | 3/2006 | Glenn et al. |
| 2006/0052331 A1 | 3/2006 | Koch et al. |
| 2006/0111362 A1 | 5/2006 | Kira et al. |
| 2006/0116383 A1 | 6/2006 | Bloxham et al. |
| 2006/0148830 A1 | 7/2006 | Terakado et al. |
| 2006/0154977 A1 | 7/2006 | Morand et al. |
| 2006/0160872 A1 | 7/2006 | Norman et al. |
| 2007/0032493 A1 | 2/2007 | Foley et al. |
| 2007/0043043 A1 | 2/2007 | Chen et al. |
| 2007/0049622 A1 | 3/2007 | Dimitroff et al. |
| 2007/0093544 A1 | 4/2007 | Parmee et al. |
| 2007/0105930 A1 | 5/2007 | Parmee et al. |
| 2007/0112048 A1 | 5/2007 | Bavari et al. |
| 2007/0173527 A1 | 7/2007 | Bressi et al. |
| 2007/0197450 A1 | 8/2007 | Fushimi et al. |
| 2007/0219235 A1 | 9/2007 | Mjalli et al. |
| 2007/0249637 A1 | 10/2007 | Collins et al. |
| 2007/0275984 A1 | 11/2007 | Imogai et al. |
| 2008/0008682 A1 | 1/2008 | Chong et al. |
| 2008/0009488 A1 | 1/2008 | Anand et al. |
| 2008/0032936 A1 | 2/2008 | Gai et al. |
| 2008/0058297 A1 | 3/2008 | Ono et al. |
| 2008/0096903 A1 | 4/2008 | Chen et al. |
| 2008/0132501 A1 | 6/2008 | Sun et al. |
| 2008/0161254 A1 | 7/2008 | Green et al. |
| 2008/0194803 A1 | 8/2008 | Sinclair et al. |
| 2008/0221148 A1 | 9/2008 | Ibrahim et al. |
| 2008/0284322 A1 | 11/2008 | Hosokawa et al. |
| 2009/0047249 A1 | 2/2009 | Graupe et al. |
| 2009/0118200 A1 | 5/2009 | Bergman et al. |
| 2009/0140637 A1 | 6/2009 | Hosokawa et al. |
| 2009/0176778 A1 | 7/2009 | Schmitz et al. |
| 2009/0232844 A1 | 9/2009 | Sutton et al. |
| 2009/0233946 A1 | 9/2009 | Krasinski et al. |
| 2009/0278115 A1 | 11/2009 | Hosokawa et al. |
| 2010/0010217 A1 | 1/2010 | Valiante et al. |
| 2010/0029709 A1 | 2/2010 | Menet et al. |
| 2010/0093747 A1 | 4/2010 | Goodhew |
| 2010/0197688 A1 | 8/2010 | Nantermet et al. |
| 2010/0204265 A1 | 8/2010 | Baskaran et al. |
| 2010/0210598 A1 | 8/2010 | Carson et al. |
| 2010/0216810 A1 | 8/2010 | Okaniwa et al. |
| 2010/0249119 A1 | 9/2010 | Hirose et al. |
| 2010/0256188 A1 | 10/2010 | Pfau et al. |
| 2010/0261679 A1 | 10/2010 | Sutton et al. |
| 2010/0267714 A1 | 10/2010 | Jorgensen et al. |
| 2011/0021518 A1 | 1/2011 | Magnuson et al. |
| 2011/0039895 A1 | 2/2011 | Chai et al. |
| 2011/0059962 A1 | 3/2011 | Alekshun et al. |
| 2011/0105498 A1 | 5/2011 | Pettus et al. |
| 2011/0117073 A1 | 5/2011 | Singh et al. |
| 2011/0172186 A1 | 7/2011 | Behnke et al. |
| 2011/0201605 A1 | 8/2011 | Baumann et al. |
| 2011/0237620 A1 | 9/2011 | Okaniwa |
| 2011/0263598 A1 | 10/2011 | Sampson et al. |
| 2011/0281865 A1 | 11/2011 | Muthuppalaniappan et al. |
| 2011/0312935 A1 | 12/2011 | Pfau et al. |
| 2012/0028969 A1 | 2/2012 | Barnes et al. |
| 2012/0115902 A1 | 5/2012 | Pfau et al. |
| 2012/0122930 A1 | 5/2012 | Pfau et al. |
| 2012/0172351 A1 | 7/2012 | Negoro et al. |
| 2012/0202287 A1 | 8/2012 | Adams et al. |
| 2012/0208839 A1 | 8/2012 | Priepke et al. |
| 2012/0214786 A1 | 8/2012 | Priepke et al. |
| 2012/0258967 A1 | 10/2012 | Qiao et al. |
| 2013/0059851 A1 | 3/2013 | Garraway et al. |
| 2013/0079342 A1 | 3/2013 | Dransfield et al. |
| 2013/0084346 A1 | 4/2013 | Wolkenberg et al. |
| 2013/0090327 A1 | 4/2013 | Hata et al. |
| 2013/0096136 A1 | 4/2013 | Hata et al. |
| 2013/0136782 A1 | 5/2013 | Blackwell et al. |
| 2013/0149717 A1 | 6/2013 | Krause et al. |
| 2013/0165446 A1 | 6/2013 | Fujita et al. |
| 2013/0184240 A1 | 7/2013 | Tonogaki et al. |
| 2013/0184248 A1 | 7/2013 | Grauert et al. |
| 2013/0190320 A1 | 7/2013 | Xu et al. |
| 2013/0224195 A1 | 8/2013 | Costales et al. |
| 2013/0225596 A1 | 8/2013 | Kai et al. |
| 2013/0261125 A1 | 10/2013 | Shipps, Jr. et al. |
| 2013/0310333 A1 | 11/2013 | Chesworth et al. |
| 2013/0345261 A1 | 12/2013 | Waters et al. |
| 2014/0011763 A1 | 1/2014 | Lakshman |
| 2014/0031339 A1 | 1/2014 | Abeywardane et al. |
| 2014/0155379 A1 | 6/2014 | Ho et al. |
| 2014/0194420 A1 | 7/2014 | Kojima et al. |
| 2014/0303102 A1 | 10/2014 | Choe et al. |
| 2014/0303360 A1 | 10/2014 | Schroeder et al. |
| 2014/0364386 A1 | 12/2014 | Choe et al. |
| 2015/0018291 A1 | 1/2015 | Choe et al. |
| 2015/0057309 A1 | 2/2015 | Vakkalanka et al. |
| 2015/0126436 A1 | 5/2015 | Phillips et al. |
| 2015/0133500 A1 | 5/2015 | Tafesse et al. |
| 2015/0152065 A1 | 6/2015 | Brookings et al. |
| 2015/0197497 A1 | 7/2015 | Abeywickrama et al. |
| 2015/0216168 A1 | 8/2015 | Frackenpohl et al. |
| 2015/0243903 A1 | 8/2015 | Zeng et al. |
| 2015/0249221 A1 | 9/2015 | Zeng et al. |
| 2016/0024072 A1 | 1/2016 | Kai et al. |
| 2016/0052922 A1 | 2/2016 | Chesworth et al. |
| 2016/0096804 A1 | 4/2016 | Shuttleworth et al. |
| 2016/0168165 A1 | 6/2016 | Koehler et al. |
| 2016/0176825 A1 | 6/2016 | Gray et al. |
| 2016/0229837 A1 | 8/2016 | Xi et al. |
| 2016/0257641 A1 | 9/2016 | Kobayashi et al. |
| 2016/0297795 A1 | 10/2016 | Heer et al. |
| 2016/0304511 A1 | 10/2016 | Jackson et al. |
| 2016/0304513 A1 | 10/2016 | Deligny et al. |
| 2017/0114078 A1 | 4/2017 | McGowan et al. |
| 2017/0121349 A1 | 5/2017 | Kim et al. |
| 2017/0129883 A1 | 5/2017 | Jackson et al. |
| 2017/0158688 A1 | 6/2017 | Jackson et al. |
| 2017/0222157 A1 | 8/2017 | Jatsch et al. |
| 2017/0333398 A1 | 11/2017 | Kojima et al. |
| 2018/0030453 A1 | 2/2018 | Zakharenko et al. |
| 2018/0072688 A1 | 3/2018 | Qian et al. |
| 2018/0079727 A1 | 3/2018 | Ohyabu et al. |
| 2018/0086725 A1 | 3/2018 | Kumar et al. |
| 2018/0153877 A1 | 6/2018 | Azam |
| 2018/0273511 A1 | 9/2018 | Long |
| 2019/0002442 A1 | 1/2019 | Zhao et al. |
| 2019/0022074 A1 | 1/2019 | Hadari et al. |
| 2019/0038603 A1 | 2/2019 | Jakobsson |
| 2019/0119217 A1 | 4/2019 | Long et al. |
| 2019/0134042 A1 | 5/2019 | Miao et al. |
| 2019/0135834 A1 | 5/2019 | Tamura et al. |
| 2019/0183866 A1 | 6/2019 | Tamura et al. |
| 2019/0382377 A1 | 12/2019 | Li et al. |
| 2019/0388426 A1 | 12/2019 | Nguyen et al. |
| 2020/0039933 A1 | 2/2020 | Gaisina et al. |
| 2020/0039961 A1 | 2/2020 | Campbell et al. |
| 2020/0039998 A1 | 2/2020 | Campbell et al. |
| 2020/0054635 A1 | 2/2020 | Campbell et al. |
| 2020/0062758 A1 | 2/2020 | Liu et al. |
| 2020/0101091 A1 | 4/2020 | Peyrottes et al. |
| 2020/0113901 A1 | 4/2020 | Campbell et al. |
| 2020/0113907 A1 | 4/2020 | Hagiwara et al. |
| 2020/0237717 A1 | 7/2020 | Jensen et al. |
| 2020/0268753 A1 | 8/2020 | Nguyen et al. |
| 2020/0274072 A1 | 8/2020 | Kugler |
| 2020/0317642 A1 | 10/2020 | Campbell et al. |
| 2021/0008046 A1 | 1/2021 | Bravo et al. |
| 2022/0127260 A1 | 4/2022 | Gray et al. |

(56) References Cited

U.S. PATENT DOCUMENTS

| | | | |
|---|---|---|---|
| 2022/0127284 A1 | 4/2022 | Gray et al. | |
| 2023/0099203 A1 | 3/2023 | Masse et al. | |

FOREIGN PATENT DOCUMENTS

| | | | |
|---|---|---|---|
| CN | 107383014 A | 11/2017 | |
| CN | 108689942 A | 10/2018 | |
| CN | 110092798 A | 8/2019 | |
| EP | 639573 A1 | 2/1995 | |
| EP | 3059225 A1 | 8/2016 | |
| EP | 3279187 A1 | 2/2018 | |
| EP | 3450435 A1 | 3/2019 | |
| JP | H11-283746 A | 10/1999 | |
| JP | 2000299186 A | 10/2000 | |
| JP | 2004067629 A | 3/2004 | |
| JP | 2005289921 A | 10/2005 | |
| JP | 2009149589 A | 7/2009 | |
| JP | 2016132649 A | 7/2016 | |
| KR | 10-2019-0064508 A | 6/2019 | |
| WO | WO-93/05163 A1 | 3/1993 | |
| WO | WO-97/11065 A1 | 3/1997 | |
| WO | WO-99/26932 A1 | 6/1999 | |
| WO | WO-2001/044259 A1 | 6/2001 | |
| WO | WO-2002/076960 A1 | 10/2002 | |
| WO | WO-2003/082272 A1 | 10/2003 | |
| WO | WO-2004/006849 A2 | 1/2004 | |
| WO | WO-2004/085425 A1 | 10/2004 | |
| WO | WO-2004/087153 A2 | 10/2004 | |
| WO | WO-2005/032548 A1 | 4/2005 | |
| WO | WO-2005/035526 A1 | 4/2005 | |
| WO | WO-2005/037273 A1 | 4/2005 | |
| WO | WO-2006/027365 A1 | 3/2006 | |
| WO | WO-2006/128129 A2 | 11/2006 | |
| WO | WO-2006/130469 A1 | 12/2006 | |
| WO | WO-2007/091950 A1 | 8/2007 | |
| WO | WO-2007/121484 A2 | 10/2007 | |
| WO | WO-2008/016666 A2 | 2/2008 | |
| WO | WO-2008/124145 A1 | 10/2008 | |
| WO | WO-2008/144062 A1 | 11/2008 | |
| WO | WO-2008/150015 A1 | 12/2008 | |
| WO | WO-2009/011775 A1 | 1/2009 | |
| WO | WO-2009/017954 A1 | 2/2009 | |
| WO | WO-2009/034386 A1 | 3/2009 | |
| WO | WO-2009/050228 A2 | 4/2009 | |
| WO | WO-2009/155565 A1 | 12/2009 | |
| WO | WO-2010/002492 A1 | 1/2010 | |
| WO | WO-2010/141796 A2 | 12/2010 | |
| WO | WO-2010/144909 A1 | 12/2010 | |
| WO | WO-2011/063908 A1 | 6/2011 | |
| WO | WO-2011/127833 A1 | 10/2011 | |
| WO | WO-2012/016133 A2 | 2/2012 | |
| WO | WO-2013/024078 A1 | 2/2013 | |
| WO | WO-2014/069426 A1 | 5/2014 | |
| WO | WO-2014/072435 A1 | 5/2014 | |
| WO | WO-2014/175330 A1 | 10/2014 | |
| WO | WO-2015/008861 A1 | 1/2015 | |
| WO | WO-2016/014576 A1 | 1/2016 | |
| WO | WO-2016/119700 A1 | 8/2016 | |
| WO | WO-2017/143014 A1 | 8/2017 | |
| WO | WO-2017/175068 A1 | 10/2017 | |
| WO | WO-2018/039557 A1 | 3/2018 | |
| WO | WO-2018/064498 A1 | 4/2018 | |
| WO | WO-2018/066545 A1 | 4/2018 | |
| WO | WO-2018/191146 A1 | 10/2018 | |
| WO | WO-2018/200786 A1 | 11/2018 | |
| WO | WO-2018/203099 A1 | 11/2018 | |
| WO | WO-2018/204765 A1 | 11/2018 | |
| WO | WO-2019/000683 A1 | 1/2019 | |
| WO | WO-2019/018119 A1 | 1/2019 | |
| WO | WO-2019/038683 A1 | 2/2019 | |
| WO | WO-2019/079596 A1 | 4/2019 | |
| WO | WO-2019/079607 A1 | 4/2019 | |
| WO | WO-2019/088159 A1 | 5/2019 | |
| WO | WO-2019/217838 A1 | 11/2019 | |
| WO | WO-2020/014599 A1 | 1/2020 | |
| WO | WO-2020/081450 A1 | 4/2020 | |
| WO | WO-2020/089455 A1 | 5/2020 | |
| WO | WO-2020/093905 A1 | 5/2020 | |
| WO | WO-2020/097396 A1 | 5/2020 | |
| WO | WO-2020/097398 A1 | 5/2020 | |
| WO | WO-2020/097400 A1 | 5/2020 | |
| WO | WO-2020/118045 A1 | 6/2020 | |
| WO | WO-2020/165907 A1 | 8/2020 | |
| WO | WO-2020/176597 A1 | 9/2020 | |
| WO | WO-2020/180768 A1 | 9/2020 | |
| WO | WO-2020/181050 A1 | 9/2020 | |
| WO | WO-2020/210481 A1 | 10/2020 | |
| WO | WO-2020/243457 A1 | 12/2020 | |
| WO | WO-2021/067682 A1 | 4/2021 | |
| WO | WO-2021/091575 A1 | 5/2021 | |
| WO | WO-2021/113557 A1 | 6/2021 | |
| WO | WO-2021/226261 A1 | 11/2021 | |
| WO | WO-2022/140527 A1 | 6/2022 | |

OTHER PUBLICATIONS

Jutzi, J. et al., LSD1 Inhibition Prolongs Survival in Mouse Models of MPN by Selectivity Targeting the Disease Clone, HemaSphere, 2:3, 13 pages (2018).
Meyer, S. and Levine, R., Molecular Pathways: Molecular Basis for Sensitivity and Resistance to JAK Kinase Inhibitors, Clin. Cancer Res., 20(8):2051-2059 (2014).
O'Hare, T. et al., AP24534, a Pan-BCR-ABL Inhibitor for Chronic Myeloid Leukemia, Potently Inhibits the T315I Mutant and Overcomes Mutation-Based Resistance, Cancer Cell, 16(5):401-412 (2009).
O'Shea, J. et al., Janus kinase Inhibitors in autoimmune diseases, Ann Rheum. Dis., 72, 11 pages (2013).
Ramurthy, S. et al., Design and Synthesis of Orally Bioavailable Benzimidazoles as Raf Kinase Inhibitors, J. Med. Chem., 51:7049-7052 (2008).
Ramurthy, S. et al., Supporting Information Design and Synthesis of Benzimidazoles Amides as Raf Kinase Inibitors, Novartis Institutes of Biomedical Research, 38 pages (2018).
Rodrigues, M.A. and Torres, T., JAK/STAT inhibitors for the treatment of atopic dermatitis, Journal of Dermatological Treatment, 31(1):33-40 (2020).
Rzymski, T. et al., SEL120-34A is a novel CDK8 inhibitor active in AML cells with high levels of serine phosphorylation of STAT1 and STAT5 transactivation domains, Oncotarget, 8(20):33779-33795 (2017).
Subramanian, S. et al., Design and Synthesis of Orally Bioavailable Benzimidazole Reverse Amides as Pan RAF Kinase Inhibitors, ACS Med. Chem. Lett., 5:989-992 (2014).
Vainchenker, W. et al., JAK inhibitors for the treatment of myeloproliferative neoplasms and other disorders, F1000 Research, 7(F1000 Faculty Rev), 19 pages (last updated Jan. 17, 2018).
Wu, S. et al., Activity of the Type II JAK2 Inhibitor CHZ868 in B Cell Acute Lymphoblastic Leukemia, Cancer Cell, 28:29-41 (2015).
Yumeen, S. et al., JAK inhibition synergistically potentiates BCL2, BET, HDAC, and proteasome inhibition in advanced CTCL, Blood Advances, 4(10):2213-2226 (2020).
Aaronson, D. S. and Horvath, C. M., A Road Map for Those Who Don't Know JAK-STAT, Science, 296(5573):1653-1655 (2002).
Andraos, R. et al., Modulation of activation-loop phosphorylation by JAK inhibitors is binding mode dependent, Cancer Discovery, 2(6):512-523 (2012).
Elf, S. et al., Mutant calreticulin requires both its mutant C-terminus and the thrombopoietin receptor for oncogenic transformation, Science Discovery, 6(4):368-381 (2016).
Harrison, C. et al., JAK Inhibition with Ruxolitinib versus Best Available Therapy for Myelofibrosis, The New England Journal of Medicine, 366(9):787-798 (2012).
International Search Report for PCT/US2019/060358, dated Mar. 3, 2020.
International Search Report for PCT/US2019/060360, dated Mar. 3, 2020.

(56) References Cited

OTHER PUBLICATIONS

International Search Report for PCT/US2019/060363, dated Mar. 9, 2020.
International Search Report for PCT/US2020/053922, dated Mar. 8, 2021.
International Search Report for PCT/US2021/030926, 7 pages (dated Sep. 8, 2021).
International Search Report for PCT/US2021/064830, 4 pages (dated Mar. 25, 2022).
Koppikar, P. et al., Heterodimeric JAK-STAT Activation as a Mechanism of Persistence to JAK2 Inhibitor Therapy, Nature, 489(7414):155-159 (2012).
Leroy, E. et al., Rethinking JAK2 inhibition: towards novel strategies of more specific and versatile janus kinase inhibition, Leukemia, 31(5):1023-1038 (2017).
Levine, R. L., JAK-mutant Myeloproliferative Neoplasms, Current Topics in Microbiology and Immunology, 355:119-133 (2011).
Pandey, A. et al., Cloning of a receptor subunit required for signaling by thymic stromal lymphopoietin, Nature Immunology, 1(1):59-64 (2000).
Roberts, K. G. et al., Targetable Kinase-Activating Lesions in Ph-like Acute Lymphoblastic Leukemia, New England Journal of Medicine, 371(11):1005-1015 (2014).
Rui, L. et al., Cooperative Epigenetic Modulation by Cancer Amplicon Genes, Cancer Cell., 18(6):590-605 (2010).
Shiels, M. S. et al., Cancer Burden in the HIV-Infected Population in the United States, J Natl Cancer Inst., 103(9):753-762 (2011).
Smith, A. et al., Imidazo[1,2-a]pyridin-6-yl-benzamide analogs as potent RAF inhibitors, Bioorg Med Chem Lett., 27(23):5221-5224 (2017).
Verstovsek, S. et al., A Double-Blind Placebo-Controlled Trial of Ruxolitinib for Myelofibrosis, N Engl J Med., 366(9):799-807 (2012).
Yuanyuan, W. et al., Design, synthesis, biological evaluation and molecular modeling of novel 1H-pyrazolo [3,4-d] pyrimidine derivatives as BRAFV600E and VEGFR-2 dual inhibitors, European Journal of Medicinal Chemistry, 155:210-228 (2018).
Bundgard, Design of Prodrugs, Amsterdam, New York, Oxford, Elsevier, pp. 7-9, 21-24 (1985).
Dymock et al., Inhibitors of JAK2 and JAK3: an update on the patent literature 2010-2012, Expert Opin Ther Pat., 23(4):449-501 (2013).
Extended European Search Report for Application No. EP19882411.2, dated Jun. 21, 2022.
Extended European Search Report for EP 19882880.8 dated Jul. 11, 2022.
Extended European Search Report for EP19881035.0 dated Jun. 29, 2022.
Li, et al., AutoT&T v.2: An Efficient and Versatile Tool for Lead Structure Generation and Optimization, J. Chem. Inf. Model, 56(2):435-453 (2016).
Okaniwa, et al., Design and synthesis of novel DFG-out RAF/vascular endothelial growth factor receptor 2 (VEGF2) inhibitors. 1. Exploration of [5,6]-fused bicyclic scaffolds, J Med Chem., 55(7):3452-78 (2012).
Rai, S. et al., The Second Generation Type II JAK2 inhibitor, AJ1-10502, Demonstrates Enhanced Selectivity Improved Therapeutic Efficacy and Reduced Mutant Cell Fraction Compared to Type I JAK2 inhibitors in Models of Myeloproliferative Neoplasms (MPNs), 64th American Society of Hematology Annual Meeting, 1-4 (2022).
Rai, S. et al., The Second Generation Type II JAK2 inhibitor, AJ1-10502, Demonstrates Enhanced Selectivity Improved Therapeutic Efficacy and Reduced Mutant Cell Fraction Compared to Type I JAK2 inhibitors in Models of Myeloproliferative Neoplasms (MPNs), Poster (1 page), Presented at the 64th American Society of Hematology Annual Meeting from Dec. 10-13, 2022.
Steelman, L. S. et al., JAK/STAT, Raf/MEK/ERK, PI3K/Akt and BCR-ABL in cell cycle progression and leukemogenesis, Leukemia, 18:189-218 (2004).
Williams et al., Discovery of RAF265: A Potent mut-B-RAF Inhibitor for the Treatment of Metastatic Melanoma, ACS Med. Chem Lett., 6(9):961-965 (2015).
Zhao, et al., Exploration of type II binding mode: A privileged approach for kinase inhibitor focused drug discovery?, ACS Chem Biol., 9(6):1230-41 (2014).

6-HETEROARYLOXY BENZIMIDAZOLES AND AZABENZIMIDAZOLES AS JAK2 INHIBITORS

RELATED APPLICATIONS

This application claims priority to and benefit of U.S. Application No. 63/020,645, filed May 6, 2020, U.S. Application No. 63/087,717, filed Oct. 5, 2020, and U.S. Application No. 63/130,254, filed Dec. 23, 2020, the entire contents of each of which are hereby incorporated by reference in their entirety.

BACKGROUND

Janus kinase 2 (JAK2) is a non-receptor tyrosine kinase involved in the JAK-STAT signaling pathway, which plays a role in cell processes such as immunity, cell division, and cell death. Dysfunction of the JAK-STAT pathway is implicated in various diseases, including cancer and other proliferative diseases, as well as diseases of the immune system. For example, essentially all BCR-ABL1-negative myeloproliferative neoplasms are associated with mutations that activate JAK2. In particular, JAK2V617F is the most prevalent mutation in myeloproliferative neoplasms, occurring in approx. 70% of all patients, and in up to 95% of patients with polycythemia vera. (Vainchenker, W., Kralovics, R. Blood 2017, 129(6):667-79). Even less common mutations, such as in MPL and CALR, have been shown to effect activation of JAK2, thereby initiating and/or driving disease progression. (Vainchenker, W. et al., F1000Research 2018, 7(F1000 Faculty Rev):82). Furthermore, polymorphisms in JAK2 have been linked to various autoimmune diseases and inflammatory conditions, such as psoriasis and inflammatory bowel disease. (O'Shea, J. J. et al., Ann. Rheum. Dis. 2013 April, 72:ii111-ii115). Increased signaling through JAK2, as well as other members of the JAK family, is also associated with atopic dermatitis. (Rodrigues, M. A. and Torres, T. J. Derm. Treat. 2019, 31(1):33-40).

Inhibitors of JAKs (e.g., JAK2) are classified based on their binding mode. All currently approved JAK inhibitors are Type I inhibitors, which are those that bind the ATP-binding site in the active conformation of the kinase domain, thereby blocking catalysis (Vainchenker, W. et al.). However, increased phosphorylation of the JAK2 activation loop is observed with Type I inhibitors and may lead to acquired resistance in certain patients (Meyer S. C., Levine, R. L. Clin. Cancer Res. 2014, 20(8):2051-9). Type II inhibitors, on the other hand, bind the ATP-binding site of the kinase domain in the inactive conformation and, therefore, may avoid hyperphosphorylation observed with Type I inhibitors (Wu, S. C. et al. Cancer Cell 2015 Jul. 13, 28(1):29-41).

SUMMARY

The present disclosure provides compounds useful for inhibiting JAK2. In some embodiments, provided compounds are useful for, among other things, treating and/or preventing diseases, disorders, or conditions associated with JAK2.

In some embodiments, the present disclosure provides a compound of Formula I-1:

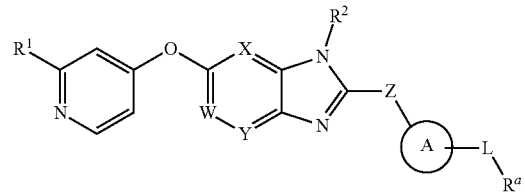

I-1 or a pharmaceutically acceptable salt thereof, wherein Ring A, L, W, X, Y, Z, $R^1$, $R^2$, and $R^a$ are as defined herein.

In some embodiments, the present disclosure provides a compound of Formula I:

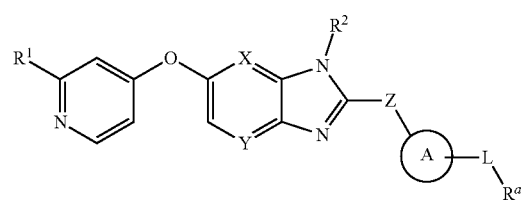

I or a pharmaceutically acceptable salt thereof, wherein Ring A, L, X, Y, Z, $R^1$, $R^2$, and $R^a$ are as defined herein.

DETAILED DESCRIPTION

Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

Unless otherwise stated, structures depicted herein are meant to include all stereoisomeric (e.g., enantiomeric or diastereomeric) forms of the structure, as well as all geometric or conformational isomeric forms of the structure. For example, the R and S configurations of each stereocenter are contemplated as part of the disclosure. Therefore, single stereochemical isomers, as well as enantiomeric, diastereomic, and geometric (or conformational) mixtures of provided compounds are within the scope of the disclosure. For example, in some case, Table 1 shows one or more stereoisomers of a compound, and unless otherwise indicated, represents each stereoisomer alone and/or as a mixture. Unless otherwise stated, all tautomeric forms of provided compounds are within the scope of the disclosure.

Unless otherwise indicated, structures depicted herein are meant to include compounds that differ only in the presence of one or more isotopically enriched atoms. For example, compounds having the present structures including replacement of hydrogen by deuterium or tritium, or replacement of a carbon by $^{13}$C- or $^{14}$C-enriched carbon are within the scope of this disclosure.

Aliphatic: The term "aliphatic" refers to a straight-chain (i.e., unbranched) or branched, optionally substituted hydrocarbon chain that is completely saturated or that contains one or more units of unsaturation, or a monocyclic or bicyclic hydrocarbon that is completely saturated or that contains one or more units of unsaturation but which is not aromatic (also referred to herein as "carbocyclic" or "cycloaliphatic"), that has a single point of attachment to the rest of the molecule. Unless otherwise specified, aliphatic groups contain 1-12 aliphatic carbon atoms. In some embodiments, aliphatic groups contain 1-6 aliphatic carbon atoms (e.g., $C_{1-6}$). In some embodiments, aliphatic groups contain 1-5 aliphatic carbon atoms (e.g., $C_{1-5}$). In other embodiments, aliphatic groups contain 1-4 aliphatic carbon atoms (e.g., $C_{1-4}$). In still other embodiments, aliphatic groups contain 1-3 aliphatic carbon atoms (e.g., $C_{1-3}$), and in yet other embodiments, aliphatic groups contain 1-2 aliphatic carbon atoms (e.g., $C_{1-2}$). Suitable aliphatic groups include, but are not limited to, linear or branched, substituted or unsubstituted alkyl, alkenyl, alkynyl groups and hybrids thereof. In some embodiments, "aliphatic" refers to a straight-chain (i.e., unbranched) or branched, optionally substituted hydrocarbon chain that is completely saturated or that contains one or more units of unsaturation that has a single point of attachment to the rest of the molecule.

Alkyl: The term "alkyl", used alone or as part of a larger moiety, refers to a saturated, optionally substituted straight or branched hydrocarbon group having (unless otherwise specified) 1-12, 1-10, 1-8, 1-6, 1-4, 1-3, or 1-2 carbon atoms (e.g., $C_{1-12}$, $C_{1-10}$, $C_{1-8}$, $C_{1-6}$, $C_{1-4}$, $C_{1-3}$, or $C_{1-2}$). Exemplary alkyl groups include methyl, ethyl, propyl, butyl, pentyl, hexyl, and heptyl.

Carbocyclyl: The terms "carbocyclyl," "carbocycle," and "carbocyclic ring" as used herein, refer to saturated or partially unsaturated cyclic aliphatic monocyclic, bicyclic, or polycyclic ring systems, as described herein, having from 3 to 14 members, wherein the aliphatic ring system is optionally substituted as described herein. Carbocyclic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, "carbocyclyl" (or "cycloaliphatic") refers to an optionally substituted monocyclic $C_3$-$C_8$ hydrocarbon, or an optionally substituted $C_7$-$C_{10}$ bicyclic hydrocarbon that is completely saturated or that contains one or more units of unsaturation, but which is not aromatic, that has a single point of attachment to the rest of the molecule. The term "cycloalkyl" refers to an optionally substituted saturated ring system of about 3 to about 10 ring carbon atoms. In some embodiments, cycloalkyl groups have 3-6 carbons. Exemplary monocyclic cycloalkyl rings include cyclopropyl, cyclobutyl, cyclopentyl, cyclohexyl, and cycloheptyl. The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentenyl, cyclohexenyl, and cycloheptenyl.

Alkenyl: The term "alkenyl", used alone or as part of a larger moiety, refers to an optionally substituted straight or branched hydrocarbon chain having at least one double bond and having (unless otherwise specified) 2-12, 2-10, 2-8, 2-6, 2-4, or 2-3 carbon atoms (e.g., $C_{2-12}$, $C_{2-10}$, $C_{2-8}$, $C_{2-6}$, $C_{2-4}$, or $C_{2-3}$). Exemplary alkenyl groups include ethenyl, propenyl, butenyl, pentenyl, hexenyl, and heptenyl.

Alkynyl: The term "alkynyl", used alone or as part of a larger moiety, refers to an optionally substituted straight or branched chain hydrocarbon group having at least one triple bond and having (unless otherwise specified) 2-12, 2-10, 2-8, 2-6, 2-4, or 2-3 carbon atoms (e.g., $C_{2-12}$, $C_{2-10}$, $C_{2-8}$, $C_{2-6}$, $C_{2-4}$, or $C_{2-3}$). Exemplary alkynyl groups include ethynyl, propynyl, butynyl, pentynyl, hexynyl, and heptynyl.

Aryl: The term "aryl" refers to monocyclic and bicyclic ring systems having a total of six to fourteen ring members (e.g., $C_{6-14}$), wherein at least one ring in the system is aromatic and wherein each ring in the system contains three to seven ring members. The term "aryl" may be used interchangeably with the term "aryl ring". In some embodiments, "aryl" refers to an aromatic ring system which includes, but not limited to, phenyl, naphthyl, anthracyl and the like, which may bear one or more substituents. Unless otherwise specified, "aryl" groups are hydrocarbons.

Heteroaryl: The terms "heteroaryl" and "heteroar-", used alone or as part of a larger moiety, e.g., "heteroaralkyl", or "heteroaralkoxy", refer to monocyclic or bicyclic ring groups having 5 to 10 ring atoms (e.g., 5- to 6-membered monocyclic heteroaryl or 9- to 10-membered bicyclic heteroaryl); having 6, 10, or 14 π electrons shared in a cyclic array; and having, in addition to carbon atoms, from one to five heteroatoms. Exemplary heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridonyl, pyridazinyl, pyrimidinyl, pyrazinyl, indolizinyl, purinyl, naphthyridinyl, pteridinyl, imidazo[1,2a]-imidazo[1,2-a]pyridinyl, thienopyrimidinyl, triazolopyridinyl, and benzoisoxazolyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring (i.e., a bicyclic heteroaryl ring having 1 to 3 heteroatoms). Nonlimiting examples include indolyl, isoindolyl, benzothienyl, benzofuranyl, dibenzofuranyl, indazolyl, benzimidazolyl, benzothiazolyl, benzothiadiazolyl, benzoxazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, pyrido[2,3-b]-1,4-oxazin-3(4H)-one, and benzoisoxazolyl. The term "heteroaryl" may be used interchangeably with the terms "heteroaryl ring", "heteroaryl group", or "heteroaromatic", any of which terms include rings that are optionally substituted.

Heteroatom: The term "heteroatom" as used herein refers to nitrogen, oxygen, or sulfur, and includes any oxidized form of nitrogen or sulfur, and any quaternized form of a basic nitrogen.

Heterocycle: As used herein, the terms "heterocycle", "heterocyclyl", and "heterocyclic ring" are used interchangeably and refer to a stable 3- to 8-membered monocyclic or 7- to 10-membered bicyclic heterocyclic moiety that is either saturated or partially unsaturated, and having, in addition to carbon atoms, one or more, such as one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR$^+$ (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, preferably mono-, bi-, or tricyclic, more preferably mono- or bicyclic. A bicyclic heterocyclic ring also includes groups in which the heterocyclic ring is fused to one or more aryl, heteroaryl, or cycloaliphatic rings. Exemplary bicyclic heterocyclic groups include indolinyl, isoindolinyl, benzodioxolyl, 1,3-dihydroisobenzofuranyl, 2,3-dihydrobenzofuranyl, and tetrahydroquinolinyl. A bicyclic heterocyclic ring can also be a spirocyclic ring system (e.g., 7- to 11-membered spirocyclic fused heterocyclic ring having, in addition to carbon atoms, one or more heteroatoms as defined above (e.g., one, two, three or four heteroatoms)).

Partially Unsaturated: As used herein, the term "partially unsaturated", when referring to a ring moiety, means a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

Patient or subject: As used herein, the term "patient" or "subject" refers to any organism to which a provided composition is or may be administered, e.g., for experimental, diagnostic, prophylactic, cosmetic, and/or therapeutic purposes. Typical patients or subjects include animals (e.g., mammals such as mice, rats, rabbits, non-human primates, and/or humans). In some embodiments, a patient is a human. In some embodiments, a patient or a subject is suffering from or susceptible to one or more disorders or conditions. In some embodiments, a patient or subject displays one or more symptoms of a disorder or condition. In some embodiments, a patient or subject has been diagnosed with one or more disorders or conditions. In some embodiments, a patient or a subject is receiving or has received certain therapy to diagnose and/or to treat a disease, disorder, or condition.

Substituted or optionally substituted: As described herein, compounds of this disclosure may contain "optionally substituted" moieties. In general, the term "substituted," whether preceded by the term "optionally" or not, means that one or more hydrogens of the designated moiety are replaced with a suitable substituent. "Substituted" applies to one or more hydrogens that are either explicit or implicit from the structure (e.g.,

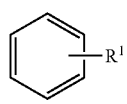

refers to at least

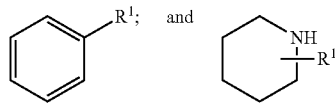

refers to at least

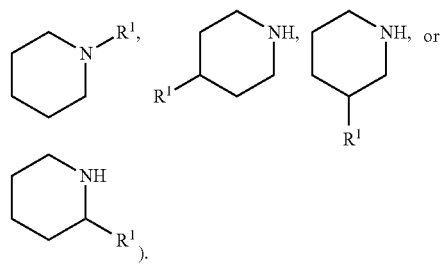

Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes provided herein. Groups described as being "substituted" preferably have between 1 and 4 substituents, more preferably 1 or 2 substituents. Groups described as being "optionally substituted" may be unsubstituted or be "substituted" as described above.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5- to 6-membered heteroaryl ring), or a 3- to 6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3- to 12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$, —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 3- to 6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O ("oxo"), =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 3- to 6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 3- to 6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, or an unsubstituted 3- to 6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3- to 12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 3- to 6-membered saturated, partially unsaturated, or aryl ring having 0-4 heteroatoms independently selected from nitrogen, oxygen, or sulfur.

Treat: As used herein, the term "treat" (also "treatment" or "treating") refers to any administration of a therapy that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition.

Provided Compounds

The present disclosure provides a compound of Formula I-1:

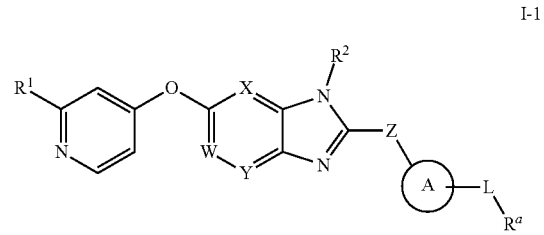

I-1 or a pharmaceutically acceptable salt thereof, wherein:
W is CR$^w$ or N;
X is CR$^x$ or N;
Y is CR$^y$ or N;
Z is —O— or —NR$^z$—;
R$^w$, R$^x$ and R$^y$ are each independently hydrogen, halogen, —OR$^3$, —N(R$^3$)$_2$, —SR$^3$, optionally substituted C$_{1-6}$ aliphatic, or —CN;
R$^z$ is hydrogen or optionally substituted C$_{1-6}$ aliphatic;
R$^1$ is —N(R)$_2$, —N(R)C(O)R', —C(O)N(R)$_2$, or —N(R)C(O)N(R)$_2$;
R$^2$ is optionally substituted C$_{1-6}$ aliphatic;
each R$^3$ is independently hydrogen or optionally substituted C$_{1-6}$ aliphatic;
Ring A is optionally substituted phenyl, optionally substituted 5- to 6-membered monocyclic heteroaryl having 1-4 heteroatoms independently selected from nitrogen, oxygen, and sulfur, optionally substituted 8- to 10-membered bicyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur;
L is a covalent bond or a bivalent C$_{1-3}$ straight or branched hydrocarbon chain;
R$^a$ is hydrogen, halogen, optionally substituted C$_{1-6}$ aliphatic, optionally substituted phenyl, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur;

each R is independently hydrogen, optionally substituted $C_{1-6}$ aliphatic, optionally substituted 3- to 7-membered saturated or partially unsaturated carbocyclyl, or optionally substituted 3- to 7-membered saturated or partially unsaturated monocyclic heterocyclyl having 1-3 heteroatoms independently selected from nitrogen, oxygen, and sulfur, or two R when attached to the same nitrogen atom are taken together form an optionally substituted 3- to 7-membered saturated or partially unsaturated monocyclic heterocyclyl having 0-2 additional heteroatoms independently selected from nitrogen, oxygen, and sulfur; and each R' is independently optionally substituted $C_{1-6}$ aliphatic or optionally substituted 3- to 7-membered saturated or partially unsaturated carbocyclyl.

In some embodiments, the present disclosure provides a compound of Formula I-1, or a pharmaceutically acceptable salt thereof, wherein:

W is $CR^w$ or N;
X is $CR^x$ or N;
Y is $CR^y$ or N;
Z is —O— or —$NR^z$—;
$R^w$, $R^x$ and $R^y$ are each independently hydrogen, halogen, —$OR^3$, —$N(R^3)_2$, —$SR^3$, optionally substituted $C_{1-6}$ aliphatic, or —CN;
$R^z$ is hydrogen or optionally substituted $C_{1-6}$ aliphatic;
$R^1$ is —$N(R)_2$, —N(R)C(O)R', —C(O)N(R)$_2$, or —N(R)C(O)N(R)$_2$;
$R^2$ is optionally substituted $C_{1-6}$ aliphatic;
each $R^3$ is independently hydrogen or optionally substituted $C_{1-6}$ aliphatic;
Ring A is optionally substituted phenyl, optionally substituted 5- to 6-membered monocyclic heteroaryl having 1-4 heteroatoms independently selected from nitrogen, oxygen, and sulfur, optionally substituted 8- to 10-membered bicyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur;
L is a covalent bond or a bivalent $C_{1-3}$ straight or branched hydrocarbon chain;
$R^a$ is hydrogen, halogen, optionally substituted $C_{1-6}$ aliphatic, optionally substituted phenyl, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur;

each R is independently hydrogen, optionally substituted $C_{1-6}$ aliphatic, optionally substituted 3- to 7-membered saturated or partially unsaturated carbocyclyl, or optionally substituted 3- to 7-membered saturated or partially unsaturated monocyclic heterocyclyl having 1-3 heteroatoms independently selected from nitrogen, oxygen, and sulfur, or two R when attached to the same nitrogen atom are taken together form a 3- to 7-membered saturated or partially unsaturated monocyclic heterocyclyl having 0-2 additional heteroatoms independently selected from nitrogen, oxygen, and sulfur; and each R' is independently optionally substituted $C_{1-6}$ aliphatic or optionally substituted 3- to 7-membered saturated or partially unsaturated carbocyclyl.

In some embodiments, the present disclosure provides a compound of Formula I:

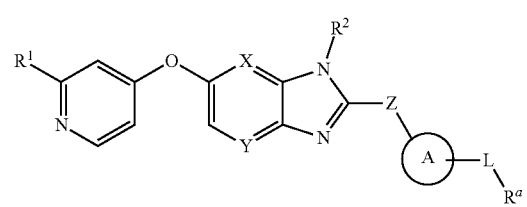

or a pharmaceutically acceptable salt thereof, wherein:
X is $CR^x$ or N;
Y is $CR^y$ or N;
Z is —O— or —$NR^z$—;
$R^x$ and $R^y$ are each independently hydrogen, optionally substituted $C_{1-6}$ aliphatic, or —CN;
$R^z$ is hydrogen or optionally substituted $C_{1-6}$ aliphatic;
$R^1$ is —$N(R)_2$, —N(R)C(O)R', —C(O)N(R)$_2$, or —N(R)C(O)N(R)$_2$;
$R^2$ is optionally substituted $C_{1-6}$ aliphatic;
Ring A is optionally substituted phenyl, optionally substituted 5- to 6-membered monocyclic heteroaryl having 1-4 heteroatoms independently selected from nitrogen, oxygen, and sulfur, optionally substituted 8- to 10-membered bicyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur;
L is a covalent bond or a bivalent $C_{1-3}$ straight or branched hydrocarbon chain;
$R^a$ is hydrogen, halogen, optionally substituted $C_{1-6}$ aliphatic, optionally substituted phenyl, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur;

each R is independently hydrogen, optionally substituted C$_{1-6}$ aliphatic, optionally substituted 3- to 7-membered saturated or partially unsaturated carbocyclyl, or optionally substituted 3- to 7-membered saturated or partially unsaturated monocyclic heterocyclyl having 1-3 heteroatoms independently selected from nitrogen, oxygen, and sulfur, or two R when attached to the same nitrogen atom are taken together form a 3- to 7-membered saturated or partially unsaturated monocyclic heterocyclyl having 0-2 additional heteroatoms independently selected from nitrogen, oxygen, and sulfur; and each R' is independently optionally substituted C$_{1-6}$ aliphatic or optionally substituted 3- to 7-membered saturated or partially unsaturated carbocyclyl.

In some embodiments, the present disclosure provides a compound of Formula II:

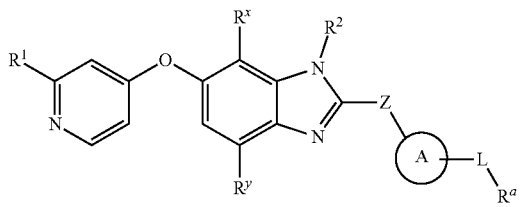

II or a pharmaceutically acceptable salt thereof, wherein Ring A, L, Z, R$^1$, R$^2$, R$^a$, R$^x$, and R$^y$ are as defined above for Formula I-1 and described in classes and subclasses herein, both singly and in combination. In some embodiments, Ring A, L, Z, R$^1$, R$^2$, R$^a$, and R$^y$ are as defined above for Formula I.

In some embodiments, the present disclosure provides a compound of Formula III:

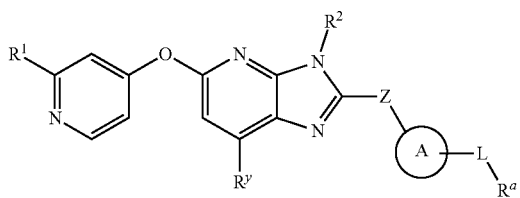

III or a pharmaceutically acceptable salt thereof, wherein Ring A, L, Z, R$^1$, R$^2$, R$^a$, R$^x$, and R$^y$ are as defined above for Formula I-1 and described in classes and subclasses herein, both singly and in combination. In some embodiments, Ring A, L, Z, R$^1$, R$^2$, R$^a$, R$^x$, and R$^y$ are as defined above for Formula I.

In some embodiments, the present disclosure provides a compound of Formula IV:

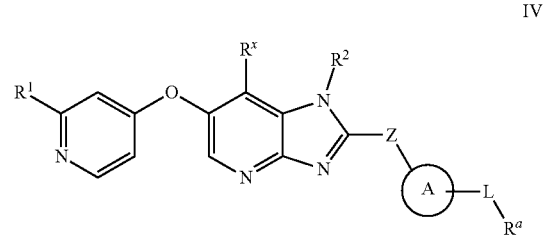

IV or a pharmaceutically acceptable salt thereof, wherein Ring A, L, Z, R$^1$, R$^2$, R$^a$, and R$^x$ are as defined above for Formula I-1 and described in classes and subclasses herein, both singly and in combination. In some embodiments, Ring A, L, Z, R$^1$, R$^2$, R$^a$, and R$^x$ are as defined above for Formula I.

In some embodiments, the present disclosure provides a compound of Formula I':

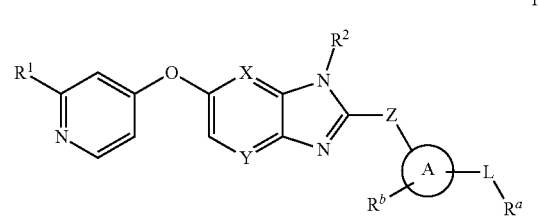

I' or a pharmaceutically acceptable salt thereof, wherein Ring A, L, Z, R$^1$, R$^2$, R$^a$, X, and Y are as defined above for Formula I-1 and described in classes and subclasses herein, both singly and in combination; and R$^b$ is hydrogen, halogen, —CN, —OR, —SR, —N(R)$_2$, —NO$_2$, —C(O)R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R', —SO$_2$N(R)$_2$, —SO$_3$R', optionally substituted C$_{1-6}$ aliphatic, optionally substituted 3- to 6-membered saturated or partially unsaturated carbocyclyl, optionally substituted 3- to 6-membered saturated or partially unsaturated monocyclic heterocyclyl having 1-3 heteroatoms independently selected from nitrogen, oxygen, and sulfur, optionally substituted 5- to 6-membered monocyclic heteroaryl having 1-4 heteroatoms independently selected from nitrogen, oxygen, and sulfur.

In some embodiments of Formula I', Ring A, L, Z, R$^1$, R$^2$, R$^a$, X, and Y are as defined above for Formula I, and R$^b$ is as defined above for Formula I'.

In some embodiments, the present disclosure provides a compound of Formula II':

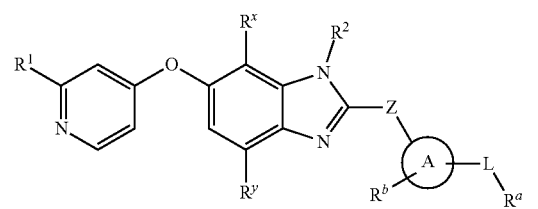

II' or a pharmaceutically acceptable salt thereof, wherein Ring A, L, Z, $R^1$, $R^2$, $R^a$, $R^x$, and $R^y$ are as defined above for Formula I-1 and $R^b$ is as defined above for Formula I', and described in classes and subclasses herein, both singly and in combination. In some embodiments, Ring A, L, Z, $R^1$, $R^2$, $R^a$, $R^x$, and $R^y$ are as defined above for Formula I and $R^b$ is as defined above for Formula I'.

In some embodiments, the present disclosure provides a compound of Formula III':

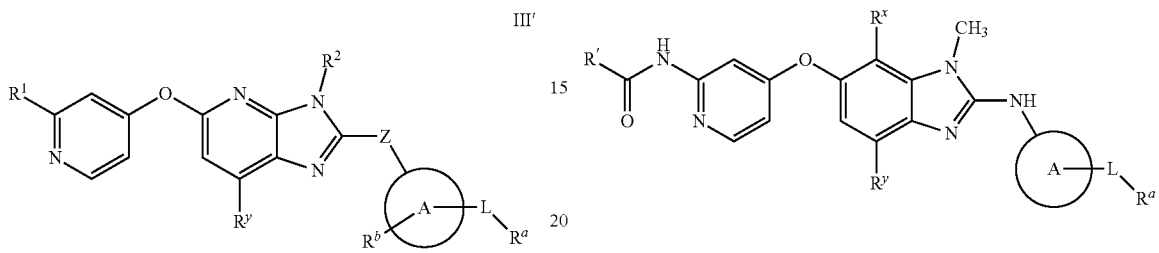

III' or a pharmaceutically acceptable salt thereof, wherein Ring A, L, Z, $R^1$, $R^2$, $R^a$, $R^x$, and $R^y$ are as defined above for Formula I-1 and $R^b$ is as defined above for Formula I', and described in classes and subclasses herein, both singly and in combination. In some embodiments, Ring A, L, Z, $R^1$, $R^2$, $R^a$, $R^x$, and $R^y$ are as defined above for Formula I and $R^b$ is as defined above for Formula I'.

In some embodiments, the present disclosure provides a compound of Formula IV':

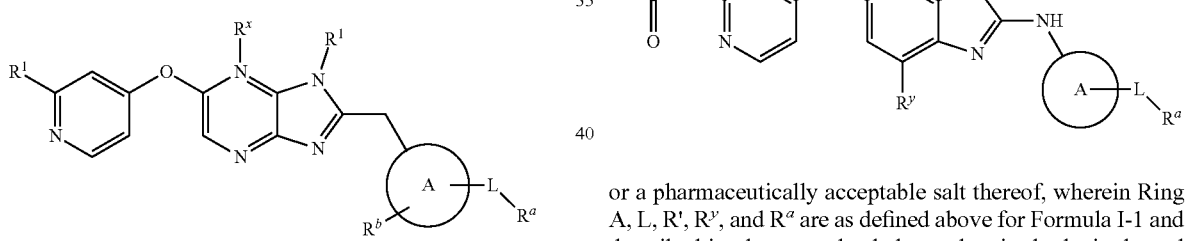

IV' or a pharmaceutically acceptable salt thereof, wherein Ring A, L, Z, $R^1$, $R^2$, $R^a$, and $R^x$ are as defined above for Formula I-1 and $R^b$ is as defined above for Formula I', and described in classes and subclasses herein, both singly and in combination. In some embodiments, Ring A, L, Z, $R^1$, $R^2$, $R^a$, and $R^x$ are as defined above for Formula I and $R^b$ is as defined above for Formula I'.

In some embodiments, the present disclosure provides a compound of Formula I-A:

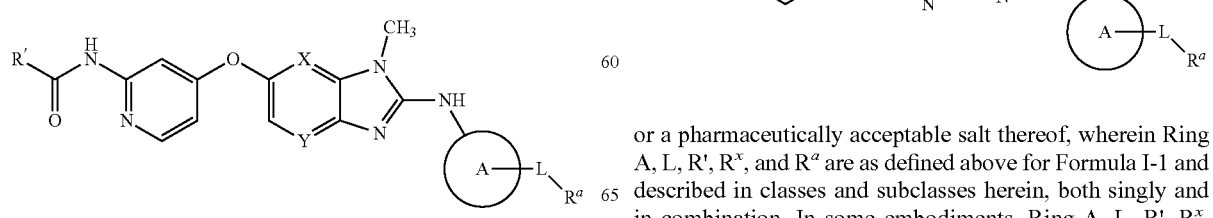

I-A or a pharmaceutically acceptable salt thereof, wherein Ring A, L, X, Y, R', and $R^a$ are as defined above for Formula I-1 and described in classes and subclasses herein, both singly and in combination. In some embodiments, Ring A, L, X, Y, R', and $R^a$ are as defined above for Formula I.

In some embodiments, the present disclosure provides a compound of Formula II-A:

II-A or a pharmaceutically acceptable salt thereof, wherein Ring A, L, R', $R^x$, $R^y$, and $R^a$ are as defined above for Formula I-1 and described in classes and subclasses herein, both singly and in combination. In some embodiments, Ring A, L, R', $R^x$, $R^y$, and $R^a$ are as defined above for Formula I.

In some embodiments, the present disclosure provides a compound of Formula III-A:

III-A or a pharmaceutically acceptable salt thereof, wherein Ring A, L, R', $R^y$, and $R^a$ are as defined above for Formula I-1 and described in classes and subclasses herein, both singly and in combination. In some embodiments, Ring A, L, R', $R^y$, and $R^a$ are as defined above for Formula I.

In some embodiments, the present disclosure provides a compound of Formula IV-A:

IV-A or a pharmaceutically acceptable salt thereof, wherein Ring A, L, R', $R^x$, and $R^a$ are as defined above for Formula I-1 and described in classes and subclasses herein, both singly and in combination. In some embodiments, Ring A, L, R', $R^x$, and $R^a$ are as defined above for Formula I.

In some embodiments, the present disclosure provides a compound of Formula I-B:

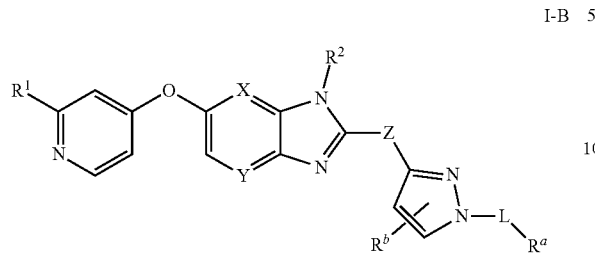

I-B or a pharmaceutically acceptable salt thereof, wherein L, X, Y, Z, $R^1$, $R^2$, and $R^a$ are as defined above for Formula I-1 and $R^b$ is as defined above for Formula I', and described in classes and subclasses herein, both singly and in combination. In some embodiments, L, X, Y, Z, $R^1$, $R^2$, and $R^a$ are as defined above for Formula I and $R^b$ is as defined above for Formula I'.

In some embodiments, the present disclosure provides a compound of Formula II-B:

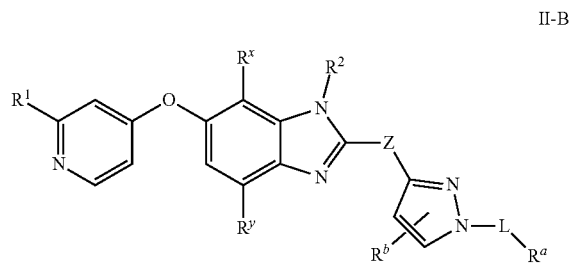

II-B or a pharmaceutically acceptable salt thereof, wherein L, Z, $R^1$, $R^2$, $R^x$, and $R^a$ are as defined above for Formula I-1 and $R^b$ is as defined above for Formula I', and described in classes and subclasses herein, both singly and in combination. In some embodiments, L, Z, $R^1$, $R^2$, $R^x$, $R^y$, and $R^a$ are as defined above for Formula I and $R^b$ is as defined above for Formula I'.

In some embodiments, the present disclosure provides a compound of Formula III-B:

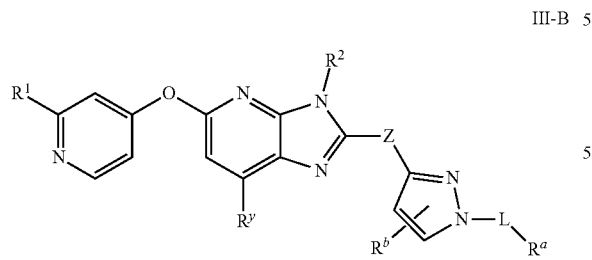

III-B or a pharmaceutically acceptable salt thereof, wherein L, Z, $R^1$, $R^2$, $R^y$, and $R^a$ are as defined above for Formula I-1 and $R^b$ is as defined above for Formula I', and described in classes and subclasses herein, both singly and in combination. In some embodiments, L, Z, $R^1$, $R^2$, $R^y$, and $R^a$ are as defined above for Formula I and $R^b$ is as defined above for Formula I'.

In some embodiments, the present disclosure provides a compound of Formula IV-B:

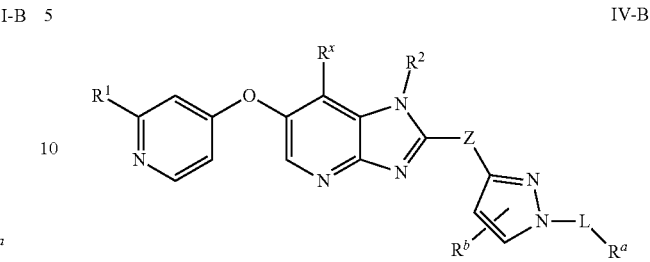

IV-B or a pharmaceutically acceptable salt thereof, wherein L, Z, $R^1$, $R^2$, $R^x$, and $R^a$ are as defined above for Formula I-1 and $R^b$ is as defined above for Formula I', and described in classes and subclasses herein, both singly and in combination. In some embodiments, L, Z, $R^1$, $R^2$, $R^x$, and $R^a$ are as defined above for Formula I and $R^b$ is as defined above for Formula I'.

In some embodiments, the present disclosure provides a compound of Formula I-C:

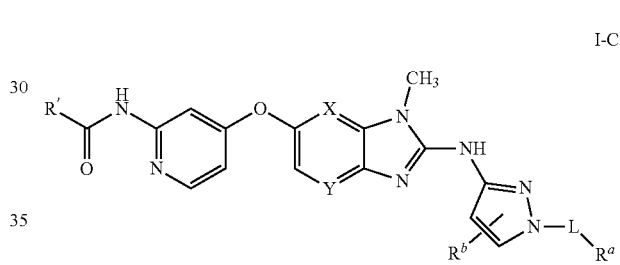

I-C or a pharmaceutically acceptable salt thereof, wherein L, X, Y, R', and $R^a$ are as defined above for Formula I-1 and $R^b$ is as defined above for Formula I', and described in classes and subclasses herein, both singly and in combination. In some embodiments, L, X, Y, R', and $R^a$ are as defined above for Formula I and $R^b$ is as defined above for Formula I'.

In some embodiments, the present disclosure provides a compound of Formula II-C:

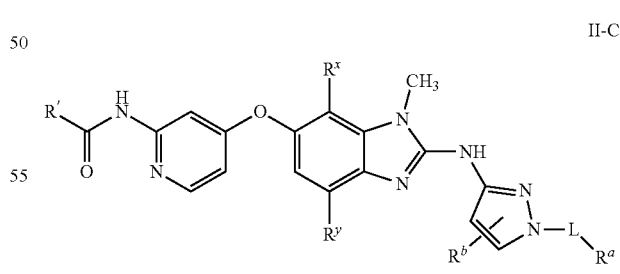

II-C or a pharmaceutically acceptable salt thereof, wherein L, R', $R^x$, $R^y$, and $R^a$ are as defined above for Formula I-1 and $R^b$ is as defined above for Formula I', and described in classes and subclasses herein, both singly and in combination. In some embodiments, L, R', $R^x$, $R^y$, and $R^a$ are as defined above for Formula I and $R^b$ is as defined above for Formula I'.

In some embodiments, the present disclosure provides a compound of Formula III-C:

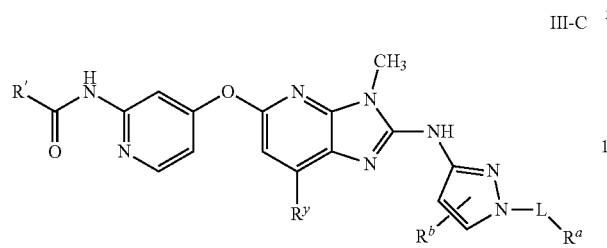

III-C or a pharmaceutically acceptable salt thereof, wherein L, R', $R^y$, and $R^a$ are as defined above for Formula I-1 and $R^b$ is as defined above for Formula I', and described in classes and subclasses herein, both singly and in combination. In some embodiments, L, R', $R^y$, and $R^a$ are as defined above for Formula I and $R^b$ is as defined above for Formula I'.

In some embodiments, the present disclosure provides a compound of Formula IV-C:

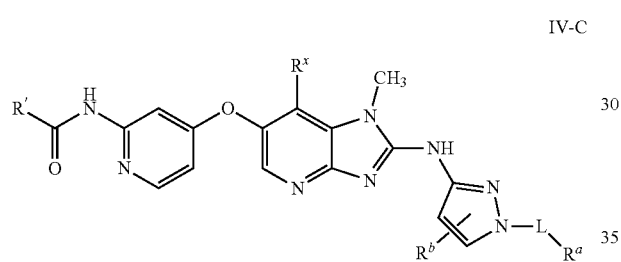

IV-C or a pharmaceutically acceptable salt thereof, wherein L, R', $R^x$, and $R^a$ are as defined above for Formula I-1 and $R^b$ is as defined above for Formula I', and described in classes and subclasses herein, both singly and in combination. In some embodiments, L, R', $R^x$, and $R^a$ are as defined above for Formula I and $R^b$ is as defined above for Formula I'.

In some embodiments, the present disclosure provides a compound of Formula I-D:

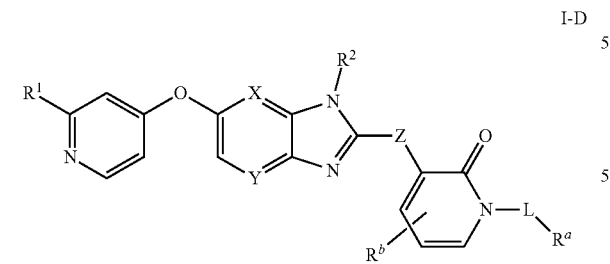

I-D or a pharmaceutically acceptable salt thereof, wherein L, X, Y, Z, $R^1$, $R^2$, and $R^a$ are as defined above for Formula I-1 and $R^b$ is as defined above for Formula I', and described in classes and subclasses herein, both singly and in combination. In some embodiments, L, X, Y, Z, $R^1$, $R^2$, and $R^a$ are as defined above for Formula I and $R^b$ is as defined above for Formula I'.

In some embodiments, the present disclosure provides a compound of Formula II-D:

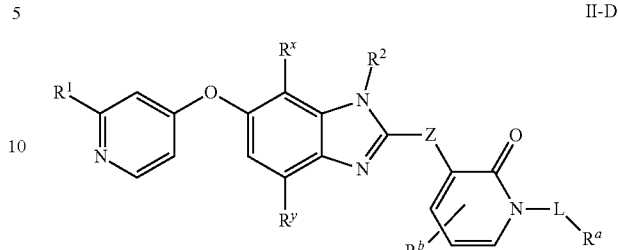

II-D or a pharmaceutically acceptable salt thereof, wherein L, Z, $R^x$, $R^y$, $R^1$, $R^2$, and $R^a$ are as defined above for Formula I-1 and $R^b$ is as defined above for Formula I', and described in classes and subclasses herein, both singly and in combination. In some embodiments, L, Z, $R^x$, $R^y$, $R^1$, $R^2$, and $R^a$ are as defined above for Formula I and $R^b$ is as defined above for Formula I'.

In some embodiments, the present disclosure provides a compound of Formula III-D:

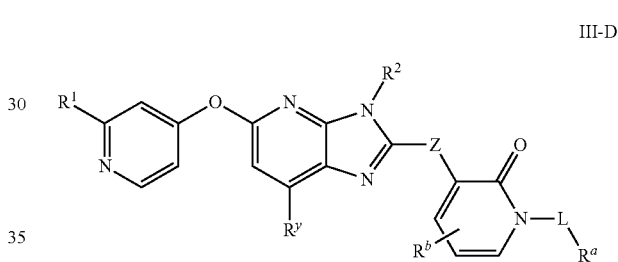

III-D or a pharmaceutically acceptable salt thereof, wherein L, Z, $R^y$, $R^1$, $R^2$, and $R^a$ are as defined above for Formula I-1 and $R^b$ is as defined above for Formula I', and described in classes and subclasses herein, both singly and in combination. In some embodiments, L, Z, $R^y$, $R^1$, $R^2$, and $R^a$ are as defined above for Formula I and $R^b$ is as defined above for Formula I'.

In some embodiments, the present disclosure provides a compound of Formula IV-D:

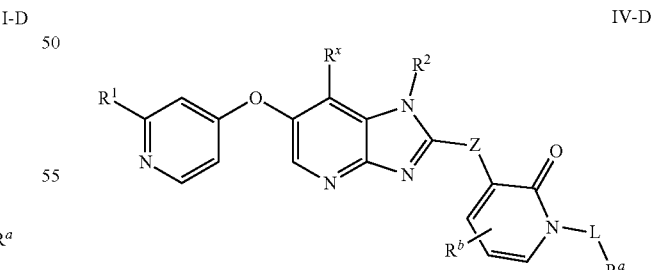

IV-D or a pharmaceutically acceptable salt thereof, wherein L, Z, $R^x$, $R^1$, $R^2$, and $R^a$ are as defined above for Formula I-1 and $R^b$ is as defined above for Formula I', and described in classes and subclasses herein, both singly and in combination. In some embodiments, L, Z, $R^x$, $R^1$, $R^2$, and $R^a$ are as defined above for Formula I and $R^b$ is as defined above for Formula I'.

In some embodiments, the present disclosure provides a compound of Formula I-E:

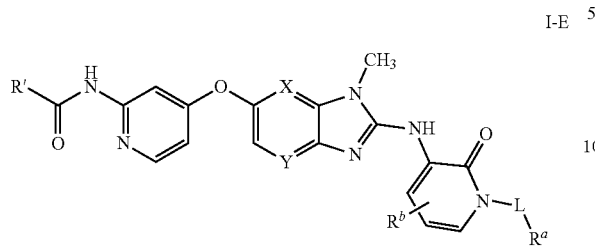

I-E or a pharmaceutically acceptable salt thereof, wherein L, X, Y, R', and $R^a$ are as defined above for Formula I-1 and $R^b$ is as defined above for Formula I', and described in classes and subclasses herein, both singly and in combination. In some embodiments, L, X, Y, R', and $R^a$ are as defined above for Formula I and $R^b$ is as defined above for Formula I'.

In some embodiments, the present disclosure provides a compound of Formula II-E:

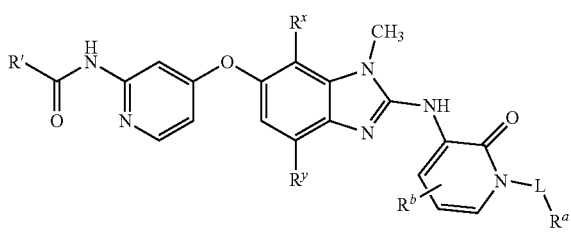

II-E or a pharmaceutically acceptable salt thereof, wherein L, R', $R^x$, $R^y$, and $R^a$ are as defined above for Formula I-1 and $R^b$ is as defined above for Formula I', and described in classes and subclasses herein, both singly and in combination. In some embodiments, L, R', $R^x$, $R^y$, and $R^a$ are as defined above for Formula I and $R^b$ is as defined above for Formula I'.

In some embodiments, the present disclosure provides a compound of Formula III-E:

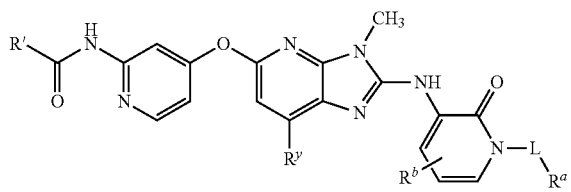

III-E or a pharmaceutically acceptable salt thereof, wherein L, R', $R^y$, and $R^a$ are as defined above for Formula I-1 and $R^b$ is as defined above for Formula I', and described in classes and subclasses herein, both singly and in combination. In some embodiments, L, R', $R^y$, and $R^a$ are as defined above for Formula I and $R^b$ is as defined above for Formula I'.

In some embodiments, the present disclosure provides a compound of Formula IV-E:

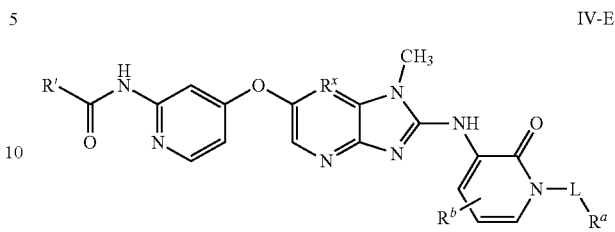

IV-E or a pharmaceutically acceptable salt thereof, wherein L, R', $R^x$, and $R^a$ are as defined above for Formula I-1 and $R^b$ is as defined above for Formula I', and described in classes and subclasses herein, both singly and in combination. In some embodiments, L, R', $R^x$, and $R^a$ are as defined above for Formula I and $R^b$ is as defined above for Formula I'.

In some embodiments of Formulae I-1, W is $CR^w$. In some embodiments, W is N.

In some embodiments of any of Formulae I-1, I, I', I-A, I-B, I-C, I-D, and I-E, X is $CR^x$. In some embodiments, X is N.

In some embodiments of any of Formulae I-1, I, I', I-A, I-B, I-C, I-D, and I-E, Y is $CR^y$. In some embodiments, Y is N.

In some embodiments of Formulae I-1, W is $CR^w$ or N, X is $CR^x$ or N, and Y is $CR^y$ or N, and no more than one of W, X, and Y is N. In some embodiments of Formulae I-1, W is $CR^w$ or N, X is $CR^x$ or N, and Y is $CR^y$ or N, and no more than two of W, X, and Y is N.

In some embodiments of any of Formulae I-1, I, II, III, IV, I', II', III', IV', I-B, II-B, III-B, IB-B, I-D, II-D, III-D, and IV-D, Z is —O—. In some embodiments, Z is —$NR^z$—. In some embodiments Z is —NH—.

In some embodiments of any of Formulae I-1, $R^w$ is hydrogen, halogen, optionally substituted $C_{1-6}$ aliphatic, or —CN. In some embodiments, $R^w$ is hydrogen, optionally substituted $C_{1-6}$ aliphatic, or —CN. In some embodiments, $R^w$ is hydrogen or methyl. In some embodiments, $R^w$ is hydrogen, methyl, or —CN. In some embodiments, $R^w$ is hydrogen. In some embodiments, $R^w$ is halogen. In some embodiments, $R^w$ is fluoro. In some embodiments, $R^w$ is chloro. In some embodiments, $R^w$ is bromo. In some embodiments, $R^w$ is iodo. In some embodiments, $R^w$ is —$OR^3$. In some embodiments, $R^w$ is —$OR^3$, wherein $R^3$ is optionally substituted $C_{1-6}$ aliphatic. In some embodiments, Y is N, W is $CR^w$, and $R^w$ is —$OR^3$ wherein $R^3$ is optionally substituted $C_{1-6}$ aliphatic. In some embodiments, $R^w$ is —$N(R^3)_2$. In some embodiments, $R^w$ is —$SR^3$. In some embodiments, $R^w$ is —$SR^3$, wherein $R^3$ is optionally substituted $C_{1-6}$ aliphatic. In some embodiments, Y is N, W is $CR^w$, and $R^w$ is —$SR^3$ wherein $R^3$ is optionally substituted $C_{1-6}$ aliphatic. In some embodiments, $R^w$ is optionally substituted $C_{1-6}$ aliphatic. In some embodiments, $R^w$ is optionally substituted straight-chain or branched $C_{1-6}$ aliphatic (i.e., optionally substituted acyclic $C_{1-6}$ aliphatic). In some embodiments, $R^w$ is optionally substituted $C_{1-6}$ alkyl. In some embodiments, $R^w$ is optionally substituted $C_{1-4}$ alkyl. In some embodiments, $R^w$ is unsubstituted $C_{1-4}$ alkyl. In some embodiments, $R^w$ is optionally substituted $C_{1-2}$ alkyl. In some embodiments, $R^w$ is optionally substituted methyl (e.g., methyl optionally substituted with one or more fluoro). In some embodiments, $R^w$ is methyl. In some embodiments, $R^w$ is —CN.

In some embodiments of any of Formulae I-1, I, II, IV, I', II', IV', I-A, II-A, IV-A, I-B, II-B, IV-B, I-C, II-C, IV-C, I-D, II-D, IV-D, I-E, II-E, and IV-E, $R^x$ is hydrogen, halogen, optionally substituted $C_{1-6}$ aliphatic, or —CN. In some embodiments, $R^x$ is hydrogen, halogen, —OR³, optionally substituted $C_{1-6}$ aliphatic, or —CN. In some embodiments, $R^x$ is hydrogen, optionally substituted $C_{1-6}$ aliphatic, or —CN. In some embodiments, $R^x$ is halogen, —OR³, —N(R³)₂, —SR³, or —CN. In some embodiments, $R^x$ is halogen, —OR³, or —CN. In some embodiments, $R^x$ is hydrogen or methyl. In some embodiments, $R^x$ is hydrogen, methyl, or —CN. In some embodiments, $R^x$ is hydrogen. In some embodiments, $R^x$ is halogen. In some embodiments, $R^x$ is fluoro. In some embodiments, $R^x$ is chloro. In some embodiments, $R^x$ is bromo. In some embodiments, $R^x$ is iodo. In some embodiments, $R^x$ is —OR³. In some embodiments, $R^x$ is —OCH₃. In some embodiments, $R^x$ is —N(R³)₂. In some embodiments, $R^x$ is —SR³. In some embodiments, $R^x$ is optionally substituted $C_{1-6}$ aliphatic. In some embodiments, $R^x$ is optionally substituted straight-chain or branched $C_{1-6}$ aliphatic (i.e., optionally substituted acyclic $C_{1-6}$ aliphatic). In some embodiments, $R^x$ is optionally substituted $C_{1-6}$ alkyl. In some embodiments, $R^x$ is optionally substituted $C_{1-4}$ alkyl. In some embodiments, $R^x$ is unsubstituted $C_{1-4}$ alkyl. In some embodiments, $R^x$ is optionally substituted $C_{1-2}$ alkyl. In some embodiments, $R^x$ is ethyl. In some embodiments, $R^x$ is optionally substituted methyl (e.g., methyl optionally substituted with one or more fluoro, e.g., —CHF₂). In some embodiments, $R^x$ is methyl. In some embodiments, $R^x$ is —CN.

In some embodiments of any of Formulae I-1, I, II, III, I', II', III', I-A, II-A, III-A, I-B, II-B, III-B, I-C, II-C, III-C, I-D, II-D, III-D, I-E, II-E, and III-E, $R^y$ is hydrogen, halogen, optionally substituted $C_{1-6}$ aliphatic, or —CN. In some embodiments, $R^y$ is hydrogen, optionally substituted $C_{1-6}$ aliphatic, or —CN. In some embodiments, $R^y$ is hydrogen or methyl. In some embodiments, $R^y$ is hydrogen, methyl, or —CN. In some embodiments, $R^y$ is hydrogen. In some embodiments, $R^y$ is halogen. In some embodiments, $R^y$ is fluoro. In some embodiments, $R^y$ is chloro. In some embodiments, $R^y$ is bromo. In some embodiments, $R^y$ is iodo. In some embodiments, $R^y$ is —OR³. In some embodiments, $R^y$ is —OR³, wherein R³ is optionally substituted $C_{1-6}$ aliphatic. In some embodiments, W is N, Y is CR^y, and $R^y$ is —OR³ wherein R³ is optionally substituted $C_{1-6}$ aliphatic. In some embodiments, $R^y$ is —N(R³)₂. In some embodiments, $R^y$ is —SR³. In some embodiments, $R^y$ is —SR³, wherein R³ is optionally substituted $C_{1-6}$ aliphatic. In some embodiments, W is N, Y is CR^y, and $R^y$ is —SR³ wherein R³ is optionally substituted $C_{1-6}$ aliphatic. In some embodiments, $R^y$ is optionally substituted $C_{1-6}$ aliphatic. In some embodiments, $R^y$ is optionally substituted straight-chain or branched $C_{1-6}$ aliphatic (i.e., optionally substituted acyclic $C_{1-6}$ aliphatic). In some embodiments, $R^y$ is optionally substituted $C_{1-6}$ alkyl. In some embodiments, $R^y$ is optionally substituted $C_{1-4}$ alkyl. In some embodiments, $R^y$ is unsubstituted $C_{1-4}$ alkyl. In some embodiments, $R^y$ is optionally substituted $C_{1-2}$ alkyl. In some embodiments, $R^y$ is optionally substituted methyl (e.g., methyl optionally substituted with one or more fluoro). In some embodiments, $R^y$ is methyl. In some embodiments, $R^y$ is —CN.

In some embodiments of any of Formulae I-1, I, II, III, IV, I', II', III', IV', I-B, II-B, III-B, IV-B, I-D, II-D, III-D, IV-D, I-E, II-E, III-E, and IV-E, $R^z$ is hydrogen. In some embodiments, $R^z$ is optionally substituted $C_{1-6}$ aliphatic. In some embodiments, $R^z$ is optionally substituted straight-chain or branched $C_{1-6}$ aliphatic (i.e., optionally substituted acyclic $C_{1-6}$ aliphatic). In some embodiments, $R^z$ is optionally substituted $C_{1-6}$ alkyl. In some embodiments, $R^z$ is optionally substituted $C_{1-4}$ alkyl. In some embodiments, $R^z$ is unsubstituted $C_{1-4}$ alkyl. In some embodiments, $R^z$ is optionally substituted $C_{1-2}$ alkyl. In some embodiments, $R^z$ is unsubstituted $C_{1-2}$ alkyl.

In some embodiments of any of Formulae I-1, I, II, III, IV, I', II', III', IV', I-B, II-B, III-B, IV-B, I-D, II-D, III-D, and IV-D, $R^1$ is —N(R)C(O)R' or —C(O)N(R)₂. In some embodiments, $R^1$ is —N(R)C(O)R', —C(O)N(R)₂, or —N(R)C(O)N(R)₂. In some embodiments, $R^1$ is —N(R)C(O)R'. In some embodiments, $R^1$ is —N(H)C(O)R'. In some embodiments, $R^1$ is —N(R)C(O)(optionally substituted $C_{1-6}$ aliphatic). In some embodiments, $R^1$ is —N(H)C(O)(optionally substituted $C_{1-6}$ aliphatic). In some embodiments, $R^1$ is —N(R)C(O)R', wherein R' is $C_{1-6}$ aliphatic optionally substituted with —OC₁₋₆ alkyl or a 3- to 7-membered saturated monocyclic heterocyclyl having 1-2 heteroatoms independently selected from nitrogen, oxygen, and sulfur. In some embodiments, $R^1$ is —N(H)C(O)R', wherein R' is $C_{1-6}$ aliphatic optionally substituted with —OC₁₋₆ alkyl or a 3- to 7-membered saturated monocyclic heterocyclyl having 1-2 heteroatoms independently selected from nitrogen, oxygen, and sulfur. In some embodiments, $R^1$ is —N(R)C(O)($C_{1-6}$ aliphatic). In some embodiments, $R^1$ is —N(H)C(O)($C_{1-6}$ aliphatic). In some embodiments, $R^1$ is —N(R)C(O)(straight-chain or branched $C_{1-6}$ aliphatic). In some embodiments, $R^1$ is —N(H)C(O)(straight-chain or branched $C_{1-6}$ aliphatic). In some embodiments, $R^1$ is —N(R)C(O)(optionally substituted $C_{1-6}$ alkyl). In some embodiments, $R^1$ is —N(H)C(O)(optionally substituted $C_{1-6}$ alkyl). In some embodiments, $R^1$ is —N(R)C(O)R', wherein R' is $C_{1-6}$ alkyl optionally substituted with —OC₁₋₆ alkyl or a 3- to 7-membered saturated monocyclic heterocyclyl having 1-2 heteroatoms independently selected from nitrogen, oxygen, and sulfur. In some embodiments, $R^1$ is —N(H)C(O)R', wherein R' is $C_{1-6}$ alkyl optionally substituted with —OC₁₋₆ alkyl or a 3- to 7-membered saturated monocyclic heterocyclyl having 1-2 heteroatoms independently selected from nitrogen, oxygen, and sulfur. In some embodiments, $R^1$ is —N(R)C(O)($C_{1-6}$ alkyl). In some embodiments, $R^1$ is —N(H)C(O)($C_{1-6}$ alkyl). In some embodiments, $R^1$ is —N(R)C(O)(optionally substituted $C_{1-4}$ alkyl). In some embodiments, $R^1$ is —N(H)C(O)(optionally substituted $C_{1-4}$ alkyl). In some embodiments, $R^1$ is —N(R)C(O)R', wherein R' is $C_{1-4}$ alkyl optionally substituted with —OC₁₋₆ alkyl or a 3- to 7-membered saturated monocyclic heterocyclyl having 1-2 heteroatoms independently selected from nitrogen, oxygen, and sulfur. In some embodiments, $R^1$ is —N(H)C(O)R', wherein R' is $C_{1-4}$ alkyl optionally substituted with —OC₁₋₆ alkyl or a 3- to 7-membered saturated monocyclic heterocyclyl having 1-2 heteroatoms independently selected from nitrogen, oxygen, and sulfur. In some embodiments, $R^1$ is —N(R)C(O)($C_{1-4}$ alkyl). In some embodiments, $R^1$ is —N(H)C(O)($C_{1-4}$ alkyl). In some embodiments, $R^1$ is —N(R)C(O)(optionally substituted $C_{1-2}$ alkyl). In some embodiments, $R^1$ is —N(H)C(O)(optionally substituted $C_{1-2}$ alkyl). In some embodiments, $R^1$ is —N(R)C(O)R', wherein R' is $C_{1-2}$ alkyl optionally substituted with —OC₁₋₆ alkyl or a 3- to 7-membered saturated monocyclic heterocyclyl having 1-2 heteroatoms independently selected from nitrogen, oxygen, and sulfur. In some embodiments, $R^1$ is —N(H)C(O)R', wherein R' is $C_{1-2}$ alkyl optionally substituted with —OC₁₋₆ alkyl or a 3- to 7-membered saturated monocyclic heterocyclyl having 1-2 heteroatoms independently selected from nitrogen, oxygen, and sulfur. In some embodiments, $R^1$ is —N(R)C(O)($C_{1-2}$ alkyl). In some embodiments, $R^1$ is —N(H)C(O)($C_{1-2}$ alkyl). In some embodiments, $R^1$ is —N(R)C(O)CH₃. In some embodiments, $R^1$ is —N(H)C(O)CH₃. In some embodiments, $R^1$ is —N(R)C(O)(optionally substituted $C_{3-7}$ carbocyclyl). In some embodiments, $R^1$ is —N(H)C(O)(optionally substituted $C_{3-7}$ carbocyclyl). In some embodiments, $R^1$ is —N(R)C(O)(optionally substituted cyclopropyl). In some embodiments, $R^1$ is —N(H)C(O)(optionally substituted cyclopropyl). In some embodiments, $R^1$ is —N(R)C(O)CH$_3$ or —N(R)C(O)(cyclopropyl). In some embodiments, $R^1$ is $R^1$ is —N(H)C(O)CH$_3$ or —N(H)C(O)(cyclopropyl).

In some embodiments, $R^1$ is —C(O)N(R)$_2$. In some embodiments, $R^1$ is —C(O)N(R)(C$_{1-6}$ aliphatic). In some embodiments, $R^1$ is —C(O)N(H)(C$_{1-6}$ aliphatic). In some embodiments, $R^1$ is —C(O)N(R)(straight-chain or branched C$_{1-6}$ aliphatic). In some embodiments, $R^1$ is —C(O)N(H)(straight-chain or branched C$_{1-6}$ aliphatic). In some embodiments, $R^1$ is —C(O)N(R)(C$_{1-6}$ alkyl). In some embodiments, $R^1$ is —C(O)N(H)(C$_{1-6}$ alkyl). In some embodiments, $R^1$ is —C(O)N(R)(C$_{1-4}$ alkyl). In some embodiments, $R^1$ is —C(O)N(H)(C$_{1-4}$ alkyl). In some embodiments, $R^1$ is —C(O)N(R)(C$_{1-2}$ alkyl). In some embodiments, $R^1$ is —C(O)N(H)(C$_{1-2}$ alkyl). In some embodiments, $R^1$ is —C(O)N(R)CH$_3$. In some embodiments, $R^1$ is —C(O)N(H)(R).

In some embodiments, $R^1$ is —N(R)$_2$. In some embodiments, $R^1$ is —N(H)(R).

In some embodiments, $R^1$ is —N(R)C(O)N(R)$_2$. In some embodiments, $R^1$ is —N(R)C(O)N(R)$_2$, wherein the two R groups attached to the same nitrogen are taken together to form an optionally substituted 3- to 7-membered saturated or partially unsaturated monocyclic heterocyclyl having 0-2 additional heteroatoms independently selected from nitrogen, oxygen, and sulfur. In some embodiments, $R^1$ is —N(R)C(O)N(R)$_2$, wherein the two R groups attached to the same nitrogen are taken together to form a 3- to 7-membered saturated or partially unsaturated monocyclic heterocyclyl having 0-2 additional heteroatoms independently selected from nitrogen, oxygen, and sulfur optionally substituted with one or more halogen, C$_{1-6}$ alkyl, and —O(C$_{1-6}$ alkyl). In some embodiments, $R^1$ is —N(R)C(O)N(R)$_2$, wherein the two R groups attached to the same nitrogen are taken together to form an optionally substituted 3- to 5-membered saturated monocyclic heterocyclyl having 0-1 additional heteroatoms. In some embodiments, $R^1$ is —N(R)C(O)N(R)$_2$, wherein the two R groups attached to the same nitrogen are taken together to form an optionally substituted 4-membered saturated monocyclic heterocyclyl having 0-1 additional heteroatoms. In some embodiments, $R^1$ is —N(R)C(O)N(R)$_2$, wherein the two R groups attached to the same nitrogen are taken together to form a 3- to 5-membered saturated monocyclic heterocyclyl having 0-1 additional heteroatoms optionally substituted with one or more halogen, C$_{1-6}$ alkyl, and —O(C$_{1-6}$ alkyl). In some embodiments, $R^1$ is —N(R)C(O)N(R)$_2$, wherein the two R groups attached to the same nitrogen are taken together to form a 4-membered saturated monocyclic heterocyclyl having 0-1 additional heteroatoms optionally substituted with one or more halogen, C$_{1-6}$ alkyl, and —O(C$_{1-6}$ alkyl). In some embodiments, $R^1$ is —N(H)C(O)N(R)$_2$. In some embodiments, $R^1$ is —N(H)C(O)N(R)$_2$, wherein the two R groups attached to the same nitrogen are taken together to form an optionally substituted 3- to 7-membered saturated or partially unsaturated monocyclic heterocyclyl having 0-2 additional heteroatoms independently selected from nitrogen, oxygen, and sulfur. In some embodiments, $R^1$ is —N(H)C(O)N(R)$_2$, wherein the two R groups attached to the same nitrogen are taken together to form a 3- to 7-membered saturated or partially unsaturated monocyclic heterocyclyl having 0-2 additional heteroatoms independently selected from nitrogen, oxygen, and sulfur optionally substituted with one or more halogen, C$_{1-6}$ alkyl, and —O(C$_{1-6}$ alkyl). In some embodiments, $R^1$ is —N(H)C(O)N(R)$_2$, wherein the two R groups attached to the same nitrogen are taken together to form an optionally substituted 3- to 5-membered saturated monocyclic heterocyclyl having 0-1 additional heteroatoms. In some embodiments, $R^1$ is —N(H)C(O)N(R)$_2$, wherein the two R groups attached to the same nitrogen are taken together to form an optionally substituted 4-membered saturated monocyclic heterocyclyl having 0-1 additional heteroatoms. In some embodiments, $R^1$ is —N(H)C(O)N(R)$_2$, wherein the two R groups attached to the same nitrogen are taken together to form a 3- to 5-membered saturated monocyclic heterocyclyl having 0-1 additional heteroatoms optionally substituted with one or more halogen, C$_{1-6}$ alkyl, and —O(C$_{1-6}$ alkyl). In some embodiments, $R^1$ is —N(H)C(O)N(R)$_2$, wherein the two R groups attached to the same nitrogen are taken together to form a 4-membered saturated monocyclic heterocyclyl having 0-1 additional heteroatoms optionally substituted with one or more halogen, C$_{1-6}$ alkyl, and —O(C$_{1-6}$ alkyl). In some embodiments, $R^1$ is

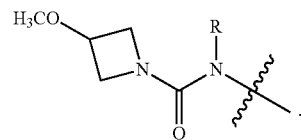

In some embodiments, $R^1$ is

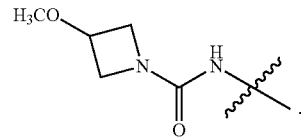 [SMILES: *NC(=O)N1CC(OC)C1]

In some embodiments, $R^1$ is selected from:

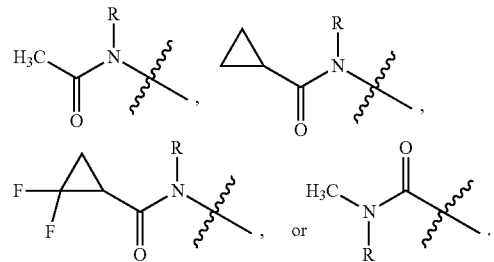

In some embodiments, $R^1$ is selected from:

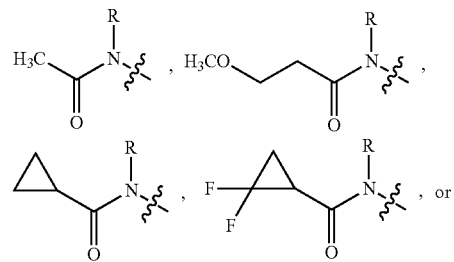

-continued
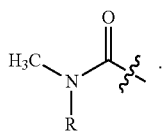
In some embodiments, $R^1$ is selected from:
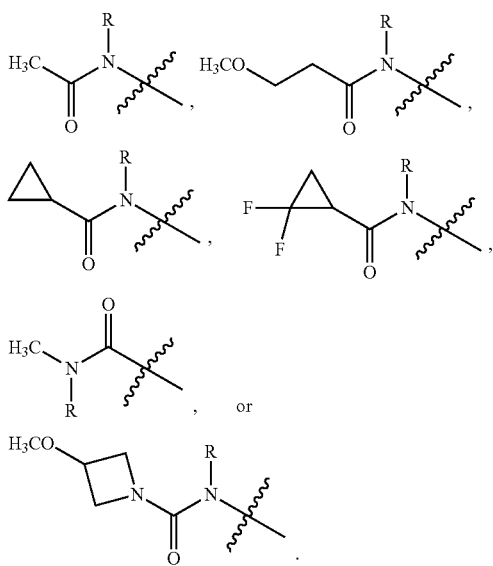
In some embodiments, $R^1$ is selected from:
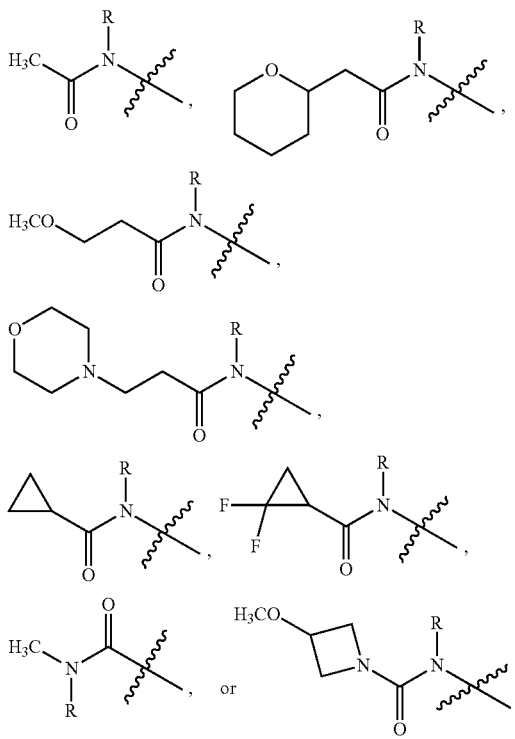
In some embodiments, $R^1$ is selected from:
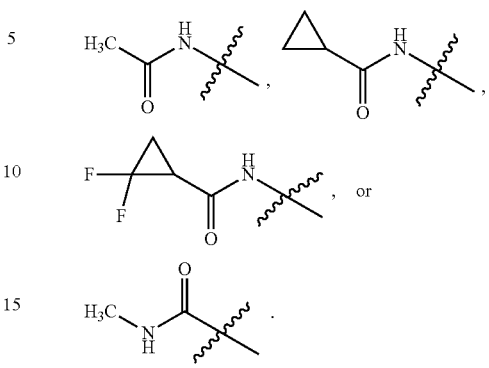
In some embodiments, $R^1$ is selected from:
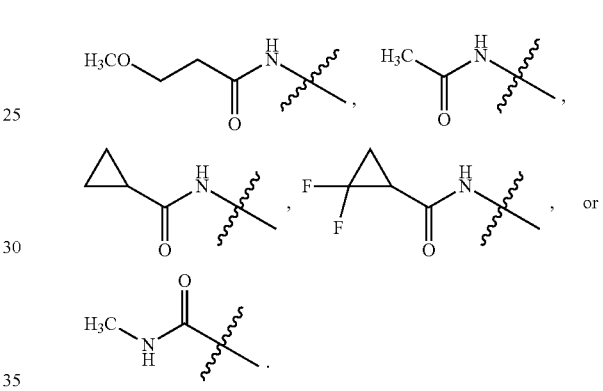
In some embodiments, $R^1$ is selected from:
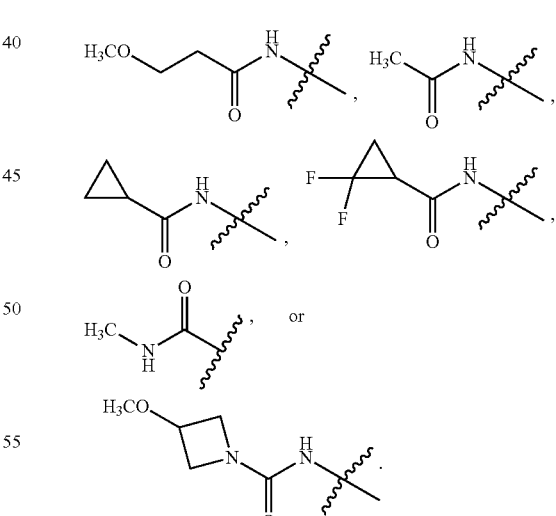
In some embodiments, $R^1$ is selected from:
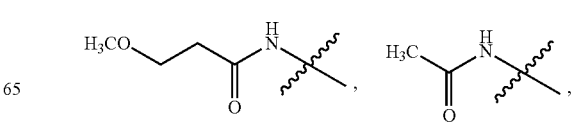

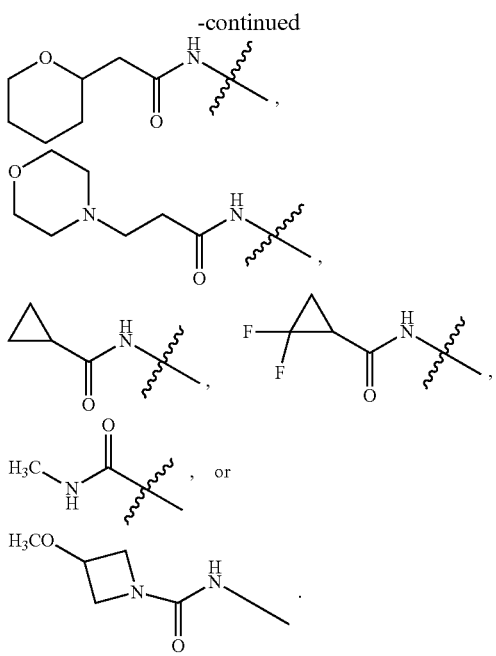

In some embodiments, $R^1$ is —C(O)N(H)CH$_3$.

In some embodiments of any of Formulae I-1, I, II, III, IV, I', II', III', IV', I-B, II-B, III-B, IV-B, I-D, II-D, III-D, and IV-D, $R^2$ is optionally substituted straight-chain or branched $C_{1-6}$ aliphatic (i.e., optionally substituted acyclic $C_{1-6}$ aliphatic). In some embodiments, $R^2$ is optionally substituted $C_{1-6}$ alkyl. In some embodiments, $R^2$ is optionally substituted $C_{1-4}$ alkyl. In some embodiments, $R^2$ is unsubstituted $C_{1-4}$ alkyl. In some embodiments, $R^2$ is optionally substituted $C_{1-2}$ alkyl. In some embodiments, $R^2$ is unsubstituted $C_{1-2}$ alkyl. In some embodiments, $R^2$ is methyl.

In some embodiments of any of Formulae I-1, I, II, III, IV, I', II', III', IV', I-A, II-A, III-A, IV-A, I-B, II-B, III-B, IV-B, I-C, II-C, III-C, IV-C, I-D, II-D, III-D, IV-D, I-E, II-E, III-E, and IV-E, each $R^3$ is independently hydrogen or optionally substituted $C_{1-4}$ aliphatic. In some embodiments, each $R^3$ is independently hydrogen or optionally substituted $C_{1-2}$ aliphatic. In some embodiments, each $R^3$ is hydrogen. In some embodiments, each $R^3$ is independently optionally substituted $C_{1-6}$ aliphatic. In some embodiments, each $R^3$ is independently optionally substituted straight-chain or branched $C_{1-6}$ aliphatic (i.e., optionally substituted acyclic $C_{1-6}$ aliphatic). In some embodiments, each $R^3$ is independently optionally substituted $C_{1-4}$ aliphatic. In some embodiments, each $R^3$ is independently optionally substituted straight-chain or branched $C_{1-4}$ aliphatic (i.e., optionally substituted acyclic $C_{1-4}$ aliphatic). In some embodiments, each $R^3$ is independently optionally substituted $C_{1-2}$ aliphatic. In some embodiments, each $R^3$ is methyl. In some embodiments, each $R^3$ is independently hydrogen or $C_{1-6}$ alkyl. In some embodiments, each $R^3$ is independently hydrogen or $C_{1-4}$ alkyl. In some embodiments, each $R^3$ is independently hydrogen or $C_{1-2}$ alkyl.

In some embodiments of any of Formulae I-1, I, II, III, IV, I', II', III', IV', I-A, II-A, III-A, and IV-A, Ring A is (i) optionally substituted on a substitutable carbon atom with one or more groups independently selected from oxo, halogen, R°, —CN, —OR°, —SR°, —N(R°)$_2$, —NO$_2$, —C(O)R°, —C(O)OR°, —C(O)NR°$_2$, —OC(O)R°, —OC(O)NR°$_2$, —OS(O)$_2$R°, —OS(O)$_2$NR°$_2$, —N(R°)C(O)R°, —N(R°)S(O)$_2$R°, —S(O)$_2$R°, and (ii) optionally substituted on a substitutable nitrogen atom with one or more groups selected from —R$^†$, —NR$^†_2$, —C(O)R$^†$, —C(O)OR$^†$, —S(O)$_2$R$^†$, —S(O)$_2$NR$^†_2$, and —S(O)$_2$OR°.

In some embodiments, Ring A is (i) optionally substituted on a substitutable carbon atom with one or more groups independently selected from oxo, halogen, R°, —CN, —OR°, —SR°, —N(R°)$_2$, —NO$_2$, —C(O)R°, —C(O)OR°, —C(O)NR°$_2$, —OC(O)R°, —OC(O)NR°$_2$, —OC(O)OR°, —OS(O)$_2$R°, —OS(O)$_2$NR°$_2$, —N(R°C)(O)R°, —N(R$^a$)S(O)$_2$R°, —S(O)$_2$R°, —SO$_2$NR°$_2$, and —S(O)$_2$OR°, and (ii) optionally substituted on a substitutable nitrogen atom with one or more groups selected from —R$^†$, —NR$^†_2$, —C(O)R$^†$, —C(O)OR$^†$, —S(O)$_2$†, and —S(O)$_2$NR$^†_2$. In some embodiments, Ring A is (i) optionally substituted on a substitutable carbon atom with one or more groups independently selected from oxo, halogen, and R°, and (ii) optionally substituted on a substitutable nitrogen atom with one or more groups selected from —R$^†$.

In some embodiments, Ring A is optionally substituted with one or more $R^b$ (i.e., in addition to being substituted with -L-R$^a$), wherein $R^b$ is as defined in Formula I' above and described in classes and subclasses herein. In some embodiments, Ring A is substituted with zero, one, two, three, four, or five $R^b$, as valency allows.

In some embodiments, Ring A is optionally substituted 5- to 6-membered monocyclic heteroaryl having 1-4 heteroatoms independently selected from nitrogen, oxygen, and sulfur, optionally substituted 8- to 10-membered bicyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur.

In some embodiments, Ring A is optionally substituted phenyl. In some embodiments, Ring A is not optionally substituted phenyl.

In some embodiments, Ring A is optionally substituted 5- to 6-membered monocyclic heteroaryl having 1-4 heteroatoms independently selected from nitrogen, oxygen, and sulfur. In some embodiments, Ring A is optionally substituted 5-membered monocyclic heteroaryl having 1-4 heteroatoms independently selected from nitrogen, oxygen, and sulfur. In some embodiments, Ring A is optionally substituted isoxazolyl or pyrazolyl. In some embodiments, Ring A is optionally substituted isoxazolyl, pyrazolyl, or thiazolyl. In some embodiments, Ring A is optionally substituted isoxazolyl, pyrazolyl, imidazolyl, or thiazolyl. In some embodiments, Ring A is optionally substituted 6-membered monocyclic heteroaryl having 1-4 heteroatoms independently selected from nitrogen, oxygen, and sulfur. In some embodiments, Ring A is optionally substituted pyridyl, pyridonyl, or pyridazinonyl.

In some embodiments, Ring A is optionally substituted 8- to 10-membered bicyclic heteroaryl having 1-4 heteroatoms independently selected from nitrogen, oxygen, and sulfur. In some embodiments, Ring A is optionally substituted 8-membered bicyclic heteroaryl having 1-4 heteroatoms independently selected from nitrogen, oxygen, and sulfur. In some embodiments, Ring A is optionally substituted 9-membered bicyclic heteroaryl having 1-4 heteroatoms independently selected from nitrogen, oxygen, and sulfur. In some embodiments, Ring A is optionally substituted 10-membered bicyclic heteroaryl having 1-4 heteroatoms independently selected from nitrogen, oxygen, and sulfur.

In some embodiments, Ring A is optionally substituted 3- to 7-membered saturated or partially unsaturated monocyclic carbocyclyl. In some embodiments, Ring A is optionally substituted 3-membered saturated or partially unsaturated monocyclic carbocyclyl. In some embodiments, Ring A is optionally substituted 4-membered saturated or partially unsaturated monocyclic carbocyclyl. In some embodiments, Ring A is optionally substituted 5-membered saturated or partially unsaturated monocyclic carbocyclyl. In some embodiments, Ring A is optionally substituted 6-membered saturated or partially unsaturated monocyclic carbocyclyl. In some embodiments, Ring A is optionally substituted cyclohexyl. In some embodiments, Ring A is optionally substituted 7-membered saturated or partially unsaturated monocyclic carbocyclyl.

In some embodiments, Ring A is optionally substituted 3- to 7-membered saturated or partially unsaturated monocyclic heterocyclyl having 1-3 heteroatoms independently selected from nitrogen, oxygen, and sulfur. In some embodiments, Ring A is optionally substituted 3-membered saturated or partially unsaturated monocyclic heterocyclyl having 1-2 heteroatoms independently selected from nitrogen, oxygen, and sulfur. In some embodiments, Ring A is optionally substituted 4-membered saturated or partially unsaturated monocyclic heterocyclyl having 1-3 heteroatoms independently selected from nitrogen, oxygen, and sulfur. In some embodiments, Ring A is optionally substituted 5-membered saturated or partially unsaturated monocyclic heterocyclyl having 1-3 heteroatoms independently selected from nitrogen, oxygen, and sulfur. In some embodiments, Ring A is optionally substituted 6-membered saturated or partially unsaturated monocyclic heterocyclyl having 1-3 heteroatoms independently selected from nitrogen, oxygen, and sulfur. In some embodiments, Ring A is optionally substituted 7-membered saturated or partially unsaturated monocyclic heterocyclyl having 1-3 heteroatoms independently selected from nitrogen, oxygen, and sulfur.

In some embodiments, Ring A is optionally substituted 7- to 10-membered saturated or partially unsaturated bicyclic heterocyclyl having 1-4 heteroatoms independently selected from nitrogen, oxygen, and sulfur. In some embodiments, Ring A is optionally substituted 7-membered saturated or partially unsaturated bicyclic heterocyclyl having 1-4 heteroatoms independently selected from nitrogen, oxygen, and sulfur. In some embodiments, Ring A is optionally substituted 8-membered saturated or partially unsaturated bicyclic heterocyclyl having 1-4 heteroatoms independently selected from nitrogen, oxygen, and sulfur. In some embodiments, Ring A is optionally substituted 9-membered saturated or partially unsaturated bicyclic heterocyclyl having 1-4 heteroatoms independently selected from nitrogen, oxygen, and sulfur. In some embodiments, Ring A is optionally substituted tetrahydrobenzo[d]thiazolyl, tetrahydropyrazole[1,5-a]pyridyl, isoindolinonyl, indolinonyl, or tetrahydroimidazo[1,2-a]pyridyl. In some embodiments, Ring A is optionally substituted 10-membered saturated or partially unsaturated bicyclic heterocyclyl having 1-4 heteroatoms independently selected from nitrogen, oxygen, and sulfur. In some embodiments, Ring A is optionally substituted tetrahydroisoquinolinyl.

In some embodiments of any of Formulae I-1, I, II, III, IV, I', II', III', IV', I-A, II-A, III-A, IV-A, I-B, II-B, III-B, IV-B, I-C, II-C, III-C, IV-C, I-D, II-D, III-D, IV-D, I-E, II-E, III-E, and IV-E, L is a covalent bond. In some embodiments, L is a bivalent $C_{1-3}$ straight or branched hydrocarbon chain. In some embodiments, L is a bivalent $C_{1-2}$ straight or branched hydrocarbon chain. In some embodiments, L is methylene (—CH$_2$—). In some embodiments, L is —CH$_2$CH$_2$—. In some embodiments, L is —CH$_2$CH$_2$CH$_2$—. In some embodiments, L is a covalent bond or —CH$_2$—.

In some embodiments of any of Formulae I-1, I, II, III, IV, I', II', III', IV', I-A, II-A, III-A, IV-A, I-B, II-B, III-B, IV-B, I-C, II-C, III-C, IV-C, I-D, II-D, III-D, IV-D, I-E, II-E, III-E, and IV-E, $R^a$ is halogen, optionally substituted $C_{1-6}$ aliphatic, optionally substituted phenyl, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur.

In some embodiments, $R^a$ is halogen, optionally substituted $C_{1-4}$ alkyl, optionally substituted 5-membered monocyclic heteroaryl having 1-4 heteroatoms independently selected from nitrogen, oxygen, and sulfur, optionally substituted 3- to 6-membered saturated monocyclic carbocyclyl, optionally substituted 3- to 6-membered saturated monocyclic heterocyclyl having 1-3 heteroatoms independently selected from nitrogen, oxygen, and sulfur, or optionally substituted 7-membered saturated, spirocyclic, bicyclic heterocyclyl having 1-4 heteroatoms independently selected from nitrogen, oxygen, and sulfur.

In some embodiments, $R^a$ is $C_{1-4}$ alkyl, 3- to 6-membered saturated monocyclic heterocyclyl having 1-2 heteroatoms independently selected from nitrogen, oxygen, and sulfur, or 7- to 8-membered saturated, spirocyclic, bicyclic heterocyclyl having 1-2 heteroatoms independently selected from nitrogen, oxygen, and sulfur.

In some embodiments, $R^a$ is hydrogen. In some embodiments, $R^a$ is not hydrogen.

In some embodiments, $R^a$ is halogen. In some embodiments, $R^a$ is fluoro, chloro, bromo, or iodo. In some embodiments, $R^a$ is fluoro. In some embodiments, $R^a$ is chloro. In some embodiments, $R^a$ is not halogen. In some embodiments, $R^a$ is not fluoro. In some embodiments, $R^a$ is not chloro.

In some embodiments, $R^a$ is optionally substituted $C_{1-6}$ aliphatic. In some embodiments, $R^a$ is optionally substituted straight-chain or branched $C_{1-6}$ aliphatic (i.e., optionally substituted acyclic $C_{1-6}$ aliphatic). In some embodiments, $R^a$ is $C_{1-6}$ aliphatic optionally substituted with one or more oxo, halogen, —CN, or —O(C$_{1-6}$ alkyl). In some embodiments, $R^a$ is $C_{1-6}$ aliphatic optionally substituted with one or more oxo, halogen, —CN, —OH, or —O(C$_{1-6}$ alkyl). In some embodiments, $R^a$ is $C_{1-6}$ aliphatic optionally substituted with one or more oxo, halogen, —CN, or —OCH$_3$. In some embodiments, $R^a$ is $C_{1-6}$ aliphatic optionally substituted with one or more oxo, halogen, —CN, —OH, or —OCH$_3$. In some embodiments, $R^a$ is optionally substituted $C_{1-6}$ alkyl. In some embodiments, $R^a$ is $C_{1-6}$ alkyl. In some embodiments, $R^a$ is $C_{1-6}$ alkyl optionally substituted with one or more oxo, halogen, —CN, or —OCH$_3$. In some embodiments, $R^a$ is $C_{1-6}$ alkyl optionally substituted with one or more oxo, halogen, —CN, —OH, or —O(C$_{1-6}$ alkyl) (e.g., —OCH$_3$). In some embodiments, $R^a$ is optionally substituted $C_{1-4}$ alkyl. In some embodiments, $R^a$ is $C_{1-4}$ alkyl. In some embodiments, $R^a$ is $C_{1-4}$ alkyl optionally substituted with one or more oxo, halogen, —CN, or —OCH₃. In some embodiments, R^a is C_{1-4} alkyl optionally substituted with one or more oxo, halogen, —CN, —OH, or —O(C_{1-6} alkyl) (e.g., —OCH₃). In some embodiments, R^a is optionally substituted C₁ alkyl (e.g., methyl). In some embodiments, R^a is methyl, —CF₃, or —CH₂OCH₃. In some embodiments, R^a is methyl, —CF₃, —CH₂OCH₃, or —CH₂CN. In some embodiments, R^a is optionally substituted C₂ alkyl. In some embodiments, R^a is —CH₂CH₂OCH₃, —CH₂CH₂OH, or —C(O)CH₃. In some embodiments, R^a is —CH₂CH₂OCH₃, —CH₂CH₂OH, —C(O)CH₃—CH₂CH₂F, —CH₂CHF₂, or —CH₂CH₂CN. In some embodiments, R^a is optionally substituted C₃ alkyl. In some embodiments, R^a is isopropyl or —C(CH₃)₂CN. In some embodiments, R^a is isopropyl, —C(CH₃)₂CN, or —CH₂CH(OH)CH₃. In some embodiments, R^a is optionally substituted C₄ alkyl. In some embodiments, R^a is tert-butyl. In some embodiments, R^a is tert-butyl or —CH₂CH(CH₃)CH₂OH. In some embodiments, R^a is not —CF₃.

In some embodiments, R^a is optionally substituted phenyl.

In some embodiments, R^a is optionally substituted 5- to 6-membered monocyclic heteroaryl having 1-4 heteroatoms independently selected from nitrogen, oxygen, and sulfur. In some embodiments, R^a is optionally substituted 5-membered monocyclic heteroaryl having 1-4 heteroatoms independently selected from nitrogen, oxygen, and sulfur. In some embodiments, R^a is 5-membered monocyclic heteroaryl having 1-4 heteroatoms independently selected from nitrogen, oxygen, and sulfur optionally substituted with one or more C_{1-6} alkyl (e.g., methyl). In some embodiments, R^a is optionally substituted imidazolyl, pyrazolyl, or oxazolyl. In some embodiments, R^a is imidazolyl, pyrazolyl, or oxazolyl optionally substituted with one or more C_{1-6} alkyl (e.g., methyl). In some embodiments, R^a is optionally substituted

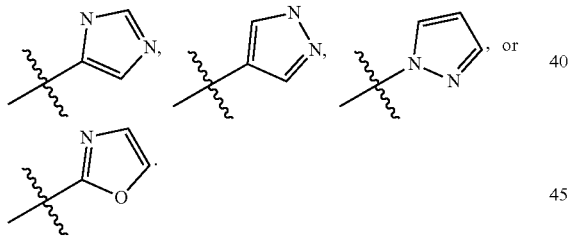

In some embodiments, R^a is

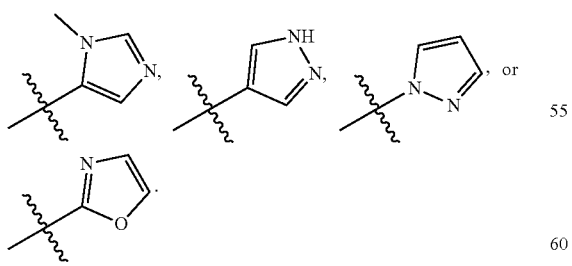

In some embodiments, R^a is optionally substituted 6-membered monocyclic heteroaryl having 1-4 heteroatoms independently selected from nitrogen, oxygen, and sulfur.

In some embodiments, R^a is optionally substituted 3- to 7-membered saturated or partially unsaturated monocyclic carbocyclyl. In some embodiments, R^a is 3- to 7-membered saturated or partially unsaturated monocyclic carbocyclyl optionally substituted with one or more —(C_{1-6} alkylene)OH, —CN, —OH, or —O(C_{1-6} alkyl). In some embodiments, R^a is 3- to 7-membered saturated or partially unsaturated monocyclic carbocyclyl optionally substituted with one or more —CH₂OH, —CN, —OH, or —OCH₃. In some embodiments, R^a is optionally substituted C_{3-6} cycloalkyl. In some embodiments, R^a is C_{3-6} cycloalkyl optionally substituted with one or more —(C_{1-6} alkylene)OH, —CN, —OH, or —O(C_{1-6} alkyl). In some embodiments, R^a is C_{3-6} cycloalkyl optionally substituted with one or more —CH₂OH, —CN, —OH, or —OCH₃. In some embodiments, R^a is optionally substituted C₃ cycloalkyl. In some embodiments, R^a is

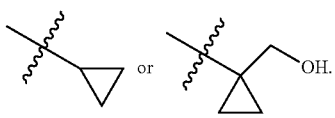

In some embodiments, R^a is optionally substituted C₄ cycloalkyl. In some embodiments, R^a is

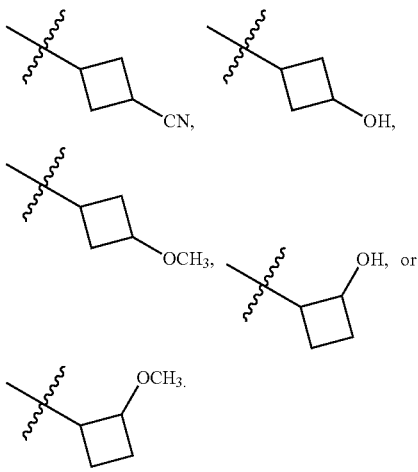

In some embodiments, R^a is

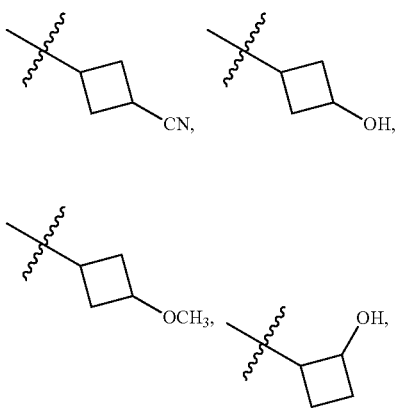

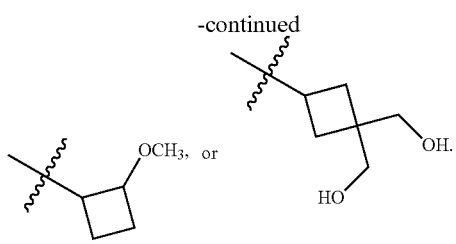

In some embodiments, $R^a$ is optionally substituted $C_5$ cycloalkyl. In some embodiments, $R^a$ is

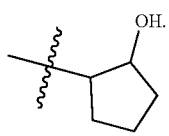 [SMILES: *C1CCCC1O]

In some embodiments, $R^a$ is optionally substituted $C_6$ cycloalkyl. In some embodiments, $R^a$ is

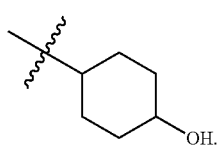 [SMILES: *C1CCC(O)CC1]

In some embodiments, $R^a$ is optionally substituted 3- to 7-membered saturated or partially unsaturated monocyclic heterocyclyl having 1-3 heteroatoms independently selected from nitrogen, oxygen, and sulfur. In some embodiments, $R^a$ is 3- to 7-membered saturated or partially unsaturated monocyclic heterocyclyl having 1-3 heteroatoms independently selected from nitrogen, oxygen, and sulfur optionally substituted with one or more oxo, $C_{1-4}$ alkyl, —C(O)($C_{1-4}$ alkyl), or —O($C_{1-4}$ alkyl). In some embodiments, $R^a$ is 3- to 7-membered saturated or partially unsaturated monocyclic heterocyclyl having 1-3 heteroatoms independently selected from nitrogen, oxygen, and sulfur optionally substituted with one or more oxo, $C_{1-4}$ alkyl optionally substituted with one or more halogen, —C(O)($C_{1-4}$ alkyl), or —O($C_{1-4}$ alkyl). In some embodiments, $R^a$ is 3- to 7-membered saturated or partially unsaturated monocyclic heterocyclyl having 1-3 heteroatoms independently selected from nitrogen, oxygen, and sulfur optionally substituted with one or more oxo, halogen, —C(O)($C_{1-4}$ alkyl), —O($C_{1-4}$ alkyl), or $C_{1-4}$ alkyl optionally substituted with one or more halogen and —O($C_{1-4}$ alkyl). In some embodiments, $R^a$ is 3- to 7-membered saturated or partially unsaturated monocyclic heterocyclyl having 1-3 heteroatoms independently selected from nitrogen, oxygen, and sulfur optionally substituted with one or more oxo, $C_{1-2}$ alkyl, —C(O)CH$_3$, or —OCH$_3$. In some embodiments, $R^a$ is 3- to 7-membered saturated or partially unsaturated monocyclic heterocyclyl having 1-3 heteroatoms independently selected from nitrogen, oxygen, and sulfur optionally substituted with one or more oxo, $C_{1-2}$ alkyl optionally substituted with one or more fluoro, —C(O)CH$_3$, or —OCH$_3$. In some embodiments, $R^a$ is 3- to 7-membered saturated or partially unsaturated monocyclic heterocyclyl having 1-3 heteroatoms independently selected from nitrogen, oxygen, and sulfur optionally substituted with one or more oxo, fluoro, —C(O)CH$_3$, —OCH$_3$, or $C_{1-2}$ alkyl optionally substituted with one or more fluoro and —OCH$_3$.

In some embodiments, $R^a$ is optionally substituted 3- to 6-membered saturated monocyclic heterocyclyl having 1-3 heteroatoms independently selected from nitrogen, oxygen, and sulfur. In some embodiments, $R^a$ is 3- to 6-membered saturated monocyclic heterocyclyl having 1-3 heteroatoms independently selected from nitrogen, oxygen, and sulfur optionally substituted with one or more oxo, $C_{1-4}$ alkyl, —C(O)($C_{1-4}$ alkyl), or —O($C_{1-4}$ alkyl). In some embodiments, $R^a$ is 3- to 6-membered saturated monocyclic heterocyclyl having 1-3 heteroatoms independently selected from nitrogen, oxygen, and sulfur optionally substituted with one or more oxo, $C_{1-4}$ alkyl optionally substituted with one or more halogen, —C(O)($C_{1-4}$ alkyl), or —O($C_{1-4}$ alkyl). In some embodiments, $R^a$ is 3- to 6-membered saturated monocyclic heterocyclyl having 1-3 heteroatoms independently selected from nitrogen, oxygen, and sulfur optionally substituted with one or more oxo, halogen, —C(O)($C_{1-4}$ alkyl), —O($C_{1-4}$ alkyl), or $C_{1-4}$ alkyl optionally substituted with one or more halogen and —O($C_{1-4}$ alkyl). In some embodiments, $R^a$ is 3- to 6-membered saturated monocyclic heterocyclyl having 1-3 heteroatoms independently selected from nitrogen, oxygen, and sulfur optionally substituted with one or more oxo, $C_{1-2}$ alkyl, —C(O)CH$_3$, or —OCH$_3$. In some embodiments, $R^a$ is 3- to 6-membered saturated monocyclic heterocyclyl having 1-3 heteroatoms independently selected from nitrogen, oxygen, and sulfur optionally substituted with one or more oxo, $C_{1-2}$ alkyl optionally substituted with one or more fluoro, —C(O)CH$_3$, or —OCH$_3$. In some embodiments, $R^a$ is 3- to 6-membered saturated monocyclic heterocyclyl having 1-3 heteroatoms independently selected from nitrogen, oxygen, and sulfur optionally substituted with one or more oxo, fluoro, —C(O)CH$_3$, —OCH$_3$, or $C_{1-2}$ alkyl optionally substituted with one or more fluoro and —OCH$_3$. In some embodiments, $R^a$ is 3- to 6-membered saturated monocyclic heterocyclyl having 1-3 heteroatoms independently selected from nitrogen, oxygen, and sulfur. In some embodiments, $R^a$ is 3- to 6-membered saturated monocyclic heterocyclyl having 1-2 heteroatoms independently selected from nitrogen, oxygen, and sulfur. In some embodiments, $R^a$ is optionally substituted 3-membered saturated monocyclic heterocyclyl having 1-3 heteroatoms independently selected from nitrogen, oxygen, and sulfur. In some embodiments, $R^a$ is optionally substituted 3-membered saturated monocyclic heterocyclyl having 1 heteroatom independently selected from nitrogen, oxygen, and sulfur. In some embodiments, $R^a$ is optionally substituted 4-membered saturated monocyclic heterocyclyl having 1-3 heteroatoms independently selected from nitrogen, oxygen, and sulfur. In some embodiments, $R^a$ is optionally substituted 4-membered saturated monocyclic heterocyclyl having 1 heteroatom independently selected from nitrogen, oxygen, and sulfur. In some embodiments, $R^a$ is optionally substituted azetidinyl or oxetanyl. In some embodiments, $R^a$ is

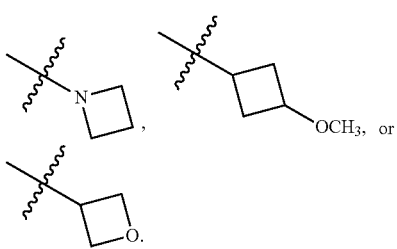

In some embodiments, $R^a$ is optionally substituted 5-membered saturated monocyclic heterocyclyl having 1-3 heteroatoms independently selected from nitrogen, oxygen, and sulfur. In some embodiments, $R^a$ is 5-membered saturated monocyclic heterocyclyl having 1 heteroatom independently selected from nitrogen, oxygen, and sulfur. In some embodiments, $R^a$ is optionally substituted pyrrolidinyl or tetrahydrofuranyl. In some embodiments, $R^a$ is

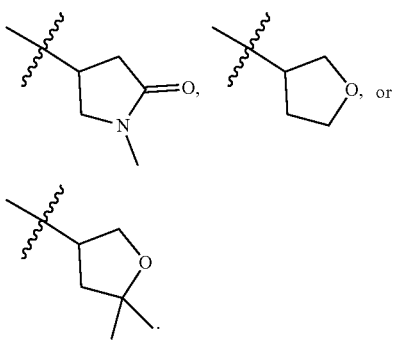

In some embodiments, $R^a$ is

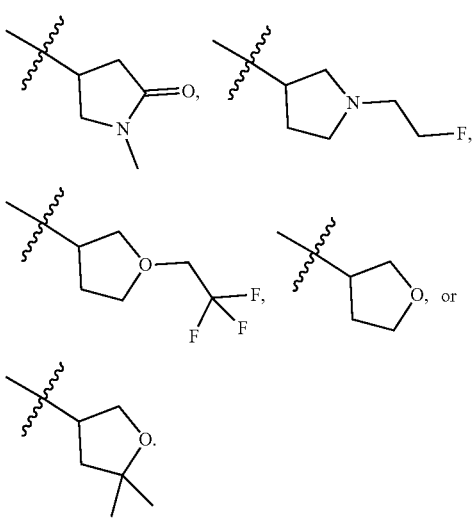

In some embodiments, $R^a$ is

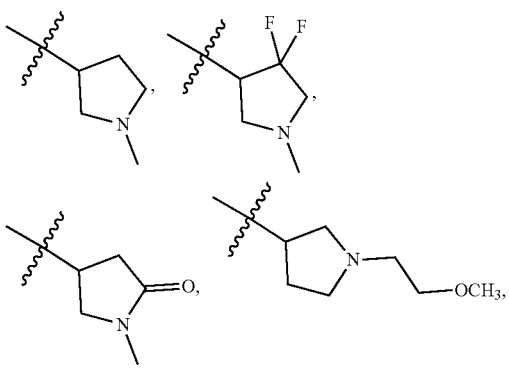

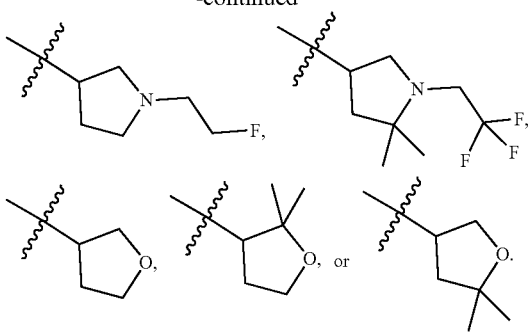

In some embodiments, $R^a$ is optionally substituted 6-membered saturated monocyclic heterocyclyl having 1-3 heteroatoms independently selected from nitrogen, oxygen, and sulfur. In some embodiments, $R^a$ is optionally substituted 6-membered saturated monocyclic heterocyclyl having 1-2 heteroatoms independently selected from nitrogen, oxygen, and sulfur. In some embodiments, $R^a$ is optionally substituted piperizinyl, morpholinyl, tetrahydropyranyl, or 1,4-dioxanyl. In some embodiments, $R^a$ is optionally substituted piperidinyl, piperizinyl, morpholinyl, tetrahydropyranyl, or 1,4-dioxanyl. In some embodiments, $R^a$ is

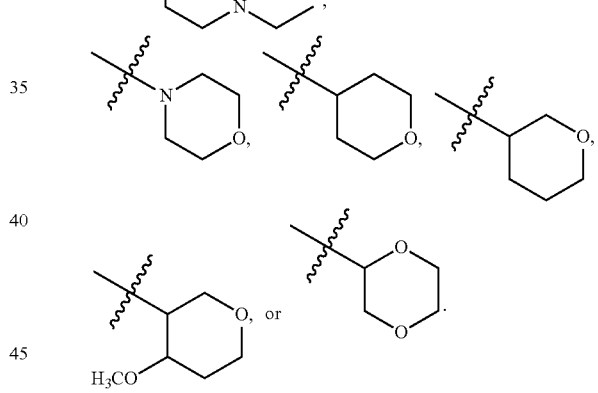

In some embodiments, $R^a$ is

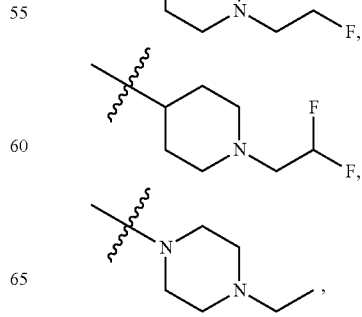

-continued

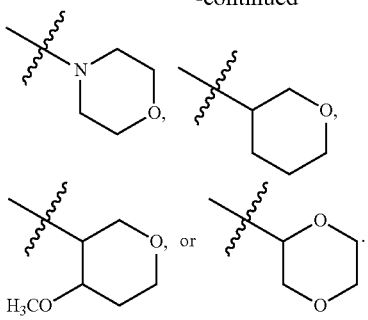

In some embodiments, $R^a$ is

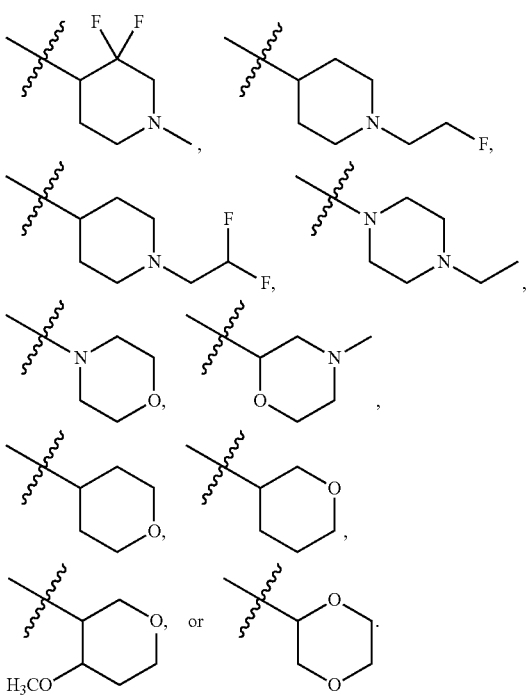

In some embodiments, $R^a$ is not

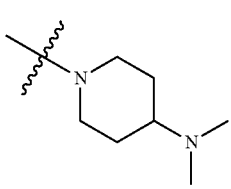 [SMILES: *N1CCC(N(C)C)CC1]

In some embodiments, $R^a$ is not

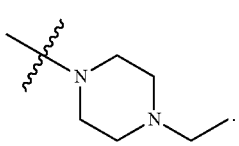 [SMILES: *N1CCN(CC)CC1]

In some embodiments, $R^a$ is optionally substituted 7- to 10-membered saturated or partially unsaturated bicyclic heterocyclyl having 1-4 heteroatoms independently selected from nitrogen, oxygen, and sulfur. In some embodiments, $R^a$ is 7- to 10-membered saturated or partially unsaturated bicyclic heterocyclyl having 1-4 heteroatoms independently selected from nitrogen, oxygen, and sulfur optionally substituted with one or more —C(O)(C$_{1-4}$ alkyl). In some embodiments, $R^a$ is 7- to 10-membered saturated or partially unsaturated bicyclic heterocyclyl having 1-4 heteroatoms independently selected from nitrogen, oxygen, and sulfur optionally substituted with one or more —C(O)CH$_3$. In some embodiments, $R^a$ is optionally substituted 7- to 10-membered saturated, spirocyclic, bicyclic heterocyclyl having 1-4 heteroatoms independently selected from nitrogen, oxygen, and sulfur. In some embodiments, $R^a$ is optionally substituted 7- to 8-membered saturated, spirocyclic, bicyclic heterocyclyl having 1-2 heteroatoms independently selected from nitrogen, oxygen, and sulfur. In some embodiments, $R^a$ is 7- to 8-membered saturated, spirocyclic, bicyclic heterocyclyl having 1-2 heteroatoms independently selected from nitrogen, oxygen, and sulfur. In some embodiments, $R^a$ is 7- to 10-membered saturated, spirocyclic, bicyclic heterocyclyl having 1-4 heteroatoms independently selected from nitrogen, oxygen, and sulfur optionally substituted with one or more —C(O)(C$_{1-4}$ alkyl). In some embodiments, $R^a$ is 7- to 10-membered saturated, spirocyclic, bicyclic heterocyclyl having 1-4 heteroatoms independently selected from nitrogen, oxygen, and sulfur optionally substituted with one or more —C(O)CH$_3$. In some embodiments $R^a$ is optionally substituted 7-membered saturated, spirocyclic, bicyclic heterocyclyl having 1-4 heteroatoms independently selected from nitrogen, oxygen, and sulfur. In some embodiments $R^a$ is optionally substituted 7-membered saturated, spirocyclic, bicyclic heterocyclyl having 1-2 heteroatoms independently selected from nitrogen, oxygen, and sulfur. In some embodiments, $R^a$ is optionally substituted 2-oxaspiro[3.3]heptanyl or 2-azaspiro[3.3]heptanyl. In some embodiments, $R^a$ is optionally substituted 2-oxaspiro[3.3]heptanyl, 2-azaspiro[3.3]heptanyl, or 4-oxaspiro[2.4]heptanyl. In some embodiments, $R^a$ is

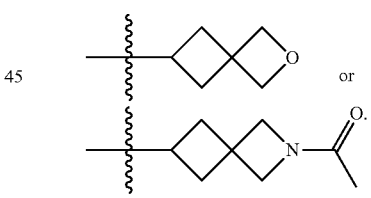

In some embodiments, $R^a$ is

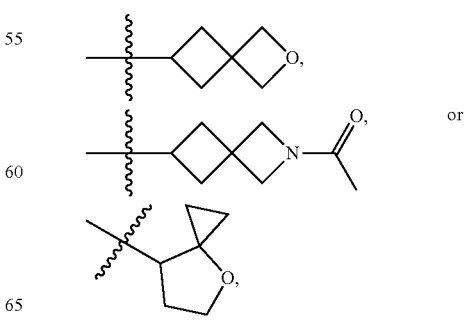

In some embodiments, $R^a$ is selected from the group consisting of:

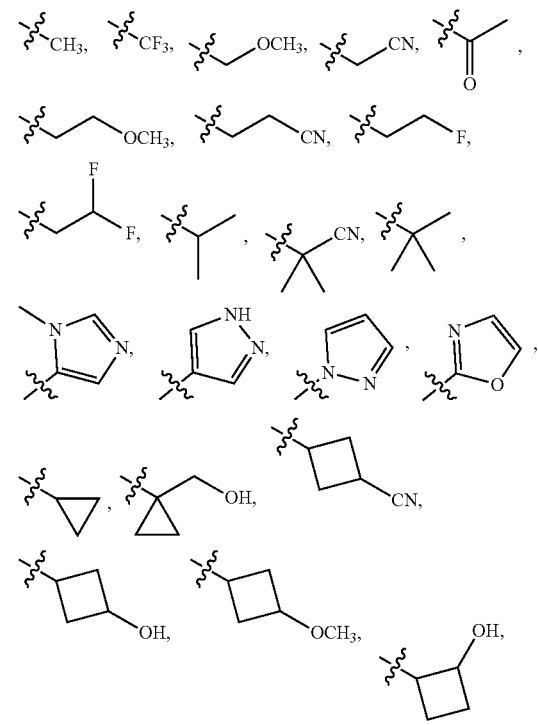
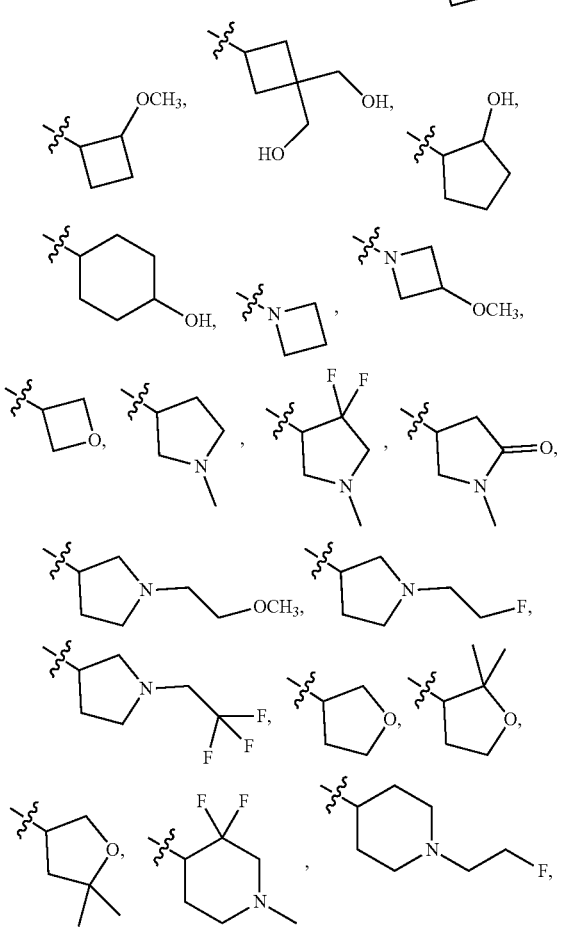
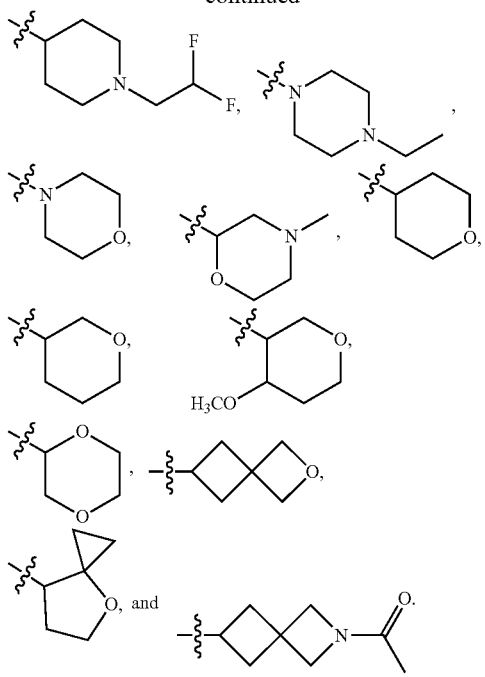

In some embodiments, $R^a$ is not fluoro, chloro, bromo, —$CF_3$,

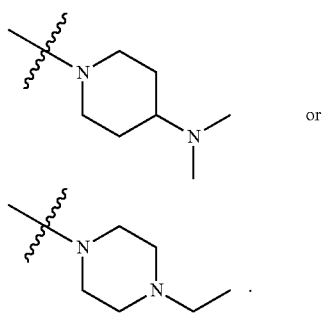

or

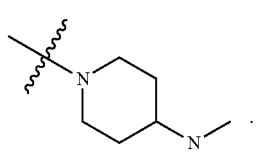

In some embodiments, $R^a$ is not chloro, bromo, or

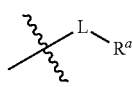

In some embodiments of any of Formulae I-1, I, II, III, IV, I', II', III', IV', I-A, II-A, III-A, IV-A, I-B, II-B, III-B, IV-B, I-C, II-C, III-C, IV-C, I-D, II-D, III-D, IV-D, I-E, II-E, III-E, and IV-E, $$\overset{\xi}{\diagdown} L\diagdown R^a$$

is —$R^a$ (i.e., L is a covalent bond). In some embodiments,

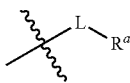

is —(C$_{1-3}$ alkylene)-R$^a$ (i.e., L is a C$_{1-3}$ straight or branched hydrocarbon chain). In some embodiments,

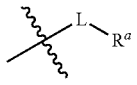

is —(C$_{1-2}$ alkylene)-R$^a$ (i.e., L is a C$_{1-2}$ straight or branched hydrocarbon chain). In some embodiments

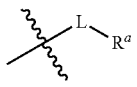

is —CH$_2$—R$^a$ (i.e., L is a C$_1$ hydrocarbon chain). In some embodiments,

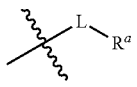

is —CH$_2$CH$_2$—R$^a$ (i.e., L is a C$_2$ straight hydrocarbon chain). In some embodiments,

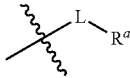

is —CH$_2$CH$_2$CH$_2$—R$^a$ (i.e., L is a C$_3$ straight hydrocarbon chain).

In some embodiments of any of Formulae I', II', III', IV', I-B, II-B, III-B, IV-B, I-C, II-C, III-C, IV-C, I-D, II-D, III-D, IV-D, I-E, II-E, III-E, and IV-E, up to five occurrences of R$^b$ may be present, as allowed by valency rules, and is each independently halogen, —CN, —OR, —SR, —N(R)$_2$, —NO$_2$, —C(O)R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R', —SO$_2$N(R)$_2$, —SO$_3$R', optionally substituted C$_{1-6}$ aliphatic, optionally substituted 3- to 6-membered saturated or partially unsaturated carbocyclyl, optionally substituted 3- to 6-membered saturated or partially unsaturated monocyclic heterocyclyl having 1-3 heteroatoms independently selected from nitrogen, oxygen, and sulfur, optionally substituted 5- to 6-membered monocyclic heteroaryl having 1-4 heteroatoms independently selected from nitrogen, oxygen, and sulfur. In some embodiments, each occurrence of R$^b$ is independently hydrogen, halogen, optionally substituted C$_{1-4}$ alkyl, optionally substituted C$_{3-4}$ cycloalkyl, optionally substituted 3- to 5-membered saturated or partially unsaturated monocyclic heterocyclyl having 1-3 heteroatoms independently selected from nitrogen, oxygen, and sulfur, or optionally substituted 5-membered monocyclic heteroaryl having 1-4 heteroatoms independently selected from nitrogen, oxygen, and sulfur. In some embodiments, R$^b$ is halogen, optionally substituted C$_{1-4}$ alkyl or optionally substituted C$_{3-4}$ cycloalkyl. In some embodiments, R$^b$ is optionally substituted C$_{1-4}$ alkyl or optionally substituted C$_{3-4}$ cycloalkyl. In some embodiments, R$^b$ is C$_{3-4}$ cycloalkyl or C$_{1-4}$ alkyl optionally substituted with one or more fluoro.

In some embodiments, R$^b$ is hydrogen.

In some embodiments, R$^b$ is halogen. In some embodiments, R$^b$ is fluoro, chloro, bromo, or iodo. In some embodiments, R$^b$ is fluoro. In some embodiments, R$^b$ is chloro. In some embodiments, R$^b$ is not halogen. In some embodiments, R$^b$ is not fluoro. In some embodiments, R$^b$ is not chloro.

In some embodiments, R$^b$ is —CN, —OR, —SR, —N(R)$_2$, —NO$_2$, —C(O)R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R, —SO$_2$N(R)$_2$, or —SO$_3$R'. In some embodiments, R$^b$ is —CN, —SR, —N(R)$_2$, —NO$_2$, —C(O)R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R, —SO$_2$N(R)$_2$, or —SO$_3$R'. In some embodiments, R$^b$ is not —OR. In some embodiments, R$^b$ is not

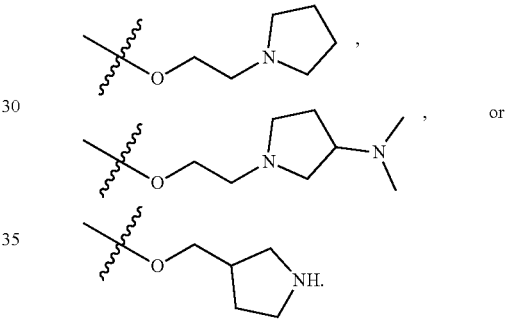

In some embodiments, R$^b$ is optionally substituted C$_{1-6}$ aliphatic. In some embodiments, R$^b$ is optionally substituted straight-chain or branched C$_{1-6}$ aliphatic (i.e., optionally substituted acyclic C$_{1-6}$ aliphatic). In some embodiments, R$^b$ is optionally substituted C$_{1-6}$ alkyl. In some embodiments, R$^b$ is optionally substituted C$_{1-4}$ alkyl. In some embodiments, R$^b$ is C$_{1-4}$ alkyl optionally substituted with one or more halogen. In some embodiments, R$^b$ is C$_{1-4}$ alkyl optionally substituted with one or more of halogen and —CN. In some embodiments, R$^b$ is methyl. In some embodiments, R$^b$ is —CF$_3$. In some embodiments, R$^b$ is tert-butyl. In some embodiments, R$^b$ is —CF$_2$CF$_3$. In some embodiments, R$^b$ is —C(CH$_3$)$_2$CN.

In some embodiments, R$^b$ is optionally substituted 3- to 6-membered saturated or partially unsaturated carbocyclyl. In some embodiments, R$^b$ is optionally substituted C$_{3-6}$ cycloalkyl. In some embodiments, R$^b$ is cyclopropyl. In some embodiments, R$^b$ is cyclobutyl.

In some embodiments, R$^b$ is optionally substituted 3- to 6-membered saturated or partially unsaturated monocyclic heterocyclyl having 1-3 heteroatoms independently selected from nitrogen, oxygen, and sulfur. In some embodiments, R$^b$ is optionally substituted 3- to 6-membered saturated monocyclic heterocyclyl having 1-3 heteroatoms independently selected from nitrogen, oxygen, and sulfur. In some embodiments, R$^b$ is optionally substituted 3- to 5-membered saturated or partially unsaturated monocyclic heterocyclyl having 1-3 heteroatoms independently selected from nitrogen, oxygen, and sulfur. In some embodiments, $R^b$ is azetidinyl.

In some embodiments, $R^b$ is optionally substituted 5- to 6-membered monocyclic heteroaryl having 1-4 heteroatoms independently selected from nitrogen, oxygen, and sulfur. In some embodiments, $R^b$ is optionally substituted 5-membered monocyclic heteroaryl having 1-4 heteroatoms independently selected from nitrogen, oxygen, and sulfur. In some embodiments, $R^b$ is pyrazolyl.

In some embodiments, $R^b$ is not fluoro, chloro, bromo, —OR, or —CF$_3$. In some embodiments, $R^b$ is not fluoro, chloro, bromo,

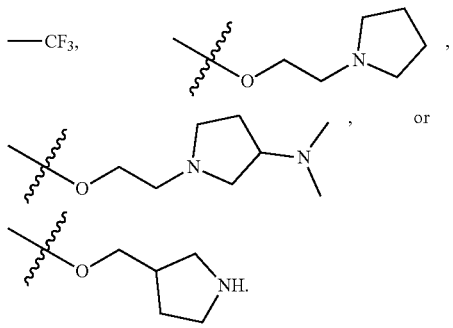

In some embodiments, $R^b$ is not chloro, bromo, or —OR. In some embodiments, $R^b$ is not chloro, bromo,

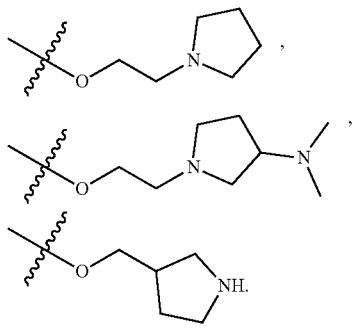

In some embodiments of any of Formulae I, II, III, IV, I-A, II-A, III-A, and IV-A, optionally substituted

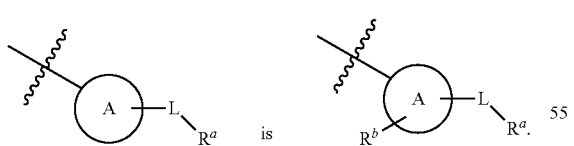

In some embodiments, optionally substituted

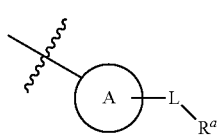

is an optionally substituted group selected from:

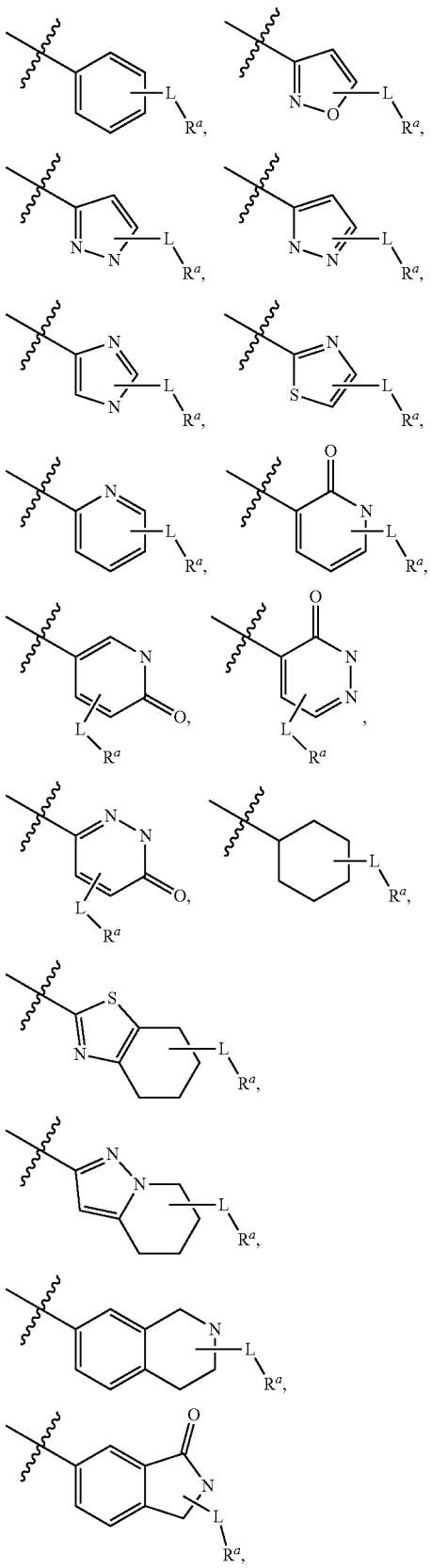

-continued

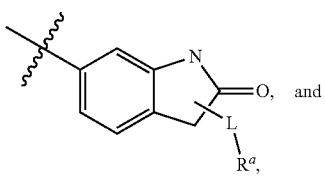

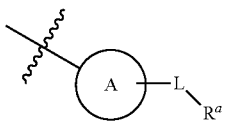

In some embodiments, optionally substituted

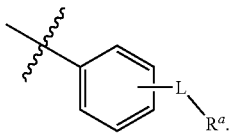

is an optionally substituted group selected from:

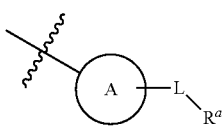

In some embodiments, optionally substituted

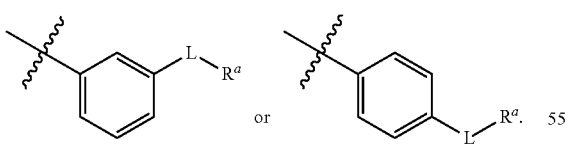

is an optionally substituted group selected from:

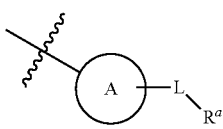

is an optionally substituted group selected from:

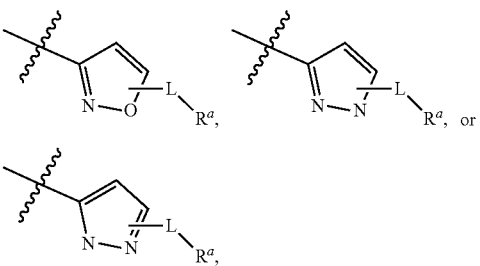

In some embodiments, optionally substituted

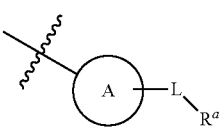

is an optionally substituted group selected from:

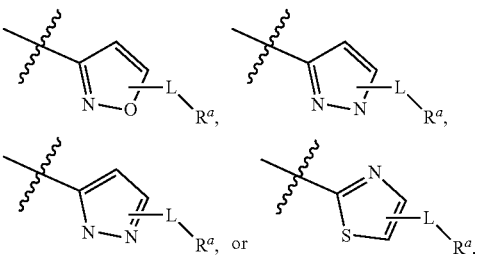

In some embodiments, optionally substituted

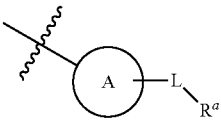

is an optionally substituted group selected from:

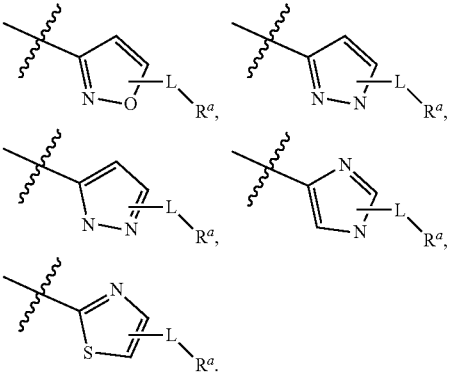

In some embodiments, optionally substituted

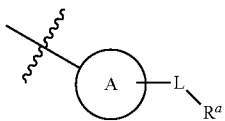

is an optionally substituted group selected from:

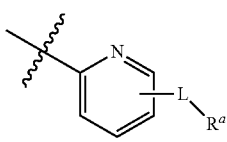

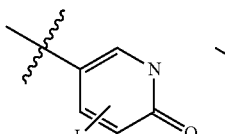

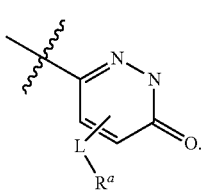

In some embodiments, optionally substituted

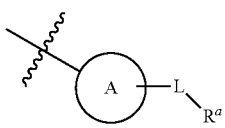

is an optionally substituted group selected from:

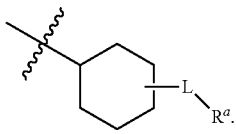

In some embodiments, optionally substituted

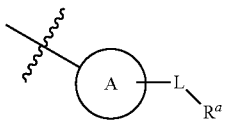

is an optionally substituted group selected from:

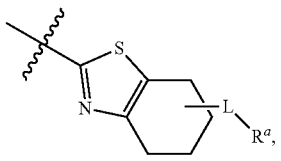

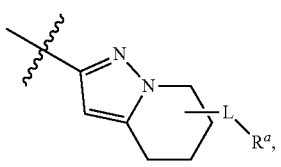

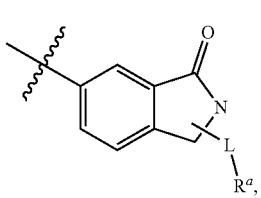

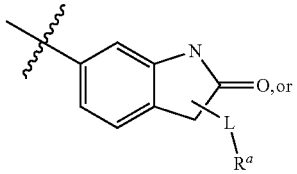

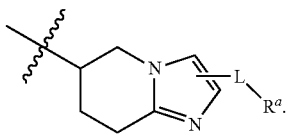

In some embodiments, optionally substituted

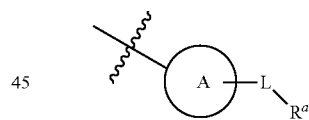

is optionally substituted

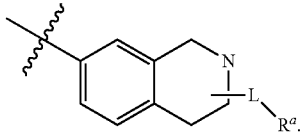

In some embodiments,

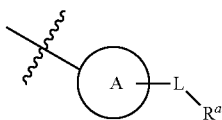

is selected from:
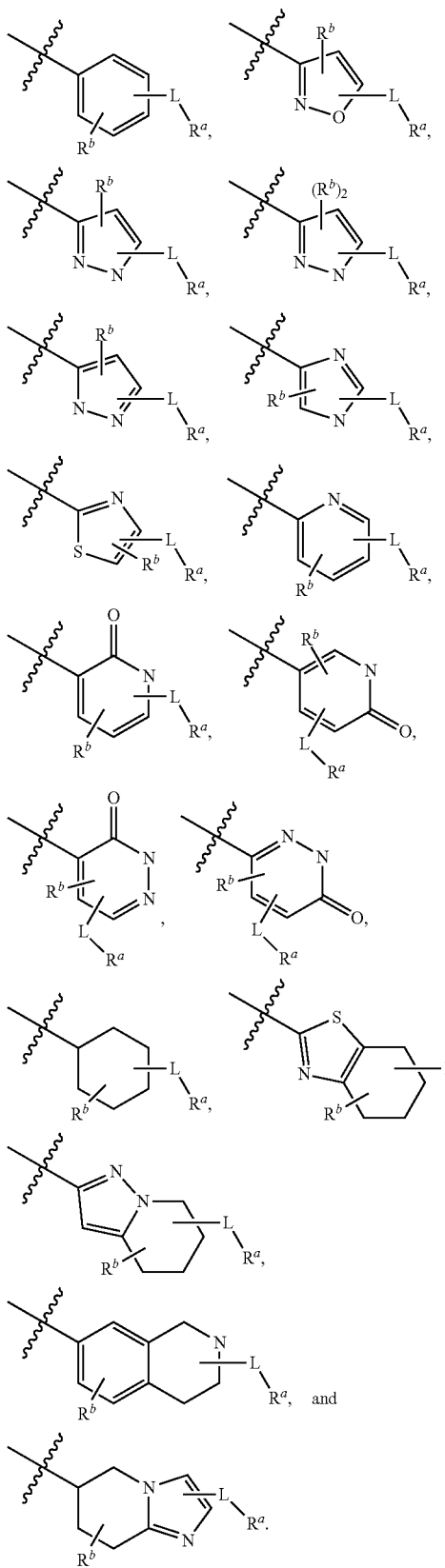
In some embodiments,
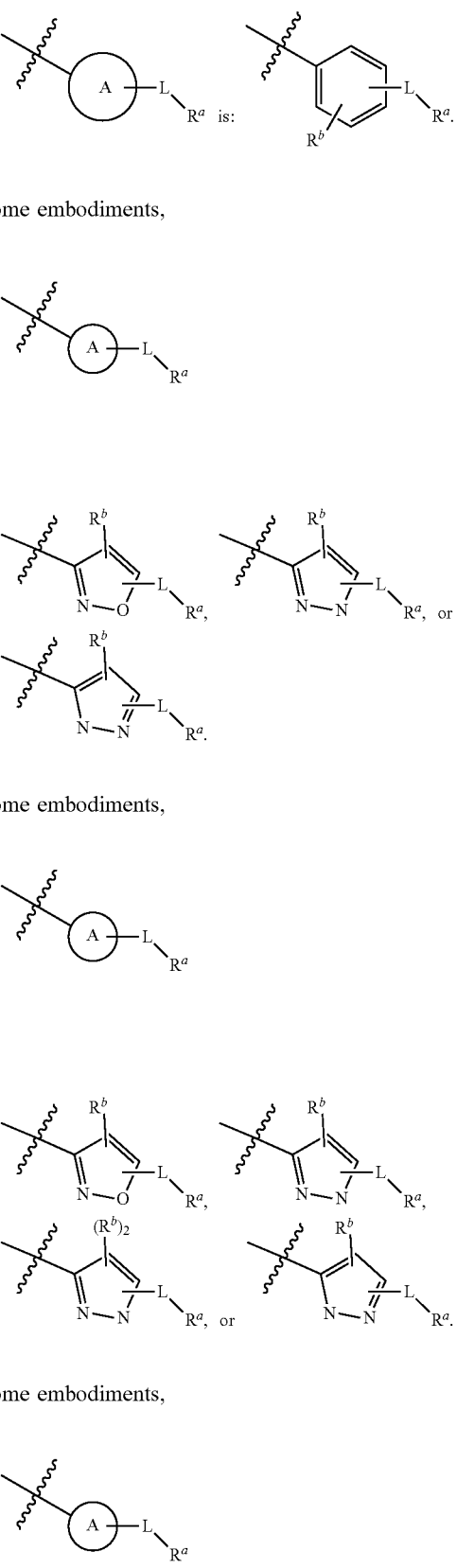

is:
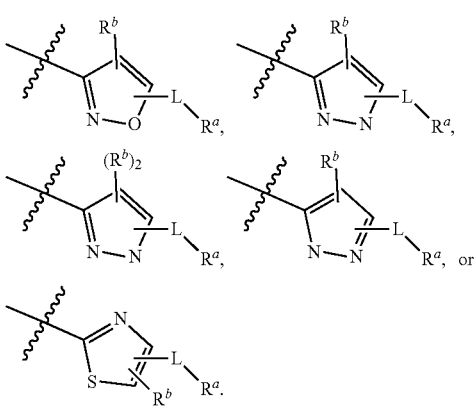
In some embodiments,
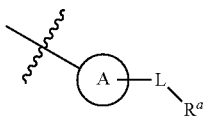
is:
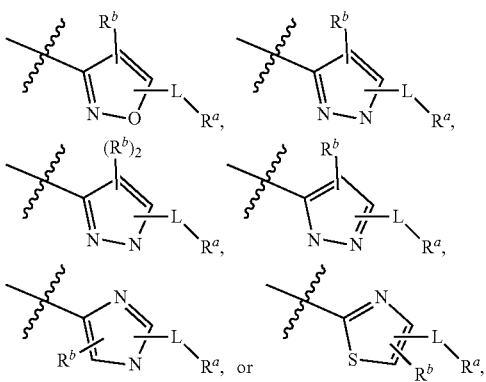
In some embodiments,
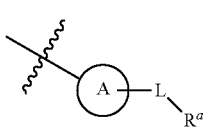
is:
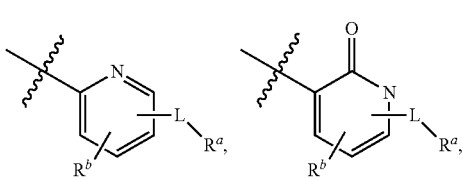
-continued
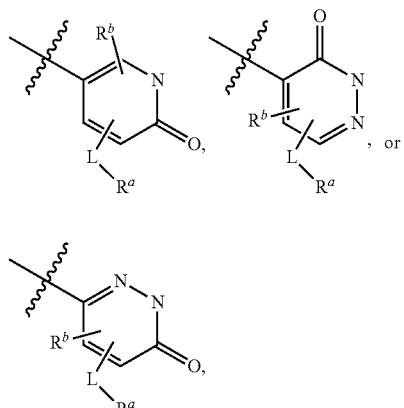
In some embodiments,
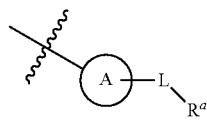
is:

In some embodiments,
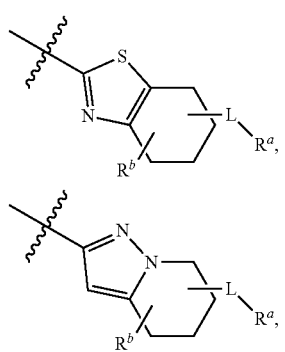

-continued
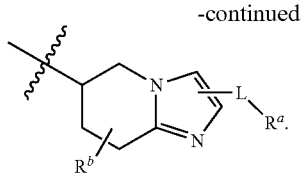
In some embodiments,
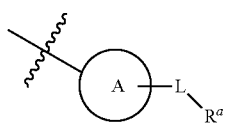
is:
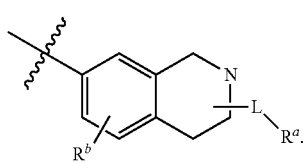
In some embodiments,
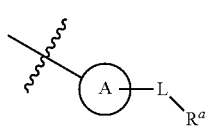
is:
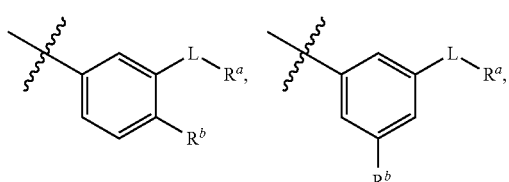
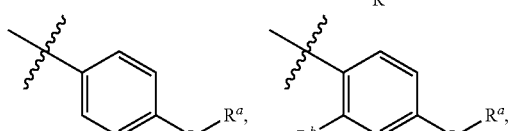
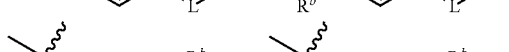
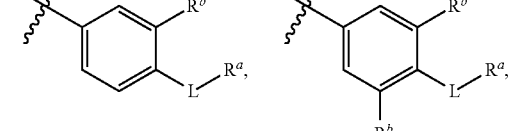
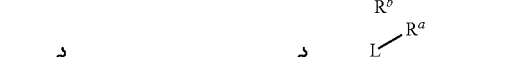
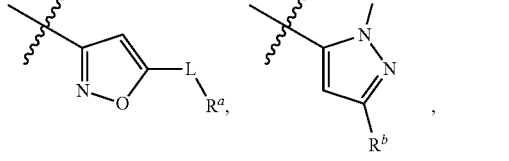
-continued
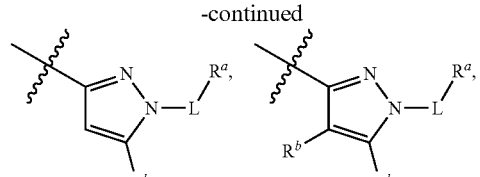
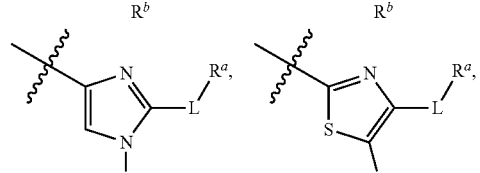
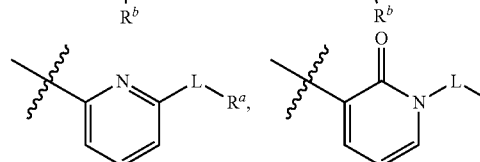
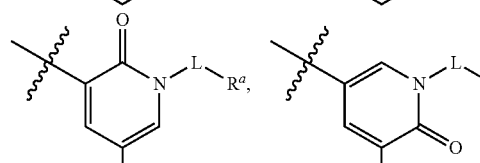
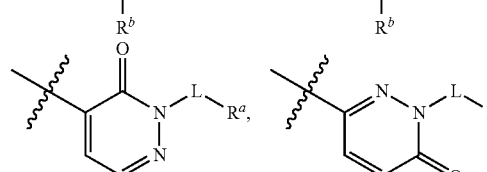
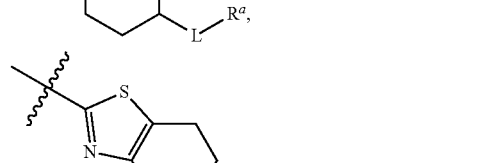
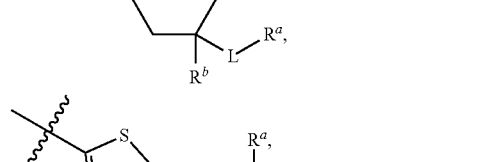
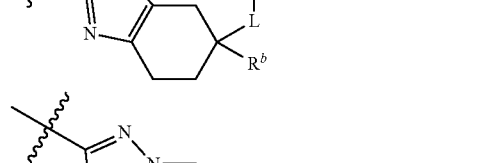
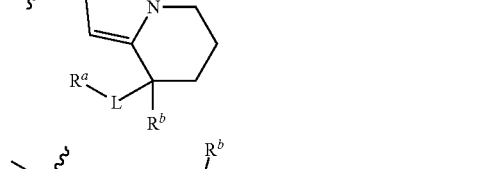
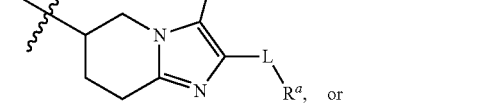, or

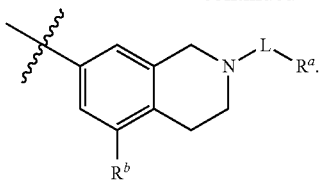
In some embodiments,
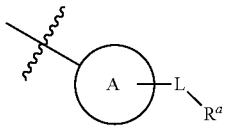
is:
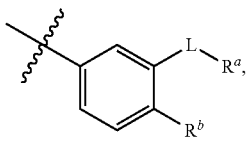
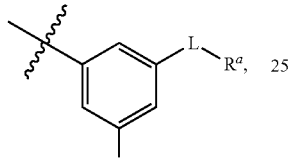
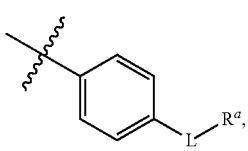
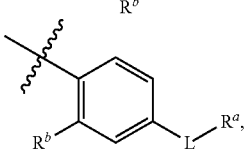
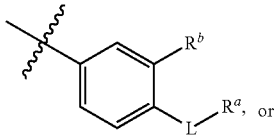
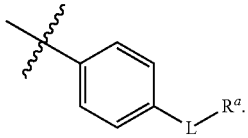
In some embodiments,
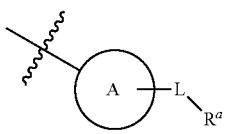
is:
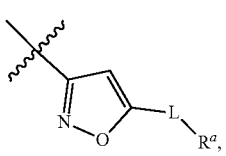
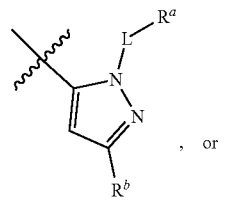, or
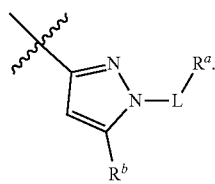
In some embodiments,
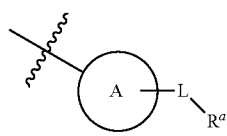
is:
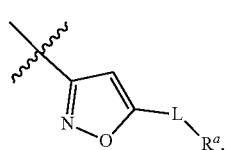
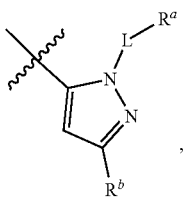,
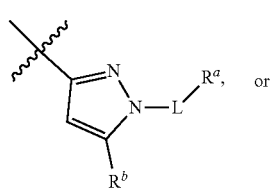
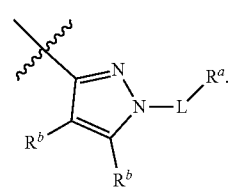
In some embodiments,
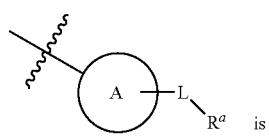 is 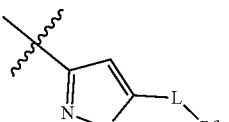,
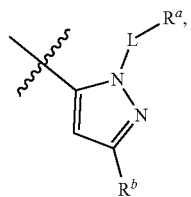
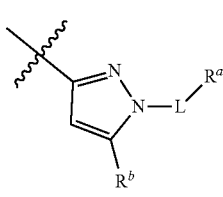,
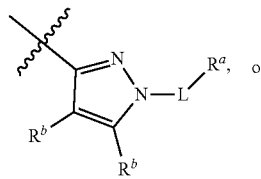, or 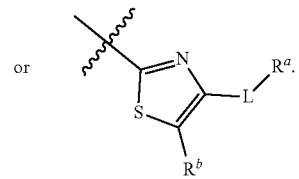

In some embodiments,
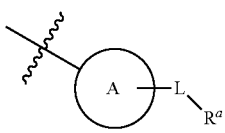
is:
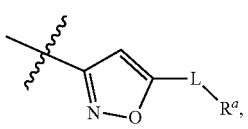
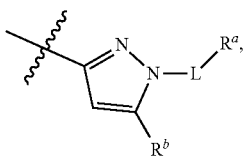
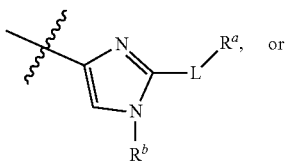
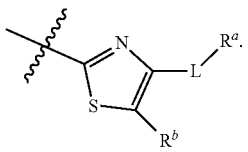
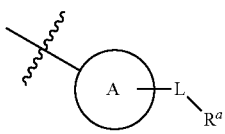
In some embodiments,
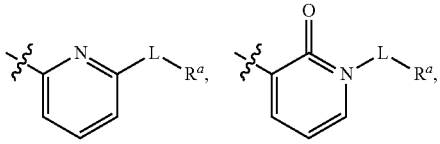
is:
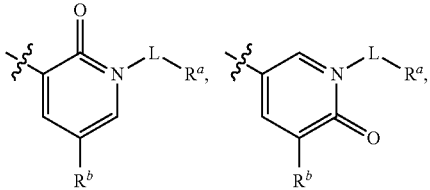
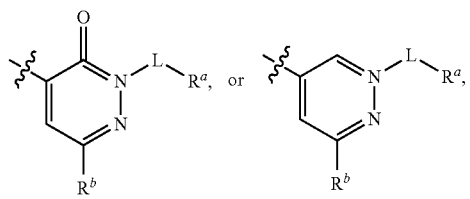
In some embodiments,
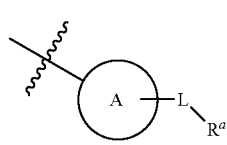
is:
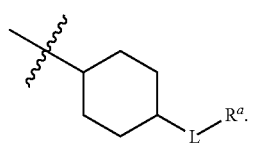
In some embodiments,
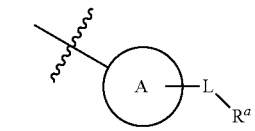
is:
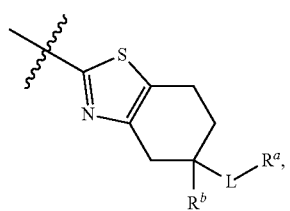
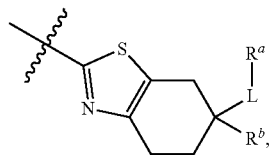
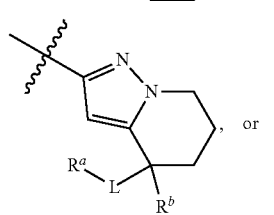

-continued
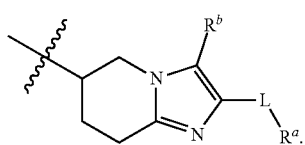
In some embodiments,
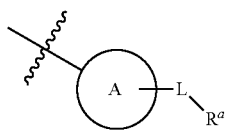
is:
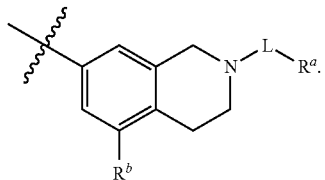
In some embodiments,
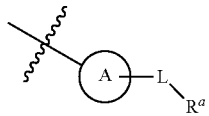
is selected from:
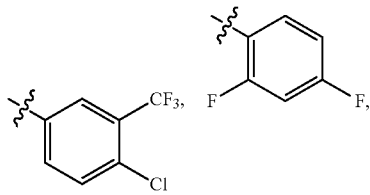
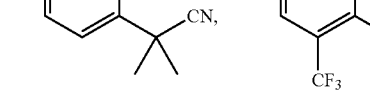
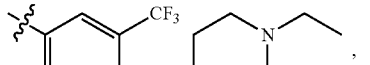
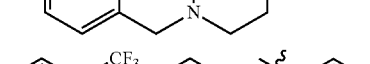
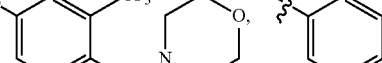

-continued
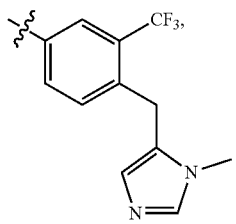
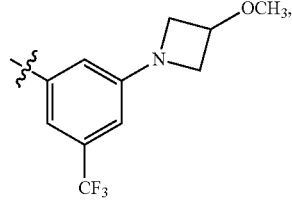
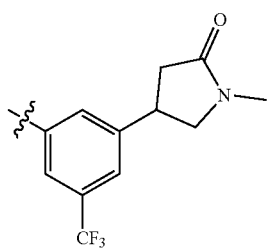
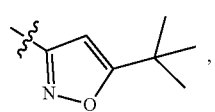
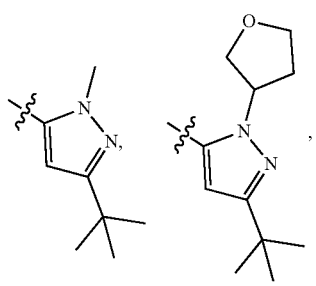

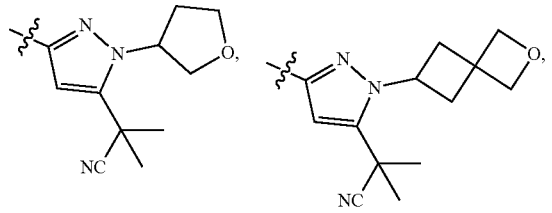
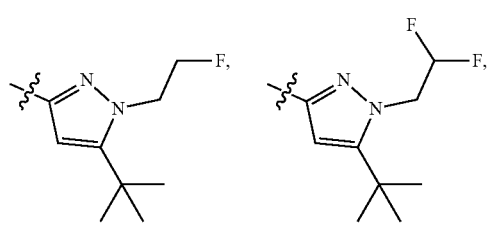
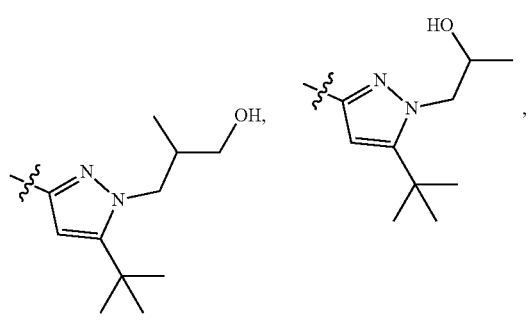
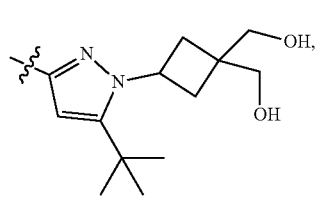
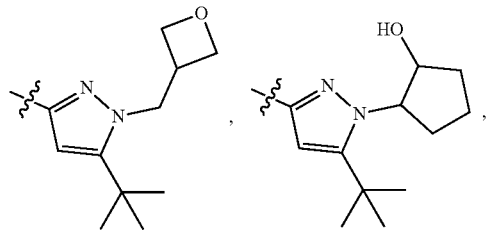
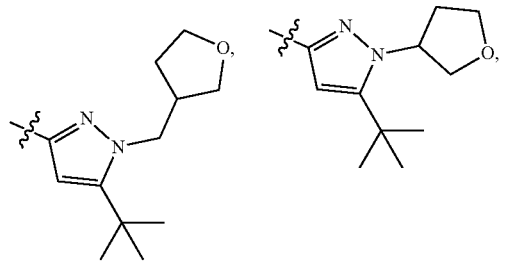
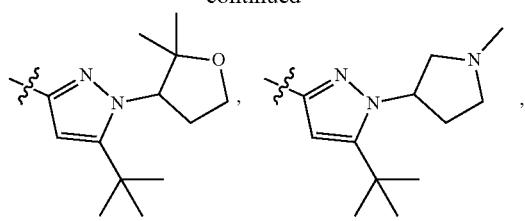
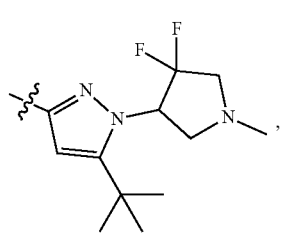
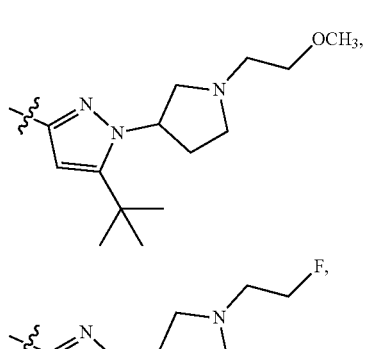
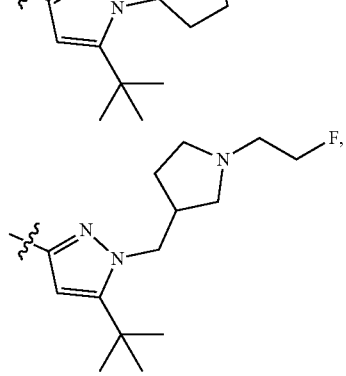
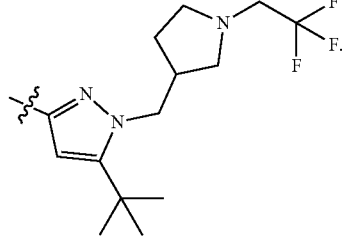
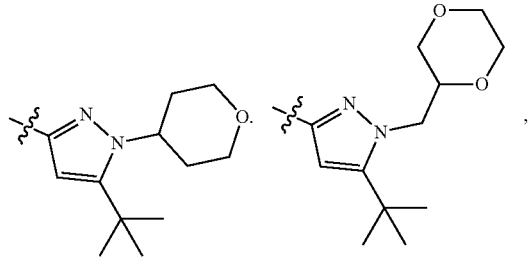

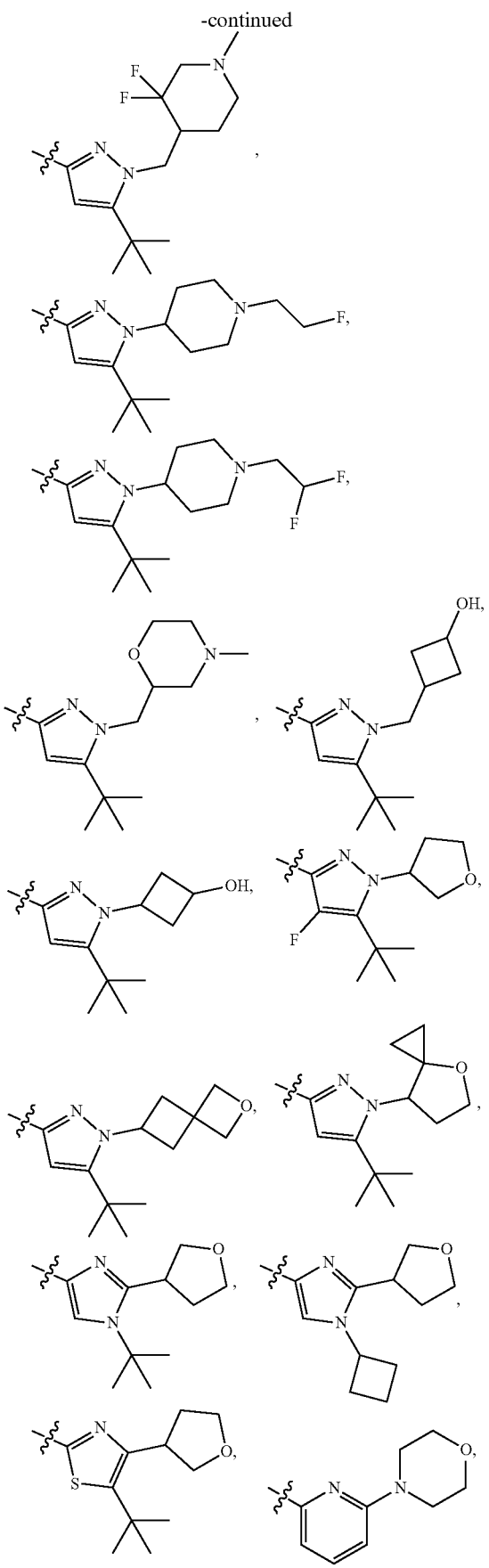
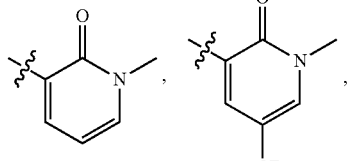

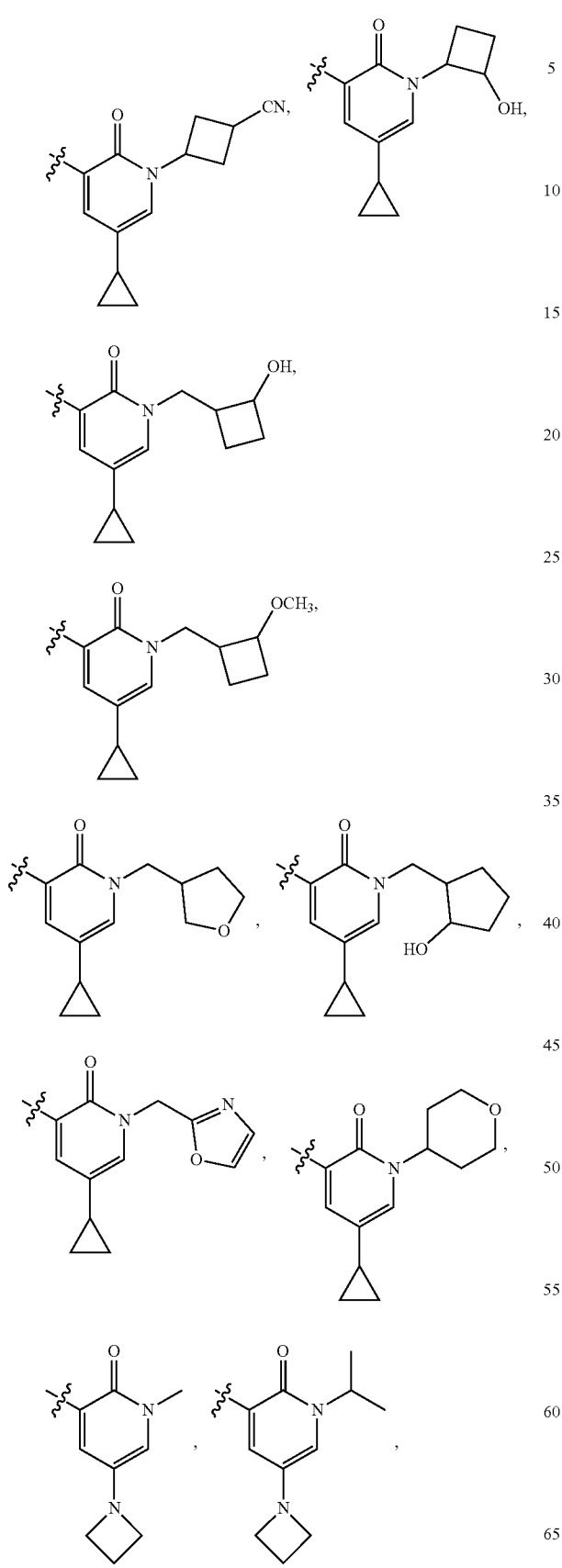
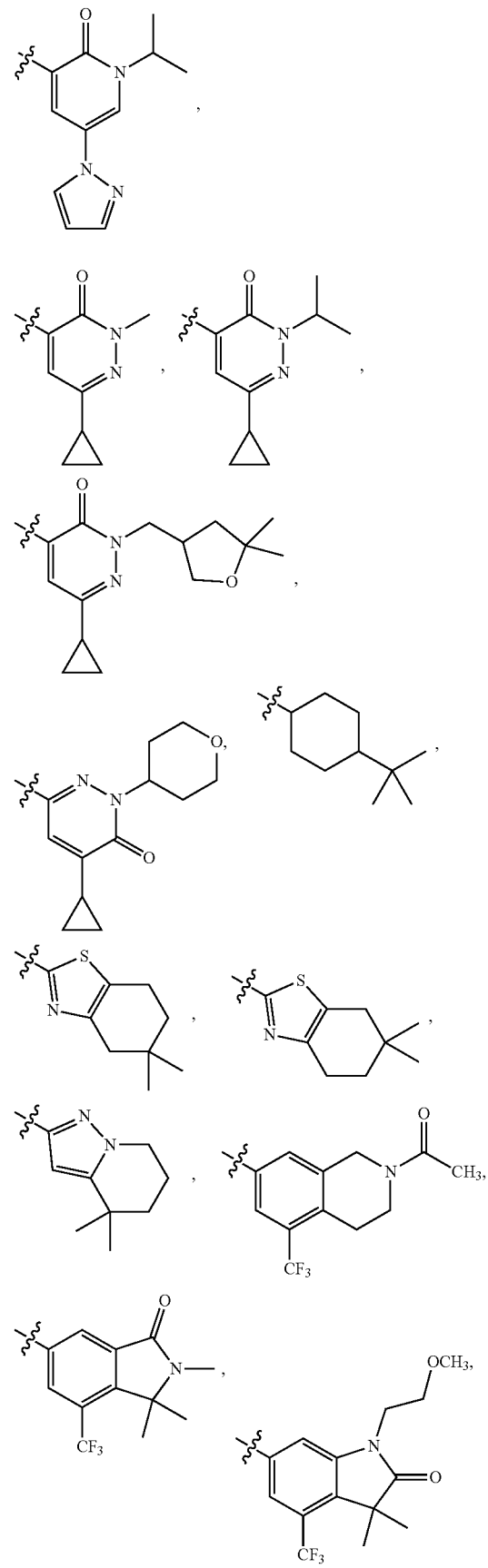

-continued
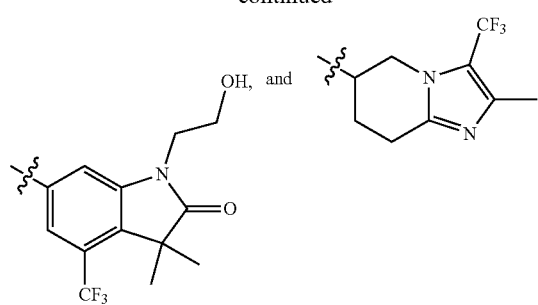
In some embodiments,
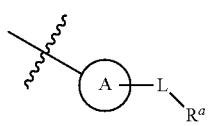
is:
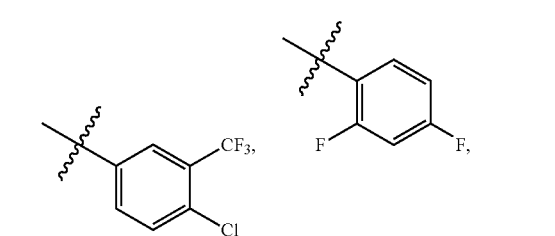
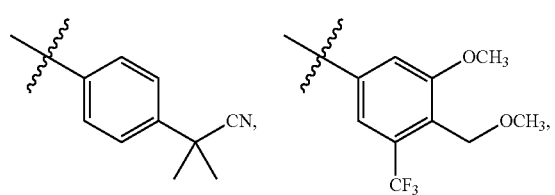
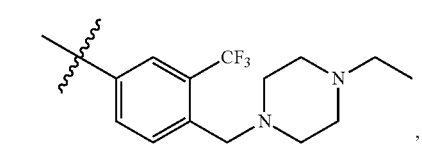
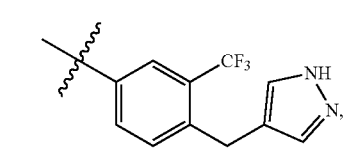
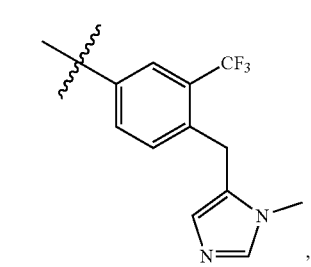
-continued
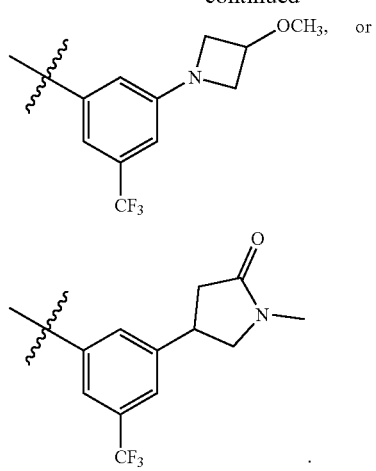
In some embodiments,
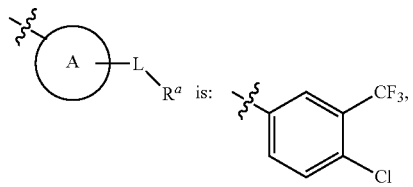
is:
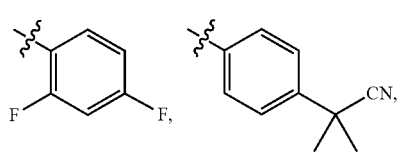
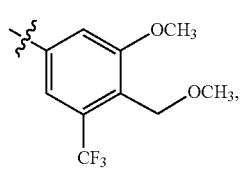
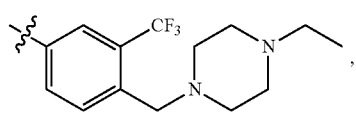
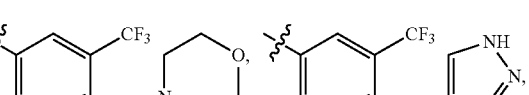
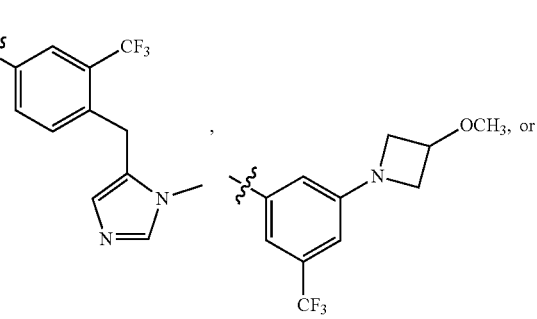

-continued
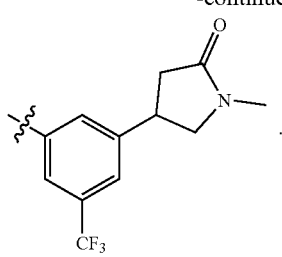
In some embodiments,
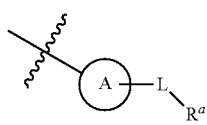
is:
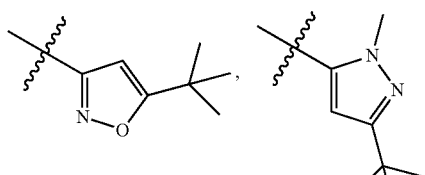
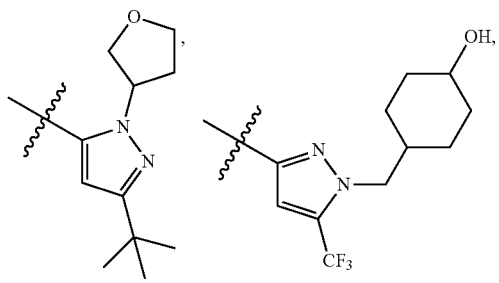
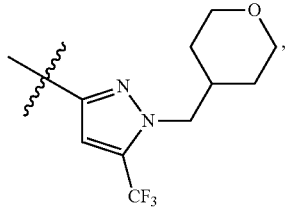
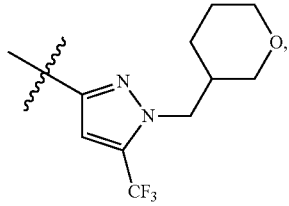
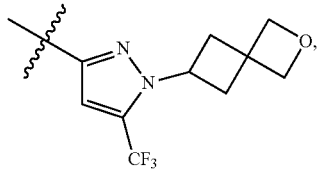
-continued
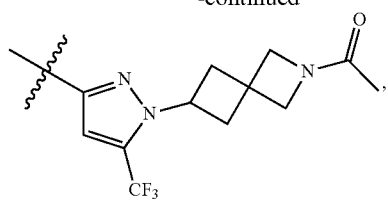
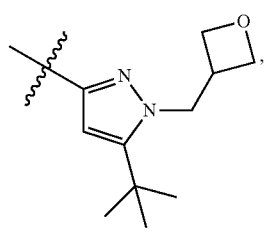
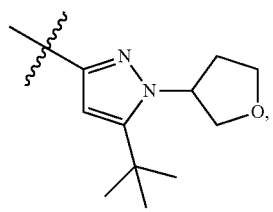
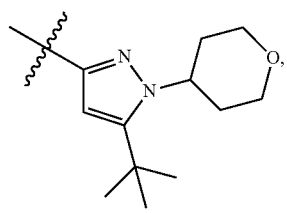
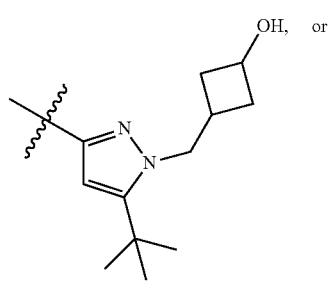
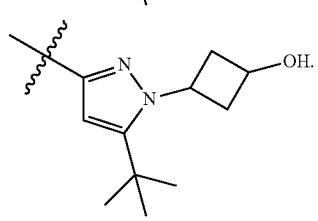
In some embodiments,
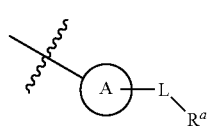

is:
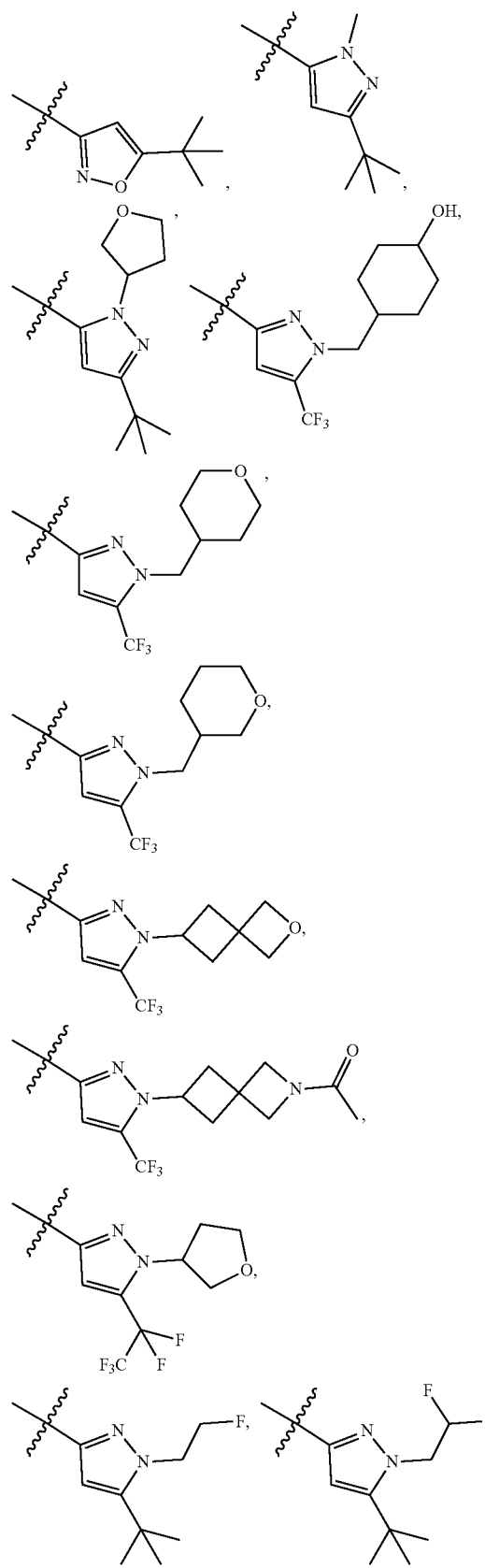
-continued
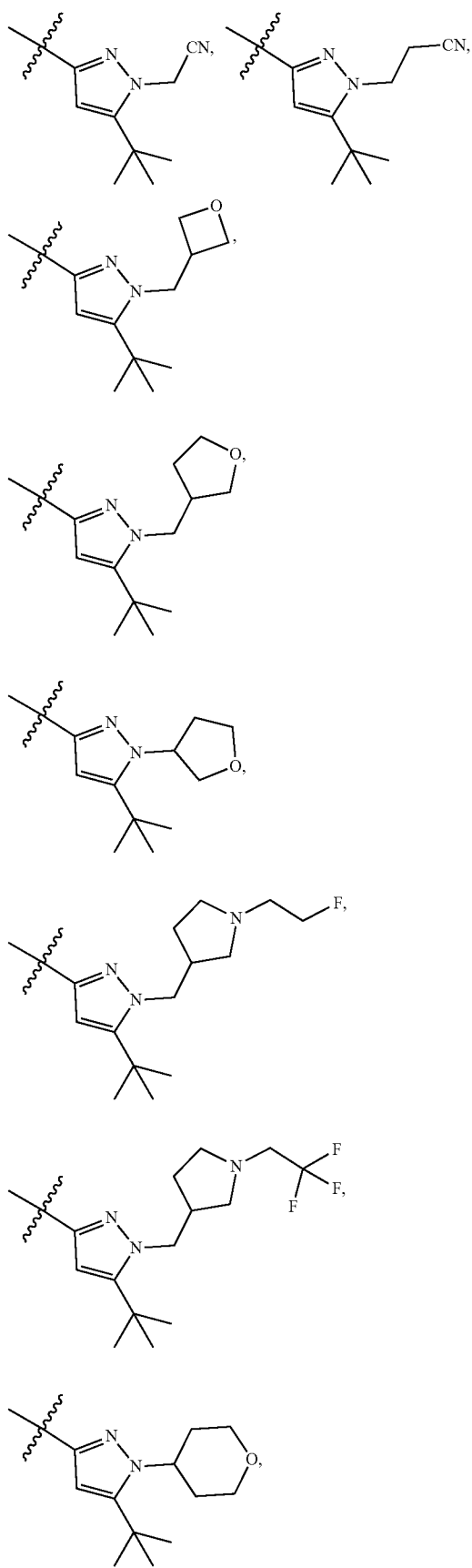

-continued
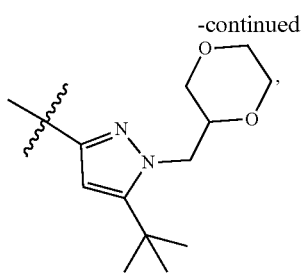
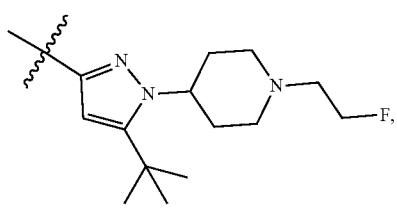
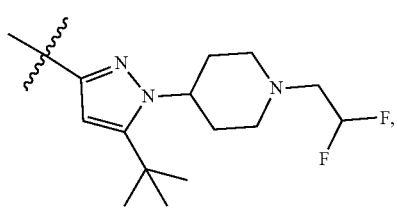
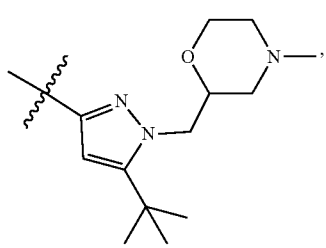
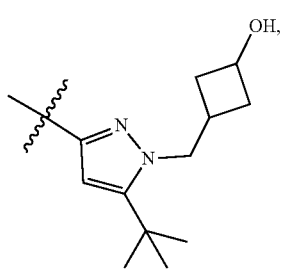
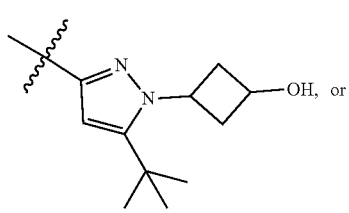
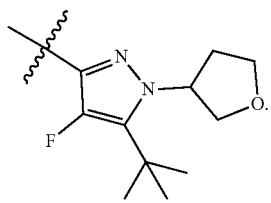
In some embodiments,
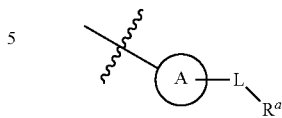
is:
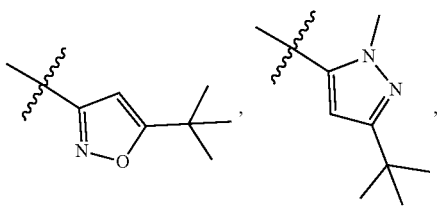
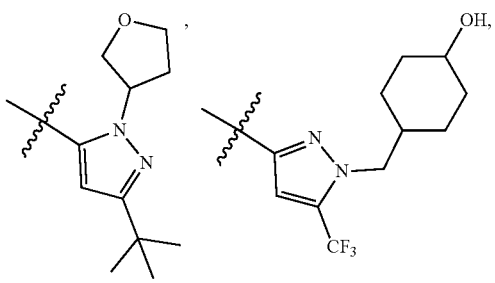
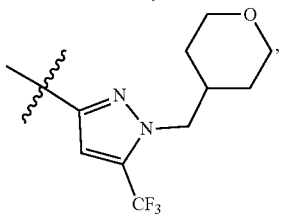
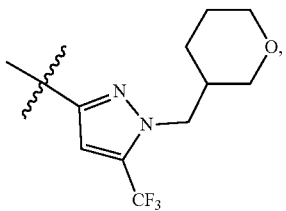
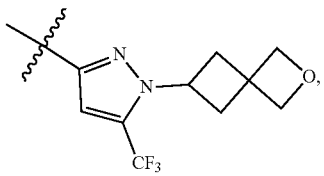
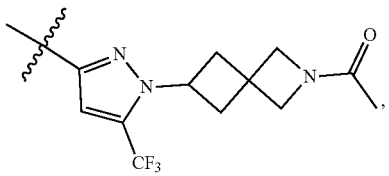
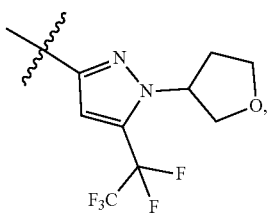

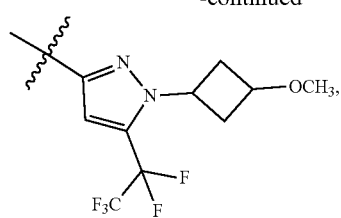
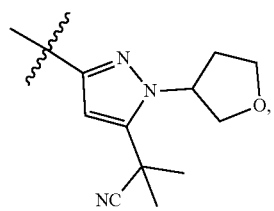
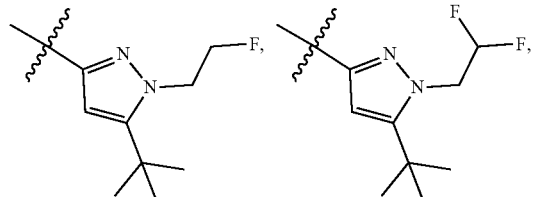
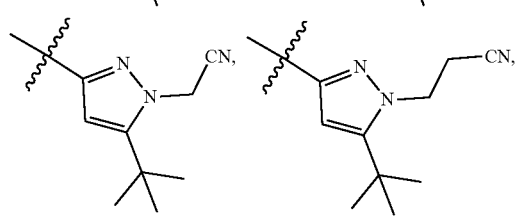
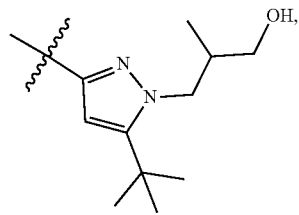
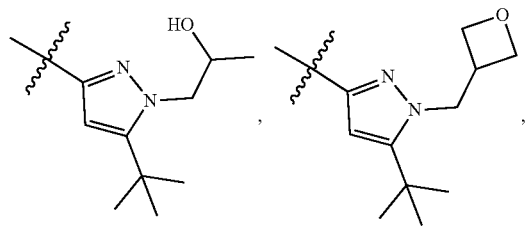
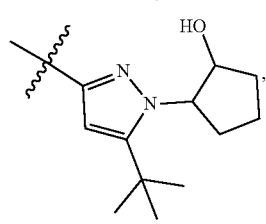
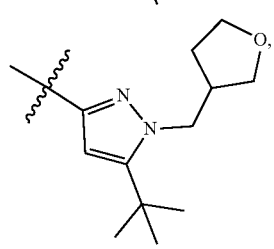
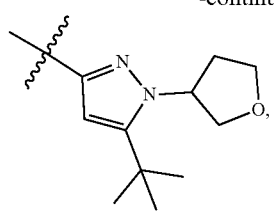
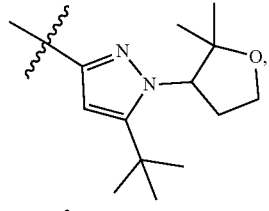
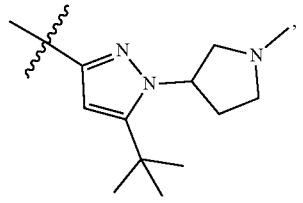
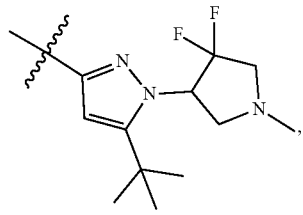
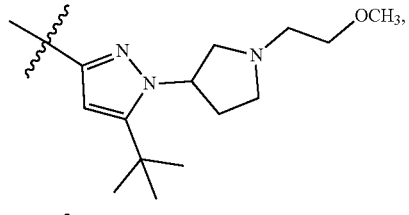
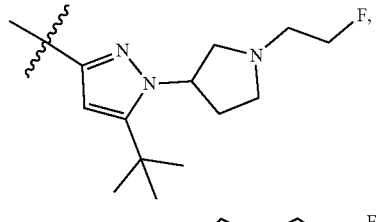
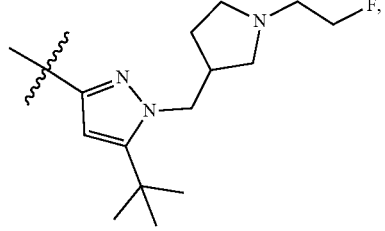
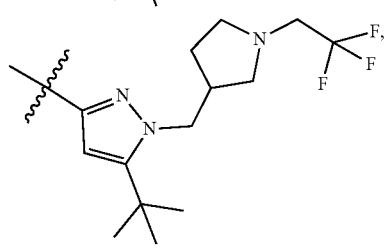

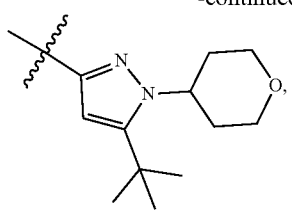
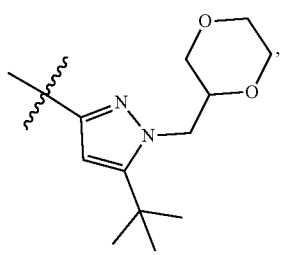
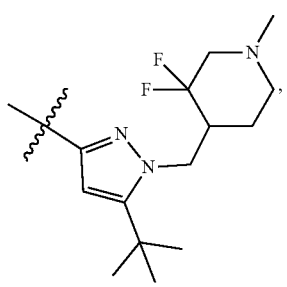
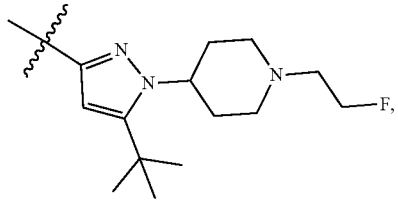
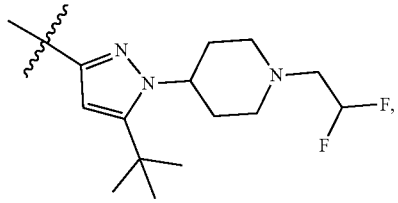
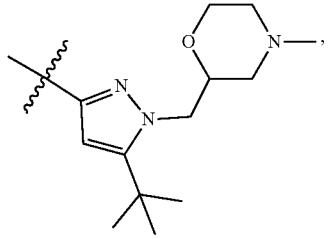
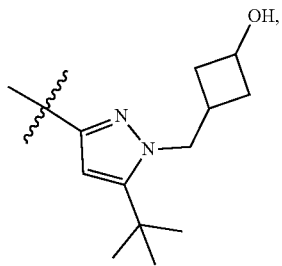
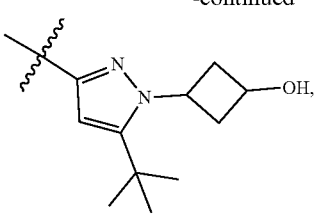
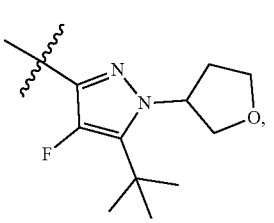
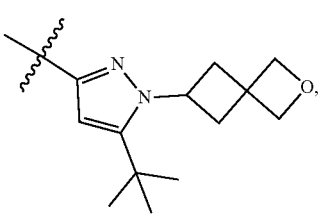
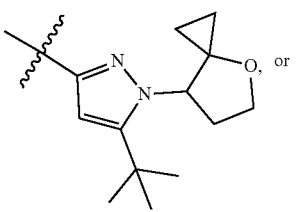
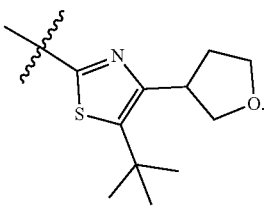
In some embodiments,
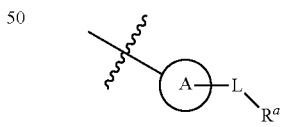
is:
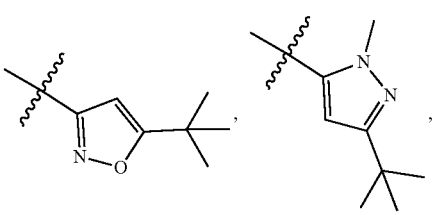

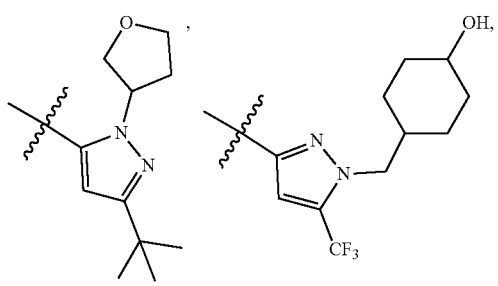
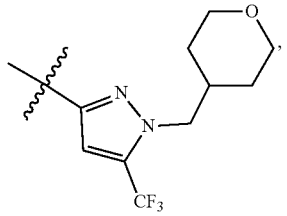
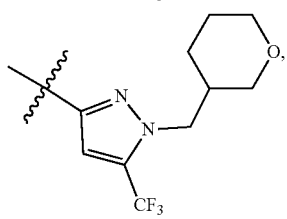
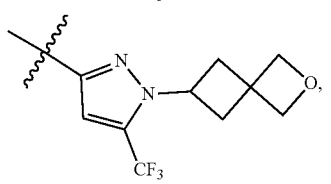
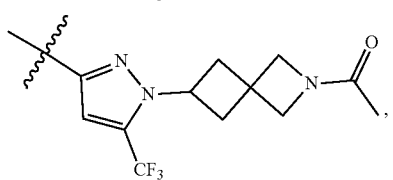
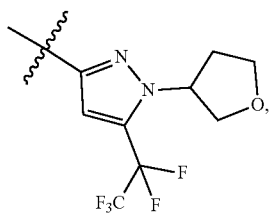
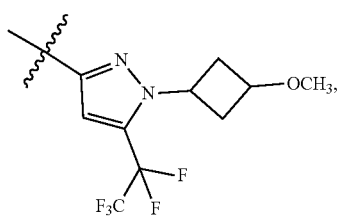
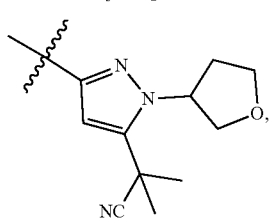
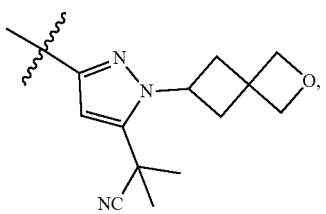
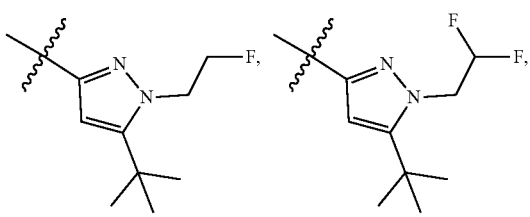
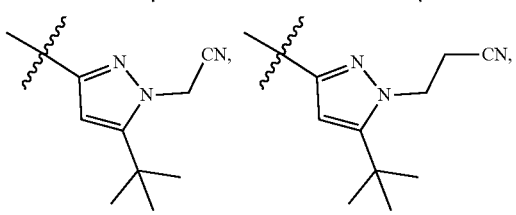
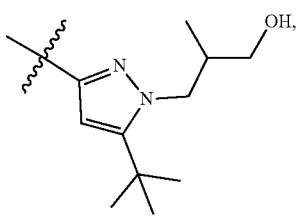
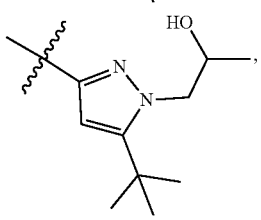
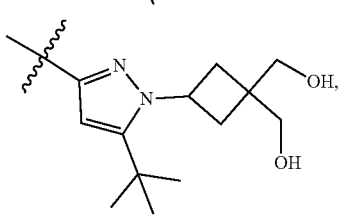
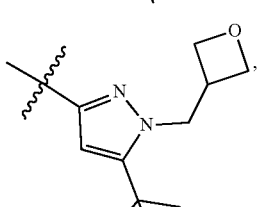
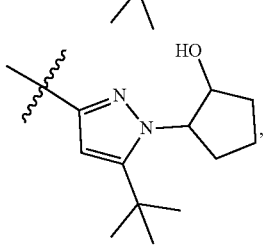

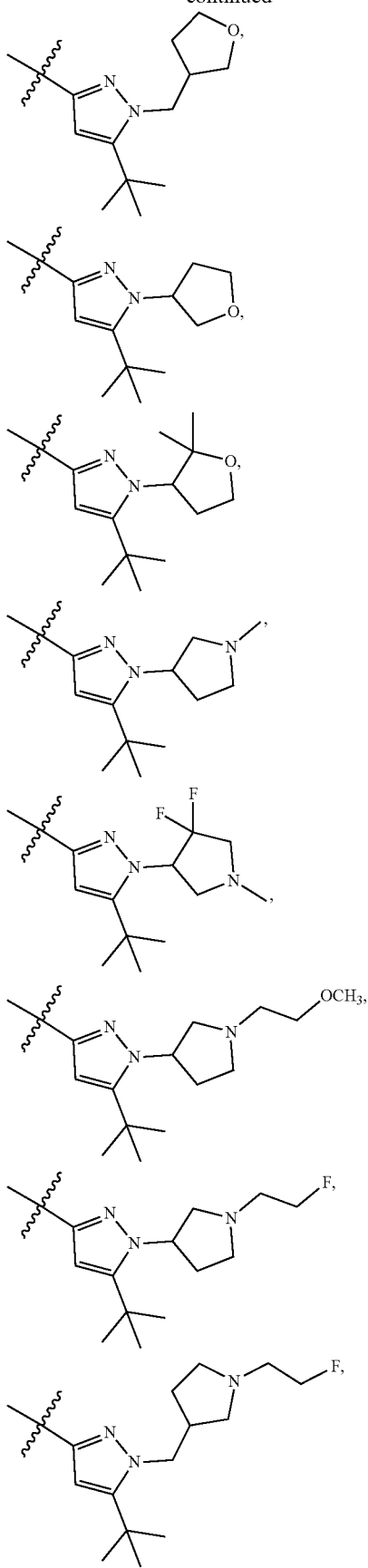
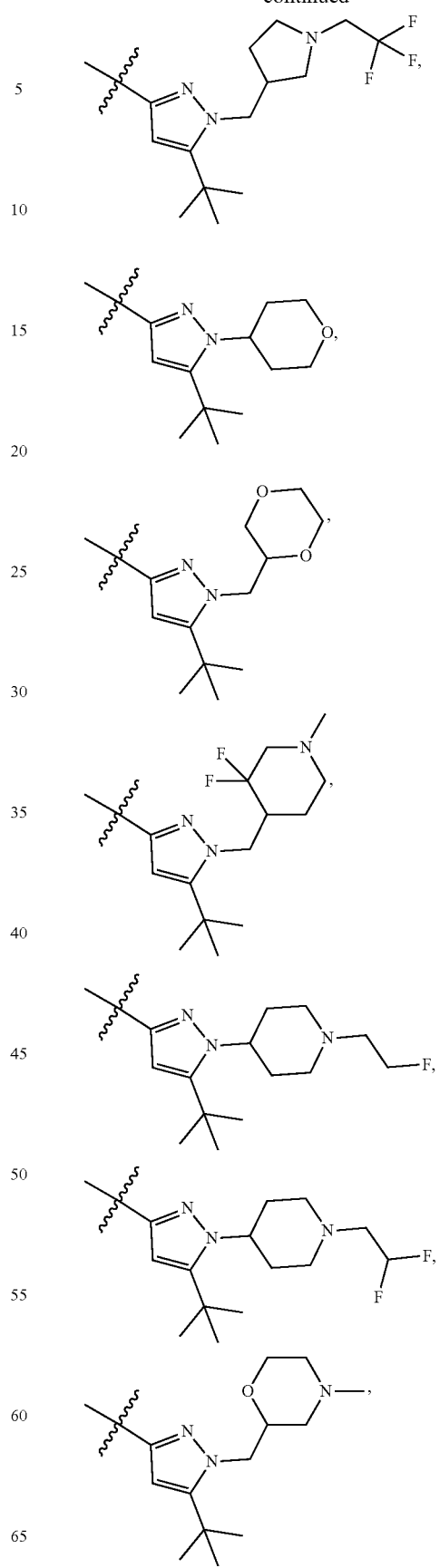

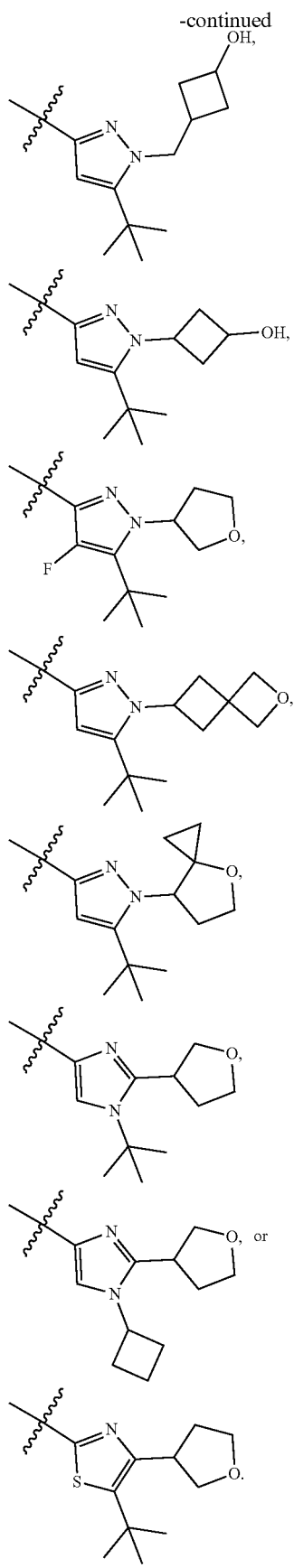
In some embodiments,
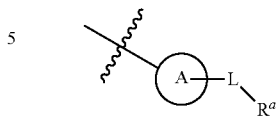
is:
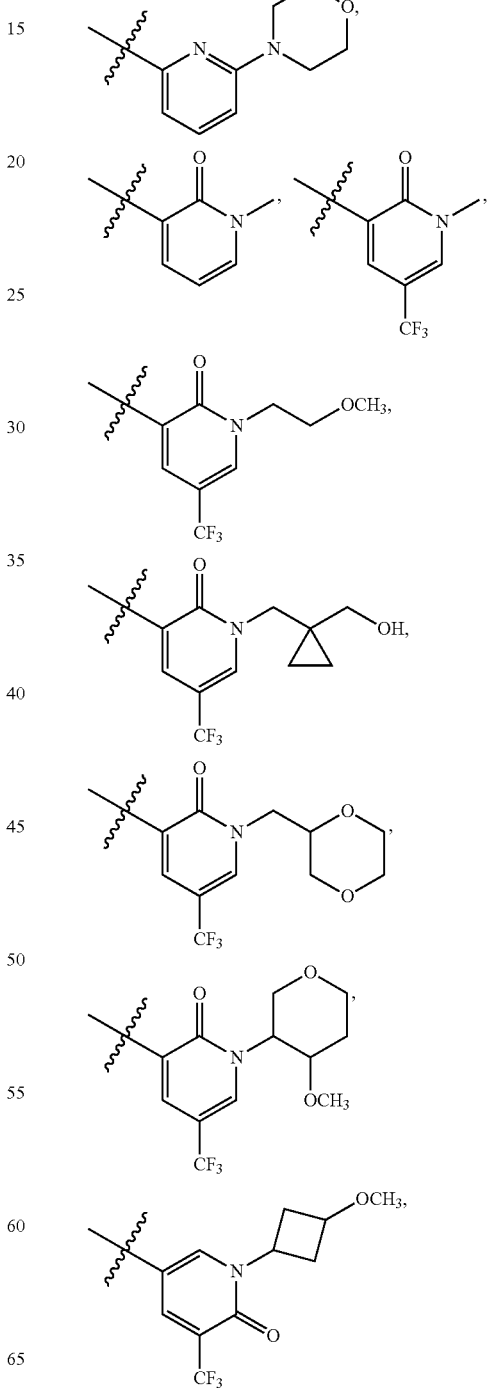

-continued
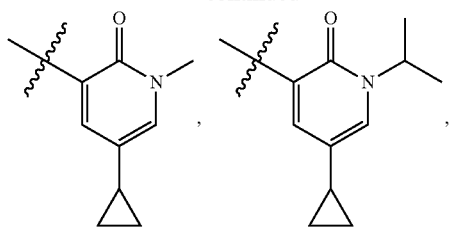
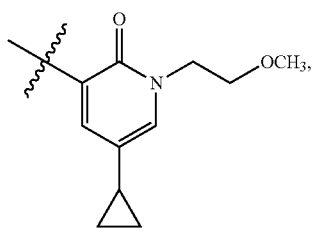
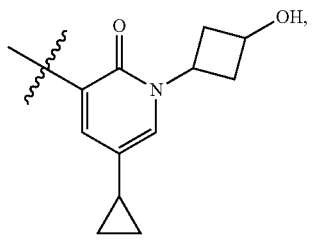
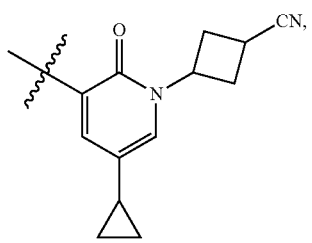
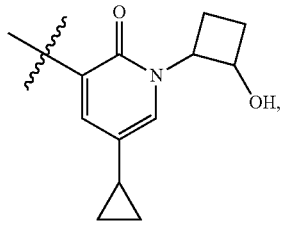
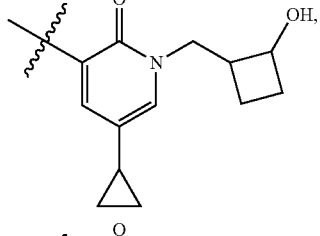
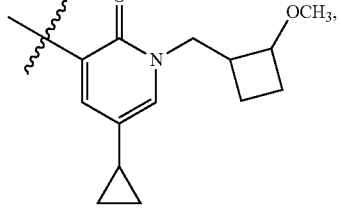
-continued
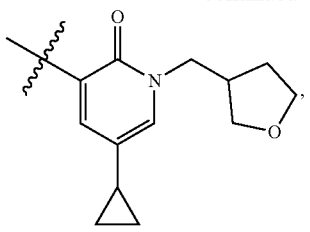
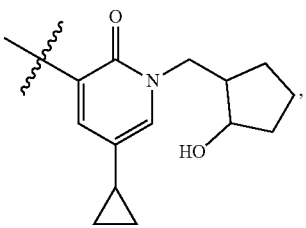
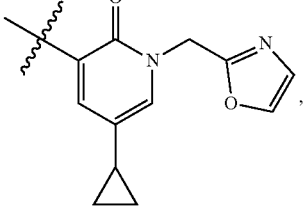
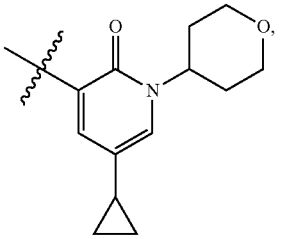
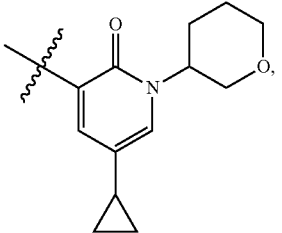
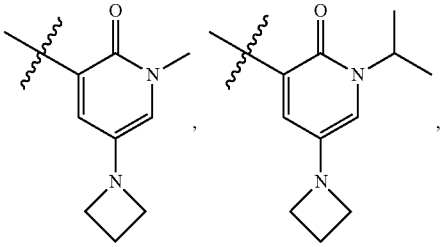
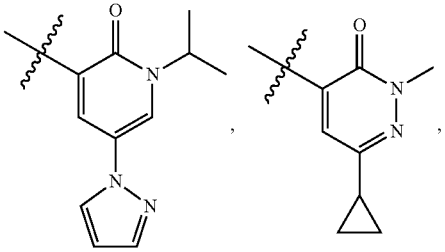

-continued
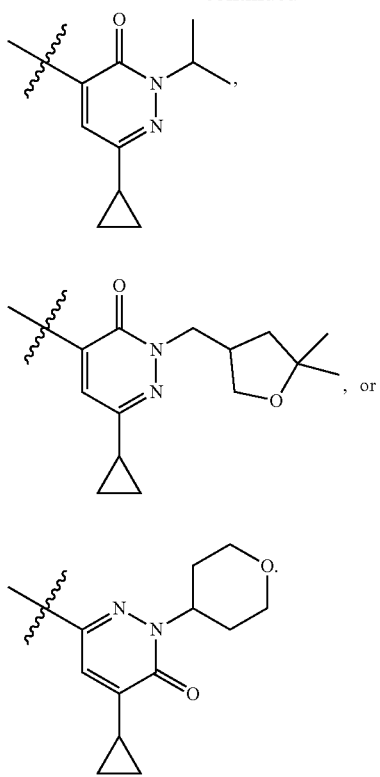
In some embodiments,
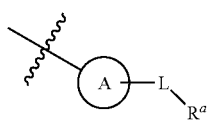
is:
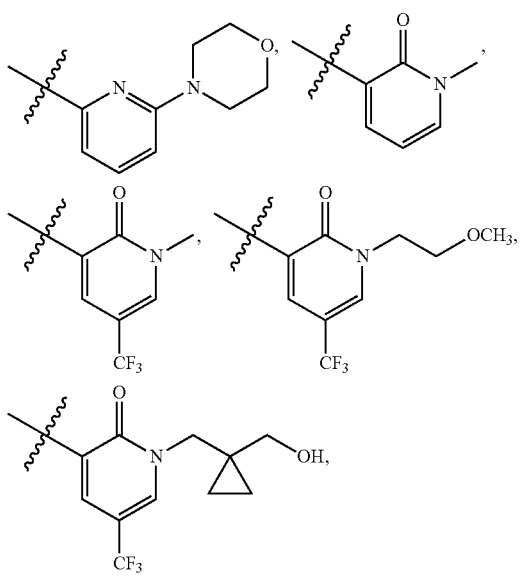
-continued
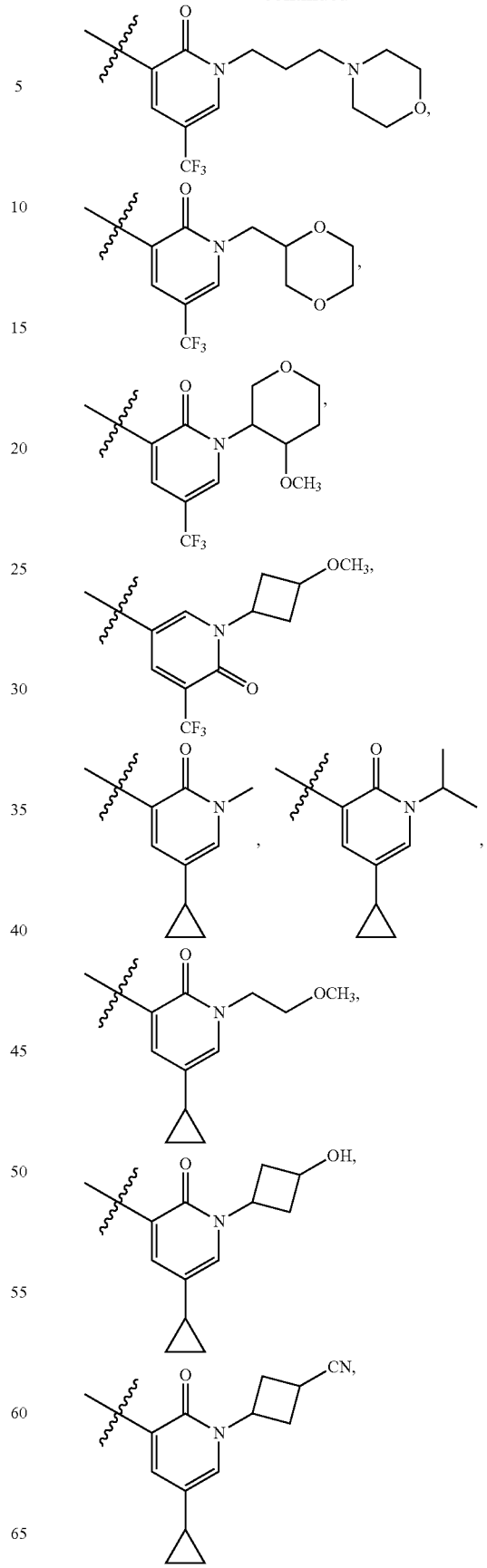

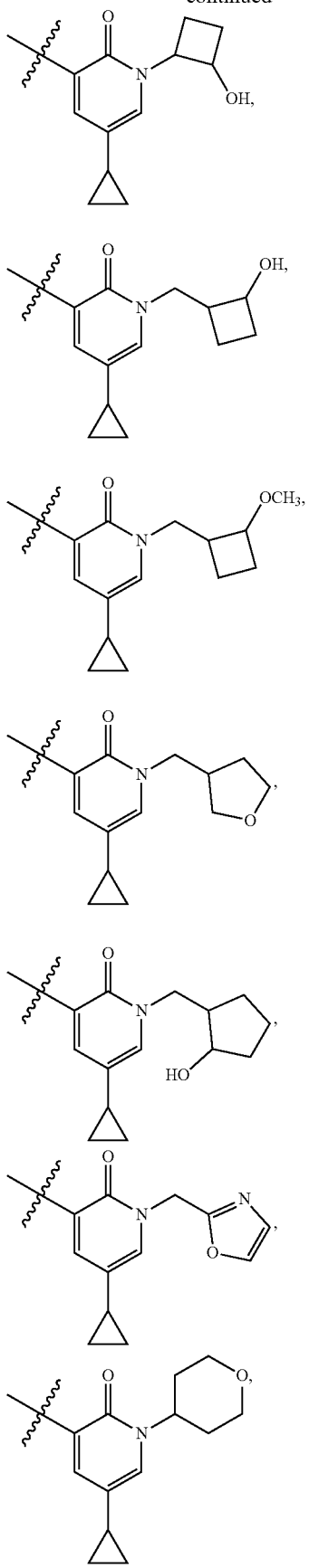
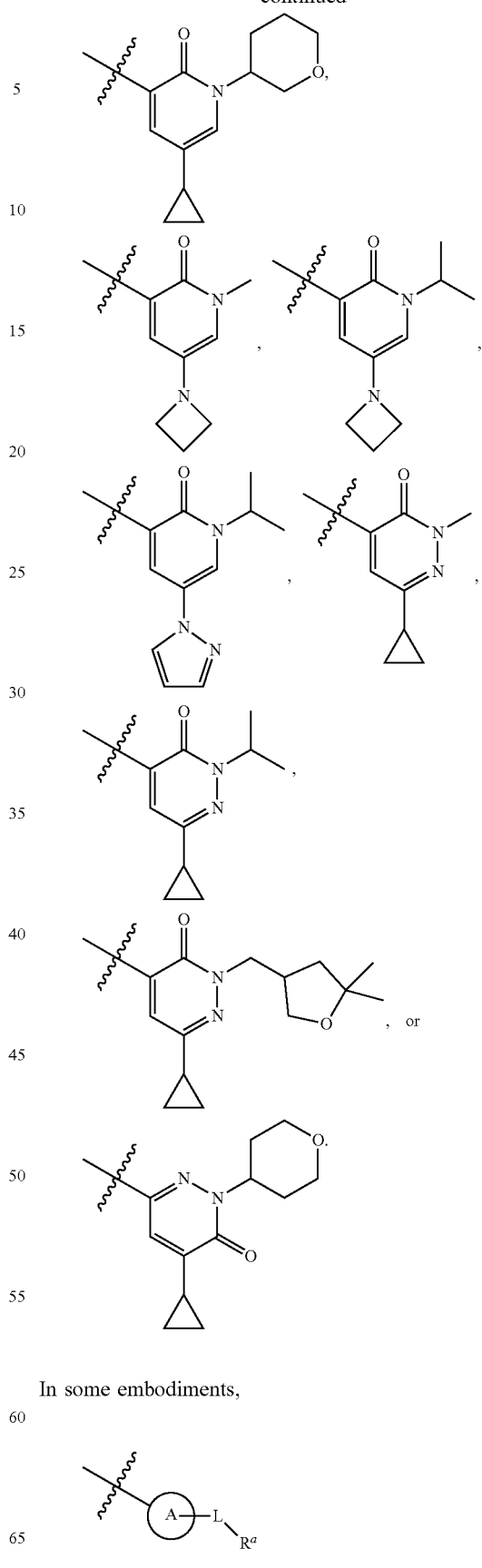
In some embodiments, is:
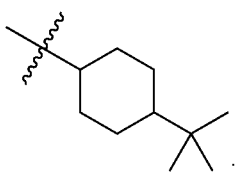 [SMILES: *C1CCC(C(C)(C)C)CC1]
In some embodiments,
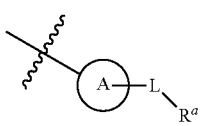
is:
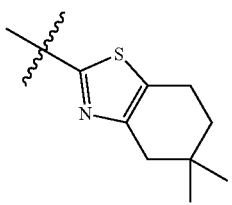 , 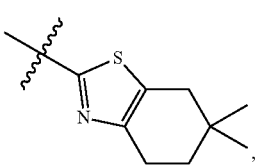 ,
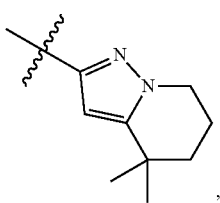 , 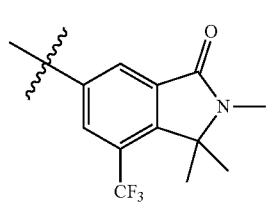 ,
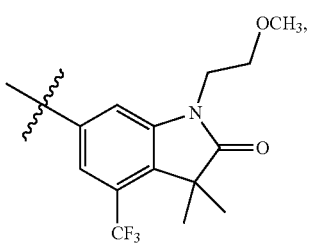 ,
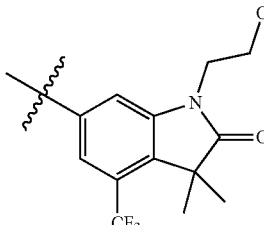 , or
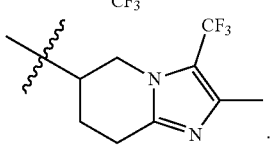 .
In some embodiments,
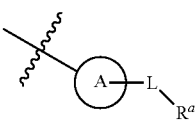
is:
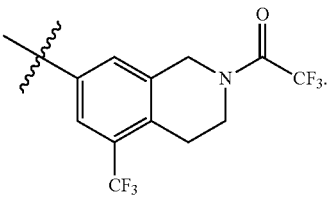 [SMILES: *c1cc2c(c(C(F)(F)F)c1)CCN(C(=O)C(F)(F)F)C2]
In some embodiments,
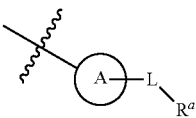
is not:
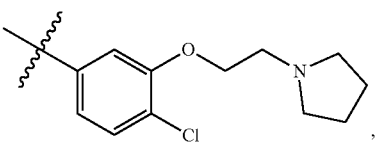 ,
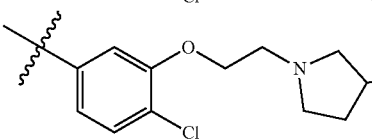 ,
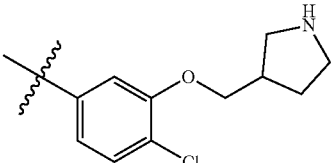 ,
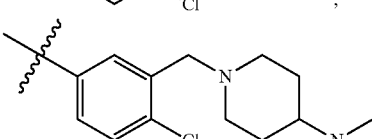 ,
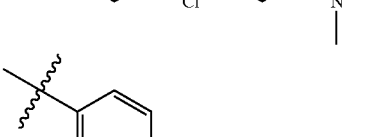 ,
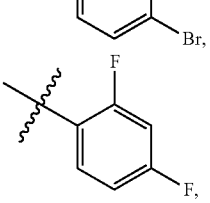
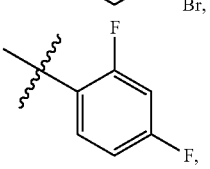

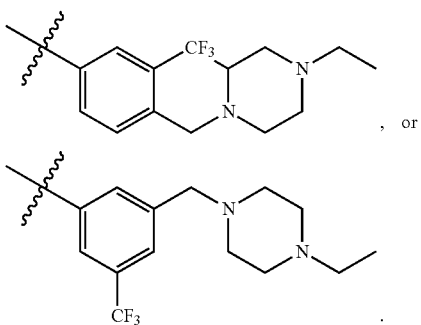

In some embodiments,

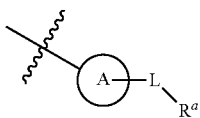

is not:

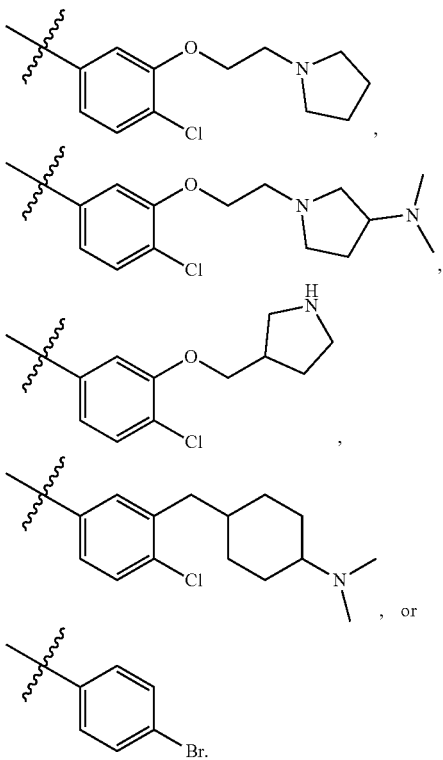

In some embodiments of any of Formulae I-1, I, II, III, IV, I', II', III', IV', I-A, II-A, III-A, IV-A, I-B, II-B, III-B, IV-B, I-C, II-C, III-C, IV-C, I-D, II-D, III-D, IV-D, I-E, II-E, III-E, and IV-E, each R is independently hydrogen or optionally substituted $C_{1-6}$ aliphatic. In some embodiments, each R is independently hydrogen or optionally substituted $C_{1-6}$ alkyl. In some embodiments, each R is independently hydrogen or $C_{1-6}$ alkyl. In some embodiments, each R is independently hydrogen or optionally substituted $C_{1-4}$ alkyl. In some embodiments, each R is independently hydrogen or $C_{1-4}$ alkyl. In some embodiments, each R is independently hydrogen or methyl.

In some embodiments, R is hydrogen.

In some embodiments, R is optionally substituted $C_{1-6}$ aliphatic. In some embodiments, R is optionally substituted straight-chain or branched $C_{1-6}$ aliphatic (i.e., optionally substituted acyclic $C_{1-6}$ aliphatic). In some embodiments, R is optionally substituted $C_{1-6}$ alkyl. In some embodiments, R is optionally substituted $C_{1-4}$ alkyl. In some embodiments, R is unsubstituted $C_{1-4}$ alkyl. In some embodiments, R is optionally substituted $C_{1-2}$ alkyl. In some embodiments, R is unsubstituted $C_{1-2}$ alkyl. In some embodiments, R is methyl.

In some embodiments, R is optionally substituted 3- to 7-membered saturated or partially unsaturated carbocyclyl.

In some embodiments, R is optionally substituted 3- to 7-membered saturated or partially unsaturated monocyclic heterocyclyl having 1-3 heteroatoms independently selected from nitrogen, oxygen, and sulfur.

In some embodiments, two R when attached to the same nitrogen atom are taken together form a 3- to 7-membered saturated or partially unsaturated monocyclic heterocyclyl having 0-2 additional heteroatoms independently selected from nitrogen, oxygen, and sulfur. In some embodiments, two R groups when attached to the same nitrogen are taken together to form a 3- to 7-membered saturated or partially unsaturated monocyclic heterocyclyl having 0-2 additional heteroatoms independently selected from nitrogen, oxygen, and sulfur optionally substituted with one or more halogen, $C_{1-6}$ alkyl, and —O($C_{1-6}$ alkyl). In some embodiments, two R groups when attached to the same nitrogen are taken together to form an optionally substituted 3- to 5-membered saturated monocyclic heterocyclyl having 0-1 additional heteroatoms. In some embodiments, two R groups when attached to the same nitrogen are taken together to form an optionally substituted 4-membered saturated monocyclic heterocyclyl having 0-1 additional heteroatoms. In some embodiments, two R groups when attached to the same nitrogen are taken together to form a 3- to 5-membered saturated monocyclic heterocyclyl having 0-1 additional heteroatoms optionally substituted with one or more halogen, $C_{1-6}$ alkyl, and —O($C_{1-6}$ alkyl). In some embodiments, two R groups when attached to the same nitrogen are taken together to form a 4-membered saturated monocyclic heterocyclyl having 0-1 additional heteroatoms optionally substituted with one or more halogen, $C_{1-6}$ alkyl, and —O($C_{1-6}$ alkyl).

In some embodiments of any of Formulae I-1, I, II, III, IV, I', II', III', IV', I-A, II-A, III-A, IV-A, I-B, II-B, III-B, IV-B, I-C, II-C, III-C, IV-C, I-D, II-D, III-D, IV-D, I-E, II-E, III-E, and IV-E, each R' is independently optionally substituted $C_{1-6}$ alkyl or optionally substituted $C_{3-6}$ cycloalkyl. In some embodiments, each R' is independently optionally substituted $C_{1-2}$ alkyl or optionally substituted $C_{3-4}$ cycloalkyl. In some embodiments, each R' is independently methyl or optionally substituted $C_3$ cycloalkyl. In some embodiments, each R' is independently $C_{1-2}$ alkyl or $C_{3-4}$ cycloalkyl. In some embodiments, each R' is independently methyl or cyclopropyl. In some embodiments, each R' is independently methyl,

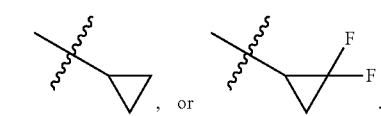

In some embodiments, each R' is independently methyl, —CH₂CH₂OCH₃,

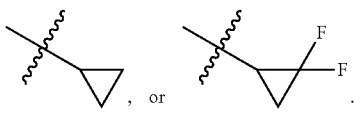

, or

In some embodiments, each R' is independently methyl, —CH₂CH₂OCH₃,

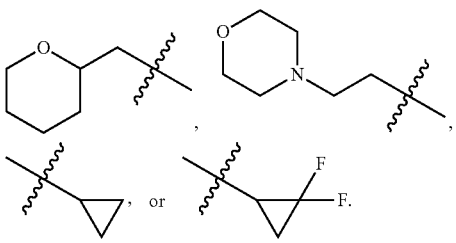

, or

In some embodiments, R' is optionally substituted $C_{1-6}$ aliphatic. In some embodiments, R' is optionally substituted straight-chain or branched $C_{1-6}$ aliphatic (i.e., optionally substituted acyclic $C_{1-6}$ aliphatic). In some embodiments, R' is optionally substituted $C_{1-6}$ alkyl. In some embodiments, R' is $C_{1-6}$ alkyl optionally substituted with —$OC_{1-6}$ alkyl or a 3- to 7-membered saturated monocyclic heterocyclyl having 1-2 heteroatoms independently selected from nitrogen, oxygen, and sulfur. In some embodiments, R' is optionally substituted $C_{1-4}$ alkyl. In some embodiments, R' is $C_{1-4}$ alkyl optionally substituted with —$OC_{1-6}$ alkyl or a 3- to 7-membered saturated monocyclic heterocyclyl having 1-2 heteroatoms independently selected from nitrogen, oxygen, and sulfur. In some embodiments, R' is unsubstituted $C_{1-4}$ alkyl. In some embodiments, R' is optionally substituted $C_{1-2}$ alkyl.

In some embodiments, R' is $C_{1-2}$ alkyl optionally substituted with —$OC_{1-6}$ alkyl or a 3- to 7-membered saturated monocyclic heterocyclyl having 1-2 heteroatoms independently selected from nitrogen, oxygen, and sulfur. In some embodiments, R' is unsubstituted $C_{1-2}$ alkyl. In some embodiments, R' is methyl. In some embodiments, R' is —CH₂CH₂OCH₃. In some embodiments, R' is $C_{1-2}$ alkyl optionally substituted with a 3- to 7-membered saturated monocyclic heterocyclyl having 1-2 heteroatoms independently selected from nitrogen, oxygen, and sulfur (e.g., morpholinyl or tetrahydopyranyl).

In some embodiments, R' is optionally substituted $C_{1-6}$ aliphatic or optionally substituted 3- to 7-membered saturated or partially unsaturated carbocyclyl. In some embodiments, R' is 3- to 7-membered saturated or partially unsaturated carbocyclyl optionally substituted with one or more halogen. In some embodiments, R' is optionally substituted $C_{3-6}$ cycloalkyl. In some embodiments, R' is $C_{3-6}$ cycloalkyl optionally substituted with one or more halogen. In some embodiments, R' is optionally substituted $C_3$ cycloalkyl. In some embodiments, R' is

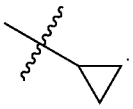

In some embodiments, R' is

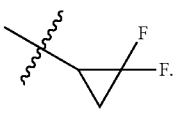 [SMILES: *C1CC1(F)F]

In some embodiments of any of Formulae I-1, I, II, III, IV, I', II', III', IV', I-A, II-A, III-A, and IV-A, the compound is not:

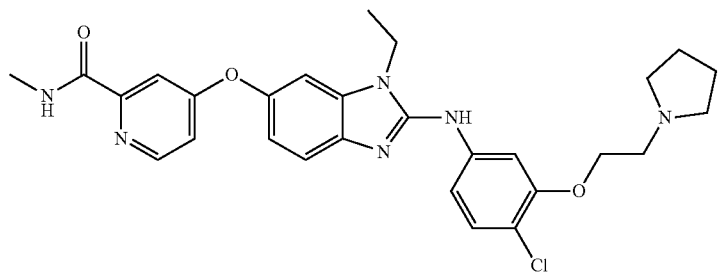

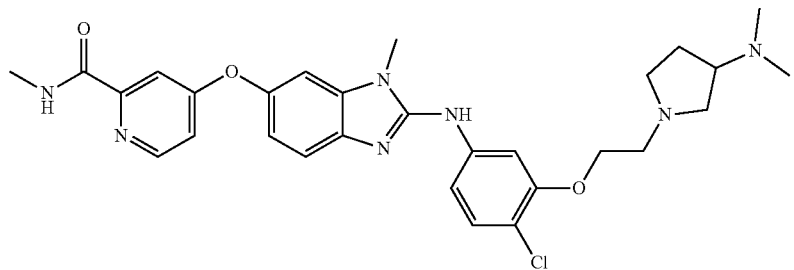

-continued
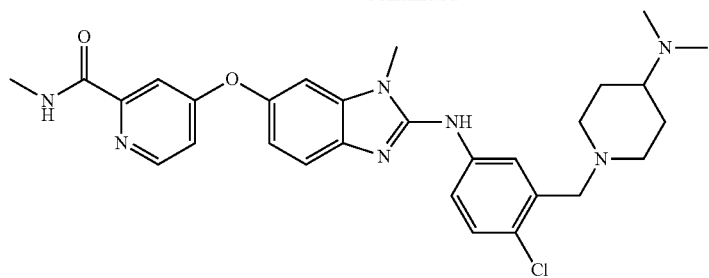
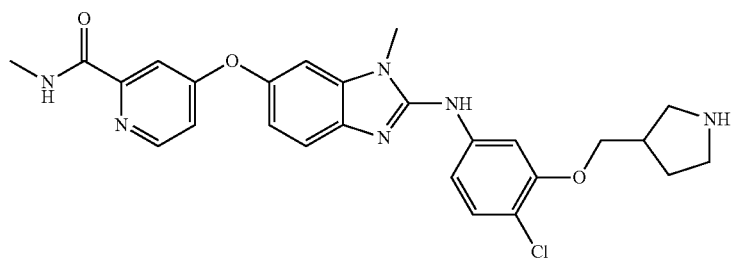
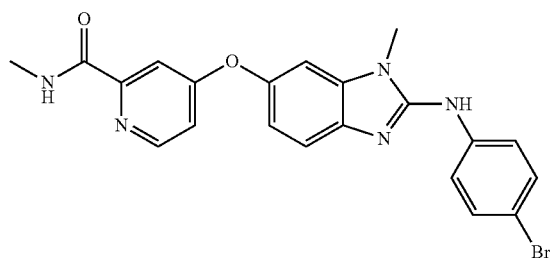
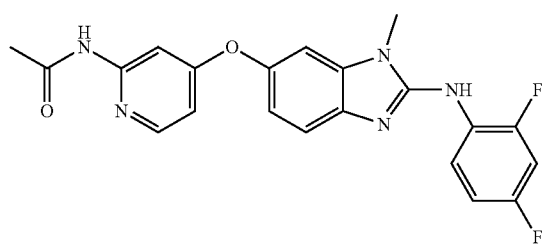
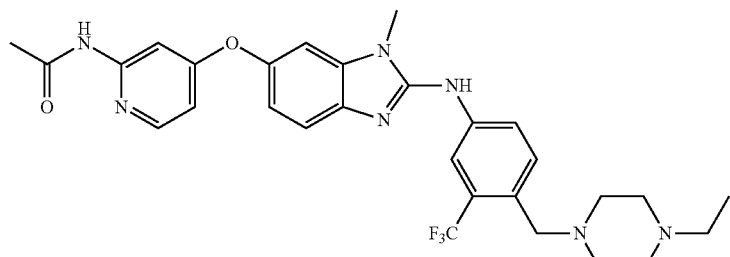
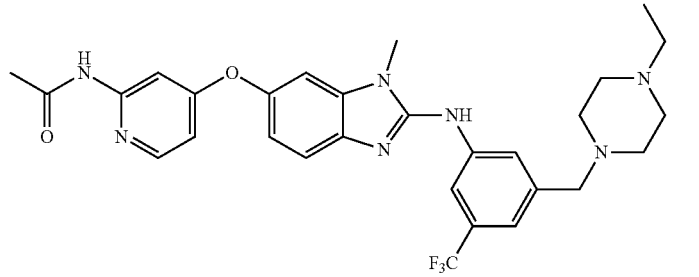

-continued
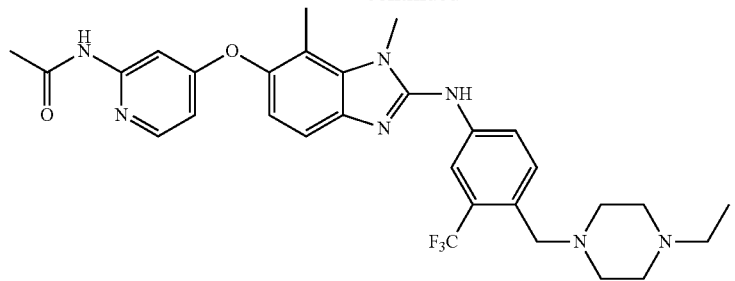
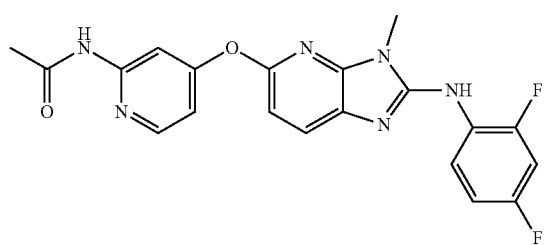
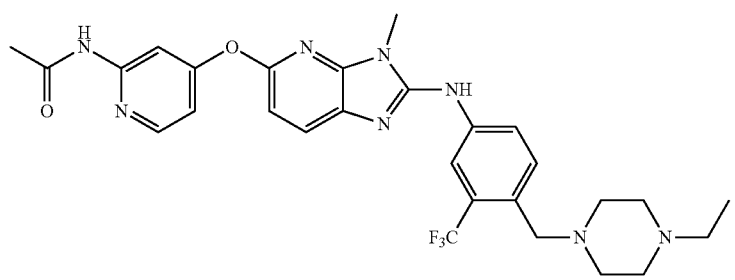
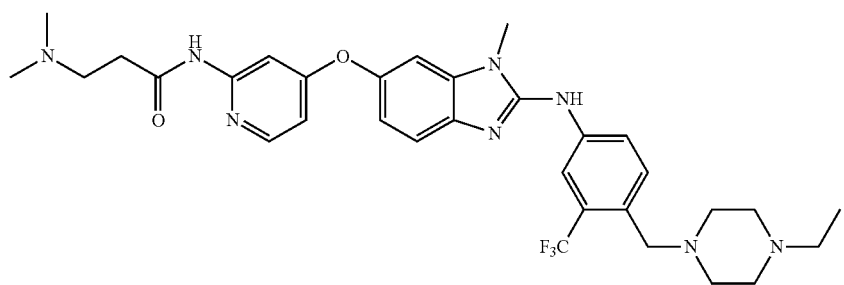
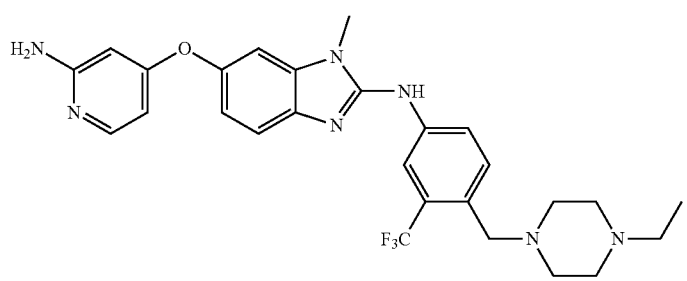

In some embodiments of any of Formulae I-1, I, II, III, IV, I', II', III', IV', I-A, II-A, III-A, and IV-A, the compound is not:
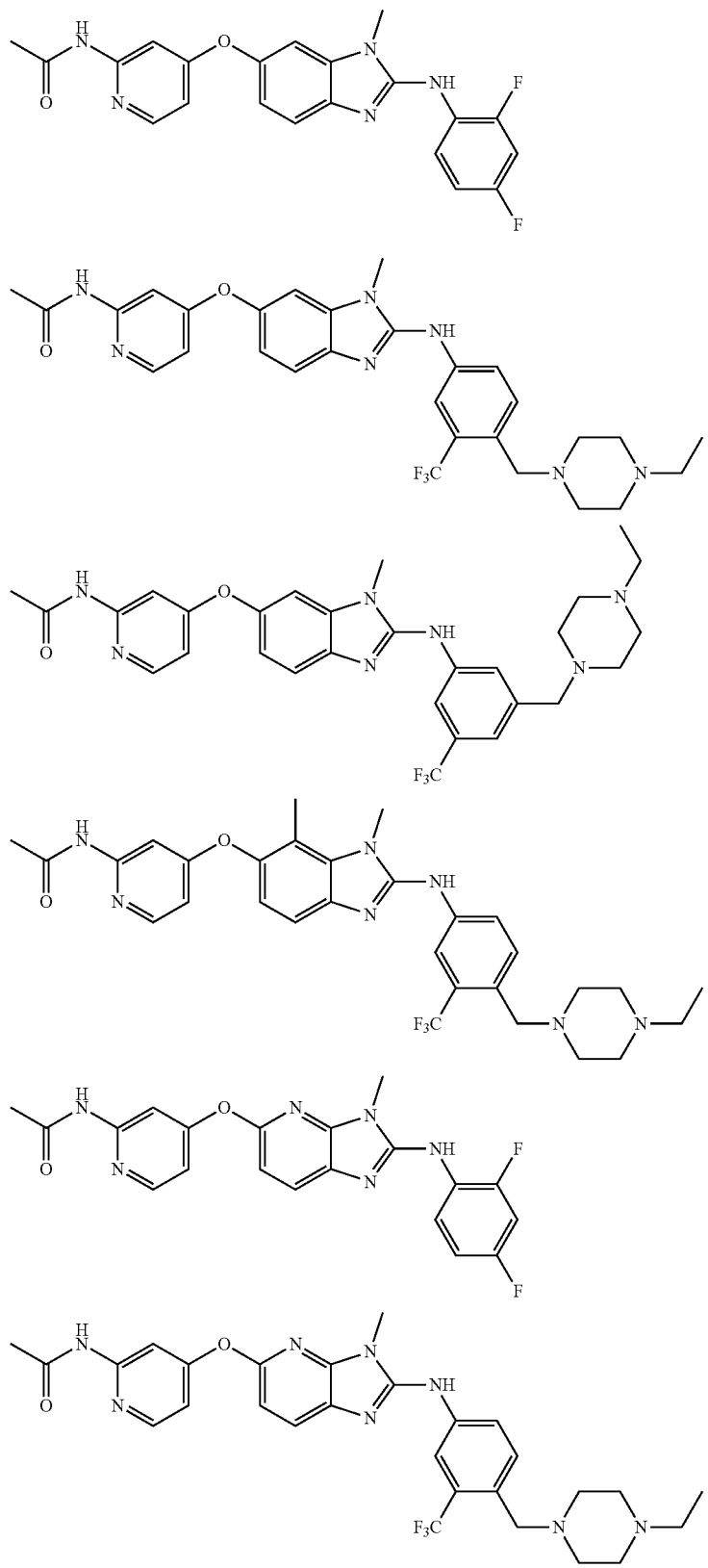

-continued
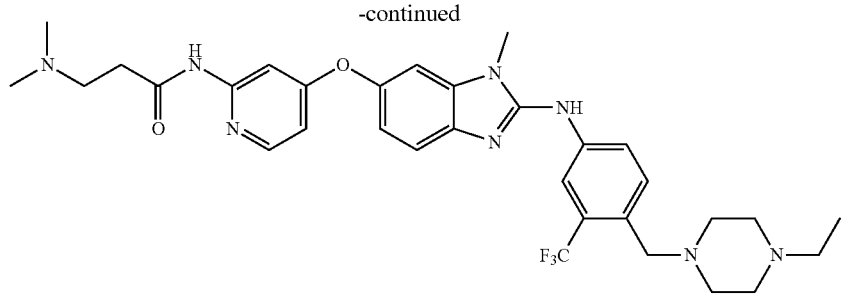
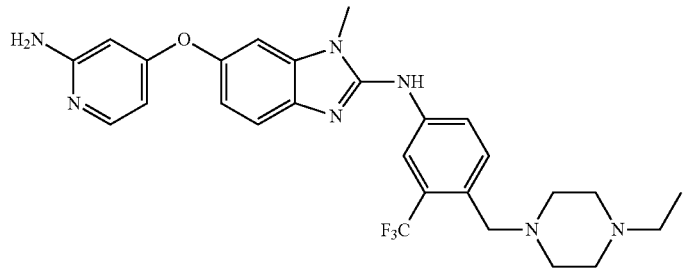
In some embodiments of any of Formulae I-1, I, II, III, IV, I', II', III', IV', I-A, II-A, III-A, and IV-A, the compound is not:
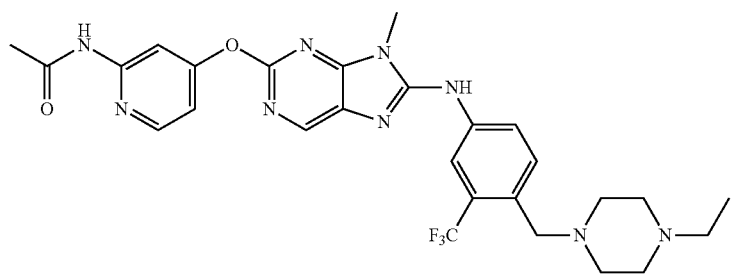
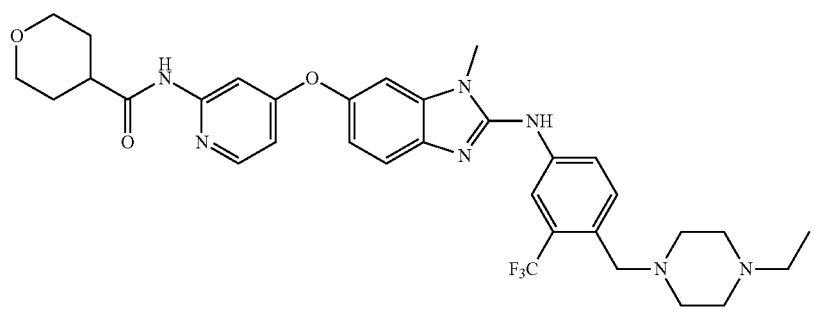
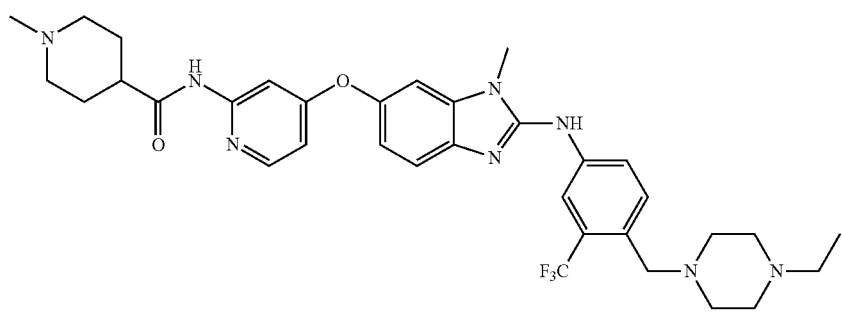

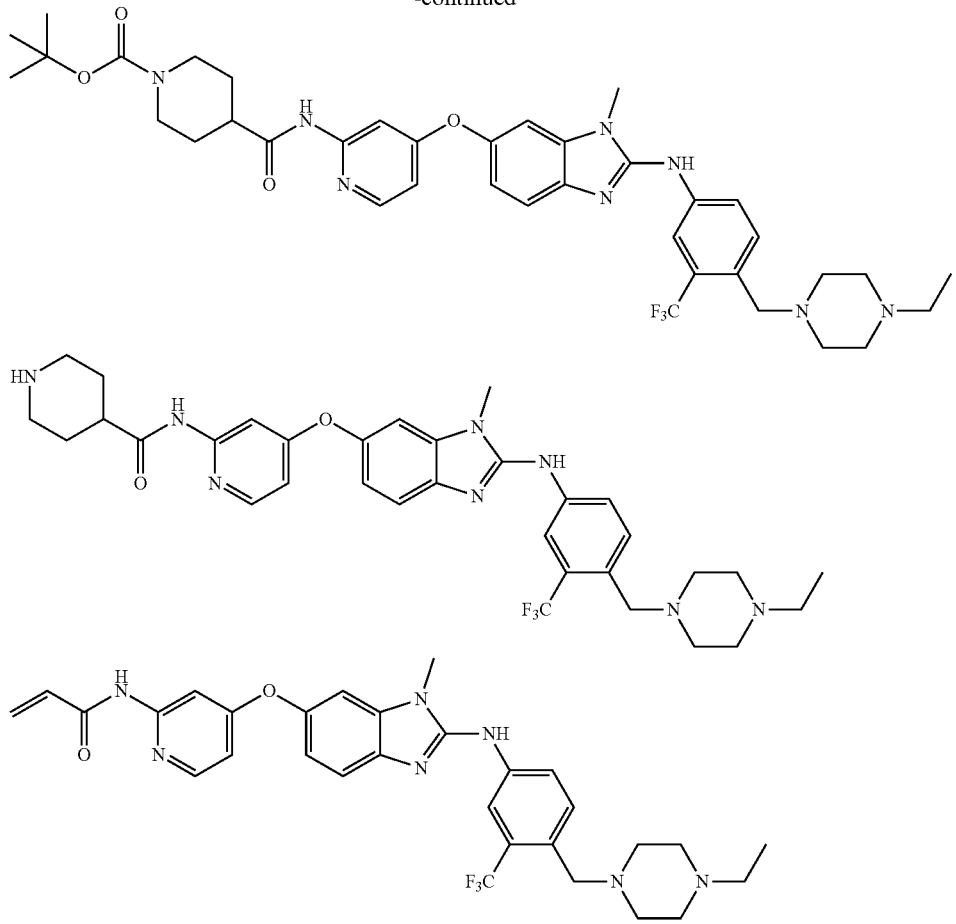

In some embodiments of any of Formulae I-1, I, II, III, IV, I', II', III', IV', I-A, II-A, III-A, and IV-A, when $R^1$ is —N(H)C(O)R' and R' is optionally substituted $C_{1-6}$ aliphatic (e.g., optionally substituted $C_{1-6}$ alkyl, e.g., optionally substituted $C_{1-2}$ alkyl), then Ring A is not phenyl.

In some embodiments of any of Formulae I-1, I, II, III, IV, I', II', III', IV', I-A, II-A, III-A, and IV-A, when $R^1$ is —N(H)C(O)R' and R' is methyl, then Ring A is not phenyl.

In some embodiments of any of Formulae I-1, I, II, III, IV, I', II', III', IV', I-A, II-A, III-A, and IV-A, when $R^1$ is —N(H)C(O)R', R' is optionally substituted $C_{1-6}$ aliphatic (e.g., optionally substituted $C_{1-6}$ alkyl, e.g., optionally substituted $C_{1-2}$ alkyl), and Ring A is phenyl, then $R^a$ is not fluoro.

In some embodiments of any of Formulae I-1, I, II, III, IV, I', II', III', IV', I-A, II-A, III-A, and IV-A, when $R^1$ is —N(H)C(O)R', R' is optionally substituted $C_{1-6}$ aliphatic (e.g., optionally substituted $C_{1-6}$ alkyl, e.g., optionally substituted $C_{1-2}$ alkyl), and Ring A is phenyl, then $R^a$ is not —CF$_3$ or optionally substituted piperazinyl.

In some embodiments of any of Formulae I-1, I, II, III, IV, I', II', III', IV', I-A, II-A, III-A, and IV-A, when $R^1$ is —N(H)C(O)R', R' is optionally substituted $C_{1-6}$ aliphatic (e.g., optionally substituted $C_{1-6}$ alkyl, e.g., optionally substituted $C_{1-2}$ alkyl), and Ring A is phenyl, then $R^a$ is not —CF$_3$ or

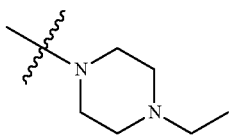

In some embodiments of any of Formulae I-1, I, II, III, IV, I', II', III', IV', I-A, II-A, III-A, and IV-A, when $R^1$ is —N(H)C(O)R', R' is optionally substituted $C_{1-6}$ aliphatic (e.g., optionally substituted $C_{1-6}$ alkyl, e.g., optionally substituted $C_{1-2}$ alkyl), and Ring A is phenyl, then $R^b$ is not —CF$_3$ or

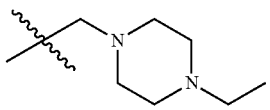

In some embodiments of any of Formulae I-1, I, II, III, IV, I', II', III', IV', I-A, II-A, III-A, and IV-A, when $R^1$ is —C(O)NH(R) and R is optionally substituted $C_{1-6}$ aliphatic (e.g., optionally substituted $C_{1-6}$ alkyl, e.g., optionally substituted $C_{1-2}$ alkyl, e.g., methyl), then Ring A is not phenyl.

In some embodiments of any of Formulae I-1, I, II, III, IV, I', II', III', IV', I-A, II-A, III-A, and IV-A, when $R^1$ is —C(O)NH(R), R is optionally substituted $C_{1-6}$ aliphatic (e.g., optionally substituted $C_{1-6}$ alkyl, e.g., optionally substituted $C_{1-2}$ alkyl, e.g., methyl), and Ring A is phenyl, then neither $R^a$ nor $R^b$ is chloro or bromo.

In some embodiments of any of Formulae I-1, I, II, III, IV, I', II', III', IV', I-A, II-A, III-A, and IV-A, when $R^1$ is —C(O)NH(R), R is optionally substituted $C_{1-6}$ aliphatic (e.g., optionally substituted $C_{1-6}$ alkyl, e.g., optionally substituted $C_{1-2}$ alkyl, e.g., methyl), and Ring A is phenyl, then $R^a$ is not chloro or bromo.

In some embodiments of any of Formulae I-1, I, II, III, IV, I', II', III', IV', I-A, II-A, III-A, and IV-A, when $R^1$ is —C(O)NH(R), R is optionally substituted $C_{1-6}$ aliphatic (e.g., optionally substituted $C_{1-6}$ alkyl, e.g., optionally substituted $C_{1-2}$ alkyl, e.g., methyl), and Ring A is phenyl, then $R^x$ is not

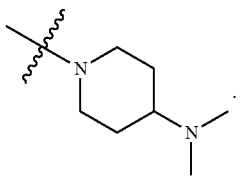 [SMILES: *N1CCC(N(C)C)CC1]

In some embodiments of any of Formulae I-1, I, II, III, IV, I', II', III', IV', I-A, II-A, III-A, and IV-A, when $R^1$ is —C(O)NH(R), R is optionally substituted $C_{1-6}$ aliphatic (e.g., optionally substituted $C_{1-6}$ alkyl, e.g., optionally substituted $C_{1-2}$ alkyl, e.g., methyl), and Ring A is phenyl, then $R^b$ is not —OR.

In some embodiments of any of Formulae I-1, I, II, III, IV, I', II', III', IV', I-A, II-A, III-A, and IV-A, when $R^1$ is —C(O)NH(R), R is optionally substituted $C_{1-6}$ aliphatic (e.g., optionally substituted $C_{1-6}$ alkyl, e.g., optionally substituted $C_{1-2}$ alkyl, e.g., methyl), and Ring A is phenyl, then $R^b$ is not

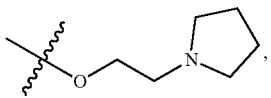

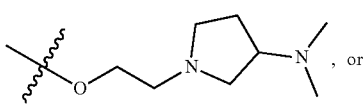, or

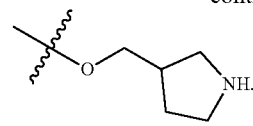

In some embodiments of any of Formulae I-1, I, II, III, IV, I', II', III', IV', I-A, II-A, III-A, and IV-A, when Ring A is phenyl, $R^1$ is —NHC(O)R' or —NH$_2$, $R^2$ is —CH$_3$, X is CH, and R' is optionally substituted $C_{1-2}$ aliphatic, then $R^a$ and $R^b$ are not fluoro or

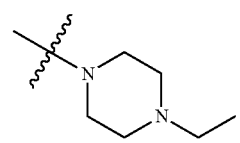

In some embodiments of any of Formulae I-1, I, II, III, IV, I', II', III', IV', I-A, II-A, III-A, and IV-A, when Ring A is phenyl, $R^1$ is —NHC(O)CH$_3$, $R^2$ is —CH$_3$, and X is N, then $R^a$ and $R^b$ are not fluoro or

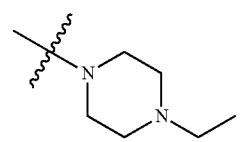

In some embodiments of any of Formulae I-1, I, II, III, IV, I', II', III', IV', I-A, II-A, III-A, and IV-A, when Ring A is phenyl, $R^1$ is —NHC(O)CH$_3$, $R^2$ is —CH$_3$, and X is CCH$_3$, then $R^a$ and $R^b$ are not

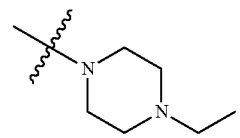

In some embodiments of any of Formulae I-1, I, II, III, IV, I', II', III', IV', I-A, II-A, III-A, and IV-A, when Ring A is phenyl, $R^1$ is —C(O)NHCH$_3$, $R^2$ is $C_{1-2}$ alkyl, and X is CH, then $R^a$ and $R^b$ are not halogen.

In some embodiments, the present disclosure provides compounds selected from Table 1:

I-1

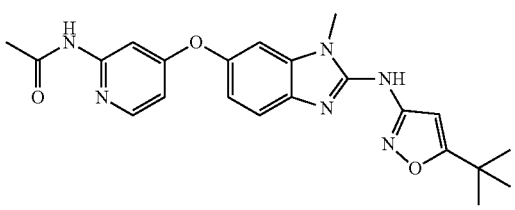

I-2

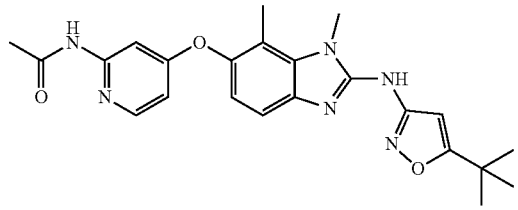

-continued
I-3
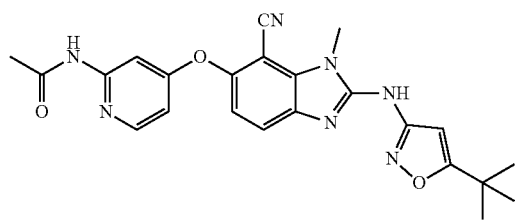
I-4
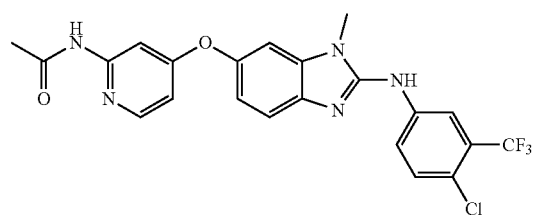
I-5
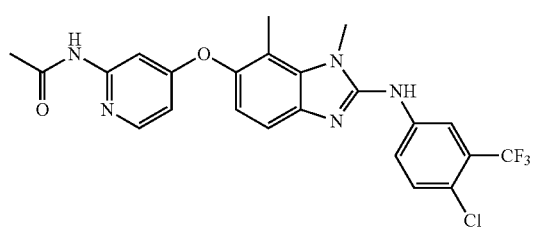
I-6
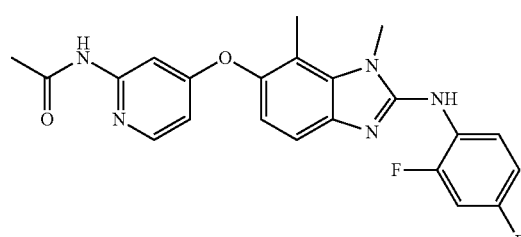
I-7
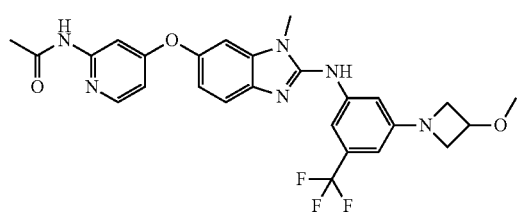
I-8
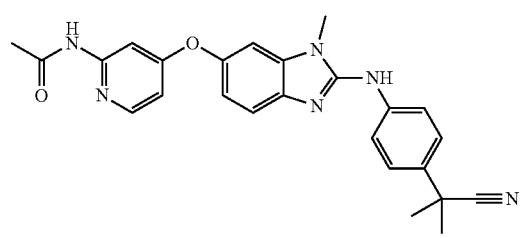
I-9
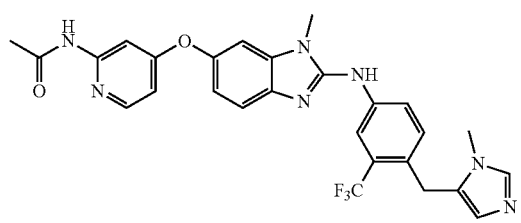
I-10
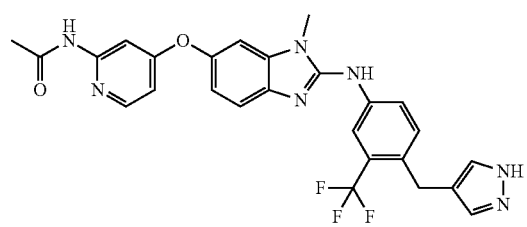
I-11
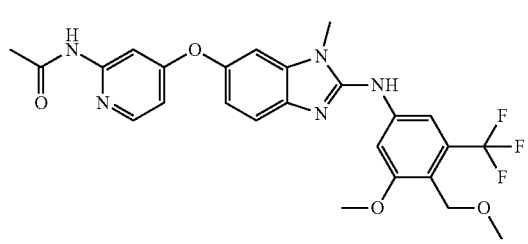
I-12
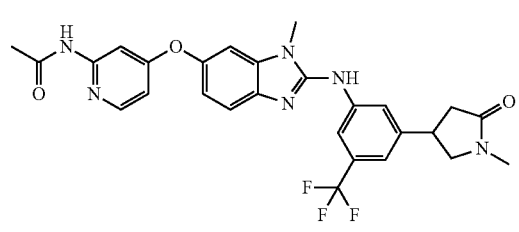
I-12-i
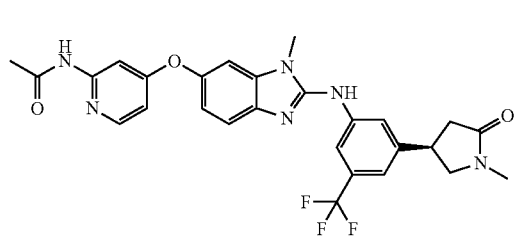
I-12-ii
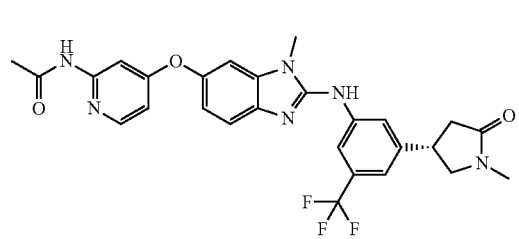

-continued
I-13
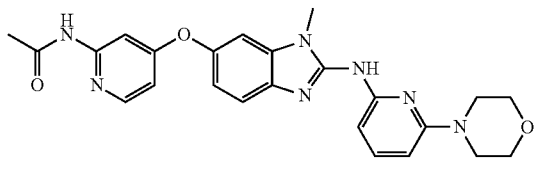
I-14
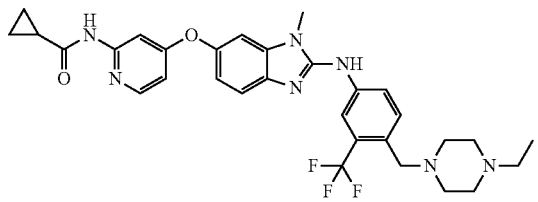
I-15
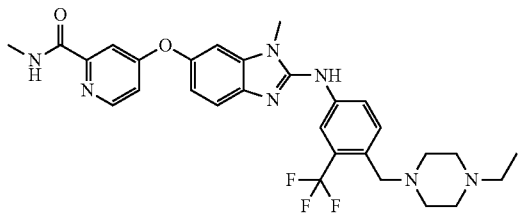
I-16
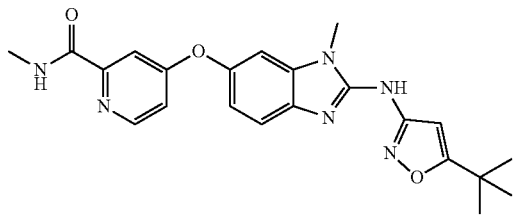
I-17
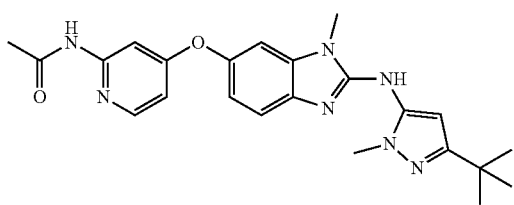
I-18
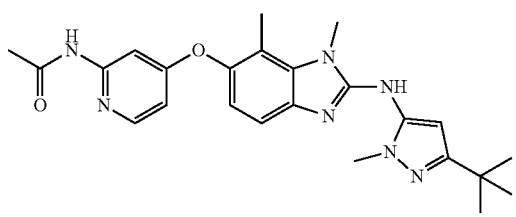
I-19'
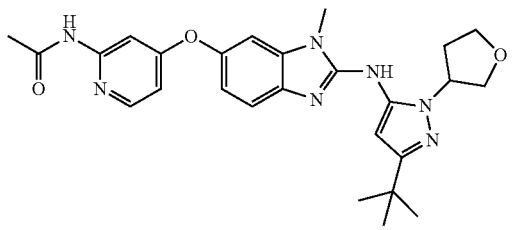
I-19
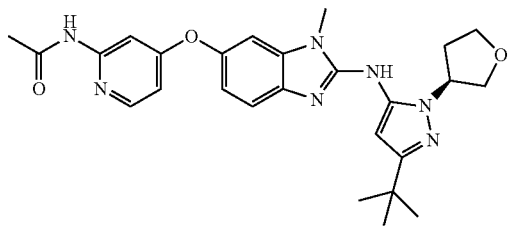
I-23
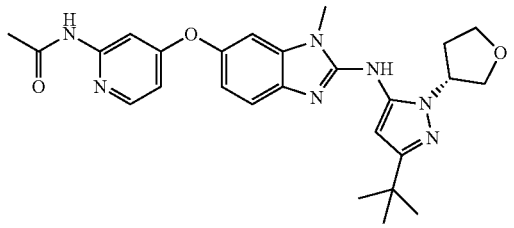
I-20'
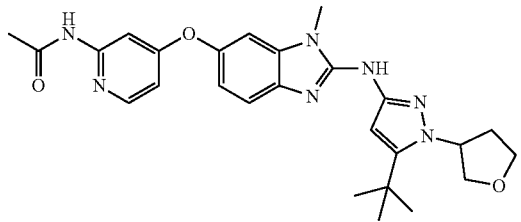
I-20
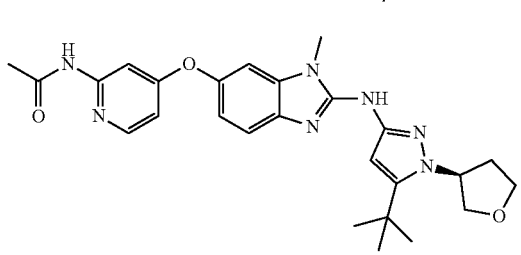
I-24
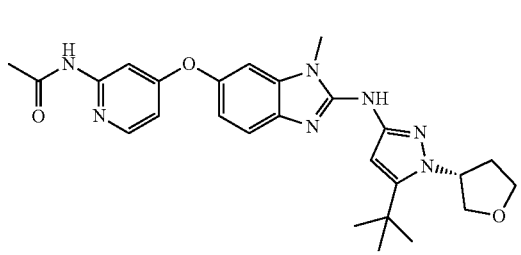
I-21'
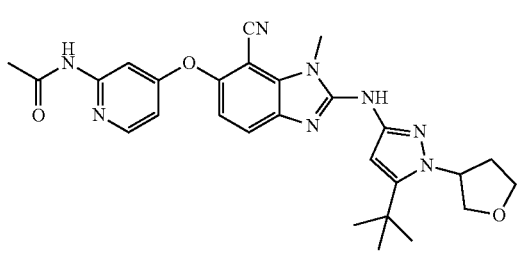
I-21
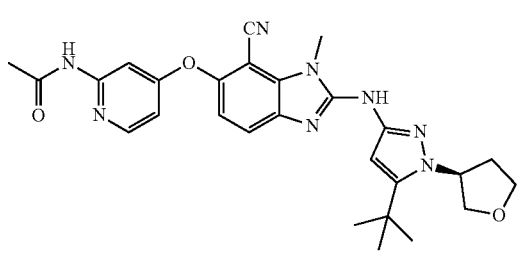

I-25
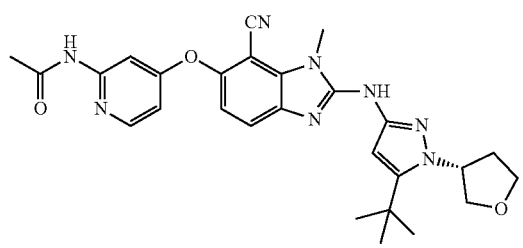
I-22'
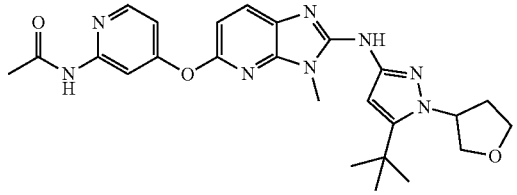
I-22
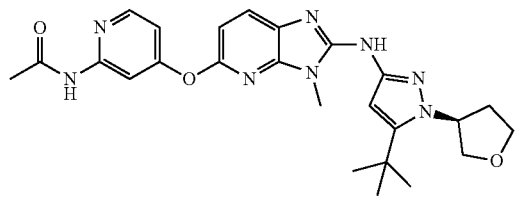
I-26
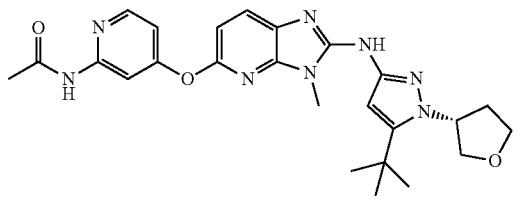
I-27
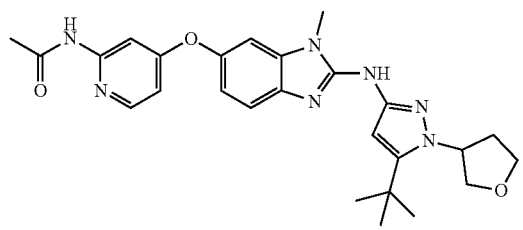
I-28
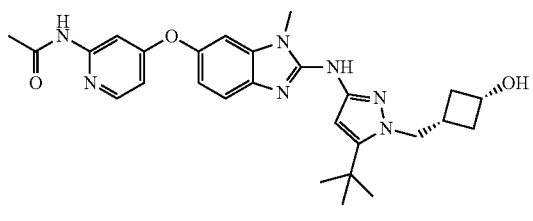
I-29
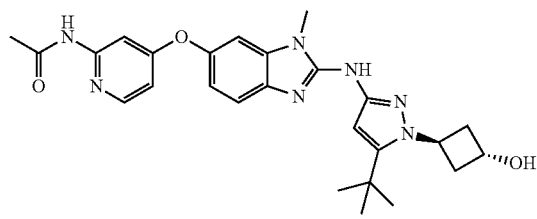
I-30
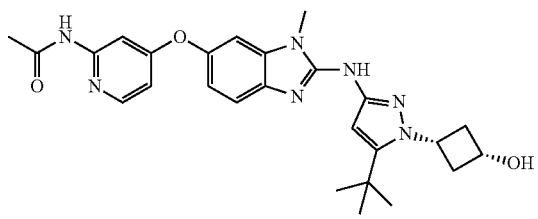
I-31
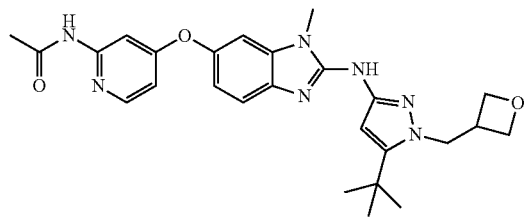
I-32
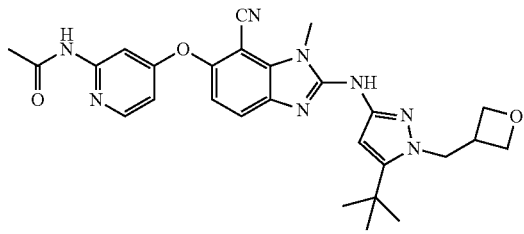
I-33
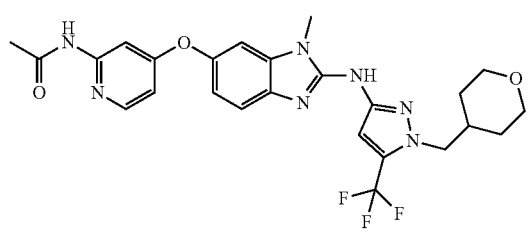
I-34
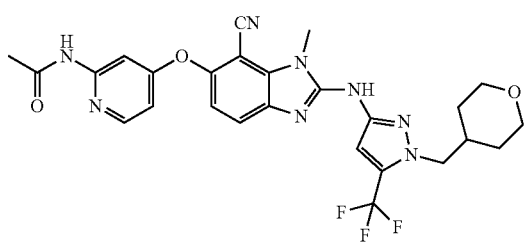

I-35
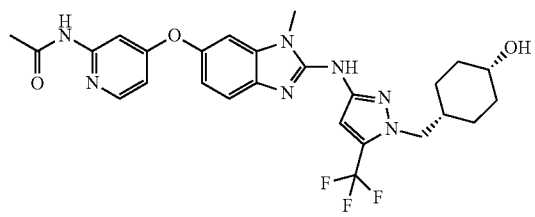
I-36
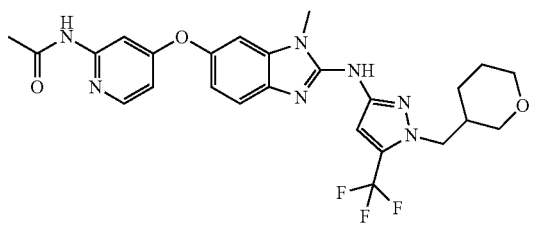
I-36-i
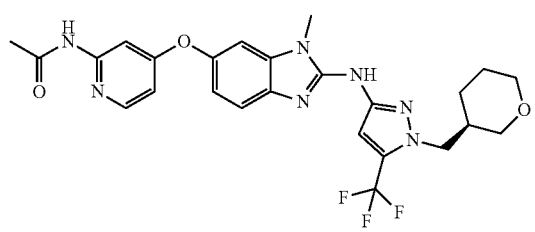
I-36-ii
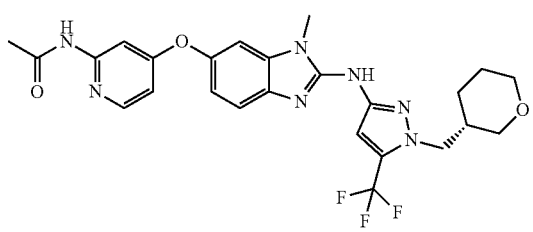
I-37
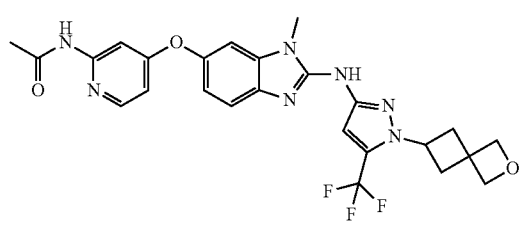
I-38
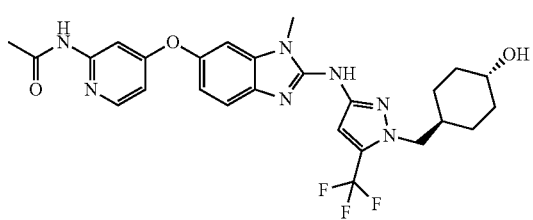
I-39
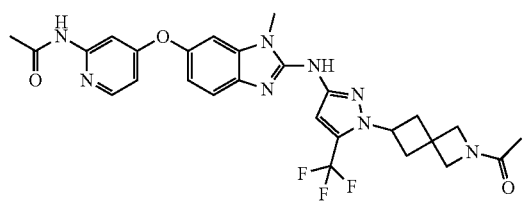
I-40
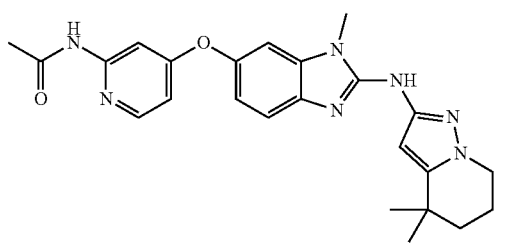
I-41
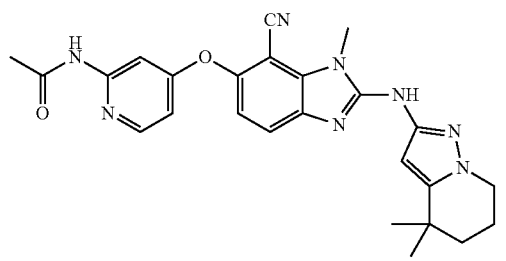
I-42
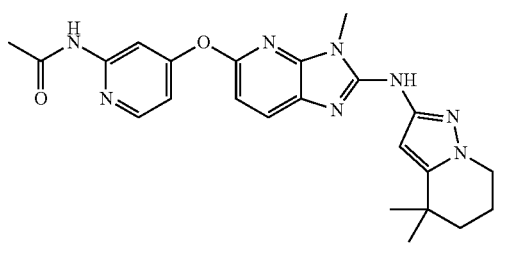
I-43
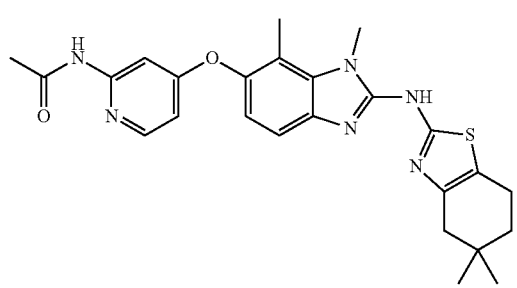
I-44
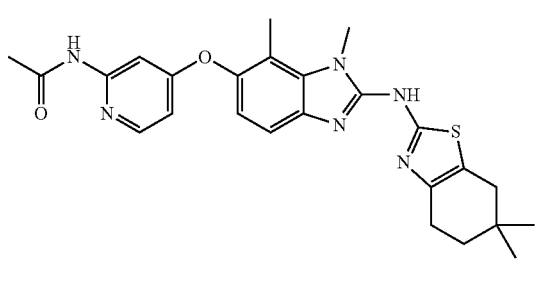

-continued
I-45
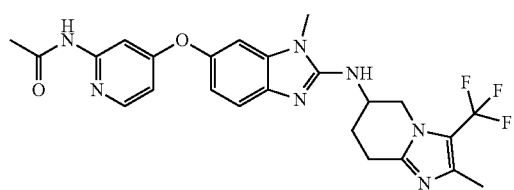
I-45-i
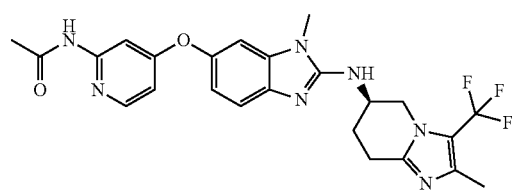
I-45-ii
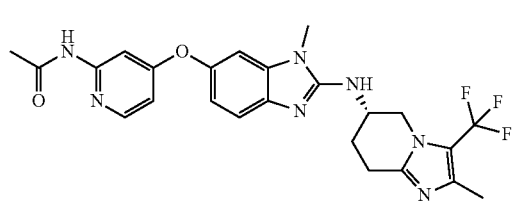
I-46
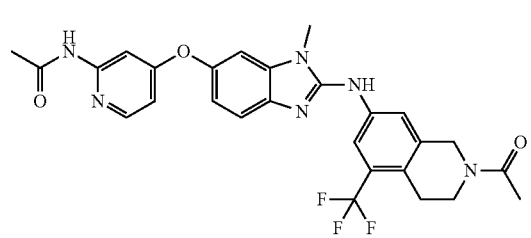
I-47
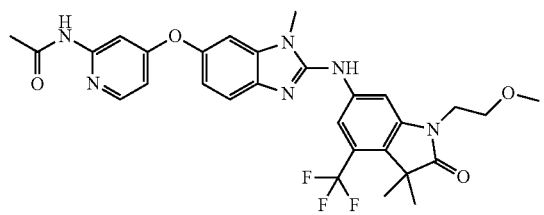
I-48
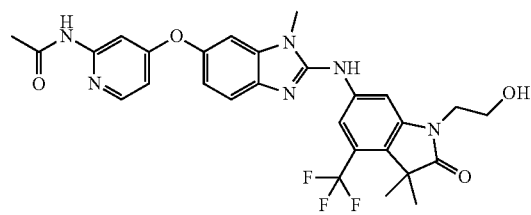
I-49
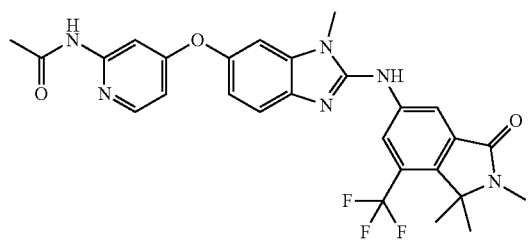
I-50
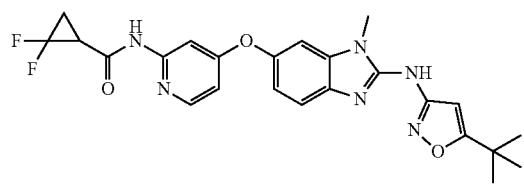
I-50-i
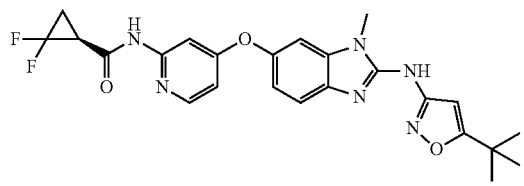
I-50-ii
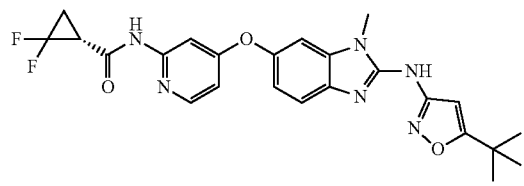
I-51
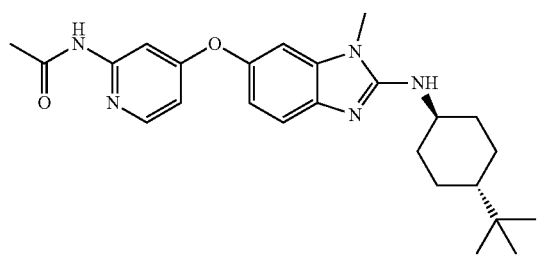
I-52
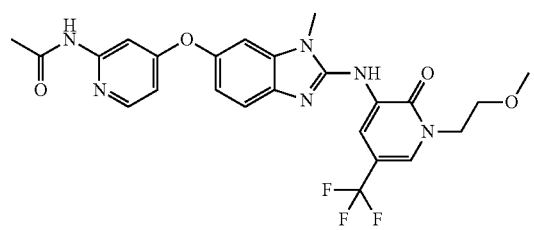

-continued
I-53
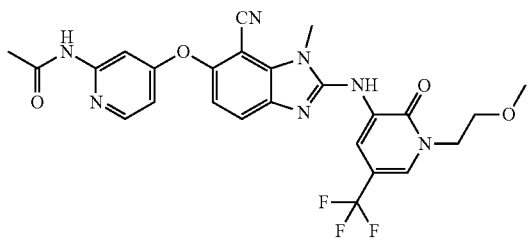
I-54
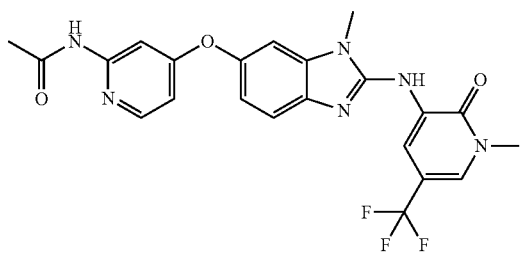
I-55
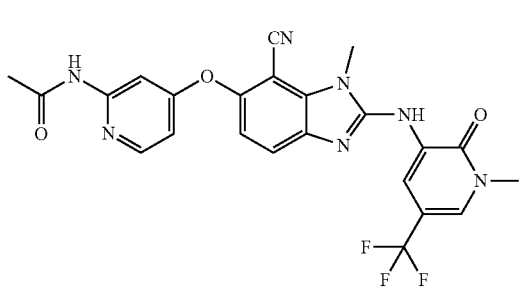
I-56
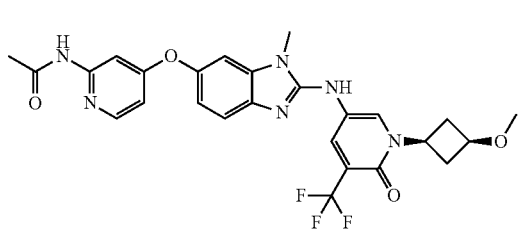
I-57
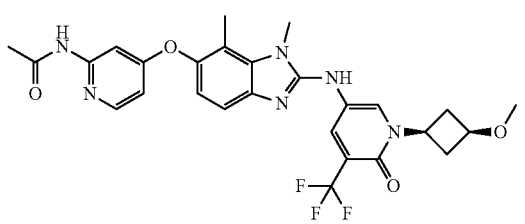
I-58
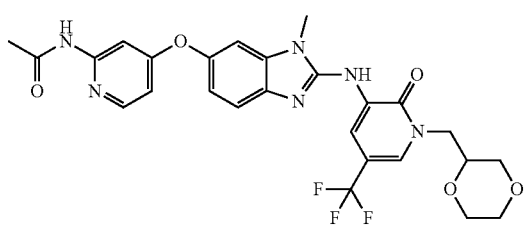
I-58-i
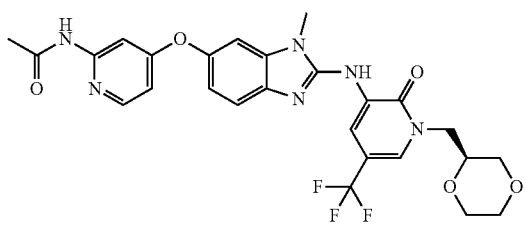
I-58-ii
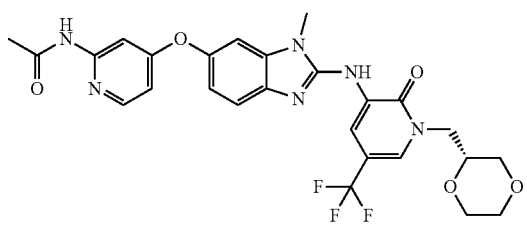
I-59'
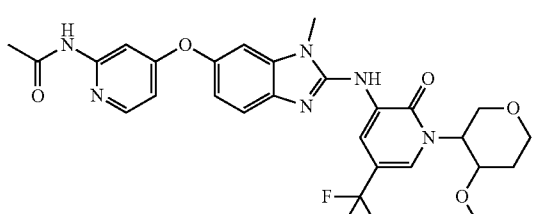
I-59-i
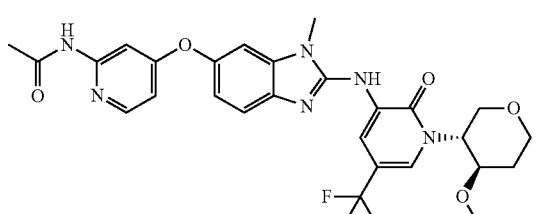
I-59-ii
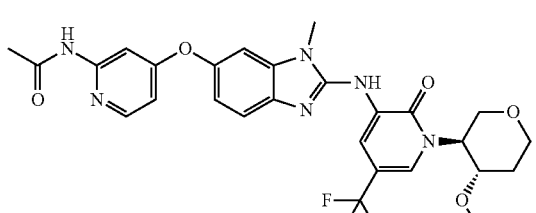
I-60-i
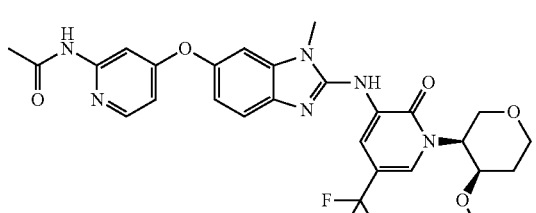

-continued
I-60-ii
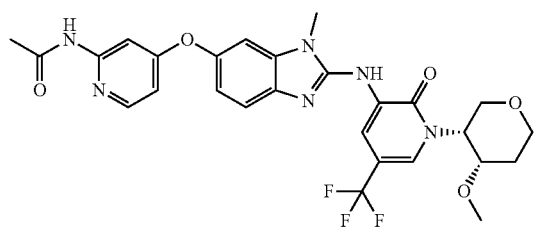
I-61
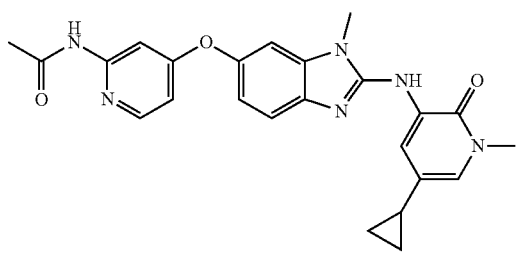
I-62
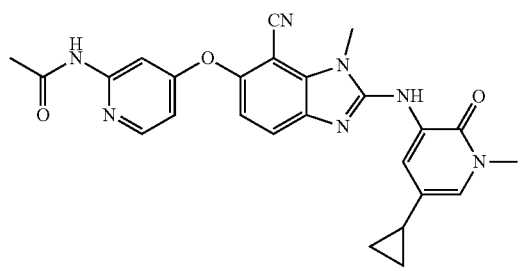
I-63
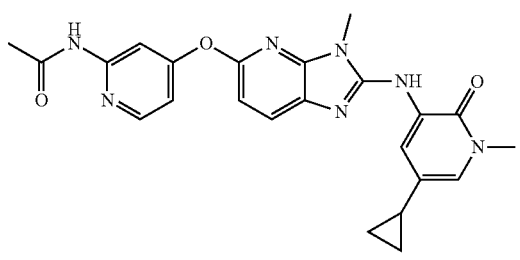
I-64
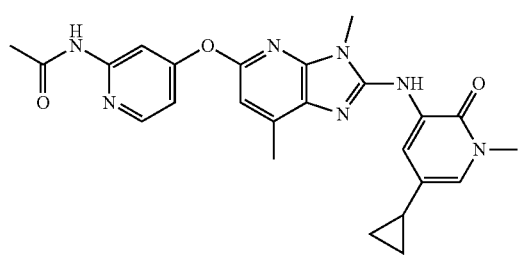
I-65
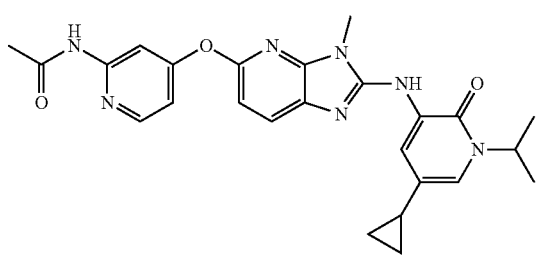
I-66
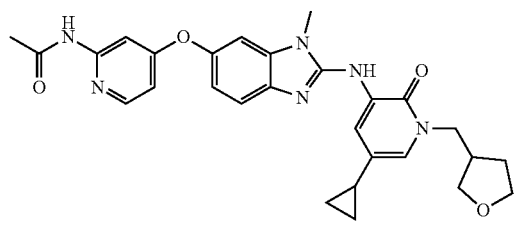
I-66-i
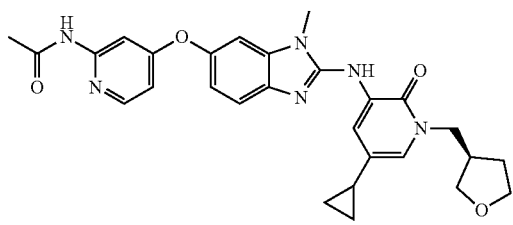
I-66-ii
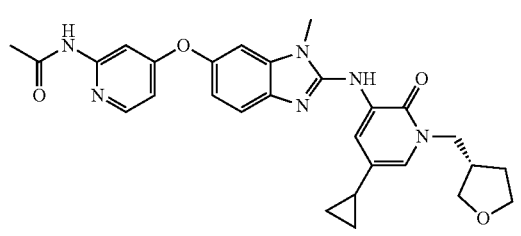
I-67
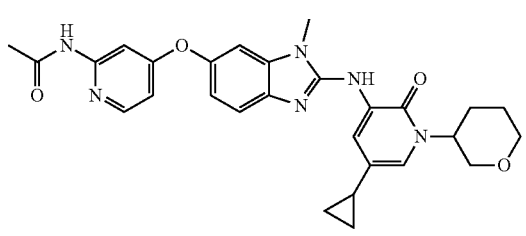
I-67-i
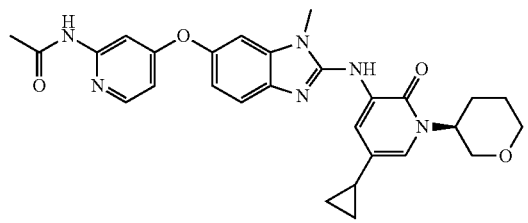
I-67-ii
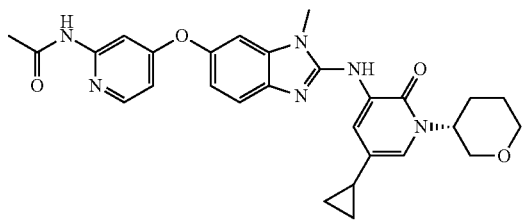

-continued
I-68
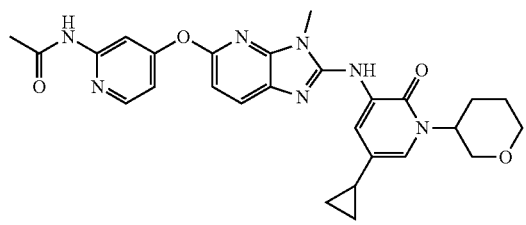
I-68-i
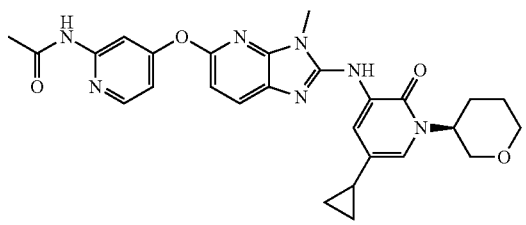
I-68-ii
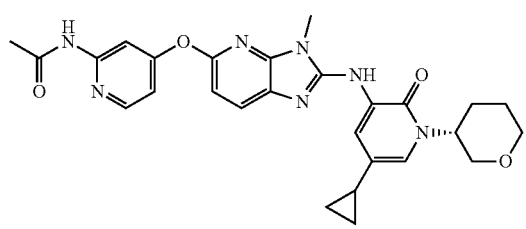
I-69
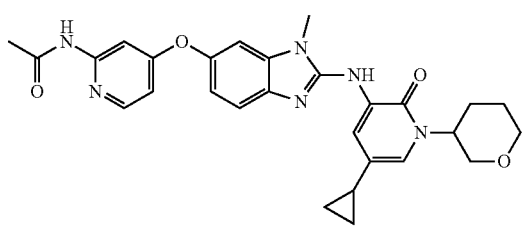
I-70
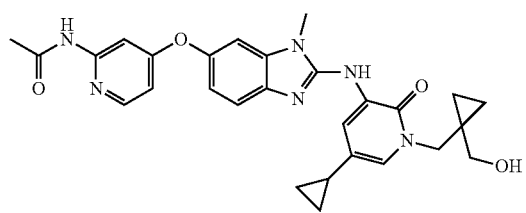
I-71
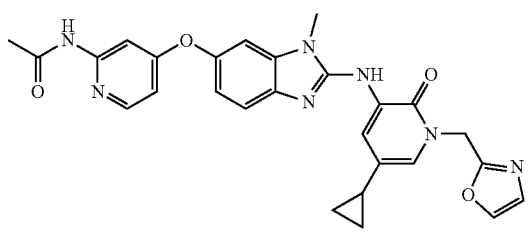
I-72
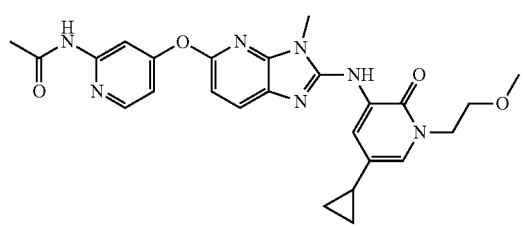
I-73
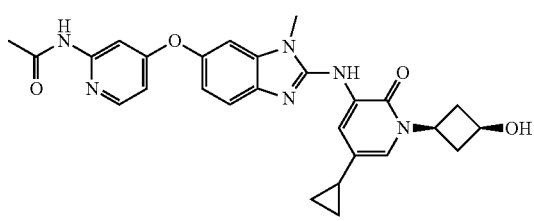
I-74
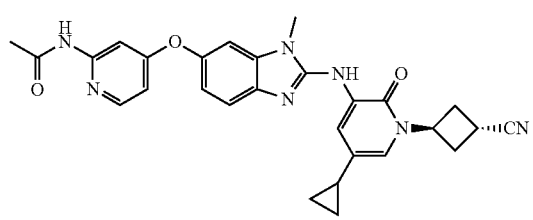
I-75
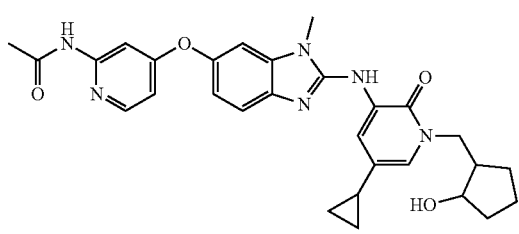
I-75-i
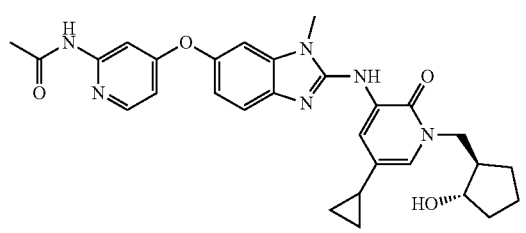
I-75-ii
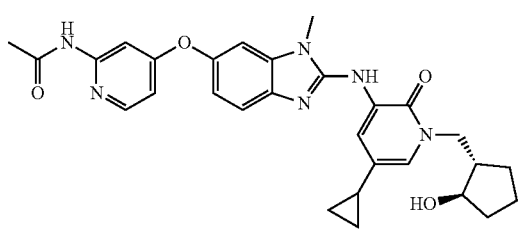

-continued
I-76
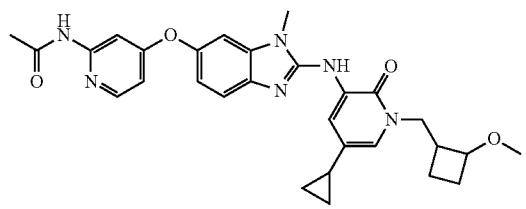
I-76-i
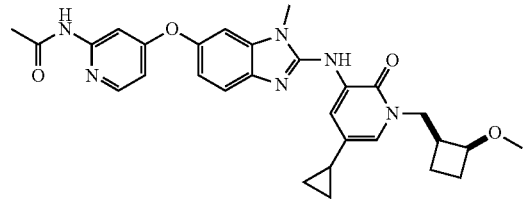
I-76-ii
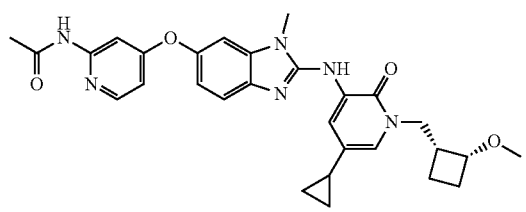
I-77
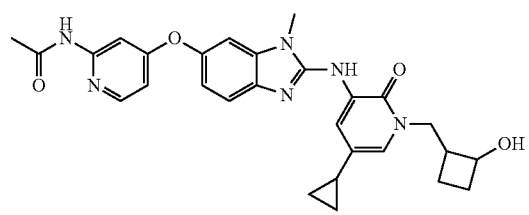
I-77-i
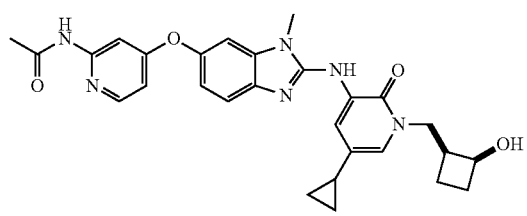
I-77-ii
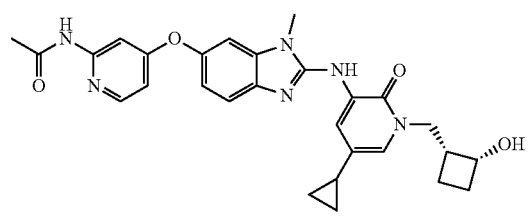
I-78
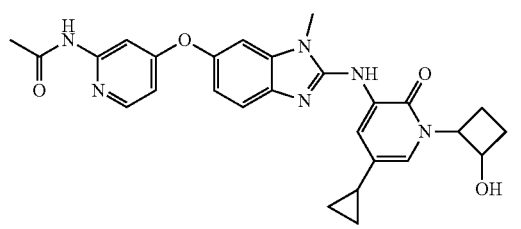
I-78-i
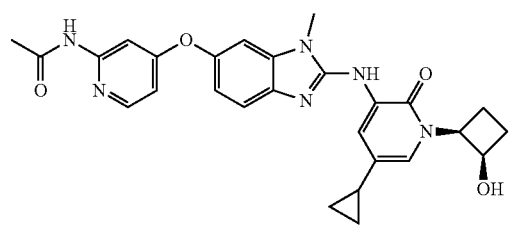
I-78-ii
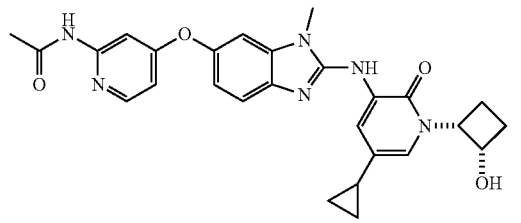
I-79-i
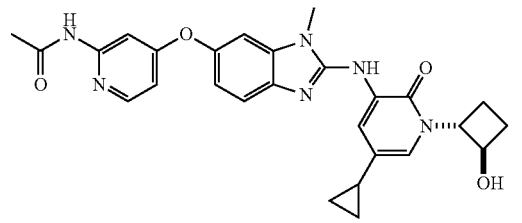
I-79-ii
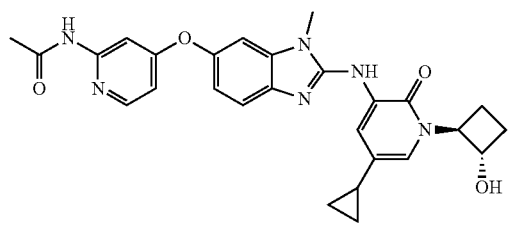
I-80
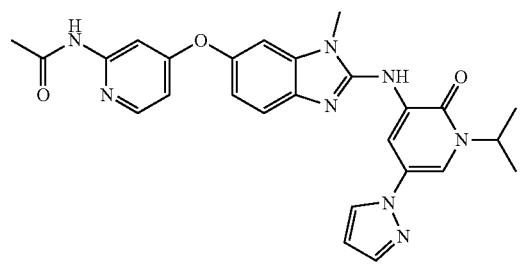

-continued
I-81
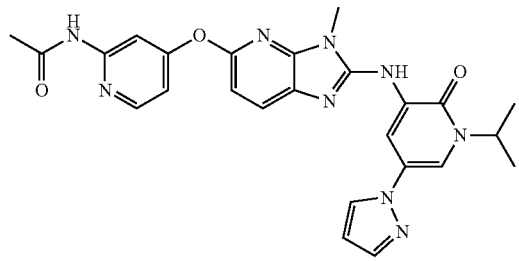
I-82
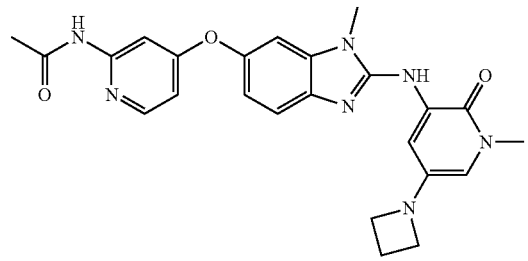
I-83
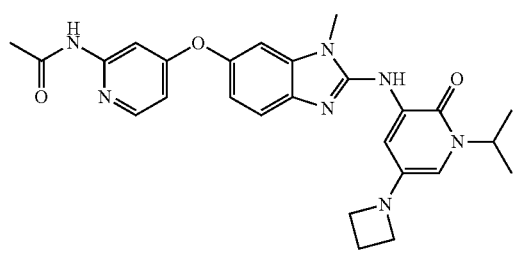
I-84
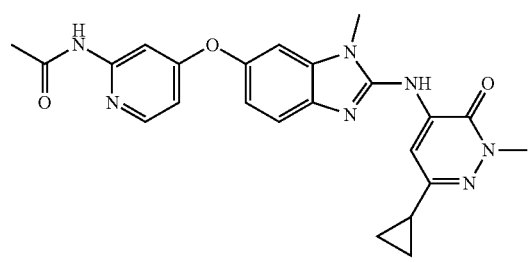
I-85
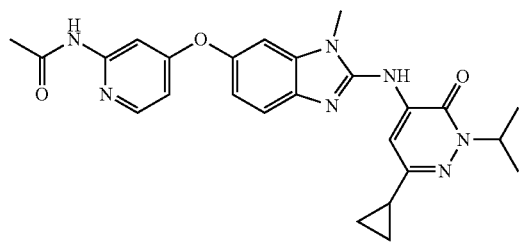
I-86
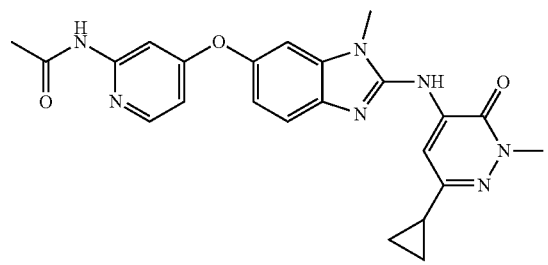
I-87
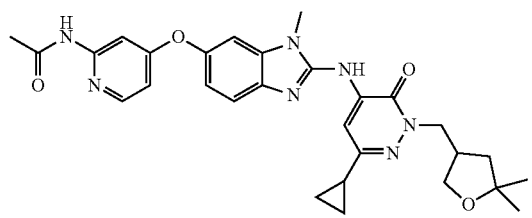
I-87-i
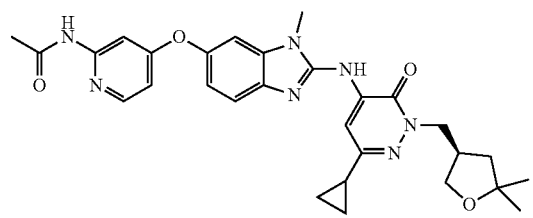
I-87-ii
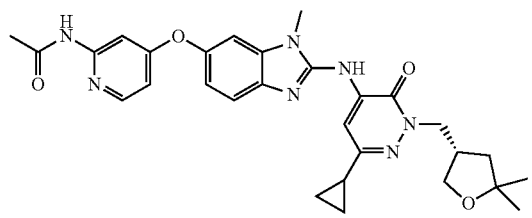
I-88
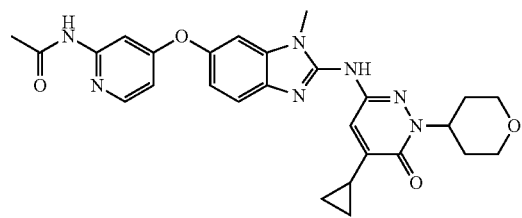
I-89
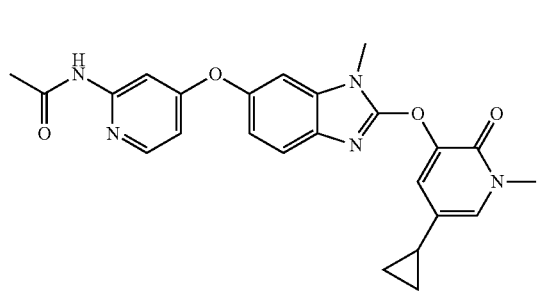
I-90
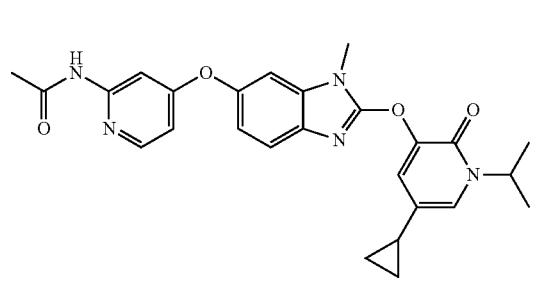

-continued
I-91
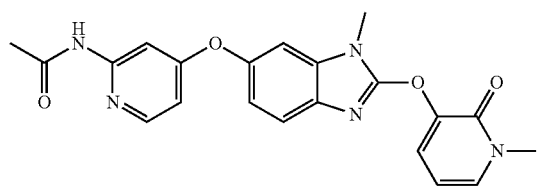
I-92
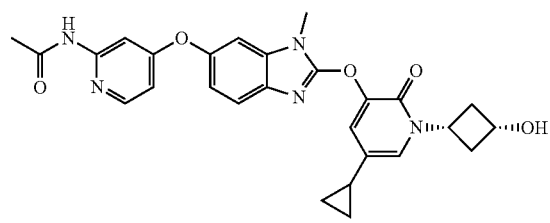
I-93
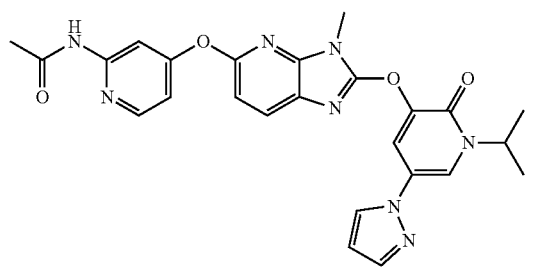
I-94
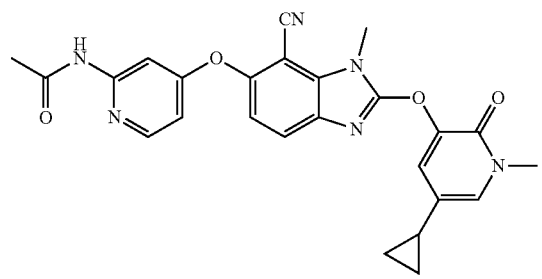
I-95
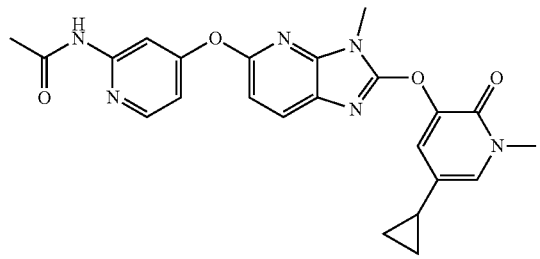
I-96
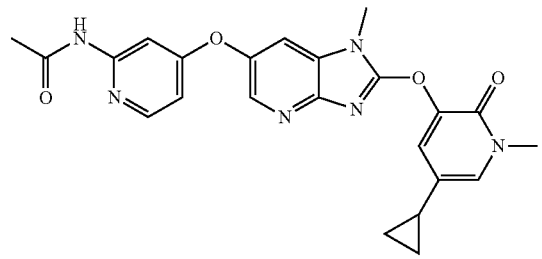
I-97
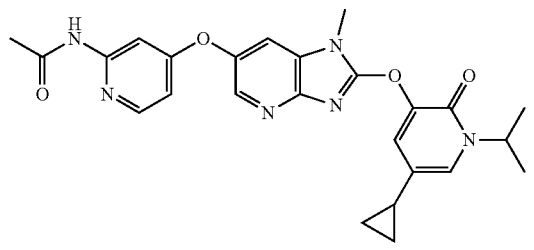
I-98
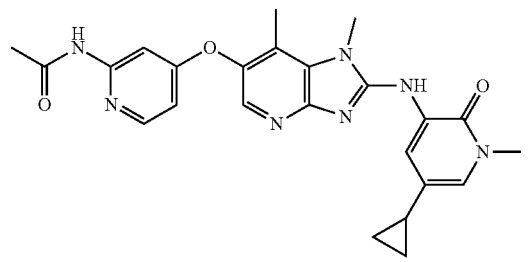
I-99
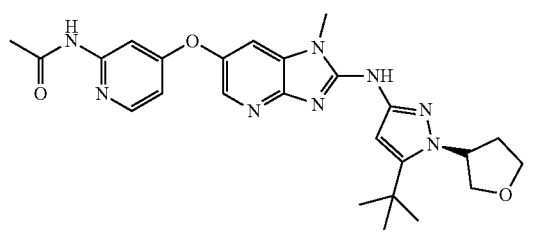
I-100
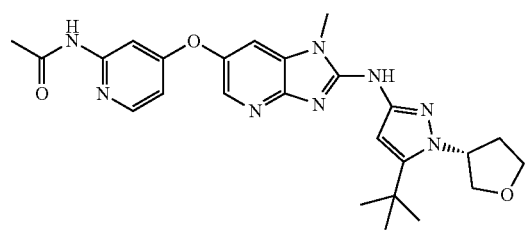

-continued
I-101
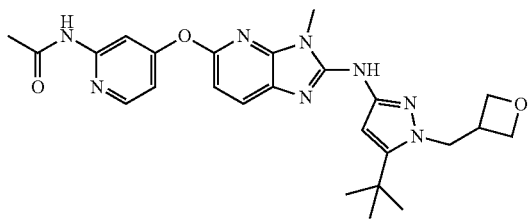
I-102
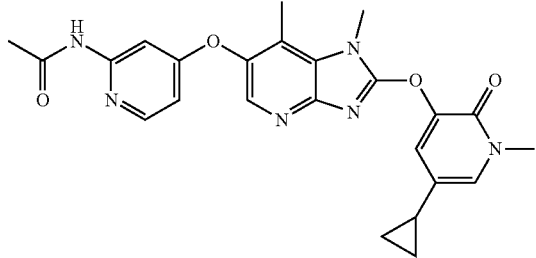
I-103
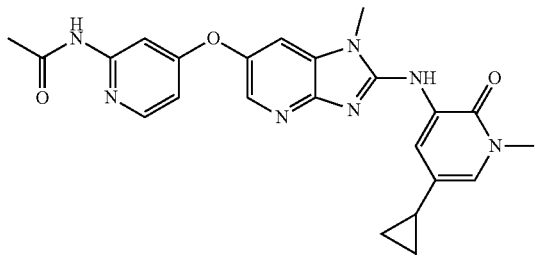
I-104
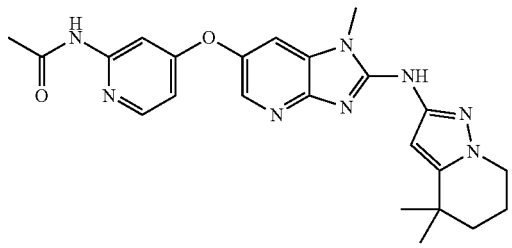
I-105'
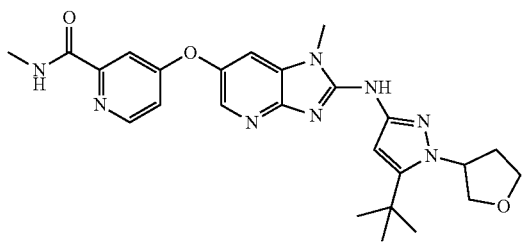
I-105
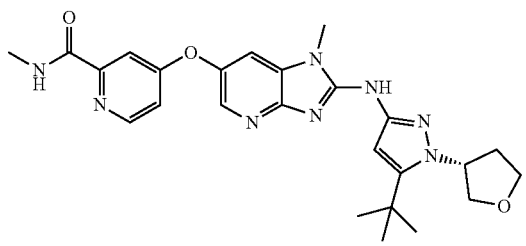
I-106
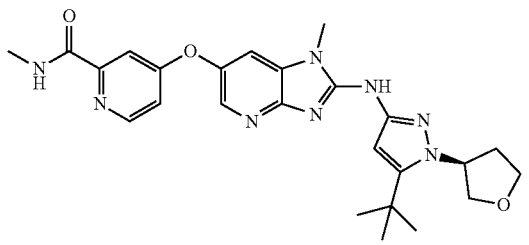
I-107
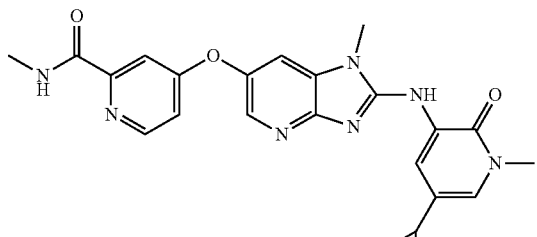
I-108'
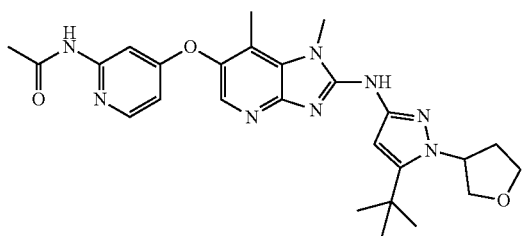
I-108
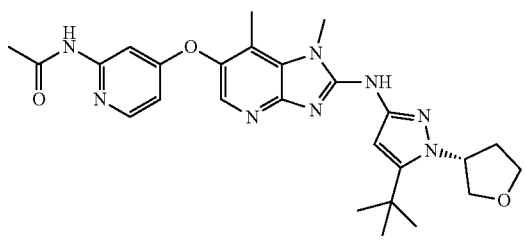
I-109'
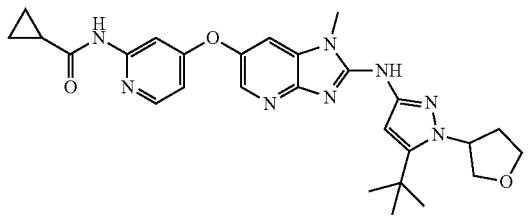
I-109
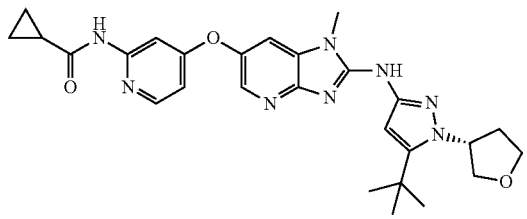

-continued
I-110
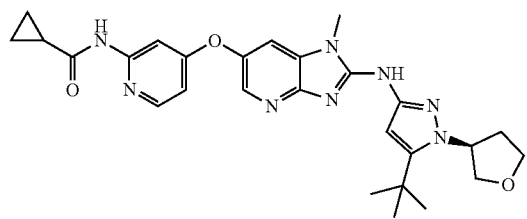
I-111
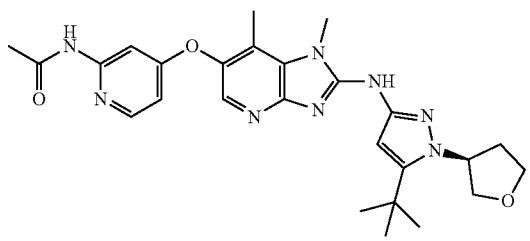
I-112
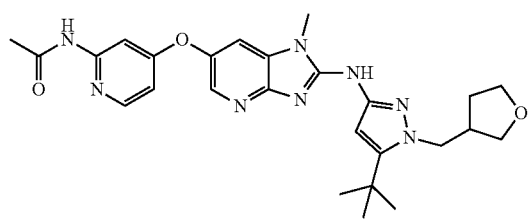
I-112-i
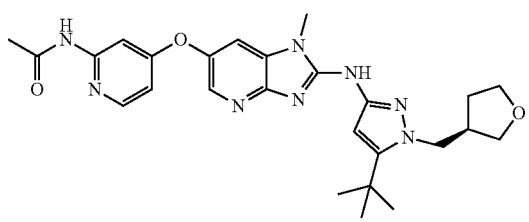
I-112-ii
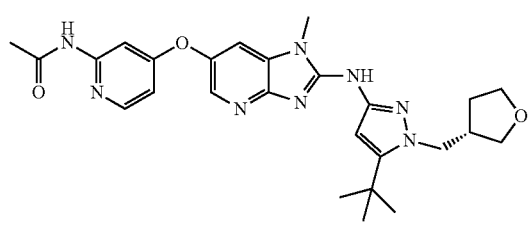
I-113
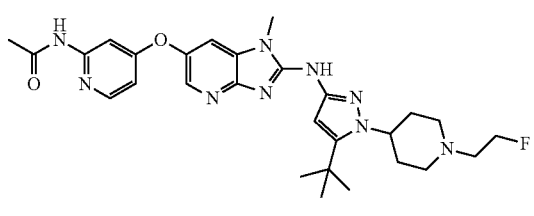
I-114
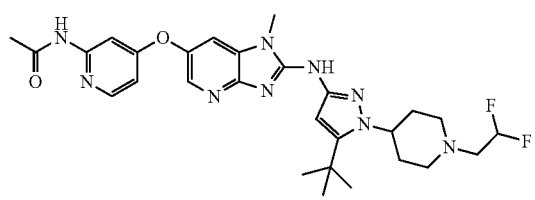
I-115'
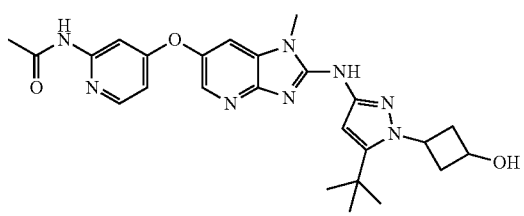
I-115
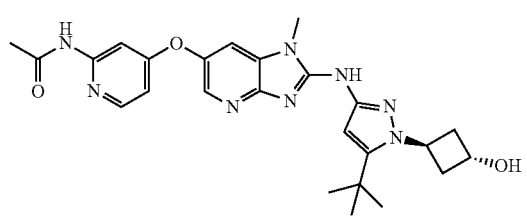
I-116
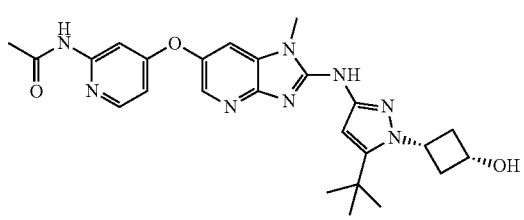
I-117
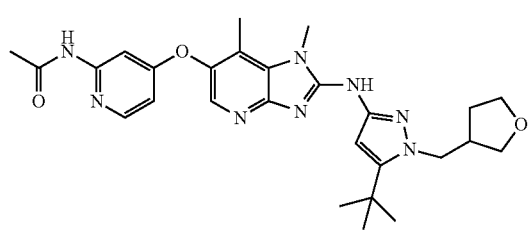
I-117-i
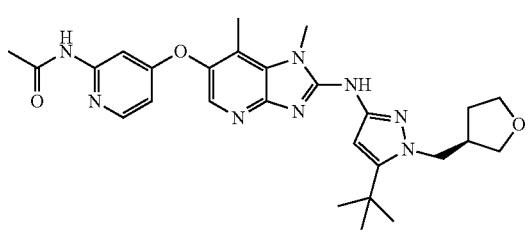

I-117-ii 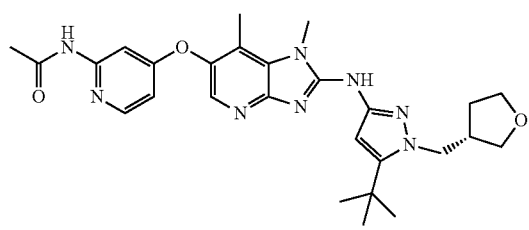
I-118' 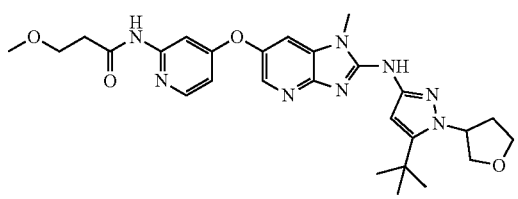
I-118 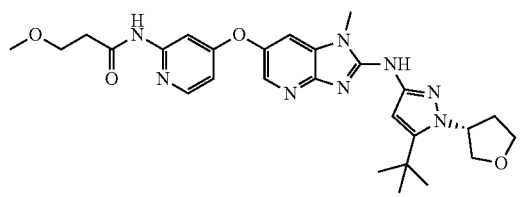
I-119 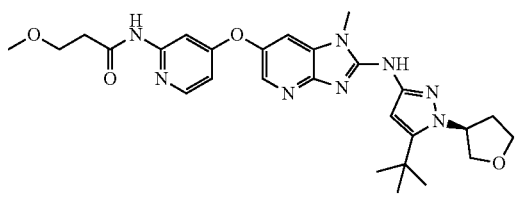
I-120' 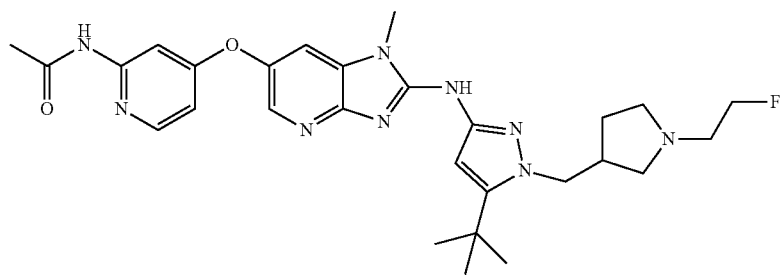
I-120 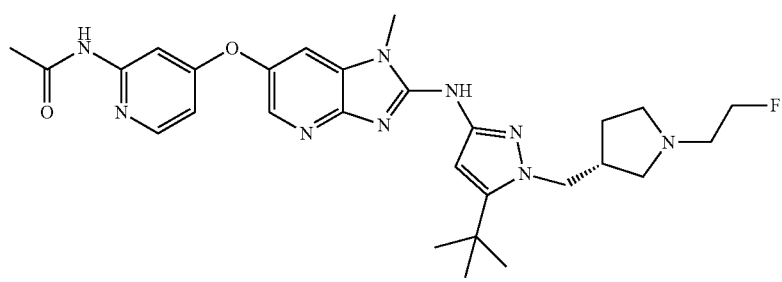
I-121 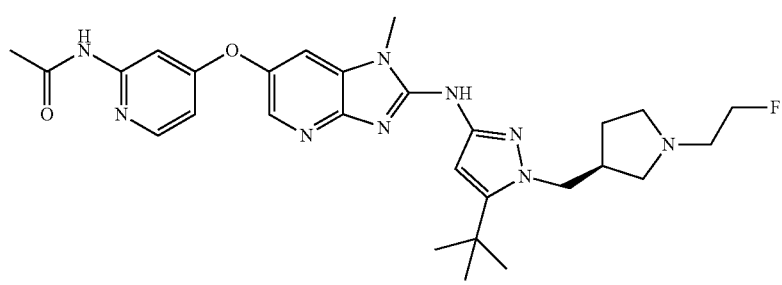
I-122' 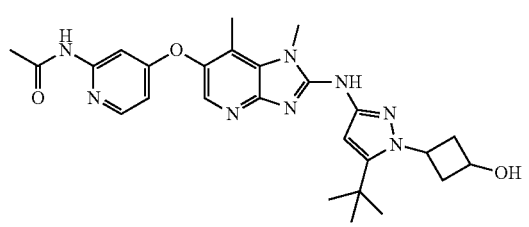
I-122 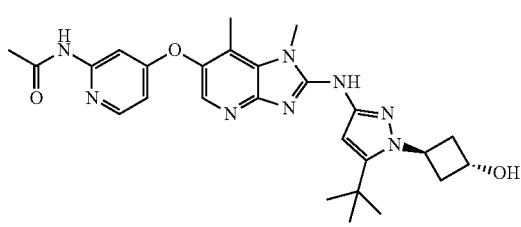

-continued
I-123
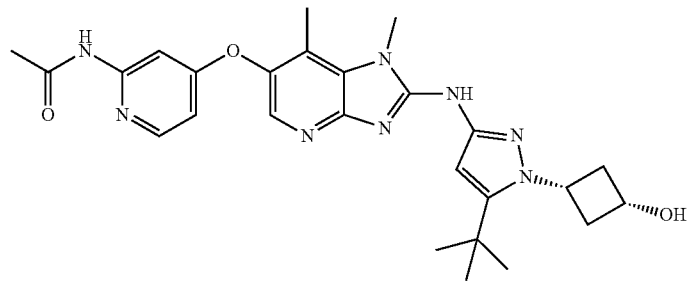
I-124'
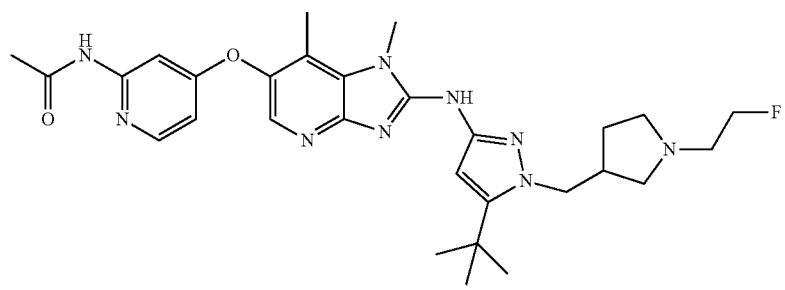
I-124
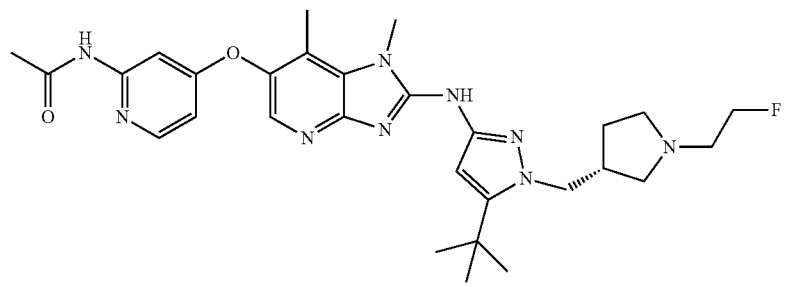
I-125
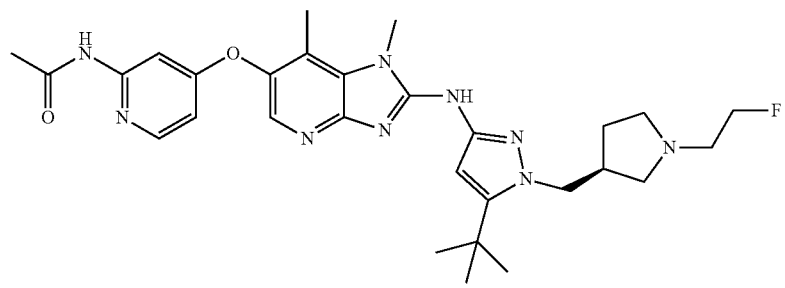
I-126'
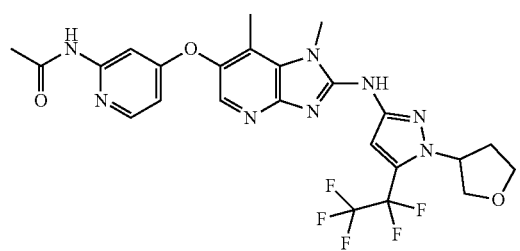
I-126
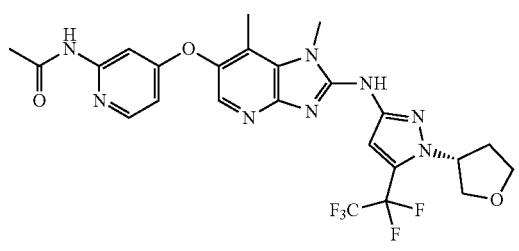

-continued
I-127
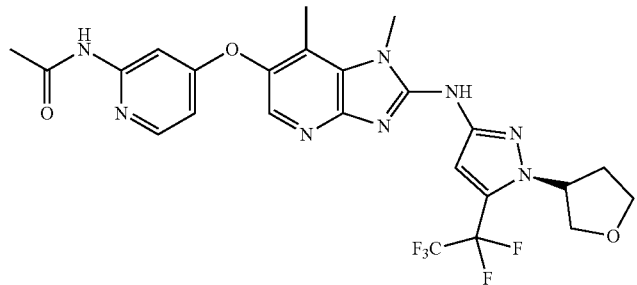
I-128
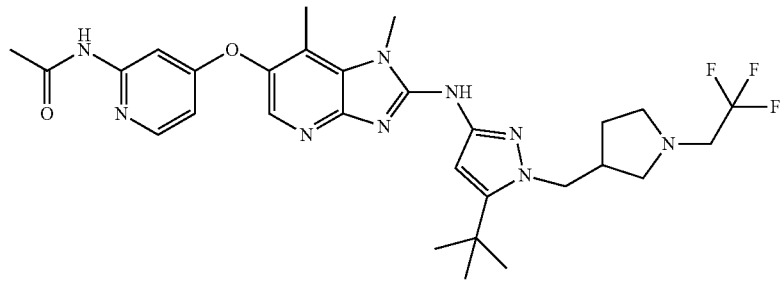
I-128-i
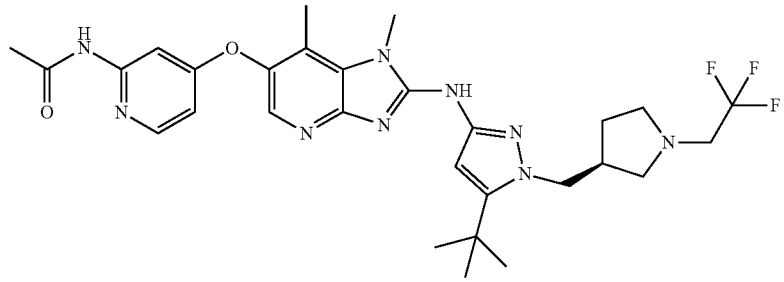
I-128-ii
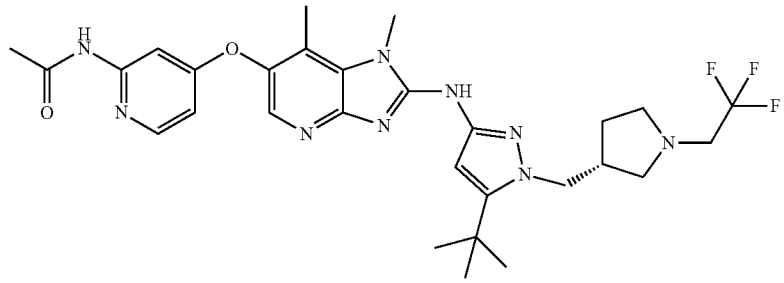
I-129
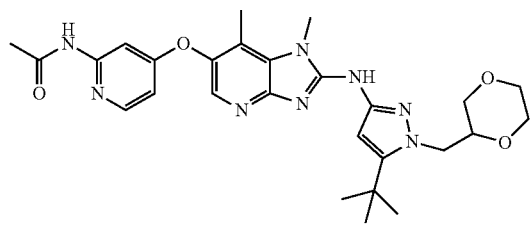
I-129-i
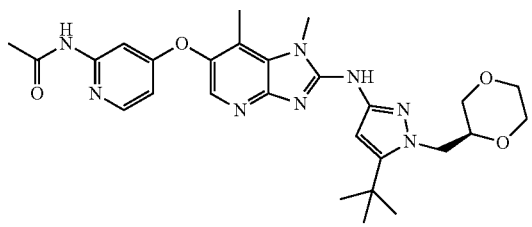

I-129-ii
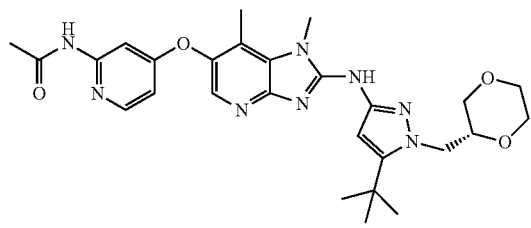
I-130
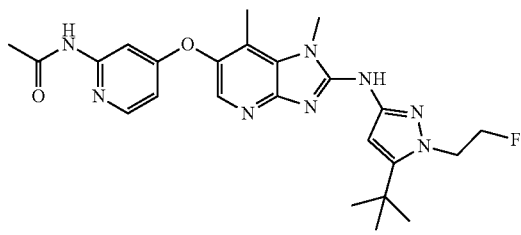
I-131
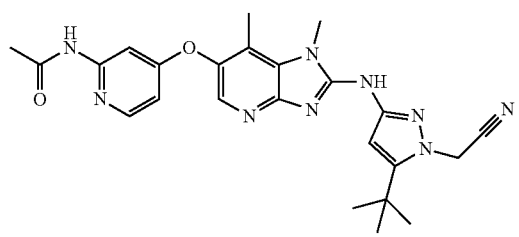
I-132
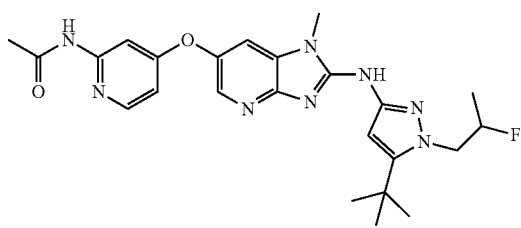
I-133'
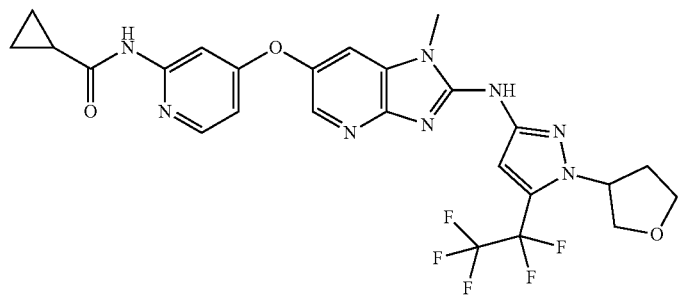
I-133
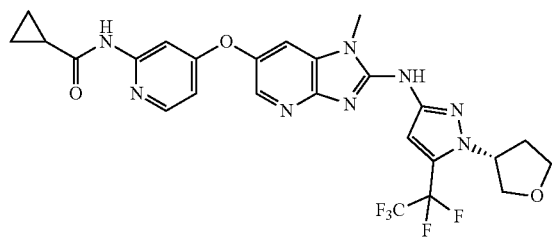
I-134
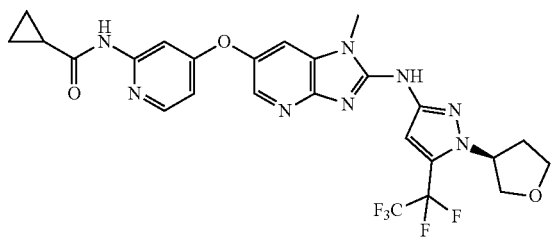
I-135
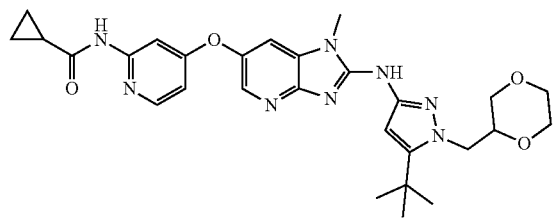
I-135-i
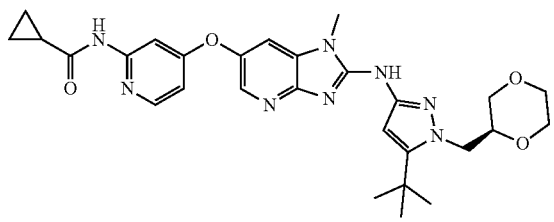

-continued
I-135-ii
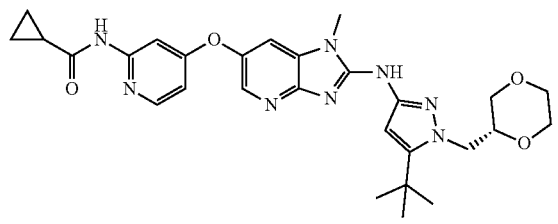
I-136
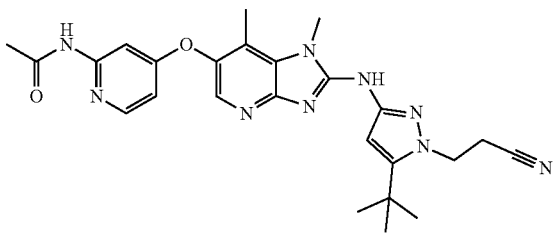
I-137
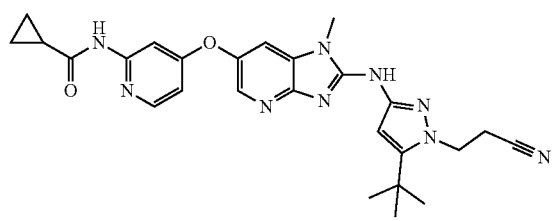
I-138'
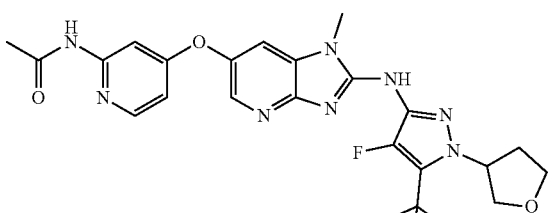
I-138
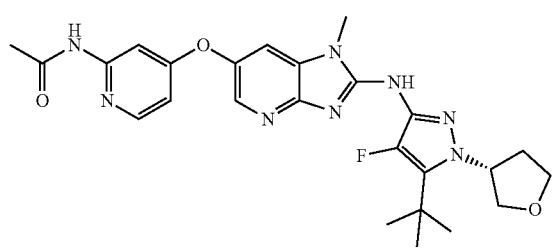
I-139
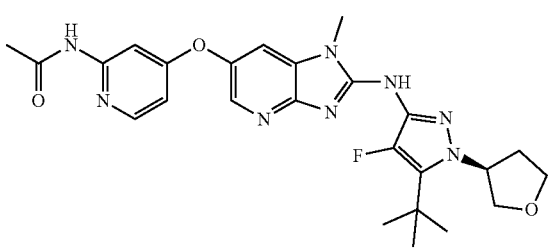
I-140
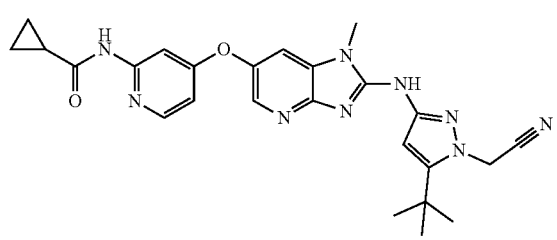
I-141'
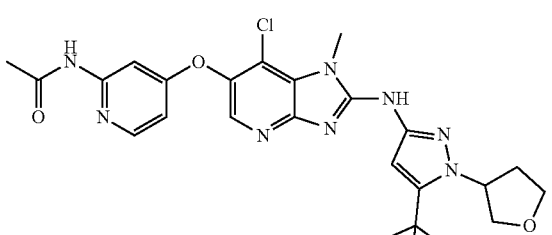
I-141
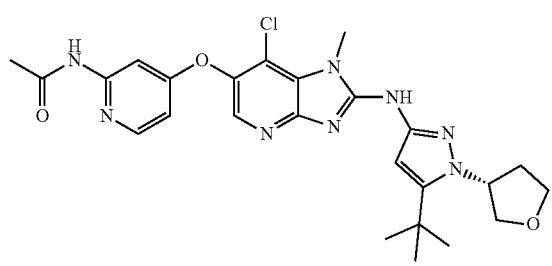
I-142
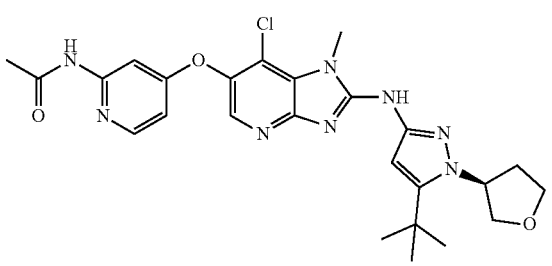
I-143'
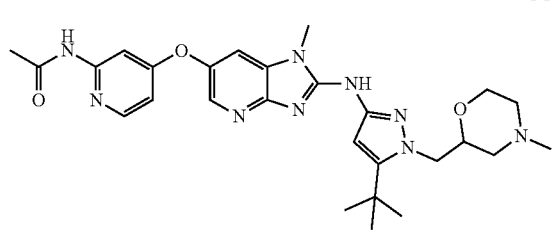
I-143
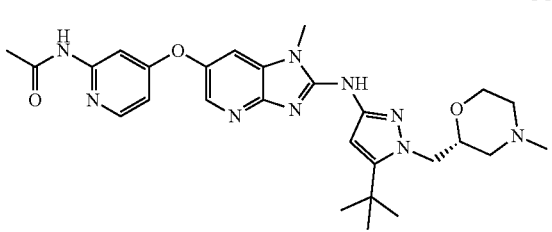

-continued
I-144
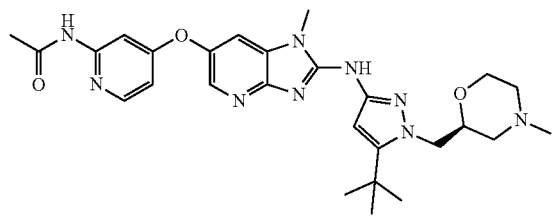
I-145'
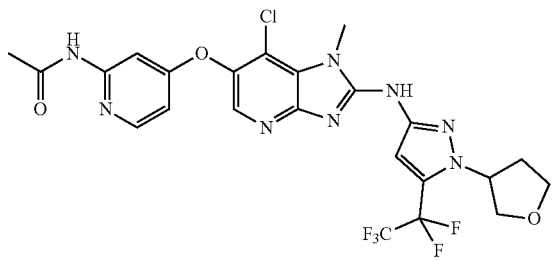
I-145
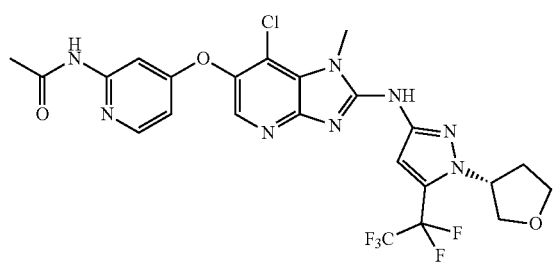
I-146
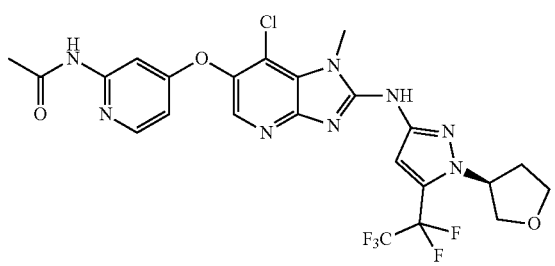
I-147'
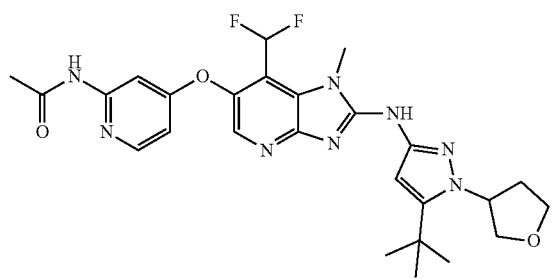
I-147
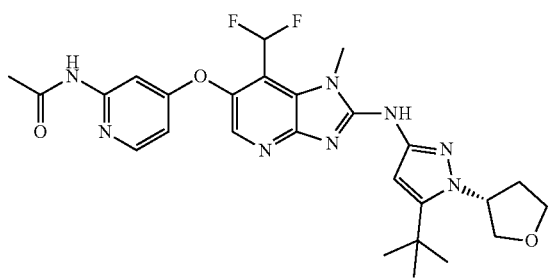
I-148
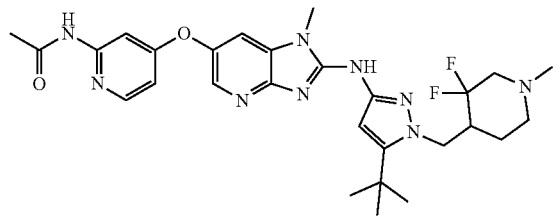
I-148-i
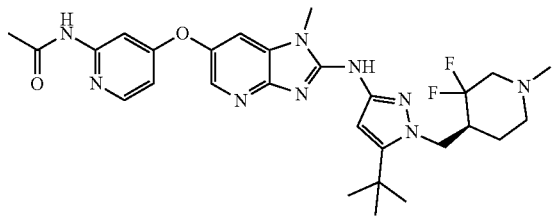
I-148-ii
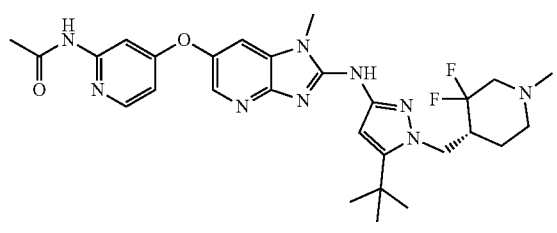
I-149
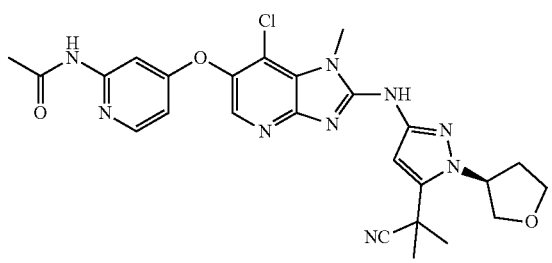

-continued
I-150'
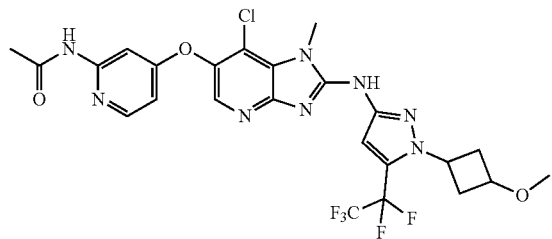
I-150
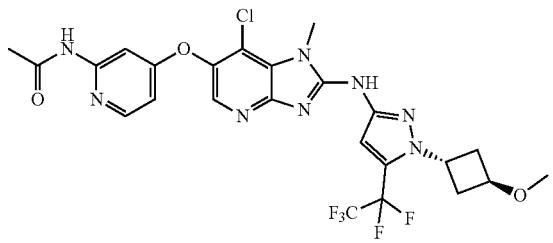
I-151'
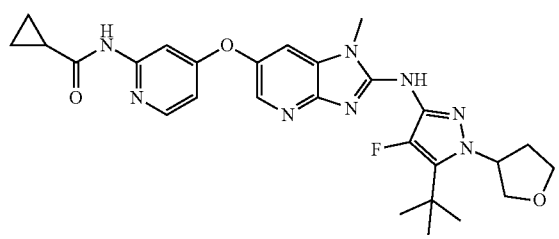
I-151
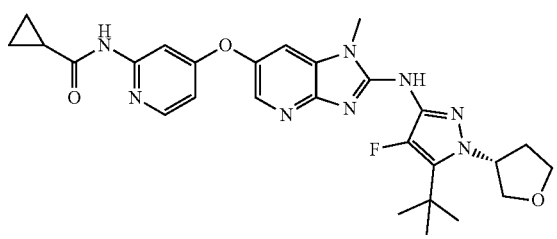
I-152
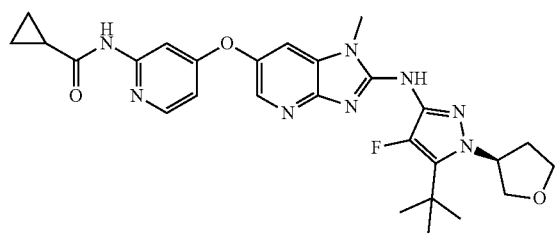
I-153'
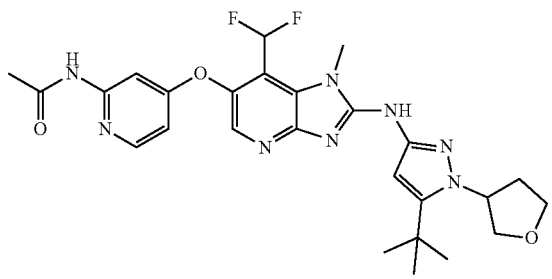
I-153
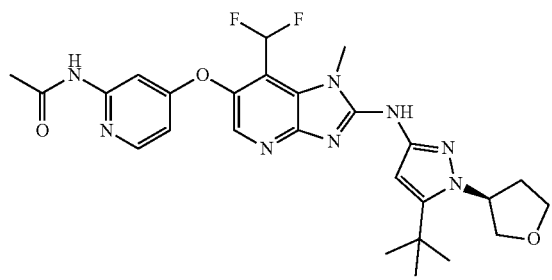
I-154'
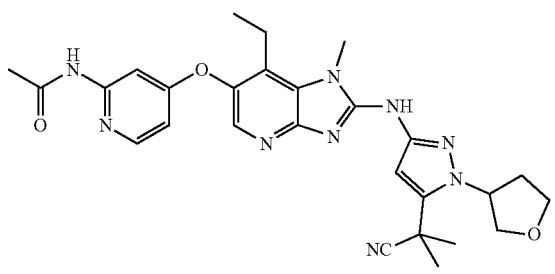
I-154
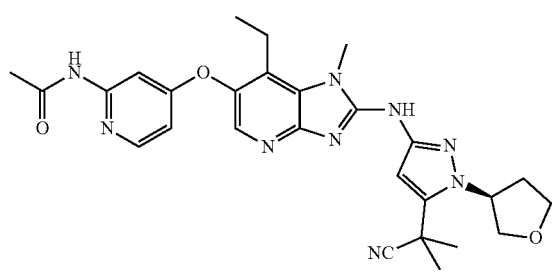
I-155'
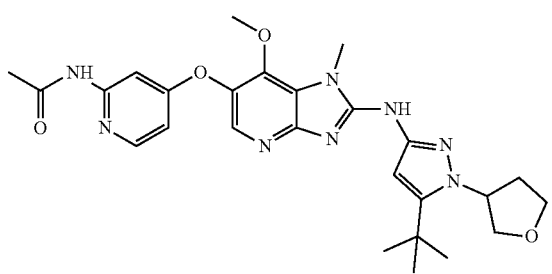

-continued
I-155
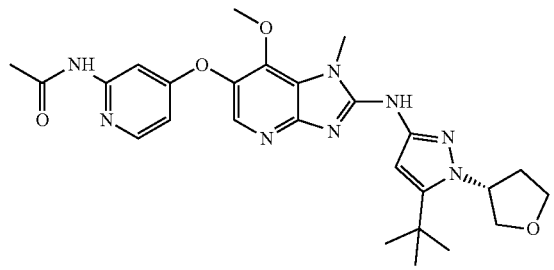
I-156
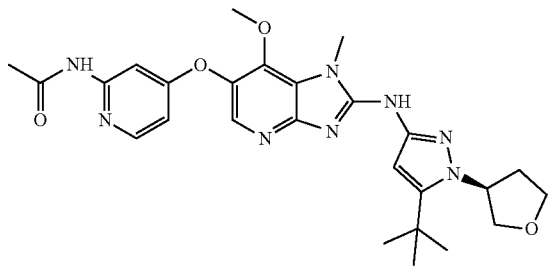
I-157'
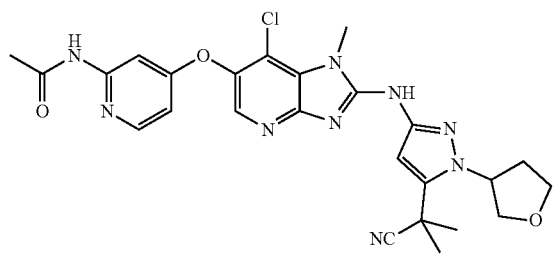
I-157
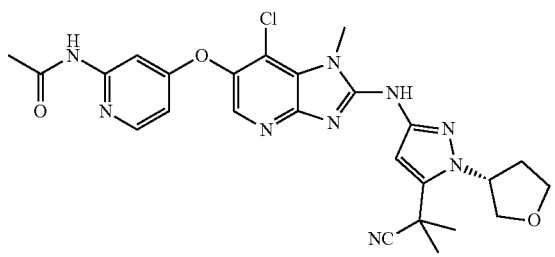
I-158
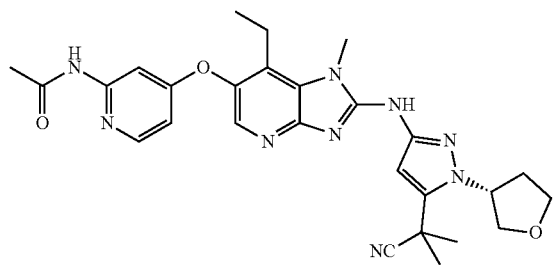
I-159
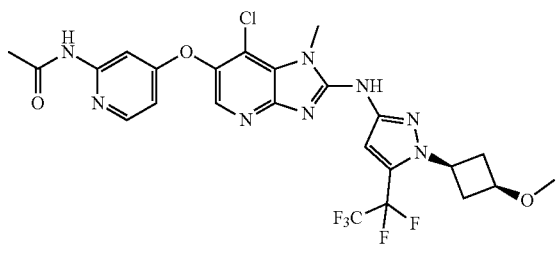
I-160'
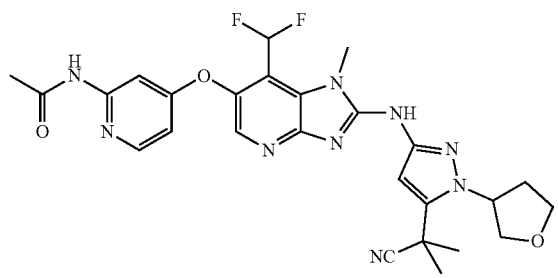
I-160
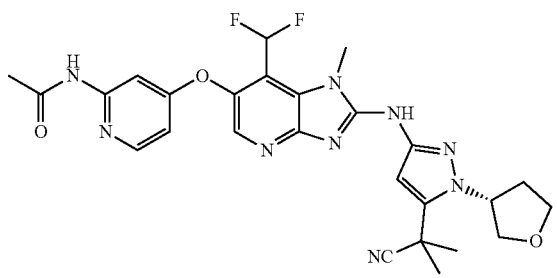
I-161
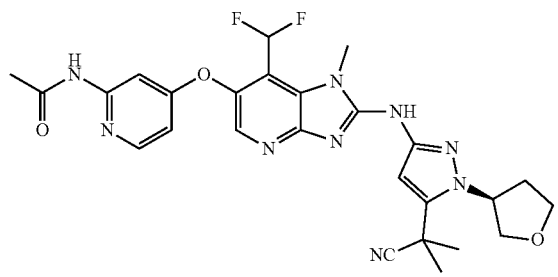
I-162
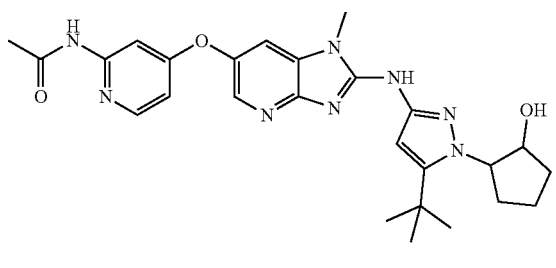

-continued
I-162-i
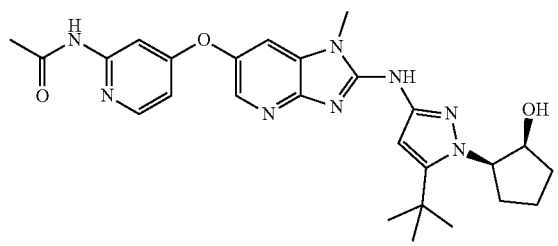
I-162-ii
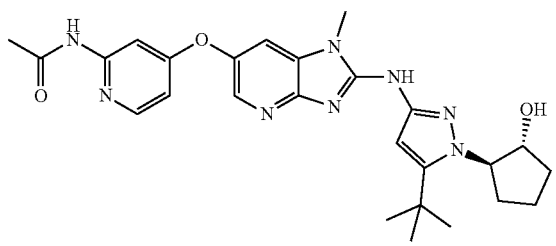
I-162-iii
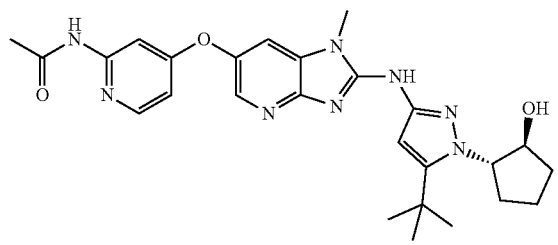
I-162-iv
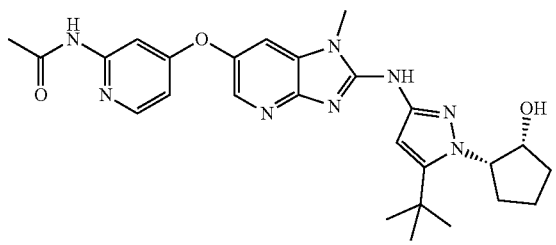
I-163
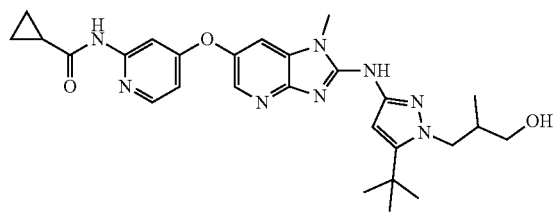
I-163-i
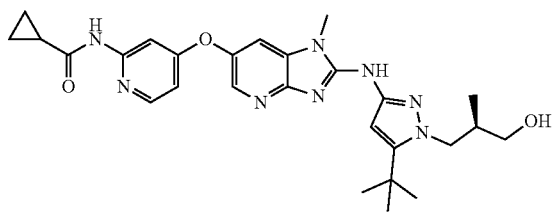
I-163-ii
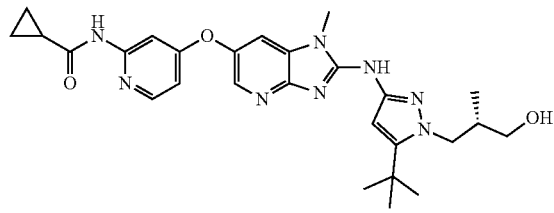
I-164
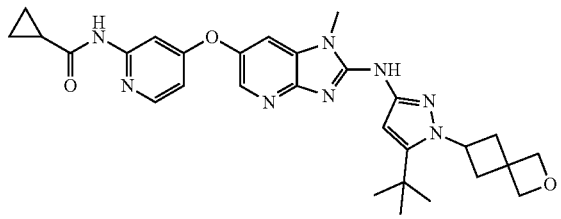
I-165'
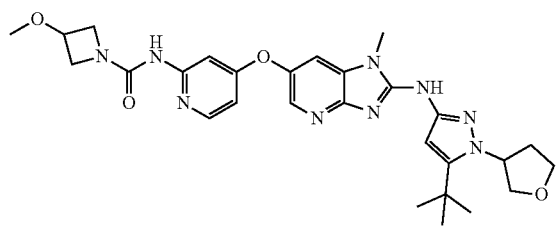
I-165
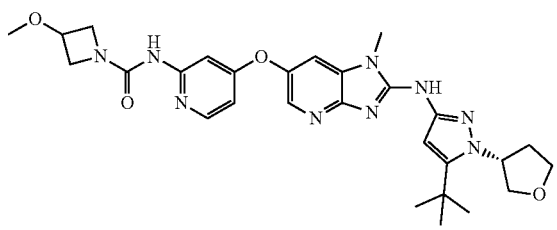
I-166
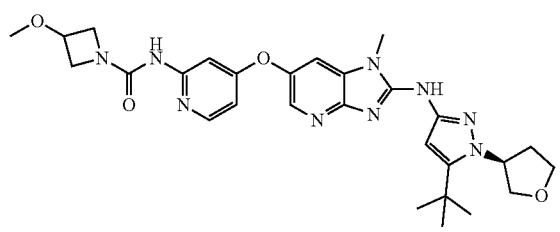
I-167'
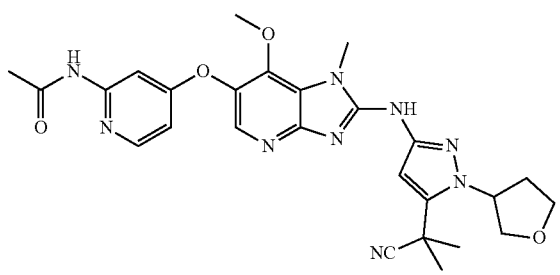

I-167
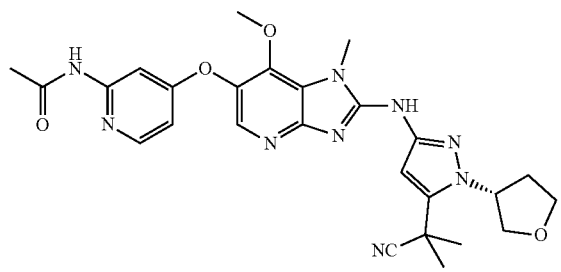
I-168
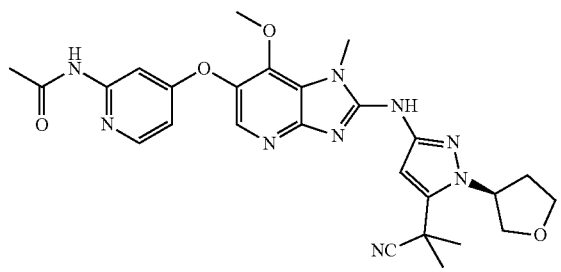
I-169
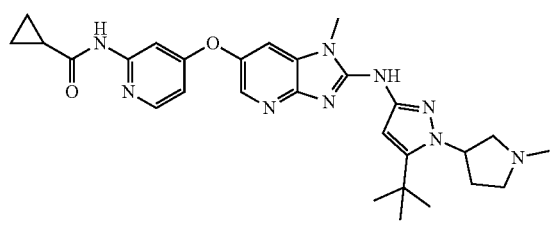
I-169-i
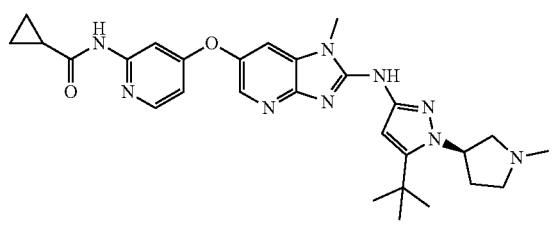
I-169-ii
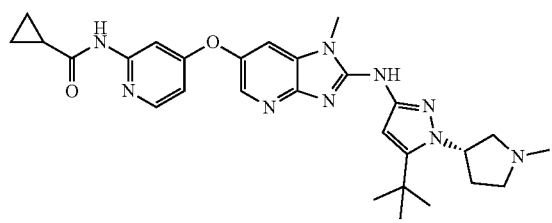
I-170'
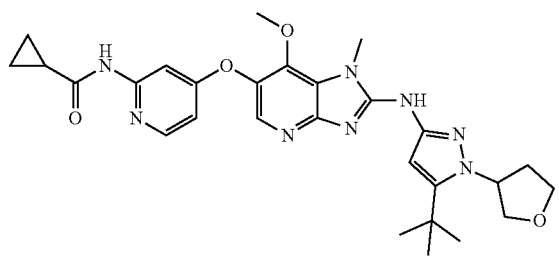
I-170
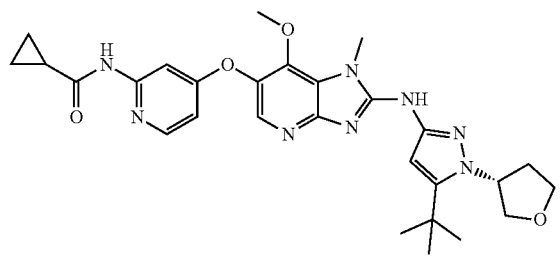
I-171
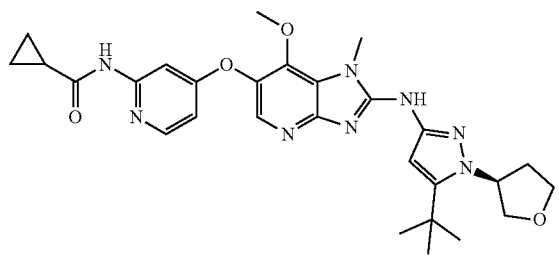
I-172
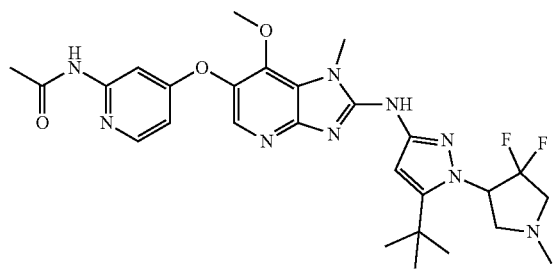
I-172-i
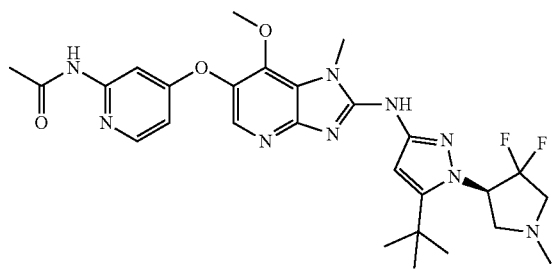

-continued
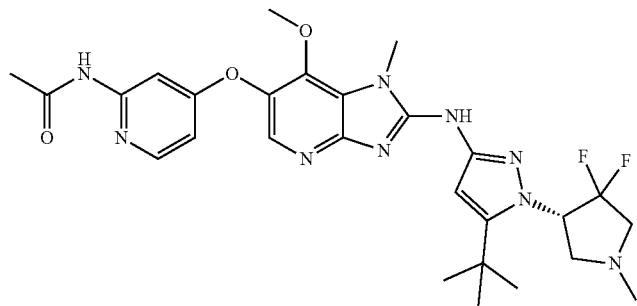
I-172-ii
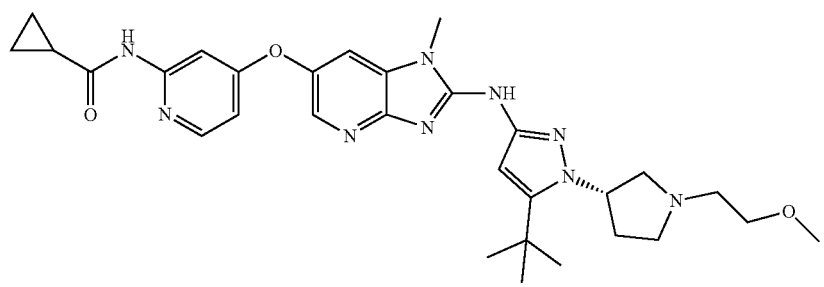
I-173'
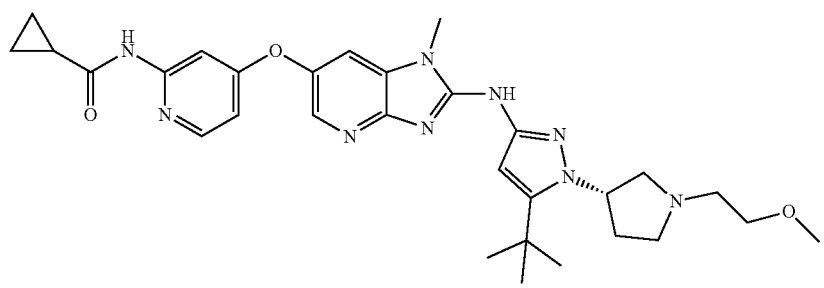
I-173
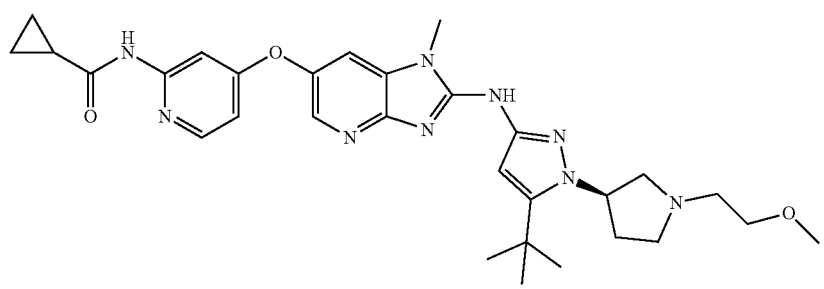
I-174
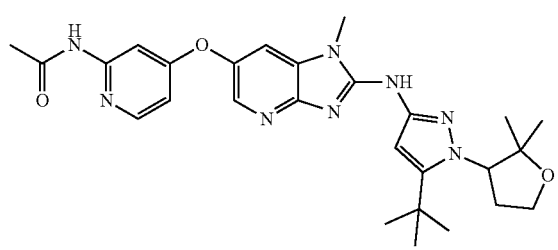
I-175
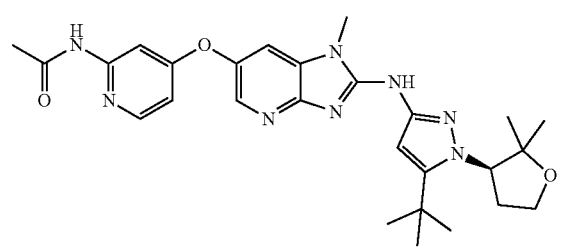
I-175-i -continued
I-175-ii
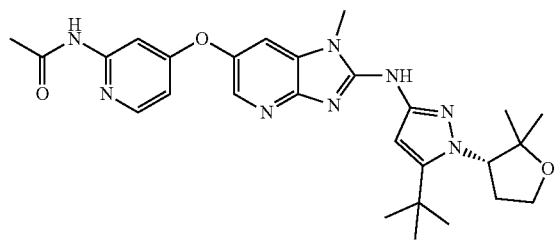
I-176
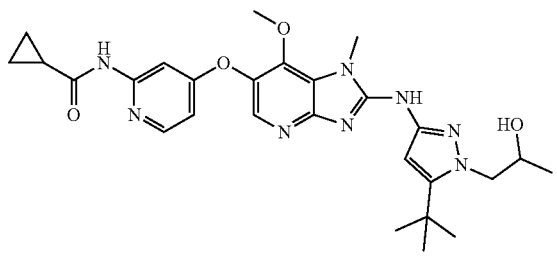
I-176-i
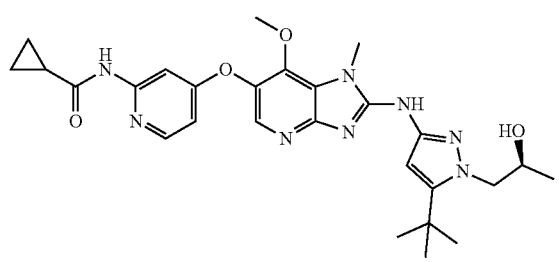
I-176-ii
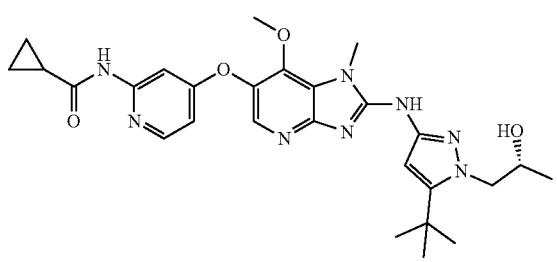
I-177'
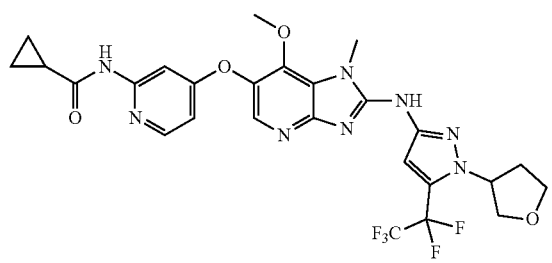
I-177
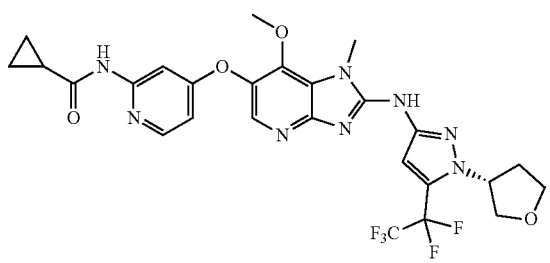
I-178
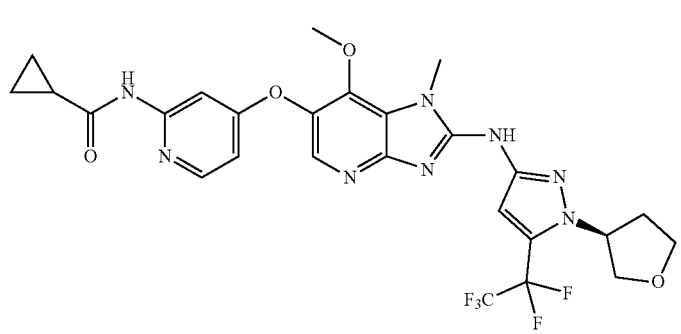
I-179'
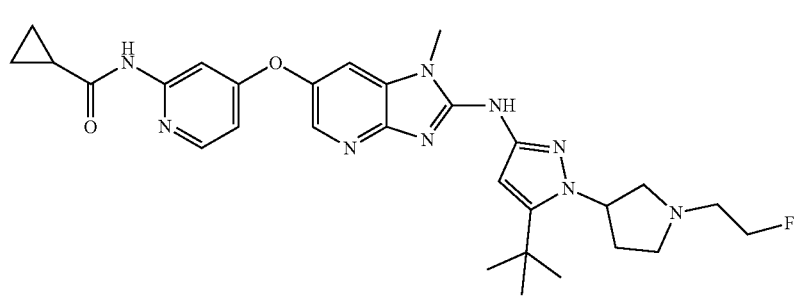

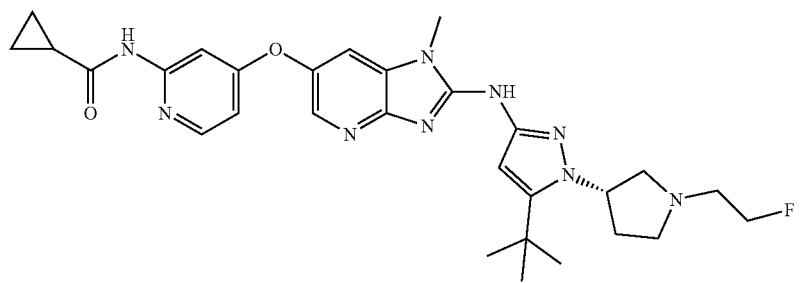
I-179
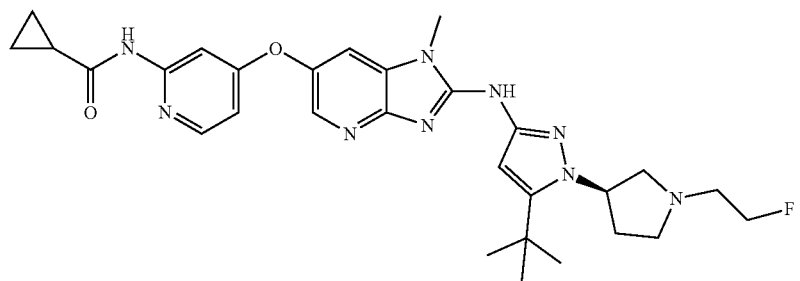
I-180
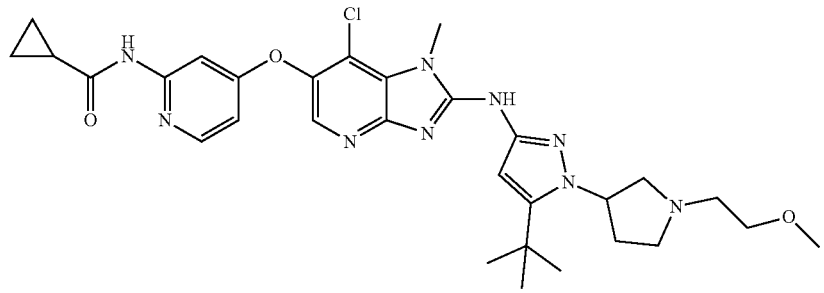
I-181'
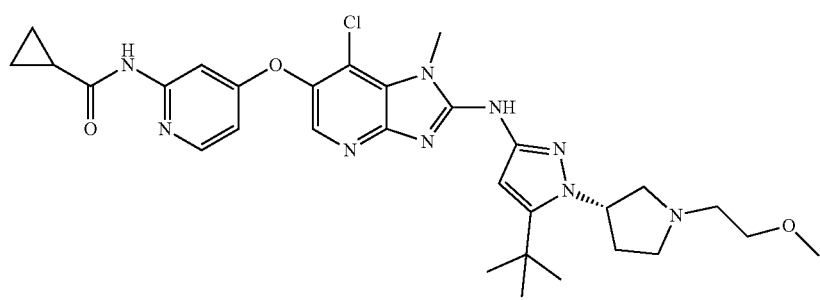
I-181
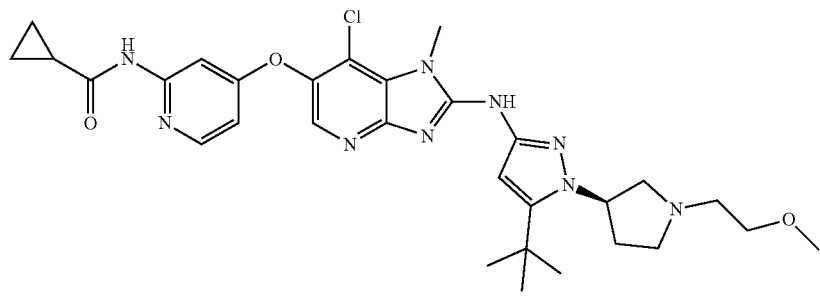
I-182

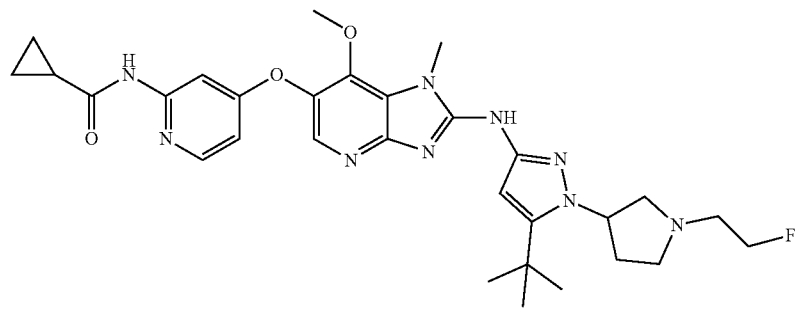
I-183'
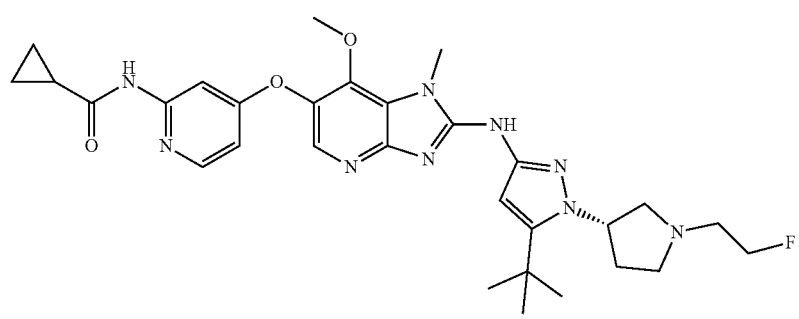
I-183
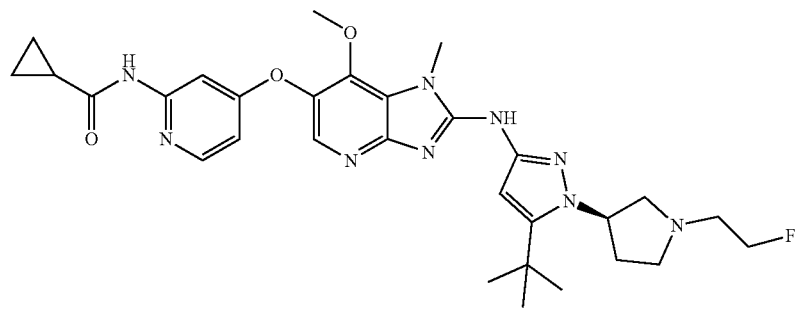
I-184
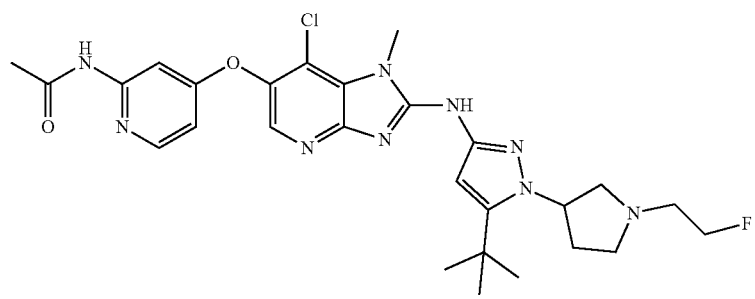
I-185'
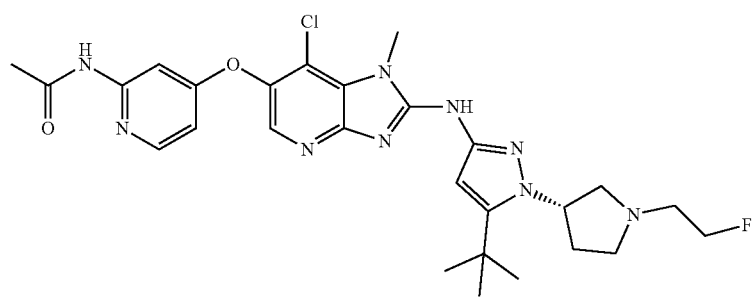
I-185

-continued
I-186
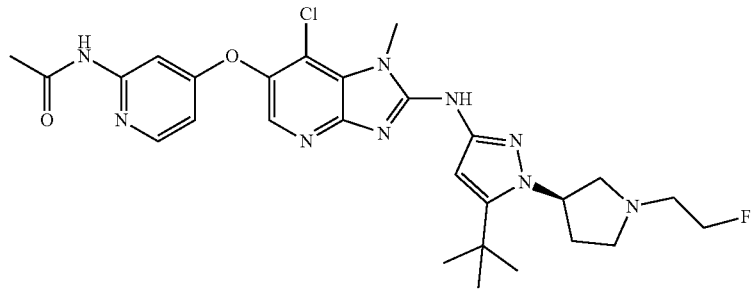
I-187
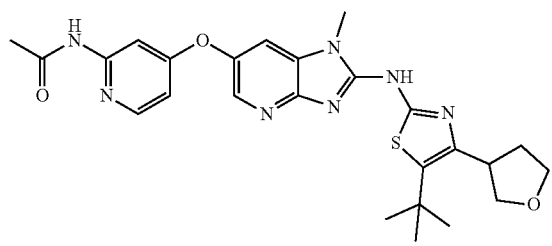
I-187-i
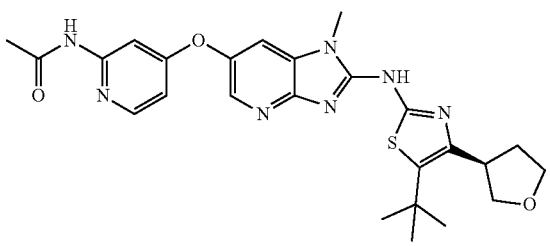
I-187-ii
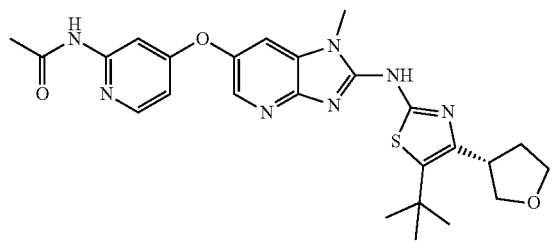
I-188
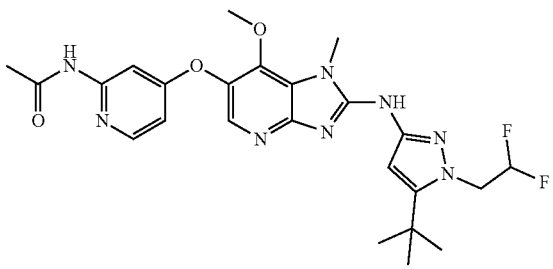
I-189
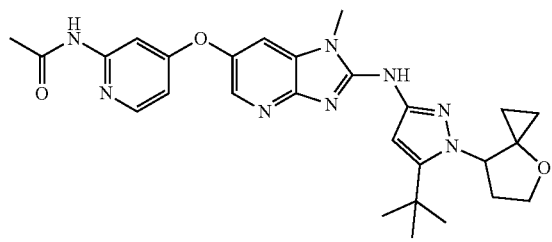
I-189-i
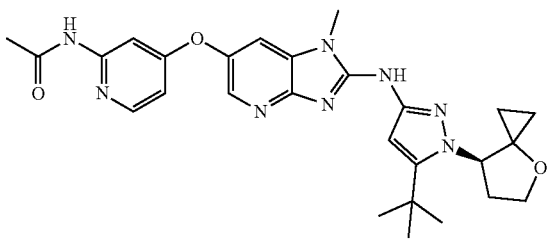
I-189-ii
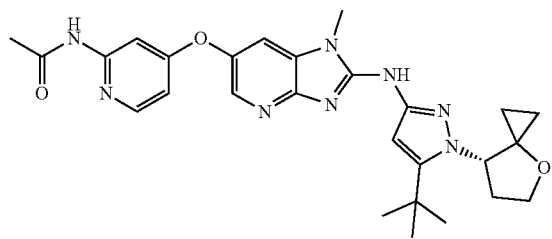
I-190
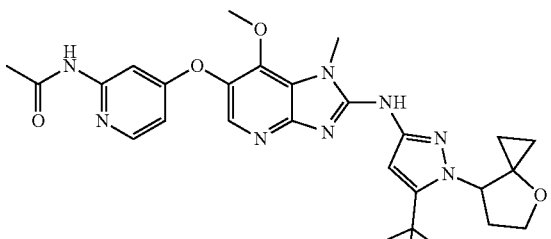

-continued
I-190-i
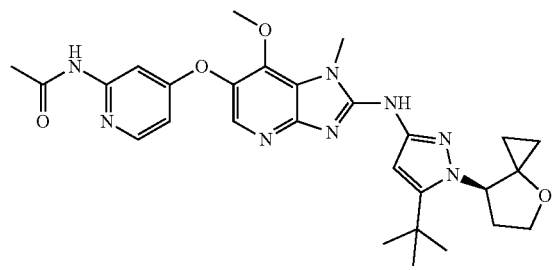
I-190-ii
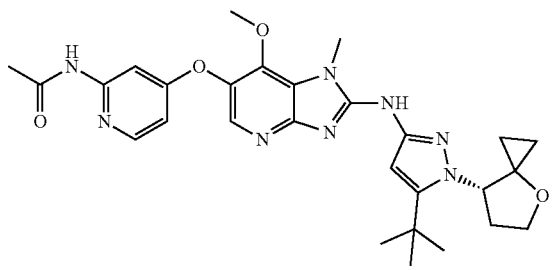
I-191
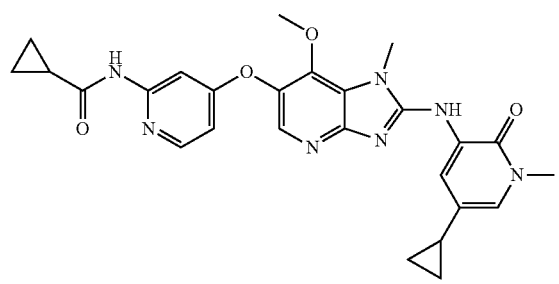
I-192
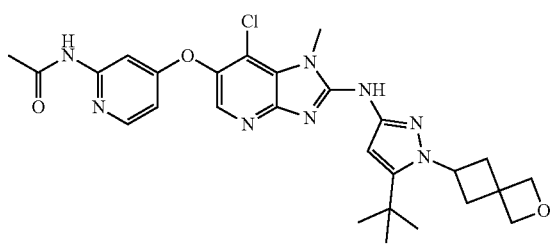
I-193
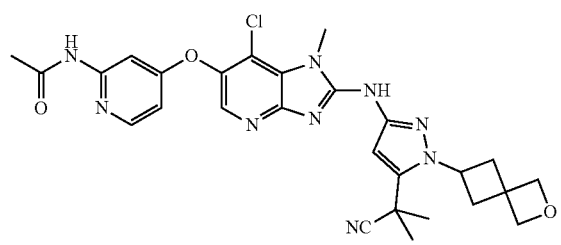
I-194
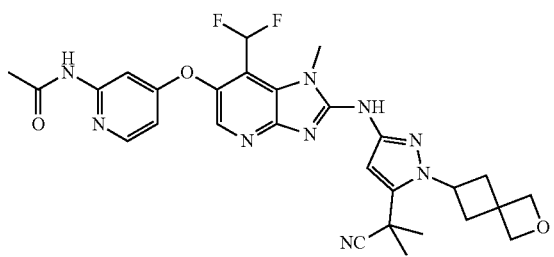
I-195
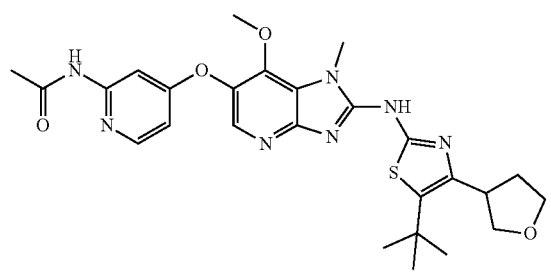
I-195-i
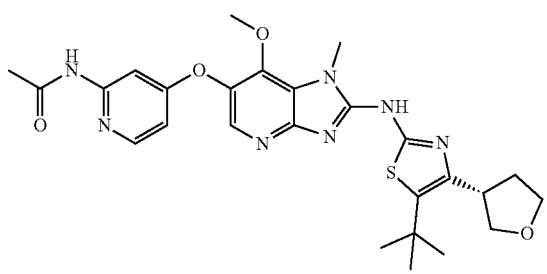
I-195-ii
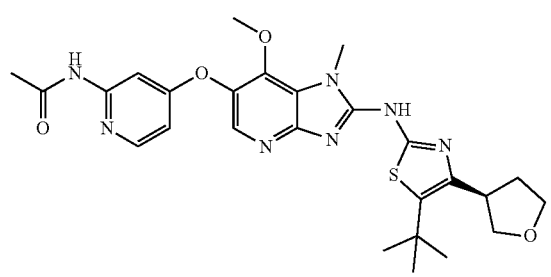
I-196
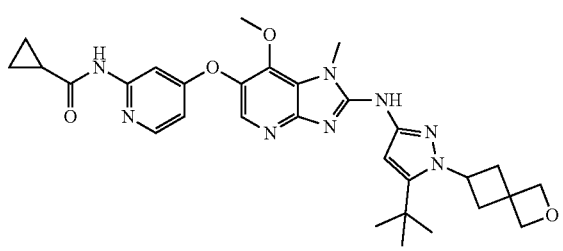

-continued
I-197
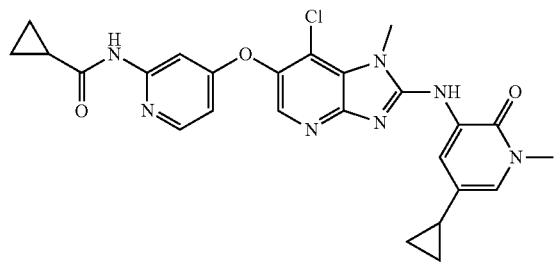
I-198
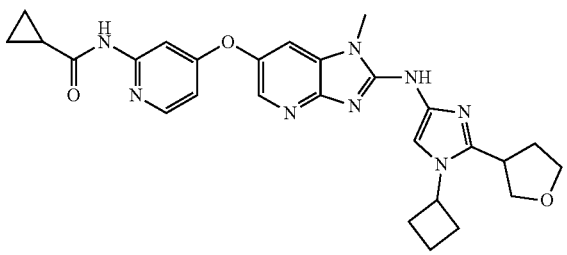
I-198-i
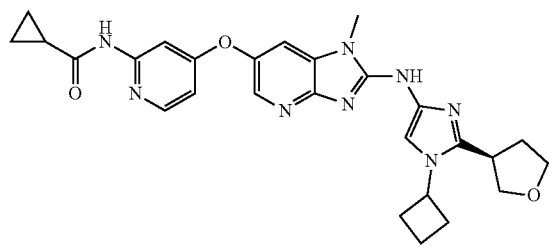
I-198-ii
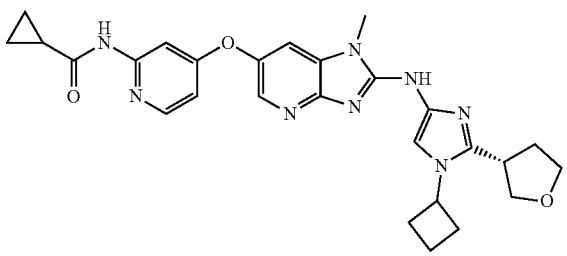
I-199
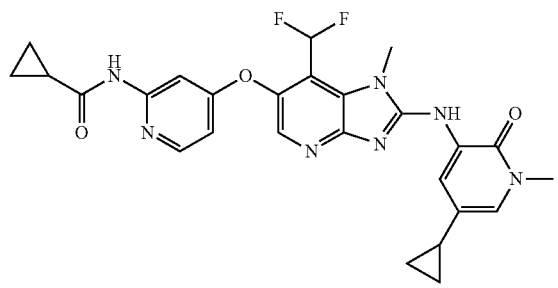
I-200
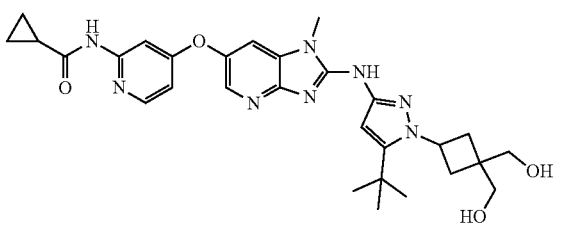
I-201
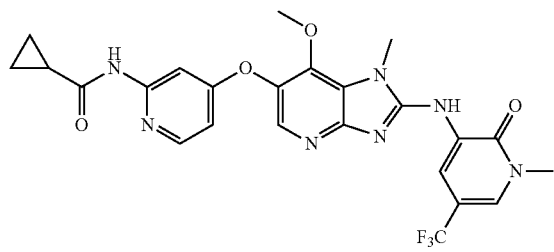
I-202
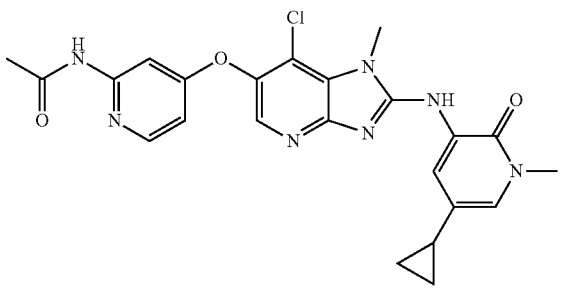
I-203
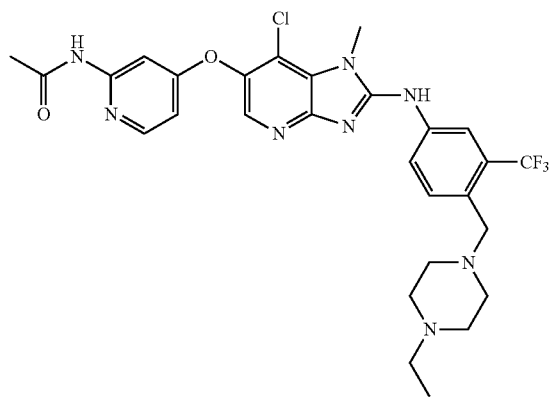
I-204
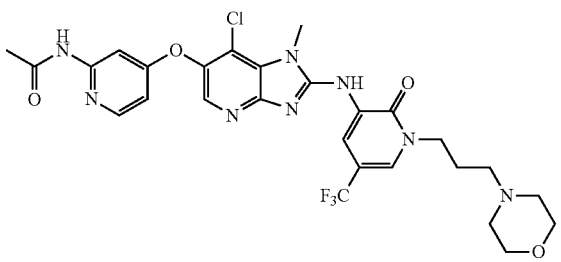

-continued
I-205
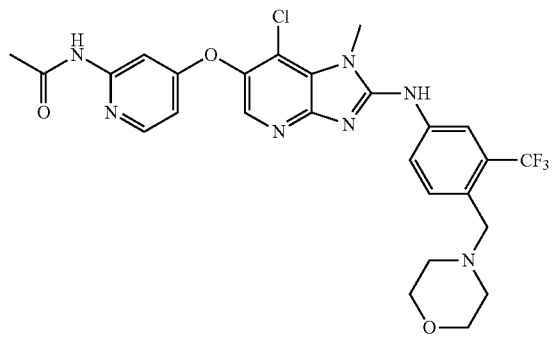
I-206
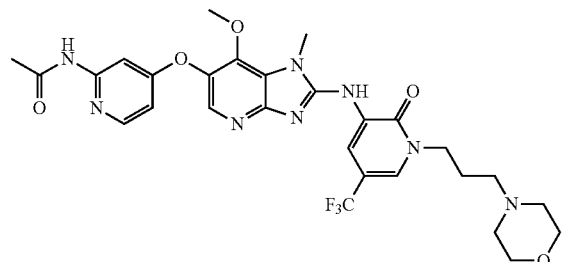
I-207
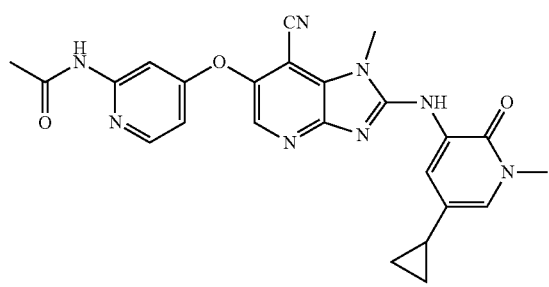
I-208
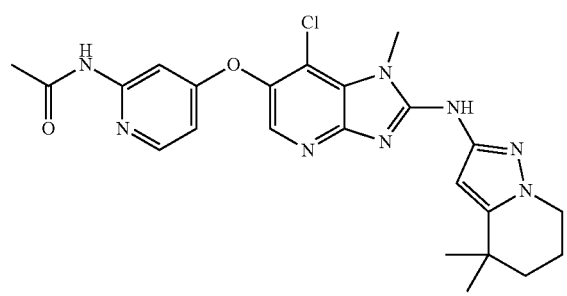
I-209
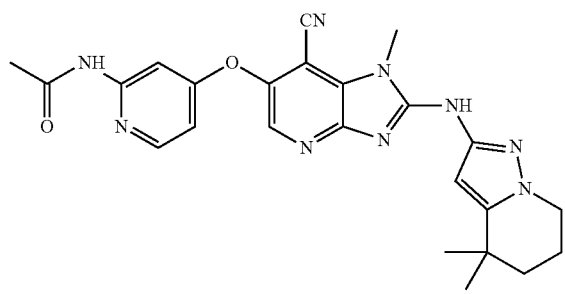
I-210
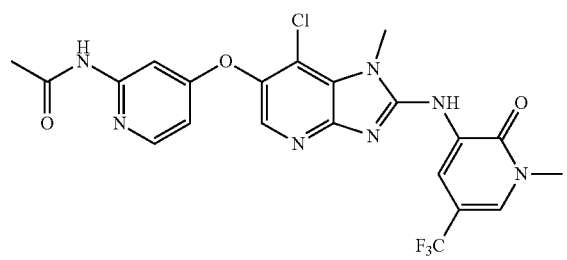
I-211
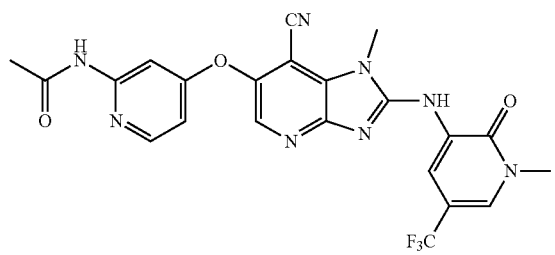
I-212
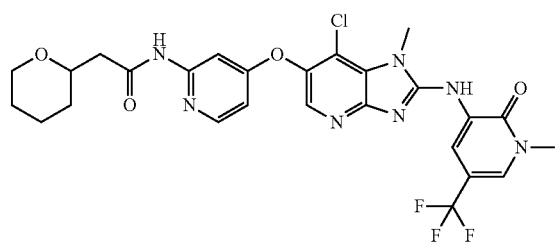
I-212-i
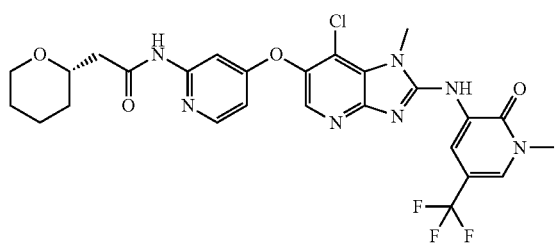
I-212-ii
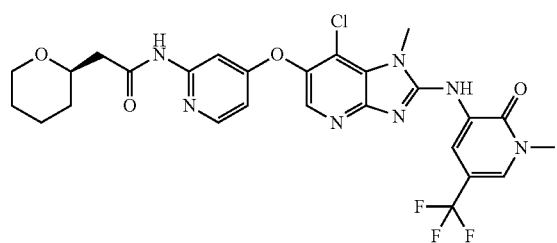

-continued

I-213
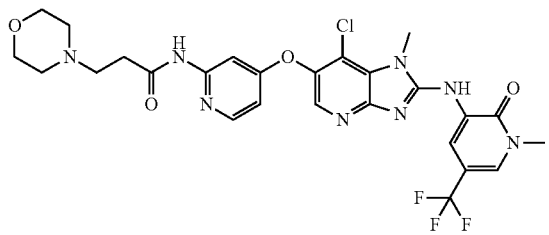

I-214
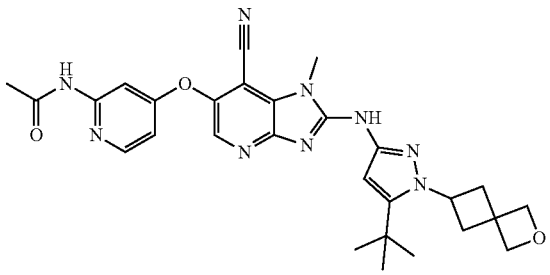

I-215
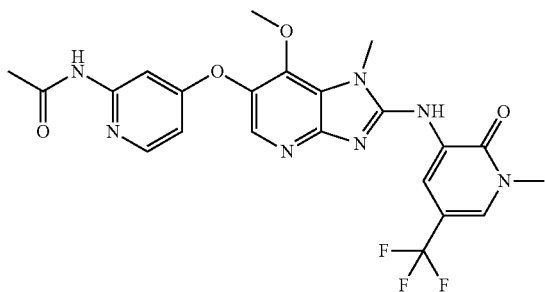

I-216
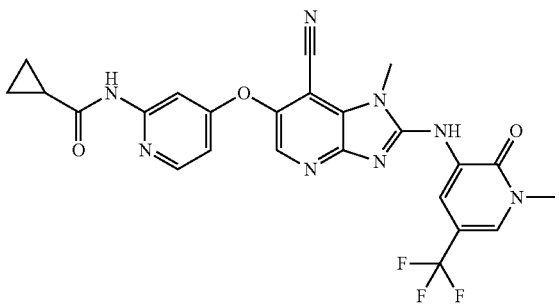

or a pharmaceutically acceptable salt thereof.

In some embodiments, the present disclosure encompasses the recognition that provided compounds display certain desirable characteristics, e.g., as compared to other known compounds. For example, in some embodiments, provided compounds are more potent in one or more biochemical or cellular assays (e.g., the JAK2 Binding Assay or SET2-pSTAT5 Cellular Assay described herein) and/or have one or more other characteristics that make them more suitable for drug development, such as better selectivity over other kinases and/or better ADME (absorption, distribution, metabolism, and excretion) properties including but not limited to better permeability, cytotoxicity, hepatocyte stability, solubility, and/or plasma protein binding profiles (e.g., based on assays described in the ensuing examples), than other known compounds. In some embodiments, provided compounds display certain desirable characteristics in one or more assays described herein, e.g., compared to other known compounds. Without wishing to be bound by any particular theory, the present disclosure encompasses the recognition that 6-heteroaryloxy benzimidazoles and azabenzimidazoles (e.g., compounds described herein) display certain more desirable characteristics (such as better properties in one or more assays described herein) than corresponding 5-heteroaryloxy benzimidazoles and azabenzimidazoles.

In some embodiments, provided compounds are provided and/or utilized in a salt form (e.g., a pharmaceutically acceptable salt form). Reference to a compound provided herein is understood to include reference to salts thereof, unless otherwise indicated. Pharmaceutically acceptable salt forms are known in the art. For example, S. M. Berge, et al. describes pharmaceutically acceptable salts in detail in J. Pharmaceutical Sciences, 66:1-19(1977).

It will be appreciated that throughout the present disclosure, unless otherwise indicated, reference to a compound of Formula I-1 is intended to also include Formulae I, I', II, II', III, III', IV, IV', II, III, IV, I-A, II-A, III-A, IV-A, I-B, II-B, III-B, IV-B, I-C, II-C, III-C, IV-C, I-D, II-D, III-D, IV-D, I-E, II-E, III-E, and IV-E, and compound species of such formulas disclosed herein.

Preparing Provided Compounds

In some embodiments, provided compounds (e.g., compounds of Formula I-1 wherein Z is —NH—) are prepared according to the following Scheme:

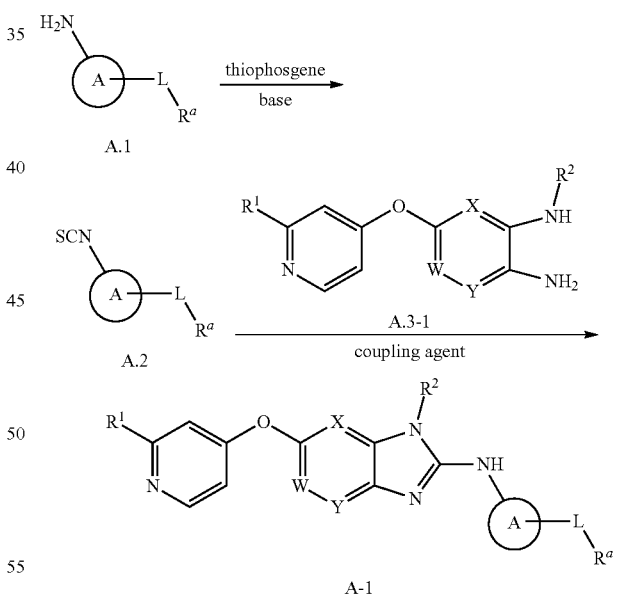

wherein Ring A, L, W, X, Y, $R^1$, $R^2$, and $R^a$ are as defined above for Formula I-1. Accordingly, in some embodiments, intermediate A.2 is prepared by a process comprising contacting intermediate A.1 with thiophosgene in the presence of a suitable base (e.g., $NaHCO_3$ or triethylamine). In some embodiments, compound A-1 is prepared by a process comprising contacting intermediate A.2 with intermediate A.3-1 in the presence of a suitable coupling agent (e.g., 1-ethyl-3-(3-dimethylaminopropyl)carbodiimide hydrochloride or N,N'-diisopropylcarbodiimide).

In some embodiments, provided compounds (e.g., compounds of Formula I wherein Z is —NH—) are prepared according to the following Scheme:

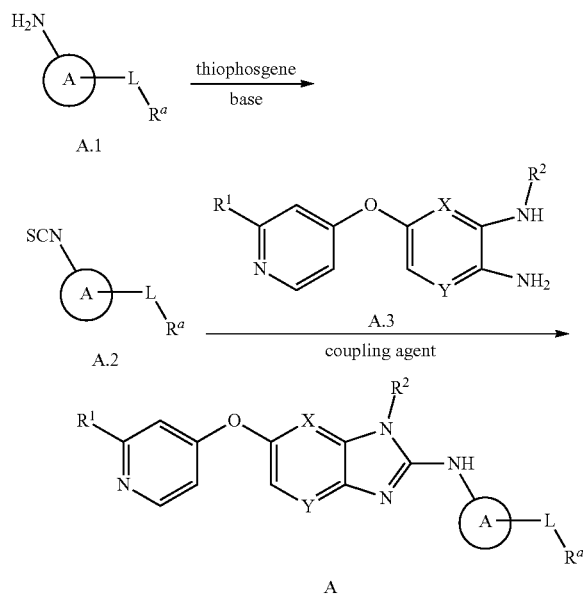

wherein Ring A, L, X, Y, $R^1$, $R^2$, and $R^a$ are as defined above for Formula I. Accordingly, in some embodiments, intermediate A.2 is prepared by a process comprising contacting intermediate A.1 with thiophosgene in the presence of a suitable base (e.g., NaHCO$_3$ or triethylamine). In some embodiments, compound A is prepared by a process comprising contacting intermediate A.2 with intermediate A.3 in the presence of a suitable coupling agent (e.g., 1-ethyl-3-(3-dimethylaminopropyl)carbodiimide hydrochloride or N,N'-diisopropylcarbodiimide).

In some embodiments, provided compounds (e.g., compounds of Formula I-1 wherein Z is —O—) are prepared according to the following Scheme:

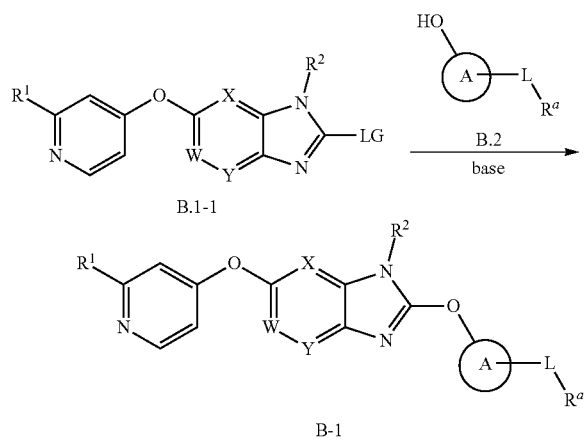

wherein LG is a suitable leaving group (e.g., halogen, e.g., chloro) and Ring A, L, W, X, Y, $R^1$, $R^2$, and $R^a$ are as defined above for Formula I-1. Accordingly, in some embodiments, compound B-1 is prepared by a process comprising contacting intermediate B.1-1 with intermediate B.2 in the presence of a suitable base (e.g., K$_2$CO$_3$).

In some embodiments, provided compounds (e.g., compounds of Formula I-1 wherein Z is —O—) are prepared according to the following Scheme:

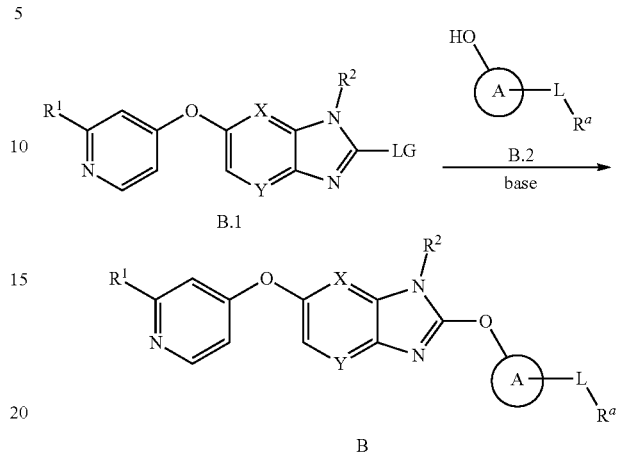

wherein LG is a suitable leaving group (e.g., halogen, e.g., chloro) and Ring A, L, X, Y, $R^1$, $R^2$, and $R^a$ are as defined above for Formula I. Accordingly, in some embodiments, compound B is prepared by a process comprising contacting intermediate B.1 with intermediate B.2 in the presence of a suitable base (e.g., K$_2$CO$_3$).

In some embodiments, a provided compound is obtained by a process comprising a purification method described in the Examples section. In some such embodiments, a compound is the 1$^{st}$ eluting isomer. In some such embodiments, a compound is the 2$^{nd}$ eluting isomer. In some embodiments, a compound is the 3$^{rd}$ eluting isomer. In some embodiments, a compound is the 4$^{th}$ eluting isomer. In some embodiments, a compound is the 5$^{th}$, 6$^{th}$, 7$^{th}$, 8$^{th}$, or more eluting isomer.

Compositions

The present disclosure also provides compositions comprising a compound provided herein with one or more other components. In some embodiments, provided compositions comprise and/or deliver a compound described herein (e.g., compounds of Formulae I-1, I, II, III, IV, I', II', III', IV', I-A, II-A, III-A, IV-A, I-B, II-B, III-B, IV-B, I-C, II-C, III-C, IV-C, I-D, II-D, III-D, IV-D, I-E, II-E, III-E, and IV-E).

In some embodiments, a provided composition is a pharmaceutical composition that comprises and/or delivers a compound provided herein (e.g., compounds of Formulae I-1, I, II, III, IV, I', II', III', IV', I-A, II-A, III-A, IV-A, I-B, II-B, III-B, IV-B, I-C, II-C, III-C, IV-C, I-D, II-D, III-D, IV-D, I-E, II-E, III-E, and IV-E) and further comprises a pharmaceutically acceptable carrier. Pharmaceutical compositions typically contain an active agent (e.g., a compound described herein) in an amount effective to achieve a desired therapeutic effect while avoiding or minimizing adverse side effects. In some embodiments, provided pharmaceutical compositions comprise a compound described herein and one or more fillers, disintegrants, lubricants, glidants, anti-adherents, and/or anti-statics, etc. Provided pharmaceutical compositions can be in a variety of forms including oral dosage forms, topical creams, topical patches, iontophoresis forms, suppository, nasal spray and/or inhaler, eye drops, intraocular injection forms, depot forms, as well as injectable and infusible solutions. Methods of preparing pharmaceutical compositions are well known in the art.

In some embodiments, provided compounds are formulated in a unit dosage form for ease of administration and uniformity of dosage. The expression "unit dosage form" as used herein refers to a physically discrete unit of an active agent (e.g., a compound described herein) for administration to a subject. Typically, each such unit contains a predetermined quantity of active agent. In some embodiments, a unit dosage form contains an entire single dose of the agent. In some embodiments, more than one unit dosage form is administered to achieve a total single dose. In some embodiments, administration of multiple unit dosage forms is required, or expected to be required, in order to achieve an intended effect. A unit dosage form may be, for example, a liquid pharmaceutical composition containing a predetermined quantity of one or more active agents, a solid pharmaceutical composition (e.g., a tablet, a capsule, or the like) containing a predetermined amount of one or more active agents, a sustained release formulation containing a predetermined quantity of one or more active agents, or a drug delivery device containing a predetermined amount of one or more active agents, etc.

Provided compositions may be administered using any amount and any route of administration effective for treating or lessening the severity of any disease or disorder described herein.

Uses

The present disclosure provides uses for compounds and compositions described herein. In some embodiments, provided compounds and compositions are useful in medicine (e.g., as therapy). In some embodiments, provided compounds and compositions are useful in research as, for example, analytical tools and/or control compounds in biological assays.

In some embodiments, the present disclosure provides methods of administering provided compounds or compositions to a subject in need thereof. In some embodiments, the present disclosure provides methods of administering provided compounds or compositions to a subject suffering from or susceptible to a disease, disorder, or condition associated with JAK2.

In some embodiments, provided compounds are useful as JAK2 inhibitors. In some embodiments, provided compounds are useful as Type II JAK2 inhibitors. In some embodiments, the present disclosure provides methods of inhibiting JAK2 in a subject comprising administering a provided compound or composition. In some embodiments, the present disclosure provides methods of inhibiting JAK2 in a biological sample comprising contacting the sample with a provided compound or composition.

JAK (e.g., JAK2) has been implicated in various diseases, disorders, and conditions, such as myeloproliferative neoplasms (Vainchenker, W. et al., F1000Research 2018, 7(F1000 Faculty Rev):82), atopic dermatitis (Rodrigues, M. A. and Torres, T. J. Derm. Treat. 2019, 31(1), 33-40) and acute respiratory syndrome, hyperinflammation, and/or cytokine storm syndrome (*The Lancet*. doi:10.1016/S0140-6736(20)30628-0). Accordingly, in some embodiments, the present disclosure provides methods of treating a disease, disorder or condition associated with JAK2 in a subject in need thereof comprising administering to the subject a provided compound or composition. In some embodiments, a disease, disorder or condition is associated with overexpression of JAK2.

In some embodiments, the present disclosure provides methods of treating cancer, comprising administering a provided compound or composition to a subject in need thereof. In some embodiments, the present disclosure provides methods of treating proliferative diseases, comprising administering a provided compound or composition to a subject in need thereof.

In some embodiments, the present disclosure provides methods of treating a hematological malignancy, comprising administering a provided compound or composition to a subject in need thereof. In some embodiments, a hematological malignancy is leukemia (e.g., chronic lymphocytic leukemia, acute lymphoblastic leukemia, T-cell acute lymphoblastic leukemia, chronic myelogenous leukemia, acute myelogenous leukemia, or acute monocytic leukemia). In some embodiments, a hematological malignancy is lymphoma (e.g., Burkitt's lymphoma, Hodgkin's lymphoma, or non-Hodgkin's lymphoma). In some embodiments, a non-Hodgkin's lymphoma is a B-cell lymphoma. In some embodiments, a non-Hodgkin's lymphoma is a NK/T-cell lymphoma (e.g., cutaneous T-cell lymphoma). In some embodiments, a hematological malignancy is myeloma (e.g., multiple myeloma). In some embodiments, a hematological malignancy is myeloproliferative neoplasm (e.g., polycythemia vera, essential thrombocytopenia, or myelofibrosis). In some embodiments, a hematological malignancy is myelodysplastic syndrome.

In some embodiments, the present disclosure provides methods of treating an inflammatory disease, disorder, or condition (e.g., acute respiratory syndrome, hyperinflammation, and/or cytokine storm syndrome (including those associated with COVID-19) or atopic dermatitis), comprising administering a provided compound or composition to a subject in need thereof.

In some embodiments, a provided compound or composition is administered as part of a combination therapy. As used herein, the term "combination therapy" refers to those situations in which a subject is simultaneously exposed to two or more therapeutic or prophylactic regimens (e.g., two or more therapeutic or prophylactic agents). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition.

For example, in some embodiments, a provided compound or composition is administered to a subject who is receiving or has received one or more additional therapies (e.g., an anti-cancer therapy and/or therapy to address one or more side effects of such anti-cancer therapy, or otherwise to provide palliative care). Exemplary additional therapies include, but are not limited to, BCL2 inhibitors (e.g., venetoclax), HDAC inhibitors (e.g., vorinostat), BET inhibitors (e.g., mivebresib), proteasome inhibitors (e.g., bortezomib), LSD1 inhibitors (e.g., IMG-7289), and CXCR2 inhibitors. Useful combinations of a JAK2 inhibitor with BCL2, HDAC, BET, and proteasome inhibitors have been demonstrated in cells derived from cutaneous T-cell lymphoma patients (Yumeen, S., et al., Blood Adv. 2020, 4(10), 2213-2226). A combination of a JAK2 inhibitor with a LSD1 inhibitor demonstrated good efficacy in a mouse model of myeloproliferative neoplasms (Jutzi, J. S., et al., HemaSphere 2018, 2(3), dx.doi.org/10.1097/HS9.000000000-0000054). CXCR2 activity has been shown to modulate signaling pathways involved in tumor growth, angiogenesis, and/or metastasis, including the JAK-STAT3 pathway (Jaffer, T., Ma, D. Transl. Cancer Res. 2016, 5 (Suppl. 4), S616-S628).

Exemplary Embodiments

The following numbered embodiments, while non-limiting, are exemplary of certain aspects of the present disclosure:

A1. A compound of Formula I-1:

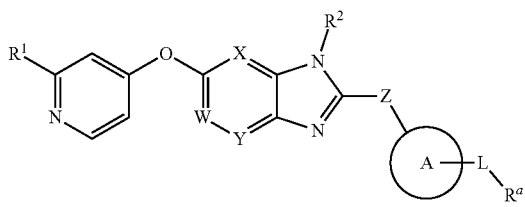

I-1 or a pharmaceutically acceptable salt thereof, wherein:
W is $CR^w$ or N;
X is $CR^x$ or N;
Y is $CR^y$ or N;
Z is —O— or —$NR^z$—;
$R^w$, $R^x$, and $R^y$ are each independently hydrogen, halogen, —$OR^3$, —$N(R^3)_2$, —$SR^3$, optionally substituted $C_{1-6}$ aliphatic, or —CN;
$R^z$ is hydrogen or optionally substituted $C_{1-6}$ aliphatic;
$R^1$ is —$N(R)_2$, —N(R)C(O)R', —C(O)N(R)$_2$, or —N(R)C(O)N(R)$_2$;
$R^2$ is optionally substituted $C_{1-6}$ aliphatic;
$R^3$ is hydrogen or optionally substituted $C_{1-6}$ aliphatic;
Ring A is optionally substituted phenyl, optionally substituted 5- to 6-membered monocyclic heteroaryl having 1-4 heteroatoms independently selected from nitrogen, oxygen, and sulfur, optionally substituted 8- to 10-membered bicyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur;
L is a covalent bond or a bivalent $C_{1-3}$ straight or branched hydrocarbon chain;
$R^a$ is hydrogen, halogen, optionally substituted $C_{1-6}$ aliphatic, optionally substituted phenyl, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur;
each R is independently hydrogen, optionally substituted $C_{1-6}$ aliphatic, optionally substituted 3- to 7-membered saturated or partially unsaturated carbocyclyl, or optionally substituted 3- to 7-membered saturated or partially unsaturated monocyclic heterocyclyl having 1-3 heteroatoms independently selected from nitrogen, oxygen, and sulfur, or two R when attached to the same nitrogen atom are taken together form an optionally substituted 3- to 7-membered saturated or partially unsaturated monocyclic heterocyclyl having 0-2 additional heteroatoms independently selected from nitrogen, oxygen, and sulfur; and
each R' is independently optionally substituted $C_{1-6}$ aliphatic or optionally substituted 3- to 7-membered saturated or partially unsaturated carbocyclyl.

A2. The compound of embodiment A1, wherein:
W is $CR^w$ or N;
X is $CR^x$ or N;
Y is $CR^y$ or N;
Z is —O— or —$NR^z$—;
$R^w$, $R^x$, and $R^y$ are each independently hydrogen, halogen, —$OR^3$, —$N(R^3)_2$, —$SR^3$, optionally substituted $C_{1-6}$ aliphatic, or —CN;
$R^z$ is hydrogen or optionally substituted $C_{1-6}$ aliphatic;
$R^1$ is —$N(R)_2$, —N(R)C(O)R', —C(O)N(R)$_2$, or —N(R)C(O)N(R)$_2$;
$R^2$ is optionally substituted $C_{1-6}$ aliphatic;
$R^3$ is hydrogen or optionally substituted $C_{1-6}$ aliphatic;
Ring A is optionally substituted phenyl, optionally substituted 5- to 6-membered monocyclic heteroaryl having 1-4 heteroatoms independently selected from nitrogen, oxygen, and sulfur, optionally substituted 8- to 10-membered bicyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur;
L is a covalent bond or a bivalent $C_{1-3}$ straight or branched hydrocarbon chain;
$R^a$ is hydrogen, halogen, optionally substituted $C_{1-6}$ aliphatic, optionally substituted phenyl, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur;
each R is independently hydrogen, optionally substituted $C_{1-6}$ aliphatic, optionally substituted 3- to 7-membered saturated or partially unsaturated carbocyclyl, or optionally substituted 3- to 7-membered saturated or partially unsaturated monocyclic heterocyclyl having 1-3 heteroatoms independently selected from nitrogen, oxygen, and sulfur, or two R when attached to the same nitrogen atom are taken together form a 3- to 7-membered saturated or partially unsaturated monocyclic heterocyclyl having 0-2 additional heteroatoms independently selected from nitrogen, oxygen, and sulfur; and each R' is independently optionally substituted $C_{1-6}$ aliphatic or optionally substituted 3- to 7-membered saturated or partially unsaturated carbocyclyl.

A3. The compound of embodiment A1 or A2, wherein:

W is CH;
X is $CR^x$ or N;
Y is $CR^y$ or N;
Z is —O— or —$NR^z$—;
$R^x$ and $R^y$ are each independently hydrogen, optionally substituted $C_{1-6}$ aliphatic, or —CN;
$R^z$ is hydrogen or optionally substituted $C_{1-6}$ aliphatic;
$R^1$ is —$N(R)_2$, —N(R)C(O)R', —C(O)N(R)$_2$, or —N(R)C(O)N(R)$_2$;
$R^2$ is optionally substituted $C_{1-6}$ aliphatic;

Ring A is optionally substituted phenyl, optionally substituted 5- to 6-membered monocyclic heteroaryl having 1-4 heteroatoms independently selected from nitrogen, oxygen, and sulfur, optionally substituted 8- to 10-membered bicyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur;

L is a covalent bond or a bivalent $C_{1-3}$ straight or branched hydrocarbon chain;

$R^a$ is hydrogen, halogen, optionally substituted $C_{1-6}$ aliphatic, optionally substituted phenyl, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur;

each R is independently hydrogen, optionally substituted $C_{1-6}$ aliphatic, optionally substituted 3- to 7-membered saturated or partially unsaturated carbocyclyl, or optionally substituted 3- to 7-membered saturated or partially unsaturated monocyclic heterocyclyl having 1-3 heteroatoms independently selected from nitrogen, oxygen, and sulfur, or two R when attached to the same nitrogen atom are taken together form a 3- to 7-membered saturated or partially unsaturated monocyclic heterocyclyl having 0-2 additional heteroatoms independently selected from nitrogen, oxygen, and sulfur; and each R' is independently optionally substituted $C_{1-6}$ aliphatic or optionally substituted 3- to 7-membered saturated or partially unsaturated carbocyclyl.

A4. The compound of any one of the preceding embodiments, wherein the compound is not:

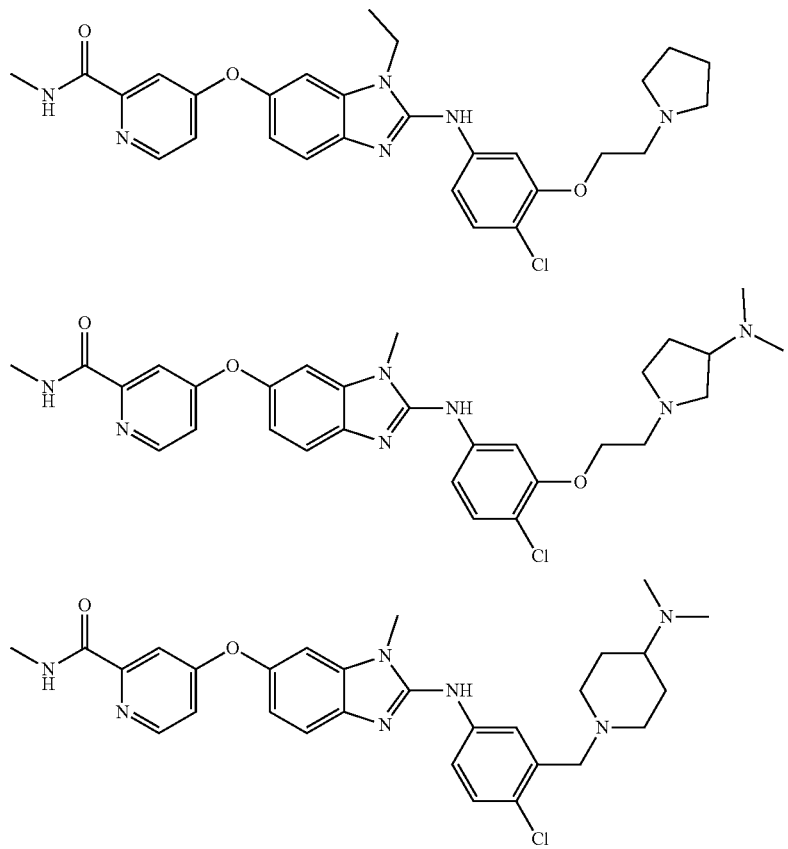

-continued
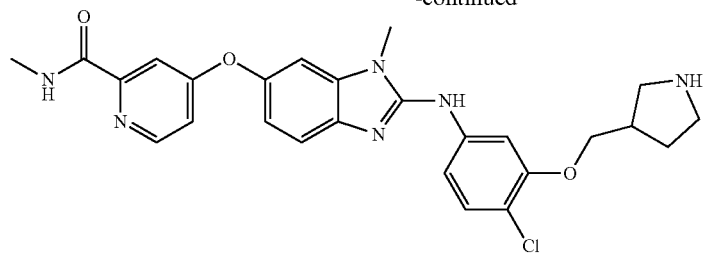
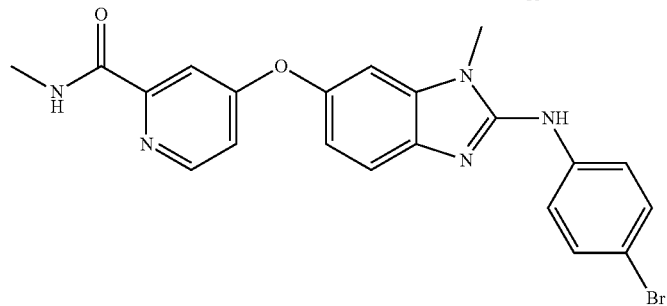
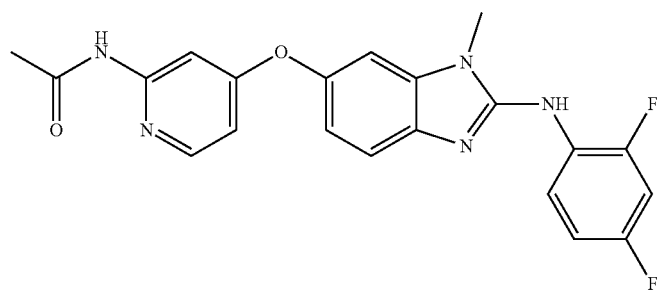
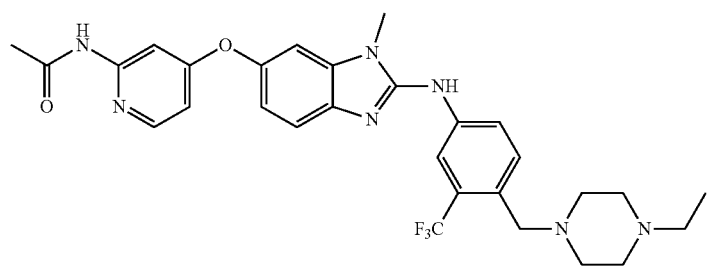
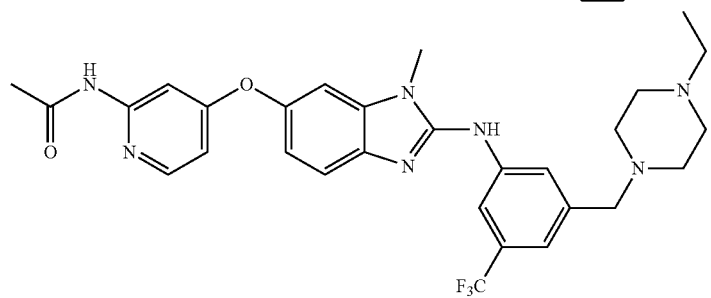
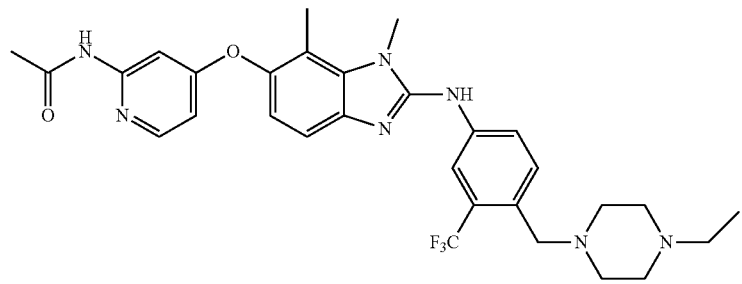

-continued
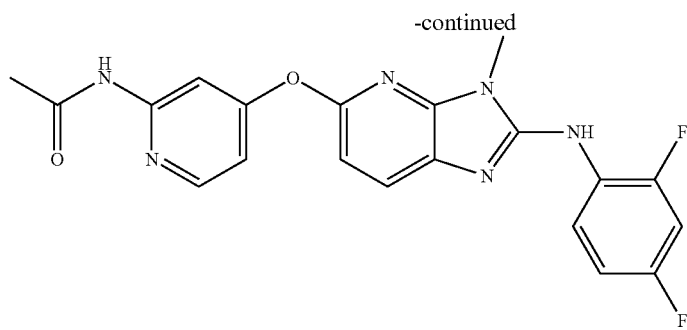
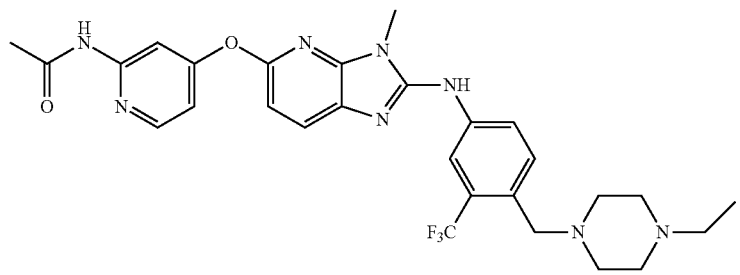
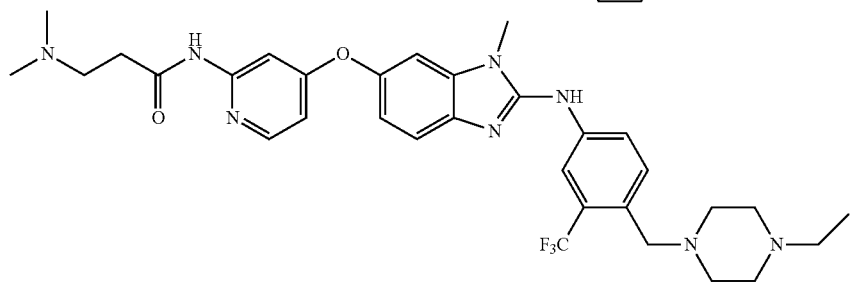
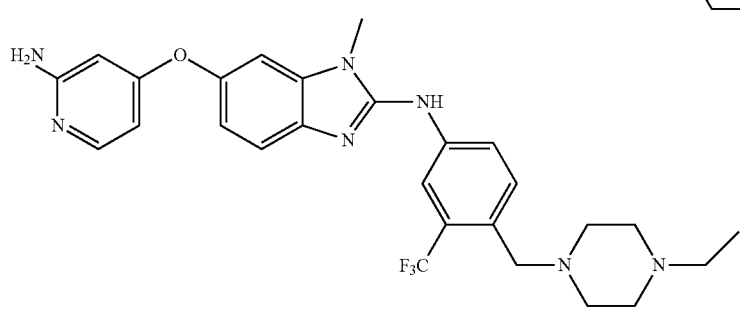
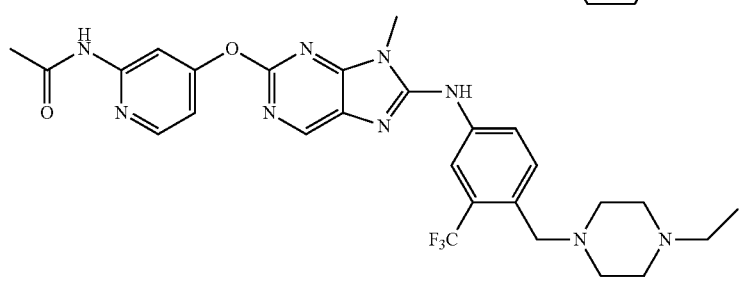
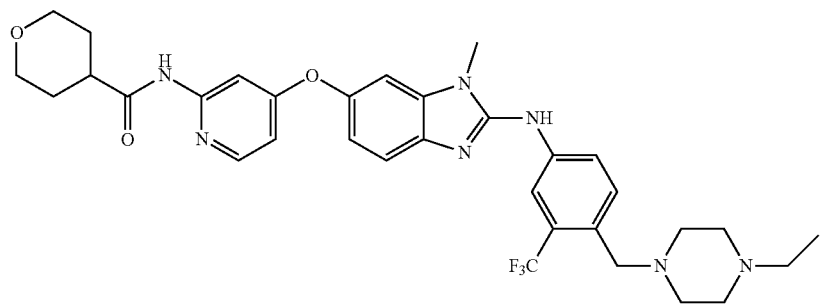

-continued

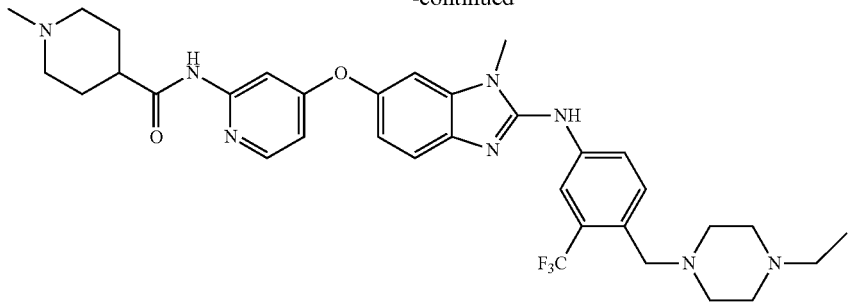

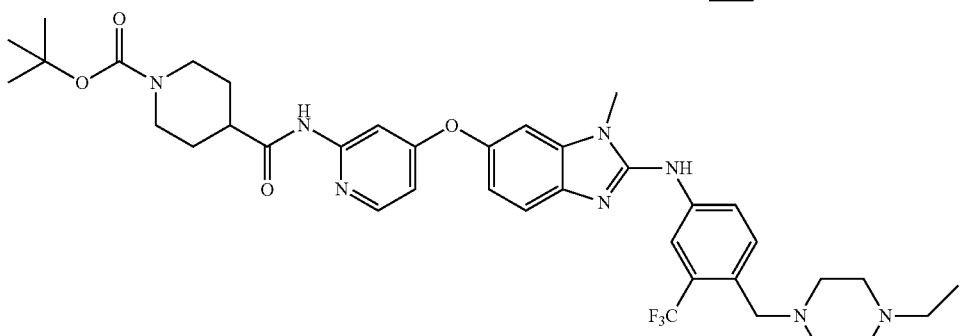

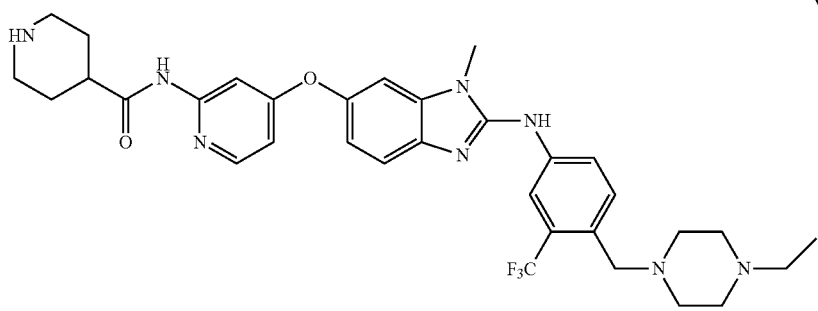

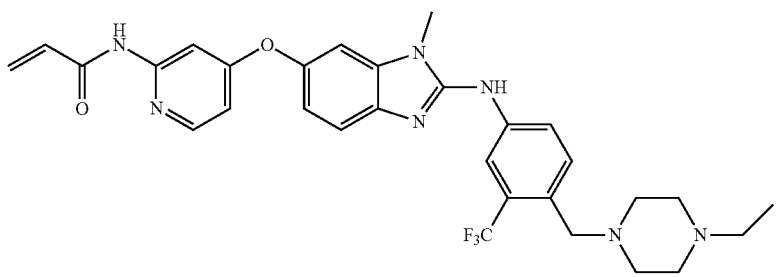

A5. The compound of any one of the preceding embodiments, wherein Ring A is optionally substituted 5- to 6-membered monocyclic heteroaryl having 1-4 heteroatoms independently selected from nitrogen, oxygen, and sulfur, optionally substituted 8- to 10-membered bicyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur.

A5. The compound of any one of the preceding embodiments, wherein Ring A is optionally substituted 5- to 6-membered monocyclic heteroaryl having 1-4 heteroatoms independently selected from nitrogen, oxygen, and sulfur.

A6. The compound of any one of the preceding embodiments, wherein $R^a$ is halogen, optionally substituted $C_{1-4}$ alkyl, optionally substituted 5-membered monocyclic heteroaryl having 1-4 heteroatoms independently selected from nitrogen, oxygen, and sulfur, optionally substituted 3- to 6-membered saturated monocyclic carbocyclyl, optionally substituted 3- to 6-membered saturated monocyclic heterocyclyl having 1-3 heteroatoms independently selected from nitrogen, oxygen, and sulfur, or optionally substituted 7-membered saturated, spirocyclic, bicyclic heterocyclyl having 1-4 heteroatoms independently selected from nitrogen, oxygen, and sulfur.

A7. The compound of any one of the preceding embodiments, wherein:

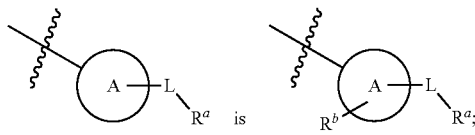 is and

R$^b$ hydrogen, halogen, —CN, —OR, —SR, —N(R)$_2$, —NO$_2$, —C(O)R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R', —SO$_2$N(R)$_2$, —SO$_3$R', optionally substituted C$_{1-6}$ aliphatic, optionally substituted 3- to 6-membered saturated or partially unsaturated carbocyclyl, optionally substituted 3- to 6-membered saturated or partially unsaturated monocyclic heterocyclyl having 1-3 heteroatoms independently selected from nitrogen, oxygen, and sulfur, optionally substituted 5- to 6-membered monocyclic heteroaryl having 1-4 heteroatoms independently selected from nitrogen, oxygen, and sulfur.

A8. The compound of embodiment A7, wherein

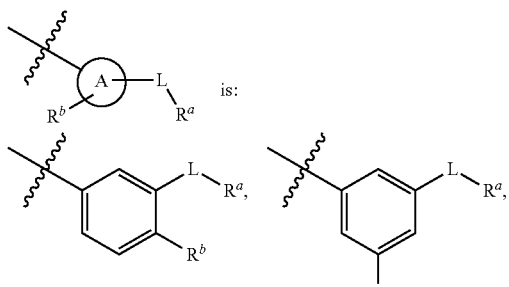
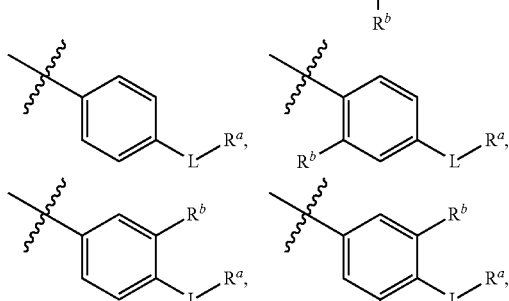
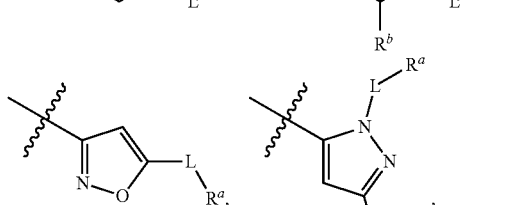
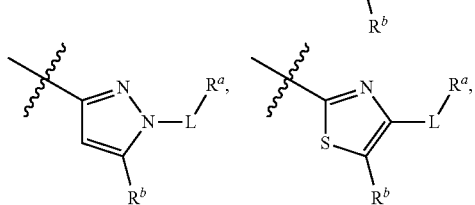

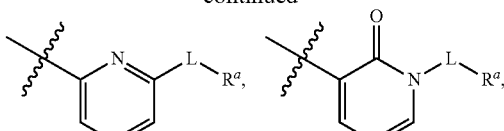
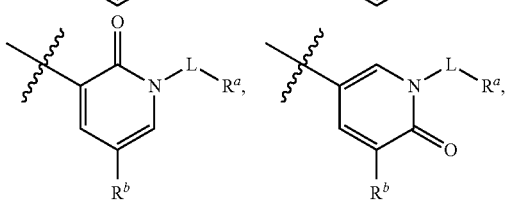
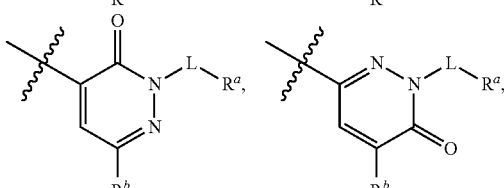
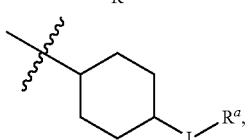
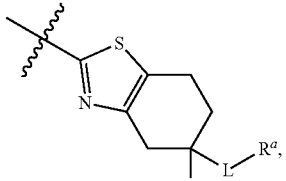
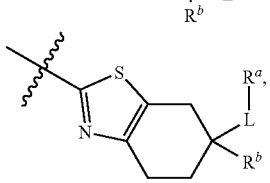
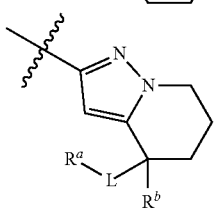
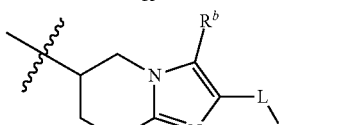
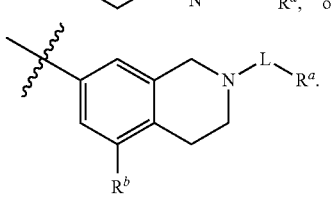

A9. The compound of embodiment A7 or A8, wherein R$^b$ is halogen, optionally substituted C$_{1-4}$ alkyl or optionally substituted C$_{3-4}$ cycloalkyl.

A10. The compound of any one of the preceding embodiments, wherein R$^1$ is —N(R)$_2$.

A11. The compound of embodiment A10, wherein $R^1$ is —N(H)(R).

A12. The compound of any one of embodiments A1-A9, wherein $R^1$ is —N(R)C(O)R'.

A13. The compound of embodiment A12, wherein $R^1$ is —N(H)C(O)R'.

A14. The compound of embodiment A13, wherein $R^1$ is —N(H)C(O)CH$_3$.

A15. The compound of any one of embodiments A1-A9, wherein $R^1$ is —C(O)N(R)$_2$.

A16. The compound of embodiment A15, wherein $R^1$ is —C(O)N(H)CH$_3$.

A17. The compound of any one of embodiments A1-A9, wherein $R^1$ is —N(R)C(O)N(R)$_2$.

A18. The compound of embodiment A17, wherein $R^1$ is —N(H)C(O)N(R)$_2$.

A19. The compound of any one of the preceding embodiments, wherein $R^2$ is $C_{1-4}$ alkyl.

A20. The compound of any one of the preceding embodiments, wherein X is $CR^x$.

A21. The compound of embodiment A20, wherein $R^x$ is hydrogen, halogen, —OR$^3$, optionally substituted $C_{1-6}$ aliphatic, or —CN.

A22. The compound of embodiment A21, wherein $R^x$ is hydrogen.

A23. The compound of any one of embodiments A1-A19, wherein X is N.

A24. The compound of any one of the preceding embodiments, wherein Y is $CR^y$.

A25. The compound of embodiment A24, wherein $R^y$ is hydrogen.

A26. The compound of any one of embodiments A1-A23, wherein Y is N.

A27. The compound of any one of the preceding embodiments, wherein Z is $NR^z$—.

A28. The compound of embodiment 27, wherein $R^z$ is hydrogen.

A29. The compound of any one of embodiments A1-A26, wherein Z is —O—.

A30. The compound of any one of the preceding embodiments, wherein the compound is of Formula I-A:

I-A

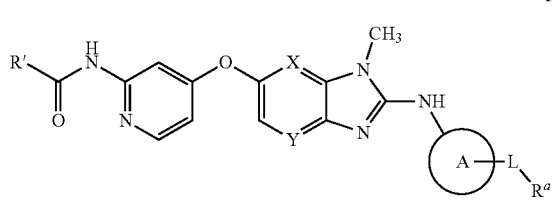

or a pharmaceutically acceptable salt thereof.

A31. The compound of any one of the preceding embodiments, wherein the compound is of Formula I-B:

I-B

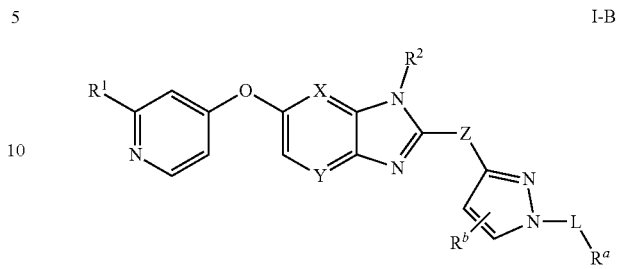

or a pharmaceutically acceptable salt thereof.

A32. The compound of any one of the preceding embodiments, wherein the compound is of Formula I-C:

I-C

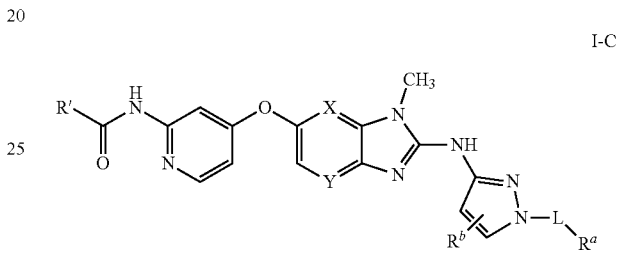

or a pharmaceutically acceptable salt thereof.

A33. The compound of any one of the preceding embodiments, wherein the compound is of Formula I-D:

I-D

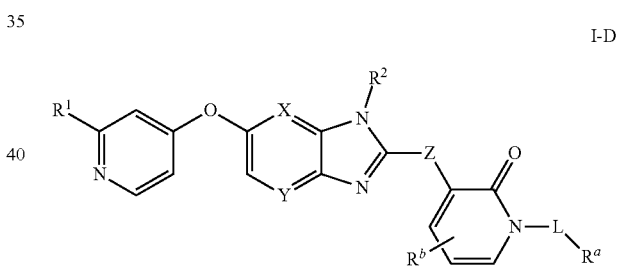

or a pharmaceutically acceptable salt thereof.

A34. The compound of any one of the preceding embodiments, wherein the compound is of Formula I-E:

I-E

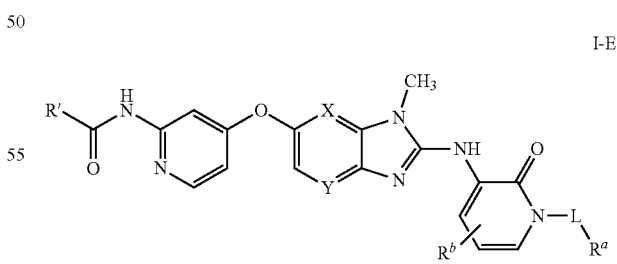

or a pharmaceutically acceptable salt thereof.

A35. The compound of embodiment 1, wherein the compound is a compound of Table 1.

A36. A pharmaceutical composition comprising a compound of any one of the preceding embodiments, or a pharmaceutically acceptable salt thereof, and a pharmaceutically acceptable carrier.

A37. A method of inhibiting JAK2 in a subject comprising administering the compound of any one of embodiments A1-A35 or the composition of embodiment A36.

A38. A method of treating a disease, disorder, or condition associated with JAK2, comprising administering to a subject in need thereof the compound of any one of embodiments A1-A35 or the composition of embodiment A36.

A39. A method of treating cancer, comprising administering to a subject in need thereof the compound of any one of embodiments A1-A35 or the composition of embodiment A36.

A40. A method of treating a hematological malignancy, comprising administering to a subject in need thereof the compound of any one of embodiments A1-A35 or the composition of embodiment A36.

A41. The method of embodiment A40, wherein the hematological malignancy is leukemia or lymphoma.

A42. A method of treating a myeloproliferative neoplasm, comprising administering to a subject in need thereof the compound of any one of embodiments A1-A35 or the composition of embodiment A36.

A43. The method of embodiment A42, wherein the myeloproliferative neoplasm is polycythemia vera, essential thrombocytopenia or myelofibrosis.

B1. A compound of Formula I-1:

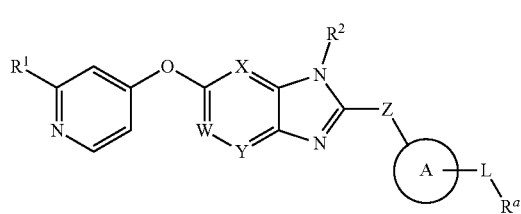

I-1 or a pharmaceutically acceptable salt thereof, wherein:
W is $CR^w$ or N;
X is $CR^x$ or N;
Y is $CR^y$ or N;
Z is —O— or —$NR^z$—;
$R^w$, $R^x$, and $R^y$ are each independently hydrogen, halogen, —$OR^3$, —$N(R^3)_2$, —$SR^3$, optionally substituted $C_{1-6}$ aliphatic, or —CN;
$R^z$ is hydrogen or optionally substituted $C_{1-6}$ aliphatic;
$R^1$ is —$N(R)_2$, —N(R)C(O)R', —C(O)N(R)$_2$, or —N(R)C(O)N(R)$_2$;
$R^2$ is optionally substituted $C_{1-6}$ aliphatic;
$R^3$ is hydrogen or optionally substituted $C_{1-6}$ aliphatic;
Ring A is optionally substituted 5- to 6-membered monocyclic heteroaryl having 1-4 heteroatoms independently selected from nitrogen, oxygen, and sulfur, optionally substituted 8- to 10-membered bicyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur;
L is a covalent bond or a bivalent $C_{1-3}$ straight or branched hydrocarbon chain;
$R^a$ is hydrogen, halogen, optionally substituted $C_{1-6}$ aliphatic, optionally substituted phenyl, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur;
each R is independently hydrogen, optionally substituted $C_{1-6}$ aliphatic, optionally substituted 3- to 7-membered saturated or partially unsaturated carbocyclyl, or optionally substituted 3- to 7-membered saturated or partially unsaturated monocyclic heterocyclyl having 1-3 heteroatoms independently selected from nitrogen, oxygen, and sulfur, or two R when attached to the same nitrogen atom are taken together form an optionally substituted 3- to 7-membered saturated or partially unsaturated monocyclic heterocyclyl having 0-2 additional heteroatoms independently selected from nitrogen, oxygen, and sulfur; and
each R' is independently optionally substituted $C_{1-6}$ aliphatic or optionally substituted 3- to 7-membered saturated or partially unsaturated carbocyclyl.

B2. The compound of embodiment B1, wherein Ring A is optionally substituted 5- to 6-membered monocyclic heteroaryl having 1-4 heteroatoms independently selected from nitrogen, oxygen, and sulfur.

B3. The compound of embodiment B1, wherein Ring A is optionally substituted 8- to 10-membered bicyclic heteroaryl having 1-4 heteroatoms independently selected from nitrogen, oxygen, and sulfur.

B4. The compound of embodiment B1, wherein Ring A is optionally substituted 3- to 7-membered saturated or partially unsaturated monocyclic carbocyclyl.

B5. The compound of embodiment B1, wherein Ring A is optionally substituted 3- to 7-membered saturated or partially unsaturated monocyclic heterocyclyl having 1-3 heteroatoms independently selected from nitrogen, oxygen, and sulfur.

B6. The compound of embodiment B1, wherein Ring A is optionally substituted 7- to 10-membered saturated or partially unsaturated bicyclic heterocyclyl having 1-4 heteroatoms independently selected from nitrogen, oxygen, and sulfur.

B7. The compound of any one of the preceding embodiments, wherein $R^a$ is halogen, optionally substituted $C_{1-4}$ alkyl, optionally substituted 5-membered monocyclic heteroaryl having 1-4 heteroatoms independently selected from nitrogen, oxygen, and sulfur, optionally substituted 3- to 6-membered saturated monocyclic carbocyclyl, optionally substituted 3- to 6-membered saturated monocyclic heterocyclyl having 1-3 heteroatoms independently selected from nitrogen, oxygen, and sulfur, or optionally substituted 7-membered saturated, spirocyclic, bicyclic heterocyclyl having 1-4 heteroatoms independently selected from nitrogen, oxygen, and sulfur.

B8. The compound of any one of the preceding embodiments, wherein $R^a$ is $C_{1-4}$ alkyl optionally substituted with one or more oxo, halogen, —CN, —OH, or —O($C_{1-6}$ alkyl).

B9. The compound of any one of the embodiments B1-B7, wherein $R^a$ is 3- to 6-membered saturated monocyclic carbocyclyl optionally substituted with one or more —($C_{1-6}$ alkylene)OH, —CN, —OH, or —O($C_{1-6}$ alkyl).

B10. The compound of any one of embodiments B1-B7, wherein $R^a$ is 3- to 6-membered saturated monocyclic heterocyclyl having 1-3 heteroatoms independently selected from nitrogen, oxygen, and sulfur optionally substituted with one or more oxo, halogen, —C(O)($C_{1-4}$ alkyl), —O($C_{1-4}$ alkyl), or $C_{1-4}$ alkyl optionally substituted with one or more halogen and —O($C_{1-4}$ alkyl).

B11. The compound of any one of embodiments B1-B7, wherein $R^a$ is optionally substituted 7- to 8-membered saturated, spirocyclic, bicyclic heterocyclyl having 1-2 heteroatoms independently selected from nitrogen, oxygen, and sulfur.

B12. The compound of any one of the preceding embodiments, wherein $R^a$ is $C_{1-4}$ alkyl, 3- to 6-membered saturated monocyclic heterocyclyl having 1-2 heteroatoms independently selected from nitrogen, oxygen, and sulfur, or 7- to 8-membered saturated, spirocyclic, bicyclic heterocyclyl having 1-2 heteroatoms independently selected from nitrogen, oxygen, and sulfur.

B13. The compound of any one of the preceding embodiments, wherein:

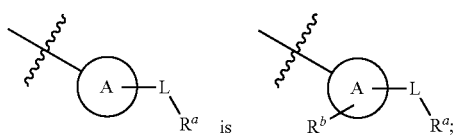

and $R^b$ hydrogen, halogen, —CN, —OR, —SR, —N(R)$_2$, —NO$_2$, —C(O)R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R', —SO$_2$N(R)$_2$, —SO$_3$R', optionally substituted $C_{1-6}$ aliphatic, optionally substituted 3- to 6-membered saturated or partially unsaturated carbocyclyl, optionally substituted 3- to 6-membered saturated or partially unsaturated monocyclic heterocyclyl having 1-3 heteroatoms independently selected from nitrogen, oxygen, and sulfur, optionally substituted 5- to 6-membered monocyclic heteroaryl having 1-4 heteroatoms independently selected from nitrogen, oxygen, and sulfur.

B14. The compound of embodiment B13, wherein

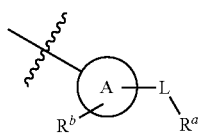

is:

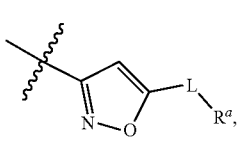

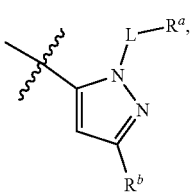

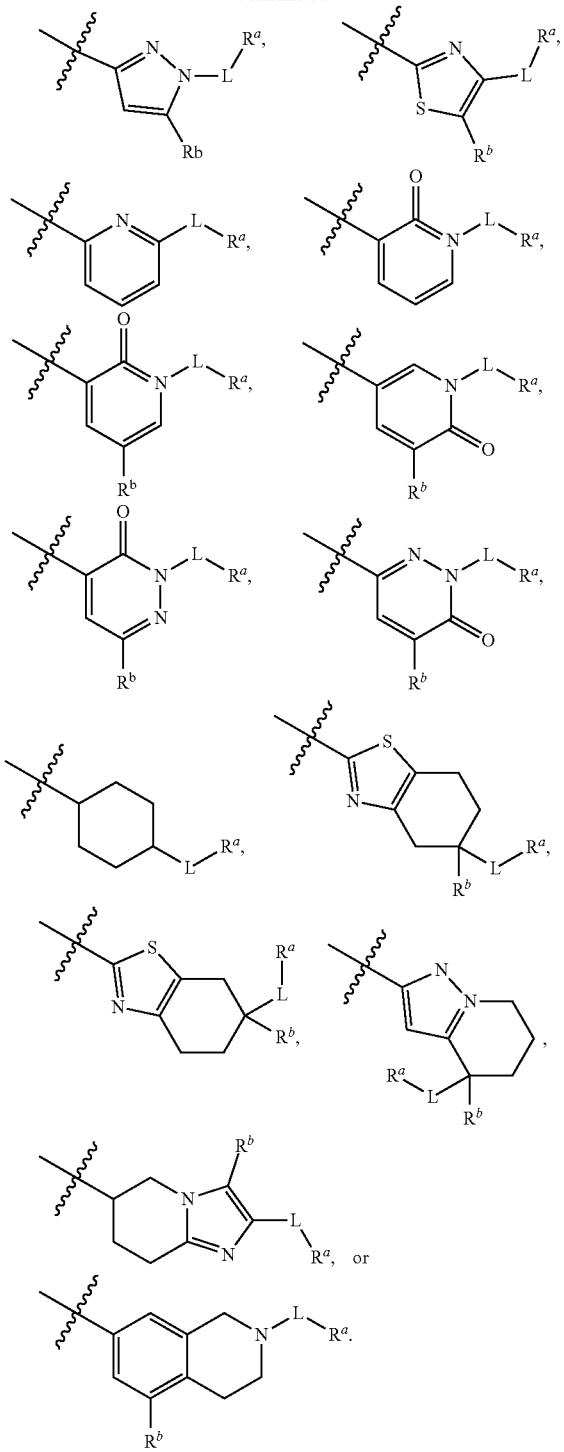

B15. The compound of embodiment B13 or B14, wherein

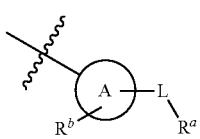

is:

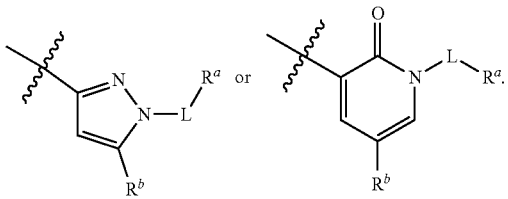

B16. The compound of any one of embodiments B13-B15, wherein $R^b$ is hydrogen, halogen, optionally substituted $C_{1-4}$ alkyl, optionally substituted $C_{3-4}$ cycloalkyl, optionally substituted 3- to 5-membered saturated or partially unsaturated monocyclic heterocyclyl having 1-3 heteroatoms independently selected from nitrogen, oxygen, and sulfur, or optionally substituted 5-membered monocyclic heteroaryl having 1-4 heteroatoms independently selected from nitrogen, oxygen, and sulfur.

B17. The compound of any one of embodiments B13-B16, wherein $R^b$ is halogen, optionally substituted $C_{1-4}$ alkyl or optionally substituted $C_{3-4}$ cycloalkyl.

B18. The compound of any one of embodiments B13-B16, wherein $R^b$ is $C_{3-4}$ cycloalkyl or $C_{1-4}$ alkyl optionally substituted with one or more fluoro.

B19. The compound of any one of the preceding embodiments, wherein the compound is of Formula I-B:

I-B

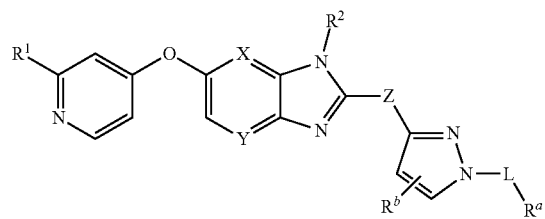

or a pharmaceutically acceptable salt thereof.

B20. The compound of any one of the preceding embodiments, wherein the compound is of Formula I-C:

I-C

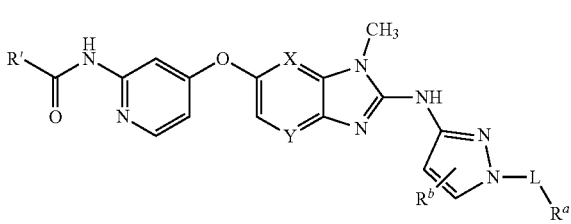

or a pharmaceutically acceptable salt thereof.

B21. The compound of any one of the preceding embodiments, wherein the compound is of Formula I-D:

I-D

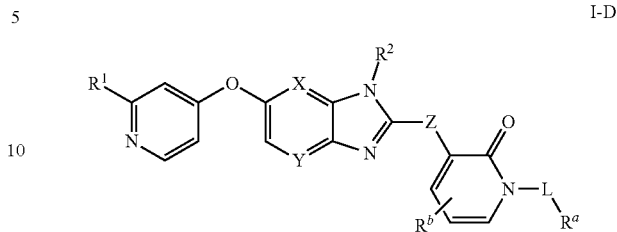

or a pharmaceutically acceptable salt thereof.

B22. The compound of any one of the preceding embodiments, wherein the compound is of Formula I-E:

I-E

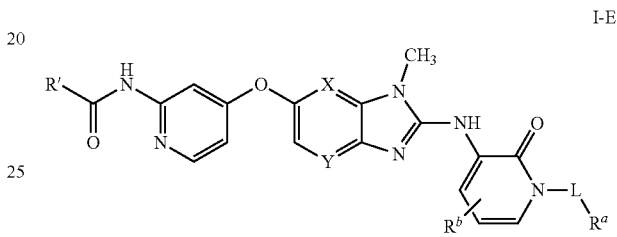

or a pharmaceutically acceptable salt thereof.

B23. A compound of Formula I-1:

I-1

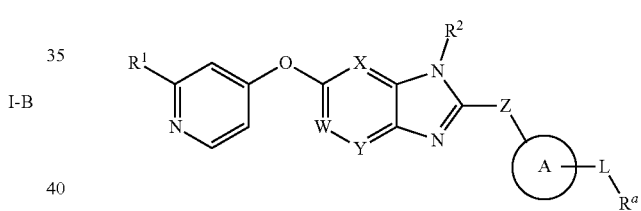

or a pharmaceutically acceptable salt thereof, wherein:
W is $CR^w$ or N;
X is $CR^x$ or N;
Y is $CR^y$ or N;
Z is —O— or —$NR^z$—;
$R^w$, $R^x$, and $R^y$ are each independently hydrogen, halogen, —$OR^3$, —$N(R^3)_2$, —$SR^3$, optionally substituted $C_{1-6}$ aliphatic, or —CN;
$R^z$ is hydrogen or optionally substituted $C_{1-6}$ aliphatic;
$R^1$ is —$N(R)_2$, —N(R)C(O)R', —C(O)N(R)$_2$, or —N(R)C(O)N(R)$_2$;
$R^2$ is optionally substituted $C_{1-6}$ aliphatic;
$R^3$ is hydrogen or optionally substituted $C_{1-6}$ aliphatic;
Ring A is optionally substituted phenyl;
L is a covalent bond or a bivalent $C_{1-3}$ straight or branched hydrocarbon chain;
$R^a$ is hydrogen, halogen, optionally substituted $C_{1-6}$ aliphatic, optionally substituted phenyl, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur;

each R is independently hydrogen, optionally substituted $C_{1-6}$ aliphatic, optionally substituted 3- to 7-membered saturated or partially unsaturated carbocyclyl, or optionally substituted 3- to 7-membered saturated or partially unsaturated monocyclic heterocyclyl having 1-3 heteroatoms independently selected from nitrogen, oxygen, and sulfur, or two R when attached to the same nitrogen atom are taken together form an optionally substituted 3- to 7-membered saturated or partially unsaturated monocyclic heterocyclyl having 0-2 additional heteroatoms independently selected from nitrogen, oxygen, and sulfur; and each R' is independently optionally substituted $C_{1-6}$ aliphatic or optionally substituted 3- to 7-membered saturated or partially unsaturated carbocyclyl.

B22. The compound of embodiment B21, wherein the compound is not:

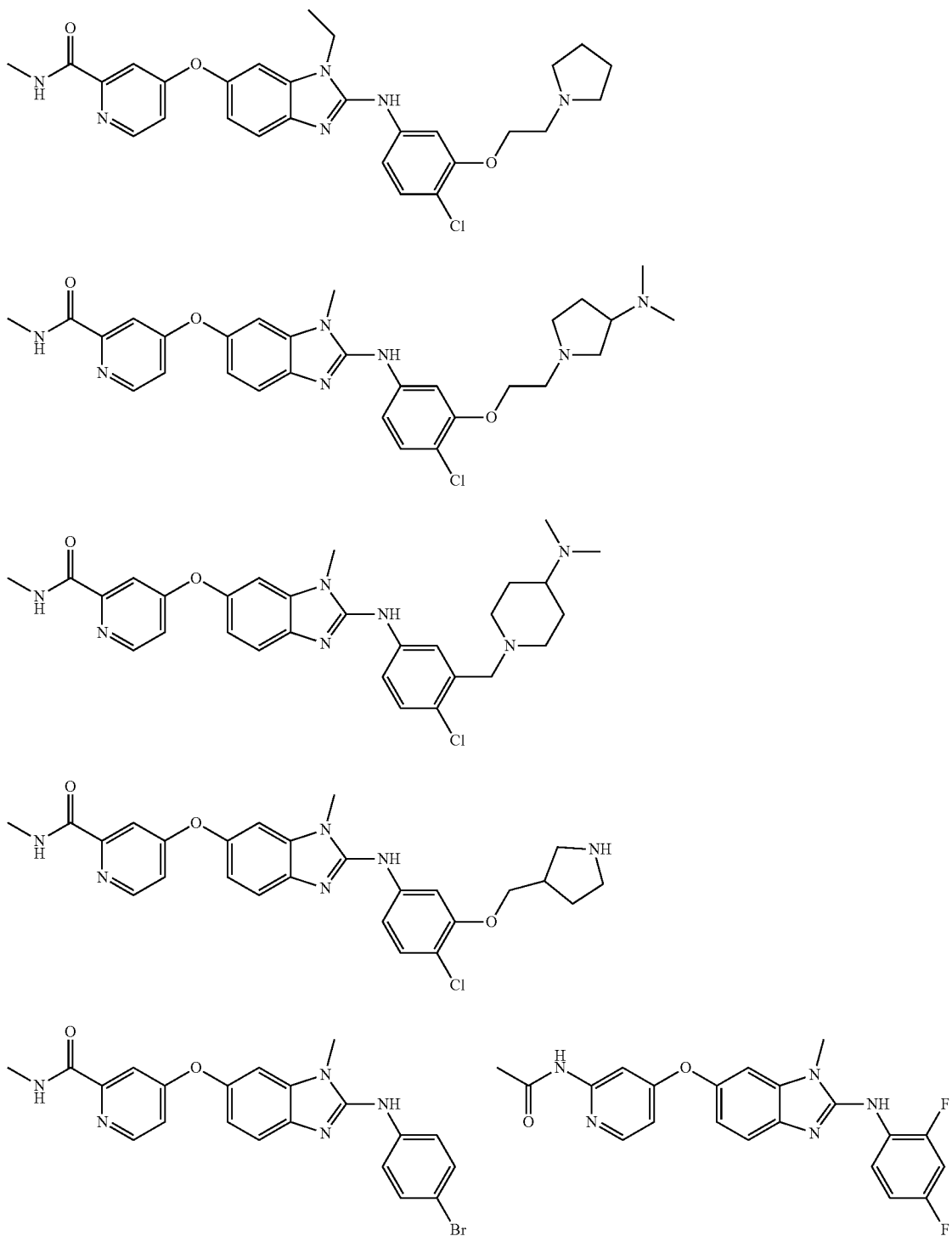

-continued
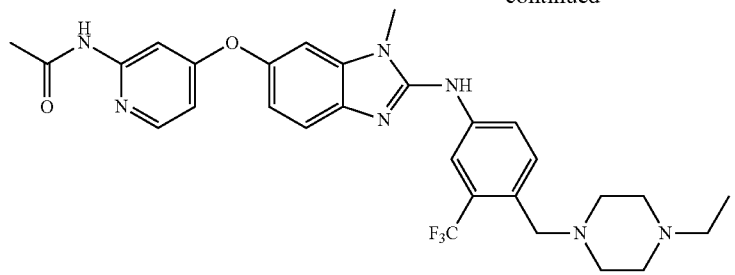
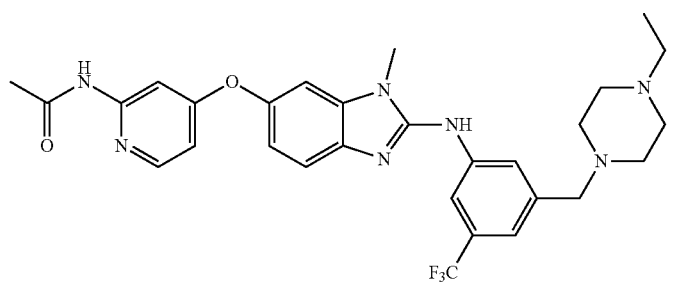
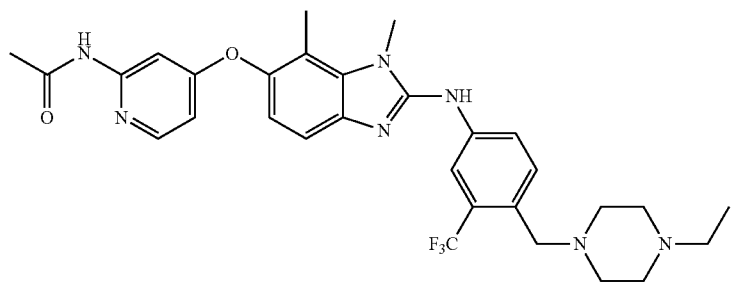
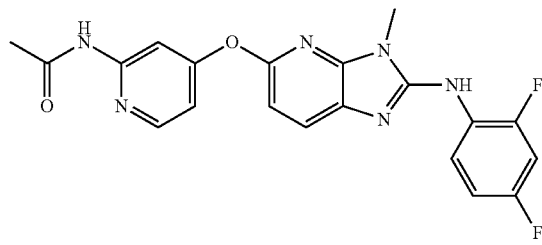
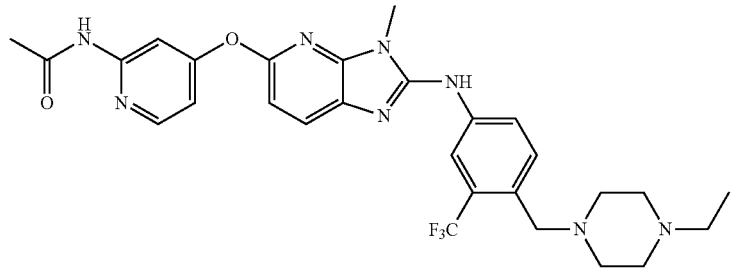
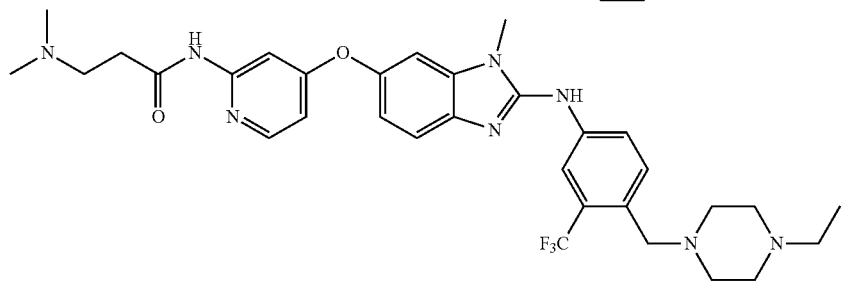

-continued
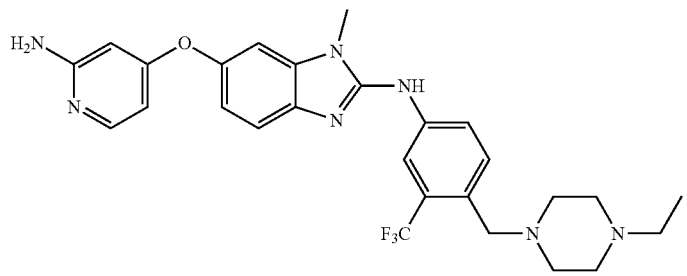
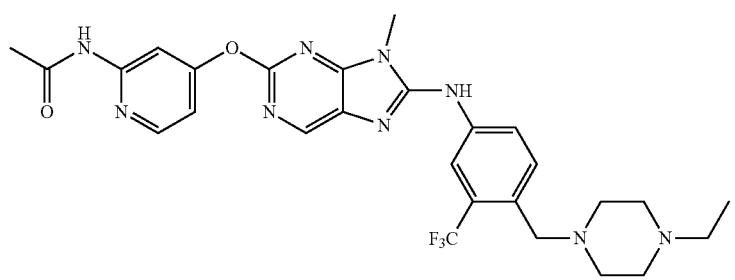
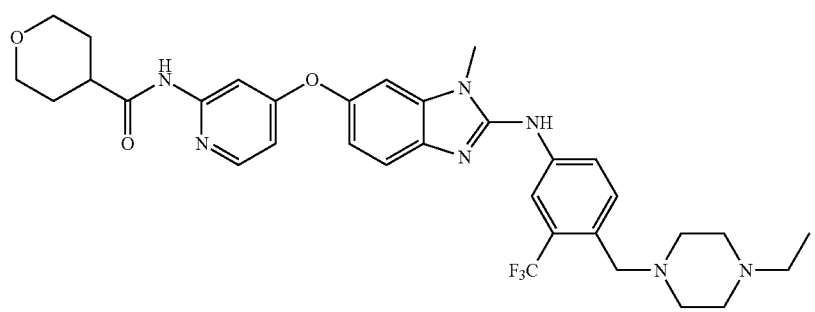
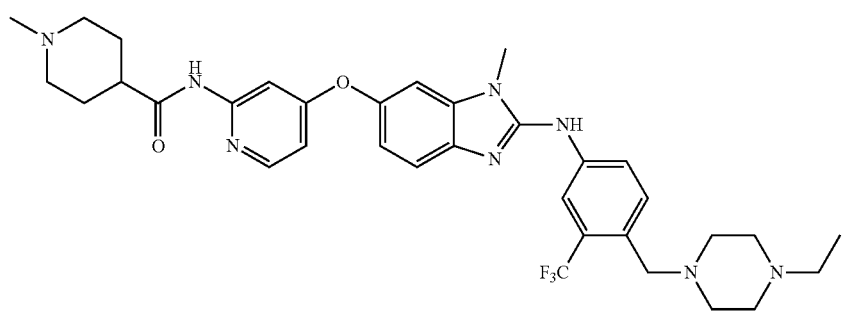
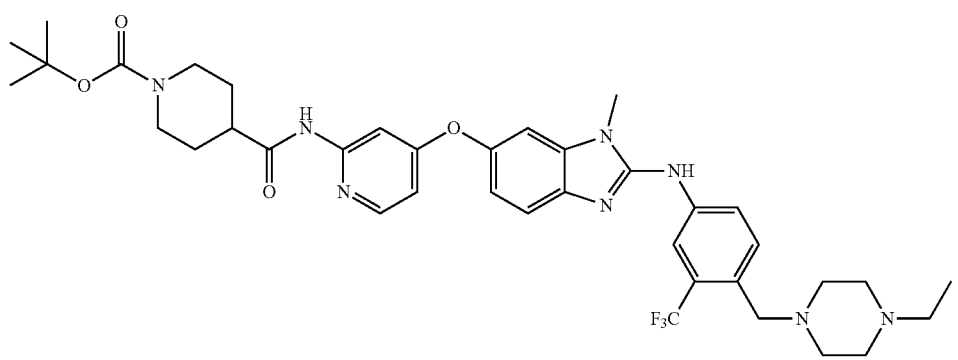

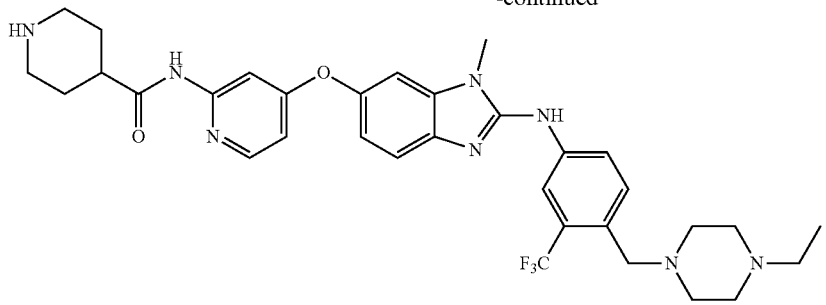

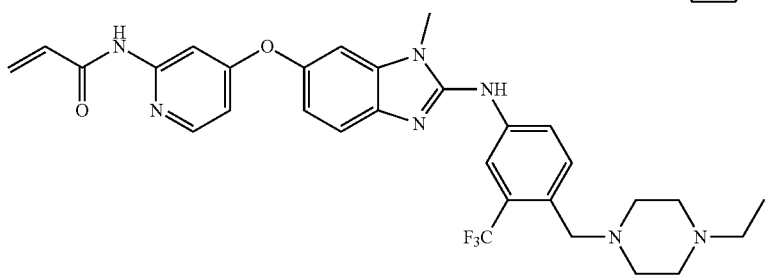

B24. The compound of embodiment B22 or B23, wherein:
(i) if $R^1$ is —NHC(O)R' or —NH$_2$, $R^2$ is —CH$_3$, X is CH, and R' is optionally substituted $C_{1-2}$ aliphatic, then $R^a$ and $R^b$ are not fluoro or

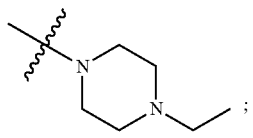 [SMILES: *N1CCN(CC)CC1]

(ii) if $R^1$ is —NHC(O)CH$_3$, $R^2$ is —CH$_3$, and X is N, then $R^a$ and $R^b$ are not fluoro or

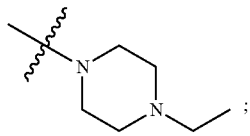 [SMILES: *N1CCN(CC)CC1]

(iii) if $R^1$ is —NHC(O)CH$_3$, $R^2$ is —CH$_3$, and X is CCH$_3$, then $R^a$ and $R^b$ are not

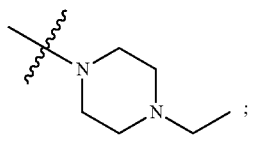 [SMILES: *N1CCN(CC)CC1]

and
(iv) if $R^1$ is —C(O)NHCH$_3$, $R^2$ is $C_{1-2}$ alkyl, and X is CH, then $R^a$ and $R^b$ are not halogen.

B25. The compound of any one of embodiments B22-B24, wherein $R^a$ is halogen, optionally substituted $C_{1-4}$ alkyl, optionally substituted 5-membered monocyclic heteroaryl having 1-4 heteroatoms independently selected from nitrogen, oxygen, and sulfur, optionally substituted 3- to 6-membered saturated monocyclic carbocyclyl, optionally substituted 3- to 6-membered saturated monocyclic heterocyclyl having 1-3 heteroatoms independently selected from nitrogen, oxygen, and sulfur, or optionally substituted 7-membered saturated, spirocyclic, bicyclic heterocyclyl having 1-4 heteroatoms independently selected from nitrogen, oxygen, and sulfur.

B26. The compound of any one of embodiments B22-B25, wherein $R^a$ is $C_{1-4}$ alkyl optionally substituted with one or more oxo, halogen, —CN, —OH, or —O($C_{1-6}$ alkyl).

B27. The compound of any one of embodiments B22-B25, wherein $R^a$ is 5-membered monocyclic heteroaryl having 1-4 heteroatoms independently selected from nitrogen, oxygen, and sulfur optionally substituted with one or more $C_{1-6}$ alkyl.

B28. The compound of any one of embodiments B22-B25, wherein $R^a$ is 3- to 7-membered saturated or partially unsaturated monocyclic heterocyclyl having 1-3 heteroatoms independently selected from nitrogen, oxygen, and sulfur optionally substituted with one or more oxo, halogen, —C(O)($C_{1-4}$ alkyl), —O($C_{1-4}$ alkyl), or $C_{1-4}$ alkyl optionally substituted with one or more halogen and —O($C_{1-4}$ alkyl).

B29. The compound of any one of embodiments B22-B28, wherein:

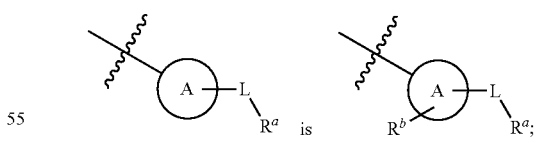

and
$R^b$ hydrogen, halogen, —CN, —OR, —SR, —N(R)$_2$, —NO$_2$, —C(O)R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R', —SO$_2$N(R)$_2$, —SO$_3$R', optionally substituted $C_{1-6}$ aliphatic, optionally substituted 3- to 6-membered saturated or partially unsaturated carbocyclyl, optionally substituted 3- to 6-membered saturated or partially unsaturated monocyclic heterocyclyl having 1-3 heteroatoms independently selected from nitrogen, oxygen, and sulfur, optionally substituted 5- to 6-membered monocyclic heteroaryl having 1-4 heteroatoms independently selected from nitrogen, oxygen, and sulfur.

B30. The compound of any one of embodiments B22-B29, wherein

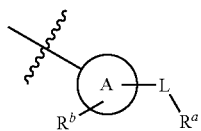

is:

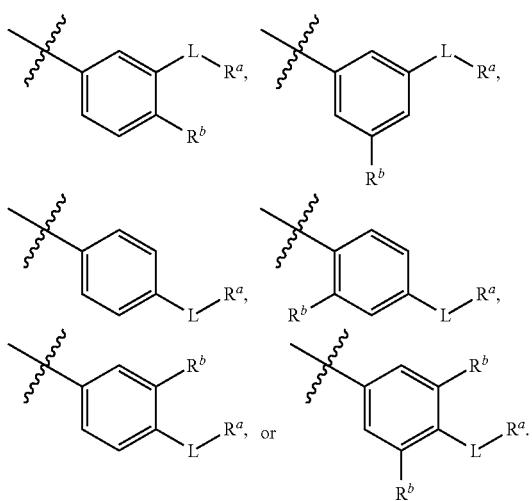

B31. The compound of embodiment B29 or B30, wherein $R^b$ is halogen, optionally substituted $C_{1-4}$ alkyl or optionally substituted $C_{3-4}$ cycloalkyl.

B32. The compound of any one of the preceding embodiments, wherein L is a covalent bond or —CH$_2$—.

B33. The compound of any one of the preceding embodiments, wherein $R^1$ is —N(R)$_2$.

B34. The compound of any one of embodiments B1-B32, wherein $R^1$ is —N(H)(R).

B35. The compound of any one of embodiments B1-B32, wherein $R^1$ is —N(R)C(O)R'.

B36. The compound of any one of embodiments B1-B32, wherein $R^1$ is —N(H)C(O)R'.

B37. The compound of any one of embodiments B1-B32, wherein $R^1$ is —N(H)C(O)(optionally substituted $C_{1-4}$ alkyl).

B38. The compound of any one of embodiments B1-B32, wherein $R^1$ is —N(H)C(O)CH$_3$ or —N(H)C(O)(cyclopropyl).

B39. The compound of any one of embodiments B1-B32, wherein $R^1$ is —C(O)N(R)$_2$.

B40. The compound of any one of embodiments B1-B32, wherein $R^1$ is —C(O)N(H)CH$_3$.

B41. The compound of any one of embodiments B1-B32, wherein $R^1$ is —N(R)C(O)N(R)$_2$.

B42. The compound of any one of embodiments B1-B32, wherein $R^1$ is —N(H)C(O)N(R)$_2$.

B43. The compound of any one of embodiments B1-B32, wherein $R^1$ is —N(R)C(O)N(R)$_2$, wherein the two R groups attached to the same nitrogen are taken together to form a 3- to 5-membered saturated monocyclic heterocyclyl having 0-1 additional heteroatoms optionally substituted with one or more halogen, $C_{1-6}$ alkyl, and —O($C_{1-6}$ alkyl).

B44. The compound of any one of the preceding embodiments, wherein $R^2$ is $C_{1-4}$ alkyl.

B45. The compound of any one of the preceding embodiments, wherein $R^2$ is methyl.

B46. The compound of any one of the preceding embodiments, wherein X is CR$^x$.

B47. The compound of embodiment B46, wherein $R^x$ is hydrogen, halogen, —OR$^3$, optionally substituted $C_{1-6}$ aliphatic, or —CN.

B48. The compound of embodiment B46, wherein $R^x$ is halogen, —OR$^3$, or —CN.

B49. The compound of embodiment B46, wherein $R^x$ is halogen, —OR$^3$, —N(R$^3$)$_2$, —SR$^3$, or —CN.

B50. The compound of any one of embodiments B1-B45, wherein X is N.

B51. The compound of any one of the preceding embodiments, wherein Y is CR$^y$.

B52. The compound of embodiment B51, wherein $R^y$ is hydrogen.

B53. The compound of any one of embodiments B1-B50, wherein Y is N.

B54. The compound of any one of the preceding embodiments, wherein W is CR$^w$.

B55. The compound of embodiment B54, wherein $R^w$ is hydrogen.

B56. The compound of any one of embodiments B1-B53, wherein W is N.

B57. The compound of any one of the preceding embodiments, wherein Z is —NR$^z$—.

B58. The compound of embodiment B57, wherein $R^z$ is hydrogen.

B59. The compound of any one of embodiments B1-B56, wherein Z is —O—.

B60. The compound of any one of the preceding embodiments, wherein each R is independently hydrogen, optionally substituted $C_{1-6}$ aliphatic, optionally substituted 3- to 7-membered saturated or partially unsaturated carbocyclyl, or optionally substituted 3- to 7-membered saturated or partially unsaturated monocyclic heterocyclyl having 1-3 heteroatoms independently selected from nitrogen, oxygen, and sulfur, or two R when attached to the same nitrogen atom are taken together form a 3- to 7-membered saturated or partially unsaturated monocyclic heterocyclyl having 0-2 additional heteroatoms independently selected from nitrogen, oxygen, and sulfur.

B61. The compound of any one of the preceding embodiments, wherein each R is independently hydrogen or optionally substituted $C_{1-6}$ aliphatic.

B62. The compound of any one of the preceding embodiments, wherein each R' is independently optionally substituted $C_{1-2}$ alkyl or optionally substituted $C_{3-4}$ cycloalkyl.

B63. The compound of any one of the preceding embodiments, wherein:

W is CH;

$R^x$ and $R^y$ are each independently hydrogen, optionally substituted $C_{1-6}$ aliphatic, or —CN;

each R is independently hydrogen, optionally substituted $C_{1-6}$ aliphatic, optionally substituted 3- to 7-membered saturated or partially unsaturated carbocyclyl, or optionally substituted 3- to 7-membered saturated or partially unsaturated monocyclic heterocyclyl having 1-3 heteroatoms independently selected from nitrogen, oxygen, and sulfur, or two R when attached to the same nitrogen atom are taken together form a 3- to 7-membered saturated or partially unsaturated monocyclic heterocyclyl having 0-2 additional heteroatoms independently selected from nitrogen, oxygen, and sulfur.

B64. The compound of any one of the preceding embodiments, wherein the compound is of Formula I-A:

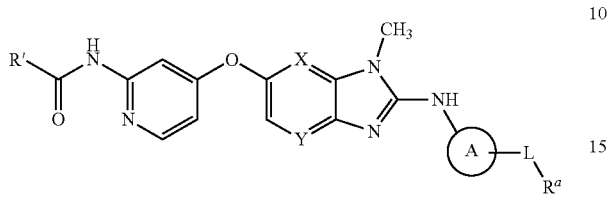

or a pharmaceutically acceptable salt thereof.

B65. A compound selected from Table 1, or a pharmaceutically acceptable salt thereof.

B66. A pharmaceutical composition comprising a compound of any one of the preceding embodiments, or a pharmaceutically acceptable salt thereof, and a pharmaceutically acceptable carrier.

B67. A method of inhibiting JAK2 in a subject comprising administering the compound of any one of embodiments B1-B63 or the composition of embodiment B64.

B68. The method of embodiment B67, wherein the compound or composition administered is characterized in that it is a Type II inhibitor of JAK2.

B69. A method of treating a disease, disorder, or condition associated with JAK2, comprising administering to a subject in need thereof the compound of any one of embodiments B1-B65 or the composition of embodiment B66.

B70. A method of treating cancer, comprising administering to a subject in need thereof the compound of any one of embodiments B1-B65 or the composition of embodiment B66.

B71. A method of treating a hematological malignancy, comprising administering to a subject in need thereof the compound of any one of embodiments B1-B65 or the composition of embodiment B66.

B72. The method of embodiment B71, wherein the hematological malignancy is leukemia or lymphoma.

B73. A method of treating a myeloproliferative neoplasm, comprising administering to a subject in need thereof the compound of any one of embodiments B1-B65 or the composition of embodiment B66.

B74. The method of embodiment B73, wherein the myeloproliferative neoplasm is polycythemia vera, essential thrombocytopenia or myelofibrosis.

EXAMPLES

As described in the Examples below, in certain exemplary embodiments, compounds are prepared according to the following general procedures. It will be appreciated that, although the general methods depict the synthesis of certain compounds of the present disclosure, the following general methods and other methods known to one of ordinary skill in the art can be applied to all compounds and subclasses and species of each of these compounds, as described herein.

Preparation of Intermediates

Preparation of Intermediate Int-1: N-(4-Hydroxypyridin-2-yl)acetamide

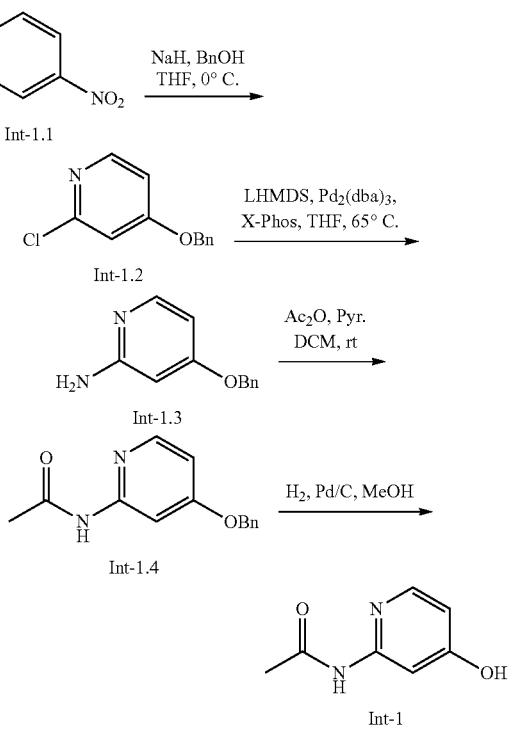

Synthesis of compound Int-1.2. To a solution of benzyl alcohol (17.05 g, 157.69 mmol, 1.0 equiv) in THF (250 mL) at 0° C. was added sodium hydride (12.61 g, 315.38 mmol, 2.0 equiv) in small portions. The mixture was stirred for 1 h and 2-chloro-4-nitropyridine (Int-1.1, 25 g, 157.69 mmol, 1.0 equiv) was added in portions. The reaction mixture was stirred at 0° C. for 2 h. It was poured over ice, stirred and extracted with ethyl acetate three times. The combined organic layers were washed with brine, dried over anhydrous sodium sulfate, filtered and concentrated under reduced pressure. The residue was purified by flash column chromatography on silica gel (CombiFlash®, 10% ethyl acetate in hexane as eluant) to afford Int-1.2. MS (ES): m/z 220.13 [M+H]$^+$.

Synthesis of compound Int-1.3. A solution of compound Int-1.2 (20 g, 91.05 mmol, 1.0 equiv) in THF (200 mL) was degassed by bubbling argon through for 10 min. 2-dicyclohexylphosphino-2',4',6'-triisopropylbiphenyl (4.34 g, 9.105 mmol, 0.1 equiv) and tris(dibenzylideneacetone)dipalladium (4.17 g, 4.55 mmol, 0.05 equiv) were added under argon atmosphere and again degassed for 5 min. To the mixture was added a solution of lithium bis(trimethylsilyl) amide (1 M in THF, 182 mL, 182.1 mmol, 2.0 equiv) and it was stirred at 60° C. for 1 h. The reaction mixture was cooled to room temperature, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 3% methanol in dichloromethane as eluant) to afford Int-1.3. MS (ES): m/z 201.2 [M+H]$^+$.

Synthesis of compound Int-1.4. To a solution of compound Int-1.3 (11.2 g, 55.93 mmol, 1.0 equiv) in dichloromethane (110 mL) and pyridine (6.3 mL, 78.30 mmol, 1.4 equiv) was added slowly acetic anhydride (6.34 mL, 67.11 mmol, 1.2 equiv) at room temperature and stirred for 1 h. The reaction mixture was poured over ice, stirred and extracted with dichloromethane three times. The combined organic layers were washed with brine, dried over anhydrous sodium sulfate, filtered and concentrated under reduced pressure. The residue was purified by flash column chromatography on silica gel (CombiFlash®, 1% methanol in dichloromethane as eluant) to afford Int-1.4. MS (ES): m/z 243.21 [M+H]$^+$.

Synthesis of compound Int-1. A round bottom flask charged with compound Int-1.4 (6.1 g, 25.18 mmol, 1.0 equiv), 10% palladium on carbon (2 g) and methanol (60 mL) was vacuumed and purged with hydrogen three times. The reaction mixture was stirred under 1 atm of hydrogen at rt for 1 h. The flask was vacuumed and purged with nitrogen before it was opened to air. The reaction mixture was filtered through a pad of Celite® and rinsed with methanol. The filtrate was concentrated under reduced pressure and the residue was purified by flash column chromatography on silica gel (CombiFlash®, 5% methanol in dichloromethane as eluant) to afford Int-1. MS (ES): m/z 153.2 [M+H]$^+$.

Preparation of Intermediate Int-2: N-(4-(4-amino-3-(methylamino)phenoxy)pyridin-2-yl)acetamide

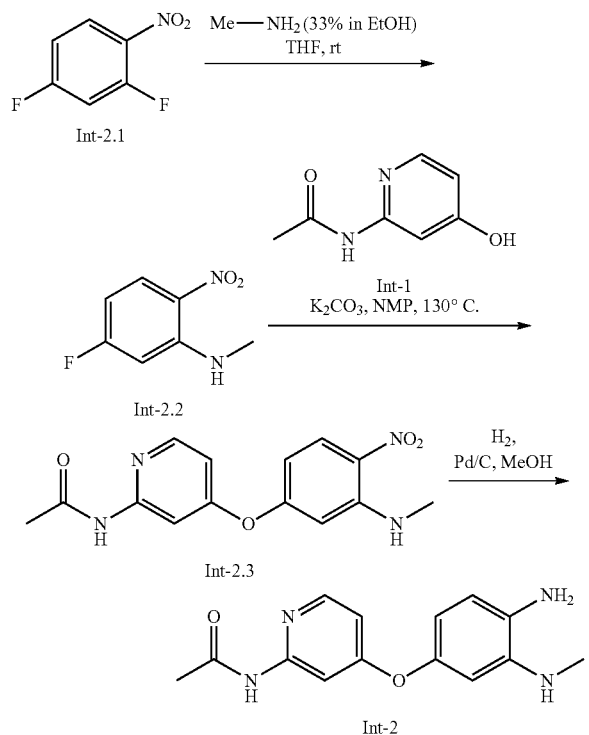

Synthesis of compound Int-2.2. To a solution of 2,4-difluoro-1-nitrobenzene (Int-2.1, 1.0 g, 6.29 mmol, 1.0 equiv) in THF (10 mL) was added a solution of methylamine (33% in ethanol, 1.18 mL, 12.58 mmol, 2.0 equiv) dropwise at 0° C. The reaction mixture was stirred at room temperature for 2 h. It was poured over ice and was extracted with ethyl acetate three times. The combined organic layers were washed with brine, dried over sodium sulfate, filtered and concentrated under reduced pressure to afford Int-2.2. MS (ES): m/z 171.2 [M+H]$^+$.

Synthesis of compound Int-2.3. A mixture of Int-2.2 (0.170 g, 0.99 mmol, 1.0 equiv), Int-1 (0.152 g, 0.99 mmol, 1.0 equiv) and potassium carbonate (0.273 g, 1.98 mmol, 2.0 equiv) in N-methyl-2-pyrrolidone (1.7 mL) was stirred at 130° C. for 12 h under nitrogen. It was cooled to room temperature, poured over ice and extracted with ethyl acetate three times. The combined organic layers were washed with brine, dried over anhydrous sodium sulfate, filtered and concentrated under reduced pressure. The residue was purified by flash column chromatography on silica gel (CombiFlash®, 2.5% methanol in dichloromethane as eluant) to afford Int-2.3. MS (ES): m/z 303.3 [M+H]$^+$.

Synthesis of compound Int-2. A round bottom flask charged with Int-2.3 (0.180 g, 0.59 mmol, 1.0 equiv), 10% palladium on carbon (0.1 g) and methanol (2 mL) was vacuumed and purged with hydrogen. The reaction mixture was stirred under 1 atm hydrogen at rt for 2 h. The flask was vacuumed and purged with nitrogen before it was opened to air. The mixture was filtered through a pad of Celite® and rinsed with methanol. The filtrate was concentrated under reduced pressure and the residue was purified by flash column chromatography on silica gel (CombiFlash®, 5% methanol in dichloromethane as eluant) to afford Int-2. MS (ES): m/z 273.3 [M+H]$^+$.

Preparation of Intermediate Int-3: N-(4-(4-amino-2-methyl-3-(methylamino)phenoxy)pyridin-2-yl)acetamide

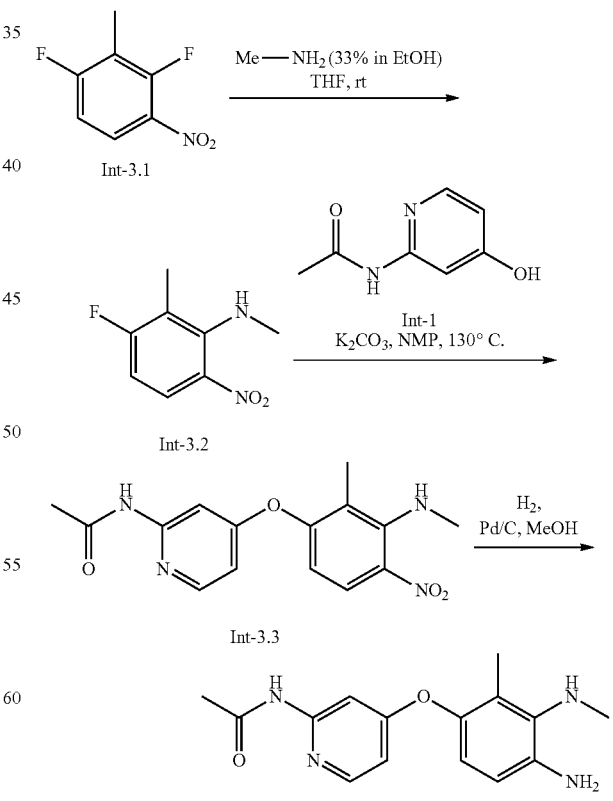

Synthesis of compound Int-3.2. Int-3.2 was prepared from 1,3-difluoro-2-methyl-4-nitrobenzene (Int-3.1) following the procedure described in the synthesis of compound Int-2.2. MS (ES): m/z 185.2 [M+H]+.

Synthesis of compound Int-3.3. Int-3.3 was prepared from Int-3.2 following the procedure described in the synthesis of compound Int-2.3. The product was purified by flash column chromatography on silica gel (CombiFlash®, 2.5% methanol in dichloromethane as eluant). MS (ES): m/z 317.03 [M+H]+.

Synthesis of compound Int-3. Int-3 was prepared from Int-3.3 following the procedure described in the synthesis of compound Int-2. The product was purified by flash column chromatography on silica gel (CombiFlash®, 5% methanol in dichloromethane as eluant). MS (ES): m/z 287.3 [M+H]+.

Preparation of Intermediate Int-4: N-(4-(4-amino-2-cyano-3-(methylamino)phenoxy)pyridin-2-yl)acetamide

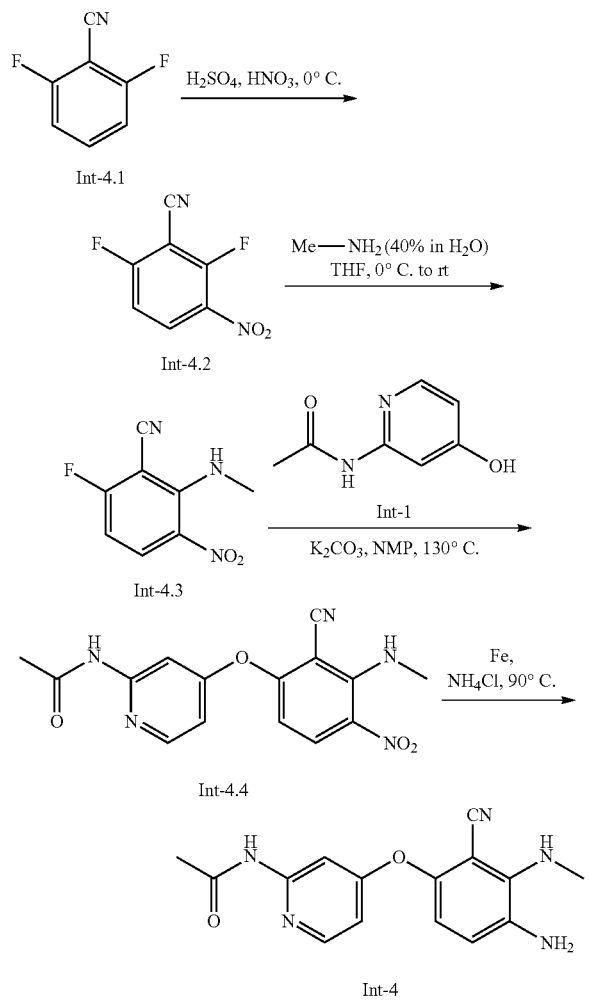

Synthesis of compound Int-4.2: To a solution of 2,6-difluorobenzonitrile (Int-4.1, 5.0 g, 35.94 mmol, 1.0 equiv) in concentrated sulfuric acid (15 mL) was slowly added concentrated nitric acid (6 mL) at −10° C. The reaction mixture was stirred at room temperature for 15 min. It was poured over crushed ice. The precipitates were collected by filtration, rinsed with a small amount of water and air-dried to afford Int-4.2. MS (ES): m/z 185.1 [M+H]+.

Synthesis of compound Int-4.3. To a solution of Int-4.2 (2.6 g, 14.12 mmol, 1.0 equiv) in THF (25 mL) was added methylamine solution (40% in water, 2.19 mL, 28.24 mmol, 2.0 equiv) dropwise at 0° C. The reaction mixture was stirred at room temperature for 2 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 6% ethyl acetate in hexane as eluant) to afford Int-4.3. MS (ES): m/z 196.2 [M+H]+.

Synthesis of compound Int-4.4. Int-4.4 was prepared from Int-4.3 following the procedure described in the synthesis of compound Int-2.3. The residue was purified by flash column chromatography on silica gel (CombiFlash®, 2.5% methanol in dichloromethane as eluant). MS (ES): m/z 328.3 [M+H]+.

Synthesis of compound Int-4. A mixture of compound Int-4.4 (0.860 g, 2.63 mmol, 1.0 equiv), ammonium chloride (1.406 g, 26.3 mmol, 10 equiv), iron powder (1.472, 26.3 mmol, 10 equiv) in ethanol (9 mL) and water (3 mL) was stirred at 80° C. for 3 h under nitrogen. It was filtered through a pad of Celite®. The filtrate was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 3.5% methanol in dichloromethane as eluant) to afford Int-4. MS (ES): m/z 298.3 [M+H]+.

Preparation of Intermediate Int-5: N-(4-((5-amino-6-(methylamino)pyridin-2-yl)oxy)pyridin-2-yl)acetamide

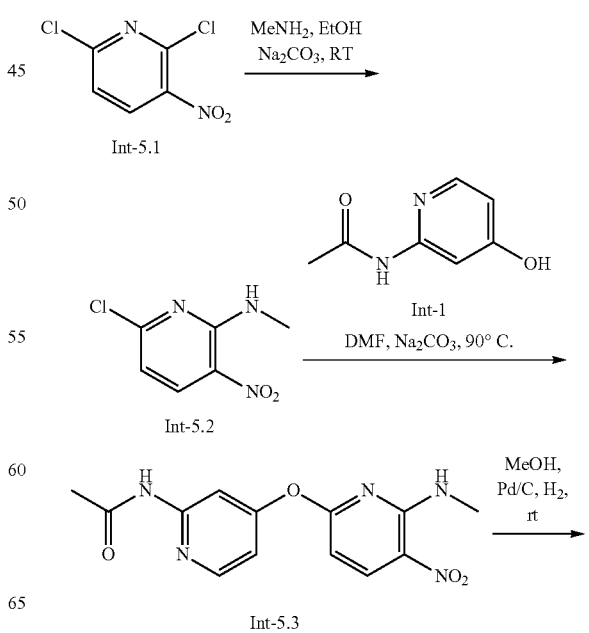

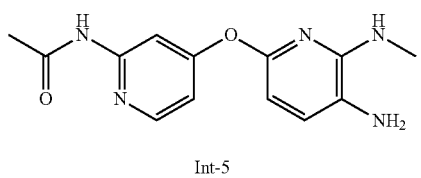

Int-5

Synthesis of compound Int-5.2. To a solution of 2,6-dichloro-3-nitropyridine (Int-5.1, 5.0 g, 25.91 mmol, 1.0 equiv) in ethanol (30 mL) was added methylamine solution (33% in ethanol, 4.9 mL, 51.82 mmol, 2.0 equiv) dropwise at 0° C. followed by sodium carbonate (4.10 g, 38.7 mmol, 1.5 equiv). The reaction mixture was stirred at room temperature for 16 h. It was poured over ice-water and extracted with ethyl acetate. The combined organic layers were washed with brine, dried over anhydrous sodium sulfate, filtered and concentrated under reduced pressure to obtain Int-5.2. MS (ES): m/z 188.5 [M+H]$^+$.

Synthesis of compound Int-5.3. A mixture of Int-5.2 (0.500 g, 2.67 mmol, 1.0 equiv), Int-1 (0.405 g, 2.67 mmol, 1.0 equiv) and sodium carbonate (0.311 g, 2.93 mmol, 1.1 equiv) in DMF (5 mL) was stirred at 90° C. for 12 h under nitrogen. It was cooled to room temperature, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 25% ethyl acetate in hexane as eluant) to afford 1.3. MS (ES): m/z 304.3 [M+H]$^+$.

Synthesis of compound Int-5. Int-5 was prepared from Int-5.3 following the procedure described in the synthesis of compound Int-2. The product was purified by flash column chromatography on silica gel (CombiFlash®, 5% methanol in dichloromethane as eluant). MS (ES): m/z 274.3 [M+H]$^+$.

Preparation of Compounds

Example 1: N-(4-((2-((5-(tert-butyl)isoxazol-3-yl)amino)-1-methyl-1H-benzo[d]imidazol-6-yl)oxy)pyridin-2-yl)acetamide

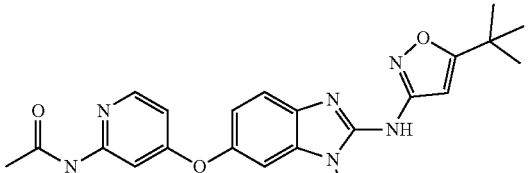

I-1

Synthesis of compound 1.2. To a solution of 1.1 (0.8 g, 5.71 mmol, 1.0 equiv) and triethylamine (2.38 mL, 17.13 mmol, 3.0 equiv) in THF (8 mL) was added thiophosgene (0.52 mL, 6.85 mmol, 1.2 equiv) dropwise at 0° C. The reaction mixture was stirred at 0° C. for 30 min. It was poured into ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 10% ethyl acetate in hexane as eluant) to afford 1.2. MS (ES): m/z 183.2 [M+H]$^+$.

Synthesis of compound I-1. To a solution of Int-2 (0.100 g, 0.37 mmol, 1.0 equiv) and 1.2 (0.087 g, 0.47 mmol, 1.3 equiv) in THF (2 mL) was added N-ethyl-N'-(3-dimethylaminopropyl)carbodiimide hydrochloride (0.141 g, 0.74 mmol, 2.0 equiv). The reaction mixture was stirred at 50° C. for 4 h. It was cooled to room temperature, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 4% methanol in dichloromethane as eluant) to afford I-1. MS (ES): m/z: 421.6 [M+H]$^+$; $^1$H NMR (DMSO-d6, 400 M Hz): δ 10.14 (bs, 2H), 8.15-8.14 (d, J=5.6 Hz, 1H), 7.65 (s, 1H), 7.42-7.40 (d, J=8.4 Hz, 1H), 7.13 (s, 1H), 6.86-6.84 (d, J=8.0 Hz, 1H), 6.63-6.62 (d, J=3.6 Hz, 1H), 3.56 (s, 3H), 2.06 (s, 3H), 1.34 (s, 9H).

Example 2: N-(4-((2-((5-(tert-butyl)isoxazol-3-yl)amino)-1,7-dimethyl-1H-benzo[d]imidazol-6-yl)oxy)pyridin-2-yl)acetamide

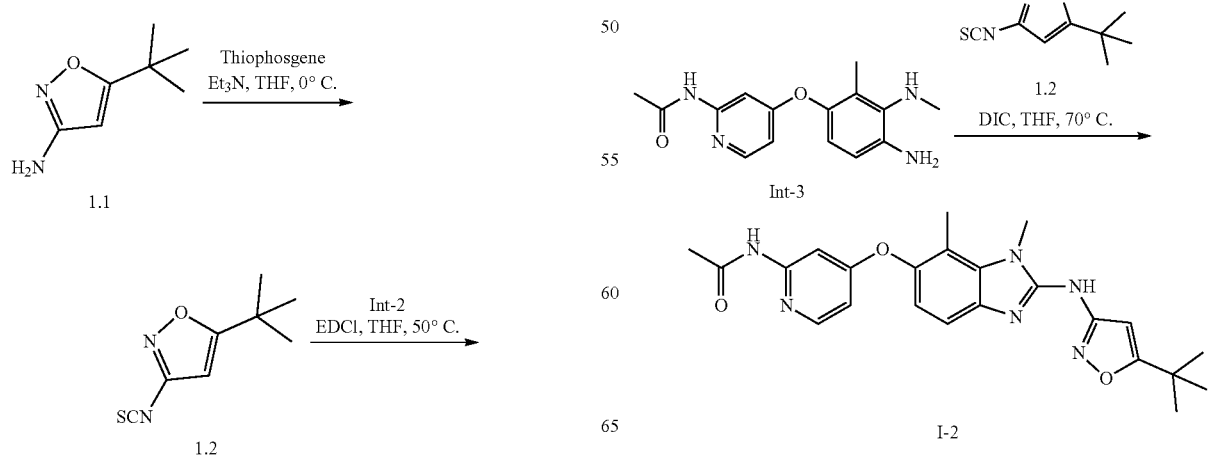

Synthesis of I-2. To a solution of Int-3 (0.150 g, 0.52 mmol, 1.0 equiv) and 1.2 (0.124 g, 0.68 mmol, 1.3 equiv) in THF (3 mL) was added N,N'-diisopropylcarbodiimide (0.087 mL, 1.04 mmol, 2.0 equiv). The reaction mixture was stirred at 70° C. for 5 h. It was cooled to room temperature, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 8% methanol in dichloromethane as eluant) to afford I-2. MS (ES): m/z: 435.1[M+H]$^+$; $^1$H NMR (DMSO-d6, 400 MHz): δ 10.50 (s, 1H), 10.10 (s, 1H), 8.14-8.13 (d, J=5.2 Hz, 1H), 7.58 (s, 1H), 7.31-7.29 (d, J=8.4 Hz, 1H), 6.84-6.80 (t, 1H), 6.73 (bs, 1H), 6.55 (bs, 1H), 3.77 (s, 3H), 2.39 (s, 3H), 2.02 (s, 3H), 1.30 (s, 9H).

Example 3: N-(4-((2-((5-(tert-butyl)isoxazol-3-yl)amino)-7-cyano-1-methyl-1H-benzo[d]imidazol-6-yl)oxy)pyridin-2-yl)acetamide

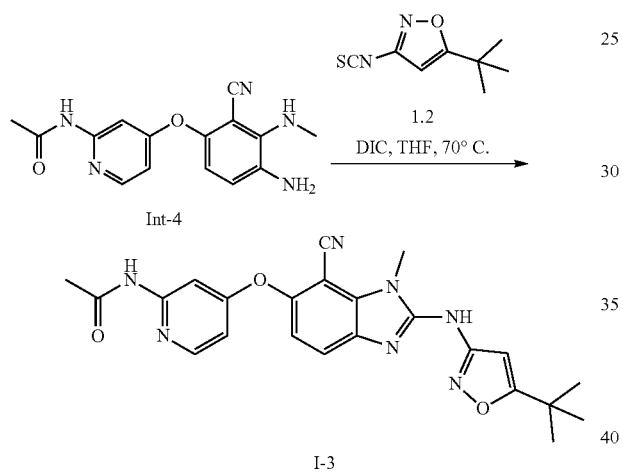

Synthesis of compound I-3. Compound I-3 was prepared from Int-4 and 1.2 following the procedure described in the synthesis of compound I-2. The product was purified by flash column chromatography on silica gel (CombiFlash®, 5% methanol in dichloromethane as eluant). MS (ES): m/z: 446.45 [M+H]$^+$; $^1$H NMR (DMSO-d6, 400 MHz): δ 10.24 (s, 1H), 8.22-8.21 (d, J=5.6 Hz, 1H), 7.70 (bs, 2H), 7.01 (s, 1H), 6.69 (bs, 2H), 3.95 (bs, 3H), 3.78 (bs, 1H), 2.07-2.06 (d, 3H), 1.27 (s, 9H).

Example 4: N-(4-((2-((4-chloro-3-(trifluoromethyl)phenyl)amino)-1-methyl-1H-benzo[d]imidazol-6-yl)oxy)pyridin-2-yl)acetamide

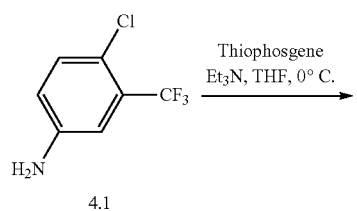

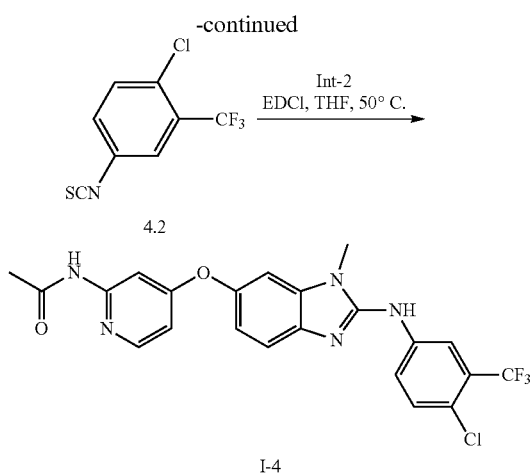

Synthesis of compound 4.2. Compound 4.2 was prepared from 4-chloro-3-(trifluoromethyl)aniline (4.1) following the procedure described in the synthesis of compound 1.2. The product was purified by flash column chromatography on silica gel (CombiFlash®, 8% ethyl acetate in hexane as eluant). MS (ES): m/z 238.5 [M+H]$^+$.

Synthesis of I-4. Compound I-4 was prepared from 4.2 and Int-2 following the procedure described in the synthesis of compound I-1. The product was purified by flash column chromatography on silica gel (CombiFlash®, 5% methanol in dichloromethane as eluant). MS (ES): m/z: 476.6 [M+H]$^+$, $^1$H NMR (DMSO-d6, 400 MHz): δ 10.48 (s, 1H), 9.49 (s, 1H), 8.41 (s, 1H), 8.33-8.31 (d, J=8.8 Hz, 1H), 8.16-8.14 (d, J=5.6 Hz, 1H), 7.70-7.65 (m, 2H), 7.49-7.47 (d, J=8.8 Hz, 1H), 7.29 (s, 1H), 6.90-6.88 (d, J=8.4 Hz, 1H), 6.63-6.61 (t, J=3.6 Hz, 1H), 3.77 (s, 3H), 2.03 (s, 3H).

Example 5: N-(4-((2-((4-chloro-3-(trifluoromethyl)phenyl)amino)-1,7-dimethyl-1H-benzo[d]imidazol-6-yl)oxy)pyridin-2-yl)acetamide

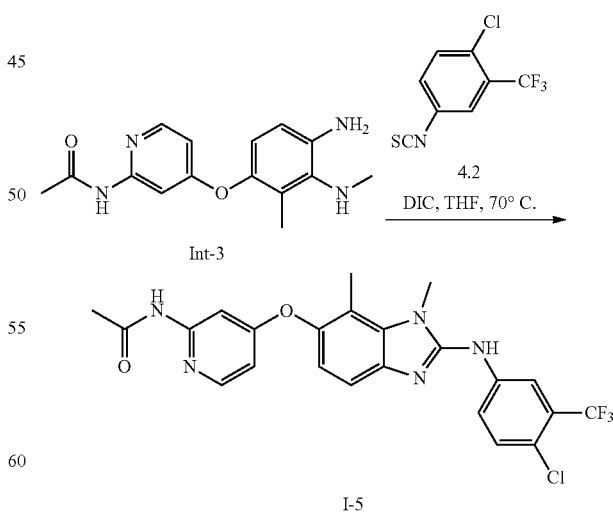

Synthesis of compound I-5. Compound I-5 was prepared from Int-3 and 4.2 following the procedure described in the synthesis of compound I-2. The product was purified by flash column chromatography on silica gel (CombiFlash®, 4% methanol in dichloromethane as eluant). MS (ES): m/z: 490.71 [M+H]+, 1H NMR (DMSO-d6, 400 MHz): δ 10.48 (s, 1H), 9.43 (s, 1H), 8.35 (s, 1H), 8.26-8.24 (d, J=8.4 Hz, 1H), 8.14-8.13 (d, J=5.6 Hz, 1H), 7.68-7.66 (d, J=8.8 Hz, 1H), 7.59 (s, 1H), 7.34-7.32 (d, J=8.4 Hz, 1H), 6.85-6.83 (d, J=7.6 Hz, 1H), 6.55-6.54 (d, J=4 Hz, 1H), 3.97 (s, 3H), 2.50 (s, 3H), 2.02 (s, 3H).

Example 6: N-(4-((2-((2,4-difluorophenyl)amino)-1,7-dimethyl-1H-benzo[d]imidazol-6-yl)oxy)pyridin-2-yl)acetamide

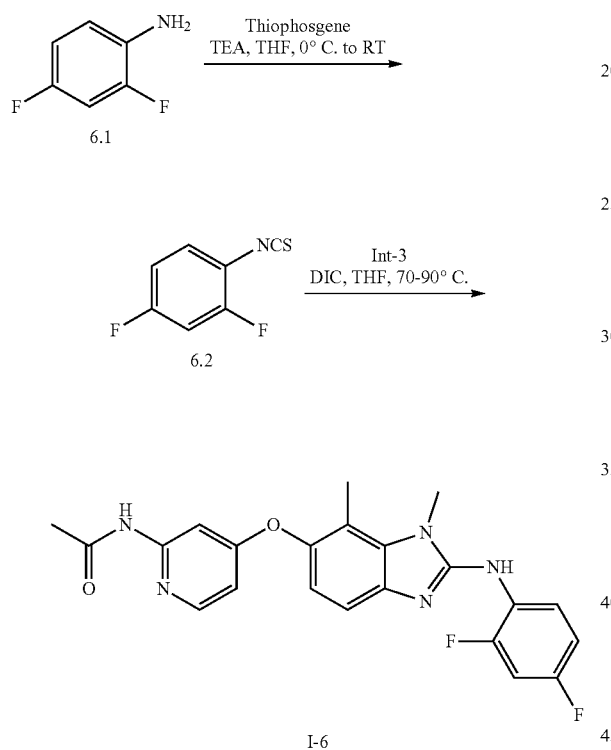

Example 7: N-(4-((2-((3-(3-methoxyazetidin-1-yl)-5-(trifluoromethyl)phenyl)amino)-1-methyl-1H-benzo[d]imidazol-6-yl)oxy)pyridin-2-yl)acetamide

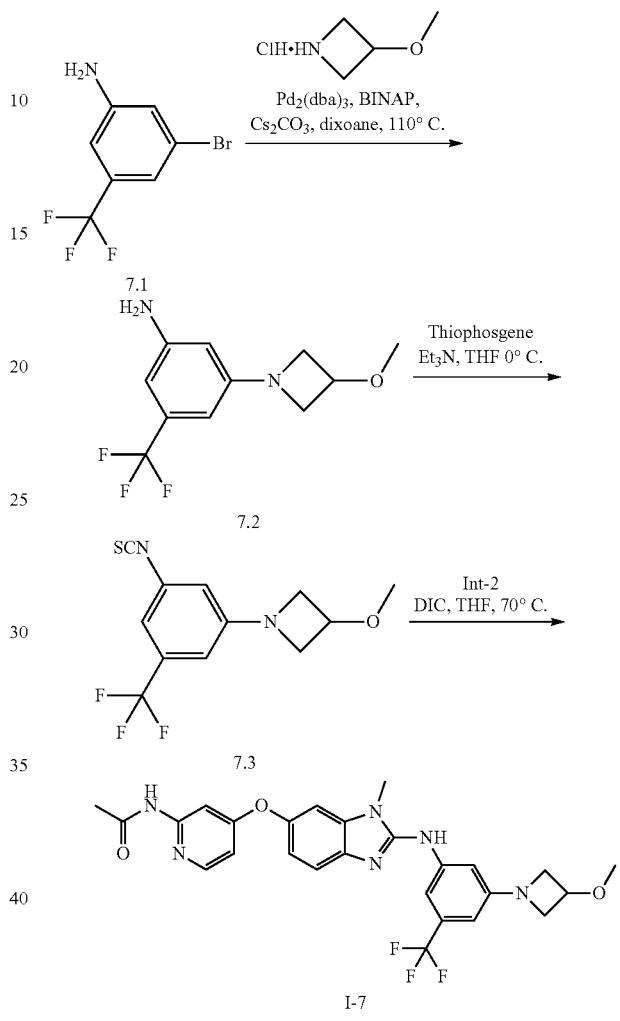

Synthesis of compound 6.2. Compound 6.2 was prepared from 2,4-difluoroaniline (6.1) following the procedure described in the synthesis of compound 1.2. The product was purified by flash column chromatography on silica gel (CombiFlash®, 10% ethyl acetate in hexane as eluant). MS (ES): m/z 172.2 [M+H]+.

Synthesis of compound I-6. Compound I-6 was prepared from Int-3 and 6.2 following the procedure described in the synthesis of compound I-2. The product was purified by flash column chromatography on silica gel (CombiFlash®, 2% methanol in dichloromethane as eluant). MS (ES): m/z: 424.0 [M+H]+; 1H NMR (DMSO-d6, 400 MHz): δ 10.53 (s, 1H), 8.68 (s, 1H), 8.18-8.16 (d, J=5.2 Hz, 1H), 7.86 (s, 1H), 7.63 (s, 1H), 7.37 (bs, 1H), 7.23 (s, 1H), 7.14 (s, 1H), 6.84-6.82 (d, J=7.6 Hz, 1H), 6.57 (bs, 1H), 3.94 (s, 3H), 2.46 (s, 3H), 2.07 (s, 3H).

Synthesis of compound 7.2. A mixture of 3-bromo-5-(trifluoromethyl)aniline (7.1, 0.7 g, 2.92 mmol, 1.0 equiv), 3-methoxyazetidine hydrochloride (0.72 g, 5.83 mmol, 2.0 equiv), cesium carbonate (2.37 g, 7.3 mmol, 2.5 equiv) in 1,4-dioxane (20 mL) was degassed by bubbling through argon for 10 min. BINAP (2,2'-bis(diphenylphosphino)-1,1'-binaphthyl) (0.363 g, 0.584 mmol, 0.2 equiv) and Pd2(dba)3 (0.267 g, 0.292 mmol, 0.1 equiv) was added, and degassed for 5 min. The reaction mixture was stirred at 110° C. under argon for 5 h. It was cooled to room temperature, filtered through a pad of Celite®. The filtrate was poured over water, extracted with ethyl acetate. The combined organic layers were washed with brine, dried over anhydrous sodium sulfate, filtered and concentrated under reduced pressure. The residue was purified by flash column chromatography on silica gel (CombiFlash®, 10-15% ethyl acetate in hexane as eluant) to afford 7.2. MS (ES): m/z 247.2 [M+H]+.

Synthesis of compound 7.3. Compound 7.3 was prepared from 7.2 following the procedure described in the synthesis of compound 1.2. MS (ES): m/z 289.3 [M+H]+.

Synthesis of I-7. Compound I-7 was prepared from 7.3 and Int-2 following the procedure described in the synthesis of compound I-2. The product was purified by trituration with methanol and dried under vacuum. MS (ES): m/z: 527.49 [M−H]+, 1H NMR (DMSO-d6, 400 MHz): δ 10.49 (s, 1H), 9.16 (s, 1H), 8.15-8.14 (d, J=5.6 Hz, 1H), 7.68 (s, 1H), 7.65 (s, 1H), 7.46-7.44 (d, J=8.4 Hz, 1H), 7.26-7.22 (m, 2H), 6.87-6.85 (d, J=8.0 Hz, 1H), 6.62-6.61 (t, 1H), 6.30 (s, 1H), 4.36 (bs, 1H), 4.15-4.11 (t, 2H), 3.69 (s, 5H), 3.27 (s, 3H), 1.99 (s, 3H).

Example 8: N-(4-((2-((4-(2-cyanopropan-2-yl)phenyl)amino)-1-methyl-1H-benzo[d]imidazol-6-yl)oxy)pyridin-2-yl)acetamide

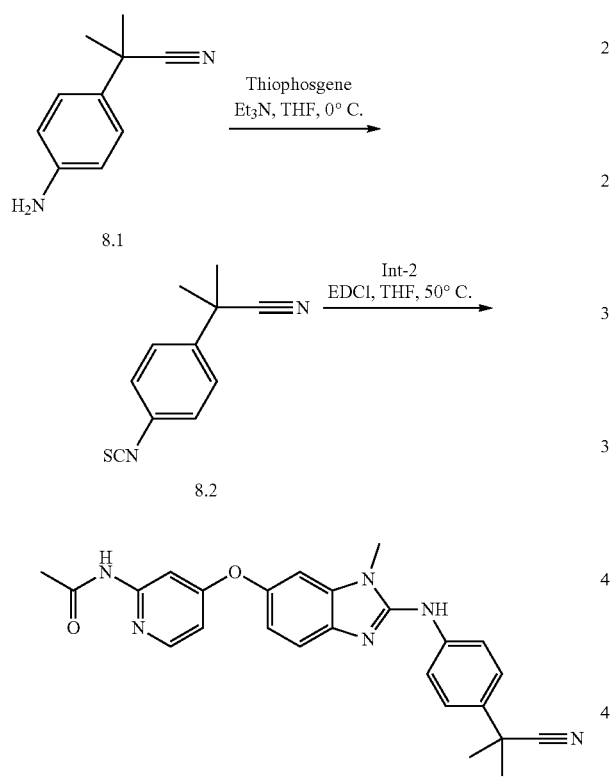

Synthesis of compound 8.2. Compound 8.2 was prepared from 2-(4-aminophenyl)-2-methylpropanenitrile (8.1) following the procedure described in the synthesis of compound 1.2. The product was purified by flash column chromatography on silica gel (CombiFlash®, 8% ethyl acetate in hexane as eluant). MS (ES): m/z 203.2 [M+H]+.

Synthesis of I-8. Compound I-8 was prepared from 8.2 and Int-2 following the procedure described in the synthesis of compound I-1. The product was purified by flash column chromatography on silica gel (CombiFlash®, 10% methanol in dichloromethane as eluant). MS (ES): m/z: 441.29[M+H]+, 1H NMR (DMSO-d6, 400 MHz): δ 10.49 (s, 1H), 9.12 (s, 1H), 8.15-8.14 (d, J=5.2 Hz, 1H), 7.67 (s, 1H), 7.91-7.89 (d, J=8 Hz, 1H), 7.65 (s, 1H), 7.49-7.47 (m, 2H), 7.43-7.41 (d, J=8 Hz, 1H), 7.24 (s, 1H), 6.87-6.85 (d, J=8 Hz, 1H), 6.62 (bs, 1H), 3.70 (s, 3H), 2.03 (s, 3H), 1.69 (s, 6H).

Example 9: N-(4-((1-methyl-2-((4-(1-methyl-1H-imidazol-5-yl)methyl)-3-(trifluoromethyl)phenyl)amino)-1H-benzo[d]imidazol-6-yl)oxy)pyridin-2-yl)acetamide

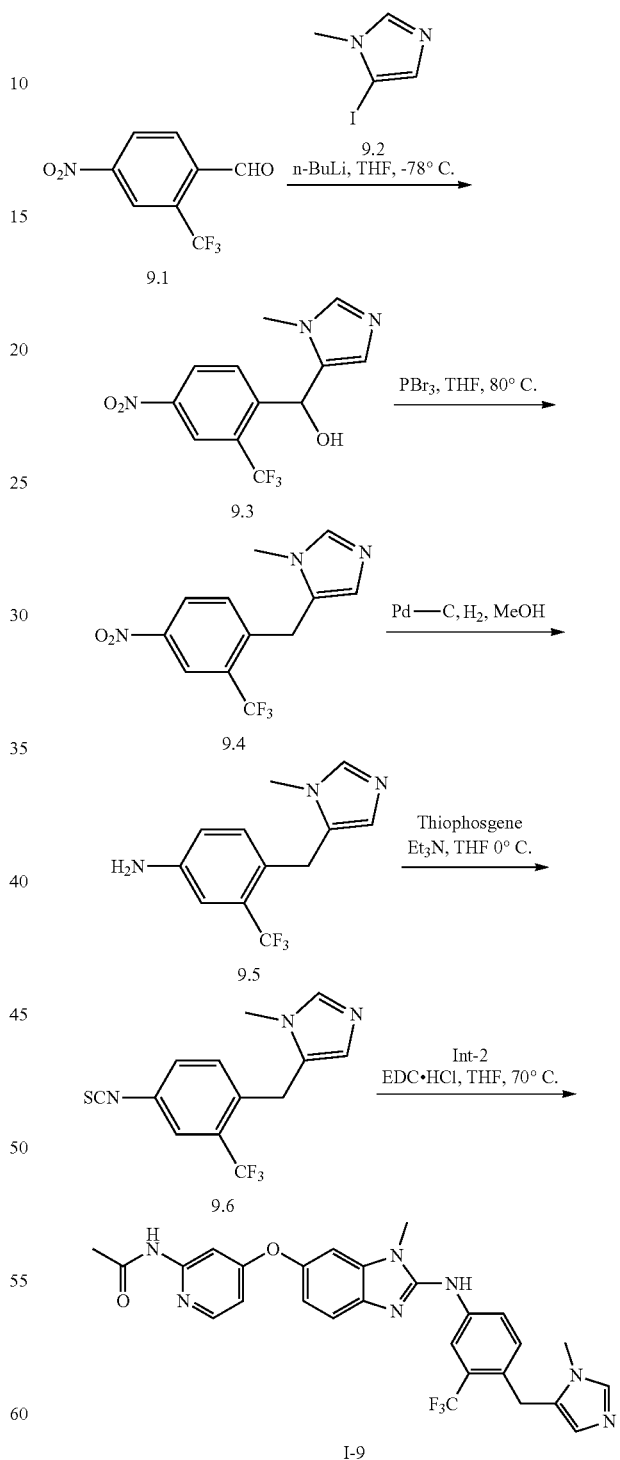

Synthesis of compound 9.3. To a solution of 5-iodo-1-methyl-1H-imidazole (9.2, 1.9 g, 9.13 mmol, 1.0 equiv) in THF (20 mL) was added n-butyl lithium dropwise (2.5 M in hexane, 7.3 mL, 18.26 mmol, 2.0 equiv) at −78° C. over 5 min. To the reaction mixture was added a solution of 4-nitro-2-(trifluoromethyl)benzaldehyde (9.1, 2.00 g, 9.13 mmol, 1.0 equiv) in THF (5 mL) and stirred at −78° C. for 10 min. It was poured over saturated ammonium chloride solution, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 4% methanol in dichloromethane as eluant) to afford 9.3. MS (ES): m/z 302.2 [M+H]$^+$.

Synthesis of compound 9.4. To a solution of compound 9.3 (0.460 g, 1.53 mmol, 1.0 equiv) in THF (10 mL) was added phosphorus tribromide (0.44 mL, 4.59 mmol, 3.0 equiv) and the reaction mixture was stirred at 80° C. for 2 h. It poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 1% methanol in dichloromethane as eluant) to afford 9.4. MS (ES): m/z 286.2 [M+H]$^+$.

Synthesis of compound 9.5. A mixture of compound 9.4 (0.210 g, 0.736 mmol, 1.0 equiv) and 10% palladium on carbon (0.1 g) in in methanol (10 mL) was stirred at rt under 1 atm of hydrogen for 2 h. It was filtered through a pad of Celite® and rinsed with methanol. The filtrate was concentrated under reduced pressure and the residue was purified by flash column chromatography on silica gel (CombiFlash®, 3% methanol in dichloromethane as eluant) to afford 9.5. MS (ES): m/z 256.3 [M+H]$^+$.

Synthesis of compound 9.6. Compound 9.6 was prepared from 9.4 following the procedure described in the synthesis of compound 1.2. MS (ES): m/z 298.3 [M+H]$^+$.

Synthesis of I-9. Compound I-9 was prepared from 9.6 and Int-2 following the procedure described in the synthesis of compound I-1. The product was purified by flash column chromatography on silica gel (CombiFlash®, 3.5% methanol in dichloromethane as eluant). MS (ES): m/z: 534.15 [M−H]$^+$, $^1$H NMR (DMSO-d6, 400 MHz): δ 10.48 (s, 1H), 9.32 (s, 1H), 8.32 (s, 1H), 8.15-8.08 (m, 2H), 7.65 (s, 1H), 7.46-7.42 (d, J=8.4 Hz, 1H), 7.26 (s, 1H), 7.12 (s, 1H), 7.01-6.99 (m, 1H), 6.87-6.82 (m, 2H), 6.62-6.61 (m, 1H), 4.14 (s, 2H), 3.70 (s, 3H), 3.51 (s, 3H), 1.99 (s, 3H).

Example 10: N-(4-((2-((4-((1H-pyrazol-4-yl)methyl)-3-(trifluoromethyl)phenyl)amino)-1-methyl-1H-benzo[d]imidazol-6-yl)oxy)pyridin-2-yl)acetamide

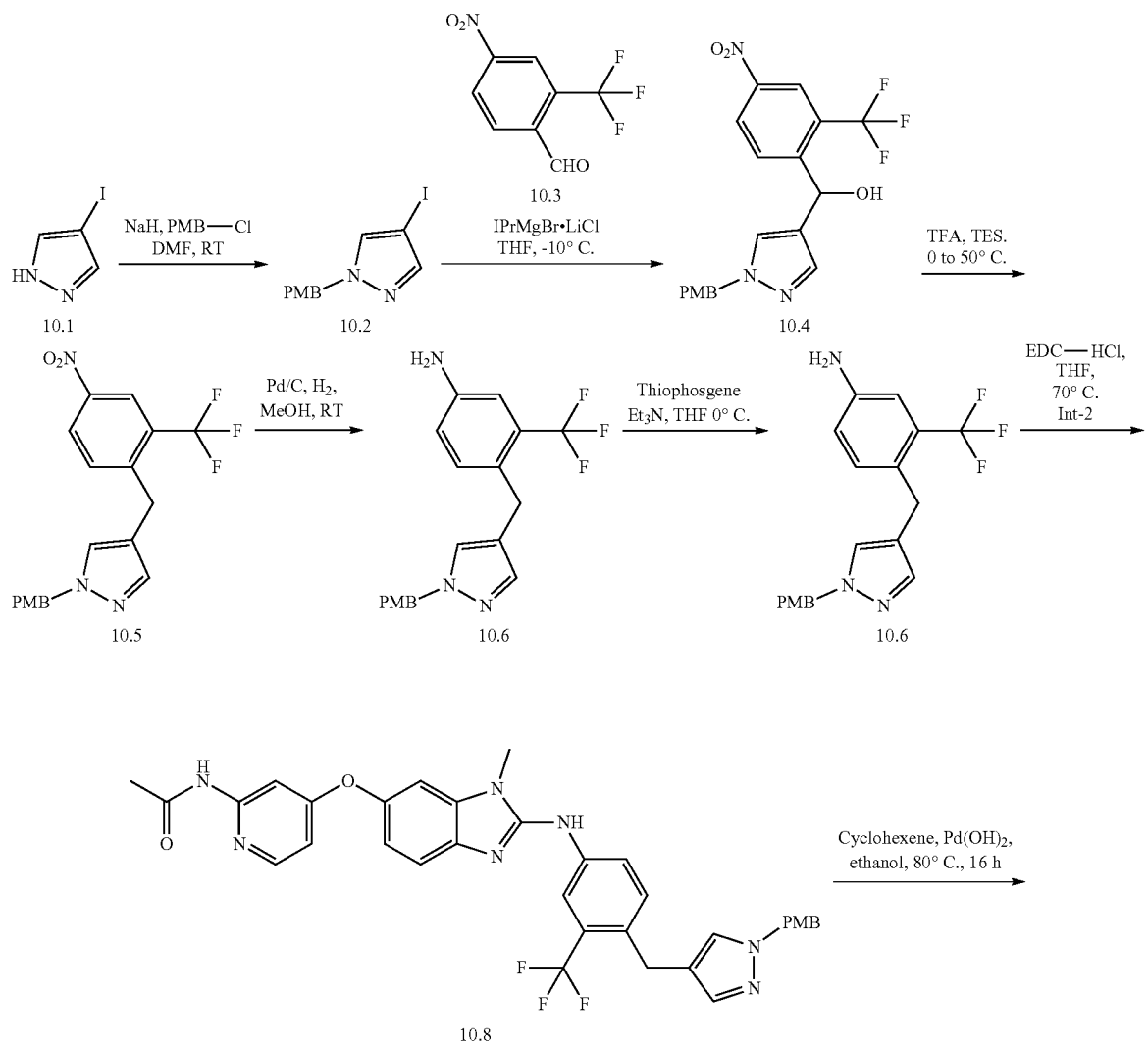

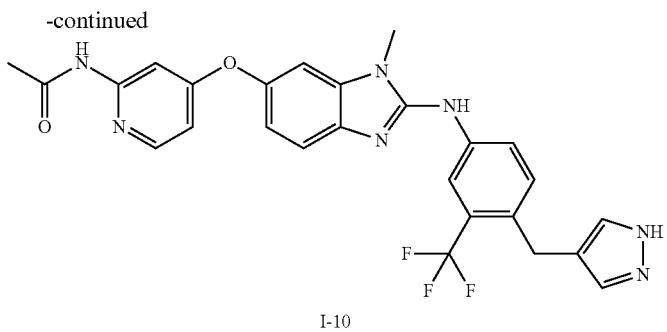

I-10

Synthesis of compound 10.2. To a solution of 4-iodo-1H-pyrazole (10.1, 5.0 g, 25.78 mmol, 1.0 equiv) in DMF (50 mL) was added sodium hydride (1.48 g, 30.93 mmol, 1.2 equiv) in small portions at 0° C. After the addition, the mixture was stirred for 15 min followed by the addition of 4-methoxybenzyl chloride (4.85 g, 30.93 mmol, 1.2 equiv) and stirred at room temperature for 2 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 6% ethyl acetate in hexane as eluant) to afford 10.2. MS (ES): m/z 315.13 [M+H]$^+$.

Synthesis of compound 10.4. To a solution of 10.2 (2.06 g, 6.37 mmol, 1.0 equiv) in THF (20 mL) was added a solution of isopropyl magnesium chloride lithium chloride complex (1.3 M in THF, 12.25 mL, 15.92 mmol, 2.5 equiv) at −10° C. The reaction mixture was stirred for 30 min at −10° C. and was added a solution of 4-nitro-2-(trifluoromethyl)benzaldehyde (10.3, 1.12 g, 5.09 mmol, 0.8 equiv) in THF (10 mL) and stirred for 5 min. It was poured over ice, stirred and acidified with 1 N hydrochloric acid and extracted with ethyl acetate. The combined organic layers were washed with brine, dried over anhydrous sodium sulfate, filtered and concentrated under reduced pressure. The residue was purified by flash column chromatography on silica gel (CombiFlash®, 25% ethyl acetate in hexane as eluant) to afford 10.4. MS (ES): m/z 408.4 [M+H]$^+$.

Synthesis of compound 10.5. To a solution of 10.4 (0.700 g, 1.72 mmol, 1.0 equiv) in dichloromethane (10 mL) and added trifluoroacetic acid (7 mL) was added triethylsilane (3.5 mL) at 0° C. It was allowed to warm to 50° C. and stirred for 1 h. It was carefully poured over cold saturated sodium bicarbonate solution, stirred and extracted with dichloromethane. The combined organic layers were washed with brine, dried over anhydrous sodium sulfate, filtered and concentrated under reduced pressure. The residue was purified by flash column chromatography on silica gel (CombiFlash®, 15% ethyl acetate in hexane as eluant) to afford 10.5. MS (ES): m/z 392.4 [M+H]$^+$.

Synthesis of compound 10.6. Compound 10.6 was prepared from 10.5 following the procedure described in the synthesis of compound 9.5. MS (ES): m/z 362.4 [M+H]$^+$.

Synthesis of compound 10.7. Compound 10.7 was prepared from 10.6 following the procedure described in the synthesis of compound 1.2. MS (ES): m/z 404.4 [M+H]$^+$.

Synthesis of compound 10.8. Compound 10.8 was prepared from 10.7 and Int-2 following the procedure described in the synthesis of compound I-1. The product was purified by flash column chromatography on silica gel (CombiFlash®, 2.6% methanol in dichloromethane as eluant). MS (ES): m/z 626.6 [M+H]$^+$.

Synthesis of I-10. A mixture of 10.8 (0.162 g, 0.258 mmol, 1.0 equiv) and palladium hydroxide (0.200 g) in ethanol (8 mL) and cyclohexene (4 mL) was stirred at 80° C. for 16 h. The reaction mixture was filtered through a pad of Celite® and rinsed with ethanol. The filtrate was concentrated under reduced pressure and the residue was purified by flash column chromatography on silica gel (CombiFlash®, 3.5% methanol in dichloromethane as eluant) to afford I-10. MS (ES): m/z: 522.7 [M+H]$^+$, $^1$H NMR (DMSO-d6, 400 MHz): δ 10.49 (s, 1H), 9.28 (s, 1H), 8.24 (s, 1H), 8.15-8.14 (d, J=5.6 Hz, 1H), 7.65 (s, 1H), 7.45-7.39 (m, 4H), 7.26 (s, 1H), 7.06 (bs, 2H), 6.87-6.81 (m, 1H), 6.62-6.61 (d, J=3.6 Hz, 1H), 3.90 (bs, 2H), 3.70 (s, 3H), 2.02 (s, 3H).

Example 11: N-(4-((2-((3-methoxy-4-(methoxymethyl)-5-(trifluoromethyl)phenyl)amino)-1-methyl-1H-benzo[d]imidazol-6-yl)oxy)pyridin-2-yl)acetamide

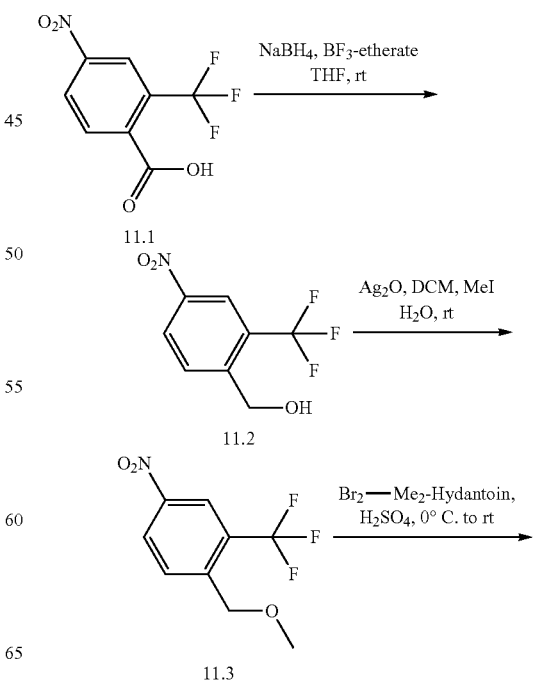

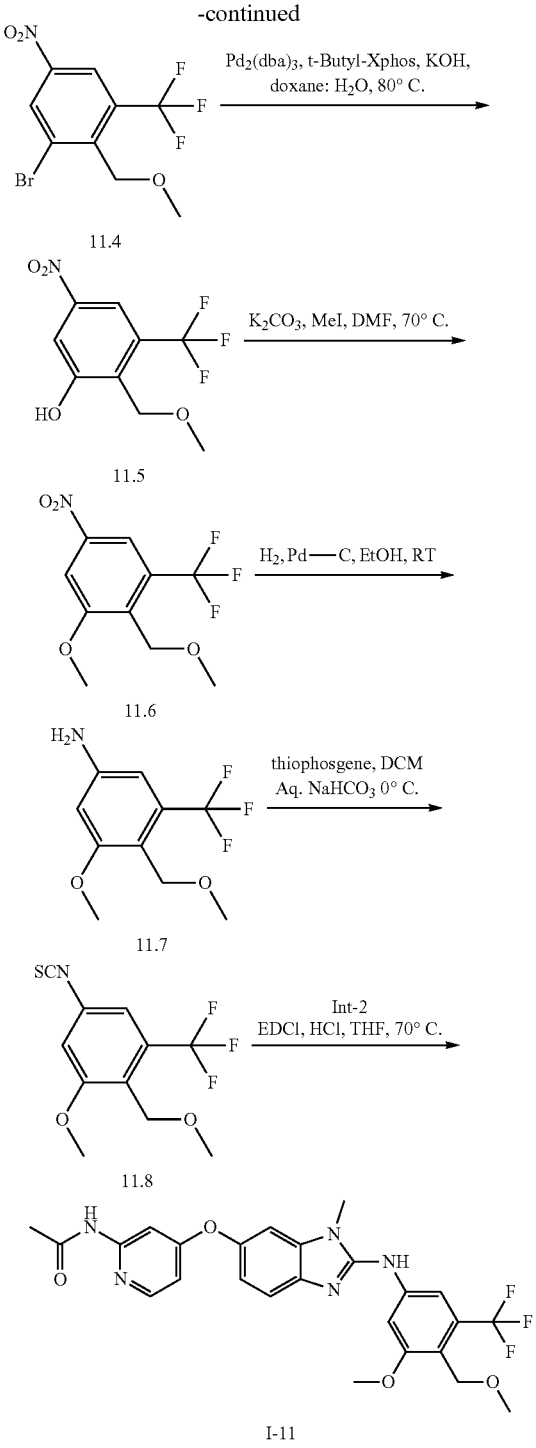

Synthesis of compound 11.2. To a solution of 4-nitro-2-(trifluoromethyl)benzoic acid (11.1, 10 g, 42.53 mmol, 1.0 equiv) in THF (200 mL) was added sodium borohydride (4.84 g, 127.59 mmol, 3.0 equiv) in portions at 0° C. followed by the addition of boron trifluoride etherate (15.7 mL, 127.59 mmol, 3.0 equiv) slowly over a period of 30 min. The reaction mixture was stirred at room temperature for 16 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 9% ethyl acetate in hexane as eluant) to afford 11.2. MS (ES): m/z 222.1 [M+H]$^+$.

Synthesis of compound 11.3. To a solution of 11.2 (9.0 g, 40.7 mmol, 1.0 equiv) in dichloromethane (90 mL) was added silver oxide (47 g, 203.5 mmol, 5.0 equiv), water (9 mL) followed by methyl iodide (25 mL, 407 mmol, 10 equiv). The reaction mixture was stirred at room temperature for 16 h in dark. It was filtered through a pad of Celite® and the filtrate was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 4% ethyl acetate in hexane as eluant) to afford 11.3. MS (ES): m/z 236.2 [M+H]$^+$.

Synthesis of compound 11.4. To a solution of 11.3 (4.6 g, 19.56 mmol, 1.0 equiv) in sulfuric acid (46 mL) was added 1,3-dibromo-5,5-dimethylhydantoin (5.59 g, 19.56 mmol, 1.0 equiv). The reaction mixture was stirred at room temperature for 16 h. It was poured over ice-water and stirred. The precipitates were collected by filtration, rinsed with water and dried under vacuum. MS (ES): m/z 315.1 [M+H]$^+$.

Synthesis of compound 11.5. To a solution of 11.4 (1.5 g, 4.78 mmol, 1.0 equiv) in 1,4-dioxane (12 mL) and water (12 mL) was added potassium hydroxide (0.602 g, 10.75 mmol, 2.25 equiv). The reaction mixture was degassed by bubbling argon for 10 min. 2-Di-tert-butylphosphino-2',4',6'-triiso-propylbiphenyl (0.052 g, 0.123 mmol, 0.18 equiv) and tris(dibenzylideneacetone)dipalladium (O) (0.131 g, 0.143 mmol, 0.03 equiv) were added, again degassed for 5 min. The reaction mixture was stirred at 80° C. under argon for 1 h. It was cooled to room temperature, filtered through a pad of Celite®. The filtrate was poured over water, extracted with ethyl acetate. The combined organic layers were washed with brine, dried over anhydrous sodium sulfate, filtered and concentrated under reduced pressure. The residue was purified by flash column chromatography on silica gel (CombiFlash®, 9% ethyl acetate in hexane as eluant) to afford 11.5. MS (ES): m/z 252.2 [M+H]$^+$.

Synthesis of compound 11.6. To a mixture of 11.5 (0.45 g, 1.79 mmol, 1.0 equiv) and potassium carbonate (0.494 g, 3.58 mmol, 2.0 equiv) in DMF (4 mL) was added methyl iodide (0.381 g, 2.68 mmol, 1.5 equiv). The reaction mixture was stirred at 70° C. under argon for 1 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 5% ethyl acetate in hexane as eluant) to afford 11.6. MS (ES): m/z 266.2 [M+H]$^+$.

Synthesis of compound 11.7. Compound 11.7 was prepared from 11.6 following the procedure described in the synthesis of compound 9.5. MS (ES): m/z 236.3 [M+H]$^+$.

Synthesis of compound 11.8. To a solution of 11.7 (0.120 g, 0.510 mmol, 1.0 equiv) in dichloromethane (3 mL) was added solution of sodium bicarbonate (0.214 g, 2.55 mmol, 5.0 equiv) in water (1 mL) followed by thiophosgene (0.146 g, 1.27 mmol, 2.5 equiv) at 0° C. The reaction mixture was stirred at room temperature for 1 h. It was poured over ice-water and extracted with dichloromethane. The combined organic layers were washed with brine, dried over anhydrous sodium sulfate, filtered and concentrated under reduced pressure to obtain 11.8. MS (ES): m/z 278.3 [M+H]$^+$.

Synthesis of I-11. Compound I-11 was prepared from 11.8 and Int-2 following the procedure described in the synthesis of compound I-1. The product was purified by flash column chromatography on silica gel (CombiFlash®, 2.7% methanol in dichloromethane as eluant). MS (ES): m/z: 516.5 [M+H]+, 1H NMR (DMSO-d6, 400 MHz): δ 10.49 (s, 1H), 9.41 (s, 1H), 8.16-8.15 (d, J=5.6 Hz, 1H), 8.01 (s, 1H), 7.65 (s, 1H), 7.48-7.46 (d, J=8.4 Hz, 1H), 7.29 (s, 1H), 7.07 (s, 1H), 6.89-6.81 (m, 1H), 6.63-6.62 (d, J=3.6 Hz, 1H), 4.43 (s, 2H), 3.90 (s, 3H), 3.72 (s, 3H), 3.28 (s, 3H), 2.02 (s, 3H).

Example 12: (R)—N-(4-((1-methyl-2-((3-(1-methyl-5-oxopyrrolidin-3-yl)-5-(trifluoromethyl)phenyl)amino)-1H-benzo[d]imidazol-6-yl)oxy)pyridin-2-yl)acetamide and (S)—N-(4-((1-methyl-2-((3-(1-methyl-5-oxopyrrolidin-3-yl)-5-(trifluoromethyl)phenyl)amino)-1H-benzo[d]imidazol-6-yl)oxy)pyridin-2-yl)acetamide

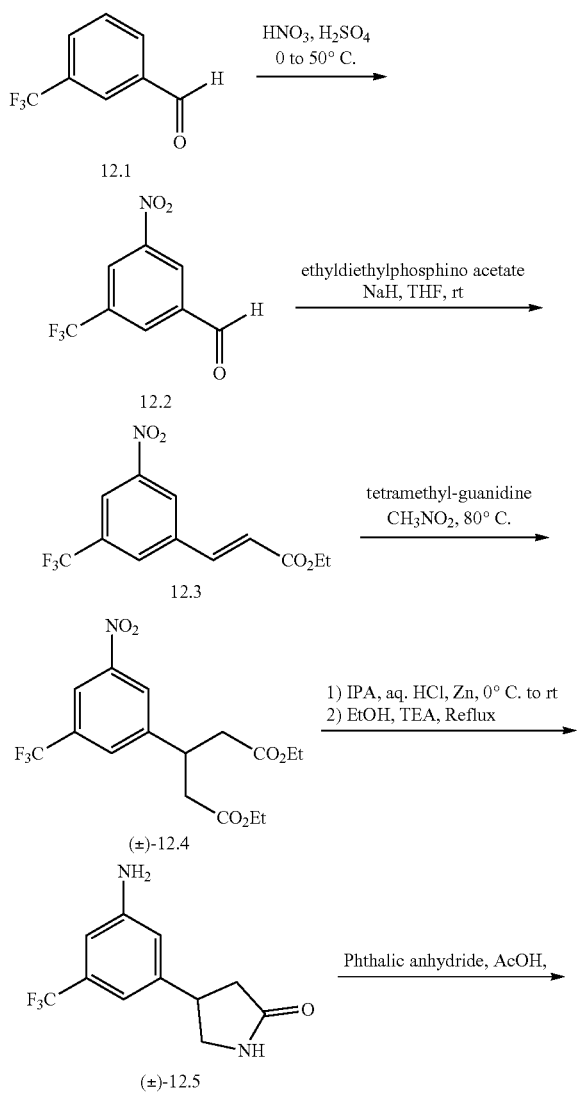

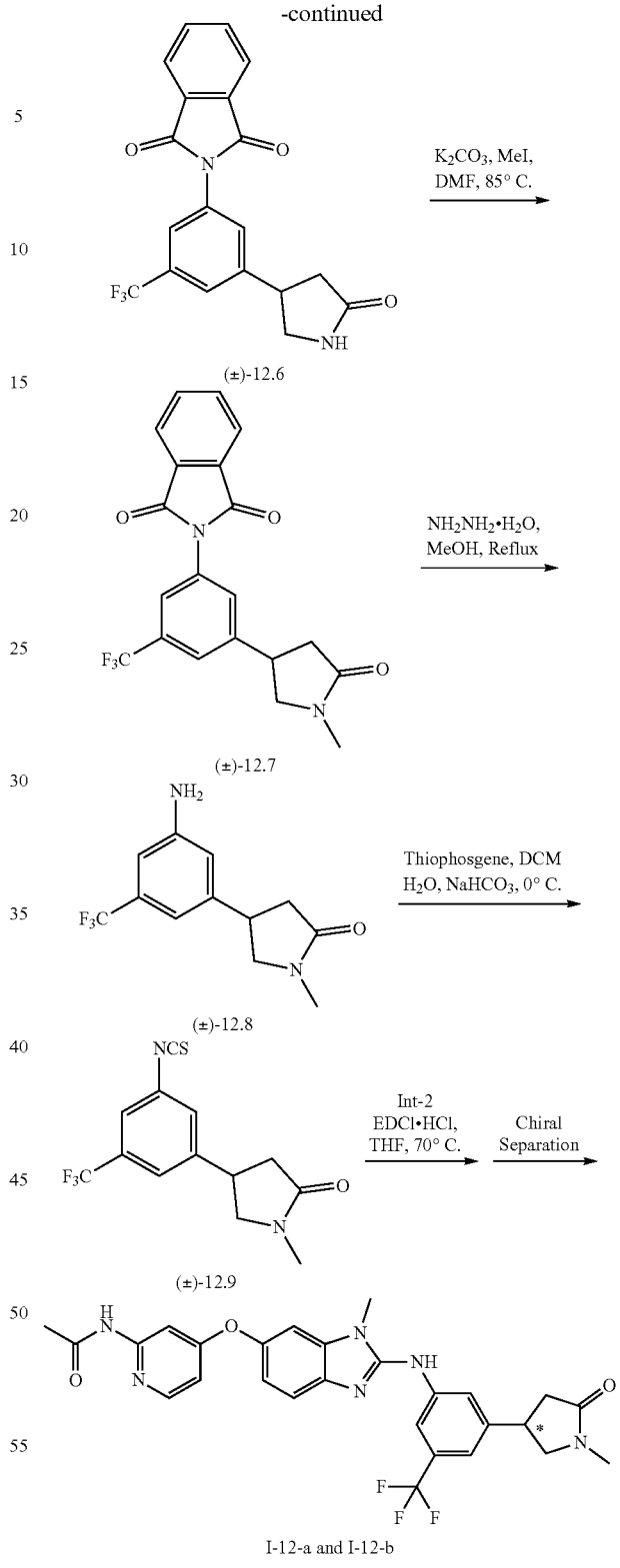

Synthesis of compound 12.2. To a mixture of 3-(trifluoromethyl)benzaldehyde (12.1, 10 g, 57.43 mmol, 1.0 equiv) in concentrated sulfuric acid (98%, 20 mL) at 0° C. was slowly added nitric acid (2.5 mL). The reaction mixture was stirred at 50° C. for 8 h. It was poured over crushed ice, stirred and extracted with ethyl acetate. The combined organic layers were washed with saturated sodium bicarbonate, brine, dried over anhydrous sodium sulfate, filtered and concentrated under reduced pressure. The residue was purified by flash column chromatography on silica gel (CombiFlash®, 10% ethyl acetate in hexane as eluant) to afford 12.2. MS (ES): m/z 220.2 [M+H]$^+$.

Synthesis of compound 12.3. To a solution of ethyldiethylphosphinoacetate (4.74 g, 22.59 mmol, 1.1 equiv) in THF (50 mL) was added sodium hydride (1.18 g, 24.64 mmol, 1.2 equiv) at 0° C. and stirred for 30 min. To the solution was added 12.2 (4.5 g, 20.54 mmol, 1.2 equiv) and the mixture was stirred at room temperature for 3 h. It was poured into ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 20% ethyl acetate in hexane as eluant) to afford 12.3. MS (ES): m/z 290.2 [M+H]$^+$.

Synthesis of compound (±)-12.4. A solution of compound 12.3 (4.0 g, 13.83 mmol, 1.0 equiv) and tetramethylguanidine (0.6 mL) in nitromethane (40 mL) was stirred at 80° C. for 2 h. It was poured into ice-water, stirred and extracted with dichloromethane. The combined organic layers were washed with brine, dried over anhydrous sodium sulfate, filtered and concentrated under reduced pressure. The residue was purified by flash column chromatography on silica gel (CombiFlash®, 12% ethyl acetate in hexane as eluant) to afford (±)-12.4. MS (ES): m/z 351.3 [M+H]$^+$.

Synthesis of compound (±)-12.5. To a solution of (±)-12.4 (1.1 g, 3.14 mmol, 1.0 equiv) in isopropyl alcohol (60 mL) and 1 N aqueous hydrochloric acid (30 mL) was added zinc dust (3.9 g, 61.23 mmol, 19.5 equiv) in portions at 0° C. After the addition, the reaction mixture was allowed to warm to rt and stirred for 2 h. It was slowly poured into a stirring saturated aqueous solution of sodium bicarbonate, and the mixture was extracted with ethyl acetate. The combined organic layers were washed with brine, dried over anhydrous sodium sulfate, filtered and concentrated under reduced pressure. The residue was purified by flash column chromatography on silica gel (CombiFlash®, 10% methanol in dichloromethane as eluant) to afford the amine, which was dissolved in ethanol (20 mL), added triethylamine (2 mL) and heated to reflux for 16 h. The reaction mixture was poured into ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 4.1% methanol in dichloromethane as eluant) to afford (±)-12.5. MS (ES): m/z 245.2 [M+H]$^+$.

Synthesis of compound (±)-12.6. To a solution of 12.5 (0.4 g, 1.64 mmol, 1.0 equiv) in acetic acid (5 mL) was added phthalic anhydride (0.485 g, 3.28 mmol, 2.0 equiv) and stirred at 80° C. for 4 h. It was poured into ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 10% methanol in dichloromethane as eluant) to afford (±)-12.6. MS (ES): m/z 375.3 [M+H]$^+$.

Synthesis of compound (±)-12.7. A mixture of (±)-12.6 (0.271 g, 0.723 mmol, 1.0 equiv) and potassium carbonate (0.209 g, 1.51 mmol, 2.1 equiv) in DMF (3 mL) was stirred for 15 min and was added methyl iodide (0.123 g, 0.867 mmol, 1.2 equiv). The reaction mixture was stirred at 85° C. for 3 h. It was poured into ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 4.7% methanol in dichloromethane as eluant) to afford (±)-12.7. MS (ES): m/z 389.4 [M+H]$^+$.

Synthesis of compound (±)-12.8. To a solution of (±)-12.7 (0.190 g, 0.489 mmol, 1.0 equiv) in methanol (10 mL) was added hydrazine (99%, 1 mL) and the mixture was heated to reflux for 2 h. It was poured into ice-water and extracted with ethyl acetate. The combined organic layers were washed with brine, dried over anhydrous sodium sulfate, filtered and concentrated under reduced pressure to obtain (±)-12.8. MS (ES): m/z 259.2 [M+H]$^+$.

Synthesis of compound (±)-12.9. Compound (±)-12.9 was prepared from compound (±)-12.8 following the procedure described in the synthesis of 11.8. MS (ES): m/z 301.3 [M+H]$^+$.

Synthesis of compound (±)-I-12. Compound (±)-I-12 was prepared from (±)-12.9 and Int-2 following the procedure described in the synthesis of compound I-1. The residue was purified by flash column chromatography on silica gel (CombiFlash®, 4.8% methanol in dichloromethane as eluant). MS (ES): m/z 539.5 [M+H]$^+$.

I-12-a and I-12-b. Enantiomers of (±)-I-12 were separated on HPLC (CHIRALPAK IH (250 mm×21 mm, 5 μm); mobile phase: (A) 0.1% diethylamine/n-hexane (B) 0.1% diethylamine/isopropanol:acetonitrile (70:30); flow rate: 20 mL/min) to get first eluting fraction (I-12-a) and second eluting fraction (I-12-b). (*Absolute stereochemistry not determined.) I-12-a: MS (ES): m/z: 539.8 [M+H]$^+$; $^1$H NMR (DMSO-d6, 400 MHz): δ 10.50 (s, 1H), 9.37 (s, 1H), 8.34 (s, 1H), 8.16-8.14 (d, J=5.6 Hz, 1H), 8.01 (s, 1H), 7.65 (s, 1H), 7.48-7.46 (d, J=8.4 Hz, 1H), 7.29 (s, 1H), 7.25 (s, 1H), 6.89-6.87 (m, 1H), 6.63-6.62 (m, 1H), 3.82-3.80 (m, 1H), 3.72 (s, 3H), 3.69-3.65 (m, 1H), 3.40-3.35 (m, 1H), 2.81 (s, 3H), 2.79-2.72 (m, 1H), 2.42-2.33 (m, 1H), 2.02 (s, 3H).

I-12-b: MS (ES): m/z: 539.4 [M+H]$^+$; $^1$H NMR (DMSO-d6, 400 MHz): δ 10.50 (s, 1H), 9.37 (s, 1H), 8.34 (s, 1H), 8.16-8.14 (d, J=5.6 Hz, 1H), 8.01 (s, 1H), 7.65 (s, 1H), 7.48-7.46 (d, J=8.4 Hz, 1H), 7.29 (s, 1H), 7.25 (s, 1H), 6.89-6.86 (m, 1H), 6.63-6.61 (m, 1H), 3.82-3.80 (m, 1H), 3.72 (s, 3H), 3.69-3.65 (m, 1H), 3.40-3.35 (m, 1H), 2.81 (s, 3H), 2.79-2.72 (m, 1H), 2.42-2.33 (m, 1H), 2.02 (s, 3H).

Example 13: N-(4-((1-methyl-2-((6-morpholinopyridin-2-yl)amino)-1H-benzo[d]imidazol-6-yl)oxy)pyridin-2-yl)acetamide

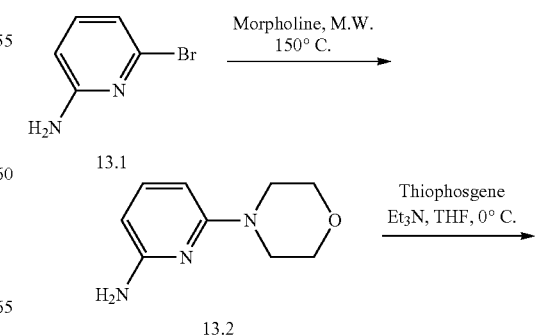

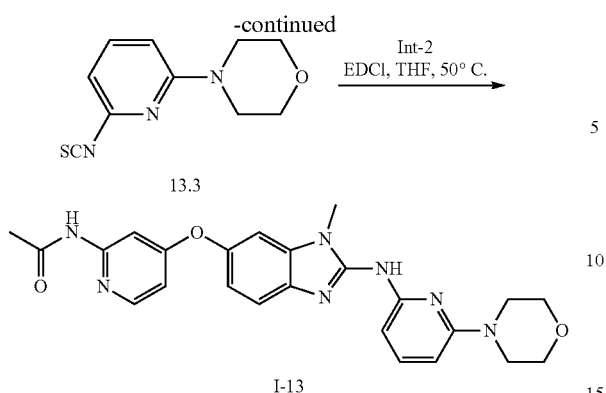

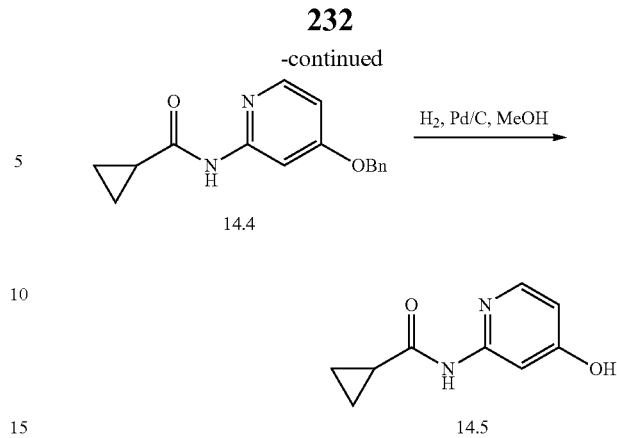

Synthesis of compound 13.2. A mixture of 6-bromopyridin-2-amine (13.1, 1.5 g, 8.67 mmol, 1.0 equiv) and morpholine (7.47 mL, 86.7 mmol, 10 equiv) was stirred in a microwave reactor at 150° C. for 4 h. It was cooled to room temperature, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 40% ethyl acetate in hexane as eluant) to afford 13.2. MS (ES): m/z 180.3 [M+H]$^+$.

Synthesis of compound 13.3. Compound 13.3 was prepared from 13.2 following the procedure described in the synthesis of compound 1.2. The residue was purified by flash column chromatography on silica gel (CombiFlash®, 15% ethyl acetate in hexane as eluant). MS (ES): m/z 222.3 [M+H]$^+$.

Synthesis of I-13. Compound I-12 was prepared from 13.3 and Int-2 following the procedure described in the synthesis of compound I-1. The residue was purified by flash column chromatography on silica gel (CombiFlash®, 8% methanol in dichloromethane as eluant). MS (ES): m/z: 460.45 [M+H]$^+$, $^1$H NMR (DMSO-d6, 400 MHz): δ 10.49 (s, 1H), 9.13 (s, 1H), 8.15-8.14 (d, J=5.6 Hz, 1H), 7.65 (s, 1H), 7.57-7.46 (m, 3H), 7.29 (s, 1H), 6.90-6.88 (d, J=8.4 Hz, 1H), 6.63-6.62 (d, J=3.6 Hz, 1H), 6.40-6.38 (d, J=8 Hz, 1H), 3.69 (bs, 8H), 3.55 (s, 3H), 2.02 (s, 3H).

Example 14: N-(4-((2-((4-((4-ethylpiperazin-1-yl)methyl)-3-(trifluoromethyl)phenyl)amino)-1-methyl-1H-benzo[d]imidazol-6-yl)oxy)pyridin-2-yl)cyclopropanecarboxamide

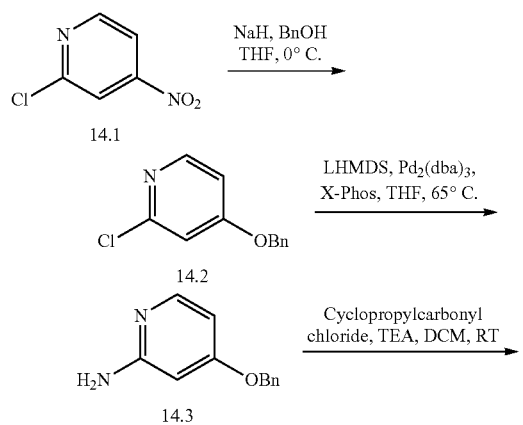

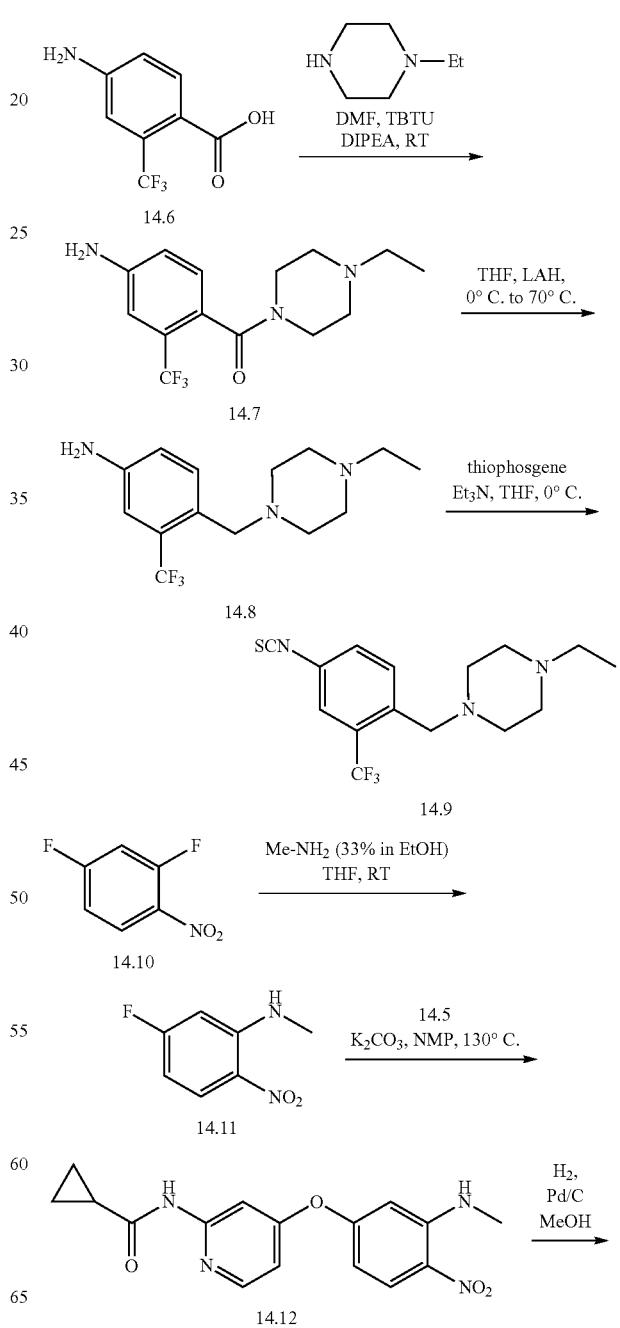

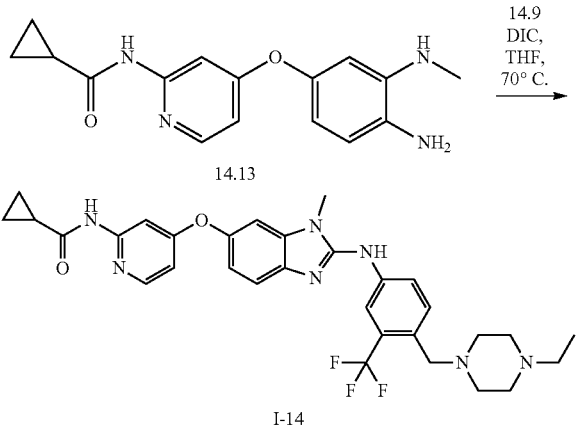

Synthesis of compound 14.2. To a solution of benzyl alcohol (17.05 g, 157.69 mmol, 1.0 equiv) in THF (250 mL) was added sodium hydride (12.61 g, 315.38 mmol, 2 equiv) at 0° C. and stirred for 1 h. 2-Chloro-4-nitropyridine (14.1, 25 g, 157.69 mmol, 1.0 equiv) was added and the reaction mixture was stirred at 0° C. for 2 h. It was poured over ice, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 10% ethyl acetate in hexane as eluant) to afford 1.1. MS (ES): m/z 220.13 $[M+H]^+$.

Synthesis of compound 14.3. A solution of 14.2 (20 g, 91.05 mmol, 1.0 equiv) in THF (200 mL) was degassed by bubbling argon for 10 min. 2-Dicyclohexylphosphino-2',4',6'-triisopropylbiphenyl (4.34 g, 9.105 mmol, 0.1 equiv) and tris(dibenzylideneacetone)dipalladium (0) (4.17 g, 4.55 mmol, 0.05 equiv) were added, and degassed for 5 min. To the mixture was added a solution of lithium bis(trimethylsilyl)amide (1 M in THF, 182 mL, 182.1 mmol, 2.0 equiv) and the reaction mixture was stirred at 60° C. under argon for 1 h. It was cooled to room temperature, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 3% methanol in dichloromethane as eluant) to afford 14.3. MS (ES): m/z 201.2 $[M+H]^+$.

Synthesis of compound 14.4. To a solution of 14.3 (0.8 g, 4.0 mmol, 1.0 equiv) in dichloromethane (10 mL) was added triethylamine (1.67 mL, 12.0 mmol, 3.0 equiv) followed by cyclopropyl carbonyl chloride (0.49 g, 4.8 mmol, 1.2 equiv) at room temperature and stirred for 1 h. It was poured over ice, stirred and extracted with dichloromethane. The combined organic layers were washed with brine, dried over anhydrous sodium sulfate, filtered and concentrated under reduced pressure. The residue was purified by flash column chromatography on silica gel (CombiFlash®, 1.2% methanol in dichloromethane as eluant) to afford 14.4. MS (ES): m/z 269.3 $[M+H]^+$.

Synthesis of compound 14.5. Compound 14.5 was prepared from 14.4 following the procedure described in the synthesis of Int-1. The product was purified by flash column chromatography on silica gel (CombiFlash®, 5% methanol in dichloromethane as eluant). MS (ES): m/z 179.2 $[M+H]^+$.

Synthesis of compound 14.7. To a solution of 4-amino-2-(trifluoromethyl)benzoic acid (14.6, 10 g, 48.75 mmol, 1.0 equiv) in DMF (30 mL) was added O-(benzotriazol-1-yl)-N,N,N',N'-tetramethyluronium tetrafluoroborate (18.4 g, 58.5 mmol, 1.2 equiv) at 0° C. The reaction mixture was stirred for 30 min and was added 1-ethylpiperazine (6.67, 58.5 mmol, 1.2 equiv) followed by N,N-diisopropylethylamine (24 mL, 146.25 mmol, 3.0 equiv). It was stirred at room temperature for 3 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.5% methanol in dichloromethane as eluant) to afford 14.7. MS (ES): m/z 302.3 $[M+H]^+$.

Synthesis of compound 14.8. To a solution of 14.7 (2 g, 6.64 mmol, 1.0 equiv) in THF (20 mL) was added a solution of lithium aluminum hydride (1 M in THF, 19.9 mL, 19.92 mmol, 3.0 equiv) at 0° C. The reaction mixture was heated to reflux for 3 h. It was cooled to room temperature, carefully poured over ice-water and extracted with ethyl acetate. The combined organic layers were washed with brine, dried over anhydrous sodium sulfate, filtered and concentrated under reduced pressure to obtain 14.8. MS (ES): m/z 288.3 $[M+H]^+$.

Synthesis of compound 14.9. Compound 14.9 was prepared from 14.8 following the procedure described in the synthesis of compound 1.2. The product was purified by flash column chromatography on silica gel (CombiFlash®, 3.0% methanol in dichloromethane as eluant). MS (ES): m/z 330.3 $[M+H]^+$.

Synthesis of compound 14.11. To a solution of 2,4-difluoro-1-nitrobenzene (14.10, 1.0 g, 6.29 mmol, 1.0 equiv) in THF (10 mL) was added methylamine solution (33% in ethanol, 1.18 mL, 12.58 mmol, 2.0 equiv) dropwise at 0° C. The reaction mixture was stirred at room temperature for 2 h. It was poured over ice-water and extracted with ethyl acetate. The combined organic layers were washed with brine, dried over anhydrous sodium sulfate, filtered and concentrated under reduced pressure to obtain 14.11. MS (ES): m/z 171.2 $[M+H]^+$.

Synthesis of compound 14.12. Compound 14.12 was prepared from 14.11 and 14.5 following the procedure described in the synthesis of compound Int-2.3. The product was purified by flash column chromatography on silica gel (CombiFlash®, 2.5% methanol in dichloromethane as eluant). MS (ES): m/z 329.3 $[M+H]^+$.

Synthesis of compound 14.13. Compound 14.13 was prepared from 14.12 following the procedure described in the synthesis of compound Int-2. The product was purified by flash column chromatography on silica gel (CombiFlash®, 5% methanol in dichloromethane as eluant). MS (ES): m/z 299.3 $[M+H]^+$.

Synthesis of I-14. Compound I-14 was prepared from 14.9 and 14.13 following the procedure described in the synthesis of compound I-2. The product was purified by flash column chromatography on silica gel (CombiFlash®, 10% methanol in dichloromethane as eluant). MS (ES): m/z: 594.30 $[M+H]^+$, $^1$H NMR (DMSO-d6, 400 MHz): δ 10.79 (s, 1H), 9.31 (s, 1H), 8.24 (s, 1H), 8.19-8.15 (m, 2H), 7.68-7.66 (d, J=8.4 Hz, 1H), 7.62 (s, 1H), 7.45-7.43 (d, J=7.6 Hz, 1H), 7.26 (s, 1H), 6.87-6.85 (d, J=10.4 Hz, 1H), 6.66-6.65 (d, J=3.2 Hz, 1H), 3.70 (s, 3H), 3.55 (s, 2H), 2.33 (bs, 10H), 1.95 (bs, 1H), 1.01-0.97 (t, 3H), 0.75 (bs, 4H).

Example 15: 4-((2-((4-((4-ethylpiperazin-1-yl)methyl)-3-(trifluoromethyl)phenyl)amino)-1-methyl-1H-benzo[d]imidazol-6-yl)oxy)-N-methylpicolinamide

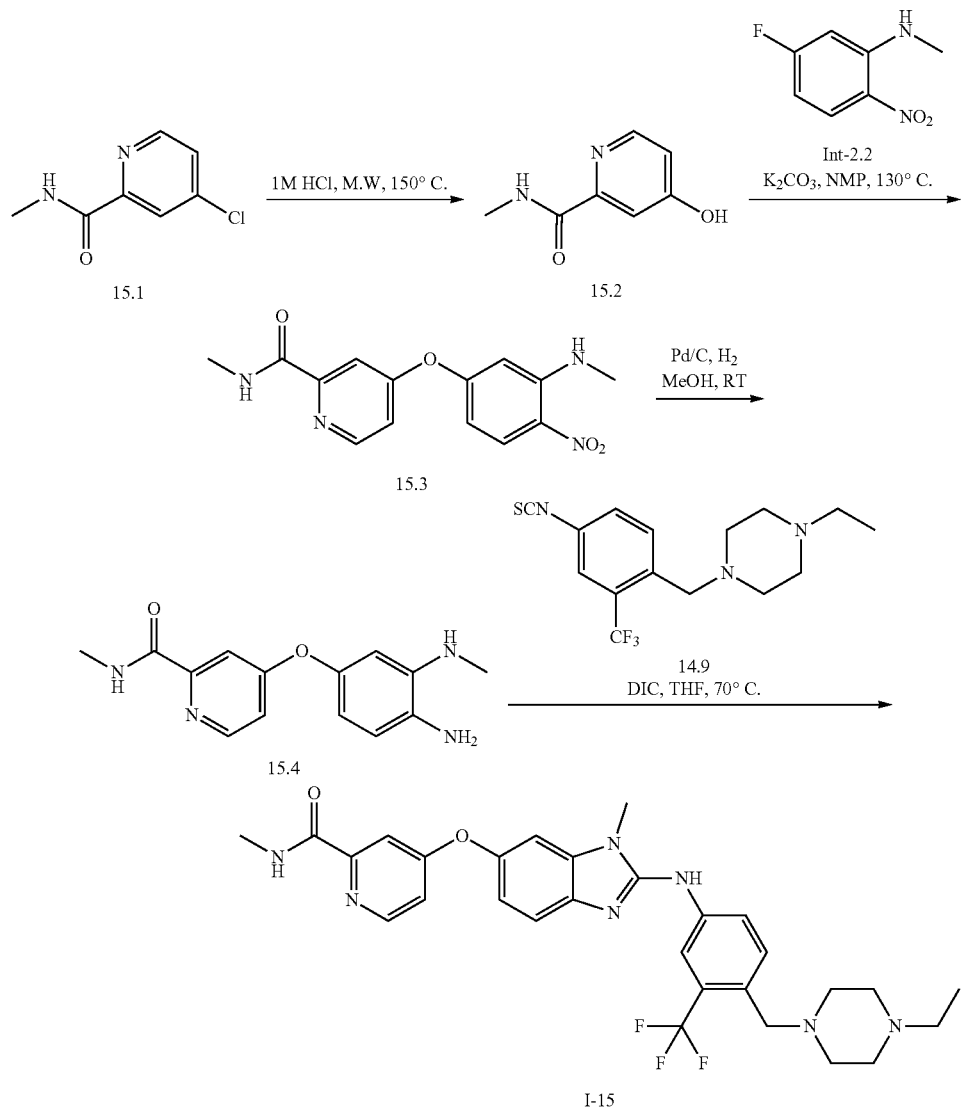

Synthesis of compound 15.2. A mixture of compound 15.1 (0.5 g, 2.93 mmol, 1.0 equiv) and 1 M hydrochloric acid (5 mL) was stirred at 150° C. in a microwave reactor for 2 h. It was poured over saturated sodium bicarbonate solution and extracted with ethyl acetate. The combined organic layers were washed with brine, dried over anhydrous sodium sulfate, filtered and concentrated under reduced pressure. The residue was purified by flash column chromatography on silica gel (CombiFlash®, 3% methanol in dichloromethane as eluant) to afford 15.2. MS (ES): m/z 153.2 [M+H]⁺.

Synthesis of compound 15.3. Compound 15.3 was prepared from Int-2.2 and 15.2 following the procedure described in the synthesis of compound Int-2.3. The product was purified by flash column chromatography on silica gel (CombiFlash®, 2.0% methanol in dichloromethane as eluant). MS (ES): m/z 303.3 [M+H]⁺.

Synthesis of compound 15.4. Compound 15.4 was prepared from 15.3 following the procedure described in the synthesis of compound Int-2. The product was purified by flash column chromatography on silica gel (CombiFlash®, 5% methanol in dichloromethane as eluant). MS (ES): m/z 273.3 [M+H]⁺.

Synthesis of I-15. Compound I-15 was prepared from 15.4 and 14.9 following the procedure described in the synthesis of compound I-2. The product was purified by flash column chromatography on silica gel (CombiFlash®, 10% methanol in dichloromethane as eluant). MS (ES): m/z: 568.9 [M+H]⁺, ¹H NMR (DMSO-d6, 400 MHz): δ 9.35 (s, 1H), 8.80-8.78 (d, J=4.8 Hz, 1H), 8.50-8.49 (d, J=5.6 Hz, 1H), 8.25 (s, 1H), 8.21-8.19 (d, J=8.0 Hz, 1H), 7.69-7.67 (d, J=8.4 Hz, 1H), 7.50-7.48 (d, J=8.4 Hz, 1H), 7.37-7.36 (d, J=2.4 Hz, 1H), 7.33 (s, 1H), 7.17-7.15 (m, 1H), 6.93-6.90 (t, J=8.4 Hz, 1H), 3.71 (s, 3H), 3.55 (s, 2H), 2.76 (s, 3H), 2.42 (bs, 6H), 2.33 (bs, 4H), 1.01-0.97 (t, 3H).

Example 16: 4-((2-((5-(tert-butyl) isoxazol-3-yl)amino)-1-methyl-1H-benzo[d]imidazol-6-yl)oxy)-N-methylpicolinamide

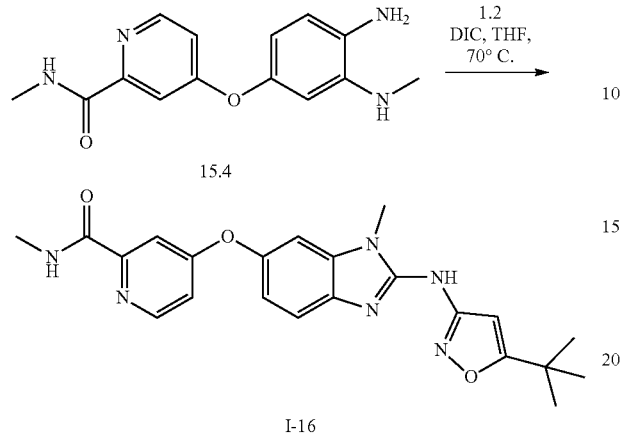

Synthesis of I-16. Compound I-16 was prepared from compound 15.4 and compound 1.2 following the procedure described in the synthesis of compound I-2. The product was purified by flash column chromatography on silica gel (CombiFlash®, 3% methanol in dichloromethane as eluant). MS (ES): m/z: 421.46 [M+H]$^+$, $^1$H NMR (DMSO-d6, 400 MHz): δ 8.49-8.48 (d, 2H), 7.46 (bs, 2H), 7.17-7.11 (m, 2H), 6.89-6.87 (d, J=7.2 Hz, 1H), 3.56 (bs, 3H), 2.84 (s, 3H), 1.35 (s, 9H).

Example 17: N-(4-((2-((3-(tert-butyl)-1-methyl-1H-pyrazol-5-yl)amino)-1-methyl-1H-benzo[d]imidazol-6-yl)oxy)pyridin-2-yl)acetamide

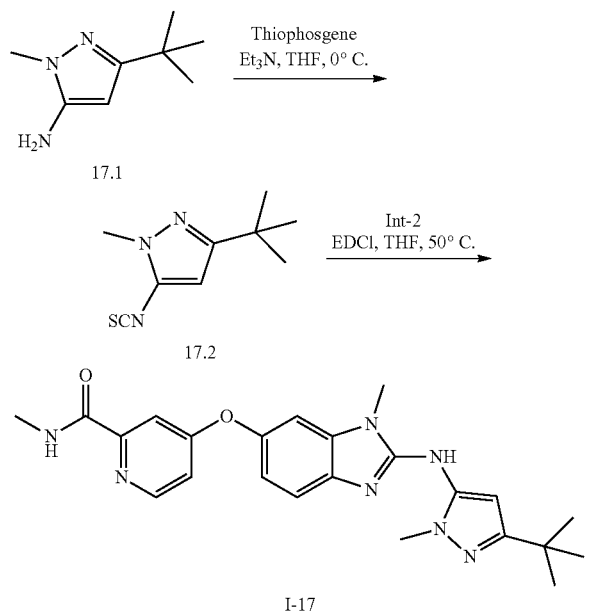

Synthesis of compound 17.2. Compound 17.2 was prepared from 17.1 following the procedure described in the synthesis of compound 1.2. The product was purified by flash column chromatography on silica gel (CombiFlash®, 12% ethyl acetate in hexane as eluant). MS (ES): m/z 196.3 [M+H]$^+$.

Synthesis of I-17. Compound I-17 was prepared from 17.2 and Int-2 following the procedure described in the synthesis of compound I-1. The product was purified by flash column chromatography on silica gel (CombiFlash®, 3% methanol in dichloromethane as eluant). MS (ES): m/z: 434.4 [M+H]$^+$, $^1$H NMR (DMSO-d6, 400 MHz): δ 10.56-10.50 (m, 2H), 8.18-8.16 (d, J=5.6 Hz, 1H), 7.67 (s, 1H), 7.35-7.16 (m, 2H), 6.84-6.78 (t, J=7.6 Hz, 1H), 6.64 (bs, 1H), 5.92 (s, 1H), 3.61 (bs, 3H), 3.42 (s, 3H), 2.04 (s, 3H), 1.27 (s, 9H).

Example 18: N-(4-((2-((3-(tert-butyl)-1-methyl-1H-pyrazol-5-yl)amino)-1,7-dimethyl-1H-benzo[d]imidazol-6-yl)oxy)pyridin-2-yl)acetamide

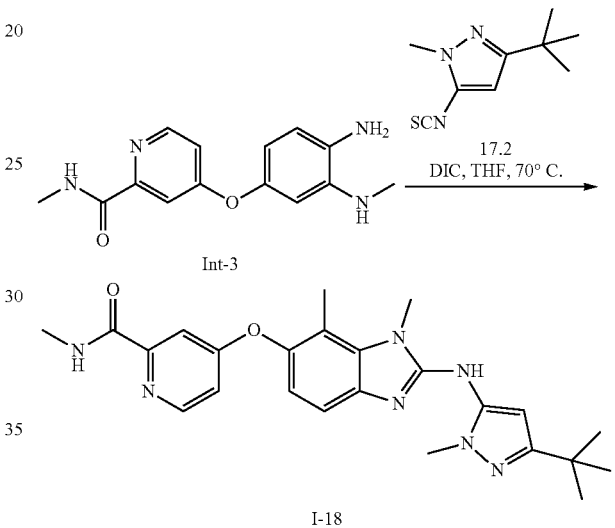

Synthesis of I-18. Compound I-18 was prepared from 17.2 and Int-3 following the procedure described in the synthesis of compound I-2. The product was purified by flash column chromatography on silica gel (CombiFlash®, 3% methanol in dichloromethane as eluant). MS (ES): m/z: 448.4 [M+H]$^+$, $^1$H NMR (DMSO-d6, 400 MHz): δ 10.53-10.48 (t, 1H), 8.76 (s, 1H), 8.15-8.12 (m, 1H), 7.58 (s, 1H), 7.07-7.05 (d, J=8.0 Hz, 1H), 6.78-6.74 (t, 1H), 6.56-6.55 (d, J=5.6 Hz, 1H), 6.07 (s, 1H), 3.72 (s, 3H), 3.61 (bs, 3H), 2.37 (s, 3H), 2.03 (s, 3H), 1.26 (s, 9H).

Example 19: (S)—N-(4-((2-((3-(tert-butyl)-1-(tetrahydrofuran-3-yl)-1H-pyrazol-5-yl)amino)-1-methyl-1H-benzo[d]imidazol-6-yl)oxy)pyridin-2-yl)acetamide

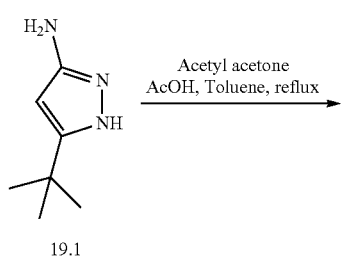

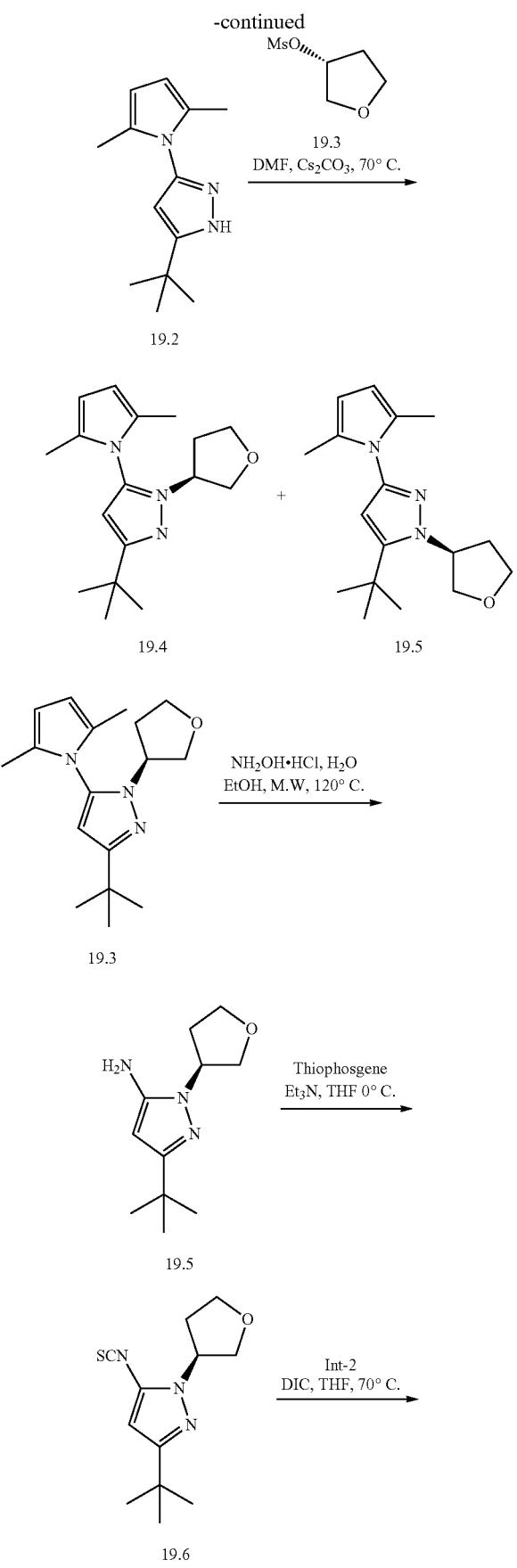
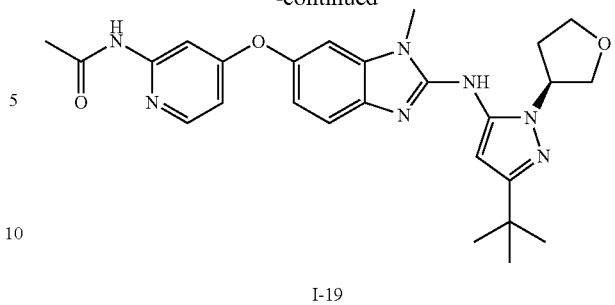

I-19

Synthesis of compound 19.1. To a round-bottom flask equipped with a Dean-Stark apparatus and a condenser was charged with 5-(tert-butyl)-1H-pyrazol-3-amine (17.1, 5.0 g, 35.92 mmol, 1.0 equiv), 2, 5-hexanedione (4.09 g, 35.92 mmol, 1.0 equiv), toluene (100 mL) and a few drops of acetic acid (catalytic). The reaction mixture was heated to reflux for 3 hours. It was cooled rt and concentrated under reduced pressure. The residue was purified by flash column chromatography on silica gel (CombiFlash®, 12% ethyl acetate in hexane as eluant) to afford 19.1. MS (ES): m/z 218.3 [M+H]$^+$.

Synthesis of compound 19.3 and 19.4. A mixture of 19.1 (2.5 g, 11.50 mmol, 1.0 equiv), 19.2 (1.91 g, 11.50 mmol, 1.0 equiv) and cesium carbonate (7.49 g, 23 mmol, 2.0 equiv) in DMF (15 mL) was stirred at 70° C. for 12 h under nitrogen. It was poured into ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 2% ethyl acetate in hexane as eluant) to afford 19.3. MS (ES): m/z 287.4 [M+H]$^+$ and 19.4. MS (ES): m/z 248.3 [M+H]$^+$.

Synthesis of compound 19.5 A solution of 19.3 (0.100 g, 0.347 mmol, 1.0 equiv) and hydroxylamine hydrochloride (0.239 g, 3.47 mmol, 10 equiv) in ethanol-water (2/1, v/v, 3 mL) was stirred at 120° C. by a microwave reactor for 1 h. It was poured into ice-water and pH was adjusted to about 10 by the addition of 2 N aqueous sodium hydroxide solution. The mixture was extracted with dichloromethane. The combined organic layers were washed with brine, dried over anhydrous sodium sulfate, filtered and concentrated under reduced pressure to afford 19.5. MS (ES): m/z 210.3 [M+H]$^+$.

Synthesis of compound 19.6. Compound 19.6 was prepared from 19.5 following the procedure described in the synthesis of compound 1.2. MS (ES): m/z 252.3 [M+H]$^+$.

Synthesis of I-19. Compound I-19 was prepared from 19.6 and Int-2 following the procedure described in the synthesis of compound I-2. The product was purified by flash column chromatography on silica gel (CombiFlash®, 1.4% methanol in dichloromethane as eluant). MS (ES): m/z: 490.85 [M+H]$^+$, $^1$H NMR (CDCl$_3$, 400 M Hz): δ 8.14-8.12 (d, J=5.6 Hz, 1H), 7.99 (bs, 1H), 7.82 (bs, 1H), 7.17-7.15 (d, J=7.6 Hz, 1H), 6.86-6.84 (d, J=8.0 Hz, 1H), 6.64 (bs, 1H), 5.27 (bs, 1H), 4.39 (bs, 1H), 4.25 (bs, 1H), 4.14 (bs, 2H), 4.02 (bs, 1H), 3.49 (s, 3H), 2.54 (bs, 2H), 2.20 (s, 3H), 1.35 (s, 9H).

Example 20: (S)—N-(4-((2-((5-(tert-butyl)-1-(tetrahydrofuran-3-yl)-1H-pyrazol-3-yl)amino)-1-methyl-1H-benzo[d]imidazol-6-yl)oxy)pyridin-2-yl)acetamide

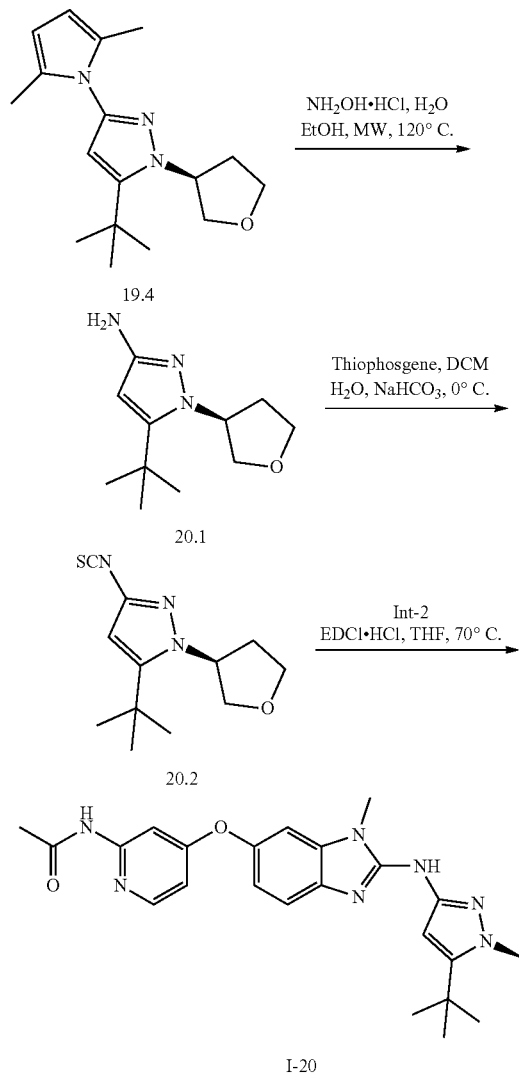

Synthesis of compound 20.1. Compound 20.1 was prepared from compound 19.4 following the procedure described in the synthesis of compound 19.5. MS (ES): m/z 210.3 [M+H]⁺.

Synthesis of compound 20.2. Compound 20.2 was prepared from compound 20.1 following the procedure described in the synthesis of 11.8. The crude product was used without further purification. MS (ES): m/z 252.3 [M+H]⁺.

Synthesis of compound I-20. Compound I-20 was prepared from 20.2 and Int-2 following the procedure described in the synthesis of compound I-1. The product was purified by flash column chromatography on silica gel (Combi-Flash®, 1.5% methanol in dichloromethane as eluant). MS (ES): m/z: 490.25 [M+H]⁺, ¹H NMR (DMSO-d6, 400 MHz): δ 10.48 (s, 1H), 9.51 (s, 1H), 8.14-8.13 (d, J=6.0 Hz, 1H), 7.64 (s, 1H), 7.36-7.34 (d, J=8.0 Hz, 1H), 7.16 (s, 1H), 7.08-7.06 (d, J=8 Hz, 1H), 6.81-6.79 (m, 1H), 6.61-6.60 (d, J=3.6 Hz, 1H), 5.22 (bs, 1H), 4.08-4.07 (m, 2H), 3.99-3.95 (m, 1H), 3.85-3.82 (m, 2H), 3.62 (s, 3H), 2.24 (bs, 1H), 2.02 (s, 3H), 1.39 (s, 9H).

Example 21: (S)—N-(4-((2-((5-(tert-butyl)-1-(tetrahydrofuran-3-yl)-1H-pyrazol-3-yl)amino)-7-cyano-1-methyl-1H-benzo[d]imidazol-6-yl)oxy)pyridin-2-yl)acetamide

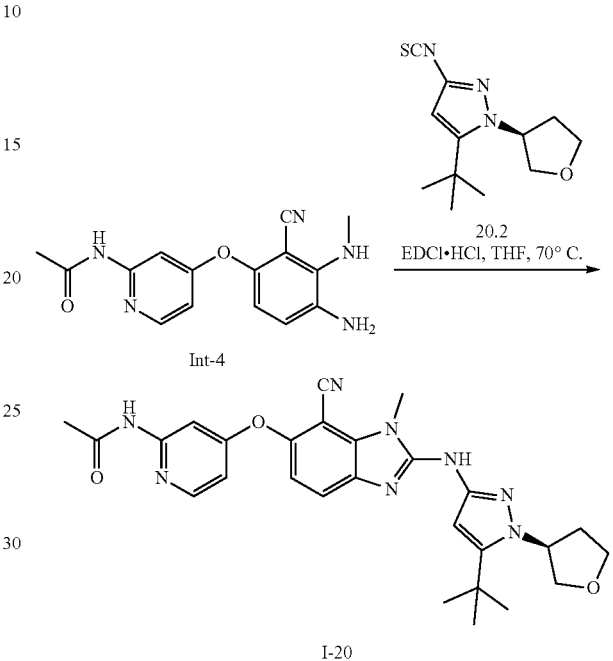

Synthesis of I-21. Compound I-21 was prepared from 20.2 and Int-4 following the procedure described in the synthesis of compound I-1. The product was purified by preparative HPLC. MS (ES): m/z: 515.8 [M+H]⁺, ¹H NMR (DMSO-d6, 400 MHz): δ 10.60 (s, 1H), 9.88 (s, 1H), 8.22-8.20 (d, J=5.6 Hz, 1H), 7.68 (s, 1H), 7.65 (s, 1H), 7.02-7.00 (d, J=8.4 Hz, 1H), 6.70-6.68 (m, 1H), 6.51 (s, 1H), 5.25 (bs, 1H), 4.10-4.07 (m, 2H), 3.91 (s, 3H), 3.87-3.81 (m, 2H), 2.37-2.34 (m, 1H), 2.24-2.20 (m, 1H), 2.04 (s, 3H), 1.39 (s, 9H).

Example 22: (S)—N-(4-((2-((5-(tert-butyl)-1-(tetrahydrofuran-3-yl)-1H-pyrazol-3-yl)amino)-3-methyl-3H-imidazo[4,5-b]pyridin-5-yl)oxy)pyridin-2-yl)acetamide

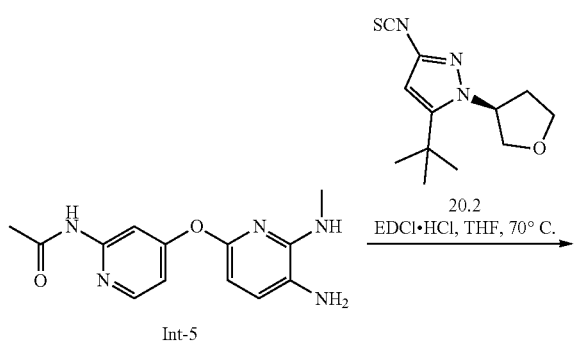

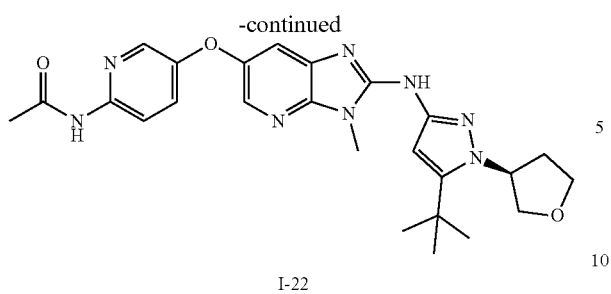

I-22

Synthesis of I-22. Compound I-22 was prepared from 20.2 and Int-5 following the procedure described in the synthesis of compound I-1. The product was purified by flash column chromatography on silica gel (CombiFlash®, 3.2% methanol in dichloromethane as a eluant). MS (ES): m/z: 491.45 [M+H]$^+$, $^1$H NMR (DMSO-d6, 400 MHz): δ 10.54 (s, 1H), 9.81 (s, 1H), 8.19-8.18 (d, J=5.6 Hz, 1H), 7.79-7.77 (d, J=8 Hz, 1H), 7.75 (s, 1H), 6.84-6.82 (d, J=8 Hz, 1H), 6.71-6.70 (d, J=4 Hz, 1H), 6.56 (s, 1H), 5.24 (bs, 1H), 4.08 (bs, 2H), 3.87-3.81 (m, 2H), 3.59 (s, 3H), 2.33 (bs, 1H), 2.25-2.22 (m, 1H), 2.04 (s, 3H), 1.39 (s, 9H).

Example 23: (R)—N-(4-((2-((3-(tert-butyl)-1-(tetrahydrofuran-3-yl)-1H-pyrazol-5-yl)amino)-1-methyl-1H-benzo[d]imidazol-6-yl)oxy)pyridin-2-yl)acetamide

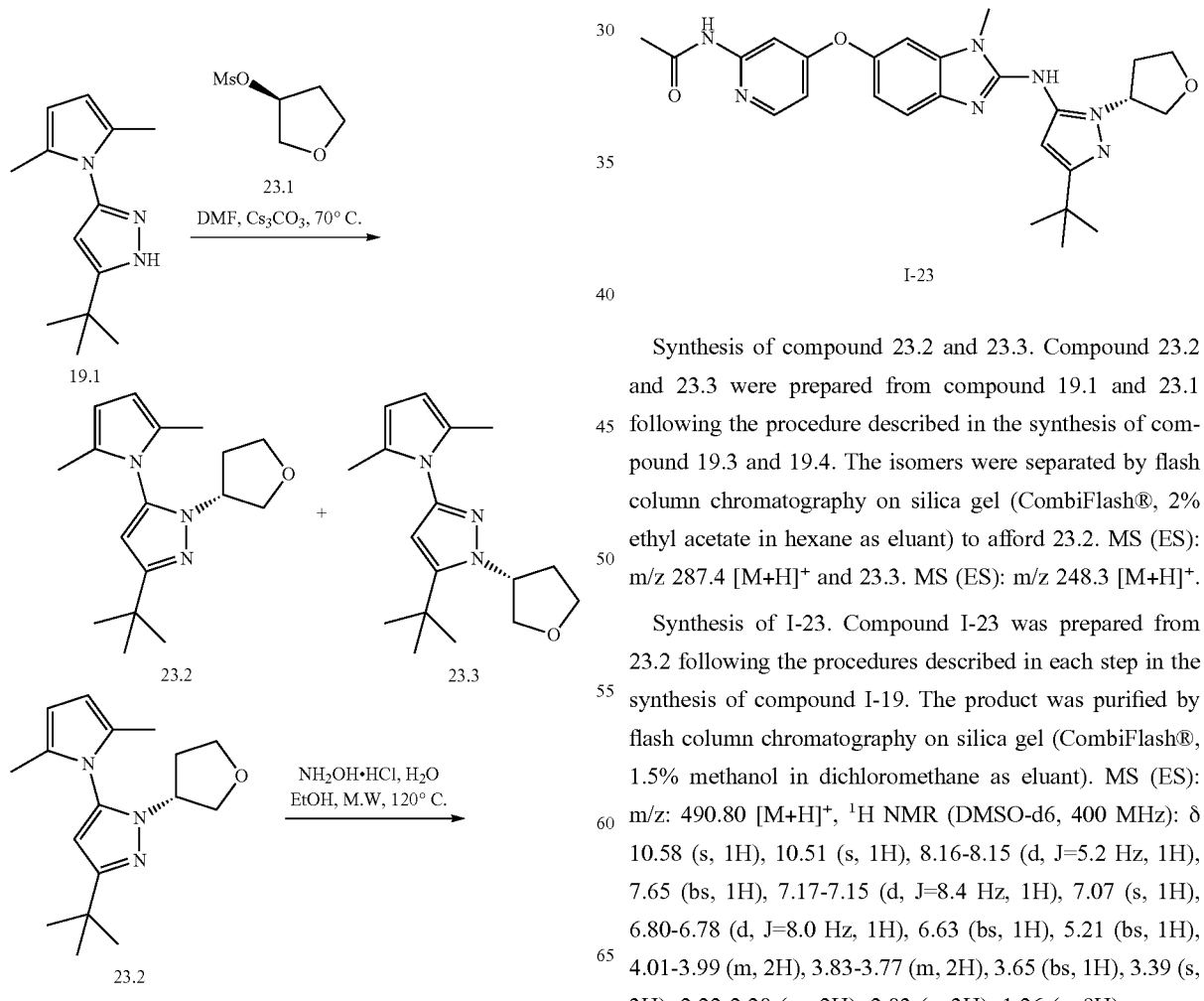

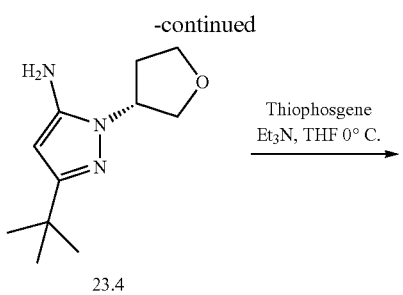

Synthesis of compound 23.2 and 23.3. Compound 23.2 and 23.3 were prepared from compound 19.1 and 23.1 following the procedure described in the synthesis of compound 19.3 and 19.4. The isomers were separated by flash column chromatography on silica gel (CombiFlash®, 2% ethyl acetate in hexane as eluant) to afford 23.2. MS (ES): m/z 287.4 [M+H]$^+$ and 23.3. MS (ES): m/z 248.3 [M+H]$^+$.

Synthesis of I-23. Compound I-23 was prepared from 23.2 following the procedures described in each step in the synthesis of compound I-19. The product was purified by flash column chromatography on silica gel (CombiFlash®, 1.5% methanol in dichloromethane as eluant). MS (ES): m/z: 490.80 [M+H]$^+$, $^1$H NMR (DMSO-d6, 400 MHz): δ 10.58 (s, 1H), 10.51 (s, 1H), 8.16-8.15 (d, J=5.2 Hz, 1H), 7.65 (bs, 1H), 7.17-7.15 (d, J=8.4 Hz, 1H), 7.07 (s, 1H), 6.80-6.78 (d, J=8.0 Hz, 1H), 6.63 (bs, 1H), 5.21 (bs, 1H), 4.01-3.99 (m, 2H), 3.83-3.77 (m, 2H), 3.65 (bs, 1H), 3.39 (s, 3H), 2.22-2.20 (m, 2H), 2.03 (s, 3H), 1.26 (s, 9H).

Example 24: (R)—N-(4-((2-((5-(tert-butyl)-1-(tetrahydrofuran-3-yl)-1H-pyrazol-3-yl)amino)-1-methyl-1H-benzo[d]imidazol-6-yl)oxy)pyridin-2-yl)acetamide

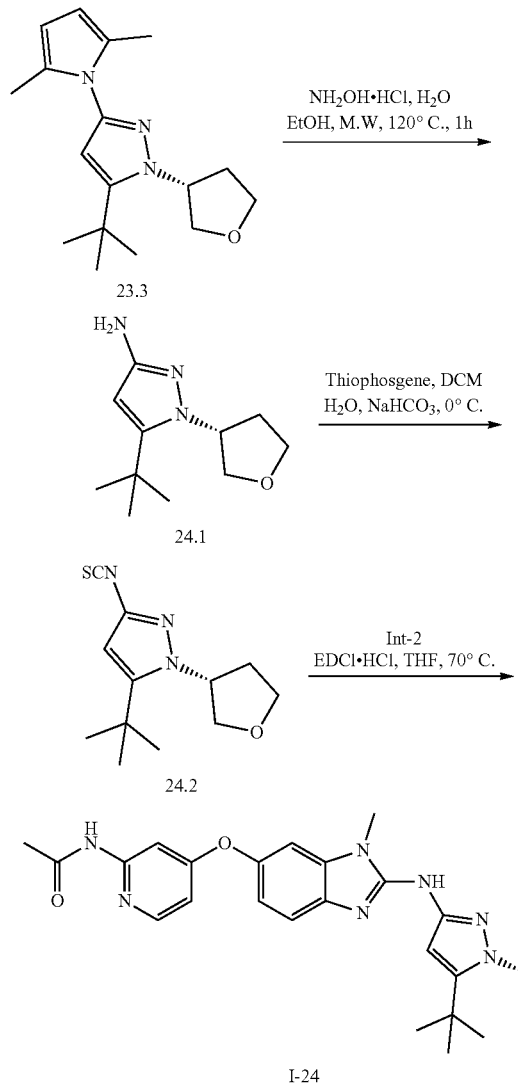

Synthesis of compound I-24. Compound I-24 was prepared from 23.3 following the procedures described in each step in the synthesis of compound I-20. The product was purified by flash column chromatography on silica gel (CombiFlash®, 1.5% methanol in dichloromethane as eluant). MS (ES): m/z: 490.37 [M+H]+, 1H NMR (DMSO-d6, 400 MHz): δ 10.48 (s, 1H), 9.56 (s, 1H), 8.16-8.14 (d, J=5.6 Hz, 1H), 7.65 (s, 1H), 7.38-7.36 (d, J=8.4 Hz, 1H), 7.19 (s, 1H), 7.10-7.04 (d, J=8 Hz, 1H), 6.84-6.82 (m, 1H), 6.62-6.61 (d, J=3.6 Hz, 1H), 5.24 (bs, 1H), 4.10-4.07 (m, 2H), 4.01-3.96 (m, 1H), 3.89-3.83 (m, 2H), 3.63 (s, 3H), 2.24 (bs, 1H), 2.03 (s, 3H), 1.39 (s, 9H).

Example 25: (R)—N-(4-((2-((5-(tert-butyl)-1-(tetrahydrofuran-3-yl)-1H-pyrazol-3-yl)amino)-7-cyano-1-methyl-1H-benzo[d]imidazol-6-yl)oxy)pyridin-2-yl)acetamide

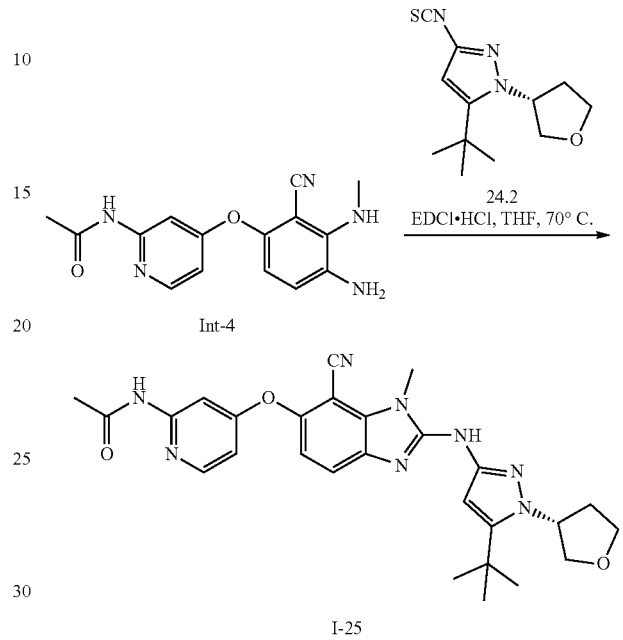

Synthesis of compound I-25. Compound I-25 was prepared from Int-4 and 24.2 following the procedure described in the synthesis of compound I-1. The product was purified by flash column chromatography on silica gel (CombiFlash®, 1.8% methanol in dichloromethane as eluant). MS (ES): m/z: 515.36 [M+H]+, 1H NMR (DMSO-d6, 400 MHz): δ 10.60 (s, 1H), 9.88 (s, 1H), 8.22-8.20 (d, J=5.6 Hz, 1H), 7.68 (s, 1H), 7.66 (s, 1H), 7.02-7.00 (d, J=8.4 Hz, 1H), 6.70-6.68 (m, 1H), 6.51 (s, 1H), 5.25 (bs, 1H), 4.10-4.07 (m, 2H), 3.91 (s, 3H), 3.88-3.84 (m, 2H), 2.37-2.34 (m, 1H), 2.23-2.22 (m, 1H), 2.04 (s, 3H), 1.39 (s, 9H).

Example 26: (R)—N-(4-((2-((5-(tert-butyl)-1-(tetrahydrofuran-3-yl)-1H-pyrazol-3-yl)amino)-3-methyl-3H-imidazo[4,5-b]pyridin-5-yl)oxy)pyridin-2-yl)acetamide

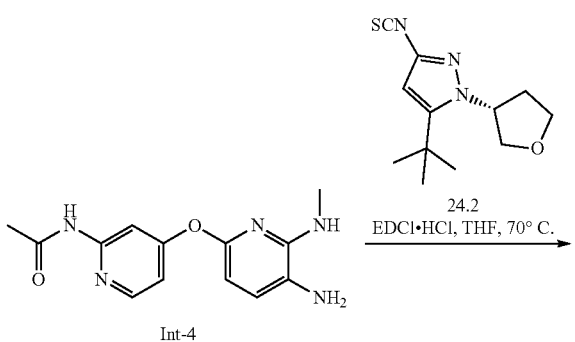

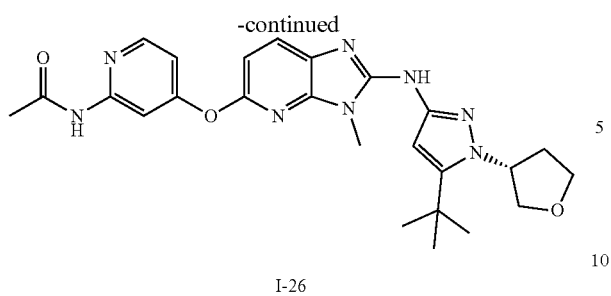

I-26

Synthesis of compound I-26. Compound I-26 was prepared from Int-5 and 24.2 following the procedure described in the synthesis of I-1. The product was purified by flash column chromatography on silica gel (CombiFlash®, 3.1% methanol in dichloromethane as eluant). MS (ES): m/z: 491.40 [M+H]+, 1H NMR (DMSO-d6, 400 MHz): δ 10.54 (s, 1H), 9.81 (s, 1H), 8.19-8.18 (d, J=5.6 Hz, 1H), 7.79-7.77 (d, J=8 Hz, 1H), 7.75 (s, 1H), 6.84-6.82 (d, J=8 Hz, 1H), 6.71-6.70 (d, J=4 Hz, 1H), 6.56 (s, 1H), 5.24 (bs, 1H), 4.08 (bs, 2H), 3.85-3.81 (m, 2H), 3.59 (s, 3H), 2.33 (bs, 1H), 2.25-2.20 (m, 1H), 2.04 (s, 3H), 1.39 (s, 9H).

Example 27: N-(4-((2-((5-(tert-butyl)-1-(tetrahydro-2H-pyran-4-yl)-1H-pyrazol-3-yl)amino)-1-methyl-1H-benzo[d]imidazol-6-yl)oxy)pyridin-2-yl)acetamide

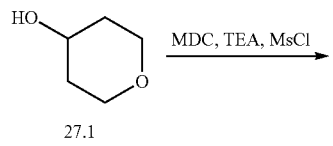

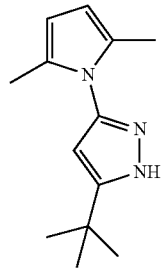

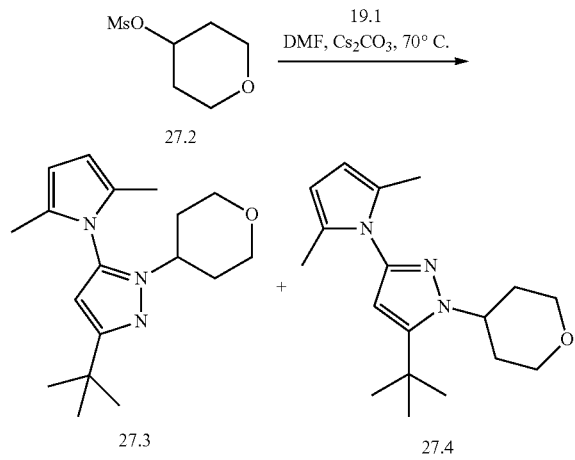

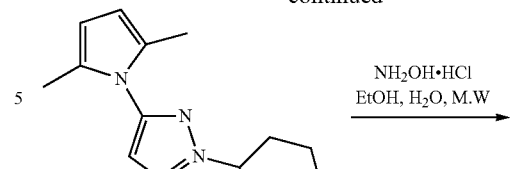

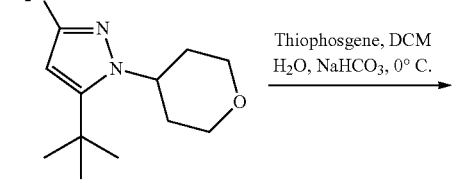

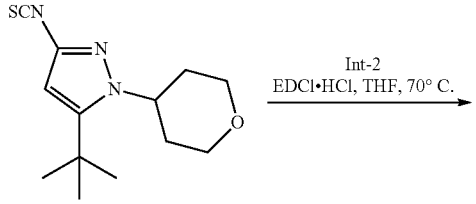

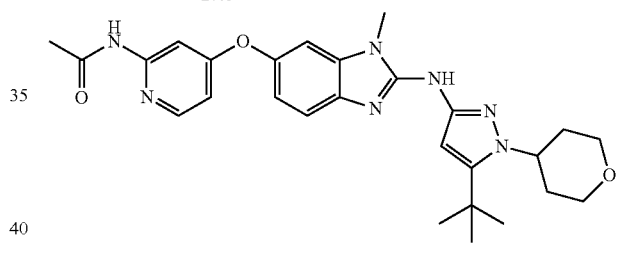

I-27

Synthesis of compound 27.2. To a solution of tetrahydro-2H-pyran-4-ol (27.1, 4.0 g, 39.16 mmol, 1.0 equiv) in dichloromethane (40 mL) and triethylamine (13.64 mL, 97.9 mmol, 2.5 equiv) at 0° C. was added methanesulfonyl chloride (3.61 mL, 46.99 mmol, 1.2 equiv) slowly. The reaction mixture was allowed to warm to at room temperature and stirred for 6 h. It was poured over ice-water, stirred and extracted with dichloromethane. The combined organic layers were washed with brine, dried over anhydrous sodium sulfate, filtered and concentrated under reduced pressure. The residue was purified by flash column chromatography on silica gel (CombiFlash®, 20% ethyl acetate in hexane as eluant) to afford 27.2. MS (ES): m/z 181.2 [M+H]+.

Synthesis of compound 27.3 and 27.4. Compound 27.3 and 27.4 were prepared from 27.2 and 19.1 following the procedure described in the synthesis of compound 19.3 and 19.4. The isomers were separated by flash column chromatography on silica gel (CombiFlash®, 8-12% ethyl acetate in hexane as eluant) to afford 27.3. MS (ES): m/z 302.4 [M+H]+ and 27.4. MS (ES): m/z 302.3 [M+H]+.

Synthesis of compound I-27. Compound I-27 was prepared from compound 27.4 following the procedures described in each step in the synthesis of I-20. The product was purified by flash column chromatography on silica gel (CombiFlash®, 2.5% methanol in dichloromethane as eluant). MS (ES): m/z: 503.85 [M+H]⁺, ¹H NMR (DMSO-d6, 400 MHz): δ 10.49 (s, 1H), 9.48 (s, 1H), 8.16-8.14 (d, J=5.6 Hz, 1H), 7.65 (s, 1H), 7.37-7.35 (d, J=8.4 Hz, 1H), 7.17 (s, 1H), 6.82-6.80 (d, J=8.4 Hz, 1H), 6.62-6.61 (d, J=3.6 Hz, 1H), 6.51 (s, 1H), 4.50 (bs, 1H), 3.98-3.96 (m, 2H), 3.64 (s, 3H), 3.59-3.53 (m, 2H), 2.21-2.16 (m, 2H), 2.04 (s, 3H), 1.79-1.76 (m, 2H), 1.40 (s, 9H).

Example 28: N-(4-((2-((5-(tert-butyl)-1-(((1s,3s)-3-hydroxycyclobutyl)methyl)-1H-pyrazol-3-yl)amino)-1-methyl-1H-benzo[d]imidazol-6-yl)oxy)pyridin-2-yl)acetamide

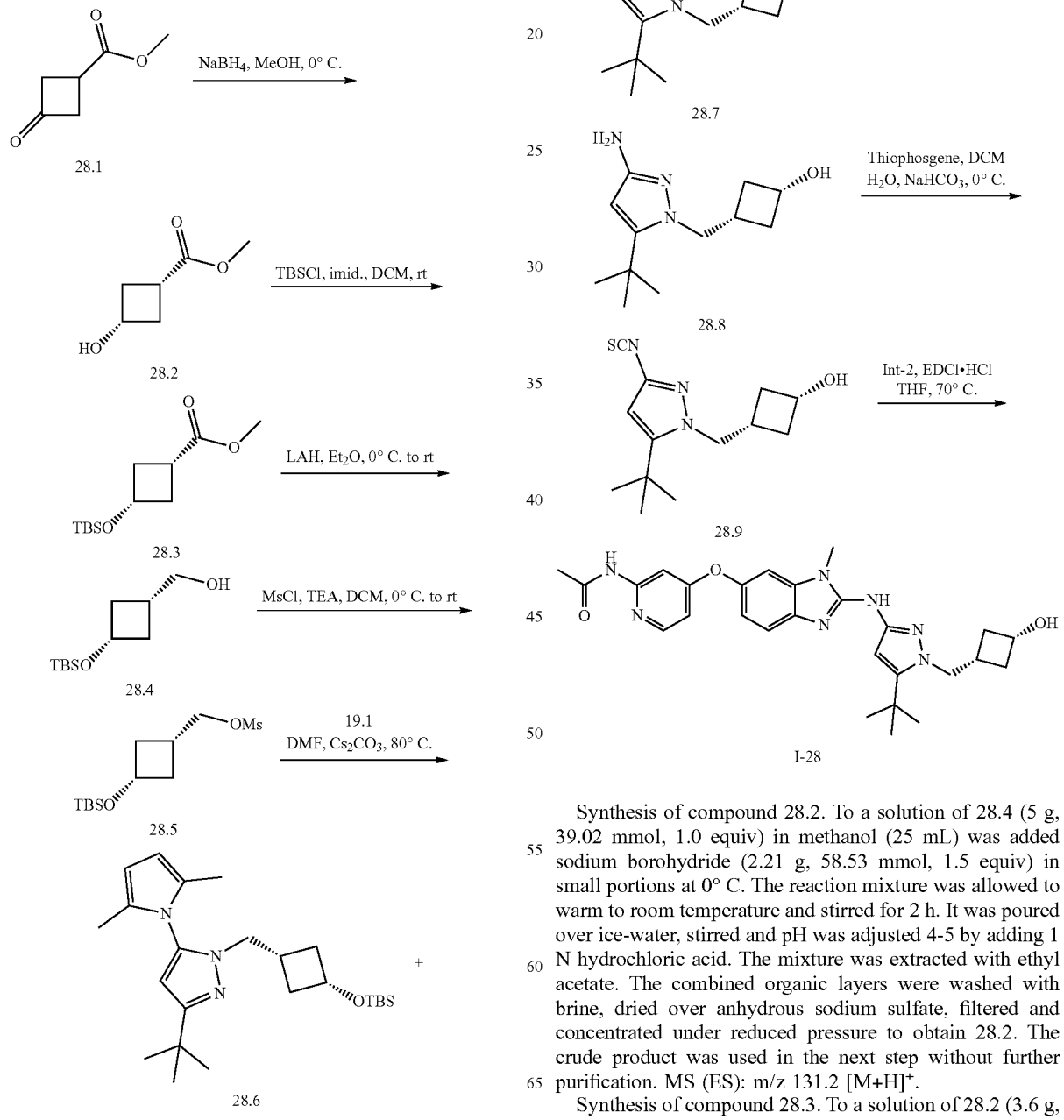

Synthesis of compound 28.2. To a solution of 28.4 (5 g, 39.02 mmol, 1.0 equiv) in methanol (25 mL) was added sodium borohydride (2.21 g, 58.53 mmol, 1.5 equiv) in small portions at 0° C. The reaction mixture was allowed to warm to room temperature and stirred for 2 h. It was poured over ice-water, stirred and pH was adjusted 4-5 by adding 1 N hydrochloric acid. The mixture was extracted with ethyl acetate. The combined organic layers were washed with brine, dried over anhydrous sodium sulfate, filtered and concentrated under reduced pressure to obtain 28.2. The crude product was used in the next step without further purification. MS (ES): m/z 131.2 [M+H]⁺.

Synthesis of compound 28.3. To a solution of 28.2 (3.6 g, 27.66 mmol, 1.0 equiv) in dichloromethane (36 mL) was added imidazole (2.82 g, 41.49 mmol, 1.5 equiv) followed by tert-butyldimethylsilyl chloride (6.22 g, 41.49 mmol, 1.5 equiv) and stirred at room temperature for 12 h. It was poured over saturated sodium bicarbonate solution, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 10% ethyl acetate in hexane as eluant) to afford 28.3. $^1$H NMR (CDCl$_3$, 400 MHz): δ 4.19-4.14 (m, 1H), 3.69 (s, 3H), 2.57-2.46 (m, 3H), 2.25-2.17 (m, 2H), 0.89 (s, 9H), 0.05 (s, 6H).

Synthesis of compound 28.4. To a solution of 28.3 (4.1 g, 16.78 mmol, 1.0 equiv) in diethyl ether (40 mL) was added lithium aluminum hydride solution (1 M in THF, 20.1 mL, 20.13 mmol, 1.2 equiv) at 0° C. The reaction mixture was stirred at room temperature for 2 h. After completion of reaction, water (4 mL) and 15% sodium hydroxide (12 mL) was added and stirred for 30 min. The reaction mixture was extracted with ethyl acetate. The combined organic layers were washed with brine, dried over anhydrous sodium sulfate, filtered and concentrated under reduced pressure. The residue was purified by flash column chromatography on silica gel (CombiFlash®, 30% ethyl acetate in hexane as eluant) to afford 28.4. $^1$H NMR (CDCl$_3$, 400 MHz): δ 4.22-4.15 (m, 1H), 3.66-3.62 (m, 2H), 2.41-2.35 (m, 2H), 2.15-2.11 (m, 1H), 2.02-1.94 (m, 1H), 1.73-1.66 (m, 2H), 0.91 (s, 9H), 0.06 (s, 6H).

Synthesis of compound 28.5. To a solution of 28.4 (2.3 g, 10.63 mmol, 1.0 equiv) in dichloromethane (25 mL) was added triethylamine (4.44 mL, 31.89 mmol, 3.0 equiv) followed by addition of methanesulfonyl chloride (2.45 mL, 31.89 mmol, 3.0 equiv) at 0° C. and stirred at room temperature for 3 h. It was poured over ice, stirred and extracted with dichloromethane. The combined organic layers were washed with saturated sodium bicarbonate solution followed brine, dried over anhydrous sodium sulfate, filtered and concentrated under reduced pressure. The residue was purified by flash column chromatography on silica gel (CombiFlash®, 12% ethyl acetate in hexane as eluant) to afford 28.5. $^1$H NMR (CDCl$_3$, 400 MHz): δ 4.24-4.16 (m, 3H), 3.03 (s, 3H), 2.45-2.39 (m, 1H), 2.20-2.14 (m, 1H), 1.78-1.69 (m, 3H), 0.89 (s, 9H), 0.05 (s, 6H).

Synthesis of compound 28.6 and 28.7. To a solution of 19.1 (2.0 g, 9.20 mmol, 1.0 equiv) and 28.5 (3.25 g, 11.04 mmol, 1.2 equiv) in DMF (7 mL) was added cesium carbonate (5.98 g, 18.40 mmol, 2.0 equiv) reaction mixture was stirred at 80° C. for 16 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 6-8% ethyl acetate in hexane as eluant) to afford 28.6. MS (ES): m/z 416.7 [M+H]$^+$ and 28.7 (0.500 g, Yield: 13.07%). MS (ES): m/z 416.6 [M+H]$^+$.

Synthesis of compound 28.8. A solution of 28.7 (0.500 g, 1.2 mmol, 1.0 equiv) and hydroxylamine hydrochloride (0.828 g, 12 mmol, 10 equiv) in ethanol:water (2:1, 10 mL) was stirred at 120° C. in a microwave reactor for 1 h. It was poured over ice-water, neutralized by 2 N sodium hydroxide and extracted with ethyl acetate. The combined organic layers were washed with brine, dried over anhydrous sodium sulfate, filtered and concentrated under reduced pressure to obtain chiral mixture which was separated by preparative HPLC to obtain 28.8. MS (ES): m/z 224.3 [M+H]$^+$ and 28.9. MS (ES): m/z 224.2 [M+H]$^+$.

Synthesis of compound 28.9. Compound 28.9 was prepared from 28.8 following the procedure described in the synthesis of 1.2. The crude product was used in the next step without purification. MS (ES): m/z 266.4 [M+H]$^+$.

Synthesis of I-28. Compound I-28 was prepared from compound 28.9 following the procedures described in each step in the synthesis of I-1. The product was purified by flash column chromatography on silica gel (CombiFlash®, 2.5% methanol in dichloromethane as eluant). MS (ES): m/z: 504.9 [M+H]$^+$, $^1$H NMR (DMSO-d6, 400 MHz): δ 10.48 (s, 1H), 9.39 (s, 1H), 8.14-8.13 (d, J=5.2 Hz, 1H), 7.64 (s, 1H), 7.35-7.33 (d, J=8.4 Hz, 1H), 7.16 (s, 1H), 6.81-6.78 (d, J=8.4 Hz, 1H), 6.61-6.60 (d, J=4 Hz, 1H), 6.50 (s, 1H), 5.02-5.01 (d, J=6.4 Hz, 1H), 4.08-4.07 (d, J=5.2 Hz, 2H), 3.93-3.91 (m, 1H), 3.62 (s, 3H), 2.32-2.29 (m, 3H), 2.02 (s, 3H), 1.70-1.68 (m, 2H), 1.37 (s, 9H).

Example 29: N-(4-((2-((5-(tert-butyl)-1-((1r,3r)-3-hydroxycyclobutyl)-1H-pyrazol-3-yl)amino)-1-methyl-1H-benzo[d]imidazol-6-yl)oxy)pyridin-2-yl)acetamide

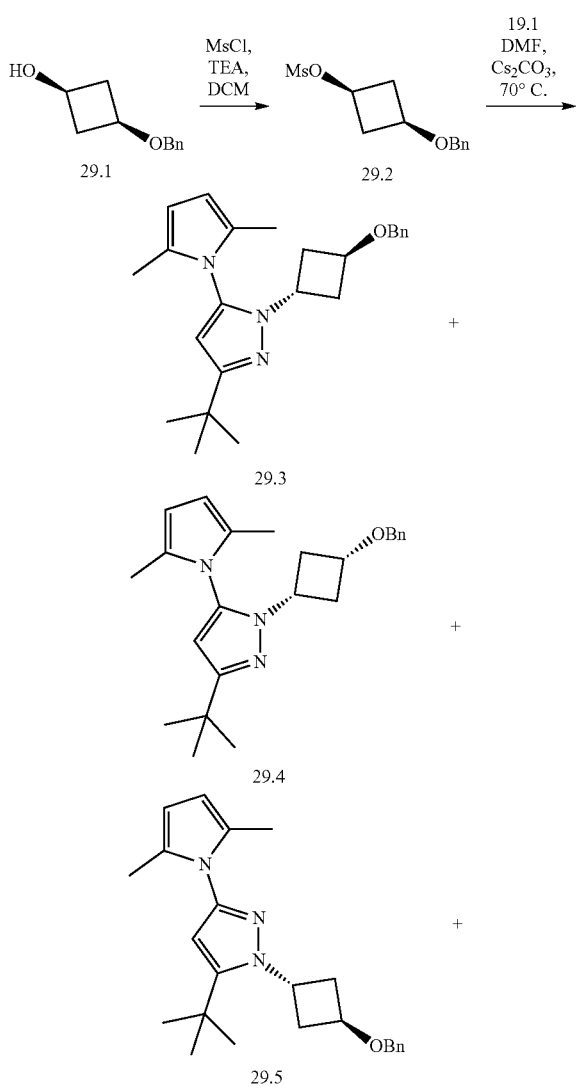

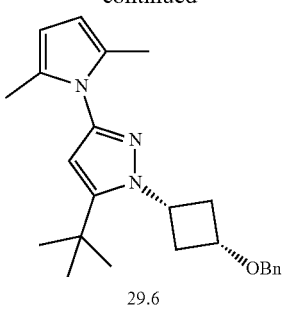

29.6

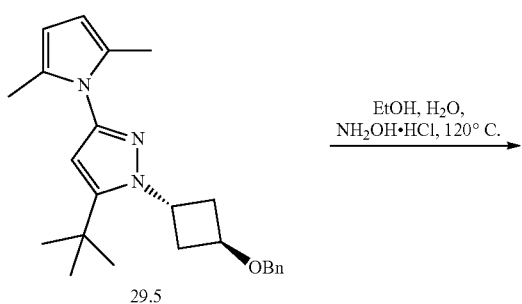

29.5

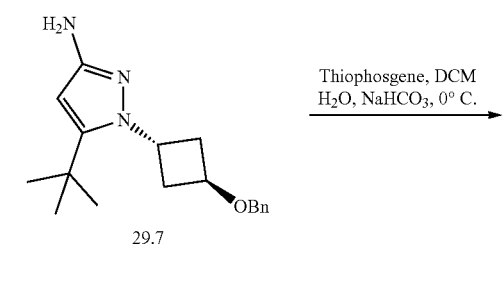

29.7

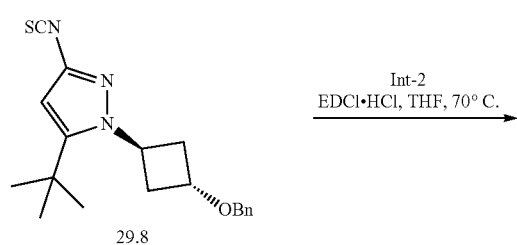

29.8

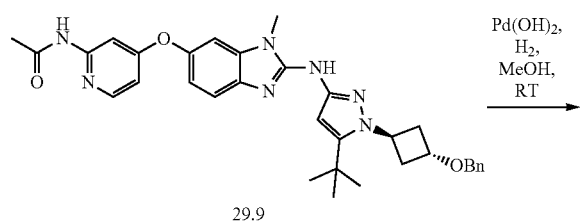

29.9

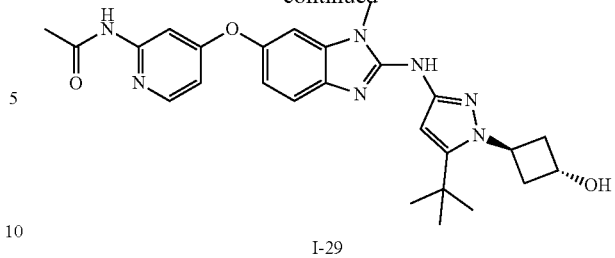

I-29

Synthesis of compound 29.2 To a solution of 29.1 (3.0 g, 16.83 mmol, 1.0 equiv) in dichloromethane (30 mL) and triethylamine (3.0 mL, 21.87 mmol, 1.3 equiv) at 0° C. was added methanesulfonyl chloride (1.7 mL, 21.87 mmol, 1.3 equiv). The reaction mixture was allowed to warm to room temperature and stirred for 12 h. It was poured over ice-water, stirred and extracted with dichloromethane. The combined organic layers were washed with brine, dried over anhydrous sodium sulfate, filtered and concentrated under reduced pressure. The residue was purified by flash column chromatography on silica gel (CombiFlash®, 20% ethyl acetate in hexane as eluant) to afford 29.2. MS (ES): m/z 257.3 [M+H]$^+$.

Synthesis of compound 29.3, 29.4, 29.5 and 29.6. Compound 29.3, 29.4, 29.5 and 29.6 were prepared from compound 19.1 and 29.2 following the procedure described in the synthesis of compound 19.3 and 19.4. The isomers were separated by flash column chromatography on silica gel (CombiFlash®, 8-12% ethyl acetate in hexane as eluant). MS (ES): m/z 378.5 [M+H]$^+$.

Synthesis of compound 29.9. Compound 29.9 was prepared from 29.5 following the procedures described in each step in the synthesis of compound I-20. The product was purified by flash column chromatography on silica gel (CombiFlash®, 2.2% methanol in dichloromethane as eluant). MS (ES): m/z 580.7 [M+H]$^+$.

Synthesis of I-29. A mixture of compound 29.9 (0.070 g, 0.120 mmol, 1.0 equiv) and 20% palladium hydroxide on carbon (0.150 g) in methanol (5 mL) was stirred at rt under 1 atm hydrogen for 12 h. The reaction mixture was filtered through a pad of Celite® and rinsed with methanol. The filtrate was concentrated under reduced pressure and the residue was purified by flash column chromatography on silica gel (CombiFlash®, 5% methanol in dichloromethane as eluant) to afford I-29. MS (ES): m/z: 490.51 [M+H]$^+$, $^1$H NMR (DMSO-d6, 400 MHz): δ 10.49 (s, 1H), 9.53 (s, 1H), 8.16-8.14 (d, J=5.2 Hz, 1H), 7.65 (s, 1H), 7.38-7.36 (d, J=8.0 Hz, 1H), 7.19 (s, 1H), 6.83-6.81 (d, J=7.6 Hz, 1H), 6.62-6.61 (d, J=3.6 Hz, 1H), 6.50 (s, 1H), 5.19-5.18 (m, 2H), 4.46 (bs, 1H), 3.64 (s, 3H), 2.74 (bs, 2H), 2.33 (bs, 2H), 2.03 (s, 3H), 1.36 (s, 9H).

Example 30: N-(4-((2-((5-(tert-butyl)-1-((1s,3s)-3-hydroxycyclobutyl)-1H-pyrazol-3-yl)amino)-1-methyl-1H-benzo[d]imidazol-6-yl)oxy)pyridin-2-yl)acetamide

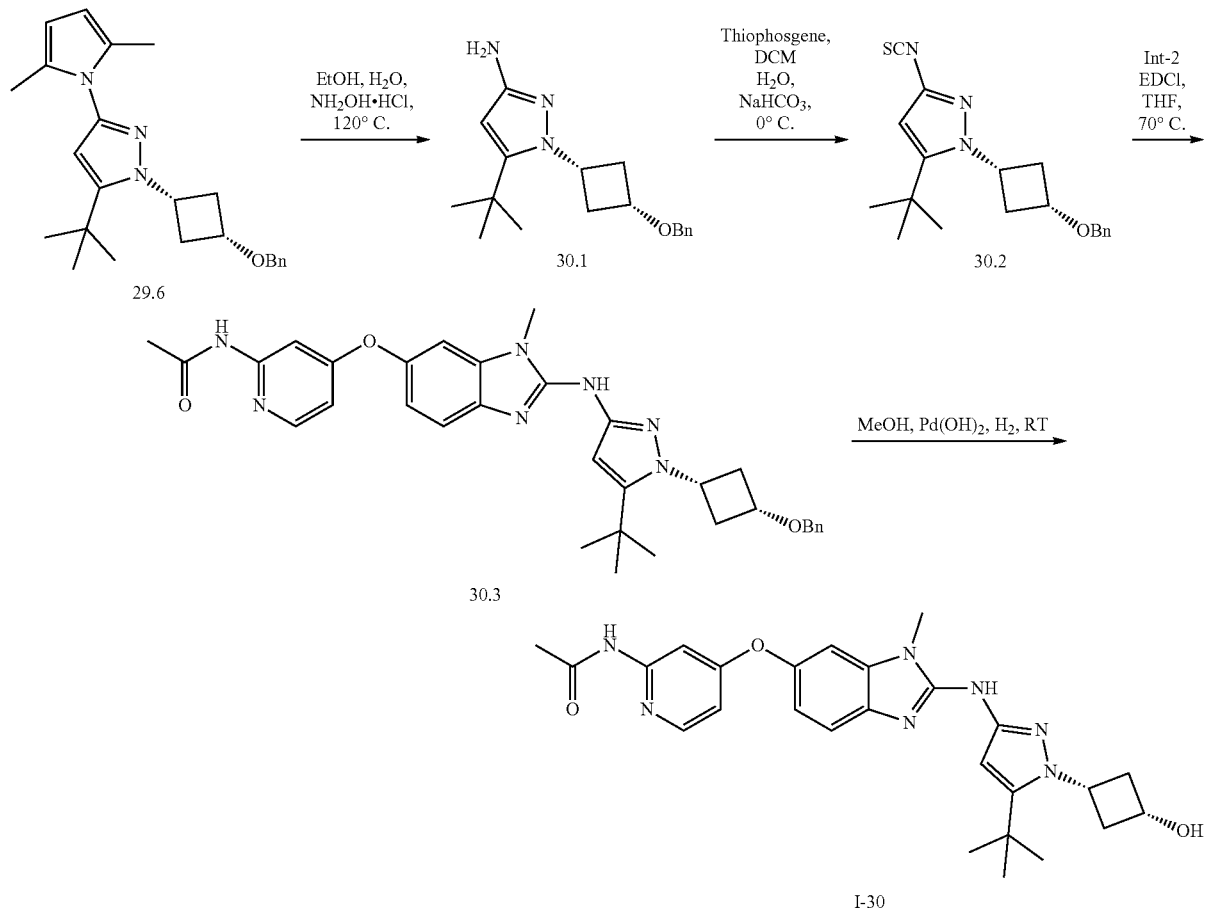

Synthesis of compound I-30. Compound I-30 was prepared from 29.6 in the same manner as that in the synthesis of I-29. The product was purified by flash column chromatography on silica gel (CombiFlash®, 5% methanol in dichloromethane as eluant). MS (ES): m/z: 490.46 [M+H]+, 1H NMR (DMSO-d6, 400 MHz): δ 10.48 (s, 1H), 9.53 (s, 1H), 8.15-8.13 (d, J=5.6 Hz, 1H), 7.64 (s, 1H), 7.36-7.34 (d, J=8.4 Hz, 1H), 7.17 (s, 1H), 6.82-6.80 (d, J=7.6 Hz, 1H), 6.61-6.60 (d, J=3.6 Hz, 1H), 6.48 (s, 1H), 5.20-5.19 (m, 2H), 4.03-4.01 (m, 1H), 3.63 (s, 3H), 3.50-3.48 (m, 2H), 2.62 (bs, 2H), 2.02 (s, 3H), 1.35 (s, 9H).

Example 31: N-(4-((2-((5-(tert-butyl)-1-(oxetan-3-ylmethyl)-1H-pyrazol-3-yl)amino)-1-methyl-1H-benzo[d]imidazol-6-yl)oxy)pyridin-2-yl)acetamide

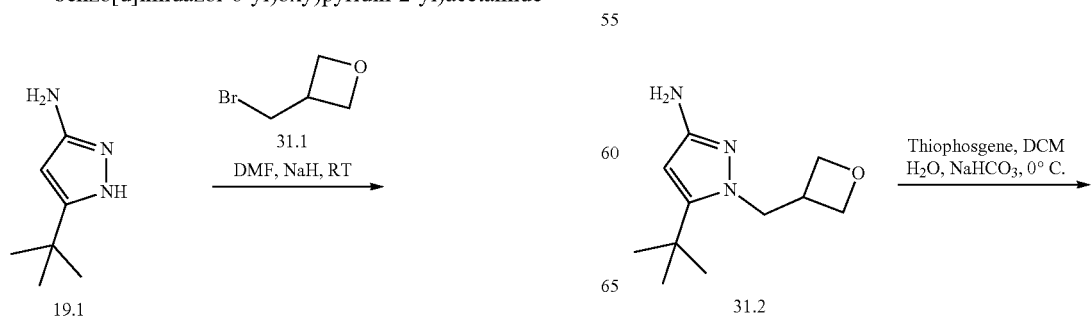

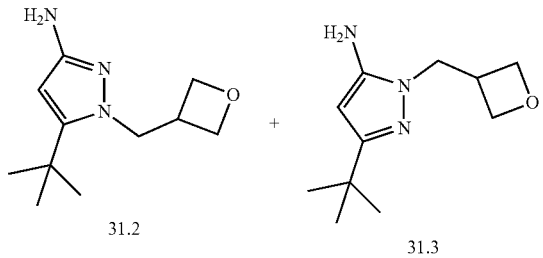

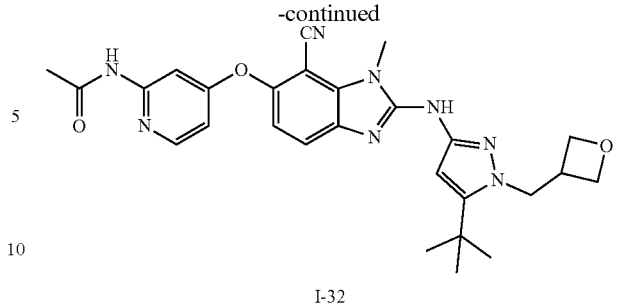

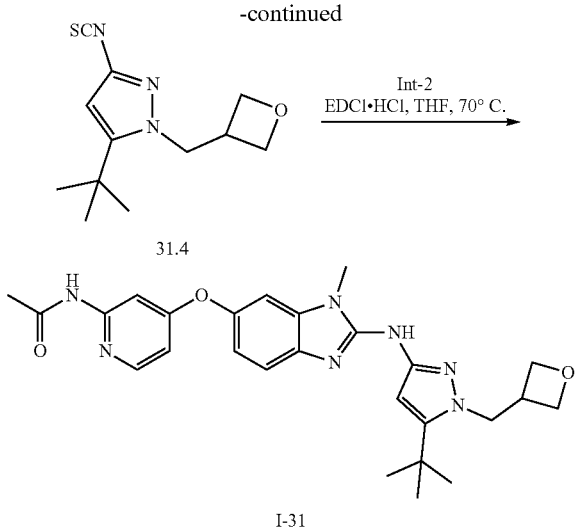

I-31

Synthesis of compound 31.2 and 31.3. To a solution of 31.1 (0.4 g, 2.65 mmol, 1.0 equiv) in DMF (5 mL) was added sodium hydride (0.165 g, 3.45 mmol, 1.3 equiv) at 0° C. and stirred for 30 min. To the solution was added 17.1 (0.0.368 g, 2.65 mmol, 1.0 equiv). The reaction mixture was stirred at room temperature for 16 h. It was poured over ice, stirred and extracted with ethyl acetate. The combined organic layers were washed with brine, dried over anhydrous sodium sulfate, filtered and concentrated under reduced pressure. The residue was purified by preparative HPLC to obtain 31.2. MS (ES): m/z 210.3 [M+H]$^+$ and 31.3. MS (ES): m/z 210.3 [M+H]$^+$.

Synthesis of compound 31.4. Compound 31.4 was prepared from 31.2 following the procedure described in the synthesis of 11.8. MS (ES): m/z 252.3 [M+H]$^+$.

Synthesis of I-31. Compound 31.4 was prepared from 31.4 and Int-2 following the procedure described in the synthesis of compound I-1. The product was purified by flash column chromatography on silica gel (CombiFlash®, 3-4% methanol in dichloromethane as eluant). MS (ES): m/z 489.8 [M+H]$^+$, $^1$H NMR (DMSO-d6, 400 MHz): δ 10.49 (s, 1H), 9.41 (s, 1H), 8.15-8.13 (d, J=5.6 Hz, 1H), 7.64 (s, 1H), 7.36-7.34 (d, J=8.4 Hz, 1H), 7.17 (s, 1H), 6.82-6.80 (d, J=7.6 Hz, 1H), 6.60 (s, 1H), 6.48 (s, 1H), 4.71-4.67 (m, 2H), 4.56-4.54 (m, 2H), 4.42-4.40 (m, 2H), 3.60 (bs, 3H), 3.50-3.47 (m, 1H), 2.02 (s, 3H), 1.37 (s, 9H).

Example 32: N-(4-((2-((5-(tert-butyl)-1-(oxetan-3-ylmethyl)-1H-pyrazol-3-yl)amino)-7-cyano-1-methyl-1H-benzo[d]imidazol-6-yl)oxy)pyridin-2-yl)acetamide

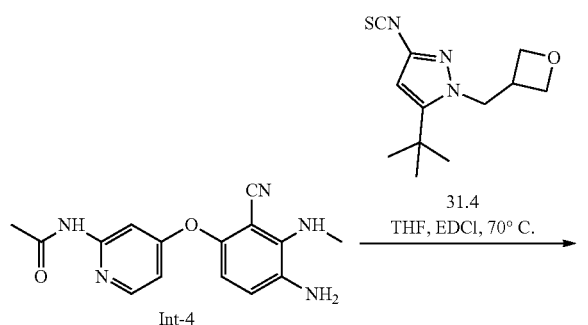

I-32

Synthesis of I-32. Compound I-32 was prepared from 31.4 and Int-4 following the procedure described in the synthesis of compound I-1. The product was purified by flash column chromatography on silica gel (CombiFlash®, 2.0% methanol in dichloromethane as eluant). MS (ES): m/z: 515.15 [M+H]$^+$, $^1$H NMR (DMSO-d6, 400 MHz): δ 10.61 (s, 1H), 9.79 (s, 1H), 8.22 (bs, 1H), 7.68-7.58 (m, 2H), 7.04 (bs, 1H), 6.70 (bs, 1H), 6.51-6.48 (m, 1H), 4.69 (bs, 2H), 4.54 (bs, 2H), 4.29 (bs, 2H), 3.90 (s, 3H), 3.77 (s, 1H), 2.04 (s, 3H), 1.38 (s, 9H).

Example 33: N-(4-((1-methyl-2-((1-((tetrahydro-2H-pyran-4-yl)methyl)-5-(trifluoromethyl)-1H-pyrazol-3-yl)amino)-1H-benzo[d]imidazol-6-yl)oxy)pyridin-2-yl)acetamide

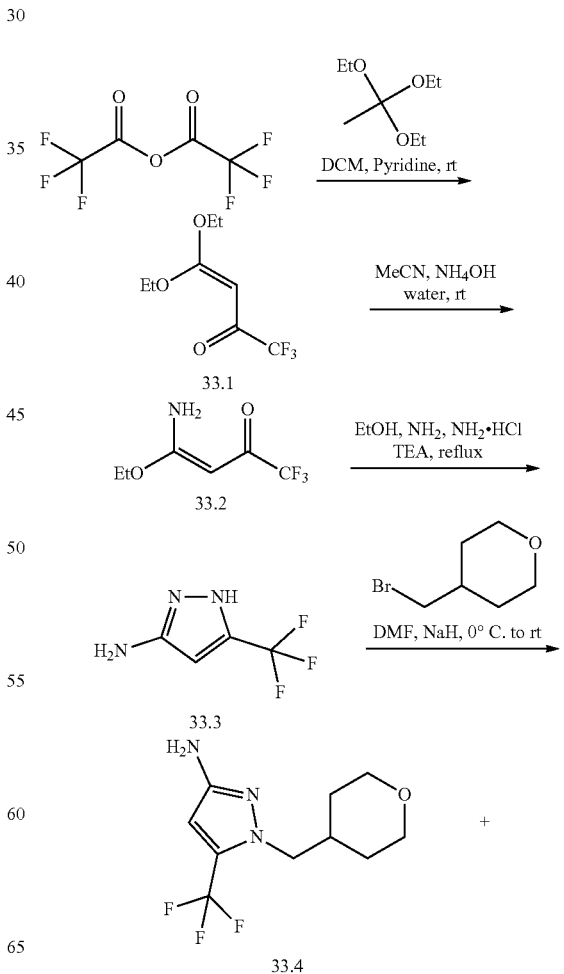

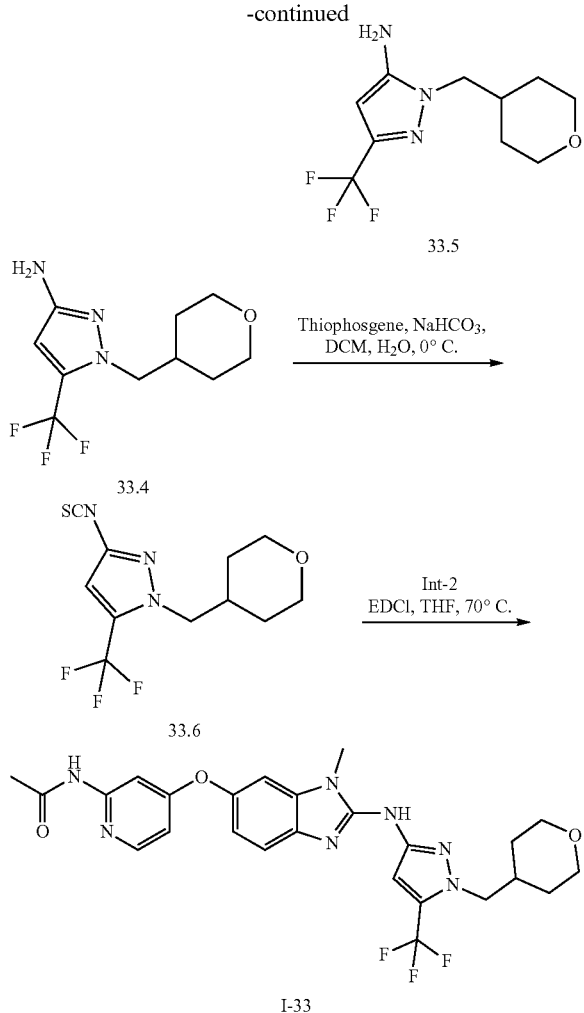

Synthesis of compound 33.1. To a solution of 1,1,1-triethoxyethane (20 g, 123.28 mmol, 1.0 equiv) and pyridine (21 mL, 258.8 mmol, 2.1 equiv) in dichloromethane (200 mL) at 0° C. was added trifluoroacetic anhydride (52 g, 246.57 mmol, 2.0 equiv). The reaction solution was allowed to warm to rt and stirred for 16 h. It was poured over saturated sodium bicarbonate solution, stirred and extracted with ethyl acetate. The combined organic layers were washed with brine, dried over anhydrous sodium sulfate, filtered and concentrated under reduced pressure to obtain 33.1. MS (ES): m/z 213.2 [M+H]$^+$.

Synthesis of compound 33.2. To a solution of 33.1 (14.2 g, 66.93 mmol, 1.0 equiv) in acetonitrile (150 mL) was added aqueous ammonia solution (28 mL) at 0° C. The reaction mixture was allowed to warm to rt and stirred for 24 h. It was poured over ice-water, stirred and extracted with ethyl acetate. The combined organic layers were washed with brine, dried over anhydrous sodium sulfate, filtered and concentrated under reduced pressure to obtain crude which was triturated with n-pentane to obtain 33.2. MS (ES): m/z 184.2 [M+H]$^+$.

Synthesis of compound 33.3. To a solution of 33.2 (7.0 g, 38.22 mmol, 1.0 equiv) in ethanol (70 mL) was added triethylamine (5.3 mL, 38.22 mmol, 1.0 equiv) followed by addition of hydrazine hydrochloride (2.61 g, 38.22 mmol, 1.0 equiv). The reaction mixture was heated to reflux for 12 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 30% ethyl acetate in hexane as eluant) to afford 33.3. MS (ES): m/z 152.1 [M+H]$^+$.

Synthesis of compound 33.4 and 33.5. To a solution of 4-(bromomethyl)tetrahydro-2H-pyran (0.7 g, 4.63 mmol, 1.0 equiv) in DMF (8 mL) was added sodium hydride (0.288 g, 6.019 mmol, 1.3 equiv) at 0° C. and stirred for 30 min. To the solution was added 33.3 (0.829 g, 4.63 mmol, 1.0 equiv). The reaction mixture was allowed to warm to rt and stirred for 16 h. It was poured over ice, stirred and extracted with ethyl acetate. The combined organic layers were washed with brine, dried over anhydrous sodium sulfate, filtered and concentrated under reduced pressure. The residue was purified by preparative HPLC to obtain 33.4. MS (ES): m/z 250.4 [M+H]$^+$ and 33.5. MS (ES): m/z 250.4 [M+H]$^+$.

Synthesis of compound 33.6. Compound 33.6 was prepared from 33.4 following the procedure described in the synthesis of 11.8. The crude product was used without further purification. MS (ES): m/z 292.3 [M+H]$^+$.

Synthesis of I-33. Compound I-33 was prepared from 33.6 and Int-2, following the procedure described in the synthesis of I-1. The product was purified by flash column chromatography on silica gel (CombiFlash®, 10% methanol in dichloromethane as eluant). MS (ES): m/z: 530.49 [M+H]$^+$, $^1$H NMR (DMSO-d6, 400 MHz): δ 10.48 (s, 1H), 10.07 (s, 1H), 8.15-8.13 (d, J=6.0 Hz, 1H), 7.64 (s, 1H), 7.43-7.41 (d, J=8.4 Hz, 1H), 7.32 (s, 1H), 7.23 (s, 1H), 6.85-6.83 (d, J=6.8 Hz, 1H), 6.61-6.60 (d, J=3.2 Hz, 1H), 4.04-4.02 (m, 2H), 3.87-3.84 (m, 2H), 3.67 (s, 3H), 2.20 (bs, 1H), 2.02 (s, 3H), 1.56 (bs, 1H), 1.48-1.45 (m, 2H), 1.35-1.23 (m, 3H).

Example 34: N-(4-((7-cyano-1-methyl-2-((1-((tetrahydro-2H-pyran-4-yl)methyl)-5-(trifluoromethyl)-1H-pyrazol-3-yl)amino)-1H-benzo[d]imidazol-6-yl)oxy)pyridin-2-yl)acetamide

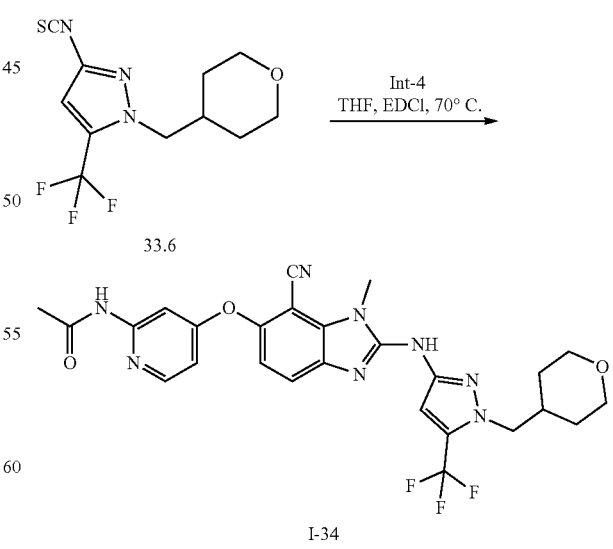

Synthesis of I-34. Compound I-34 was prepared from 33.6 and Int-4, following the procedure described in the synthesis of I-1. The residue was purified by flash column chromatography on silica gel (CombiFlash®, 1.8% methanol in dichloromethane as eluant). MS (ES): m/z: 555.42 [M+H]+, $^1$H NMR (DMSO-d6, 400 MHz): δ 10.61 (s, 1H), 10.41 (s, 1H), 8.22-8.21 (d, J=5.6 Hz, 1H), 7.75-7.73 (d, J=8.4 Hz, 1H), 7.68 (s, 1H), 7.30 (s, 1H), 7.07-7.05 (d, J=8.4 Hz, 1H), 6.71-6.70 (d, J=4 Hz, 1H), 4.06-4.04 (m, 2H), 3.94 (s, 3H), 3.87-3.85 (m, 2H), 3.27-3.24 (m, 2H), 2.20 (bs, 1H), 2.04 (s, 3H), 1.48-1.45 (m, 2H), 1.35-1.27 (m, 2H).
Example 35: N-(4-((2-((1-(((1s,4s)-4-hydroxycyclohexyl)methyl)-5-(trifluoromethyl)-1H-pyrazol-3-yl)amino)-1-methyl-1H-benzo[d]imidazol-6-yl)oxy)pyridin-2-yl)acetamide
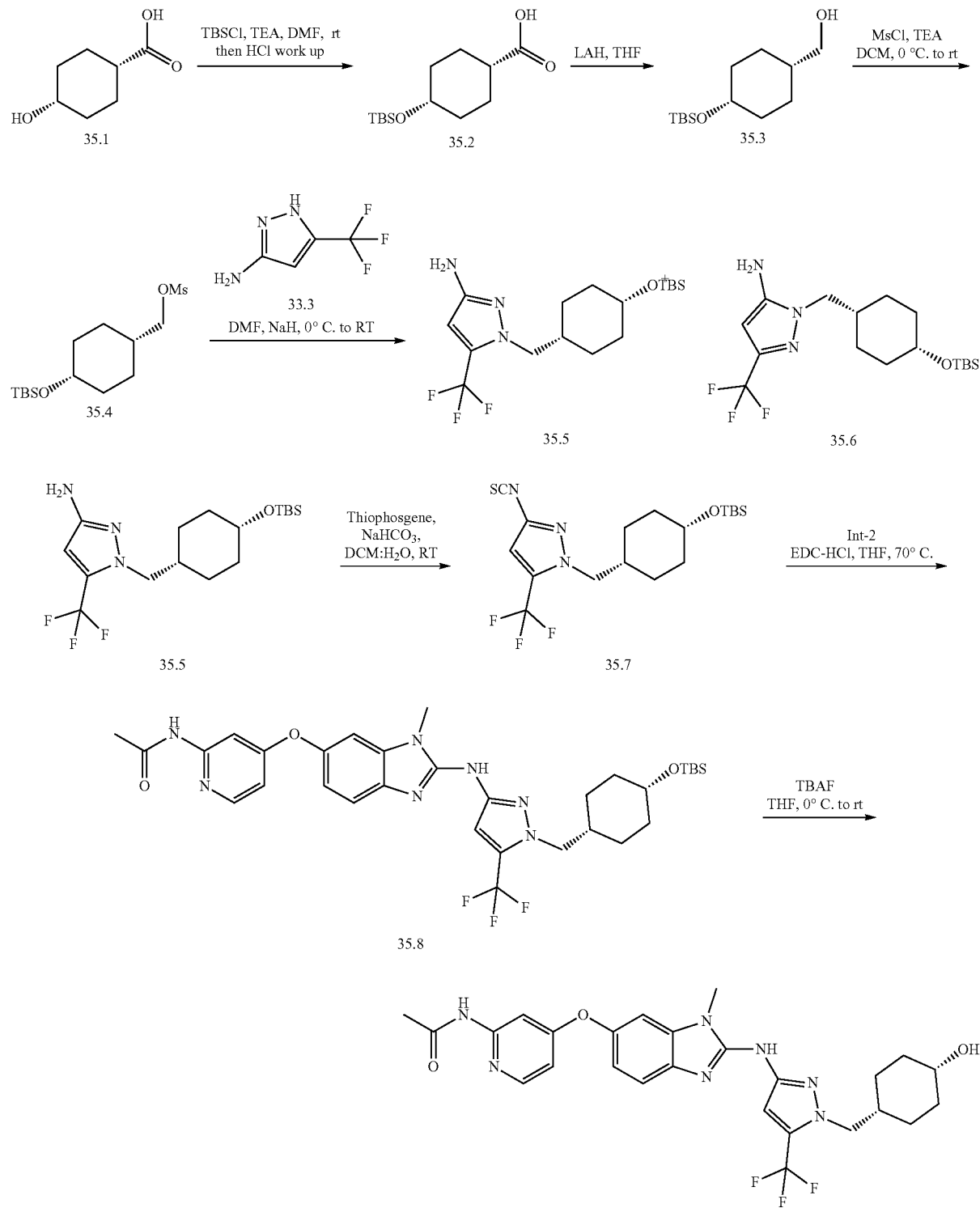

Synthesis of compound 35.2. To a solution of 35.1 (5.0 g, 34.68 mmol, 1.0 equiv) and triethylamine (10.6 mL, 76.29 mmol, 2.2 equiv) in DMF (30 mL) was added tert-butyldimethylsilyl chloride (11.5 g, 76.29 mmol, 2.2 equiv) and stirred at room temperature for 2 h. It was poured over ice-water, acidified with 1 M hydrochloric acid to pH=4, and extracted with diethyl ether. The organic layer was separated washed with brine and concentrated under reduced pressure to obtain a crude product. It was dissolved in a mixture of methanol and THF (1:1, 20 mL) and was added a 5 M aqueous solution of sodium hydroxide (10 mL) at room temperature. The mixture was stirred for 3 h and was concentrated to one-half volume. It was acidified with 2 M hydrochloric acid to pH=4 and extracted with diethyl ether. The combined organic layers were washed with brine, dried over anhydrous sodium sulfate, filtered and concentrated under reduced pressure to obtain 35.2. MS (ES): m/z 259.4 $[M+H]^+$.

Synthesis of compound 35.3. To a solution of 35.2 (3.0 g, 11.61 mmol, 1.0 equiv) in THF (30 mL) was added a solution of lithium aluminum hydride (1 M in THF, 23.2 mL, 23.2 mmol, 2.0 equiv) at 0° C. The reaction mixture was allowed to warm to rt and stirred or 3 h. It was carefully poured over ice-water, neutralized with 1 M hydrochloric acid and extracted with ethyl acetate. The combined organic layers were washed with brine, dried over anhydrous sodium sulfate, filtered and concentrated under reduced pressure to obtain 35.3. MS (ES): m/z 245.5 $[M+H]^+$.

Synthesis of compound 35.4. To a solution of 35.3 (1.7 g, 6.95 mmol, 1.0 equiv) and triethylamine (1.25 mL, 9.035 mmol, 1.3 equiv) in dichloromethane (25 mL) was added methanesulfonyl chloride (1.6 mL, 20.85 mmol, 1.3 equiv) at 0° C. The reaction solution was allowed to warm to rt and stirred for 12 h. It was poured over ice, stirred and extracted with dichloromethane. The combined organic layers were washed with brine, dried over anhydrous sodium sulfate, filtered and concentrated under reduced pressure. The residue was purified by flash column chromatography on silica gel (CombiFlash®, 5% ethyl acetate in hexane as eluant) to afford 35.4. MS (ES): m/z 323.5 $[M+H]^+$.

Synthesis of compound 35.5 and 35.6. To a solution of 33.3 (0.6 g, 3.97 mmol, 1.0 equiv) in DMF (8 mL) was added sodium hydride (0.247 g, 5.161 mmol, 1.3 equiv) at 0° C. and stirred for 30 min. To the mixture was added 35.4 (1.28 g, 3.97 mmol, 1.0 equiv). The reaction mixture was stirred at room temperature for 16 h. It was poured over ice, stirred and extracted with ethyl acetate. The combined organic layers were washed with brine, dried over anhydrous sodium sulfate, filtered and concentrated under reduced pressure. The residue was purified by preparative HPLC to obtain 35.5. MS (ES): m/z 378.5 $[M+H]^+$ and 35.6. MS (ES): m/z 378.5 $[M+H]^+$.

Synthesis of compound 35.7. Compound 35.7 was prepared from 35.5 following the procedure described in the synthesis of 11.8. The crude product was used in the next step without further purification. MS (ES): m/z 420.5 $[M+H]^+$.

Synthesis of compound 35.8. Compound 35.8 was prepared from 35.5 and Int-2 following the procedure described in the synthesis of I-1. The product was purified by flash column chromatography on silica gel (CombiFlash®, 2% methanol in dichloromethane as eluant). MS (ES): m/z 658.8 $[M+H]^+$.

Synthesis of I-35. To a solution of 35.8 (0.062 g, 0.094 mmol, 1.0 equiv) in THF (2 mL) was added a solution of tetrabutylammonium fluoride (1 M in THF, 5 mL). The reaction mixture was stirred at 50° C. for 3 h. It was cooled to room temperature, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 5% methanol in dichloromethane as eluant) to afford I-35. MS (ES): m/z: 544.57 $[M+H]^+$, $^1$H NMR (DMSO-d6, 400 MHz): δ 10.49 (s, 1H), 10.06 (s, 1H), 8.15-8.13 (d, J=5.6 Hz, 1H), 7.64 (s, 1H), 7.43-7.41 (d, J=8.4 Hz, 1H), 7.30 (s, 1H), 7.23 (s, 1H), 6.85-6.83 (d, J=7.2 Hz, 1H), 6.62-6.60 (d, J=5.2 Hz, 1H), 4.57-4.56 (d, 1H), 4.02-3.95 (m, 2H), 3.67 (s, 3H), 3.03 (bs, 1H), 2.02 (s, 3H), 1.85-1.82 (m, 2H), 1.55 (bs, 2H), 1.34-1.30 (m, 1H), 1.30 (bs, 2H), 1.11-1.03 (m, 2H).

Example 36: (S)—N-(4-((1-methyl-2-((1-((tetrahydro-2H-pyran-3-yl)methyl)-5-(trifluoromethyl)-1H-pyrazol-3-yl)amino)-1H-benzo[d]imidazol-6-yl)oxy)pyridin-2-yl)acetamide and (R)—N-(4-((1-methyl-2-((1-((tetrahydro-2H-pyran-3-yl)methyl)-5-(trifluoromethyl)-1H-pyrazol-3-yl)amino)-1H-benzo[d]imidazol-6-yl)oxy)pyridin-2-yl)acetamide

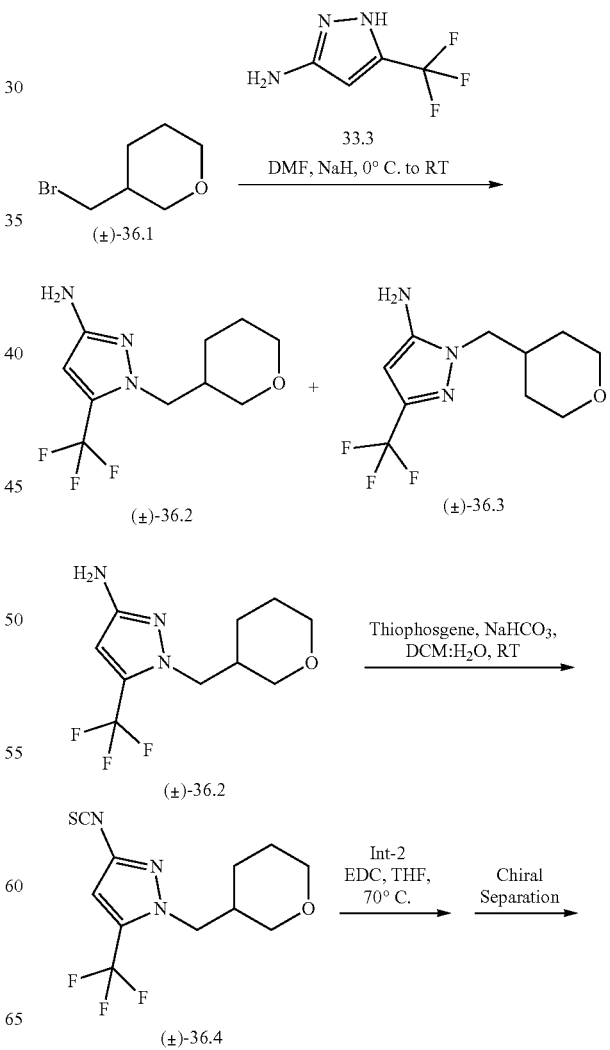

-continued

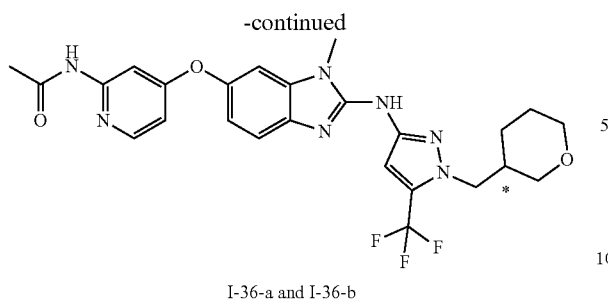

I-36-a and I-36-b

Synthesis of compound (±)-36.2 and (±)-36.3. To a solution of 33.3 (0.5 g, 3.31 mmol, 1.0 equiv) in DMF (8 mL) was added sodium hydride (0.206 g, 4.303 mmol, 1.3 equiv) at 0° C. and stirred for 30 min. To the mixture was added 3-(bromomethyl)tetrahydro-2H-pyran ((±)-36.1, 0.592 g, 3.31 mmol, 1.0 equiv). The reaction mixture was stirred at room temperature for 16 h. It was poured over ice, stirred and extracted with ethyl acetate. The combined organic layers were washed with brine, dried over anhydrous sodium sulfate, filtered and concentrated under reduced pressure. The residue was purified by preparative HPLC to obtain (±)-36.2. MS (ES): m/z 250.3 [M+H]$^+$ and (±)-36.3. MS (ES): m/z 250.3 [M+H]$^+$.

Synthesis of compound (±)-36.4. Compound (±)-36.4 was prepared from (±)-36.2 following the procedure as described in the synthesis of 11.8. The crude product was used in the next step without further purification. MS (ES): m/z 292.3 [M+H]$^+$.

Synthesis of compound (±)-I-36. Compound (±)-I-36 was prepared from (±)-36.4 and Int-2 following the procedure described in the synthesis of I-1. MS (ES): m/z 530.5 [M+H]$^+$.

I-36-a and I-36-b. Enantiomers of (±)-I-36 were separated on SFC (column: CHIRALCEL OJ-H (250 mm×4.6 mm, 5 μm); eluant: 0.1% DEA in methanol; flow rate: 4 mL/min) to afford first eluting fraction (I-36-a) and second eluting fraction (I-36-b). (*Absolute stereochemistry not determined.)

I-36-a. MS (ES): m/z: 530.44 [M+H]$^+$, $^1$H NMR (DMSO-d6, 400 MHz): δ 10.48 (s, 1H), 10.06 (s, 1H), 8.15-8.13 (d, J=6 Hz, 1H), 7.64 (s, 1H), 7.43-7.41 (m, 1H), 7.32 (s, 1H), 7.23 (s, 1H), 6.86-6.83 (d, J=10.4 Hz, 1H), 6.62-6.60 (d, J=6.4 Hz, 1H), 4.07-4.01 (m, 2H), 3.71 (bs, 1H), 3.67 (s, 3H), 3.27-3.23 (m, 2H), 2.19 (bs, 1H), 2.02 (s, 3H), 1.69-1.60 (m, 3H), 1.49 (bs, 1H), 1.34-1.23 (m, 1H).

I-36-b. MS (ES): m/z: 530.49 [M+H]$^+$, $^1$H NMR (DMSO-d6, 400 MHz): δ 10.49 (s, 1H), 10.08 (s, 1H), 8.16-8.14 (d, J=6 Hz, 1H), 7.65 (s, 1H), 7.44-7.42 (d, J=8.4 Hz, 1H), 7.33 (s, 1H), 7.23 (s, 1H), 6.86-6.84 (d, J=8.4 Hz, 1H), 6.62-6.61 (d, J=5.6 Hz, 1H), 4.11-4.00 (m, 2H), 3.71 (bs, 1H), 3.68 (s, 3H), 3.28-3.23 (m, 2H), 2.20 (bs, 1H), 2.03 (s, 3H), 1.70-1.61 (m, 3H), 1.50 (bs, 1H), 1.34-1.24 (m, 1H).

Example 37: N-(4-((2-((1-(2-oxaspiro[3.3]heptan-6-yl)-5-(trifluoromethyl)-1H-pyrazol-3-yl)amino)-1-methyl-1H-benzo[d]imidazol-6-yl)oxy)pyridin-2-yl)acetamide

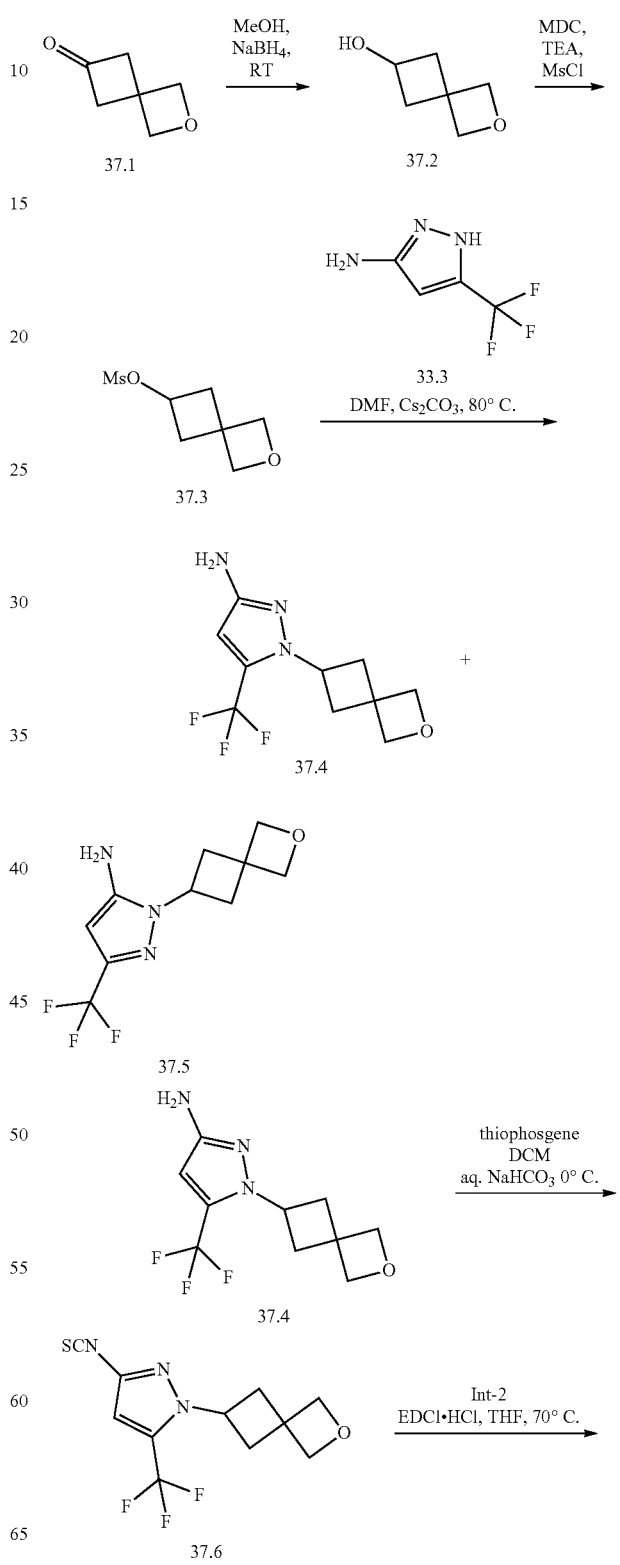

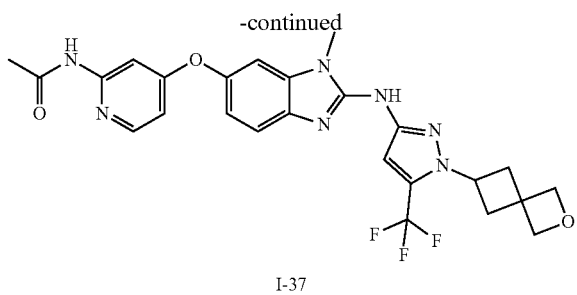

I-37

Synthesis of compound 37.2. To a solution of 37.1 (0.600 g, 5.35 mmol, 1.0 equiv) in methanol (10 mL) was added sodium borohydride (0.203 g, 5.35 mmol, 1.0 equiv) in small portions at 0° C. The reaction mixture was stirred at 0° C. for 2 h. It was poured over ice-water, stirred and extracted with ethyl acetate. The combined organic layers were washed with brine, dried over anhydrous sodium sulfate, filtered and concentrated under reduced pressure to obtain 37.2. MS (ES): m/z 115.2 [M+H]$^+$.

Synthesis of compound 37.3. To a solution of 37.2 (0.540 g, 4.73 mmol, 1.0 equiv) and triethylamine (1.64 mL, 11.82 mmol, 2.5 equiv) in dichloromethane (10 mL) was added methanesulfonyl chloride (0.71 mL, 9.46 mmol, 2.0 equiv) at 0° C. The reaction mixture was stirred at room temperature for 12 h. It was poured over ice-water, stirred and extracted with dichloromethane. The combined organic layers were washed with brine, dried over anhydrous sodium sulfate, filtered and concentrated under reduced pressure. The residue was purified by flash column chromatography on silica gel (CombiFlash®, 40% ethyl acetate in hexane as eluant) to afford 37.3. MS (ES): m/z 193.2 [M+H]$^+$.

Synthesis of compound 37.4 and 37.5. To a solution of 37.3 (0.4 g, 2.08 mmol, 1.0 equiv) and 33.3 (0.314 g, 2.08 mmol, 1.0 equiv) in DMF (7 mL) was added cesium carbonate (1.352 g, 4.16 mmol, 2.0 equiv) reaction mixture was stirred at 80° C. for 5 h. It was poured over ice-water, stirred and extracted with ethyl acetate. The combined organic layers were washed with brine, dried over anhydrous sodium sulfate, filtered and concentrated under reduced pressure. The residue was purified by preparative HPLC to obtain 37.4. MS (ES): m/z 248.2 [M+H]$^+$ and 37.5. MS (ES): m/z 248.3 [M+H]$^+$.

Synthesis of compound 37.6. Compound 37.6 was prepared from 37.4 following the procedure described in the synthesis of 11.8. The crude product was used in the next step without further purification. MS (ES): m/z 290.2 [M+H]$^+$.

Synthesis of I-37. Compound I-37 was prepared from 37.6 following the procedure described in the synthesis of I-1. The product was purified by flash column chromatography on silica gel (CombiFlash®, 1.5% methanol in dichloromethane as eluant). MS (ES): m/z: 527.8 [M+H]$^+$, $^1$H NMR (DMSO-d6, 400 MHz): δ 10.49 (s, 1H), 10.10 (s, 1H), 8.15-8.13 (d, J=6.0 Hz, 1H), 7.64 (s, 1H), 7.42-7.40 (d, J=8.4 Hz, 1H), 7.32 (s, 1H), 7.23-7.22 (d, J=1.6 Hz, 1H), 6.85-6.83 (m, 1H), 6.62-6.60 (m, 1H), 4.70 (s, 2H), 4.58 (s, 2H), 3.67 (s, 3H), 3.41-3.39 (m, 1H), 2.80-2.78 (m, 4H), 2.02 (s, 3H).

Example 38: N-(4-((2-(((1-(((1r,4r)-4-hydroxycyclohexyl)methyl)-5-(trifluoromethyl)-1H-pyrazol-3-yl)amino)-1-methyl-1H-benzo[d]imidazol-6-yl)oxy)pyridin-2-yl)acetamide

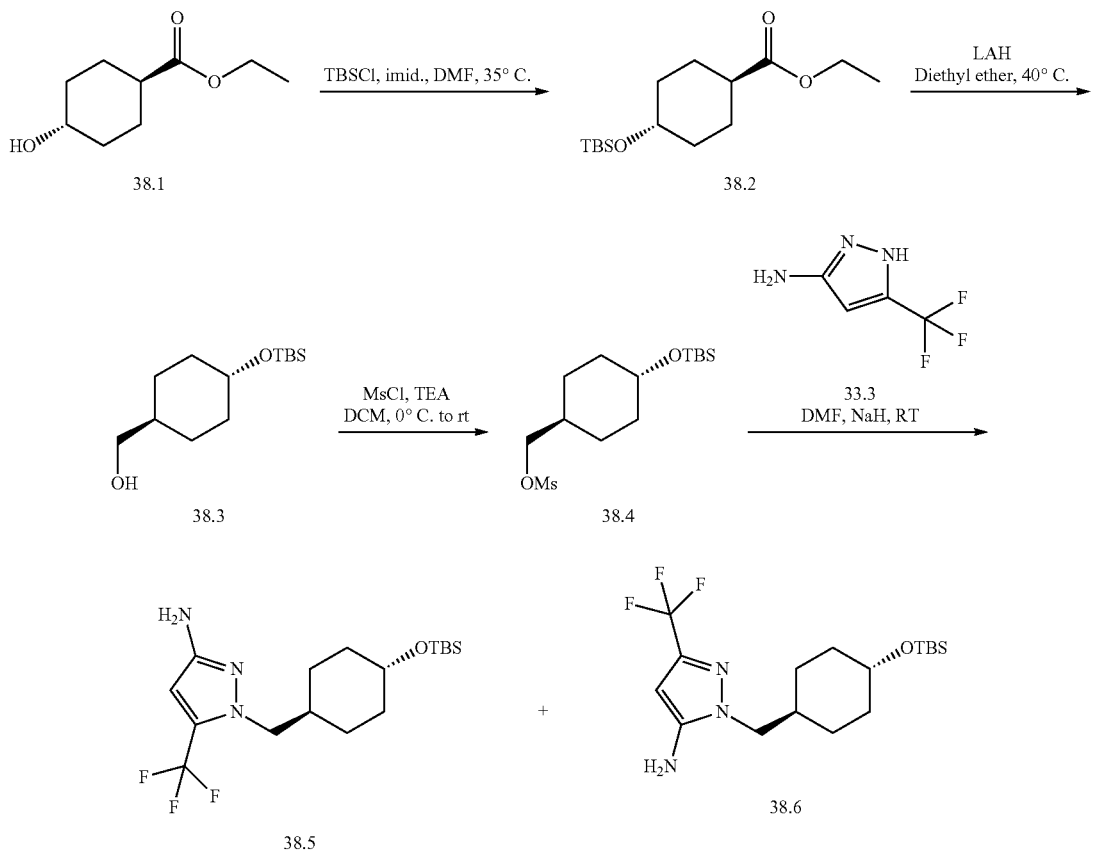

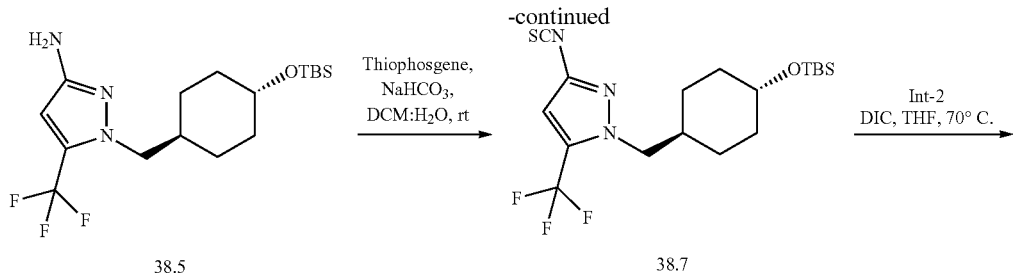

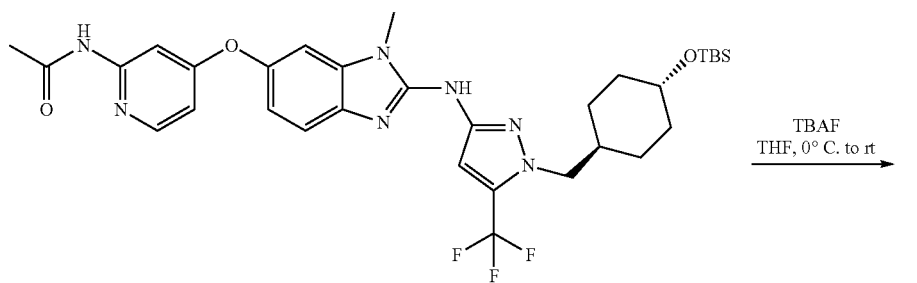

38.8

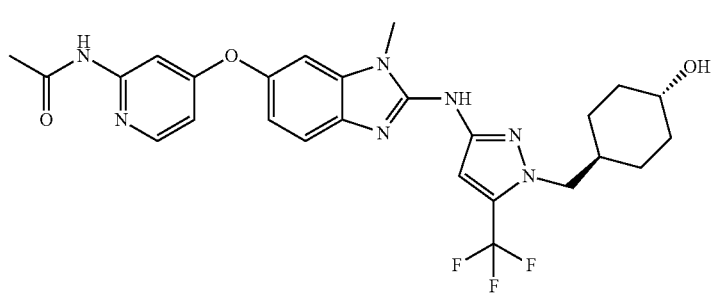

I-38

Synthesis of compound 38.2. To a solution of 38.1 (5.0 g, 29.03 mmol, 1.0 equiv) and imidazole (5.0 g, 72.57 mmol, 1.2 equiv) in DMF (25 mL) was added tert-butyldimethylsilyl chloride (5.2 g, 34.83 mmol, 1.2 equiv) and stirred at room temperature for 16 h. It was poured over saturated sodium bicarbonate solution, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 10% ethyl acetate in hexane as eluant) to afford 38.2. MS (ES): m/z 287.5 [M+H]+.

Synthesis of compound 38.3. To a solution of 38.2 (4.2 g, 14.66 mmol, 1.0 equiv) in diethyl ether (42 mL) was added a solution of lithium aluminum hydride (1 M in THF, 16.1 mL, 16.12 mmol, 1.1 equiv) at 0° C. The reaction mixture was allowed to warm to rt and stirred for 4 h. It was carefully poured over ice, stirred and extracted with ethyl acetate. The combined organic layers were washed with brine, dried over anhydrous sodium sulfate, filtered and concentrated under reduced pressure to obtain 38.3. MS (ES): m/z 245.5 [M+H]+.

Synthesis of compound 38.4. Compound 38.4 was prepared from 38.3 following the procedure described in the synthesis of 35.4. The product was purified by flash column chromatography on silica gel (CombiFlash®, 12% ethyl acetate in hexane as eluant). MS (ES): m/z 323.5 [M+H]+.

Synthesis of compound 38.5 and 38.6. Compounds 38.5 and 38.6 were prepared from 38.4 and 33.3 following the procedure described in the synthesis of 35.5 and 35.6. The isomers were isolated by preparative HPLC to obtain 38.5. MS (ES): m/z 378.5 [M+H]+ and 38.6. MS (ES): m/z 378.5 [M+H]+.

Synthesis of compound 38.7. Compound 38.7 was prepared from 38.5 following the procedures described in the synthesis of 11.8. The crude product was used in the next step without further purification. MS (ES): m/z 420.5 [M+H]+.

Synthesis of compound 38.8. Compound 38.8 was prepared from 38.7 and Int-2 following the procedure described in the synthesis of 1-2. The product was purified by flash column chromatography on silica gel (CombiFlash®, 2% methanol in dichloromethane as eluant). MS (ES): m/z 658.8 [M+H]+.

Synthesis of compound I-38. Compound I-38 was prepared from 38.8 following the procedure described in the synthesis of I-35. The product was purified by flash column chromatography on silica gel (CombiFlash®, 5% methanol in dichloromethane as eluant). MS (ES): m/z: 544.49 [M+H]+, 1H NMR (DMSO-d6, 400 MHz): δ 10.48 (s, 1H), 10.05 (s, 1H), 8.15-8.13 (d, J=5.6 Hz, 1H), 7.64 (s, 1H), 7.43-7.41 (d, J=8.4 Hz, 1H), 7.30 (s, 1H), 7.22 (s, 1H), 6.85-6.83 (d, J=7.2 Hz, 1H), 6.62-6.60 (d, J=5.2 Hz, 1H), 4.56-4.55 (d, 1H), 4.04-4.02 (m, 2H), 3.67 (s, 3H), 2.02 (s, 3H), 1.85-1.82 (m, 2H), 1.55 (bs, 2H), 1.34-1.30 (m, 1H), 1.30 (bs, 2H), 1.11-1.03 (m, 2H).

Example 39: N-(4-((2-((1-(2-acetyl-2-azaspiro[3.3]heptan-6-yl)-5-(trifluoromethyl)-1H-pyrazol-3-yl)amino)-1-methyl-1H-benzo[d]imidazol-6-yl)oxy)pyridin-2-yl)acetamide
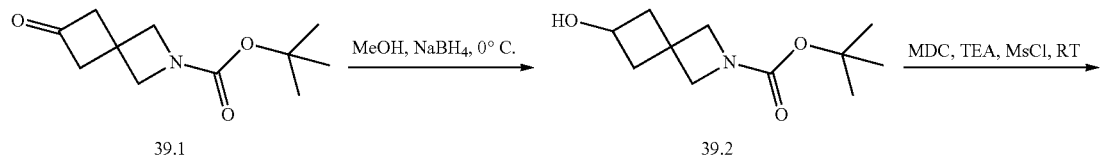
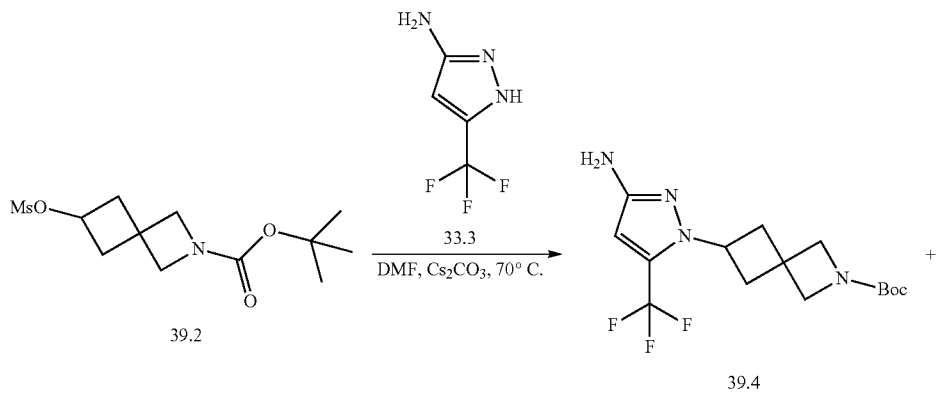
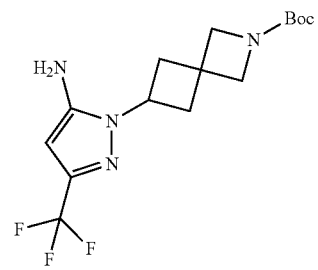
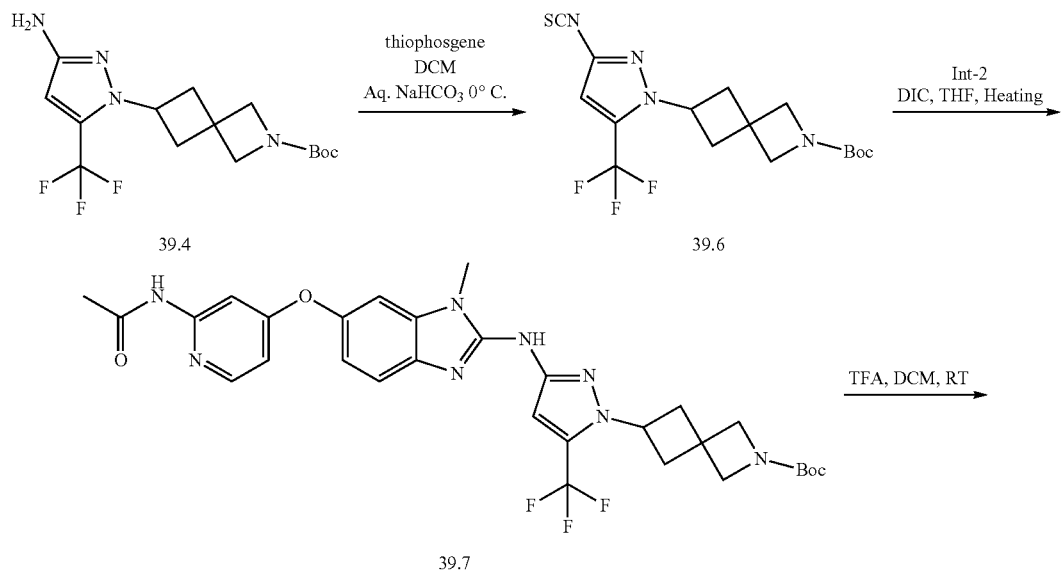

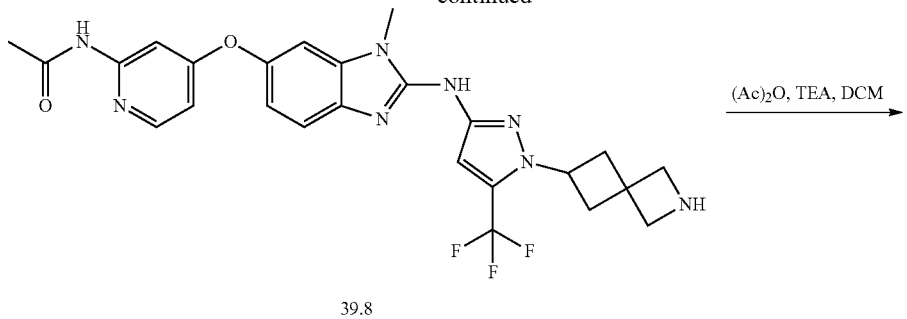

39.8

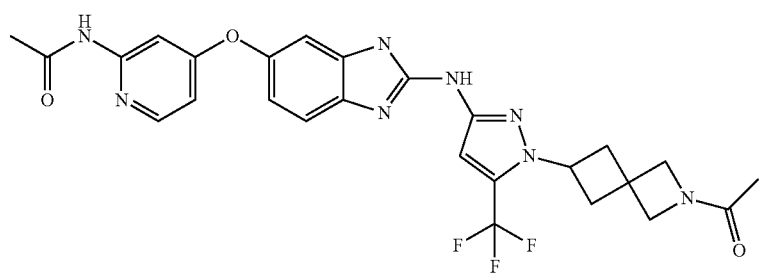

I-39

Synthesis of compound 39.2. To a solution of 39.1 (2.0 g, 9.47 mmol, 1.0 equiv) in methanol (20 mL) was added sodium borohydride (1.439 g, 37.88 mmol, 4.0 equiv) in small portions at 0° C. The reaction mixture was stirred at 0° C. for 2 h. It was poured over ice-water, stirred and extracted with ethyl acetate. The combined organic layers were washed with brine, dried over anhydrous sodium sulfate, filtered and concentrated under reduced pressure to obtain 39.2. MS (ES): m/z 214.3 [M+H]+.

Synthesis of compound 39.3. To a solution of 39.2 (1.6 g, 7.5 mmol, 1.0 equiv) and triethylamine (1.35 mL, 9.75 mmol, 1.3 equiv) in dichloromethane (20 mL) was added methanesulfonyl chloride (0.75 mL, 9.75 mmol, 1.3 equiv) at 0° C. The reaction mixture was stirred at room temperature for 12 h. It was poured over ice-water, stirred and extracted with dichloromethane. The combined organic layers were washed with brine, dried over anhydrous sodium sulfate, filtered and concentrated under reduced pressure to 39.3. MS (ES): m/z 292.3 [M+H]+.

Synthesis of compound 39.4 and 39.5. Compound 39.4 and 39.5 were prepared from 39.3 and 17.1 following the procedure described in the synthesis of 37.4 and 37.5. The isomers were isolated by preparative HPLC to obtain 39.4, MS (ES): m/z 347.3 [M+H]+ and 39.5, MS (ES): m/z 347.3 [M+H]+.

Synthesis of compound 39.6. Compound 39.6 was prepared from 39.4 following the procedure described in the synthesis of 11.8. The crude product was used in the next step without further purification. MS (ES): m/z 389.4 [M+H]+.

Synthesis of compound 39.7. Compound 39.7 was prepared from 39.6 following the procedure described in the synthesis of 1-2. The product was purified by flash column chromatography on silica gel (CombiFlash®, 1.5% methanol in dichloromethane as eluant). MS (ES): m/z: 627.6 [M+H]+.

Synthesis of compound 39.8. To a solution of 39.7 (0.110 g, 0.175 mmol, 1.0 equiv) in dichloromethane (5 mL) was added trifluoroacetic acid (0.199 g, 1.75 mmol, 10.0 equiv) at 0° C. The reaction mixture was stirred at room temperature for 2 h. It was poured over ice-cold saturated sodium bicarbonate solution and extracted with dichloromethane. The combined organic layers were washed with brine, dried over anhydrous sodium sulfate, filtered and concentrated under reduced pressure to obtain 39.8. MS (ES): m/z 526.5 [M+H]+.

Synthesis of I-39. To a solution of 39.8 (0.074 g, 0.140 mmol, 1.0 equiv) and triethylamine (0.058 mL, 0.42 mmol, 1.5 equiv) in dichloromethane (3 mL) was added acetic anhydride (0.014 g, 0.140 mmol, 1.0 equiv) dropwise at 0° C. The reaction mixture was stirred for 15 min. It was poured over ice-water, stirred and extracted with dichloromethane. This was further purified by flash column chromatography on silica gel (CombiFlash®, 0.5% methanol in dichloromethane as eluant) to afford I-39. MS (ES): m/z: 569.5 [M+H]+, 1H NMR (DMSO-d6, 400 MHz): δ 10.50 (s, 1H), 10.14 (s, 1H), 8.15-8.14 (d, J=5.6 Hz, 1H), 7.64-7.40 (m, 2H), 7.32 (s, 1H), 7.23 (s, 1H), 6.86-6.83 (d, J=8.8 Hz, 1H), 6.62-6.61 (d, J=4.4 Hz, 1H), 4.94-4.85 (m, 1H), 4.25 (s, 1H), 4.14 (s, 1H), 4.05-3.97 (m, 1H), 3.87 (s, 1H), 3.67 (s, 3H), 2.82 (s, 3H), 2.74 (bs, 1H), 2.02 (s, 3H), 1.75-1.74 (m, 3H).

Example 40: N-(4-((2-((4,4-dimethyl-4,5,6,7-tetrahydropyrazolo[1,5-c]pyridin-2-yl)amino)-1-methyl-1H-benzo[d]imidazol-6-yl)oxy)pyridin-2-yl)acetamide

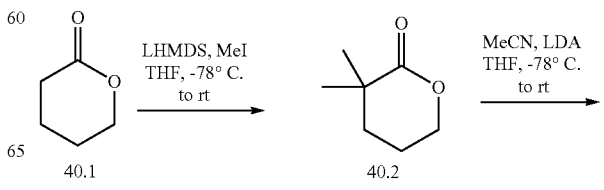

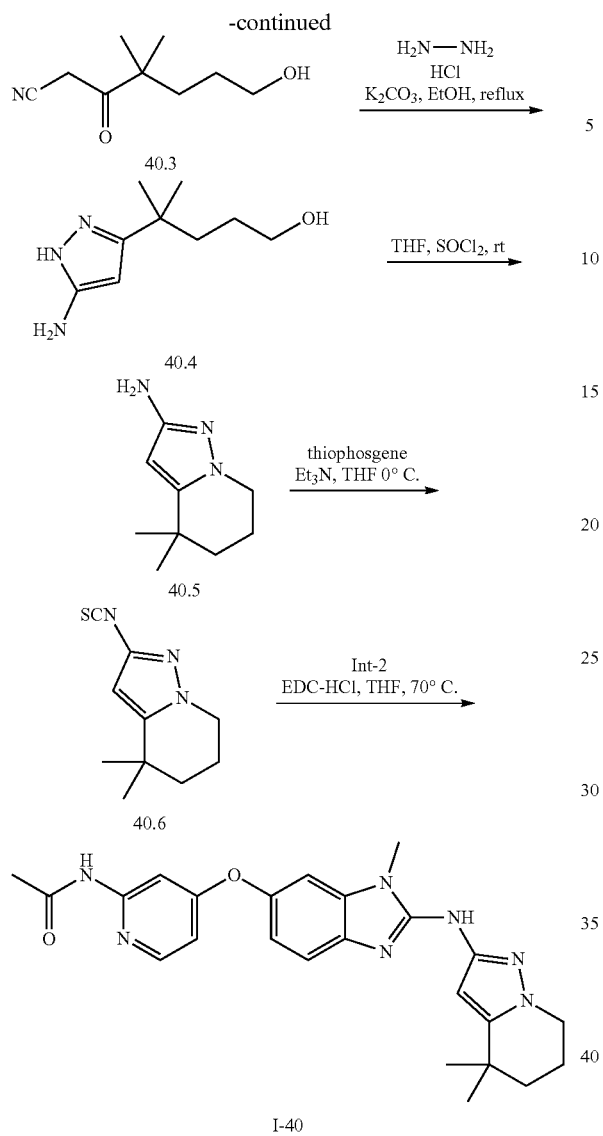

extracted with ethyl acetate. The combined organic layers were washed with brine, dried over anhydrous sodium sulfate, filtered and concentrated under reduced pressure. The residue was purified by flash column chromatography on silica gel (CombiFlash®, 20% ethyl acetate in hexane as eluant) to afford 40.3. MS (ES): m/z 170.2 [M+H]$^+$.

Synthesis of compound 40.4. To a solution of 40.3 (3.9 g, 23.05 mmol, 1.0 equiv) in ethanol (40 mL) was added hydrazine hydrochloride (2.35 g, 34.57 mmol, 1.5 equiv) followed by addition of potassium carbonate (4.77 g, 34.57 mmol, 1.5 equiv). The reaction mixture was heated to reflux for 16 h. It was concentrated under reduced pressure. The residue was purified by flash column chromatography on silica gel (CombiFlash®, 3-4% methanol in dichloromethane as eluant) to afford 40.4. MS (ES): m/z 184.26 [M+H]$^+$.

Synthesis of compound 40.5. To a solution of 40.4 (1.1 g, 6.0 mmol, 1.0 equiv) in THF (20 mL) was added thionyl chloride (2.15 mL, 30 mmol, 5.0 equiv). The reaction mixture was stirred at room temperature for 2 h. It was poured over saturated sodium bicarbonate solution, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 2% methanol in dichloromethane as eluant) to afford 40.5. MS (ES): m/z 166.24 [M+H]$^+$.

Synthesis of compound 40.6. Compound 40.6 was prepared from 40.5 following the procedure described in the synthesis of 1.2. The crude product was used in the next step without further purification. MS (ES): m/z 208.3 [M+H]$^+$.

Synthesis of compound I-40. Compound I-40 was prepared from 40.6 following the procedure described in the synthesis of I-1. The product was purified by preparative HPLC. MS (ES): m/z: 446.41 [M+H]$^+$, $^1$H NMR (DMSO-d6, 400 MHz): δ 10.48 (s, 1H), 9.48 (s, 1H), 8.15-8.14 (d, J=5.6 Hz, 1H), 7.65 (s, 1H), 7.38-7.36 (d, J=8 Hz, 1H), 7.16 (s, 1H), 6.82-6.80 (d, J=7.6 Hz, 1H), 6.61-6.56 (m, 2H), 3.94 (bs, 2H), 3.62 (s, 3H), 2.03 (s, 6H), 1.68 (s, 3H), 1.25 (bs, 4H).

Example 41: N-(4-((7-cyano-2-((4,4-dimethyl-4,5,6,7-tetrahydropyrazolo[1,5-a]pyridin-2-yl)amino)-1-methyl-1H-benzo[d]imidazol-6-yl)oxy)pyridin-2-yl)acetamide

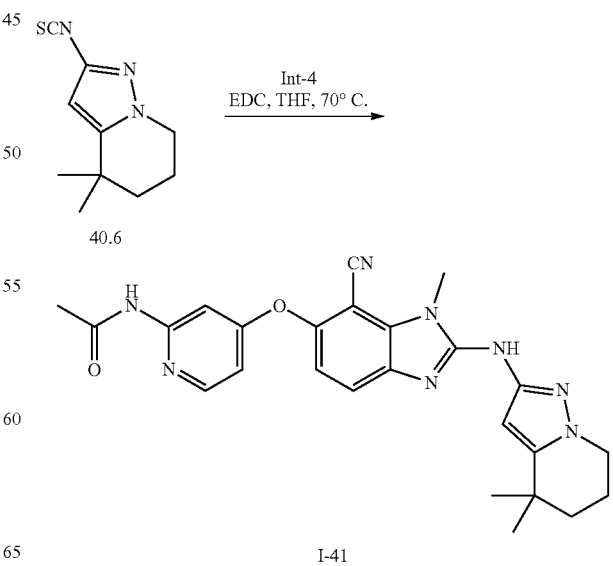

Synthesis of compound 40.2. To a solution of 40.1 (10 g, 99.88 mmol, 1.0 equiv) and methyl iodide (24.8 mL, 399.52 mmol, 4.0 equiv) in THF (200 mL) was added lithium bis(trimethylsilyl)amide (1 M in THF, 219 mL, 219.7 mmol, 2.2 equiv) at −78° C. The reaction mixture was stirred at room temperature for 16 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 10% ethyl acetate in hexane as eluant) to afford 40.2. MS (ES): m/z 129.2 [M+H]$^+$.

Synthesis of compound 40.3. To a solution of diisopropylamine (4.88 g, 48.37 mmol, 1.0 equiv) in THF (100 mL) at −78° C. was slowly added a solution of n-butyl lithium (2.5M in hexane, 24.2 mL, 60.46 mmol, 1.25 equiv). The reaction mixture was stirred for 5 min followed by addition of acetonitrile (2.5 mL, 48.37 mmol, 1.0 equiv). The reaction mixture stirred for 10 min and compound 40.3 (6.20 g, 48.37 mmol, 1.0 equiv) in THF (30 mL) was added to it. The reaction mixture was stirred at 5° C. for 6 h. It was poured over cold saturated ammonium chloride solution and Synthesis of I-41. Compound I-41 was prepared from 40.6 and Int-4 following the procedure described in the synthesis of I-1. The product was purified by flash column chromatography on silica gel (CombiFlash®, 5-7% methanol in dichloromethane as eluant). MS (ES): m/z: 470.83 [M+H]$^+$, $^1$H NMR (DMSO-d6, 400 MHz): δ 10.59 (s, 1H), 9.85 (s, 1H), 8.22-8.20 (d, J=5.6 Hz, 1H), 7.68 (bs, 2H), 7.03-7.01 (d, J=8.4 Hz, 1H), 6.69 (bs, 1H), 6.55 (s, 1H), 4.02-3.90 (m, 4H), 2.04 (s, 6H), 1.67 (bs, 2H), 1.30 (bs, 6H).

Example 42: N-(4-((2-((4,4-dimethyl-4,5,6,7-tetra-hydropyrazolo[1,5-c]pyridin-2-yl)amino)-3-methyl-3H-imidazo[4,5-b]pyridin-5-yl)oxy)pyridin-2-yl)acetamide

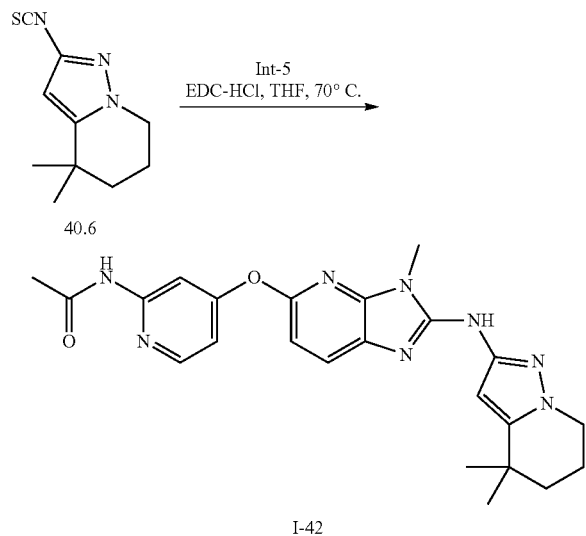

I-42

Synthesis of I-42. Compound I-42 was prepared from 40.6 and Int-5 following the procedure described in the synthesis of I-1. The product was purified by flash column chromatography on silica gel (CombiFlash®, 5-6% methanol in dichloromethane as eluant). MS (ES): m/z: 447.45 [M+H]$^+$, $^1$H NMR (DMSO-d6, 400 MHz): δ 10.53 (s, 1H), 9.79 (s, 1H), 8.19-8.17 (d, J=5.6 Hz, 1H), 7.81-7.75 (m, 2H), 6.84-6.82 (d, J=8 Hz, 1H), 6.71-6.70 (t, 1H), 6.58 (s, 1H), 5.76 (s, 1H), 3.95-3.93 (m, 2H), 3.58 (s, 3H), 2.04 (bs, 4H), 1.67 (bs, 2H), 1.30 (bs, 6H).

Example 43: N-(4-((2-((5,5-dimethyl-4,5,6,7-tetra-hydrobenzo[d]thiazol-2-yl)amino)-1,7-dimethyl-1H-benzo[d]imidazol-6-yl)oxy)pyridin-2-yl)acetamide

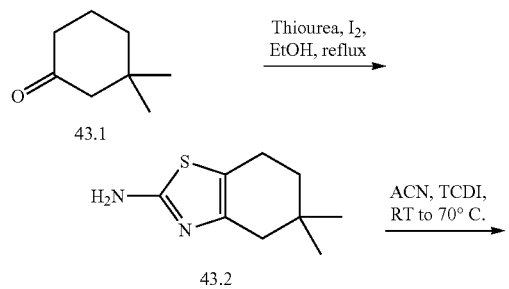

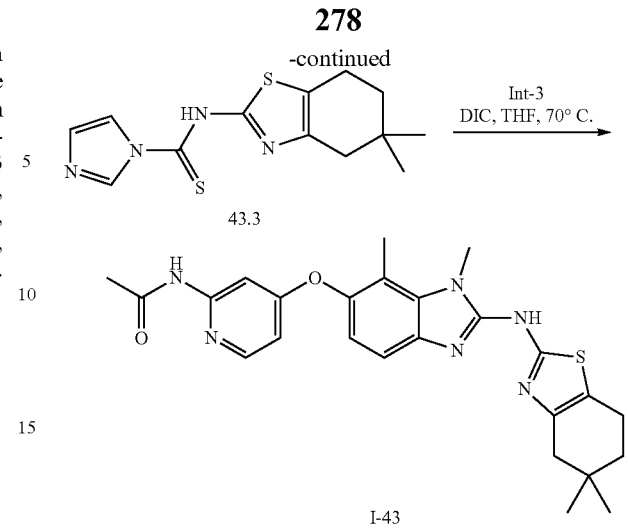

I-43

Synthesis of compound 43.2. To a solution of 3,3-dimethylcyclohexan-1-one (43.1, 6.0 g, 47.54 mmol, 1.0 equiv) in ethanol (60 mL) was added thiourea (10.86 g, 142 mmol, 3.0 equiv) followed by iodine (12.02 g, 47.54 mmol, 1.0 equiv). The reaction mixture was heated to reflux for 8 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 25% ethyl acetate in hexane as eluant) to afford 43.2. MS (ES): m/z 183.3 [M+H]$^+$.

Synthesis of compound 43.3. To a solution of 43.2 (0.200 g, 1.1 mmol, 1.0 equiv) in acetonitrile (4 mL) was added thiocarbonyldiimidazole (0.214, 1.208 mmol, 1.1 equiv). The reaction mixture was stirred at room temperature for 2 h. After completion of reaction, precipitated solid was filtered out, dried well to obtain 43.3. MS (ES): m/z 293.4 [M+H]$^+$.

Synthesis of I-43. To a solution of 43.3 (0.100 g, 0.349 mmol, 1.0 equiv) and Int-3 (0.122 g, 0.417 mmol, 1.2 equiv) in DMF (2 mL) was added N,N-diisopropylethylamine (0.2 mL, 1.047 mmol, 3.0 equiv). The reaction mixture was stirred at 70° C. for 6 h. It was cooled to room temperature, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 5% methanol in dichloromethane as eluant) to afford I-43. MS (ES): m/z: 477.81 [M+H]$^+$, $^1$H NMR (DMSO-d6, 400 MHz): δ 11.83 (s, 1H), 10.47 (s, 1H), 8.13-8.11 (d, J=5.2 Hz, 1H), 7.59 (s, 1H), 7.28 (s, 1H), 6.79 (s, 1H), 6.53 (s, 1H), 3.87 (s, 3H), 2.43-2.42 (m, 2H), 2.27 (s, 3H), 2.03-2.02 (d, 3H), 1.55 (bs, 2H), 1.00 (s, 6H), 0.99-0.84 (m, 2H).

Example 44: N-(4-((2-((6,6-dimethyl-4,5,6,7-tetra-hydrobenzo[d]thiazol-2-yl)amino)-1,7-dimethyl-1H-benzo[d]imidazol-6-yl)oxy)pyridin-2-yl)acetamide

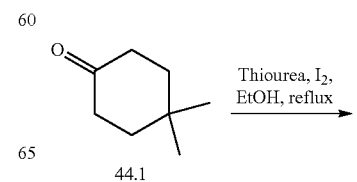

44.1

279

-continued

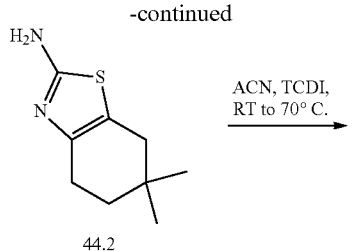

44.2

Int-3
DIC, THF, 70° C.
→

44.3

I-44

Synthesis of compound 44.2. Compound 44.2 was prepared from 4,4-dimethylcyclohexan-1-one (44.1) following the procedure described in the synthesis of 43.2. The residue was purified by flash column chromatography on silica gel (CombiFlash®, 30% ethyl acetate in hexane as eluant). MS (ES): m/z 183.3 [M+H]$^+$.

Synthesis of compound 44.3. Compound 44.3 was prepared from 44.2 following the procedure described in the synthesis of 43.3. The crude product was used in the next step without further purification. MS (ES): m/z 293.4 [M+H]$^+$.

Synthesis of I-44. A solution of 44.3 (0.100 g, 0.349 mmol, 1.0 equiv), Int-3 (0.113 g, 0.384 mmol, 1.1 equiv) and N,N-diisopropylethylamine (0.2 mL, 1.047 mmol, 3.0 equiv) in DMF (2 mL) was stirred at 70° C. for 12 h under nitrogen. It was cooled to room temperature, poured over ice-water and extracted with ethyl acetate. The combined organic layers were washed with brine, dried over anhydrous sodium sulfate, filtered and concentrated under reduced pressure. The residue was purified by preparative HPLC to obtain I-44. MS (ES): m/z: 477.81 [M+H]$^+$, $^1$H NMR (DMSO-d6, 400 MHz): δ 11.88 (s, 1H), 10.49 (s, 1H), 8.14-8.13 (d, J=5.6 Hz, 1H), 7.60 (s, 1H), 7.28 (s, 1H), 6.81-6.79 (d, J=8.4 Hz, 1H), 6.55-6.53 (m, 1H), 3.88 (s, 3H), 2.43 (bs, 4H), 2.34 (s, 3H), 2.03 (s, 3H), 1.58-1.55 (m, 2H), 1.01 (s, 6H).

280

Example 45: (R)—N-(4-((1-methyl-2-((2-methyl-3-(trifluoromethyl)-5,6,7,8-tetrahydroimidazo[1,2-c]pyridin-6-yl)amino)-1H-benzo[d]imidazol-6-yl)oxy)pyridin-2-yl)acetamide and (S)—N-(4-((1-methyl-2-((2-methyl-3-(trifluoromethyl)-5,6,7,8-tetrahydroimidazo[1,2-a]pyridin-6-yl)amino)-1H-benzo[d]imidazol-6-yl)oxy)pyridin-2-yl)acetamide

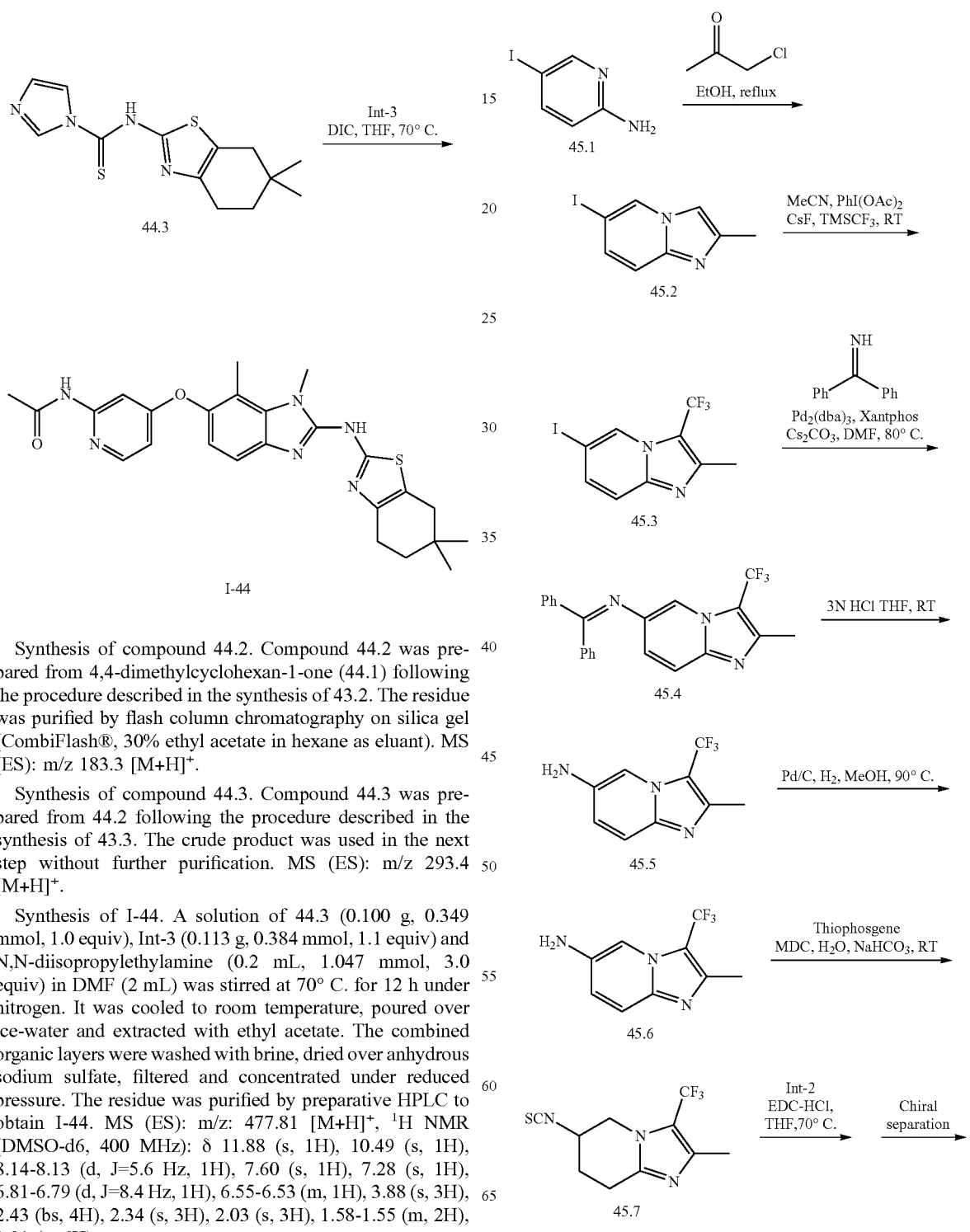

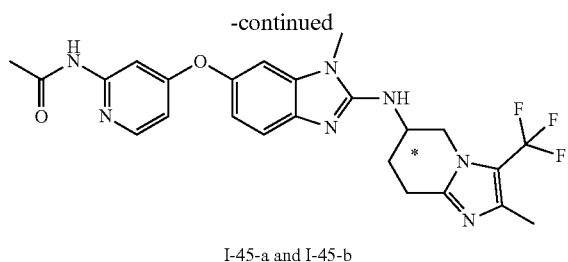

I-45-a and I-45-b

Synthesis of compound 45.2. To a solution of 45.1 (8.0 g, 36.36 mmol, 1.0 equiv) in ethanol (50 mL) was added 1-chloropropan-2-one (5.05 g, 54.54 mmol, 1.5 equiv). The reaction mixture was heated to reflux for 24 h. It was concentrated under reduced pressure. The residue was taken in water and basified to pH 8 with saturated sodium carbonate solution. The aqueous solution was extracted with dichloromethane. The combined organic layers were washed with brine, dried over anhydrous sodium sulfate, filtered and concentrated under reduced pressure. The residue was purified by flash column chromatography on silica gel (CombiFlash®, 50% ethyl acetate in hexane as eluant) to afford 45.2. MS (ES): m/z 259.2 [M+H]$^+$.

Synthesis of compound 45.3. To a solution of 45.2 (4.8 g, 18.16 mmol, 1.0 equiv) in acetonitrile (100 mL) was added (diacetoxyiodo)benzene (11.69 g, 36.32 mmol, 2.0 equiv), cesium fluoride (11.04 g, 72.64 mmol, 4.0 equiv) followed by trifluoromethyltrimethylsilane (10.314 g, 72.64 mmol, 4.0 equiv) and stirred at room temperature for 4 h. It was filtered with Celite® bed and washed with ethyl acetate. The filtrate was concentrated under reduced pressure. The residue was purified by flash column chromatography on silica gel (CombiFlash®, 12% ethyl acetate in hexane as eluant) to afford 45.3. MS (ES): m/z 327.2 [M+H]$^+$.

Synthesis of compound 45.4. A mixture of 45.3 (1.7 g, 5.21 mmol, 1.0 equiv), diphenylmethanimine (1.037 g, 5.73 mmol, 1.1 equiv) and cesium carbonate (3.39 g, 10.42 mmol, 2.0 equiv) in DMF (20 mL) was degassed by bubbling argon through for 10 min. 4,5-Bis (diphenylphosphino)-9,9-dimethylxanthene (0.090 g, 0.156 mmol, 0.03 equiv) and tris (dibenzylideneacetone) dipalladium (0, 0.071 g, 0.078 mmol, 0.015 equiv) was added, and degassed for 5 min. The reaction mixture was stirred at 80° C. for 4 h. It was cooled to room temperature, filtered through a pad of Celite®. The filtrate was poured over water, extracted with ethyl acetate. The combined organic layers were washed with brine, dried over anhydrous sodium sulfate, filtered and concentrated under reduced pressure. The residue was purified by flash column chromatography on silica gel (CombiFlash®, 15% ethyl acetate in hexane as eluant) to afford 45.4. MS (ES): m/z 380.4 [M+H]$^+$.

Synthesis of compound 45.5. To a solution of 45.4 (1.62 g, 4.27 mmol, 1.0 equiv) in THF (16 mL) was added 1N hydrochloric acid (16 mL, 10 v) and stirred at room temperature for 30 min. It was poured over ice-water, stirred and extracted with ethyl acetate. Aqueous layer separated, neutralized with saturated sodium bicarbonate solution and extracted with ethyl acetate. The combined organic layers were washed with brine, dried over anhydrous sodium sulfate, filtered and concentrated under reduced pressure to obtain 45.5. MS (ES): m/z 216.2 [M+H]$^+$.

Synthesis of compound 45.6. A mixture of compound 45.5 (0.500 g, 2.32 mmol, 1.0 eq), 10% palladium on carbon (0.500 g) in methanol (10 mL) was stirred at 90° C. under 280 psi hydrogen for 12 h. After completion of the reaction, the reaction mixture was filtered through a pad of Celite® and rinsed with methanol. The filtrate was concentrated under reduced pressure to obtain 45.6. MS (ES): m/z 220.2 [M+H]$^+$.

Synthesis of compound (±)-45.7. Compound (±)-45.7 was prepared from 45.6 following the procedure described in the synthesis of 11.8. The crude product was used in the next step without further purification. MS (ES): m/z 262.3 [M+H]$^+$.

Synthesis of compound (±)-I-45. Compound (±)-I-45 was prepared from (±)-45.6 following the procedure described in the synthesis of I-1. The product was purified by flash column chromatography on silica gel (CombiFlash®, 3.0% methanol in dichloromethane as eluant) to afford. MS (ES): m/z: 500.5 [M+H]$^+$.

I-45-a and I-45-b. Enantiomers of I-45 were isolated by SFC (CHIRALPAK AD-H (250 mm×4.6 mm, 5 μm), eluent: 0.1% DEA in MEOH; flow rate: 4 mL/min) to get first eluting fraction (I-45-a) and second eluting fraction (I-45-b). (*Absolute stereochemistry not determined.)

I-45-a: MS (ES): m/z: 500.8 [M+H]$^+$, $^1$H NMR (DMSO-d6, 400 MHz): δ 10.47 (s, 1H), 8.13-8.12 (d, J=5.6 Hz, 1H), 7.62 (s, 1H), 7.29-7.27 (d, J=8.4 Hz, 1H), 7.11 (s, 1H), 6.90-6.88 (d, J=6.4 Hz, 1H), 6.78-6.75 (m, 1H), 6.59-6.58 (m, 1H), 4.43 (bs, 1H), 4.37-4.33 (m, 1H), 4.06-3.97 (m, 2H), 3.51 (s, 3H), 2.99-2.85 (m, 2H), 2.22 (bs, 3H), 2.15-2.10 (m, 1H), 2.02 (s, 3H).

I-45-b: MS (ES): m/z: 500.77 [M+H]$^+$, $^1$H NMR (DMSO-d6, 400 MHz): δ 10.46 (s, 1H), 8.13-8.12 (d, J=5.6 Hz, 1H), 7.62 (s, 1H), 7.29-7.27 (d, J=8.4 Hz, 1H), 7.11 (s, 1H), 6.89-6.88 (d, J=6.4 Hz, 1H), 6.78-6.76 (m, 1H), 6.59-6.58 (m, 1H), 4.43 (bs, 1H), 4.37-4.33 (m, 1H), 4.04-3.97 (m, 2H), 3.51 (s, 3H), 2.99-2.89 (m, 2H), 2.22 (bs, 3H), 2.13-2.12 (m, 1H), 2.02 (s, 3H).

Example 46: N-(4-((2-((2-acetyl-5-(trifluoromethyl)-1,2,3,4-tetrahydroisoquinolin-7-yl)amino)-1-methyl-1H-benzo[d]imidazol-6-yl)oxy)pyridin-2-yl)acetamide

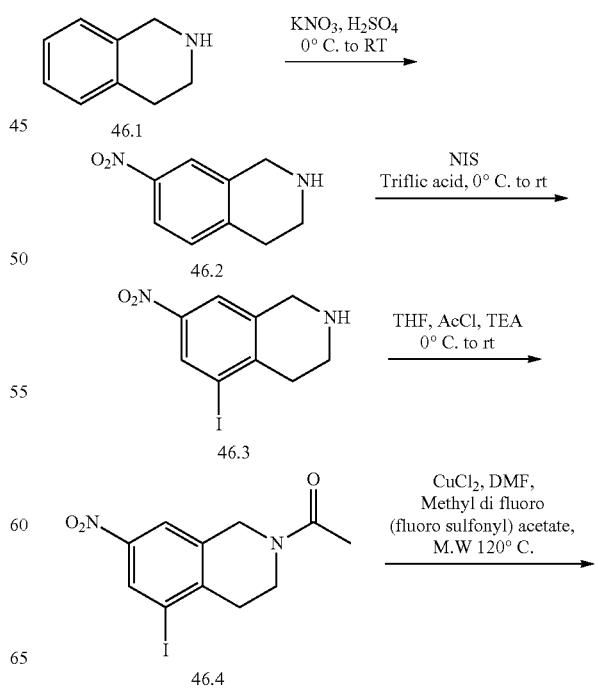

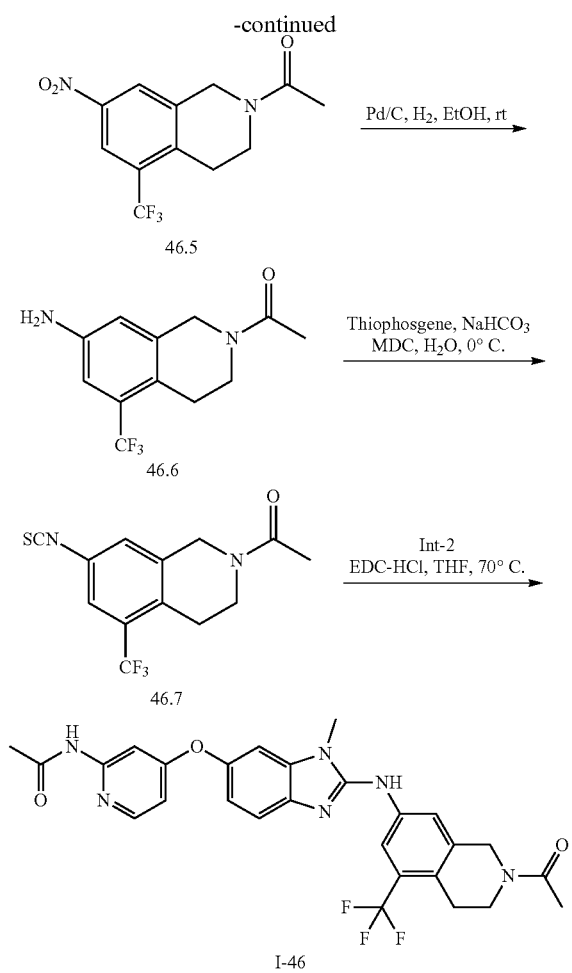

Synthesis of compound 46.2 To a solution of 46.1 (5.0 g, 35.94 mmol, 1.0 equiv) in concentrated sulfuric acid (20 mL) was added potassium nitrate (4.17 g, 41.35 mmol, 1.1 equiv) at 0° C. The reaction mixture was stirred at room temperature for 3 h. It was poured over crushed ice, neutralized by aqueous ammonium hydroxide, and extracted with ethyl acetate. The combined organic layers were washed with brine, dried over anhydrous sodium sulfate, filtered and concentrated under reduced pressure. The residue was purified by flash column chromatography on silica gel (CombiFlash®, 3-4% methanol in dichloromethane as eluant) to afford 46.2. MS (ES): m/z 179.2 [M+H]$^+$.

Synthesis of compound 46.3. To a solution of 46.2 (1.3 g, 7.30 mmol, 1.0 equiv) in triflic acid (2.5 mL) was added N-iodo-succinimide (1.97 g, 8.76 mmol, 1.2 equiv) at 0° C. The reaction mixture was stirred at room temperature for 3 h. It was poured over cold saturated sodium bicarbonate solution and extracted with ethyl acetate. The combined organic layers were washed with brine, dried over anhydrous sodium sulfate, filtered and concentrated under reduced pressure. The residue was purified by flash column chromatography on silica gel (CombiFlash®, 3% methanol in dichloromethane as eluant) to afford 46.3. MS (ES): m/z 305.1 [M+H]$^+$.

Synthesis of compound 46.4. To a solution of 46.3 (0.9 g, 2.96 mmol, 1.0 equiv) in THF (20 mL) was added triethylamine (1.23 mL, 8.88 mmol, 3.0 equiv) followed by addition of acetyl chloride (0.25 mL, 3.55 mmol, 1.2 equiv) at 0° C. and stirred at room temperature for 4 h. It was cooled to room temperature poured over water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 60% ethyl acetate in hexane as eluant) to afford 46.4. MS (ES): m/z 347.12 [M+H]$^+$.

Synthesis of compound 46.5. To a mixture of 46.4 (0.350 g, 1.01 mmol, 1.0 equiv), copper(II) chloride (0.027 g, 0.202 mmol, 0.2 equiv), methyl 2,2-difluoro-2-(fluorosulfonyl) acetate (0.582 g, 3.03 mmol, 3.0 equiv) in N,N-dimethylformamide (10 mL) was heated at 120° C. by a microwave reactor for 2 h. The reaction mixture was transferred into saturated sodium bicarbonate solution, stirred and extracted with ethyl acetate. The combined organic layers were washed with brine, dried over anhydrous sodium sulfate filtered and concentrated under reduced pressure. The residue was purified by flash column chromatography on silica gel (CombiFlash®, 30% ethyl acetate in hexane as eluant). MS (ES): m/z 289.23 [M+H]$^+$.

Synthesis of compound 46.6. A mixture of compound 46.5 (0.155 g, 0.537 mmol, 1.0 equiv) and 10% palladium on carbon (0.050 g) in ethanol (10 mL) was vacuumed and purged with hydrogen three times. The reaction mixture was stirred at rt under 1 atm hydrogen for 2 h. It was filtered through a pad of Celite® and rinsed with methanol. The filtrate was concentrated under reduced pressure and the residue was purified by flash column chromatography on silica gel (CombiFlash®, 5% methanol in dichloromethane as eluant) to afford 46.6. MS (ES): m/z 259.24 [M+H]$^+$.

Synthesis of compound 46.7. Compound 46.7 was prepared from 46.6 following the procedure described in the synthesis of 11.8. The crude product was used in the next step without further purification. MS (ES): m/z 301.3 [M+H]$^+$.

Synthesis of I-46. Compound I-46 was prepared from 46.7 following the procedure described in the synthesis of I-1. The product was purified by flash column chromatography on silica gel (CombiFlash®, 5% methanol in dichloromethane as eluant). MS (ES): m/z: 539.57 [M+H]$^+$, $^1$H NMR (DMSO-d6, 400 MHz): δ 10.49 (s, 1H), 9.29 (s, 1H), 8.16 (bs, 2H), 8.10 (s, 1H), 7.66 (s, 1H), 7.50-7.48 (d, J=7.6 Hz, 1H), 7.27 (s, 1H), 6.89-6.87 (d, J=8 Hz, 1H), 6.63 (s, 1H), 4.77-4.70 (m, 2H), 3.71 (bs, 5H), 2.96 (bs, 1H), 2.83 (bs, 1H), 2.14-2.11 (d, 3H), 2.00 (s, 3H).

Example 47: N-(4-((2-((1-(2-methoxyethyl)-3,3-dimethyl-2-oxo-4-(trifluoromethyl)indolin-6-yl)amino)-1-methyl-1H-benzo[d]imidazol-6-yl)oxy)pyridin-2-yl)acetamide

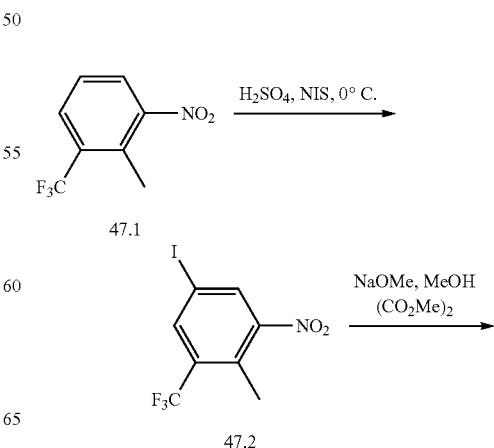

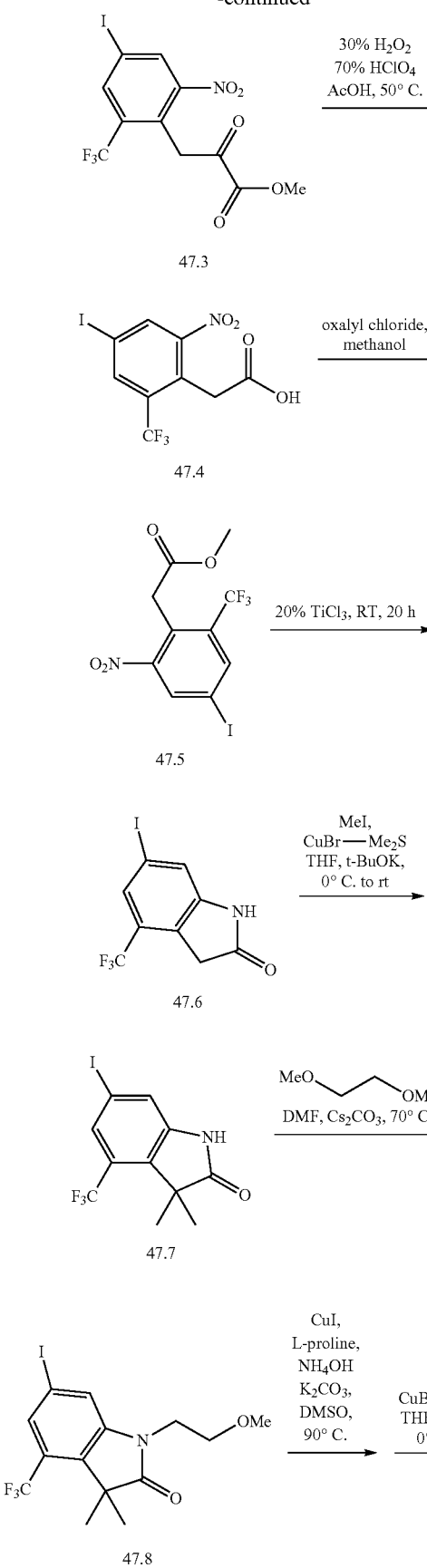
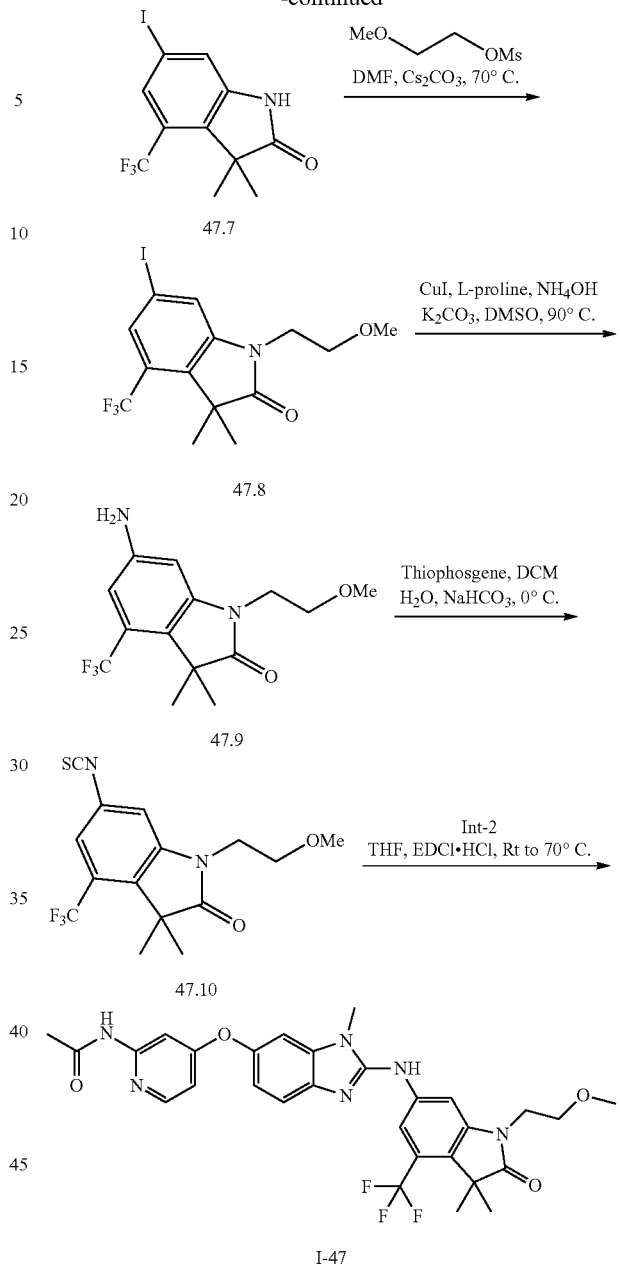

Synthesis of compound 47.2. To a solution of 47.1 (10 g, 4.90 mmol, 1.0 equiv) in sulfuric acid (10 mL) was added solution of N-iodosuccinimide (1.32 g, 5.88 mmol, 1.2 equiv) at 0° C. The reaction mixture was stirred at room temperature for 12 h. It was carefully poured over ice-water, stirred and extracted with ethyl acetate. The combined organic layers were washed with brine, dried over anhydrous sodium sulfate, filtered and concentrated under reduced pressure to obtain 47.2. MS (ES): m/z 332.2 [M+H]$^+$.

Synthesis of compound 47.3. Dimethyl oxalate (4.27 g, 36.25 mmol, 1.0 equiv) was added to sodium methoxide solution (21%) in methanol (9.3 mL, 36.25 mmol, 1.0 equiv) at room temperature and stirred for 1.5 h. To the mixture was added a solution of 47.2 (12 g, 36.25 mmol, 1.0 equiv) in methanol (10 mL) and stirred at room temperature for 12 h. It was added to ice-cold 2.5 M hydrochloric acid until pH 4-5, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 10% ethyl acetate in hexane as eluant) to afford 47.3. MS (ES): m/z 418.2 [M+H]$^+$.

Synthesis of compound 47.4. To a solution of 47.3 (10 g, 23.98 mmol, 1.0 equiv) in acetic acid (20 mL) was added perchloric acid (10 mL) at rt. The mixture was heated at 80° C. for 1 h. It was cooled to room temperature and added 30% hydrogen peroxide solution (59 mL, 527 mmol, 22 equiv). The reaction mixture was stirred at 60° C. for 5 h. It was poured over a saturated aqueous sodium sulphite solution, stirred and extracted with ethyl acetate. The combined organic layers were washed with brine and 2 N sodium hydroxide solution Aqueous layer was acidified with conc. hydrochloric acid to pH 3. The precipitates were collected by filtration, rinsed with water and dried under vacuum to afford 47.4. MS (ES): m/z 376.1 [M+H]$^+$.

Synthesis of compound 47.5. To a solution of 47.4 (2.5 g, 6.67 mmol, 1.0 equiv) in methanol (25 mL) was added oxalyl chloride (3.75 mL, 43.7 mmol, 6.5 equiv). The reaction mixture was stirred at 70° C. for 4 h. It was poured over saturated sodium bicarbonate solution, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 20% ethyl acetate in hexane as eluant) to afford 47.5. MS (ES): m/z 390.1 [M+H]$^+$.

Synthesis of compound 47.6. To a solution of 47.5 (2.0 g, 5.14 mmol, 1.0 equiv) in methanol (20 mL) was added a commercial 15% titanium (III) chloride solution (9.8 g, 63.73 mmol, 12.4 equiv) at 0° C. The reaction mixture was stirred at room temperature for 12 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 10% ethyl acetate in hexane as eluant) to afford 47.6. MS (ES): m/z 328.2 [M+H]$^+$.

Synthesis of compound 47.7. To a solution of 47.6 (1.4 g, 4.28 mmol, 1.0 equiv) in THF (15 mL) was added potassium tert-butoxide (2.39 g, 21.4 mmol, 5.0 equiv) at 0° C. followed by copper (I) bromide dimethyl sulfide complex (0.087 g, 0.428 mmol, 0.1 equiv). Methyl iodide (1.27 g, 8.98 mmol, 2.1 equiv) was slowly added at 0° C. The reaction mixture was stirred at room temperature for 3 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 8% ethyl acetate in hexane as eluant) to afford 47.7. MS (ES): m/z 356.1 [M+H]$^+$.

Synthesis of compound 47.8. To a solution of 47.7 (0.5 g, 1.41 mmol, 1.0 equiv) and 2-methoxyethyl methanesulfonate (0.260 g, 1.69 mmol, 1.2 equiv) in DMF (5 mL) was added cesium carbonate (1.14 g, 3.52 mmol, 2.5 equiv) reaction mixture was stirred at 80° C. for 16 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 5-8% ethyl acetate in hexane as eluant) to afford 47.8. MS (ES): m/z 414.5 [M+H]$^+$.

Synthesis of compound 47.9. To a solution of 47.8 (0.370 g, 0.895 mmol, 1.0 equiv) in dimethyl sulfoxide (4 mL) was added L-proline (0.020 g, 0.179 mmol, 0.2 equiv), copper iodide (0.068 g, 0.358 mmol, 0.4 equiv) and potassium carbonate (0.432 g, 3.13 mmol, 3.5 equiv) followed by ammonium hydroxide solution (0.13 mL). The reaction mixture was stirred at 90° C. for 16 h. It was cooled to room temperature, poured over water, extracted with ethyl acetate. The combined organic layers were washed with brine, dried over anhydrous sodium sulfate, filtered and concentrated under reduced pressure. The residue was purified by flash column chromatography on silica gel (CombiFlash®, 25% ethyl acetate in hexane as eluant) to afford 47.9. MS (ES): m/z 303.3 [M+H]$^+$.

Synthesis of compound 47.10. Compound 47.10 was prepared from 47.9 following the procedure described in the synthesis of 11.8. The crude product was used in the next step without further purification. MS (ES): m/z 345.4 [M+H]$^+$.

Synthesis of I-47. Compound I-47 was prepared from 47.10 and Int-2 following the procedure described in the synthesis of I-1. The product was purified by flash column chromatography on silica gel (CombiFlash®, 3-5% methanol in dichloromethane as eluant). MS (ES): m/z: 583.9 [M+H]$^+$, $^1$H NMR (DMSO-d6, 400 MHz): δ 10.48 (s, 1H), 9.42 (s, 1H), 8.16-8.15 (d, J=6.0 Hz, 1H), 8.01 (s, 1H), 7.97 (s, 1H), 7.65 (s, 1H), 7.45-7.43 (d, J=8.4 Hz, 1H), 7.28 (s, 1H), 6.89-6.87 (d, J=7.2 Hz, 1H), 6.63-6.62 (d, J=3.6 Hz, 1H), 3.90-3.89 (m, 2H), 3.72 (s, 3H), 3.65-3.62 (m, 2H), 3.24 (s, 3H), 2.03 (s, 3H), 1.36 (s, 6H).

Example 48: N-(4-((2-((1-(2-hydroxyethyl)-3,3-dimethyl-2-oxo-4-(trifluoromethyl)indolin-6-yl)amino)-1-methyl-1H-benzo[d]imidazol-6-yl)oxy)pyridin-2-yl)acetamide

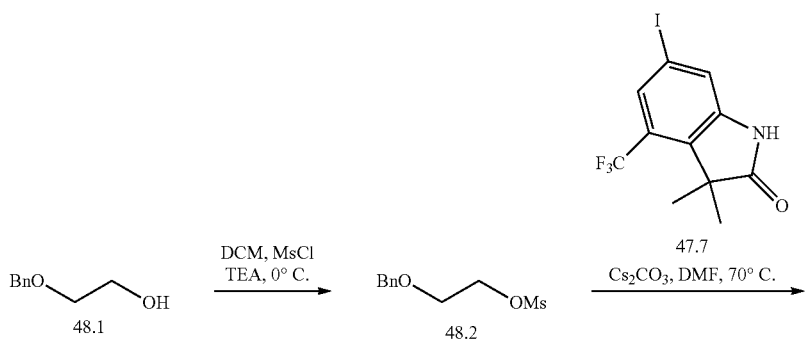

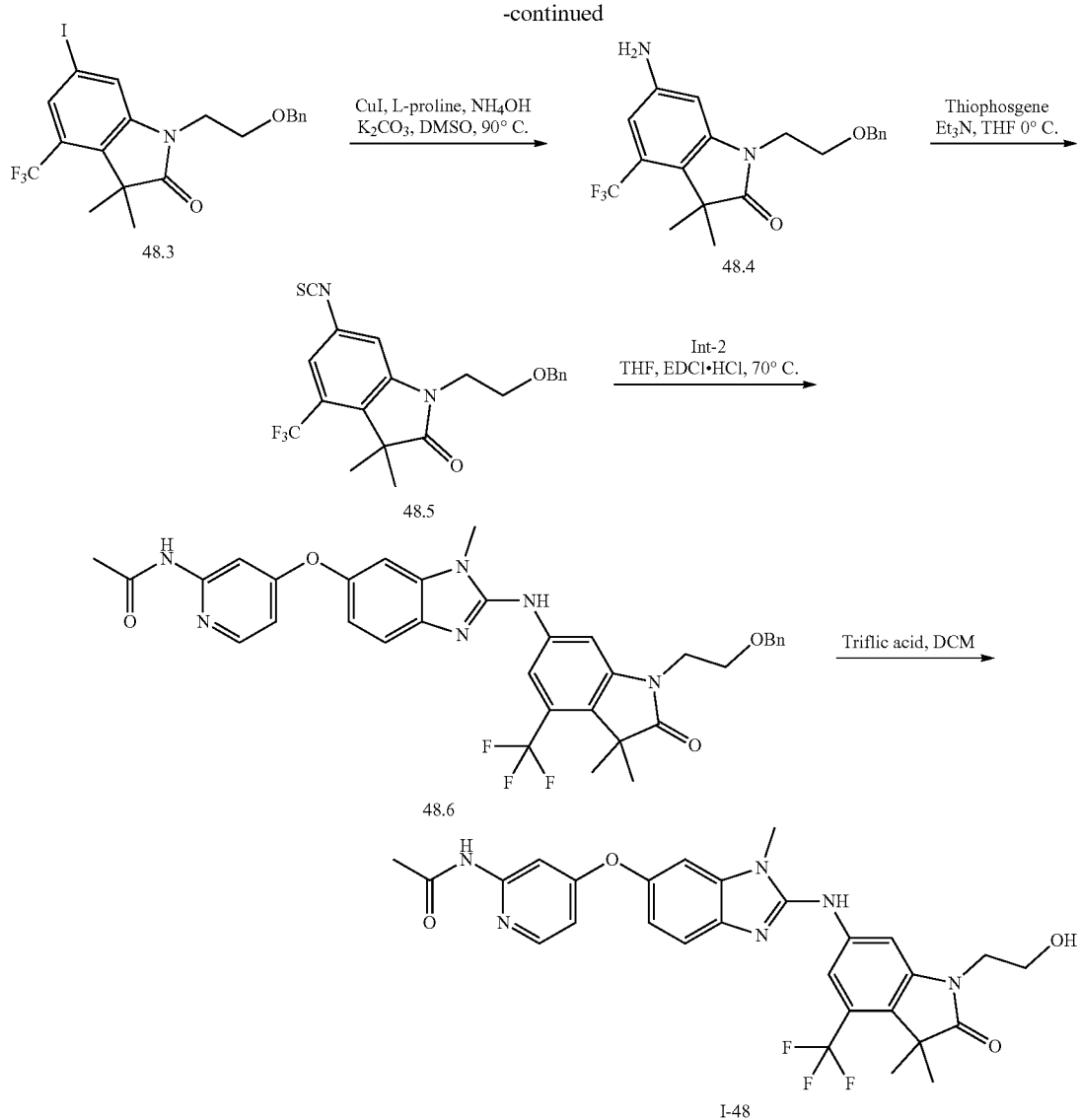

Synthesis of compound 48.2. To a solution of 48.1 (1.0 g, 6.57 mmol, 1.0 equiv) and triethylamine (2.74 mL, 19.71 mmol, 3.0 equiv) in dichloromethane (10 mL) was added methanesulfonyl chloride (0.76 mL, 9.85 mmol, 1.5 equiv) at 0° C. The reaction mixture was stirred at room temperature for 3 h. It was poured over ice-water, stirred and extracted with dichloromethane. The combined organic layers were washed with brine, dried over anhydrous sodium sulfate, filtered and concentrated under reduced pressure to obtain 48.2. MS (ES): m/z 231.3 [M+H]$^+$.

Synthesis of compound 48.3. Compound 48.3 was prepared from 48.1 and 47.7 following the procedure described in the synthesis of 47.8. The residue was purified by flash column chromatography on silica gel (CombiFlash®, 10-12% ethyl acetate in hexane as eluant). MS (ES): m/z 490.3 [M+H]$^+$.

Synthesis of compound 48.4. Compound 48.4 was prepared from 48.3 following the procedure described in the synthesis of 47.9. The residue was purified by flash column chromatography on silica gel (CombiFlash®, 20-22% ethyl acetate in hexane as eluant). MS (ES): m/z 379.4 [M+H]$^+$.

Synthesis of compound 48.5. Compound 48.5 was prepared from 48.4 following the procedure described in the synthesis of 11.8. The crude product was used in the next step without further purification. MS (ES): m/z 421.5 [M+H]$^+$.

Synthesis of compound 48.6. Compound 48.6 was prepared from 48.5 following the procedure described in the synthesis of I-1. The product was purified by flash column chromatography on silica gel (CombiFlash®, 3-4% methanol in dichloromethane as eluant). MS (ES): m/z: 659.6 [M+H]$^+$.

Synthesis of compound I-48. To a solution of compound 48.6 (0.100 g, 0.151 mmol, 1.0 equiv) in dichloromethane (5 mL) was added triflic acid (0.5 mL) at 0° C. The reaction mixture was stirred at 0° C. for 30 min. It was poured over saturated sodium bicarbonate solution and extracted with dichloromethane. The combined organic layers were washed with brine, dried over anhydrous sodium sulfate, filtered and concentrated under reduced pressure. The residue was purified by trituration with methanol to obtain I-48. MS (ES): m/z: 569.9 [M+H]$^+$, $^1$H NMR (DMSO-d6, 400 MHz): δ

10.50 (s, 1H), 9.42 (s, 1H), 8.16-8.15 (d, J=5.6 Hz, 1H), 8.03 (s, 1H), 7.92 (s, 1H), 7.65 (s, 1H), 7.47-7.45 (d, J=8.4 Hz, 1H), 7.29 (s, 1H), 6.89-6.87 (d, J=8.4 Hz, 1H), 6.64-6.63 (d, J=3.6 Hz, 1H), 4.99-4.97 (m, 1H), 3.79-3.78 (m, 2H), 3.72 (s, 3H), 3.70-3.67 (m, 2H), 2.02 (s, 3H), 1.37 (s, 6H).

Example 49: N-(4-((1-methyl-2-((1,1,2-trimethyl-3-oxo-7-(trifluoromethyl)isoindolin-5-yl)amino)-1H-benzo[d]imidazol-6-yl)oxy)pyridin-2-yl)acetamide

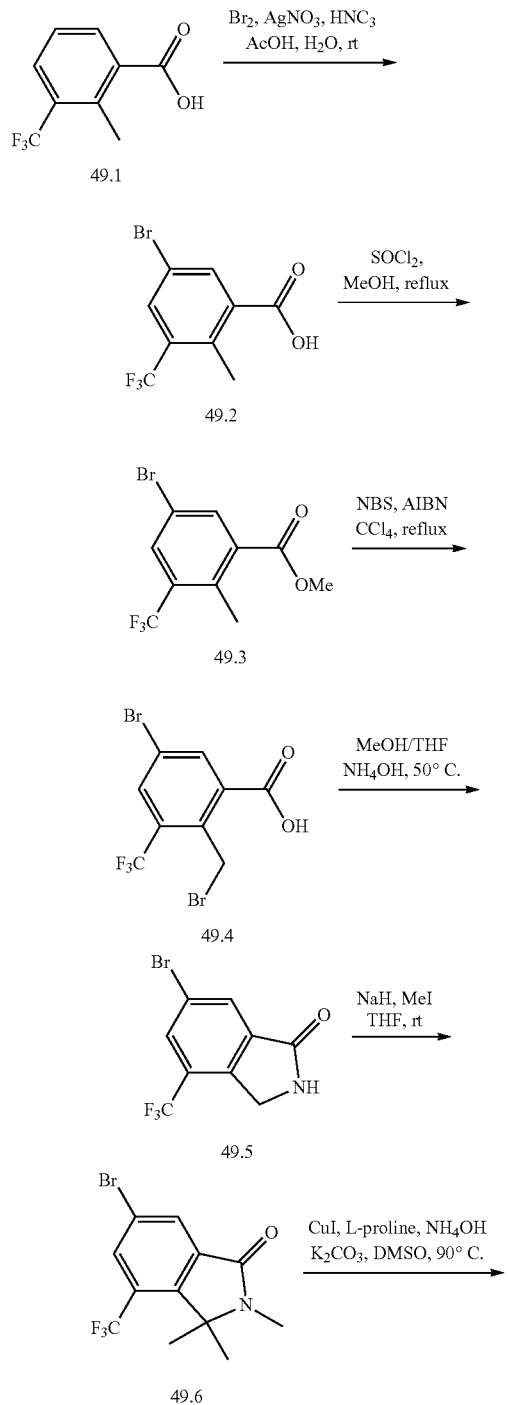

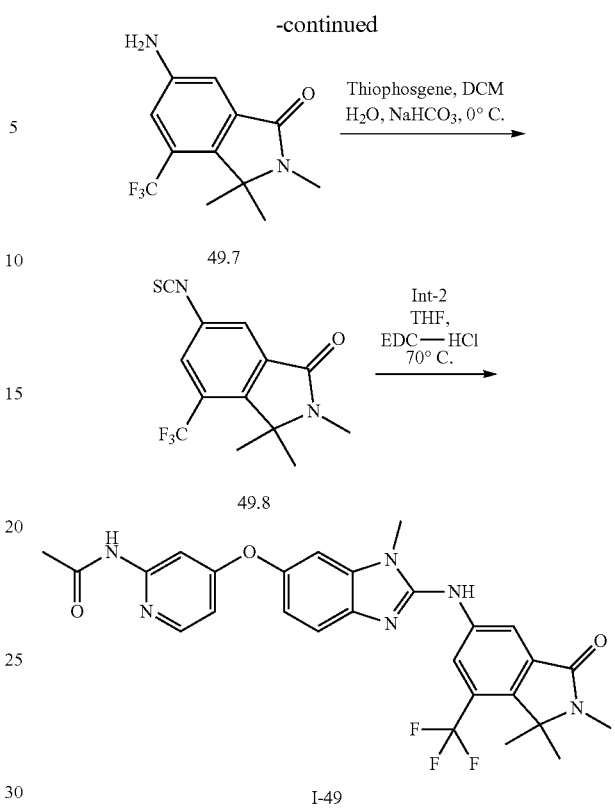

Synthesis of compound 49.2. To a solution of 49.1 (1.0 g, 4.90 mmol, 1.0 equiv) in 0.2 M aqueous acetic acid (20 mL) was added nitric acid (2.08 mL, 49 mmol, 10 equiv), bromine (0.86 g, 5.39 mmol, 1.1 equiv) followed by addition of 2.5 M aqueous silver nitrate solution (2.5 mL, 6.37 mmol, 1.3 equiv) over a period of 30 min. The reaction mixture was stirred at room temperature for 48 h. It was poured over ice-water, stirred and extracted with ethyl acetate. The combined organic layers were washed with brine, dried over anhydrous sodium sulfate, filtered and concentrated under reduced pressure to obtain 49.2. MS (ES): m/z 284.1 [M+H]$^+$.

Synthesis of compound 49.3. To a solution of 49.2 (1.6 g, 5.65 mmol, 1.0 equiv) in methanol (20 mL) was added thionyl chloride (0.82 mL, 11.3 mmol, 2.0 equiv) at 0° C. The reaction mixture was heated to reflux for 4-5 h. It was poured over ice-water, stirred and extracted with ethyl acetate. The combined organic layers were washed with brine, dried over anhydrous sodium sulfate, filtered and concentrated under reduced pressure to obtain 49.3. MS (ES): m/z 298.1 [M+H]$^+$.

Synthesis of compound 49.4. To a solution of 49.3 (0.710 g, 2.39 mmol, 1.0 equiv) in carbon tetrachloride (10 mL) was added N-bromosuccinimide (0.425 g, 2.39 mmol, 1.0 equiv) followed by azobisisobutyronitrile (0.078 g, 0.478 mmol, 0.2 equiv). The reaction mixture was heated to reflux for 1 h. It was poured over ice-water, stirred and extracted with dichloromethane. The combined organic layers were washed with brine, dried over anhydrous sodium sulfate, filtered and concentrated under reduced pressure to obtain 49.4. MS (ES): m/z 362.9 [M+H]$^+$.

Synthesis of compound 49.5. To a solution of 49.4 (0.480 g, 1.33 mmol, 1.0 equiv) in methanol (5 mL) and THF (5 mL) was added aqueous ammonium hydroxide solution (2.5 mL). The reaction mixture was stirred at 50° C. heated to reflux for 4 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 3.0% methanol in dichloromethane as eluant) to afford 49.5. MS (ES): m/z 281.1 [M+H]+.

Synthesis of compound 49.6. To a solution of 49.5 (0.205 g, 0.732 mmol, 1.0 equiv) in THF (3 mL) was added sodium hydride (0.175 g, 3.66 mmol, 5.0 equiv) in small portions at 0° C. and stirred for 20 min. To the mixture was added methyl iodide (0.620 g, 4.39 mmol, 6.0 equiv). The reaction mixture was stirred at room temperature for 24 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 17% ethyl acetate in hexane as eluant) to afford 49.6. MS (ES): m/z 323.2 [M+H]+.

Synthesis of compound 49.7. Compound 49.7 was prepared from 49.6 following the procedure described in the synthesis of 47.9. The residue was purified by flash column chromatography on silica gel (CombiFlash®, 30% ethyl acetate in hexane as eluant) to afford 49.7. MS (ES): m/z 259.3 [M+H]+.

Synthesis of compound 49.8. Compound 49.8 was prepared from 49.7 following the procedure described in the synthesis of 11.8. The crude product was used in the next step without further purification. MS (ES): m/z 301.3 [M+H]+.

Synthesis of compound I-49. Compound I-49 was prepared from 49.8 following the procedure described in the synthesis of I-1. The residue was purified by flash column chromatography on silica gel (CombiFlash®, 4.2% methanol in dichloromethane as eluant). MS (ES): m/z: 539.5 [M+H]+, 1H NMR (DMSO-d6, 400 MHz): δ 10.51 (s, 1H), 9.60 (s, 1H), 8.71 (s, 1H), 8.44 (s, 1H), 8.16-8.15 (d, J=5.6 Hz, 1H), 7.66 (s, 1H), 7.55-7.53 (d, J=8.4 Hz, 1H), 7.31 (s, 1H), 6.91-6.89 (d, J=6.4 Hz, 1H), 6.63-6.62 (d, J=3.6 Hz, 1H), 3.74 (s, 3H), 2.99 (s, 3H), 2.02 (s, 3H), 1.52 (s, 6H).

Example 50: (R)—N-(4-((2-((5-(tert-butyl) isoxazol-3-yl)amino)-1-methyl-1H-benzo[d]imidazol-6-yl)oxy)pyridin-2-yl)-2,2-difluorocyclopropane-1-carboxamide and (S)—N-(4-((2-((5-(tert-butyl) isoxazol-3-yl)amino)-1-methyl-1H-benzo[d]imidazol-6-yl)oxy)pyridin-2-yl)-2,2-difluorocyclopropane-1-carboxamide

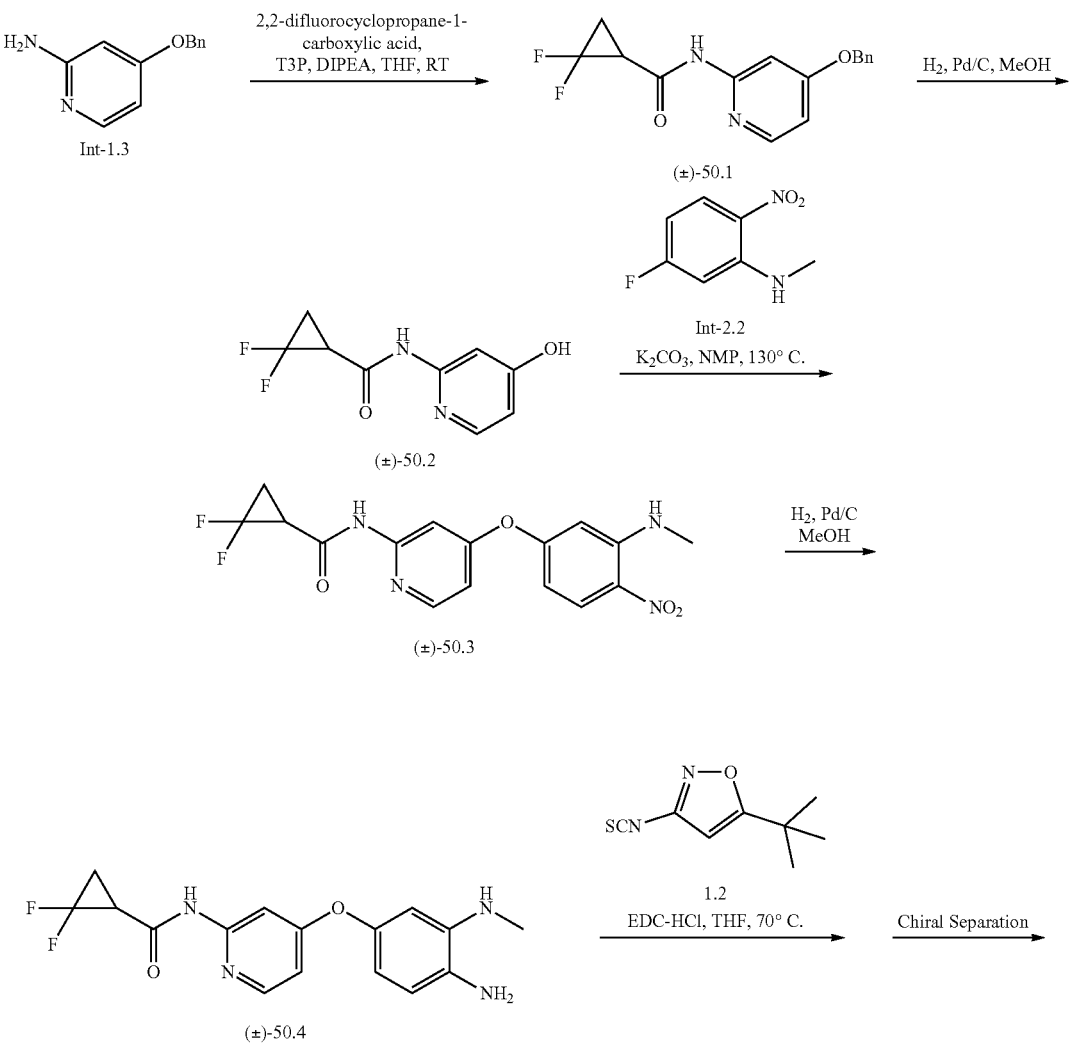

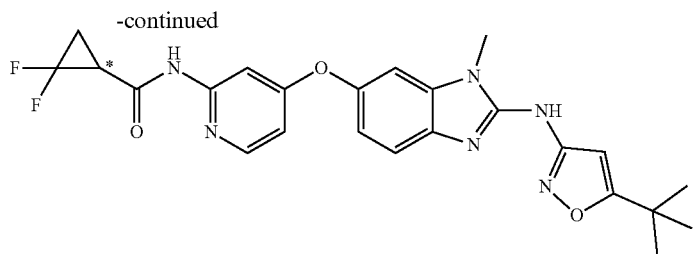

I-50-a and I-50-b

Synthesis of compound (±)-50.1. To a solution of Int-1.3 (1.0 g, 4.99 mmol, 1.0 equiv) and 2,2-difluorocyclopropane-1-carboxylic acid (0.913 g, 7.485 mmol, 1.5 equiv) in THF (10 mL) was added N,N-diisopropylethylamine (2.17 mL, 12.48 mmol, 2.5 equiv) and stirred at room temperature for 30 min. To the mixture was added propylphosphonic anhydride (~50% in ethyl acetate, 2.38 g, 7.485 mmol, 1.5 equiv) at 0° C. The reaction mixture was stirred at room temperature for 2 h. It was poured over ice water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 20-25% ethyl acetate in hexane as eluant) to afford (±)-50.1. MS (ES): m/z 305.3 [M+H]$^+$.

Synthesis of compound (±)-50.2. A mixture of compound (±)-50.1 (0.75 g, 2.46 mmol, 1.0 equiv) and 10% palladium on carbon (0.3 g) in methanol (15 mL) was added vacuumed on and purged with hydrogen three times. The reaction mixture was stirred at rt under 1 atm hydrogen for 2 h. It was filtered through a pad of Celite® and rinsed with methanol. The filtrate was concentrated under reduced pressure and the residue was purified by flash column chromatography on silica gel (CombiFlash®, 30-35% ethyl acetate in hexane as eluant) to afford (±)-50.2. MS (ES): m/z 215.2 [M+H]$^+$.

Synthesis of compound (±)-50.3. Compound (±)-50.3 was prepared from (±)-50.2 and Int-2.2 following the procedure described in the synthesis of Int-2.3. The product was purified by flash column chromatography on silica gel (CombiFlash®, 25-30% ethyl acetate in hexane as eluant). MS (ES): m/z 365.3 [M+H]$^+$.

Synthesis of compound (±)-50.4. Compound (±)-50.4 was prepared from (±)-50.3 following the procedure described in the synthesis of Int-2. The product was purified by flash column chromatography on silica gel (CombiFlash®, 35-40% ethyl acetate in hexane as eluant). MS (ES): m/z 335.3 [M+H]$^+$.

Synthesis of compound (±)-I-50. Compound (±)-I-50 was prepared from compound (±)-50.4 and compound 1.2 following the procedure described in the synthesis of I-1. The product was purified by flash column chromatography on silica gel (CombiFlash®, 1% methanol in dichloromethane as eluant). MS (ES): m/z 483.7 [M+H]$^+$.

I-50-a and I-50-b. Enantiomers of 1.7 (0.090 g) were separated using SFC (CHIRALCEL OJ-H (250 mm×4.6 mm, 5 μm); eluent: 0.1% DEA in MEOH:ACN (50:50); flow rate=4 mL/min) to get first eluting fraction (I-50-a) and second eluting fraction (I-50-b). (*Absolute stereochemistry not determined.)

I-50-a. MS (ES): m/z: 483.76 [M+H]$^+$, $^1$H NMR (MeOD, 400 MHz): δ 8.17-8.16 (d, J=5.6 Hz, 1H), 7.69 (s, 1H), 7.43 (bs, 1H), 7.15 (s, 1H), 6.95-6.93 (d, J=7.2 Hz, 1H), 6.73-6.71 (m, 1H), 5.99 (s, 1H), 3.63 (s, 3H), 2.84-2.76 (m, 1H), 2.09-2.01 (m, 1H), 1.87-1.78 (m, 1H), 1.39 (s, 9H).

I-50-b. MS (ES): m/z: 483.76 [M+H]$^+$, $^1$H NMR (MeOD, 400 MHz): δ 8.17-8.16 (d, J=5.6 Hz, 1H), 7.68 (s, 1H), 7.43 (bs, 1H), 7.15 (s, 1H), 6.95-6.93 (d, J=7.2 Hz, 1H), 6.73-6.71 (m, 1H), 6.00 (s, 1H), 3.63 (s, 3H), 2.84-2.76 (m, 1H), 2.09-2.01 (m, 1H), 1.87-1.78 (m, 1H), 1.39 (s, 9H).

Example 51: N-(4-((2-(((1r,4r)-4-(tert-butyl)cyclohexyl)amino)-1-methyl-1H-benzo[d]imidazol-6-yl)oxy)pyridin-2-yl)acetamide

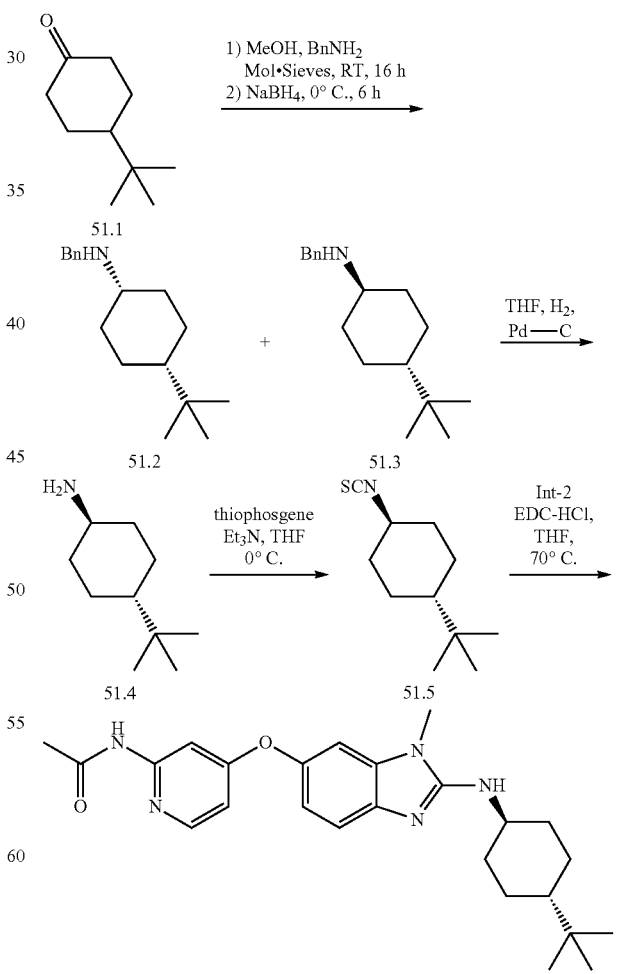

Synthesis of compound 51.2 and 51.3. A mixture of 4-(tert-butyl)cyclohexan-1-one (51.1, 10 g, 64.83 mmol, 1.0 equiv), benzylamine (8.32 g, 77.79 mmol, 1.2 equiv) and molecular sieves (5.0 g) in methanol (100 mL) was stirred at room temperature for 16 h. To the reaction mixture was added sodium borohydride (4.9 g, 129.6 mmol, 2.0 equiv) in small portions at 0° C. It was allowed to warm to room temperature and stirred for 6 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 20% ethyl acetate in hexane as eluant) to afford 51.2. MS (ES): m/z 246.4 [M+H]+ and 51.3. MS (ES): m/z 246.4 [M+H]+.

Synthesis of compound 51.4. A mixture of compound 51.3 (3.9 g, 15.89 mmol, 1.0 equiv) and 10% palladium on carbon (2.0 g) in methanol (40 mL) was vacuumed and purged with 1 atm hydrogen and stirred at rt for 16 h. It was vacuumed and purged with nitrogen before opened to air. The mixture was filtered through a pad of Celite® and rinsed with methanol. The filtrate was concentrated under reduced pressure to obtain 51.4. MS (ES): m/z 156.2 [M+H]+.

Synthesis of compound 51.5. Compound 51.5 was prepared from 51.4 following the procedure described in the synthesis of 1.2. The crude product was used in the next step without further purification. MS (ES): m/z 198.3 [M+H]+.

Synthesis of I-51. Compound I-51 was prepared from 51.5 and Int-2 following the procedure described in the synthesis of I-1. The product was purified by flash column chromatography on silica gel (CombiFlash®, 3.5% methanol in dichloromethane as eluant). MS (ES): m/z: 436.5 [M+H]+, 1H NMR (DMSO-d6, 400 MHz): δ 10.47 (s, 1H), 8.13-8.12 (d, J=6.0 Hz, 1H), 7.62 (s, 1H), 7.22-7.20 (d, J=8.4 Hz, 1H), 7.04 (bs, 1H), 6.84-6.82 (d, J=8.0 Hz, 1H), 6.74-6.72 (d, J=6.8 Hz, 1H), 6.59-6.57 (m, 1H), 3.65-3.63 (m, 1H), 3.47 (s, 3H), 2.13-2.10 (m, 2H), 2.03 (s, 3H), 1.82-1.79 (m, 2H), 1.56 (bs, 1H), 1.35-1.26 (m, 2H), 1.17-1.02 (m, 2H), 0.88 (s, 9H).

Example 52: N-(4-((2-(((1-(2-methoxyethyl)-2-oxo-5-(trifluoromethyl)-1,2-dihydropyridin-3-yl)amino)-1-methyl-1H-benzo[d]imidazol-6-yl)methyl)pyridin-2-yl)acetamide

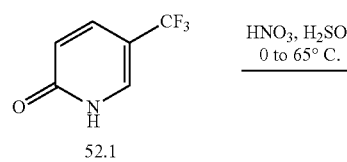

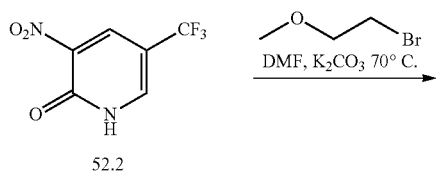

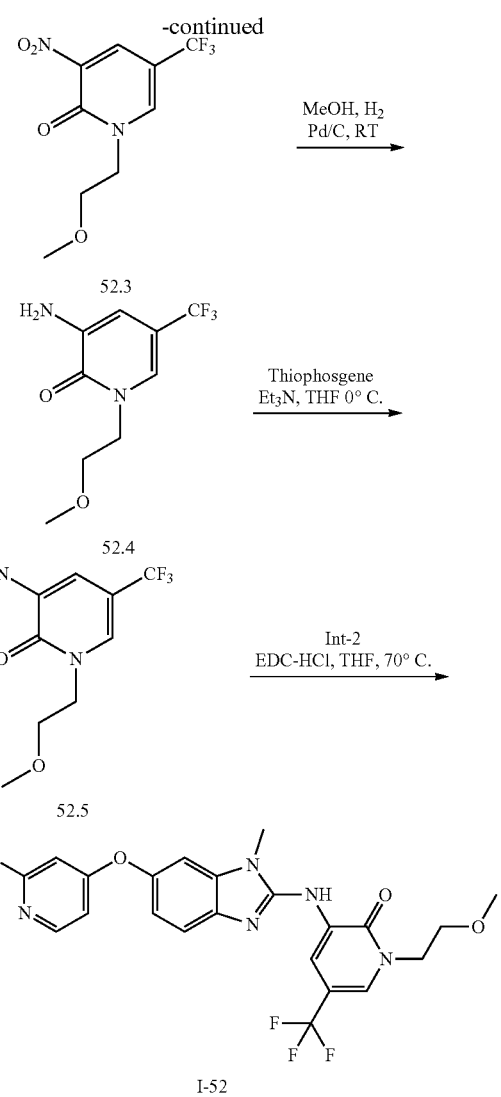

Synthesis of compound 52.2. To a solution of 52.1 (5.0 g, 30.66 mmol, 1.0 equiv) in conc. sulfuric acid (25 mL) was added fuming nitric acid (8 mL) at 0° C. The reaction mixture was stirred at 65° C. for 6 h. It was poured over crushed ice, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.5% methanol in dichloromethane as eluant) to afford 52.2. MS (ES): m/z 209.10 [M+H]+.

Synthesis of compound 52.3. A mixture of 52.2 (1.0 g, 4.81 mmol, 1.0 equiv) and potassium carbonate (1.3 g, 9.62 mmol, 2.0 equiv) in DMF (15 mL) was stirred at rt for 15 min. 1-Bromo-2-methoxyethane (1.0 g, 7.21 mmol, 1.5 equiv) was added and the reaction mixture was stirred at 70° C. for 2 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 40% ethyl acetate in hexane as eluant) to afford 52.3. MS (ES): m/z 267.2 [M+H]+.

Synthesis of compound 52.4. A flask charged with compound 52.3 (0.6 g, 2.25 mmol, 1.0 equiv), 10% palladium on carbon (0.3 g) and methanol (18 mL) was vacuumed and purged with hydrogen three times. The mixture was stirred at rt under 1 atm hydrogen atmosphere for 1 h. The flask was vacuumed and purged with nitrogen three times before it was opened to air. The reaction mixture was filtered through a pad of Celite® and rinsed with methanol. The filtrate was concentrated under reduced pressure to obtain 52.4. MS (ES): m/z 237.2 [M+H]+.

Synthesis of compound 52.5. Compound 52.5 was prepared from 52.4 following the procedure described in the synthesis of 1.2. The crude product was used in the next step without further purification. MS (ES): m/z 279.3 [M+H]+.

Synthesis of I-52. Compound I-52 was synthesized from compound 52.5 and Int-2 following the synthetic protocol described in the synthesis of I-12. The product was purified by preparative HPLC. MS (ES): m/z: 517.92 [M+H]+, $^1$H NMR (DMSO-d6, 400 MHz): δ 10.49 (s, 1H), 8.65 (s, 1H), 8.53 (s, 1H), 8.16-8.14 (d, J=5.6 Hz, 1H), 7.93 (s, 1H), 7.65 (s, 1H), 7.58-7.56 (d, J=8.4 Hz, 1H), 7.36 (s, 1H), 6.92-6.90 (d, J=7.6 Hz, 1H), 6.62-6.61 (d, J=3.6 Hz, 1H), 4.29-4.28 (m, 2H), 3.73 (s, 3H), 3.70-3.67 (t, 2H), 3.28 (s, 3H), 2.02 (s, 3H).

Example 53: N-(4-((7-cyano-2-((1-(2-methoxy-ethyl)-2-oxo-5-(trifluoromethyl)-1,2-dihydropyridin-3-yl)amino)-1-methyl-1H-benzo[d]imidazol-6-yl)oxy)pyridin-2-yl)acetamide Synthesis of compound I-53. Compound I-53 was prepared from 52.5 and Int-4 following the procedure described in the synthesis of I-1. The product was purified by flash column chromatography on silica gel (CombiFlash®, 1.8% methanol in dichloromethane as eluant). MS (ES): m/z: 542.8 [M+H]+, $^1$H NMR (DMSO-d6, 400 MHz): δ 10.64 (s, 1H), 8.82 (s, 1H), 8.59 (s, 1H), 8.24-8.23 (d, J=5.6 Hz, 1H), 8.00 (s, 1H), 7.92-7.90 (d, J=8.4 Hz, 1H), 7.71 (s, 1H), 7.14-7.12 (d, J=8.8 Hz, 1H), 6.74-6.72 (m, 1H), 4.32-4.30 (t, 2H), 3.97 (s, 3H), 3.71-3.68 (t, 2H), 3.28 (s, 3H), 2.05 (s, 3H).

Example 54: N-(4-((1-methyl-2-((1-methyl-2-oxo-5-(trifluoromethyl)-1,2-dihydropyridin-3-yl)amino)-1H-benzo[d]imidazol-6-yl)oxy)pyridin-2-yl)acetamide

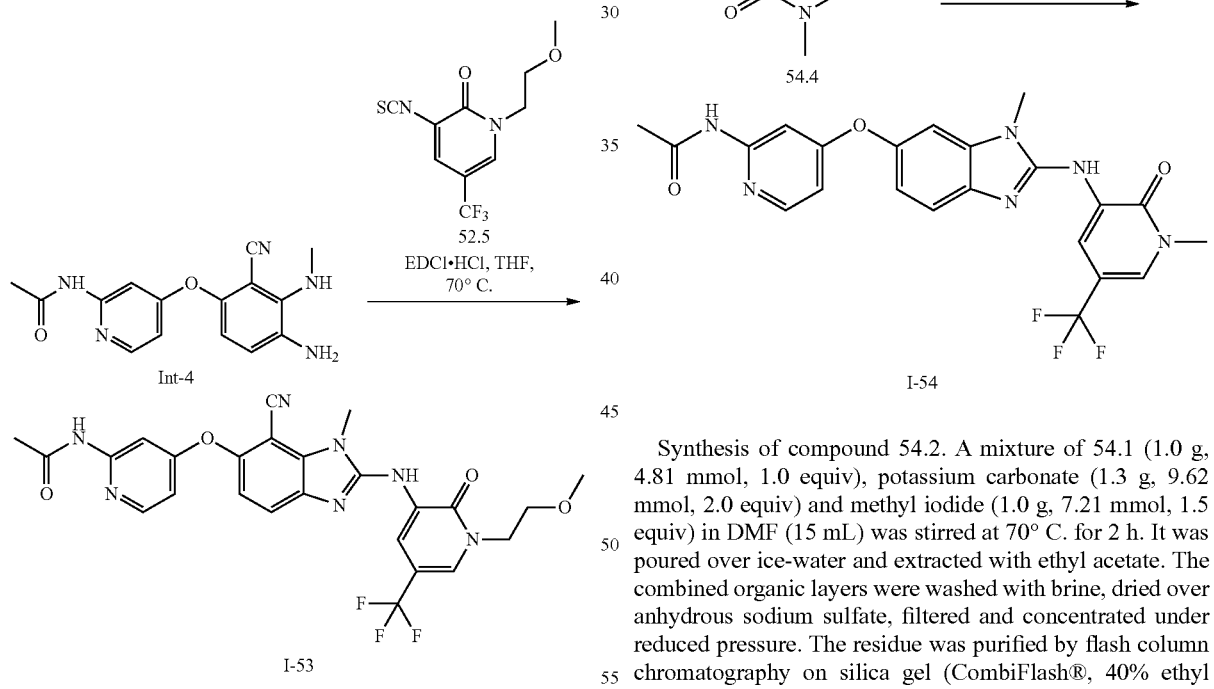

Synthesis of compound 54.2. A mixture of 54.1 (1.0 g, 4.81 mmol, 1.0 equiv), potassium carbonate (1.3 g, 9.62 mmol, 2.0 equiv) and methyl iodide (1.0 g, 7.21 mmol, 1.5 equiv) in DMF (15 mL) was stirred at 70° C. for 2 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 40% ethyl acetate in hexane as eluant) to afford 54.2. MS (ES): m/z 223.12 [M+H]+.

Synthesis of compound 54.3. Compound 54.3 was prepared from 54.2 following the procedure described in the synthesis of 52.4. MS (ES): m/z 193.14 [M+H]+.

Synthesis of compound 54.4. Compound 54.4 was prepared from 54.3 following the procedure described in the synthesis of 1.2. The crude product was used in the next step without further purification. MS (ES): m/z 192.15 [M+H]+.

Synthesis of compound I-54. Compound I-54 was prepared from 54.4 and Int-2 following the procedure described in the synthesis of I-1. The product was purified by preparative HPLC. MS (ES): m/z: 473.39 [M+H]+, 1H NMR (DMSO-d6, 400 MHz): δ 10.49 (s, 1H), 8.63 (s, 1H), 8.50 (s, 1H), 8.16-8.14 (d, J=5.6 Hz, 1H), 8.04 (s, 1H), 7.65 (s, 1H), 7.57-7.55 (d, J=8.4 Hz, 1H), 7.36 (s, 1H), 6.92-6.90 (d, J=7.6 Hz, 1H), 6.62-6.61 (d, J=3.6 Hz, 1H), 3.73 (s, 3H), 3.65 (s, 3H), 2.03 (s, 3H).

Example 55: N-(4-((7-cyano-1-methyl-2-((1-methyl-2-oxo-5-(trifluoromethyl)-1,2-dihydropyridin-3-yl)amino)-1H-benzo[d]imidazol-6-yl)oxy)pyridin-2-yl)acetamide

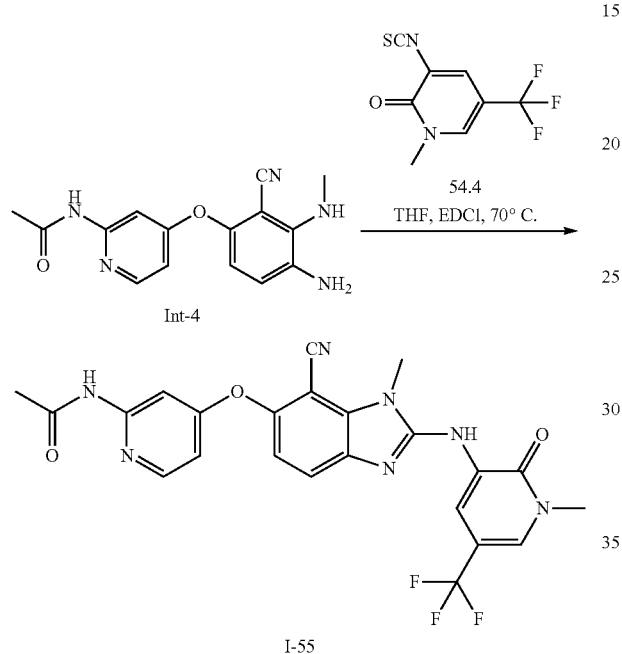

Synthesis of compound I-55. Compound I-55 was prepared from 54.4 and Int-4 following the procedure described in the synthesis of I-1. The product was purified by flash column chromatography on silica gel (CombiFlash®, 2% methanol in dichloromethane as eluant). MS (ES): m/z: 498.76 [M+H]+, 1H NMR (DMSO-d6, 400 MHz): δ 10.62 (s, 1H), 8.80 (s, 1H), 8.56 (s, 1H), 8.23-8.22 (d, J=5.6 Hz, 1H), 8.11 (s, 1H), 7.92-7.90 (d, J=8.4 Hz, 1H), 7.70 (s, 1H), 7.14-7.12 (d, J=8.4 Hz, 1H), 6.72-6.71 (m, 1H), 3.96 (s, 3H), 3.65 (s, 3H), 2.04 (s, 3H).

Example 56: N-(4-((2-((1-(((1s,3s)-3-methoxycyclobutyl)-6-oxo-5-(trifluoromethyl)-1,6-dihydropyridin-3-yl)amino)-1-methyl-1H-benzo[d]imidazol-6-yl)oxy)pyridin-2-yl)acetamide

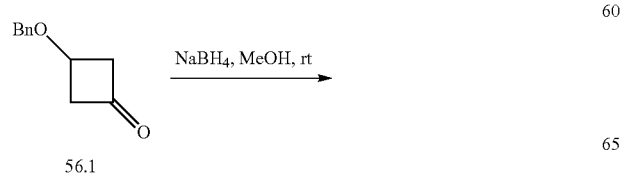

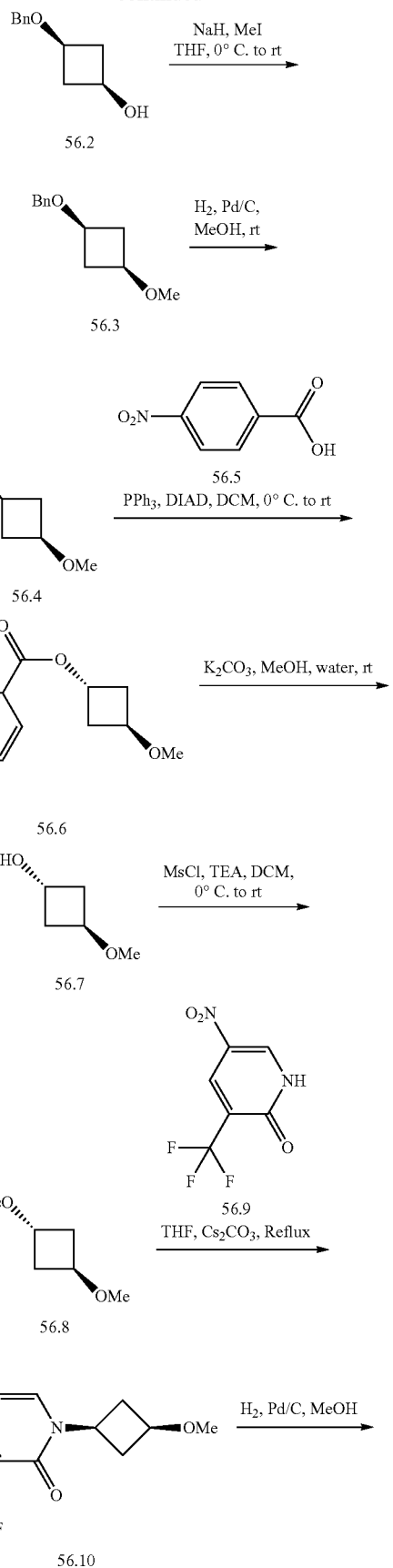

-continued

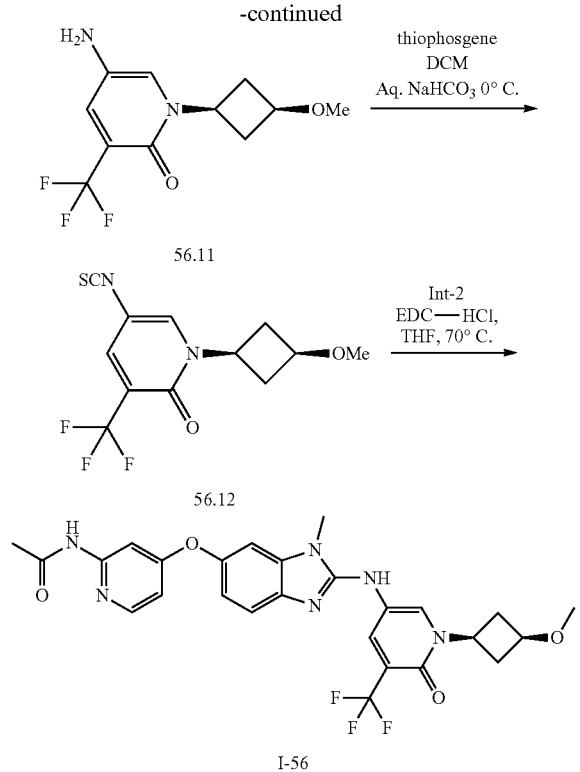

Synthesis of compound 56.2. To a solution of 56.1 (10 g, 56.75 mmol, 1.0 equiv) in methanol (100 mL) was added sodium borohydride (6.4 g, 170.2 mmol, 3.0 equiv) in small portions at 0° C. The reaction mixture was stirred at room temperature for 3 h. It was poured over ice-water, stirred and extracted with ethyl acetate. The combined organic layers were washed with brine, dried over anhydrous sodium sulfate, filtered and concentrated under reduced pressure to obtain 56.2. MS (ES): m/z 179.3 [M+H]⁺.

Synthesis of compound 56.3. To a solution of 56.2 (9.2 g, 51.62 mmol, 1.0 equiv) in THF (100 mL) was added sodium hydride (3.71 g, 77.43 mmol, 1.5 equiv) at 0° C. and stirred for 30 min. Methyl iodide (8.73 g, 61.94 mmol, 1.2 equiv) was added. The reaction mixture was stirred at room temperature for 3 h. It was poured over ice, stirred and extracted with ethyl acetate. The combined organic layers were washed with brine, dried over anhydrous sodium sulfate, filtered and concentrated under reduced pressure to obtain 56.3. MS (ES): m/z 193.3 [M+H]⁺.

Synthesis of compound 56.4. A flask charged with compound 56.3 (8.1 g, 42.13 mmol, 1.0 equiv), 10% palladium on carbon (4.0 g) and methanol (80 mL) was vacuumed and purged with hydrogen three times. The mixture was stirred at rt under 1 atm hydrogen atmosphere for 1 h. The flask was vacuumed and purged with nitrogen three times before it was opened to air. The reaction mixture was filtered through a pad of Celite® and rinsed with methanol. The filtrate was concentrated under reduced pressure and the residue was purified by flash column chromatography on silica gel (CombiFlash®, 5% methanol in dichloromethane as eluant) to afford 56.4. MS (ES): m/z 103.2 [M+H]⁺.

Synthesis of compound 56.6. To a solution of compound 56.4 (3.4 g, 33.29 mmol, 1.0 equiv), 4-nitrobenzoic acid (56.5, 5.56 g, 33.29 mmol, 1.0 equiv) and triphenyl phosphine (10.46 g, 39.94 mmol, 1.2 equiv) in dichloromethane (40 mL) was added diisopropyl azodicarboxylate (8.067 g, 39.94 mmol, 1.2 equiv) 0° C. The reaction mixture was stirred at room temperature for 4 h. It poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 20% ethyl acetate in hexane as eluant) to afford 56.6. MS (ES): m/z 252.24 [M+H]⁺.

Synthesis of compound 56.7. To a solution of 56.6 (3.9 g, 15.52 mmol, 1.0 equiv) in methanol (40 mL) and water (8 mL) was added potassium carbonate (4.28 g, 31.04 mmol, 2.0 equiv). The reaction mixture was stirred at room temperature for 3 h. It was poured over ice-water, stirred and extracted with ethyl acetate. The combined organic layers were washed with brine, dried over anhydrous sodium sulfate, filtered and concentrated under reduced pressure to obtain 56.7. MS (ES): m/z 103.3 [M+H]⁺.

Synthesis of compound 56.8. To a solution of 56.7 (1.1 g, 10.77 mmol, 1.0 equiv) in dichloromethane (10 mL) was added triethylamine (1.95 mL, 14.0 mmol, 1.3 equiv) at 0° C. followed by addition of methanesulfonyl chloride (1.59 g, 14.0 mmol, 1.3 equiv). The reaction mixture was stirred at room temperature for 2 h. It was poured over ice-water, stirred and extracted with dichloromethane. The combined organic layers were washed with brine, dried over anhydrous sodium sulfate, filtered and concentrated under reduced pressure. The residue was purified by flash column chromatography on silica gel (CombiFlash®, 10% ethyl acetate in hexane as eluant) to afford 56.8. MS (ES): m/z 181.2 [M+H]⁺.

Synthesis of compound 56.10. A mixture of 56.9 (0.2 g, 0.961 mmol, 1.0 equiv) and 56.8 (0.207 g, 1.15 mmol, 1.2 equiv) and cesium carbonate (0.468 g, 1.44 mmol, 1.5 equiv) in THF (7 mL) was heated to reflux for 72 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 15% ethyl acetate in hexane as eluant) to afford 56.10. MS (ES): m/z 293.2 [M+H]⁺.

Synthesis of compound 56.11. Compound 56.11 was prepared from 56.10 following the procedure described in the synthesis of Int-2. The crude product was used in the next step without further purification. MS (ES): m/z 263.2 [M+H]⁺.

Synthesis of compound 56.12. Compound 56.12 was prepared from 56.11 following the procedure described in the synthesis of 11.8. The crude product was used in the next step without further purification. MS (ES): m/z 305.3 [M+H]⁺.

Synthesis of compound I-56. Compound I-56 was prepared from 56.12 and Int-2 following the procedure described in the synthesis of I-1. The product was purified by flash column chromatography on silica gel (CombiFlash®, 3.5% methanol in dichloromethane as eluant). MS (ES): m/z: 540.8 [M−H]⁺, ¹H NMR (DMSO-d6, 400 MHz): δ 10.50 (s, 1H), 8.95 (s, 1H), 8.80 (s, 1H), 8.38 (s, 1H), 8.16-8.15 (d, J=5.6 Hz, 1H), 7.64 (s, 1H), 7.38-7.36 (d, J=8.4 Hz, 1H), 7.26 (s, 1H), 6.86-6.84 (d, J=8.0 Hz, 1H), 6.63-6.62 (d, J=5.2 Hz, 1H), 4.80-4.76 (m, 1H), 3.86-3.82 (m, 1H), 3.67 (s, 3H), 3.24 (s, 3H), 2.86 (bs, 2H), 2.13-2.11 (m, 2H), 2.03 (s, 3H).

Example 57: N-(4-((2-((1-((1s,3s)-3-methoxycyclobutyl)-6-oxo-5-(trifluoromethyl)-1,6-dihydropyridin-3-yl)amino)-1,7-dimethyl-1H-benzo[d]imidazol-6-yl)oxy)pyridin-2-yl)acetamide

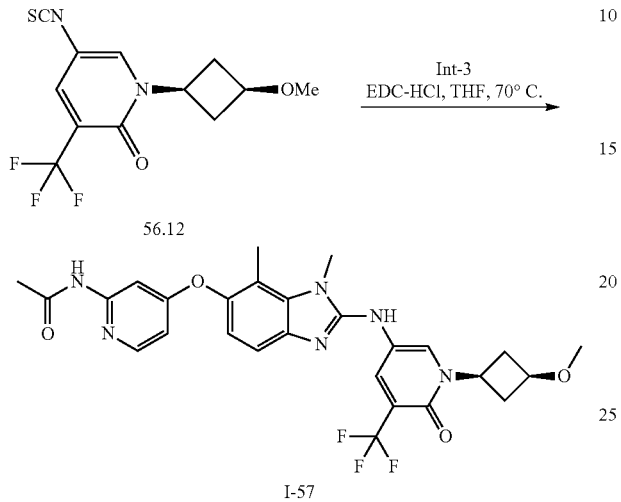

Synthesis of compound I-57. Compound I-57 was prepared from 56.12 and Int-3 following the procedure described in the synthesis of I-1. The product was purified by flash column chromatography on silica gel (CombiFlash®, 3-4% methanol in dichloromethane as eluant). MS (ES): m/z: 557.4 [M+H]$^+$, $^1$H NMR (DMSO-d6, 400 MHz): δ 10.49 (s, 1H), 8.85 (s, 1H), 8.78 (s, 1H), 8.35 (s, 1H), 8.15-8.13 (d, J=5.2 Hz, 1H), 7.58 (s, 1H), 7.22-7.20 (d, J=8 Hz, 1H), 6.82-6.80 (d, J=8.4 Hz, 1H), 6.55 (bs, 1H), 4.80-4.76 (m, 1H), 3.89 (s, 3H), 3.85-3.82 (m, 1H), 3.23 (s, 3H), 3.18-3.17 (d, 1H), 2.87 (bs, 2H), 2.43 (s, 3H), 2.12-2.10 (m, 1H), 2.03 (s, 3H).

Example 58: (R)—N-(4-((2-((1-(1,4-dioxan-2-yl)methyl)-2-oxo-5-(trifluoromethyl)-1,2-dihydropyridin-3-yl)amino)-1-methyl-1H-benzo[d]imidazol-6-yl)oxy)pyridin-2-yl)acetamide and (S)—N-(4-((2-((1-((1,4-dioxan-2-yl)methyl)-2-oxo-5-(trifluoromethyl)-1,2-dihydropyridin-3-yl)amino)-1-methyl-1H-benzo[d]imidazol-6-yl)oxy)pyridin-2-yl)acetamide

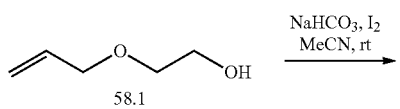

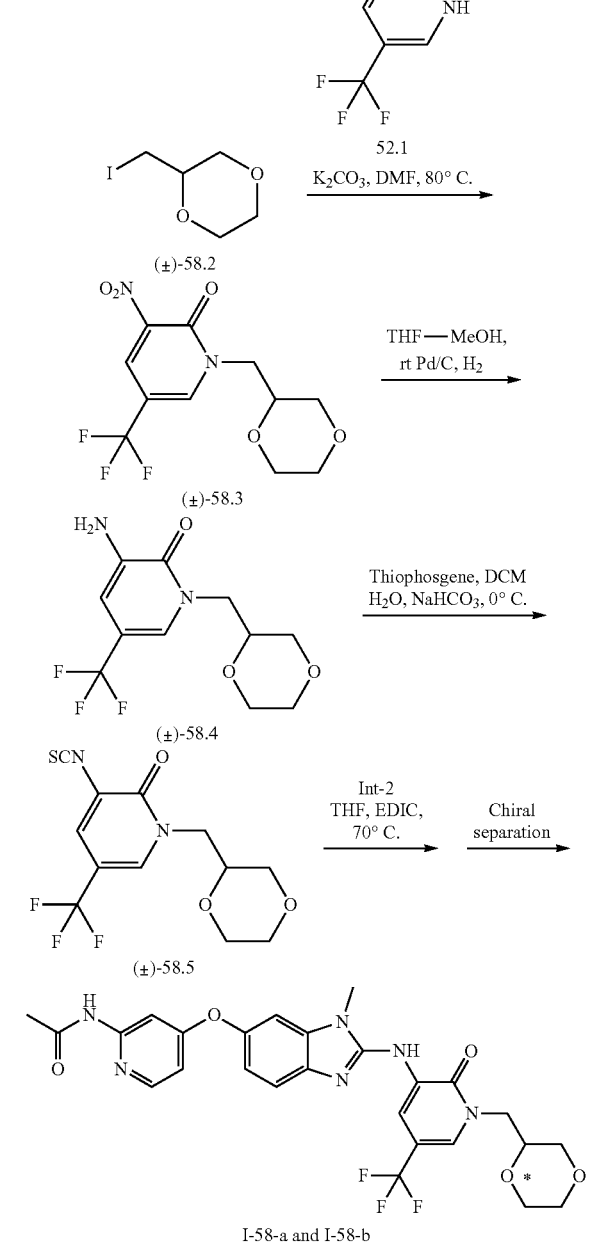

Synthesis of compound (±)-58.2. A mixture of 58.1 (5.0 g, 48.96 mmol, 1.0 equiv), sodium bicarbonate (12.337 g, 146.88 mmol, 3.0 equiv) and iodine (37.3 g, 146.88 mmol, 3.0 equiv) in acetonitrile (25 mL) was stirred at room temperature for 16 h. It was poured over crushed ice, stirred and extracted with ethyl acetate. The combined organic layers were washed with aqueous sodium thiosulphate followed by brine, dried over anhydrous sodium sulfate, filtered and concentrated under reduced pressure. The residue was purified by flash column chromatography on silica gel (CombiFlash®, 15% ethyl acetate in hexane as eluant) to afford (±)-58.2. MS (ES): m/z 229.10 [M+H]$^+$.

Synthesis of compound (±)-58.3. To a solution of 52.1 (2.25 g, 10.81 mmol, 1.0 equiv) in DMF (25 mL) was added

307 potassium carbonate (2.98 g, 21.62 mmol, 2.0 equiv) and stirred for 15 min. To the mixture was added (±)-58.2 (2.96 g, 12.97 mmol, 1.2 equiv). The reaction mixture was stirred at 80° C. for 16 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 20% ethyl acetate in hexane as eluant) to afford (±)-58.3. MS (ES): m/z 309.2 [M+H]$^+$.

Synthesis of compound (±)-58.4. A mixture of compound (±)-58.3 (1.2 g, 3.89 mmol, 1.0 equiv), 10% palladium on carbon (0.6 g) in methanol (10 mL) and THF (4 mL) was vacuumed and purged with hydrogen. It was stirred at rt under 1 atm of hydrogen for 1 h. It was filtered through a pad of Celite® and rinsed with methanol. The filtrate was concentrated under reduced pressure to obtain (±)-58.4. MS (ES): m/z 279.3 [M+H]$^+$.

Synthesis of compound (±)-58.5. Compound (±)-58.5 was prepared from (±)-58.4 following the procedure described in the synthesis of 11.8. The crude product was used in the next step without further purification. MS (ES): m/z 321.3 [M+H]$^+$.

Synthesis of compound (±)-I-58. Compound (±)-I-58 was prepared from (±)-58.5 and Int-2 following the procedure described in the synthesis of I-1. The product was purified by flash column chromatography on silica gel (CombiFlash®, 2% methanol in dichloromethane as eluant). MS (ES): m/z: 559.8 [M+H]$^+$.

I-58-a and I-58-b. Enantiomers of I-58 were separated on SFC (column: CHIRALCEL OJ-H (250 mm×4.6 mm, 5 µm); eluent: 0.1% DEA in IPA:ACN (50:50); flow rate=4 mL/min) to get first eluting fraction (I-58-a) and second eluting fraction (I-58-b). (*Absolute stereochemistry not determined.)

I-58-a. MS (ES): m/z: 559.8 [M+H]$^+$, $^1$H NMR (DMSO-d6, 400 MHz): δ 10.50 (s, 1H), 8.65-8.64 (d, J=2.0 Hz, 1H), 8.54 (s, 1H), 8.16-8.14 (d, J=5.6 Hz, 1H), 7.91 (s, 1H), 7.65 (s, 1H), 7.58-7.56 (d, J=8.4 Hz, 1H), 7.37 (bs, 1H), 6.92 (m, 1H), 6.63-6.61 (m, 1H), 4.23-4.19 (m, 1H), 4.13-4.08 (m, 1H), 3.93 (bs, 1H), 3.82-3.76 (m, 4H), 3.66-3.64 (m, 2H), 3.48 (s, 3H), 2.02 (s, 3H).

I-58-b. MS (ES): m/z: 559.8 [M+H]$^+$, $^1$H NMR (DMSO-d6, 400 MHz): δ 10.50 (s, 1H), 8.65-8.64 (d, J=2.0 Hz, 1H), 8.54 (s, 1H), 8.16-8.14 (d, J=5.6 Hz, 1H), 7.91 (s, 1H), 7.65 (s, 1H), 7.58-7.56 (d, J=8.4 Hz, 1H), 7.37 (bs, 1H), 6.92 (m, 1H), 6.63-6.61 (m, 1H), 4.23-4.19 (m, 1H), 4.13-4.08 (m, 1H), 3.93 (bs, 1H), 3.82-3.76 (m, 4H), 3.66-3.64 (m, 2H), 3.48 (s, 3H), 2.02 (s, 3H).

308

Example 59: N-(4-((2-((1-((3R,4R)-4-methoxytetrahydro-2H-pyran-3-yl)-2-oxo-5-(trifluoromethyl)-1,2-dihydropyridin-3-yl)amino)-1-methyl-1H-benzo[d]imidazol-6-yl)oxy)pyridin-2-yl)acetamide and N-(4-((2-((1-((3S,4S)-4-methoxytetrahydro-2H-pyran-3-yl)-2-oxo-5-(trifluoromethyl)-1,2-dihydropyridin-3-yl)amino)-1-methyl-1H-benzo[d]imidazol-6-yl)oxy)pyridin-2-yl)acetamide

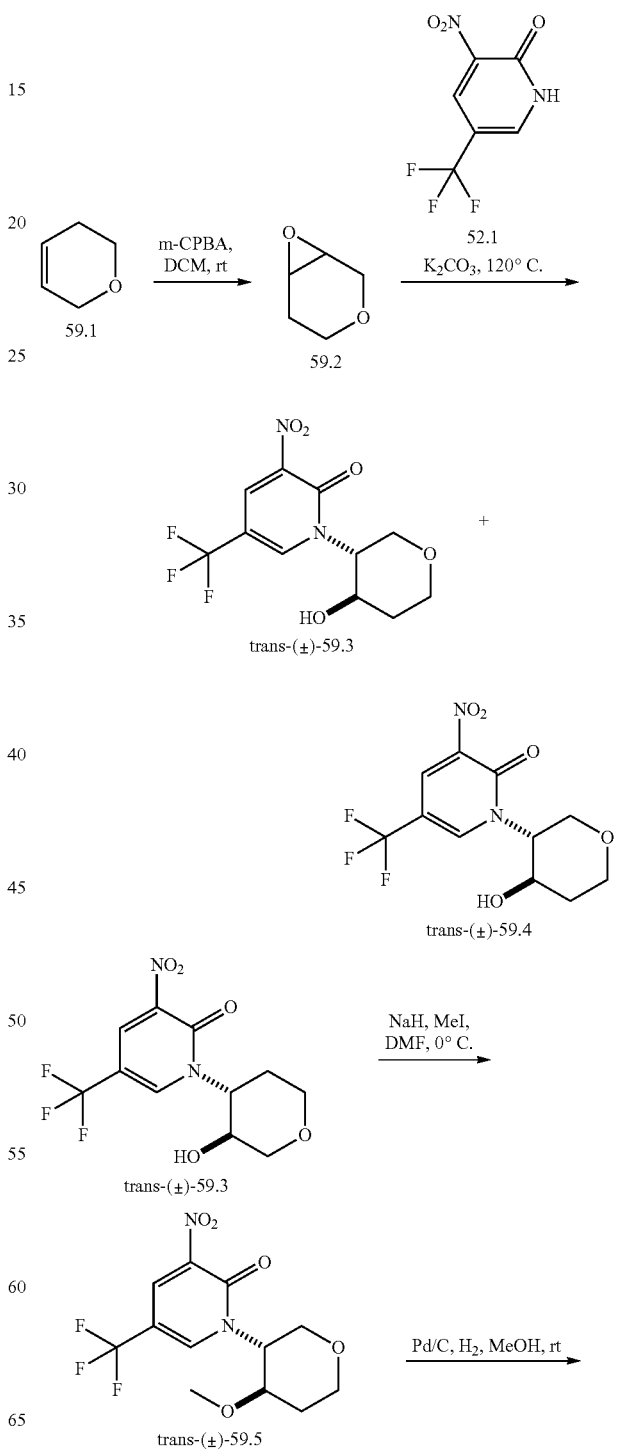

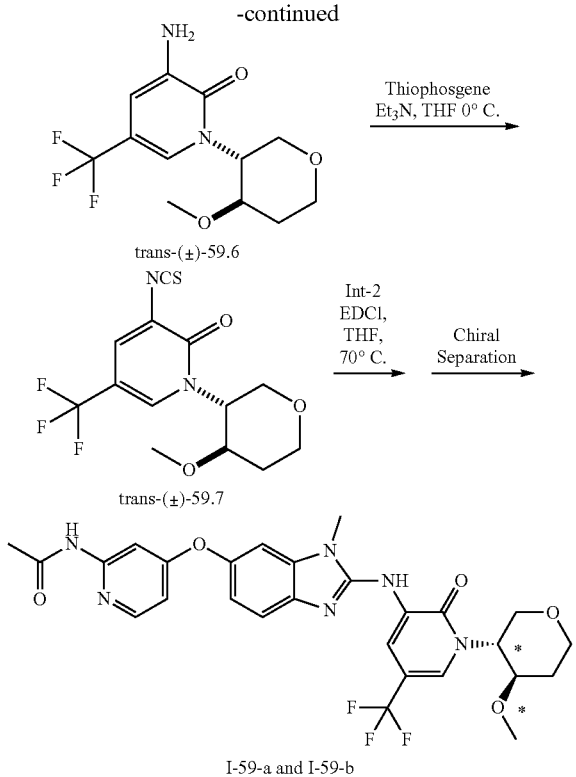

Synthesis of compound trans-(±)-59.6. Compound trans-(±)-59.6 was prepared from trans-(±)-59.5 following the procedure described in the synthesis of 52.4. The crude product was used in the next step without further purification. MS (ES): m/z 293.3 [M+H]⁺.

Synthesis of compound trans-(±)-59.7. Compound trans-(±)-59.7 was prepared from trans-(±)-59.6 following the procedure described in the synthesis of 1.2. The crude product was used in the next step without further purification. MS (ES): m/z 335.3 [M+H]⁺.

Synthesis of compound trans-(±)-I-59. Compound trans-(±)-I-59 was prepared from trans-(±)-I-57 and Int-2 following the procedure described in the synthesis of 1-2. MS (ES): m/z: 573.8 [M+I-1]⁺.

I-59-a and I-59-b. trans-(±)-I-59 was separated on HPLC (CHIRALCEL OX-H (250 mm×21.0 mm, 5 μm), mobile phases: (A) 0.1% diethylamine in Hexane (B) 0.1% diethylamine in isopropanol/acetonitrile (70:30); flow rate:19 mL/min) to get first eluting fraction (I-59-a) and second eluting fraction (I-59-b). (*Absolute stereochemistry not determined.)

I-59-a: MS (ES): m/z: 573.8 [M+H]⁺, ¹H NMR (DMSO-d6, 400 MHz): δ 10.51 (s, 1H), 8.64 (s, 1H), 8.58 (s, 1H), 8.16-8.14 (d, J=5.6 Hz, 1H), 8.07 (s, 1H), 7.65 (s, 1H), 7.58-7.56 (d, J=8.4 Hz, 1H), 7.38 (s, 1H), 6.92-6.90 (d, J=8.4 Hz, 1H), 6.63-6.62 (d, J=3.2 Hz, 1H), 4.83 (bs, 1H), 4.13 (bs, 1H), 3.97-3.88 (m, 2H), 3.74 (s, 3H), 3.58-3.52 (m, 1H), 3.21 (s, 3H), 2.33-2.26 (m, 1H), 2.02 (s, 3H), 1.54-1.51 (m, 2H).

I-59-b: MS (ES): m/z: 573.8 [M+H]⁺, ¹H NMR (DMSO-d6, 400 MHz): δ 10.51 (s, 1H), 8.64 (s, 1H), 8.58 (s, 1H), 8.16-8.14 (d, J=5.6 Hz, 1H), 8.07 (s, 1H), 7.65 (s, 1H), 7.58-7.56 (d, J=8.4 Hz, 1H), 7.37 (s, 1H), 6.92-6.90 (d, J=8.4 Hz, 1H), 6.63-6.62 (d, J=3.2 Hz, 1H), 4.83 (bs, 1H), 4.13 (bs, 1H), 3.97-3.88 (m, 2H), 3.74 (s, 3H), 3.58-3.52 (m, 1H), 3.21 (s, 3H), 2.33-2.26 (m, 1H), 2.02 (s, 3H), 1.54-1.51 (m, 2H).

Synthesis of compound 59.2. To a solution of 59.1 (10 g, 118.8 mmol, 1.0 equiv) in dichloromethane (100 mL) was added m-chloroperbenzoic acid (22.5 g, 130.68 mmol, 1.1 equiv) portion-wise at 0° C. The reaction mixture was stirred at room temperature for 18 h. It was poured into a saturated aqueous solution of sodium bicarbonate and stirred for a few minutes. The organic layer was separated washed with brine, dried over anhydrous sodium sulfate, filtered and concentrated under reduced pressure to obtain 59.2. ¹H NMR (DMSO-d6, 400 MHz): δ 3.84 (dd, J=2.7 Hz, 13.4 Hz, 1H), 3.74-3.70 (m, 1H), 3.38-3.26 (m, 3H), 3.10-3.09 (m, 1H), 1.87-1.82 (m, 2H).

Synthesis of compound trans-(±)-59.3 and trans-(±)-59.4. A mixture of 59.2 (2.5 g, 12.01 mmol, 1.0 equiv), 52.1 (6.01 g, 60.07 mmol, 5.0 equiv) and potassium carbonate (4.143 g, 30.02 mmol, 2.5 equiv) in DMF was stirred at 120° C. for 16 h. The reaction mixture was cooled to room temperature, poured into ice-water and extracted with ethyl acetate. The combined organic layers were washed with brine, dried over anhydrous sodium sulfate, filtered and concentrated under reduced pressure. The residue was purified by flash column chromatography on silica gel followed by preparative HPLC to obtain trans-(±)-59.3. MS (ES): m/z 309.2 [M+H]⁺ and trans-(±)-59.4. MS (ES): m/z 309.3 [M+H]⁺.

Synthesis of compound trans-(±)-59.5. To a solution of trans-(±)-59.3 (0.135 g, 0.438 mmol, 1.0 equiv) in DMF (1 mL) was added sodium hydride (0.042 g, 0.876 mmol, 2.0 equiv) at 0° C. The reaction mixture was stirred for 30 min and was added methyl iodide (0.168 g, 0.876 mmol, 2.0 equiv). It was stirred at room temperature for 1 h before it was poured over ice, stirred and extracted with ethyl acetate. The combined organic layers were washed with brine, dried over anhydrous sodium sulfate, filtered and concentrated under reduced pressure to obtain trans-(±)-59.5. MS (ES): m/z 323.2 [M+H]⁺.

Example 60: N-(4-((2-(((1-((3R,4S)-4-methoxytetrahydro-2H-pyran-3-yl)-2-oxo-5-(trifluoromethyl)-1,2-dihydropyridin-3-yl)amino)-1-methyl-1H-benzo[d]imidazol-6-yl)oxy)pyridin-2-yl)acetamide and N-(4-((2-((1-((3S,4R)-4-methoxytetrahydro-2H-pyran-3-yl)-2-oxo-5-(trifluoromethyl)-1,2-dihydropyridin-3-yl)amino)-1-methyl-1H-benzo[d]imidazol-6-yl)oxy)pyridin-2-yl)acetamide

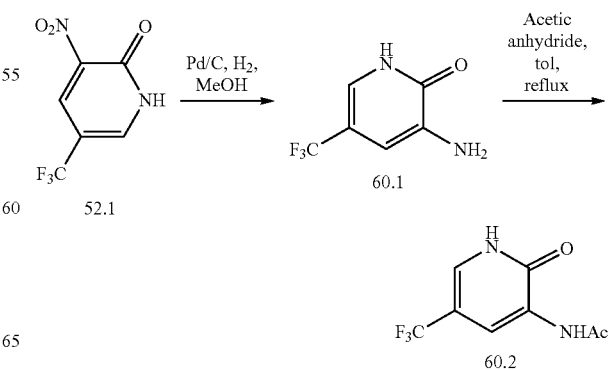

-continued

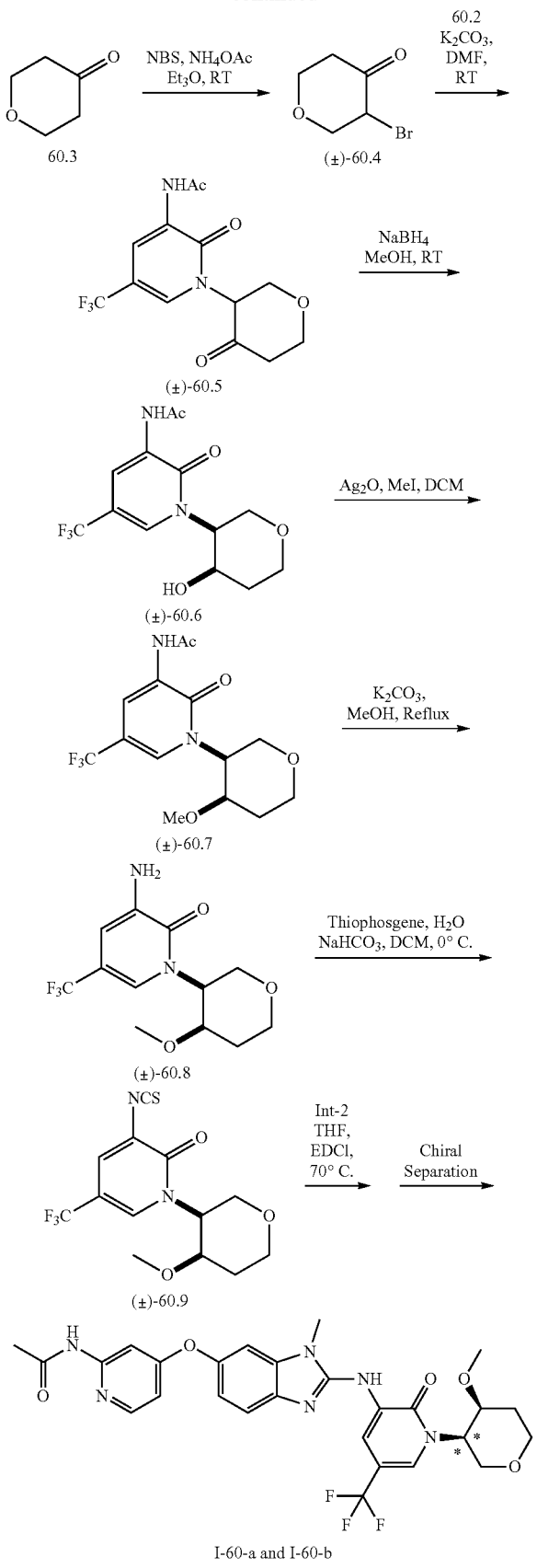

Synthesis of compound 60.1. Compound 60.1 was prepared from 52.1 following the procedure described in the synthesis of 52.4. The crude product was used in the next step without further purification. MS (ES): m/z 179.1 [M+H]$^+$.

Synthesis of compound 60.2. To a solution of 60.1 (6.5 g, 36.49 mmol, 1.0 equiv) in toluene (25 mL) was added acetic anhydride (17 mL, 182.45 mmol, 5.0 equiv). The reaction mixture was heated to reflux for 2 h. It was concentrated under reduced pressure. The residue was further purified by trituration with diethyl ether to obtain 60.2. MS (ES): m/z 221.3 [M+H]$^+$.

Synthesis of compound (±)-60.4. To a mixture of 60.3 (5.0 g, 49.94 mmol, 1.0 equiv) and ammonium acetate (0.384 g, 4.99 mmol, 0.1 equiv) in diethyl ether (50 mL) at 0° C. was added N-bromosuccinimide (9.28 g, 52.43 mmol, 1.05 equiv). The reaction mixture was stirred at room temperature for 16 h. It was filtered through a pad of Celite® and the filtrate was concentrated under reduced pressure. The residue was purified by flash column chromatography on silica gel (CombiFlash®, 10% ethyl acetate in hexane as eluant) to afford (±)-60.4. MS (ES): m/z 180.1 [M+H]$^+$.

Synthesis of compound (±)-60.5. To a solution of (±)-60.4 (4.6 g, 25.7 mmol, 1.0 equiv) and 60.2 (5.66 g, 25.7 mmol, 1.0 equiv) in DMF (50 mL) was added potassium carbonate (5.67 g, 41.12 mmol, 1.6 equiv) and stirred at room temperature for 12 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 40% ethyl acetate in hexane as eluant) to afford (±)-60.5. MS (ES): m/z 319.1 [M+H]$^+$.

Synthesis of compound (±)-60.6. To a solution of (±)-60.5 (2.5 g, 7.86 mmol, 1.0 equiv) in methanol (25 mL) was added sodium borohydride (0.348 g, 9.43 mmol, 1.2 equiv) in small portions at 0° C. and stirred for 30 min. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 60% ethyl acetate in hexane as eluant) to afford (±)-60.6. MS (ES): m/z 321.3 [M+H]$^+$.

Synthesis of compound (±)-60.7. To a solution of (±)-60.6 (1.2 g, 3.75 mmol, 1.0 equiv) in dichloromethane (7.5 mL) and water (2.5 mL) was added silver oxide (4.33 g, 18.75 mmol, 5.0 equiv) and stirred at room temperature for 15 min. To the mixture was added methyl iodide (0.798 g, 5.62 mmol, 1.5 equiv). The reaction mixture was stirred at room temperature for 72 h. It was poured over ice-water, stirred and extracted with dichloromethane. The combined organic layers were washed with brine, dried over anhydrous sodium sulfate, filtered and concentrated under reduced pressure. The residue was purified by flash column chromatography on silica gel (CombiFlash®, 30% ethyl acetate in hexane as eluant) to afford (±)-60.7. MS (ES): m/z 335.3 [M+H]$^+$.

Synthesis of compound (±)-60.8. A mixture of (±)-60.7 (0.680 g, 2.03 mmol, 1.0 equiv) and potassium carbonate (5.6 g, 40.6 mmol, 20 equiv) in methanol (10 mL) was heated to reflux for 16 h. It was poured over ice-water, stirred and extracted with ethyl acetate. The combined organic layers were washed with brine, dried over anhydrous sodium sulfate, filtered and concentrated under reduced pressure to obtain (±)-60.8. MS (ES): m/z 293.3 [M+H]$^+$.

Synthesis of compound (±)-60.9. Compound (±)-60.9 was prepared from (±)-60.8 following the procedure described in the synthesis of 11.8. The crude product was used in the next step without further purification. MS (ES): m/z 335.3 [M+H]+.

Synthesis of compound (±)-I-60. Compound (±)-I-60 was prepared from (±)-60.9 following the procedure described in the synthesis of I-1. The product was purified by flash column chromatography on silica gel (CombiFlash®, 2.5% methanol in dichloromethane as eluant). MS (ES): m/z: 573.5 [M+H]+.

I-60-a and I-60-b. Compound (±)-I-60 was separated on HPLC (column: CHIRALPAK IC (250 mm×21 mm, 5 μm); mobile phase: (A) 0.1% DEA in n-hexane (B) 0.1% DEA in 2-propanol:acetonitrile (70:30); flow rate: 20 mL/min) to get first eluting fraction (I-60-a) and second eluting fraction (I-60-b). (*Absolute stereochemistry not determined.)

I-60-a. MS (ES): m/z: 573.7 [M+H]+, $^1$H NMR (DMSO-d6, 400 MHz): δ 10.51 (s, 1H), 8.64 (s, 1H), 8.59 (s, 1H), 8.16-8.14 (d, J=5.6 Hz, 1H), 8.07 (s, 1H), 7.65 (s, 1H), 7.58-7.56 (d, J=9.2 Hz, 1H), 7.38 (s, 1H), 6.93-6.91 (d, J=8.4 Hz, 1H), 6.63-6.62 (m, 1H), 5.76 (s, 1H), 4.83 (bs, 1H), 4.13 (bs, 1H), 3.97-3.87 (m, 2H), 3.73 (s, 3H), 3.58-3.52 (m, 1H), 3.21 (s, 3H), 2.33-2.26 (m, 1H), 2.02 (s, 3H), 1.54-1.51 (m, 1H).

I-60-b. MS (ES): m/z: 573.4 [M+H]+, $^1$H NMR (DMSO-d6, 400 MHz): δ 10.50 (s, 1H), 8.64 (s, 1H), 8.59 (s, 1H), 8.16-8.14 (d, J=5.6 Hz, 1H), 8.07 (s, 1H), 7.65 (s, 1H), 7.58-7.56 (d, J=8.4 Hz, 1H), 7.38 (s, 1H), 6.93-6.91 (d, J=8.4 Hz, 1H), 6.62 (bs, 1H), 5.76 (s, 1H), 4.83 (bs, 1H), 4.13 (bs, 1H), 3.94-3.88 (m, 2H), 3.74 (s, 3H), 3.55-3.53 (m, 1H), 3.21 (s, 3H), 2.33-2.26 (m, 1H), 2.02 (s, 3H), 1.51 (bs, 1H).

Example 61: N-(4-((2-((5-cyclopropyl-1-methyl-2-oxo-1,2-dihydropyridin-3-yl)amino)-1-methyl-1H-benzo[d]imidazol-6-yl)oxy)pyridin-2-yl)acetamide

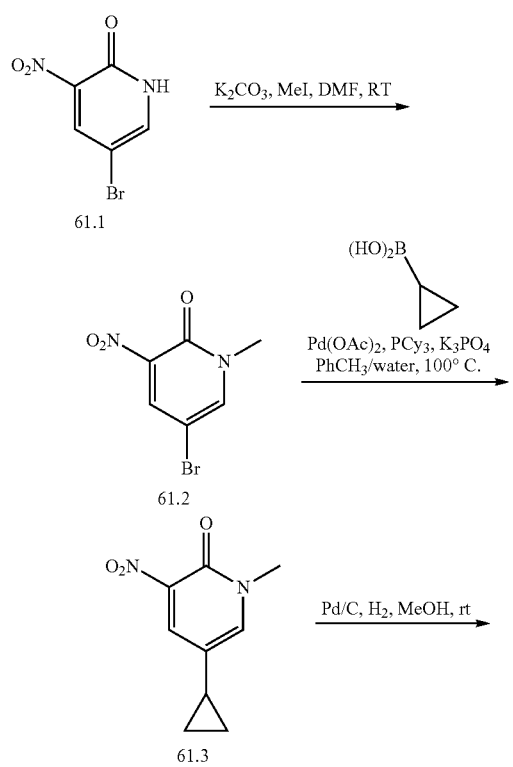

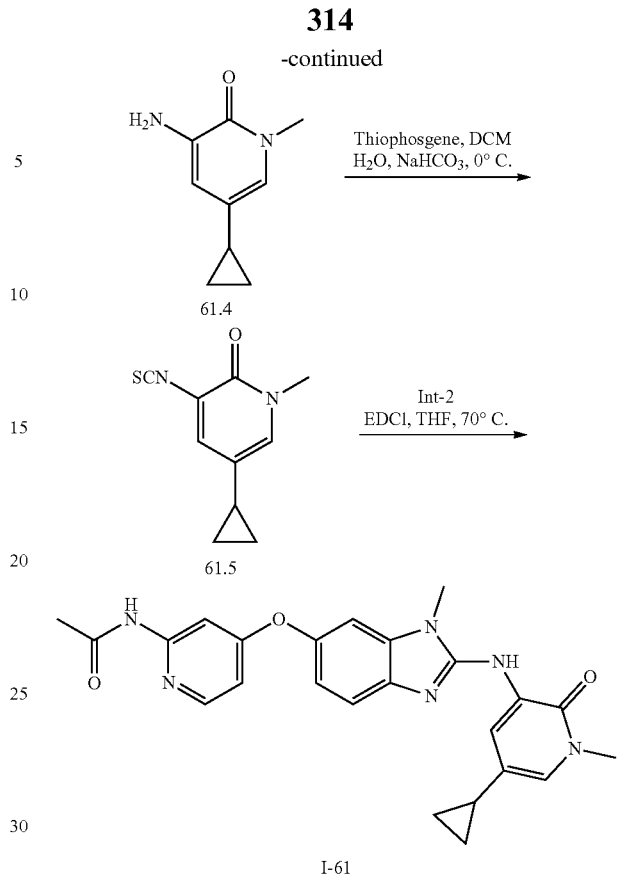

Synthesis of compound 61.2. To a solution of 61.1 (5.0 g, 22.83 mmol, 1.0 equiv) in DMF (50 mL) was added potassium carbonate (6.6 g, 47.94 mmol, 2.1 equiv) and stirred for 15 min. To the mixture was added methyl iodide (3.56 g, 25.11 mmol, 1.1 equiv). The reaction mixture was stirred at room temperature for 1 h. It was poured over ice-water and extracted with ethyl acetate. The combined organic layers were washed with brine, dried over anhydrous sodium sulfate, filtered and concentrated under reduced pressure to obtain 61.2. MS (ES): m/z 234.02 [M+H]+.

Synthesis of compound 61.3. A mixture of 61.2 (0.7 g, 3.0 mmol, 1.0 equiv), cyclopropylboronic acid (0.774 g, 9.0 mmol, 3.0 equiv), potassium phosphate (1.9 g, 9.0 mmol, 3.0 equiv) and tricyclohexylphosphine (0.168 g, 0.6 mmol, 0.2 equiv) in toluene (10 mL) and water (1 mL) was degassed by bubbling argon for 10 min. Palladium(II) acetate (0.336 g, 1.5 mmol, 0.5 equiv) was added under argon, and degassed again for 5 min. The reaction mixture was stirred at 100° C. for 2 h. It was cooled to room temperature, filtered through a pad of Celite®. The filtrate was poured over water, extracted with ethyl acetate. The combined organic layers were washed with brine, dried over anhydrous sodium sulfate, filtered and concentrated under reduced pressure. The residue was purified by flash column chromatography on silica gel (CombiFlash®, 30% ethyl acetate in hexane as eluant) to afford 61.3. MS (ES): m/z 195.2 [M+H]+.

Synthesis of compound 61.4. Compound 61.4 was prepared from 61.3 following the procedure described in the synthesis of 52.4. The crude product was used in the next step without further purification. MS (ES): m/z 165.21 [M+H]+.

Synthesis of compound 61.5. Compound 61.5 was prepared from 61.4 following the procedure described in the synthesis of 11.8. The crude product was used in the next step without further purification. MS (ES): m/z 207.3 [M+H]⁺.

Synthesis of compound I-61. Compound I-61 was prepared from 61.5 and Int-2 following the procedure described in the synthesis of I-1. The product was purified by preparative HPLC. MS (ES): m/z: 445.31 [M–H]⁺, $^1$H NMR (DMSO-d6, 400 MHz): δ 10.49 (s, 1H), 8.32-8.31 (d, J=1.6 Hz, 1H), 8.21 (s, 1H), 8.15-8.14 (d, J=5.6 Hz, 1H), 7.65 (s, 1H), 7.52-7.50 (d, J=8.4 Hz, 1H), 7.33-7.32 (d, J=1.6 Hz, 1H), 7.14 (s, 1H), 6.90-6.87 (m, 1H), 6.63-6.61 (m, 1H), 3.69 (s, 3H), 3.54 (s, 3H), 2.02 (s, 3H), 1.82-1.77 (m, 1H), 0.88-0.83 (m, 2H), 0.59-0.58 (m, 2H).

Example 62: N-(4-((7-cyano-2-((5-cyclopropyl-1-methyl-2-oxo-1,2-dihydropyridin-3-yl)amino)-1-methyl-1H-benzo[d]imidazol-6-yl)oxy)pyridin-2-yl)acetamide

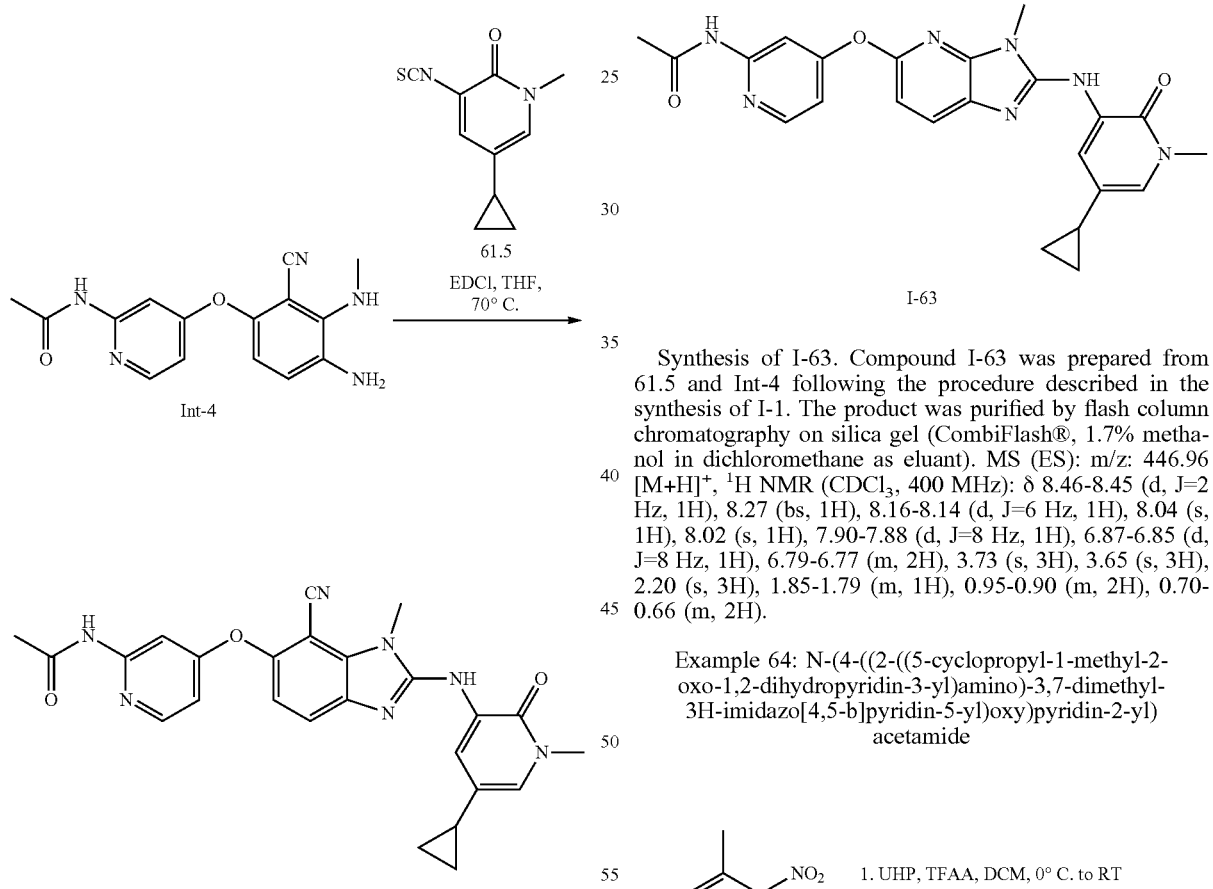

Synthesis of compound I-62. Compound I-62 was prepared from 61.5 and Int-2 following the procedure described in the synthesis of I-1. The residue was purified by preparative HPLC. MS (ES): m/z: 470.75 [M+H]⁺, H NMR (DMSO-d6, 400 MHz): δ 10.61 (s, 1H), 8.47 (s, 1H), 8.25-8.22 (m, 2H), 7.85-7.83 (d, J=8.4 Hz, 1H), 7.69 (s, 1H), 7.20 (s, 1H), 7.11-7.09 (d, J=8.4 Hz, 1H), 6.72-6.71 (d, J=3.2 Hz, 1H), 3.93 (s, 3H), 3.55 (s, 3H), 2.04 (s, 3H), 1.80 (bs, 1H), 0.86-0.85 (m, 2H), 0.59-0.58 (m, 2H).

Example 63: N-(4-((2-((5-cyclopropyl-1-methyl-2-oxo-1,2-dihydropyridin-3-yl)amino)-3-methyl-3H-imidazo[4,5-b]pyridin-5-yl)oxy)pyridin-2-yl)acetamide

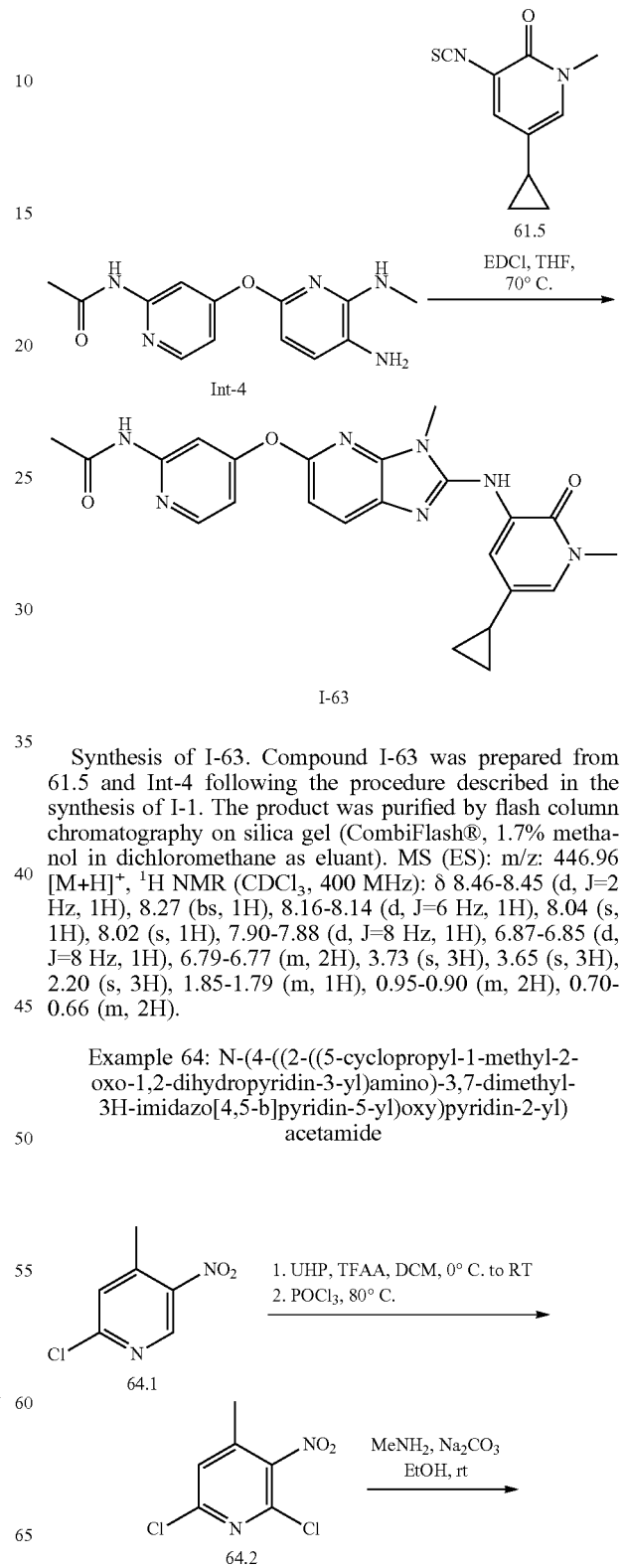

Synthesis of I-63. Compound I-63 was prepared from 61.5 and Int-4 following the procedure described in the synthesis of I-1. The product was purified by flash column chromatography on silica gel (CombiFlash®, 1.7% methanol in dichloromethane as eluant). MS (ES): m/z: 446.96 [M+H]⁺, $^1$H NMR (CDCl₃, 400 MHz): δ 8.46-8.45 (d, J=2 Hz, 1H), 8.27 (bs, 1H), 8.16-8.14 (d, J=6 Hz, 1H), 8.04 (s, 1H), 8.02 (s, 1H), 7.90-7.88 (d, J=8 Hz, 1H), 6.87-6.85 (d, J=8 Hz, 1H), 6.79-6.77 (m, 2H), 3.73 (s, 3H), 3.65 (s, 3H), 2.20 (s, 3H), 1.85-1.79 (m, 1H), 0.95-0.90 (m, 2H), 0.70-0.66 (m, 2H).

Example 64: N-(4-((2-((5-cyclopropyl-1-methyl-2-oxo-1,2-dihydropyridin-3-yl)amino)-3,7-dimethyl-3H-imidazo[4,5-b]pyridin-5-yl)oxy)pyridin-2-yl)acetamide

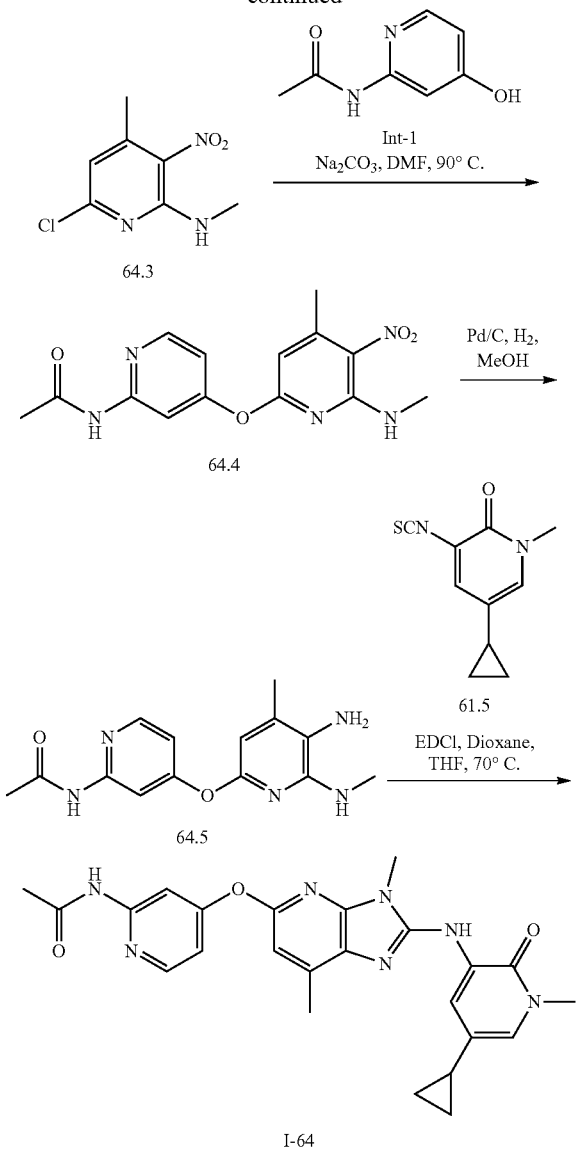

Synthesis of compound 64.2 To a solution of 2-chloro-4-methyl-5-nitropyridine (64.1, 3.0 g, 17.38 mmol, 1.0 equiv) and urea hydrogen peroxide (3.43 g, 36.49 mmol, 2.1 equiv) in dichloromethane (30 mL) at 0° C. was added trifluoroacetic anhydride (4.8 mL, 34.76 mmol, 2.0 equiv) dropwise. The reaction mixture was stirred at room temperature for 3 h. It was poured over ice-water and extracted with dichloromethane. The combined organic layers were washed with brine, dried over anhydrous sodium sulfate, filtered and concentrated under reduced pressure to obtain residue. The residue was dissolved in phosphorousoxy chloride (15 mL) and stirred at 80° C. for 12 h under nitrogen. It was poured over crushed ice, stirred and extracted with dichloromethane. The combined organic layers were washed with saturated sodium bicarbonate solution followed by brine, dried over anhydrous sodium sulfate, filtered and concentrated under reduced pressure to obtain 64.2. MS (ES): m/z 208.1 [M+H]$^+$.

Synthesis of compound 64.3. Compound 64.3 was prepared from 64.2 following the procedure described in the synthesis of Int-2.2. The product was purified by flash column chromatography on silica gel (CombiFlash®, 2% ethyl acetate in hexane as eluant). MS (ES): m/z 202.6 [M+H]$^+$.

Synthesis of compound 64.4. To a solution of 64.3 (0.150 g, 0.744 mmol, 1.0 equiv) in N, N-dimethylformamide (1.5 mL) was added Int-1 (0.113 g, 0.744 mmol, 1.0 equiv) followed by sodium carbonate (0.118 g, 1.116 mmol, 1.5 equiv). The reaction mixture was stirred at 90° C. for 12 h under nitrogen. It was cooled to room temperature, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 40% ethyl acetate in hexane) to afford 64.4. MS (ES): m/z 318.3 [M+H]$^+$.

Synthesis of compound 64.5. Compound 64.5 was prepared from 64.4 following the procedure described in the synthesis of Int-2. The crude product was used in the next step without further purification. MS (ES): m/z 288.3 [M+H]$^+$.

Synthesis of compound I-64. Compound I-64 was prepared from compound 64.5 and compound 61.5 following the procedure described in the synthesis of I-1. The product was purified by flash column chromatography on silica gel (CombiFlash®, 2.5% methanol in dichloromethane as eluant). MS (ES): m/z: 460.40 [M+H]$^+$, $^1$H NMR (DMSO-d6, 400 MHz): δ 10.55 (s, 1H), 8.38 (s, 1H), 8.29 (s, 1H), 8.20-8.19 (d, J=5.2 Hz, 1H), 7.76 (s, 1H), 7.20 (s, 1H), 6.80 (s, 1H), 6.73 (bs, 1H), 3.62 (s, 3H), 3.54 (s, 3H), 2.55 (s, 3H), 2.05 (s, 3H), 1.80 (bs, 1H), 0.88-0.87 (d, 2H), 0.60 (bs, 2H).

Example 65: N-(4-((2-((5-cyclopropyl-1-isopropyl-2-oxo-1,2-dihydropyridin-3-yl)amino)-3-methyl-3H-imidazo[4,5-b]pyridin-5-yl)oxy)pyridin-2-yl)acetamide

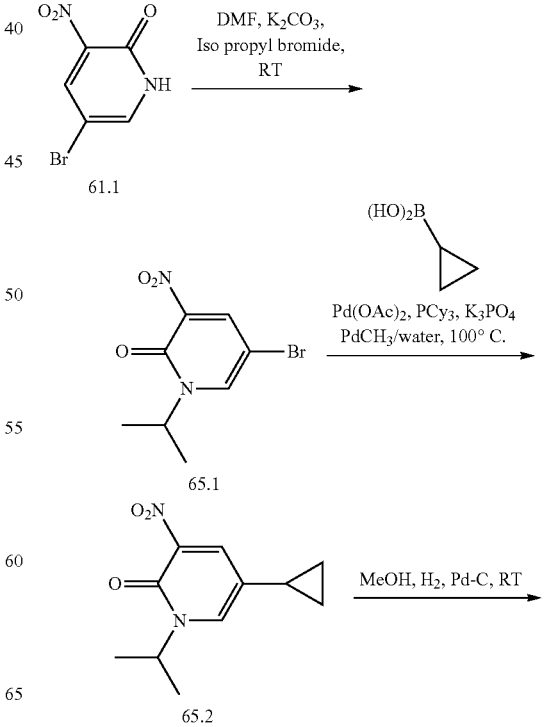

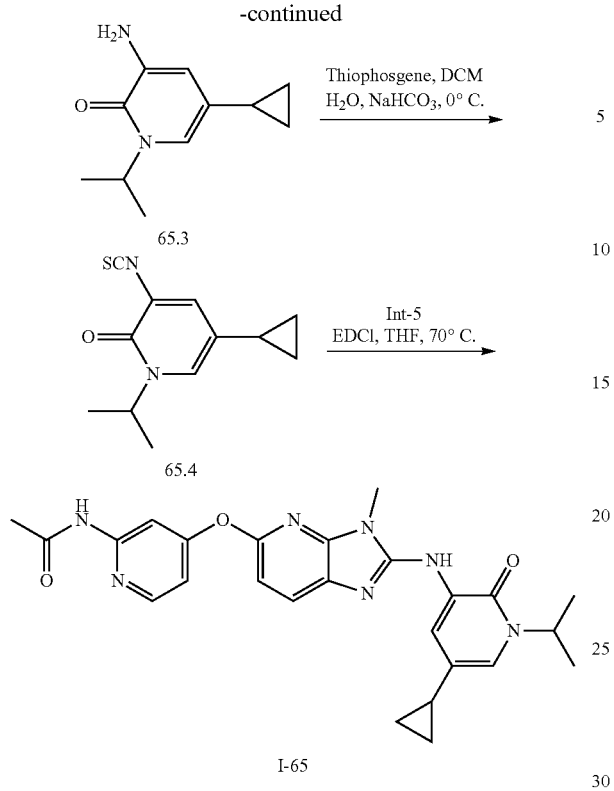

Hz, 1H), 6.77-6.75 (m, 1H), 5.18-5.14 (m, 1H), 3.65 (s, 3H), 2.06 (s, 3H), 1.90-1.86 (m, 1H), 1.36 (s, 6H), 0.91-0.87 (m, 2H), 0.65-0.61 (m, 2H).

Example 66: (R)—N-(4-((2-((5-cyclopropyl-2-oxo-1-((tetrahydrofuran-3-yl)methyl)-1,2-dihydropyridin-3-yl)amino)-1-methyl-1H-benzo[d]imidazol-6-yl)oxy)pyridin-2-yl)acetamide and (S)—N-(4-((2-((5-cyclopropyl-2-oxo-1-((tetrahydrofuran-3-yl)methyl)-1,2-dihydropyridin-3-yl)amino)-1-methyl-1H-benzo[d]imidazol-6-yl)oxy)pyridin-2-yl)acetamide

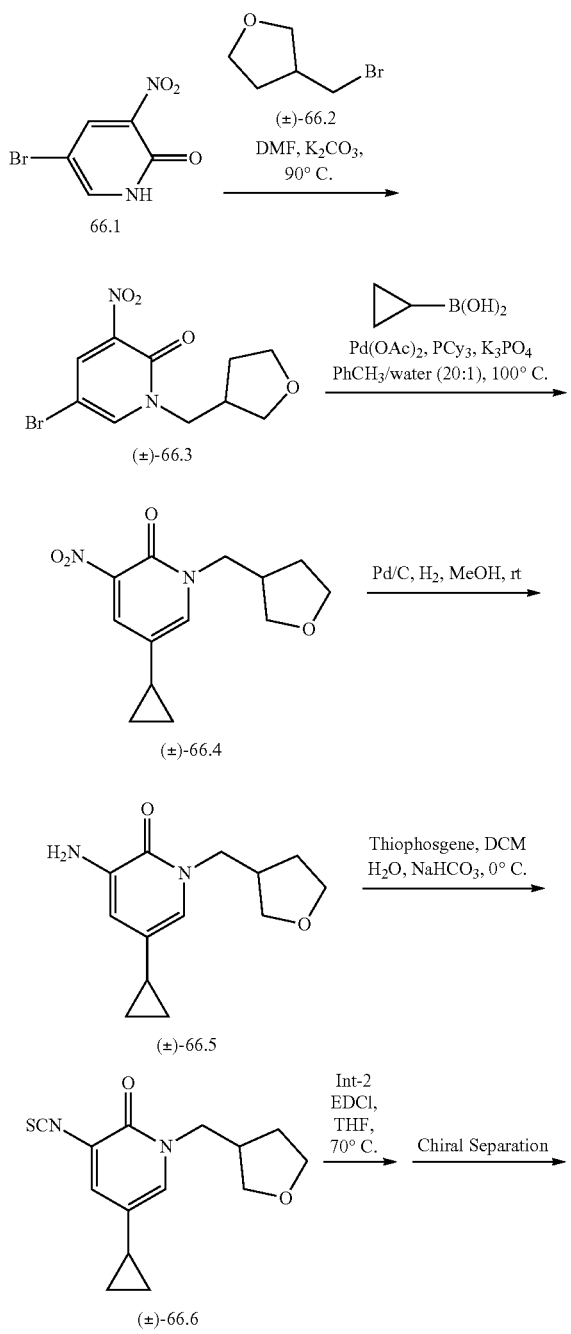

Synthesis of compound 65.1. To a solution of 61.1 (5.0 g, 22.83 mmol, 1.0 equiv) in DMF (50 mL) was added potassium carbonate (6.6 g, 47.94 mmol, 2.1 equiv) and stirred for 15 min. To the mixture was added isopropyl bromide (3.36 g, 27.39 mmol, 1.2 equiv). The reaction mixture was stirred at 85° C. for 16 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 7-8% ethyl acetate in hexane as eluant) to afford 65.1. MS (ES): m/z 262.2 [M+H]$^+$.

Synthesis of compound 65.2. Compound 65.2 was prepared from 65.1 following the procedure described in the synthesis of 61.3. The residue was purified by flash column chromatography on silica gel (CombiFlash®, 20% ethyl acetate in hexane as eluant). MS (ES): m/z 223.3 [M+H]$^+$.

Synthesis of compound 65.3. Compound 65.3 was prepared from 65.2 following the procedure described in the synthesis of 52.4. The crude product was used in the next step without further purification. MS (ES): m/z 193.3 [M+H]$^+$.

Synthesis of compound 65.4. Compound 65.4 was prepared from 65.3 following the procedure described in the synthesis of 11.8. The crude product was used in the next step without further purification. MS (ES): m/z 235.3 [M+H]$^+$.

Synthesis of compound I-65. Compound I-65 was prepared from 65.4 following the procedure described in the synthesis of I-1. The residue was purified by preparative HPLC. MS (ES): m/z: 474.40 [M+H]$^+$, $^1$H NMR (DMSO-d6, 400 MHz): δ 10.57 (s, 1H), 8.37 (s, 1H), 8.26-8.25 (d, J=1.6 Hz, 1H), 8.22-8.21 (d, J=5.6 Hz, 1H), 7.98-7.96 (d, J=8.4 Hz, 1H), 7.78 (s, 1H), 7.20 (s, 1H), 6.93-6.91 (d, J=8.4

-continued

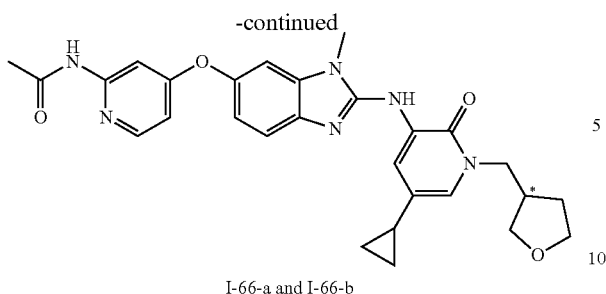

I-66-a and I-66-b

Synthesis of compound (±)-66.3. To a solution of 66.1 (1.5 g, 6.85 mmol, 1.0 equiv) in DMF (15 mL) was added potassium carbonate (1.89 g, 13.7 mmol, 2.0 equiv) and stirred for 15 min. To the mixture was added 3-(bromomethyl)tetrahydrofuran ((±)-66.2, 1.36 g, 8.22 mmol, 1.2 equiv). The reaction mixture was stirred at 90° C. for 6 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 50% ethyl acetate in hexane as eluant) to afford (±)-66.3. MS (ES): m/z 304.1 [M+H]$^+$.

Synthesis of compound (±)-66.4. Compound (±)-66.4 was prepared from (±)-66.3 following the procedure described in the synthesis of 61.3. The residue was purified by flash column chromatography on silica gel (CombiFlash®, 5% methanol in dichloromethane as eluant). MS (ES): m/z 265.2 [M+H]$^+$.

Synthesis of compound (±)-66.5. Compound (±)-66.5 was prepared from (±)-66.4 following the procedure described in the synthesis of 52.4. The crude product was used in the next step without further purification. MS (ES): m/z 235.3 [M+H]$^+$.

Synthesis of compound (±)-66.6. Compound (±)-66.6 was prepared from (±)-66.5 following the procedure described in the synthesis of 11.8. The crude product was used in the next step without further purification. MS (ES): m/z 277.3 [M+H]$^+$.

Synthesis of compound (±)-I-66. Compound (±)-I-66 was prepared from (±)-66.6 following the procedure described in the synthesis of I-1. The residue was purified by flash column chromatography on silica gel (CombiFlash®, 3% methanol in dichloromethane as eluant). MS (ES): m/z: 515.5 [M+H]$^+$.

I-66-a and I-66-b. (±)-I-66 was separated on SFC (column: CHIRALCEL OJ-H (250 mm×4.6 mm, 5 μm); mobile phase: 0.1% DEA in MeOH; flow rate: 4 mL/min) to get first eluting fraction (I-66-a) and second eluting fraction (I-66-b). (*Absolute stereochemistry not determined.)

I-66-a. MS (ES): m/z: 515.3 [M+H]$^+$, $^1$H NMR (DMSO-d6, 400 MHz): δ 10.50 (s, 1H), 8.33-8.32 (d, J=2.0 Hz, 1H), 8.24 (s, 1H), 8.16-8.15 (d, J=5.6 Hz, 1H), 7.66 (s, 1H), 7.53-7.51 (d, J=8.4 Hz, 1H), 7.34 (bs, 1H), 7.18 (s, 1H), 6.91-6.88 (m, 1H), 6.64-6.62 (m, 1H), 4.00-3.99 (m, 2H), 3.85-3.80 (m, 1H), 3.70 (s, 3H), 3.67-3.62 (m, 2H), 3.53-3.50 (m, 1H), 2.78-2.75 (m, 1H), 2.03 (s, 3H), 1.94-1.81 (m, 2H), 1.70-1.62 (m, 1H), 0.95-0.93 (m, 2H), 0.62-0.61 (m, 2H).

I-66-b. MS (ES): m/z: 515.3 [M+H]$^+$, $^1$H NMR (DMSO-d6, 400 MHz): δ 10.50 (s, 1H), 8.33-8.32 (d, J=2.0 Hz, 1H), 8.24 (s, 1H), 8.16-8.15 (d, J=5.6 Hz, 1H), 7.66 (s, 1H), 7.53-7.51 (d, J=8.4 Hz, 1H), 7.34 (bs, 1H), 7.18 (s, 1H), 6.91-6.88 (m, 1H), 6.64-6.62 (m, 1H), 4.00-3.99 (m, 2H), 3.85-3.80 (m, 1H), 3.70 (s, 3H), 3.67-3.62 (m, 2H), 3.53-3.50 (m, 1H), 2.78-2.75 (m, 1H), 2.03 (s, 3H), 1.94-1.81 (m, 2H), 1.70-1.62 (m, 1H), 0.95-0.93 (m, 2H), 0.62-0.61 (m, 2H).

Example 67: (R)—N-(4-((2-((5-cyclopropyl-2-oxo-1-(tetrahydro-2H-pyran-3-yl)-1,2-dihydropyridin-3-yl)amino)-3-methyl-3H-imidazo[4,5-b]pyridin-5-yl)oxy)pyridin-2-yl)acetamide and (S)—N-(4-((2-((5-cyclopropyl-2-oxo-1-(tetrahydro-2H-pyran-3-yl)-1,2-dihydropyridin-3-yl)amino)-3-methyl-3H-imidazo[4,5-b]pyridin-5-yl)oxy)pyridin-2-yl)acetamide

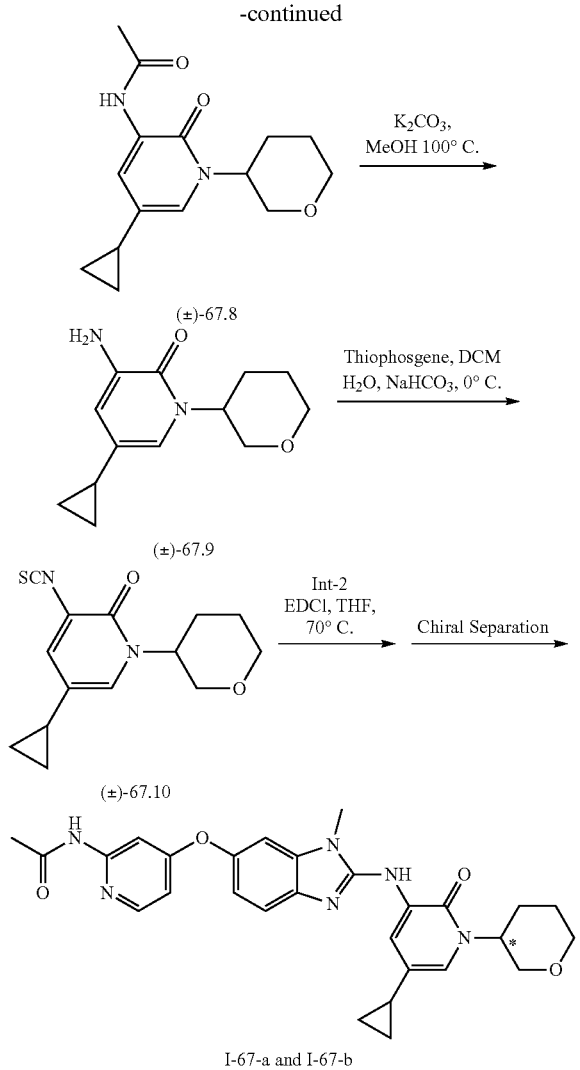

I-67-a and I-67-b

Synthesis of compound 67.2. To a solution of 67.1 (20 g, 238 mmol, 1.0 equiv) in dichloromethane (200 mL) was added bromine (12.2 mL, 238 mmol, 1.0 equiv) in dichloromethane (100 mL) at −78° C. dropwise. The reaction mixture was stirred at −78° C. for 2 h, then it was allowed to warm to room temperature stirred for 16 h. To the mixture was added dropwise triethylamine (66 mL, 476 mmol, 2.0 equiv) in dichloromethane (100 mL). It was stirred for 5 h. The reaction mixture was concentrated under reduced pressure. To the residue was added diethyl ether. Solids was removed by filtration. The filtrate was concentrated under reduced pressure. The crude product was purified by vacuum distillation (80° C., 0.02 mm Hg) to obtained pure compound 67.2. $^1$H NMR (400 M Hz, CDCl$_3$): 6.68 (s, 1H), 4.02-4.00 (t, J=4 Hz, 2H), 2.45-2.42 (m, 2H), 2.06-2.00 (m, 2H).

Synthesis of compound 67.4. To a solution of 67.2 (8 g, 49.08 mmol, 1.0 equiv) and 67.3 (6.48 g, 58.89 mmol, 1.2 equiv) in 1,4-dioxane (100 mL) was added potassium carbonate (13.6 g, 98.16 mmol, 2.0 equiv) and degassed by bubbling argon through for 15 min. Copper iodide (1.4 g, 7.40 mmol, 0.15 equiv) and 1,2-dimethylethylenediamine (1.60 mL, 14.72 mmol, 0.30 equiv) was added. The reaction mixture again degassed with argon for 5 min. It was stirred at 110° C. for 12 h under argon. It was cooled to room temperature, poured over water and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.2% methanol in dichloromethane to obtain 67.4. MS (ES): m/z 193.09 [M+H]$^+$.

Synthesis of compound (±)-67.5. A mixture of 67.4 (8 g, 41.62 mmol, 1.0 equiv) and palladium on charcoal (4 g) in methanol (100 mL) was stirred at rt under 1 atm hydrogen for 16 h. It was filtered through a pad of Celite® and rinsed with methanol. The filtrate was concentrated under reduced pressure. The residue was purified by trituration with n-pentane to obtain (±)-67.5. MS (ES): m/z 195.11 [M+H]$^+$.

Synthesis of compound (±)-67.6. To a solution of (±)-67.5 (2 g, 10.30 mmol, 1.0 equiv) in dichloromethane (20 mL) at 0° C. was added triethylamine (4.33 mL, 30.9 mmol, 3.0 equiv) and acetic anhydride (1.55 mL, 16.49 mmol, 1.6 equiv). The reaction mixture was stirred at room temperature for 2 h. It was poured over water and extracted with dichloromethane. The combined organic layers were dried over anhydrous sodium sulfate, filtered and concentrated under reduced pressure. The residue was purified by flash column chromatography on silica gel (CombiFlash®, 0-5% methanol in dichloromethane) to afford (±)-67.6. MS (ES): m/z 237.12 [M+H]$^+$.

Synthesis of compound (±)-67.7. To a solution of (±)-67.6 (0.9 g, 3.81 mmol, 1.0 equiv) in DMF (10 mL) was added N-bromosuccinimide (1.017 g, 5.71 mmol, 1.5 equiv) and stirred at room temperature for 1 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 60% ethyl acetate in hexane as eluant) to afford (±)-67.7. MS (ES): m/z 316.2 [M+H]$^+$.

Synthesis of compound (±)-67.8. Compound (±)-67.8 was prepared from (±)-67.7 following the procedure described in the synthesis of 61.3. The product was purified by flash column chromatography on silica gel (CombiFlash®, ethyl acetate as eluant). MS (ES): m/z 277.3 [M+H]$^+$.

Synthesis of compound (±)-67.9. To a solution of compound (±)-67.8 (0.182 g, 0.658 mmol, 1.0 equiv) in methanol (10 mL) was added potassium carbonate (1.816 g, 13.16 mmol, 20.0 equiv). The reaction mixture was heated to reflux for 16 h. It was poured over water, extracted with ethyl acetate. The combined organic layers were washed with brine, dried over anhydrous sodium sulfate, filtered and concentrated under reduced pressure. The residue was purified by flash column chromatography on silica gel (CombiFlash®, 2.0% methanol in dichloromethane as eluant) to afford (±)-67.9. MS (ES): m/z 235.3 [M+H]$^+$.

Synthesis of compound (±)-67.10. Compound (±)-67.10 was prepared from (±)-67.9 following the procedure described in the synthesis of 11.8. The crude product was used in the next step without further purification. MS (ES): m/z 277.4 [M+H]$^+$.

Synthesis of compound (±)-I-67. Compound (±)-I-67 was prepared from (±)-67.10 and Int-2 following the procedure described in the synthesis of IA. The product was purified by flash column chromatography on silica gel (CombiFlash®, 1.2% methanol in dichloromethane as eluant). MS (ES): m/z: 515.4 [M+H]$^+$.

I-67-a and I-67-b. (±)-I-67 was separated on HPLC (column: CHIRALPAK IH (250 mm×21 mm, 5 μm); mobile phase: (A) 0.1% diethylamine in n-hexane (B) 0.1% diethylamine in 2-propanol:acetonitrile (70:30); flow rate: 20 mL/min) to afford first eluting fraction (I-67-a) and second eluting fraction (I-67-b). (*Absolute stereochemistry not determined.)

I-67-a. MS (ES): m/z: 515.4 [M+H]+, 1H NMR (DMSO-d6, 400 MHz): δ 10.50 (s, 1H), 8.26-8.25 (d, J=3.2 Hz, 2H), 8.15-8.14 (d, J=5.6 Hz, 1H), 7.64 (s, 1H), 7.52-7.50 (d, J=8.4 Hz, 1H), 7.33 (bs, 1H), 7.22 (s, 1H), 6.89-6.87 (m, 1H), 6.63-6.61 (m, 1H), 4.97 (bs, 1H), 3.85-3.80 (m, 2H), 3.69 (s, 3H), 3.50-3.45 (m, 1H), 2.18-2.12 (m, 1H), 2.08 (s, 3H), 1.93-1.83 (m, 4H), 1.23 (bs, 1H), 1.07-1.03 (m, 2H), 0.67 (bs, 2H).

I-67-b. MS (ES): m/z: 515.4 [M+H]+, 1H NMR (DMSO-d6, 400 MHz): δ 10.50 (s, 1H), 8.25 (bs, 2H), 8.16-8.14 (d, J=5.6 Hz, 1H), 7.64 (s, 1H), 7.52-7.50 (d, J=8.4 Hz, 1H), 7.34 (bs, 1H), 7.24 (s, 1H), 6.90-6.88 (d, J=7.6 Hz, 1H), 6.63-6.62 (d, J=3.6 Hz, 1H), 4.86 (bs, 1H), 3.85-3.80 (m, 2H), 3.69 (s, 3H), 3.50-3.45 (m, 1H), 2.14-2.12 (m, 1H), 2.08 (s, 3H), 1.93-1.77 (m, 4H), 1.23 (bs, 1H), 0.88-0.86 (m, 2H), 0.62-0.61 (bs, 2H).

Example 68: (R)—N-(4-((2-((5-cyclopropyl-2-oxo-1-(tetrahydro-2H-pyran-3-yl)-1,2-dihydropyridin-3-yl)amino)-3-methyl-3H-imidazo[4,5-b]pyridin-5-yl)oxy)pyridin-2-yl)acetamide and (S)—N-(4-((2-((5-cyclopropyl-2-oxo-1-(tetrahydro-2H-pyran-3-yl)-1,2-dihydropyridin-3-yl)amino)-3-methyl-3H-imidazo[4,5-b]pyridin-5-yl)oxy)pyridin-2-yl)acetamide Synthesis of compound (±)-I-68. Compound (±)-I-68 was prepared from (±)-67.10 and Int-4 following the procedure described in the synthesis of I-1. The product was purified by flash column chromatography on silica gel (CombiFlash®, 4.1% methanol in dichloromethane as eluant). MS (ES): m/z: 516.41 [M+H]+.

I-68-a and I-68-b. (±)-I-68 were separated on HPLC (column CHIRALPAK IC (250 mm×21 mm, 5 μm); mobile phase: (A) 0.1% diethylamine in n-hexane (B) 0.1% diethylamine in 2-propanol:acetonitrile (70:30); flow rate: 20 mL/min) to afford first eluting fraction (I-68-a) and second eluting fraction (I-68-b). (*Absolute stereochemistry not determined.)

I-68-a. MS (ES): m/z: 516.4 [M+H]+, 1H NMR (DMSO-d6, 400 MHz): δ 10.57 (s, 1H), 8.37 (s, 1H), 8.28 (s, 1H), 8.21-8.20 (d, J=4.4 Hz, 1H), 7.99-7.96 (m, 1H), 7.78 (bs, 1H), 7.26 (bs, 1H), 6.94-6.91 (m, 1H), 6.76 (bs, 1H), 4.86 (bs, 1H), 3.82 (bs, 2H), 3.65 (s, 3H), 3.48 (bs, 2H), 3.19-3.17 (m, 1H), 2.06 (s, 3H), 1.93-1.77 (m, 4H), 0.88-0.86 (m, 2H), 0.63 (bs, 2H).

I-68-b. MS (ES): m/z: 516.4 [M+H]+, 1H NMR (DMSO-d6, 400 MHz): δ 10.57 (s, 1H), 8.37 (s, 1H), 8.28 (s, 1H), 8.22-8.21 (d, J=4.4 Hz, 1H), 7.98-7.96 (d, J=8.0 Hz, 1H), 7.78 (bs, 1H), 7.27 (bs, 1H), 6.93-6.91 (d, J=8.4 Hz, 1H), 6.76-6.75 (d, J=3.6 Hz, 1H), 4.87 (bs, 1H), 3.83 (bs, 2H), 3.65 (s, 3H), 3.48 (bs, 2H), 3.18-3.17 (m, 1H), 2.06 (s, 3H), 1.94 (bs, 1H), 1.86 (bs, 1H), 1.77-1.73 (m, 2H), 0.89-0.87 (m, 2H), 0.63-0.62 (m, 2H).

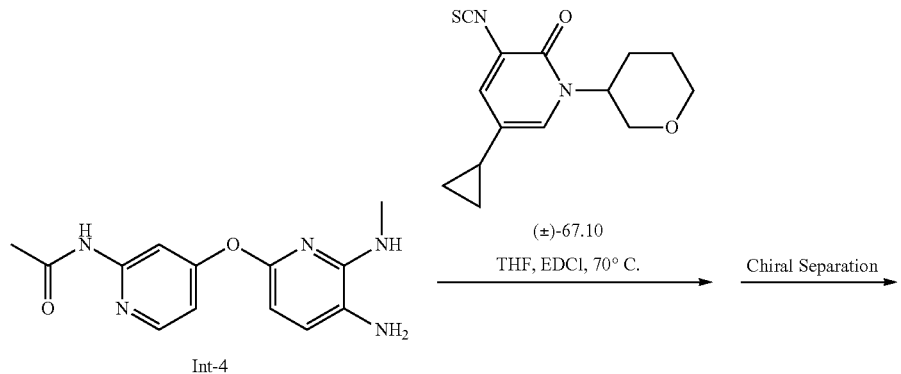

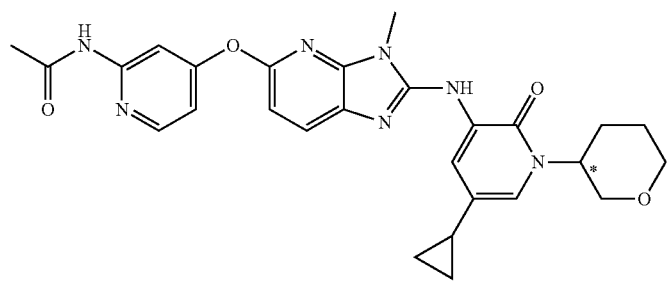

I-68-a and I-68-b

Example 69: N-(4-((2-((5-cyclopropyl-2-oxo-1-(tetrahydro-2H-pyran-4-yl)-1,2-dihydropyridin-3-yl)amino)-1-methyl-1H-benzo[d]imidazol-6-yl)oxy)pyridin-2-yl)acetamide

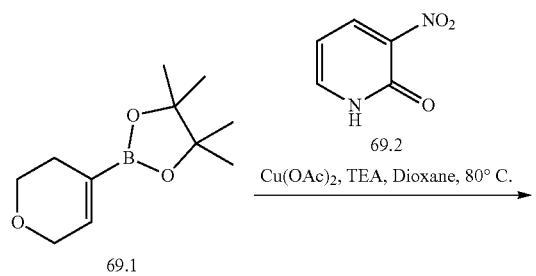

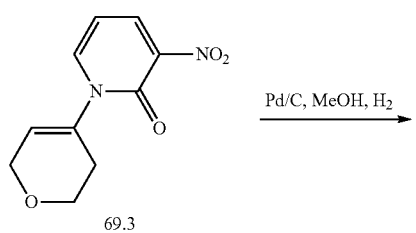

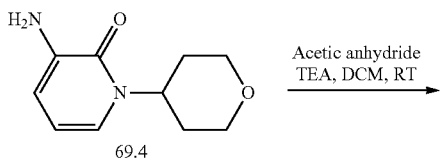

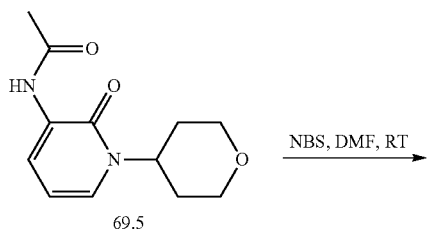

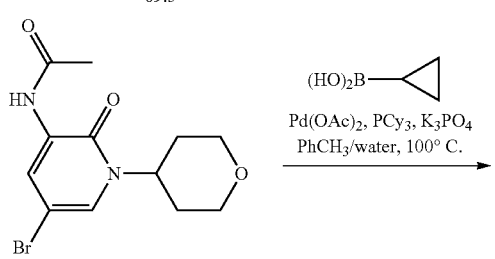

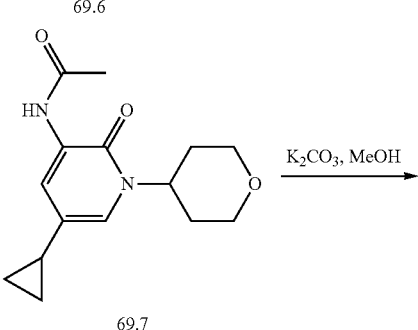

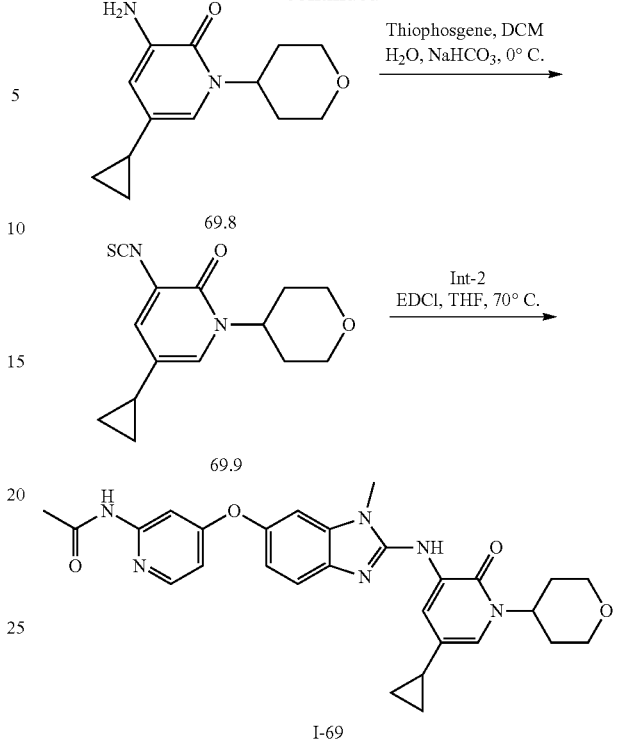

Synthesis of compound 69.3. To a solution of 69.1 (3 g, 14.28 mmol, 1.0 equiv) and 69.2 (2.4 g, 17.14 mmol, 1.2 equiv) in dioxane (30 mL) was added copper acetate (2.60 g, 14.28 mmol, 1.0 equiv) and triethylamine (5.0 mL, 35.7 mmol, 2.5 equiv) under nitrogen. The reaction was stirred at 80° C. for 5 h. It was poured over ice-water and extracted with ethyl acetate. The combined organic layers were dried over anhydrous sodium sulfate, filtered and concentrated under reduced pressure. The residue was purified by flash column chromatography on silica gel (CombiFlash®, 10% ethyl acetate in hexane to obtain 69.3. MS (ES): m/z 222.20 [M+H]$^+$.

Synthesis of compound 69.4. Compound 69.4 was prepared from 69.3 following the procedure described in the synthesis of 52.4. The crude product was used in the next step without further purification. MS (ES): m/z 195.23 [M+H]$^+$.

Synthesis of compound 69.5. To a solution of 69.4 (0.500 g, 2.57 mmol, 1.0 equiv) in dichloromethane (5 mL) was added triethylamine (1.07 mL, 7.71 mmol, 3.0 equiv) at 0° C. followed by addition of acetic anhydride (0.51 mL, 5.14 mmol, 2.0 equiv) dropwise. The reaction mixture was stirred at room temperature for 2 h. It was poured over ice-water, stirred and extracted with dichloromethane. The combined organic layers were washed with brine, dried over anhydrous sodium sulfate, filtered and concentrated under reduced pressure. The residue was purified by flash column chromatography on silica gel (CombiFlash®, 1.4% methanol in dichloromethane) to afford 69.5. MS (ES): m/z 237.3 [M+H]$^+$.

Synthesis of compound 69.6. To a solution of 69.5 (0.4 g, 1.69 mmol, 1.0 equiv) in DMF (5 mL) was added N-bromosuccinimide (0.448 g, 2.53 mmol, 1.5 equiv) and stirred at room temperature for 1 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 80% ethyl acetate in hexane as eluant) to afford 69.6. MS (ES): m/z 316.2 [M+H]⁺.

Synthesis of compound 69.7. Compound 69.7 was prepared from 69.6 following the procedure described in the synthesis of 61.3. The product was purified by flash column chromatography on silica gel (CombiFlash®, 1.4% methanol in dichloromethane as eluant). MS (ES): m/z 277.3 [M+H]⁺.

Synthesis of compound 69.8. To a solution of compound 69.7 (0.185 g, 0.669 mmol, 1.0 equiv) in methanol (5 mL) was added potassium carbonate (1.846 g, 13.38 mmol, 20.0 equiv). The reaction mixture was heated to reflux for 16 h. It was poured over water, extracted with ethyl acetate. The combined organic layers were washed with brine, dried over anhydrous sodium sulfate, filtered and concentrated under reduced pressure. The residue was purified by flash column chromatography on silica gel (CombiFlash®, 2.0% methanol in dichloromethane as eluant) to afford 69.8. MS (ES): m/z 235.3 [M+H]⁺.

Synthesis of compound 69.9. Compound 69.9 was prepared from 69.8 following the procedure described in the synthesis of 11.8. The crude product was used in the next step without further purification. MS (ES): m/z 277.4 [M+H]⁺.

Synthesis of compound I-69. Compound I-69 was prepared from 69.9 following the procedure described in the synthesis of I-1. The product was purified by flash column chromatography on silica gel (CombiFlash®, 2.5% methanol in dichloromethane as eluant). MS (ES): m/z: 515.46 [M+H]⁺, ¹H NMR (DMSO-d6, 400 MHz): δ 10.57 (s, 1H), 8.25 (s, 1H), 8.24-8.23 (d, J=2.0 Hz, 1H), 8.15-8.14 (d, J=5.6 Hz, 1H), 7.65 (s, 1H), 7.52-7.50 (d, J=8.4 Hz, 1H), 7.34-7.33 (d, J=2.0 Hz, 1H), 7.20-7.19 (d, J=2.0 Hz, 1H), 6.89-6.87 (m, 1H), 6.63-6.61 (m, 1H), 5.01 (bs, 1H), 4.03-4.00 (m, 2H), 3.69 (s, 3H), 3.52-3.47 (m, 2H), 2.02 (s, 3H), 1.91-1.85 (m, 1H), 1.73-1.70 (m, 2H), 1.11-1.07 (m, 2H), 0.89-0.84 (m, 2H), 0.65-0.63 (m, 2H).

Example 70: N-(4-((2-((5-cyclopropyl-1-((1-(hydroxymethyl)cyclopropyl)methyl)-2-oxo-1,2-dihydropyridin-3-yl)amino)-1-methyl-1H-benzo[d]imidazol-6-yl)oxy)pyridin-2-yl)acetamide

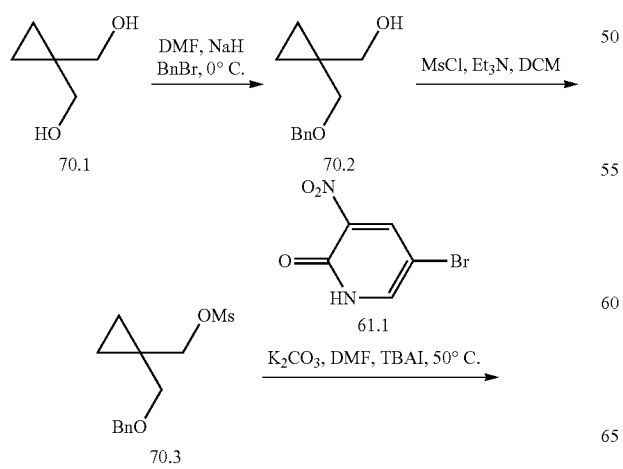

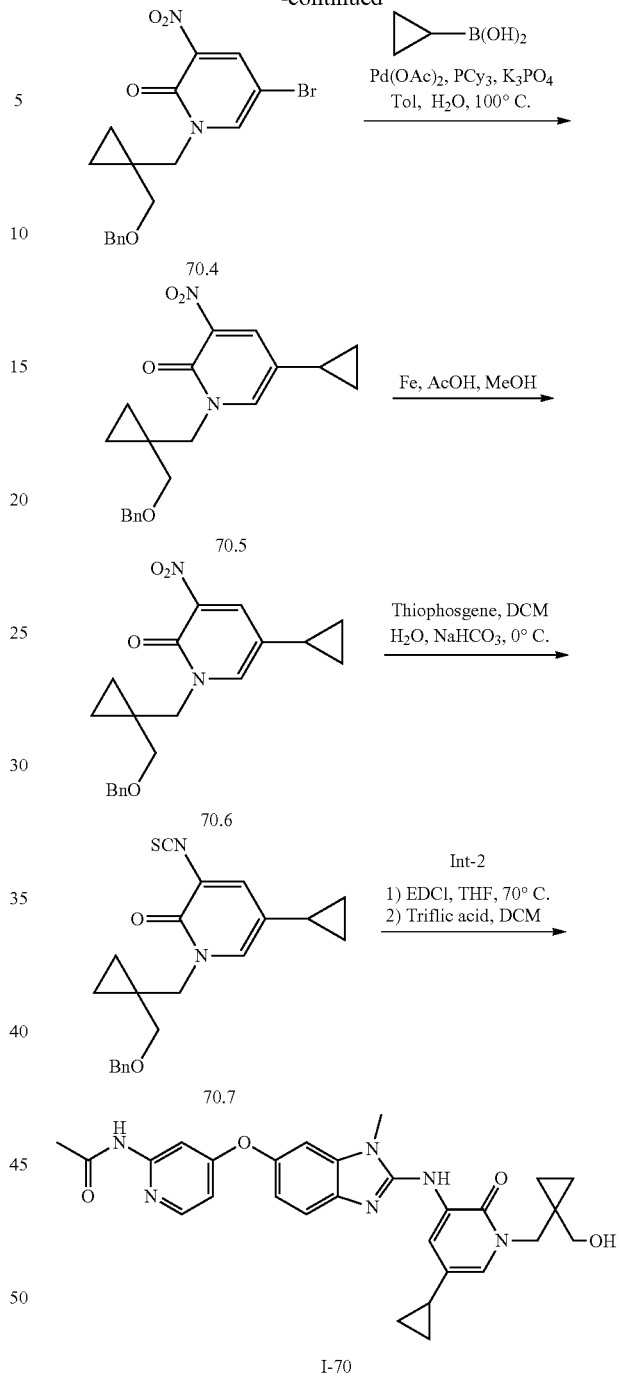

Synthesis of compound 70.2. To a solution of 70.1 (2.0 g, 19.58 mmol, 1.0 equiv) in DMF (20 mL) was added sodium hydride (0.798 g, 16.64 mmol, 0.85 equiv) at 0° C. and stirred for 30 min. Benzyl bromide (2.34 g, 13.70 mmol, 0.7 equiv) was added. The reaction mixture was stirred at 0° C. for 2 h. It was poured over ice, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 12% ethyl acetate in hexane as eluant) to afford 70.2. MS (ES): m/z 193.3 [M+H]⁺.

Synthesis of compound 70.3. To a solution of 70.2 (1.05 g, 5.46 mmol, 1.0 equiv) in dichloromethane (10 mL) was added triethylamine (2.28 mL, 16.38 mmol, 3.0 equiv) at 0° C. followed by addition of methanesulfonyl chloride (1.27 mL, 16.38 mmol, 3.0 equiv). The reaction mixture was stirred at room temperature for 1 h. It was poured over ice-water, stirred and extracted with dichloromethane. The combined organic layers were washed with brine, dried over anhydrous sodium sulfate, filtered and concentrated under reduced pressure to obtain 70.3. MS (ES): m/z 271.3 $[M+H]^+$.

Synthesis of compound 70.4. To a solution of 70.3 (0.4 g, 1.83 mmol, 1.0 equiv) in DMF (20 mL) was added potassium carbonate (0.505 g, 3.66 mmol, 2.0 equiv) and tetrabutyl ammonium iodide (0.073 g, 0.201 mmol, 0.11 equiv) followed by 61.1 (0.987 g, 3.65 mmol, 2.0 equiv). The reaction mixture was stirred at 50° C. for 4 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 50% ethyl acetate in hexane as eluant) to afford 70.4. MS (ES): m/z 394.2 $[M+H]^+$.

Synthesis of compound 70.5. Compound 70.5 was prepared from 70.4 following the procedure described in the synthesis of 61.3. The product was purified by flash column chromatography on silica gel (CombiFlash®, 70% ethyl acetate in hexane as eluant). MS (ES): m/z 355.4 $[M+H]^+$.

Synthesis of compound 70.6. A mixture of 70.5 (0.200 g, 0.564 mmol, 1.0 equiv) and iron powder (0.157 g, 2.82 mmol, 5.0 equiv) in methanol (5 mL) and water (1 mL) was added a few drops of acetic acid. The reaction mixture was stirred at 90° C. for 2 h. It was filtered through a pad of Celite® and rinsed with methanol. The filtrate was concentrated under reduced pressure to obtain 70.6. MS (ES): m/z 325.4 $[M+H]^+$.

Synthesis of compound 70.7. Compound 70.7 was prepared from 70.6 following the procedure described in the synthesis of 11.8. The crude product was used in the next step without further purification. MS (ES): m/z 367.4 $[M+H]^+$.

Synthesis of compound I-70. To a solution of Int-2 (0.074 g, 0.272 mmol, 1.0 equiv) in THF (2 mL) was added 70.7 (0.100 g, 0.272 mmol, 1.0 equiv) followed by N-(3-dimethylaminopropyl)-N'-ethylcarbodiimide hydrochloride (0.103 g, 0.544 mmol, 2.0 equiv). The reaction mixture was stirred at 70° C. for 2 h. It was cooled to room temperature, poured over ice-water and extracted with ethyl acetate. The combined organic layers were washed with brine, dried over anhydrous sodium sulfate, filtered and concentrated under reduced pressure to obtain product that was dissolved in dichloromethane (2 mL) and triflic acid (0.5 mL) was added dropwise at 0° C. The reaction mixture was stirred at 0° C. for 30 min, poured over saturated sodium bicarbonate solution and extracted with ethyl acetate. The combined organic layers were washed with brine, dried over anhydrous sodium sulfate, filtered and concentrated under reduced pressure. The residue was purified by flash column chromatography on silica gel (CombiFlash®, 4% methanol in dichloromethane as eluant) to afford I-70. MS (ES): m/z: 515.8 $[M+H]^+$, $^1$H NMR (DMSO-d6, 400 MHz): δ 10.50 (s, 1H), 8.33 (s, 1H), 8.24 (s, 1H), 8.16 (s, 1H), 7.65 (s, 1H), 7.53-7.50 (d, J=8.4 Hz, 1H), 7.34 (s, 1H), 7.11 (s, 1H), 6.90-6.88 (d, J=8.4 Hz, 1H), 6.63-6.61 (m, 1H), 4.03 (s, 2H), 3.70 (s, 3H), 3.19 (s, 2H), 2.02 (s, 3H), 1.85-1.81 (m, 1H), 0.88-0.87 (m, 2H), 0.69 (bs, 2H), 0.59-0.58 (m, 2H), 0.44 (bs, 2H).

Example 71: N-(4-((2-((5-cyclopropyl-1-(oxazol-2-ylmethyl)-2-oxo-1,2-dihydropyridin-3-yl)amino)-1-methyl-1H-benzo[d]imidazol-6-yl)oxy)pyridin-2-yl)acetamide

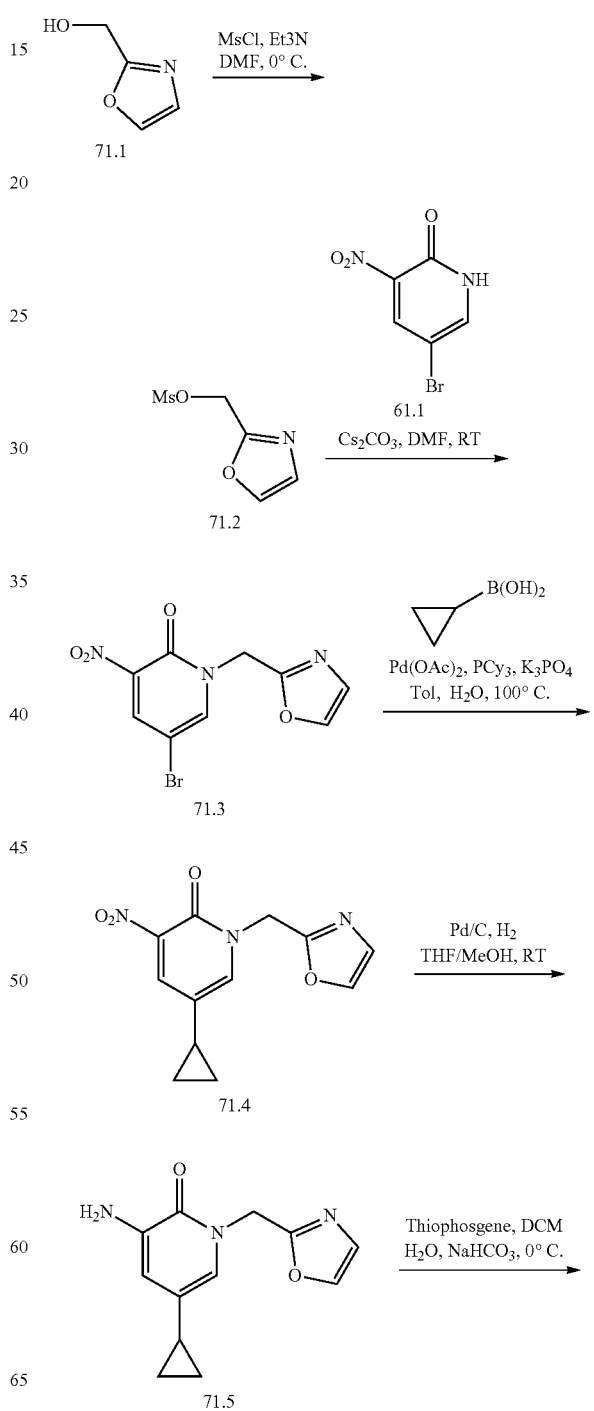

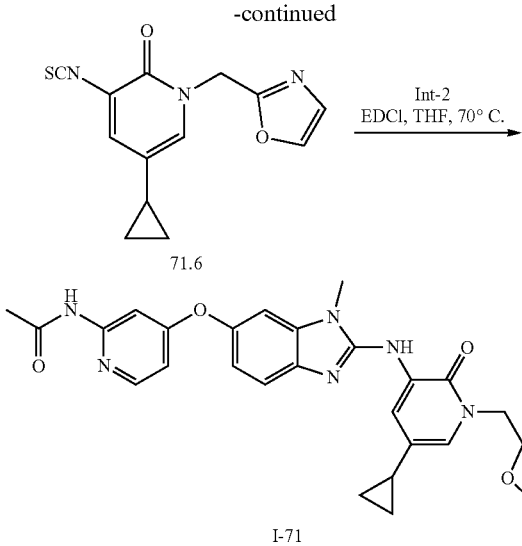

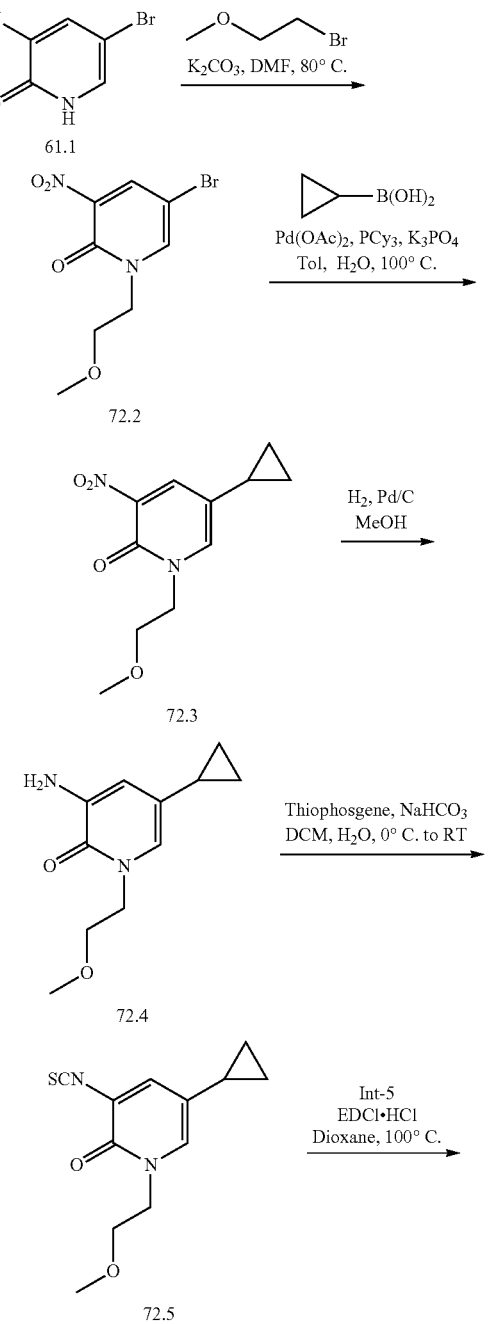

Synthesis of compound 71.2. To a solution of 71.1 (1.0 g, 10.09 mmol, 1.0 equiv) in DMF (10 mL) was added triethylamine (1.82 mL, 13.11 mmol, 1.3 equiv) at 0° C. followed by addition of methanesulfonyl chloride (1.00 mL, 13.11 mmol, 1.3 equiv). The reaction mixture was stirred at room temperature for 1 h. It was poured over ice-water, stirred and extracted with dichloromethane. The combined organic layers were washed with brine, dried over anhydrous sodium sulfate, filtered and concentrated under reduced pressure to obtain 71.2. MS (ES): m/z 178.2 [M+H]$^+$.

Synthesis of compound 71.3. To a solution of 61.1 (1.0 g, 5.64 mmol, 1.0 equiv) in DMF (10 mL) was added cesium carbonate (3.66 g, 11.28 mmol, 2.0 equiv) and stirred for 15 min. To the mixture was added 71.2 (1.24 g, 7.00 mmol, 1.2 equiv). The reaction mixture was stirred at room temperature for 16 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.5% methanol in dichloromethane as eluant) to afford 71.3. MS (ES): m/z 301.1 [M+H]$^+$.

Synthesis of compound 71.4. Compound 71.4 was prepared from 71.3 following the procedure described in the synthesis of 61.3. The product was purified by flash column chromatography on silica gel (CombiFlash®, 2.5% methanol in dichloromethane as eluant). MS (ES): m/z 262.2 [M+H]$^+$.

Synthesis of compound 71.5. A mixture of compound 71.4 (0.070 g, 0.267 mmol, 1.0 equiv) and 10% palladium on carbon (0.040 g) in methanol (5 mL) was stirred at rt under 1 atm hydrogen for 2 h. It was filtered through a pad of Celite® and rinsed with methanol. The filtrate was concentrated under reduced pressure to obtain 71.5. MS (ES): m/z 232.3 [M+H]$^+$.

Synthesis of compound 71.6. Compound 71.6 was prepared from 71.5 following the procedure described in the synthesis of 11.8. The crude product was used in the next step without further purification. MS (ES): m/z 274.3 [M+H]$^+$.

Synthesis of compound I-71. Compound I-71 was prepared from 71.6 and Int-2 following the procedure described in the synthesis of I-1. The product was purified by flash column chromatography on silica gel (CombiFlash®, 3% methanol in dichloromethane as eluant). MS (ES): m/z: 512.4 [M+H]$^+$, $^1$H NMR (CDCl$_3$, 400 MHz): δ 8.46 (s, 1H), 8.20 (s, 1H), 8.08-8.07 (d, J=5.6 Hz, 1H), 7.90 (s, 1H), 7.85 (s, 1H), 7.69 (s, 1H), 7.63-7.61 (d, J=8.8 Hz, 1H), 7.15 (s, 1H), 6.94 (bs, 2H), 6.88 (s, 1H), 6.58 (bs, 1H), 5.34 (bs, 2H), 3.66 (s, 3H), 2.18 (s, 3H), 1.83-1.81 (m, 1H), 0.93-0.91 (m, 2H), 0.70-0.69 (m, 2H).

Example 72: N-(4-((2-((5-cyclopropyl-1-(2-methoxyethyl)-2-oxo-1,2-dihydropyridin-3-yl)amino)-3-methyl-3H-imidazo[4,5-b]pyridin-5-yl)oxy)pyridin-2-yl)acetamide

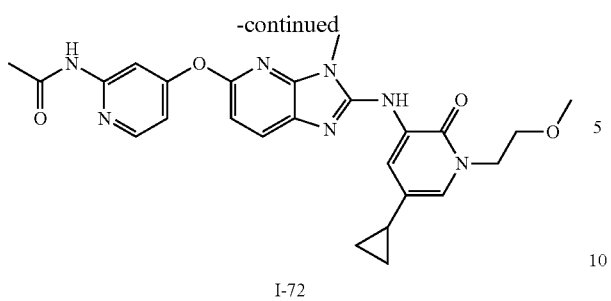

I-72

Synthesis of compound 72.1. Compound 73.1 was prepared from 61.1 following the procedure described in the synthesis of 52.3. The product was purified by flash column chromatography on silica gel (CombiFlash®, 7-8% ethyl acetate in hexane as eluant). MS (ES): m/z 278.1 [M+H]$^+$.

Synthesis of compound 72.2. Compound 72.2 was prepared from 72.1 following the procedure described in the synthesis of 61.3. The product was purified by flash column chromatography on silica gel (CombiFlash®, 30% ethyl acetate in hexane as eluant). MS (ES): m/z 239.2 [M+H]$^+$.

Synthesis of compound 72.3. Compound 72.3 was prepared from 72.2 following the procedure described in the synthesis of 52.4. The crude product was used in the next step without further purification. MS (ES): m/z 209.3 [M+H]$^+$.

Synthesis of compound 72.4. Compound 72.4 was prepared from 72.3 following the procedure described in the synthesis of 11.8. The crude product was used in the next step without further purification. MS (ES): m/z 251.3 [M+H]$^+$.

Synthesis of I-72. To a solution of Int-5 (0.071 g, 0.259 mmol, 1.0 equiv) in 1,4-dioxane (2 mL) was added 72.4 (0.065 g, 0.259 mmol, 1.0 equiv) followed by N-(3-dimethylaminopropyl)-N'-ethylcarbodiimide hydrochloride (0.098 g, 0.518 mmol, 2.0 equiv). The reaction mixture was stirred at 100° C. for 2 h. It was cooled to room temperature, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 3.0% methanol in dichloromethane as eluant) to afford I-72. MS (ES): m/z: 490.40 [M+H]$^+$, $^1$H NMR (DMSO-d6, 400 MHz): δ 10.57 (s, 1H), 8.35 (s, 1H), 8.33 (s, 1H), 8.22-8.21 (d, J=5.6 Hz, 1H), 7.98-7.96 (d, J=8.4 Hz, 1H), 7.78 (s, 1H), 7.14 (s, 1H), 6.93-6.91 (d, J=8.4 Hz, 1H), 6.77-6.75 (m, 1H), 4.16-4.15 (m, 2H), 3.65 (bs, 5H), 3.27 (s, 3H), 2.06 (s, 3H), 1.82-1.81 (m, 1H), 0.88-0.86 (m, 2H), 0.60-0.59 (m, 2H).

Example 73: N-(4-((2-((5-cyclopropyl-1-((1s,3s)-3-hydroxycyclobutyl)-2-oxo-1,2-dihydropyridin-3-yl)amino)-1-methyl-1H-benzo[d]imidazol-6-yl)oxy)pyridin-2-yl)acetamide

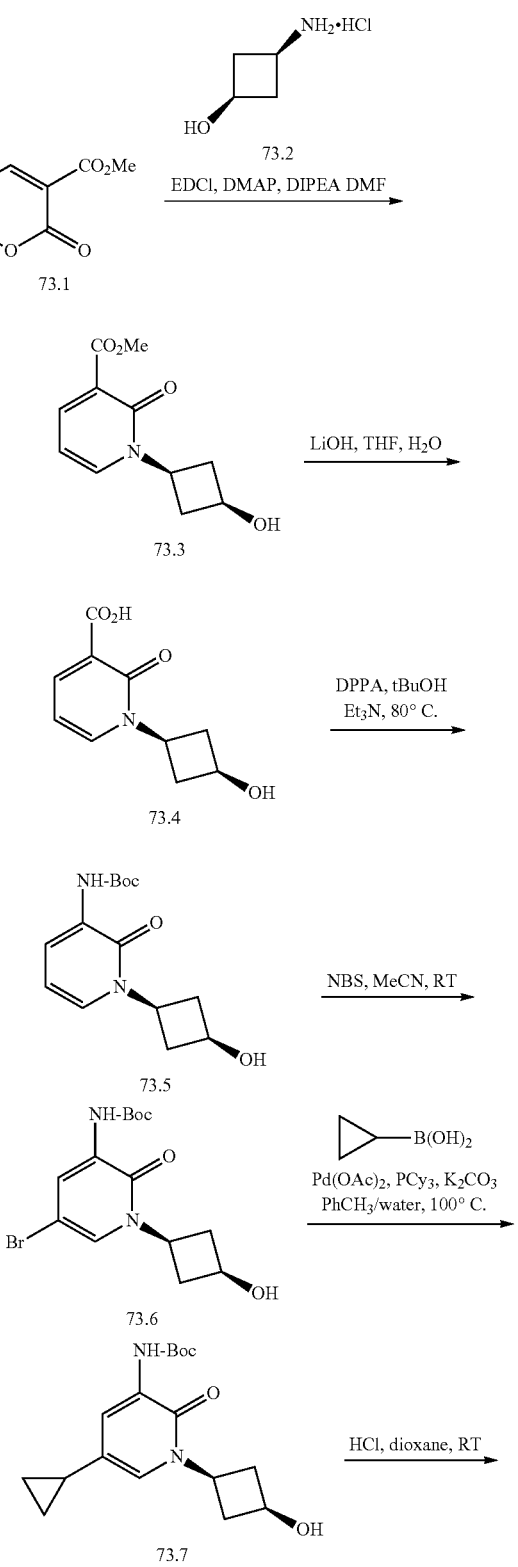

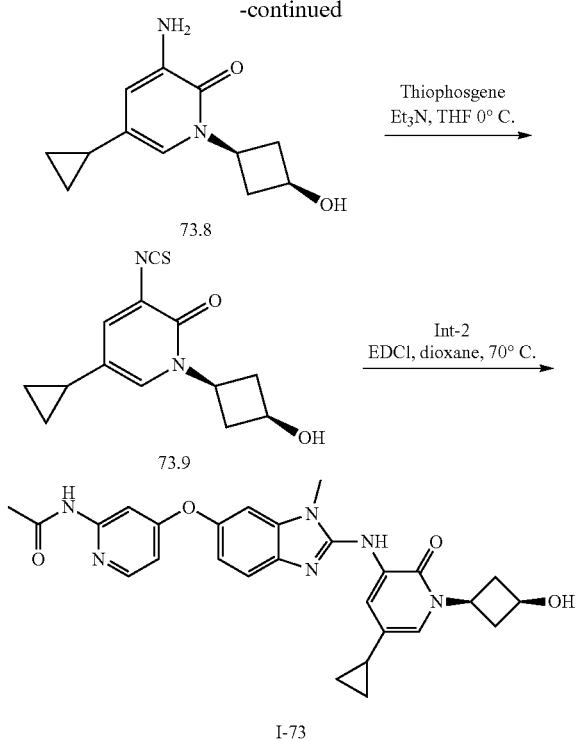

Synthesis of compound 73.3. To a mixture of 73.1 (5.0 g, 32.44 mmol, 1.0 equiv) and 73.2 (5.21 g, 42.17 mmol, 1.3 equiv) in DMF (50 mL) was added diisopropylethylamine (11.1 mL, 64.88 mmol, 2.0 equiv) at 0° C. The reaction mixture was stirred at 0° C. for 2 h and was added N-ethyl-N'-(3-dimethylaminopropyl)carbodiimide hydrochloride (8.7 g, 45.36 mmol, 1.4 equiv) and 4-dimethylaminopyridine (0.989 g, 8.11 mmol, 0.25 equiv). It was allowed to warm to rt and stirred for 16 h. It was poured over water and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.5% methanol in dichloromethane) to afford 73.3. MS (ES): m/z 224.09 [M+H]⁺.

Synthesis of compound 73.4. To a solution of lithium hydroxide (1.22 g, 29.1 mmol, 5.0 equiv) in THF:water (15 mL, 2:1) was added 73.3 (1.3 g, 5.82 mmol, 1.0 equiv). The reaction was stirred at room temperature for 24 h. Most organic solvents were removed under reduced pressure. The aqueous residue was acidified with 1 N hydrochloric acid to approx. pH 3. It was extracted with 10% methanol in dichloromethane. The combined organic layers were washed with brine, dried over anhydrous sodium sulfate, filtered and concentrated under reduced pressure to obtain 73.4. MS (ES): m/z 210.2 [M+H]⁺.

Synthesis of compound 73.5. A solution of 73.4 (0.8 g, 3.82 mmol, 1.0 equiv) and triethylamine (0.91 mL, 6.49 mmol, 1.7 equiv) in tert-butanol (15 mL) was added diphenyl phosphoryl azide (1.36 g, 4.96 mmol, 1.3 equiv) under nitrogen. The reaction mixture was stirred at 80° C. for 16 h. It cooled to room temperature, poured over water and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.5% methanol in dichloromethane to obtain 73.5. MS (ES): m/z 281.3 [M+H]⁺.

Synthesis of compound 73.6. To a solution of 73.5 (0.4 g, 1.43 mmol, 1.0 equiv) in acetonitrile (10 mL) at 0° C. was N-bromosuccinimide (0.354 g, 2.00 mmol, 1.4 equiv) in portions. The reaction mixture was stirred at 0° C. for 15 min. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 40% ethyl acetate in hexane as eluant) to afford 73.6. MS (ES): m/z 360.2 [M+H]⁺.

Synthesis of compound 73.7. Compound 73.7 was prepared from 73.6 following the procedure described in the synthesis of 61.3. The product was purified by flash column chromatography on silica gel (CombiFlash®, 70% ethyl acetate in hexane as eluant). MS (ES): m/z 321.4 [M+H]⁺.

Synthesis of compound 73.8. To a solution of 73.7 (0.059 g, 0.184 mmol, 1 equiv) in dioxane (2 mL) at 0° C. was added 4 N hydrochloric acid in dioxane (1 mL) dropwise. The reaction mixture was stirred at room temperature for 30 min. It was poured over saturated aqueous solution of sodium bicarbonate and extracted with dichloromethane. The combined organic layers were washed with brine, dried over anhydrous sodium sulfate, filtered and concentrated under reduced pressure to obtain 73.8. MS (ES): m/z 221.3 [M+H]⁺.

Synthesis of compound 73.9. Compound 73.9 was prepared from 73.8 following the procedure described in the synthesis of 1.2. The crude product was used in the next step without further purification. MS (ES): m/z 263.3 [M+H]⁺.

Synthesis of compound I-73. Compound I-73 was prepared from 73.9 and Int-2 following the procedure described in the synthesis of I-1. The product was purified by flash column chromatography on silica gel (CombiFlash®, 4% methanol in dichloromethane as eluant). MS (ES): m/z: 501.7 [M+H]⁺, ¹H NMR (DMSO-d6, 400 MHz): δ 10.50 (s, 1H), 8.25 (bs, 2H), 8.16-8.14 (d, J=5.6 Hz, 1H), 7.64 (s, 1H), 7.52-7.50 (d, J=8.4 Hz, 1H), 7.34 (s, 1H), 7.20 (s, 1H), 6.90-6.88 (m, 1H), 6.63-6.61 (m, 1H), 5.27 (bs, 1H), 4.68-4.64 (m, 1H), 4.06-3.98 (m, 1H), 3.69 (s, 3H), 2.18-2.11 (m, 2H), 2.02 (s, 3H), 1.94-1.87 (m, 1H), 1.23-1.16 (m, 2H), 0.91-0.86 (m, 2H), 0.65-0.61 (m, 2H).

Example 74: N-(4-((2-((1-((1r,3r)-3-cyanocyclobutyl)-5-cyclopropyl-2-oxo-1,2-dihydropyridin-3-yl)amino)-1-methyl-1H-benzo[d]imidazol-6-yl)oxy)pyridin-2-yl)acetamide

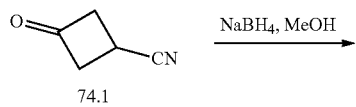

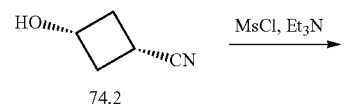

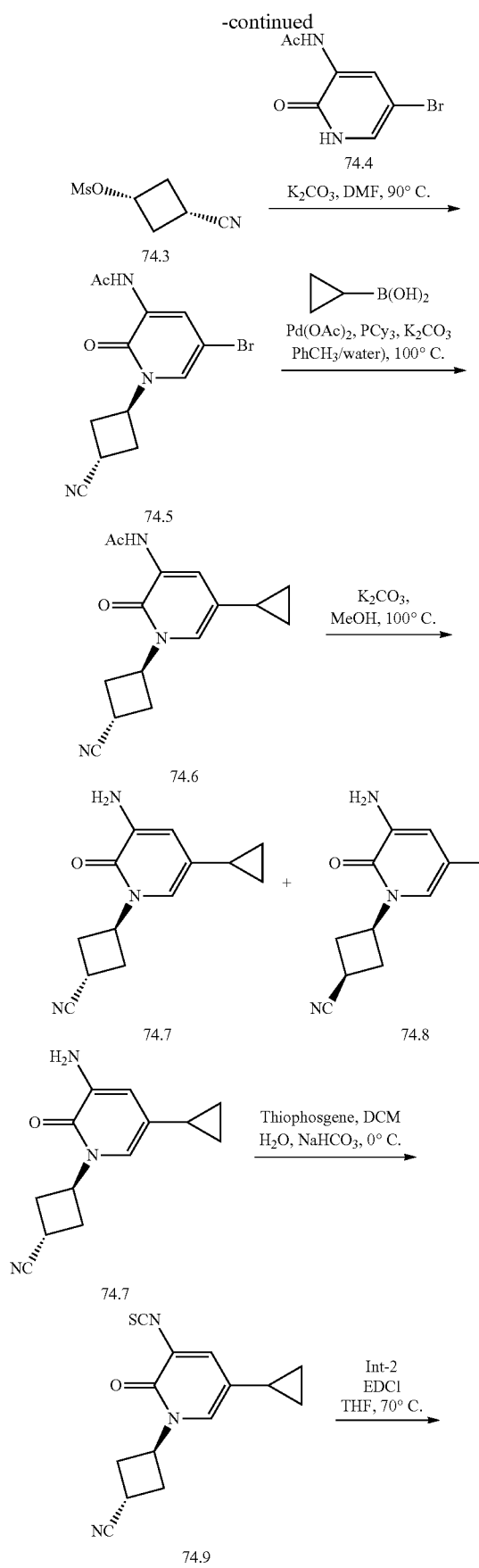

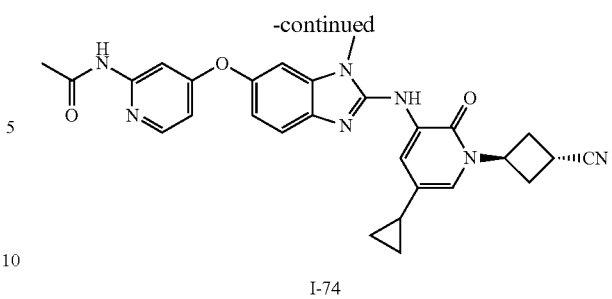

I-74

Synthesis of compound 74.2. To a solution of 74.1 (1.0 g, 10.52 mmol, 1.0 equiv) in methanol (10 mL) was added sodium borohydride (0.778 g, 21.04 mmol, 2.0 equiv) in small portions at 0° C. The reaction mixture was stirred at room temperature for 3 h. It was poured over ice-water, stirred and extracted with ethyl acetate. The combined organic layers were washed with brine, dried over anhydrous sodium sulfate, filtered and concentrated under reduced pressure to obtain 74.2. $^1$H NMR (CDCl$_3$, 400 MHz): 4.35-4.27 (m, 1H), 2.83-2.79 (m, 2H), 2.69-2.58 (m, 1H), 2.41-2.34 (m, 2H), 2.00 (bs, 1H).

Synthesis of compound 74.3. To a solution of 74.2 (0.600 g, 6.18 mmol, 1.0 equiv) in dichloromethane (10 mL) was added triethylamine (2.58 mL, 18.54 mmol, 3.0 equiv) at 0° C. followed by addition of methanesulfonyl chloride (0.571 mL, 7.41 mmol, 1.2 equiv). The reaction mixture was stirred at room temperature for 2 h. It was poured over ice-water, stirred and extracted with dichloromethane. The combined organic layers were washed with brine, dried over anhydrous sodium sulfate, filtered and concentrated under reduced pressure. The residue was purified by flash column chromatography on silica gel (CombiFlash®, 15% ethyl acetate in hexane as eluant) to afford 74.3. $^1$H NMR (CDCl$_3$, 400 MHz): 5.03-4.96 (m, 1H), 3.18-3.12 (m, 1H), 3.07 (s, 3H), 2.98-2.94 (m, 2H), 2.87-2.61 (m, 2H).

Synthesis of compound 74.4. To a solution of 3-amino-5-bromopyridin-2(1H)-one (0.5 g, 2.65 mmol, 1.0 equiv) in toluene (5 mL) was added acetic anhydride (0.30 mL, 3.18 mmol, 1.2 equiv). The reaction mixture was heated to reflux for 2 h. It was concentrated under reduced pressure, and the residue was purified by trituration with diethyl ether to obtain 74.4. MS (ES): m/z 232.2 [M+H]$^+$.

Synthesis of compound 74.5. To a solution of 74.3 (0.900 g, 5.14 mmol, 1.0 equiv) and 74.4 (1.19 g, 5.14 mmol, 1.0 equiv) in DMF (10 mL) was added potassium carbonate (1.773 g, 12.85 mmol, 2.5 equiv). The reaction mixture was stirred at 90° C. for 16 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 25% ethyl acetate in hexane as eluant) to afford 74.5. MS (ES): m/z 311.2 [M+H]$^+$.

Synthesis of compound 74.6. Compound 74.6 was prepared from 74.5 following the procedure described in the synthesis of 61.3. The product was purified by flash column chromatography on silica gel (CombiFlash®, 25% ethyl acetate in hexane as eluant). MS (ES): m/z 272.3 [M+H]$^+$.

Synthesis of compound 74.7 and 74.8. To a solution of 74.6 (0.150 g, 0.552 mmol, 1.0 equiv) in methanol (5 mL) was added potassium carbonate (1.52 g, 11.04 mmol, 20 equiv). The reaction mixture was stirred at 100° C. for 16 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 15% ethyl acetate in hexane as eluant) to afford mixture of 74.7 and 74.8. This was further separated on SFC purification to obtain 74.7, MS (ES): m/z 230.3 [M+H]+ and 74.8, MS (ES): m/z 230.3 [M+H]+.

Synthesis of compound 74.9. Compound 74.9 was prepared from 74.7 following the procedure described in the synthesis of 11.8. The crude product was used in the next step without further purification. MS (ES): m/z 272.3 [M+H]+.

Synthesis of I-74. Compound I-74 was prepared from 74.9 and Int-2 following the procedure described in the synthesis of I-1. The residue was purified by flash column chromatography on silica gel (CombiFlash®, 1.2% methanol in dichloromethane as eluant). MS (ES): m/z: 510.48 [M+H]+, 1H NMR (DMSO-d6, 400 MHz): δ 10.51 (s, 1H), 8.27 (s, 1H), 8.16 (s, 1H), 8.02 (s, 1H), 7.65 (s, 1H), 7.59 (s, 1H), 7.47-7.45 (d, J=6.8 Hz, 1H), 7.30 (s, 1H), 6.89-6.87 (d, J=7.6 Hz, 1H), 6.63 (s, 1H), 5.42 (s, 1H), 3.70 (s, 3H), 3.46 (bs, 1H), 2.77 (bs, 2H), 2.67 (bs, 2H), 2.02 (s, 3H), 1.93 (bs, 1H), 0.95-0.94 (m, 2H), 0.66 (bs, 2H).

Example 75: N-(4-((2-((5-cyclopropyl-1-(((1S,2R)-2-hydroxycyclopentyl)methyl)-2-oxo-1,2-dihydropyridin-3-yl)amino)-1-methyl-1H-benzo[d]imidazol-6-yl)oxy)pyridin-2-yl)acetamide and N-(4-((2-((5-cyclopropyl-1-(((1R,2S)-2-hydroxycyclopentyl)methyl)-2-oxo-1,2-dihydropyridin-3-yl)amino)-1-methyl-1H-benzo[d]imidazol-6-yl)oxy)pyridin-2-yl)acetamide

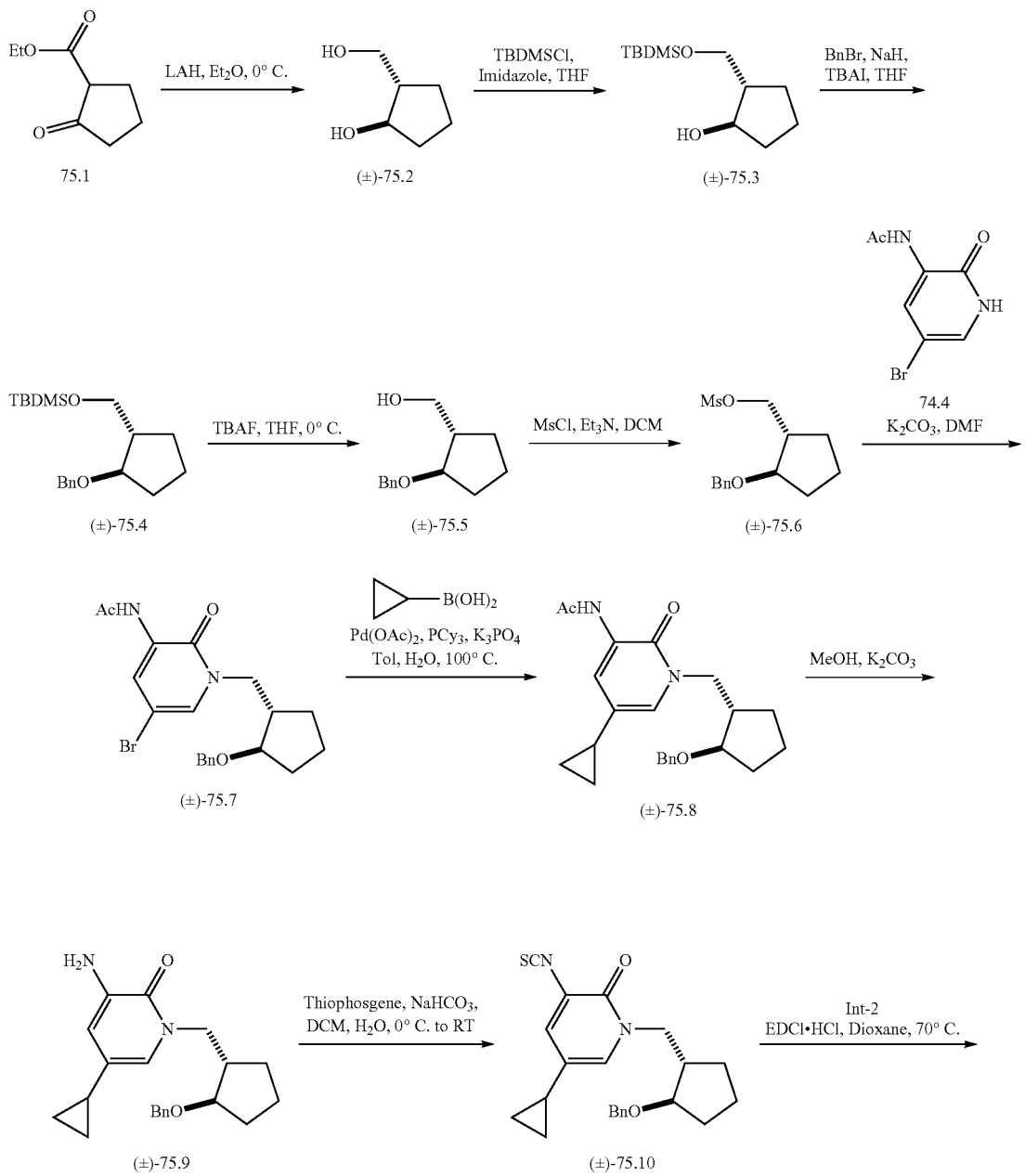

-continued

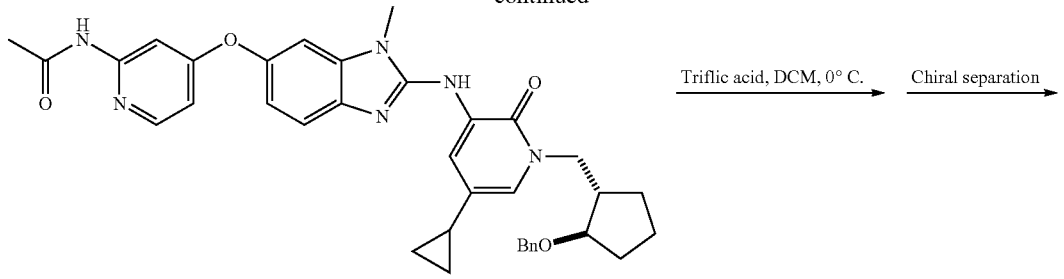

(±)-75.10

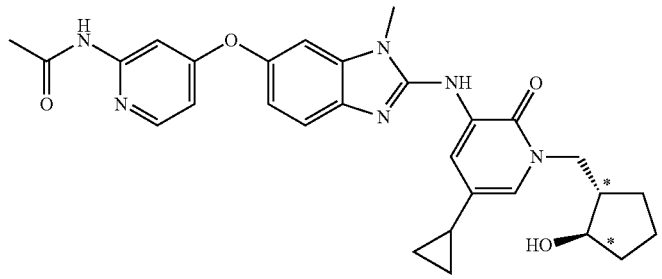

I-75-a and I-75-b

Synthesis of compound trans-(±)-75.2. To a solution of 75.1 (10 g, 64.03 mmol, 1.0 equiv) in diethyl ether (100 mL) was added lithium aluminum hydride solution (1 M in THF, 89 mL, 89.6 mmol, 1.4 equiv) at 0° C. The reaction mixture was stirred at room temperature for 4 h. It was treated with ice-water (3 mL) and 15% sodium hydroxide (3 mL), filtered through a pad of Celite® and washed with diethyl ether. Organic layer dried over anhydrous sodium sulfate, filtered and concentrated under reduced pressure. The residue was purified by flash column chromatography on silica gel (CombiFlash®, 2-2.4% methanol in dichloromethane as eluant) to afford trans-(±)-75.2. MS (ES): m/z 117.2 [M+H]$^+$.

Synthesis of compound trans-(±)-75.3. To a solution of trans-(±)-75.2 (1.5 g, 12.91 mmol, 1.0 equiv) in THF (15 mL) was added tert-butyldimethylsilyl chloride (2.32 g, 15.49 mmol, 1.2 equiv) followed by imidazole (2.10 g, 30.98 mmol, 2.4 equiv). The mixture was stirred at room temperature for 5 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 8-10% ethyl acetate in hexane as eluant) to afford trans-(±)-75.3. MS (ES): m/z 231.4 [M+H]$^+$.

Synthesis of compound trans-(±)-75.4. To a solution of trans-(±)-75.3 (1.2 g, 5.21 mmol, 1.0 equiv) in THF (12 mL) was added sodium hydride (0.5 g, 10.42 mmol, 2 equiv) at 0° C. and stirred for 1 h followed by addition of benzyl bromide (1.336 g, 7.815 mmol, 1.5 equiv) and tetrabutylammonium iodide (0.192 g, 0.521 mmol, 0.1 equiv). The reaction mixture was stirred at room temperature for 12 h. It was poured over ice, stirred and extracted with diethyl ether. The combined organic layers were washed with brine, dried over anhydrous sodium sulfate, filtered and concentrated under reduced pressure. The residue was purified by flash column chromatography on silica gel (CombiFlash®, 5% ethyl acetate in hexane as eluant) to afford trans-(±)-75.4. MS (ES): m/z 321.5 [M+H]$^+$.

Synthesis of compound trans-(±)-75.5. To a solution of trans-(±)-75.4 (0.960 g, 2.99 mmol, 1.0 equiv) in THF (10 mL) was added tetrabutylammoniumfluoride solution (1 M in THF, 3.6 mL, 3.58 mmol, 1.2 equiv) at 0° C. and stirred for 1 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 15% ethyl acetate in hexane as eluant) to afford trans-(±)-75.5. MS (ES): m/z 207.3 [M+H]$^+$.

Synthesis of compound trans-(±)-75.6. To a solution of trans-(±)-75.5 (0.600 g, 14.32 mmol, 1.0 equiv) in dichloromethane (10 mL) was added triethylamine (2.9 mL, 21.48 mmol, 1.5 equiv) followed by addition of methanesulfonyl chloride (1.1 mL, 14.32 mmol, 1.0 equiv) at 0° C. and stirred at room temperature for 1 h. It was poured over ice, stirred and extracted with dichloromethane. The combined organic layers were washed with brine, dried over anhydrous sodium sulfate, filtered and concentrated under reduced pressure to obtain trans-(±)-75.6. MS (ES): m/z 285.4 [M+H]$^+$.

Synthesis of compound trans-(±)-75.7. To a solution of 74.4 (0.610 g, 2.15 mmol, 1.0 equiv) in DMF (10 mL) was added potassium carbonate (0.593 g, 4.3 mmol, 2.0 equiv) followed by trans-(±)-75.6 (0.495 g, 2.15 mmol, 1.0 equiv). The reaction mixture stirred at 65° C. for 2 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 45% ethyl acetate in hexane as eluant) to afford (±)-75.7. MS (ES): m/z 420.3 [M+H]$^+$.

Synthesis of compound trans-(±)-75.8. Compound trans-(±)-75.8 was prepared from (±)-75.7 following the procedure described in the synthesis of 61.3. The product was purified by flash column chromatography on silica gel (CombiFlash®, 50% ethyl acetate in hexane as eluant). MS (ES): m/z 381.5 [M+H]$^+$.

Synthesis of compound trans-(±)-75.9. To a solution of trans-(±)-75.8 (0.225 g, 0.591 mmol, 1.0 equiv) in methanol (5 mL) was added potassium carbonate (0.163 g, 1.182 mmol, 2.0 equiv). The mixture was heated to reflux for 16 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.6% methanol in dichloromethane as eluant) to afford (±)-75.9. MS (ES): m/z 339.5 [M+H]$^+$.

Synthesis of compound (±)-75.10. Compound (±)-75.10 was prepared from (±)-75.9 following the procedure described in the synthesis of 11.8. The crude product was used in the next step without further purification. MS (ES): m/z 381.5 [M+H]$^+$.

Synthesis of compound (±)-75.11. Compound (±)-75.11 was prepared from (±)-75.10 following the procedure described in the synthesis of I-1. The product was purified by flash column chromatography on silica gel (CombiFlash®, 1.5% methanol in dichloromethane as eluant). MS (ES): m/z: 619.7 [M+H]$^+$.

Synthesis of compound (±)-I-75. To a solution of (±)-75.11 (0.125 g, 0.202 mmol, 1.0 equiv) in dichloromethane (3 mL) was added triflic acid (0.5 mL) at 0° C. and stirred for 30 min. It was poured over ice-cold saturated sodium bicarbonate solution and extracted with dichloromethane. The combined organic layers were washed with brine, dried over anhydrous sodium sulfate, filtered and concentrated under reduced pressure. The residue was purified by flash column chromatography on silica gel (CombiFlash®, 2.5-3.0% methanol in dichloromethane as eluant) to afford (±)-I-75. MS (ES): m/z: 529.2 [M+H]$^+$.

I-75-a and I-75-b. Compound (±)-I-75 was separated on SFC (column: CHIRALPAK IH (250 mm×4.6 mm, 5 μm); mobile phase: 0.1% DEA in MEOH; flow rate: 4 mL/min) to afford first eluting fraction (I-75-a) and second eluting fraction (I-75-b). (*Absolute stereochemistry not determined.)

I-75-a. MS (ES): m/z: 529.14 [M+H]$^+$, $^1$H NMR (DMSO-d6, 400 MHz): δ 10.52 (s, 1H), 8.30 (s, 1H), 8.24 (s, 1H), 8.16-8.15 (d, J=5.2 Hz, 1H), 7.66 (s, 1H), 7.53-7.51 (d, J=8.4 Hz, 1H), 7.35-7.34 (d, J=2.0 Hz, 1H), 7.13 (s, 1H), 6.90-6.88 (m, 1H), 6.64-6.62 (m, 1H), 4.62-4.61 (d, 1H), 4.08-4.03 (m, 1H), 3.83-3.78 (t, 2H), 3.70 (s, 3H), 2.24 (bs, 2H), 2.03 (s, 3H), 1.86-1.82 (m, 2H), 1.68-1.56 (m, 2H), 1.50-1.47 (m, 1H), 1.34-1.24 (m, 1H), 0.88-0.86 (d, 2H), 0.61-0.60 (d, 2H).

I-75-b. MS (ES): m/z: 529.19 [M+H]$^+$, $^1$H NMR (DMSO-d6, 400 MHz): δ 10.51 (s, 1H), 8.30 (s, 1H), 8.24 (s, 1H), 8.16-8.15 (d, J=5.2 Hz, 1H), 7.66 (s, 1H), 7.53-7.51 (d, J=8.4 Hz, 1H), 7.34 (s, 1H), 7.13 (s, 1H), 6.90-6.88 (d, J=6.8 Hz, 1H), 6.63-6.62 (m, 1H), 4.62-4.61 (d, 1H), 4.05-4.03 (m, 1H), 3.83-3.78 (t, 2H), 3.70 (s, 3H), 2.24 (bs, 2H), 2.03 (s, 3H), 1.86-1.83 (m, 2H), 1.64-1.60 (m, 2H), 1.50-1.47 (m, 1H), 1.34-1.24 (m, 1H), 0.88-0.86 (d, 2H), 0.61-0.60 (d, 2H).

Example 76: N-(4-((2-((5-cyclopropyl-1-(((1R,2R)-2-methoxycyclobutyl)methyl)-2-oxo-1,2-dihydropyridin-3-yl)amino)-1-methyl-1H-benzo[d]imidazol-6-yl)oxy)pyridin-2-yl)acetamide and N-(4-((2-((5-cyclopropyl-1-((1S,2S)-2-methoxycyclobutyl)methyl)-2-oxo-1,2-dihydropyridin-3-yl)amino)-1-methyl-1H-benzo[d]imidazol-6-yl)oxy)pyridin-2-yl)acetamide

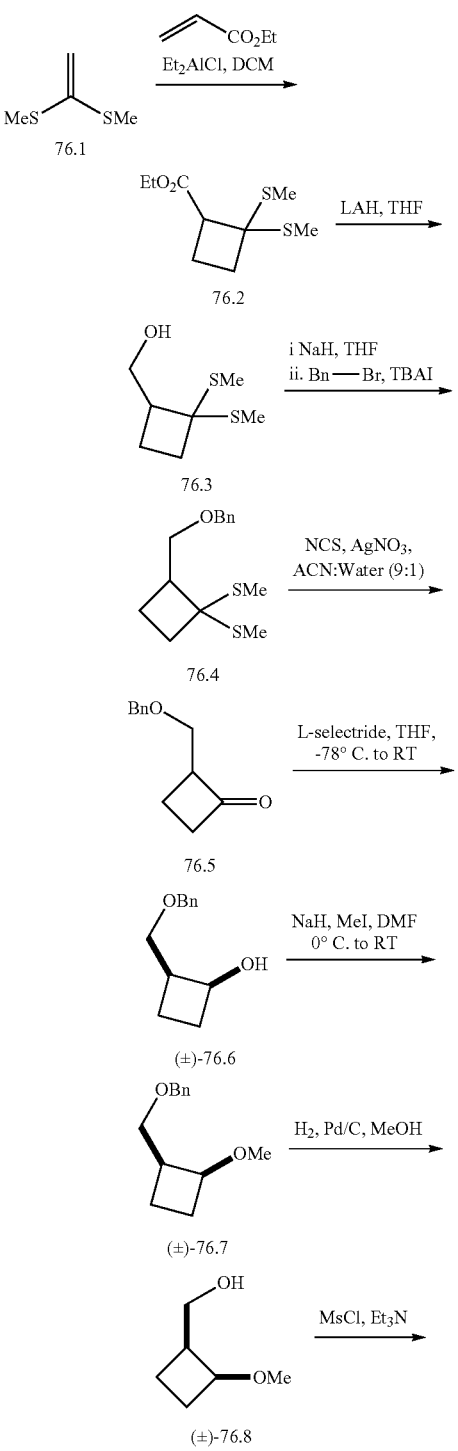

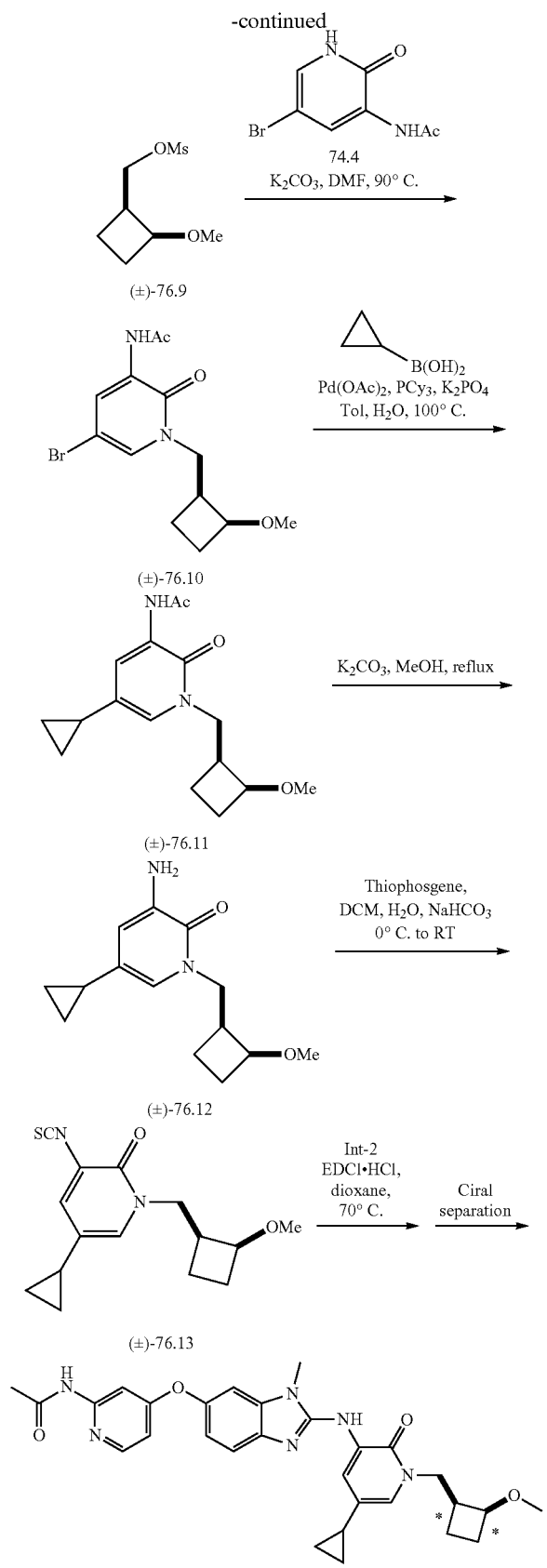

Synthesis of compound 76.2. To a solution of 76.1 (4.0 g, 33.27 mmol, 1.0 equiv) in dichloromethane (75 mL) was added ethyl acrylate (7.33 g, 78.99 mmol, 2.2 equiv) at 0° C. followed by addition of diethylaluminum chloride solution (1 M in hexane, 50 mL, 49.9 mmol, 1.5 equiv). The reaction mixture was stirred at room temperature for 2-3 h. After completion of reaction, triethyl amine (5 mL) followed by 10% aqueous sodium bicarbonate was added, filtered through a pad of Celite® and washed with dichloromethane. Organic layer dried over anhydrous sodium sulfate, filtered and concentrated under reduced pressure. The residue was purified by flash column chromatography on silica gel (CombiFlash®, 0.5% ethyl acetate in hexane as eluant) to afford 76.2. $^1$H NMR (CDCl$_3$, 400 MHz): δ 4.25-4.19 (m, 2H), 3.45-3.41 (m, 1H), 2.59-2.53 (m, 1H), 2.34-2.30 (m, 3H), 2.15 (s, 3H), 2.05 (s, 3H), 1.35-1.29 (t, 3H).

Synthesis of compound 76.3. To a solution of 76.2 (2.0 g, 9.08 mmol, 1.0 equiv) in THF (20 mL) was added lithium aluminum hydride solution (1 M in THF, 13.6 mL, 13.62 mmol, 1.5 equiv) at 0° C. The reaction mixture was stirred at room temperature for 1 h. After completion of reaction, saturated aqueous sodium sulfate was added, reaction mixture filtered through a pad of Celite® and washed with diethyl ether. Organic layer dried over anhydrous sodium sulfate, filtered and concentrated under reduced pressure. The residue was purified by flash column chromatography on silica gel (CombiFlash®, 8% ethyl acetate in hexane as eluant) to afford 76.3. $^1$H NMR (CDCl$_3$, 400 MHz): δ 3.90-3.85 (m, 1H), 3.79-3.75 (m, 1H), 2.75-2.68 (m, 1H), 2.34-2.22 (m, 3H), 2.11 (s, 3H), 2.08 (s, 3H), 2.00-1.91 (m, 2H).

Synthesis of compound 76.4. To a solution of 76.3 (1.5 g, 8.41 mmol, 1.0 equiv) in THF (15 mL) was added sodium hydride (0.807 g, 16.82 mmol, 2 equiv) at 0° C. It was stirred for 1 h and was added benzyl bromide (1.72 g, 10.09 mmol, 1.2 equiv) and tetrabutylammonium iodide (0.031 g, 0.0841 mmol, 0.01 equiv). The reaction mixture was stirred at room temperature for 16 h. It was poured over ice, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 2% ethyl acetate in hexane as eluant) to afford 76.4. $^1$H NMR (CDCl$_3$, 400 MHz): δ 7.41-7.37 (m, 5H), 4.60-4.50 (m, 2H), 3.80-3.75 (m, 1H), 3.52-3.48 (m, 1H), 2.92-2.89 (m, 1H), 2.30-2.19 (m, 3H), 2.09 (s, 3H), 2.05 (s, 2H), 1.29 (bs, 2H).

Synthesis of compound 76.5. To a solution of silver nitrate (3.87 g, 22.81 mmol, 3.4 equiv) and N-chlorosuccinimide (2.67 g, 20.13 mmol, 3.0 equiv) in acetonitrile (10 mL) and water (1.8 mL) at 0° C. was added 76.4 (1.8 g, 6.71 mmol, 1.0 equiv) in acetonitrile (6 mL) and stirred for 30 min. It was poured over saturated aqueous sodium sulfite solution, stirred and precipitated solid was filtered washed with ethyl acetate. Organic layer separated washed with brine, dried over anhydrous sodium sulfate, filtered and concentrated under reduced pressure. The residue was purified by flash column chromatography on silica gel (CombiFlash®, 5% ethyl acetate in hexane as eluant) to afford 76.5. $^1$H NMR (CDCl$_3$, 400 MHz): δ 7.39-7.32 (m, 5H), 4.59-4.53 (m, 2H), 3.77-3.73 (m, 1H), 3.65-3.57 (m, 2H), 3.11-3.04 (m, 2H), 2.26-2.04 (m, 2H).

Synthesis of compound (±)-76.6. To a solution of 76.5 (1.0 g, 5.26 mmol, 1.0 equiv) in THF (10 mL) was added L-selectride (1.49 g, 7.89 mmol, 1.5 equiv) at −78° C. and stirred for 30 min. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 10% ethyl acetate in hexane as eluant) to afford (±)-76.6. $^1$H NMR (CDCl$_3$, 400 MHz): δ 7.37-7.26 (m, 5H), 4.84-4.82 (m, 1H), 4.50-4.44 (m, 1H), 4.24-4.20 (m, 1H), 3.67-3.56 (m, 1H), 2.15-2.10 (m, 1H), 1.95-1.87 (m, 1H), 1.67-1.50 (m, 2H), 1.36-1.33 (m, 1H), 0.86-0.81 (m, 2H).

Synthesis of compound (±)-76.7. To a solution of (±)-76.6 (0.700 g, 3.64 mmol, 1.0 equiv) in DMF (10 mL) was added sodium hydride (0.436 g, 10.92 mmol, 3.0 equiv) in small portions at 0° C. and stirred for 20 min. To the mixture was added methyl iodide (1.033 g, 7.28 mmol, 2.0 equiv). The reaction mixture was stirred at room temperature for 16 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 8% ethyl acetate in hexane as eluant) to afford (±)-76.7. MS (ES): m/z 207.3 [M+H]$^+$.

Synthesis of compound (±)-76.8. A mixture of compound (±)-76.7 (0.600 g, 2.91 mmol, 1.0 equiv), methanol (10 mL) and 10% palladium on carbon (0.300 g) was stirred at rt under 1 atm hydrogen for 2 h. It was filtered through a pad of Celite® and rinsed with methanol. The filtrate was concentrated under reduced pressure to obtain (±)-76.8. $^1$H NMR (DMSO-d6, 400 MHz): δ 4.26-4.23 (m, 1H), 3.89-3.84 (m, 1H), 3.67-3.62 (m, 1H), 3.50-3.44 (m, 1H), 3.12 (s, 3H), 2.11-2.09 (m, 1H), 1.94-1.85 (m, 1H), 1.63-1.46 (m, 2H).

Synthesis of compound (±)-76.9. To a solution of (±)-76.8 (0.300 g, 2.58 mmol, 1.0 equiv) and triethylamine (1.07 mL, 7.74 mmol, 3.0 equiv) in dichloromethane (5 mL) was added methanesulfonyl chloride (0.4 mL, 5.16 mmol, 2.0 equiv) at 0° C. and stirred at room temperature for 2 h. It was poured over ice, stirred and extracted with dichloromethane. The combined organic layers were washed with brine, dried over anhydrous sodium sulfate, filtered and concentrated under reduced pressure to obtain (±)-76.9. MS (ES): m/z 195.3 [M+H]$^+$.

Synthesis of compound (±)-76.10. To a solution of 74.4 (0.350 g, 1.51 mmol, 1.0 equiv) in DMF (5 mL) was added potassium carbonate (0.416 g, 3.02 mmol, 2.0 equiv) followed by (±)-76.9 (0.35 g, 1.82 mmol, 1.2 equiv). The reaction mixture stirred at 90° C. for 24 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 11% ethyl acetate in hexane as eluant) to afford (±)-76.10. MS (ES): m/z 330.2 [M+H]$^+$.

Synthesis of compound (±)-76.11. Compound (±)-76.11 was prepared from (±)-76.10 following the procedure described in the synthesis of 61.3. The product was purified by flash column chromatography on silica gel (CombiFlash®, 1% methanol in dichloromethane as eluant). MS (ES): m/z 291.4 [M+H]$^+$.

Synthesis of compound (±)-76.12. A mixture of (±)-76.11 (0.163 g, 0.561 mmol, 1.0 equiv) and potassium carbonate (1.54 g, 11.22 mmol, 20.0 equiv) in methanol (5 mL) was added heated to reflux for 16 h. It was poured over ice-water and extracted with dichloromethane. The combined organic layers were washed with brine, dried over anhydrous sodium sulfate, filtered and concentrated under reduced pressure. The residue was purified by flash column chromatography on silica gel (CombiFlash®, 1.6% methanol in dichloromethane as eluant) to afford (±)-76.12. MS (ES): m/z 249.3 [M+H]$^+$.

Synthesis of compound (±)-76.13. Compound (±)-76.13 was prepared from (±)-76.12 following the procedure described in the synthesis of 11.8. The crude product was used in the next step without further purification. MS (ES): m/z 291.4 [M+H]$^+$.

Synthesis of compound (±)-I-76. Compound (±)-I-76 was prepared from (±)-76.13 and Int-2 following the procedure described in the synthesis of I-1 The product was purified by flash column chromatography on silica gel (CombiFlash®, 2.5% methanol in dichloromethane as eluant). MS (ES): m/z: 529.6 [M+H]$^+$.

I-76-a and I-76-b. (±)-I-76 was separated on HPLC (column: CHIRALPAK IB-N (250 mm×4.6 mm, 5 μm); mobile phase: (A) 0.1% diethylamine in n-hexane (B) 0.1% diethylamine in 2-propanol:acetonitrile (70:30); flow rate: 20 mL/min) to afford first eluting fraction (I-76-a) and second eluting fraction (I-76-b). (*Absolute stereochemistry not determined.)

I-76-a. MS (ES): m/z: 530.09 [M+H]$^+$, $^1$H NMR (DMSO-d6, 400 MHz): δ 10.50 (s, 1H), 8.31 (s, 1H), 8.22 (s, 1H), 8.15-8.14 (d, J=5.6 Hz, 1H), 7.65 (s, 1H), 7.52-7.50 (d, J=8.0 Hz, 1H), 7.33 (s, 1H), 7.18 (s, 1H), 6.89-6.87 (d, J=8.0 Hz, 1H), 6.62 (bs, 1H), 4.29-4.23 (m, 1H), 4.08-4.06 (m, 1H), 3.95-3.93 (m, 1H), 3.69 (s, 3H), 3.19 (s, 3H), 2.97 (bs, 1H), 2.15-2.13 (m, 1H), 2.02 (s, 3H), 1.56 (bs, 2H), 1.23 (bs, 2H), 0.86 (bs, 2H), 0.59 (bs, 2H).

I-76-b. MS (ES): m/z: 529.6 [M+H]$^+$, $^1$H NMR (DMSO-d6, 400 MHz): δ 10.50 (s, 1H), 8.31 (s, 1H), 8.23 (s, 1H), 8.15-8.14 (d, J=5.6 Hz, 1H), 7.65 (s, 1H), 7.52-7.50 (d, J=8.0 Hz, 1H), 7.33 (s, 1H), 7.18 (s, 1H), 6.89-6.87 (d, J=8.0 Hz, 1H), 6.62-6.61 (m, 1H), 4.29-4.23 (m, 1H), 4.10-4.05 (m, 1H), 3.97-3.92 (m, 1H), 3.69 (s, 3H), 3.19 (s, 3H), 2.96 (bs, 1H), 2.17-2.11 (m, 1H), 2.02 (s, 3H), 1.58-1.56 (m, 2H), 1.17 (bs, 2H), 0.87 (bs, 2H), 0.59 (bs, 2H).

Example 77: N-(4-((2-((5-cyclopropyl-1-(((1R,2R)-2-hydroxycyclobutyl)methyl)-2-oxo-1,2-dihydropyridin-3-yl)amino)-1-methyl-1H-benzo[d]imidazol-6-yl)oxy)pyridin-2-yl)acetamide and N-(4-((2-((5-cyclopropyl-1-(((1S,2S)-2-hydroxycyclobutyl)methyl)-2-oxo-1,2-dihydropyridin-3-yl)amino)-1-methyl-1H-benzo[d]imidazol-6-yl)oxy)pyridin-2-yl)acetamide

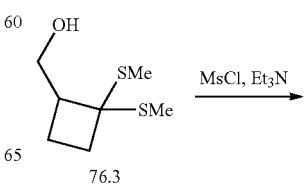

76.3

-continued

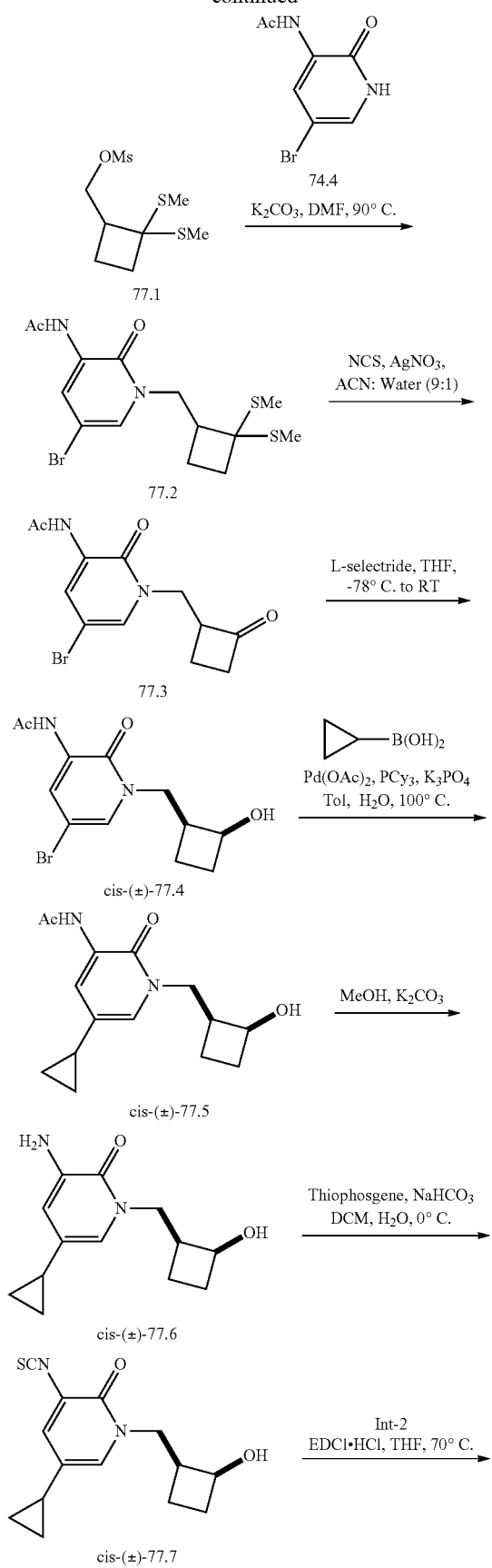

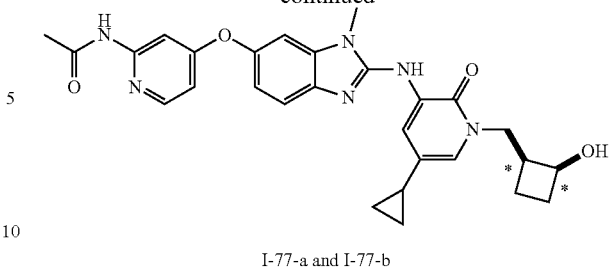

I-77-a and I-77-b

Synthesis of compound 77.1. To a solution of 76.3 (2.4 g, 13.46 mmol, 1.0 equiv) in dichloromethane (25 mL) was added triethylamine (5.62 mL, 40.38 mmol, 3.0 equiv) followed by addition of methanesulfonyl chloride (2.1 mL, 26.92 mmol, 2.0 equiv) at 0° C. and stirred at room temperature for 3 h. It was poured over ice, stirred and extracted with dichloromethane. The combined organic layers were washed with brine, dried over anhydrous sodium sulfate, filtered and concentrated under reduced pressure to obtain 77.1. MS (ES): m/z 257.4 [M+H]$^+$.

Synthesis of compound 77.2. To a solution of 74.4 (1.6 g, 6.92 mmol, 1.0 equiv) in DMF (20 mL) was added potassium carbonate (1.90 g, 13.84 mmol, 2.0 equiv) followed by 77.1 (2.31 g, 9.0 mmol, 1.3 equiv). The reaction mixture stirred at 90° C. for 24 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 30% ethyl acetate in hexane as eluant) to afford 77.3. MS (ES): m/z 392.3 [M+H]$^+$.

Synthesis of compound 77.3. To a solution of silver nitrate (1.167 g, 6.868 mmol, 3.4 equiv) and N-chlorosuccinimide (2.67 g, 20.13 mmol, 3.0 equiv) in acetonitrile (12 mL) and water (2 mL) at 0° C. was added 77.2 (0.790 g, 2.02 mmol, 1.0 equiv) in acetonitrile (8 mL) and stirred for 30 min. It was poured over saturated aqueous sodium sulfite solution, stirred and precipitated solid was filtered washed with ethyl acetate. Organic layer separated washed with brine, dried over anhydrous sodium sulfate, filtered and concentrated under reduced pressure. The residue was purified by flash column chromatography on silica gel (CombiFlash®, ethyl acetate as eluant) to afford 77.3. MS (ES): m/z 314.3 [M+H]$^+$.

Synthesis of compound (±)-77.4 To a solution of 77.3 (0.500 g, 1.60 mmol, 1.0 equiv) in THF (10 mL) was added L-selectride (0.456 g, 2.4 mmol, 1.5 equiv) at −78° C. and stirred for 30 min. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.2% methanol in dichloromethane as eluant) to afford (±)-77.4. MS (ES): m/z 316.2 [M+H]$^+$.

Synthesis of compound (±)-77.5. Compound (±)-77.5 was prepared from (±)-77.4 following the procedure described in the synthesis of 61.3. The product was purified by flash column chromatography on silica gel (CombiFlash®, 1.8% methanol in dichloromethane as eluant). MS (ES): m/z 277.3 [M+H]$^+$.

Synthesis of compound (±)-77.6. A mixture of (±)-77.5 (0.160 g, 0.579 mmol, 1.0 equiv), methanol (5 mL) and potassium carbonate (1.59 g, 11.58 mmol, 20.0 equiv) was heated to reflux for 16 h. It was poured over ice-water and extracted with dichloromethane. The combined organic layers were washed with brine, dried over anhydrous sodium sulfate, filtered and concentrated under reduced pressure. The residue was purified by flash column chromatography on silica gel (CombiFlash®, 2.0% methanol in dichloromethane as eluant) to afford (±)-77.6. MS (ES): m/z 235.3 [M+H]⁺.

Synthesis of compound (±)-77.7. Compound (±)-77.7 was prepared from (±)-77.6 following the procedure described in the synthesis of 11.8. The crude product was used in the next step without further purification. MS (ES): m/z 277.4 [M+H]⁺.

Synthesis of compound (±)-I-77. Compound (±)-I-77 was prepared from (±)-77.7 and Int-2 following the procedure described in the synthesis of I-1. The product was purified by flash column chromatography on silica gel (CombiFlash®, 2.5% methanol in dichloromethane as eluant). MS (ES): m/z: 515.5 [M+H]⁺.

I-77-a and I-77-b. Compound (±)-I-77 was separated on SFC (column CHIRALPAK 1H (250 mm×4.6 mm, 5 μm); mobile phase: 0.1% diethylamine in MeOH; flow rate: 4 mL/min) to afford first eluting fraction (I-77-a) and second eluting fraction (I-77-b). (*Absolute stereochemistry not determined.)

I-77-a. MS (ES): m/z: 515.6 [M+H]⁺, ¹H NMR (DMSO-d6, 400 MHz): δ 10.51 (s, 1H), 8.31 (s, 1H), 8.23 (s, 1H), 8.16-8.14 (d, J=5.6 Hz, 1H), 7.65 (s, 1H), 7.52-7.50 (d, J=8.4 Hz, 1H), 7.33 (s, 1H), 7.19 (s, 1H), 6.89-6.87 (d, J=8.4 Hz, 1H), 6.63-6.61 (d, J=4.4 Hz, 1H), 4.34-4.19 (m, 2H), 4.15-4.10 (m, 1H), 3.70 (s, 3H), 3.17 (s, 3H), 2.82 (bs, 1H), 2.16 (bs, 1H), 2.03 (s, 2H), 1.81 (bs, 1H), 1.60-1.58 (d, 1H), 1.24 (bs, 1H), 0.87-0.85 (d, 2H), 0.60-0.59 (d, 2H).

I-77-b. MS (ES): m/z: 515.7 [M+H]⁺, ¹H NMR (DMSO-d6, 400 MHz): δ 10.50 (s, 1H), 8.31 (s, 1H), 8.22 (s, 1H), 8.16-8.14 (d, J=5.6 Hz, 1H), 7.65 (s, 1H), 7.52-7.50 (d, J=8.4 Hz, 1H), 7.33 (s, 1H), 7.19 (s, 1H), 6.90-6.87 (d, J=8.4 Hz, 1H), 6.63-6.62 (d, J=3.6 Hz, 1H), 4.34-4.19 (m, 2H), 4.15-4.10 (m, 1H), 3.70 (s, 3H), 3.17 (s, 3H), 2.81 (bs, 1H), 2.17 (bs, 1H), 2.03 (s, 2H), 1.81 (bs, 1H), 1.60-1.58 (d, 1H), 1.24 (bs, 1H), 0.87-0.85 (d, 2H), 0.60-0.59 (d, 2H).

Example 78: N-(4-((2-((5-cyclopropyl-1-((1R,2S)-2-hydroxycyclobutyl)-2-oxo-1,2-dihydropyridin-3-yl)amino)-1-methyl-1H-benzo[d]imidazol-6-yl)oxy)pyridin-2-yl)acetamide and N-(4-((2-((5-cyclopropyl-1-((1S,2R)-2-hydroxycyclobutyl)-2-oxo-1,2-dihydropyridin-3-yl)amino)-1-methyl-1H-benzo[d]imidazol-6-yl)oxy)pyridin-2-yl)acetamide

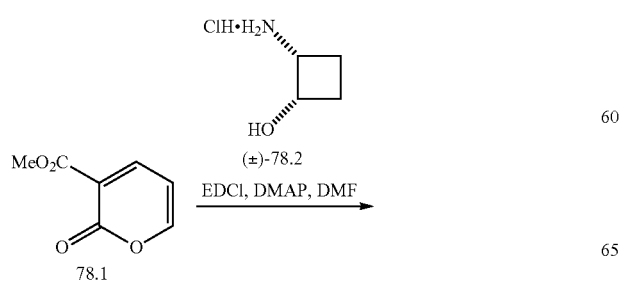

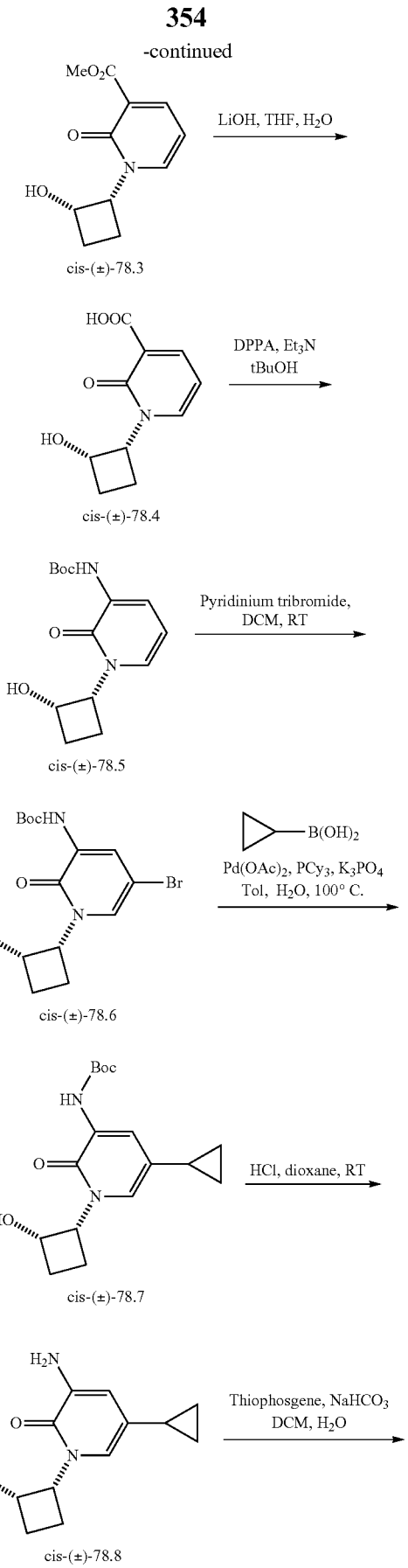

-continued

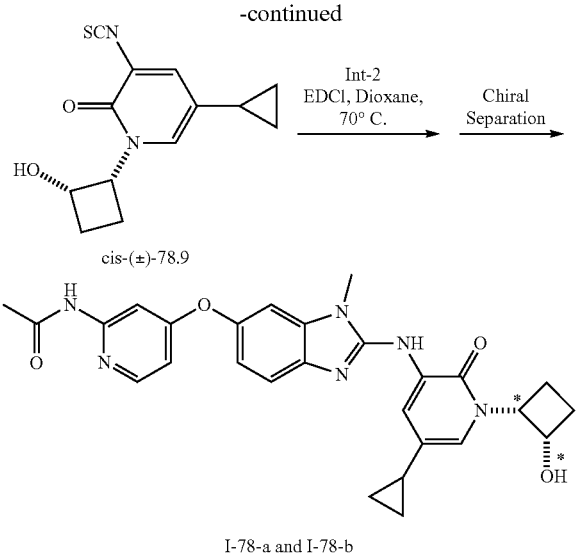

cis-(±)-78.9

I-78-a and I-78-b

Synthesis of compound cis-(±)-78.3. To a solution of 78.1 (2.0 g, 12.98 mmol, 1.0 equiv) and (±)-78.2 (1.92 g, 15.57 mmol, 1.2 equiv) in DMF (20 mL) was added diisopropylethylamine (4.5 mL, 25.96 mmol, 2.0 equiv) at 0° C. The reaction mixture was stirred for 2 h and was added N-ethyl-N'-(3-dimethylaminopropyl)carbodiimide hydrochloride (3.48 g, 18.17 mmol, 1.4 equiv) and 4-dimethylaminopyridine (0.395 g, 3.24 mmol, 0.25 equiv). The reaction mixture was stirred at room temperature for 16 h. It was poured over water and extracted with ethyl acetate. The combined organic layers were washed with brine, dried over anhydrous sodium sulfate, filtered and concentrated under reduced pressure. The residue was purified by column chromatography and the compound was eluted in 2.0% methanol in dichloromethane to obtain (±)-78.3. MS (ES): m/z 224.09 $[M+H]^+$.

Synthesis of compound cis-(±)-78.4. To a solution of lithium hydroxide (1.50 g, 35.85 mmol, 5.0 equiv) in THF:methanol:water (15 mL, 2:1:1) was added cis-(±)-78.3 (1.6 g, 7.17 mmol, 1.0 equiv) and stirred at room temperature for 24 h. Most organic solvent was removed under reduced pressure. The aqueous residue was acidified with 1 N hydrochloric acid to adjust approx. pH 3. It was extracted with 10% methanol in dichloromethane. The combined organic layers were washed with brine, dried over anhydrous sodium sulfate, filtered and concentrated under reduced pressure to obtain cis-(±)-78.4. MS (ES): m/z 210.2 $[M+H]^+$.

Synthesis of compound cis-(±)-78.5. To a solution of cis-(±)-78.4 (1.1 g, 5.26 mmol, 1.0 equiv) in tert-butanol (10 mL) was added triethylamine (2.19 mL, 15.78 mmol, 3.0 equiv) and diphenylphosphorylazide (3.6 g, 13.15 mmol, 2.5 equiv) under nitrogen. The mixture was stirred at 80° C. for 16 h. It cooled to room temperature, poured over water and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.2% methanol in dichloromethane to obtain cis-(±)-78.5. MS (ES): m/z 281.3 $[M+H]^+$.

Synthesis of compound cis-(±)-78.6. To a solution of cis-(±)-78.5 (0.6 g, 2.14 mmol, 1.0 equiv) in dichloromethane (10 mL) at 0° C. was added pyridinium tribromide (1.03 g, 3.21 mmol, 1.5 equiv) portionwise. The reaction mixture stirred at room temperature for 4 h. It concentrated under reduced pressure. The residue was purified by flash column chromatography on silica gel (CombiFlash®, 20% ethyl acetate in hexane as eluant) to afford cis-(±)-78.6. MS (ES): m/z 360.2 $[M+H]^+$.

Synthesis of compound cis-(±)-78.7. Compound cis-(±)-78.7 was prepared from cis-(±)-78.6 following the procedure described in the synthesis of 61.3. The product was purified by flash column chromatography on silica gel (CombiFlash®, 30% ethyl acetate in hexane as eluant). MS (ES): m/z 321.4 $[M+H]^+$.

Synthesis of compound cis-(±)-78.8. To a solution of cis-(±)-78.7 (0.110 g, 0.343 mmol, 1.0 equiv) in dioxane (1 mL) was added 4 N hydrochloric acid in dioxane (1 mL) dropwise at 0° C. The reaction mixture was stirred at room temperature for 30 min. It was poured over saturated aqueous solution of sodium bicarbonate and extracted with dichloromethane. The combined organic layers were washed with brine, dried over anhydrous sodium sulfate, filtered and concentrated under reduced pressure to obtain cis-(±)-78.8. MS (ES): m/z 221.3 $[M+H]^+$.

Synthesis of compound cis-(±)-78.9. Compound cis-(±)-78.9 was prepared from cis-(±)-78.8 following the procedure described in the synthesis of 11.8. The crude product was used in the next step without further purification. MS (ES): m/z 263.3 $[M+H]^+$.

Synthesis of compound cis-(±)-I-78. Compound cis-(±)-I-78 was prepared from cis-(±)-78.9 and Int-2 following the procedure described in the synthesis of I-1. The product was purified by flash column chromatography on silica gel (CombiFlash®, 4% methanol in dichloromethane as eluant). MS (ES): m/z: 501.7 $[M+H]^+$.

I-78-a and I-78-b. Compound (±)-I-78 was separated on HPLC (column: CHIRALPAK IB-N (250 mm×21 mm, 5 μm); mobile phase: (A) 0.1% diethylamine in n-hexane (B) 0.1% diethylamine in 2-propanol:acetonitrile (70:30); flow rate: 20 mL/min) to afford first eluting fraction (I-78-a) and second eluting fraction (I-78-b). (*Absolute stereochemistry not determined.)

I-78-a. MS (ES): m/z: 501.1 $[M+H]^+$, $^1$H NMR (DMSO-d6, 400 MHz): δ 10.50 (s, 1H), 8.27 (s, 1H), 8.19 (s, 1H), 8.15-8.14 (d, J=5.6 Hz, 1H), 7.65 (s, 1H), 7.52-7.50 (d, J=8.4 Hz, 1H), 7.33 (bs, 1H), 7.17 (s, 1H), 6.89-6.87 (m, 1H), 6.63-6.61 (m, 1H), 5.20-5.15 (m, 1H), 4.51 (bs, 1H), 3.69 (s, 3H), 2.79-2.72 (m, 1H), 2.02 (s, 3H), 1.91-1.86 (m, 1H), 1.75-1.70 (m, 1H), 1.23 (bs, 1H), 1.11-1.03 (m, 2H), 0.89-0.87 (m, 2H), 0.62-0.59 (m, 2H).

I-78-b. MS (ES): m/z: 501.2 $[M+H]^+$, $^1$H NMR (DMSO-d6, 400 MHz): δ 10.50 (s, 1H), 8.27 (s, 1H), 8.19 (s, 1H), 8.15-8.14 (d, J=5.6 Hz, 1H), 7.65 (s, 1H), 7.52-7.50 (d, J=8.4 Hz, 1H), 7.33 (s, 1H), 7.17 (s, 1H), 6.89-6.87 (m, 1H), 6.63-6.61 (m, 1H), 5.19-5.15 (m, 1H), 4.51 (bs, 1H), 3.69 (s, 3H), 2.79-2.72 (m, 1H), 2.02 (s, 3H), 1.90 (bs, 1H), 1.76-1.70 (m, 1H), 1.23 (bs, 1H), 1.11-1.03 (m, 2H), 0.89-0.87 (m, 2H), 0.62 (bs, 2H).

Example 79: N-(4-((2-((5-cyclopropyl-1-((1R,2R)-2-hydroxycyclobutyl)-2-oxo-1,2-dihydropyridin-3-yl)amino)-1-methyl-1H-benzo[d]imidazol-6-yl)oxy)pyridin-2-yl)acetamide and N-(4-((2-((5-cyclopropyl-1-((1S,2S)-2-hydroxycyclobutyl)-2-oxo-1,2-dihydropyridin-3-yl)amino)-1-methyl-1H-benzo[d]imidazol-6-yl)oxy)pyridin-2-yl)acetamide

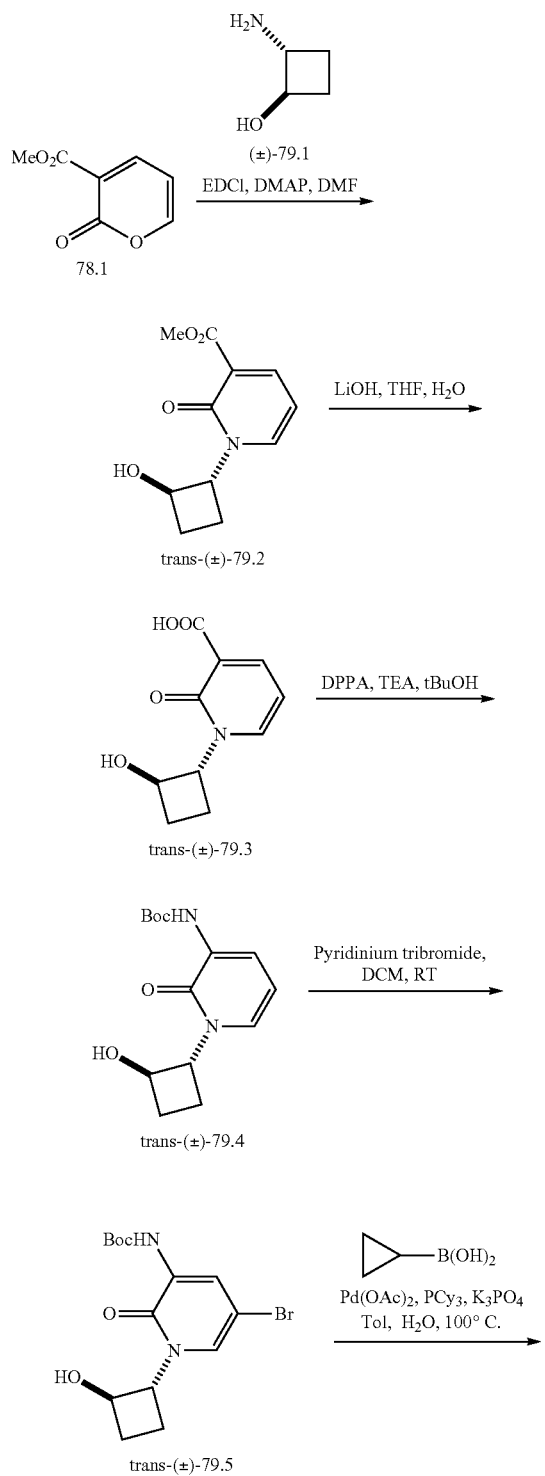

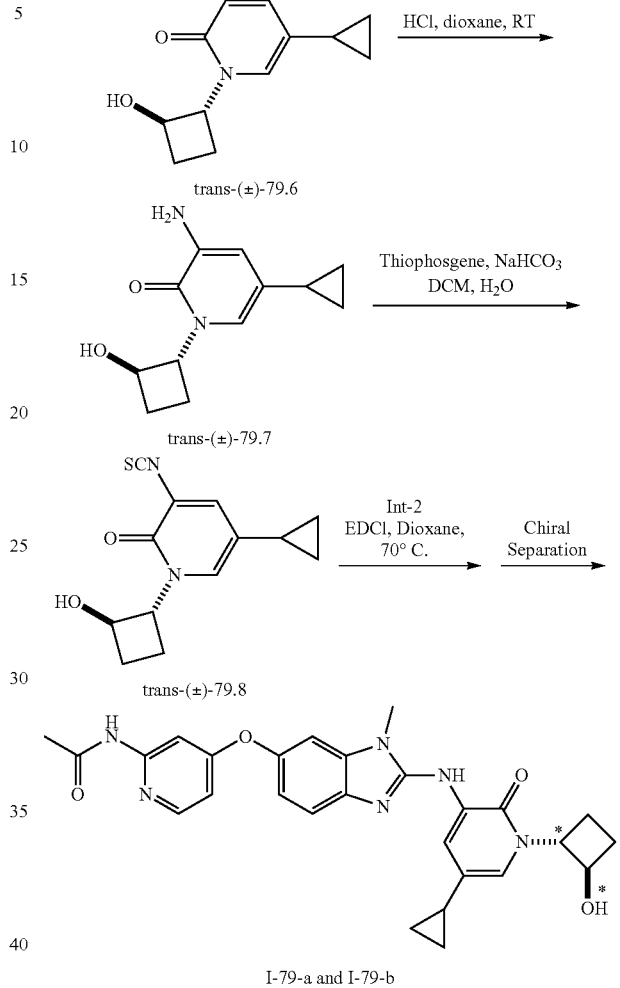

Synthesis of compound (±)-I-79. Compound (±)-I-79 was prepared from compound 78.1 and (±)-79.1 following the procedures described in each step in the synthesis of (±)-I-78. The product was purified by flash column chromatography on silica gel (CombiFlash®, 3.5% methanol in dichloromethane as eluant). MS (ES): m/z: 501.7 [M+H]$^+$.

I-79-a and I-79-b. Compound (±)-I-79 was separated on HPLC (column: CHIRALPAK IH (250 mm×21 mm, 5 μm); mobile phase (A) 0.1% diethylamine in n-hexane (B) 0.1% diethylamine in 2-propanol:acetonitrile (70:30); flow rate: 20 mL/min) to afford first eluting fraction (I-79-a) and second eluting fraction (I-79-b). (*Absolute stereochemistry not determined.)

I-79-a. MS (ES): m/z: 501.2 [M+H]$^+$, $^1$H NMR (DMSO-d6, 400 MHz): δ 10.50 (s, 1H), 8.27 (s, 1H), 8.24 (s, 1H), 8.15-8.14 (d, J=5.2 Hz, 1H), 7.64 (s, 1H), 7.52-7.50 (d, J=8.4 Hz, 1H), 7.33 (bs, 1H), 7.20 (s, 1H), 6.89-6.87 (d, J=8.4 Hz, 1H), 6.62-6.61 (d, J=3.6 Hz, 1H), 5.62-5.60 (d, J=6.4 Hz, 1H), 4.92-4.87 (m, 1H), 4.44-4.40 (m, 1H), 3.69 (s, 3H), 2.13-2.08 (m, 2H), 2.02 (s, 3H), 1.87 (bs, 1H), 1.23 (bs, 1H), 1.14-1.07 (m, 1H), 0.88-0.86 (m, 2H), 0.64 (bs, 2H).

I-79-b. MS (ES): m/z: 501.2 [M+H]$^+$, $^1$H NMR (DMSO-d6, 400 MHz): δ 10.50 (s, 1H), 8.28 (s, 1H), 8.28 (s, 1H), 8.16-8.15 (d, J=5.6 Hz, 1H), 7.65 (s, 1H), 7.53-7.51 (d, J=8.4

Hz, 1H), 7.34 (bs, 1H), 7.21 (s, 1H), 6.90-6.88 (d, J=8.0 Hz, 1H), 6.63 (bs, 1H), 5.63-5.61 (d, J=6.8 Hz, 1H), 4.92-4.90 (m, 1H), 4.45-4.43 (m, 1H), 3.70 (s, 3H), 2.12-2.09 (m, 2H), 2.03 (s, 3H), 1.88 (bs, 1H), 1.24 (bs, 1H), 1.14-1.10 (m, 1H), 0.89-0.87 (m, 2H), 0.65 (bs, 2H).

Example 80: N-(4-((2-((1-isopropyl-2-oxo-5-(1H-pyrazol-1-yl)-1,2-dihydropyridin-3-yl)amino)-1-methyl-1H-benzo[d]imidazol-6-yl)oxy)pyridin-2-yl)acetamide

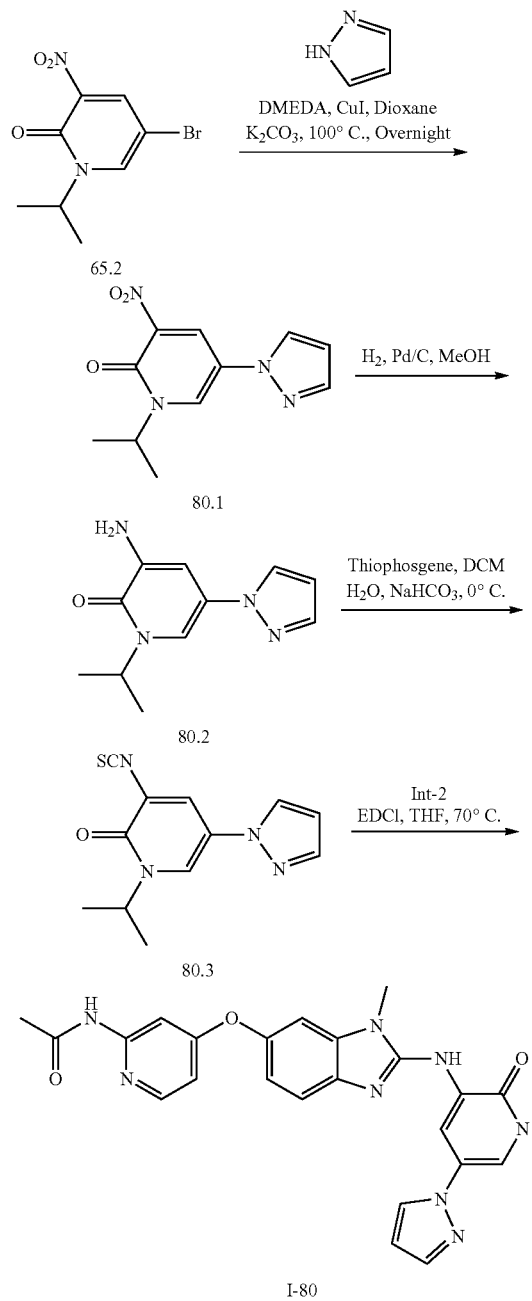

Synthesis of compound 80.1. A mixture of 65.2 (0.3 g, 1.15 mmol, 1.0 equiv), 1,4-dioxane (12 mL), pyrazole (0.093 g, 1.38 mmol, 1.2 equiv) and potassium carbonate (0.396 g, 2.87 mmol, 2.5 equiv) was degassed by bubbling argon for 10 min and added 1,2-dimethylethylenediamine (0.015 g, 0.172 mmol, 0.15 equiv) and copper iodide (0.065 g, 0.345 mmol, 0.3 equiv). The reaction mixture was degassed for 5 min and was stirred at 100° C. for 12 h. It was cooled to room temperature, poured over water, extracted with ethyl acetate. The combined organic layers were washed with brine, dried over anhydrous sodium sulfate, filtered and concentrated under reduced pressure. The residue was purified by flash column chromatography on silica gel (CombiFlash®, 25% ethyl acetate in hexane as eluant) to afford 80.1. MS (ES): m/z 249.2 [M+H]$^+$.

Synthesis of compound 80.2. A mixture of compound 80.1 (0.150 g, 0.604 mmol, 1.0 equiv), methanol (5 mL) and 10% palladium on carbon (0.065 g) was stirred at rt under 1 atm hydrogen for 2 h. It was filtered through a pad of Celite® and rinsed with methanol. The filtrate was concentrated under reduced pressure to obtain 80.2. MS (ES): m/z 219.3 [M+H]$^+$.

Synthesis of compound 80.3. Compound 80.3 was prepared from 80.2 following the procedure described in the synthesis of 11.8. The crude product was used in the next step without further purification. MS (ES): m/z 261.3 [M+H]$^+$.

Synthesis of compound I-80. Compound I-80 was prepared from 80.3 following the procedure described in the synthesis of I-1. The product was purified by preparative HPLC. MS (ES): m/z: 499.41 [M+H]$^+$, $^1$H NMR (DMSO-d6, 400 MHz): δ 10.50 (s, 1H), 8.93-8.92 (d, J=2.8 Hz, 1H), 8.49 (s, 1H), 8.34-8.33 (d, J=2.4 Hz, 1H), 8.16-8.14 (d, J=5.6 Hz, 1H), 7.80-7.79 (d, J=2.4 Hz, 1H), 7.77-7.76 (d, J=1.6 Hz, 1H), 7.66 (s, 1H), 7.55-7.53 (d, J=8.8 Hz, 1H), 7.38-7.37 (d, J=2.4 Hz, 1H), 6.92-6.89 (m, 1H), 6.63-6.61 (m, 1H), 6.55-6.54 (m, 1H), 5.27-5.23 (m, 1H), 3.74 (s, 3H), 2.02 (s, 3H), 1.45-1.44 (d, 6H).

Example 81: N-(4-((2-((1-isopropyl-2-oxo-5-(1H-pyrazol-1-yl)-1,2-dihydropyridin-3-yl)amino)-3-methyl-3H-imidazo[4,5-b]pyridin-5-yl)oxy)pyridin-2-yl)acetamide

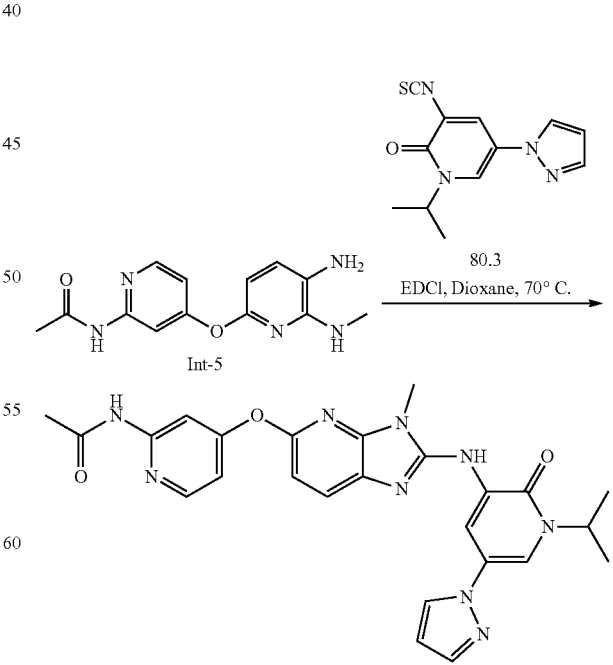

Synthesis of compound I-81. Compound I-81 was prepared from 80.3 and Int-5 following the procedure described in the synthesis of I-1. The product was purified by flash column chromatography on silica gel (CombiFlash®, 2.4% methanol in dichloromethane as eluant). MS (ES): m/z: 497.99 [M−H]+, $^1$H NMR (DMSO-d6, 400 MHz): δ 10.58 (s, 1H), 8.96 (s, 1H), 8.60 (s, 1H), 8.35 (s, 1H), 8.22-8.20 (d, J=5.6 Hz, 1H), 8.02-7.99 (d, J=8.4 Hz, 1H), 7.83 (s, 1H), 7.79-7.77 (d, J=6.0 Hz, 2H), 6.95-6.93 (d, J=8.0 Hz, 1H), 6.77-6.76 (d, J=4.0 Hz, 1H), 6.55 (s, 1H), 5.26-5.23 (m, 1H), 3.69 (s, 3H), 2.05 (s, 3H), 1.45-1.43 (d, 6H).

Example 82: N-(4-((2-((5-(azetidin-1-yl)-1-methyl-2-oxo-1,2-dihydropyridin-3-yl)amino)-1-methyl-1H-benzo[d]imidazol-6-yl)oxy)pyridin-2-yl)acetamide

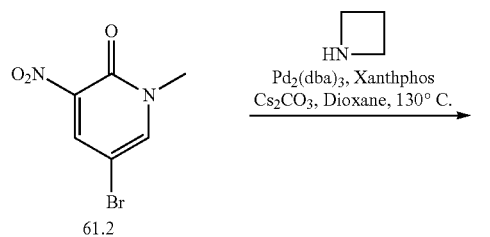

61.2

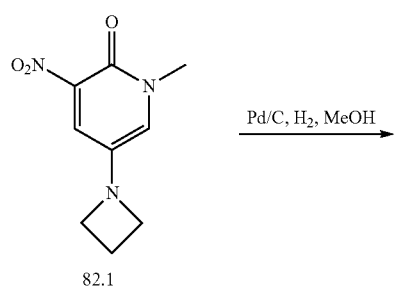

82.1

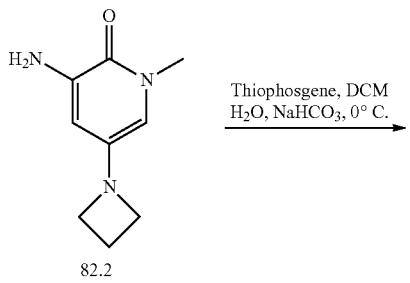

82.2

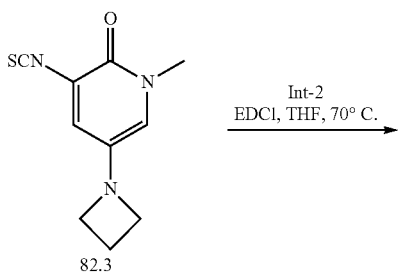

82.3

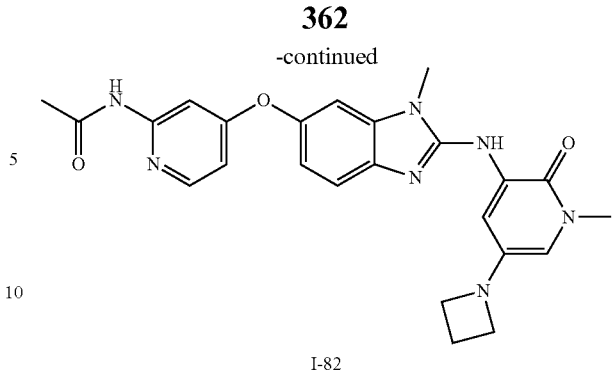

I-82

Synthesis of compound 82.1. To a solution of 61.2 (0.5 g, 2.15 mmol, 1.0 equiv) in toluene (50 mL) and water (5 mL) was added azetidine (0.367 g, 6.45.0 mmol, 3.0 equiv), cesium carbonate (1.7 g, 5.36 mmol, 2.5 equiv). The reaction mixture was degassed by bubbling argon through for 10 min. Under argon atmosphere was added 4,5-bis(diphenylphosphino)-9,9-dimethylxanthene (0.124 g, 0.215 mmol, 0.1 equiv) and tris(dibenzylideneacetone)dipalladium (0.098 g, 0.1075 mmol, 0.05 equiv). The reaction mixture was degassed for 5 min and was stirred at 130° C. for 1 h. It was cooled to room temperature, filtered through a pad of Celite®. The filtrate was poured over water, extracted with ethyl acetate. The combined organic layers were washed with brine, dried over anhydrous sodium sulfate, filtered and concentrated under reduced pressure. The residue was purified by preparative HPLC to obtain 82.1. MS (ES): m/z 210.21 [M+H]+.

Synthesis of compound 82.2. A mixture of compound 82.1 (0.040 g, 0.191 mmol, 1.0 equiv), methanol (3 mL) and 10% palladium on carbon (0.020 g) was stirred at rt under 1 atm of hydrogen for 1 h. It was filtered through a pad of Celite® and rinsed with methanol. The filtrate was concentrated under reduced pressure to obtain 82.2. MS (ES): m/z 180.2 [M+H]+.

Synthesis of compound 82.3. Compound 82.3 was prepared from 82.2 following the procedure described in the synthesis of 11.8. The crude product was used in the next step without further purification. MS (ES): m/z 222.3 [M+H]+.

Synthesis of compound I-82. Compound I-82 was prepared from 82.3 and Int-2 following the procedure described in the synthesis of IA. The product was purified by preparative HPLC. MS (ES): m/z: 460.77 [M−H]+, $^1$H NMR (DMSO-d6, 400 MHz): δ 10.48 (s, 1H), 8.12-8.11 (d, J=5.6 Hz, 1H), 7.65 (s, 1H), 7.50 (s, 1H), 7.43-7.41 (d, J=7.6 Hz, 1H), 7.18-7.16 (d, J=8.4 Hz, 1H), 7.08 (s, 1H), 6.74-6.72 (d, J=7.2 Hz, 1H), 6.57-6.56 (d, J=3.6 Hz, 1H), 5.61-5.59 (d, J=7.6 Hz, 1H), 4.03-3.99 (m, 4H), 3.58 (s, 3H), 3.31 (bs, 3H), 2.18-2.14 (m, 2H), 2.03 (s, 3H).

Example 83: N-(4-((2-((5-(azetidin-1-yl)-1-isopropyl-2-oxo-1,2-dihydropyridin-3-yl)amino)-1-methyl-1H-benzo[d]imidazol-6-yl)oxy)pyridin-2-yl)acetamide

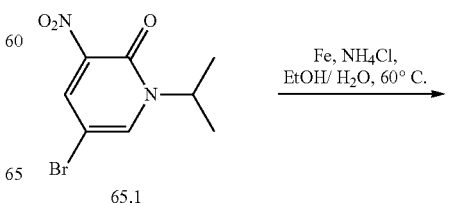

65.1

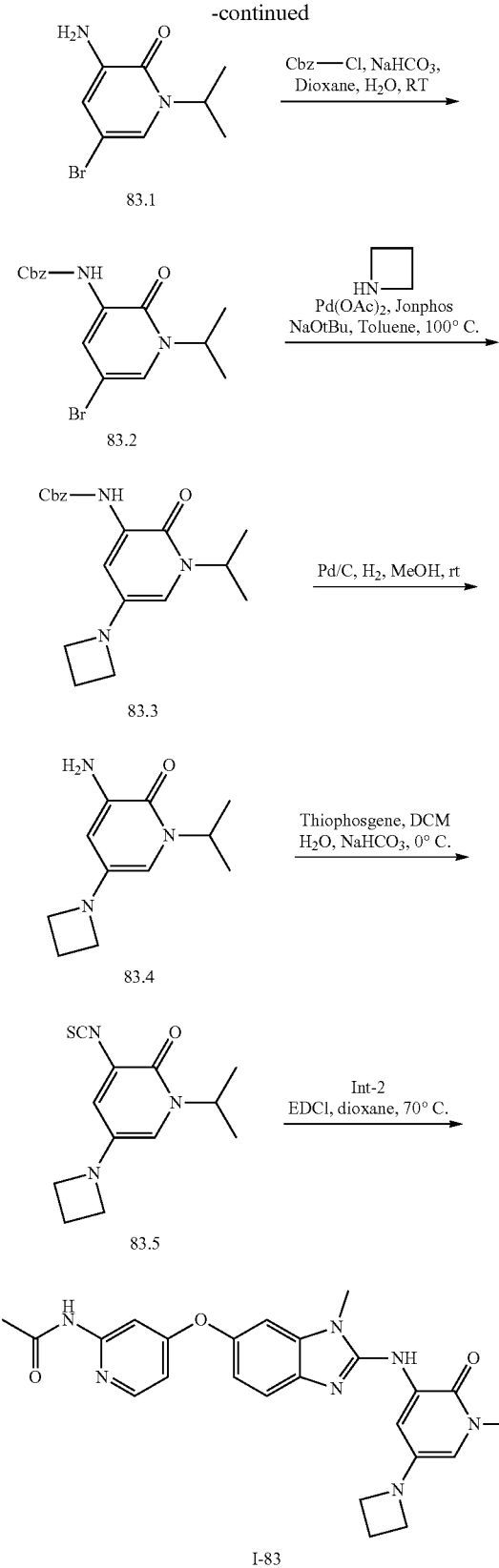

followed by ammonium chloride (2.06 g, 38.3 mmol, 10 equiv). The reaction mixture was stirred at 60° C. for 3 h. It was filtered through a pad of Celite® and rinsed with ethanol. The filtrate was concentrated under reduced pressure and the residue was purified by flash column chromatography on silica gel (CombiFlash®, 30% ethyl acetate in hexane as eluant) to afford 83.1. MS (ES): m/z 232.1 [M+H]$^+$.

Synthesis of compound 83.2. To a solution of 83.1 (0.725 g, 3.14 mmol, 1.0 equiv) in 1,4-dioxane (10 mL) and water (1 mL) was added sodium bicarbonate (1.055 g, 12.56 mmol, 4.0 equiv) followed by benzyl chloroformate (2.66 g, 15.7 mmol, 5.0 equiv). The reaction mixture was stirred at room temperature for 16 h. It was poured over water, extracted with ethyl acetate. The combined organic layers were washed with brine, dried over anhydrous sodium sulfate, filtered and concentrated under reduced pressure. The residue was purified by flash column chromatography on silica gel (CombiFlash®, 20% ethyl acetate in hexane as eluant) to afford 83.2. MS (ES): m/z 366.2 [M+H]$^+$.

Synthesis of compound 83.3. To a solution of 83.2 (0.55 g, 1.51 mmol, 1.0 equiv) in toluene (10 mL) was added azetidine (0.429 g, 7.53 mmol, 5.0 equiv) and sodium tert-butoxide (0.289 g, 3.02 mmol, 2.0 equiv). The reaction mixture was degassed by bubbling argon through for 10 min and was added (2-biphenyl)di-tert-butylphosphine (0.044 g, 0.151 mmol, 0.1 equiv) and palladium acetate (0.016 g, 0.075 mmol, 0.05 equiv). It was degassed for 5 min. The reaction mixture was stirred at 100° C. for 15 min. It was cooled to room temperature, filtered through a pad of Celite®. The filtrate was poured over water, extracted with ethyl acetate. The combined organic layers were washed with brine, dried over anhydrous sodium sulfate, filtered and concentrated under reduced pressure. The residue was purified by flash column chromatography on silica gel (CombiFlash®, 30% ethyl acetate in hexane as eluant) to afford 83.3. MS (ES): m/z 342.4 [M+H]$^+$.

Synthesis of compound 83.4. A mixture of compound 83.3 (0.090 g, 0.263 mmol, 1.0 equiv), methanol (2 mL) and 10% palladium on carbon (0.045 g) was stirred at rt under 1 atm hydrogen for 15 min. It was filtered through a pad of Celite® and rinsed with methanol. The filtrate was concentrated under reduced pressure to obtain 83.4. MS (ES): m/z 208.3 [M+H]$^+$.

Synthesis of compound 83.5. Compound 83.5 was prepared from 83.5 following the procedure described in the synthesis of 11.8. The crude product was used in the next step without further purification. MS (ES): m/z 250.3 [M+H]$^+$.

Synthesis of compound I-83. Compound I-83 was prepared from 83.5 and Int-2 following the procedure described in the synthesis of I-1. The product was purified by preparative HPLC. MS (ES): m/z: 488.46 [M+H]$^+$, $^1$H NMR (DMSO-d6, 400 MHz): δ 10.49 (s, 1H), 8.13-8.12 (d, J=5.2 Hz, 1H), 7.66 (s, 1H), 7.48 (bs, 2H), 7.20 (s, 1H), 7.10 (s, 1H), 6.75 (s, 1H), 6.58 (s, 1H), 5.68 (bs, 1H), 4.98-4.94 (m, 1H), 4.03 (bs, 4H), 3.60 (s, 3H), 2.17 (s, 2H), 2.04 (s, 3H), 1.25-1.24 (d, 6H).

Synthesis of compound 83.1 To a solution of 65.1 (1.0 g, 3.83 mmol, 1.0 equiv) in ethanol (10 mL) and water (2 mL), iron powder (2.14 g, 38.3 mmol, 10 equiv) was added

Example 84: N-(4-((2-((6-cyclopropyl-2-methyl-3-oxo-2,3-dihydropyridazin-4-yl)amino)-1-methyl-1H-benzo[d]imidazol-6-yl)oxy)pyridin-2-yl)acetamide

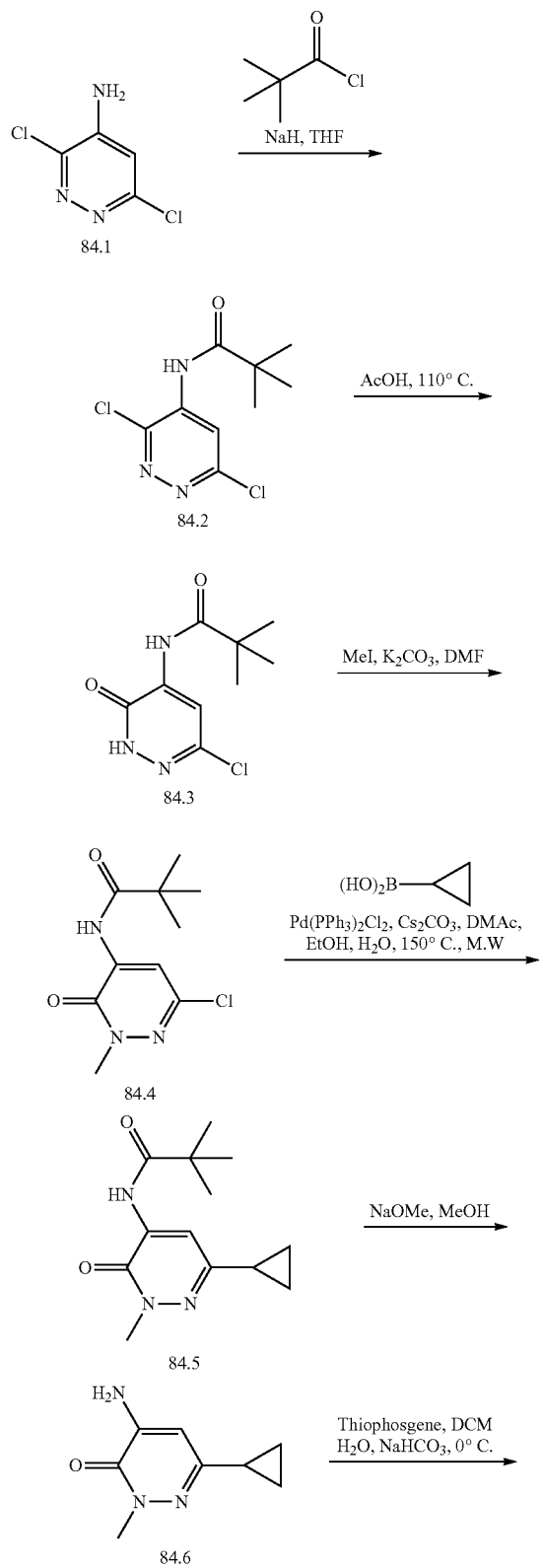

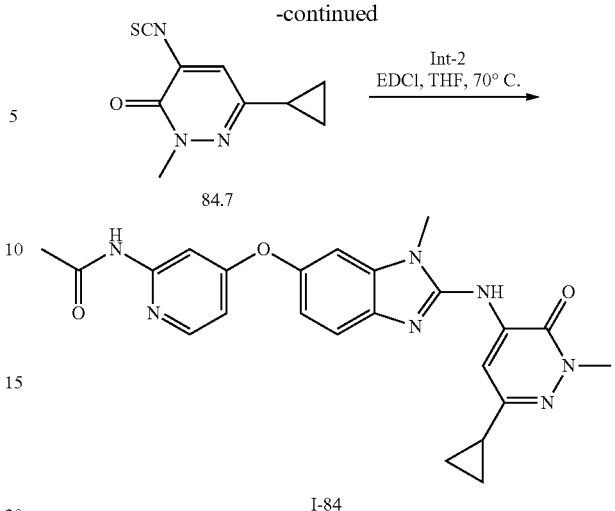

Synthesis of compound 84.2. To a solution of 84.1 (0.9 g, 5.49 mmol, 1.0 equiv) in THF (20 mL) was added sodium hydride (0.579 g, 12.07 mmol, 2.2 q) at 0° C. and stirred for 10 min. Pivaloyl chloride (0.7 mL, 5.76 mmol, 1.05 equiv) was added dropwise. The reaction mixture was stirred at room temperature for 15 min. It was poured over ice-water, stirred and extracted with ethyl acetate. The combined organic layers were washed with brine, dried over anhydrous sodium sulfate, filtered and concentrated under reduced pressure to obtain 84.2. MS (ES): m/z 230.6 [M+H]$^+$.

Synthesis of compound 84.3. A solution of 84.2 (1.1 g, 4.43 mmol, 1.0 equiv) in acetic acid (10 mL) was stirred at 110° C. for 3 h. It was poured over ice, stirred and neutralized with saturated sodium bicarbonate solution. Precipitated solid was filtered out and dried well to obtain 84.3. MS (ES): m/z 271.3 [M+H]$^+$.

Synthesis of compound 84.4. To a solution of 84.3 (0.7 g, 3.05 mmol, 1.0 equiv) in DMF (7 mL) was added potassium carbonate (0.841 g, 6.1 mmol, 2.0 equiv) at room temperature and stirred for 15 min followed by addition of methyl iodide (0.519 g, 3.66 mmol, 1.2 equiv). The reaction mixture was stirred at room temperature for 16 h. It was poured over ice-water and extracted with ethyl acetate. The combined organic layers were washed with brine, dried over anhydrous sodium sulfate, filtered and concentrated under reduced pressure. The residue was purified by trituration with n-pentane to obtain 84.4. MS (ES): m/z 244.6 [M+H]$^+$.

Synthesis of compound 84.5. To a solution of 84.4 (0.350 g, 1.44 mmol, 1.0 equiv) in dimethylacetamide (2 mL), water (1 mL) and ethanol (0.7 mL) was added cyclopropylboronic acid (0.27 g, 3.16 mmol, 2.2 equiv), cesium carbonate (0.938 g, 2.88 mmol, 2.0 equiv) and dichlorobis (triphenylphosphine) palladium (II) (0.090 g, 0.129 mmol, 0.09 equiv). The reaction mixture was heated in MW at 150° C. for 30 min. It was cooled to room temperature, filtered through Celite®. Filtrate was poured over water, extracted with dichloromethane. The combined organic layers were washed with brine, dried over anhydrous sodium sulfate, filtered and concentrated under reduced pressure. The residue was purified by flash column chromatography on silica gel (CombiFlash®, 10% ethyl acetate in hexane as eluant) to afford 84.5. MS (ES): m/z 250.3 [M+H]$^+$.

Synthesis of compound 84.6. To a solution of 84.5 (0.155 g, 0.621 mmol, 1.0 equiv) in methanol (2.5 mL) was added sodium methoxide solution (25% in methanol, 0.4 mL, 1.86 mmol, 3.0 equiv). The reaction mixture was stirred at 65° C. for 2 h. Most solvent was removed under reduced pressure and the residue was poured over water, extracted with ethyl acetate. The combined organic layers were washed with brine, dried over anhydrous sodium sulfate, filtered and concentrated under reduced pressure to obtain 84.6. MS (ES): m/z 166.2 [M+H]⁺.

Synthesis of compound 84.7. Compound 84.7 was prepared from 84.6 following the procedure described in the synthesis of 11.8. The crude product was used in the next step without further purification. MS (ES): m/z 208.3 [M+H]⁺.

Synthesis of compound I-84. Compound I-84 was prepared from 84.7 and Int-2 following the procedure described in the synthesis of I-1. The product was purified by flash column chromatography on silica gel (CombiFlash®, 2.2% methanol in dichloromethane as eluant). MS (ES): m/z: 446.35 [M+H]⁺, ¹H NMR (DMSO-d6, 400 MHz): δ 10.51 (s, 1H), 8.96 (s, 1H), 8.16-8.14 (d, J=5.2 Hz, 1H), 7.97 (s, 1H), 7.65 (s, 1H), 7.62-7.60 (d, J=8.4 Hz, 1H), 7.41 (s, 1H), 6.96-6.94 (d, J=8.4 Hz, 1H), 6.64-6.63 (d, J=3.2 Hz, 1H), 3.74 (s, 3H), 3.69 (s, 3H), 2.02 (s, 3H), 1.19-1.16 (m, 1H), 0.94 (bs, 2H), 0.81 (bs, 2H).

Example 85: N-(4-((2-((6-cyclopropyl-2-isopropyl-3-oxo-2,3-dihydropyridazin-4-yl)amino)-1-methyl-1H-benzo[d]imidazol-6-yl)oxy)pyridin-2-yl)acetamide

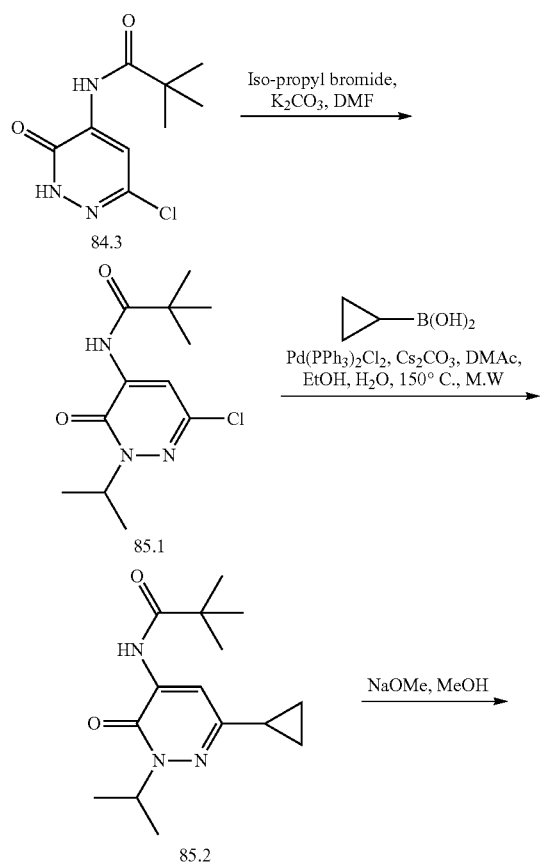

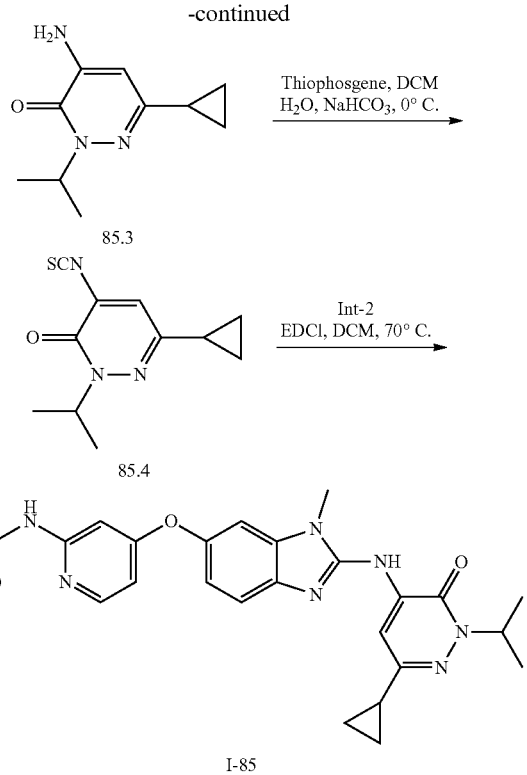

Synthesis of compound 85.1. To a solution of 84.3 (1.0 g, 4.35 mmol, 1.0 equiv) in DMF (10 mL) was added potassium carbonate (1.2 g, 8.7 mmol, 2.0 equiv) at room temperature and stirred for 15 min followed by addition of isopropyl bromide (0.642 g, 5.22 mmol, 1.2 equiv). The reaction mixture was stirred at room temperature for 16 h. It was poured over ice-water and extracted with ethyl acetate. The combined organic layers were washed with brine, dried over anhydrous sodium sulfate, filtered and concentrated under reduced pressure. The residue was purified by trituration with n-pentane to obtain 85.1. MS (ES): m/z 272.7 [M+H]⁺.

Synthesis of compound 85.2. Compound 85.2 was prepared from 85.1 following the procedure described in the synthesis of 84.5. The product was purified by flash column chromatography on silica gel (CombiFlash®, 12% ethyl acetate in hexane as eluant). MS (ES): m/z 278.4 [M+H]⁺.

Synthesis of compound 85.3. Compound 85.3 was prepared from 85.2 following the procedure described in the synthesis of 84.6. MS (ES): m/z 194.2 [M+H]⁺.

Synthesis of compound 85.4. Compound 85.4 was prepared from 85.3 following the procedure described in the synthesis of 11.8. The crude product was used in the next step without further purification. MS (ES): m/z 236.3 [M+H]⁺.

Synthesis of compound I-85. Compound I-85 was prepared from 85.4 and Int-2 following the procedure described in the synthesis of I-1. The product was purified by flash column chromatography on silica gel (CombiFlash®, 2.4% methanol in dichloromethane as eluant). MS (ES): m/z: 475.06 [M+H]⁺, ¹H NMR (DMSO-d6, 400 MHz): δ 10.52 (s, 1H), 8.93 (s, 1H), 8.17-8.16 (d, J=6.0 Hz, 1H), 7.99 (s, 1H), 7.66 (s, 1H), 7.62-7.60 (d, J=8.4 Hz, 1H), 7.42 (s, 1H), 6.97-6.95 (m, 1H), 6.65-6.63 (m, 1H), 5.24-5.18 (m, 1H), 3.75 (s, 3H), 2.03 (s, 3H), 2.00-1.98 (m, 1H), 1.33-1.31 (d, 6H), 0.97-0.95 (m, 2H), 0.85-0.83 (m, 2H).

Example 86: N-(4-((2-((6-cyclopropyl-2-methyl-3-oxo-2,3-dihydropyridazin-4-yl)amino)-3-methyl-3H-imidazo[4,5-b]pyridin-5-yl)oxy)pyridin-2-yl)acetamide

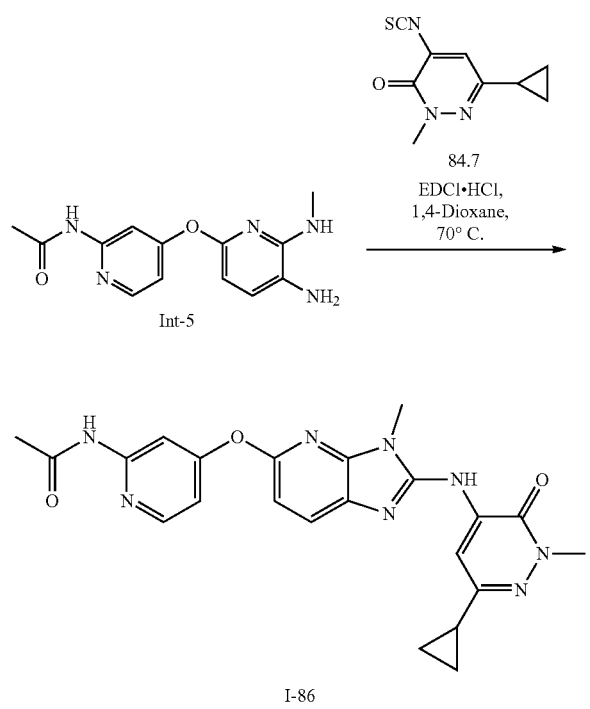

Synthesis of compound I-86. Compound I-86 was prepared from 84.7 and Int-5 following the procedure described in the synthesis of I-1. The product was purified by trituration with methanol:diethyl ether (1:1). MS (ES): m/z: 447.81 [M+H]$^+$, $^1$H NMR (DMSO-d6, 400 MHz): δ 10.58 (s, 1H), 9.05 (s, 1H), 8.23-8.21 (d, J=5.6 Hz, 1H), 8.09-8.07 (d, J=8.4 Hz, 1H), 8.02 (s, 1H), 7.80 (s, 1H), 7.00-6.98 (d, J=8.4 Hz, 1H), 6.79-6.77 (m, 1H) 3.69 (s, 3H), 2.50 (s, 3H), 2.05 (s, 3H), 2.00-1.95 (m, 1H), 0.97-0.92 (m, 2H), 0.83-0.82 (m, 2H).

Example 87: (R)—N-(4-((2-((6-cyclopropyl-2-((5,5-dimethyltetrahydrofuran-3-yl)methyl)-3-oxo-2,3-dihydropyridazin-4-yl)amino)-1-methyl-1H-benzo[d]imidazol-6-yl)oxy)pyridin-2-yl)acetamide and (S)—N-(4-((2-((6-cyclopropyl-2-((5,5-dimethyltetrahydrofuran-3-yl)methyl)-3-oxo-2,3-dihydropyridazin-4-yl)amino)-1-methyl-1H-benzo[d]imidazol-6-yl)oxy)pyridin-2-yl)acetamide

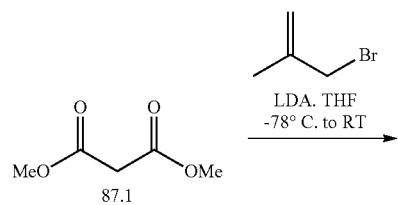

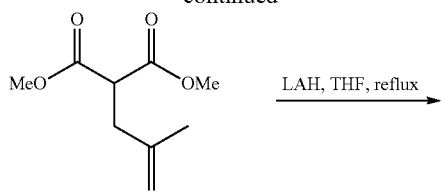

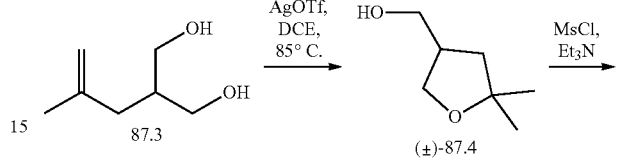

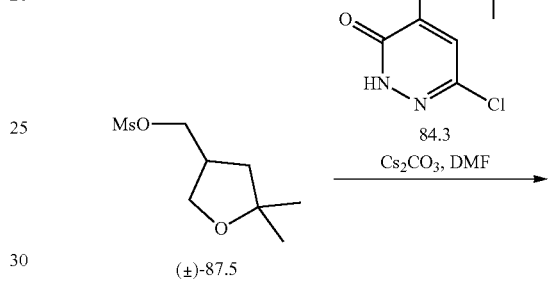

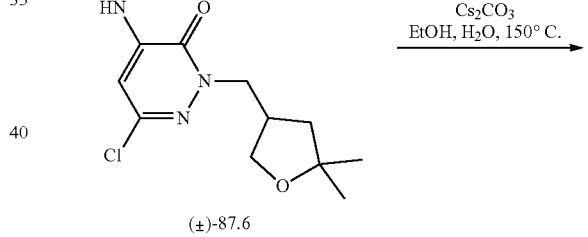

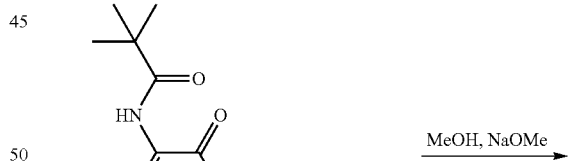

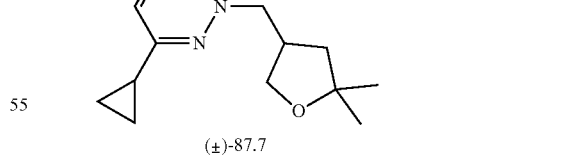

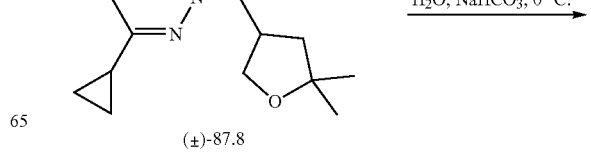

-continued

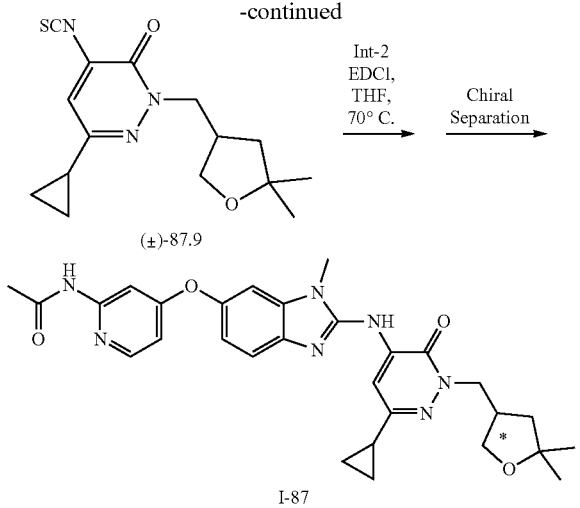

Synthesis of compound 87.2. To a solution of 87.1 (4.0 g, 30.28 mmol, 1.0 equiv) in THF (40 mL) was added lithium diisopropylamide (2 M in THF, 18.15 mL, 36.3 mmol, 1.2 equiv) at −78° C. and stirred for 15 min followed by addition of 3-bromo-2-methylprop-1-ene (4.8 g, 36.3 mmol, 1.2 equiv). The reaction mixture was stirred at room temperature for 12 h. It was poured over 3 N hydrochloric acid solution, stirred and extracted with diethyl ether. The combined organic layers were washed with brine, dried over anhydrous sodium sulfate, filtered and concentrated under reduced pressure to obtain crude which was purified by flash column chromatography on silica gel (CombiFlash®, 2.5% ethyl acetate in hexane as eluant) to afford 87.2. MS (ES): m/z 187.2 [M+H]$^+$.

Synthesis of compound 87.3. To a solution of 87.2 (2 g, 10.74 mmol, 1.0 equiv) in THF (40 mL) was added a solution of lithium aluminum hydride (1 M in THF, 21.5 mL, 21.48 mmol, 2.0 equiv) at 0° C. The reaction mixture was heated to reflux for 2 h. It was cooled to 0° C. and was carefully added ice-water (2 mL) and 15% sodium hydroxide (2 mL). The suspension was filtered through a pad of Celite® and rinsed with diethyl ether. The filtrate was separated by a separatory funnel. The organic layer was dried over anhydrous sodium sulfate, filtered and concentrated under reduced pressure. The residue was purified by flash column chromatography on silica gel (CombiFlash®, 50% ethyl acetate in hexane as eluant) to 87.3. MS (ES): m/z 131.2 [M+H]$^+$.

Synthesis of compound (±)-87.4. To a solution of 87.3 (1.2 g, 9.22 mmol, 1.0 equiv) in 1,2-dichloroethane (12 mL) was added silver trifluoromethanesulfonate (0.118 g, 0.461 mmol, 0.05 equiv). The reaction mixture was stirred at 85° C. for 12 h in dark. It was filtered through a pad of Celite® and rinsed with ethyl acetate. The filtrate was separated by a separatory funnel. The organic layer was dried over anhydrous sodium sulfate, filtered and concentrated under reduced pressure. The residue was purified by flash column chromatography on silica gel (CombiFlash®, 45% ethyl acetate in hexane as eluant) to (±)-87.4. MS (ES): m/z 131.2 [M+H]$^+$.

Synthesis of compound (±)-87.5. To a solution of (±)-87.4 (0.810 g, 6.22 mmol, 1.0 equiv) and triethylamine (2.16 mL, 15.55 mmol, 2.5 equiv) in dichloromethane (10 mL) was added methanesulfonyl chloride (0.72 mL, 9.33 mmol, 1.5 equiv) at 0° C. and stirred at room temperature for 12 h. It was poured over ice, stirred and extracted with dichloromethane. The combined organic layers were washed with brine, dried over anhydrous sodium sulfate, filtered and concentrated under reduced pressure to obtain (±)-87.5. MS (ES): m/z 209.3 [M+H]$^+$.

Synthesis of compound (±)-87.6. To a solution of 84.3 (0.750 g, 3.27 mmol, 1.0 equiv) in DMF (15 mL) was added cesium carbonate (2.66 g, 8.17 mmol, 2.5 equiv) at room temperature and stirred for 15 min followed by addition of (±)-87.5 (0.816 g, 3.92 mmol, 1.2 equiv). The reaction mixture was stirred at 70° C. for 3 h. It was poured over ice-water and extracted with ethyl acetate. The combined organic layers were washed with brine, dried over anhydrous sodium sulfate, filtered and concentrated under reduced pressure. The residue was purified by trituration with n-pentane to obtain (±)-87.6. MS (ES): m/z 342.8 [M+H]$^+$.

Synthesis of compound (±)-87.7. Compound (±)-87.7 was prepared from (±)-87.6 following the procedure described in the synthesis of 84.5. The product was purified by flash column chromatography on silica gel (CombiFlash®, 12% ethyl acetate in hexane as eluant). MS (ES): m/z 348.5 [M+H]$^+$.

Synthesis of compound (±)-87.8. Compound (±)-87.8 was prepared from (±)-87.7 following the procedure described in the synthesis of 84.6. MS (ES): m/z 264.3 [M+H]$^+$.

Synthesis of compound (±)-87.9. Compound (±)-87.9 was prepared from (±)-87.8 following the procedure described in the synthesis of 11.8. The crude product was used in the next step without further purification. MS (ES): m/z 306.4 [M+H]$^+$.

Synthesis of compound (±)-I-87. Compound (±)-I-87 was prepared from (±)-87.9 following the procedure described in the synthesis of I-1. The residue was purified by flash column chromatography on silica gel (CombiFlash®, 3.0% methanol in dichloromethane as eluant). MS (ES): m/z: 544.6 [M+H]$^+$.

I-87-a and I-87-b. Compound (±)-I-87 was separated on HPLC (column: CHIRALCEL OX-H (250 mm×21.0 mm, 5 μm); mobile phases: (A) 0.1% diethylamine in hexane (B) 0.1% diethylamine in 2-propanol:methanol (50:50); flow rate: 19 mL/min) to afford first eluting fraction (I-87-a) and second eluting fraction (I-87-b). (*Absolute stereochemistry not determined.)

I-87-a. MS (ES): m/z: 544.4 [M+H]$^+$, $^1$H NMR (DMSO-d6, 400 MHz): δ 10.52 (s, 1H), 8.97 (s, 1H), 8.17-8.16 (d, J=6.0 Hz, 1H), 8.01 (s, 1H), 7.66 (s, 1H), 7.62-7.60 (d, J=8.4 Hz, 1H), 7.42 (bs, 1H), 6.98-6.95 (m, 1H), 6.65-6.63 (m, 1H), 4.20-4.15 (m, 1H), 4.10-4.05 (m, 1H), 3.82-3.78 (m, 1H), 3.75 (s, 3H), 2.86-2.82 (m, 1H), 2.02 (s, 3H), 2.00-1.96 (m, 2H), 1.87-1.81 (m, 1H), 1.56-1.51 (m, 1H), 1.26 (s, 6H), 0.97-0.94 (m, 2H), 0.86-0.82 (m, 2H).

I-87-b. MS (ES): m/z: 544.5 [M+H]$^+$, $^1$H NMR (DMSO-d6, 400 MHz): δ 10.51 (s, 1H), 8.97 (s, 1H), 8.17-8.16 (d, J=6.0 Hz, 1H), 8.00 (s, 1H), 7.65 (s, 1H), 7.62-7.59 (d, J=8.4 Hz, 1H), 7.41 (bs, 1H), 6.97-6.94 (m, 1H), 6.64-6.62 (m, 1H), 4.18-4.15 (m, 1H), 4.10-4.05 (m, 1H), 3.81-3.77 (m, 1H), 3.75 (s, 3H), 2.85-2.82 (m, 1H), 2.02 (s, 3H), 2.00-1.96 (m, 2H), 1.87-1.81 (m, 1H), 1.56-1.51 (m, 1H), 1.26 (s, 6H), 0.97-0.94 (m, 2H), 0.86-0.82 (m, 2H).

Example 88: N-(4-((2-((5-cyclopropyl-6-oxo-1-(tetrahydro-2H-pyran-4-yl)-1,6-dihydropyridazin-3-yl)amino)-1-methyl-1H-benzo[d]imidazol-6-yl)oxy)pyridin-2-yl)acetamide

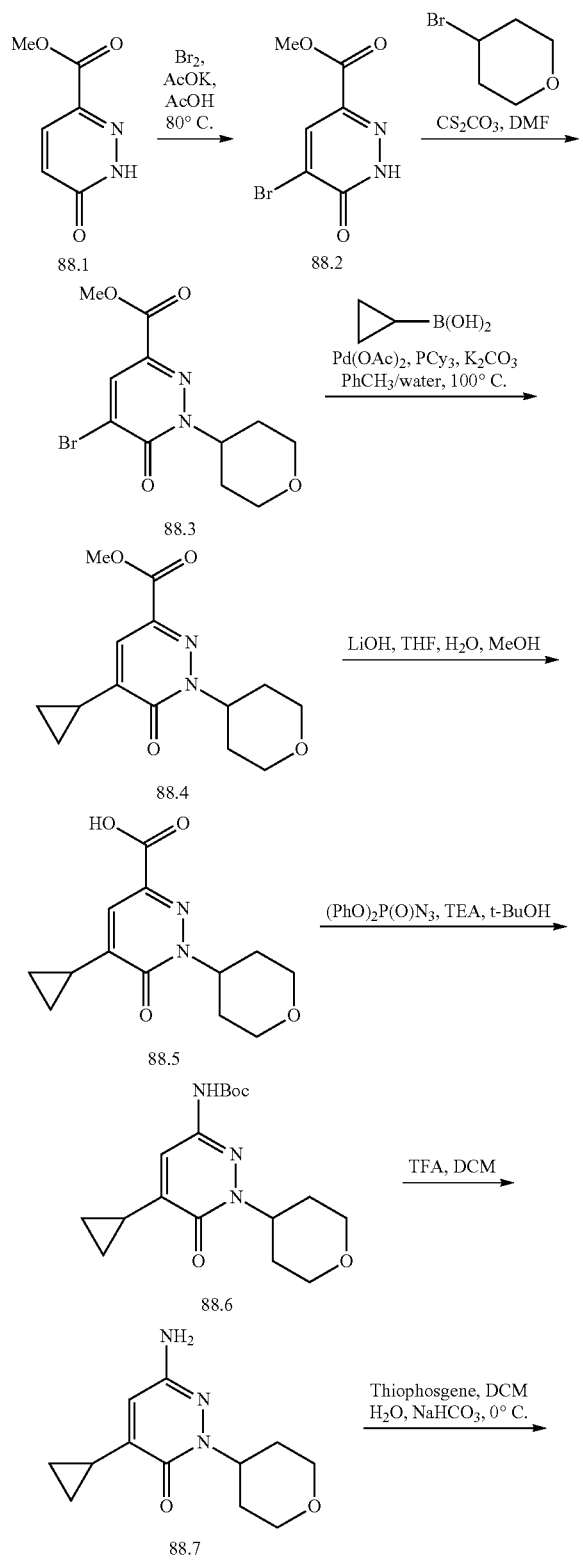

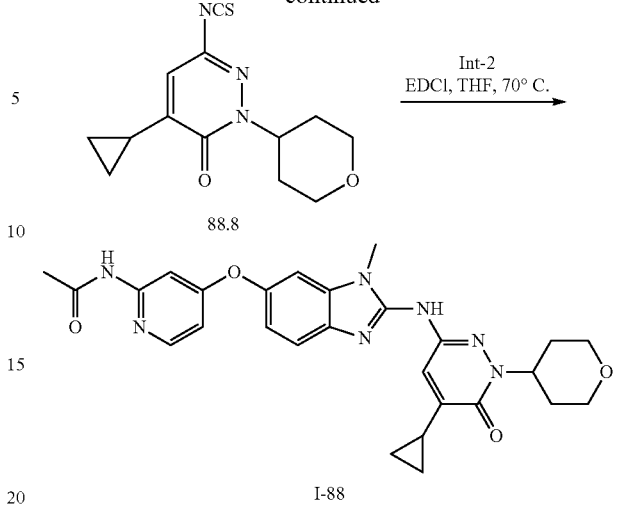

Synthesis of compound 88.2. To a solution of 88.1 (2.0 g, 12.98 mmol, 1.0 equiv) in acetic acid (40 mL) was added potassium acetate (4.57 g, 46.72 mmol, 3.6 equiv) followed by addition of bromine (4.56 g, 28.55 mmol, 2.2 equiv). The reaction mixture was stirred at 80° C. for 6-7 h. It was poured over water and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.1% methanol in dichloromethane) to afford 88.2. MS (ES): m/z 234.1 [M+H]$^+$.

Synthesis of compound 88.3. To a solution of 88.2 (1.2 g, 5.15 mmol, 1.0 equiv) in DMF (10 mL) was added cesium carbonate (3.34 g, 10.3 mmol, 2.0 equiv) and stirred for 15 min. To the mixture was added 4-bromotetrahydro-2H-pyran (1.7 g, 10.3 mmol, 2.0 equiv). The reaction mixture was stirred at 80° C. for 16 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 30% ethyl acetate in hexane as eluant) to afford 88.3. MS (ES): m/z 318.2 [M+H]$^+$.

Synthesis of compound 88.4. To a solution of 88.3 (0.700 g, 2.21 mmol, 1.0 equiv) in toluene (10 mL) and water (1 mL) was added cyclopropylboronic acid (0.568 g, 6.62 mmol, 3.0 equiv), potassium carbonate (0.609 g, 4.42 mmol, 2.0 equiv) and tricyclohexylphosphine (0.123 g, 0.442 mmol, 0.2 equiv). The reaction mixture was degassed for 10 min under argon atmosphere then palladium(II) acetate (0.039 g, 0.176 mmol, 0.08 equiv) was added, again degassed for 5 min. The reaction mixture was stirred at 100° C. for 1-2 h. It was cooled to room temperature, filtered through a pad of Celite®. The filtrate was poured over water, extracted with ethyl acetate. The combined organic layers were washed with brine, dried over anhydrous sodium sulfate, filtered and concentrated under reduced pressure. The residue was purified by flash column chromatography on silica gel (CombiFlash®, 35% ethyl acetate in hexane as eluant) to afford 88.4. MS (ES): m/z 279.3 [M+H]$^+$.

Synthesis of compound 88.5. To a solution of 88.4 (0.275 g, 0.988 mmol, 1.0 equiv) in THF:methanol:water (10 mL, 2:1:1) was added lithium hydroxide (0.207 g, 4.94 mmol, 5.0 equiv). The reaction stirred at room temperature for 16 h. It was concentrated under reduced pressure to obtain residue. To the mixture was added water and acidified with 1 N hydrochloric acid to adjust pH-3. It was extracted with ethyl acetate. The combined organic layers were washed with brine, dried over anhydrous sodium sulfate, filtered and concentrated under reduced pressure to obtain 88.5. MS (ES): m/z 265.3 [M+H]$^+$.

Synthesis of compound 88.6. To a solution of 88.5 (0.210 g, 0.794 mmol, 1.0 equiv) in tert-butanol (5 mL) was added triethylamine (0.33 mL, 2.38 mmol, 3.0 equiv) and diphenylphosphorylazide (0.436 g, 1.58 mmol, 2.0 equiv) under nitrogen. The mixture was stirred at 80° C. for 3-4 h. It cooled to room temperature, poured over water and extracted with ethyl acetate. The combined organic layers were washed with brine, dried over anhydrous sodium sulfate, filtered and concentrated under reduced pressure. The residue was purified by flash column chromatography on silica gel (CombiFlash®, 50% ethyl acetate in hexane) to afford 88.6. MS (ES): m/z 336.4 [M+H]$^+$.

Synthesis of compound 88.7. To a solution of 88.6 (0.110 g, 0.327 mmol, 1.0 equiv) in dichloromethane (2 mL) was added trifluoroacetic acid (0.5 mL) dropwise at 0° C. The reaction mixture was stirred at room temperature for 2 h. It was poured over saturated aqueous solution of sodium bicarbonate and extracted with dichloromethane. The combined organic layers were washed with brine, dried over anhydrous sodium sulfate, filtered and concentrated under reduced pressure to obtain 88.7. MS (ES): m/z 236.3 [M+H]$^+$.

Synthesis of compound 88.8. Compound 88.8 was prepared from 88.7 following the procedure described in the synthesis of 11.8. The crude product was used in the next step without further purification. MS (ES): m/z 278.3 [M+H]$^+$.

Synthesis of compound I-88. Compound I-88 was prepared from 88.8 and Int-2 following the procedure described in the synthesis of I-1. The residue was purified by flash column chromatography on silica gel (CombiFlash®, 4% methanol in dichloromethane as eluant). MS (ES): m/z: 516.8 [M+H]$^+$, $^1$H NMR (DMSO-d6, 400 MHz): δ 10.51 (s, 1H), 9.57 (s, 1H), 8.16-8.15 (d, J=5.6 Hz, 1H), 7.65 (s, 1H), 7.41 (s, 1H), 7.39-7.37 (d, J=8.4 Hz, 1H), 7.30 (s, 1H), 6.89-6.87 (m, 1H), 6.64-6.63 (m, 1H), 5.08-4.97 (m, 1H), 4.04-3.96 (m, 2H), 3.65 (bs, 2H), 3.46 (s, 3H), 2.18-2.16 (m, 2H), 2.02 (s, 3H), 1.99-1.98 (m, 1H), 1.78-1.69 (m, 2H), 1.05-1.01 (m, 2H), 0.82 (bs, 2H).

Example 89: N-(4-((2-((5-cyclopropyl-1-methyl-2-oxo-1,2-dihydropyridin-3-yl)oxy)-1-methyl-1H-benzo[d]imidazol-6-yl)oxy)pyridin-2-yl)acetamide

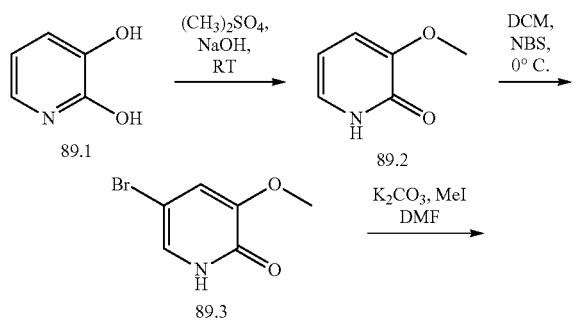

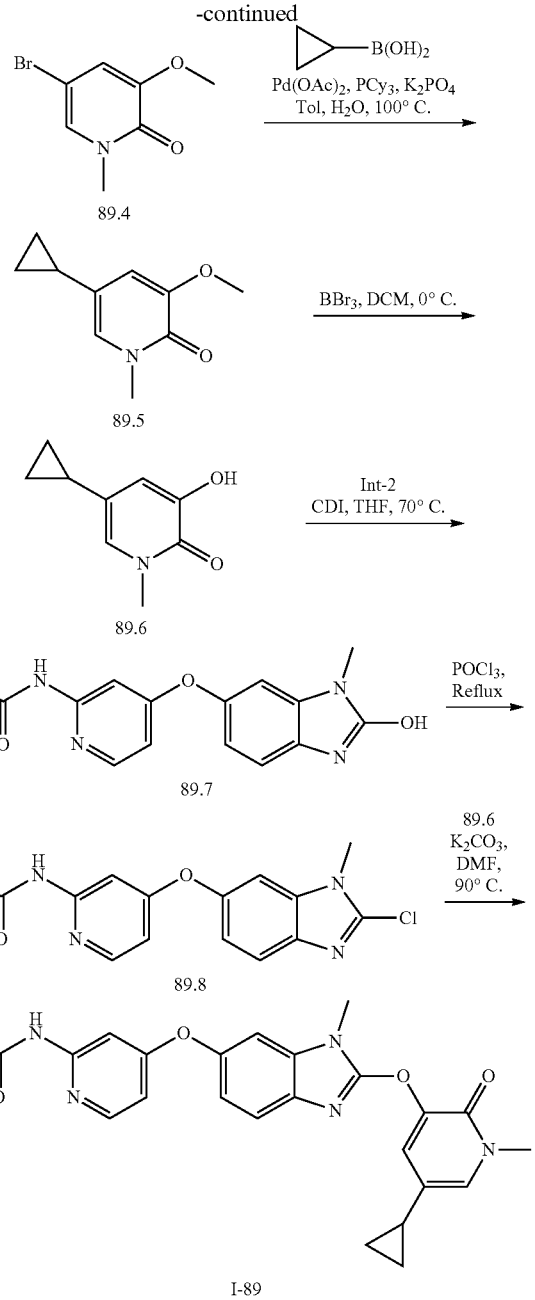

Synthesis of compound 89.2. To a 1 M aqueous solution of sodium hydroxide (51 mL, 135 mmol, 1.0 equiv) at 0° C. was added 89.1 (15 g, 135 mmol, 1.0 equiv). After 15 min dimethyl sulfate (12.8 mL, 135 mmol, 1.0 equiv) was added at 0° C. The reaction mixture was stirred at room temperature for 3 h. It was neutralized with acetic acid to pH 7 and extracted with dichloromethane. The combined organic layers were washed with brine, dried over anhydrous sodium sulfate, filtered and concentrated under reduced pressure. The residue was purified by flash column chromatography on silica gel (CombiFlash®, 3.2% methanol in dichloromethane as eluant) to afford 89.2. MS (ES): m/z 126.2 [M+H]$^+$.

Synthesis of compound 89.3. To a solution of 89.2 (4.0 g, 31.97 mmol, 1.0 equiv) in dichloromethane (40 mL) was added N-bromosuccinimide (6.79 g, 38.36 mmol, 1.2 equiv)

at 0° C. The reaction mixture was stirred at room temperature for 30 min. It was poured over ice-water, stirred and extracted with dichloromethane. The combined organic layers were washed with brine, dried over anhydrous sodium sulfate, filtered and concentrated under reduced pressure. The residue was purified by flash column chromatography on silica gel (CombiFlash®, 3% methanol in dichloromethane as eluant) to afford 89.3. MS (ES): m/z 205.1 [M+H]$^+$.

Synthesis of compound 89.4. To a solution of 89.3 (3.0 g, 14.7 mmol, 1.0 equiv) in DMF (30 mL) was added potassium carbonate (4.46 g, 32.34 mmol, 2.2 equiv) and stirred at room temperature for 15 min. To the mixture was added methyl iodide (1.04 mL, 16.17 mmol, 1.1 equiv). The reaction mixture was stirred at room temperature for 30 min. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.2% methanol in dichloromethane as eluant) to afford 89.4. MS (ES): m/z 219.1 [M+H]$^+$.

Synthesis of compound 89.5. Compound 89.5 was prepared from 89.4 following the procedure described in the synthesis of 61.3. The product was purified by flash column chromatography on silica gel (CombiFlash®, 2.5% methanol in dichloromethane as eluant). MS (ES): m/z 180.2 [M+H]$^+$.

Synthesis of compound 89.6. To a solution of 89.5 (0.675 g, 3.77 mmol, 1.0 equiv) in dichloromethane (10 mL) was added boron tribromide (0.73 mL, 7.54 mmol, 2.0 equiv) at 0° C. The reaction mixture was stirred for 30 min. It was poured over saturated sodium bicarbonate solution, stirred and extracted with dichloromethane. The combined organic layers were washed with brine, dried over anhydrous sodium sulfate, filtered and concentrated under reduced pressure. The residue was purified by flash column chromatography on silica gel (CombiFlash®, 3.5% methanol in dichloromethane as eluant) to afford 89.6. MS (ES): m/z 166.2 [M+H]$^+$.

Synthesis of compound 89.7. To a solution of Int-2 (0.300 g, 1.10 mmol, 1.0 equiv) in THF (3 mL) was added 1,1'-carbonyldiimidazole (0.213 g, 1.32 mmol, 1.2 equiv). The reaction mixture was stirred at 70° C. for 3 h. It was cooled to room temperature and concentrated under reduced pressure. This was further triturated with hexane to obtain 89.7. MS (ES): m/z: 299.3 [M+H]$^+$.

Synthesis of compound 89.8. Compound 89.7 (0.220 g, 0.737 mmol, 1.0 equiv) in phosphoryl chloride (5 mL) was stirred at 100° C. for 4 h. It was cooled and poured over saturated sodium bicarbonate solution, stirred and extracted with dichloromethane. The combined organic layers were washed with brine, dried over anhydrous sodium sulfate, filtered and concentrated under reduced pressure. The residue was purified by flash column chromatography on silica gel (CombiFlash®, 2.6% methanol in dichloromethane as eluant) to afford 89.8. MS (ES): m/z 317.7 [M+H]$^+$.

Synthesis of I-89. A mixture of 89.8 (0.065 g, 0.205 mmol, 1.0 equiv), 89.6 (0.051 g, 0.307 mmol, 1.5 equiv) and potassium carbonate (0.056 g, 0.41 mmol, 2.0 equiv) in DMF (2 mL) was stirred at 90° C. for 16 h. It was cooled to room temperature, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.4% methanol in dichloromethane as eluant). MS (ES): m/z: 446.35 [M+H]$^+$, $^1$H NMR (DMSO-d6, 400 MHz): 10.52 (s, 1H), 8.16-8.15 (d, J=6.0 Hz, 1H), 7.65 (s, 1H), 7.55 (s, 1H), 7.44-7.40 (m, 3H), 6.93-6.88 (m, 1H), 6.63-6.62 (d, J=6.0 Hz, 1H), 3.69 (s, 3H), 3.46 (s, 3H), 2.04 (s, 3H), 1.79 (bs, 1H), 0.86-0.84 (m, 2H), 0.63-0.62 (m, 2H).

Example 90: N-(4-((2-((5-cyclopropyl-1-isopropyl-2-oxo-1,2-dihydropyridin-3-yl)oxy)-1-methyl-1H-benzo[d]imidazol-6-yl)oxy)pyridin-2-yl)acetamide

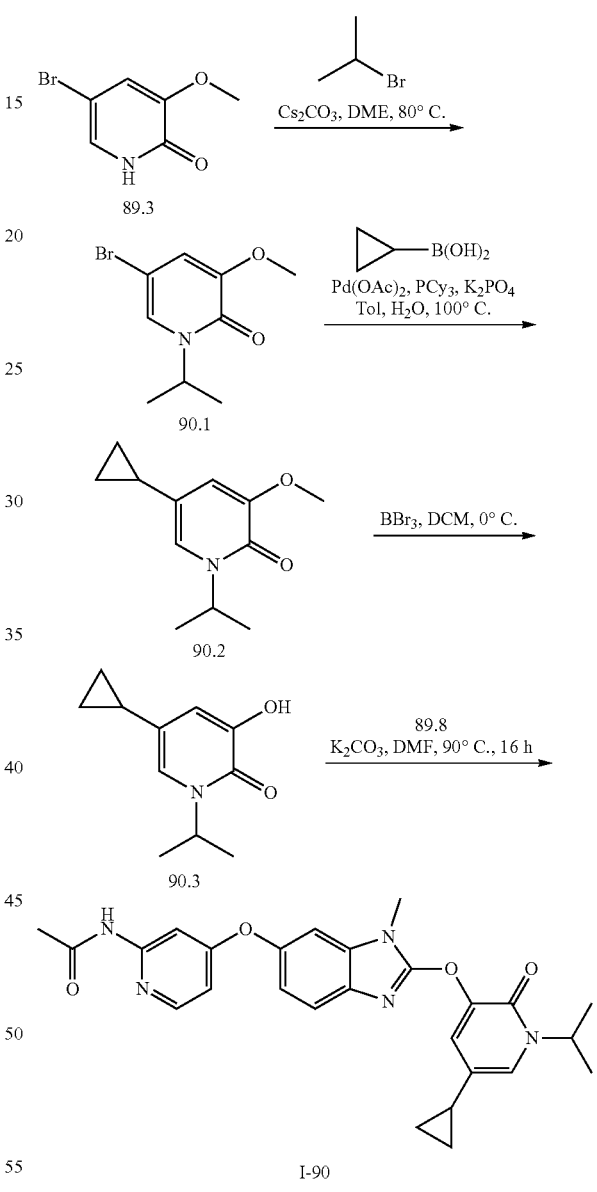

Synthesis of compound 90.1. To a solution of 89.3 (2.0 g, 9.8 mmol, 1.0 equiv) in dimethoxyethane (20 mL) was added cesium carbonate (7.96 g, 24.5 mmol, 2.5 equiv) and stirred at room temperature for 15 min. To the mixture was added 2-bromopropane (2.41 g, 19.61 mmol, 1.5 equiv). The reaction mixture was stirred at 80° C. for 16 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.1% methanol in dichloromethane as eluant) to afford 90.1. MS (ES): m/z 247.1 [M+H]$^+$.

Synthesis of compound 90.2. Compound 90.2 was prepared from 90.1 following the procedure described in the synthesis of 61.3. The product was purified by flash column chromatography on silica gel (CombiFlash®, 2.5% methanol in dichloromethane as eluant). MS (ES): m/z 180.2 [M+H]$^+$.

Synthesis of compound 90.3. To a solution of 90.2 (0.950 g, 4.58 mmol, 1.0 equiv) in dichloromethane (10 mL) was added boron tribromide (0.88 mL, 9.16 mmol, 2.0 equiv) at 0° C. The reaction mixture was stirred for 30 min. It was poured over saturated sodium bicarbonate solution, stirred and extracted with dichloromethane. The combined organic layers were washed with brine, dried over anhydrous sodium sulfate, filtered and concentrated under reduced pressure. The residue was purified by flash column chromatography on silica gel (CombiFlash®, 1.5% methanol in dichloromethane as eluant) to afford 90.3. MS (ES): m/z 194.3 [M+H]$^+$.

Synthesis of compound I-90. A mixture of 89.8 (0.065 g, 0.205 mmol, 1.0 equiv), 90.3 (0.059 g, 0.307 mmol, 1.5 equiv) and potassium carbonate (0.056 g, 0.41 mmol, 2.0 equiv) in DMF (2 mL) was stirred at 90° C. for 16 h. It was cooled to room temperature, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.2% methanol in dichloromethane as eluant) to afford I-90. MS (ES): m/z: 474.40 [M+H]$^+$, $^1$H NMR (DMSO-d6, 400 MHz): δ 10.52 (s, 1H), 8.16-8.15 (d, J=6.0 Hz, 1H), 7.65 (s, 1H), 7.58 (s, 1H), 7.43-7.39 (m, 2H), 7.34-7.33 (d, J=2.0 Hz, 1H), 6.94-6.91 (m, 1H), 6.63-6.61 (m, 1H), 5.02 (s, 1H), 3.69 (s, 3H), 2.04 (s, 3H), 1.90-1.87 (m, 1H), 1.33-1.32 (d, 6H), 0.87-0.85 (m, 2H), 0.66-0.65 (m, 2H).

Example 91: N-(4-((1-methyl-2-((1-methyl-2-oxo-1,2-dihydropyridin-3-yl)oxy)-1H-benzo[d]imidazol-6-yl)oxy)pyridin-2-yl)acetamide

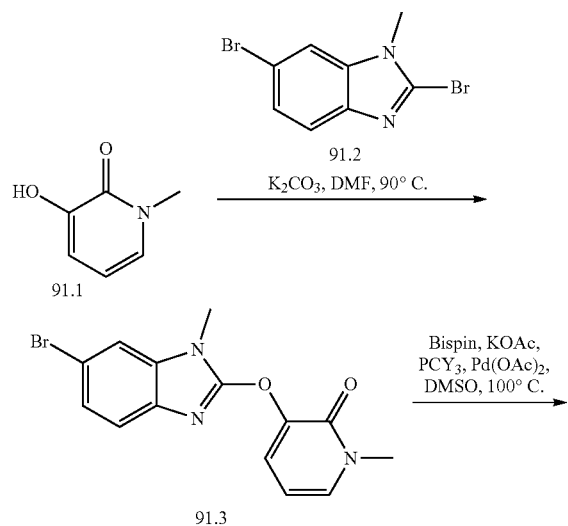

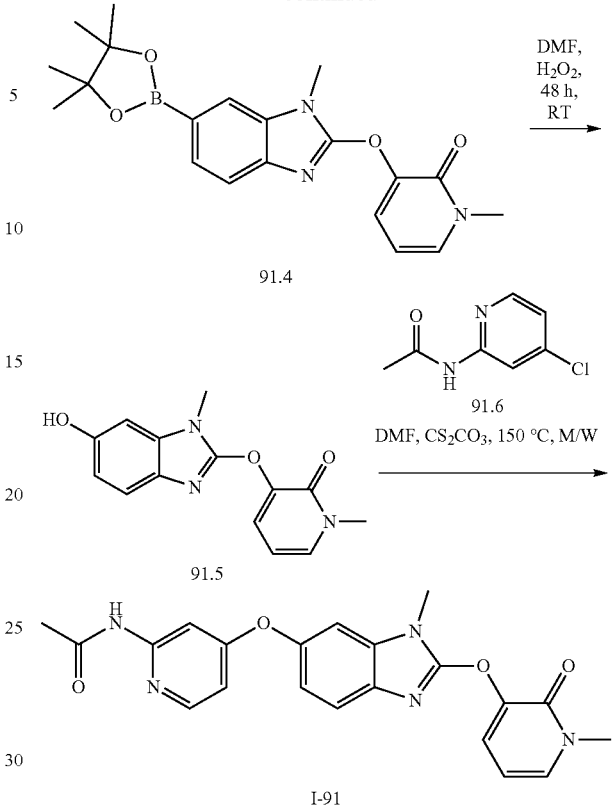

Synthesis of compound 91.3. A mixture of 91.2 (1.0 g, 3.45 mmol, 1.0 equiv), potassium carbonate (0.952 g, 6.9 mmol, 2.0 equiv) and 91.1 (0.647 g, 5.17 mmol, 1.5 equiv) in DMF (10 mL) was stirred at 90° C. for 16 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 0.8% methanol in dichloromethane as eluant) to afford 91.3. MS (ES): m/z 335.2 [M+H]$^+$.

Synthesis of compound 91.4. To a solution of 91.3 (0.500 g, 1.50 mmol, 1.0 equiv) in dimethyl sulfoxide (5 mL) was added bis(pinacolato)diboron (0.571 g, 2.25 mmol, 1.5 equiv), potassium acetate (0.441 g, 4.5 mmol, 3.0 equiv) and tricyclohexylphosphine (0.084 g, 0.3 mmol, 0.2 equiv). The reaction mixture was degassed for 10 min under argon atmosphere then palladium(II) acetate (0.034 g, 0.15 mmol, 0.1 equiv) was added, again degassed for 5 min. The reaction mixture was stirred at 100° C. for 2 h. It was cooled to room temperature, filtered through a pad of Celite®. The filtrate was poured over water, extracted with ethyl acetate. The combined organic layers were washed with brine, dried over anhydrous sodium sulfate, filtered and concentrated under reduced pressure. The residue was purified by flash column chromatography on silica gel (CombiFlash®, 1.0% methanol in dichloromethane as eluant) to afford 91.4. MS (ES): m/z 382.2 [M+H]$^+$.

Synthesis of compound 91.5. To a solution of 91.4 (0.335 g, 0.878 mmol, 1.0 equiv) in DMF (3 mL) was added hydrogen peroxide solution (30%, 0.25 mL, 2.19 mmol, 2.5 equiv). The reaction mixture was stirred at room temperature for 48 h. It was poured over water, extracted with ethyl acetate. The combined organic layers were washed with brine, dried over anhydrous sodium sulfate, filtered and concentrated under reduced pressure. The residue was purified by flash column chromatography on silica gel (CombiFlash®, 1.5% methanol in dichloromethane as eluant) to afford 91.5. MS (ES): m/z 272.3 [M+H]$^+$.

Synthesis of I-91. A mixture of 91.5 (0.150 g, 0.552 mmol, 1.0 equiv), 91.6 (0.094 g, 0.552 mmol, 1.0 equiv) and cesium carbonate (0.448 g, 1.38 mmol, 2.5 equiv) in DMF (3 mL) was stirred at 150° C. in a microwave reactor for 2 h. It was cooled to room temperature, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.4% methanol in dichloromethane as eluant) to afford material which was further purified by prep HPLC to obtain I-91. MS (ES): m/z: 406.21 [M+H]$^+$, $^1$H NMR (DMSO-d6, 400 MHz): δ 10.51 (s, 1H), 8.15 (s, 1H), 7.72 (bs, 1H), 7.64 (bs, 1H), 7.62 (s, 1H), 7.42 (s, 1H), 7.40 (s, 1H), 6.93 (bs, 1H), 6.61 (bs, 1H), 6.31 (bs, 1H), 3.69 (s, 3H), 3.49 (s, 3H), 2.02 (s, 3H).

Example 92: N-(4-((2-((5-cyclopropyl-1-((1s,3s)-3-hydroxycyclobutyl)-2-oxo-1,2-dihydropyridin-3-yl)oxy)-1-methyl-1H-benzo[d]imidazol-6-yl)oxy)pyridin-2-yl)acetamide

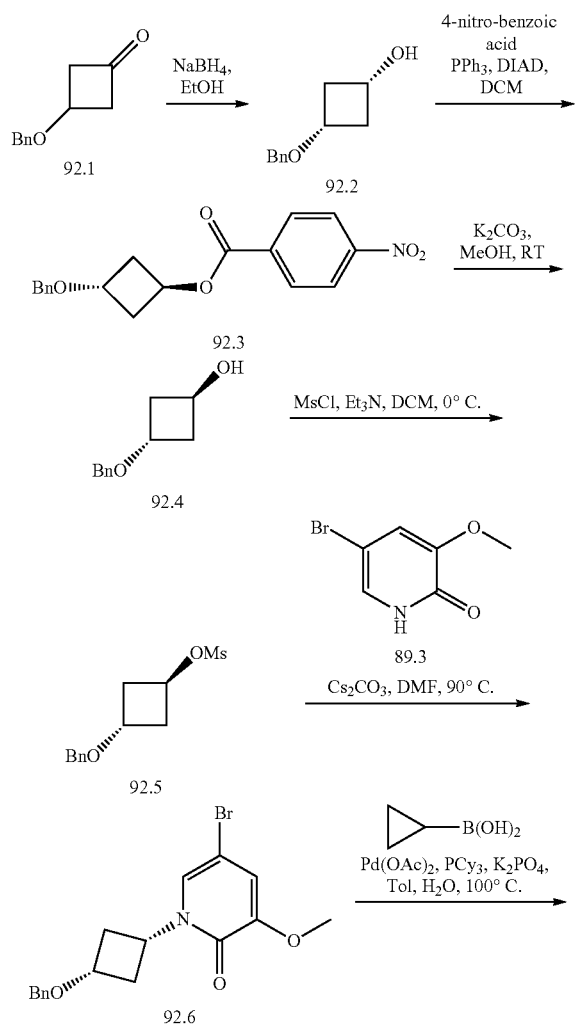

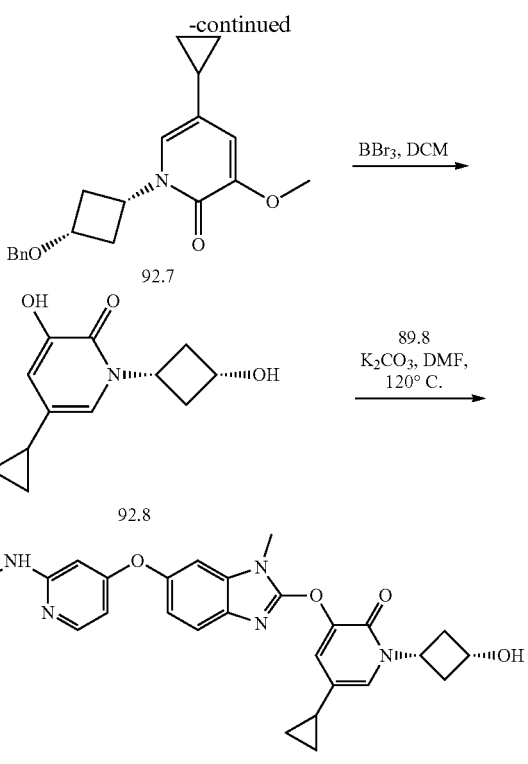

Synthesis of compound 92.2. To a solution of 92.1 (5 g, 28.37 mmol, 1.0 equiv) in methanol (50 mL) was added sodium borohydride (1.401 g, 36.88 mmol, 1.3 equiv) in small portions at 0° C. The reaction mixture was stirred at room temperature for 3 h. It was poured over ice-water, stirred and extracted with ethyl acetate. The combined organic layers were washed with brine, dried over anhydrous sodium sulfate, filtered and concentrated under reduced pressure to obtain 92.2. MS (ES): m/z 179.3 [M+H]$^+$.

Synthesis of compound 92.3. To a mixture of compound 92.2 (3.2 g, 17.95 mmol, 1.0 equiv), 4-nitrobenzoic acid (3.0 g, 17.95 mmol, 1.0 equiv) and triphenylphosphine (5.64 g, 21.54 mmol, 1.2 equiv) in dichloromethane (30 mL) at 0° C. was added diisopropylazodicarboxylate (1.35 g, 21.54 mmol, 1.2 equiv). The reaction mixture was stirred at room temperature for 4 h. It poured over ice-water and extracted with dichloromethane. The combined organic layers were washed with brine, dried over anhydrous sodium sulfate, filtered and concentrated under reduced pressure. The residue was purified by flash column chromatography on silica gel (CombiFlash®, 10% ethyl acetate in hexane as eluant) to afford 92.3. MS (ES): m/z 328.3 [M+H]$^+$.

Synthesis of compound 92.4. To a solution of 92.3 (2.45 g, 7.48 mmol, 1.0 equiv) in methanol (25 mL) was added potassium carbonate (3.09 g, 22.44 mmol, 3.0 equiv). The reaction mixture was stirred at room temperature for 3 h. It was poured over ice-water, stirred and extracted with ethyl acetate. The combined organic layers were washed with brine, dried over anhydrous sodium sulfate, filtered and concentrated under reduced pressure to obtain 92.4. MS (ES): m/z 179.2 [M+H]$^+$.

Synthesis of compound 92.5. To a solution of 92.4 (1.1 g, 6.17 mmol, 1.0 equiv) in dichloromethane (10 mL) was added triethylamine (1.1 mL, 8.02 mmol, 1.3 equiv) at 0° C. followed by addition of methanesulfonylchloride (0.62 mL, 8.02 mmol, 1.3 equiv). The reaction mixture was stirred at room temperature for 3 h. It was poured over ice-water, stirred and extracted with dichloromethane. The combined organic layers were washed with brine, dried over anhydrous sodium sulfate, filtered and concentrated under reduced pressure. The residue was purified by flash column chromatography on silica gel (CombiFlash®, 12% ethyl acetate in hexane as eluant) to afford 92.5. MS (ES): m/z 257.3 [M+H]$^+$.

Synthesis of compound 92.6. To a solution of 89.3 (2.7 g, 13.23 mmol, 1.0 equiv) in DMF (50 mL) was added cesium carbonate (12.93 g, 39.69 mmol, 3.0 equiv) and stirred for 30 min. The reaction mixture cooled to 0° C. and solution of 92.5 (4.07 g, 15.88 mmol, 1.2 equiv) in DMF (10 mL) was added dropwise. The reaction mixture was stirred at 90° C. for 16 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 50% ethyl acetate in hexane as eluant) to afford 92.6. MS (ES): m/z 365.2 [M+H]$^+$.

Synthesis of compound 92.7. Compound 92.7 was prepared from 92.6 following the procedure described in the synthesis of 61.3. The product was purified by flash column chromatography on silica gel (CombiFlash®, 2.2% methanol in dichloromethane as eluant). MS (ES): m/z 326.4 [M+H]$^+$.

Synthesis of compound 92.8. To a solution of 92.7 (0.400 g, 1.23 mmol, 1.0 equiv) in dichloromethane (12 mL) was added boron tribromide (0.6 mL, 6.15 mmol, 5.0 equiv) at 0° C. The reaction mixture was stirred at room temperature for 1 h. It was poured over saturated sodium bicarbonate solution, stirred and extracted with dichloromethane. The combined organic layers were washed with brine, dried over anhydrous sodium sulfate, filtered and concentrated under reduced pressure. The residue was purified by flash column chromatography on silica gel (CombiFlash®, 5.0% methanol in dichloromethane as eluant) to afford 92.8. MS (ES): m/z 222.3 [M+H]$^+$.

Synthesis of compound I-92. To a solution of Int-2 (0.095 g, 0.299 mmol, 1.0 equiv) in DMF (2 mL) was added 92.8 (0.100 g, 0.449 mmol, 1.5 equiv) followed by potassium carbonate (0.082 g, 0.598 mmol, 2.0 equiv). The reaction mixture was stirred at 120° C. for 3 h. It was cooled to room temperature, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 10% methanolic ammonia in dichloromethane as eluant) to afford I-92. MS (ES): m/z: 502.1 [M+H]$^+$, $^1$H NMR (DMSO-d6, 400 MHz): δ 10.51 (s, 1H), 8.15-8.14 (d, J=5.6 Hz, 1H), 7.64 (s, 1H), 7.61 (s, 1H), 7.41-7.37 (m, 3H), 6.92-6.90 (d, J=8.4 Hz, 1H), 6.62-6.61 (d, J=3.6 Hz, 1H), 5.28-5.26 (d, 1H), 4.59-4.55 (m, 1H), 3.96-3.91 (m, 1H), 3.67 (s, 3H), 2.71-2.69 (d, 2H), 2.13-2.10 (d, 2H), 2.03 (s, 3H), 1.91 (bs, 1H), 0.88-0.86 (m, 2H), 0.66-0.65 (m, 2H).

Example 93: N-(4-((2-((1-isopropyl-2-oxo-5-(1H-pyrazol-1-yl)-1,2-dihydropyridin-3-yl)oxy)-3-methyl-3H-imidazo[4,5-b]pyridin-5-yl)oxy)pyridin-2-yl)acetamide

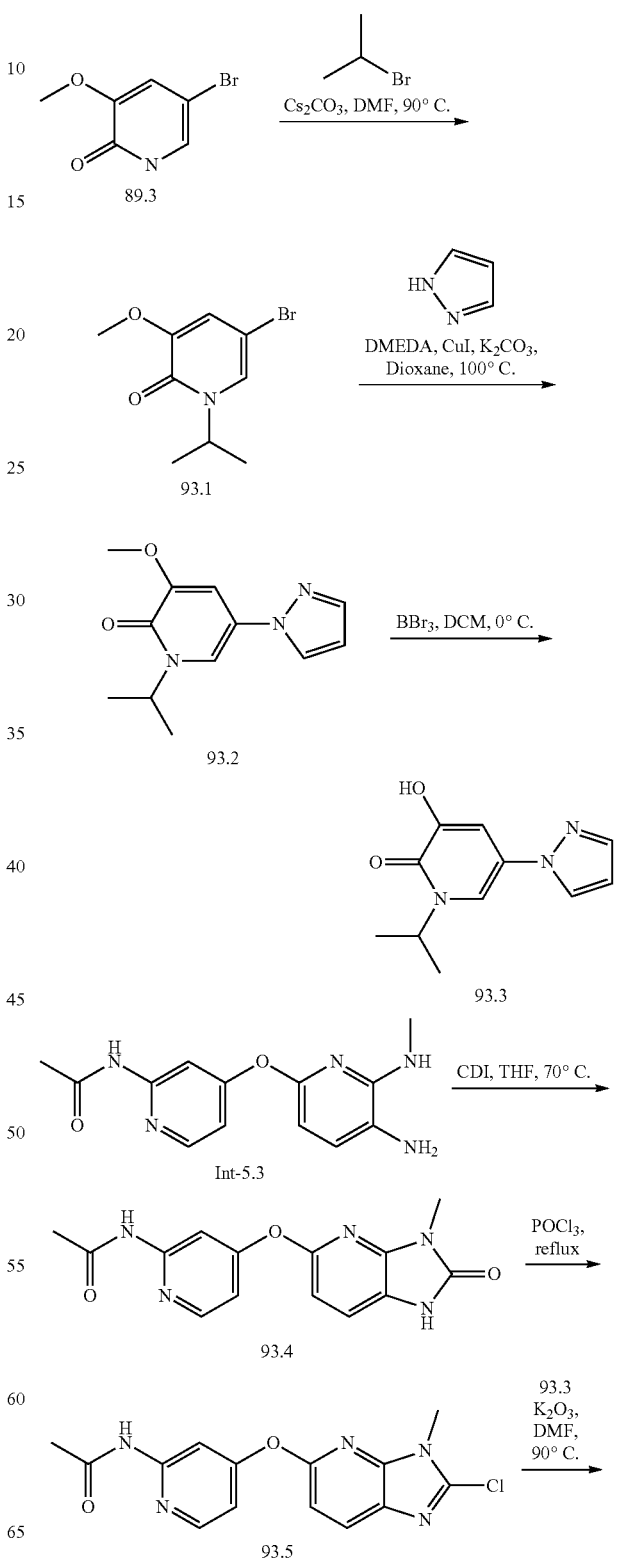

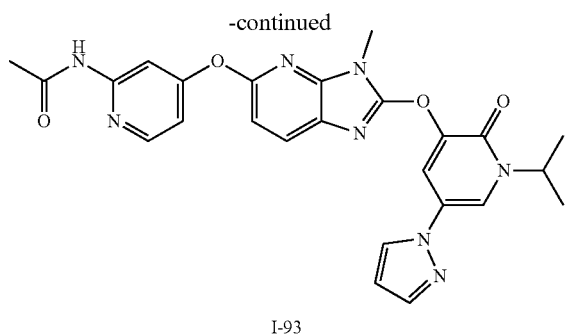

I-93

Synthesis of compound 93.1. To a solution of 89.3 (2.0 g, 9.8 mmol, 1.0 equiv) in dimethoxyethane (20 mL) was added cesium carbonate (7.96 g, 24.5 mmol, 2.5 equiv) and stirred at room temperature for 15 min. To the mixture was added 2-bromopropane (2.41 g, 19.61 mmol, 1.5 equiv). The reaction mixture was stirred at 80° C. for 16 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.1% methanol in dichloromethane as eluant) to afford 93.1. MS (ES): m/z 247.1 [M+H]$^+$.

Synthesis of compound 93.2. To a solution of 93.1 (1.4 g, 5.69 mmol, 1.0 equiv) in 1,4-dioxane (15 mL) was added pyrazole (0.464 g, 6.83 mmol, 1.2 equiv), potassium carbonate (1.96 g, 14.22 mmol, 2.5 equiv). The reaction mixture was degassed for 10 min under argon atmosphere then 1,2-dimethylethylenediamine (0.075 g, 0.85 mmol, 0.15 equiv) and copper iodide (0.326 g, 1.707 mmol, 0.3 equiv) was added, again degassed for 5 min. The reaction mixture was stirred at 100° C. for 12 h. It was cooled to room temperature, poured over water, extracted with ethyl acetate. The combined organic layers were washed with brine, dried over anhydrous sodium sulfate, filtered and concentrated under reduced pressure. The residue was purified by flash column chromatography on silica gel (CombiFlash®, 2.5% methanol in dichloromethane as eluant) to afford 93.2. MS (ES): m/z 234.3 [M+H]$^+$.

Synthesis of compound 93.3. To a solution of 93.5 (0.610 g, 2.61 mmol, 1.0 equiv) in dichloromethane (10 mL) was added boron tribromide (0.49 mL, 5.22 mmol, 2.0 equiv) at 0° C. The reaction mixture was stirred for 2 h. It was poured over saturated sodium bicarbonate solution, stirred and extracted with dichloromethane. The combined organic layers were washed with brine, dried over anhydrous sodium sulfate, filtered and concentrated under reduced pressure. The residue was purified by flash column chromatography on silica gel (CombiFlash®, 3.5% methanol in dichloromethane as eluant) to afford 93.3. MS (ES): m/z 220.2 [M+H]$^+$.

Synthesis of compound 93.4. To a solution of Int-5.3 (0.900 g, 3.29 mmol, 1.0 equiv) in THF (9 mL) was added 1,1'-carbonyldiimidazole (0.638 g, 3.94 mmol, 1.2 equiv). The reaction mixture was stirred at 70° C. for 3 h. It was cooled to room temperature and concentrated under reduced pressure. This was further triturated with hexane to obtain 93.4. MS (ES): m/z: 300.3 [M+H]$^+$.

Synthesis of compound 93.5. Compound 93.4 (0.800 g, 2.67 mmol, 1.0 equiv) in phosphorylchloride (8 mL) was stirred at 100° C. for 4 h. It was cooled and poured over saturated sodium bicarbonate solution, stirred and extracted with dichloromethane. The combined organic layers were washed with brine, dried over anhydrous sodium sulfate, filtered and concentrated under reduced pressure. The residue was purified by flash column chromatography on silica gel (CombiFlash®, 2.8% methanol in dichloromethane as eluant) to afford 93.5. MS (ES): m/z 318.7 [M+H]$^+$.

Synthesis of compound I-93. A mixture of 93.8 (0.070 g, 0.220 mmol, 1.0 equiv), 93.6 (0.058 g, 0.264 mmol, 1.2 equiv) and potassium carbonate (0.091 g, 0.66 mmol, 3.0 equiv) in DMF (2 mL) was stirred at 90° C. for 5 h. It was cooled to room temperature, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 4.5% methanol in dichloromethane as eluant) to afford I-93. MS (ES): m/z: 501.22 [M+H]$^+$, $^1$H NMR (DMSO-d6, 400 MHz): δ 10.59 (s, 1H), 8.42 (s, 1H), 8.28 (s, 1H), 8.24-8.22 (d, J=5.6 Hz, 1H), 8.19 (s, 1H), 7.97-7.95 (d, J=8.4 Hz, 1H), 7.83 (s, 1H), 7.76 (s, 1H), 7.01-6.99 (d, J=8.0 Hz, 1H), 6.80-6.79 (d, J=3.6 Hz, 1H), 5.12-5.09 (m, 1H), 3.65 (s, 3H), 3.41-3.38 (m, 1H), 2.07 (s, 3H), 1.41-1.40 (d, 6H).

Example 94: N-(4-((7-cyano-2-((5-cyclopropyl-1-methyl-2-oxo-1,2-dihydropyridin-3-yl)oxy)-1-methyl-1H-benzo[d]imidazol-6-yl)oxy)pyridin-2-yl) acetamide

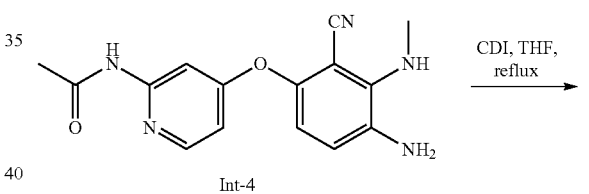

Int-4

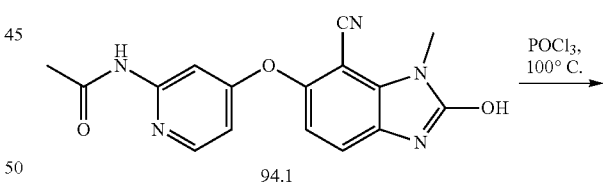

94.1

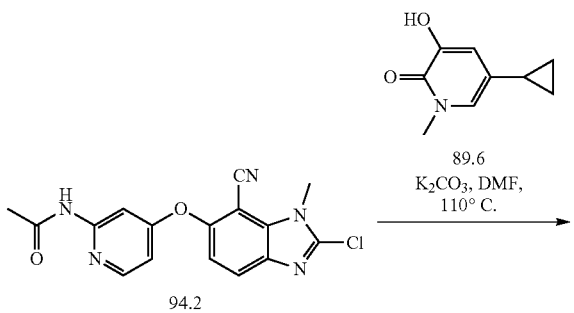

94.2

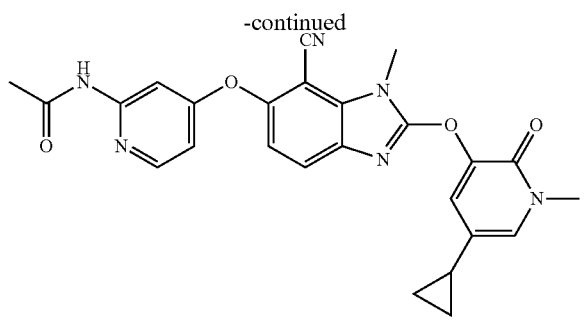

I-94

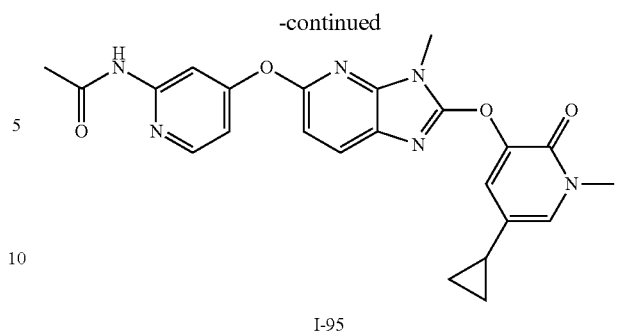

I-95

Synthesis of compound 94.1. To a solution of Int-4 (0.200 g, 0.672 mmol, 1.0 equiv) in THF (3 mL) was added 1,1'-carbonyldiimidazole (0.130 g, 0.806 mmol, 1.2 equiv). The reaction mixture was stirred at 70° C. for 3 h. It was cooled to room temperature and poured over ice-water. Precipitated solid was filtered out and triturated with hexane to obtain 94.1. MS (ES): m/z: 324.3 [M+H]+.

Synthesis of compound 94.2. compound 94.1 (0.180 g, 0.556 mmol, 1.0 equiv) in phosphorylchloride (5 mL) was stirred at 100° C. for 8 h. It was cooled and poured over saturated sodium bicarbonate solution, stirred and extracted with dichloromethane. The combined organic layers were washed with brine, dried over anhydrous sodium sulfate, filtered and concentrated under reduced pressure. The residue was purified by flash column chromatography on silica gel (CombiFlash®, 1.8% methanol in dichloromethane as eluant) to afford 94.2. MS (ES): m/z 342.5 [M+H]+.

Synthesis of compound I-94. A mixture of 94.2 (0.090 g, 0.263 mmol, 1.0 equiv), 89.6 (0.108 g, 0.658 mmol, 2.5 equiv) and potassium carbonate (0.108 g, 0.789 mmol, 3.0 equiv) in DMF (3 mL) was stirred at 110° C. for 3 h. It was cooled to room temperature, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 3.0% methanol in dichloromethane as eluant) to afford I-94. MS (ES): m/z: 471.5 [M+H]+, $^1$H NMR (DMSO-d6, 400 MHz): δ 10.63 (s, 1H), 8.23-8.22 (d, J=6.0 Hz, 1H), 7.80-7.78 (d, J=8.8 Hz, 1H), 7.69 (s, 1H), 7.58 (s, 1H), 7.49 (s, 1H), 7.16-7.14 (d, J=8.8 Hz, 1H), 6.74-6.72 (m, 1H), 3.93 (s, 3H), 3.46 (s, 3H), 2.04 (s, 3H), 1.79 (bs, 1H), 0.86-0.84 (d, 2H), 0.62-0.61 (d, 2H).

Example 95: N-(4-((2-((5-cyclopropyl-1-methyl-2-oxo-1,2-dihydropyridin-3-yl)oxy)-3-methyl-3H-imidazo[4,5-b]pyridin-5-yl)oxy)pyridin-2-yl)acetamide

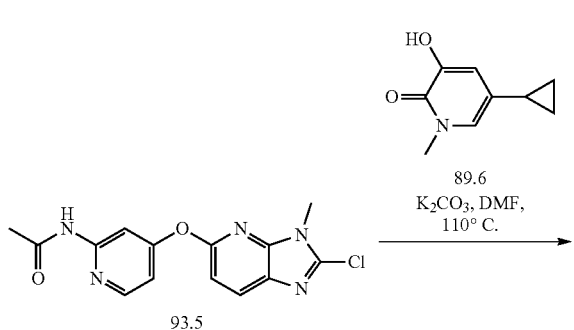

Synthesis of compound I-95. Compound I-95 was prepared from 93.5 and 89.5 following the procedure described in the synthesis of I-94. The product was purified by flash column chromatography on silica gel (CombiFlash®, 3.2% methanol in dichloromethane as eluant). MS (ES): m/z: 447.5 [M+H]+, $^1$H NMR (DMSO-d6, 400 MHz): δ 10.57 (s, 1H), 8.22-8.20 (d, J=5.6 Hz, 1H), 7.92-7.90 (d, J=7.6 Hz, 1H), 7.80 (s, 1H), 7.57 (s, 1H), 7.47 (s, 1H), 6.98-6.96 (d, J=8.0 Hz, 1H), 6.78 (bs, 1H), 3.62 (s, 3H), 3.42 (s, 3H), 2.05 (s, 3H), 1.78 (bs, 1H), 0.85 (bs, 2H), 0.62 (bs, 2H).

Example 96: N-(4-((2-((5-cyclopropyl-1-methyl-2-oxo-1,2-dihydropyridin-3-yl)oxy)-1-methyl-1H-imidazo[4,5-b]pyridin-6-yl)oxy)pyridin-2-yl)acetamide

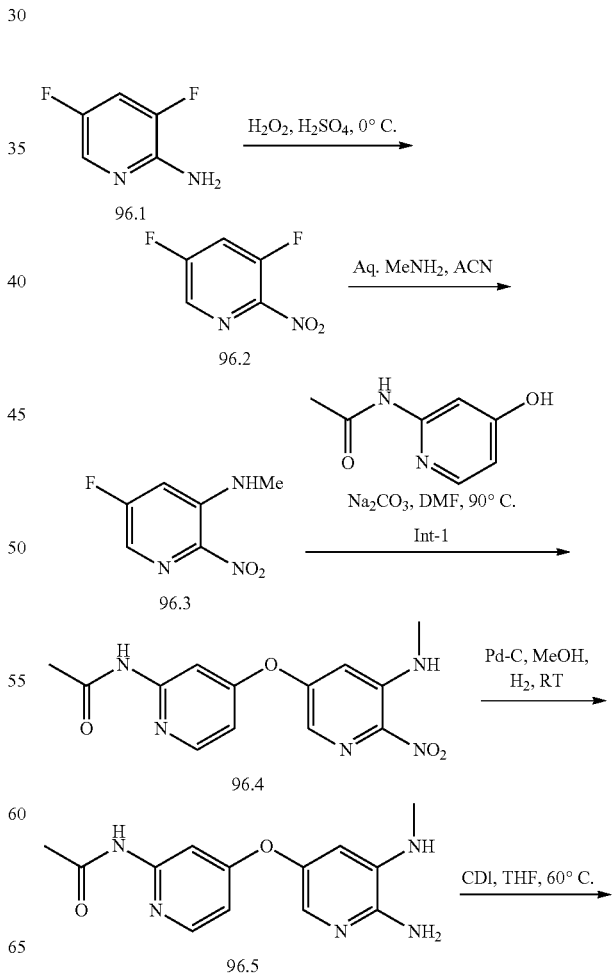

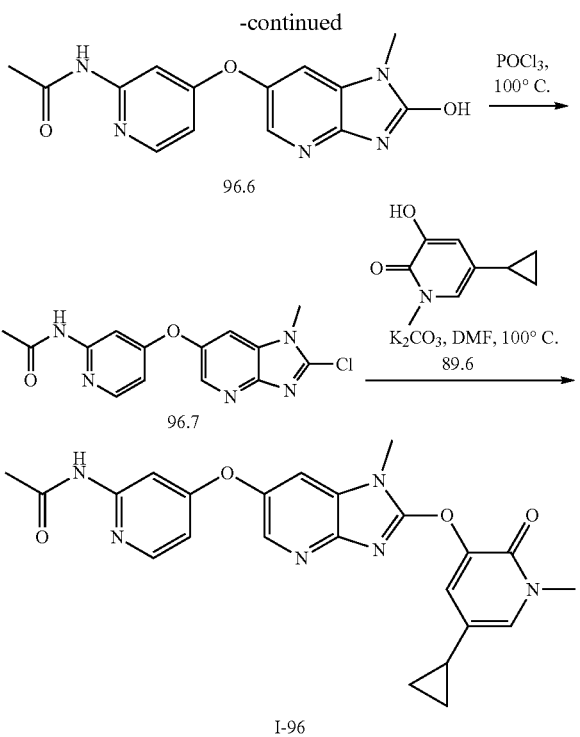

Synthesis of compound 96.2 Hydrogen peroxide (30 wt. %) (31 mL) was added dropwise to concentrated sulfuric acid (60 mL) at 0° C. To the solution was added a solution of 96.1 (5.0 g, 38.43 mmol, 1.0 eq) in concentrated sulfuric acid (60 mL) dropwise at 0° C. The reaction mixture was stirred at room temperature for 48 h. It was carefully poured over crushed ice and stirred. The aqueous mixture was basified with saturated aqueous sodium bicarbonate. Precipitates were removed by filtration and the filtrate was extracted with ethyl acetate. The combined organic layers were washed with brine, dried over anhydrous sodium sulfate, filtered and concentrated under reduced pressure to afford 96.2. $^1$H NMR (CDCl$_3$, 400 MHz): δ 8.35 (bs, 1H), 7.62-7.58 (m, 1H).

Synthesis of compound 96.3. To a solution of 96.2 (2.3 g, 14.37 mmol, 1.0 eq) in acetonitrile (20 mL) was added aqueous methylamine solution (40%) (1.1 mL, 14.37 mmol, 1.0 eq) dropwise at 0° C. The reaction mixture was stirred at room temperature for 1 h. It was poured over ice-water and extracted with ethyl acetate. The combined organic layers were washed with brine, dried over anhydrous sodium sulfate, filtered and concentrated under reduced pressure to afford 96.3. $^1$H NMR (CDCl$_3$, 400 MHz): δ 7.93 (bs, 1H), 7.78-7.75 (d, 1H), 7.02-6.99 (m, 1H), 3.06 (s, 3H).

Synthesis of compound 96.4. A mixture of 96.3 (1.6 g, 9.35 mmol, 1.0 eq), Int-1 (1.71 g, 11.22 mmol, 1.2 eq) and sodium carbonate (1.98 g, 18.7 mmol, 2.0 eq) in DMF (15 mL) was stirred at 90° C. for 12 h. The reaction mixture was cooled to room temperature, transferred into ice-water and extracted with ethyl acetate. The combined organic layers were with brine, dried over anhydrous sodium sulfate, filtered and concentrated under reduced pressure. The residue was purified by flash column chromatography on silica gel (CombiFlash®, 2% methanol in dichloromethane) to afford 96.4. MS (ES): m/z 304.3 [M+H]$^+$.

Synthesis of compound 96.5. Compound 96.5 was prepared from compound 96.4 following the procedure described in the synthesis of compound Int-2. The crude product was used in the next step without further purification. MS (ES): m/z 274.3 [M+H]$^+$.

Synthesis of compound 96.6. A mixture of 96.5 (0.550 g, 2.01 mmol, 1.0 eq) and 1,1'-carbonyldiimidazole (1.041 g, 6.43 mmol, 3.2 eq) in THF (6 mL) was stirred at 70° C. for 3 h. It was cooled to room temperature and poured over ice-water. Precipitates were collected by filtration and triturated with hexane to obtain 96.6. MS (ES): m/z: 300.3 [M+H]$^+$.

Synthesis of compound 96.7. Compound 96.6 (0.370 g, 1.24 mmol, 1.0 eq) in phosphorylchloride (10 mL) was heated to reflux for 8 h. It was cooled to rt and slowly poured into ice-saturated sodium bicarbonate solution, stirred and extracted with dichloromethane. The combined organic layers were with brine, dried over anhydrous sodium sulfate, filtered and concentrated under reduced pressure. The residue was purified by flash column chromatography on silica gel (CombiFlash®, 3.2% methanol in dichloromethane as eluant) to obtain 96.7. MS (ES): m/z 318.7 [M+H]$^+$.

Synthesis of compound I-96. A mixture of 96.7 (0.040 g, 0.125 mmol, 1.0 eq), 89.6 (0.031 g, 0.188 mmol, 1.5 eq) and potassium carbonate (0.051 g, 0.375 mmol, 3.0 eq) in DMF (2 mL) was stirred at 100° C. for 2 h. It was cooled to room temperature, poured over ice-water and extracted with ethyl acetate. The combined organic layers were with brine, dried over anhydrous sodium sulfate, filtered and concentrated under reduced pressure. The residue was purified by flash column chromatography on silica gel (CombiFlash®, 4.0% methanol in dichloromethane as eluant) to afford I-96. MS (ES): m/z: 447.19 [M+H]$^+$, $^1$H NMR (DMSO-d6, 400 MHz): δ 10.57 (s, 1H), 8.20-8.15 (m, 2H), 7.96-7.95 (d, J=2.0 Hz, 1H), 7.67 (s, 1H), 7.60 (s, 1H), 7.50 (s, 1H), 6.69-6.68 (d, 3.6 Hz, 1H), 3.73 (s, 3H), 3.48 (s, 3H), 2.05 (s, 3H), 1.81 (bs, 1H), 0.87-0.86 (d, 2H), 0.65-0.64 (d, 2H).

Example 97: N-(4-((2-((5-cyclopropyl-1-isopropyl-2-oxo-1,2-dihydropyridin-3-yl)oxy)-1-methyl-1H-imidazo[4,5-b]pyridin-6-yl)oxy)pyridin-2-yl)acetamide

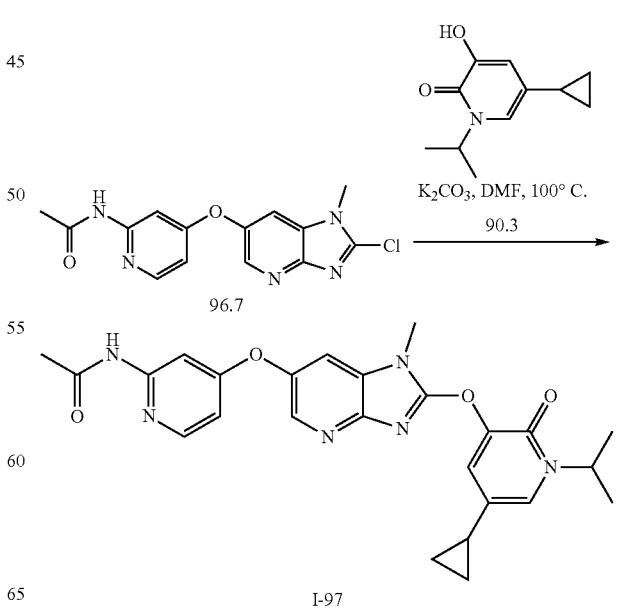

Synthesis of Compound I-97. Compound I-97 was prepared from compound 96.7 and compound 90.3 following the procedure described in the synthesis of compound I-96. The product was purified by flash column chromatography on silica gel (CombiFlash®, 3.8% methanol in dichloromethane as eluant). MS (ES): m/z: 475.20 [M+H]$^+$, $^1$H NMR (DMSO-d6, 400 MHz): δ 10.57 (s, 1H), 8.19-8.18 (d, J=5.6 Hz, 1H), 8.15 (s, 1H), 7.95 (s, 1H), 7.67 (s, 1H), 7.62 (s, 1H), 7.38 (s, 1H), 6.69-6.68 (d, 3.2 Hz, 1H), 5.05-5.02 (m, 1H), 3.72 (s, 3H), 2.05 (s, 3H), 1.90 (bs, 1H), 1.35-1.33 (d, 6H), 0.89-0.87 (d, 2H), 0.67-0.66 (d, 2H).

Example 98: N-(4-((2-((5-cyclopropyl-1-methyl-2-oxo-1,2-dihydropyridin-3-yl)amino)-1,7-dimethyl-1H-imidazo[4,5-b]pyridin-6-yl)oxy)pyridin-2-yl)acetamide

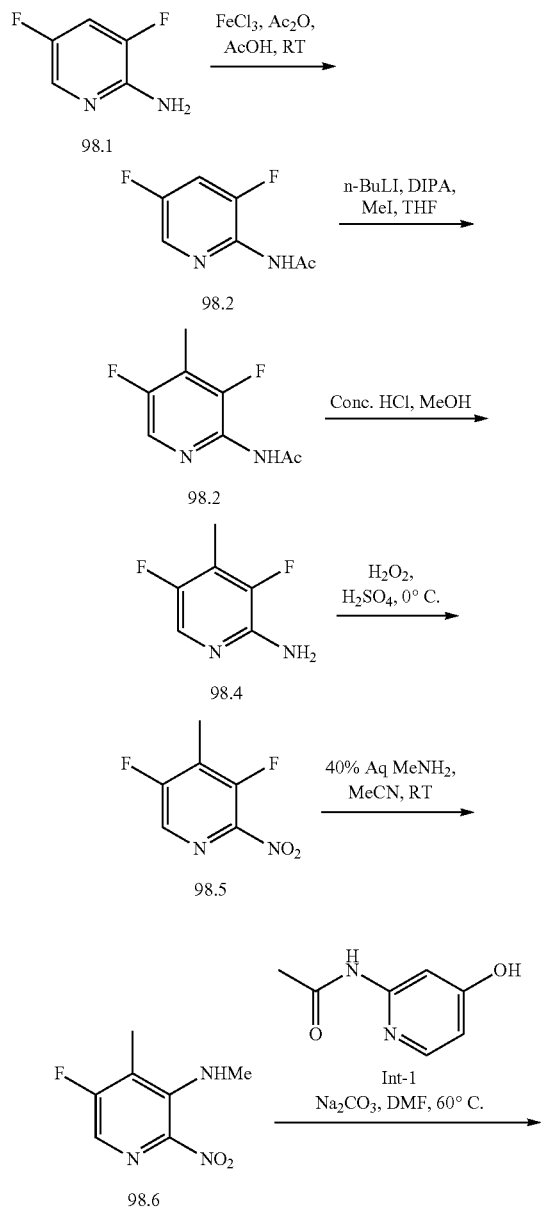

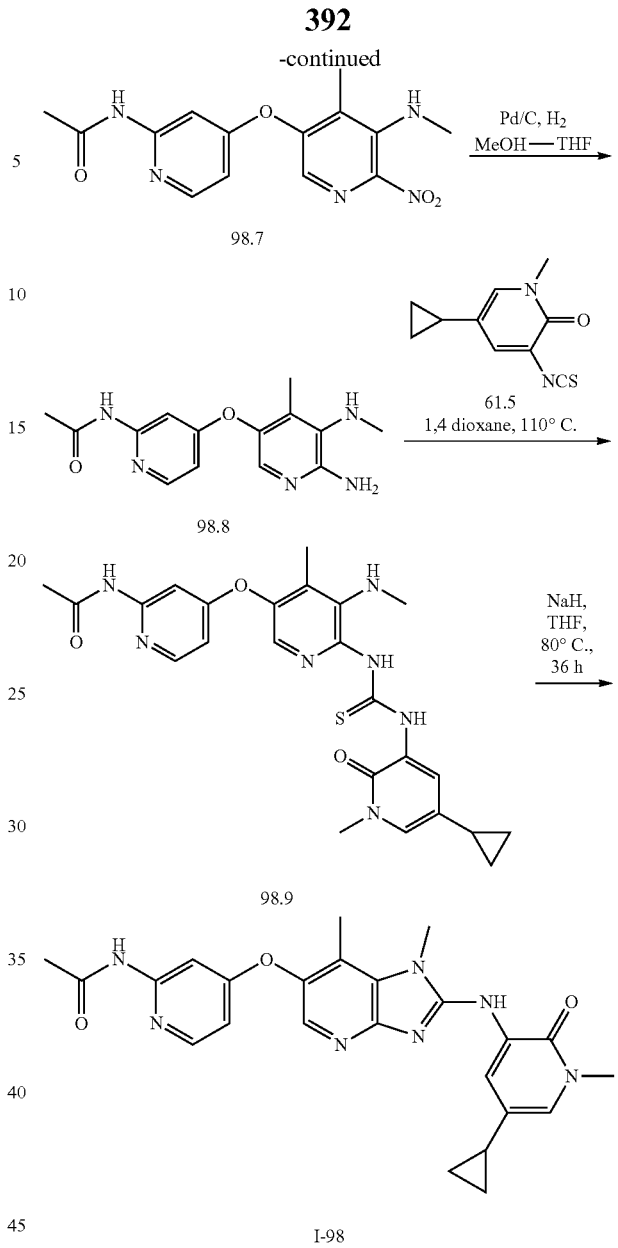

Synthesis of compound 98.2 To a solution of 3,5-difluoropyridin-2-amine (98.1, 20 g, 153.73 mmol, 1.0 equiv) in acetic acid (13.3 mL, 230.59 mmol, 1.5 equiv) was added acetic anhydride (18.9 mL, 199.84 mmol, 1.3 equiv) followed by ferric chloride (catalytic) at room temperature and stirred for 3 h. The reaction mixture was poured over ice-water and extracted with ethyl acetate. The combined organic layers were washed with brine, dried over anhydrous sodium sulfate, filtered and concentrated under reduced pressure. The residue was triturated with hexane to afford 98.2. $^1$H NMR (CDCl$_3$, 400 MHz): δ 8.16 (s, 1H), 7.73 (s, 1H), 7.36-7.30 (m, 1H), 2.35 (s, 3H).

Synthesis of compound 98.3. To a solution of 98.2 (18 g, 104.57 mmol, 1.0 equiv) and diisopropylamine (36.2 mL, 261.4 mmol, 2.5 equiv) in THF (200 mL) at −78° C. was added n-butyl lithium (2.5 M in hexane) (104 mL, 261.4 mmol, 2.5 equiv). The reaction mixture was stirred at −78° C. for 2 h and was added iodomethane (13 mL, 209.12 mmol, 2.0 equiv). The reaction was stirred for 2 h and was quenched by the addition of 1 N hydrochloric acid. It was warmed to room temperature and extracted with ethyl acetate. The combined organic layers were washed with brine, dried over anhydrous sodium sulfate, filtered and concentrated under reduced pressure. The residue was triturated with hexane to obtain 98.3. ¹H NMR (CDCl₃, 400 MHz): δ 10.22 (s, 1H), 8.26 (s, 1H), 2.25 (s, 3H), 2.06 (s, 3H).

Synthesis of compound 98.4. To a solution of 98.3 (9.00 g, 48.35 mmol, 1.0 equiv) in methanol (20 mL) was added concentrated hydrochloric acid (15 mL). The reaction mixture was refluxed for 4 h. It was concentrated under reduced pressure. To this residue was added ice-water and pH of the aqueous solution was adjusted to 9-10 by the addition of 3 N sodium hydroxide solution. The mixture is extracted with diethyl ether. The combined organic layers were washed with brine, dried over anhydrous sodium sulfate, filtered and concentrated under reduced pressure. The residue was purified by flash column chromatography on silica gel (CombiFlash®, 10% ethyl acetate in hexane as eluant) to afford 98.4. ¹H NMR (CDCl₃, 400 MHz): δ 7.74 (s, 1H), 4.47 (bs, 2H), 2.24 (s, 3H).

Synthesis of compound 98.5. Hydrogen peroxide (30 wt. %) (31 mL) was added dropwise to concentrated sulfuric acid (60 mL) at 0° C. To the solution was added a solution of 98.4 (4.5 g, 31.22 mmol, 1.0 equiv) in concentrated sulfuric acid (60 mL) drop wise at 0° C. The reaction mixture was stirred at room temperature for 48 h. It was carefully poured over crushed ice, stirred and basified with saturated sodium bicarbonate. Insoluble solids was removed by filtration and the filtrate was extracted with ethyl acetate. The combined organic layers were washed with brine, dried over anhydrous sodium sulfate, filtered and concentrated under reduced pressure. The residue was purified by flash column chromatography on silica gel (CombiFlash®, 6% ethyl acetate in hexane as eluant) to afford 98.5. ¹H NMR (CDCl₃, 400 MHz): δ 8.54 (bs, 1H), 2.35 (s, 3H).

Synthesis of compound 98.6. To a solution of 98.5 (0.480 g, 2.76 mmol, 1.0 equiv) in acetonitrile (5 mL) was added aqueous methylamine solution (40%) (0.2 mL, 2.76 mmol, 1.0 equiv) dropwise at 0° C. The reaction mixture was stirred at room temperature for 4 h. It was poured over ice-water and extracted with ethyl acetate. The combined organic layers were washed with brine, dried over anhydrous sodium sulfate, filtered and concentrated under reduced pressure to obtain 98.6. ¹H NMR (CDCl₃, 400 MHz): δ 7.82 (s, 1H), 7.21 (bs, 1H), 3.13 (s, 3H), 2.41 (s, 3H).

Synthesis of compound 98.7. A mixture of 98.6 (0.43 g, 2.32 mmol, 1.0 equiv), Int-1 (0.424 g, 2.79 mmol, 1.2 equiv) and sodium carbonate (0.491 g, 4.64 mmol, 2.0 equiv) in N,N-dimethylformamide (5 mL) was stirred at 60° C. for 12 h. The reaction mixture was cooled to room temperature, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 60% ethyl acetate in hexane) to afford 98.7. MS (ES): m/z 318.3 [M+H]⁺.

Synthesis of compound 98.8. A mixture of compound 98.7 (0.320 g, 1.01 mmol, 1.0 equiv), 10% palladium on carbon (0.300 g), methanol (1 mL) and THF (4 mL) was stirred at rt under 1 atm hydrogen for 3 h. The reaction mixture was filtered through a pad of Celite® and rinsed with methanol. The filtrate was concentrated under reduced pressure. The residue was purified by flash column chromatography on silica gel (CombiFlash®, 4% methanol in dichloromethane as eluant) to afford 98.8 (0.210 g, 72.47%). MS (ES): m/z 288.4 [M+H]⁺.

Synthesis of compound 98.9. A solution of 98.8 (0.210 g, 0.730 mmol, 1.0 equiv) and 61.5 (0.150 g, 0.730 mmol, 1.0 equiv) in 1,4-dioxane (2 mL) was stirred at 110° C. for 2 h. The reaction mixture was cooled to room temperature, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 4.2% methanol in dichloromethane as eluant) to afford 98.9. MS (ES): m/z 494.6 [M+H]⁺.

Synthesis of I-98. To a solution of 98.9 (0.154 g, 0.312 mmol, 1.0 equiv) in THF (2 mL) was added sodium hydride (0.124 g, 3.12 mmol, 10 equiv). The reaction mixture was stirred at 80° C. for 36 h. The reaction mixture was cooled to room temperature, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 4.0% methanol in dichloromethane as eluant) to afford I-98. MS (ES): m/z: 460.25 [M+H]⁺; ¹H NMR (DMSO-d6, 400 MHz): δ 10.54 (s, 1H), 8.42 (s, 1H), 8.32 (s, 1H), 8.17 (bs, 1H), 8.00 (s, 1H), 7.62 (bs, 1H), 7.21 (bs, 1H), 6.60 (s, 1H), 3.90 (s, 3H), 3.56 (s, 3H), 2.45 (s, 3H), 2.04 (s, 3H), 1.83 (bs, 1H), 0.87 (bs, 2H), 0.60 (bs, 2H).

Example 99: (S)—N-(4-((2-((5-(tert-butyl)-1-(tetrahydrofuran-3-yl)-1H-pyrazol-3-yl)amino)-1-methyl-1H-imidazo[4,5-b]pyridin-6-yl)oxy)pyridin-2-yl)acetamide

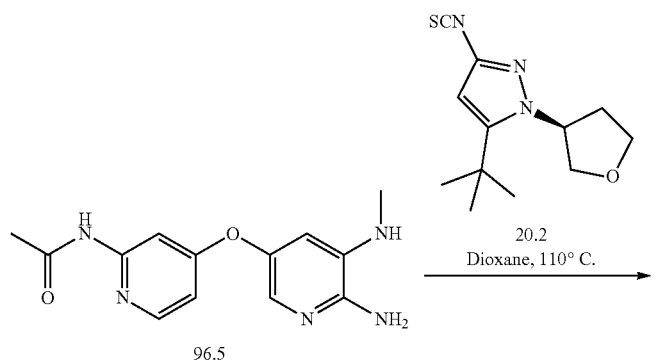

96.5

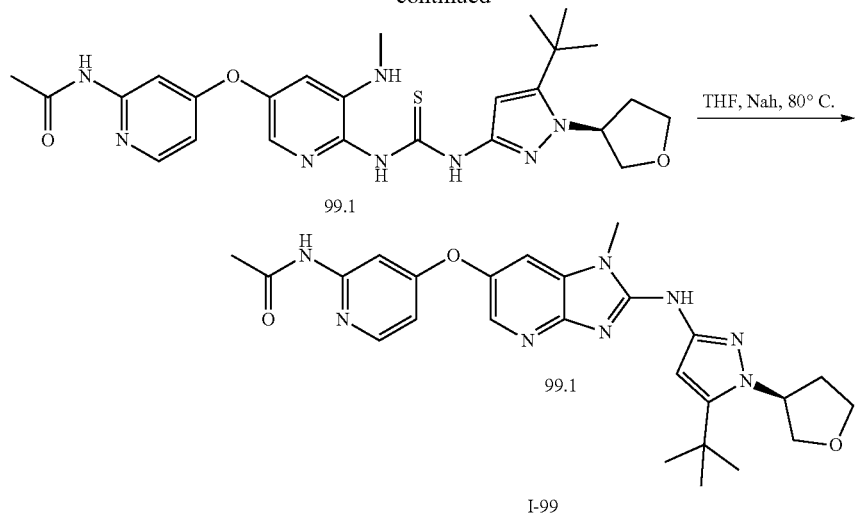

Synthesis of compound 99.1. Compound 99.1 was prepared from compound 96.5 and 20.2 following the procedure described in the synthesis of compound 98.9. The product was purified by flash column chromatography on silica gel (CombiFlash®, 3.8% methanol in dichloromethane as eluant). MS (ES): m/z 525.6 [M+H]⁺.

Synthesis of I-99. Compound I-99 was prepared from compound 99.1 following the procedure described in the synthesis of compound I-98. The product was purified by flash column chromatography on silica gel (CombiFlash®, 3.6% methanol in dichloromethane as eluant). MS (ES): m/z: 491.28 [M+H]⁺; ¹H NMR (DMSO-d6, 400 MHz): δ 10.55 (s, 1H), 9.91 (s, 1H), 8.19-8.17 (d, J=6 Hz, 1H), 7.97 (s, 1H), 7.66-7.64 (m, 2H), 6.67-6.66 (d, J=3.6 Hz, 1H), 6.60 (s, 1H), 5.26 (bs, 1H), 4.11-4.09 (m, 2H), 3.88-3.83 (m, 2H), 3.67 (s, 3H), 2.36-2.34 (m, 2H), 2.04 (s, 3H), 1.41 (s, 9H).

Example 100: (R)—N-(4-((2-((5-(tert-butyl)-1-(tetrahydrofuran-3-yl)-1H-pyrazol-3-yl)amino)-1-methyl-1H-imidazo[4,5-b]pyridin-6-yl)oxy)pyridin-2-yl)acetamide

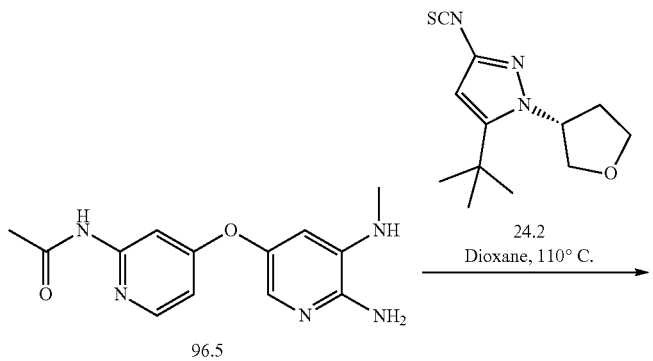

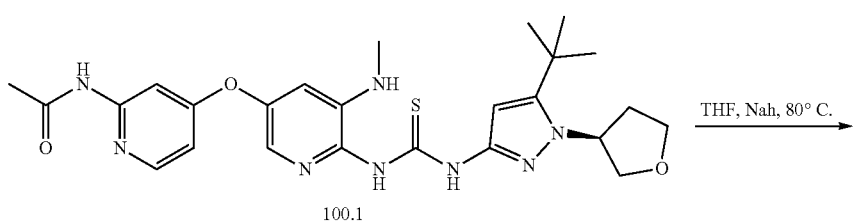

-continued

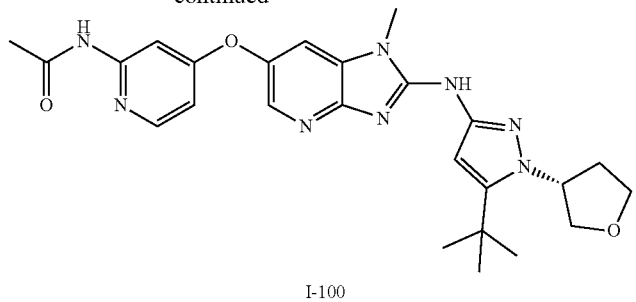

I-100

Synthesis of compound 100.1 Compound 100.1 was prepared from compound 96.5 and compound 24.2 following the procedure described in the synthesis of compound 98.9. The product was purified by flash column chromatography on silica gel (CombiFlash®, 3.9% methanol in dichloromethane as eluant). MS (ES): m/z 525.5 [M+H]$^+$.

Synthesis of I-100. Compound I-100 was prepared from compound 100.1 following the procedure described in the synthesis of compound I-98. The product was purified by flash column chromatography on silica gel (CombiFlash®, 3.5% methanol in dichloromethane as eluant). MS (ES): m/z: 491.28 [M+H]$^+$, $^1$H NMR (DMSO-d6, 400 MHz): δ 10.52 (s, 1H), 9.88 (s, 1H), 8.17-8.16 (d, J=5.6 Hz, 1H), 7.96 (s, 1H), 7.66-7.63 (m, 2H), 6.66-6.65 (m, 1H), 6.59 (s, 1H), 5.25 (bs, 1H), 4.10-4.09 (m, 2H), 3.85-3.82 (m, 2H), 3.66 (s, 3H), 2.38-2.33 (m, 2H), 2.03 (s, 3H), 1.41 (s, 9H).

Example 101: N-(4-((2-((5-(tert-butyl)-1-(oxetan-3-ylmethyl)-1H-pyrazol-3-yl)amino)-3-methyl-3H-imidazo[4,5-b]pyridin-5-yl)oxy)pyridin-2-yl)acetamide

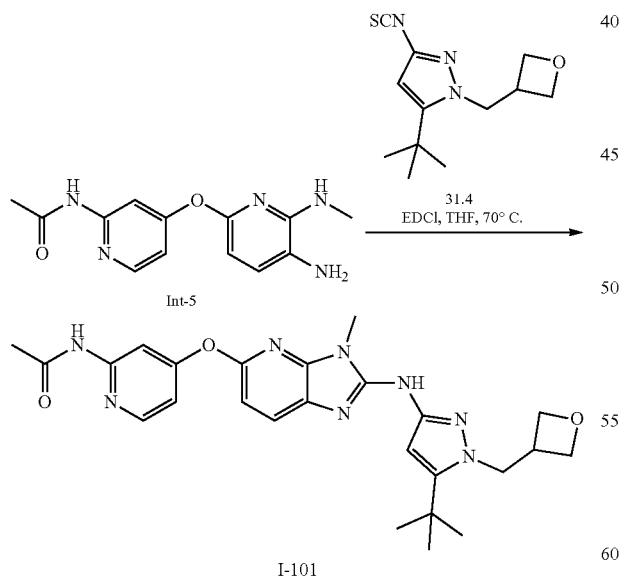

I-101

Synthesis of I-101. Compound I-101 was prepared from compound Int-5 and compound 31.4 following the procedure described in the synthesis of compound I-1. The product was purified by flash column chromatography on silica gel (CombiFlash®, 3.2% methanol in dichlorometh-ane as eluant). MS (ES): m/z: 491.2 [M+H]$^+$; $^1$H NMR (DMSO-d$_6$, 400 MHz): δ 10.74 (s, 1H), 10.56 (S, 1H), 9.05 (s, 1H), 8.21-8.19 (d, J=5.2 Hz, 1H), 7.77-7.75 (m, 2H), 7.47-7.45 (d, J=8.0 Hz, 1H), 6.13 (s, 1H), 4.61-4.58 (m, 2H), 4.49-4.43 (m, 2H), 3.60 (bs, 2H), 3.37 (s, 3H), 2.05 (s, 3H), 1.25 (s, 9H), 1.11-1.07 (m, 1H).

Example 102: N-(4-((2-((5-cyclopropyl-1-methyl-2-oxo-1,2-dihydropyridin-3-yl)oxy)-1,7-dimethyl-1H-imidazo[4,5-b]pyridin-6-yl)oxy)pyridin-2-yl)acetamide

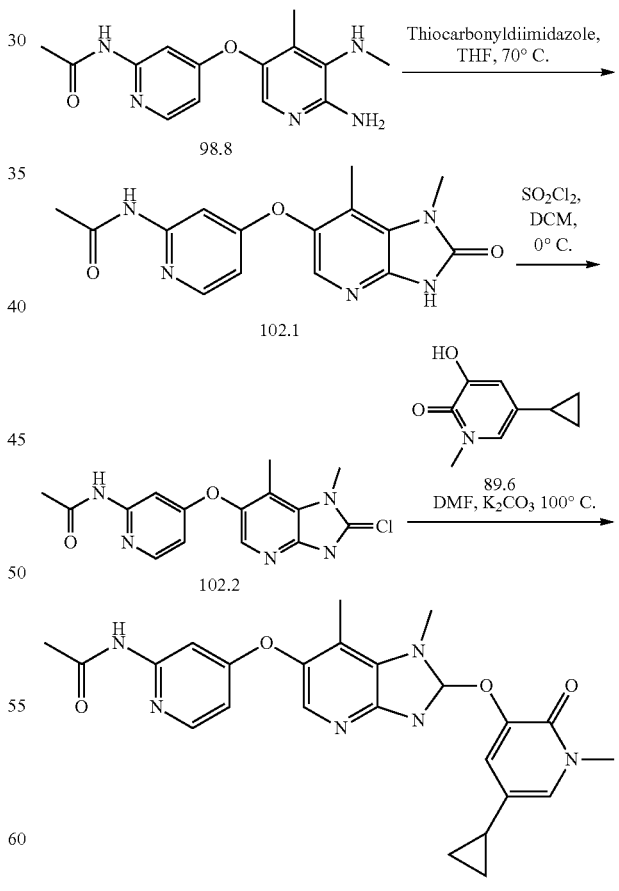

I-102

Synthesis of compound 102.1. A solution of 98.8 (0.162 g, 0.563 mmol, 1.0 equiv) and 1,1'-thiocarbonyldiimidazole (0.501 g, 2.815 mmol, 5.0 equiv) in THF (3 mL) was stirred at 70° C. for 16 h. The reaction mixture was cooled to room temperature and poured over ice-water. Precipitated solids were collected by filtration and air dried. The solids were triturated with hexane to afford 102.1. MS (ES): m/z: 330.3 [M+H]⁺.

Synthesis of compound 102.2. Compound 102.1 (0.086 g, 0.261 mmol, 1.0 equiv) was added to sulfuryl chloride (0.7 mL, 9.135 mmol, 35 equiv) at 0° C. and stirred for 10 min. The reaction mixture was slowly poured into a saturated aqueous sodium bicarbonate solution and extracted with dichloromethane. The combined organic layers were washed with brine, dried over anhydrous sodium sulfate, filtered and concentrated under reduced pressure. The residue was purified by flash column chromatography on silica gel (Combi-Flash®, 2.4% methanol in dichloromethane) to afford 102.2. MS (ES): m/z 332.5 [M+H]⁺.

Synthesis of I-102. Compound I-102 was prepared from compound 102.2 and compound 89.6 following the procedure described in the synthesis of compound I-96. The product was purified by flash column chromatography on silica gel (CombiFlash®, 3.8% methanol in dichloromethane). MS (ES): m/z: 461.39 [M+H]⁺, ¹H NMR (DMSO-d₆, 400 MHz): δ 10.56 (s, 1H), 8.17-8.15 (d, J=5.6 Hz, 1H), 8.04 (s, 1H), 7.60 (bs, 2H), 7.21 (bs, 1H), 6.60 (bs, 1H), 3.92 (s, 3H), 3.47 (s, 3H), 2.46 (s, 3H), 2.03 (s, 3H), 1.83 (bs, 1H), 0.86 (bs, 2H), 0.64 (bs, 2H).

Example 103: N-(4-((2-((5-cyclopropyl-1-methyl-2-oxo-1,2-dihydropyridin-3-yl)amino)-1-methyl-1H-imidazo[4,5-b]pyridin-6-yl)oxy)pyridin-2-yl)acetamide

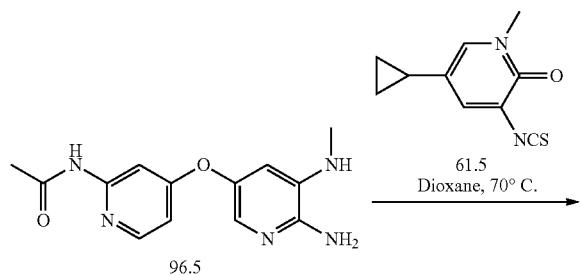

Synthesis of compound 103.1. A mixture of 96.5 (0.120 g, 0.439 mmol, 1.0 equiv) and 61.5 (0.091 g, 0.439 mmol, 1.0 equiv) in 1,4-dioxane (2 mL) was stirred at 70° C. for 5 h. It was cooled to room temperature, poured over ice-water and extracted with ethyl acetate. The combined organic layers were washed with brine solution, dried over anhydrous sodium sulfate, filtered and concentrated under reduced pressure. The residue was purified by flash column chromatography on silica gel (CombiFlash®, 3.2% methanol in dichloromethane) to afford 103.1. MS (ES): m/z 480.5 [M+H]⁺.

Synthesis of I-103. To a solution of 103.1 (0.076 g, 0.158 mmol, 1.0 equiv) in THF (2 mL) was added sodium hydride (0.031 g, 0.79 mmol, 5.0 equiv). The reaction mixture was stirred at 90° C. for 4 h. It was cooled to room temperature, poured over ice-water and extracted with ethyl acetate. The combined organic layers were washed with brine solution, dried over anhydrous sodium sulfate, filtered and concentrated under reduced pressure. The residue was purified by flash column chromatography on silica gel (CombiFlash®, 3.4% methanol in dichloromethane) to afford I-103. MS (ES): m/z: 446.0 [M+H]⁺, ¹H NMR (CDCl₃/MeOD, 400 MHz): δ 8.54 (bs, 1H), 8.08 (bs, 1H), 8.03 (bs, 1H), 7.78 (bs, 1H), 7.28 (s, 1H), 7.24 (bs, 1H), 6.80 (s, 1H), 6.54 (bs, 1H), 3.68 (s, 3H), 3.60 (s, 3H), 2.13 (s, 3H), 1.77-1.74 (m, 1H), 0.87-0.85 (m, 2H), 0.63 (bs, 2H).

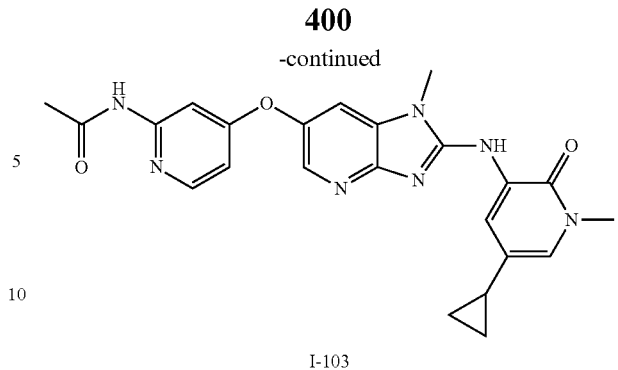

I-103

Example 104: N-(4-((2-((4,4-dimethyl-4,5,6,7-tetrahydropyrazolo[1,5-c]pyridin-2-yl)amino)-1-methyl-1H-imidazo[4,5-b]pyridin-6-yl)oxy)pyridin-2-yl)acetamide

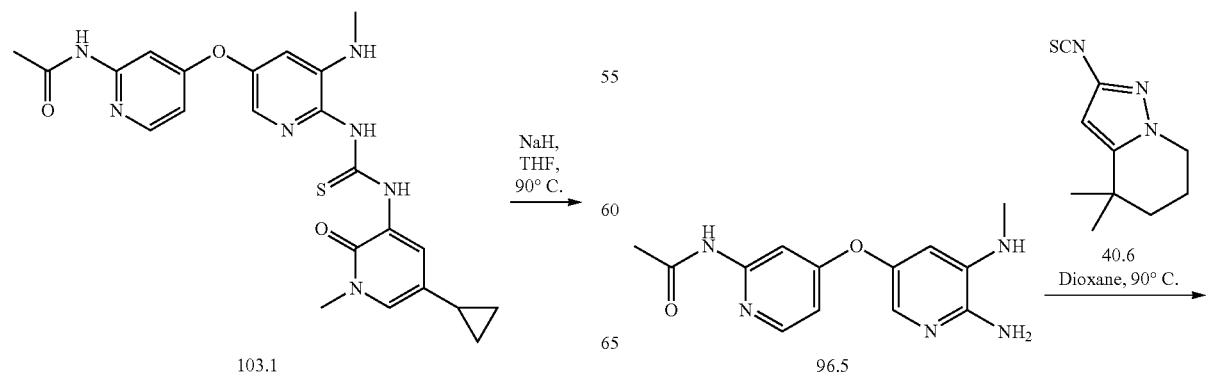

401

-continued

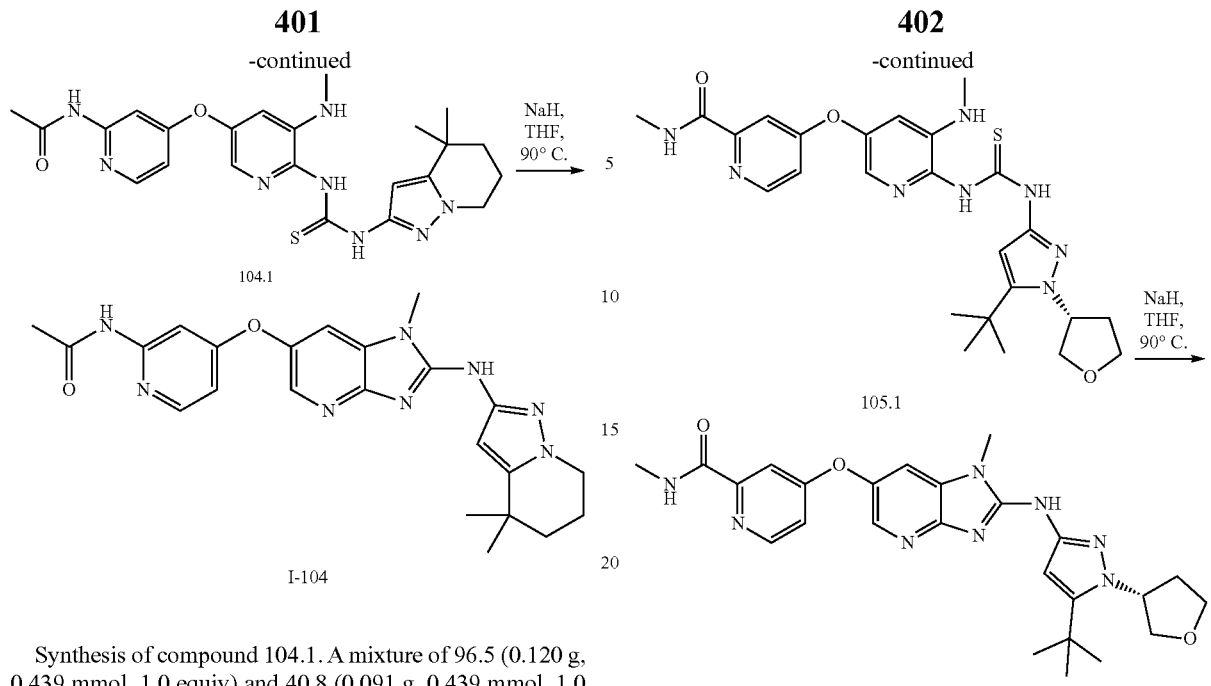

104.1

I-104

Synthesis of compound 104.1. A mixture of 96.5 (0.120 g, 0.439 mmol, 1.0 equiv) and 40.8 (0.091 g, 0.439 mmol, 1.0 equiv) in 1,4-dioxane (2 mL) was stirred at 90° C. for 3 h. It was cooled to room temperature, poured over ice-water and extracted with ethyl acetate. The combined organic layers were washed with brine solution, dried over anhydrous sodium sulfate, filtered and concentrated under reduced pressure. The residue was purified by flash column chromatography on silica gel (CombiFlash®, 2.3% methanol in dichloromethane) to afford 104.1. MS (ES): m/z 481.5 [M+H]⁺.

Synthesis of I-104. Compound I-104 was prepared from compound 104.1 following the procedure described in the synthesis of compound I-103. The product was purified by flash column chromatography on silica gel (CombiFlash®, 3.6% methanol in dichloromethane). MS (ES): m/z: 447.5 [M+H]⁺, ¹H NMR (DMSO-d₆, 400 MHz): δ 10.5 (s, 1H), 9.89 (s, 1H), 8.18-8.16 (d, J=5.6 Hz, 1H), 7.96 (bs, 1H), 7.66 (s, 1H), 7.62 (bs, 1H), 7.07 (bs, 1H), 6.83 (bs, 1H), 6.65-6.63 (m, 2H), 3.95 (s, 1H), 3.65 (bs, 2H), 2.03 (s, 3H), 1.68 (bs, 2H), 1.55 (bs, 2H), 1.32 (s, 6H).

Example 105: (R)-4-((2-((5-(tert-butyl)-1-(tetrahydrofuran-3-yl)-1H-pyrazol-3-yl)amino)-1-methyl-1H-imidazo[4,5-b]pyridin-6-yl)oxy)-N-methylpicolinamide

402

-continued 105.1

I-105

Synthesis of compound 105.1. Compound 105.1 was prepared from compound 15.4 and 24.2 following the procedure described in the synthesis of compound 104.1. The product was purified by flash column chromatography on silica gel (CombiFlash®, 2.5% methanol in dichloromethane). MS (ES): m/z 525.6 [M+H]⁺.

Synthesis of I-105. Compound I-105 was prepared from compound 105.1 following the procedure described in the synthesis of compound I-103. The product was purified by flash column chromatography on silica gel (CombiFlash®, 3.5% methanol in dichloromethane). MS (ES): m/z: 491.62 [M+H]⁺, Chiral HPLC purity: 96.8%, ¹H NMR (DMSO-d6, 400 MHz): δ 9.92 (s, 1H), 8.78 (s, 1H), 8.53-8.52 (d, J=5.6 Hz, 1H), 8.02-8.01 (d, J=2.4 Hz, 1H), 7.69 (s, 1H), 7.40 (s, 1H), 7.20-7.19 (m, 1H), 6.61 (s, 1H), 5.29 (bs, 1H), 4.10 (bs, 2H), 3.87-3.83 (m, 2H), 3.68 (s, 3H), 2.80 (s, 3H), 2.27-2.24 (m, 2H), 1.42 (s, 9H).

Example 106: (S)-4-((2-((5-(tert-butyl)-1-(tetrahydrofuran-3-yl)-1H-pyrazol-3-yl)amino)-1-methyl-1H-imidazo[4,5-b]pyridin-6-yl)oxy)-N-methylpicolinamide

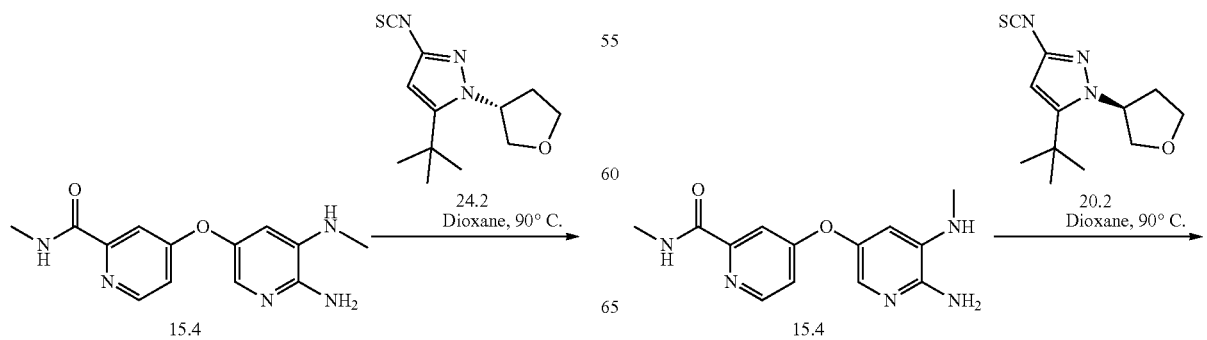

-continued

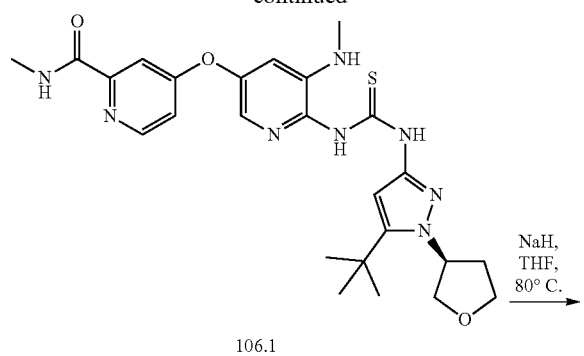

106.1

NaH, THF, 80° C.

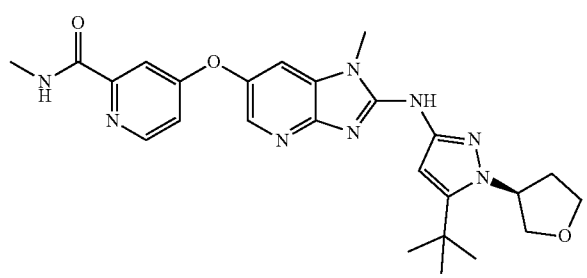

I-106

Synthesis of I-106. Compound I-106 was prepared from compound 15.4 and 20.2 following the procedure described in each step in the synthesis of compound I-105. The product was purified by flash column chromatography on silica gel (CombiFlash®, 3.7% methanol in dichloromethane). MS (ES): m/z: 491.32 [M+H]$^+$, Chiral HPLC purity: 98%, $^1$H NMR (DMSO-d$_6$, 400 MHz): δ 9.93 (s, 1H), 8.80-8.79 (d, J=4.4 Hz, 1H), 8.52-8.51 (d, J=5.6 Hz, 1H), 8.01-8.00 (d, J=2.4 Hz, 1H), 7.69 (s, 1H), 7.39 (s, 1H), 7.19-7.18 (m, 1H), 6.60 (s, 1H), 5.26 (bs, 1H), 4.11 (bs, 2H), 3.86-3.82 (m, 2H), 3.67 (s, 3H), 2.79 (s, 3H), 2.26-2.23 (m, 2H), 1.41 (s, 9H).

Example 107: 4-((2-((5-cyclopropyl-1-methyl-2-oxo-1,2-dihydropyridin-3-yl)amino)-1-methyl-1H-benzo[d]imidazol-6-yl)oxy)-N-methylpicolinamide

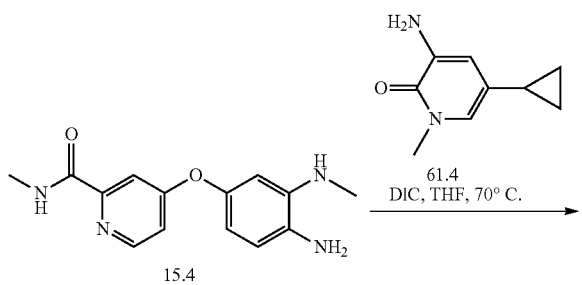

15.4

61.4
DIC, THF, 70° C.

-continued

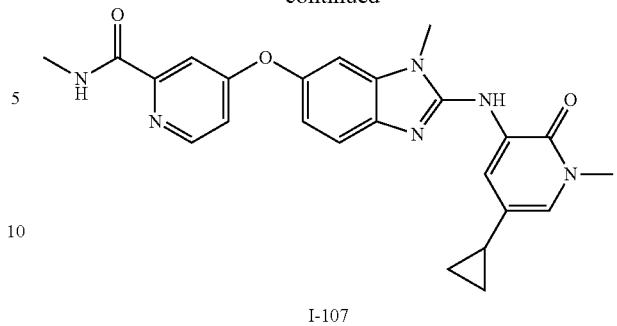

I-107

Synthesis of I-107. Compound I-107 was prepared from compound 15.4 and compound 61.4 following the procedure described in the synthesis of compound I-2. The product was purified by flash column chromatography on silica gel (CombiFlash®, 3.5% methanol in dichloromethane). MS (ES): m/z: 445.49 [M+H]$^+$, $^1$H NMR (DMSO-d$_6$, 400 MHz): δ 8.79-8.78 (d, J=4.4 Hz, 1H), 8.52-8.50 (d, J=5.6 Hz, 1H), 8.34 (s, 1H), 8.23 (s, 1H), 7.58-7.56 (d, J=8.4 Hz, 1H), 7.40-7.38 (m, 2H), 7.16 (s, 2H), 6.95-6.93 (d, J=6.4 Hz, 1H), 3.71 (s, 3H), 3.55 (s, 3H), 2.79 (d, 3H), 1.83-1.82 (m, 1H), 0.88-0.86 (m, 2H), 0.61-0.60 (m, 2H).

Example 108: (R)—N-(4-((2-((5-(tert-butyl)-1-(tetrahydrofuran-3-yl)-1H-pyrazol-3-yl)amino)-1,7-dimethyl-1H-imidazo[4,5-b]pyridin-6-yl)oxy)pyridin-2-yl)acetamide

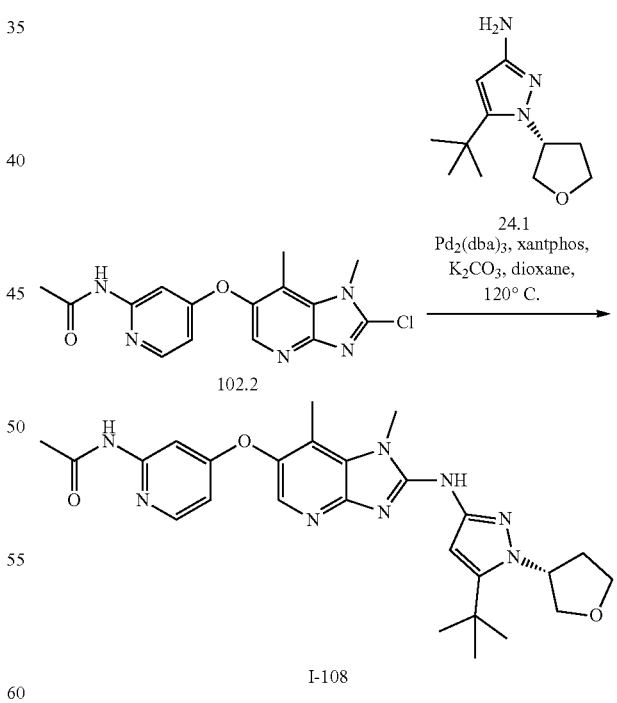

102.2

24.1
Pd$_2$(dba)$_3$, xantphos, K$_2$CO$_3$, dioxane, 120° C.

I-108

Synthesis of I-108. A mixture of 102.2 (0.032 g, 0.096 mmol, 1.0 equiv), 24.1 (0.024 g, 0.115 mmol, 1.2 equiv) and potassium carbonate (0.033 g, 0.24 mmol, 2.5 equiv) in 1,4-dioxane (1 mL) was degassed for 10 min by bubbling through argon. 4,5-Bis(diphenylphosphino)-9,9-dimethylxanthene (0.006 g, 0.0096 mmol, 0.1 equiv) and tris(dibenzylideneacetone)dipalladium(0) (0.004 g, 0.0048 mmol, 0.05 equiv) were added, and degassed for another 5 min. The reaction mixture was stirred at 120° C. for 1 h in a sealed tube. It was cooled to room temperature, poured into water and extracted with ethyl acetate. The combined organic layers were washed with brine solution, dried over anhydrous sodium sulfate, filtered and concentrated under reduced pressure. The residue was purified by flash column chromatography on silica gel (CombiFlash®, 4.2% methanol in dichloromethane). MS (ES): m/z: 505.46 [M+H]⁺, Chiral HPLC purity: 97%, ¹H NMR (DMSO-d₆, 400 MHz): 10.54 (s, 1H), 9.78 (s, 1H), 8.17-8.15 (d, J=5.6 Hz, 1H), 7.89 (s, 1H), 7.61 (s, 1H), 6.60-6.56 (m, 2H), 5.26 (s, 1H), 4.00 (bs, 2H), 3.83 (bs, 5H), 2.41 (s, 3H), 2.34 (bs, 1H), 2.26 (bs, 1H), 2.04 (s, 3H), 1.41 (s, 9H).

Example 109: (R)—N-(4-((2-((5-(tert-butyl)-1-(tetrahydrofuran-3-yl)-1H-pyrazol-3-yl)amino)-1-methyl-1H-imidazo[4,5-b]pyridin-6-yl)oxy)pyridin-2-yl)cyclopropanecarboxamide

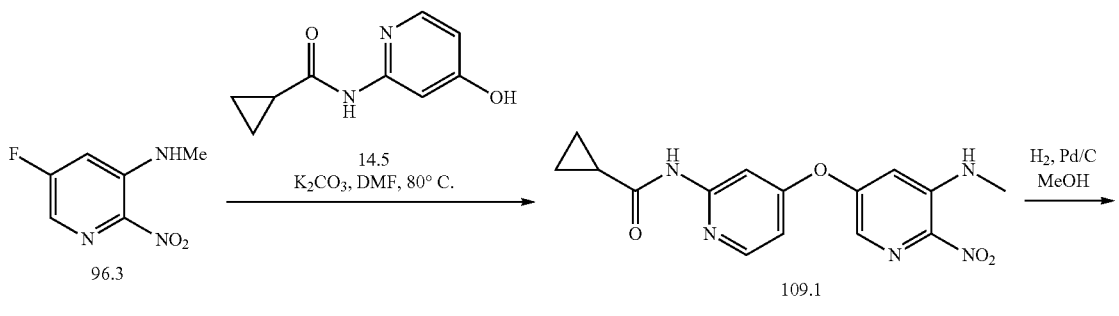

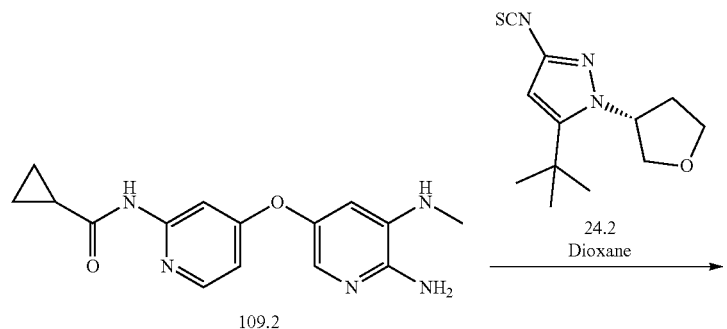

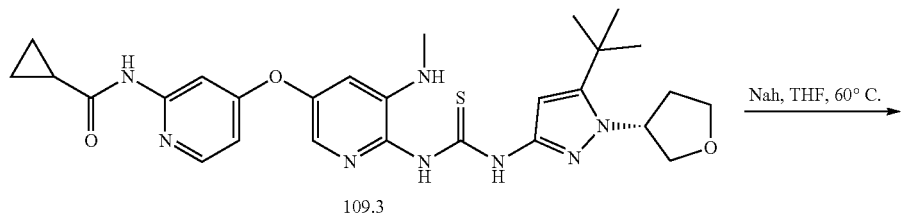

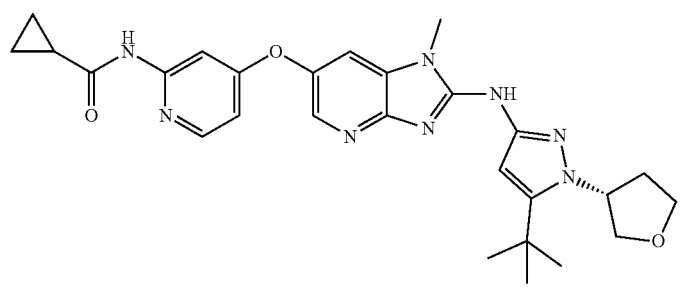

Synthesis of compound 109.1. A mixture of 96.3 (0.460 g, 2.58 mmol, 1.0 equiv), 14.5 (0.441 g, 2.58 mmol, 1.0 equiv) and potassium carbonate (1.068 g, 7.74 mmol, 3.0 equiv) in DMF (5 mL) was stirred at 80° C. for 12 h. It was cooled to room temperature, poured over ice-water and extracted with ethyl acetate. The combined organic layers were washed with brine solution, dried over anhydrous sodium sulfate, filtered and concentrated under reduced pressure. The residue was purified by flash column chromatography on silica gel (CombiFlash®, 35-40% ethyl acetate in hexane). MS (ES): m/z 330.3 [M+H]$^+$.

Synthesis of compound 109.2. Compound 109.2 was prepared from 109.1 following the procedure described in the synthesis of compound Int-2. The product was purified by flash column chromatography on silica gel (CombiFlash®, 45-50% ethyl acetate in hexane). MS (ES): m/z 300.3 [M+H]$^+$.

Synthesis of compound 109.3. Compound 109.3 was prepared from compound 109.2 and 24.2 following the procedure described in the synthesis of compound 104.1. The product was purified by flash column chromatography on silica gel (CombiFlash®, 2.4% methanol in dichloromethane). MS (ES): m/z 551.6 [M+H]$^+$.

Synthesis of I-109. To a solution of 109.3 (0.100 g, 0.181 mmol, 1.0 equiv) in THF (5 mL) was added sodium hydride (0.036 g, 0.905 mmol, 5.0 equiv). The reaction mixture was stirred at 60° C. for 16 h. It was cooled to room temperature, poured over ice-water and extracted with ethyl acetate. The combined organic layers were washed with brine solution, dried over anhydrous sodium sulfate, filtered and concentrated under reduced pressure. The residue was purified by preparative HPLC to afford I-109. MS (ES): m/z: 517.20 [M+H]$^+$, Chiral HPLC purity: 99%, $^1$H NMR (DMSO-d$_6$, 400 MHz): δ 10.84 (s, 1H), 9.92 (s, 1H), 8.20-8.18 (d, J=6.0 Hz, 1H), 7.96 (s, 1H), 7.64-7.63 (d, J=2.4 Hz, 2H), 6.71-6.69 (m, 1H), 6.59 (s, 1H), 5.27-5.24 (m, 1H), 4.12-4.06 (m, 2H), 3.88-3.83 (m, 2H), 3.67 (s, 3H), 2.39-2.34 (m, 1H), 2.28-2.20 (m, 1H), 1.41 (s, 9H), 1.20-1.16 (m, 1H), 0.77-0.75 (m, 4H).

Example 110: (S)—N-(4-((2-((5-(tert-butyl)-1-(tetrahydrofuran-3-yl)-1H-pyrazol-3-yl)amino)-1-methyl-1H-imidazo[4,5-b]pyridin-6-yl)oxy)pyridin-2-yl)cyclopropanecarboxamide

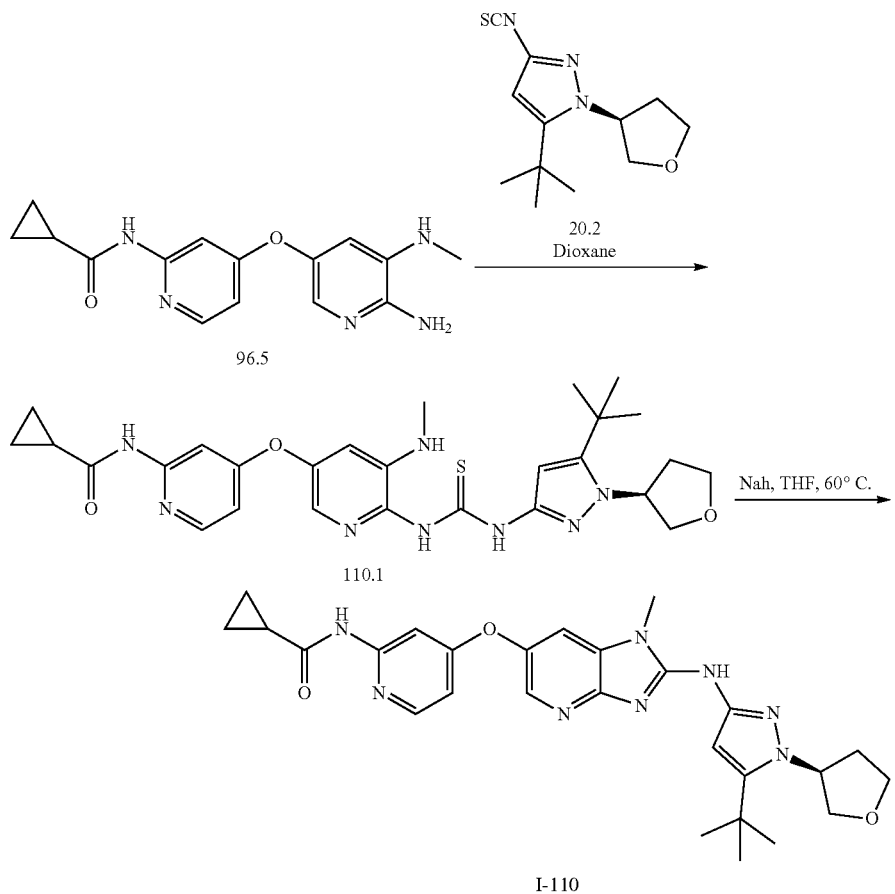

Synthesis of compound 110.1. Compound 110.1 was prepared from compound 109.2 and 20.2 following the procedure described in the synthesis of compound 104.1. The product was purified by flash column chromatography on silica gel (CombiFlash®, 2.4% methanol in dichloromethane). MS (ES): m/z 551.6 [M+H]$^+$.

Synthesis of I-110. Compound I-110 was prepared from compound 110.1 following the procedure described in the synthesis of compound I-109. The product was purified by preparative HPLC to afford I-110. MS (ES): m/z: 517.16 [M+H]$^+$, Chiral HPLC purity: 100%, $^1$H NMR (DMSO-d$_6$, 400 MHz): δ 10.84 (s, 1H), 9.90 (s, 1H), 8.19-8.18 (d, J=6.0 Hz, 1H), 7.96-7.95 (d, J=2.4 Hz, 1H), 7.64-7.63 (d, J=2.4 Hz, 2H), 6.71-6.69 (m, 1H), 6.60 (s, 1H), 5.29-5.23 (m, 1H), 4.11-4.04 (m, 2H), 3.88-3.83 (m, 2H), 3.67 (s, 3H), 2.40-2.32 (m, 1H), 2.28-2.20 (m, 1H), 1.41 (s, 9H), 1.20-1.18 (m, 1H), 0.77-0.75 (m, 4H).

Example 111: (S)—N-(4-((2-((5-(tert-butyl)-1-(tetrahydrofuran-3-yl)-1H-pyrazol-3-yl)amino)-1,7-dimethyl-1H-imidazo[4,5-b]pyridin-6-yl)oxy)pyridin-2-yl)acetamide

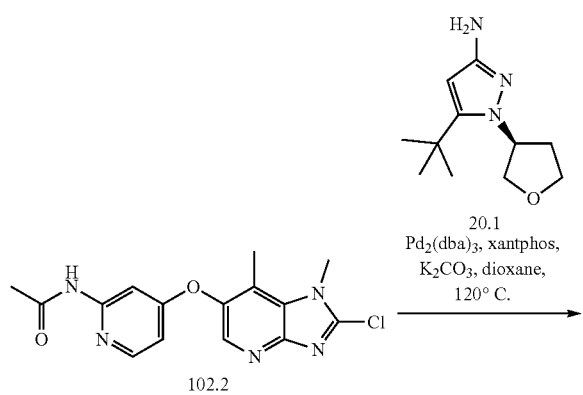

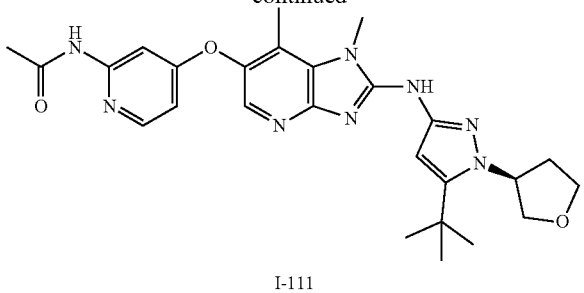

I-111

Synthesis of I-111. Compound I-111 was prepared from compound 102.2 and 20.1 following the procedure described in the synthesis of compound I-108. The product was purified by flash column chromatography on silica gel (CombiFlash®, 4.0% methanol in dichloromethane). MS (ES): m/z: 505.17 [M+H]$^+$, Chiral HPLC purity: 96%, $^1$H NMR (DMSO-d$_6$, 400 MHz): 10.24 (s, 1H), 9.46 (s, 1H), 8.15-8.14 (d, J=5.6 Hz, 1H), 7.87 (s, 1H), 7.60 (s, 1H), 6.58-6.55 (m, 2H), 5.22 (s, 1H), 4.11-4.09 (m, 2H), 3.86 (bs, 5H), 2.42 (s, 3H), 2.35 (bs, 1H), 2.30-2.27 (m, 1H), 2.05 (s, 3H), 1.42 (s, 9H).

Example 112: (S)—N-(4-((2-((5-(tert-butyl)-1-((tetrahydrofuran-3-yl)methyl)-1H-pyrazol-3-yl)amino)-1-methyl-1H-imidazo[4,5-b]pyridin-6-yl)oxy)pyridin-2-yl)acetamide and (R)—N-(4-((2-((5-(tert-butyl)-1-((tetrahydrofuran-3-yl)methyl)-1H-pyrazol-3-yl)amino)-1-methyl-1H-imidazo[4,5-b]pyridin-6-yl)oxy)pyridin-2-yl)acetamide

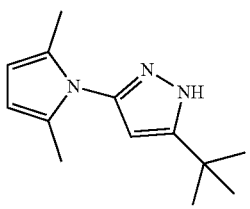

19.2

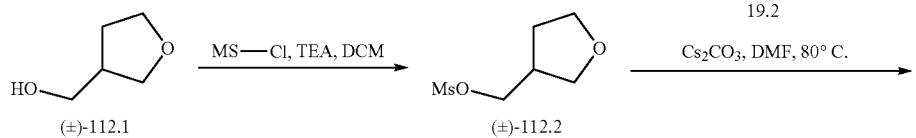

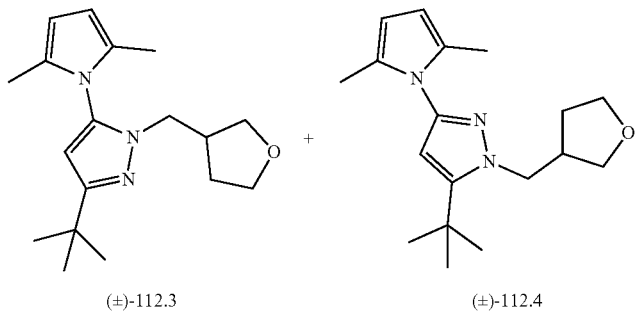

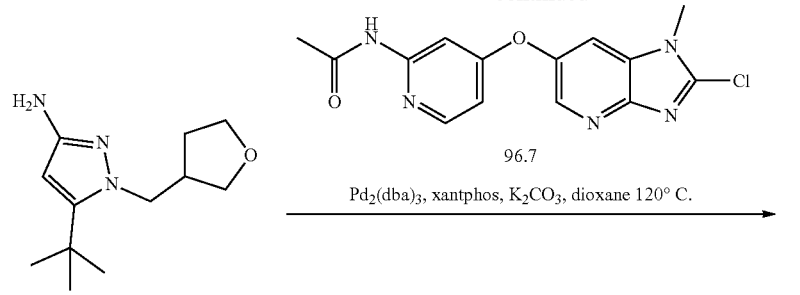

(±)-112.5

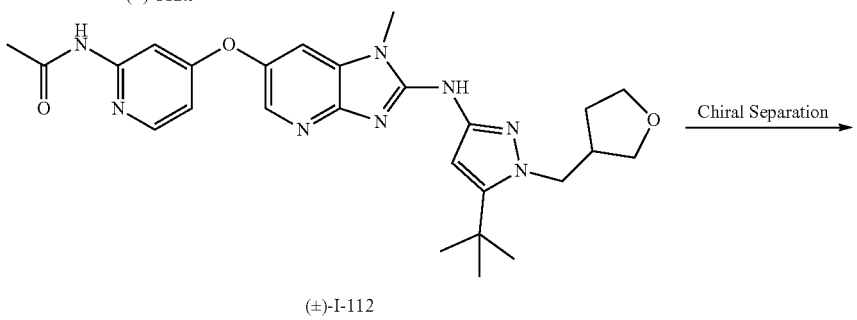

(±)-I-112

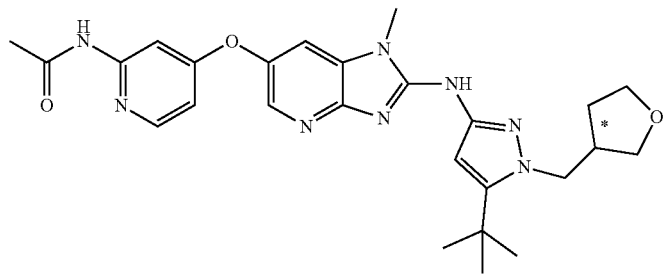

I-112-a and I-112-b

Synthesis of compound (±)-112.2. To a solution of (tetrahydrofuran-3-yl)methanol ((±)-112.1) (5.0 g, 48.96 mmol, 1.0 equiv) and triethylamine (20.5 mL, 146.88 mmol, 3.0 equiv) in dichloromethane (50 mL) at 0° C. was added MsCl (4.56 mL, 58.75 mmol, 1.2 equiv). The reaction mixture was stirred at room temperature for 2 h. It was poured over ice-water, stirred and extracted with dichloromethane. The combined organic layers were washed with saturated sodium bicarbonate followed by brine, dried over anhydrous sodium sulfate, filtered and concentrated under reduced pressure to afford (±)-112.2. MS (ES): m/z 181.2 [M+H]$^+$.

Synthesis of compound (±)-112.4. Compound (±)-112.4 was prepared from compound (±)-112.2 and 19.2 following the procedure described in the synthesis of compound 28.7. The product was purified by flash column chromatography on silica gel (CombiFlash®, 8-12% ethyl acetate in hexane). MS (ES): m/z 302.3 [M+H]$^+$.

Synthesis of compound (±)-112.5. Compound (±)-112.5 was prepared from compound (±)-112.4 following the procedure described in the synthesis of compound 19.6. The product was purified by flash column chromatography on silica gel (CombiFlash®, 2-3% methanol in dichloromethane) to afford (±)-112.5. MS (ES): m/z 224.3 [M+H]$^+$.

Synthesis of compound (±)-112. Compound (±)-112 was prepared from compound (±)-112.5 and 96.7 following the procedure described in the synthesis of compound I-108. The product was purified by flash column chromatography on silica gel (CombiFlash®, 4.0% methanol in dichloromethane). MS (ES): m/z: 505.6 [M+H]$^+$.

I-112-a and I-112-b. Enantiomers of (±)-I-112 were separated on HPLC (CHIRALPAK IH (250 mm×21 mm, 5 μm); eluant: (A) 0.1% DEA in n-hexane (B) 0.1% DEA in propane-2-ol:methanol (30:70); flow rate: 20 mL/min) to afford first eluting fraction (I-112-a) and second eluting fraction (I-112-b). (*Absolute stereochemistry not determined.)

I-112-a. MS (ES): m/z: 503.1 [M−H]$^+$, $^1$H NMR (DMSO-d$_6$, 400 MHz): δ 10.52 (s, 1H), 9.80 (s, 1H), 8.17-8.16 (d, J=5.6 Hz, 1H), 7.88 (s, 1H), 7.66 (s, 1H), 7.50 (s, 1H), 6.66-6.64 (m, 1H), 6.59 (bs, 1H), 4.07-4.03 (m, 2H), 3.84-3.80 (m, 1H), 3.73-3.65 (m, 1H), 3.61 (s, 3H), 3.58-3.57 (m, 2H), 2.89 (bs, 1H), 2.04 (s, 3H), 1.74-1.69 (m, 1H), 1.56 (bs, 1H), 1.39 (s, 9H).

I-112-b. MS (ES): m/z: 505.18 [M+H]$^+$, $^1$H NMR (DMSO-d$_6$, 400 MHz): δ 10.52 (s, 1H), 9.80 (s, 1H), 8.17-8.16 (d, J=5.6 Hz, 1H), 7.88 (s, 1H), 7.66 (s, 1H), 7.50 (s, 1H), 6.66-6.64 (m, 1H), 6.59 (bs, 1H), 4.07-4.03 (m, 2H), 3.84-3.80 (m, 1H), 3.73-3.65 (m, 1H), 3.61 (s, 3H), 3.58-3.57 (m, 2H), 2.89 (bs, 1H), 2.04 (s, 3H), 1.74-1.69 (m, 1H), 1.56 (bs, 1H), 1.39 (s, 9H).

Example 113: N-(4-((2-((5-(tert-butyl)-1-(1-(2-fluoroethyl)piperidin-4-yl)-1H-pyrazol-3-yl)amino)-1-methyl-1H-imidazo[4,5-b]pyridin-6-yl)oxy)pyridin-2-yl)acetamide
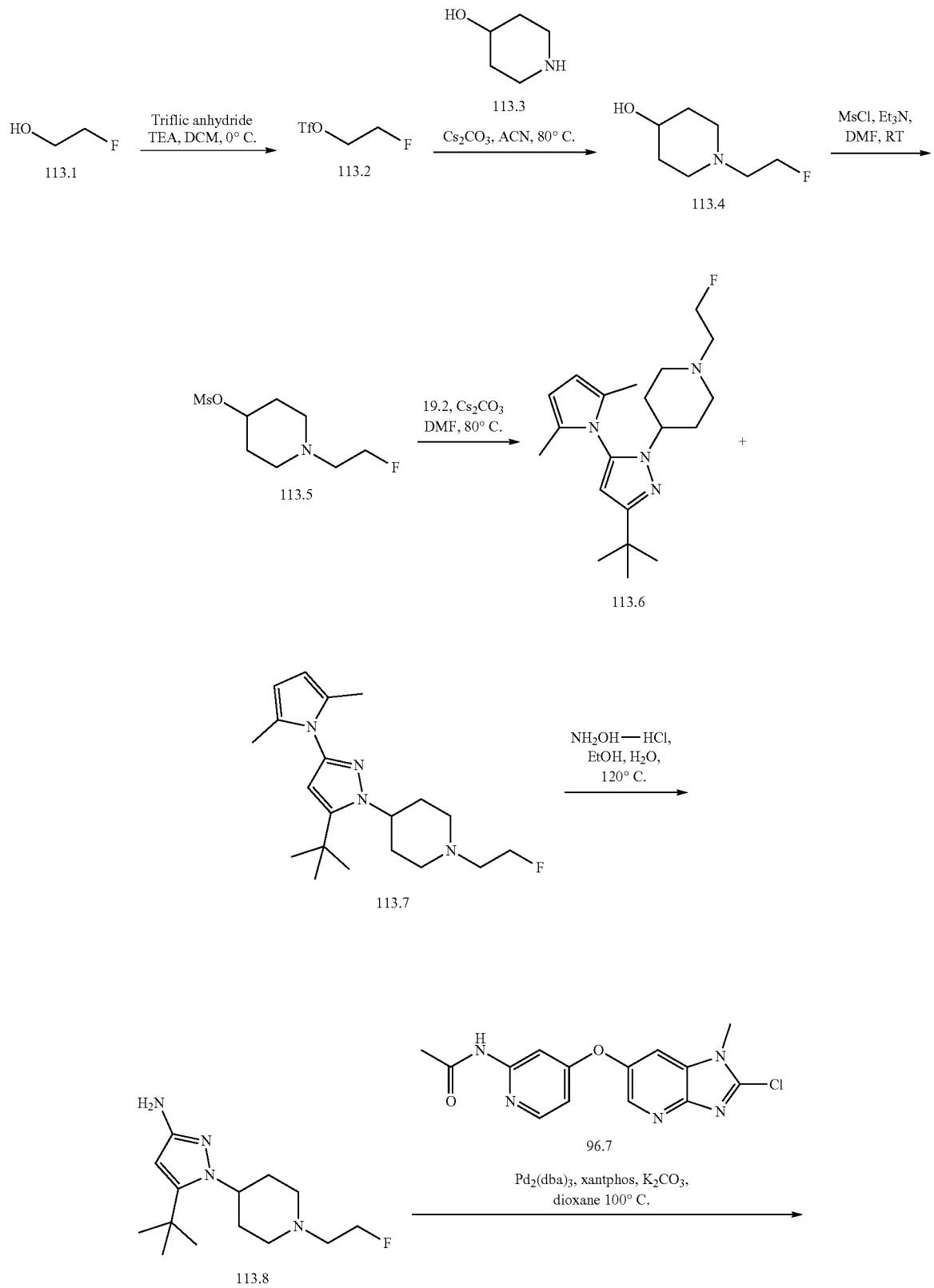

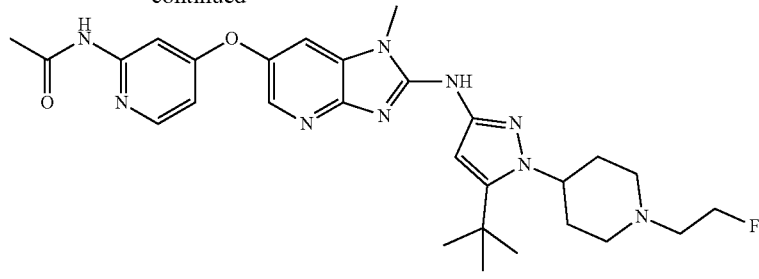

I-113

Synthesis of compound 113.2. To a solution of 113.1 (8.0 g, 124.88 mmol, 1.0 equiv) and triethylamine (19.1 mL, 137.36 mmol, 1.1 equiv) in dichloromethane (80 mL) at 0° C. was added triflic anhydride (22.4 mL, 133.6 mmol, 1.07 equiv) slowly. The reaction mixture was stirred at 0° C. for 30 min. It was poured over ice-water, stirred and extracted with dichloromethane. The combined organic layers were washed with saturated sodium bicarbonate followed by brine, dried over anhydrous sodium sulfate, filtered and concentrated under reduced pressure to afford 113.2, which was used in the next reaction without further purification.

Synthesis of compound 113.4. A mixture of 113.3 (1.5 g, 14.83 mmol, 1.0 equiv), 113.2 (4.36 g, 22.24 mmol, 1.5 equiv) and cesium carbonate (9.63 g, 29.66 mmol, 2.0 equiv) in acetonitrile (15 mL) was stirred at 80° C. for 12 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 2-3% methanol in dichloromethane) to afford 113.4. $^1$H NMR (CDCl$_3$, 400 MHz): δ 4.68-4.66 (m, 1H), 4.56-4.54 (m, 1H), 3.78-3.76 (m, 1H), 2.92-2.87 (m, 2H), 2.80-2.77 (m, 1H), 2.73-2.70 (m, 1H), 2.35-2.31 (m, 2H), 1.98-1.94 (m, 2H), 1.71-1.62 (m, 2H).

Synthesis of compound 113.5. To a solution of 113.4 (1.3 g, 8.83 mmol, 1.0 equiv) and triethylamine (3 mL, 22.07 mmol, 2.5 equiv) in dichloromethane (15 mL) at 0° C. was added MSCl (0.82 mL, 10.59 mmol, 1.2 equiv). The reaction mixture was stirred at room temperature for 1 h. It was poured over ice-water, stirred and extracted with dichloromethane. The combined organic layers were washed with saturated sodium bicarbonate followed by brine, dried over anhydrous sodium sulfate, filtered and concentrated under reduced pressure to afford 113.5. $^1$H NMR (CDCl$_3$, 400 MHz): δ 4.82 (bs, 1H), 4.70-4.67 (m, 1H), 4.58-4.55 (m, 1H), 3.07 (s, 3H), 2.86-2.82 (m, 3H), 2.75 (bs, 2H), 2.53 (bs, 2H), 2.11 (bs, 2H), 2.02-1.99 (m, 2H).

Synthesis of compound 113.7. Compound 113.7 was prepared from compound 113.5 and 19.2 following the procedure described in the synthesis of compound 28.7. The product was purified by flash column chromatography on silica gel (CombiFlash®, 50-55% ethyl acetate in hexane). MS (ES): m/z 347.5 [M+H]$^+$.

Synthesis of compound 113.8. Compound 113.8 was prepared from compound 113.7 following the procedure described in the synthesis of compound 19.6. The product was purified by flash column chromatography on silica gel (CombiFlash®, 4-5% methanol in dichloromethane). MS (ES): m/z 269.4 [M+H]$^+$.

Synthesis of I-113. A mixture of 96.7 (0.059 g, 0.186 mmol, 1.0 equiv), 113.8 (0.050 g, 0.186 mmol, 1.0 equiv) and potassium carbonate (0.077 g, 0.558 mmol, 3.0 equiv) in 1,4-dioxane (2 mL) was degassed by bubbling argon through for 10 min. 4,5-Bis(diphenylphosphino)-9,9-dimethylxanthene (0.021 g, 0.037 mmol, 0.2 equiv) and tris (dibenzylideneacetone)dipalladium(0) (0.017 g, 0.0186 mmol, 0.1 equiv) were added, and degassed for 5 min. The reaction mixture was stirred at 100° C. for 4 h. It was cooled to room temperature, transferred into water and extracted with ethyl acetate. The combined organic layers were washed with brine solution, dried over anhydrous sodium sulfate, filtered and concentrated under reduced pressure. The residue was purified by flash column chromatography on silica gel (CombiFlash®, 6-7% methanol in dichloromethane) to afford I-113. MS (ES): m/z: 550.2 [M+H]$^+$, $^1$H NMR (DMSO-d$_6$, 400 MHz): δ 10.54 (s, 1H), 9.84 (s, 1H), 8.18-8.16 (d, J=5.6 Hz, 1H), 7.96-7.95 (d, J=2.4 Hz, 1H), 7.66-7.50 (m, 2H), 6.67-6.65 (m, 1H), 6.55 (s, 1H), 4.62-4.50 (m, 2H), 4.24 (bs, 1H), 3.67 (s, 3H), 3.02 (bs, 2H), 2.73-2.68 (m, 3H), 2.24-2.19 (m, 4H), 2.03 (bs, 2H), 1.81 (bs, 2H), 1.39 (s, 9H).

Example 114: N-(4-((2-((5-(tert-butyl)-1-(1-(2,2-difluoroethyl)piperidin-4-yl)-1H-pyrazol-3-yl)amino)-1-methyl-1H-imidazo[4,5-b]pyridin-6-yl)oxy)pyridin-2-yl)acetamide

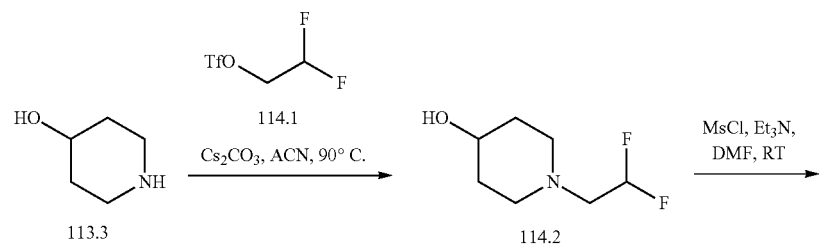

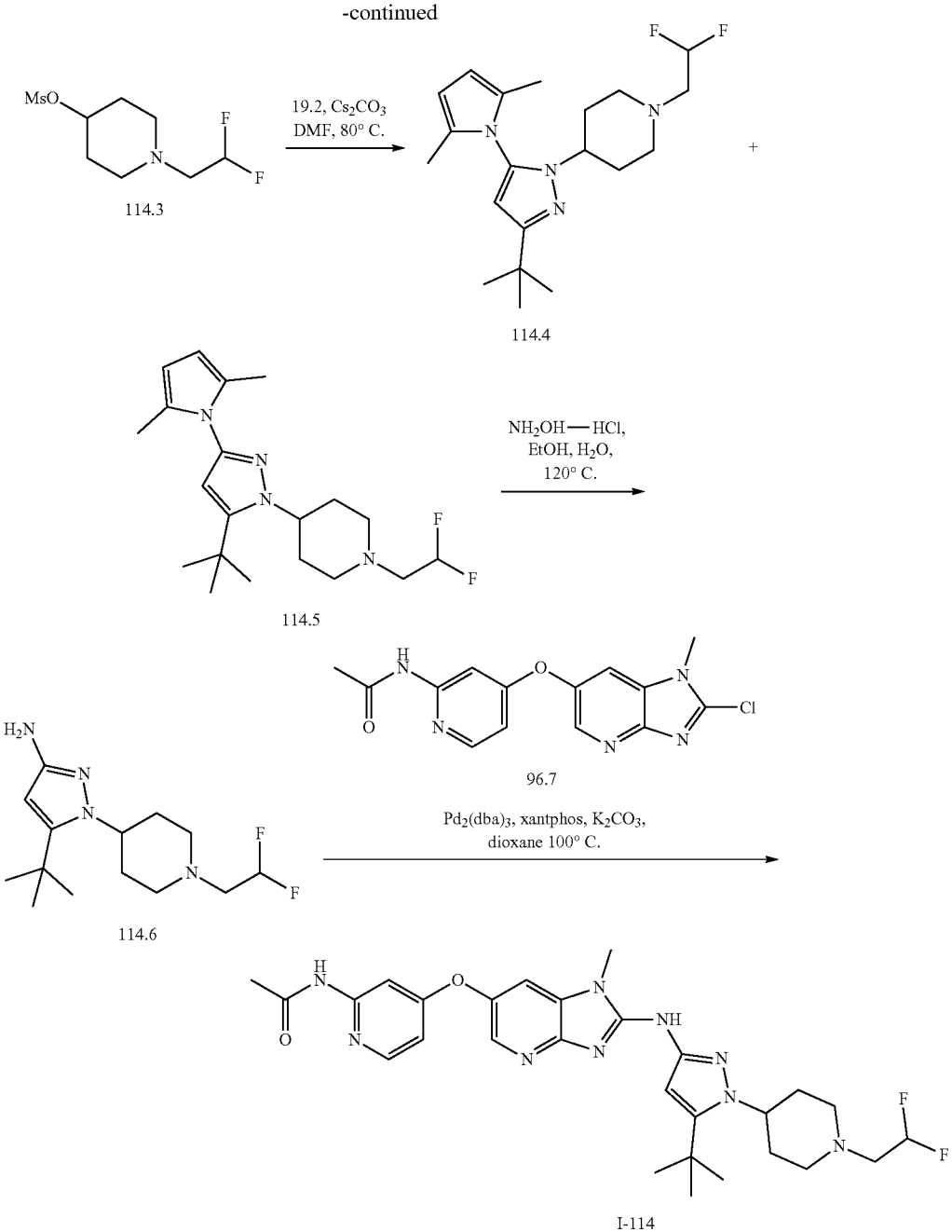

Synthesis of compound 114.2. A mixture of 113.3 (1.5 g, 14.83 mmol, 1.0 equiv), 2,2-difluoroethyl trifluoromethanesulfonate (114.1) (3.18 g, 14.83 mmol, 1.0 equiv) and cesium carbonate (9.63 g, 29.66 mmol, 2.0 equiv) in acetonitrile (30 mL) was stirred at 90° C. for 4 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 60% ethyl acetate in hexane) to afford 114.2. $^1$H NMR (CDCl$_3$, 400 MHz): δ 6.06-5.75 (m, 1H), 3.74 (bs. 1H), 2.89-2.86 (m, 2H), 2.81-2.72 (m, 2H), 2.42-2.36 (m, 2H), 1.94-1.90 (m, 2H), 1.68-1.61 (m, 3H).

Synthesis of compound 114.3 To a solution of 114.2 (1.1 g, 6.66 mmol, 1.0 equiv) and triethylamine (1.8 mL, 13.32 mmol, 2.0 equiv) in dichloromethane (15 mL) at 0° C. was added MSCl (0.62 mL, 7.99 mmol, 1.2 equiv). The reaction mixture was stirred at room temperature for 12 h. It was poured over ice-water, stirred and extracted with dichloromethane. The combined organic layers were washed with saturated sodium bicarbonate followed by brine, dried over anhydrous sodium sulfate, filtered and concentrated under reduced pressure. The residue was purified by flash column chromatography on silica gel (CombiFlash®, 40% ethyl acetate in hexane) to afford 114.3. $^1$H NMR (CDCl$_3$, 400 MHz): δ 6.26-5.98 (m, 1H), 4.68 (bs, 1H), 3.19 (s, 3H), 2.77-2.69 (m, 4H), 2.47-2.42 (m, 2H), 1.92 (bs, 2H), 1.73-1.68 (m, 2H).

Synthesis of compound 114.5. Compound 114.5 was prepared from compound 114.3 and 19.2 following the procedure described in the synthesis of compound 28.7. The product was purified by flash column chromatography on silica gel (CombiFlash®, 6-8% ethyl acetate in hexane). MS (ES): m/z 365.5 [M+H]$^+$.

Synthesis of compound 114.6. Compound 114.6 was prepared from compound 114.5 following the procedure described in the synthesis of compound 19.6. The product was purified by flash column chromatography on silica gel (CombiFlash®, 4-5% methanol in dichloromethane). MS (ES): m/z 287.4 [M+H]$^+$.

Synthesis of I-114. Compound I-114 was prepared from compound 114.6 following the procedure described in the synthesis of compound I-113. The product was purified by flash column chromatography on silica gel (CombiFlash®, 6% methanol in dichloromethane). MS (ES): m/z: 568.6 [M+H]$^+$, $^1$H NMR (DMSO-$d_6$, 400 MHz): δ 10.53 (s, 1H), 9.83 (s, 1H), 8.19-8.17 (m, 1H), 7.97-7.96 (d, J=2.8 Hz, 1H), 7.67-7.66 (d, J=2.4 Hz, 1H), 7.64-7.63 (d, J=2.8 Hz, 1H), 6.67-6.65 (m, 1H), 6.55 (s, 1H), 6.30-6.02 (m, 1H), 4.30-4.20 (m, 1H), 3.67 (s, 3H), 3.04-3.01 (m, 2H), 2.84-2.75 (m, 2H), 2.34-2.33 (m, 2H), 2.24-2.19 (m, 2H), 2.04 (s, 3H), 1.79-1.77 (m, 2H), 1.39 (s, 9H).

Example 115: N-(4-((2-((5-(tert-butyl)-1-((1r,3r)-3-hydroxycyclobutyl)-1H-pyrazol-3-yl)amino)-1-methyl-1H-imidazo[4,5-b]pyridin-6-yl)oxy)pyridin-2-yl)acetamide

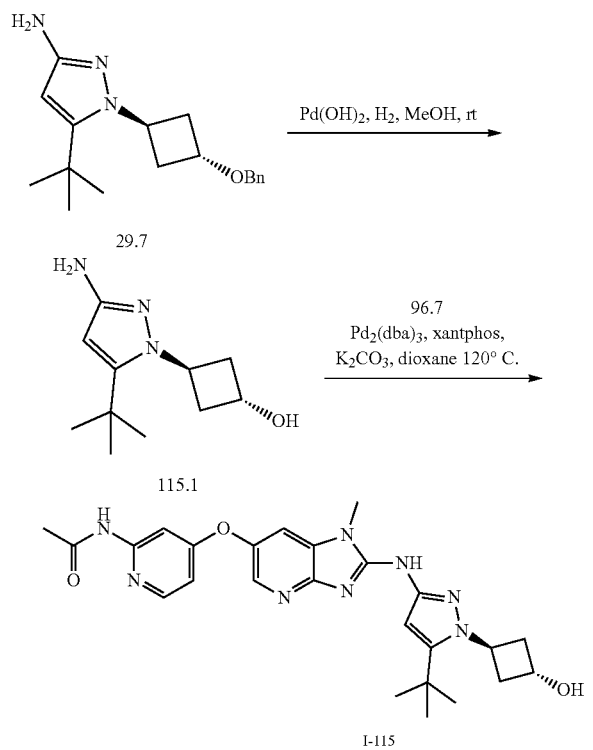

Synthesis of compound 115.1. A mixture of compound 29.7 (0.130 g, 0.434 mmol, 1.0 equiv) and 20% palladium hydroxide (0.130 g) in methanol (5 mL) was purged with hydrogen and stirred under 1 atm of hydrogen at rt for 6 h. The reaction mixture was filtered through a pad of Celite® and rinsed with methanol. The filtrate was concentrated under reduced pressure to afford 115.1. MS (ES): m/z: 210.3 [M+H]$^+$.

Synthesis of I-115. Compound I-115 was prepared from compound 115.1 and 96.7 following the procedure described in the synthesis of compound I-108. The product was purified by flash column chromatography on silica gel (CombiFlash®, 4.0% methanol in dichloromethane). MS (ES): m/z: 491.13 [M+H]$^+$, $^1$H NMR (DMSO-$d_6$, 400 MHz): 10.54 (s, 1H), 9.87 (s, 1H), 8.18-8.17 (d, J=5.6 Hz, 1H), 7.96 (s, 1H), 7.66-7.63 (d, 2H), 6.66-6.59 (m, 2H), 5.22-5.18 (m, 2H), 4.47 (bs, 1H), 3.68 (s, 3H), 2.73-2.68 (m, 2H), 2.34 (bs, 2H), 2.04 (s, 3H), 1.37 (s, 9H).

Example 116: N-(4-((2-((5-(tert-butyl)-1-((1s,3s)-3-hydroxycyclobutyl)-1H-pyrazol-3-yl)amino)-1-methyl-1H-imidazo[4,5-b]pyridin-6-yl)oxy)pyridin-2-yl)acetamide

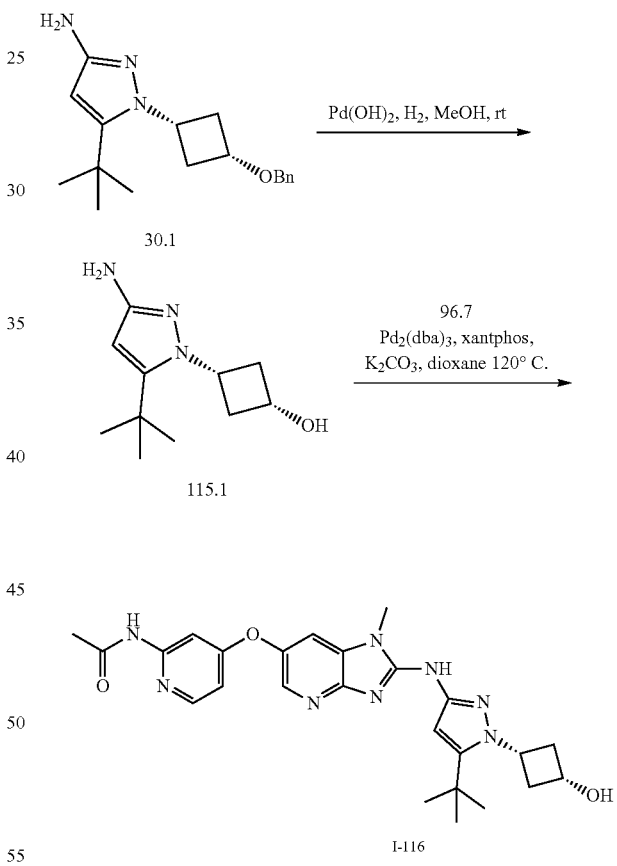

Synthesis of I-116. Compound I-116 was prepared from compound 30.1 following the procedures described in the synthesis of compound I-115. The product was purified by preparative HPLC. MS (ES): m/z: 492.3 [M+H]$^+$, $^1$H NMR (DMSO-$d_6$, 400 MHz): 10.53 (s, 1H), 9.87 (s, 1H), 8.19-8.17 (d, J=5.6 Hz, 1H), 7.97 (s, 1H), 7.67 (s, 1H), 7.64-7.63 (d, J=2.4 Hz, 1H), 6.67-6.66 (m, 1H), 6.57 (s, 1H), 5.20-5.19 (d, J=5.2 Hz, 1H), 4.56-4.52 (m, 1H), 4.12-4.02 (m, 1H), 3.69 (s, 3H), 3.19-3.18 (m, 2H), 2.68-2.65 (m, 2H), 2.05 (s, 3H), 1.38 (s, 9H).

Example I-117: (R)—N-(4-((2-((5-(tert-butyl)-1-((tetrahydrofuran-3-yl)methyl)-1H-pyrazol-3-yl)amino)-1,7-dimethyl-1H-imidazo[4,5-b]pyridin-6-yl)oxy)pyridin-2-yl)acetamide and (S)—N-(4-((2-((5-(tert-butyl)-1-((tetrahydrofuran-3-yl)methyl)-1H-pyrazol-3-yl)amino)-1,7-dimethyl-1H-imidazo[4,5-b]pyridin-6-yl)oxy)pyridin-2-yl)acetamide

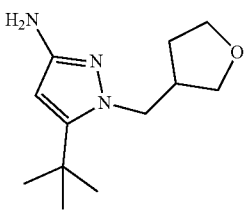

(±)-112.5

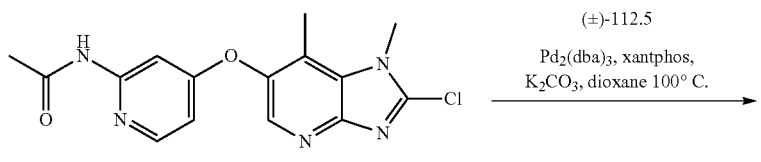

102.2

Pd₂(dba)₃, xantphos, K₂CO₃, dioxane 100° C.

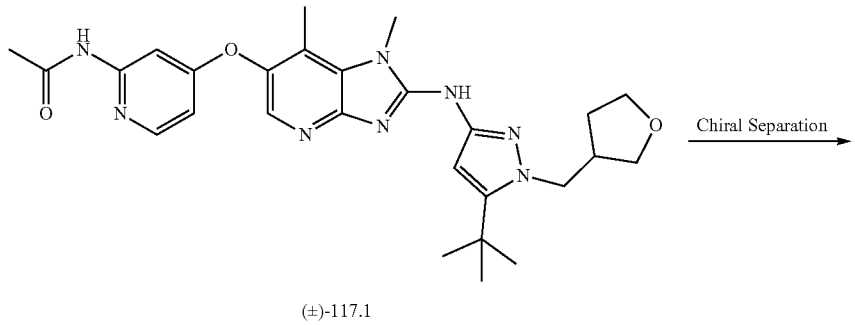

(±)-117.1

Chiral Separation

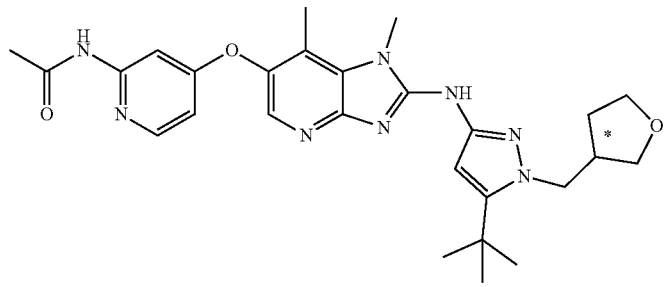

I-117-a and I-117-b

Synthesis of compound (±)-117.1. Compound (±)-117.1 was prepared from compound 102.2 and (±)-112.5 following the procedure described in the synthesis of compound I-113. The product was purified by flash column chromatography on silica gel (CombiFlash®, 4.1% methanol in dichloromethane). MS (ES): m/z: 519.6 [M+H]$^+$.

I-117-a and I-117-b. Enantiomers of (±)-117.1 were separated on HPLC (CHIRALPAK IH (250 mm×21 mm, 5 μm); eluant: (A) 0.1% DEA in n-hexane (B) 0.1% DEA in propane-2-ol:methanol (20:80); flow rate: 18 mL/min) to afford first eluting fraction (I-117-a) and second eluting fraction (I-117-b). (*Absolute stereochemistry not determined.)

I-117-a. MS (ES): m/z: 519.15 [M+H]$^+$, $^1$H NMR (DMSO-d$_6$, 400 MHz): δ 10.54 (s, 1H), 9.71 (s, 1H), 8.16-8.15 (d, J=5.6 Hz, 1H), 7.87 (s, 1H), 7.60 (s, 1H), 6.58 (bs, 2H), 4.08-4.01 (m, 2H), 3.85 (s, 3H), 3.73-3.58 (m, 2H), 2.39 (s, 3H), 2.03 (s, 3H), 1.74-1.71 (m, 1H), 1.56 (bs, 2H), 1.38 (s, 9H), 1.24 (bs, 2H).

I-117-b. MS (ES): m/z: 519.16 [M+H]$^+$, $^1$H NMR (DMSO-d$_6$, 400 MHz): δ 10.54 (s, 1H), 9.72 (s, 1H), 8.17-8.15 (d, J=5.6 Hz, 1H), 7.87 (s, 1H), 7.60 (s, 1H), 6.58-6.56 (m, 2H), 4.12-4.04 (m, 2H), 3.85 (s, 3H), 3.73-3.58 (m, 2H), 2.39 (s, 3H), 2.03 (s, 3H), 1.74-1.69 (m, 1H), 1.57 (bs, 2H), 1.38 (s, 9H), 1.24 (bs, 2H).

Example 118: (R)—N-(4-((2-((5-(tert-butyl)-1-(tetrahydrofuran-3-yl)-1H-pyrazol-3-yl)amino)-1-methyl-1H-imidazo[4,5-b]pyridin-6-yl)oxy)pyridin-2-yl)-3-methoxypropanamide
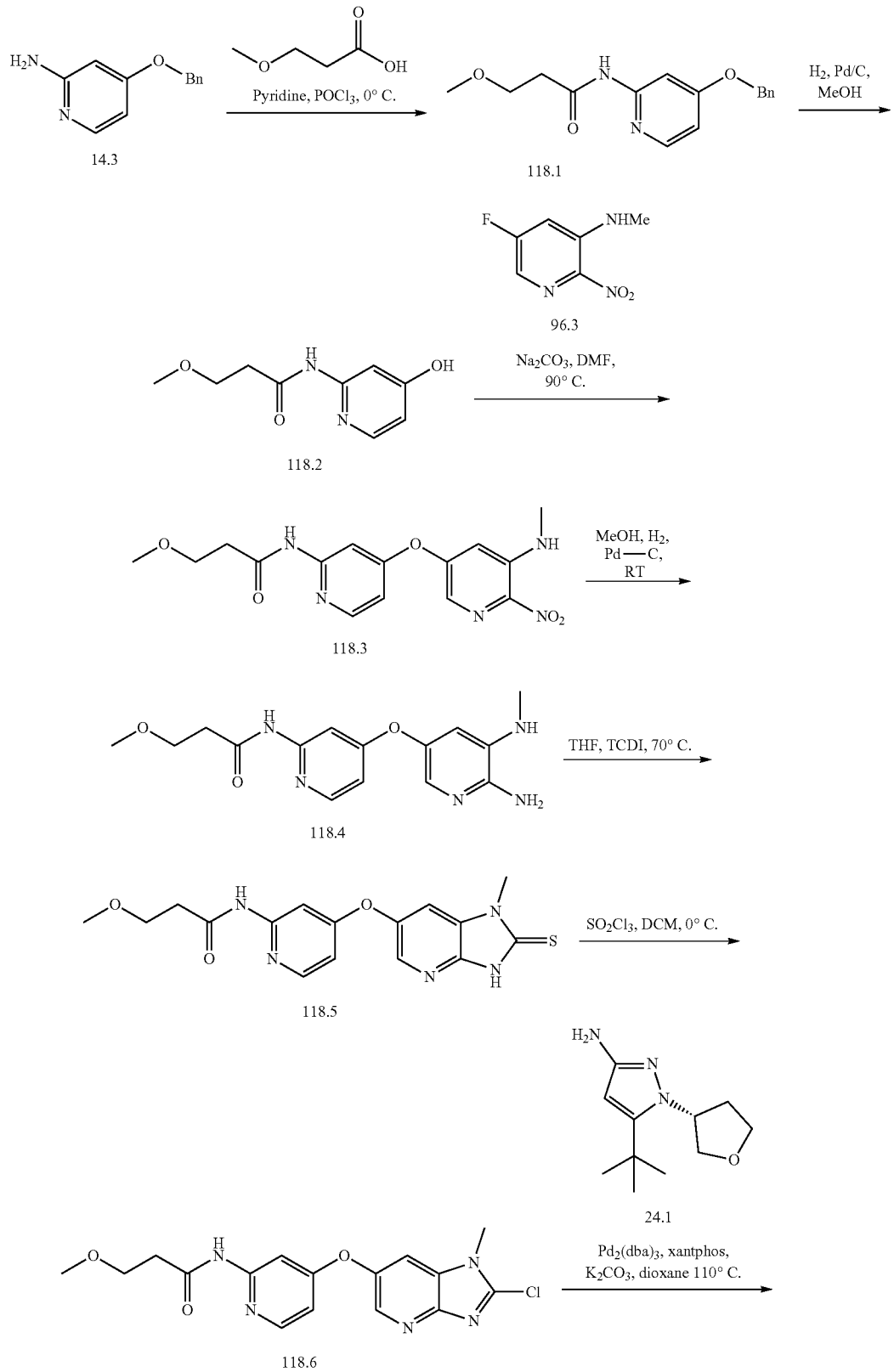

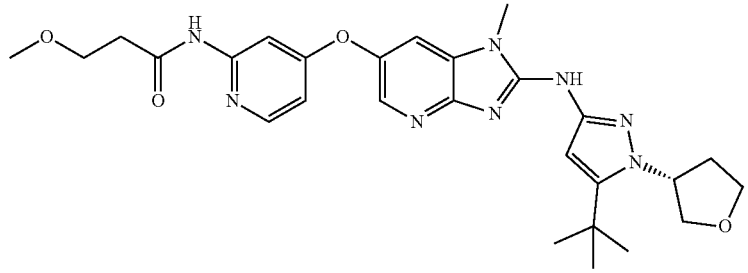

I-118

Synthesis of compound 118.1. To a solution of 14.3 (1.3 g, 6.49 mmol, 1.0 equiv) and 3-methoxypropanoic acid (0.675 g, 6.49 mmol, 1.0 equiv) in dichloromethane (50 mL) at 0° C. was added phosphorous oxychloride (1.3 mL, 1 v/w) dropwise followed by pyridine (1.3 mL, 1 v/w). The reaction mixture was stirred at 0° C. for 3 h. It was poured over ice, neutralized with saturated aqueous sodium bicarbonate solution stirred and extracted with dichloromethane. The combined organic layers were washed with brine, dried over anhydrous sodium sulfate, filtered and concentrated under reduced pressure. The residue was purified by flash column chromatography on silica gel (CombiFlash®, 2% methanol in dichloromethane) to afford 118.1. MS (ES): m/z 287.3 [M+H]$^+$.

Synthesis of compound 118.2. A mixture of compound 118.1 (0.820 g, 2.86 mmol, 1.0 equiv) and 10% palladium on carbon (0.4 g) in methanol (20 mL) was stirred under hydrogen (1 atm) at rt for 2 h. The reaction mixture was filtered through a pad of Celite® and rinsed with methanol. The filtrate was concentrated under reduced pressure. The residue was purified by flash column chromatography on silica gel (CombiFlash®, 3.0% methanol in dichloromethane) to afford 118.2. MS (ES): m/z 197.2 [M+H]$^+$.

Synthesis of compound 118.3. Compound 118.3 was prepared from compound 118.2 and 96.3 following the procedure described in the synthesis of compound 96.4. The product was purified by flash column chromatography on silica gel (CombiFlash®, 2.4-2.6% methanol in dichloromethane). MS (ES): m/z 348.3 [M+H]$^+$.

Synthesis of compound 118.4. Compound 118.4 was prepared from compound 118.3 following the procedure described in the synthesis of compound Int-2. The product was purified by flash column chromatography on silica gel (CombiFlash®, 3.6-3.8% methanol in dichloromethane). MS (ES): m/z 318.4 [M+H]$^+$.

Synthesis of compound 118.5. A solution of 118.4 (0.350 g, 1.1 mmol, 1.0 equiv) and 1,1'-thiocarbonyldiimidazole (0.979 g, 5.5 mmol, 5.0 equiv) in THF (5 mL) was stirred at 70° C. for 1.5 h. It was cooled to room temperature and poured over ice-water. The precipitated solids were collected by filtration and triturated with hexane to afford 118.5. MS (ES): m/z: 360.4 [M+H]$^+$.

Synthesis of compound 118.6. Compound 118.6 was prepared from compound 118.5 following the procedure described in the synthesis of compound 102.2. The product was purified by flash column chromatography on silica gel (CombiFlash®, 2.4% methanol in dichloromethane). MS (ES): m/z 362.8 [M+H]$^+$.

Synthesis of I-118. Compound I-118 was prepared from compound 118.6 and 24.1 following the procedure described in the synthesis of compound I-108. The product was purified by flash column chromatography on silica gel (CombiFlash®, 3.8% methanol in dichloromethane). MS (ES): m/z: 535.19 [M+H]$^+$, $^1$H NMR (DMSO-d$_6$, 400 MHz): δ 10.54 (s, 1H), 9.91 (s, 1H), 8.20-8.18 (d, J=5.6 Hz, 1H), 7.98-7.97 (d, J=2.4 Hz, 1H), 7.68-7.64 (m, 2H), 6.72-6.69 (m, 1H), 6.61 (s, 1H), 5.27 (bs, 1H), 4.11-4.07 (m, 2H), 3.89-3.83 (m, 2H), 3.68 (s, 3H), 3.56-3.53 (m, 2H), 3.21 (s, 3H), 2.60-2.52 (m, 2H), 2.35-2.32 (m, 1H), 2.27-2.22 (m, 1H), 1.42 (s, 9H).

Example 119: (S)—N-(4-((2-((5-(tert-butyl)-1-(tetrahydrofuran-3-yl)-1H-pyrazol-3-yl)amino)-1-methyl-1H-imidazo[4,5-b]pyridin-6-yl)oxy)pyridin-2-yl)-3-methoxypropanamide

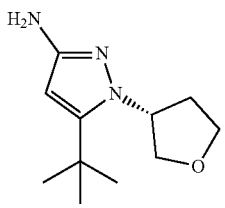

20.1

Pd$_2$(dba)$_3$, xantphos,
K$_2$CO$_3$, dioxane 110° C.

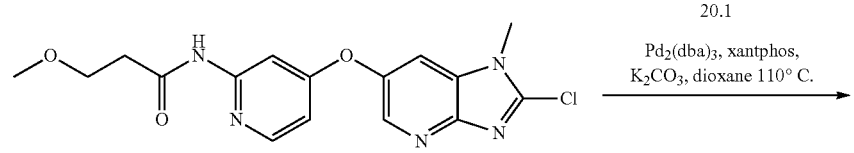

118.6

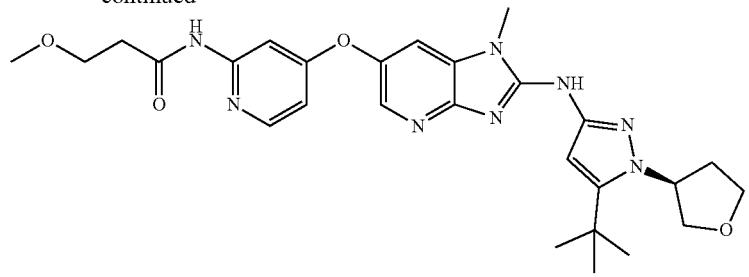
I-119

Synthesis of I-119. Compound I-119 was prepared from compound 118.6 and 20.1 following the procedure described in the synthesis of compound I-108. The product was purified by flash column chromatography on silica gel (CombiFlash®, 4.0% methanol in dichloromethane). MS (ES): m/z: 535.17 [M+H]$^+$, $^1$H NMR (DMSO-d$_6$, 400 MHz): δ 10.54 (s, 1H), 9.91 (s, 1H), 8.20-8.18 (d, J=5.6 Hz, 1H), 7.98-7.97 (d, J=2.4 Hz, 1H), 7.68-7.64 (m, 2H), 6.71-6.69 (m, 1H), 6.61 (s, 1H), 5.27 (bs, 1H), 4.12-4.08 (m, 2H), 3.87-3.83 (m, 2H), 3.68 (s, 3H), 3.56-3.53 (m, 2H), 3.21 (s, 3H), 2.62-2.57 (m, 2H), 2.35-2.34 (m, 1H), 2.26-2.25 (m, 1H), 1.42 (s, 9H).

Example 120: (R)—N-(4-((2-((5-(tert-butyl)-1-((1-(2-fluoroethyl)pyrrolidin-3-yl)methyl)-1H-pyrazol-3-yl)amino)-1-methyl-1H-imidazo[4,5-b]pyridin-6-yl)oxy)pyridin-2-yl)acetamide

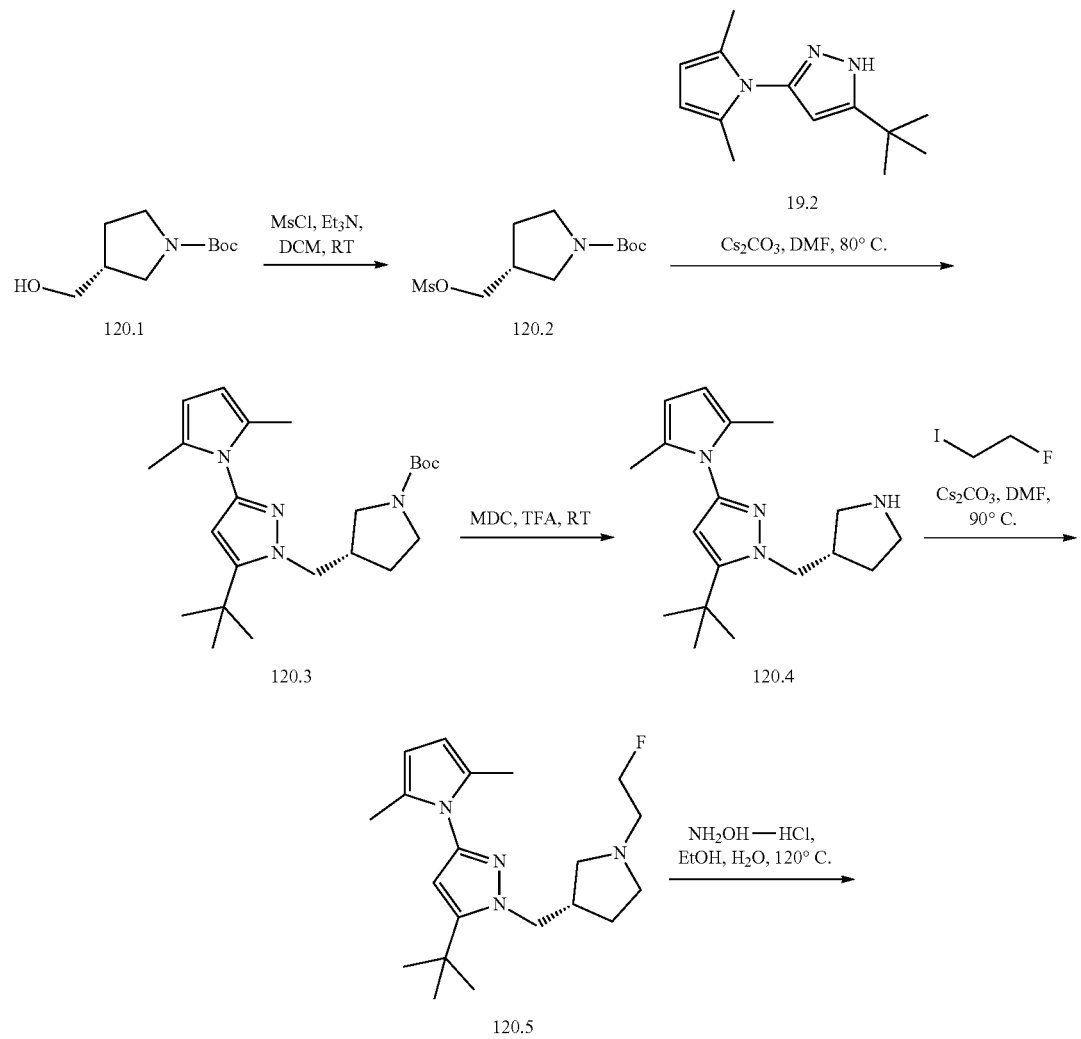

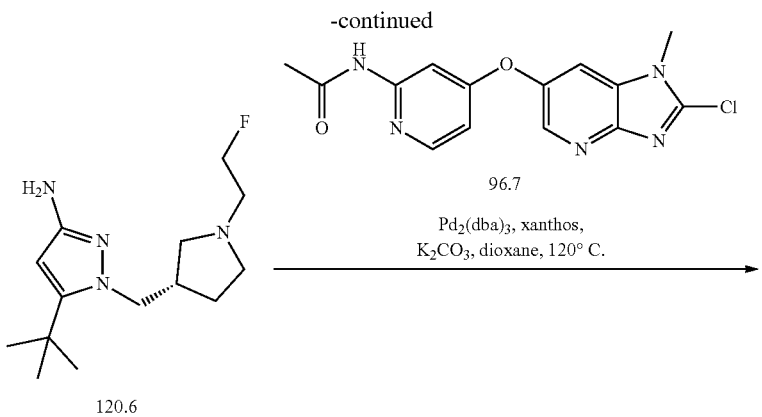

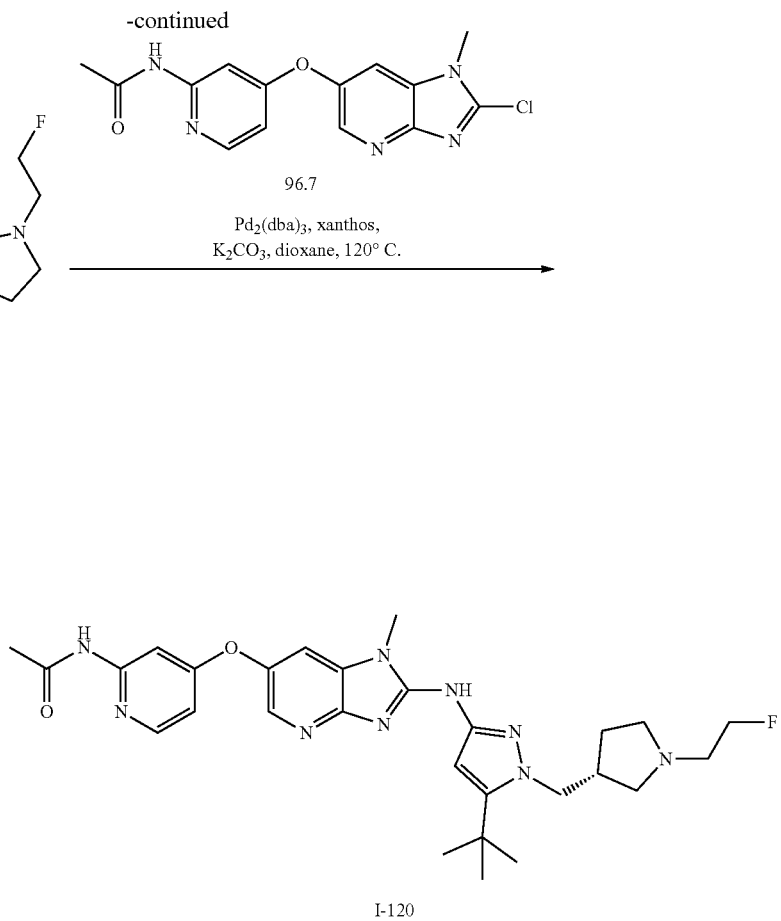

Synthesis of compound 120.2. Compound 120.2 was prepared from compound 120.1 following the procedure described in the synthesis of compound 28.5. The crude product was used in the next step without further purification. $^1$H NMR (DMSO-d$_6$, 400 MHz): δ 4.24-4.15 (m, 2H), 3.44-3.33 (m, 2H), 3.25-3.23 (m, 1H), 3.20 (s, 3H), 3.04-3.01 (m, 1H), 2.55 (bs, 1H), 1.96 (bs, 1H), 1.69-1.64 (m, 1H), 1.41 (s, 9H).

Synthesis of compound 120.3. Compound 120.3 was prepared from compound 120.2 and 19.2 following the procedure described in the synthesis of compound 28.7. The product was purified by flash column chromatography on silica gel (CombiFlash®, 8-10% ethyl acetate in hexane) to afford 120.3. MS (ES): m/z 401.5 [M+H]$^+$.

Synthesis of compound 120.4. To a solution of 120.3 (0.390 g, 0.973 mmol, 1.0 equiv) in dichloromethane (5 mL) was added trifluoroacetic acid (1.95 mL) at 0° C. The reaction mixture was stirred at room temperature for 2 h. It was poured over ice-water, neutralized with saturated aqueous sodium bicarbonate solution and extracted with dichloromethane. The combined organic layers were washed with brine, dried over anhydrous sodium sulfate, filtered and concentrated under reduced pressure to afford 120.4.

Synthesis of compound 120.5. To a solution of 120.4 (0.240 g, 0.798 mmol, 1.0 equiv) and 1-fluoro-2-iodoethane (0.208 g, 1.20 mmol, 1.5 equiv) in DMF (3 mL) was added cesium carbonate (0.518 g, 1.596 mmol, 2.0 equiv). The reaction mixture was stirred at 90° C. for 2 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 2-2.5% methanol in dichloromethane) to afford 120.5. MS (ES): m/z 347.5 [M+H]$^+$.

Synthesis of compound 120.6. A solution of 120.5 (0.180 g, 0.519 mmol, 1.0 equiv) and hydroxylamine hydrochloride (1.79 g, 25.95 mmol, 50 equiv) in ethanol-water (2:1) (8 mL) was stirred in a sealed tube at 120° C. for 3 h. It was cooled to rt and poured over ice-water. The pH of the aqueous solution was adjusted by the addition of 2 N sodium hydroxide to 10 and the mixture was extracted with ethyl acetate. The combined organic layers were washed with brine solution, dried over anhydrous sodium sulfate, filtered and concentrated under reduced pressure to afford crude product. The residue was purified by flash column chromatography on silica gel (CombiFlash®, 8-10% methanol in dichloromethane) to afford 120.6. MS (ES): m/z 269.4 [M+H]$^+$.

Synthesis 1-120. Compound I-120 was prepared from compound 120.6 and 96.7 following the procedure described in the synthesis of compound I-108. The product was purified by flash column chromatography on silica gel (CombiFlash®, 5-6% methanol in dichloromethane). MS (ES): m/z: 550.6 [M+H]$^+$, $^1$H NMR (DMSO-d$_6$, 400 MHz): δ 10.25 (s, 1H), 9.57 (s, 1H), 8.19-8.17 (m, 1H), 7.97 (s, 1H), 7.67-7.66 (d, J=1.6 Hz, 1H), 7.57 (s, 1H), 6.68-6.66 (m, 1H), 6.46 (bs, 1H), 4.66 (bs, 1H), 4.54 (bs, 1H), 4.17 (bs 2H), 3.68 (s, 3H), 2.22-2.15 (bs, 1H), 2.07 (s, 3H), 1.68-1.65 (m, 2H), 1.42 (s, 9H), 1.30-1.27 (m, 6H).

Example I-121: (S)—N-(4-((2-((5-(tert-butyl)-1-((1-(2-fluoroethyl)pyrrolidin-3-yl)methyl)-1H-pyrazol-3-yl)amino)-1-methyl-1H-imidazo[4,5-b]pyridin-6-yl)oxy)pyridin-2-yl)acetamide
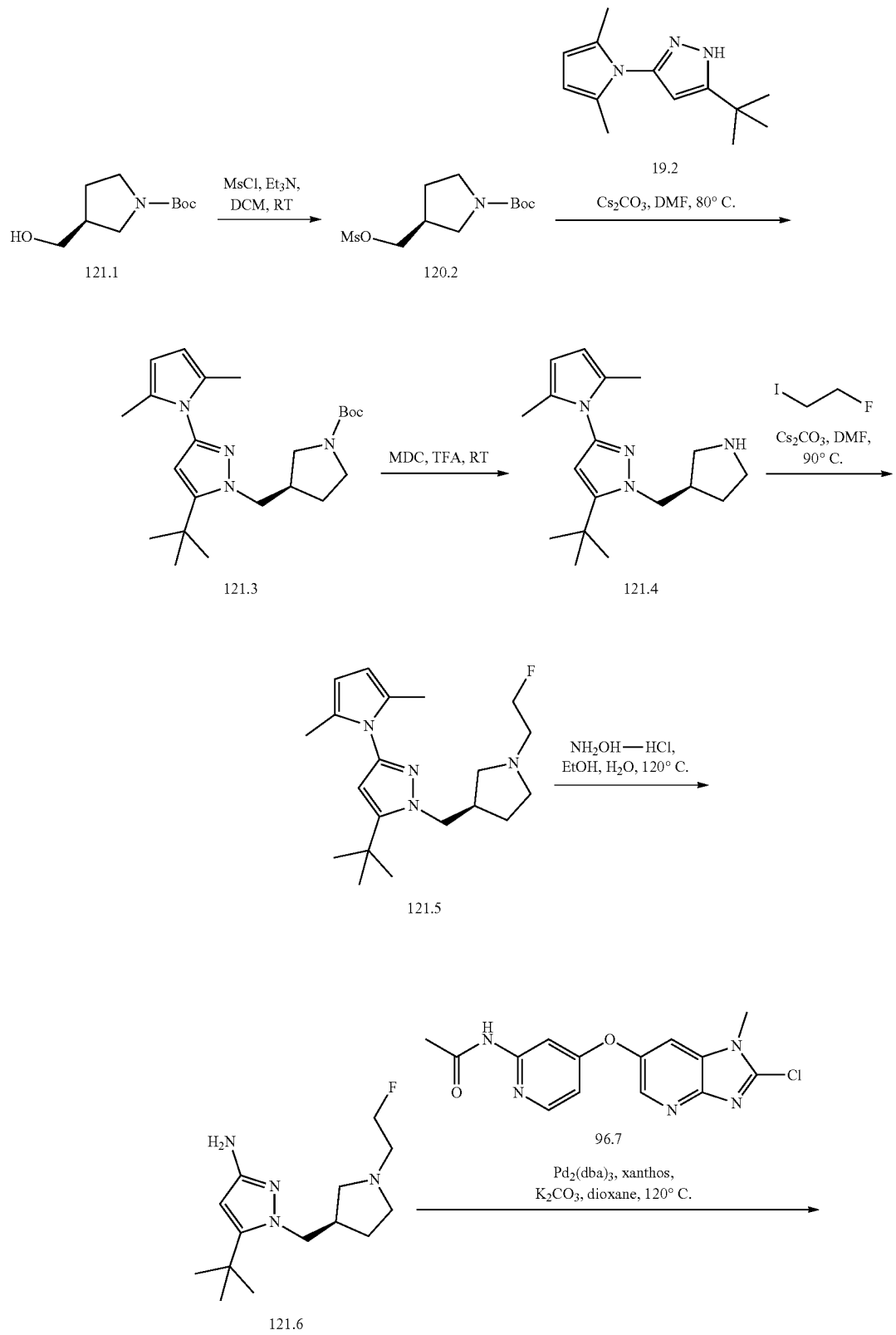

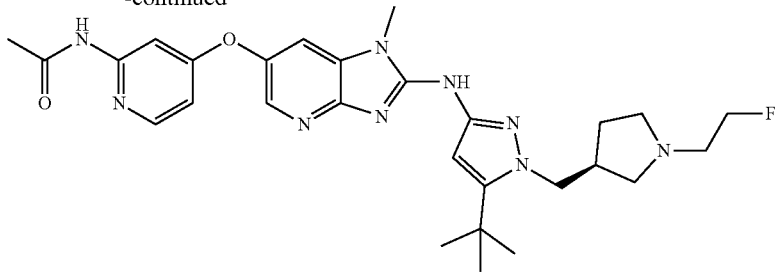

I-121

Synthesis of I-121. Compound I-121 was prepared from compound 121.1 following the procedure in each step described in the synthesis of compound I-120. The product was purified by flash column chromatography on silica gel (CombiFlash®, 6-7% methanol in dichloromethane). MS (ES): m/z: 550.67 [M+H]$^+$, $^1$H NMR (DMSO-d$_6$, 400 MHz): δ 10.24 (s, 1H), 9.53 (s, 1H), 8.19-8.17 (d, J=5.6 Hz, 1H), 7.97 (s, 1H), 7.67-7.66 (d, J=1.6 Hz, 1H), 7.58 (s, 1H), 6.67-6.66 (m, 1H), 6.44 (bs, 1H), 4.72 (bs, 1H), 4.61 (bs, 1H), 4.21-4.17 (m, 2H), 3.69 (s, 3H), 2.07 (bs, 4H), 1.79-1.66 (m, 2H), 1.42 (s, 9H), 1.28-1.18 (m, 6H).

Example I-122: N-(4-((2-((5-(tert-butyl)-1-((1r,3r)-3-hydroxycyclobutyl)-1H-pyrazol-3-yl)amino)-1,7-dimethyl-1H-imidazo[4,5-b]pyridin-6-yl)oxy)pyridin-2-yl)acetamide

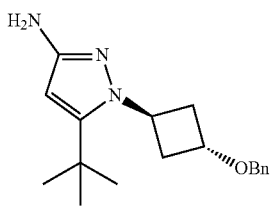

29.7

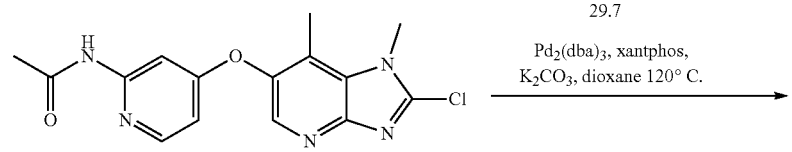

102.2

Pd$_2$(dba)$_3$, xantphos,
K$_2$CO$_3$, dioxane 120° C.

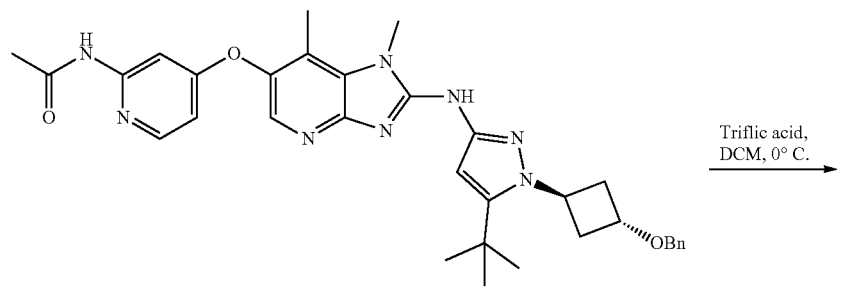

122.1

Triflic acid,
DCM, 0° C.

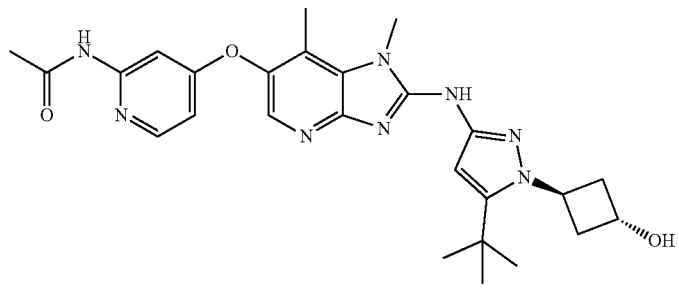

I-122

Synthesis of compound 122.1. Compound 122.1 was prepared from compound 102.2 and 29.7 following the procedure described in the synthesis of compound I-108. The product was purified by flash column chromatography on silica gel (CombiFlash®, 3% methanol in dichloromethane). MS (ES): m/z 595.7 [M+H]⁺.

Synthesis of I-122. To a solution of 122.1 (0.052 g, 0.087 mmol, 1.0 equiv) in dichloromethane (3 mL) was added triflic acid (0.2 mL) at 0° C. The reaction mixture was stirred for 10 min. It was poured over ice-water, neutralized with saturated aqueous sodium bicarbonate solution and extracted with dichloromethane. The combined organic layers were washed with brine solution, dried over anhydrous sodium sulfate, filtered and concentrated under reduced pressure. The residue was further purified by trituration with diethyl ether to afford I-122. MS (ES): m/z: 505.12 [M+H]⁺, ¹H NMR (DMSO-d₆, 400 MHz): δ 10.55 (s, 1H), 9.76 (s, 1H), 8.18-8.16 (d, J=6 Hz, 1H), 7.89 (s, 1H), 7.62 (s, 1H), 6.61-6.58 (m, 1H), 6.56 (s, 1H), 5.24-5.19 (m, 1H), 4.48 (bs, 1H), 3.88 (s, 3H), 3.41-3.39 (m, 1H), 2.78-2.69 (m, 2H), 2.41 (s, 3H), 2.37-2.32 (m, 2H), 2.04 (s, 3H), 1.37 (s, 9H).

Example I-123: N-(4-((2-((5-(tert-butyl)-1-((1s,3s)-3-hydroxycyclobutyl)-1H-pyrazol-3-yl)amino)-1,7-dimethyl-1H-imidazo[4,5-b]pyridin-6-yl)oxy)pyridin-2-yl)acetamide

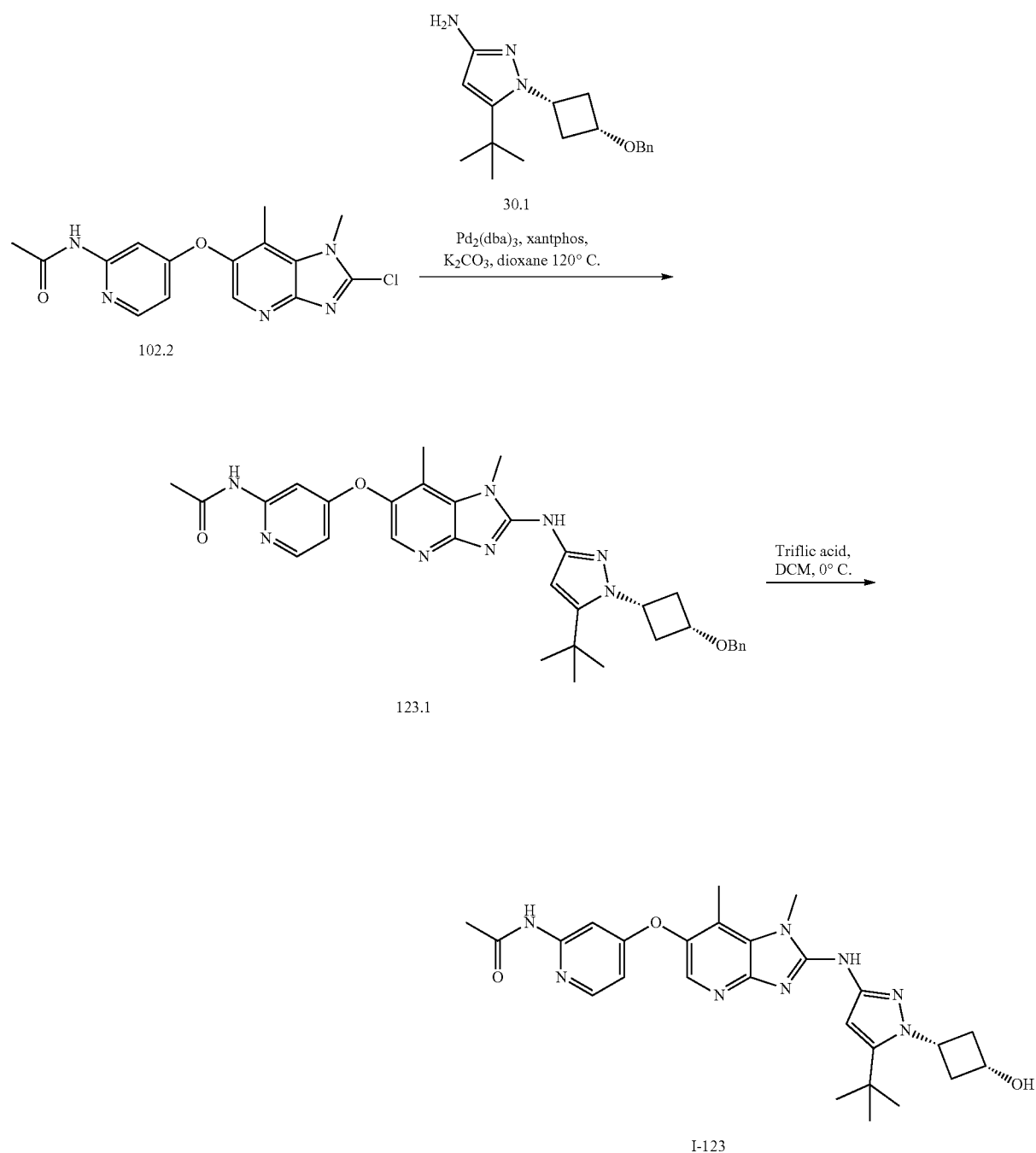

Synthesis of I-123. Compound I-123 was prepared from compound 102.2 and 30.1 following the procedures described in the synthesis of compound I-122. The product was purified by trituration with diethyl ether. MS (ES): m/z: 505.15 [M+H]$^+$, $^1$H NMR (DMSO-d$_6$, 400 MHz): δ 10.55 (s, 1H), 9.77 (s, 1H), 8.18-8.16 (d, J=6 Hz, 1H), 7.89 (s, 1H), 7.62 (s, 1H), 6.60-6.58 (m, 1H), 6.53 (s, 1H), 5.22-5.21 (m, 1H), 4.54 (bs, 1H), 4.05-4.03 (m, 1H), 3.88 (s, 3H), 3.41-3.39 (m, 1H), 2.69-2.64 (m, 2H), 2.41 (s, 3H), 2.04 (s, 3H), 2.01 (bs, 1H), 1.37 (s, 9H).

Example I-124: (R)—N-(4-((2-((5-(tert-butyl)-1-((1-(2-fluoroethyl)pyrrolidin-3-yl)methyl)-1H-pyrazol-3-yl)amino)-1,7-dimethyl-1H-imidazo[4,5-b]pyridin-6-yl)oxy)pyridin-2-yl)acetamide

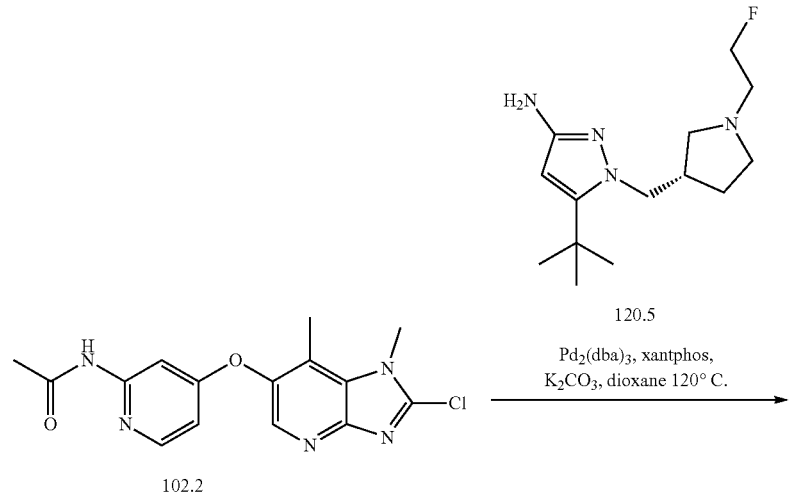

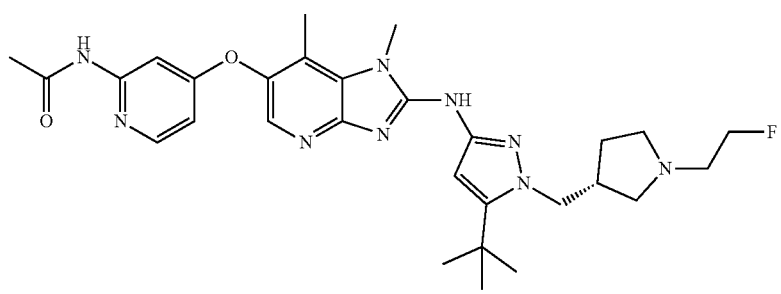

Synthesis of I-124. Compound I-124 was prepared from compound 102.2 and 120.5 following the procedure described in the synthesis of compound I-108. The product was purified by flash column chromatography on silica gel (CombiFlash®, 5-6% methanol in dichloromethane). MS (ES): m/z: 564.12 [M+H]$^+$, $^1$H NMR (DMSO-d$_6$, 400 MHz): δ 10.30 (s, 1H), 9.40 (s, 1H), 8.17-8.15 (d, J=5.6 Hz, 1H), 7.89 (s, 1H), 7.61-7.60 (d, J=2.0 Hz, 1H), 6.61-6.59 (m, 1H), 6.40 (bs, 1H), 4.67 (bs, 1H), 4.55 (bs, 1H), 4.18 (bs 2H), 3.88 (s, 3H), 2.44 (s, 3H), 2.11 (bs, 1H), 2.06 (s, 3H), 1.76 (bs, 2H), 1.41 (s, 9H), 1.30-1.28 (m, 6H).

Example I-125: (S)—N-(4-((2-((5-(tert-butyl)-1-((1-(2-fluoroethyl)pyrrolidin-3-yl)methyl)-1H-pyrazol-3-yl)amino)-1,7-dimethyl-1H-imidazo[4,5-b]pyridin-6-yl)oxy)pyridin-2-yl)acetamide

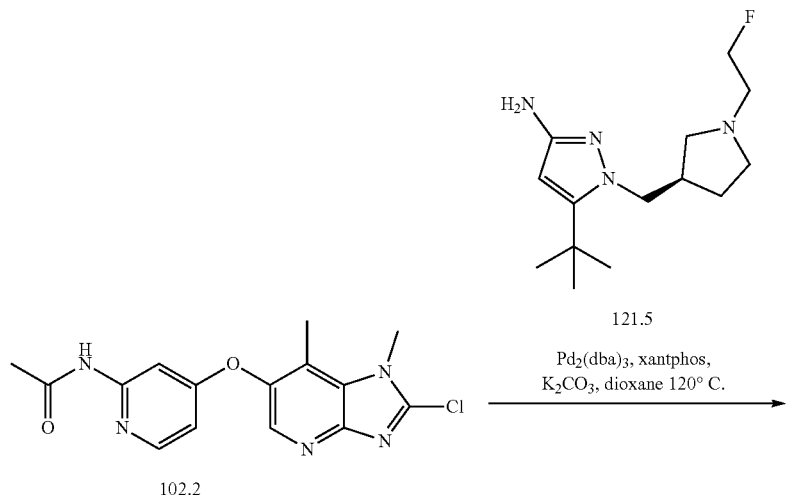

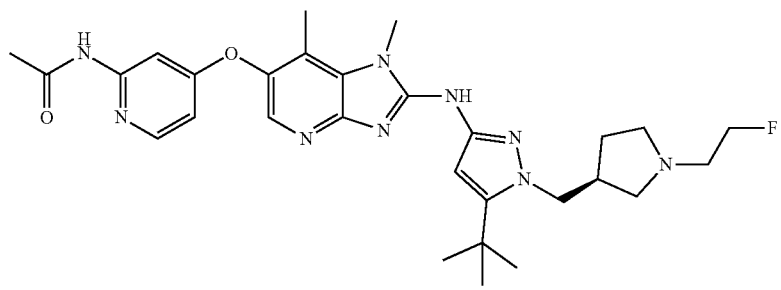

Synthesis of I-125. Compound I-125 was prepared from compound 102.2 and 121.5 following the procedure described in the synthesis of compound I-108. The product was purified by flash column chromatography on silica gel (CombiFlash®, 6-7% methanol in dichloromethane). MS (ES): m/z: 563.87 [M+H]⁺, $^1$H NMR (DMSO-d$_6$, 400 MHz): δ 10.24 (s, 1H), 9.41 (s, 1H), 8.17-8.16 (d, J=5.6 Hz, 1H), 7.90 (s, 1H), 7.61-7.60 (d, J=2.0 Hz, 1H), 6.60-6.59 (m, 1H), 6.46 (bs, 1H), 4.66 (bs, 1H), 4.54 (bs, 1H), 4.18 (bs 2H), 3.88 (s, 3H), 2.44 (s, 3H), 2.11 (bs, 1H), 2.06 (s, 3H), 1.69 (bs, 2H), 1.42 (s, 9H), 1.31-1.28 (m, 6H).

Example I-126: (R)—N-(4-((1,7-dimethyl-2-((5-(perfluoroethyl)-1-(tetrahydrofuran-3-yl)-1H-pyrazol-3-yl)amino)-1H-imidazo[4,5-b]pyridin-6-yl)oxy)pyridin-2-yl)acetamide

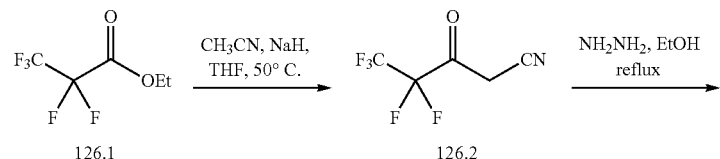

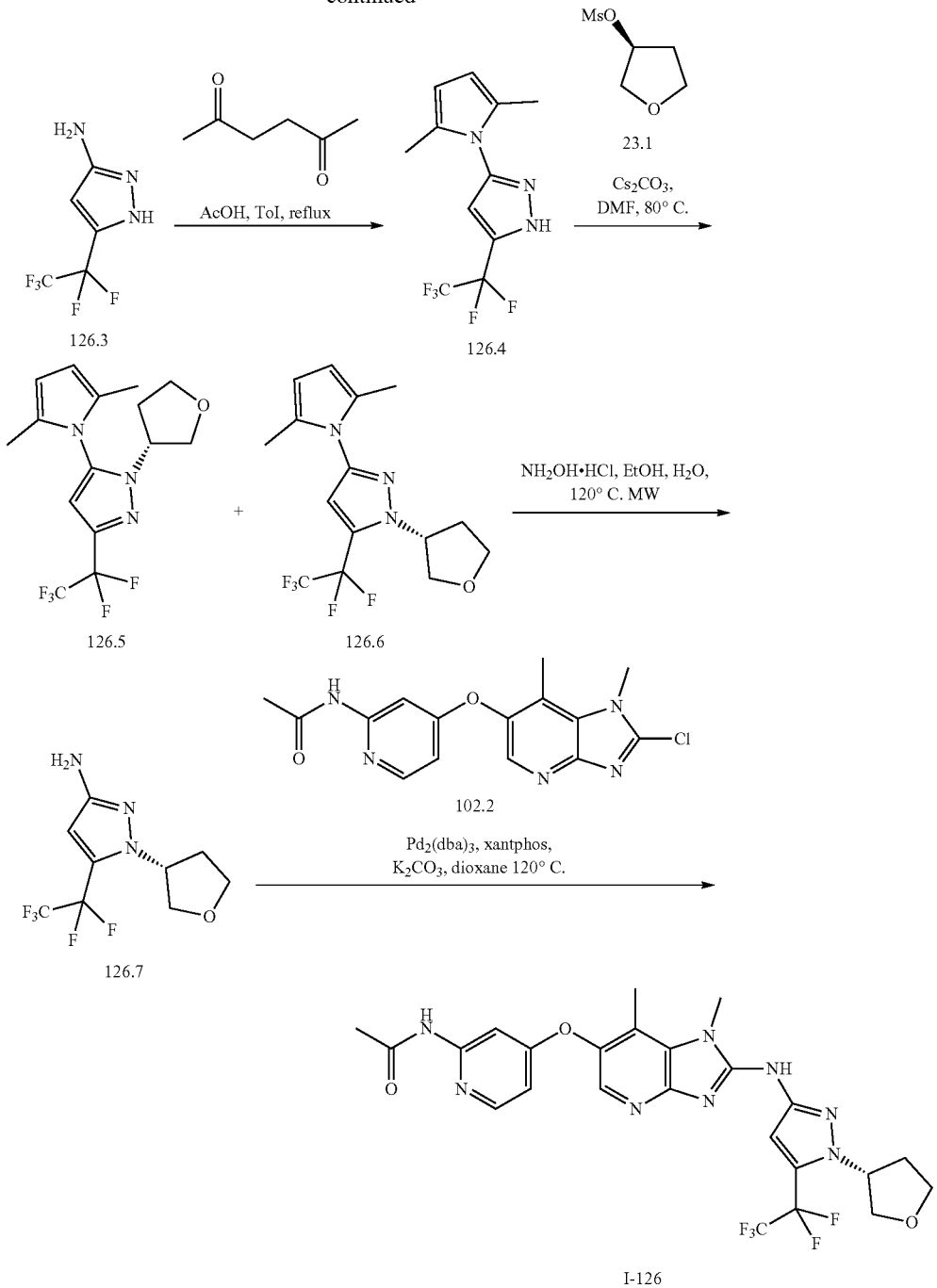

Synthesis of compound 126.2. To a suspension of sodium hydride (6.2 g, 156.18 mmol, 3.0 equiv) in THF (100 mL) was added 126.1 (10 g, 52.06 mmol, 1.0 equiv) and acetonitrile (1.68 mL, 52.06 mmol, 1.0 equiv). The reaction mixture was stirred at 50° C. for 4 h. It cooled to rt and concentrated under reduced pressure. To the residue was added 4 N hydrochloric acid and the mixture was extracted with diethyl ether. The combined organic layers were washed with brine, dried over anhydrous sodium sulfate, filtered and concentrated under reduced pressure to afford 126.2. It was used in the next step without further purification.

Synthesis of compound 126.3. To a solution of 126.2 (6.0 g, 32.07 mmol, 1.0 equiv) in ethanol (60 mL) was added hydrazine hydrate (98%) (3.14 mL, 64.14 mmol, 2.0 equiv). The reaction mixture was refluxed for 12 h. It was cooled to rt and poured over ice-water, stirred and extracted with ethyl acetate. The combined organic layers were washed with brine, dried over anhydrous sodium sulfate, filtered and concentrated under reduced pressure to afford 126.3. MS (ES): m/z 202.1 [M+H]$^+$.

Synthesis of compound 126.4. To a solution of 126.3 (3.0 g, 14.92 mmol, 1.0 equiv) in toluene (30 mL) was added hexane-2,5-dione (1.87 g, 16.41 mmol, 1.1 equiv) followed by addition of acetic acid (0.2 mL, catalytic). The reaction mixture was refluxed for 5 h. It was poured over water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 4-6% ethyl acetate in hexane) to afford 126.4. MS (ES): m/z 280.2 [M+H]$^+$.

Synthesis of compound 126.6. Compound 126.6 was prepared from compound 126.4 and 23.1 following the procedure described in the synthesis of compound 28.7. The product was purified by flash column chromatography on silica gel (CombiFlash®, 6-8% ethyl acetate in hexane) to afford 126.5, MS (ES): m/z 350.3 [M+H]$^+$ and 126.6, MS (ES): m/z 350.3 [M+H]$^+$.

Synthesis of compound 126.7. Compound 126.7 was prepared from compound 126.6 following the procedure described in the synthesis of compound 120.6. The product was purified by flash column chromatography on silica gel (CombiFlash®, 3-4% methanol in dichloromethane). MS (ES): m/z 272.2 [M+H]$^+$.

Synthesis of I-126. Compound I-126 was prepared from compound 102.2 and 126.7 following the procedure described in the synthesis of compound I-108. The product was purified by flash column chromatography on silica gel (CombiFlash®, 2-3% methanol in dichloromethane). MS (ES): m/z: 567.7 [M+H]$^+$, $^1$H NMR (DMSO-d$_6$, 400 MHz): δ 10.54 (s, 1H), 10.39 (s, 1H), 8.17-8.15 (d, J=5.6 Hz, 1H), 7.93 (s, 1H), 7.60 (s, 1H), 7.38 (s, 1H), 6.59-6.57 (m, 1H), 5.16 (bs, 1H), 4.13-4.05 (m, 2H), 3.94-3.82 (m, 5H), 2.42 (s, 3H), 2.35-2.27 (m, 1H), 2.03 (s, 3H), 1.23-1.15 (m, 1H).

Example I-127: (S)—N-(4-((1,7-dimethyl-2-((5-(perfluoroethyl)-1-(tetrahydrofuran-3-yl)-1H-pyrazol-3-yl)amino)-1H-imidazo[4,5-b]pyridin-6-yl)oxy)pyridin-2-yl)acetamide

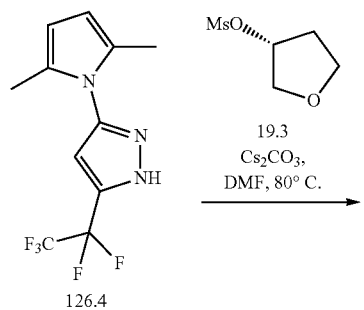

126.4

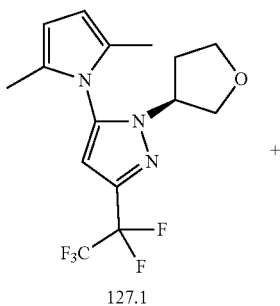

127.1

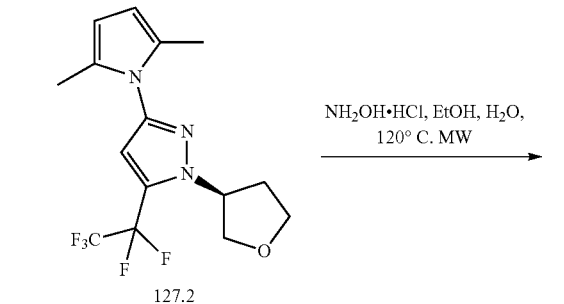

127.2

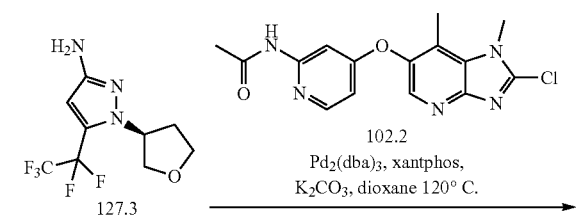

127.3

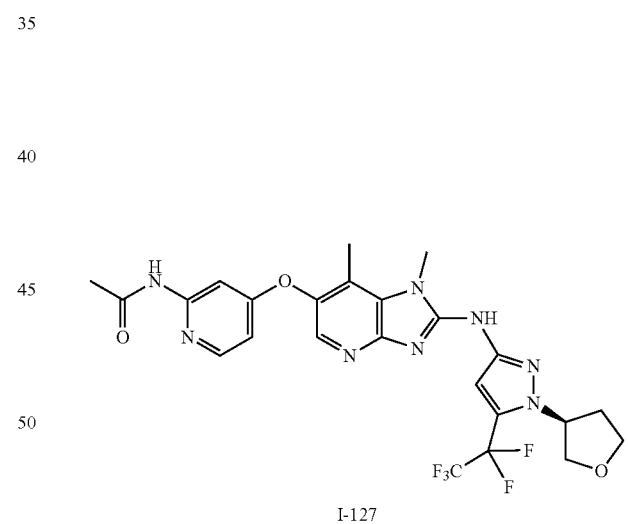

I-127

Synthesis of I-127. Compound I-127 was prepared from compound 126.4 and 19.3 following the procedures described in each step in the synthesis of compound I-126. The product was purified by flash column chromatography on silica gel (CombiFlash®, 2-3% methanol in dichloromethane). MS (ES): m/z: 567.1 [M+H]$^+$, $^1$H NMR (DMSO-d$_6$, 400 MHz): δ 10.55 (s, 1H), 10.41 (s, 1H), 8.17-8.16 (d, J=5.6 Hz, 1H), 7.94 (s, 1H), 7.61 (s, 1H), 7.39 (s, 1H), 6.60-6.58 (m, 1H), 5.17 (bs, 1H), 4.14-4.06 (m, 2H), 3.95-3.83 (m, 5H), 2.43 (s, 3H), 2.34-2.31 (m, 1H), 2.04 (s, 3H), 1.24 (bs, 1H).

Example 128: (R)—N-(4-((2-((5-(tert-butyl)-1-((1-(2,2,2-trifluoroethyl)pyrrolidin-3-yl)methyl)-1H-pyrazol-3-yl)amino)-1,7-dimethyl-1H-imidazo[4,5-b]pyridin-6-yl)oxy)pyridin-2-yl)acetamide and (S)—N-(4-((2-((5-(tert-butyl)-1-((1-(2,2,2-trifluoroethyl)pyrrolidin-3-yl)methyl)-1H-pyrazol-3-yl)amino)-1,7-dimethyl-1H-imidazo[4,5-b]pyridin-6-yl)oxy)pyridin-2-yl)acetamide
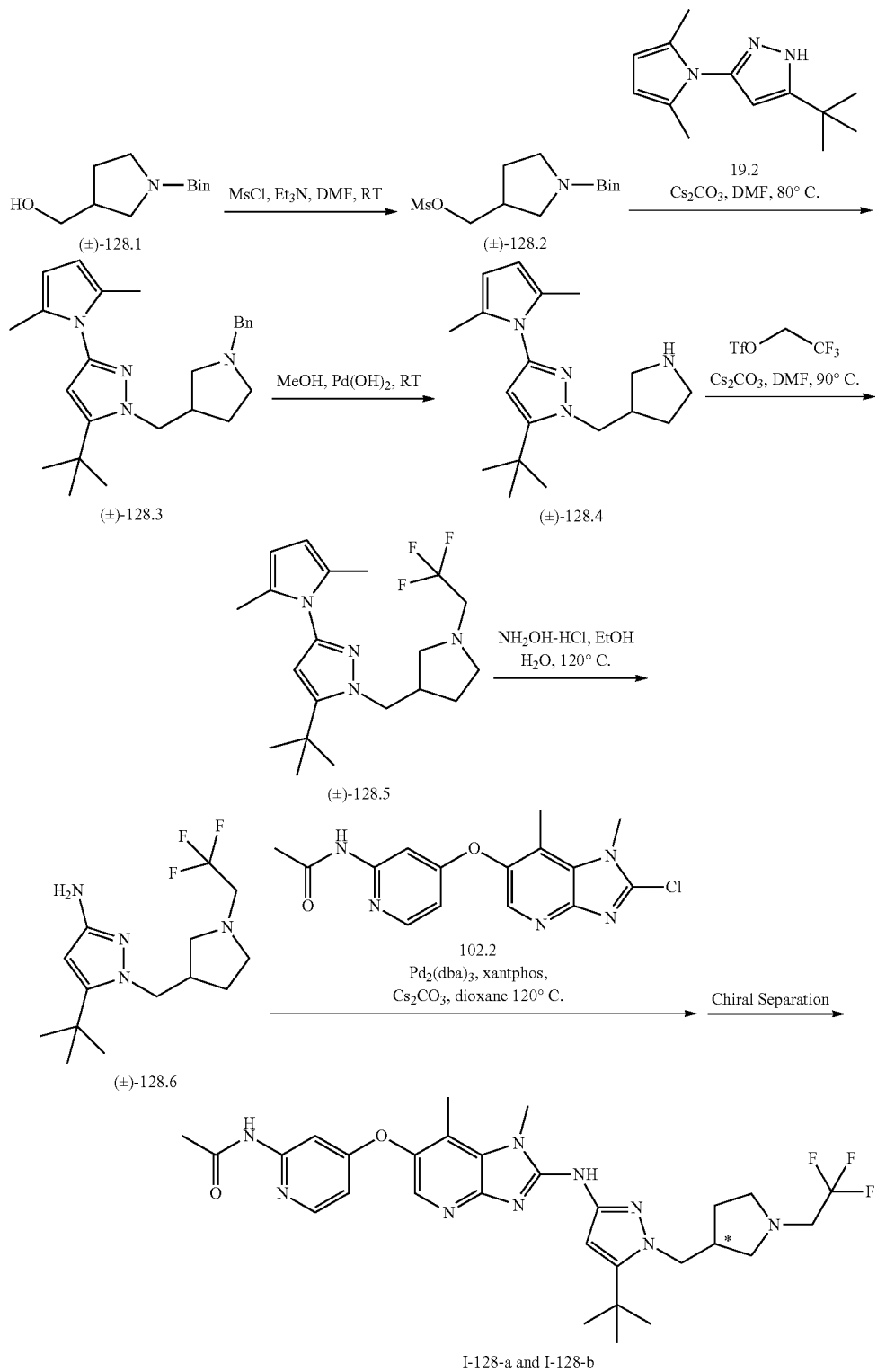

Synthesis of compound (±)-128.2. Compound (±)-128.2 was prepared from compound (±)-128.1 following the procedure described in the synthesis of compound 28.5. The crude product was used in the next step without further purification. MS (ES): m/z 218.3[M+H]$^+$.

Synthesis of compound (±)-128.3. Compound (±)-128.3 was prepared from compound (±)-128.2 following the procedure described in the synthesis of compound 28.7. The product was purified by flash column chromatography on silica gel (CombiFlash®, 30-35% ethyl acetate in hexane). MS (ES): m/z 391.6 [M+H]$^+$.

Synthesis of compound (±)-128.4. A mixture compound (±)-128.3 (0.690 g, 1.77 mmol, 1.0 equiv) and 20% palladium hydroxide (0.35 g) in methanol (20 mL) was stirred under hydrogen (1 atm) at rt for 2 h. The reaction mixture was filtered through a pad of Celite® and rinsed with 10% methanol in dichloromethane. The filtrate was concentrated under reduced pressure to afford (±)-128.4. MS (ES): m/z 300.4 [M+H]$^+$.

Synthesis of compound (±)-128.5. Compound (±)-128.5 was prepared from compound (±)-128.4 following the procedure described in the synthesis of compound 120.5. The product was purified by flash column chromatography on silica gel (CombiFlash®, 10% ethyl acetate in hexane). MS (ES): m/z 383.5 [M+H]$^+$.

Synthesis of compound (±)-128.6. Compound (±)-128.6 was prepared from compound (±)-128.5 following the procedure described in the synthesis of compound 120.6. The product was purified by flash column chromatography on silica gel (CombiFlash®, 2-3% methanol in dichloromethane). MS (ES): m/z 305.4 [M+H]$^+$.

Synthesis of compound (±)-I-128. A mixture of 102.2 (0.110 g, 0.331 mmol, 1.0 equiv), (±)-128.6 (0.111 g, 0.364 mmol, 1.1 equiv) and cesium carbonate (0.215 g, 0.662 mmol, 2.0 equiv) in 1,4-dioxane (2 mL) was degassed by bubbling argon through for 10 min. Under argon atmosphere 4,5-bis(diphenylphosphino)-9,9-dimethylxanthene (0.038 g, 0.0662 mmol, 0.2 equiv) and tris(dibenzylideneacetone) dipalladium(0) (0.030 g, 0.0331 mmol, 0.1 equiv) were added, and degassed for 5 min. The reaction mixture was stirred at 120° C. for 4 h. The reaction mixture was cooled to room temperature, transferred into water and extracted with ethyl acetate. The combined organic layers were washed with brine solution, dried over anhydrous sodium sulfate, filtered and concentrated under reduced pressure. The residue was purified by flash column chromatography on silica gel (CombiFlash®, 6-7% methanol in dichloromethane) to afford (±)-128.

I-128-a and I-128-b. Enantiomers of (±)-I-128 were isolated by HPLC (CHIRALPAK IB-N (250 mm×21 mm, 5 µm), eluent: (A) 0.1% DEA in n-hexane (B) 0.1% DEA in propane-2-ol (40:60), flow rate=18 mL/min) to give the first eluting fraction (I-128-a) and second eluting fraction (I-128-b). (*Absolute stereochemistry not determined.)

I-128-a: MS (ES): m/z: 600.26 [M+H]$^+$, $^1$H NMR (DMSO-d$_6$, 400 MHz): δ 10.53 (s, 1H), 9.70 (s, 1H), 8.16-8.15 (d, J=5.6 Hz, 1H), 7.88 (s, 1H), 7.60 (s, 1H), 6.59-6.55 (m, 2H), 4.11-3.97 (m, 2H), 3.85 (s, 3H), 3.26-3.21 (m, 2H), 2.89-2.88 (m, 2H), 2.67-2.59 (m, 2H), 2.40 (s, 3H), 2.03 (s, 3H), 1.97-1.95 (m, 1H), 1.58-1.55 (m, 2H), 1.38 (s, 9H).

I-128-b: MS (ES): m/z: 600.27 [M+H]$^+$, $^1$H NMR (DMSO-d$_6$, 400 MHz): δ 10.54 (s, 1H), 9.70 (s, 1H), 8.16-8.15 (d, J=5.6 Hz, 1H), 7.88 (s, 1H), 7.60 (s, 1H), 6.59-6.55 (m, 2H), 4.10-4.00 (m, 2H), 3.85 (s, 3H), 3.26-3.21 (m, 2H), 2.89-2.88 (m, 2H), 2.67-2.61 (m, 2H), 2.40 (s, 3H), 2.03 (s, 3H), 1.97-1.91 (m, 1H), 1.58-1.55 (m, 2H), 1.38 (s, 9H).

Example 129: (S)—N-(4-((2-((1-((1,4-dioxan-2-yl)methyl)-5-(tert-butyl)-1H-pyrazol-3-yl)amino)-1,7-dimethyl-1H-imidazo[4,5-b]pyridin-6-yl)oxy)pyridin-2-yl)acetamide and (R)—N-(4-((2-((1-((1,4-dioxan-2-yl)methyl)-5-(tert-butyl)-1H-pyrazol-3-yl)amino)-1,7-dimethyl-1H-imidazo[4,5-b]pyridin-6-yl)oxy)pyridin-2-yl)acetamide

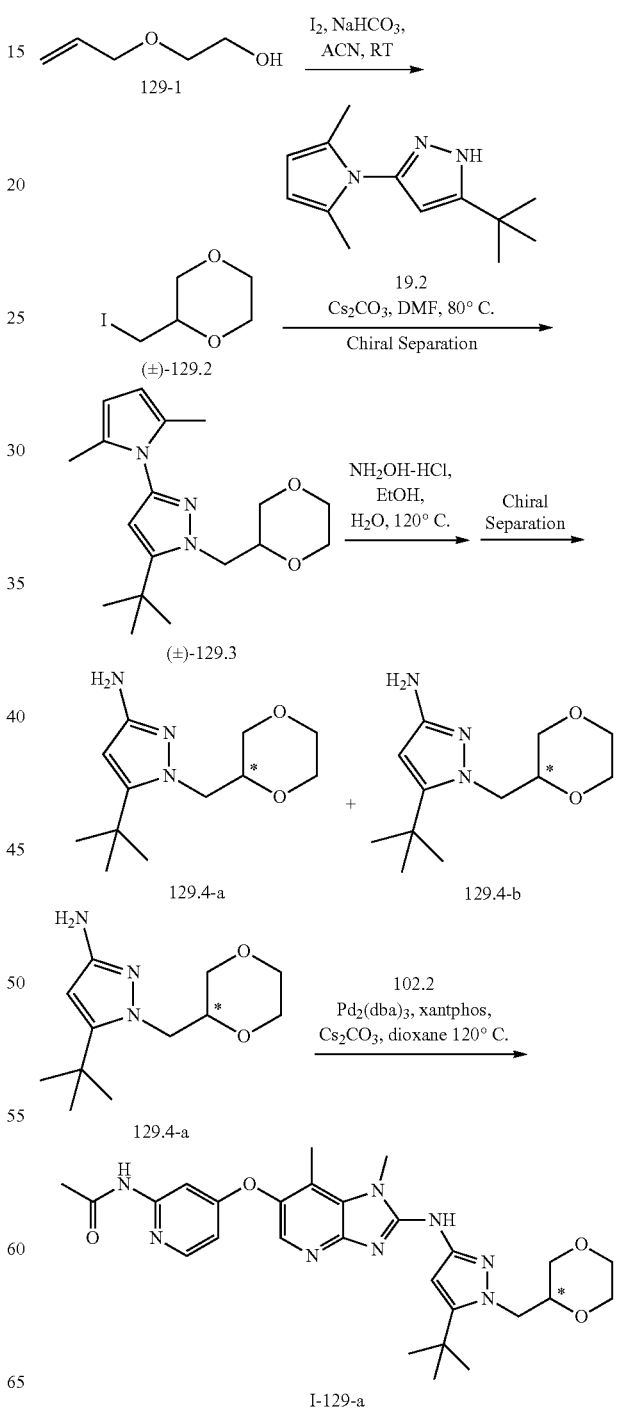

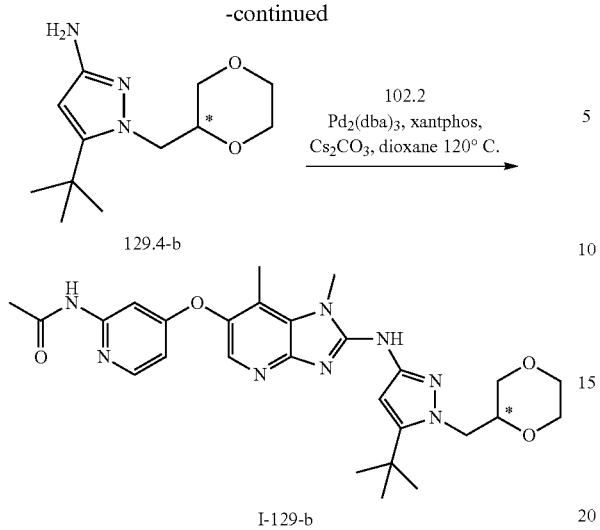

3.73 (m, 1H), 3.67-3.65 (m, 1H), 3.59-3.44 (m, 2H), 3.17 (bs, 2H), 2.40 (s, 3H), 2.03 (s, 3H), 1.38 (s, 9H).

Synthesis of I-129-b. Compound I-129-b was prepared from compound 129.4-b following the procedure described in the synthesis of compound I-128. The product was purified by flash column chromatography on silica gel (CombiFlash®, 4.0% methanol in dichloromethane). MS (ES): m/z: 535.53 [M+H]$^+$, $^1$H NMR (DMSO-d$_6$, 400 MHz): δ 10.53 (s, 1H), 9.75 (s, 1H), 8.16-8.15 (d, J=5.6 Hz, 1H), 7.88 (s, 1H), 7.60 (s, 1H), 6.59-6.56 (m, 2H), 4.20-4.09 (m, 1H), 4.06-3.98 (m, 1H), 3.86 (s, 3H), 3.84 (bs, 1H), 3.76-3.73 (m, 1H), 3.67-3.65 (m, 1H), 3.59-3.44 (m, 2H), 3.17 (bs, 2H), 2.40 (s, 3H), 2.03 (s, 3H), 1.38 (s, 9H).

Example 130: N-(4-((2-((5-(tert-butyl)-1-(2-fluoro-ethyl)-1H-pyrazol-3-yl)amino)-1-methyl-1H-imidazo[4,5-b]pyridin-6-yl)oxy)pyridin-2-yl)acetamide

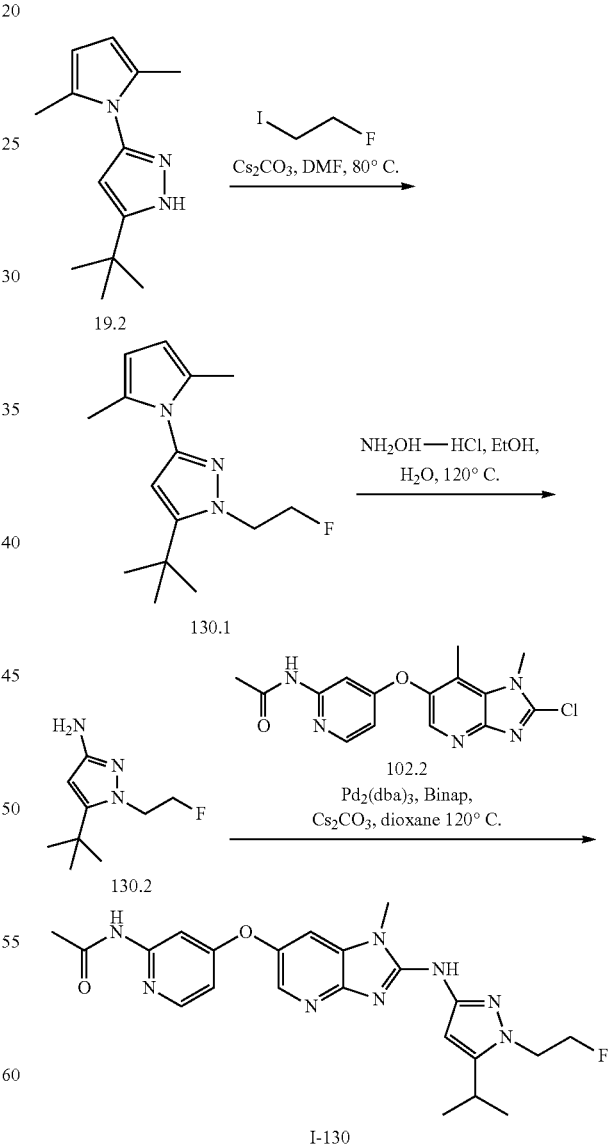

Synthesis of compound (±)-129.2. To a solution of (±)-129.1 (5.0 g, 48.96 mmol, 1.0 equiv) in acetonitrile (25 mL) was added sodium bicarbonate (12.33 g, 146.88 mmol, 3.0 equiv) and iodine (37.3 g, 146.88 mmol, 3.0 equiv). The reaction mixture was stirred at room temperature for 16 h. It was poured over crushed ice, stirred and extracted with ethyl acetate. The combined organic layers were washed with aqueous sodium thiosulfate followed by brine solution, dried over anhydrous sodium sulfate, filtered and concentrated under reduced pressure. The residue was purified by flash column chromatography on silica gel (CombiFlash®, 8-10% ethyl acetate in hexane) to afford (±)-129.2. $^1$H NMR (CDCl$_3$, 400 MHz): δ 3.99-3.95 (m, 1H), 3.92-3.96 (m, 1H), 3.84-3.80 (m, 1H), 3.70 (bs, 1H), 3.67-3.63 (m, 1H), 3.40-3.35 (m, 1H), 3.14-3.12 (m, 2H).

Synthesis of compound (±)-129.3. Compound (±)-129.3 was prepared from compound (±)-129.2 and 19.2 following the procedure described in the synthesis of compound 28.7. The product was purified by flash column chromatography on silica gel (CombiFlash®, 8% ethyl acetate in hexane). MS (ES): m/z 318.3 [M+H]$^+$.

Synthesis of compound (±)-129.4. Compound (±)-129.4 was prepared from compound (±)-129.3 following the procedure described in the synthesis of compound 120.6. The product was purified by flash column chromatography on silica gel (CombiFlash®, 2-3% methanol in dichloromethane). MS (ES): m/z 240.3 [M+H]$^+$.

Synthesis of compound 129.4-a and 129.4-b. Enantiomers of (±)-129.4 were isolated by HPLC (CHIRALPAK IG (250 mm×21 mm, 5 μm), eluent: (A) 0.1% DEA in n-hexane (B) 0.1% DEA in propane-2-ol (50:50), flow rate=20 mL/min) to get first eluting fraction (129.4-a), MS (ES): m/z: 240.3 [M+H]$^+$ and second eluting fraction (129.4-b), MS (ES): m/z: 240.3 [M+H]$^+$ (*Absolute stereochemistry not determined.)

Synthesis of I-129-a. Compound I-129-a was prepared from compound 129.4-a following the procedure described in the synthesis of compound I-128. The product was purified by flash column chromatography on silica gel (CombiFlash®, 4.0% methanol in dichloromethane). MS (ES): m/z: 535.23 [M+H]$^+$, $^1$H NMR (DMSO-d$_6$, 400 MHz): δ 10.53 (s, 1H), 9.75 (s, 1H), 8.16-8.15 (d, J=5.6 Hz, 1H), 7.88 (s, 1H), 7.60 (s, 1H), 6.59-6.56 (m, 2H), 4.20-4.09 (m, 1H), 4.06-3.98 (m, 1H), 3.86 (s, 3H), 3.84 (bs, 1H), 3.76-

Synthesis of compound 130.1. Compound 130.1 was prepared from compound 19.2 and 1-fluoro-2-iodoethane following the procedure described in the synthesis of compound 28.7. The product was purified by flash column chromatography on silica gel (CombiFlash®, 8-10% ethyl acetate in hexane). MS (ES): m/z 264.3 [M+H]$^+$.

Synthesis of compound 130.2. Compound 130.2 was prepared from compound 130.1 following the procedure described in the synthesis of compound 120.6. The product was purified by flash column chromatography on silica gel (CombiFlash®, 2-3% methanol in dichloromethane). MS (ES): m/z 186.3 [M+H]$^+$.

Synthesis of I-130. Compound I-130 was prepared from compound 130.2 and 102.2 following the procedure described in the synthesis of compound I-128. The product was purified by flash column chromatography on silica gel (CombiFlash®, 4-5% methanol in dichloromethane). MS (ES): m/z: 467.24 [M+H]$^+$, $^1$H NMR (DMSO-d$_6$, 400 MHz): 10.54 (s, 1H), 9.93 (s, 1H), 8.18-8.16 (d, J=6.0 Hz, 1H), 7.97-7.96 (d, J=2.4 Hz, 1H), 7.66-7.63 (m, 2H), 6.66-6.63 (m, 2H), 4.95 (bs, 1H), 4.83 (bs, 1H), 4.48-4.43 (m, 2H), 3.66 (s, 3H), 2.03 (s, 3H), 1.39 (s, 9H).

Example 131: N-(4-((2-((5-(tert-butyl)-1-(cyanomethyl)-1H-pyrazol-3-yl)amino)-1,7-dimethyl-1H-imidazo[4,5-b]pyridin-6-yl)oxy)pyridin-2-yl)acetamide

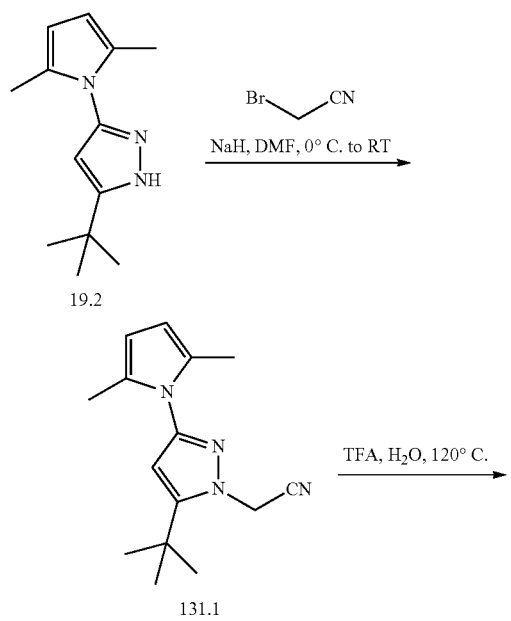

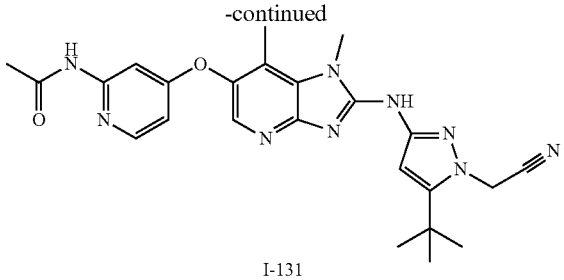

Synthesis of compound 131.1. To a solution of 19.2 (5.0 g, 23.01 mmol, 1.0 equiv) in DMF (25 mL) was added sodium hydride (3.6 g, 92.04 mmol, 4.0 equiv) in small portions at 0° C. The reaction mixture was stirred at 0° C. for 2 h followed by the addition of bromoacetonitrile (13.7 g, 115.08 mmol, 5.0 equiv) dropwise. The reaction mixture was stirred at room temperature for 16 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 6-8% ethyl acetate in hexane) to afford 131.1. MS (ES): m/z 257.3 [M+H]$^+$.

Synthesis of compound 131.2. To a suspension of 131.1 (0.465 g, 1.82 mmol, 1.0 equiv) in water (20 mL) was added trifluoroacetic acid (10 mL). The reaction mixture was stirred at 120° C. for 10 min. It was poured over ice-water, followed by addition of saturated aqueous sodium bicarbonate solution and extracted with ethyl acetate. The combined organic layers were washed with brine solution, dried over anhydrous sodium sulfate, filtered and concentrated under reduced pressure to afford crude. The residue was purified by flash column chromatography on silica gel (CombiFlash®, 70% ethyl acetate in hexane) to afford 131.2. MS (ES): m/z 179.2 [M+H]$^+$.

Synthesis of I-131. Compound I-131 was prepared from compound 131.2 and 102.2 following the procedure described in the synthesis of compound I-128. The product was purified by flash column chromatography on silica gel (CombiFlash®, 4.0% methanol in dichloromethane). MS (ES): m/z: 474.28 [M+H]$^+$, $^1$H NMR (DMSO-d$_6$, 400 MHz): 10.54 (s, 1H), 9.97 (s, 1H), 8.16-8.15 (d, J=5.6 Hz, 1H), 7.91 (s, 1H), 7.60 (s, 1H), 6.69 (s, 1H), 6.59-6.58 (m, 1H), 5.46 (s, 2H), 3.94 (s, 3H), 2.41 (s, 3H), 2.03 (s, 3H), 1.40 (s, 9H).

Example 132: N-(4-((2-((5-(tert-butyl)-1-(2,2-difluoroethyl)-1H-pyrazol-3-yl)amino)-1-methyl-1H-imidazo[4,5-b]pyridin-6-yl)oxy)pyridin-2-yl)acetamide

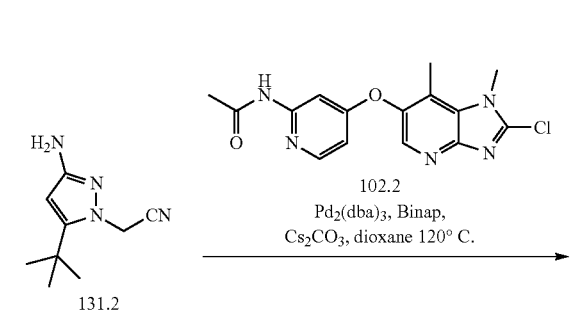

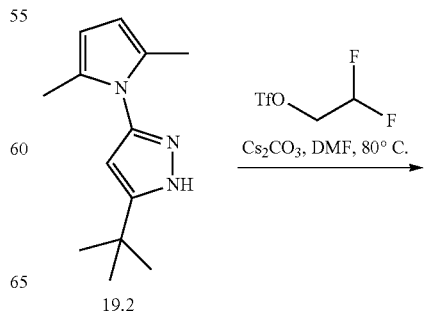

453

-continued

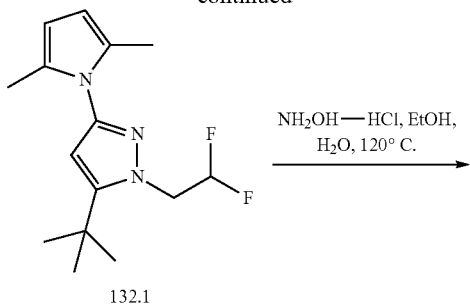
132.1

NH$_2$OH—HCl, EtOH,
H$_2$O, 120° C.

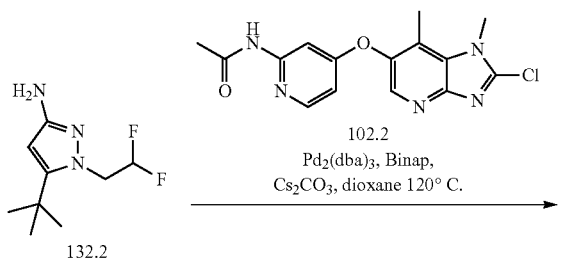
132.2

102.2
Pd$_2$(dba)$_3$, Binap,
Cs$_2$CO$_3$, dioxane 120° C.

454

-continued

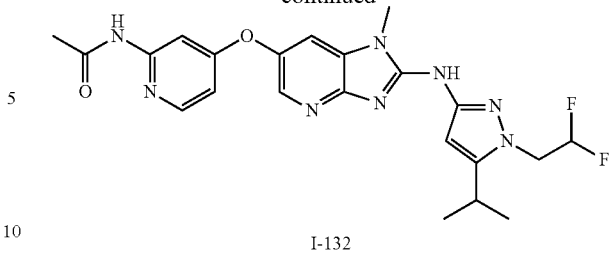
I-132

Synthesis of I-132. Compound I-132 was prepared from compound 19.2 and 2,2-difluoroethyl trifluoromethanesulfonate following the procedure described in each step in the synthesis of compound I-130. The product was purified by flash column chromatography on silica gel (CombiFlash®, 4.5% methanol in dichloromethane). MS (ES): m/z: 485.37 [M+H]$^+$, $^1$H NMR (DMSO-d$_6$, 400 MHz): 10.54 (s, 1H), 10.01 (s, 1H), 8.19-8.17 (d, J=5.6 Hz, 1H), 7.98 (s, 1H), 7.66 (s, 1H), 7.08 (bs, 1H), 6.83 (bs, 1H), 6.70-6.66 (m, 1H), 6.46 (bs, 1H), 4.65-4.59 (m, 2H), 3.68 (s, 3H), 2.04 (s, 3H), 1.40 (s, 9H).

Example 133: (R)—N-(4-((1-methyl-2-((5-(perfluoroethyl)-1-(tetrahydrofuran-3-yl)-1H-pyrazol-3-yl)amino)-1H-imidazo[4,5-b]pyridin-6-yl)oxy)pyridin-2-yl)cyclopropanecarboxamide

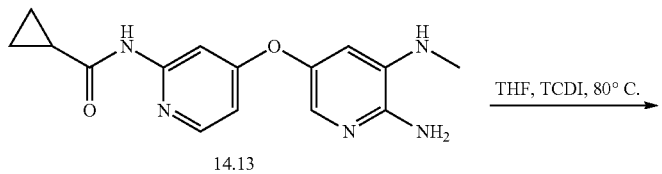
14.13

THF, TCDI, 80° C.

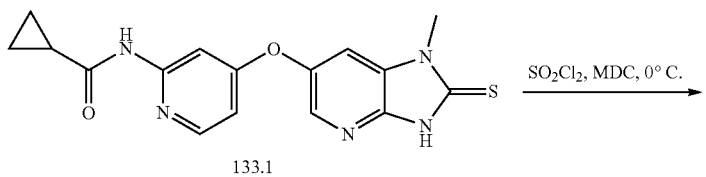
133.1

SO$_2$Cl$_2$, MDC, 0° C.

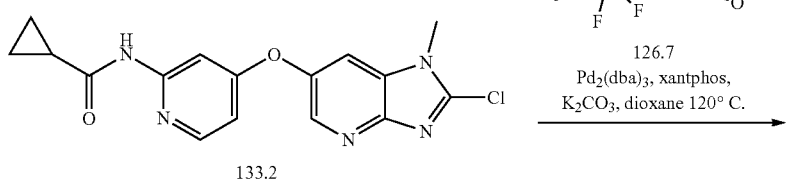
133.2

126.7
Pd$_2$(dba)$_3$, xantphos,
K$_2$CO$_3$, dioxane 120° C.

-continued

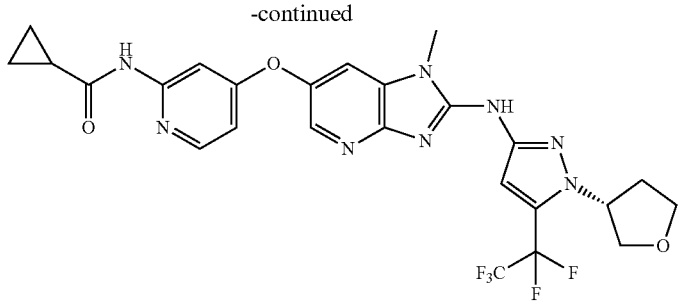

I-133

Synthesis of compound 133.1. To a solution of 14.13 (0.500 g, 1.67 mmol, 1.0 equiv) in THF (10 mL) was added 1,1'-thiocarbonyldiimidazole (1.48 g, 8.35 mmol, 5.0 equiv). The reaction mixture was stirred at 80° C. for 1 h. It was cooled to room temperature and poured over ice-water. Precipitated solid was collected by filtration and dried under vacuum to afford 133.1. MS (ES): m/z: 342.4 [M+H]$^+$.

Synthesis of compound 133.2. Compound 133.2 was prepared from compound 133.1 following the procedure described in the synthesis of compound 102.2. The product was purified by flash column chromatography on silica gel (CombiFlash®, 2.4% methanol in dichloromethane. MS (ES): m/z 344.7 [M+H]$^+$.

Synthesis of I-133. Compound I-133 was prepared from compound 133.2 and 126.7 following the procedure described in the synthesis of compound I-108. The product was purified by flash column chromatography on silica gel (CombiFlash®, 1.8-2.0% methanol in dichloromethane). MS (ES): m/z: 579.7 [M+H]$^+$, $^1$H NMR (DMSO-d$_6$, 400 MHz): δ 10.84 (s, 1H), 10.52 (s, 1H), 8.19-8.18 (d, J=5.6 Hz, 1H), 8.01-8.00 (d, J=2.4 Hz, 1H), 7.72-7.71 (d, J=2.4 Hz, 1H), 7.63-7.61 (d, J=2.0 Hz, 1H), 7.41 (s, 1H), 6.70-6.68 (m, 1H), 5.16 (bs, 1H), 4.13-4.05 (m, 2H), 3.94-3.91 (m, 1H), 3.87-3.82 (m, 1H), 3.71 (s, 3H), 2.43-2.39 (m, 1H), 2.33-2.30 (m, 1H), 1.97-1.94 (m, 1H), 0.76-0.74 (m, 4H).

Example 134: (S)—N-(4-((1-methyl-2-((5-(perfluoroethyl)-1-(tetrahydrofuran-3-yl)-1H-pyrazol-3-yl)amino)-1H-imidazo[4,5-b]pyridin-6-yl)oxy)pyridin-2-yl)cyclopropanecarboxamide

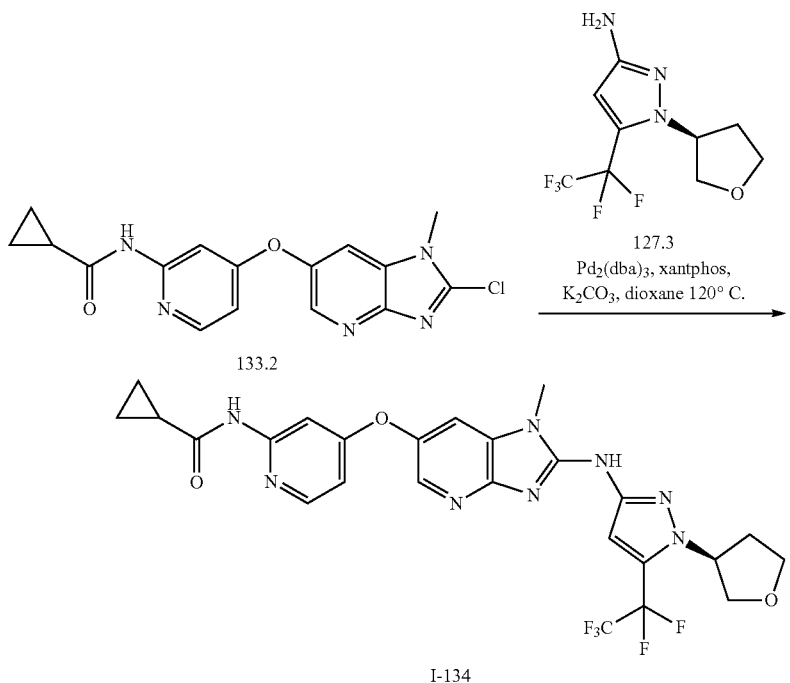

Synthesis of I-134. Compound I-134 was prepared from compound 133.2 and 127.3 following the procedure described in the synthesis of compound I-108. The product was purified by flash column chromatography on silica gel (CombiFlash®, 2.0% methanol in dichloromethane). MS (ES): m/z: 579.2 [M+H]$^+$, $^1$H NMR (DMSO-d$_6$, 400 MHz): δ 10.85 (s, 1H), 10.53 (s, 1H), 8.20-8.19 (d, J=5.6 Hz, 1H), 8.02-8.01 (d, J=2.4 Hz, 1H), 7.73-7.72 (d, J=2.4 Hz, 1H), 7.64-7.63 (d, J=2.0 Hz, 1H), 7.42 (s, 1H), 6.71-6.69 (m, 1H), 5.17 (bs, 1H), 4.14-4.06 (m, 2H), 3.95-3.92 (m, 1H), 3.87-3.82 (m, 1H), 3.72 (s, 3H), 2.43-2.42 (m, 1H), 2.34-2.29 (m, 1H), 1.98-1.95 (m, 1H), 0.77-0.75 (m, 4H).

Example 135: (S)—N-(4-((2-((1-((1,4-dioxan-2-yl)methyl)-5-(tert-butyl)-1H-pyrazol-3-yl)amino)-1-methyl-1H-imidazo[4,5-b]pyridin-6-yl)oxy)pyridin-2-yl)cyclopropanecarboxamide and (R)—N-(4-((2-((1-((1,4-dioxan-2-yl)methyl)-5-(tert-butyl)-1H-pyrazol-3-yl)amino)-1-methyl-1H-imidazo[4,5-b]pyridin-6-yl)oxy)pyridin-2-yl)cyclopropanecarboxamide (ES): m/z: 547.8 [M+H]$^+$, $^1$H NMR (DMSO-d$_6$, 400 MHz): δ 10.84 (s, 1H), 9.90 (s, 1H), 8.20-8.19 (d, J=5.6 Hz, 1H), 7.96 (s, 1H), 7.64 (s, 2H), 6.71-6.69 (m, 1H), 6.61 (s, 1H), 4.22-4.17 (m, 1H), 4.10-3.96 (m, 2H), 3.87-3.84 (m, 1H), 3.77-3.74 (m, 1H), 3.67 (s, 4H), 3.51-3.38 (m, 3H), 2.00-1.95 (m, 1H), 1.39 (s, 9H), 0.77-0.75 (m, 4H).

Synthesis of I-135-b. Compound I-135-b was prepared from compound 133.2 and 129.4-b following the procedure

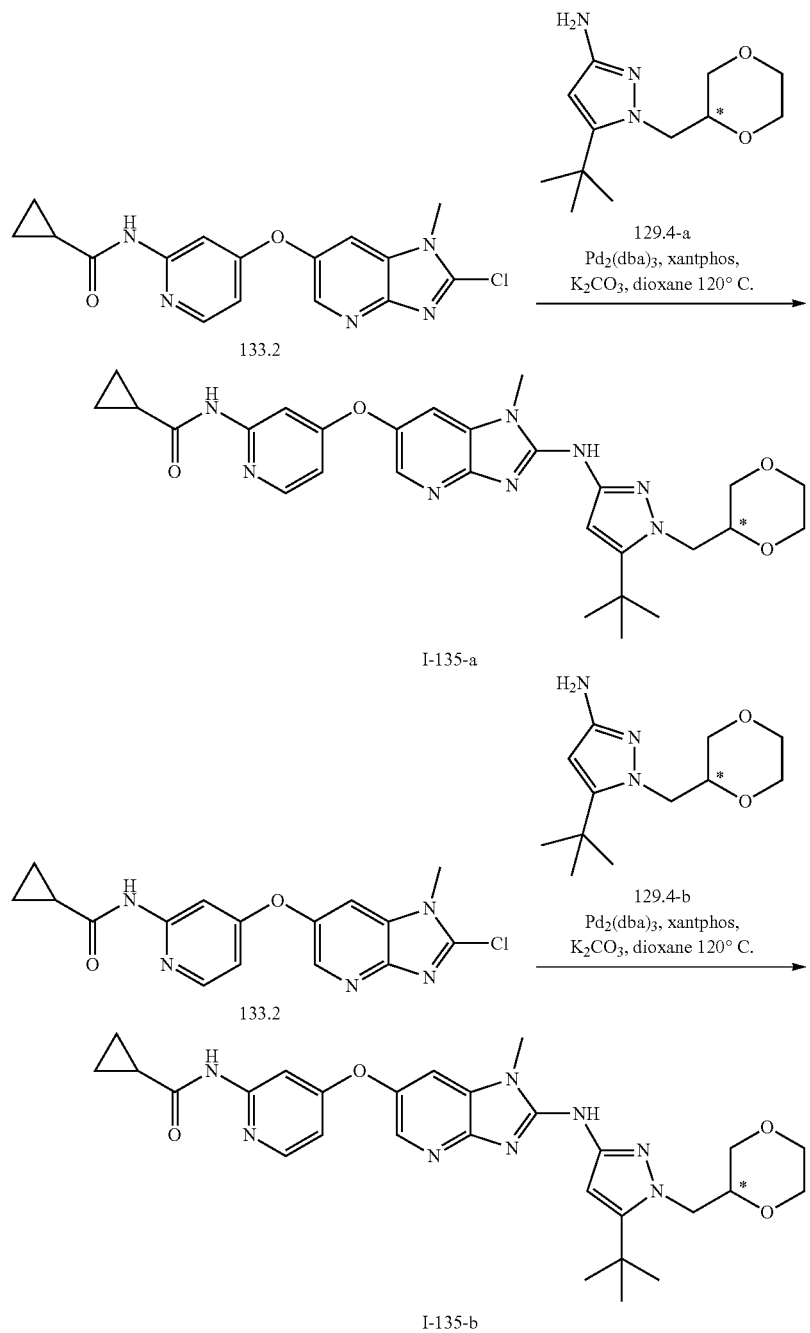

Synthesis of I-135-a. Compound I-135-a was prepared from compound 133.2 and 129.4-a following the procedure described in the synthesis of compound I-108. The product was purified by flash column chromatography on silica gel (CombiFlash®, 3.5% methanol in dichloromethane). MS described in the synthesis of compound I-108. The product was was purified by flash column chromatography on silica gel (CombiFlash®, 3.6% methanol in dichloromethane). MS (ES): m/z: 547.8 [M+H]$^+$, $^1$H NMR (DMSO-d$_6$, 400 MHz): δ 10.85 (s, 1H), 9.90 (s, 1H), 8.20-8.19 (d, J=5.6 Hz, 1H), 7.97-7.96 (d, J=2.4 Hz, 1H), 7.64 (s, 2H), 6.71-6.69 (m, 1H), 6.61 (s, 1H), 4.22-4.17 (m, 1H), 4.11-4.00 (m, 2H), 3.88-3.83 (m, 1H), 3.77-3.74 (m, 1H), 3.67 (s, 4H), 3.51-3.38 (m, 3H), 1.98-1.95 (m, 1H), 1.40 (s, 9H), 0.77-0.75 (m, 4H).

Example 136: N-(4-((2-((5-(tert-butyl)-1-(2-cyanoethyl)-1H-pyrazol-3-yl)amino)-1,7-dimethyl-1H-imidazo[4,5-b]pyridin-6-yl)oxy)pyridin-2-yl)acetamide

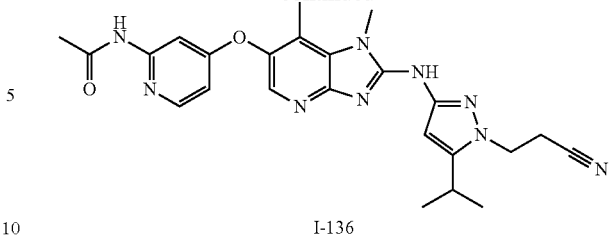

I-136

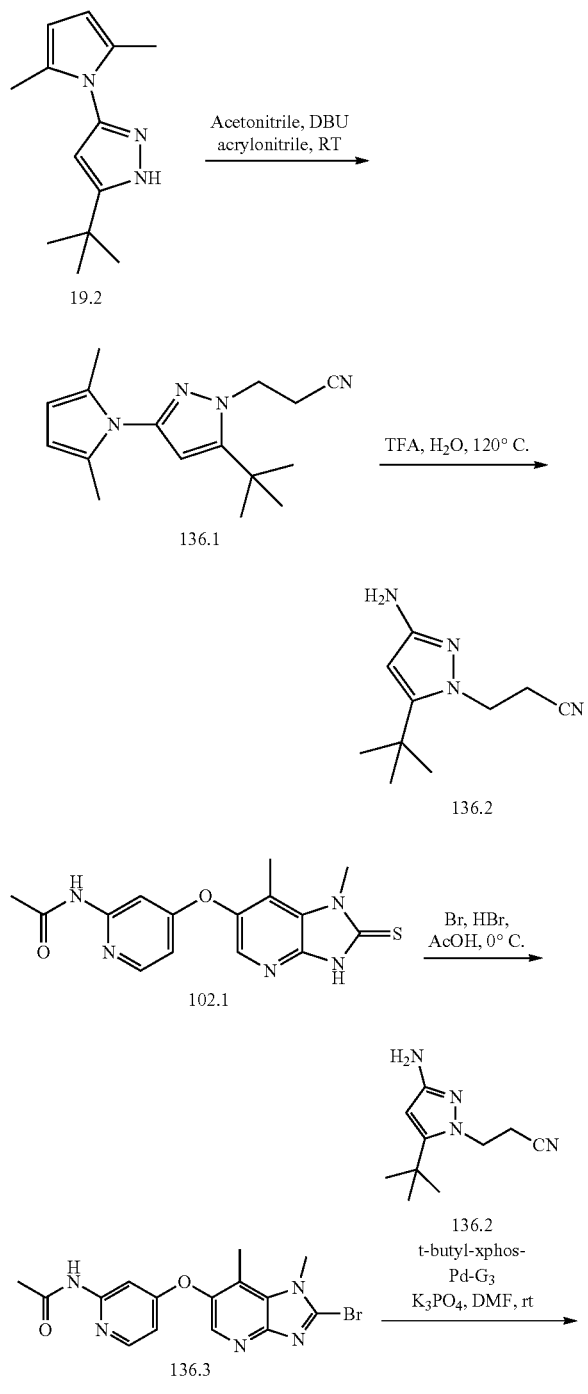

Synthesis of compound 136.1. To a solution of 19.2 (15 g, 69.02 mmol, 1.0 equiv) in acetonitrile (150 mL) was added acrylonitrile (5.4 mL, 82.8 mmol, 1.2 equiv). The reaction mixture was stirred at room temperature for 16 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 12-15% ethyl acetate in hexane) to afford 136.1. MS (ES): m/z 271.3 [M+H]$^+$.

Synthesis of compound 136.2. Compound 136.2 was prepared from compound 136.1 following the procedure described in the synthesis of compound 131.2. The product was purified by flash column chromatography on silica gel (CombiFlash®, 4% methanol in dichloromethane). MS (ES): m/z 193.2 [M+H]$^+$.

Synthesis of compound 136.3. To a solution of 102.1 (0.400 g, 0.261 mmol, 1.0 equiv) in acetic acid (10 mL) was added aqueous hydrobromic acid (0.029 g, 0.365 mmol, 1.4 equiv) at 0° C. followed by bromine (0.150 g, 0.939 mmol, 3.6 equiv). The reaction mixture was stirred for 10 min. It was poured into a saturated aqueous sodium bicarbonate solution, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.8% methanol in dichloromethane) to afford 136.3. MS (ES): m/z 377.2 [M+H]$^+$.

Synthesis of I-136. A mixture of 136.3 (0.100 g, 0.265 mmol, 1.0 equiv), 136.2 (0.051 g, 0.265 mmol, 1.0 equiv) and tripotassium phosphate (0.393 g, 1.85 mmol, 7.0 equiv) in DMF (4 mL) was degassed by bubbling argon through for 10 min. Under argon atmosphere [(2-di-tert-butylphosphino-2',4',6'-triisopropyl-1,1'-biphenyl)-2-(2'-amino-1,1'-biphenyl)] palladium(II) methanesulfonate (0.084 g, 0.106 mmol, 0.4 equiv) was added, and degassed for 5 min. The reaction mixture was stirred at room temperature for 16 h. It was poured over water and extracted with ethyl acetate. The combined organic layers were washed with brine solution, dried over anhydrous sodium sulfate, filtered and concentrated under reduced pressure. The residue was purified by flash column chromatography on silica gel (CombiFlash®, 3.2% methanol in dichloromethane) to afford I-136. MS (ES): m/z: 488.21 [M+H]$^+$, $^1$H NMR (DMSO-d$_6$, 400 MHz): 10.53 (s, 1H), 9.81 (s, 1H), 8.16-8.15 (d, J=5.6 Hz, 1H), 7.89 (s, 1H), 7.60 (s, 1H), 6.60-6.57 (m, 2H), 4.41-4.38 (m, 2H), 3.86 (s, 3H), 3.13-3.10 (m, 2H), 2.40 (s, 3H), 2.03 (s, 3H), 1.40 (s, 9H).

Example 137: N-(4-((2-((5-(tert-butyl)-1-(2-cyanoethyl)-1H-pyrazol-3-yl)amino)-1-methyl-1H-imidazo[4,5-b]pyridin-6-yl)oxy)pyridin-2-yl)cyclopropanecarboxamide

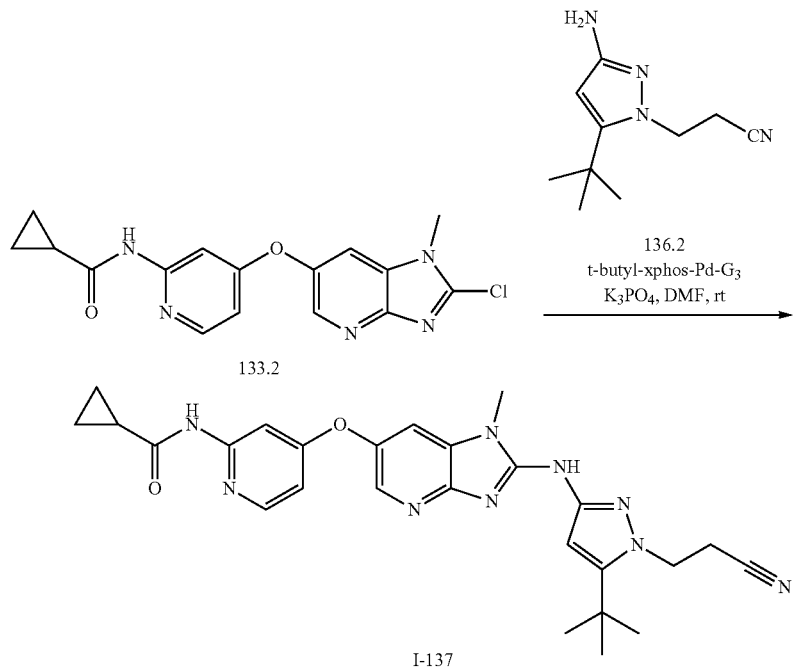

Synthesis of I-137. Compound I-137 was prepared from compound 136.2 and 133.2 following the procedure described in the synthesis of compound I-136. The product was purified by flash column chromatography on silica gel (CombiFlash®, 3.0% methanol in dichloromethane). MS (ES): m/z: 500.20 [M+H]$^+$, LCMS purity: 100%, HPLC purity: 99.24%, $^1$H NMR (DMSO-d$_6$, 400 MHz): 10.83 (s, 1H), 9.94 (s, 1H), 8.19-8.17 (d, J=5.6 Hz, 1H), 7.96 (s, 1H), 7.64-7.63 (d, J=2.8 Hz, 2H), 6.70-6.68 (m, 1H), 6.64 (bs, 1H), 4.41-4.38 (m, 2H), 3.66 (s, 3H), 3.13-3.09 (m, 2H), 1.97-1.94 (m, 1H), 1.40 (s, 9H), 0.74 (bs, 4H).

Example 138: (R)—N-(4-((2-((5-(tert-butyl)-4-fluoro-1-(tetrahydrofuran-3-yl)-1H-pyrazol-3-yl)amino)-1-methyl-1H-imidazo[4,5-b]pyridin-6-yl)oxy)pyridin-2-yl)acetamide

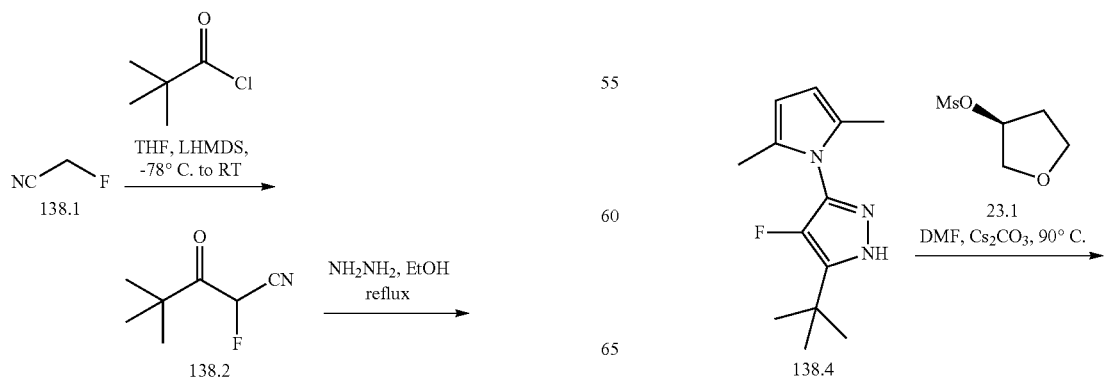

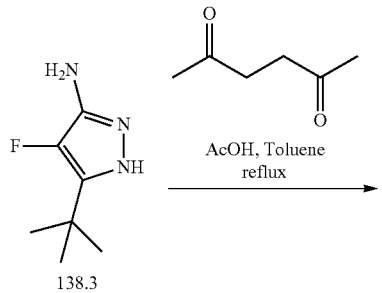

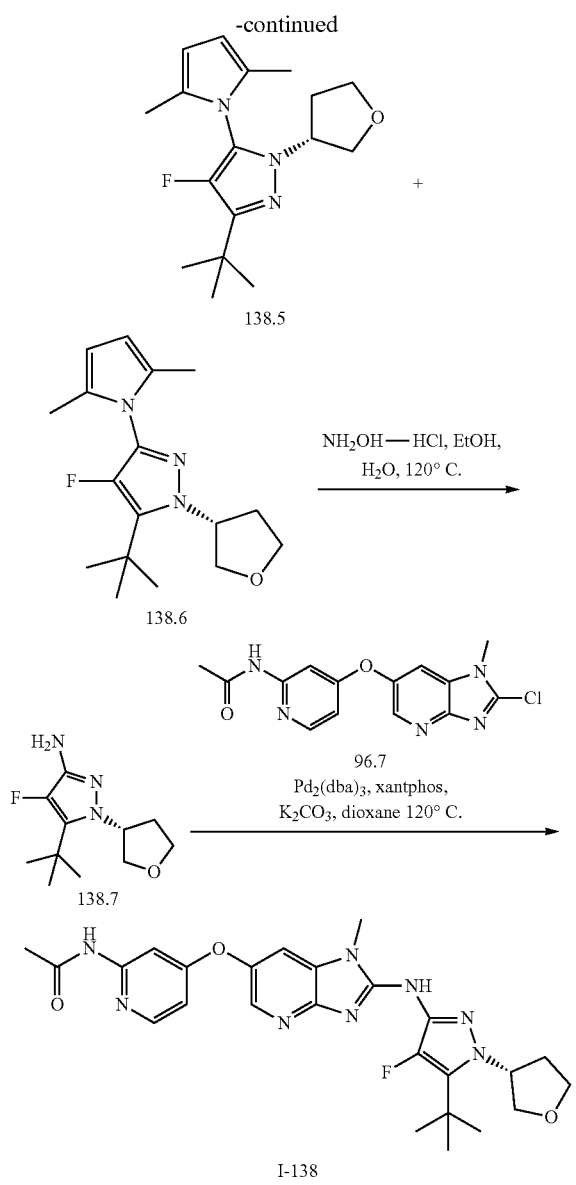

Synthesis of compound 138.4. Compound 138.4 was prepared from compound 138.3 following the procedure described in the synthesis of compound 126.4. The product was purified by flash column chromatography on silica gel (CombiFlash®, 5-7% ethyl acetate in hexane). MS (ES): m/z 236.3 [M+H]$^+$.

Synthesis of compound 138.6. Compound 138.6 was prepared from compound 138.4 and 23.1 following the procedure described in the synthesis of compound 28.7. The product was purified by flash column chromatography on silica gel (CombiFlash®, 8-10% ethyl acetate in hexane). 138.5: MS (ES): m/z 306.4 [M+H]$^+$ and 138.6: MS (ES): m/z 306.4 [M+H]$^+$.

Synthesis of compound 138.7. Compound 138.7 was prepared from compound 138.6 following the procedure described in the synthesis of compound 120.6. The product was purified by flash column chromatography on silica gel (CombiFlash®, 40% ethyl acetate in hexane). MS (ES): m/z 228.3 [M+H]$^+$.

Synthesis of I-138. Compound I-138 was prepared from compound 138.7 and 96.7 following the procedure described in the synthesis of compound I-108. The product was purified by flash column chromatography on silica gel (CombiFlash®, 2-3% methanol in dichloromethane). MS (ES): m/z: 509.44 [M+H]$^+$, $^1$H NMR (DMSO-d$_6$, 400 MHz): δ 10.53 (s, 1H), 9.39 (s, 1H), 8.18-8.16 (d, J=5.6 Hz, 1H), 7.97 (s, 1H), 7.70 (s, 1H), 7.66 (s, 1H), 6.68-6.64 (m, 1H), 5.27 (bs, 1H), 4.13-4.01 (m, 2H), 3.88-3.66 (m, 2H), 3.43 (s, 3H), 2.41-2.34 (m, 1H), 2.22-2.21 (m, 1H), 2.04 (s, 3H), 1.44 (s, 9H).

Example 139: (S)—N-(4-((2-((5-(tert-butyl)-4-fluoro-1-(tetrahydrofuran-3-yl)-1H-pyrazol-3-yl)amino)-1-methyl-1H-imidazo[4,5-b]pyridin-6-yl)oxy)pyridin-2-yl)acetamide

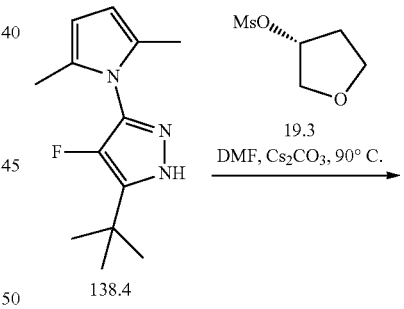

Synthesis of compound 138.2. To a solution of 138.1 (2.5 g, 42.34 mmol, 1.0 equiv) in THF (25 mL) was added pivaloyl chloride (5.11 g, 42.34 mmol, 1.0 equiv) and the reaction mixture was cooled to −78° C. To this added lithium bis(trimethylsilyl)amide (1 M in THF) (84.6 mL, 84.68 mmol, 2.0 equiv). The reaction mixture was allowed to warm to room temperature followed by addition of 1 N hydrochloric acid until pH=2. The reaction mixture was extracted with hexane. The combined organic layers were washed with brine, dried over anhydrous sodium sulfate, filtered and concentrated under reduced pressure to afford 138.2. The crude product was used in the next step without further purification.

Synthesis of compound 138.3. To a solution of 138.2 (3.5 g, 24.45 mmol, 1.0 equiv) in ethanol (35 mL) was added hydrazine hydrate (98%) (2.9 mL, 58.68 mmol, 2.4 equiv). The reaction mixture was refluxed for 4 h. It was poured over ice-water, stirred and extracted with dichloromethane. The combined organic layers were washed with brine, dried over anhydrous sodium sulfate, filtered and concentrated under reduced pressure to afford 138.3. MS (ES): m/z 158.1 [M+H]$^+$.

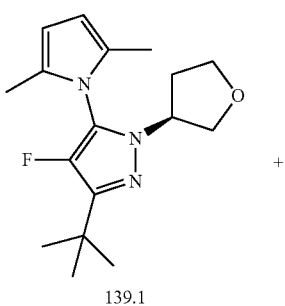

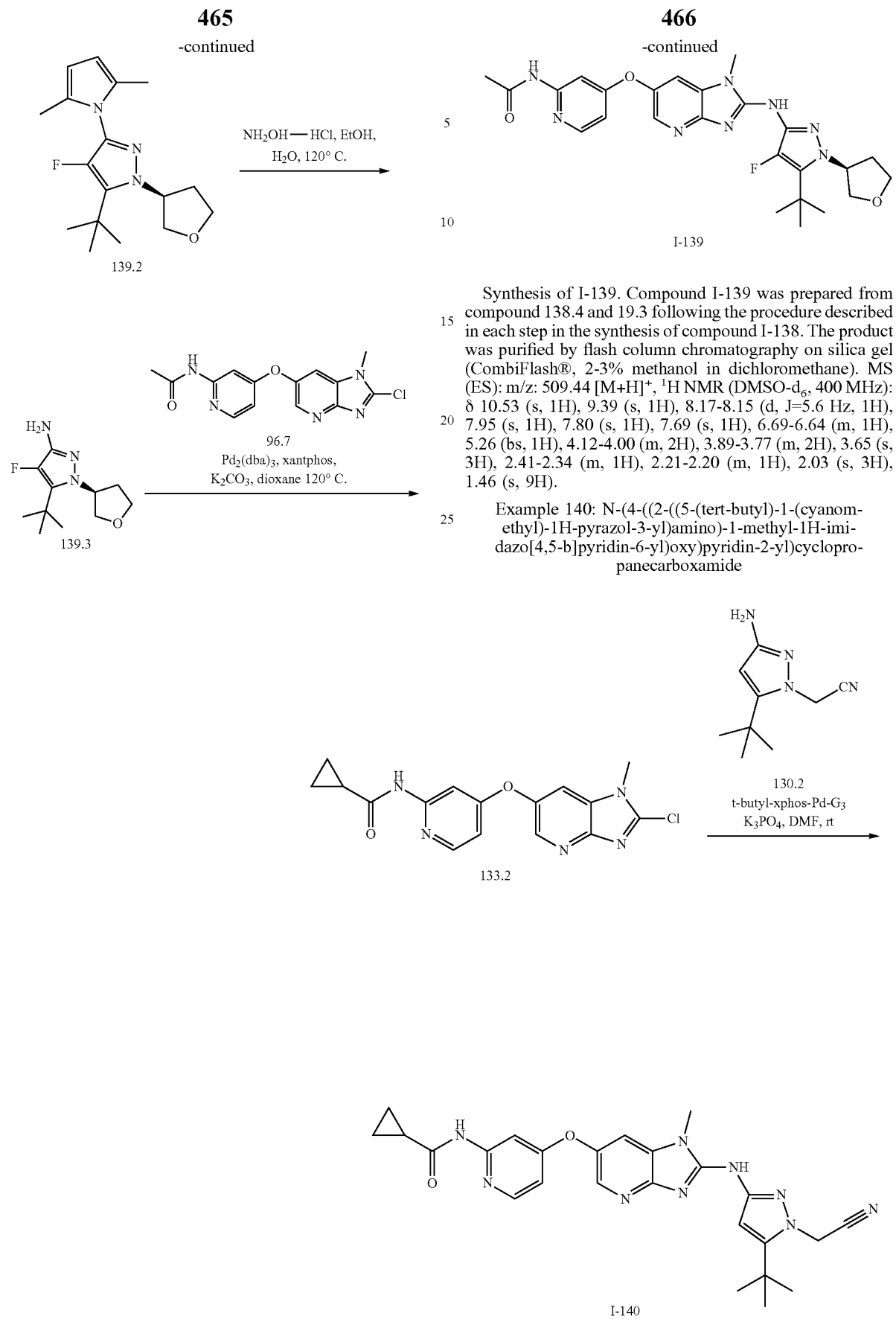

Synthesis of I-139. Compound I-139 was prepared from compound 138.4 and 19.3 following the procedure described in each step in the synthesis of compound I-138. The product was purified by flash column chromatography on silica gel (CombiFlash®, 2-3% methanol in dichloromethane). MS (ES): m/z: 509.44 [M+H]$^+$, $^1$H NMR (DMSO-d$_6$, 400 MHz): δ 10.53 (s, 1H), 9.39 (s, 1H), 8.17-8.15 (d, J=5.6 Hz, 1H), 7.95 (s, 1H), 7.80 (s, 1H), 7.69 (s, 1H), 6.69-6.64 (m, 1H), 5.26 (bs, 1H), 4.12-4.00 (m, 2H), 3.89-3.77 (m, 2H), 3.65 (s, 3H), 2.41-2.34 (m, 1H), 2.21-2.20 (m, 1H), 2.03 (s, 3H), 1.46 (s, 9H).

Example 140: N-(4-((2-((5-(tert-butyl)-1-(cyanomethyl)-1H-pyrazol-3-yl)amino)-1-methyl-1H-imidazo[4,5-b]pyridin-6-yl)oxy)pyridin-2-yl)cyclopropanecarboxamide Synthesis of I-140. Compound I-140 was prepared from compound 130.2 and 133.2 following the procedure described in the synthesis of compound I-136. The product was purified by preparative HPLC. MS (ES): m/z: 485.9 [M+H]+, $^1$H NMR (DMSO-d$_6$, 400 MHz): 10.83 (s, 1H), 10.08 (s, 1H), 8.20-8.19 (d, J=5.6 Hz, 1H), 7.99 (s, 1H), 7.67-7.64 (d, J=9.6 Hz, 2H), 6.74 (s, 1H), 6.71-6.70 (d, J=3.6 Hz, 1H), 5.48 (bs, 2H), 3.69 (s, 3H), 2.00-1.92 (m, 1H), 1.41 (s, 9H), 0.75 (bs, 4H).

Example 141: (R)—N-(4-((2-((5-(tert-butyl)-1-(tetrahydrofuran-3-yl)-1H-pyrazol-3-yl)amino)-7-chloro-1-methyl-1H-imidazo[4,5-b]pyridin-6-yl)oxy)pyridin-2-yl)acetamide

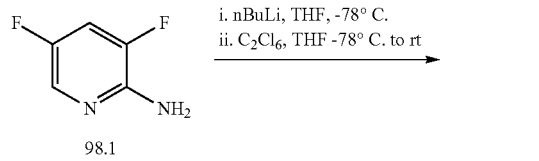

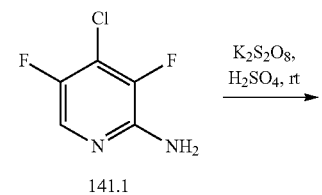

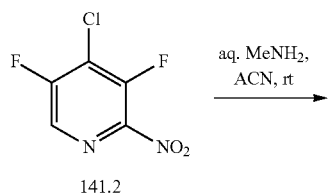

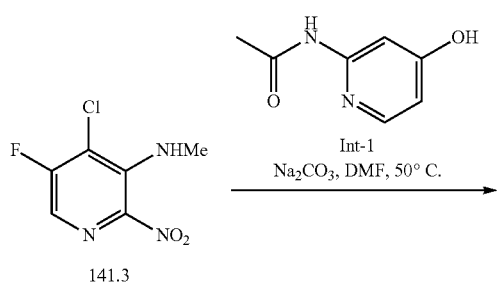

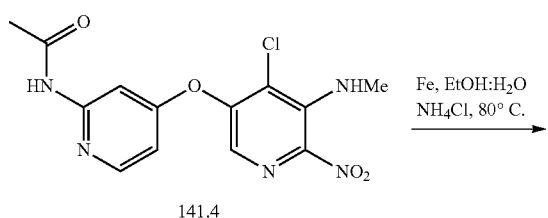

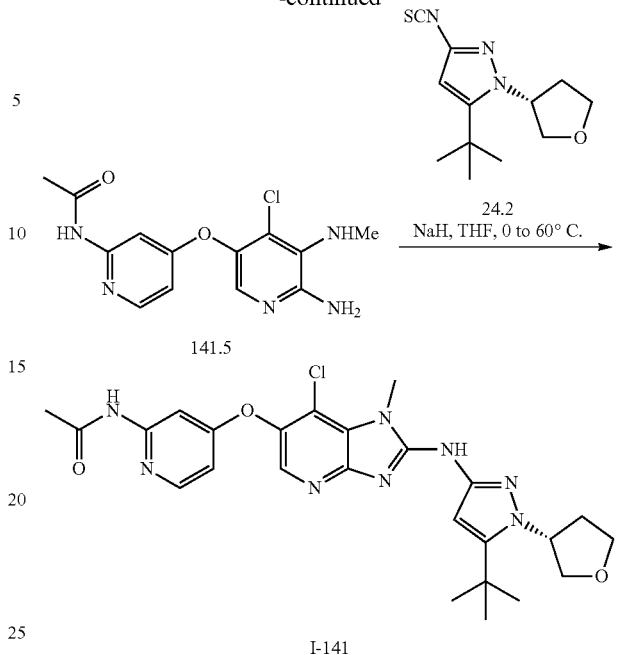

Synthesis of compound 141.1. To a solution of 98.1 (10 g, 76.87 mmol, 1.0 equiv) in THF (200 mL), was added n-butyl lithium (2.5M in hexane) (61.4 mL, 153.7 mmol, 2.0 equiv) at −78° C. and stirred for 40 min. Hexachloroethane (36.3 g, 153.7 mmol, 2.0 equiv) was added and the reaction mixture was stirred at −78° C. for 40 min. A saturated aqueous ammonium chloride solution was added carefully to quench the reaction. The mixture was extracted with ethyl acetate. The combined organic layers were washed with brine, dried over anhydrous sodium sulfate, filtered and concentrated under reduced pressure. The residue by flash column chromatography on silica gel (CombiFlash®, 12% ethyl acetate in hexane) to afford 141.1. $^1$H NMR (DMSO-d$_6$, 400 MHz): δ 7.98-7.94 (m, 1H), 6.48 (bs, 2H).

Synthesis of compound 141.2. Concentrated sulfuric acid (3 mL) was added dropwise to potassium persulfate (2.05 g, 7.6 mmol, 2.5 equiv) at room temperature and stirred for 15 min. To the mixture was added 141.1 (0.5 g, 3.04 mmol, 1.0 equiv) in small portions while maintaining temperature in the range of 30–40° C. After the addition the reaction mixture was stirred at room temperature for 3-4 h. It was poured over crushed ice, stirred and basified with saturated sodium bicarbonate and extracted with ethyl acetate. The combined organic layers were washed with brine solution, dried over anhydrous sodium sulfate, filtered and concentrated under reduced pressure. The residue was purified by flash column chromatography on silica gel (CombiFlash®, 2-3% ethyl acetate in hexane) to afford 141.2. $^1$H NMR (DMSO-d$_6$, 400 MHz): δ 8.78 (s, 1H).

Synthesis of compound 141.3. To a solution of 141.2 (0.970 g, 4.99 mmol, 1.0 equiv) in acetonitrile (10 mL) was added aqueous methylamine solution (40%) (0.8 mL, 9.98 mmol, 2.0 equiv) dropwise at 0° C. The reaction mixture was allowed to warm to at room temperature and stirred for 20 min. It was poured over ice-water and extracted with ethyl acetate. The combined organic layers were washed with brine solution, dried over anhydrous sodium sulfate, filtered and concentrated under reduced pressure. The residue was purified by flash column chromatography on silica gel (CombiFlash®, 10% ethyl acetate in hexane) to afford 141.3. ¹H NMR (DMSO-d₆, 400 MHz): δ 7.98 (s, 1H), 7.05 (bs, 1H), 2.79 (d, 3H).

Synthesis of compound 141.4. A mixture of 141.3 (0.930 g, 4.52 mmol, 1.0 equiv) in DMF (10 mL), Int-1 (0.895 g, 5.88 mmol, 1.3 equiv) and sodium carbonate (0.958 g, 9.04 mmol, 2.0 equiv) was stirred at 50° C. for 6 h. The reaction mixture was cooled to room temperature, poured over ice-water. The precipitated solids were collected by filtration, rinsed with water and dried under vacuum to afford 141.4. MS (ES): m/z 338.7 [M+H]⁺.

Synthesis of compound 141.5. To a solution of compound 141.4 (0.850 g, 2.52 mmol, 1.0 equiv) in ethanol-water (8:2, 10 mL) was added iron powder (0.705 g, 12.6 mmol, 5.0 equiv) followed by ammonium chloride (0.673 g, 12.6 mmol, 5.0 equiv). The reaction mixture was stirred at 80° C. for 2 h. It was filtered through a pad of Celite® and rinsed with ethanol. The filtrate was concentrated under reduced pressure. The residue was purified by flash column chromatography on silica gel (CombiFlash®, 2.4% methanol in dichloromethane) to afford 141.5. MS (ES): m/z 308.5 [M+H]⁺.

Synthesis of I-141. To a solution of 141.5 (0.100 g, 0.324 mmol, 1.0 equiv) in THF (5 mL) was added sodium hydride (0.065 g, 1.62 mmol, 5.0 equiv) at 0° C. and stirred for 30 min. To the mixture was added solution of 24.2 (0.163 g, 0.649 mmol, 2.0 equiv) in THF (2 mL). The reaction mixture was stirred at 60° C. for 3 h. It was cooled to room temperature, poured over ice-water and extracted with ethyl acetate. The combined organic layers were washed with brine solution, dried over anhydrous sodium sulfate, filtered and concentrated under reduced pressure. The residue was further purified by preparative HPLC to afford I-141. MS (ES): m/z: 525.45 [M+H]⁺, ¹H NMR (DMSO-d₆, 400 MHz): δ 10.57 (s, 1H), 10.03 (s, 1H), 8.18-8.17 (d, J=5.6 Hz, 1H), 8.08 (s, 1H), 7.64 (s, 1H), 6.65-6.63 (m, 1H), 6.56 (s, 1H), 5.26 (m, 1H), 4.11-4.06 (m, 2H), 3.93 (s, 3H), 3.88-3.82 (m, 2H), 2.26-2.23 (m, 2H), 2.04 (s, 3H), 1.40 (s, 9H).

Example 142: (S)—N-(4-((2-((5-(tert-butyl)-1-(tetrahydrofuran-3-yl)-1H-pyrazol-3-yl)amino)-7-chloro-1-methyl-1H-imidazo[4,5-b]pyridin-6-yl)oxy)pyridin-2-yl)acetamide

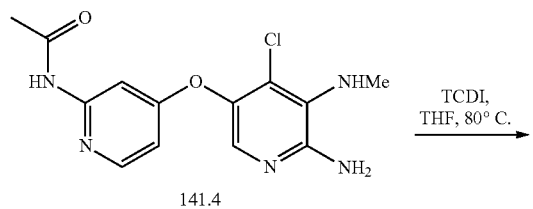

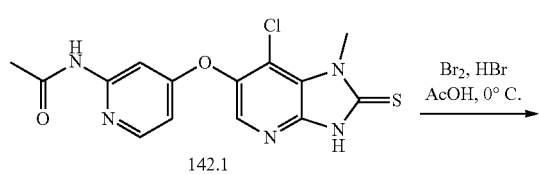

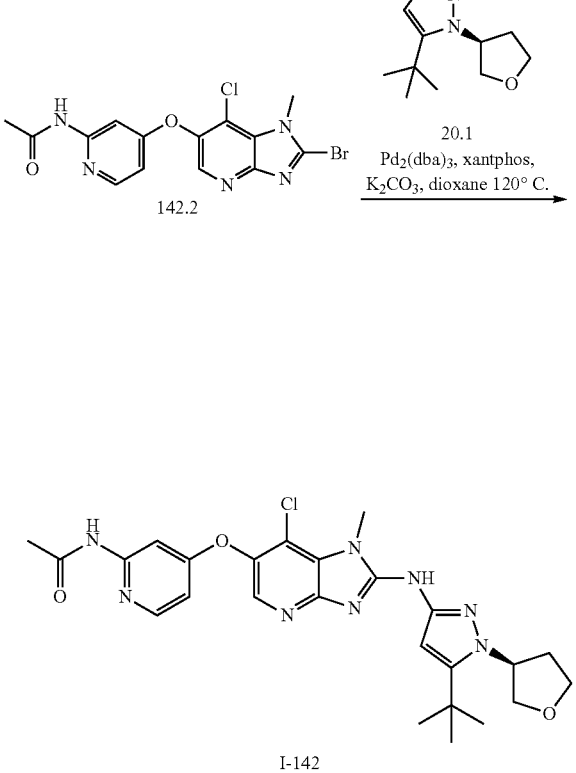

Synthesis of compound 142.1. To a solution of 141.4 (0.150 g, 0.487 mmol, 1.0 equiv) in THF (2 mL) was added 1,1'-thiocarbonyldiimidazole (0.433 g, 2.43 mmol, 5.0 equiv). The reaction mixture was stirred at 80° C. for 1 h. The reaction mixture was cooled to room temperature and poured over ice-water. Precipitated solid was filtered out and triturated with hexane to afford 142.1. MS (ES): m/z: 350.7 [M+H]⁺.

Synthesis of compound 142.2. Compound 142.2 was prepared from compound 142.1 following the procedure described in the synthesis of compound 136.3. The product was purified by flash column chromatography on silica gel (CombiFlash®, 2.5% methanol in dichloromethane). MS (ES): m/z 397.6 [M+H]⁺.

Synthesis of I-142. Compound I-142 was prepared from compound 142.2 and 20.1 following the procedure described in the synthesis of compound I-108. The product was purified by flash column chromatography on silica gel (CombiFlash®, 3.8% methanol in dichloromethane). MS (ES): m/z: 525.88 [M+H]⁺, ¹H NMR (DMSO-d₆, 400 MHz): δ 10.57 (s, 1H), 10.03 (s, 1H), 8.18-8.17 (d, J=5.6 Hz, 1H), 8.08 (s, 1H), 7.64 (s, 1H), 6.65-6.63 (m, 1H), 6.56 (s, 1H), 5.26 (m, 1H), 4.11-4.06 (m, 2H), 3.93 (s, 3H), 3.88-3.82 (m, 2H), 2.26-2.23 (m, 2H), 2.04 (s, 3H), 1.40 (s, 9H).

Example 143: (R)—N-(4-((2-((5-(tert-butyl)-1-(((4-methylmorpholin-2-yl)methyl)-1H-pyrazol-3-yl)amino)-1-methyl-1H-imidazo[4,5-b]pyridin-6-yl)oxy)pyridin-2-yl)acetamide
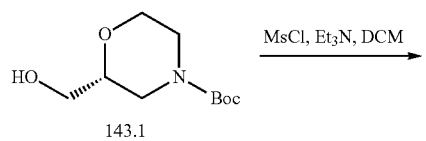
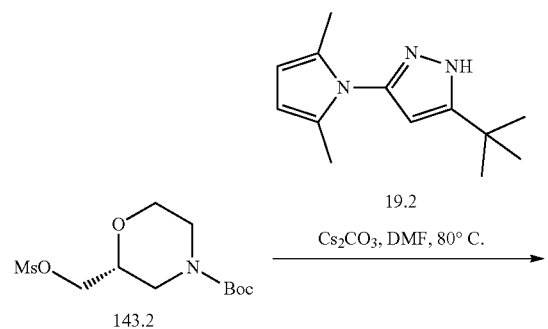
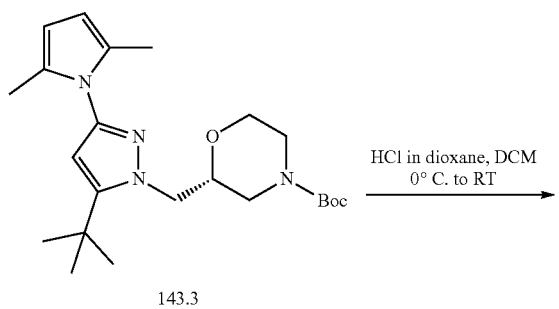
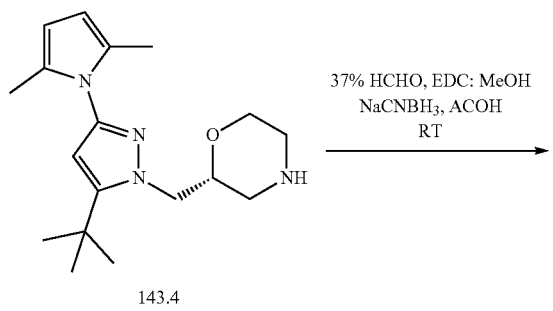
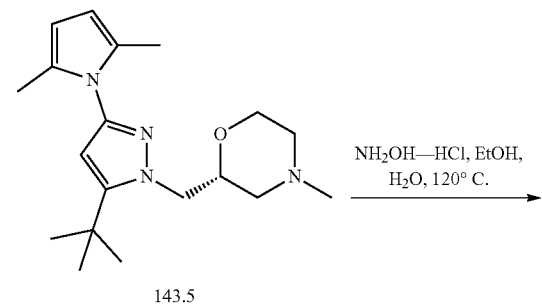

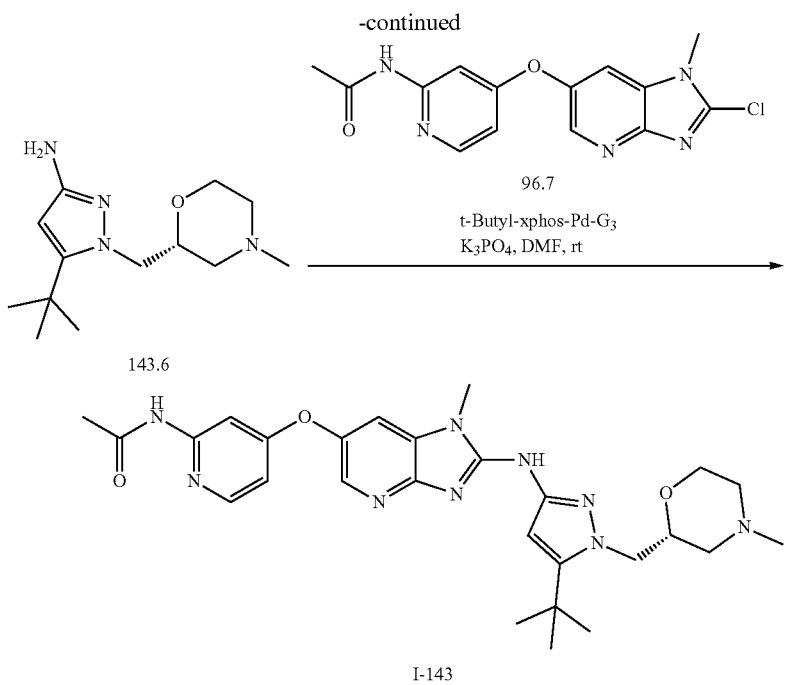

Synthesis of compound 143.2. Compound 143.2 was prepared from compound 143.1 following the procedure described in the synthesis of compound 28.5. The crude product was used without further purification. $^1$H NMR (CDCl$_3$, 400 MHz): δ 4.25-4.24 (d, 2H), 3.94-3.91 (m, 3H), 3.72-3.69 (m, 1H), 3.59-3.50 (m, 1H), 3.08 (s, 3H), 2.97 (bs, 1H), 2.78 (bs, 1H), 1.48 (s, 9H).

Synthesis of compound 143.3. Compound 143.3 was prepared from compound 143.2 following the procedure described in the synthesis of compound 28.7. The product was purified by flash column chromatography on silica gel (CombiFlash®, 10-12% ethyl acetate in hexane) to afford 143.3. MS (ES): m/z 403.5 [M+H]$^+$.

Synthesis of compound 143.4. To a solution of 143.3 (1.67 g, 4.15 mmol, 1.0 equiv) in dichloromethane (20 mL) was added hydrogen chloride solution (4.0 M in dioxane) (11.7 mL) at 0° C. The reaction mixture was stirred at room temperature for 2 h. It was transferred into ice-water, neutralized with saturated sodium bicarbonate solution and extracted with dichloromethane. The combined organic layers were washed with brine, dried over sodium sulfate, filtered and concentrated under reduced pressure to afford 143.4. It was used without further purification.

Synthesis of compound 143.5. To a solution of 143.4 (1.1 g, 3.48 mmol, 1.0 equiv) in 1,2-dichloroethane-methanol (2:1, 10 mL) was added formaldehyde solution (37% in water) (1.4 mL, 17.4 mmol, 5.0 equiv). The reaction mixture was stirred at room temperature for 30 min. To mixture was added acetic acid (0.49 mL, 8.7 mmol, 2.5 equiv) followed by sodium cyanoborohydride (1.1 g, 17.4 mmol, 5.0 equiv). After completion of reaction, it was transferred into ice-water and extracted with ethyl acetate. The combined organic layers were washed with brine, dried over sodium sulfate, filtered and concentrated under reduced pressure. The residue was purified by flash column chromatography on silica gel (CombiFlash®, 3.0-3.5% methanol in dichloromethane) to afford 143.5. MS (ES): m/z 331.5 [M+H]$^+$.

Synthesis of compound 143.6. Compound 143.6 was prepared from compound 143.5 following the procedure described in the synthesis of compound 120.6. The product was purified by flash column chromatography on silica gel (CombiFlash®, 7-8% methanol in dichloromethane) to afford 143.6. MS (ES): m/z 253.3 [M+H]$^+$.

Synthesis of I-143. Compound I-143 was prepared from compound 143.6 and 96.7 following the procedure described in the synthesis of compound I-136. The product was purified by preparative HPLC. MS (ES): m/z: 534.5 [M+H]$^+$, $^1$H NMR (DMSO-d$_6$, 400 MHz): 10.53 (s, 1H), 9.87 (s, 1H), 8.31 (s, 1H), 8.18-8.16 (d, J=6.0 Hz, 1H), 7.96 (s, 1H), 7.66-7.63 (m, 2H), 6.66-6.64 (m, 1H), 6.60 (s, 1H), 4.23-4.17 (m, 1H), 4.05-3.99 (m, 3H), 3.80-3.77 (m, 2H), 3.53-3.45 (m, 1H), 2.80-2.77 (m, 2H), 2.60-2.57 (m, 2H), 2.19 (s, 3H), 2.03 (s, 3H), 1.38 (s, 9H).

Example I-144: (S)—N-(4-((2-((5-(tert-butyl)-1-(((4-methylmorpholin-2-yl)methyl)-1H-pyrazol-3-yl)amino)-1-methyl-1H-imidazo[4,5-b]pyridin-6-yl)oxy)pyridin-2-yl)acetamide

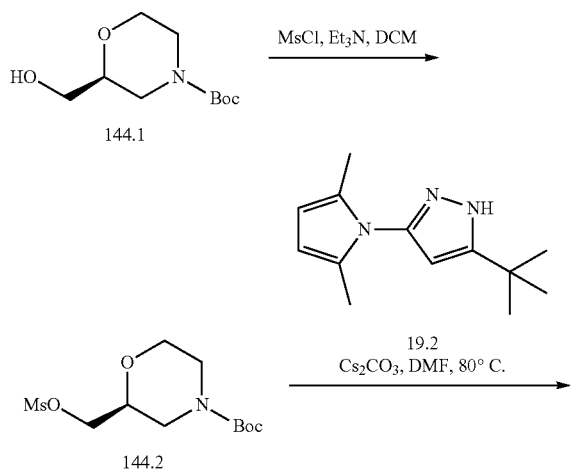

-continued

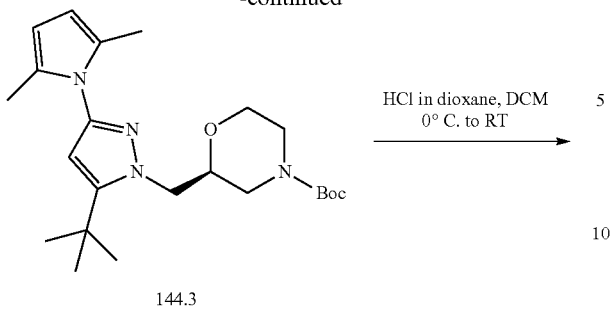

144.3

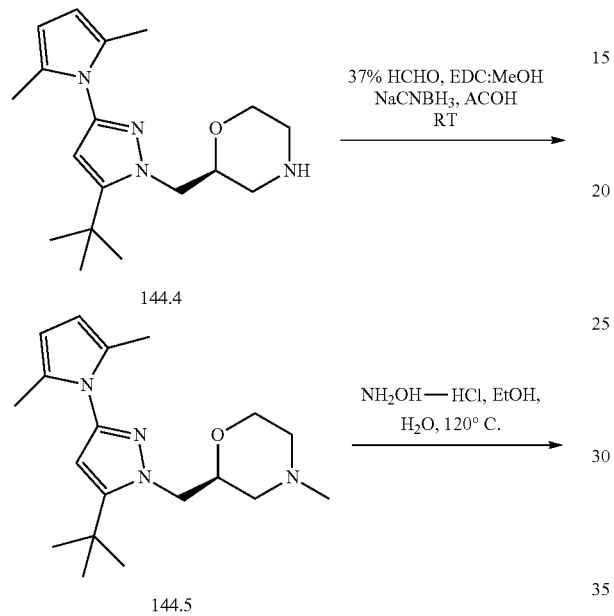

144.4

144.5

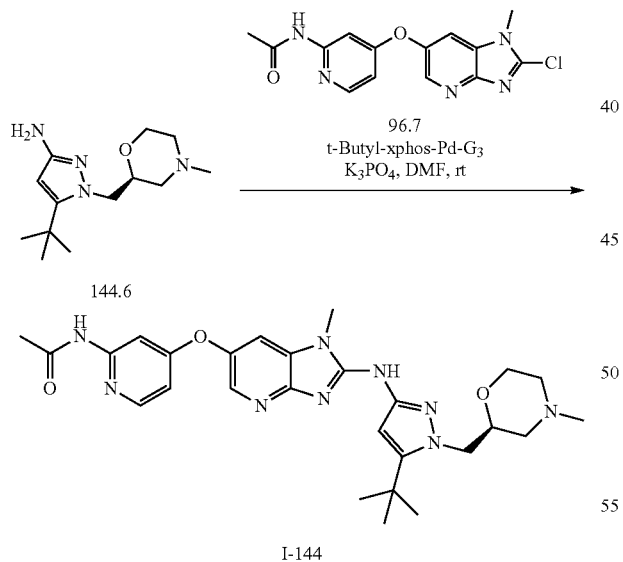

144.6

I-144

Synthesis of I-144. Compound I-144 was prepared from compound 144.1 following the procedure described in each step in the synthesis of compound I-143. The product was purified by preparative HPLC. MS(ES): m/z: 534.9 [M+H]⁺, ¹H NMR (DMSO-d₆, 400 MHz): 10.53 (s, 1H), 9.89 (s, 1H), 8.27 (s, 1H), 8.19-8.17 (d, J=5.6 Hz, 1H), 7.97 (s, 1H), 7.67-7.64 (m, 2H), 6.67-6.65 (m, 1H), 6.61 (s, 1H), 4.22-4.18 (m, 1H), 4.08-4.04 (m, 3H), 3.81-3.78 (m, 2H), 3.51-3.45 (m, 1H), 2.81-2.78 (m, 2H), 2.60-2.57 (m, 2H), 2.20 (s, 3H), 2.04 (s, 3H), 1.38 (s, 9H).

Example 145: (R)—N-(4-((7-chloro-1-methyl-2-((5-(perfluoroethyl)-1-(tetrahydrofuran-3-yl)-1H-pyrazol-3-yl)amino)-1H-imidazo[4,5-b]pyridin-6-yl)oxy)pyridin-2-yl)acetamide

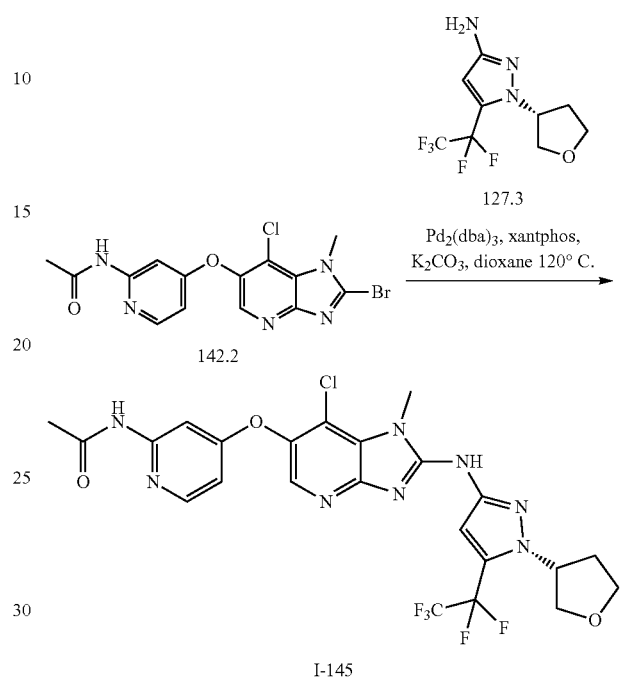

Synthesis of I-145. Compound I-145 was prepared from compound 142.2 and 127.3 following the procedure described in the synthesis of compound I-108. The product was purified by flash column chromatography on silica gel (CombiFlash®, 2.0% methanol in dichloromethane). MS (ES): m/z: 587.8 [M+H]⁺, ¹H NMR (DMSO-d₆, 400 MHz): δ 10.65 (s, 1H), 10.59 (s, 1H), 8.20-8.19 (d, J=5.6 Hz, 1H), 8.15 (s, 1H), 7.65 (s, 1H), 7.38 (s, 1H), 6.67-6.65 (m, 1H), 5.18 (bs, 1H), 4.15-4.07 (m, 2H), 3.98-3.93 (m, 4H), 3.89-3.83 (m, 1H), 2.46-2.41 (m, 1H), 2.34-2.31 (m, 1H), 2.05 (s, 3H).

Example 146: (S)—N-(4-((7-chloro-1-methyl-2-((5-(perfluoroethyl)-1-(tetrahydrofuran-3-yl)-1H-pyrazol-3-yl)amino)-1H-imidazo[4,5-b]pyridin-6-yl)oxy)pyridin-2-yl)acetamide

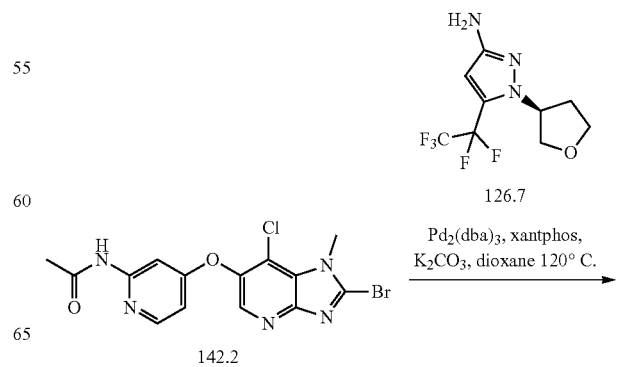

-continued

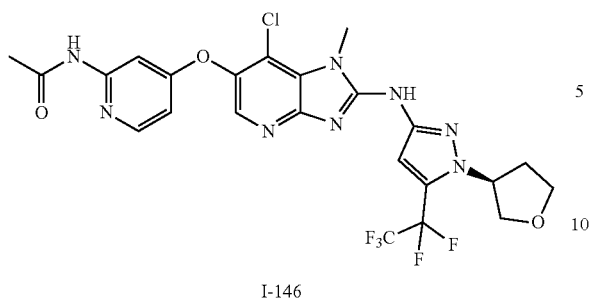

I-146

Synthesis of I-146. Compound I-146 was prepared from compound 142.2 and 126.7 following the procedure described in the synthesis of compound I-108. The product was purified by flash column chromatography on silica gel (CombiFlash®, 2.0% methanol in dichloromethane). MS (ES): m/z: 587.8 [M+H]+, $^1$H NMR (DMSO-$d_6$, 400 MHz): δ 10.65 (s, 1H), 10.59 (s, 1H), 8.20-8.19 (d, J=5.6 Hz, 1H), 8.15 (s, 1H), 7.65 (s, 1H), 7.38 (s, 1H), 6.67-6.65 (m, 1H), 5.18 (bs, 1H), 4.15-4.07 (m, 2H), 3.98-3.93 (m, 4H), 3.89-3.83 (m, 1H), 2.46-2.41 (m, 1H), 2.34-2.31 (m, 1H), 2.05 (s, 3H).

Example I-147: (R)—N-(4-((2-((5-(tert-butyl)-1-(tetrahydrofuran-3-yl)-1H-pyrazol-3-yl)amino)-7-(difluoromethyl)-1-methyl-1H-imidazo[4,5-b]pyridin-6-yl)oxy)pyridin-2-yl)acetamide -continued

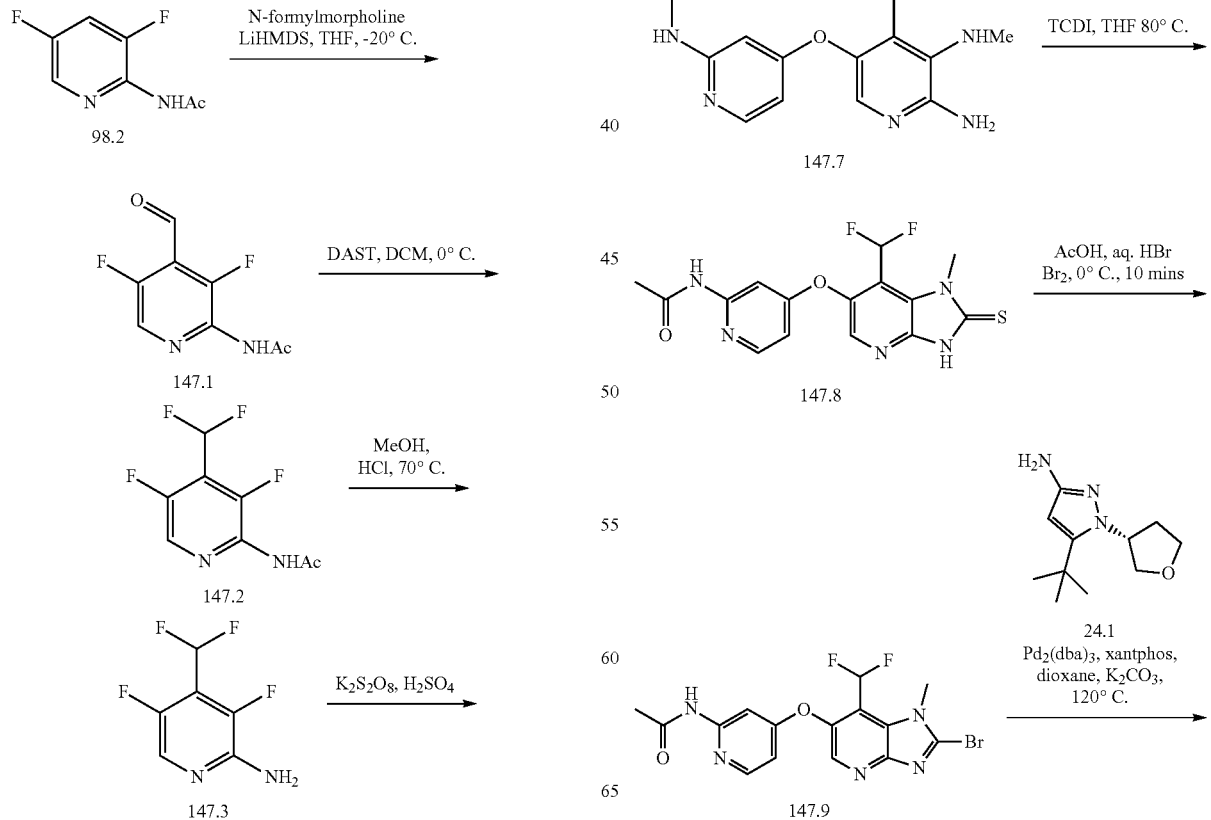

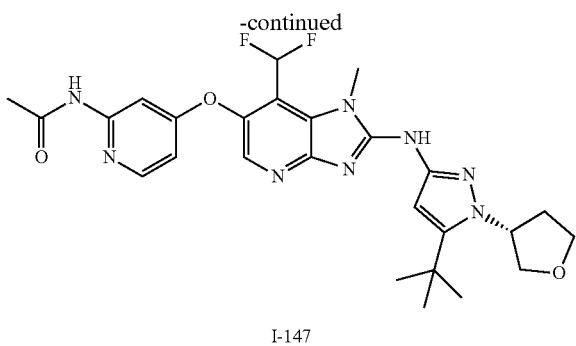

I-147

Synthesis of compound 147.1. To a solution of 98.2 (15 g, 87.14 mmol, 1.0 equiv) and N-formylmorpholine (26.1 mL, 261.4 mmol, 3.0 equiv) in THF (150 mL) was added lithium bis(trimethylsilyl)amide (1.0 M in THF) (200 mL, 200.4 mmol, 2.3 equiv) at −20° C. dropwise. After the addition, the reaction mixture was stirred at same temperature for 2 h. It was poured into a cold aqueous solution of citric acid monohydrate (60.4 g) and sodium chloride (15 g) and the mixture was stirred at 0° C. for 15 min. The organic layer was separated, washed with 50% dipotassium hydrogen phosphate aqueous solution followed by brine. It was dried over sodium sulfate, filtered and concentrated under reduced pressure. The residue was purified by flash column chromatography on silica gel (CombiFlash®, 70% ethyl acetate in hexane) to afford 147.1. $^1$H NMR (DMSO-d$_6$, 400 MHz): δ 10.46 (s, 1H), 10.22 (s, 1H), 8.53 (s, 1H), 2.09 (s, 3H).

Synthesis of compound 147.2. To a solution of 147.1 (1.0 g, 5.0 mmol, 1.0 equiv) in dichloromethane (10 mL), was added diethylaminosulfur trifluoride (0.65 mL, 5.0 mmol, 1.0 equiv) dropwise at 0° C. The reaction mixture was stirred at same temperature for 30 min. It was transferred into saturated sodium bicarbonate solution and extracted with ethyl acetate. The combined organic layers were washed with brine, dried over sodium sulfate, filtered and concentrated under reduced pressure. The residue was purified by flash column chromatography on silica gel (CombiFlash®, 35-40% ethyl acetate in hexane) to afford 147.2. $^1$H NMR (CDCl$_3$, 400 MHz): δ 8.27 (s, 1H), 7.63 (s, 1H), 7.12-6.86 (m, 1H), 2.38 (s, 3H).

Synthesis of compound 147.3. To a solution of 147.2 (1.8 g, 8.10 mmol, 1.0 equiv) in methanol (10 mL), was added concentrated hydrochloric acid (3 mL). The reaction mixture was refluxed for 1 h. It was concentrated under reduced pressure. To the residue was added ice-water and it was neutralized by saturated sodium bicarbonate solution and extracted with ethyl acetate. The combined organic layers were washed with brine, dried over sodium sulfate, filtered and concentrated under reduced pressure. The residue was purified by flash column chromatography on silica gel (CombiFlash®, 15-20% ethyl acetate in hexane) to afford 147.3. $^1$H NMR (DMSO-d$_6$, 400 MHz): δ 7.99 (s, 1H), 7.44-7.18 (m, 1H), 6.54 (s, 2H).

Synthesis of compound 147.4. Compound 147.4 was prepared from compound 147.3 following the procedure described in the synthesis of compound 141.2. The product was purified by flash column chromatography on silica gel (CombiFlash®, 8-10% ethyl acetate in hexane) to afford 147.4. $^1$H NMR (CDCl$_3$, 400 MHz): δ 8.69 (s, 1H), 7.28-6.91 (m, 1H).

Synthesis of compound 147.5. To a solution of 147.4 (0.155 g, 0.737 mmol, 1.0 equiv) in acetonitrile (3 mL) was added aqueous methylamine solution (40%) (0.06 mL, 0.737 mmol, 1.0 equiv) dropwise at 0° C. The reaction mixture was stirred at room temperature for 2-3 h. It was transferred into ice-water and extracted with ethyl acetate. The combined organic layers were washed with brine solution, dried over sodium sulfate, filtered and concentrated under reduced pressure to afford 147.5. $^1$H NMR (DMSO-d$_6$, 400 MHz): δ 7.96 (s, 1H), 7.54-7.41 (m, 1H), 2.86 (d, 3H).

Synthesis of compound 147.6. A mixture of 147.5 (0.120 g, 0.542 mmol, 1.0 equiv) in DMF (2 mL), Int-1 (0.091 g, 0.596 mmol, 1.1 equiv) and sodium carbonate (0.110 g, 1.082 mmol, 2.0 equiv) was stirred at 70° C. for 1 h. It was cooled to room temperature, transferred into ice-water and extracted with ethyl acetate. The combined organic layers were washed with brine solution, dried over sodium sulfate, filtered and concentrated under reduced pressure. The residue was purified by flash column chromatography on silica gel (CombiFlash®, 25-30% ethyl acetate in hexane) to afford 147.6. MS(ES): m/z 354.3 [M+H]$^+$.

Synthesis of compound 147.7. Compound 147.7 was prepared from compound 147.6 following the procedure described in the synthesis of compound 141.5. The product was purified by flash column chromatography on silica gel (CombiFlash®, 2.2% methanol in dichloromethane) to afford 147.7. MS(ES): m/z 324.3 [M+H]$^+$.

Synthesis of compound 147.8. To a solution of 147.7 (0.060 g, 0.185 mmol, 1.0 equiv) in THF (2 mL) was added 1,1'-thiocarbonyldiimidazole (0.164 g, 0.925 mmol, 5.0 equiv). The reaction mixture was stirred at 80° C. for 1 h. It was cooled to room temperature and poured into ice-water. The precipitates formed were collected by filtration and triturated with hexane to obtain 147.8. MS(ES): m/z: 366.3 [M+H]$^+$.

Synthesis of compound 147.9. To a solution of 147.8 (0.040 g, 0.109 mmol, 1.0 equiv) in acetic acid (2 mL) was added aqueous hydrobromic acid (0.013 g, 0.163 mmol, 1.5 equiv) at 0° C. followed by bromine (0.078 g, 0.436 mmol, 4.0 equiv). The reaction mixture was stirred for 10 min. It was poured into a saturated sodium bicarbonate solution, stirred and extracted with ethyl acetate. The combined organic layers were washed with brine, dried over sodium sulfate, filtered and concentrated under reduced pressure. The residue was further purified by flash column chromatography on silica gel (CombiFlash®, 2.3% methanol in dichloromethane) to afford 147.9. MS (ES): m/z 413.2 [M+H]$^+$.

Synthesis of I-147. Compound I-147 was prepared from compound 147.9 and 24.1 following the procedure described in the synthesis of compound I-108. The product was purified by flash column chromatography on silica gel (CombiFlash®, 4.0% methanol in dichloromethane). MS(ES): m/z: 541.56 [M+H]$^+$, $^1$H NMR (DMSO-d$_6$, 400 MHz): 10.60 (s, 1H), 10.13 (s, 1H), 8.21-8.20 (d, J=5.6 Hz, 1H), 8.08 (s, 1H), 7.68 (s, 1H), 7.49-7.23 (m, 1H), 6.67-6.65 (m, 1H), 6.58 (s, 1H), 5.28 (s, 1H), 4.12-4.09 (m, 2H), 3.89-3.80 (m, 5H), 2.39-2.35 (m, 1H), 2.27-2.23 (m, 1H), 2.05 (s, 3H), 1.42 (s, 9H).

Example 148: (R)—N-(4-((2-((5-(tert-butyl)-1-((3,3-difluoro-1-methylpiperidin-4-yl)methyl)-1H-pyrazol-3-yl)amino)-1-methyl-1H-imidazo[4,5-b]pyridin-6-yl)oxy)pyridin-2-yl)acetamide and (S)—N-(4-((2-((5-(tert-butyl)-1-((3,3-difluoro-1-methylpiperidin-4-yl)methyl)-1H-pyrazol-3-yl)amino)-1-methyl-1H-imidazo[4,5-b]pyridin-6-yl)oxy)pyridin-2-yl)acetamide
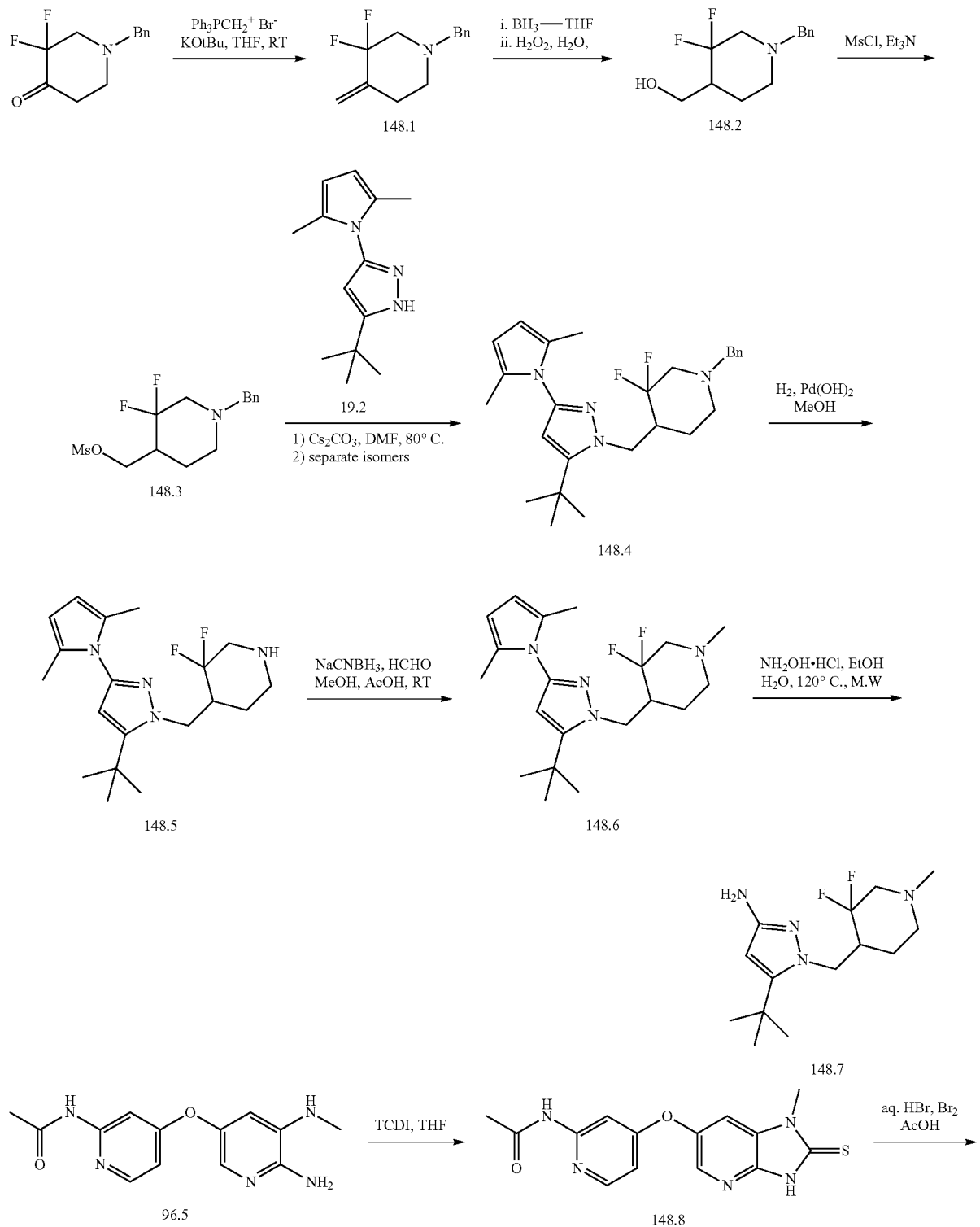

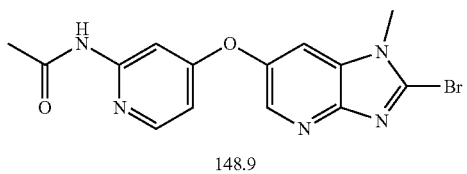 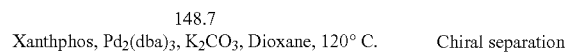

-continued 148.7

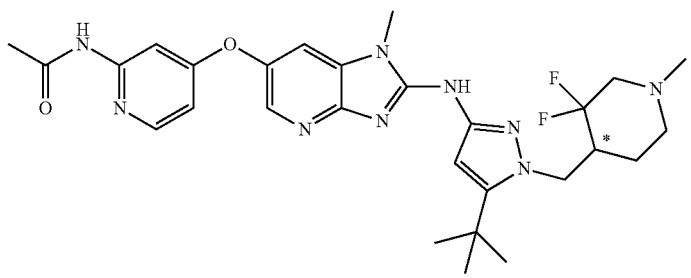

I-148-a and I-148-b

Synthesis of compound 148.1. To a solution of methyltriphenylphosphonium bromide (47.54 g, 133.18 mmol, 1.5 equiv) in THF (100 mL) was added solution of potassium tert-butoxide (1 M in THF) (133.2 mL, 133.18 mmol, 1.5 equiv) at 0° C. The solution was allowed to warm to room temperature and stirred for 30 min. It was cooled to 0° C. and was added to a solution of 1-benzyl-3,3-difluoropiperidin-4-one (20 g, 88.79 mmol, 1.0 equiv) in THF (100 mL) stirring at room temperature for 16 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 4-6% ethyl acetate in hexane) to afford the 148.1. MS (ES): m/z 224.3 [M+H]$^+$.

Synthesis of compound 148.2. To a solution of 148.1 (8.0 g, 35.83 mmol, 1.0 equiv) in THF (100 mL) was added borane-THF (1 M in THF) (72 mL, 71.66 mmol, 2.0 equiv) and stirred at 70° C. for 2 h. The reaction mixture was cooled to 0° C. and was added 2 N sodium hydroxide solution (100 mL) followed by 30% hydrogen peroxide (100 mL). It was stirred at room temperature for 15 min and 40° C. for 16 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 25-30% ethyl acetate in hexane) to afford 148.2. MS (ES): m/z 242.3 [M+H]$^+$.

Synthesis of compound 148.3. Compound 148.3 was prepared from compound 148.2 following the procedure described in the synthesis of compound 28.5. The crude product was used in the next step without further purification. MS (ES): m/z 320.4 [M+H]$^+$.

Synthesis of compound 148.4. Compound 148.4 was prepared from compound 148.3 and 19.2 following the procedure described in the synthesis of compound 28.7. The product was purified by flash column chromatography on silica gel (CombiFlash®, 2-2.5% ethyl acetate in hexane) to afford 148.4. MS (ES): m/z 441.5 [M+H]$^+$.

Synthesis of compound 148.5. A mixture of compound 148.4 (0.600 g, 1.36 mmol, 1.0 equiv) and 20% palladium hydroxide (0.600 g) in methanol (20 mL) was stirred under hydrogen (1 atm) for 3-4 h. The reaction mixture was filtered through a pad of Celite® and washed with 10% methanol in dichloromethane. The filtrate was concentrated under reduced pressure. The residue was purified by flash column chromatography on silica gel (CombiFlash®, 1.6-1.8% methanol in dichloromethane) to afford 148.5. MS (ES): m/z 351.4 [M+H]$^+$.

Synthesis of compound 148.6. To a solution of 148.5 (0.330 g, 0.941 mmol, 1.0 equiv) in methanol (10 mL) and formaldehyde (37% in water) (0.38 mL, 4.70 mmol, 5.0 equiv) was stirred at room temperature for 30 min. To the solution was added acetic acid (0.13 mL, 2.35 mmol, 2.5 equiv) followed by sodium cyanoborohydride (0.296 g, 4.70 mmol, 5.0 equiv) in portions. The reaction mixture stirred at room temperature for 10 min. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 20% ethyl acetate in hexane) to afford 148.6. MS (ES): m/z 365.5 [M+H]$^+$.

Synthesis of compound 148.7. Compound 148.7 was prepared from compound 148.6 following the procedure described in the synthesis of compound 28.8.

Synthesis of compound 148.8. To a solution of 96.5 (3.5 g, 12.81 mmol, 1.0 equiv) in THF (35 mL) was added 1,1'-thiocarbonyldiimidazole (11.4 g, 64.05 mmol, 5.0 equiv). The reaction mixture was stirred at 80° C. for 1 h. It was cooled to room temperature and poured into ice-water. Precipitated solids were collected by filtration and dried under reduced pressure to obtain 148.7. MS(ES): m/z: 316.3 [M+H]$^+$.

Synthesis of compound 148.9. To a solution of 148.8 (0.510 g, 1.62 mmol, 1.0 equiv) in acetic acid (10 mL) was added aqueous hydrobromic acid (0.524 g, 3.24 mmol, 2.0 equiv) at 0° C. followed by bromine (1.036 g, 6.48 mmol, 4.0 equiv). It was stirred for 10 min and poured into a saturated aqueous sodium bicarbonate solution, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.5-3.0% methanol in dichloromethane) to afford 148.8. MS (ES): m/z 363.2 [M+H]$^+$.

Synthesis of (±)-I-148. Compound I-148 was prepared from compound 148.7 and 148.9 following the procedure described in the synthesis of compound I-108. The product was purified by flash column chromatography on silica gel (CombiFlash®, 4.5% methanol in dichloromethane) to afford the racemic product.

Synthesis of compound I-148-a and I-148-b. The two enantiomers were separated by chiral SFC (CHIRALPAK IC (250 mm×21 mm, 5 μm), eluent: (A) Liquid Carbon dioxide and (B) 0.1% DEA in methanol, flow rate=80 mL/min) to give first eluting fraction (I-148-a) and second eluting fraction (I-148-b). (*Absolute stereochemistry not determined.)

I-148-a: MS (ES): m/z: 566.5 [M−H]$^+$, $^1$H NMR (DMSO-d$_6$, 400 MHz): δ 11.46 (s, 1H), 10.53 (s, 1H), 8.19-8.18 (d, J=5.6 Hz, 1H), 7.81 (s, 1H), 7.70 (s, 1H), 7.48 (s, 1H), 6.70-6.66 (m, 1H), 6.17 (s, 1H), 4.34-4.30 (m, 1H), 4.09-4.03 (m, 2H), 3.67 (bs, 1H), 3.40 (s, 3H), 2.95 (bs, 1H), 2.24 (s, 3H), 2.19 (s, 3H), 1.91 (bs, 2H), 1.55 (bs, 2H), 1.25 (s, 9H).

I-148-b: MS (ES): m/z: 568.5 [M+H]$^+$, $^1$H NMR (DMSO-d$_6$, 400 MHz): δ 11.46 (s, 1H), 10.55 (s, 1H), 8.19-8.18 (d, J=5.6 Hz, 1H), 7.81 (s, 1H), 7.69 (s, 1H), 7.48 (s, 1H), 6.68 (bs, 1H), 6.17 (s, 1H), 4.34-4.30 (m, 1H), 4.09-4.03 (m, 2H), 3.67 (bs, 1H), 3.40 (s, 3H), 2.97-2.95 (m, 1H), 2.19 (s, 3H), 2.11 (s, 3H), 1.91 (bs, 2H), 1.46 (bs, 2H), 1.25 (s, 9H).

Example 149: (S)—N-(4-((7-chloro-2-((5-(2-cyano-propan-2-yl)-1-(tetrahydrofuran-3-yl)-1H-pyrazol-3-yl)amino)-1-methyl-1H-imidazo[4,5-b]pyridin-6-yl)oxy)pyridin-2-yl)acetamide

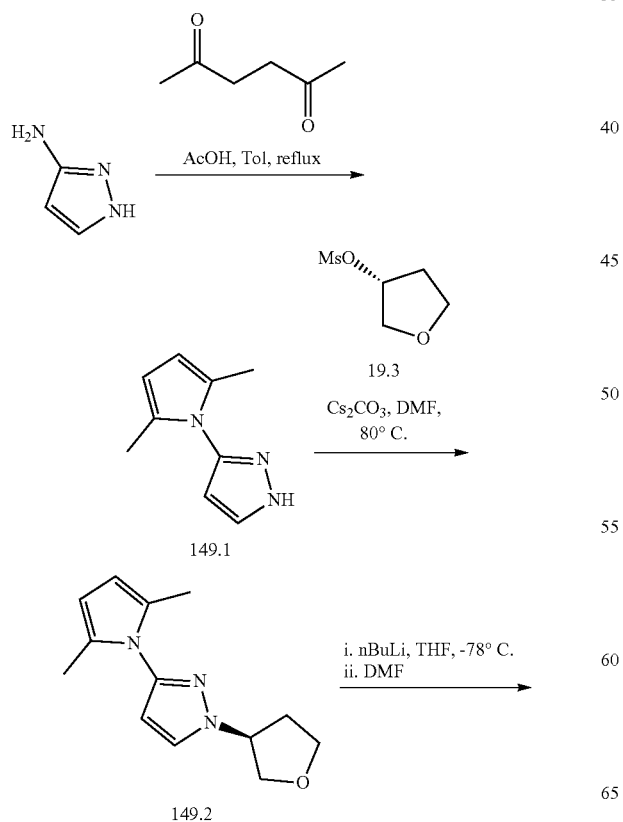
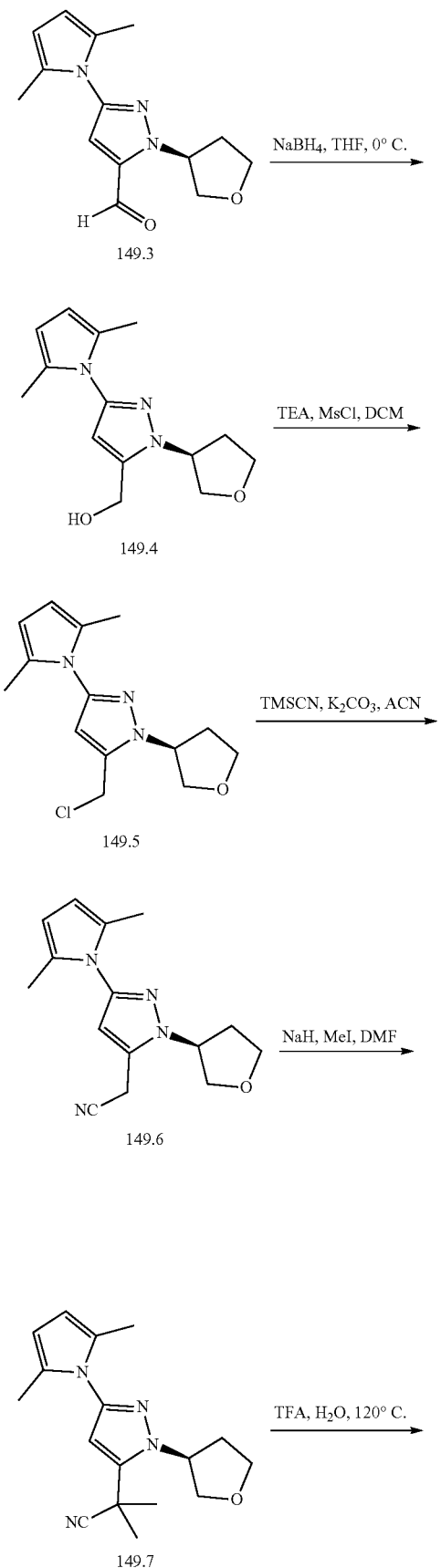

-continued

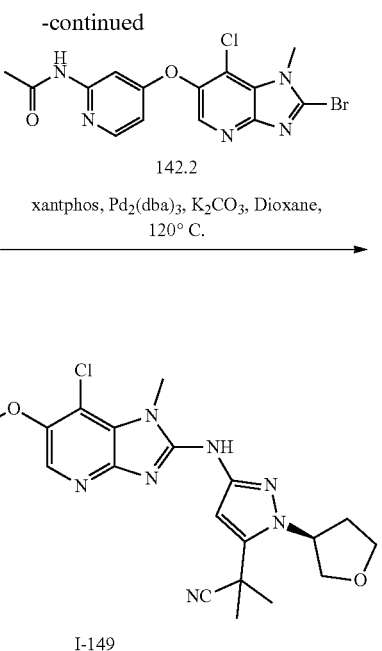

Synthesis of compound 149.1. To a solution of 1H-pyrazol-3-amine (10.0 g, 120.35 mmol, 1.0 equiv) and hexane-2,5-dione (13.74 g, 120.35 mmol, 1.0 equiv) in toluene (100 mL), was added acetic acid (catalytic). The reaction mixture was refluxed with a Dean-Stark trap to remove water. The reaction mixture was cooled to rt and concentrated under reduced pressure. The residue was purified by flash column chromatography on silica gel (CombiFlash®, 25% ethyl acetate in hexane) to afford 149.1. MS (ES): m/z 162.2 [M+H]$^+$.

Synthesis of compound 149.2. A mixture of 149.1 (15 g, 93.05 mmol, 1.0 equiv), 19.3 (18.56 g, 111.66 mmol, 1.2 equiv) and cesium carbonate (60.48 g, 186.01 mmol, 2.0 equiv) in DMF (150 mL) was stirred at 80-90° C. for 5 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (Combi-Flash®, 17% ethyl acetate in hexane) to afford 149.2. MS (ES): m/z 232.3 [M+H]$^+$.

Synthesis of compound 149.3. To a solution of 149.2 (10 g, 43.23 mmol, 1.0 equiv) in THF (100 mL), was added n-butyl lithium (2.5 M in hexane) (22.5 mL, 56.19 mmol, 1.3 equiv) dropwise at −78° C. and stirred for 1 h. To the solution was added DMF (7.3 mL, 95.10 mmol, 2.2 equiv) and the reaction mixture was stirred at −78° C. for 30-40 min. A saturated aqueous solution of ammonium chloride was added carefully to quench the reaction. The mixture was warmed to room temperature and extracted with ethyl acetate. The combined organic layers were washed with brine, dried over anhydrous sodium sulfate, filtered and concentrated under reduced pressure. The residue was purified by flash column chromatography on silica gel (Combi-Flash®, 15% ethyl acetate in hexane) to afford 149.3.

Synthesis of compound 149.4. To a solution of 149.3 (3.5 g, 13.50 mmol, 1.0 equiv) in THF (50 mL) was added sodium borohydride (0.62 g, 16.2 mmol, 1.2 equiv) at 0° C. The reaction mixture was stirred at 0° C. for 1 h. It was poured over ice-water, stirred and extracted with ethyl acetate. The combined organic layers were washed with brine, dried over anhydrous sodium sulfate, filtered and concentrated under reduced pressure to obtain 149.4.

Synthesis of compound 149.5. To a solution of 149.4 (2.5 g, 9.57 mmol, 1.0 equiv) and triethylamine (4.0 mL, 28.71 mmol, 3.0 equiv) in dichloromethane (40 mL) at 0° C. was added MSCl (1.1 mL, 14.35 mmol, 1.5 equiv). The reaction mixture was allowed to warm to rt and stirred for 1 h. It was poured over ice-water, stirred and extracted with dichloromethane. The combined organic layers were washed with saturated aqueous sodium bicarbonate followed by brine, dried over anhydrous sodium sulfate, filtered and concentrated under reduced pressure. The residue was purified by flash column chromatography on silica gel (CombiFlash®, 15% ethyl acetate in hexane) to afford 149.5. MS (ES): m/z 280.7 [M+H]$^+$.

Synthesis of compound 149.6. To a solution of 149.6 (2.0 g, 7.15 mmol, 1.0 equiv) in acetonitrile (40 mL) was added potassium carbonate (1.97 g, 14.3 mmol, 2.0 equiv) followed by addition of trimethylsilyl cyanide (1.415 g, 14.3 mmol, 2.0 equiv). The reaction mixture was stirred at 80° C. for 5 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 25% ethyl acetate in hexane) to afford 149.6. MS (ES): m/z 271.3 [M+H]$^+$.

Synthesis of compound 149.7. To a solution of 149.6 (1.0 g, 3.70 mmol, 1.0 equiv) in DMF (15 mL), was added sodium hydride (0.592 g, 14.8 mmol, 4.0 equiv) at 0° C. and stirred for 20 min. To the mixture was added methyl iodide (2.1 g, 14.8 mmol, 4.0 equiv) and it was allowed to warm to rt with stirring for 30 min. It was poured into ice, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 22% ethyl acetate in hexane) to afford 149.7. MS (ES): m/z 299.4 [M+H]$^+$.

Synthesis of compound 149.8. To a suspension of 149.7 (0.3 g, 1.01 mmol, 1.0 equiv) in water (10 mL) was added trifluoroacetic acid (3 mL) and stirred at 120° C. for 30 min. The reaction mixture was poured into a mixture of ice-saturated aqueous solution of sodium bicarbonate, stirred and extracted with dichloromethane. The combined organic layers were washed with brine, dried over anhydrous sodium sulfate, filtered and concentrated under reduced pressure. The residue was purified by flash column chromatography on silica gel (CombiFlash®, 2.4% methanol in dichloromethane) to afford 149.8. MS (ES): m/z 221.3 [M+H]$^+$.

Synthesis of I-149. Compound I-149 was prepared from compound 142.2 and 149.8 following the procedure described in the synthesis of compound I-108. The product was purified by flash column chromatography on silica gel (CombiFlash®, 3.5% methanol in dichloromethane) to afford I-149. MS (ES): m/z: 536.77 [M+H]$^+$, $^1$H NMR (DMSO-d$_6$, 400 MHz): δ 10.56 (s, 1H), 10.27 (s, 1H), 8.19-8.17 (d, J=6.0 Hz, 1H), 8.10 (s, 1H), 7.64 (s, 1H), 6.80 (s, 1H), 6.66-6.64 (m, 1H), 5.30 (bs, 1H), 4.18-4.06 (m, 2H), 3.94 (s, 3H), 3.88-3.85 (m, 2H), 2.28-2.24 (m, 2H), 2.03 (s, 3H), 1.83 (s, 6H).

489

Example 150: trans-N-(4-((7-chloro-2-((1-(3-methoxycyclobutyl)-5-(perfluoroethyl)-1H-pyrazol-3-yl)amino)-1-methyl-1H-imidazo[4,5-b]pyridin-6-yl)oxy)pyridin-2-yl)acetamide

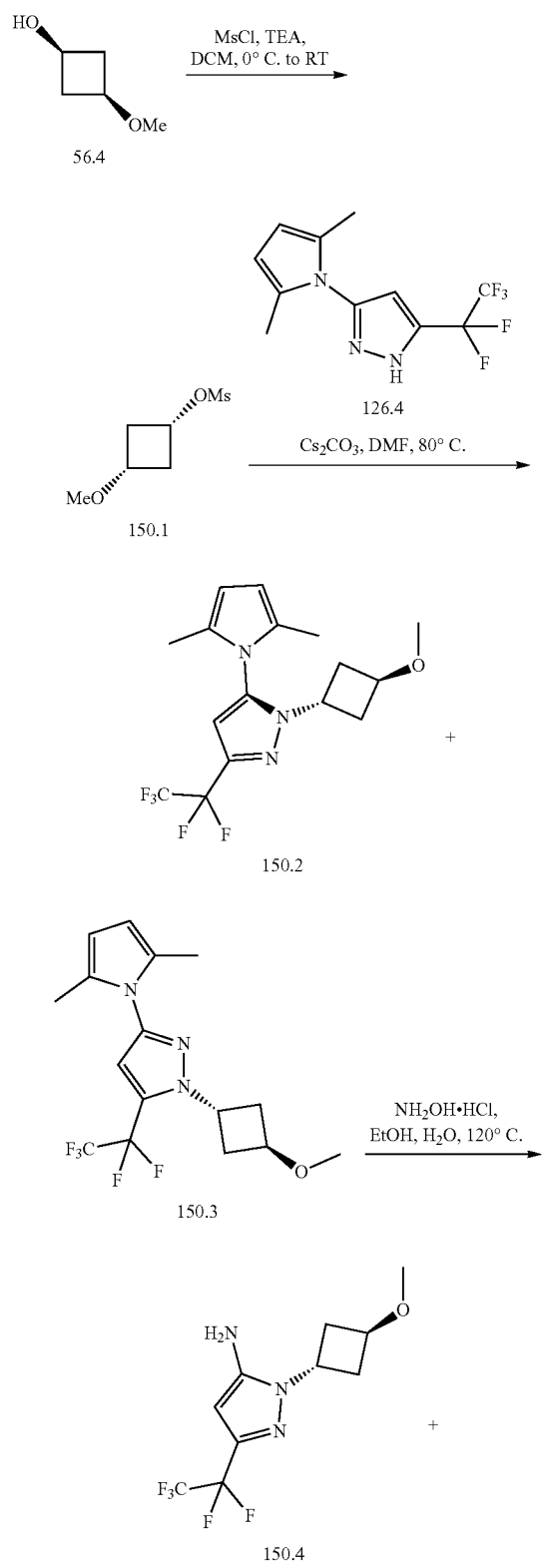

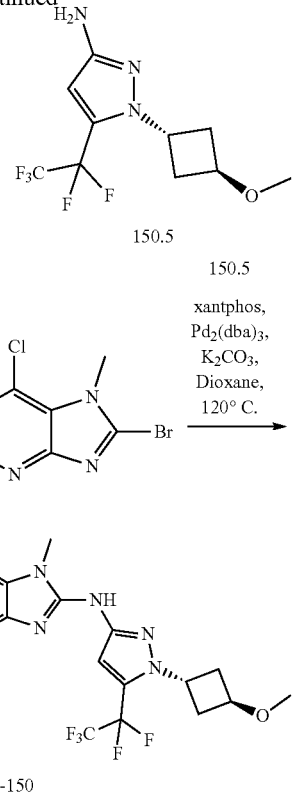

Synthesis of compound 150.1. Compound 150.1 was prepared from compound 56.4 following the procedure described in the synthesis of compound 28.5. The crude product was used in the next step without further purification. $^1$H NMR (CDCl$_3$, 400 MHz): δ 4.73-4.69 (m, 1H), 3.63-3.60 (m, 1H), 3.29 (s, 3H), 3.03 (s, 3H), 2.92-2.85 (m, 2H), 2.33-2.26 (m, 2H).

Synthesis of compound 150.2 and 150.3. To a solution of 126.4 (2.4 g, 8.60 mmol, 1.0 equiv) and 150.1 (2.32 g, 12.89 mmol, 1.5 equiv) in DMF (25 mL) was added cesium carbonate (5.59 g, 17.2 mmol, 2.0 equiv) and reaction mixture was heated at 80-90° C. for 12 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 8-10% ethyl acetate in hexane) to afford mixture of 150.2 and 150.3 (88:12). The mixture was used in the next step without further purification.

Synthesis of compound 150.5. Compound 150.5 was prepared from the above mixture of 150.2 and 150.3 following the procedure described in the synthesis of compound 120.6. The residue was purified by flash column chromatography on silica gel (CombiFlash®, 28-30% ethyl acetate in hexane) to afford 150.5. MS (ES): m/z 286.3 [M+H]$^+$.

Synthesis of I-150. Compound I-150 was prepared from compound 142.2 and 150.5 following the procedure described in the synthesis of compound I-108. The product was purified by flash column chromatography on silica gel (CombiFlash®, 3.7% methanol in dichloromethane) to afford I-150. MS (ES): m/z: 601.85 [M+H]$^+$, $^1$H NMR (DMSO-d$_6$, 400 MHz): δ 10.66 (s, 1H), 10.60 (s, 1H), 8.20-8.19 (d, J=5.6 Hz, 1H), 8.15 (s, 1H), 7.65 (s, 1H), 7.38 (s, 1H), 6.66 (d, J=3.6 Hz, 1H), 5.05 (bs, 1H), 4.23 (bs, 1H), 3.99 (s, 3H), 3.20 (s, 3H), 2.79-2.77 (m, 2H), 2.44 (bs, 2H), 2.04 (s, 3H).

Example 151: (R)—N-(4-((2-((5-(tert-butyl)-4-fluoro-1-(tetrahydrofuran-3-yl)-1H-pyrazol-3-yl)amino)-1-methyl-1H-imidazo[4,5-b]pyridin-6-yl)oxy)pyridin-2-yl)cyclopropane-carboxamide

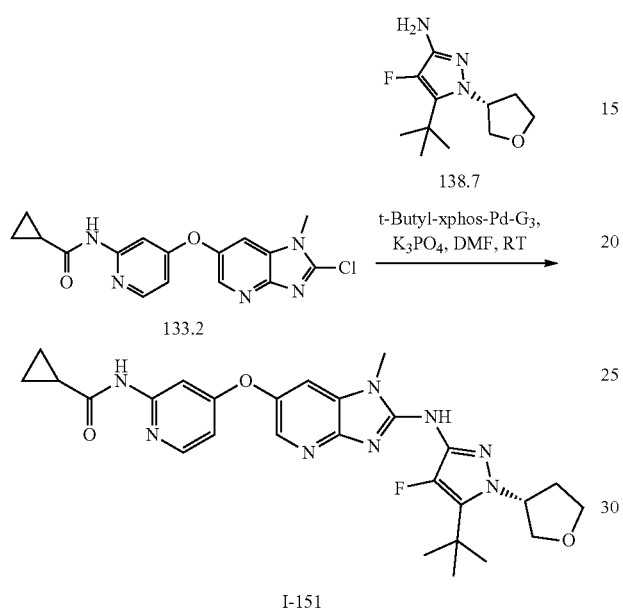

Synthesis of I-151. Compound I-151 was prepared from compound 133.2 and 138.7 following the procedure described in the synthesis of compound I-136. The product was purified by flash column chromatography on silica gel (CombiFlash®, 2.5% methanol in dichloromethane). MS (ES): m/z: 535.49 [M+H]$^+$, $^1$H NMR (DMSO-d$_6$, 400 MHz): 10.81 (s, 1H), 9.37 (s, 1H), 8.20-8.17 (m, 1H), 7.95-7.94 (d, J=2.4 Hz, 1H), 7.68-7.54 (m, 2H), 6.72-6.67 (m, 1H), 5.27-5.26 (m, 1H), 4.12-4.00 (m, 2H), 3.95-3.78 (m, 2H), 3.65 (s, 3H), 2.26-2.20 (m, 1H), 1.99-1.94 (m, 1H), 1.43 (s, 9H), 1.24-1.20 (m, 1H), 0.76-0.75 (m, 4H).

Example 152: (S)—N-(4-((2-((5-(tert-butyl)-4-fluoro-1-(tetrahydrofuran-3-yl)-1H-pyrazol-3-yl)amino)-1-methyl-1H-imidazo[4,5-b]pyridin-6-yl)oxy)pyridin-2-yl)cyclopropanecarboxamide

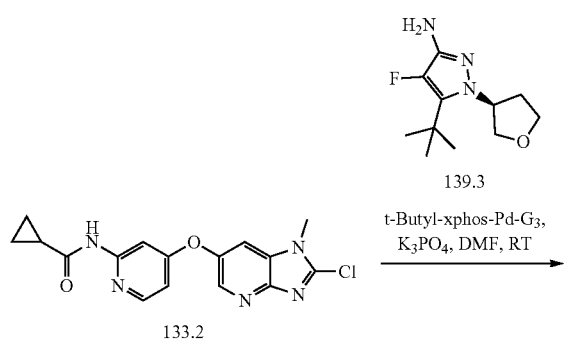

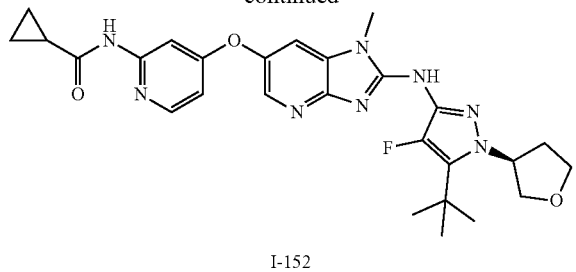

Synthesis of I-152. Compound I-152 was prepared from compound 133.2 and 139.3 following the procedure described in the synthesis of compound I-136. The product was purified by flash column chromatography on silica gel (CombiFlash®, 2.6% methanol in dichloromethane). MS (ES): m/z: 535.50 [M+H]$^+$, $^1$H NMR (DMSO-d$_6$, 400 MHz): 10.83 (s, 1H), 9.39 (s, 1H), 8.21-8.18 (m, 1H), 7.96 (bs, 1H), 7.69-7.64 (m, 2H), 6.70-6.69 (m, 1H), 5.27-5.26 (m, 1H), 4.13-4.01 (m, 2H), 3.90-3.78 (m, 2H), 3.66 (s, 3H), 2.22-2.21 (m, 1H), 2.00-1.95 (m, 1H), 1.44 (s, 9H), 1.25-1.19 (m, 1H), 0.77 (bs, 4H).

Example 153: (S)—N-(4-((2-((5-(tert-butyl)-1-(tetrahydrofuran-3-yl)-1H-pyrazol-3-yl)amino)-7-(difluoromethyl)-1-methyl-1H-imidazo[4,5-b]pyridin-6-yl)oxy)pyridin-2-yl)acetamide

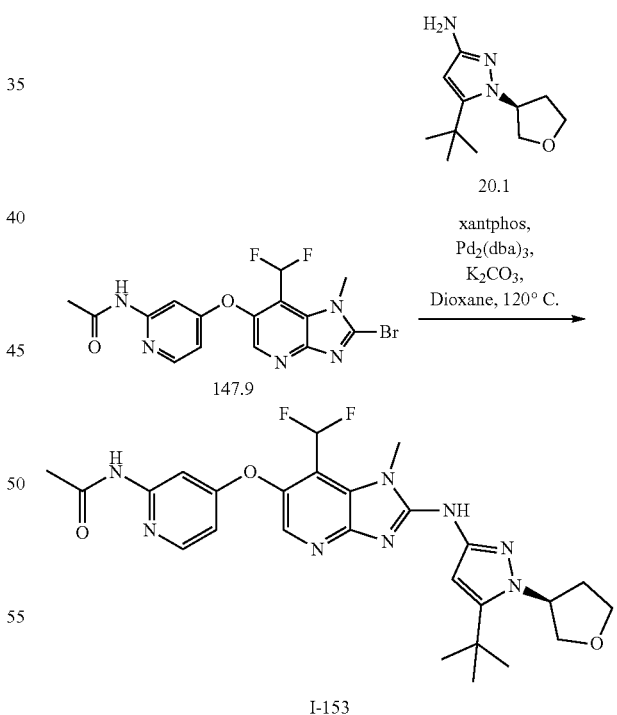

Synthesis of I-153. Compound I-153 was prepared from compound 147.9 and 20.1 following the procedure described in the synthesis of compound I-108. The product was purified by flash column chromatography on silica gel (CombiFlash®, 4.0% methanol in dichloromethane). MS (ES): m/z: 541.87 [M+H]$^+$, $^1$H NMR (DMSO-d$_6$, 400 MHz): 10.56 (s, 1H), 10.09 (s, 1H), 8.20-8.19 (d, J=5.6 Hz, 1H), 8.06 (s, 1H), 7.67 (s, 1H), 7.48-7.21 (m, 1H), 6.66-6.64 (m, 1H), 6.57 (s, 1H), 5.31-5.23 (s, 1H), 4.11-4.08 (m, 2H), 3.97-3.83 (m, 2H), 3.79 (s, 3H), 2.38-2.33 (m, 1H), 2.27-2.22 (m, 1H), 2.04 (s, 3H), 1.41 (s, 9H).

Example 154: (S)—N-(4-((2-((5-(2-cyanopropan-2-yl)-1-(tetrahydrofuran-3-yl)-1H-pyrazol-3-yl)amino)-7-ethyl-1-methyl-1H-imidazo[4,5-b]pyridin-6-yl)oxy)pyridin-2-yl)acetamide

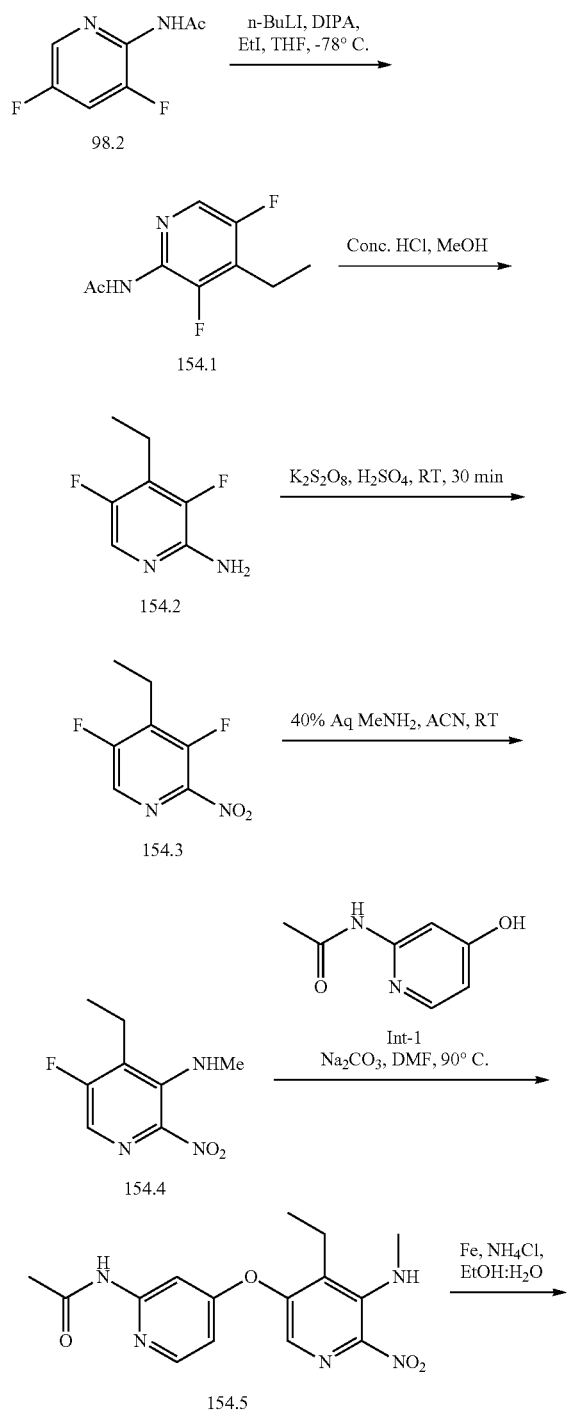

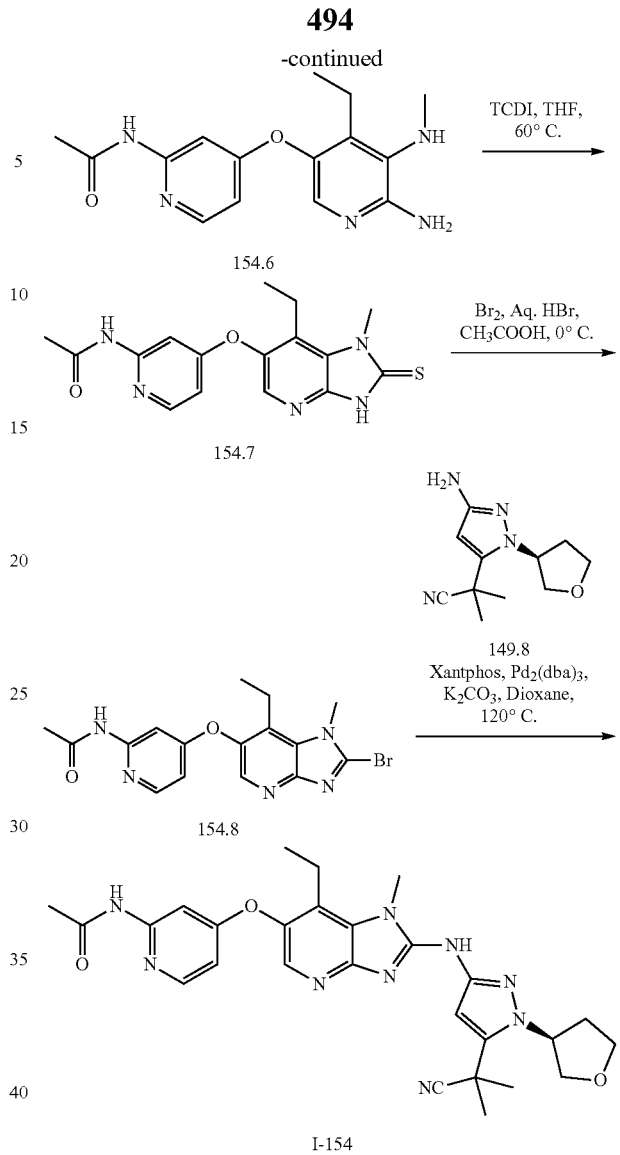

Synthesis of compound 154.1. To a solution of 98.2 (2.0 g, 11.62 mmol, 1.0 equiv) in THF (20 mL), was added diisopropylamine (4.0 mL, 29.05 mmol, 2.5 equiv), stirred and cooled to −78° C. followed by addition of n-butyl lithium (2.5 M in hexane) (11.6 mL, 29.05 mmol, 2.5 equiv). The reaction mixture was stirred at −78° C. for 1 h. Iodoethane (1.1 mL, 13.94 mmol, 1.2 equiv) was added and the reaction mixture was stirred at −60° C. to −70° C. for 2 h. Aqueous solution of ammonium chloride was added carefully to quench the reaction. The mixture was warmed to room temperature and extracted with ethyl acetate. The combined organic layers were washed with brine, dried over anhydrous sodium sulfate, filtered and concentrated under reduced pressure. The residue was purified by flash column chromatography on silica gel (CombiFlash®, 20% ethyl acetate in hexane) to afford 154.1. MS (ES): m/z 201.2 [M+H]$^+$.

Synthesis of compound 154.2. To a solution of 154.1 (1.3 g, 6.49 mmol, 1.0 equiv) in methanol (5 mL), was added concentrated hydrochloric acid (2.5 mL). The reaction mixture was refluxed for 2 h. Most solvent was removed under reduced pressure. The residue was added ice-water and pH of the mixture was adjusted to 9-10 by addition of 3 N aqueous solution of sodium hydroxide. The mixture is extracted with diethyl ether. The combined organic layers were washed with brine, dried over anhydrous sodium sulfate, filtered and concentrated under reduced pressure. The residue was purified by flash column chromatography on silica gel (CombiFlash®, 30% ethyl acetate in hexane) to afford 154.2. $^1$H NMR (DMSO-$d_6$, 400 MHz): δ 7.76 (bs, 1H), 6.02 (bs, 2H), 2.64-2.59 (q, 2H), 1.17-1.13 (t, 3H).

Synthesis of compound 154.3. To the suspension of potassium persulfate (3.34 g, 12.4 mmol, 2.8 equiv) in concentrated sulfuric acid (5 mL) was added 154.2 (0.7 g, 4.43 mmol, 1.0 equiv). The reaction mixture was stirred at room temperature for 4 h. It was poured over crushed ice, stirred, neutralized with saturated aqueous sodium bicarbonate solution and extracted with ethyl acetate. The combined organic layers were washed with brine, dried over anhydrous sodium sulfate, filtered and concentrated under reduced pressure. The residue was purified by flash column chromatography on silica gel (CombiFlash®, 10% ethyl acetate in hexane) to afford 154.3. $^1$H NMR (DMSO-$d_6$, 400 MHz): δ 8.47 (bs, 1H), 3.00-2.94 (q, 2H), 1.35-1.32 (t, 3H).

Synthesis of compound 154.4. To a solution of 154.3 (0.370 g, 1.97 mmol, 1.0 equiv) in acetonitrile (5 mL) was added aqueous methylamine solution (40%) (0.2 mL, 2.95 mmol, 1.5 equiv) dropwise at 0° C. The reaction mixture was stirred at room temperature for 1 h. The reaction mixture was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 12% ethyl acetate in hexane) to afford 154.4. (0.365 g, 93.18%). $^1$H NMR (CDCl$_3$, 400 MHz): δ 7.78 (s, 1H), 6.55-6.54 (d, J=5.6 Hz, 1H), 2.72-2.70 (q, 2H), 2.67-2.66 (d, 3H), 1.12-1.08 (t, 3H).

Synthesis of compound 154.5. A mixture of 154.4 (0.365 g, 1.83 mmol, 1.0 equiv), Int-1 (0.334 g, 2.20 mmol, 1.2 equiv) and sodium carbonate (0.387 g, 3.66 mmol, 2.0 equiv) in DMF (5 mL) was stirred at 90° C. for 12 h. It was cooled to room temperature, transferred into ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 50% ethyl acetate in hexane to afford 154.5. MS (ES): m/z 332.3 [M+H]$^+$.

Synthesis of compound 154.6. A mixture of compound 154.5 (0.229 g, 0.691 mmol, 1.0 equiv), iron powder (0.193 g, 3.45 mmol, 5.0 equiv) and ammonium chloride (0.193 g, 3.15 mmol, 5.0 equiv) in ethanol:water (8:2, 6 mL) was stirred at 80° C. for 2 h. It was filtered through a pad of Celite® and washed with ethanol. The filtrate was concentrated under reduced pressure. The residue was purified by flash column chromatography on silica gel (CombiFlash®, 2.0% methanol in dichloromethane) to afford 154.6. MS (ES): m/z 302.3 [M+H]$^+$.

Synthesis of compound 154.7. Compound 154.7 was prepared from compound 154.6 following the procedure described in the synthesis of compound 148.8. The product was triturated with hexane to afford 154.7. MS (ES): m/z: 344.4 [M+H]$^+$.

Synthesis of compound 154.8. Compound 154.8 was prepared from compound 154.7 following the procedure described in the synthesis of compound 148.9. The product was purified by flash column chromatography on silica gel (CombiFlash®, 2.3% methanol in dichloromethane). MS (ES): m/z 391.2 [M+H]$^+$.

Synthesis of I-154. Compound I-154 was prepared from compound 149.8 and 154.8 following the procedure described in the synthesis of compound I-108. The product was purified by flash column chromatography on silica gel (CombiFlash®, 3.4% methanol in dichloromethane). MS (ES): m/z: 530.5 [M+H]$^+$, $^1$H NMR (DMSO-$d_6$, 400 MHz): 10.51 (s, 1H), 10.01 (s, 1H), 8.17-8.15 (d, J=6.0 Hz, 1H), 7.89 (s, 1H), 7.62 (s, 1H), 6.79 (s, 1H), 6.63-6.61 (m, 1H), 5.32-5.25 (m, 1H), 4.16-4.12 (m, 2H), 3.85 (s, 5H), 2.85-2.80 (m, 2H), 2.30-2.22 (m, 1H), 2.03 (s, 3H), 1.82 (bs, 6H), 1.55 (bs, 1H), 1.16-1.13 (t, 3H).

Example 155: (R)—N-(4-((2-((5-(tert-butyl)-1-(tetrahydrofuran-3-yl)-1H-pyrazol-3-yl)amino)-7-methoxy-1-methyl-1H-imidazo[4,5-b]pyridin-6-yl)oxy)pyridin-2-yl)acetamide

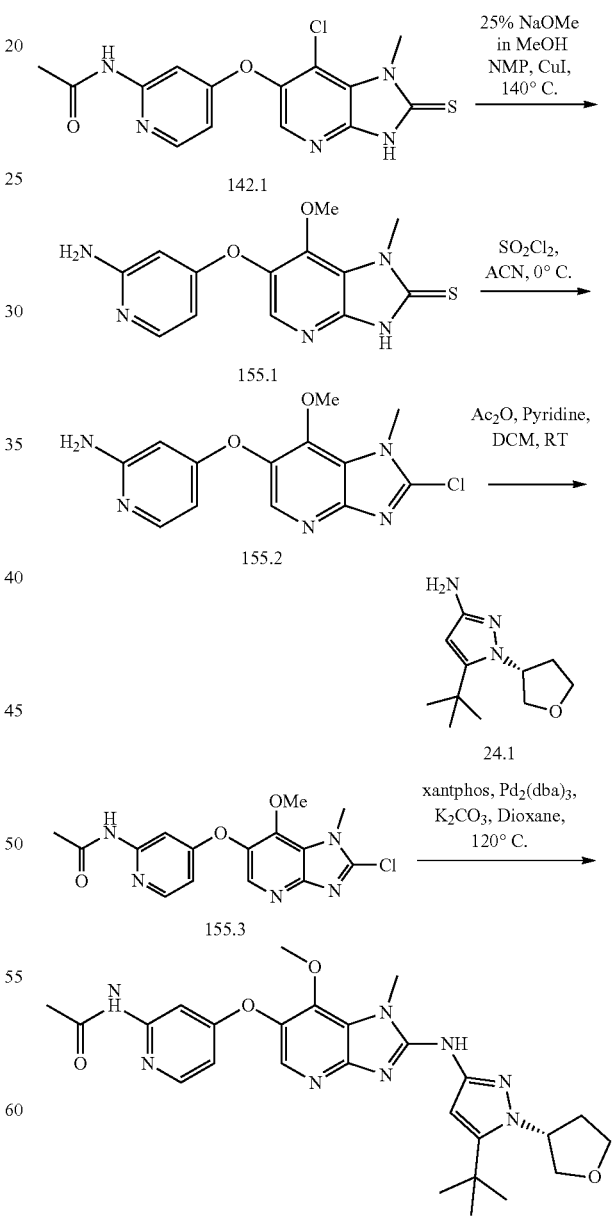

Synthesis of compound 155.1. To solution of 142.1 (1.0 g, 2.86 mmol, 1.0 equiv) in methanol (7 mL) and N-methyl-2-pyrrolidone (15 mL) was added as solution of sodium methoxide in methanol (25% w/w, 8 mL, 37.18 mmol, 13 equiv) and copper iodide (0.119 g, 0.629 mmol, 0.22 equiv). The reaction mixture was stirred at 140° C. in a sealed tube for 4 h. It was cooled to room temperature, transferred into ice-water, and extracted with dichloromethane. The combined organic layers were washed with brine, dried over anhydrous sodium sulfate, filtered and concentrated under reduced pressure. The residue was purified by flash column chromatography on silica gel (CombiFlash®, 2.5% methanol in dichloromethane as eluant). MS (ES): m/z: 304.3 [M+H]+.

Synthesis of compound 155.2. To a solution of 155.1 (0.050 g, 0.164 mmol, 1.0 equiv) in acetonitrile (5 mL) was added sulfuryl chloride (0.49 mL, 6.06 mmol, 37 equiv) at 0° C. and reaction mixture was stirred for 15 min. The reaction mixture was transferred into saturated aqueous sodium bicarbonate solution, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 3.0% methanol in dichloromethane) to afford 155.2. MS (ES): m/z 306.7 [M+H]+.

Synthesis of compound 155.3. To a solution of 155.2 (0.025 g, 0.081 mmol, 1.0 equiv) in dichloromethane (2 mL) was added pyridine (0.03 mL) at 0° C. followed by acetic anhydride (0.019 mL, 0.202 mmol, 2.5 equiv) and reaction mixture was stirred for 5 min. The reaction mixture was transferred into saturated aqueous sodium bicarbonate solution, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.8% methanol in dichloromethane) to afford 155.3. MS (ES): m/z 348.7 [M+H]+.

Synthesis of I-155. Compound I-155 was prepared from compound 24.1 and 155.3 following the procedure described in the synthesis of compound I-108. The product was purified by flash column chromatography on silica gel (CombiFlash®, 3.9% methanol in dichloromethane). MS (ES): m/z: 521.8 [M+H]+, 1H NMR (DMSO-d6, 400 MHz): δ 10.25 (s, 1H), 9.46 (s, 1H), 8.18-8.17 (d, J=5.6 Hz, 1H), 7.92 (s, 1H), 7.68 (s, 1H), 6.66-6.64 (m, 1H), 6.55 (s, 1H), 5.23 (m, 1H), 4.14-4.08 (m, 2H), 3.93 (s, 3H), 3.89-3.84 (m, 2H), 2.38-2.28 (m, 3H), 2.07 (s, 3H), 1.59 (bs, 2H), 1.43 (s, 9H).

Example 156: (S)—N-(4-((2-((5-(tert-butyl)-1-(tetrahydrofuran-3-yl)-1H-pyrazol-3-yl)amino)-7-methoxy-1-methyl-1H-imidazo[4,5-b]pyridin-6-yl)oxy)pyridin-2-yl)acetamide

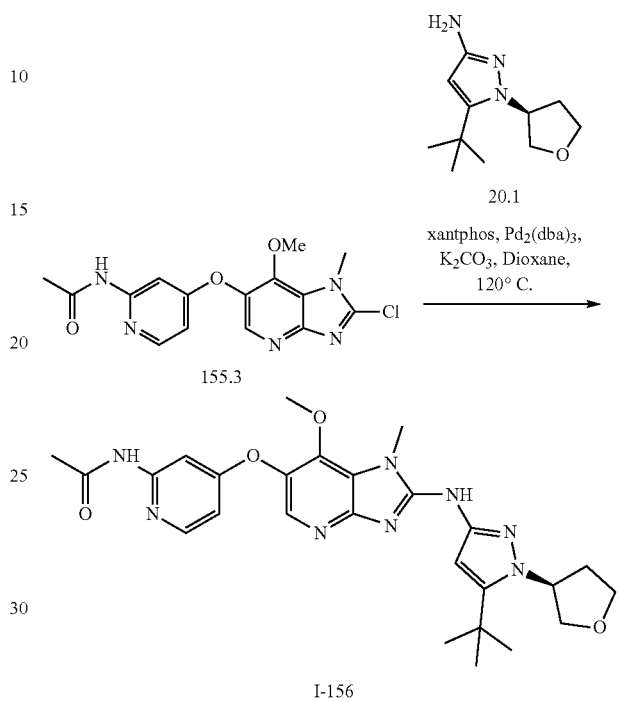

I-156

Synthesis of I-156. Compound I-156 was prepared from compound 20.1 and 155.3 following the procedure described in the synthesis of compound I-108. The product was purified by flash column chromatography on silica gel (CombiFlash®, 4.0% methanol in dichloromethane). MS (ES): m/z: 521.49 [M+H]+, 1H NMR (DMSO-d6, 400 MHz): δ 10.56 (s, 1H), 9.82 (s, 1H), 8.19-8.17 (d, J=5.6 Hz, 1H), 7.93 (s, 1H), 7.68 (s, 1H), 6.66-6.65 (d, 1H), 6.55 (s, 1H), 5.26 (bs, 1H), 4.09 (bs, 2H), 3.96 (s, 3H), 3.90-3.83 (m, 3H), 2.34-2.24 (m, 2H), 2.04 (s, 3H), 2.00 (bs, 2H), 1.41 (s, 9H).

Example 157: (R)—N-(4-((7-chloro-2-((5-(2-cyanopropan-2-yl)-1-(tetrahydrofuran-3-yl)-1H-pyrazol-3-yl)amino)-1-methyl-1H-imidazo[4,5-b]pyridin-6-yl)oxy)pyridin-2-yl)acetamide

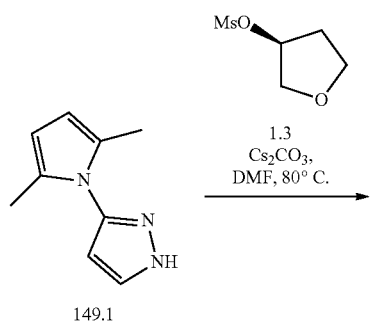

-continued

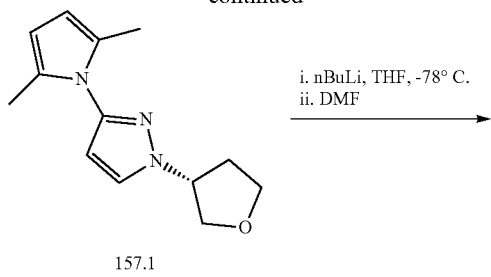
157.1 i. nBuLi, THF, -78° C.
ii. DMF

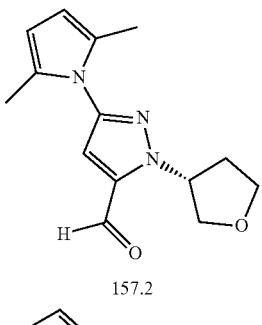
157.2

NaBH₄
THF, 0° C.

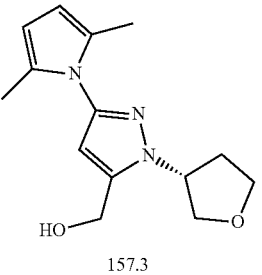
157.3

MsCl,
TEA, DCM

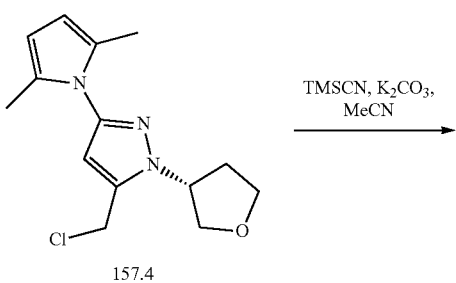
157.4

TMSCN, K₂CO₃,
MeCN

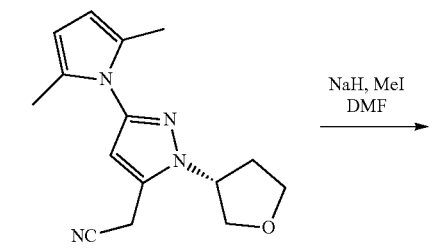
157.5

NaH, MeI
DMF

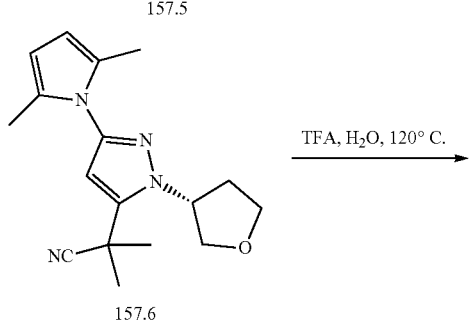
157.6

TFA, H₂O, 120° C.

-continued

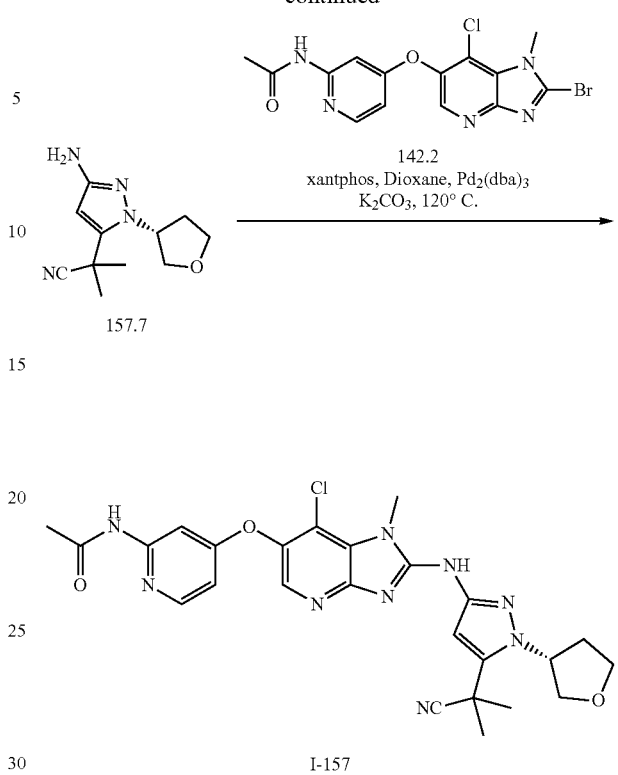
157.7

142.2
xantphos, Dioxane, Pd₂(dba)₃
K₂CO₃, 120° C.

I-157

Synthesis of I-157. Compound I-157 was prepared following the procedures described in the synthesis of compound I-149. The product was purified by flash column chromatography on silica gel (CombiFlash®, 3.5% methanol in dichloromethane). MS (ES): m/z: 536.77 [M+H]⁺, ¹H NMR (DMSO-d₆, 400 MHz): δ 10.58 (s, 1H), 10.30 (s, 1H), 8.19-8.17 (d, J=6.0 Hz, 1H), 8.11 (s, 1H), 7.64 (s, 1H), 6.80 (s, 1H), 6.66-6.64 (m, 1H), 5.30 (bs, 1H), 4.16-4.10 (m, 2H), 3.94 (s, 3H), 3.88-3.84 (m, 2H), 2.29-2.24 (m, 2H), 2.03 (s, 3H), 1.83 (s, 6H).

Example 158: (R)—N-(4-((2-((5-(2-cyanopropan-2-yl)-1-(tetrahydrofuran-3-yl)-1H-pyrazol-3-yl)amino)-7-ethyl-1-methyl-1H-imidazo[4,5-b]pyridin-6-yl)oxy)pyridin-2-yl)acetamide

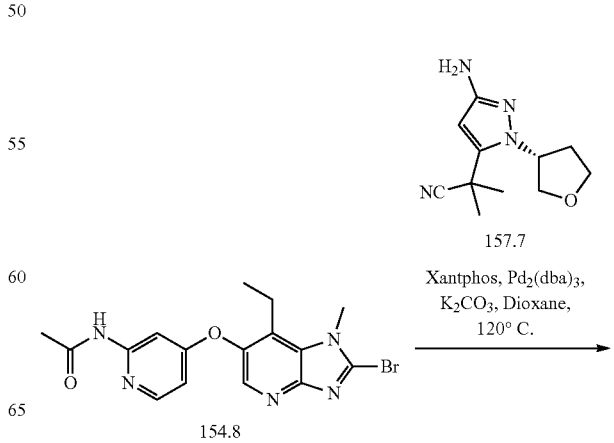
157.7

154.8

Xantphos, Pd₂(dba)₃,
K₂CO₃, Dioxane,
120° C.

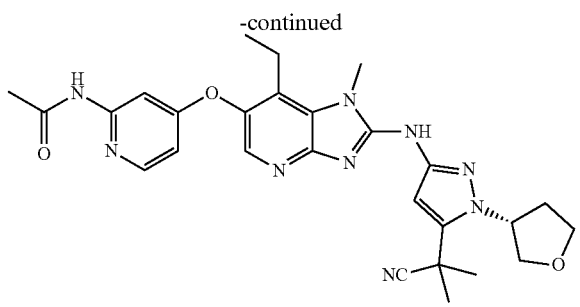

I-158

Synthesis of I-158. Compound I-158 was prepared from compound 154.8 and 157.7 following the procedure described in the synthesis of compound I-108. The product was purified by flash column chromatography on silica gel (CombiFlash®, 3.5% methanol in dichloromethane). MS (ES): m/z: 530.49 [M+H]$^+$, $^1$H NMR (DMSO-d$_6$, 400 MHz): 10.54 (s, 1H), 10.04 (s, 1H), 8.18-8.16 (d, J=6.0 Hz, 1H), 7.90 (s, 1H), 7.63 (s, 1H), 6.80 (s, 1H), 6.63-6.62 (m, 1H), 5.29 (bs, 1H), 4.19-4.09 (m, 2H), 3.91-3.86 (m, 5H), 2.86-2.81 (m, 2H), 2.29-2.25 (m, 1H), 2.03 (s, 3H), 1.82 (bs, 6H), 1.55 (bs, 1H), 1.16-1.13 (t, 3H).

Example 159: N-(4-((7-chloro-2-((1-((1s,3s)-3-methoxycyclobutyl)-5-(perfluoroethyl)-1H-pyrazol-3-yl)amino)-1-methyl-1H-imidazo[4,5-b]pyridin-6-yl)oxy)pyridin-2-yl)acetamide

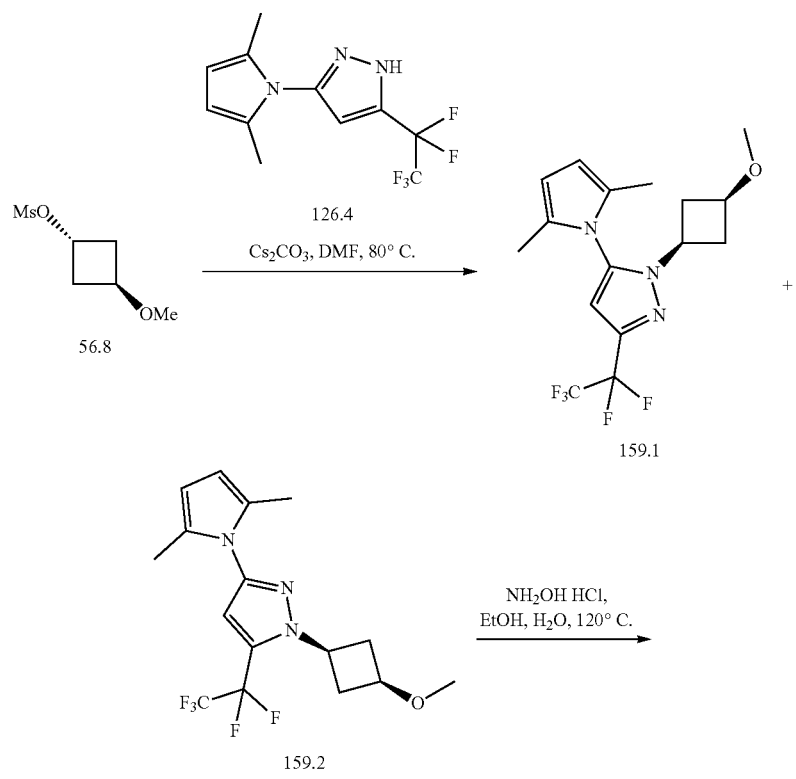

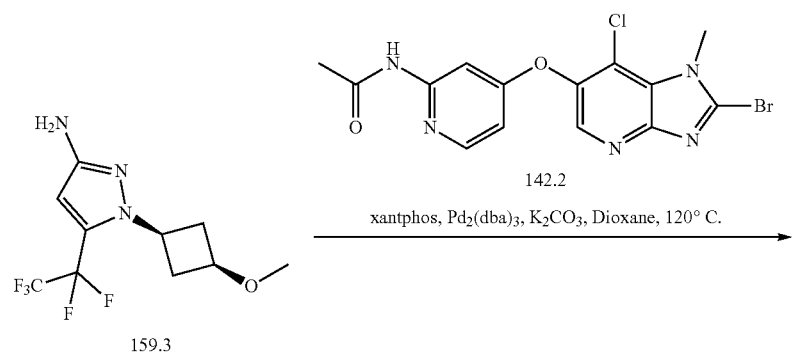

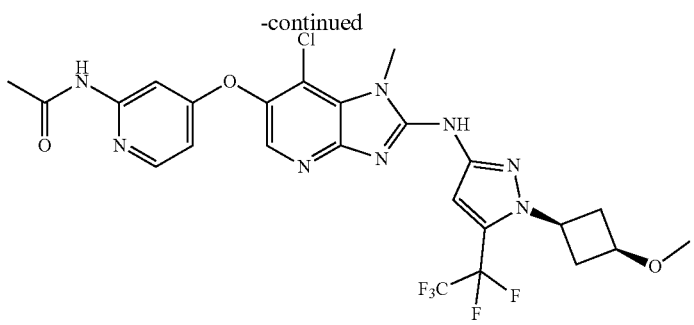

I-159

Synthesis of compound 159.1 and 159.2. A mixture of 126.4 (1.2 g, 4.3 mmol, 1.0 equiv), 56.8 (0.930 g, 5.16 mmol, 1.2 equiv) and cesium carbonate (2.8 g, 8.6 mmol, 2.0 equiv) in DMF (8 mL) was stirred at 80-90° C. for 12 h. It was poured over ice-water, stirred and extracted with ethyl acetate. The combined organic layers were washed with brine, dried over anhydrous sodium sulfate, filtered and concentrated under reduced pressure to afford a mixture (91:8) of 159.1 and 159.2. It was used in the next step without further purification.

Synthesis of compound 159.3. Compound 159.3 was prepared from the above mixture of 159.1 and 159.2 following the procedure described in the synthesis of compound 120.6. The residue was purified by flash column chromatography on silica gel (CombiFlash®, 28-30% ethyl acetate in hexane) to afford 159.3. MS (ES): m/z 286.3 [M+H]$^+$.

Synthesis of I-159. Compound I-159 was prepared from compound 159.3 and 142.2 following the procedure described in the synthesis of compound I-108. The product was purified by flash column chromatography on silica gel (CombiFlash®, 3.6% methanol in dichloromethane. MS (ES): m/z: 601.88 [M+H]$^+$, $^1$H NMR (DMSO-$d_6$, 400 MHz): δ 10.69 (s, 1H), 10.59 (s, 1H), 8.20-8.18 (d, J=5.6 Hz, 1H), 8.15 (s, 1H), 7.65 (s, 1H), 7.38 (s, 1H), 6.66 (d, J=3.6 Hz, 1H), 4.65-4.61 (m, 1H), 3.98 (s, 3H), 3.83-3.80 (m, 1H), 3.20 (s, 3H), 2.79 (bs, 2H), 2.52 (bs, 2H), 2.04 (s, 3H).

Example 160: (R)—N-(4-((2-((5-(2-cyanopropan-2-yl)-1-(tetrahydrofuran-3-yl)-1H-pyrazol-3-yl)amino)-7-(difluoromethyl)-1-methyl-1H-imidazo[4,5-b]pyridin-6-yl)oxy)pyridin-2-yl)acetamide

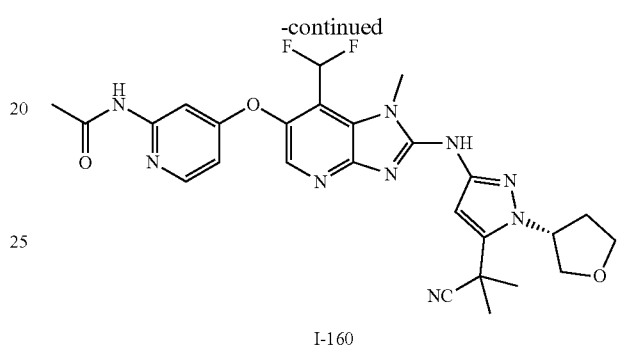

I-160

Synthesis of I-160. Compound I-160 was prepared from compound 147.9 and 157.7 following the procedure described in the synthesis of compound I-108. The product was purified by flash column chromatography on silica gel (CombiFlash®, 3.8% methanol in dichloromethane). MS (ES): m/z: 552.46 [M+H]$^+$, $^1$H NMR (DMSO-$d_6$, 400 MHz): 10.59 (s, 1H), 10.36 (s, 1H), 8.20-8.19 (d, J=5.6 Hz, 1H), 8.09 (s, 1H), 7.66 (s, 1H), 7.49-7.23 (m, 1H), 7.09-7.06 (d, J=7.6 Hz, 1H), 6.66-6.64 (m, 1H), 5.35-5.30 (m, 1H), 3.99-3.95 (m, 2H), 3.90-3.84 (m, 2H), 3.81 (s, 3H), 2.28-2.23 (m, 2H), 2.03 (s, 3H), 1.83-1.82 (d, 3H), 1.55 (bs, 3H).

Example 161: (S)—N-(4-((2-((5-(2-cyanopropan-2-yl)-1-(tetrahydrofuran-3-yl)-1H-pyrazol-3-yl)amino)-7-(difluoromethyl)-1-methyl-1H-imidazo[4,5-b]pyridin-6-yl)oxy)pyridin-2-yl)acetamide

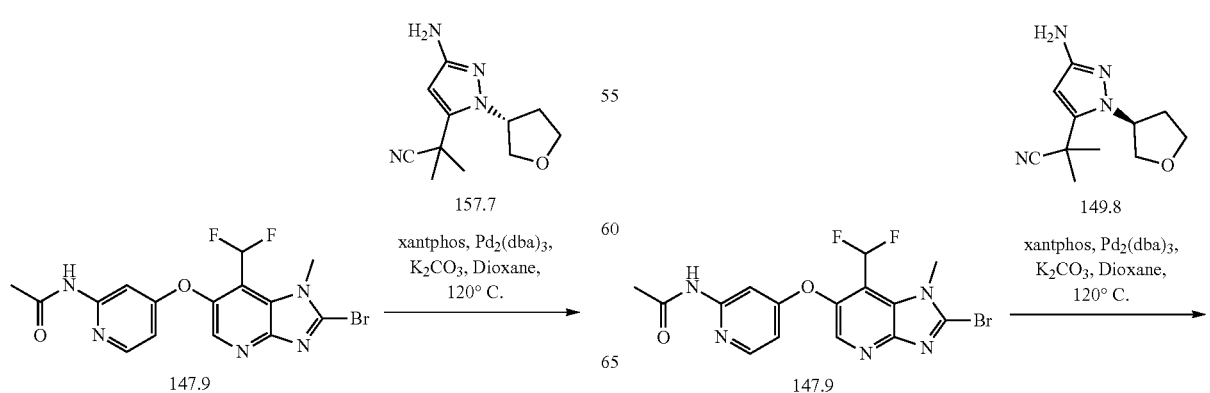

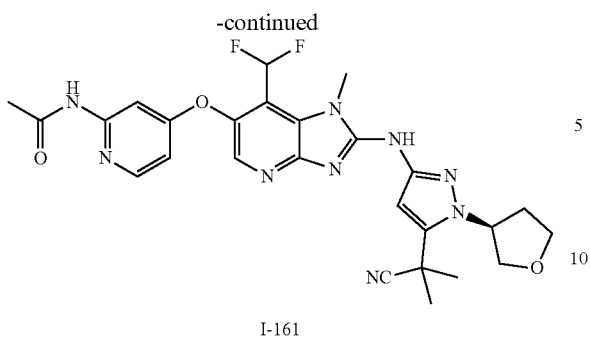

I-161

Synthesis of I-161. Compound I-161 was prepared from compound 147.9 and 149.8 following the procedure described in the synthesis of compound I-108. The product was purified by flash column chromatography on silica gel (CombiFlash®, 3.8% methanol in dichloromethane). MS (ES): m/z: 552.85 [M+H]$^+$, $^1$H NMR (DMSO-$d_6$, 400 MHz): 10.59 (s, 1H), 10.36 (s, 1H), 8.20-8.19 (d, J=5.6 Hz, 1H), 8.09 (s, 1H), 7.66 (s, 1H), 7.49-7.23 (m, 1H), 7.09-7.06 (d, J=7.6 Hz, 1H), 6.66-6.64 (m, 1H), 5.35-5.30 (m, 1H), 4.18-4.10 (m, 2H), 3.99-3.96 (m, 2H), 3.81 (s, 3H), 2.33-2.26 (m, 2H), 2.03 (s, 3H), 1.83-1.82 (d, 3H), 1.55 (bs, 3H).

Example 162: N-(4-((2-((5-(tert-butyl)-1-((1S,2R)-2-hydroxycyclopentyl)-1H-pyrazol-3-yl)amino)-1-methyl-1H-imidazo[4,5-b]pyridin-6-yl)oxy)pyridin-2-yl)acetamide and N-(4-((2-((5-(tert-butyl)-1-((1R,2S)-2-hydroxycyclopentyl)-1H-pyrazol-3-yl)amino)-1-methyl-1H-imidazo[4,5-b]pyridin-6-yl)oxy)pyridin-2-yl)acetamide

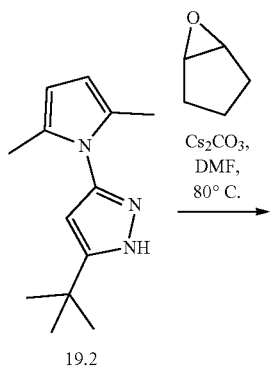

19.2

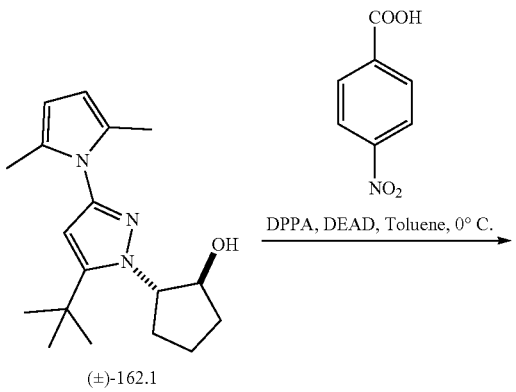

(±)-162.1

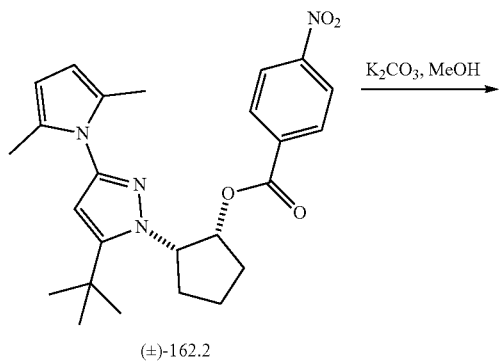

(±)-162.2

-continued
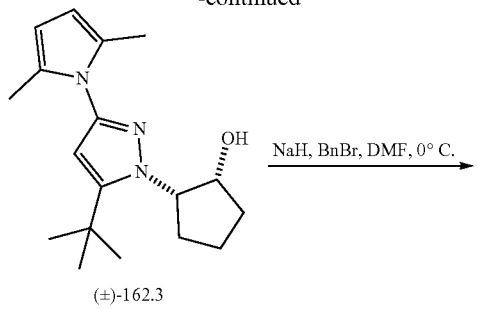
(±)-162.3
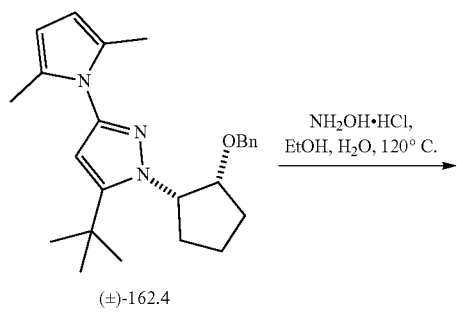
(±)-162.4
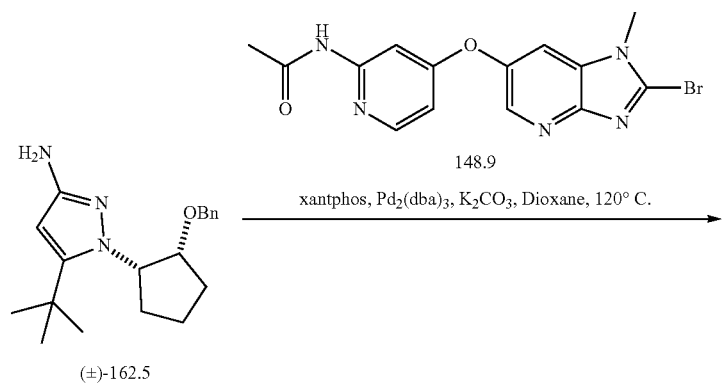
(±)-162.5
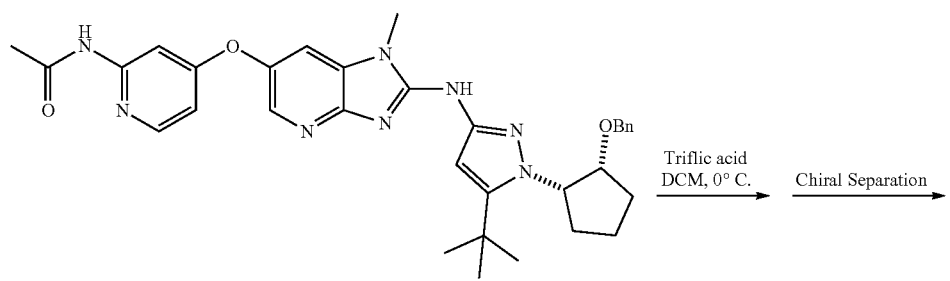
(±)-162.6
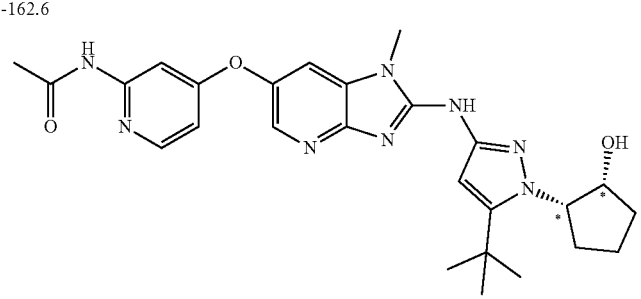
I-162-a and I-162-b Synthesis of compound (±)-162.1. A mixture of compound 19.2 (105 g, 46.02 mmol, 1.0 equiv), 6-oxabicyclo[3.1.0]hexane (5.81 g, 69.02 mmol, 1.5 equiv) and cesium carbonate (44.86 g, 138.06 mmol, 3.0 equiv) in DMF (100 mL) was stirred at 80° C. for 16 h. The reaction mixture transferred into water and product was extracted with ethyl acetate. The combined organic layers were washed with brine, dried over anhydrous sodium sulfate, filtered and concentrated under reduced pressure. The residue was purified by flash column chromatography on silica gel (CombiFlash®, 5-10% ethyl acetate in hexane) to afford (±)-162.1. MS (ES): m/z 302.4 [M+H]$^+$.

Synthesis of compound (±)-162.2. To a solution of compound (±)-162.1 (1.6 g, 5.31 mmol, 1.0 equiv) and 4-nitrobenzoic acid (1.77 g, 10.62 mmol, 2.0 equiv) in toluene (35 mL) at 0° C. was added diphenylphosphoryl azide (3.17 g, 7.96 mmol, 1.5 equiv) followed by diethylazodicarboxylate (1.38 g, 7.96 mmol, 1.5 equiv). The reaction mixture was allowed to warm to rt and stirred for 2 h. It was poured into ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 4% ethyl acetate in hexane) to afford (±)-162.2. MS (ES): m/z 451.4 [M+H]$^+$.

Synthesis of compound (±)-162.3. To a solution of (±)-162.2 (0.8 g, 1.78 mmol, 1.0 equiv) in methanol (20 mL) was added potassium carbonate (1.96 g, 14.24 mmol, 8.0 equiv) and reaction mixture was stirred at room temperature for 1 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 10% ethyl acetate in hexane) to afford (±)-162.3. MS (ES): m/z 302.4 [M+H]$^+$.

Synthesis of compound (±)-162.4. To a solution of (±)-162.3 (0.5 g, 1.66 mmol, 1.0 equiv) in DMF (10 mL), was added sodium hydride (0.132 g, 3.32 mmol, 2.0 equiv) at 0° C. and stirred for 20 min followed by the addition of benzyl bromide (0.3 mL, 2.49 mmol, 1.5 equiv). The reaction mixture was stirred at room temperature for 30 min. It was transferred into ice, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 5% ethyl acetate in hexane) to afford (±)-162.4. MS (ES): m/z 392.5 [M+H]$^+$.

Synthesis of compound (±)-162.5. Compound (±)-162.5 was prepared from (±)-162.4 following the procedure described in the synthesis of compound 120.6. The residue was purified by flash column chromatography on silica gel (CombiFlash®, 28-30% ethyl acetate in hexane). MS (ES): m/z 314.4 [M+H]$^+$.

Synthesis of compound (±)-162.6. Compound (±)-162.6 was prepared from compound (±)-162.5 and 148.8 following the procedure described in the synthesis of compound 1-108. The product was purified by flash column chromatography on silica gel (CombiFlash®, 3.0% methanol in dichloromethane). MS (ES): m/z: 595.7 [M+H]$^+$.

Synthesis of compound I-162-a and I-162-b. To a solution of (±)-162.6 (0.160 g, 0.269 mmol, 1.0 equiv) in dichloromethane (5 mL) was added triflic acid (0.6 mL) at 0° C. and stirred for 15 min. The reaction mixture was transferred into ice-water and extracted with dichloromethane. The combined organic layers were washed with brine, dried over anhydrous sodium sulfate, filtered and concentrated under reduced pressure to afford the racemate. The enantiomers were separated by HPLC (CHIRALPAK IH (250 mm×21 mm, 5 µm); elute: (A) 0.1% DEA in n-hexane, (B) 0.1% DEA in 2-propanol:methanol (30:70); flow rate=18 mL/min.) to afford first eluting fraction (I-162-a) and second eluting fraction (I-162-b). (*Absolute stereochemistry not determined.)

I-162-a: MS (ES): m/z: 505.5 [M+H]$^+$, $^1$H NMR (DMSO-d$_6$, 400 MHz): δ 10.53 (s, 1H), 9.83 (s, 1H), 8.18-8.16 (d, J=6.0 Hz, 1H), 7.96-7.95 (d, J=2.0 Hz, 1H), 7.66 (s, 1H), 7.63-7.62 (d, J=2.4 Hz, 1H), 6.66-6.64 (m, 1H), 6.56 (s, 1H), 5.03-5.02 (d, 1H), 4.60-4.45 (m, 2H), 3.66 (s, 3H), 2.13-2.07 (m, 1H), 2.03 (s, 3H), 1.99-1.91 (m, 1H), 1.89-1.83 (m, 1H), 1.82-1.75 (m, 2H), 1.66-1.59 (m, 1H), 1.41 (s, 9H).

I-162-b: MS (ES): m/z: 505.5 [M+H]$^+$, $^1$H NMR (DMSO-d$_6$, 400 MHz): δ 10.53 (s, 1H), 9.83 (s, 1H), 8.18-8.16 (d, J=6.0 Hz, 1H), 7.96-7.95 (d, J=2.4 Hz, 1H), 7.66 (s, 1H), 7.63-7.62 (d, J=2.4 Hz, 1H), 6.66-6.64 (m, 1H), 6.56 (s, 1H), 5.03-5.02 (d, 1H), 4.58-4.46 (m, 2H), 3.66 (s, 3H), 2.13-2.07 (m, 1H), 2.03 (s, 3H), 1.99-1.91 (m, 1H), 1.89-1.83 (m, 1H), 1.82-1.75 (m, 2H), 1.64-1.59 (m, 1H), 1.41 (s, 9H).

Example 163: (S)—N-(4-((2-((5-(tert-butyl)-1-(3-hydroxy-2-methylpropyl)-1H-pyrazol-3-yl)amino)-1-methyl-1H-imidazo[4,5-b]pyridin-6-yl)oxy)pyridin-2-yl)cyclopropane-carboxamide and (R)—N-(4-((2-((5-(tert-butyl)-1-(3-hydroxy-2-methylpropyl)-1H-pyrazol-3-yl)amino)-1-methyl-1H-imidazo[4,5-b]pyridin-6-yl)oxy)pyridin-2-yl)cyclopropanecarboxamide

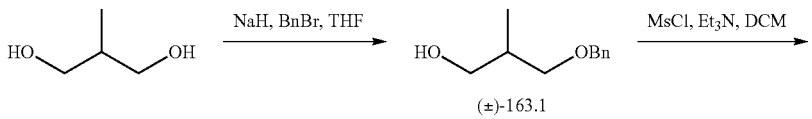

(±)-163.1

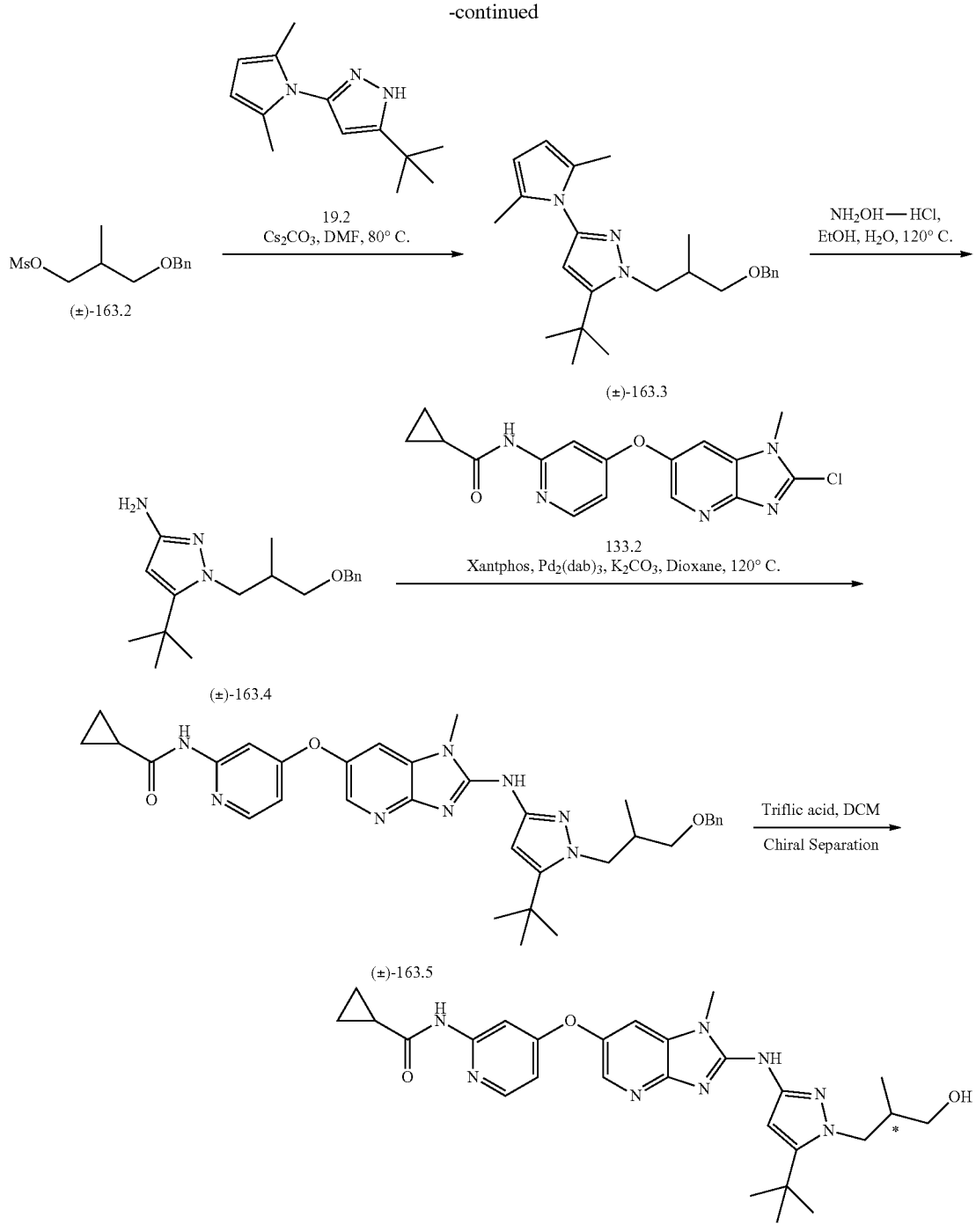

Synthesis of compound (±)-163.1. To a suspension of sodium hydride (2.2 g, 55.48 mmol, 1.0 equiv) in THF (20 mL) was added solution of 2-methylpropane-1,3-diol (5.0 g, 55.48 mmol, 1.0 equiv) in THF (25 mL) and stirred at 70° C. for 1 h. To the mixture was added benzyl bromide (6.6 mL, 55.48 mmol, 1.0 equiv) and stirred at 70° C. for 2 h. It was cooled to rt and poured into ice, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 20-25% ethyl acetate in hexane) to afford (±)-163.1. MS (ES): m/z 181.2 [M+H]$^+$.

Synthesis of compound (±)-163.2. Compound (±)-163.2 was prepared from compound (±)-163.1 following the procedure described in the synthesis of compound 28.5. The crude product was used in the next step without further purification.

Synthesis of compound (±)-163.3. Compound (±)-163.3 was prepared from compound (±)-163.2 and 19.2 following the procedure described in the synthesis of compound 28.7. The product was purified by flash column chromatography on silica gel (CombiFlash®, 2.5-3.0% ethyl acetate in hexane). MS (ES): m/z 380.5 [M+H]$^+$.

Synthesis of compound (±)-163.4. Compound (±)-163.4 was prepared from the above mixture of (±)-163.3 following the procedure described in the synthesis of compound 120.6. The product was purified by flash column chromatography on silica gel (CombiFlash®, 1.2% methanol in dichloromethane). MS (ES): m/z 302.4 [M+H]$^+$.

Synthesis of compound (±)-163.5. Compound (±)-163.5 was prepared from compound (±)-163.4 and 133.2 following the procedure described in the synthesis of compound I-108. The product was purified by flash column chromatography on silica gel (CombiFlash®, 2.6% methanol in dichloromethane). MS (ES): m/z: 609.5 [M+H]$^+$.

Synthesis of compound I-163-a and I-163-b. To a solution of (±)-163.5 (0.110 g, 0.180 mmol, 1.0 equiv) in dichloromethane (10 mL) was added triflic acid (0.4 mL) at 0° C. and stirred for 5 min. The reaction mixture was transferred into a mixture of ice and saturated aqueous sodium bicarbonate and extracted with dichloromethane. The combined organic layers were washed with brine, dried over anhydrous sodium sulfate, filtered and concentrated under reduced pressure. The residue was purified by flash column chromatography on silica gel (CombiFlash®, 4.0% methanol in dichloromethane) to afford the racemate product. The enantiomers were separated by SFC (column CHIRAL-CEL OX-H (250 mm*21 mm, 5 μm, mobile phase: (A) liquid carbon dioxide and (B) 0.3% DEA in 2-propanol:acetonitrile (50:50); flow rate=80 mL/min) to afford first eluting fraction (I-163-a) and second eluting fraction (I-163-b).

I-163-a: MS (ES): m/z: 519.5 [M+H]$^+$, LCMS purity: 98.10%, HPLC purity: 95.48%, Chiral HPLC: 100%, $^1$H NMR (DMSO-d$_6$, 400 MHz): δ 10.84 (s, 1H), 9.83 (s, 1H), 8.19-8.17 (d, J=6.0 Hz, 1H), 7.95-7.94 (d, J=2.4 Hz, 1H), 7.62-7.59 (m, 2H), 6.70-6.68 (m, 1H), 6.59 (s, 1H), 4.67-4.66 (m, 1H), 4.15-4.10 (m, 1H), 3.90-3.84 (m, 1H), 3.66 (s, 3H), 3.50 (bs, 2H), 2.70-2.67 (m, 1H), 2.01-1.88 (m, 1H), 1.39 (s, 9H), 1.25-1.24 (d, 3H), 0.90-0.84 (m, 2H), 0.81-0.74 (m, 2H).

I-163-b: MS (ES): m/z: 519.5 [M+H]$^+$, LCMS purity: 100%, HPLC purity: 99.41%, Chiral HPLC: 100%, $^1$H NMR (DMSO-d$_6$, 400 MHz): δ 10.84 (s, 1H), 9.83 (s, 1H), 8.19-8.17 (d, J=6.0 Hz, 1H), 7.95-7.94 (d, J=2.4 Hz, 1H), 7.62 (bs, 2H), 6.70-6.68 (m, 1H), 6.63 (s, 1H), 4.67-4.66 (m, 1H), 4.15-4.10 (m, 1H), 3.90-3.84 (m, 1H), 3.66 (s, 3H), 3.50 (bs, 2H), 2.67-2.58 (m, 1H), 1.99-1.95 (m, 1H), 1.39 (s, 9H), 1.25-1.24 (d, 3H), 0.90-0.84 (m, 2H), 0.81-0.74 (m, 2H).

Example 164: N-(4-((2-((5-(tert-butyl)-1-(2-oxaspiro[3.3]heptan-6-yl)-1H-pyrazol-3-yl)amino)-1-methyl-1H-imidazo[4,5-b]pyridin-6-yl)oxy)pyridin-2-yl)cyclopropanecarboxamide

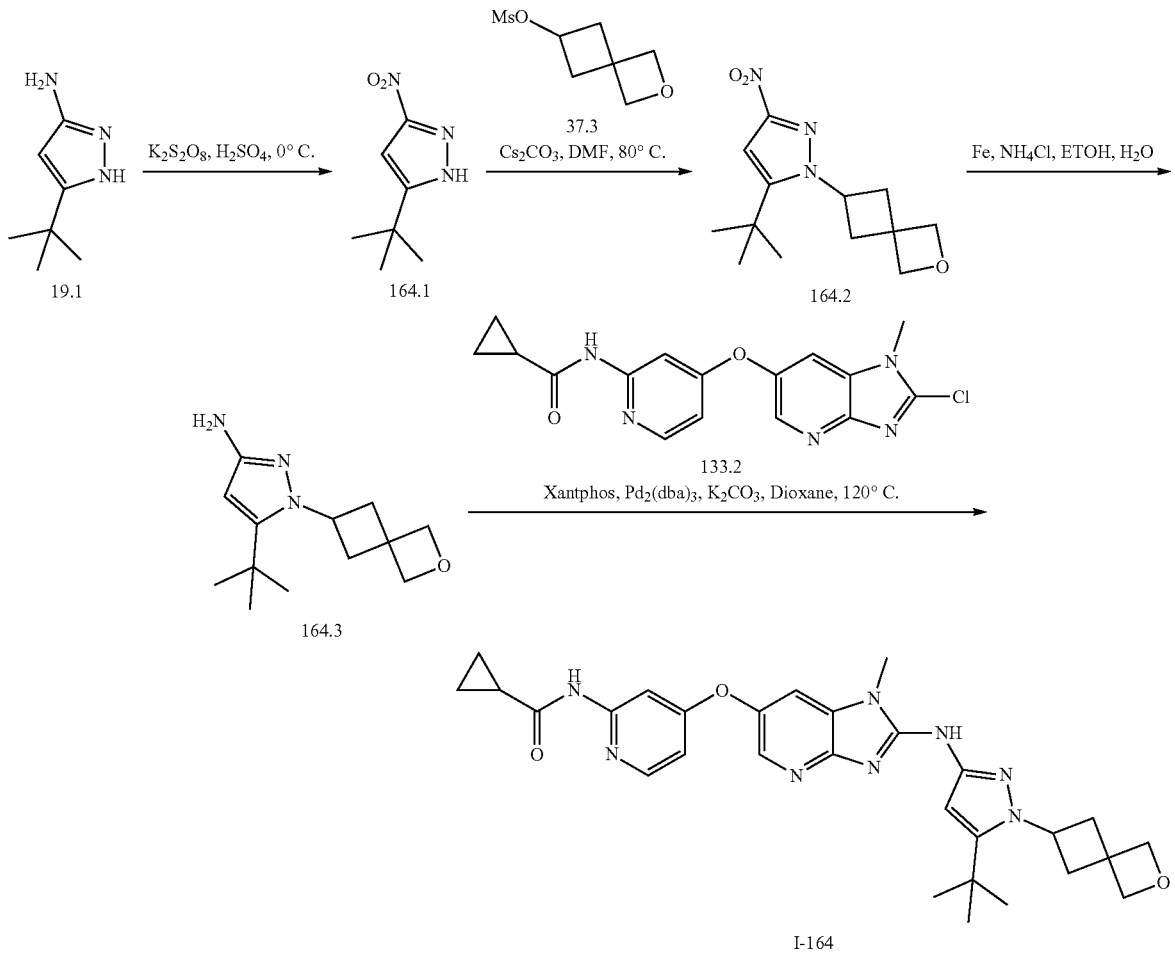

Synthesis of compound 164.1. Concentrated sulfuric acid (60 mL, 6 volumes) was added dropwise to potassium persulfate (54.31 g, 201.15 mmol, 2.8 equiv) at room temperature and stirred for 15 min. To the mixture was added 19.1 (10 g, 71.84 mmol, 1.0 equiv) in portions maintaining temperature 30-40° C. The reaction mixture was stirred at room temperature for 30 min. It was poured over crushed ice, stirred and basified with saturated aqueous sodium bicarbonate and extracted with ethyl acetate. The combined organic layers were washed with brine, dried over anhydrous sodium sulfate, filtered and concentrated under reduced pressure. The residue was purified by flash column chromatography on silica gel (CombiFlash®, 15% ethyl acetate in hexane) to afford 164.1. $^1$H NMR (DMSO-$d_6$, 400 MHz): δ 11.20 (s, 1H), 6.26 (s, 1H), 1.29 (s, 9H).

Synthesis of compound 164.2. Compound 164.2 was prepared from compound 164.2 and 37.3 following the procedure described in the synthesis of compound 28.7. The product was purified by flash column chromatography on silica gel (CombiFlash®, 15-20% ethyl acetate in hexane). MS (ES): m/z 266.3 [M+H]$^+$.

Synthesis of compound 164.3. To a solution of 164.2 (0.200 g, 0.753 mmol, 1.0 equiv) in ethanol:water (2:1, 5 mL) was added iron powder (0.210 g, 3.765 mmol, 5 equiv) followed by ammonium chloride (0.203 g, 3.765 mmol, 5 equiv). The reaction mixture was heated at 50° C. for 30 min. It was poured over ice-water, filtered and product was extracted with ethyl acetate. The combined organic layers were washed with brine, dried over anhydrous sodium sulfate, filtered and concentrated under reduced pressure to obtain 164.3. MS (ES): m/z 236.3 [M+H]$^+$.

Synthesis of I-164. Compound I-164 was prepared from compound 164.3 and 133.2 following the procedure described in the synthesis of compound I-108. The product was purified by flash column chromatography on silica gel (CombiFlash®, 3.5% methanol in dichloromethane). MS (ES): m/z: 543.9 [M+H]$^+$, $^1$H NMR (DMSO-$d_6$, 400 MHz): δ 10.83 (s, 1H), 9.88 (s, 1H), 8.19-8.17 (d, J=5.6 Hz, 1H), 7.95-7.94 (d, J=2.4 Hz, 1H), 7.63 (bs, 2H), 6.77-6.68 (m, 1H), 6.57 (s, 1H), 4.70 (s, 2H), 4.57 (s, 2H), 3.66 (s, 3H), 2.80-2.67 (m, 3H), 1.99-1.91 (m, 2H), 35 (s, 9H), 1.19-1.16 (m, 1H), 0.88-0.86 (m, 4H).

Example 165: (R)—N-(4-((2-((5-(tert-butyl)-1-(tetrahydrofuran-3-yl)-1H-pyrazol-3-yl)amino)-1-methyl-1H-imidazo[4,5-b]pyridin-6-0)oxy)pyridin-2-yl)-3-methoxyazetidine-1-carboxamide

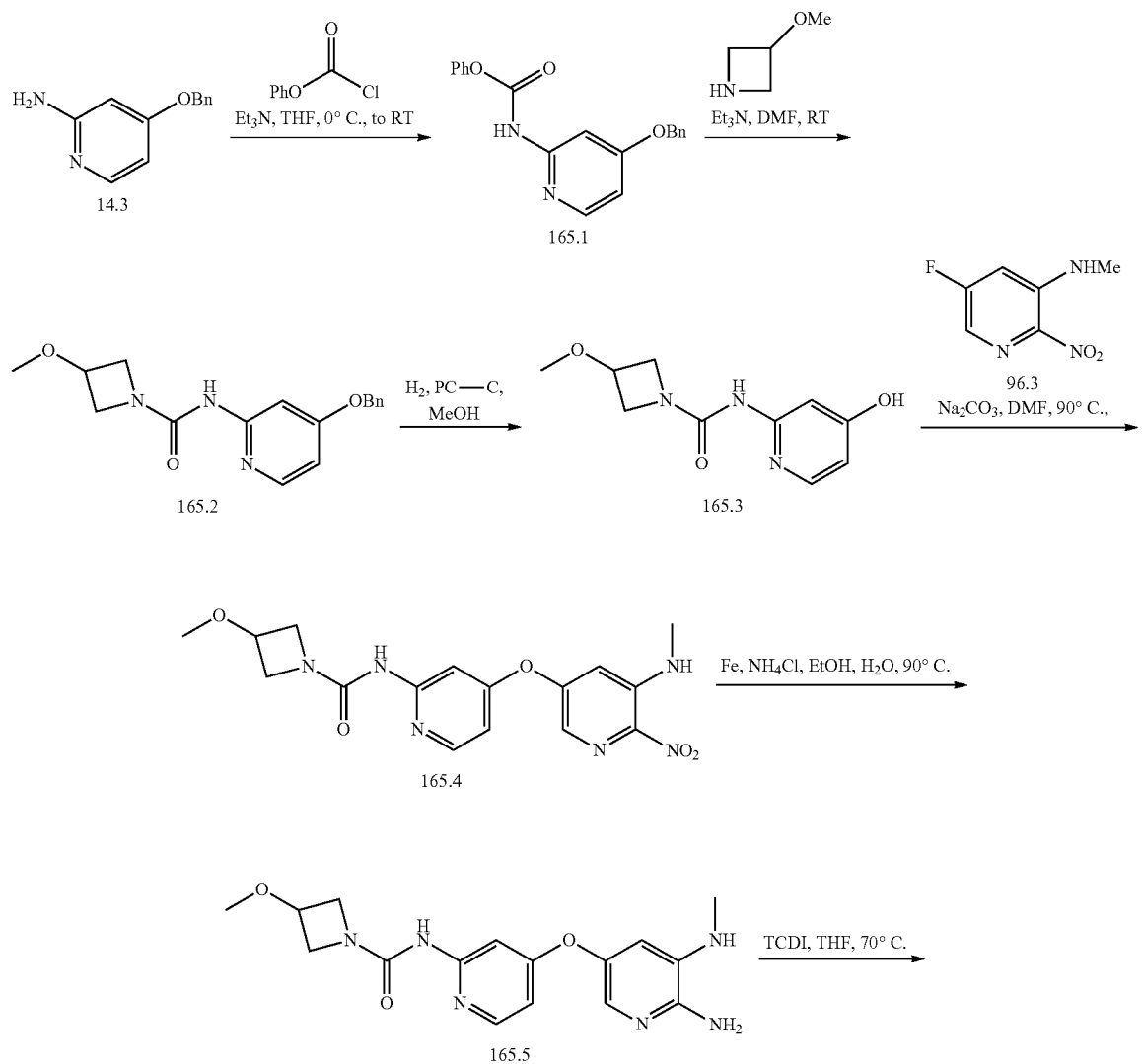

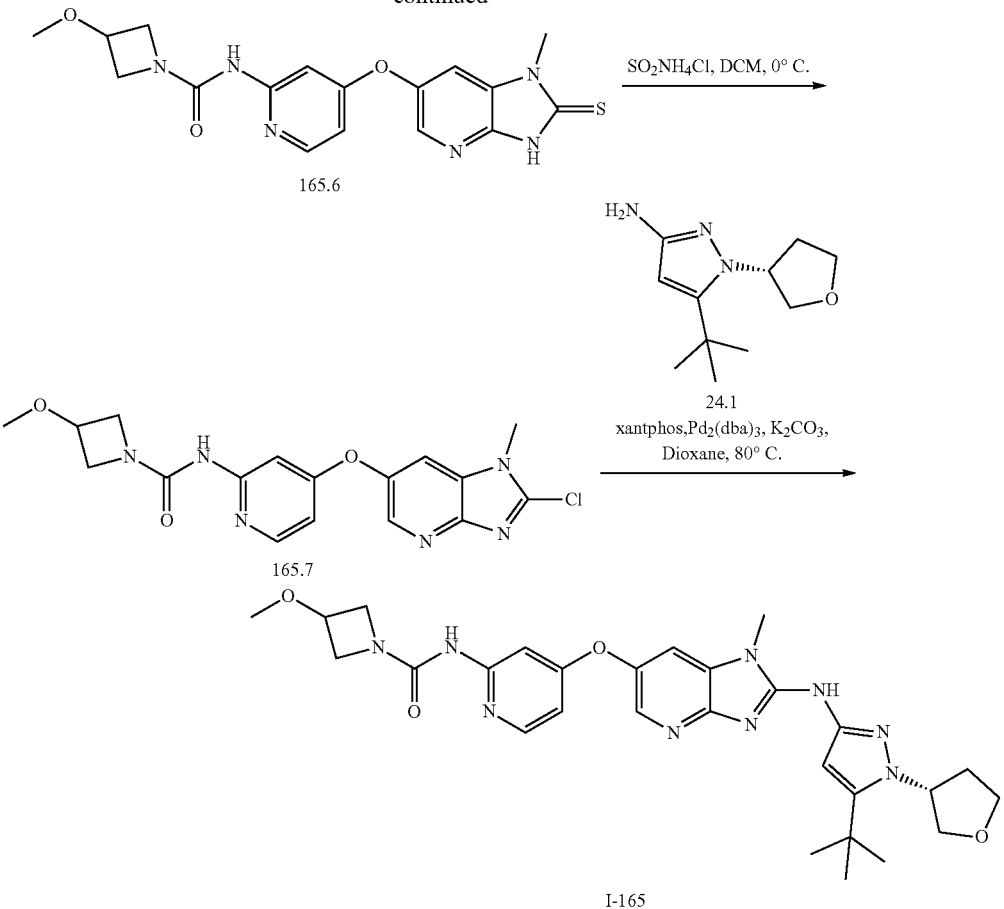

Synthesis of compound 165.1. To a solution of 14.3 (2.0 g, 9.99 mmol, 1.0 equiv) and triethylamine (4.2 mL, 29.97 mmol, 3.0 equiv) in THF (20 mL) at 0° C. was added phenyl chloroformate (4.67 g, 29.97 mmol, 3.0 equiv) dropwise. The reaction mixture was allowed to warm to rt and stirred for 3 h. It was transferred into water and extracted with ethyl acetate. The combined organic layers were washed with brine, dried over anhydrous sodium sulfate, filtered and concentrated under reduced pressure. The residue was used in the next step without further purification. MS (ES): m/z 321.3 [M+H]$^+$.

Synthesis of compound 165.2. To a solution of 165.1 (3.0 g, 9.36 mmol, 1.0 equiv) and triethylamine (12.5 mL, 84.24 mmol, 9.0 equiv) in DMF (20 mL) at 0° C. was added 3-methoxyazetidine (1.06 g, 12.17 mmol, 1.3 equiv) dropwise. The reaction mixture stirred at room temperature for 16 h. It was transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.5% methanol in dichloromethane) to afford 165.2 MS (ES): m/z 314.3 [M+H]$^+$.

Synthesis of compound 165.3. A mixture of compound 165.3 (1.1 g, 3.51 mmol, 1.0 equiv) and 10% palladium on carbon (0.5 g) in methanol (10 mL) was stirred at rt under hydrogen atmosphere (1 atm) for 3 h. The reaction mixture was filtered through a pad of Celite® and washed with methanol. The filtrate was concentrated under reduced pressure to obtain 165.3. MS (ES): m/z 224.2 [M+H]$^+$.

Synthesis of compound 165.4. Compound 165.4 was prepared from compound 165.3 and 96.3 following the procedure described in the synthesis of compound 96.4. The product was purified by flash column chromatography on silica gel (CombiFlash®, 2.8% methanol in dichloromethane). MS (ES): m/z 375.3 [M+H]$^+$.

Synthesis of compound 165.5. Compound 165.5 was prepared from compound 165.4 following the procedure described in the synthesis of compound Int-4. The product was purified by flash column chromatography on silica gel (CombiFlash®, 3.5% methanol in dichloromethane). MS (ES): m/z 345.5 [M+H]$^+$.

Synthesis of compound 165.6. Compound 165.6 was prepared from compound 165.5 following the procedure described in the synthesis of compound 102.1. The product was purified by trituration in hexane. MS (ES): m/z: 387.4 [M+H]$^+$.

Synthesis of compound 165.7. Compound 165.7 was prepared from compound 165.6 following the procedure described in the synthesis of compound 102.2. The residue was purified by flash column chromatography on silica gel (CombiFlash®, 2.4% methanol in dichloromethane). MS (ES): m/z 389.8 [M+H]$^+$.

Synthesis of I-165. Compound I-165 was prepared from compound 165.7 and 24.1 following the procedure described in the synthesis of compound I-108. The product was purified by flash column chromatography on silica gel (CombiFlash®, 3.0% methanol in dichloromethane). MS (ES): m/z: 563.05 [M+H]$^+$, $^1$H NMR (DMSO-d$_6$, 400 MHz): δ 9.89 (s, 1H), 9.20 (s, 1H), 8.11-8.10 (d, J=5.6 Hz, 1H), 7.96-7.95 (d, J=2.4 Hz, 1H), 7.63-7.62 (d, J=2.4 Hz, 1H), 7.47 (bs, 1H), 6.60-6.58 (m, 2H), 5.77 (s, 1H), 5.26 (bs, 1H), 4.13-4.07 (m, 5H), 3.88-3.83 (m, 2H), 3.75-3.73 (m, 2H), 3.68 (s, 3H), 3.19 (s, 3H), 2.27-2.24 (m, 1H), 1.41 (s, 9H).

Example 166: (S)—N-(4-((2-((5-(tert-butyl)-1-(tetrahydrofuran-3-yl)-1H-pyrazol-3-yl)amino)-1-methyl-1H-imidazo[4,5-b]pyridin-6-yl)oxy)pyridin-2-yl)-3-methoxyazetidine-1-carboxamide

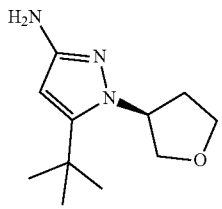
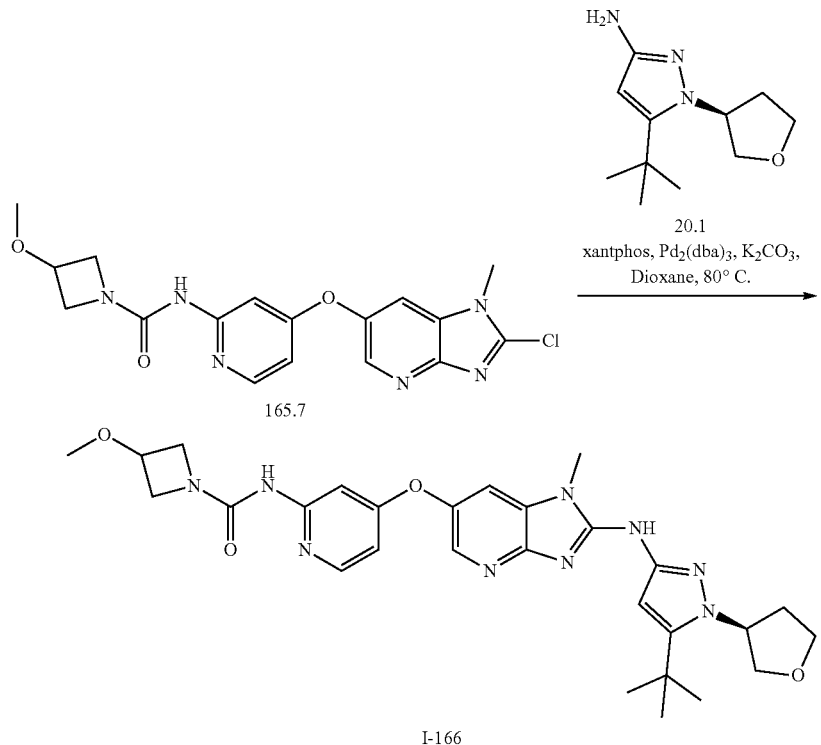

Synthesis of I-166. Compound I-166 was prepared from compound 165.7 and 20.1 following the procedure described in the synthesis of compound I-108. The product was purified by flash column chromatography on silica gel (CombiFlash®, 3.0% methanol in dichloromethane). MS (ES): m/z: 562.64 [M+H]$^+$, $^1$H NMR (DMSO-d$_6$, 400 MHz): δ 9.88 (s, 1H), 9.20 (s, 1H), 8.10-8.09 (d, J=5.6 Hz, 1H), 7.94-7.94 (d, J=2.4 Hz, 1H), 7.62-7.61 (d, J=2.4 Hz, 1H), 7.46 (bs, 1H), 6.59-6.56 (m, 2H), 5.76 (s, 1H), 5.27-5.25 (m, 1H), 4.11-4.06 (m, 5H), 3.87-3.82 (m, 2H), 3.74-3.72 (m, 2H), 3.66 (s, 3H), 3.18 (s, 3H), 2.27-2.21 (m, 1H), 1.40 (s, 9H).

Example 167: (R)—N-(4-((2-((5-(2-cyanopropan-2-yl)-1-(tetrahydrofuran-3-yl)-1H-pyrazol-3-yl)amino)-7-methoxy-1-methyl-1H-imidazo[4,5-b]pyridin-6-yl)oxy)pyridin-2-yl)acetamide

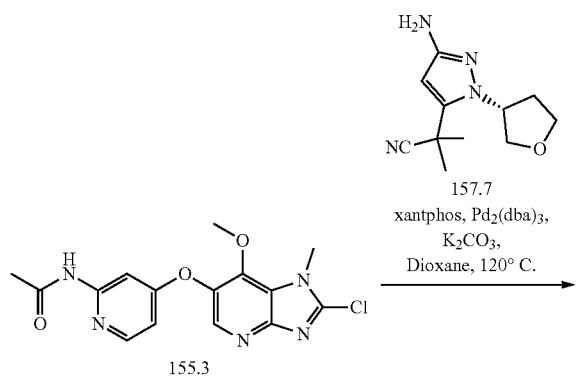

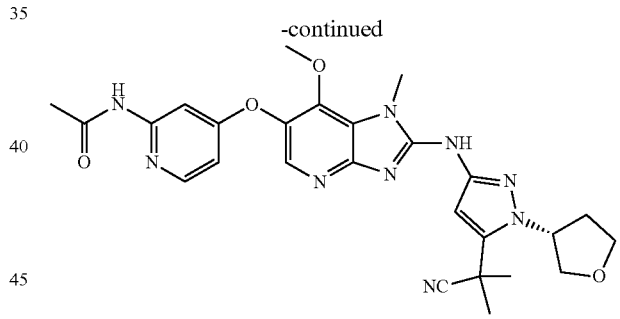

Synthesis of I-167. Compound I-167 was prepared from compound 155.3 and 157.7 following the procedure described in the synthesis of compound I-108. The product was purified by flash column chromatography on silica gel (CombiFlash®, 3.4% methanol in dichloromethane). MS (ES): m/z: 533.1 [M+H]$^+$, $^1$H NMR (DMSO-d$_6$, 400 MHz): δ 10.56 (s, 1H), 10.07 (s, 1H), 8.19-8.18 (d, J=5.6 Hz, 1H), 7.68 (s, 1H), 7.09-7.08 (d, J=5.6 Hz, 1H), 6.84-6.80 (m, 1H), 6.67-6.65 (m, 1H), 5.28 (bs, 1H), 4.19-4.11 (m, 2H), 4.01-3.95 (m, 2H), 3.91 (s, 3H), 3.84 (s, 3H), 3.40-3.35 (m, 2H), 2.04 (s, 3H), 1.83 (bs, 6H).

Example 168: (S)—N-(4-((2-((5-(2-cyanopropan-2-yl)-1-(tetrahydrofuran-3-yl)-1H-pyrazol-3-yl)amino)-7-methoxy-1-methyl-1H-imidazo[4,5-b]pyridin-6-yl)oxy)pyridin-2-yl)acetamide

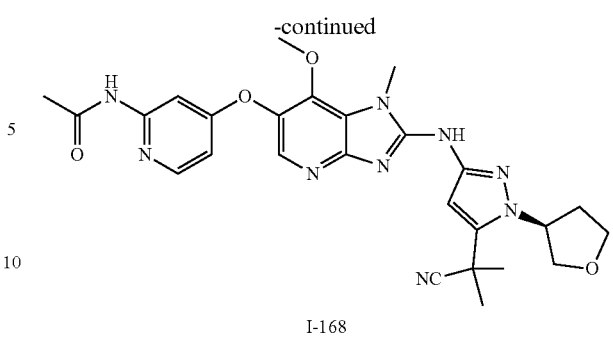

I-168

Synthesis of I-168. Compound I-168 was prepared from compound 155.3 and 149.8 following the procedure described in the synthesis of compound I-108. The product was purified by flash column chromatography on silica gel (CombiFlash®, 3.5% methanol in dichloromethane). MS (ES): m/z: 533.1 [M+H]$^+$, $^1$H NMR (DMSO-d$_6$, 400 MHz): δ 10.56 (s, 1H), 10.06 (s, 1H), 8.18-8.16 (d, J=5.6 Hz, 1H), 7.67 (s, 1H), 7.08-7.06 (d, J=5.6 Hz, 1H), 6.83-6.81 (d, J=6.4 Hz, 1H), 6.66-6.64 (m, 1H), 5.28 (bs, 1H), 4.17-4.08 (m, 2H), 4.00-3.93 (m, 2H), 3.90 (s, 3H), 3.83 (s, 3H), 3.41-3.34 (m, 2H), 2.03 (s, 3H), 1.82 (bs, 6H).

Example 169: (S)—N-(4-((2-((5-(tert-butyl)-1-(1-methylpyrrolidin-3-yl)-1H-pyrazol-3-yl)amino)-1-methyl-1H-imidazo[4,5-b]pyridin-6-yl)oxy)pyridin-2-yl)cyclopropanecarboxamide and (R)—N-(4-((2-((5-(tert-butyl)-1-(1-methylpyrrolidin-3-yl)-1H-pyrazol-3-yl)amino)-1-methyl-1H-imidazo[4,5-b]pyridin-6-yl)oxy)pyridin-2-yl)cyclopropanecarboxamide

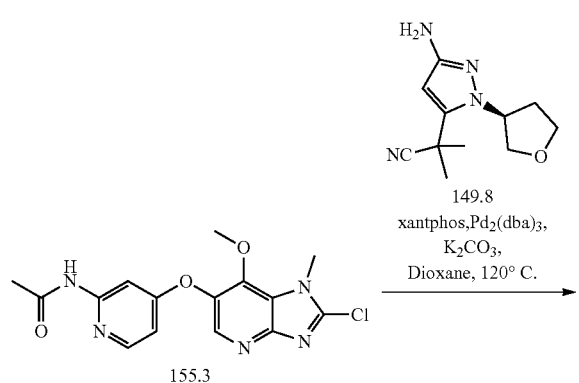

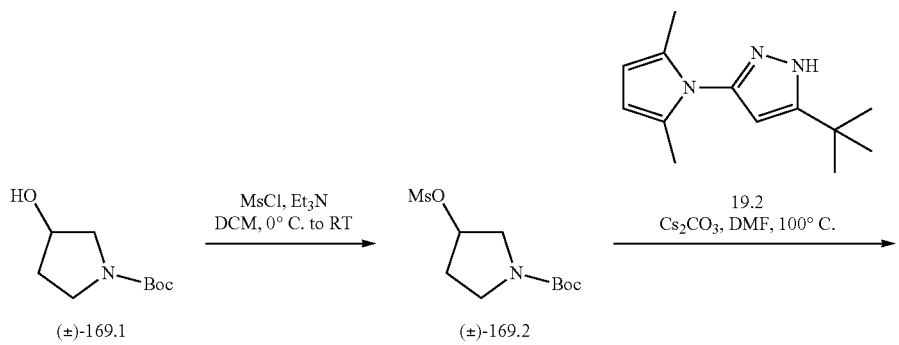

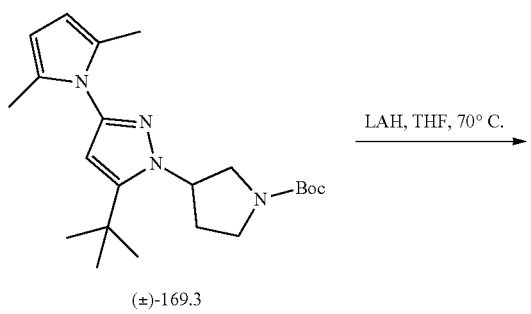

-continued
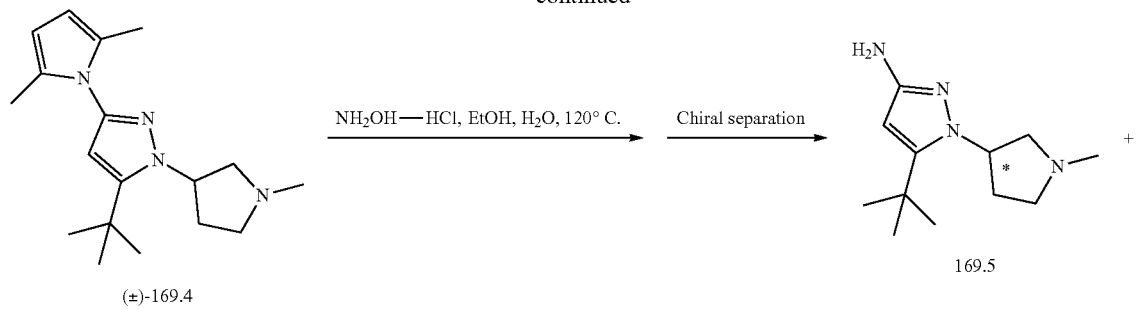
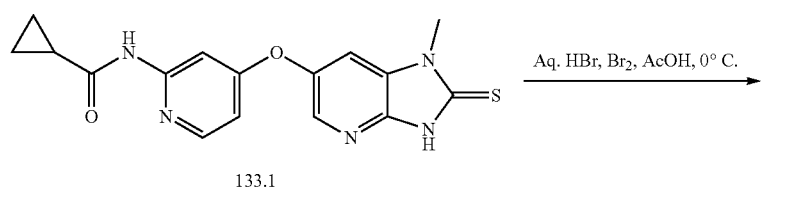
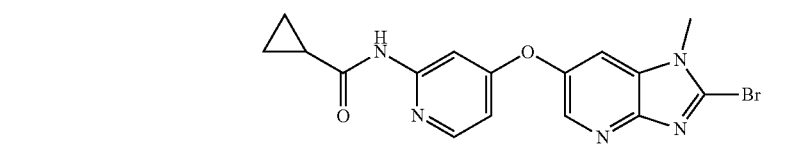
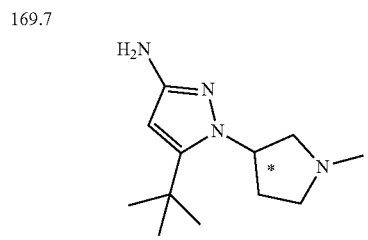
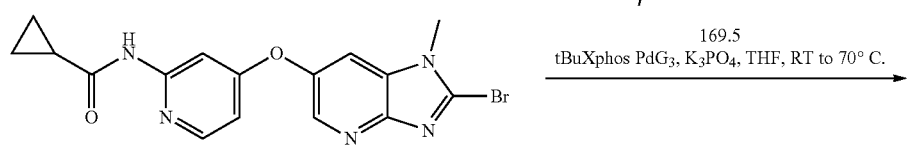
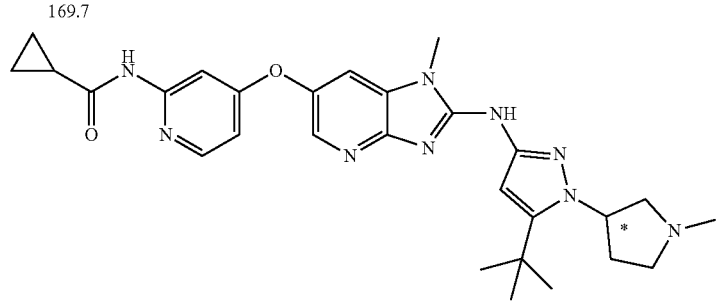

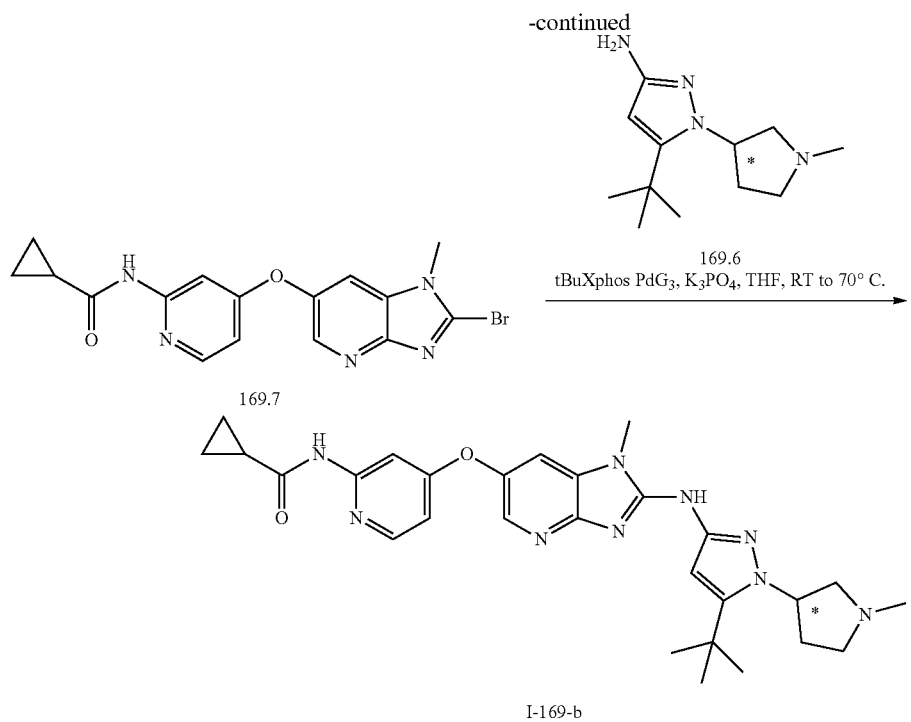

Synthesis of compound (±)-169.2. Compound (±)-169.2 was prepared from compound (±)-169.1 following the procedure described in the synthesis of compound 28.5. The crude product was used in the next step without further purification. $^1$H NMR (DMSO-d$_6$, 400 MHz): δ 5.24 (bs, 1H), 3.55-3.51 (m, 2H), 3.48-3.39 (m, 2H), 3.24 (s, 3H), 2.12 (bs, 2H), 1.41 (s, 9H).

Synthesis of compound (±)-169.3. A mixture of 19.2 (10 g, 46.02 mmol, 1.0 equiv), (±)-169.2 (18.31 g, 69.02 mmol, 1.5 equiv) and cesium carbonate (37.50 g, 115.05 mmol, 2.5 equiv) in DMF (100 mL) was stirred at 100° C. for 12 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 10-12% ethyl acetate in hexane) to afford (±)-169.3. MS (ES): m/z 387.5 [M+H]$^+$.

Synthesis of compound (±)-169.4. To a solution of (±)-169.3 (3.3 g, 8.54 mmol, 1.0 equiv) in THF (35 mL), was added lithium aluminum hydride solution (1 M in THF) (51.2 mL, 51.24 mmol, 6.0 equiv) at 0° C. The reaction mixture was stirred at 70° C. for 2 h. It was cooled to 0° C. and carefully quenched by saturated aqueous sodium sulfate. The reaction mixture was filtered through a pad of Celite® and washed with diethyl ether. The filtrate was dried over anhydrous sodium sulfate, filtered and concentrated under reduced pressure. The residue was purified by flash column chromatography on silica gel (CombiFlash®, 60% ethyl acetate in hexane) to afford (±)-169.4. MS (ES): m/z 301.5 [M+H]$^+$.

Synthesis of compound 169.5 and 169.6. The racemate was prepared from (±)-163.3 following the procedure described in the synthesis of compound 120.6. The residue was purified by flash column chromatography on silica gel (CombiFlash®, 7-8% methanol in dichloromethane). MS (ES): m/z 223.3 [M+H]$^+$. The enantiomers were separated by HPLC (column: CHIRALPAK IG (250 mm×21 mm, 5 μm); mobile phase: (A) 0.1% DEA in n-hexane, (B) 0.1% DEA in 2-propanol:methanol (50:50); flow rate=20 mL/min) to afford first eluting fraction (169.5) and second eluting fraction (169.6). (*Absolute stereochemistry not determined.)

Synthesis of compound 169.7. To a solution of 133.1 (1.8 g, 5.27 mmol, 1.0 equiv) in acetic acid (18 mL) was added aqueous hydrobromic acid (0.640 g, 7.9 mmol, 1.5 equiv) at 0° C. followed by bromine (3.37 g, 21.08 mmol, 4.0 equiv). The reaction mixture was stirred for 10 min. It was poured into saturated aqueous sodium bicarbonate solution, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.5% methanol in dichloromethane) to afford 169.7. MS (ES): m/z 389.2 [M+H]$^+$.

Synthesis of I-169-a. A mixture of 169.7 (0.070 g, 0.180 mmol, 1.0 equiv), 169.5 (0.040 g, 0.180 mmol, 1.0 equiv) and tripotassium phosphate (0.076 g, 0.36 mmol, 2.0 equiv) in THF (2 mL) was degassed by bubbling argon through for 10 min. Under argon atmosphere [(2-di-tert-butylphosphino-2',4',6'-triisopropyl-1,1'-biphenyl)-2-(2'-amino-1,1'-biphenyl)] palladium(II) methanesulfonate (0.028 g, 0.036 mmol, 0.2 equiv) was added, again degassed for 5 min. The reaction mixture was stirred at 70° C. for 3 h. The reaction mixture was transferred into water and extracted with ethyl acetate. The combined organic layers were washed with brine, dried over anhydrous sodium sulfate, filtered and concentrated under reduced pressure. The residue was purified by preparative HPLC to afford I-169-a. MS (ES): m/z: 530.5 [M+H]$^+$, $^1$H NMR (DMSO-d$_6$, 400 MHz): 10.84 (s, 1H), 8.34 (s, 1H), 8.19-8.17 (d, J=5.6 Hz, 1H), 7.95-7.94 (d, J=2.4 Hz, 1H), 7.62 (bs, 2H), 6.70-6.68 (m, 1H), 6.55 (s, 1H), 5.09-5.05 (m, 1H), 3.66 (s, 3H), 3.02-2.98 (m, 1H), 2.98-

2.67 (m, 2H), 2.25 (bs, 5H), 2.18-2.16 (m, 1H), 1.97-1.93 (m, 1H), 1.39 (s, 9H), 0.76-0.74 (m, 4H).

Synthesis of I-169-b. Compound I-169-b was prepared from compound 169.6 and 169.7 following the procedure described in the synthesis of compound I-169-a. The product was purified by preparative HPLC. MS (ES): m/z: 530.5 [M+H]$^+$, $^1$H NMR (DMSO-d$_6$, 400 MHz): 10.83 (s, 1H), 8.33 (s, 1H), 8.19-8.17 (d, J=5.6 Hz, 1H), 7.95-7.94 (d, J=2.4 Hz, 1H), 7.63-7.62 (m, 2H), 6.70-6.68 (m, 1H), 6.55 (s, 1H), 5.09-5.05 (m, 1H), 3.66 (s, 3H), 3.02-2.98 (m, 1H), 2.72-2.67 (m, 2H), 2.30 (bs, 5H), 2.18-2.16 (m, 1H), 1.97-1.93 (m, 1H), 1.39 (s, 9H), 0.76-0.74 (m, 4H).

Example 170: (R)—N-(4-((2-((5-(tert-butyl)-1-(tetrahydrofuran-3-yl)-1H-pyrazol-3-yl)amino)-7-methoxy-1-methyl-1H-imidazo[4,5-b]pyridin-6-yl)oxy)pyridin-2-yl)cyclopropanecarboxamide Synthesis of I-170. Compound I-170 was prepared from compound 170.1 and 24.1 following the procedure described in the synthesis of compound I-108. The product was purified by preparative HPLC. MS (ES): m/z: 547.5 [M+H]$^+$, $^1$H NMR (CDCl$_3$, 400 MHz): 8.70 (s, 1H), 8.12-8.11 (d, J=5.6 Hz, 1H), 7.92 (bs, 2H), 6.55-6.54 (d, J=3.6 Hz, 1H), 5.17-5.14 (m, 1H), 4.29-4.27 (m, 1H), 4.13-4.10 (m, 2H), 4.01 (s, 3H), 3.83 (s, 3H), 2.41-2.39 (m, 2H), 1.59 (bs, 2H), 1.43 (s, 9H), 1.09 (bs, 2H), 0.91-0.90 (m, 2H).

Example 171: (S)—N-(4-((2-((5-(tert-butyl)-1-(tetrahydrofuran-3-yl)-1H-pyrazol-3-yl)amino)-7-methoxy-1-methyl-1H-imidazo[4,5-b]pyridin-6-yl)oxy)pyridin-2-yl)cyclopropanecarboxamide

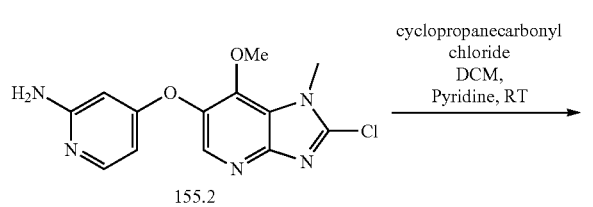

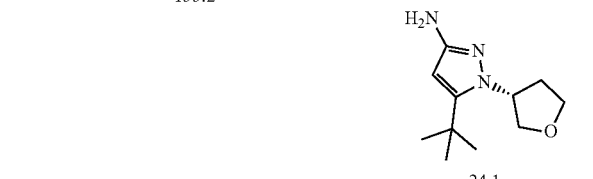

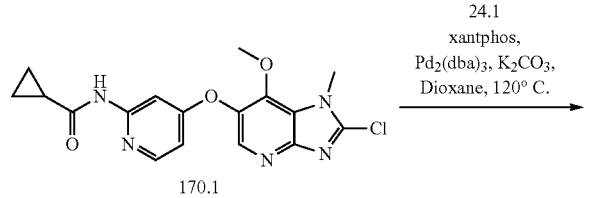

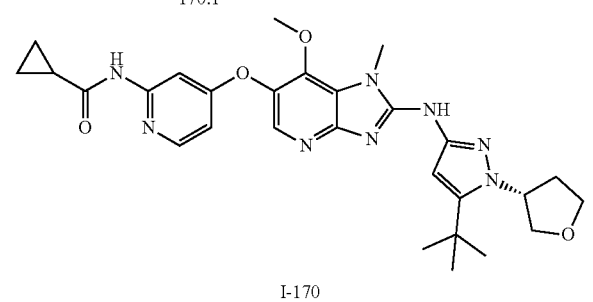

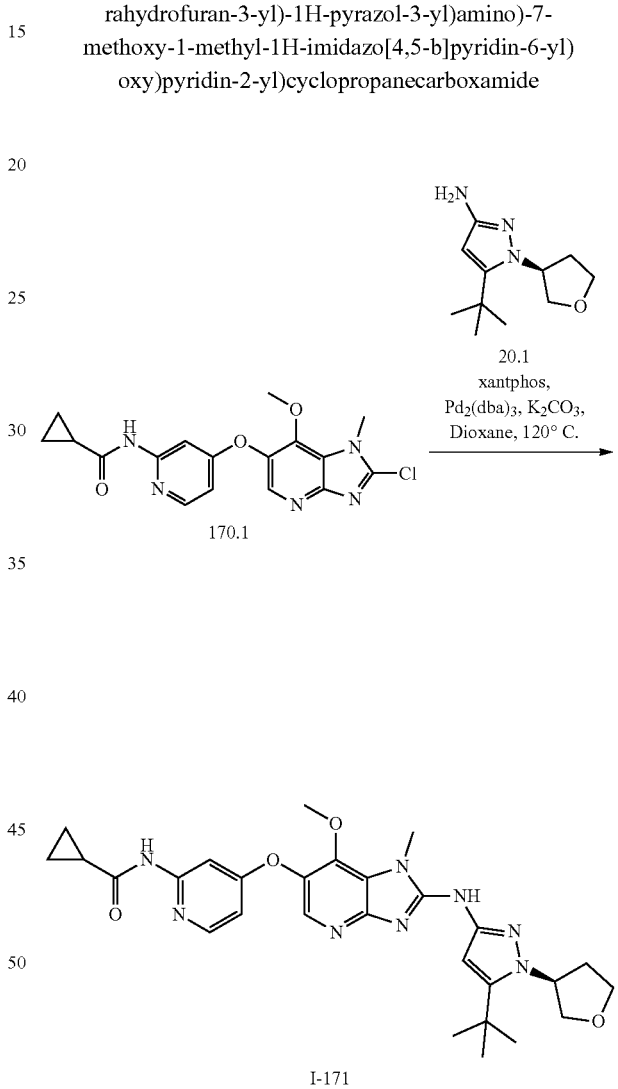

Synthesis of compound 170.1. To a solution of 155.2 (0.045 g, 0.147 mmol, 1.0 equiv) and pyridine (0.06 mL, 0.617 mmol, 4.2 equiv) in dichloromethane (2 mL) at 0° C. was added cyclopropanecarbonyl chloride (0.033 mL, 0.367 mmol, 2.5 equiv). The reaction mixture was allowed to warm to rt and stirred for 15 min. It was poured over ice-water, stirred and extracted with dichloromethane. The combined organic layers were washed with saturated aqueous sodium bicarbonate followed by brine, dried over anhydrous sodium sulfate, filtered and concentrated under reduced pressure. The residue was purified by flash column chromatography on silica gel (CombiFlash®, 2.8% methanol in dichloromethane) to afford 170.1. MS (ES): m/z 374.8 [M+H]$^+$.

Synthesis of I-171. Compound I-171 was prepared from compound 170.1 and 20.1 following the procedure described in the synthesis of compound I-108. The product was purified by preparative HPLC. MS (ES): m/z: 547.5 [M+H]$^+$, $^1$H NMR (CDCl$_3$, 400 MHz): 8.70 (s, 1H), 8.12-8.11 (d, J=5.6 Hz, 1H), 7.92 (bs, 2H), 6.55-6.54 (d, J=3.6 Hz, 1H), 5.17-5.14 (m, 1H), 4.29-4.27 (m, 1H), 4.13-4.10 (m, 2H), 4.01 (s, 3H), 3.83 (s, 3H), 2.41-2.39 (m, 2H), 1.59 (bs, 2H), 1.43 (s, 9H), 1.09 (bs, 2H), 0.91-0.90 (m, 2H).

Example 172: (R)—N-(4-((2-((5-(tert-butyl)-1-(4,4-difluoro-1-methylpyrrolidin-3-yl)-1H-pyrazol-3-yl)amino)-7-methoxy-1-methyl-1H-imidazo[4,5-b]pyridin-6-yl)oxy)pyridin-2-yl)acetamide and (S)—N-(4-((2-((5-(tert-butyl)-1-(4,4-difluoro-1-methylpyrrolidin-3-yl)-1H-pyrazol-3-yl)amino)-7-methoxy-1-methyl-1H-imidazo[4,5-b]pyridin-6-yl)oxy)pyridin-2-yl)acetamide
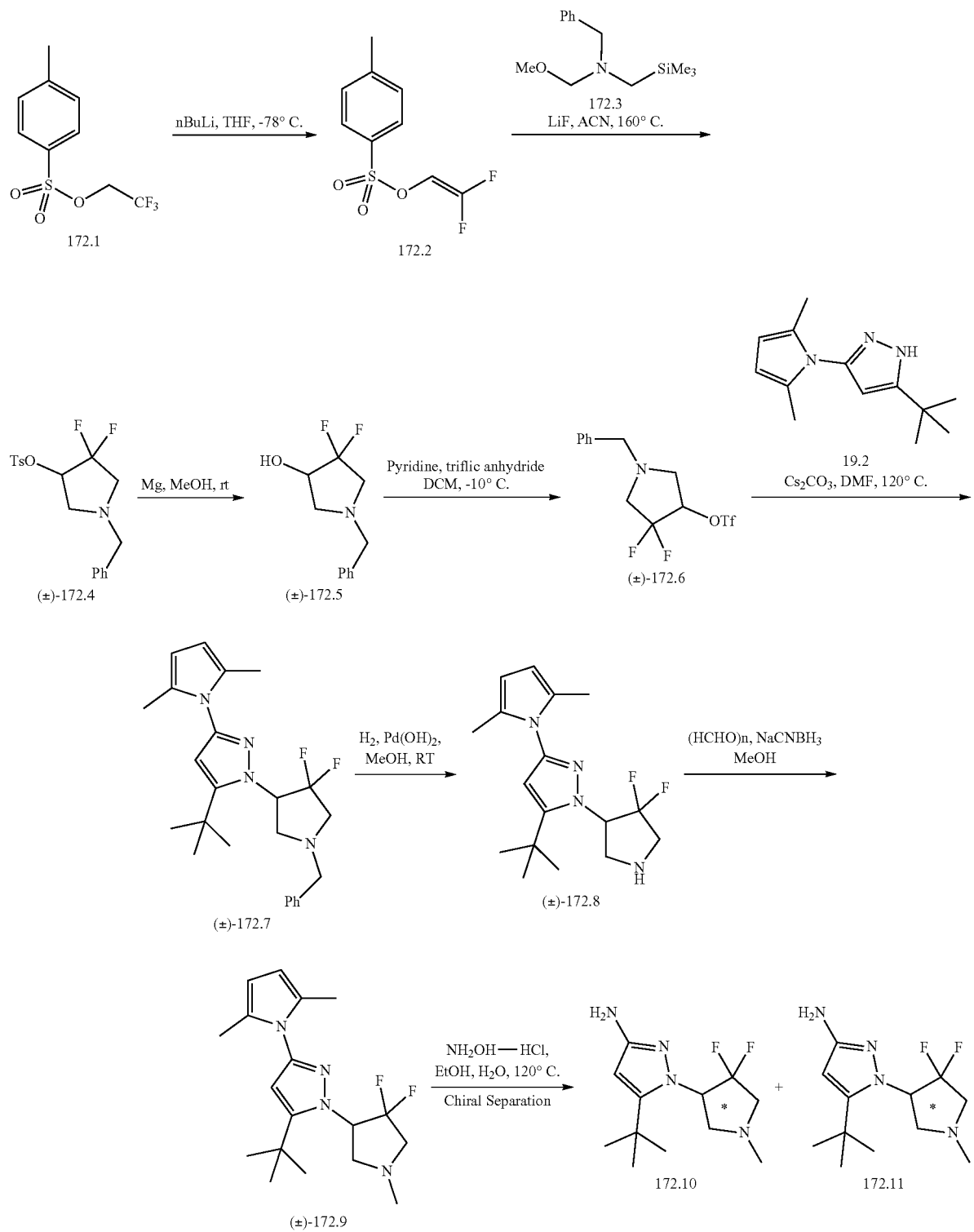

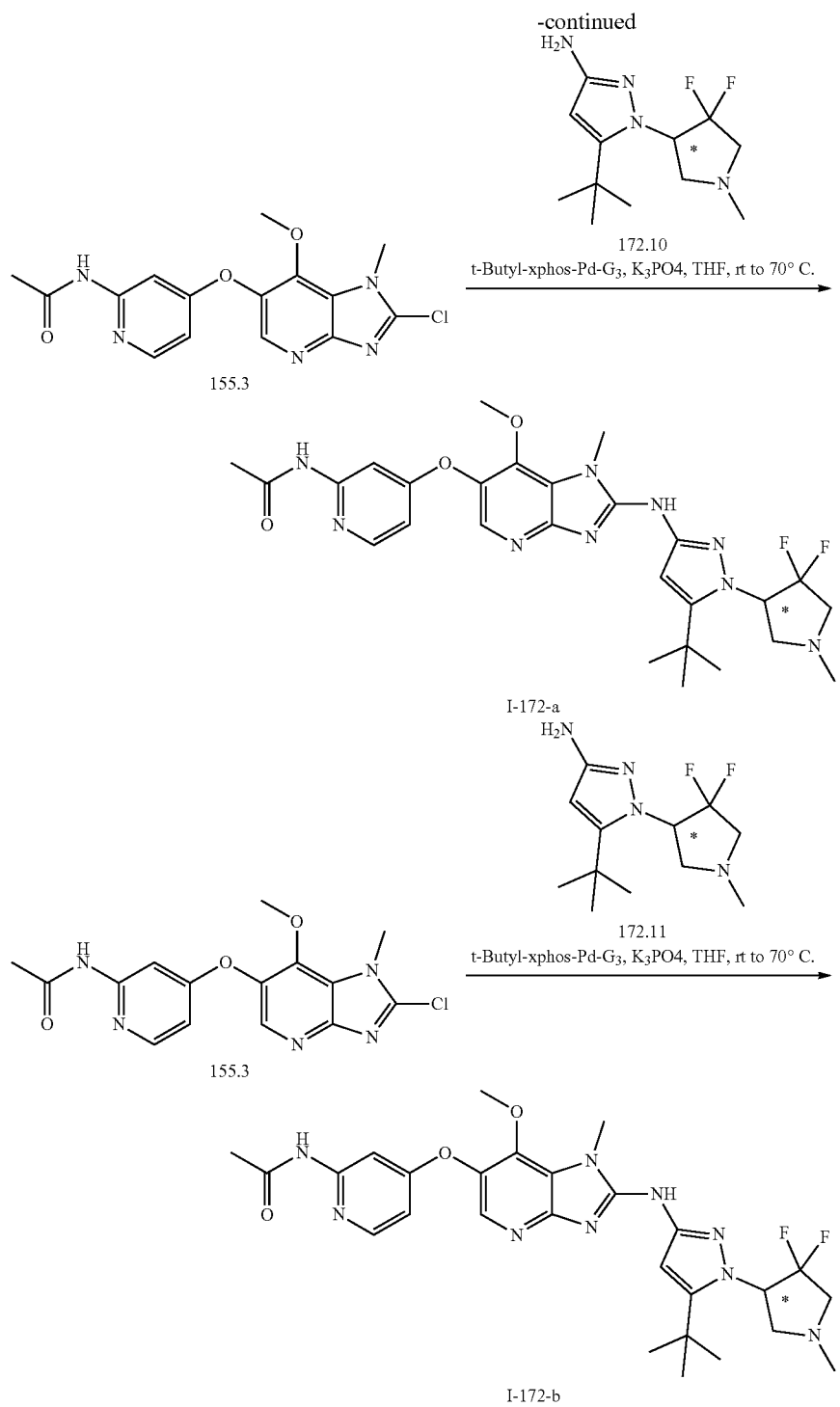

Synthesis of compound 172.2. To a solution of 172.1 (25 g, 98.34 mmol, 1.0 equiv) in THF (250 mL), was added n-butyl lithium (2.5M in Hexane) (78.6 mL, 196.68 mmol, 2.0 equiv) at −78° C. and stirred for 1 h. A saturated solution of ammonium chloride was added slowly to quench the reaction. The mixture was allowed to warmed to room temperature and extracted with ethyl acetate. The combined organic layers were washed with brine, dried over anhydrous sodium sulfate, filtered and concentrated under reduced pressure. The residue was purified by flash column chromatography on silica gel (CombiFlash®, 3% ethyl acetate in hexane) to afford 172.2. $^1$H NMR (CDCl$_3$, 400 MHz): δ 7.84-7.82 (d, J=8 Hz, 2H), 7.41-7.39 (d, J=8 Hz, 2H), 6.11-6.07 (m, 1H), 2.49 (s, 3H).

Synthesis of compound (±)-172.4. A mixture of 172.2 (0.500 g, 2.13 mmol, 1.0 equiv), 172.3 (2.03 g, 8.54 mmol, 4.0 equiv), lithium fluoride (0.165 g, 6.39 mmol, 3.0 equiv) and acetonitrile (8 mL) in a sealed tube was stirred at 160° C. for 6 h. The reaction mixture was cooled to room temperature, transferred into water, and extracted with ethyl acetate. The combined organic layers were washed with brine, dried over anhydrous sodium sulfate, filtered and concentrated under reduced pressure. The residue was purified by flash column chromatography on silica gel (CombiFlash®, 7% ethyl acetate in hexane) to afford (±)-172.4. MS (ES): m/z 368.3 [M+H]$^+$.

Synthesis of compound (±)-172.5. To a solution of (±)-172.4 (6.1 g, 16.60 mmol, 1.0 equiv) in methanol (60 mL) was added magnesium turnings (2.78 g, 116.2 mmol, 7.0 equiv) at 0° C. in portions. The reaction mixture was stirred at room temperature for 3 h. It was poured over ice-water, stirred and precipitated solids were collected by filtration. The solids were dissolved in 5 N hydrochloric acid and neutralized by addition of a saturated aqueous solution of sodium bicarbonate. The mixture was then extracted with ethyl acetate. The combined organic layers were washed with brine, dried over anhydrous sodium sulfate, filtered and concentrated under reduced pressure. The residue was purified by flash column chromatography on silica gel (CombiFlash®, 20% ethyl acetate in hexane) to afford (±)-172.5. MS (ES): m/z 214.2 [M+H]$^+$.

Synthesis of compound (±)-172.6. To a solution of (±)-172.5 (2.0 g, 9.38 mmol, 1.0 equiv) and pyridine (3.8 mL, 46.9 mmol, 5.0 equiv) in dichloromethane (20 mL) at −10° C. was added triflic anhydride (3.9 mL, 23.45 mmol, 2.5 equiv). The reaction mixture stirred at −10° C. for 30 min. It was transferred into water, neutralized using a saturated aqueous solution of sodium bicarbonate. The mixture was then extracted with ethyl acetate. The combined organic layers were washed with brine, dried over anhydrous sodium sulfate, filtered and concentrated under reduced pressure. The residue was purified by flash column chromatography on silica gel (CombiFlash®, 10% ethyl acetate in hexane) to afford (±)-172.6. MS (ES): m/z 346.24 [M+H]$^+$.

Synthesis of compound (±)-172.7. A mixture of compound (±)-172.6 (1.82 g, 5.27 mmol, 1.0 equiv), 19.2 (1.15 g, 5.27 mmol, 1.0 equiv) and cesium carbonate (5.13 g, 15.81 mmol, 3.0 equiv) in DMF (20 mL) was stirred at 120° C. for 5 h. The reaction mixture was transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 4% ethyl acetate in hexane) to afford (±)-172.7. MS (ES): m/z 413.5 [M+H]$^+$.

Synthesis of compound (±)-172.8. A mixture of compound (±)-172.7 (1.0 g, 2.42 mmol, 1.0 equiv) and 20% palladium hydroxide (0.500 g) in methanol (20 mL) was stirred under hydrogen (1 atm) for 30 min. The reaction mixture was filtered through a pad of Celite® and washed with 10% methanol in dichloromethane. The filtrate was concentrated under reduced pressure. The residue was purified by flash column chromatography on silica gel (CombiFlash®, 40% ethyl acetate in hexane) to afford (±)-172.8. MS (ES): m/z 323.4 [M+H]$^+$.

Synthesis of compound (±)-172.9. To a solution of (±)-172.8 (0.364 g, 1.13 mmol, 1.0 equiv) in methanol (7 mL) was added formaldehyde solution (37% in water) (0.5 mL, 5.65 mmol, 5.0 equiv), and the reaction mixture was stirred at room temperature for 10 min. To the mixture was added acetic acid (0.169 g, 2.82 mmol, 2.5 equiv) followed by sodium cyanoborohydride (0.350 g, 5.65 mmol, 5.0 equiv) at 0° C. The reaction mixture was stirred at 0° C. for 15 min. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 20% ethyl acetate in hexane) to afford (±)-172.9. MS (ES): m/z 337.5 [M+H]$^+$.

Synthesis of compound 172.10 and 172.11. The racemate was prepared from (±)-172.9 following the procedure described in the synthesis of compound 120.6. The residue was purified by flash column chromatography on silica gel (CombiFlash®, 40% ethyl acetate in hexane). The enantiomers were separated by HPLC (column: CHIRALPAK IB-N (250 mm×21 mm, 5 μm); mobile phase: (A) 0.1% DEA in n-hexane, (B) 0.1% DEA in 2-propanol; flow rate=18 mL/min) to afford first eluting fraction (172.10) and second eluting fraction (170.11). MS (ES): m/z 259.3 [M+H]$^+$. (*Absolute stereochemistry not determined.)

Synthesis of I-172-a. Compound I-172-a was prepared from compound 172.10 and 155.3 following the procedure described in the synthesis of compound I-169-a. The product was purified by preparative HPLC. MS (ES): m/z: 570.5 [M+H]$^+$, $^1$H NMR (DMSO-d$_6$, 400 MHz): δ 10.54 (s, 1H), 9.82 (s, 1H), 8.19-8.17 (d, J=6.0 Hz, 1H), 7.95 (s, 1H), 7.69-7.68 (d, J=2.0 Hz, 1H), 6.67-6.65 (m, 2H), 5.25-5.19 (m, 1H), 3.91 (s, 3H), 3.84 (s, 3H), 3.61-3.52 (m, 2H), 3.27-3.23 (m, 1H), 2.85-2.79 (m, 1H), 2.40 (s, 3H), 2.05 (s, 3H), 1.41 (s, 9H).

Synthesis of I-172-b. Compound I-172-b was prepared from compound 172.10 and 155.3 following the procedure described in the synthesis of compound I-169-a. The product was purified by preparative HPLC. MS (ES): m/z: 570.5 [M+H]$^+$, $^1$H NMR (DMSO-d$_6$, 400 MHz): δ 10.55 (s, 1H), 9.83 (s, 1H), 8.18-8.16 (d, J=5.6 Hz, 1H), 7.94 (s, 1H), 7.67 (bs, 1H), 6.66-6.64 (m, 2H), 5.22-5.18 (m, 1H), 3.90 (s, 3H), 3.83 (s, 3H), 3.59-3.52 (m, 2H), 3.26-3.21 (m, 1H), 2.86-2.78 (m, 1H), 2.39 (s, 3H), 2.03 (s, 3H), 1.40 (s, 9H).

Example 173: (S)—N-(4-((2-((5-(tert-butyl)-1-(1-(2-methoxyethyl)pyrrolidin-3-yl)-1H-pyrazol-3-yl)amino)-1-methyl-1H-imidazo[4,5-b]pyridin-6-yl)oxy)pyridin-2-yl)cyclopropanecarboxamide
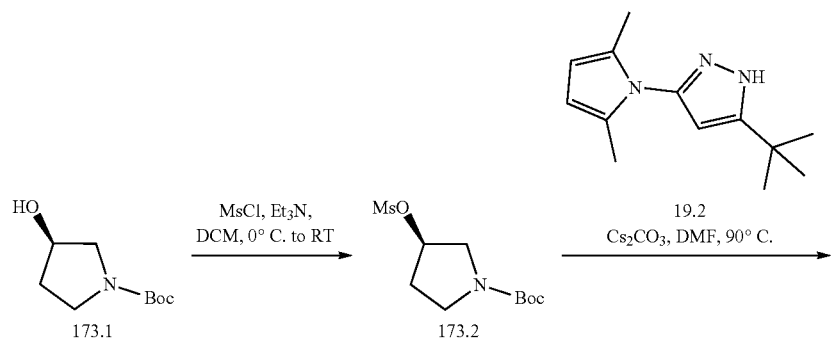
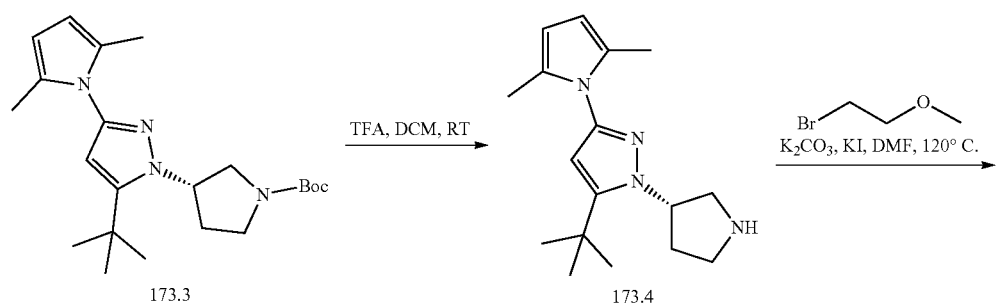
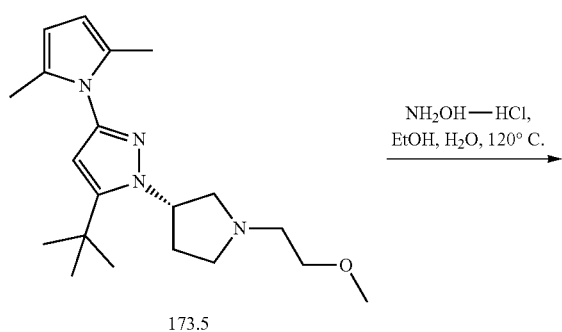
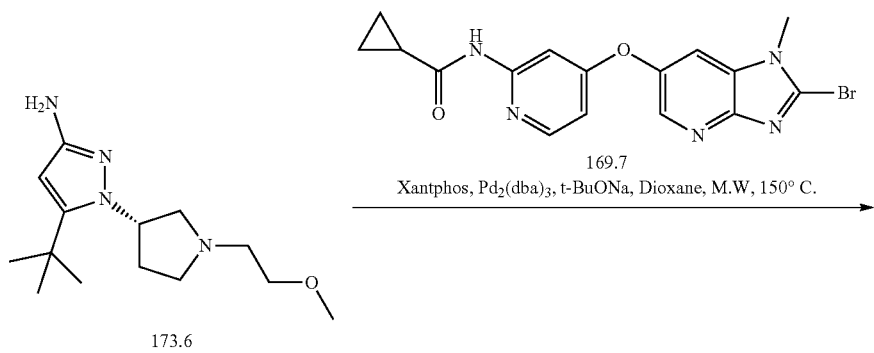

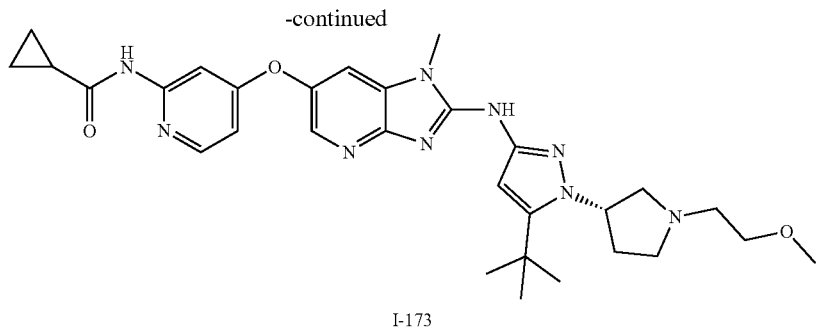

I-173

Synthesis of compound 173.2. Compound 173.2 was prepared from compound 173.1 following the procedure described in the synthesis of compound 28.5. The crude product was used in the next step without further purification. $^1$H NMR (DMSO-$d_6$, 400 MHz): δ 5.24 (bs, 1H), 3.55-3.51 (m, 2H), 3.48-3.39 (m, 2H), 3.24 (s, 3H), 2.12 (bs, 2H), 1.41 (s, 9H).

Synthesis of compound 173.3. Compound 173.3 was prepared from compound 173.2 and 19.2 following the procedure described in the synthesis of compound 28.7. The product was purified by flash column chromatography on silica gel (CombiFlash®, 10-12% ethyl acetate in hexane). MS (ES): m/z 387.5 [M+H]$^+$.

Synthesis of compound 173.4. To a solution of 173.3 (4.1 g, 10.61 mmol, 1.0 equiv) in dichloromethane (40 mL) was added trifluoroacetic acid (10 mL) at 0° C. The reaction mixture was stirred at room temperature for 3 h. It was poured over ice-water, followed by addition of saturated aqueous sodium bicarbonate solution and product was extracted with ethyl acetate. The combined organic layers were washed with brine, dried over anhydrous sodium sulfate, filtered and concentrated under reduced pressure to obtain 173.4. MS (ES): m/z 287.4 [M+H]$^+$.

Synthesis of compound 173.5. A mixture of 173.4 (1.0 g, 3.49 mmol, 1.0 equiv), 1-bromo-2-methoxyethane (0.582 g, 4.19 mmol, 1.2 equiv), potassium carbonate (1.44 g, 10.47 mmol, 3.0 equiv) and potassium iodide (0.028 g, 0.174 mmol, 0.05 equiv) in DMF (10 mL) was heated at 120° C. for 5 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 6-8% ethyl acetate in hexane) to afford 173.5. MS (ES): m/z 345.5 [M+H]$^+$.

Synthesis of compound 173.6. Compound 173.6 was prepared from 173.5 following the procedure described in the synthesis of compound 120.6. The product was purified by flash column chromatography on silica gel (CombiFlash®, 4-5% methanol in dichloromethane) to afford 173.6. MS (ES): m/z 223.3 [M+H]$^+$.

Synthesis of I-173. A mixture of 169.7 (0.100 g, 0.257 mmol, 1.0 equiv), 173.6 (0.082 g, 0.309 mmol, 1.2 equiv) and sodium tert-butoxide (0.049 g, 0.514 mmol, 2.0 equiv) in 1,4-dioxane (3 mL) was degassed by bubbling argon through for 10 min. Under argon atmosphere 4,5-bis(diphenylphosphino)-9,9-dimethylxanthene (0.029 g, 0.0514 mmol, 0.2 equiv) and tris(dibenzylideneacetone)dipalladium(0) (0.023 g, 0.0257 mmol, 0.1 equiv) were added, again degassed for 5 min. The reaction mixture was stirred at 150° C. in a microwave reactor for 1 h. The reaction mixture was cooled to room temperature, transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 6-8% methanol in dichloromethane) to afford I-173. MS (ES): m/z: 574.5 [M+H]$^+$, $^1$H NMR (DMSO-$d_6$, 400 MHz): 10.84 (s, 1H), 9.90 (s, 1H), 8.20-8.19 (d, J=5.6 Hz, 1H), 7.96 (bs, 1H), 7.64-7.63 (m, 2H), 6.71-6.69 (m, 1H), 6.58 (s, 1H), 5.08-5.04 (m, 1H), 3.68 (s, 3H), 3.47-3.44 (m, 2H), 3.25 (s, 3H), 3.12-3.07 (m, 1H), 2.82-2.65 (m, 5H), 2.27-2.25 (m, 1H), 2.20-2.17 (m, 1H), 1.98-1.95 (m, 1H), 1.40 (s, 9H), 0.77-0.75 (m, 4H).

Example 174: (R)—N-(4-((2-((5-(tert-butyl)-1-(1-(2-methoxyethyl)pyrrolidin-3-yl)-1H-pyrazol-3-yl)amino)-1-methyl-1H-imidazo[4,5-b]pyridin-6-yl)oxy)pyridin-2-yl)cyclopropanecarboxamide

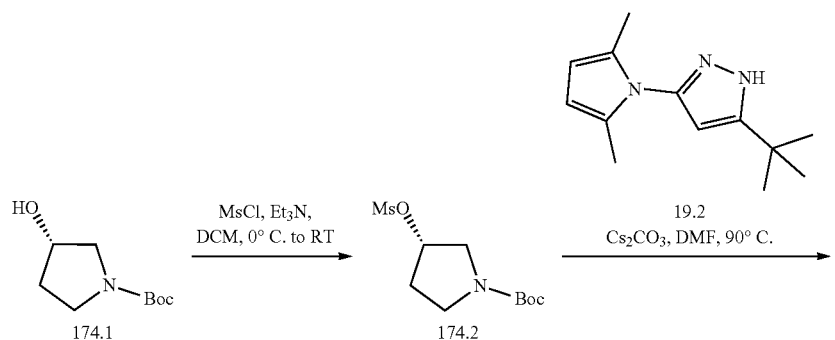

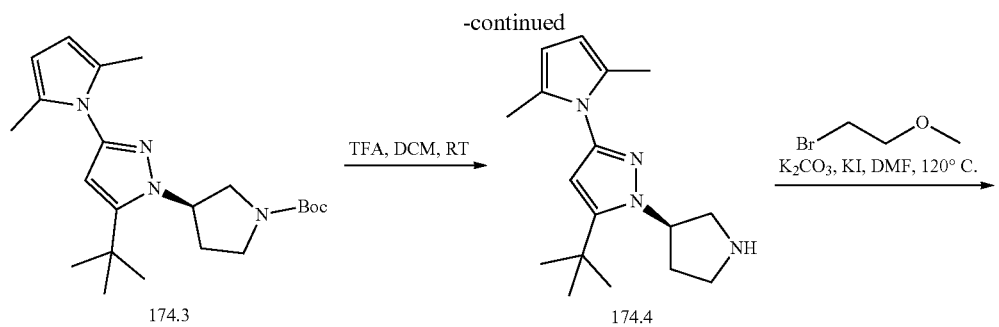
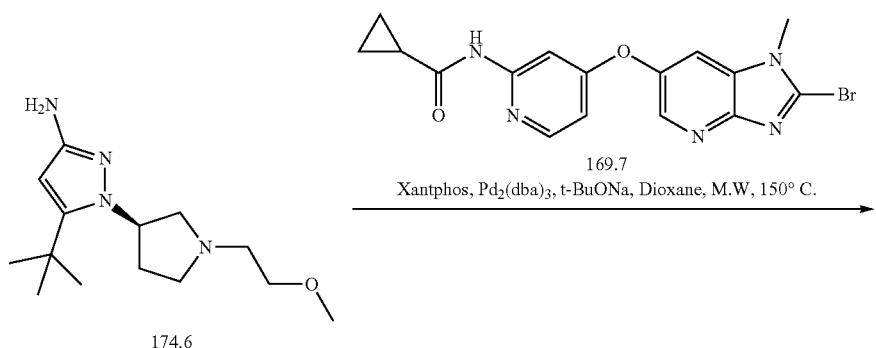
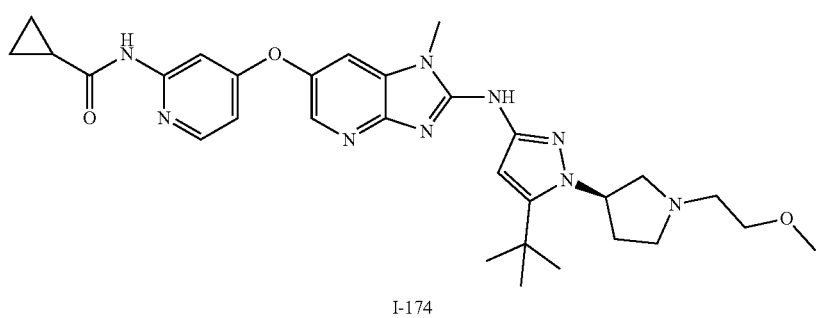
Synthesis of I-174. Compound I-174 was prepared following the procedures described in the synthesis of compound I-173. The product was purified by flash column chromatography on silica gel (CombiFlash®, 6-8% methanol in dichloromethane). MS (ES): m/z: 574.5 [M+H]$^+$, $^1$H NMR (DMSO-d$_6$, 400 MHz): 10.83 (s, 1H), 9.90 (s, 1H), 8.19-8.17 (d, J=5.6 Hz, 1H), 7.95-7.94 (d, J=2.0 Hz, 1H), 7.62 (bs, 2H), 6.69-6.68 (m, 1H), 6.56 (s, 1H), 5.05-5.03 (m, 1H), 3.66 (s, 3H), 3.45-3.42 (m, 2H), 3.24 (s, 3H), 3.10-3.06 (m, 1H), 2.82-2.75 (m, 2H), 2.71-2.55 (m, 3H), 2.27-2.25 (m, 1H), 2.20-2.17 (m, 1H), 1.96 (bs, 1H), 1.39 (s, 9H), 0.74 (bs, 4H).

Example 175: (R)—N-(4-((2-((5-(tert-butyl)-1-(2,2-dimethyltetrahydrofuran-3-yl)-1H-pyrazol-3-yl)amino)-1-methyl-1H-imidazo[4,5-b]pyridin-6-yl)oxy)pyridin-2-yl)acetamide and (S)—N-(4-((2-((5-(tert-butyl)-1-(2,2-dimethyltetrahydrofuran-3-yl)-1H-pyrazol-3-yl)amino)-1-methyl-1H-imidazo[4,5-b]pyridin-6-yl)oxy)pyridin-2-yl)acetamide

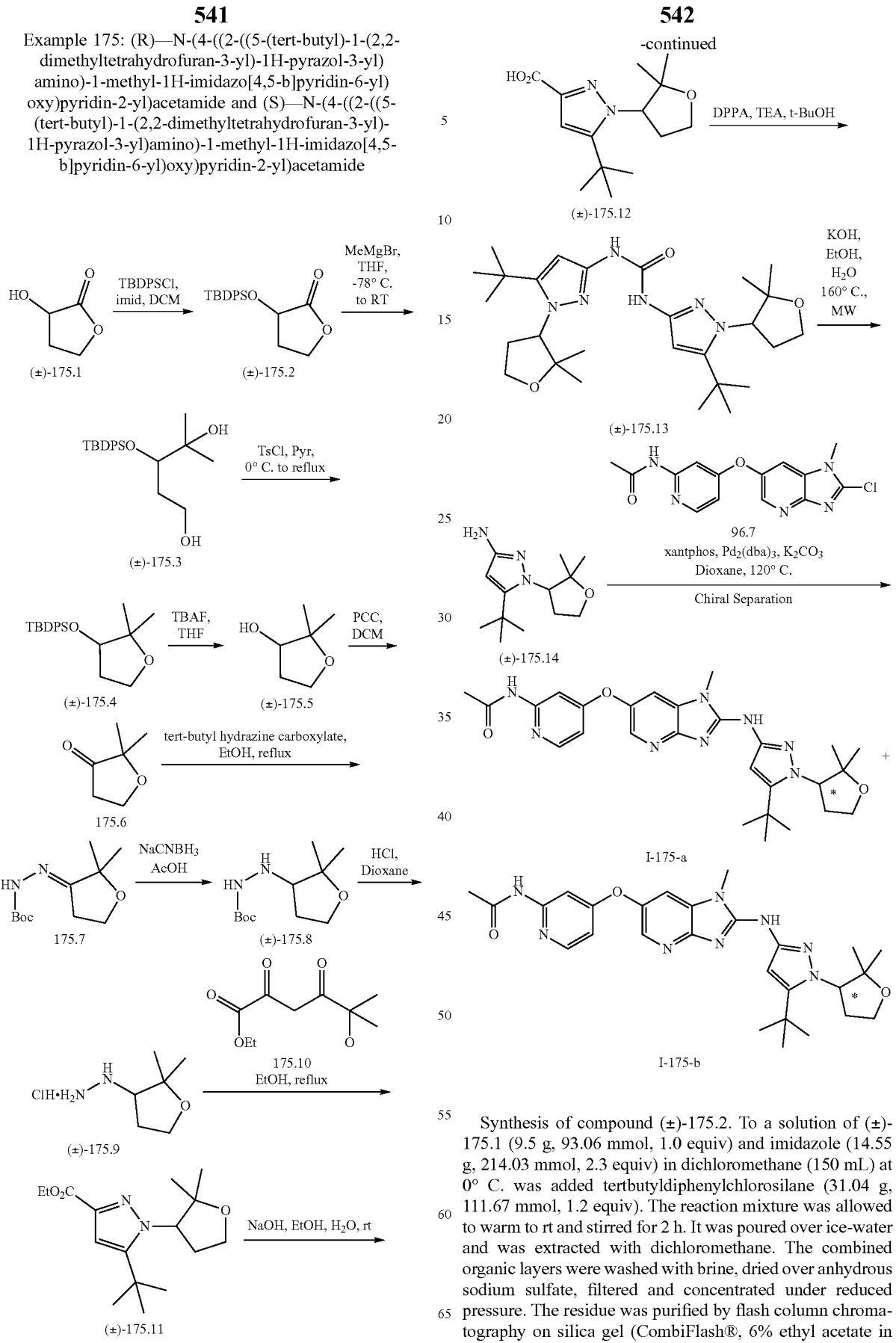

Synthesis of compound (±)-175.2. To a solution of (±)-175.1 (9.5 g, 93.06 mmol, 1.0 equiv) and imidazole (14.55 g, 214.03 mmol, 2.3 equiv) in dichloromethane (150 mL) at 0° C. was added tertbutyldiphenylchlorosilane (31.04 g, 111.67 mmol, 1.2 equiv). The reaction mixture was allowed to warm to rt and stirred for 2 h. It was poured over ice-water and was extracted with dichloromethane. The combined organic layers were washed with brine, dried over anhydrous sodium sulfate, filtered and concentrated under reduced pressure. The residue was purified by flash column chromatography on silica gel (CombiFlash®, 6% ethyl acetate in hexane) to afford (±)-175.2. $^1$H NMR (DMSO-d$_6$, 400

MHz): δ 7.74-7.65 (m, 4H), 7.51-7.39 (m, 6H), 4.61-4.56 (m, 1H), 4.28-4.24 (m, 1H), 4.10-4.04 (m, 1H), 2.29-2.14 (m, 2H), 1.03 (s, 9H).

Synthesis of compound (±)-175.3. To a solution of (±)-175.2 (28 g, 82.23 mmol, 1.0 equiv) in THF (560 mL) at −78° C. was added methyl magnesium bromide (3.0M in diethyl ether) (164 mL, 493.38 mmol, 6.0 equiv) and stirred for 15 min. It was allowed to warm to rt and stirred at for 1 h. The reaction mixture was transferred into saturated ammonium chloride and extracted with ethyl acetate. The combined organic layers were washed with brine, dried over anhydrous sodium sulfate, filtered and concentrated under reduced pressure. The residue was purified by flash column chromatography on silica gel (CombiFlash®, 50% ethyl acetate in hexane) to afford (±)-175.3. $^1$H NMR (DMSO-$d_6$, 400 MHz): δ 7.67-7.62 (m, 4H), 7.47-7.41 (m, 6H), 4.38 (s, 1H), 4.26-4.23 (m, 1H), 3.46-3.43 (m, 1H), 3.20-3.15 (m, 1H), 3.06-3.02 (m, 1H), 1.85-1.80 (m, 1H), 1.53-1.48 (m, 1H), 1.10-1.09 (d, 6H), 0.98 (s, 9H).

Synthesis of compound (±)-175.4. In a solution of (±)-175.3 (22 g, 59.05 mmol, 1.0 equiv) in pyridine (220 mL) was added p-toluenesulfonyl chloride (22.43 g, 118.1 mmol, 2.0 equiv) in portions at 0° C. It was stirred at rt for 2 h and heated to reflux for 2 h. The reaction mixture was cooled to rt and poured into water. It was extracted with dichloromethane. The combined organic layers were washed with brine, dried over anhydrous sodium sulfate, filtered and concentrated under reduced pressure. The residue was purified by flash column chromatography on silica gel (CombiFlash®, 20% ethyl acetate in hexane) to afford (±)-175.4. $^1$H NMR (DMSO-$d_6$, 400 MHz): δ 7.63-7.61 (m, 4H), 7.51-7.43 (m, 6H), 3.98-3.95 (m, 1H), 3.77-3.71 (m, 1H), 3.59-3.53 (m, 1H), 1.94-1.83 (m, 1H), 1.74-1.69 (m, 1H), 1.14 (s, 3H), 1.05 (s, 9H), 0.94 (s, 3H).

Synthesis of compound (±)-175.5. To a solution of (±)-175.4 (17 g, 47.95 mmol, 1.0 equiv) in THF (200 mL) was added tetra-N-butyl ammonium fluoride (1M in THF) (96 mL, 95.9 mmol, 2.0 equiv) at 0° C. and stir for 30 min. The reaction mixture was stirred for 6 h. It was poured over crushed ice, stirred, neutralized with saturated aqueous solution of sodium bicarbonate and extracted with ethyl acetate. The combined organic layers were washed with brine, dried over anhydrous sodium sulfate, filtered and concentrated under reduced pressure. The residue was purified by flash column chromatography on silica gel (CombiFlash®, 50% ethyl acetate in hexane) to afford (±)-175.5. $^1$H NMR (DMSO-$d_6$, 400 MHz): δ 4.83-4.82 (d, 1H), 3.77-3.72 (m, 2H), 3.66-3.61 (m, 1H), 2.18-2.10 (m, 1H), 1.76-1.69 (m, 1H), 1.06 (s, 6H).

Synthesis of compound 175.6. To a solution of (±)-175.5 (4.0 g, 34.44 mmol, 1.0 equiv) in dichloromethane (5 mL) was added pyridinium chlorochromate (22.21, 103.32 mmol, 3.0 equiv) at 0° C. The reaction mixture was stirred at room temperature for 12 h. After completion of reaction, diethyl ether was added and precipitated solids were removed by filtration through a pad of Celite®. The filtrate was concentrated under reduced pressure to afford 175.6, which was used in the next step without further purification.

Synthesis of compound 175.7. To a solution of 175.6 (3.9 g, 34.17 mmol, 1.0 equiv) in ethanol (40 mL) was added tert-butyl hydrazine carboxylate (4.96 g, 37.58 mmol, 1.1 equiv). The reaction mixture was heated to reflux for 12 h and cooled to rt. Solvent was removed under reduced pressure. The residue was purified by flash column chromatography on silica gel (CombiFlash®, 20% ethyl acetate in hexane) to afford 175.7. $^1$H NMR (DMSO-$d_6$, 400 MHz): δ 9.51 (s, 1H), 3.90-3.87 (m, 2H), 2.60-2.57 (m, 2H), 1.43 (s, 9H), 1.21 (s, 6H).

Synthesis of compound (±)-175.8. To a solution of 175.7 (3.0 g, 13.14 mmol, 1.0 equiv) in acetic acid (30 mL) was added sodium cyanoborohydride (0.814 g, 13.14 mmol, 1.0 equiv) in portions. The reaction mixture was stirred at room temperature for 3 h. It was poured over ice-water, stirred, neutralized with 1 N sodium hydroxide solution and extracted with dichloromethane. The combined organic layers were washed with brine, dried over anhydrous sodium sulfate, filtered and concentrated under reduced pressure to obtain (±)-175.8. $^1$H NMR (DMSO-$d_6$, 400 MHz): δ 8.27 (s, 1H), 4.45 (s, 1H), 3.69-3.61 (m, 2H), 3.12 (bs, 1H), 2.02-1.98 (m, 1H), 1.73-1.68 (m, 1H), 1.39 (s, 9H), 1.05 (s, 6H).

Synthesis of compound (±)-175.9. To a solution of (±)-175.8 (2.5 g, 10.86 mmol, 1.0 equiv) in 1,4-dioxane (25 mL) was added hydrogen chloride (4M in dioxane, 27 mL, 108.6 mmol, 10 equiv) at 0° C. The reaction mixture was stirred at room temperature for 12 h. It was concentrated under reduced pressure to obtain (±)-175.9. $^1$H NMR (DMSO-$d_6$, 400 MHz): δ 8.85 (bs, 1H), 3.80-3.76 (m, 1H), 3.71-3.65 (m, 2H), 3.57 (s, 2H), 3.21 (bs, 1H), 2.25-2.20 (m, 1H), 1.91 (bs, 1H), 1.19 (s, 3H), 1.08 (s, 3H).

Synthesis of compound (±)-175.11. To a solution of (±)-175.9 (1.8 g, 10.80 mmol, 1.0 equiv) in ethanol (20 mL) was added ethyl 5,5-dimethyl-2,4-dioxohexanoate (175.10, 2.16 g, 10.80 mmol, 1.0 equiv). The reaction mixture was heated to reflux for 12 h. It was concentrated under reduced pressure. The residue was purified by flash column chromatography on silica gel (CombiFlash®, 25% ethyl acetate in hexane) to afford (±)-175.11. MS (ES): m/z 295.4 [M+H]$^+$.

Synthesis of compound (±)-175.12. To a solution of (±)-175.11 (1.8 g, 6.11 mmol, 1.0 equiv) in ethanol:water (8:2, 20 mL) was added powdered sodium hydroxide (0.977 g, 24.44 mmol, 4.0 equiv) at 0° C. The reaction mixture was allowed to warm to rt and stirred for 12 h. It was poured over ice-water, stirred and adjusted pH to 2 with 1N HCl solution. The mixture was extracted with ethyl acetate. The combined organic layers were washed with brine, dried over anhydrous sodium sulfate, filtered and concentrated under reduced pressure which was triturated with diethyl ether to obtain (±)-175.12. MS (ES): m/z 267.3 [M+H]$^+$.

Synthesis of compound (±)-175.13. To a solution of (±)-175.12 (0.5 g, 1.88 mmol, 1.0 equiv) in tert-butanol (5 mL) was added triethylamine (0.52 mL, 3.76 mmol, 2.0 equiv) followed by diphenylphosphoryl azide (0.775 g, 2.82 mmol, 1.5 equiv). The reaction mixture was stirred at 90° C. for 12 h. It was poured over ice-water, stirred and extracted with ethyl acetate. The combined organic layers were washed with brine, dried over anhydrous sodium sulfate, filtered and concentrated under reduced pressure to afford (±)-175.13. MS (ES): m/z 501.6 [M+H]$^+$.

Synthesis of compound (±)-175.14. To a solution of (±)-175.13 (0.5 g, 0.998 mmol, 1.0 equiv) in ethanol:water (5:1, 10 mL) was added potassium hydroxide (20% in water 2.0 mL). The reaction mixture was stirred at 160° C. in a microwave reactor for 1 h. The reaction mixture was concentrated under reduced pressure. The residue was purified by flash column chromatography on silica gel (CombiFlash®, 1.8% methanol in dichloromethane) to afford (±)-175.14. MS (ES): m/z 238.4 [M+H]$^+$.

Synthesis of compound I-175-a and I-175-b. Compound (±)-I-175 was prepared from compound (±)-175.14 and 96.7 following the procedure described in the synthesis of compound I-108. The product was purified by flash column chromatography on C-18 silica gel (CombiFlash®, 86% acetonitrile in water). The enantiomers were separated by SFC (column: CHIRAL-cel OX-H (250 mm×21 mm, 5 μm); mobile phase: (A) liquid carbon dioxide, (B) 0.1% DEA in MeOH:acetonitrile (50:50); flow rate=80 mL/min) to afford first eluting fraction (I-175-a) and second eluting fraction (I-175-b). (*Absolute stereochemistry not determined.)

I-175-a: MS (ES): m/z: 519.4 [M+H]$^+$, $^1$H NMR (DMSO-$d_6$, 400 MHz): δ 10.54 (s, 1H), 9.82 (s, 1H), 8.50 (s, 1H), 7.95 (s, 1H), 7.65-7.63 (m, 2H), 6.65 (s, 1H), 6.60 (s, 1H), 4.79-4.77 (m, 1H), 4.23-4.21 (m, 1H), 3.84-3.82 (m, 1H), 3.67 (s, 3H), 2.33-2.28 (m, 2H), 2.03 (s, 3H), 1.40 (s, 9H), 1.27 (s, 3H), 0.94 (s, 3H).

I-175-b: MS (ES): m/z: 519.9 [M+H]$^+$, $^1$H NMR (DMSO-d$_6$, 400 MHz): δ 10.54 (s, 1H), 9.82 (s, 1H), 8.50 (s, 1H), 7.96 (s, 1H), 7.66-7.64 (m, 2H), 6.65 (s, 1H), 6.61 (s, 1H), 4.80-4.78 (m, 1H), 4.23-4.22 (m, 1H), 3.85-3.83 (m, 1H), 3.68 (s, 3H), 2.34-2.28 (m, 2H), 2.04 (s, 3H), 1.41 (s, 9H), 1.28 (s, 3H), 0.90 (s, 3H).

Example 176: (S)—N-(4-((2-((5-(tert-butyl)-1-(2-hydroxypropyl)-1H-pyrazol-3-yl)amino)-7-methoxy-1-methyl-1H-imidazo[4,5-b]pyridin-6-yl)oxy)pyridin-2-yl)cyclopropanecarboxamide and (R)—N-(4-((2-((5-(tert-butyl)-1-(2-hydroxypropyl)-1H-pyrazol-3-yl)amino)-7-methoxy-1-methyl-1H-imidazo[4,5-b]pyridin-6-yl)oxy)pyridin-2-yl)cyclopropane carboxamide

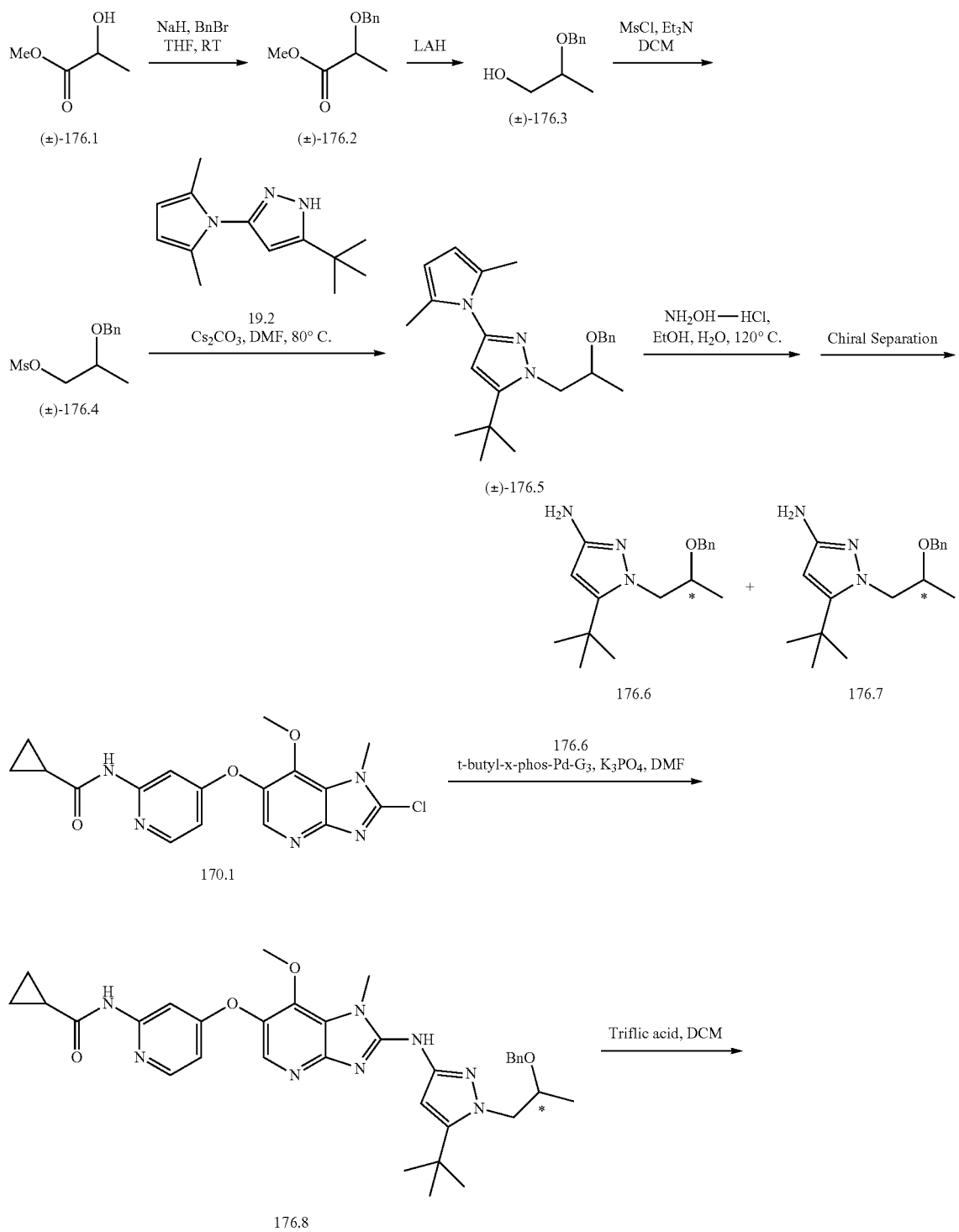

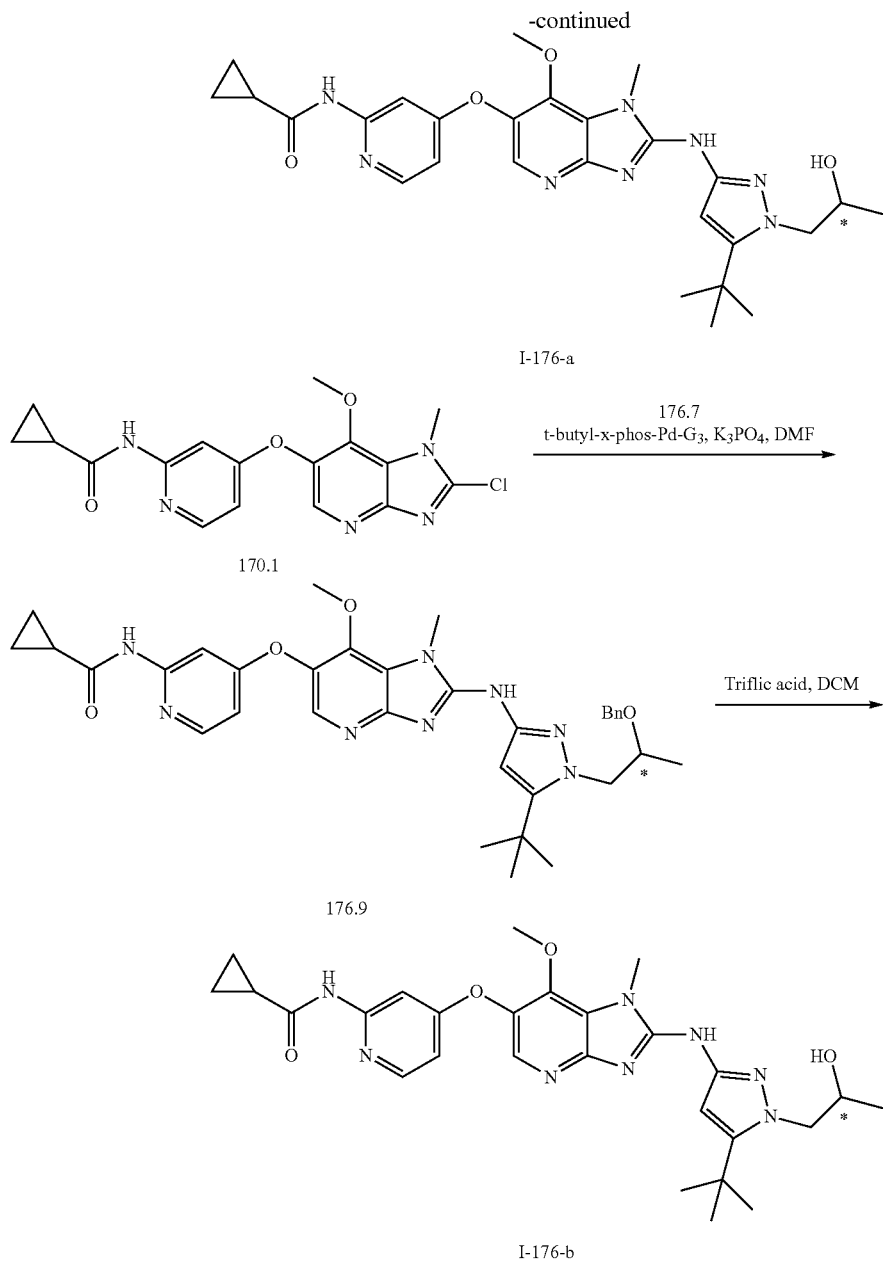

Synthesis of compound (±)-176.2. To a suspension of sodium hydride (2.88 g, 72.04 mmol, 1.5 equiv) in THF (25 mL) was added solution of methyl 2-hydroxypropanoate ((±)-176.1, 5.0 g, 48.03 mmol, 1.0 equiv) in THF (25 mL) at 0° C. and stirred for 1 h. To the reaction mixture was added benzyl bromide (6.85 mL, 57.63 mmol, 1.2 equiv) and stirred at room temperature for 2 h. It was poured over crashed ice, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 2% ethyl acetate in hexane) to afford (±)-176.2. $^1$H NMR (DMSO-$d_6$, 400 MHz): δ 7.39-7.30 (m, 5H), 4.59-4.56 (d, 1H), 4.46-4.43 (d, 1H), 4.16-4.11 (q, 1H), 3.69 (s, 3H), 1.34 (s, 3H).

Synthesis of compound (±)-176.3. To a solution of (±)-176.2 (3.0 g, 15.45 mmol, 1.0 equiv) in THF (30 mL), was added lithium aluminum hydride solution (1 M in THF) (39 mL, 38.62 mmol, 2.5 equiv) at 0° C. and stirred for 1 h. The reaction was quenched by saturated aqueous solution of sodium sulfate. Precipitated solids were removed by filtration through a pad of Celite® and washed with ethyl acetate. The organic layer was dried over anhydrous sodium sulfate, filtered and concentrated under reduced pressure to afford (±)-176.3. $^1$H NMR (DMSO-$d_6$, 400 MHz): δ 7.35-7.25 (m, 5H), 4.65-4.62 (t, 1H), 4.50 (s, 2H), 3.52-3.42 (m, 2H), 3.33 (bs, 1H), 1.10 (s, 3H).

Synthesis of compound (±)-176.4. To a solution of (±)-176.3 (2.5 g, 15.04 mmol, 1.0 equiv) and triethylamine (6.3 mL, 45.12 mmol, 3.0 equiv) in dichloromethane (25 mL) at 0° C. was added MSCl (2.3 mL, 30.08 mmol, 2.0 equiv). The reaction mixture was stirred at 0° C. for 30 min. It was poured over ice-water, stirred and extracted with dichloromethane. The combined organic layers were washed with saturated aqueous sodium bicarbonate followed by brine, dried over anhydrous sodium sulfate, filtered and concentrated under reduced pressure to afford (±)-176.4.

Synthesis of compound (±)-176.5. Compound (±)-176.5 was prepared from compound (±)-176.4 and 19.2 following the procedure described in the synthesis of compound 28.7. The product was purified by flash column chromatography on silica gel (CombiFlash®, 1-2% ethyl acetate in hexane). MS (ES): m/z 366.45 [M+H]$^+$.

Synthesis of compound 176.6 and 176.7. The racemate was prepared from (±)-176.5 following the procedure described in the synthesis of compound 120.6. The product was purified by flash column chromatography on silica gel (CombiFlash®, 25% ethyl acetate in hexane). The enantiomers were separated by HPLC (column: CHIRALPAK IG (250 mm×21 mm, 5 μm); mobile phase: (A) 0.1% DEA in n-hexane, (B) 0.1% DEA in 2-propanol; flow rate=20 mL/min) to afford first eluting fraction (176.6) and second eluting fraction (176.7). MS (ES): m/z 288.4 [M+H]$^+$. (*Absolute stereochemistry not determined.)

Synthesis of compound 176.8. Compound 176.8 was prepared from compound 176.6 and 170.1 following the procedure described in the synthesis of compound I-169-a. The product was purified by flash column chromatography on silica gel (CombiFlash®, 2.5% methanol in dichloromethane). MS (ES): m/z: 625.5 [M+H]$^+$. (*Absolute stereochemistry not determined.)

Synthesis of I-176-a. To a solution of 176.8 (0.065 g, 0.104 mmol, 1.0 equiv) in dichloromethane (2 mL) was added triflic acid (0.1 mL) at 0° C. and stirred for 5 min. The reaction mixture was transferred into ice-saturated aqueous sodium bicarbonate solution and extracted with dichloromethane. The combined organic layers were washed with brine, dried over anhydrous sodium sulfate, filtered and concentrated under reduced pressure. The residue was purified by preparative HPLC to afford I-176-a. MS (ES): m/z: 535.5 [M+H]$^+$, $^1$H NMR (DMSO-d$_6$, 400 MHz): δ 10.85 (s, 1H), 9.77 (s, 1H), 8.19-8.18 (d, J=5.6 Hz, 1H), 7.92 (s, 1H), 7.65-7.64 (d, J=2.4 Hz, 1H), 6.69-6.68 (m, 1H), 6.55 (s, 1H), 4.98-4.97 (d, 1H), 4.25-4.22 (m, 1H), 4.06-4.04 (m, 1H), 3.96-3.92 (m, 1H), 3.89 (s, 3H), 3.81 (s, 3H), 1.96 (bs, 1H), 1.39 (s, 9H), 1.14-1.13 (m, 3H), 0.76-0.74 (d, 4H). (*Absolute stereochemistry not determined.)

Synthesis of compound 176.9. Compound 176.9 was prepared from compound 176.7 and 170.1 following the procedure described in the synthesis of compound I-169-a. The product was purified by flash column chromatography on silica gel (CombiFlash®, 2.5% methanol in dichloromethane). MS (ES): m/z: 625.5 [M+H]$^+$. (*Absolute stereochemistry not determined.)

Synthesis of I-176-b. Compound I-176-b was prepared from compound 176.9 following the procedure described in the synthesis of compound I-176-a. The product was purified by preparative HPLC. MS (ES): m/z: 535.5 [M+H]$^+$, $^1$H NMR (DMSO-d$_6$, 400 MHz): δ 10.85 (s, 1H), 9.76 (s, 1H), 8.20-8.19 (d, J=5.6 Hz, 1H), 7.92 (s, 1H), 7.67-7.66 (d, J=2.4 Hz, 1H), 6.70-6.68 (m, 1H), 6.56 (s, 1H), 4.98-4.97 (d, 1H), 4.25-4.22 (m, 1H), 4.10-4.05 (m, 1H), 3.98-3.93 (m, 1H), 3.91 (s, 3H), 3.82 (s, 3H), 1.99-1.96 (m, 1H), 1.40 (s, 9H), 1.16-1.14 (m, 3H), 0.77-0.76 (d, 4H). (*Absolute stereochemistry not determined.)

Example 177: (R)—N-(4-((7-methoxy-1-methyl-2-((5-(perfluoroethyl)-1-(tetrahydrofuran-3-yl)-1H-pyrazol-3-yl)amino)-1H-imidazo[4,5-b]pyridin-6-yl)oxy)pyridin-2-yl)cyclopropanecarboxamide

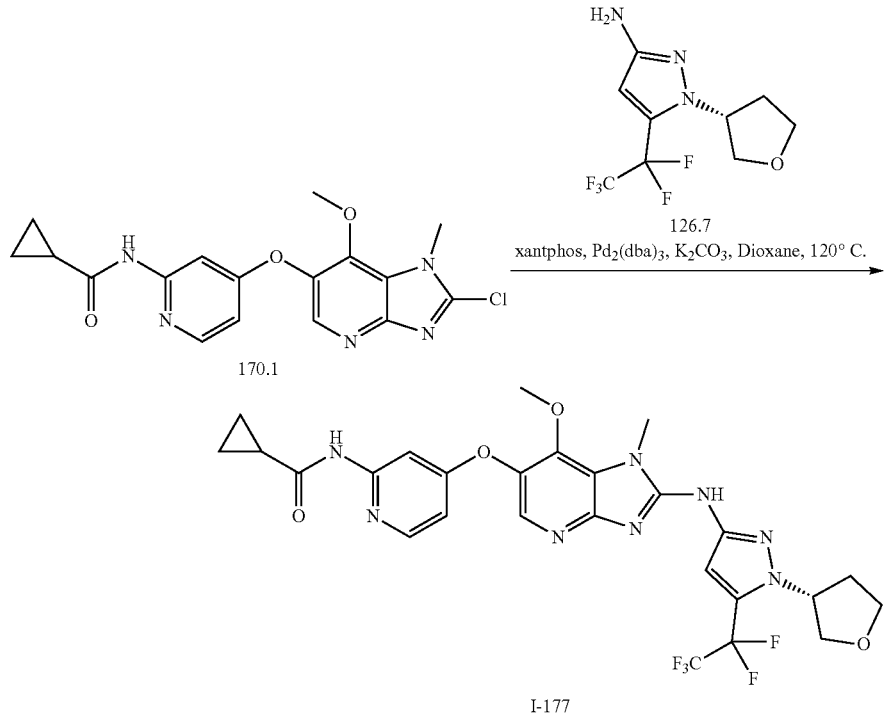

Synthesis of I-177. Compound I-177 was prepared from compound 126.7 and 170.1 following the procedure described in the synthesis of compound I-108. The product was purified by flash column chromatography on silica gel (CombiFlash®, 3% methanol in dichloromethane). MS (ES): m/z: 609.46 [M+H]⁺, ¹H NMR (DMSO-d₆, 400 MHz): δ 10.87 (s, 1H), 10.43 (s, 1H), 8.21-8.19 (d, J=5.6 Hz, 1H), 7.98 (s, 1H), 7.66 (s, 1H), 7.37 (s, 1H), 6.71-6.69 (m, 1H), 5.16 (bs, 1H), 4.12-4.06 (m, 2H), 3.92 (s, 4H), 3.86 (s, 3H), 2.68 (bs, 1H), 2.34 (bs, 1H), 1.97 (bs, 1H), 1.24 (bs, 1H), 0.75 (bs, 4H).

Example 178: (S)—N-(4-((7-methoxy-1-methyl-2-((5-(perfluoroethyl)-1-(tetrahydrofuran-3-yl)-1H-pyrazol-3-yl)amino)-1H-imidazo[4,5-b]pyridin-6-yl)oxy)pyridin-2-yl)cyclopropanecarboxamide

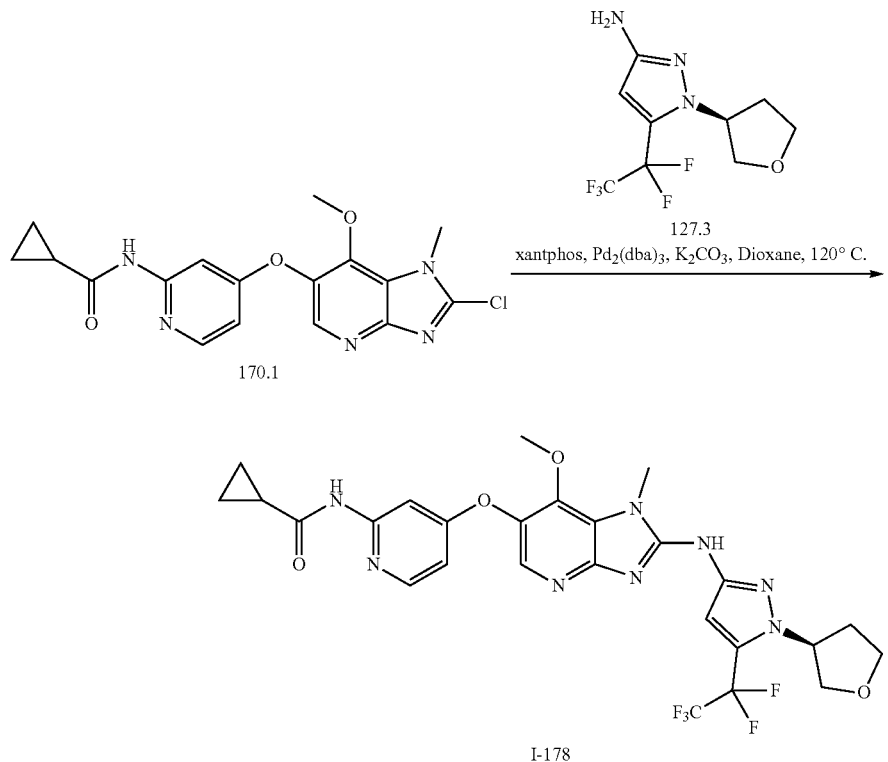

Synthesis of I-178. Compound I-178 was prepared from compound 127.3 and 170.1 following the procedure described in the synthesis of compound I-108. The product was purified by flash column chromatography on silica gel (CombiFlash®, 3% methanol in dichloromethane). MS (ES): m/z: 609.48 [M+H]⁺, ¹H NMR (DMSO-d₆, 400 MHz): δ 10.87 (s, 1H), 10.44 (s, 1H), 8.21-8.20 (d, J=5.6 Hz, 1H), 7.98 (s, 1H), 7.67-7.66 (d, J=2.0 Hz, 1H), 7.37 (s, 1H), 6.71-6.69 (m, 1H), 5.17 (bs, 1H), 4.14-4.06 (m, 2H), 3.93 (s, 4H), 3.83 (s, 3H), 2.68 (bs, 1H), 2.34 (bs, 1H), 2.00-1.94 (m, 1H), 1.25 (bs, 1H), 0.77-0.76 (m, 4H).

Example 179: (S)—N-(4-((2-((5-(tert-butyl)-1-(1-(2-fluoroethyl)pyrrolidin-3-yl)-1H-pyrazol-3-yl)amino)-1-methyl-1H-imidazo[4,5-b]pyridin-6-yl)oxy)pyridin-2-yl)cyclopropanecarboxamide

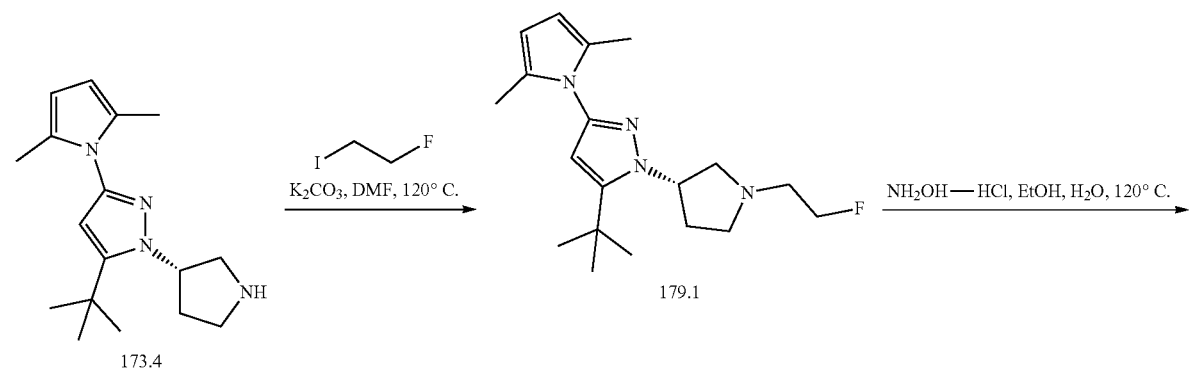

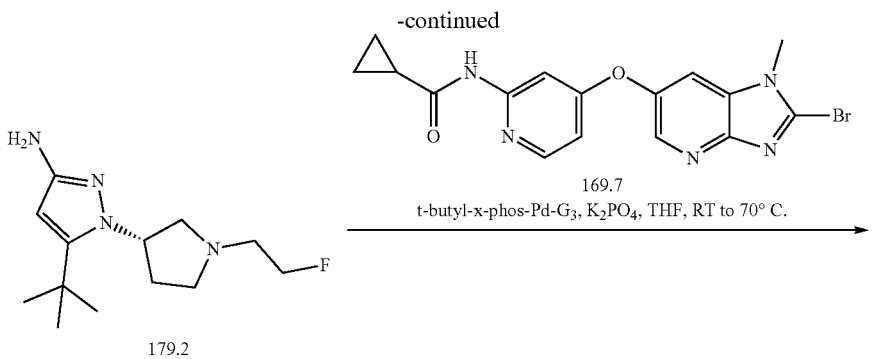

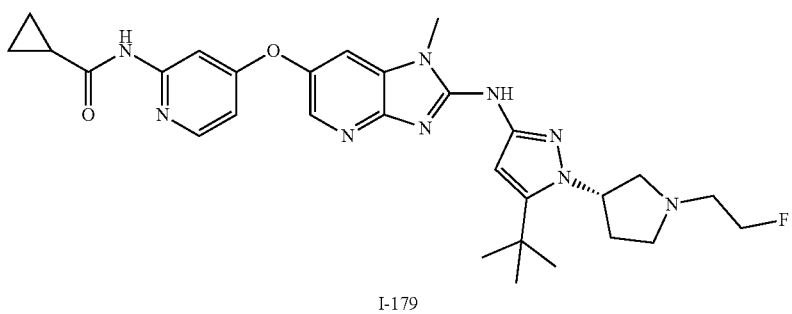

Synthesis of compound 179.1. To a solution of 173.4 (2.0 g, 6.98 mmol, 1.0 equiv) and 1-fluoro-2-iodoethane (1.82 g, 10.47 mmol, 1.5 equiv) in DMF (20 mL) was added potassium carbonate (2.89 g, 20.94 mmol, 3.0 equiv) and reaction mixture was stirred at 120° C. for 5 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 4-6% ethyl acetate in hexane) to afford 179.1. MS (ES): m/z 333.4 [M+H]$^+$.

Synthesis of compound 179.2. Compound 179.2 was prepared from 179.1 following the procedure described in the synthesis of compound 120.6. The product was purified by flash column chromatography on silica gel (CombiFlash®, 4-5% methanol in dichloromethane). MS (ES): m/z 255.3 [M+H]$^+$.

Synthesis of I-179. Compound I-179 was prepared from compound 179.2 and 169.7 following the procedure described in the synthesis of compound I-169-a. The product was purified by flash column chromatography on silica gel (CombiFlash®, 3-4% methanol in dichloromethane). MS (ES): m/z: 562.5 [M+H]$^+$, $^1$H NMR (DMSO-d$_6$, 400 MHz): 10.84 (s, 1H), 9.91 (s, 1H), 8.20-8.18 (d, J=6.0 Hz, 1H), 7.96 (bs, 1H), 7.64-7.63 (m, 2H), 6.71-6.69 (m, 1H), 6.58 (s, 1H), 5.11-5.07 (m, 1H), 4.63-4.60 (m, 1H), 4.51-4.48 (m, 1H), 3.67 (s, 3H), 3.15-3.11 (t, 2H), 2.87-2.82 (m, 2H), 2.78-2.75 (m, 2H), 2.34 (bs, 1H), 2.29-2.21 (m, 1H), 1.98-1.95 (m, 1H), 1.40 (s, 9H), 0.77-0.75 (m, 4H).

Example 180: (R)—N-(4-((2-((5-(tert-butyl)-1-(1-(2-fluoroethyl)pyrrolidin-3-yl)-1H-pyrazol-3-yl)amino)-1-methyl-1H-imidazo[4,5-b]pyridin-6-yl)oxy)pyridin-2-yl)cyclopropanecarboxamide

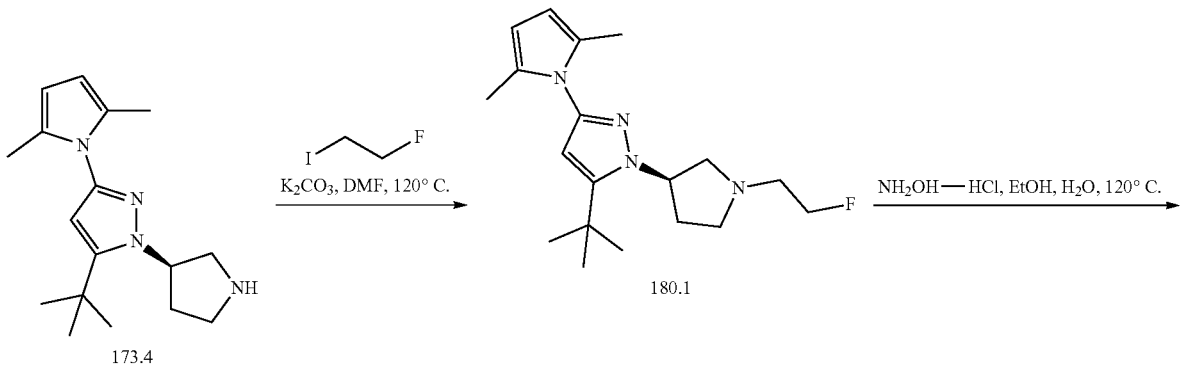

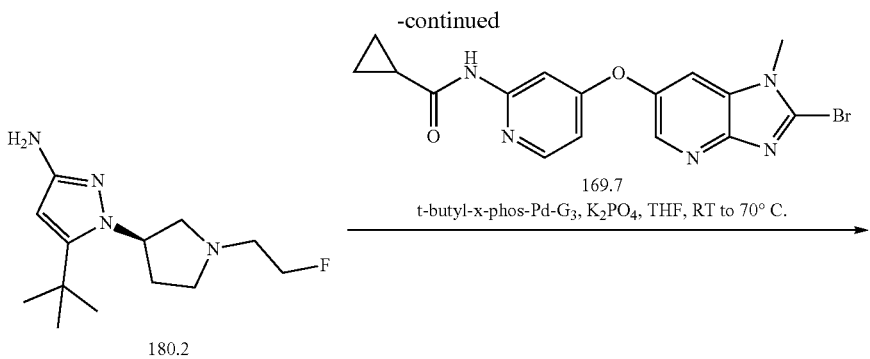

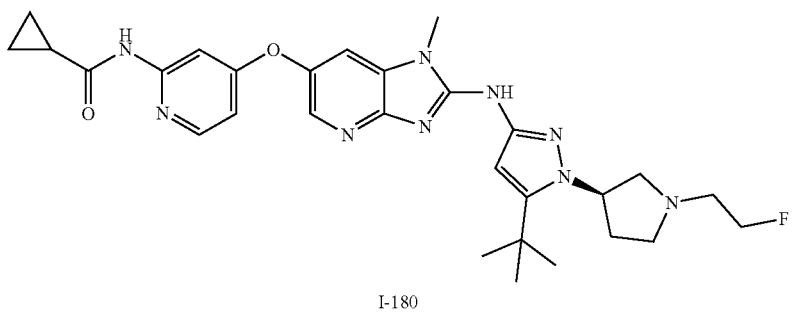

I-180

Synthesis of I-180. Compound I-180 was prepared following the procedures described in the synthesis of compound I-179. The product was purified by flash column chromatography on silica gel (CombiFlash®, 3-4% methanol in dichloromethane). MS (ES): m/z: 562.5 [M+H]$^+$, $^1$H NMR (DMSO-d$_6$, 400 MHz): 10.83 (s, 1H), 9.90 (s, 1H), 8.20-8.18 (d, J=6.0 Hz, 1H), 7.96 (bs, 1H), 7.64 (bs, 2H), 6.71-6.69 (m, 1H), 6.58 (s, 1H), 5.11-5.07 (m, 1H), 4.63-4.60 (m, 1H), 4.51-4.48 (m, 1H), 3.67 (s, 3H), 3.15-3.11 (t, 2H), 2.86-2.83 (m, 2H), 2.78-2.75 (m, 2H), 2.34 (bs, 1H), 2.21-2.20 (m, 1H), 1.98-1.97 (m, 1H), 1.40 (s, 9H), 0.76-0.75 (m, 4H).

Example 181: (S)—N-(4-((2-((5-(tert-butyl)-1-(1-(2-methoxyethyl)pyrrolidin-3-yl)-1H-pyrazol-3-yl)amino)-7-chloro-1-methyl-1H-imidazo[4,5-b]pyridin-6-yl)oxy)pyridin-2-yl)cyclopropanecarboxamide

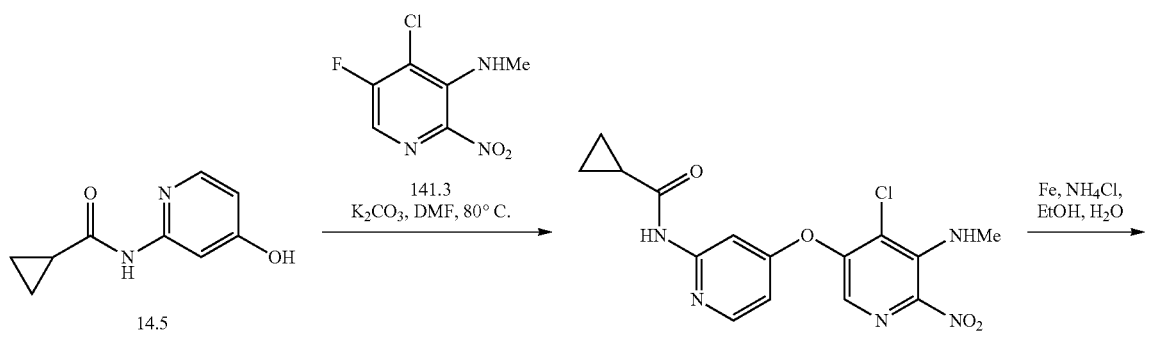

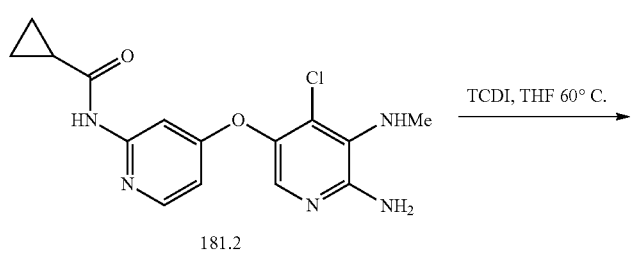

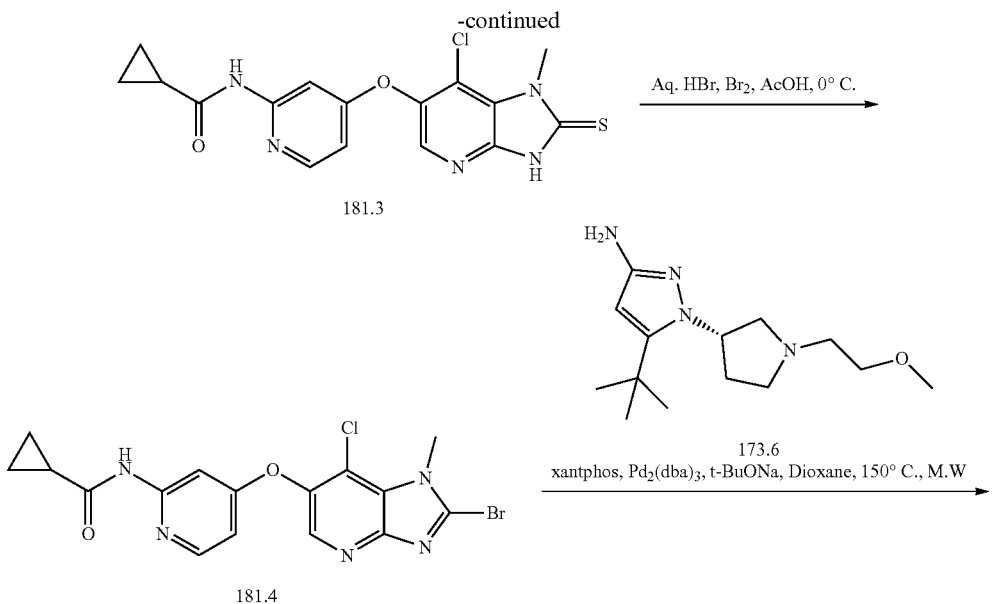

Synthesis of compound 181.1. A mixture of 14.5 (0.433 g, 2.43 mmol, 1.0 equiv), 141.3 (0.500 g, 2.43 mmol, 1.0 equiv) and potassium carbonate (0.838 g, 6.07 mmol, 2.5 equiv) in DMF (5 mL) was stirred at 80° C. for 2 h. The reaction mixture was cooled to room temperature, transferred into ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.7% methanol in dichloromethane) to afford 181.1. MS (ES): m/z 364.3 [M+H]$^+$.

Synthesis of compound 181.2. To a solution of 181.1 (0.590 g, 1.62 mmol, 1.0 equiv) in ethanol:water (2:1, 10 mL) was added iron powder (0.445 g, 8.1 mmol, 5 equiv) followed by ammonium chloride (0.445 g, 8.1 mmol, 5 equiv). The reaction mixture was stirred at 80° C. for 1 h. It was poured over ice-water, filtered and extracted with ethyl acetate. The combined organic layers were washed with brine, dried over anhydrous sodium sulfate, filtered and concentrated under reduced pressure. The residue was purified by flash column chromatography on silica gel (CombiFlash®, 3.3% methanol in dichloromethane) to afford 181.2. MS (ES): m/z 334.7 [M+H]$^+$.

Synthesis of compound 181.3. Compound 181.3 was prepared from compound 181.2 following the procedure described in the synthesis of compound 148.8. The product was triturated with hexane to afford 181.3. MS (ES): m/z: 376.7 [M+H]$^+$.

Synthesis of compound 181.4. Compound 181.4 was prepared from compound 181.3 following the procedure described in the synthesis of compound 148.9. The residue was purified by flash column chromatography on silica gel (CombiFlash®, 3.0% methanol in dichloromethane). MS (ES): m/z 423.7 [M+H]$^+$.

Synthesis of I-184. Compound I-184 was prepared from compound 181.4 and 173.6 following the procedure described in the synthesis of compound I-108. The product was purified by flash column chromatography on silica gel (CombiFlash®, 6-8% methanol in dichloromethane). MS (ES): m/z: 608.4 [M+H]$^+$, $^1$H NMR (DMSO-d$_6$, 400 MHz): δ 10.86 (s, 1H), 9.85 (s, 1H), 8.21-8.19 (d, J=5.6 Hz, 1H), 8.06 (s, 1H), 7.63-7.62 (d, J=1.6 Hz, 1H), 6.70-6.69 (d, J=3.6 Hz, 1H), 6.52 (s, 1H), 5.08-5.04 (m, 1H), 3.93 (s, 3H), 3.47-3.44 (m, 2H), 3.26 (s, 3H), 3.11-3.07 (m, 1H), 2.81-2.77 (m, 2H), 2.74-2.67 (m, 2H), 2.27-2.11 (m, 2H), 1.99-1.96 (m, 2H), 1.40 (s, 9H), 0.78-0.76 (m, 4H).

Example 182: (R)—N-(4-((2-((5-(tert-butyl)-1-(1-(2-methoxyethyl)pyrrolidin-3-yl)-1H-pyrazol-3-yl)amino)-7-chloro-1-methyl-1H-imidazo[4,5-b]pyridin-6-yl)oxy)pyridin-2-yl)cyclopropanecarboxamide

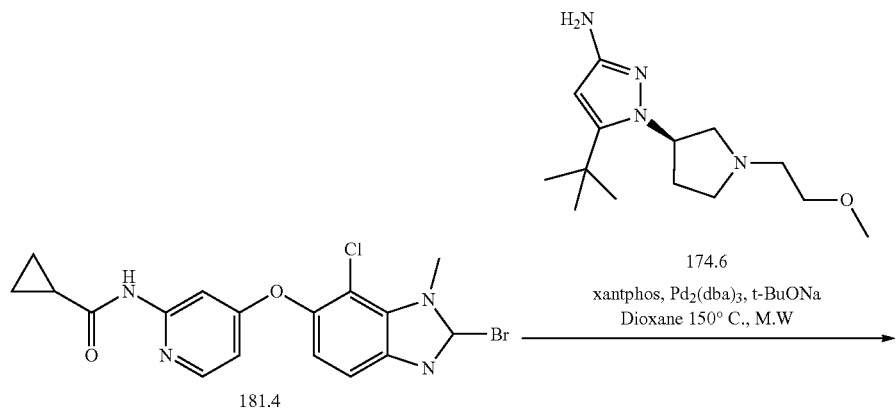

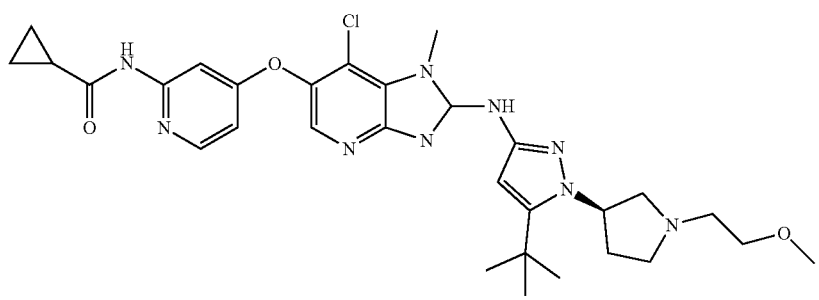

Synthesis of I-182. Compound I-182 was prepared from compound 181.4 and 174.6 following the procedure described in the synthesis of compound I-108. The product was purified by flash column chromatography on silica gel (CombiFlash®, 6-8% methanol in dichloromethane). MS (ES): m/z: 608.7 [M+H]$^+$, $^1$H NMR (DMSO-d$_6$, 400 MHz): δ 10.85 (s, 1H), 9.83 (s, 1H), 8.21-8.19 (d, J=5.6 Hz, 1H), 8.05 (s, 1H), 7.63-7.62 (d, J=2.4 Hz, 1H), 6.70-6.68 (m, 1H), 6.52 (s, 1H), 5.08-5.04 (m, 1H), 3.93 (s, 3H), 3.47-3.44 (m, 2H), 3.26 (s, 3H), 3.11-3.07 (m, 1H), 2.81-2.77 (m, 2H), 2.74-2.67 (m, 2H), 2.27-2.11 (m, 2H), 1.99-1.96 (m, 2H), 1.40 (s, 9H), 0.78-0.76 (m, 4H).

Example 183: (S)—N-(4-((2-((5-(tert-butyl)-1-(1-(2-fluoroethyl)pyrrolidin-3-yl)-1H-pyrazol-3-yl)amino)-7-methoxy-1-methyl-1H-imidazo[4,5-b]pyridin-6-yl)oxy)pyridin-2-yl)cyclopropanecarboxamide

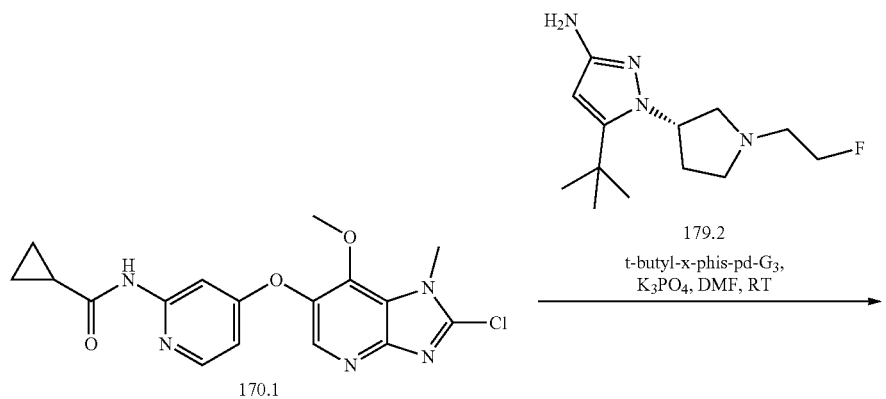

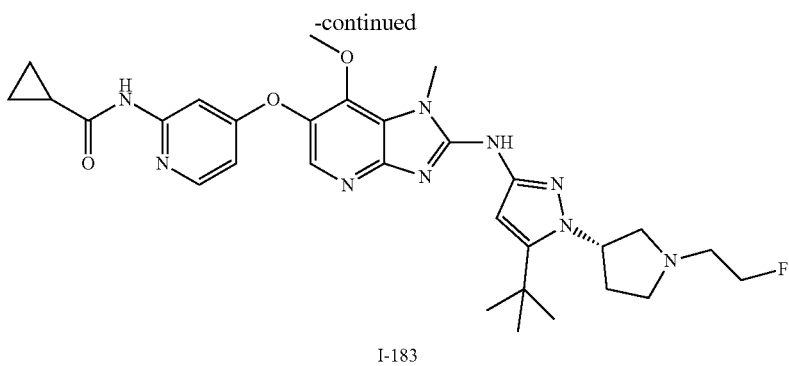

I-183

Synthesis of I-183. A mixture of 170.1 (0.070 g, 0.187 mmol, 1.0 equiv), 179.2 (0.052 g, 0.205 mmol, 1.1 equiv), tripotassium phosphate (0.119 g, 0.561 mmol, 3.0 equiv) and DMF (3 mL) was degassed by bubbling argon through for 10 min. Under argon atmosphere [(2-di-tert-butylphosphino-2', 4',6'-triisopropyl-1,1'-biphenyl)-2-(2'-amino-1,1'-biphenyl)] palladium(II) methanesulfonate (0.044 g, 0.0561 mmol, 0.3 equiv) was added, again degassed for 5 min. The reaction mixture was stirred at room temperature for 3 h. It was transferred into water and extracted with ethyl acetate. The combined organic layers were washed with brine, dried over anhydrous sodium sulfate, filtered and concentrated under reduced pressure. The residue was purified by preparative HPLC. MS (ES): m/z: 592.5 [M+H]$^+$, $^1$H NMR (DMSO-d$_6$, 400 MHz): 10.86 (s, 1H), 9.81 (s, 1H), 8.19-8.18 (d, J=5.6 Hz, 1H), 7.91 (s, 1H), 7.65 (bs, 1H), 6.70-6.68 (m, 1H), 6.52 (s, 1H), 5.09-5.06 (m, 1H), 4.61-4.59 (m, 1H), 4.49-4.47 (m, 1H), 3.89 (s, 3H), 3.82 (s, 3H), 3.17-3.09 (m, 1H), 2.85-2.73 (m, 5H), 2.28-2.18 (m, 2H), 1.98-1.95 (m, 1H), 1.39 (s, 9H), 0.76-0.75 (m, 4H).

Example 184: (R)—N-(4-((2-((5-(tert-butyl)-1-(1-(2-fluoroethyl)pyrrolidin-3-yl)-1H-pyrazol-3-yl)amino)-7-methoxy-1-methyl-1H-imidazo[4,5-b]pyridin-6-yl)oxy)pyridin-2-yl)cyclopropanecarboxamide

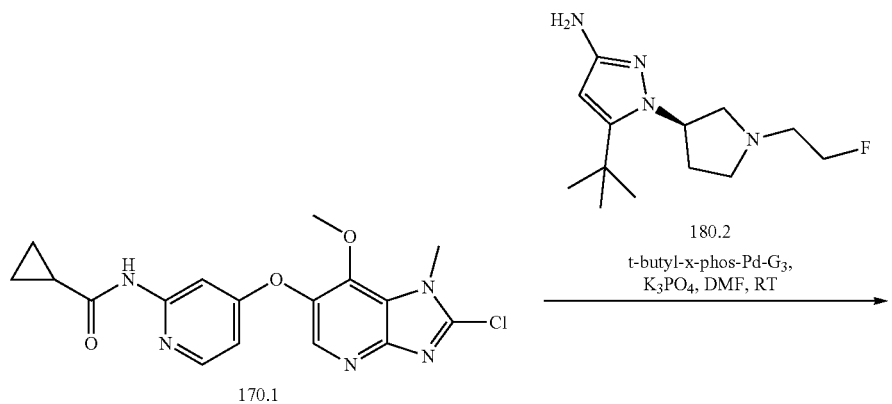

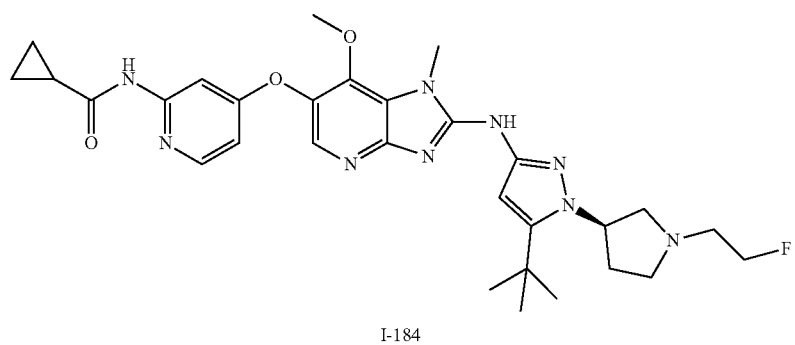

I-184

Synthesis of I-184. Compound I-184 was prepared from compound 170.1 and 180.2 following the procedure described in the synthesis of compound I-183. The product was purified by preparative HPLC. MS (ES): m/z: 592.7 [M+H]$^+$, $^1$H NMR (DMSO-d$_6$, 400 MHz): 10.86 (s, 1H), 9.82 (s, 1H), 8.19-8.18 (d, J=5.6 Hz, 1H), 7.91 (s, 1H), 7.65 (bs, 1H), 6.70-6.68 (m, 1H), 6.52 (s, 1H), 5.09-5.06 (m, 1H), 4.61-4.59 (m, 1H), 4.49-4.47 (m, 1H), 3.89 (s, 3H), 3.82 (s, 3H), 3.17-3.09 (m, 1H), 2.85-2.67 (m, 5H), 2.28-2.18 (m, 2H), 1.98-1.95 (m, 1H), 1.39 (s, 9H), 0.76-0.75 (m, 4H).

Example 185: (S)—N-(4-((2-((5-(tert-butyl)-1-(1-(2-fluoroethyl)pyrrolidin-3-yl)-1H-pyrazol-3-yl)amino)-7-chloro-1-methyl-1H-imidazo[4,5-b]pyridin-6-yl)oxy)pyridin-2-yl)acetamide

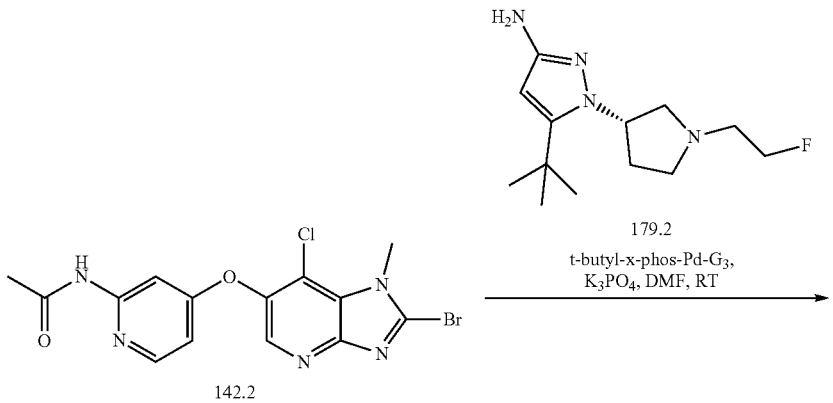

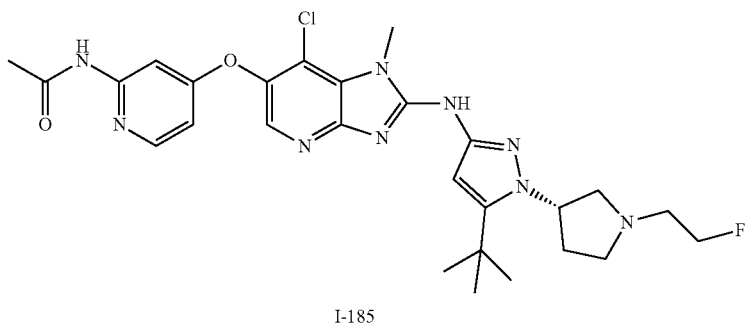

Synthesis of I-185. Compound I-185 was prepared from compound 142.2 and 179.2 following the procedure described in the synthesis of compound I-183. The product was purified by preparative HPLC. MS (ES): m/z: 570.4 [M+H]$^+$, LCMS purity: 100%, HPLC purity: 95.06%, Chiral HPLC purity: 97.51%, $^1$H NMR (DMSO-d$_6$, 400 MHz): 10.57 (s, 1H), 10.04 (s, 1H), 8.18-8.16 (d, J=5.6 Hz, 1H), 8.07 (s, 1H), 7.63 (bs, 1H), 6.51-6.63 (m, 1H), 6.52 (s, 1H), 5.10-5.06 (m, 1H), 4.61-4.58 (m, 1H), 4.49-4.46 (m, 1H), 3.92 (s, 3H), 3.17-3.09 (m, 2H), 2.85-2.73 (m, 5H), 2.21-2.19 (m, 1H), 2.03 (s, 3H), 1.38 (s, 9H).

Example 186: (R)—N-(4-((2-((5-(tert-butyl)-1-(1-(2-fluoroethyl)pyrrolidin-3-yl)-1H-pyrazol-3-yl)amino)-7-chloro-1-methyl-1H-imidazo[4,5-b]pyridin-6-yl)oxy)pyridin-2-yl)acetamide

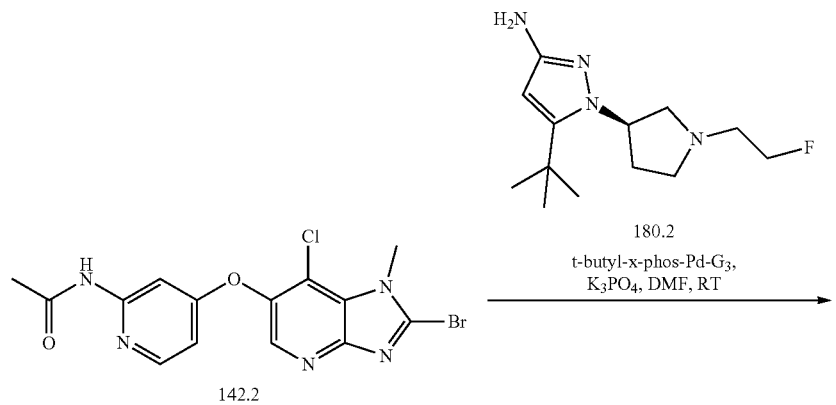

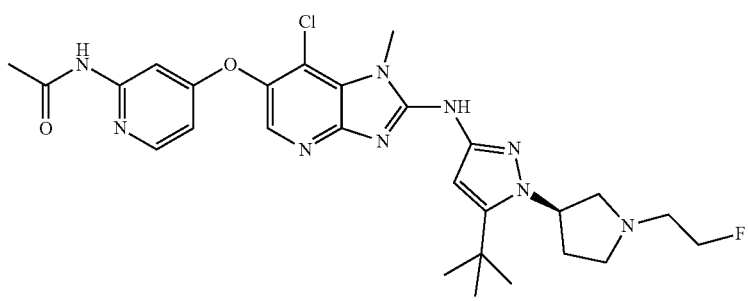

I-186

Synthesis of I-186. Compound I-186 was prepared from compound 142.2 and 180.2 following the procedure described in the synthesis of compound I-183. The product was purified by preparative HPLC. MS (ES): m/z: 570.5 [M+H]$^+$, LCMS purity: 100%, HPLC purity: 97%, Chiral HPLC purity: 98.71%, $^1$H NMR (DMSO-d$_6$, 400 MHz): 10.54 (s, 1H), 10.02 (s, 1H), 8.20-8.19 (d, J=5.6 Hz, 1H), 8.09 (s, 1H), 7.65 (bs, 1H), 6.66-6.64 (m, 1H), 6.54 (s, 1H), 5.12-5.10 (m, 1H), 4.63-4.60 (m, 1H), 4.51-4.48 (m, 1H), 3.94 (s, 3H), 3.16-3.11 (m, 2H), 2.86-2.68 (m, 5H), 2.22-2.20 (m, 1H), 2.05 (s, 3H), 1.38 (s, 9H).

Example 187: (S)—N-(4-((2-((5-(tert-butyl)-4-(tetrahydrofuran-3-yl)thiazol-2-yl)amino)-1-methyl-1H-imidazo[4,5-b]pyridin-6-yl)oxy)pyridin-2-yl)acetamide and (R)—N-(4-((2-((5-(tert-butyl)-4-(tetrahydrofuran-3-yl)thiazol-2-yl)amino)-1-methyl-1H-imidazo[4,5-b]pyridin-6-yl)oxy)pyridin-2-yl)acetamide

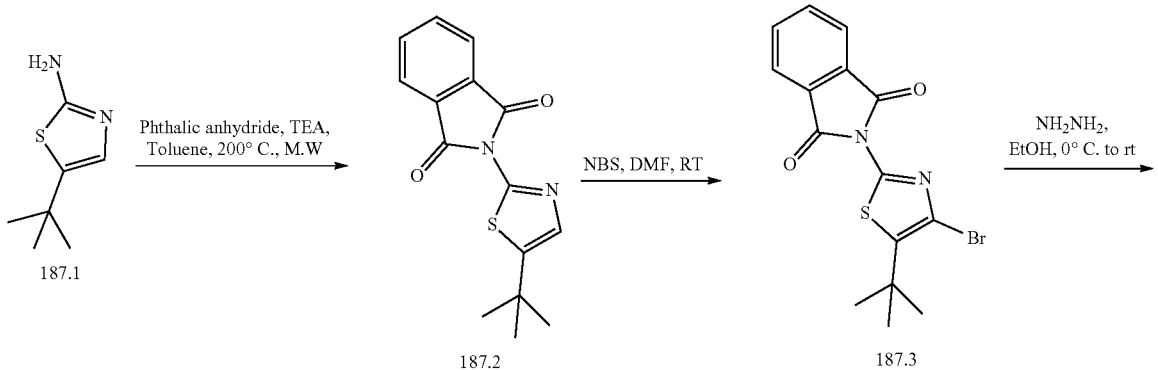

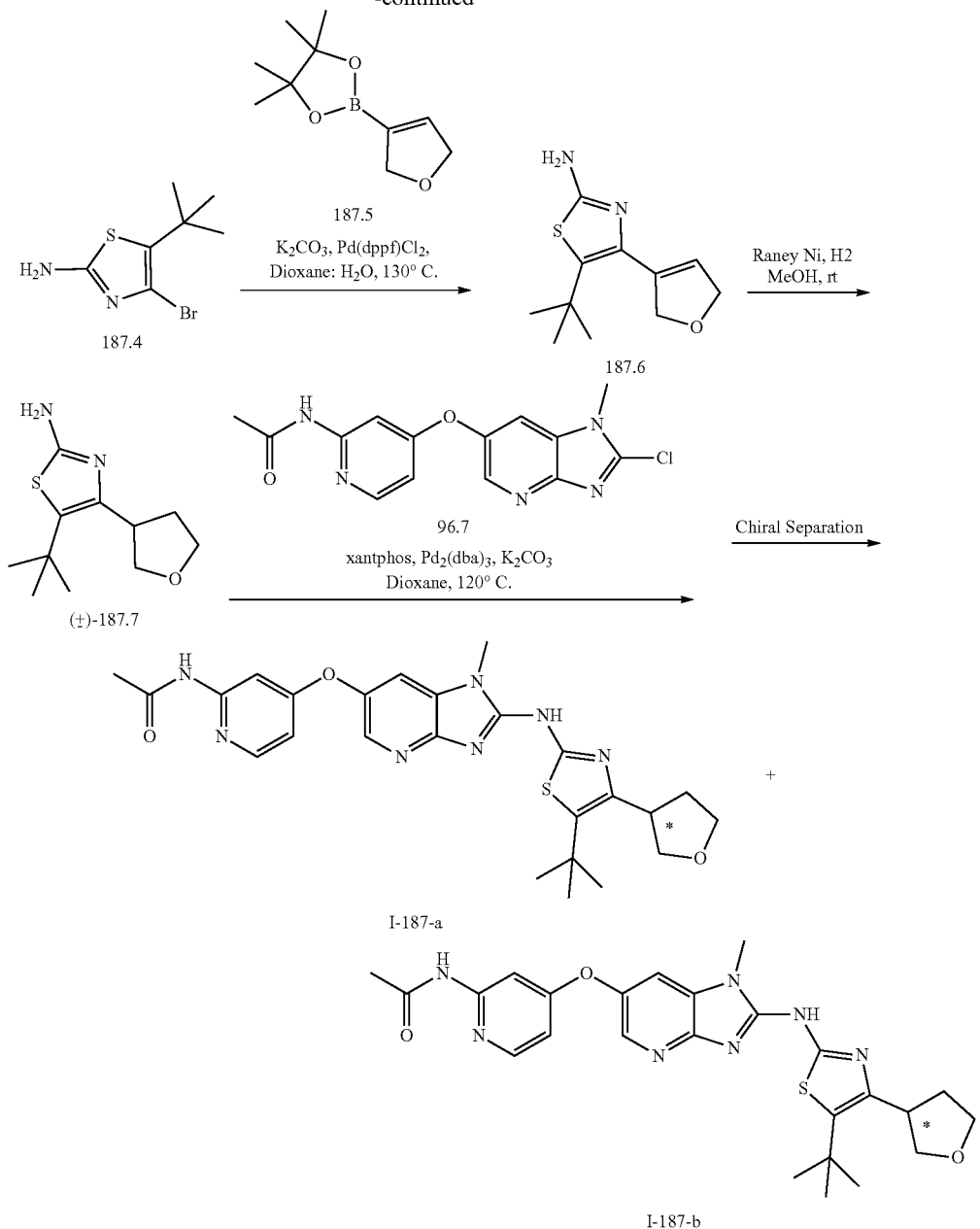

Synthesis of compound 187.2. A solution of 187.1 (2.0 g, 12.80 mmol, 1.0 equiv), phthalic anhydride (3.79 g, 25.60 mmol, 2.0 equiv) and triethylamine (5.4 mL, 38.4 mmol, 3.0 equiv) in toluene (20 mL) was stirred at 200° C. in a microwave reaction for 2 h. The reaction mixture was transferred into water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 11% ethyl acetate in hexane) to afford 187.2. MS (ES): m/z 287.3 [M+H]+.

Synthesis of compound 187.3. To a solution of 187.2 (2.1 g, 7.33 mmol, 1.0 equiv) in DMF (20 mL) was added N-bromosuccinimide (6.5 g, 36.6 mmol, 5.0 equiv). The reaction mixture was stirred at room temperature for 3 h. The reaction mixture was transferred into water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 15% ethyl acetate in hexane) to afford 187.3. MS (ES): m/z 366.2 [M+H]+.

Synthesis of compound 187.4. To a solution of 187.3 (1.9 g, 5.2 mmol, 1.0 equiv) in ethanol (20 mL) was added hydrazine (0.34 mL, 10.4 mmol, 2.0 equiv) at 0° C. The reaction mixture was stirred at room temperature for 12 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (Combi-Flash®, 70% ethyl acetate in hexane) to afford 187.4. MS (ES): m/z 236.1 [M+H]$^+$.

Synthesis of compound 187.6. To a solution of 187.4 (1.0 g, 4.25 mmol, 1.0 equiv) in 1,4-dioxane (10 mL) and water (1 mL) was added 187.5 (2.5 g, 12.76 mmol, 3.0 equiv) and potassium carbonate (1.76 g, 12.76 mmol, 3.0 equiv). The reaction mixture was degassed by bubbling argon through for 10 min. Under argon atmosphere [1,1'-bis(diphenylphosphino)ferrocene]dichloropalladium(II)-dichloromethane complex (0.173 g, 0.212 mmol, 0.05 equiv) was added, again degassed for 5 min. The reaction mixture was stirred at 130° C. for 3 h. The reaction mixture was cooled to room temperature, filtered through a pad of Celite®. The filtrate was transferred into water, extracted with ethyl acetate. The combined organic layers were washed with brine, dried over anhydrous sodium sulfate, filtered and concentrated under reduced pressure. The residue was purified by flash column chromatography on silica gel (CombiFlash®, 1% methanol in dichloromethane) to afford 187.6. MS (ES): m/z 225.3 [M+H]$^+$.

Synthesis of compound (±)-187.7. A mixture of Raney nickel (0.2 g) and compound 187.6 (0.250 g, 1.11 mmol, 1.0 equiv) in methanol (10 mL) was stirred under hydrogen atmosphere (1 atm) for 12 h. The reaction mixture was filtered through a pad of Celite® and washed with methanol. The filtrate was concentrated under reduced pressure to afford (±)-187.7. MS (ES): m/z 227.3 [M+H]$^+$.

Synthesis of compound I-187-a and I-187-b. Compound (±)-I-187 was prepared from compound (±)-187.7 and 96.7 following the procedure described in the synthesis of compound I-108. The product was purified by flash column chromatography on silica gel (CombiFlash®, 2.5% methanol in dichloromethane). The enantiomers were separated by HPLC (column: CHIRALPAK IC (250 mm×21 mm, 5 μm); mobile phase: (A) 0.1% DEA in n-hexane, (B) 0.1% DEA in propane-2-ol:acetonitrile (70:30); flow rate=20 mL/min) to afford first eluting fraction (I-187-a) and second eluting fraction (I-187-b). (*Absolute stereochemistry not determined.)

I-187-a. MS (ES): m/z: 508.4 [M+H]$^+$, $^1$H NMR (DMSO-d$_6$, 400 MHz): δ 12.18 (s, 1H), 10.53 (s, 1H), 8.18-8.16 (d, J=5.6 Hz, 1H), 8.00 (bs, 1H), 7.67 (bs, 2H), 6.67-6.65 (m, 1H), 3.99-3.95 (m, 2H), 3.88-3.82 (m, 1H), 3.74-3.51 (m, 5H), 2.18-2.15 (m, 2H), 2.03 (s, 3H), 1.42 (s, 9H).

I-187-b. MS (ES): m/z: 508.4 [M+H]$^+$, $^1$H NMR (DMSO-d$_6$, 400 MHz): δ 12.19 (s, 1H), 10.53 (s, 1H), 8.18-8.16 (d, J=5.6 Hz, 1H), 8.00 (bs, 1H), 7.67 (bs, 2H), 6.67-6.65 (m, 1H), 3.99-3.95 (m, 2H), 3.87-3.81 (m, 1H), 3.74-3.51 (m, 5H), 2.18-2.15 (m, 2H), 2.03 (s, 3H), 1.42 (s, 9H).

Example 188: N-(4-((2-((5-(tert-butyl)-1-(2,2-difluoroethyl)-1H-pyrazol-3-yl)amino)-7-methoxy-1-methyl-1H-imidazo[4,5-b]pyridin-6-yl)oxy)pyridin-2-yl)acetamide

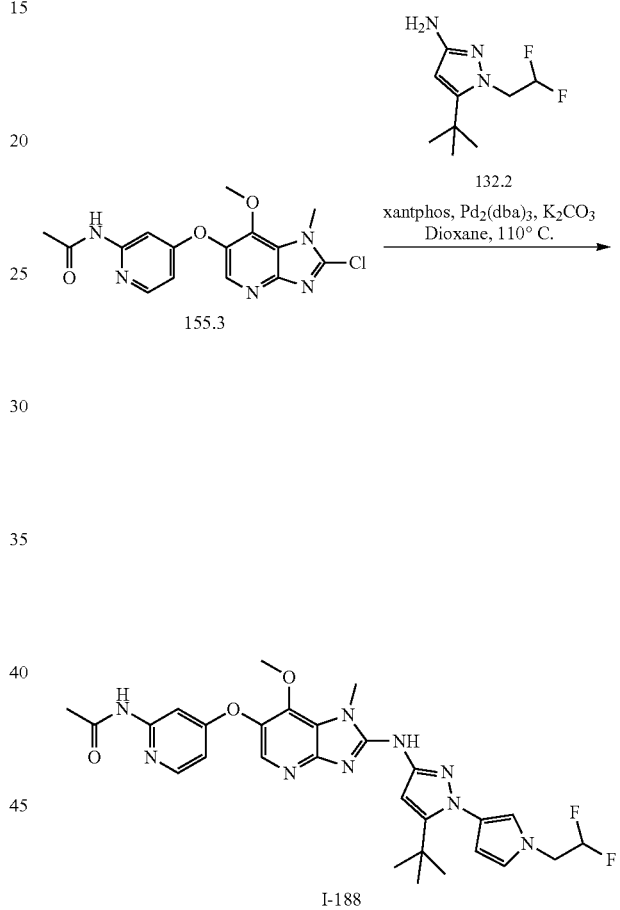

Synthesis of I-188. Compound I-188 was prepared from compound 155.3 and 132.2 following the procedure described in the synthesis of compound I-108. The product was purified by flash column chromatography on silica gel (CombiFlash®, 4.5% methanol in dichloromethane). MS (ES): m/z: 515.4 [M+H]$^+$, LCMS purity: 100%, HPLC purity: 98.79%, $^1$H NMR (DMSO-d$_6$, 400 MHz): δ 10.55 (s, 1H), 9.90 (s, 1H), 8.51 (bs, 2H), 8.18-8.16 (d, J=5.6 Hz, 1H), 7.94 (s, 1H), 6.66-6.64 (m, 1H), 6.58-6.30 (m, 1H), 4.60-4.59 (m, 2H), 3.90 (s, 3H), 3.82 (s, 3H), 2.03 (s, 3H), 1.39 (s, 9H).

Example 189: (R)—N-(4-((2-((5-(tert-butyl)-1-(4-oxaspiro[2.4]heptan-7-yl)-1H-pyrazol-3-yl)amino)-1-methyl-1H-imidazo[4,5-b]pyridin-6-yl)oxy)pyridin-2-yl)acetamide and (S)—N-(4-((2-((5-(tert-butyl)-1-(4-oxaspiro[2.4]heptan-7-yl)-1H-pyrazol-3-yl)amino)-1-methyl-1H-imidazo[4,5-b]pyridin-6-yl)oxy)pyridin-2-yl)acetamide
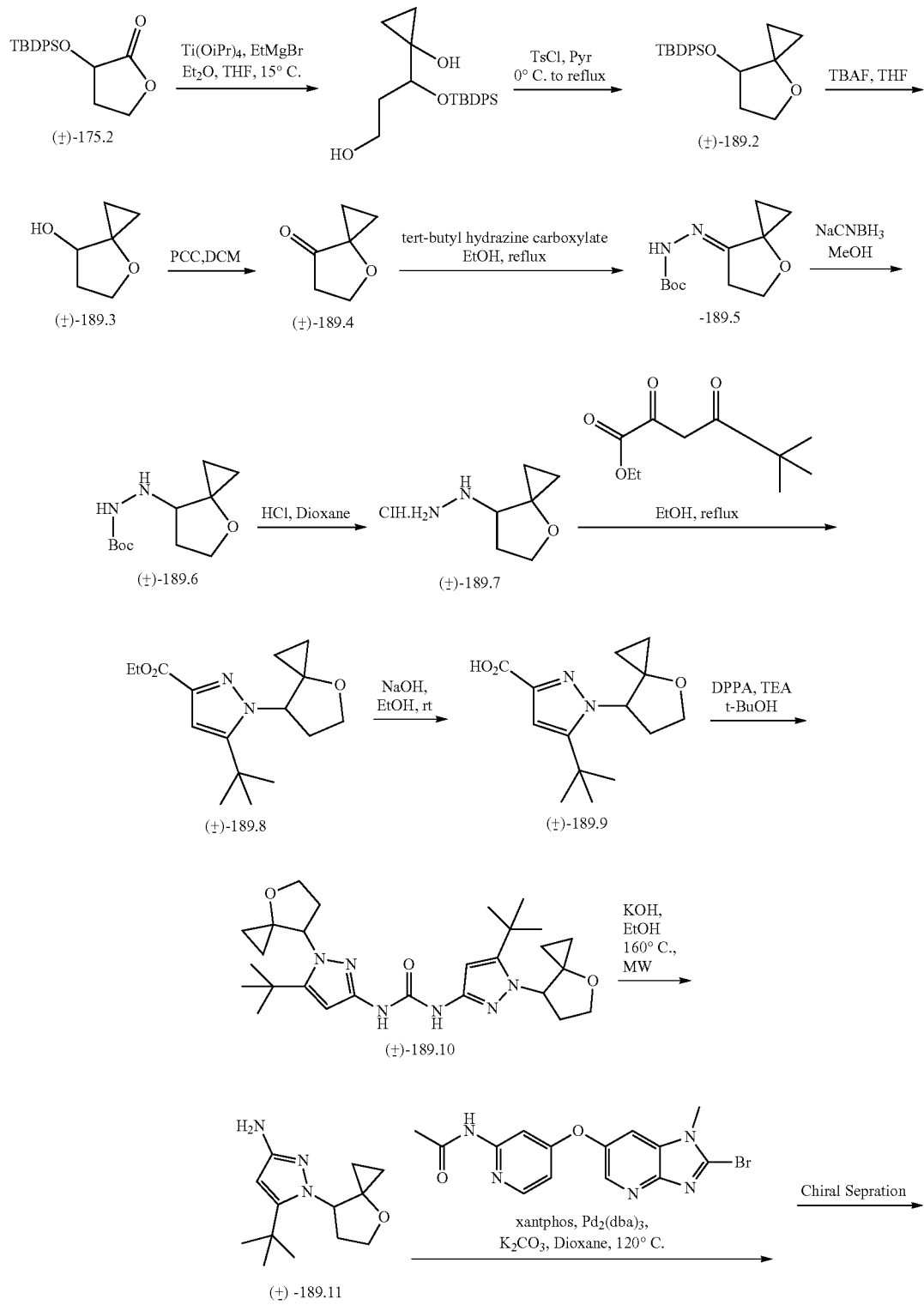

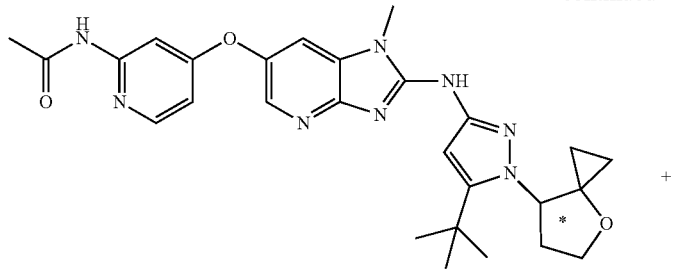

I-189-a

+

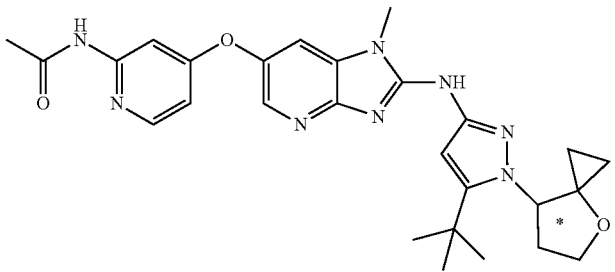

I-189-b

Synthesis of compound (±)-189.1. To a solution of (±)-175.2 (40 g, 117.48 mmol, 1.0 equiv) in THF (120 mL) and diethyl ether (120 mL) at 15° C. was added titanium isopropoxide (16.69 g, 58.74 mmol, 0.5 equiv) followed ethyl magnesium bromide (3.0M in diethyl ether) (117.5 mL, 352.4 mmol, 3.0 equiv). The reaction mixture was stirred for 1 h. It was transferred into saturated ammonium chloride and extracted with ethyl acetate. The combined organic layers were washed with brine, dried over anhydrous sodium sulfate, filtered and concentrated under reduced pressure. The residue was purified by flash column chromatography on silica gel (CombiFlash®, 40% ethyl acetate in hexane) to afford (±)-189.1. $^1$H NMR (CDCl$_3$, 400 MHz): δ 7.73-7.67 (m, 4H), 7.47-7.39 (m, 6H), 3.93-3.88 (m, 1H), 3.67-3.61 (m, 1H), 3.51 (s, 2H), 3.35-3.32 (m, 1H), 1.93-1.87 (m, 2H), 1.11 (s, 9H), 0.82-0.76 (m, 1H), 0.61-0.56 (m, 1H), 0.40-0.34 (m, 1H), 0.18-0.17 (m, 1H).

Synthesis of compound (±)-189.2. Compound (±)-189.2 was prepared from compound (±)-189.1 following the procedure described in the synthesis of compound (±)-175.4. The product was purified by flash column chromatography on silica gel (CombiFlash®, 5% ethyl acetate in hexane) to afford (±)-189.2. $^1$H NMR (CDCl$_3$, 400 MHz): δ 7.67-7.64 (m, 4H), 7.47-7.38 (m, 6H), 4.19-4.16 (m, 1H), 4.07-4.01 (m, 1H), 3.82-3.77 (m, 1H), 2.15-2.08 (m, 1H), 2.06-1.95 (m, 1H), 1.08 (s, 9H), 0.79-0.66 (m, 3H), 0.31-0.22 (m, 1H).

Synthesis of compound (±)-189.3. Compound (±)-189.3 was prepared from compound (±)-189.2 following the procedure described in the synthesis of compound (±)-175.5. The product was purified by flash column chromatography on silica gel (CombiFlash®, 50% ethyl acetate in hexane) to afford (±)-189.3. $^1$H NMR (CDCl$_3$, 400 MHz): δ 4.12-3.99 (m, 1H), 3.98-3.90 (m, 2H), 2.45-2.36 (m, 1H), 2.12-2.05 (m, 1H), 1.09-0.94 (m, 1H), 0.88-0.80 (m, 2H), 0.65-0.59 (m, 1H).

Synthesis of compound 189.4. Compound 189.4 was prepared from compound (±)-189.3 following the procedure described in the synthesis of compound 175.6. The crude product was used in the next step without purification.

Synthesis of compound 189.5. Compound 189.5 was prepared from compound 189.4 following the procedure described in the synthesis of compound 175.7. The product was purified by flash column chromatography on silica gel (CombiFlash®, 17% ethyl acetate in hexane) to afford 189.5. $^1$H NMR (DMSO-d$_6$, 400 MHz): δ 9.60 (s, 1H), 3.98-3.95 (m, 2H), 2.73-2.70 (m, 2H), 1.43 (s, 9H), 1.02-0.99 (m, 2H), 0.84-0.81 (m, 2H).

Synthesis of compound (±)-189.6. Compound (±)-189.6 was prepared from compound 189.5 following the procedure described in the synthesis of compound (±)-175.8. The crude product was used in the next step without purification. $^1$H NMR (CDCl$_3$, 400 MHz): δ 6.59 (s, 1H), 5.33 (s, 1H), 4.18-4.07 (m, 2H), 3.93-3.90 (m, 1H), 3.44 (bs, 1H), 2.34-2.31 (m, 1H), 1.50 (s, 9H), 1.09-1.06 (m, 2H), 0.75-0.73 (m, 1H), 0.56 (bs, 1H).

Synthesis of compound (±)-189.7. Compound (±)-189.7 was prepared from compound (±)-189.6 following the procedure described in the synthesis of compound (±)-175.9. The crude product was used in the next step without purification. $^1$H NMR (DMSO-d$_6$, 400 MHz): δ 9.12 (bs, 1H), 3.92-3.90 (m, 2H), 3.75-3.70 (m, 2H), 2.29 (bs, 4H), 0.66-0.54 (m, 4H).

Synthesis of compound (±)-189.8. Compound (±)-189.8 was prepared from compound (±)-189.7 following the procedure described in the synthesis of compound (±)-175.11. The product was purified by flash column chromatography on silica gel (CombiFlash®, 20% ethyl acetate in hexane) to afford (±)-189.8. MS(ES): m/z 293.4 [M+H]$^+$.

Synthesis of compound (±)-189.9. Compound (±)-189.9 was prepared from compound (±)-189.8 following the procedure described in the synthesis of compound (±)-175.12. The crude product was triturated with diethyl ether to obtain (±)-189.9. MS(ES): m/z 265.3 [M+H]$^+$.

Synthesis of compound (±)-189.10. Compound (±)-189.10 was prepared from compound (±)-189.9 following the procedure described in the synthesis of compound (±)-175.13. The crude product was used in the next step without purification. MS(ES): m/z 497.6 [M+H]$^+$.

Synthesis of compound (±)-189.11. Compound (±)-189.11 was prepared from compound (±)-189.10 following the procedure described in the synthesis of compound (±)-175.14. The product was purified by flash column chromatography on silica gel (CombiFlash®, 1.5% methanol in dichloromethane) to afford (±)-189.11. MS(ES): m/z 236.4 [M+H]$^+$.

Synthesis of compound I-189-a and I-189-b. Compound (±)-I-189 was prepared from compound (±)-189.11 and 148.9 following the procedure described in the synthesis of compound I-108. The product was purified by flash column chromatography on silica gel (CombiFlash®, 1.8% methanol in dichloromethane). The enantiomers were separated by HPLC (column: CHIRALPAK IB-N (250 mm×21 mm, 5 µm); mobile phase: (A) 0.3% DEA in n-hexane, (B) 0.3% DEA in propane-2-ol; flow rate=20 mL/min) to afford first eluting fraction (I-189-a) and second eluting fraction (I-189-b). (*Absolute stereochemistry not determined.)

I-189-a: MS(ES): m/z: 517.5 [M+H]$^+$, $^1$H NMR (DMSO-d$_6$, 400 MHz): δ 10.53 (s, 1H), 9.96 (s, 1H), 8.18-8.16 (d, J=5.6 Hz, 1H), 7.96 (s, 1H), 7.66-7.63 (m, 2H), 6.66-6.64 (m, 1H), 6.58 (s, 1H), 5.03-5.00 (m, 1H), 4.24-4.19 (m, 1H), 3.85-3.79 (m, 1H), 3.68 (s, 3H), 2.67-2.61 (m, 1H), 2.37-2.33 (m, 1H), 2.03 (s, 3H), 1.34 (s, 9H), 0.91-0.85 (m, 2H), 0.80-0.75 (m, 2H).

I-189-b: MS(ES): m/z: 517.5 [M+H]$^+$, $^1$H NMR (DMSO-d$_6$, 400 MHz): δ 10.54 (s, 1H), 9.97 (s, 1H), 8.18-8.16 (d, J=5.6 Hz, 1H), 7.96 (s, 1H), 7.66-7.63 (m, 2H), 6.66-6.64 (m, 1H), 6.58 (s, 1H), 5.03-5.00 (m, 1H), 4.24-4.19 (m, 1H), 3.85-3.79 (m, 1H), 3.68 (s, 3H), 2.67-2.63 (m, 1H), 2.39-2.33 (m, 1H), 2.03 (s, 3H), 1.34 (s, 9H), 0.91-0.86 (m, 2H), 0.80-0.75 (m, 2H).

Example 190: (R)—N-(4-((2-((5-(tert-butyl)-1-(4-oxaspiro[2.4]heptan-7-yl)-1H-pyrazol-3-yl)amino)-7-methoxy-1-methyl-1H-imidazo[4,5-b]pyridin-6-yl)oxy)pyridin-2-yl)acetamide and (S)—N-(4-((2-((5-(tert-butyl)-1-(4-oxaspiro[2.4]heptan-7-yl)-1H-pyrazol-3-yl)amino)-7-methoxy-1-methyl-1H-imidazo[4,5-b]pyridin-6-yl)oxy)pyridin-2-yl)acetamide

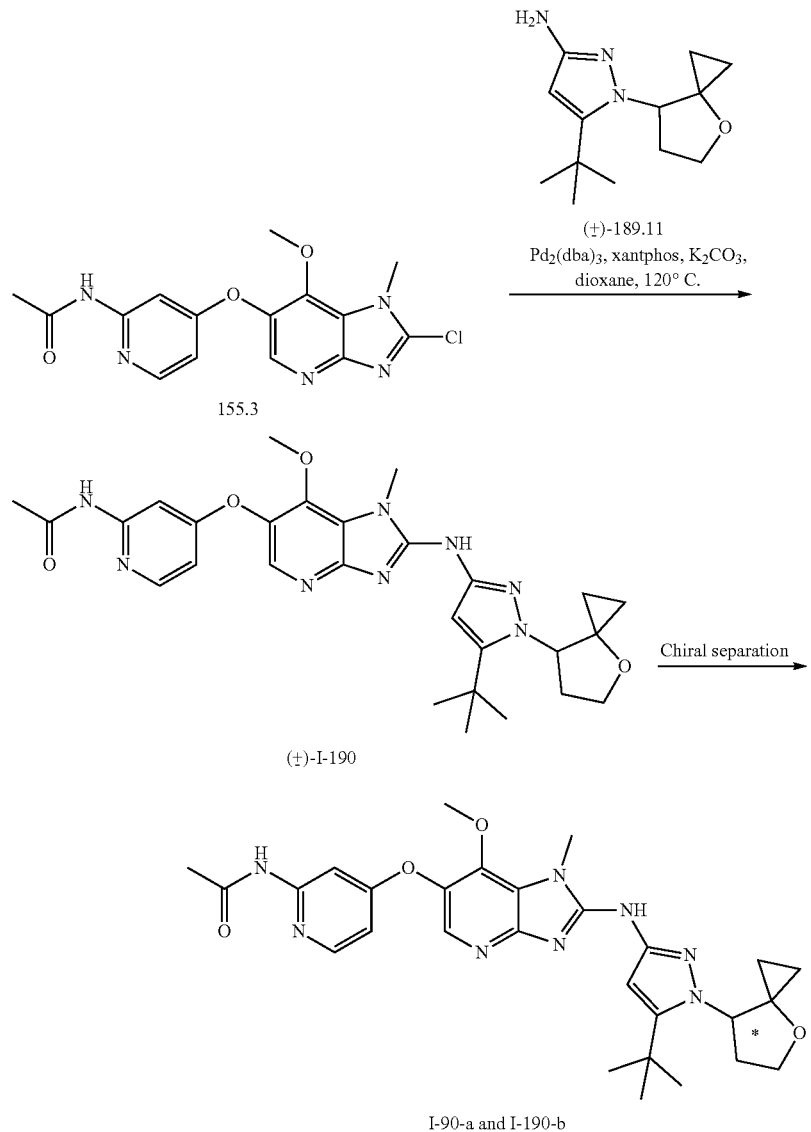

Synthesis of compound (±)-I-190. Compound (±)-I-190 was prepared from compound (±)-189.11 and 155.3 following the procedure described in the synthesis of Compound I-108. The product was purified by flash column chromatography on silica gel (CombiFlash®, 3.5% methanol in DCM). MS(ES): m/z: 547.5 [M+H]$^+$.

Synthesis of compounds I-190-a and I-190-b. The enantiomers of (±)-I-190 were separated by HPLC (column CHIRALPAK IB-N (250 mm×21 mm, 5 μm); mobile phase: (A) 0.1% diethylamine in n-hexane, (B) 0.1% diethylamine in isopropanol:methanol (50:50); flow rate=20 mL/min) to afford first eluting fraction (I-190-a) and second eluting fraction (I-190-b). (*Absolute stereochemistry not determined.)

I-190-a: MS(ES): m/z: 547.5 [M+H]$^+$, $^1$H NMR (DMSO-d$_6$, 400 MHz): δ 10.56 (s, 1H), 9.87 (s, 1H), 8.19-8.18 (d, J=5.6 Hz, 1H), 7.93 (s, 1H), 7.69 (s, 1H), 6.66-6.65 (d, J=3.6 Hz, 1H), 6.54 (s, 1H), 5.03-5.00 (m, 1H), 4.23-4.22 (m, 1H), 3.91 (s, 3H), 3.84 (s, 3H), 3.55-3.52 (m, 1H), 2.05 (s, 3H), 1.34 (s, 9H), 1.25 (s, 2H), 0.90-0.88 (m, 2H), 0.81-0.76 (m, 2H).

I-190-b: MS(ES): m/z: 547.5 [M+H]$^+$, $^1$H NMR (DMSO-d$_6$, 400 MHz): δ 10.56 (s, 1H), 9.87 (s, 1H), 8.19-8.18 (d, J=5.6 Hz, 1H), 7.93 (s, 1H), 7.69 (s, 1H), 6.66-6.65 (d, J=3.6 Hz, 1H), 6.54 (s, 1H), 5.04-5.02 (m, 1H), 4.23-4.22 (m, 1H), 3.91 (s, 3H), 3.84 (s, 3H), 3.55-3.52 (m, 1H), 2.05 (s, 3H), 1.34 (s, 9H), 1.25 (s, 2H), 0.90-0.88 (m, 2H), 0.81-0.76 (m, 2H).

Example 191: N-(4-((2-((5-cyclopropyl-1-methyl-2-oxo-1,2-dihydropyridin-3-yl)amino)-7-methoxy-1-methyl-1H-imidazo[4,5-b]pyridin-6-yl)oxy)pyridin-2-yl)cyclopropanecarboxamide

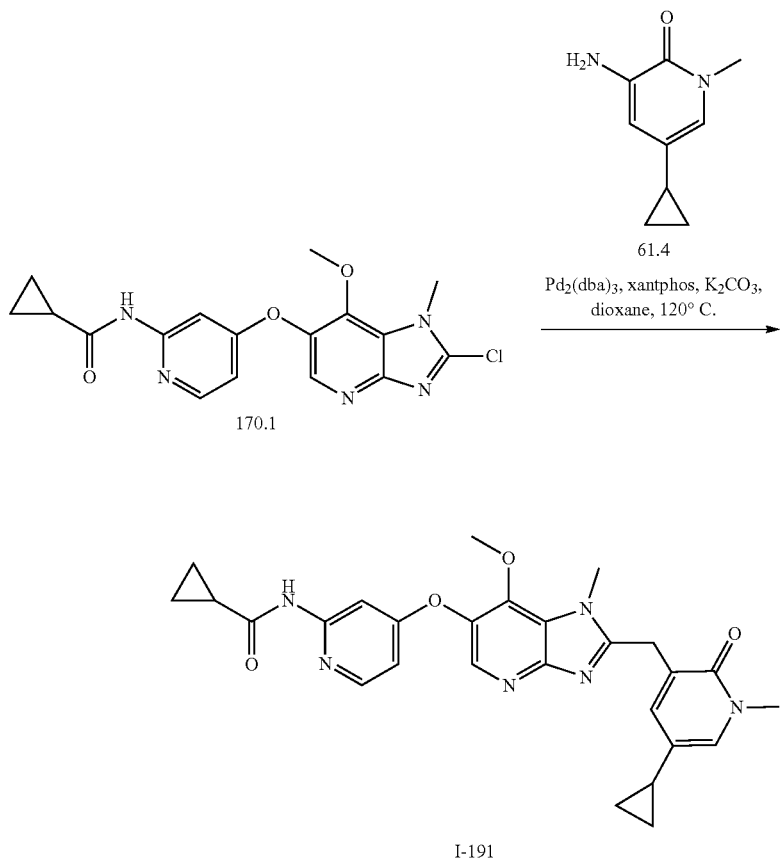

Synthesis of compound I-191. Compound I-191 was prepared from compounds 170.1 and 61.4 following the procedure described in the synthesis of compound I-108. The product was purified by flash column chromatography on silica gel (CombiFlash®, 3.1% methanol in DCM). MS(ES): m/z: 502.5 [M+H]$^+$, $^1$H NMR (DMSO-d$_6$, 400 MHz): δ 10.87 (s, 1H), 8.34 (s, 1H), 8.31-8.30 (d, J=2.0 Hz, 1H), 8.20-8.19 (d, J=5.6 Hz, 1H), 8.02 (s, 1H), 7.67-7.66 (d, J=2.0 Hz, 1H), 7.22-7.21 (d, J=2.0 Hz, 1H), 6.71-6.69 (m, 1H), 3.94 (s, 3H), 3.87 (s, 3H), 3.55 (s, 3H), 1.99-1.93 (m, 1H), 1.85-1.78 (m, 1H), 0.89-0.85 (m, 2H), 0.76-0.74 (m, 4H), 0.61-0.57 (m, 2H).

Example 192: N-(4-((7-chloro-2-((5-(2-cyanopropan-2-yl)-1-(2-oxaspiro[3.3]heptan-6-yl)-1H-pyrazol-3-yl)amino)-1-methyl-1H-imidazo[4,5-b]pyridin-6-yl)oxy)pyridin-2-yl)acetamide
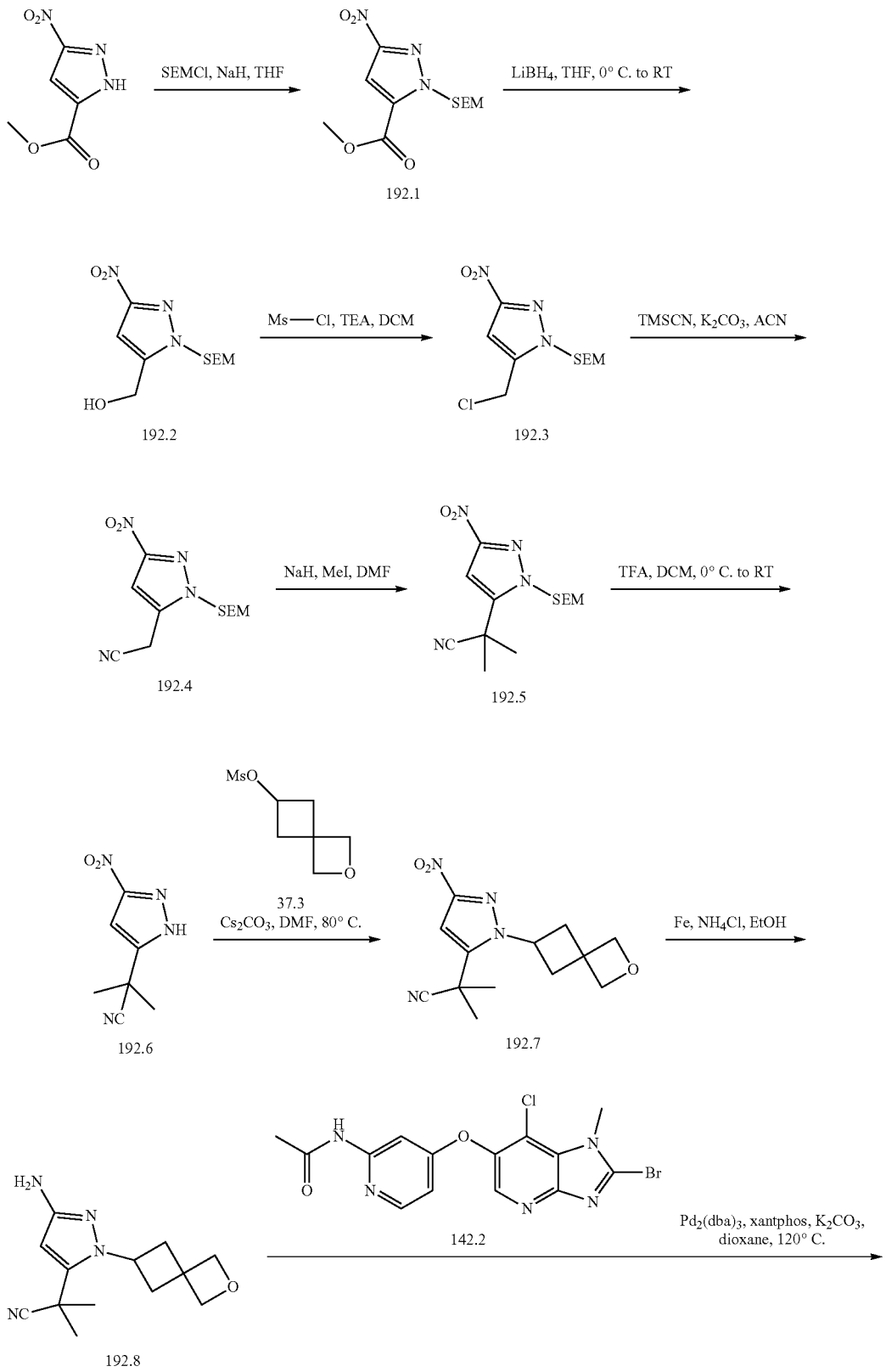

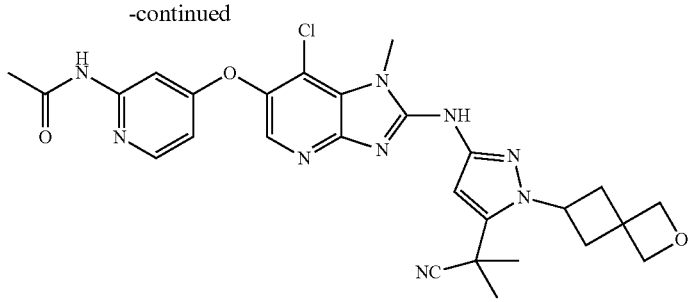

I-192

Synthesis of compound 192.1. To a suspension of sodium hydride (4.9 g, 122.7 mmol, 1.5 equiv) in THF (50 mL) was added a solution of methyl 3-nitro-1H-pyrazole-5-carboxylate (14 g, 81.82 mmol, 1.0 equiv) in THF (100 mL) at 0° C. It was stirred for 30 min followed by the addition of (2-chloromethoxyethyl)trimethylsilane (16.39 g, 98.18 mmol, 1.2 equiv). The reaction mixture was stirred at room temperature for 30 min. It was poured over ice, stirred and extracted with ethyl acetate. The combined organic layers were washed with brine, dried over sodium sulfate, filtered and concentrated under reduced pressure. The residue was purified by flash column chromatography on silica gel (CombiFlash®, 12% ethyl acetate in hexane) to afford 192.1. $^1$H NMR (DMSO-$d_6$, 400 MHz): δ 7.66 (s, 1H), 5.85 (d, 2H), 3.90 (s, 3H), 3.63-3.59 (t, 2H), 0.85-0.81 (t, 2H), 0.012 (s, 9H).

Synthesis of compound 192.2. To a solution of 192.1 (9.5 g, 31.52 mmol, 1.0 equiv) in THF (100 mL) was added lithium borohydride (1 M in THF) (63 mL, 63.04 mmol, 2.0 equiv) slowly and the reaction mixture was stirred at room temperature for 4 h. It was poured into a mixture of ice-water, stirred and extracted with ethyl acetate. The combined organic layers were washed with brine, dried over sodium sulfate, filtered and concentrated under reduced pressure. The residue was purified by flash column chromatography on silica gel (CombiFlash®, 20% ethyl acetate in hexane) to afford 192.2. $^1$H NMR (DMSO-$d_6$, 400 MHz): δ 7.24 (s, 1H), 5.73 (s, 2H), 5.69-5.66 (m, 1H), 5.41-5.38 (m, 1H), 4.62-4.60 (m, 1H), 4.46-4.45 (m, 2H), 3.59-3.55 (t, 2H), 0.04 (s, 9H).

Synthesis of compound 192.3. To a solution of 192.2 (5.1 g, 18.66 mmol, 1.0 equiv) in DCM (50 mL) was added triethylamine (7.8 mL, 55.98 mmol, 3.0 equiv) at 0° C. followed by the addition of methanesulfonyl chloride (2.15 mL, 27.99 mmol, 1.5 equiv). The reaction mixture was stirred at room temperature for 2 h. It was poured into a mixture of ice-water, stirred and extracted with DCM. The combined organic layers were washed with brine, dried over sodium sulfate, filtered and concentrated under reduced pressure. The residue was purified by flash column chromatography on silica gel (CombiFlash®, 10% ethyl acetate in hexane) to afford 192.3. $^1$H NMR (DMSO-$d_6$, 400 MHz): δ 7.26 (s, 1H), 5.66 (s, 2H), 4.98 (s, 2H), 4.78 (s, 2H), 3.63-3.58 (m, 2H), 0.02 (s, 9H).

Synthesis of compound 192.4. To a solution of 192.3 (3.0 g, 10.28 mmol, 1.0 equiv) in acetonitrile (30 mL) was added potassium carbonate (3.54 g, 25.7 mmol, 2.5 equiv) followed by the addition of trimethylsilyl cyanide (2.54 g, 25.7 mmol, 2.5 equiv). The reaction mixture was stirred at 90° C. for 5 h. It was poured into a mixture of ice-water, stirred and extracted with ethyl acetate. The combined organic layers were washed with brine, dried over sodium sulfate, filtered and concentrated under reduced pressure. The residue was purified by flash column chromatography on silica gel (CombiFlash®, 15% ethyl acetate in hexane) to afford 192.4. MS(ES): m/z 283.3 [M+H]$^+$.

Synthesis of compound 192.5. To a solution of 192.4 (1.9 g, 6.73 mmol, 1.0 equiv) in DMF (20 mL) was added sodium hydride (1.07 g, 26.92 mmol, 4.0 equiv) at 0° C. and stirred for 20 min. To the mixture was added methyl iodide (3.82 g, 26.92 mmol, 4.0 equiv) and stirred at room temperature for 30 min. The reaction mixture was poured over crushed ice, stirred and extracted with ethyl acetate. The combined organic layers were washed with brine, dried over sodium sulfate, filtered and concentrated under reduced pressure. The residue was purified by flash column chromatography on silica gel (CombiFlash®, 13% ethyl acetate in hexane) to afford 192.5. MS(ES): m/z 311.4 [M+H]$^+$.

Synthesis of compound 192.6. To a solution of 192.5 (1.2 g, 3.87 mmol, 1.0 equiv) in DCM (10 mL) was added trifluoroacetic acid (4 mL) at 0° C. and the mixture was stirred at room temperature for 6 h. The reaction mixture was poured over crushed ice-cold, saturated sodium bicarbonate solution, stirred and extracted with DCM. The combined organic layers were washed with brine, dried over sodium sulfate, filtered and concentrated under reduced pressure. The residue was purified by flash column chromatography on silica gel (CombiFlash®, 40% ethyl acetate in hexane) to afford 192.6. MS(ES): m/z 181.2 [M+H]$^+$.

Synthesis of compound 192.7. To a solution of 192.6 (0.6 g, 3.33 mmol, 1.0 equiv) and 37.3 (0.768 g, 4.0 mmol, 1.2 equiv) in DMF (10 mL) was added cesium carbonate (3.2 g, 9.99 mmol, 3.0 equiv) and heated at 80-90° C. for 5 h. The mixture was poured into a mixture of ice-water, stirred and extracted with ethyl acetate. The combined organic layers were washed with brine, dried over sodium sulfate, filtered and concentrated under reduced pressure. The residue was purified by flash column chromatography on silica gel (CombiFlash®, 45% ethyl acetate in hexane) to afford 192.7. MS (ES): m/z 277.3 [M+H]$^+$.

Synthesis of compound 192.8. To a solution of 192.7 (0.180 g, 0.651 mmol, 1.0 equiv) in ethanol:water (2:1, 10 mL) was added iron powder (0.182 g, 3.255 mmol, 5.0 equiv), followed by ammonium chloride (0.175 g, 3.255 mmol, 5.0 equiv). The reaction mixture was heated at 30° C. for 1 h. It was poured into a mixture of ice-water, filtered, and extracted with ethyl acetate. The combined organic layers were washed with brine, dried over sodium sulfate, filtered and concentrated under reduced pressure to obtain 192.8. MS(ES): m/z 247.2 [M+H]$^+$.

Synthesis of compound I-192. Compound I-192 was prepared from compound 192.8 and 142.2 following the procedure described in the synthesis of compound I-108. The product was purified by flash column chromatography on silica gel (CombiFlash®, 3.5% methanol in DCM). MS(ES): m/z: 562.8 [M+H]$^+$, $^1$H NMR (DMSO-d$_6$, 400 MHz): δ 10.58 (s, 1H), 10.13 (s, 1H), 8.19 (bs, 1H), 8.06 (s, 1H), 7.64 (s, 1H), 6.77 (s, 1H), 6.66 (s, 1H), 4.98 (bs, 1H), 4.73-4.61 (m, 4H), 3.92 (s, 3H), 3.11-3.09 (d, 4H), 2.04 (s, 3H), 1.78 (s, 6H).

Example 193: N-(4-((2-((5-(tert-butyl)-1-(2-oxaspiro[3.3]heptan-6-yl)-1H-pyrazol-3-yl)amino)-7-chloro-1-methyl-1H-imidazo[4,5-b]pyridin-6-yl)oxy)pyridin-2-yl)acetamide

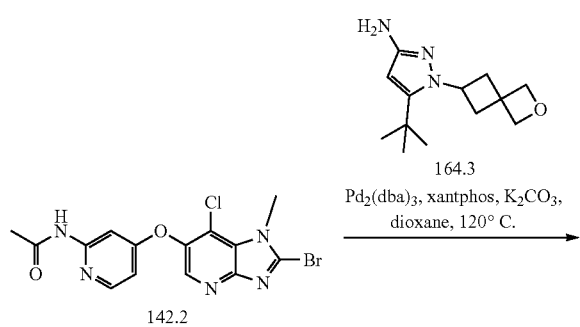

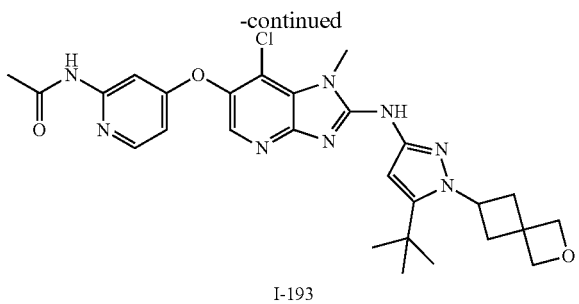

Synthesis of compound I-193. Compound I-193 was prepared from compound 164.3 and 142.2 following the procedure described in the synthesis of compound I-108. The product was purified by flash column chromatography on silica gel (CombiFlash®, 3.5% methanol in DCM). MS(ES): m/z: 551.8 [M]$^+$, $^1$H NMR (DMSO-d$_6$, 400 MHz): δ 10.57 (s, 1H), 10.02 (s, 1H), 8.18-8.17 (d, J=5.6 Hz, 1H), 7.63 (s, 1H), 6.65-6.63 (m, 1H), 6.51 (s, 1H), 5.79 (s, 1H), 4.96-4.92 (m, 1H), 4.71 (bs, 2H), 4.58 (bs, 2H), 3.91 (s, 3H), 2.80-2.70 (m, 2H), 2.02 (s, 3H), 1.55 (bs, 2H), 1.35 (s, 9H).

Example 194: N-(4-((2-((5-(2-cyanopropan-2-yl)-1-(2-oxaspiro[3.3]heptan-6-yl)-1H-pyrazol-3-yl)amino)-7-(difluoromethyl)-1-methyl-1H-imidazo[4,5-b]pyridin-6-yl)oxy)pyridin-2-yl)acetamide

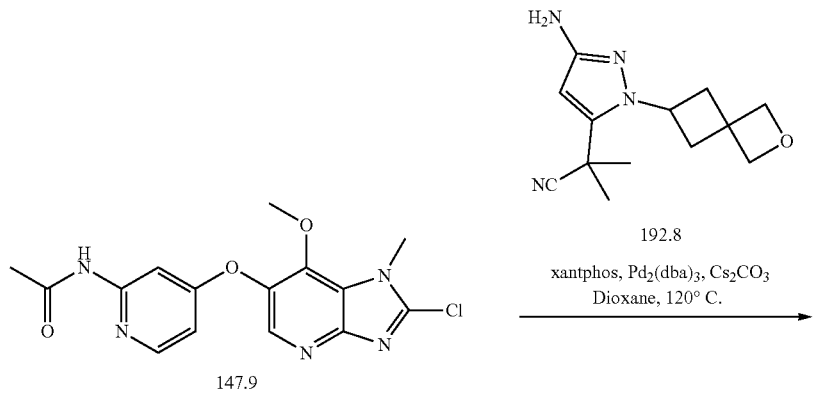

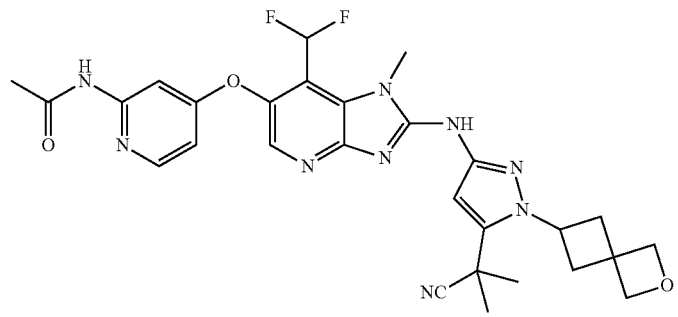

Synthesis of compound I-194. Compound I-194 was prepared from compound 170.1 and 164.3 following the procedure described in the synthesis of compound I-128. The product was purified by preparative HPLC. MS(ES): m/z: 578.8 [M]+, $^1$H NMR (CDCl$_3$, 400 MHz): δ 8.73 (bs, 1H), 8.15-8.14 (d, J=5.6 Hz, 1H), 7.93 (s, 1H), 7.16-7.03 (m, 1H), 6.62-6.61 (d, J=3.6 Hz, 1H), 6.20 (s, 1H), 4.99-4.91 (m, 1H), 4.86 (s, 2H), 3.82 (s, 2H), 2.93-2.88 (m, 2H), 2.22 (s, 3H), 1.79 (s, 3H), 1.30 (s, 6H), 0.91-0.88 (m, 2H).

Example 195: (R)—N-(4-((2-((5-(tert-butyl)-4-(tetrahydrofuran-3-yl)thiazol-2-yl)amino)-7-methoxy-1-methyl-1H-imidazo[4,5-b]pyridin-6-yl)oxy)pyridin-2-yl)acetamide and (S)—N-(4-((2-((5-(tert-butyl)-4-(tetrahydrofuran-3-yl)thiazol-2-yl)amino)-7-methoxy-1-methyl-1H-imidazo[4,5-b]pyridin-6-yl)oxy)pyridin-2-yl)acetamide on silica gel (CombiFlash®, 70% ethyl acetate in hexane). MS(ES): m/z: 538.1 [M+H]+.

Synthesis of compounds I-195-a and I-195-b. The enantiomers of (±)-I-195 were separated by HPLC (column: CHIRALPAK IC (250 mm×21 mm, 5 μm); mobile phase: (A) 0.1% DEA in n-hexane, (B) 0.1% DEA in isopropanol: acetonitrile (70:30); flow rate=20 mL/min) to afford first eluting fraction (I-195-a) and second eluting fraction (I-195-b). (*Absolute stereochemistry not determined.)

I-195-a. MS(ES): m/z: 538.1 [M+H]+, $^1$H NMR (DMSO-d$_6$, 400 MHz): δ 12.12 (s, 1H), 10.56 (s, 1H), 8.18-8.17 (d, J=5.6 Hz, 1H), 7.96 (s, 1H), 7.69 (s, 1H), 6.66-6.64 (m, 1H), 4.01-3.95 (m, 2H), 3.91 (s, 3H), 3.84-3.80 (m, 1H), 3.74 (s, 3H), 3.69-3.64 (m, 2H), 2.20-2.14 (m, 2H), 2.03 (s, 3H), 1.41 (s, 9H).

I-195-b. MS(ES): m/z: 538.1 [M+H]+, $^1$H NMR (DMSO-d$_6$, 400 MHz): δ 12.12 (s, 1H), 10.56 (s, 1H), 8.18-8.17 (d,

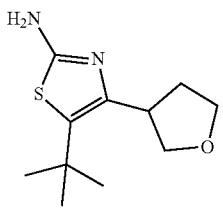

(±)-187.7

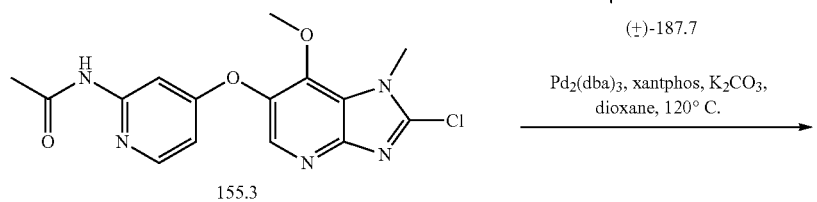

Pd$_2$(dba)$_3$, xantphos, K$_2$CO$_3$, dioxane, 120° C.

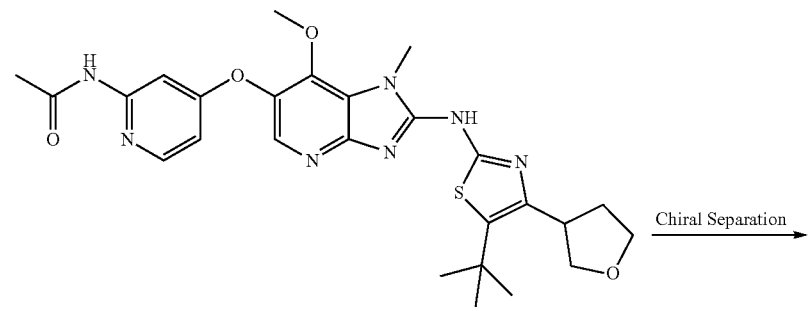

(±)-I-195

Chiral Separation

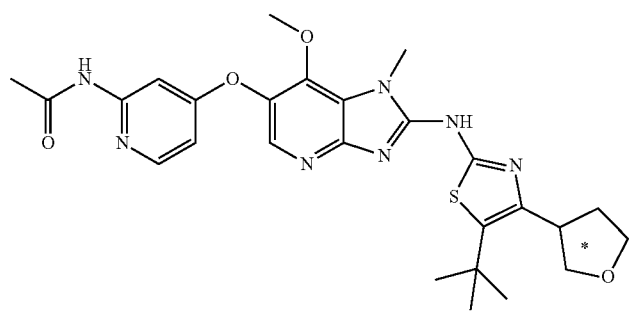

I-195-a and I-195-b

Synthesis of compound (±)-I-195. Compound (±)-I-195 was prepared from compound (±)-187.7 and 155.3 following the procedure described in the synthesis of compound I-108. The product was purified by flash column chromatography J=5.6 Hz, 1H), 7.96 (s, 1H), 7.68 (s, 1H), 6.67-6.65 (m, 1H), 4.01-3.97 (m, 2H), 3.91 (s, 3H), 3.86-3.84 (m, 1H), 3.74 (s, 3H), 3.69-3.66 (m, 2H), 2.20-2.14 (m, 2H), 2.03 (s, 3H), 1.41 (s, 9H).

Example 196: N-(4-((2-((5-(tert-butyl)-1-(2-oxas-piro[3.3]heptan-6-yl)-1H-pyrazol-3-yl)amino)-7-methoxy-1-methyl-1H-imidazo[4,5-b]pyridin-6-yl)oxy)pyridin-2-yl)cyclopropanecarboxamide

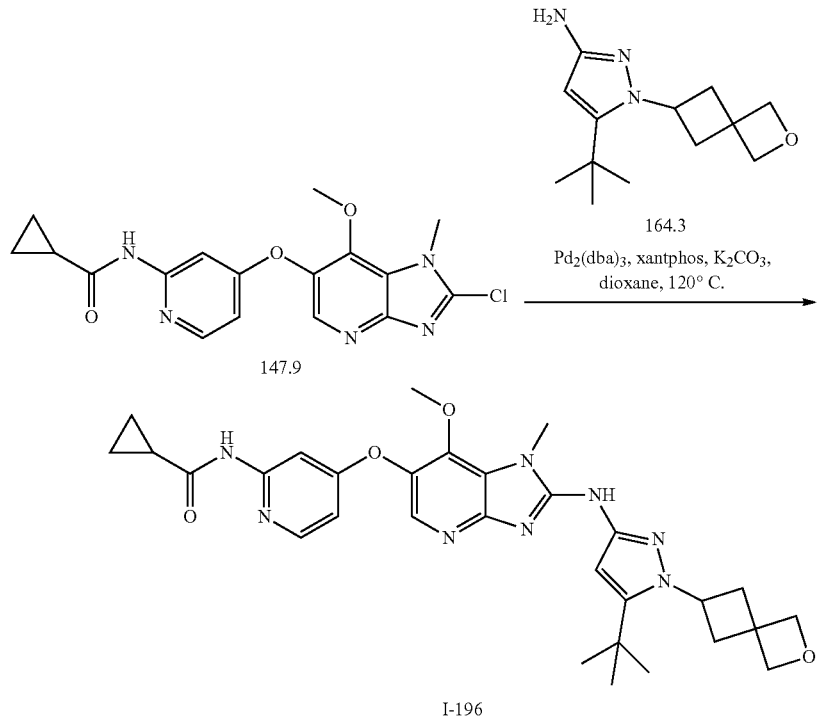

Synthesis of compound I-196. Compound I-196 was prepared from compound 170.1 and 164.3 following the procedure described in the synthesis of compound I-108. The product was purified by flash column chromatography on silica gel (CombiFlash®, 4.0% methanol in DCM). MS(ES): m/z: 573.5 [M+H]$^+$, $^1$H NMR (DMSO-d$_6$, 400 MHz): δ 10.86 (s, 1H), 9.79 (s, 1H), 8.20-8.19 (d, J=5.6 Hz, 1H), 7.92 (s, 1H), 7.66-7.65 (d, J=2.0 Hz, 1H), 6.70-6.68 (m, 1H), 6.53 (s, 1H), 4.96-4.92 (m, 1H), 4.71 (s, 2H), 4.58 (s, 2H), 3.90 (s, 3H), 3.82 (s, 3H), 2.77-2.68 (m, 4H), 1.98-1.92 (m, 1H), 1.36 (s, 9H), 0.77-0.75 (m, 4H).

Example 197: N-(4-((7-chloro-2-((5-cyclopropyl-1-methyl-2-oxo-1,2-dihydropyridin-3-yl)amino)-1-methyl-1H-imidazo[4,5-b]pyridin-6-yl)oxy)pyridin-2-yl)cyclopropanecarboxamide

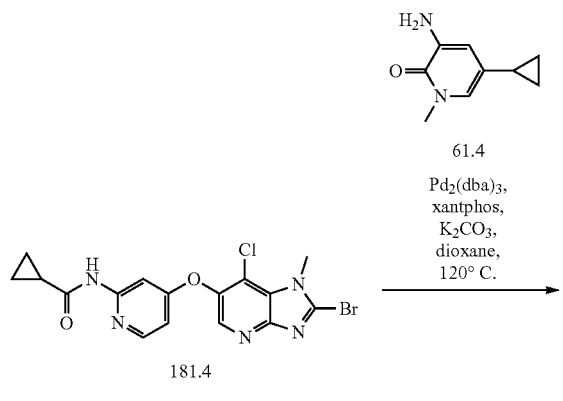

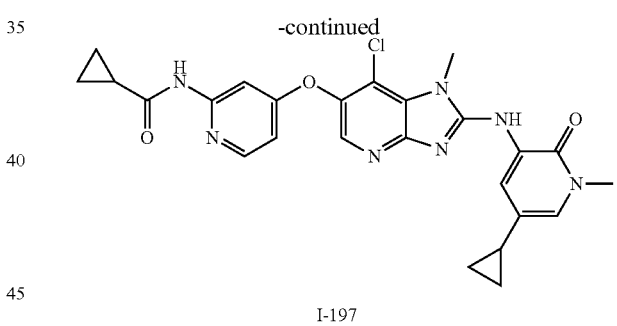

Synthesis of compound I-197. Compound I-197 was prepared from compound 181.4 and 61.4 following the procedure described in the synthesis of compound I-108. The product was purified by flash column chromatography on silica gel (CombiFlash®, 3.2% methanol in DCM). MS(ES): m/z: 506.6 [M+H]$^+$, $^1$H NMR (DMSO-d$_6$, 400 MHz): δ 10.90 (s, 1H), 8.54 (s, 1H), 8.30-8.29 (d, J=2.0 Hz, 1H), 8.21-8.20 (d, J=6.0 Hz, 1H), 8.02 (s, 1H), 7.63-7.62 (d, J=2.4 Hz, 1H), 7.25-7.24 (d, J=2.0 Hz, 1H), 6.71-6.69 (m, 1H), 3.96 (s, 3H), 3.55 (s, 3H), 1.98-1.95 (m, 1H), 1.84-1.79 (m, 1H), 0.90-0.85 (m, 2H), 0.77-0.75 (m, 4H), 0.61-0.57 (m, 2H).

Example 198: (R)—N-(4-((2-(((1-cyclobutyl-2-(tetrahydrofuran-3-yl)-1H-imidazol-4-yl)amino)-1-methyl-1H-imidazo[4,5-b]pyridin-6-yl)oxy)pyridin-2-yl)cyclopropanecarboxamide and (S)—N-(4-((2-((1-cyclobutyl-2-(tetrahydrofuran-3-yl)-1H-imidazol-4-yl)amino)-1-methyl-1H-imidazo[4,5-b]pyridin-6-yl)oxy)pyridin-2-yl)cyclopropanecarboxamide

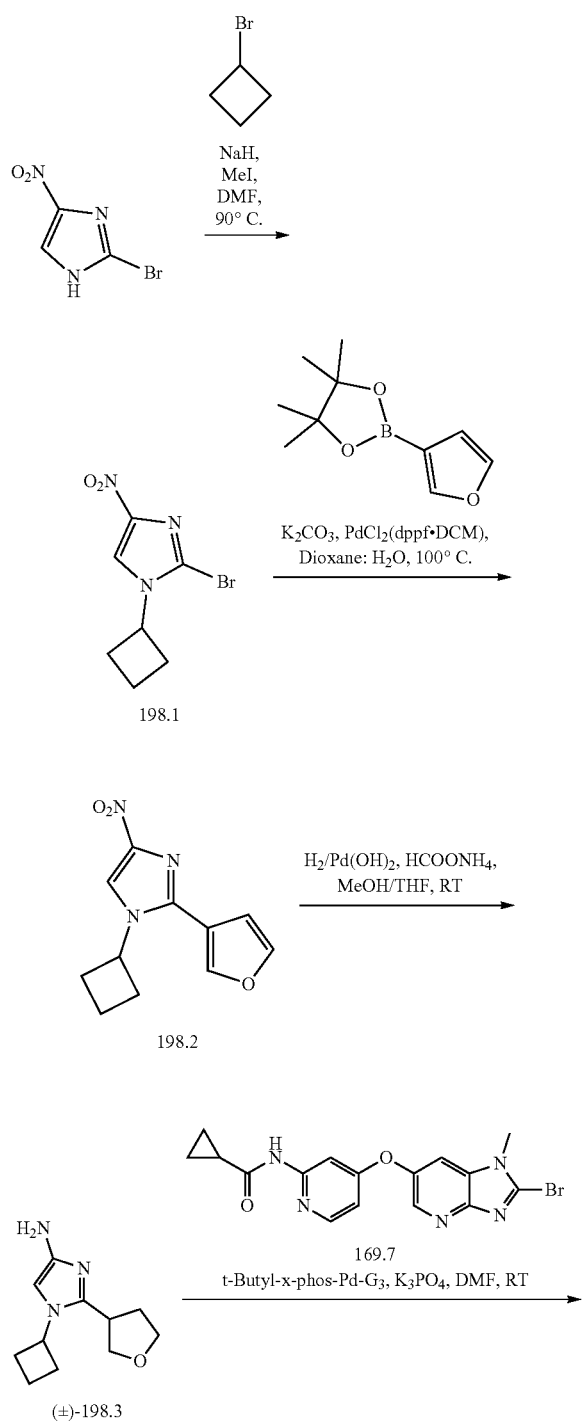

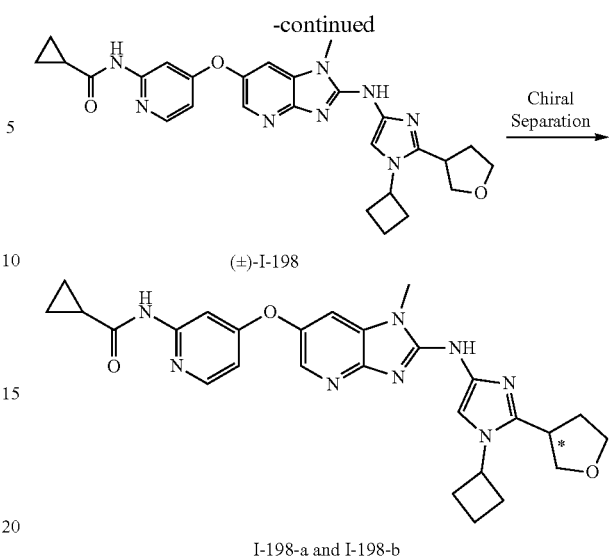

Synthesis of compound 198.1. To a solution of 2-bromo-4-nitro-1H-imidazole (1.0 g, 5.21 mmol, 1.0 equiv) in DMF (10 mL) was added sodium hydride (0.208 g, 5.21 mmol, 1.0 equiv) in portions at room temperature and stirred for 1 h followed by the addition of bromocyclobutane (1.4 g, 10.42 mmol, 2.0 equiv). The reaction mixture was stirred at 90° C. for 48 h. It was poured into a mixture of ice-water, stirred and extracted with ethyl acetate. The combined organic layers were washed with brine, dried over sodium sulfate, filtered and concentrated under reduced pressure. The residue was purified by flash column chromatography on silica gel (CombiFlash®, 20% ethyl acetate in hexane) to afford 198.1. MS (ES): m/z 247.1 [M+H]$^+$.

Synthesis of compound 198.2. A mixture of 198.1 (2.5 g, 10.16 mmol, 1.0 equiv) 2-(furan-3-yl)-4,4,5,5-tetramethyl-1,3,2-dioxaborolane (5.91 g, 30.48 mmol, 3.0 equiv), potassium carbonate (7.01 g, 50.8 mmol, 5.0 equiv), 1,4-dioxane (20 mL) and water (5 mL) was degassed by bubbling through a stream of argon for 10 min. Under the argon atmosphere [1,1'-bis(diphenylphosphino)ferrocene]dichloropalladium(II)-DCM complex (0.829 g, 1.016 mmol, 0.1 equiv) was added, and degassed for another 5 min. The reaction mixture was stirred at 100° C. for 1 h. It was cooled to room temperature and filtered through a pad of Celite®. The filtrate was transferred into water and extracted with ethyl acetate. The combined organic layers were washed with brine, dried over sodium sulfate, filtered and concentrated under reduced pressure. The residue was purified by flash column chromatography on silica gel (CombiFlash®, 25% ethyl acetate in hexane) to afford 198.2. MS(ES): m/z 234.2 [M+H]$^+$.

Synthesis of compound (±)-198.3. A mixture of 198.2 (0.500 g, 2.14 mmol, 1.0 equiv), ammonium formate (0.539 g, 8.56 mmol, 4.0 equiv), palladium hydroxide (0.350 g) in methanol (10 mL) and THF (6 mL) was stirred at room temperature for 16 h under hydrogen pressure. The reaction mixture was filtered through a pad of Celite® and washed with methanol. The filtrate was concentrated under reduced pressure. The residue was purified by flash column chromatography on silica gel (CombiFlash®, 6% methanol in DCM) to afford (±)-198.3. MS(ES): m/z 208.2 [M+H]$^+$.

Synthesis of compound (±)-I-198. Compound (±)-I-198 was prepared from compound (±)-198.3 and 169.7 following the procedure described in the synthesis of compound I-136.

The product was purified by flash column chromatography on silica gel (CombiFlash®, 5.5% methanol in DCM). MS(ES): m/z: 515.3 [M+H]⁺.

Synthesis of compounds I-198-a and I-198-b. The enantiomers of (±)-I-198 were separated by HPLC (column CHIRALPAK IB-N (250 mm×21 mm, 5 μm) and mobile phase: (A) 0.1% DEA in n-hexane, (B) 0.1% DEA in isopropanol:acetonitrile (70:30); flow rate=22 mL/min) to afford first eluting fraction (I-198-a) and second eluting fraction (I-198-b). (*Absolute stereochemistry not determined.)

I-198-a. MS(ES): m/z: 515.3 [M+H]⁺, ¹H NMR (DMSO-d₆, 400 MHz): δ 10.83 (s, 1H), 9.81 (s, 1H), 8.20-8.18 (d, J=5.6 Hz, 1H), 7.96-7.95 (d, J=2.0 Hz, 1H), 7.64-7.63 (d, J=2.0 Hz, 1H), 7.61-7.60 (d, J=2.0 Hz, 1H), 7.58 (s, 1H), 6.71-6.69 (m, 1H), 4.84-4.80 (m, 1H), 4.08-4.04 (m, 1H), 3.89-3.82 (m, 1H), 3.80-3.75 (m, 1H), 3.67 (s, 3H), 3.61-3.57 (m, 1H), 2.46 (bs, 2H), 2.38-2.34 (m, 2H), 2.28-2.25 (m, 1H), 2.16-2.13 (m, 1H), 1.86-1.79 (m, 2H), 1.24 (bs, 2H), 0.77-0.75 (m, 4H).

I-198-b. MS(ES): m/z: 515.3 [M+H]⁺, LCMS purity: 95.42%, HPLC purity: 95.00%, Chiral HPLC: 99.16%, ¹H NMR (DMSO-d₆, 400 MHz): δ 10.91 (s, 1H), 9.81 (s, 1H), 8.23-8.21 (d, J=5.6 Hz, 1H), 8.00 (bs, 1H), 7.75 (bs, 1H), 7.65 (bs, 1H), 7.59 (bs, 1H), 6.76-6.74 (m, 1H), 4.96-4.93 (m, 1H), 4.06 (bs, 1H), 3.96-3.94 (m, 1H), 3.80-3.76 (m, 1H), 3.59 (s, 3H), 3.61-3.57 (m, 1H), 2.46 (bs, 2H), 2.34 (bs, 2H), 2.28-2.25 (m, 1H), 2.16-2.13 (m, 1H), 2.00-1.98 (m, 2H), 1.24 (bs, 2H), 0.79-0.77 (m, 4H).

Example 199: N-(4-((2-((5-cyclopropyl-1-methyl-2-oxo-1,2-dihydropyridin-3-yl)amino)-7-(difluoromethyl)-1-methyl-1H-imidazo[4,5-b]pyridin-6-yl)oxy)pyridin-2-yl)cyclopropanecarboxamide

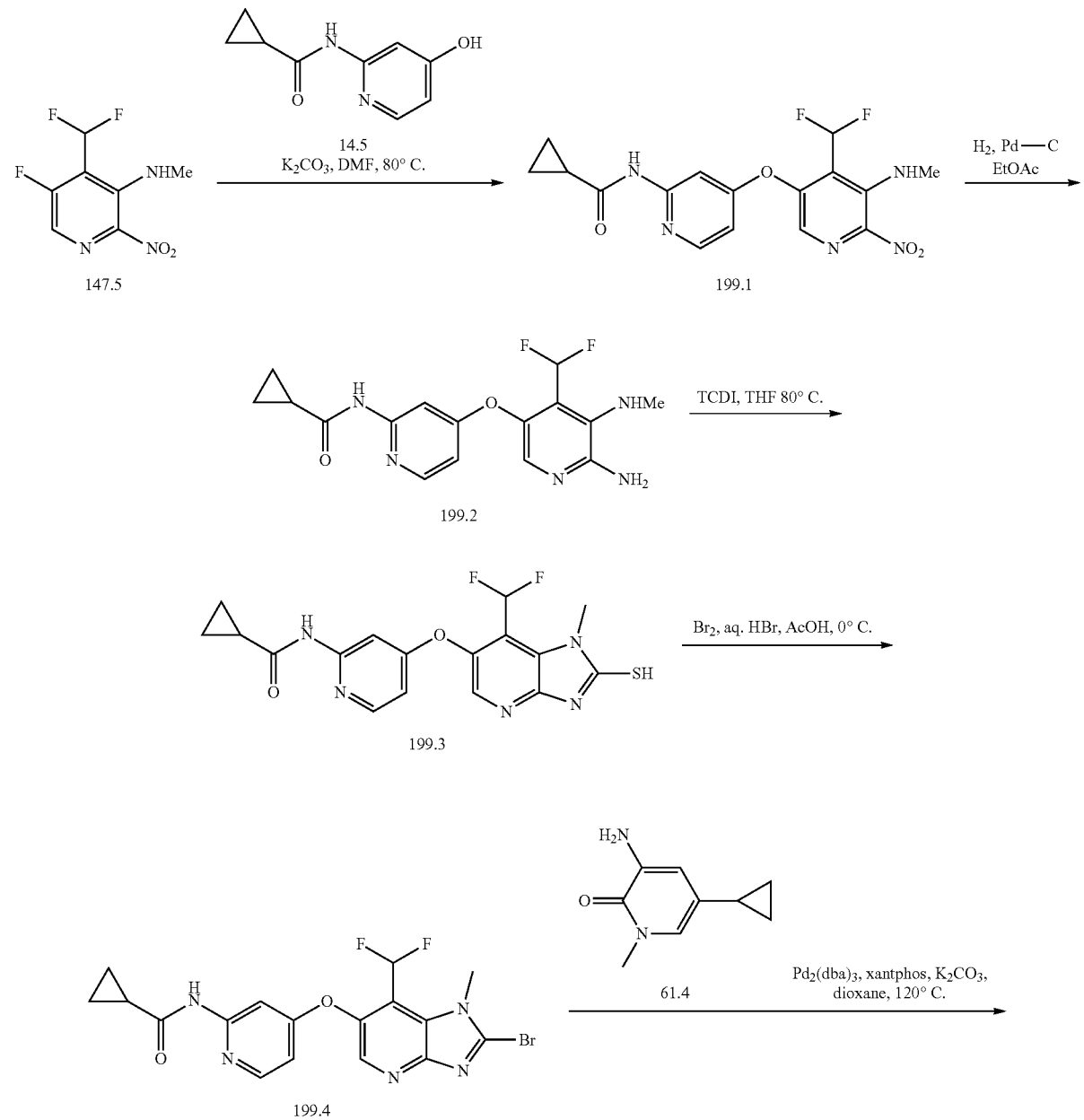

-continued

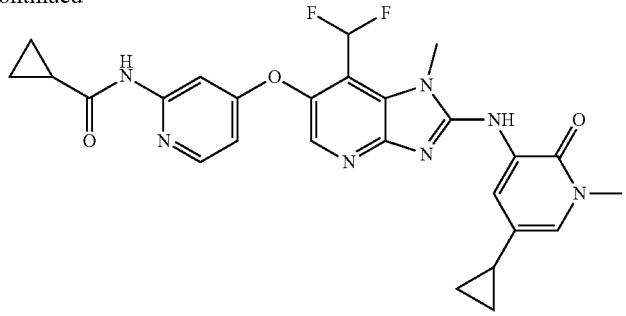

I-199

Synthesis of compound 199.1. A mixture of 147.5 (0.170 g, 0.768 mmol, 1.0 equiv), 14.5 (0.205 g, 1.15 mmol, 1.5 equiv) and potassium carbonate (0.317 g, 2.304 mmol, 3.0 equiv) in DMF (5 mL) was stirred at 80° C. for 1 h. The reaction mixture was cooled to room temperature, transferred into ice-water, and product extracted with ethyl acetate. The combined organic layers were washed with brine, dried over sodium sulfate, filtered and concentrated under reduced pressure. The residue was purified by flash column chromatography on silica gel (CombiFlash®, 20% ethyl acetate in hexane) to afford 199.1. MS(ES): m/z 380.3 [M+H]+.

Synthesis of compound 199.2. A mixture of 199.1 (0.169 g, 0.445 mmol, 1.0 equiv) and 10% palladium on carbon (0.100 g) in ethyl acetate (20 mL) was stirred under hydrogen (1 atm) at rt for 2 h. The reaction mixture was filtered through a pad of Celite® and rinsed with ethyl acetate. The filtrate was concentrated under reduced pressure to obtain 199.2. MS(ES): m/z 350.3 [M+H]+.

Synthesis of compound 199.3. To a solution of 199.2 (0.090 g, 0.257 mmol, 1.0 equiv) in THF (2 mL) was added 1,1'-thiocarbonyldiimidazole (0.228 g, 1.285 mmol, 5.0 equiv). The reaction mixture was stirred at 80° C. for 1 h. It was cooled to room temperature and transferred into ice-water. The precipitated solids were collected by filtration and triturated with hexane to obtain 199.3. MS(ES): m/z: 392.4 [M+H]+.

Synthesis of compound 199.4. To a solution of 199.3 (0.090 g, 0.229 mmol, 1.0 equiv) in acetic acid (3.5 mL) was added aqueous hydrobromic acid (0.027 g, 0.343 mmol, 1.5 equiv) at 0° C. followed by bromine (0.145 g, 0.916 mmol, 4.0 equiv). The reaction mixture was stirred for 15 min, and it was transferred into a saturated sodium bicarbonate solution, stirred and extracted with ethyl acetate. The combined organic layers were washed with brine, dried over sodium sulfate, filtered and concentrated under reduced pressure. The residue was purified by flash column chromatography on silica gel (CombiFlash®, 2.5% methanol in DCM) to afford 199.4. MS (ES): m/z 439.2 [M+H]+.

Synthesis of I-199. Compound I-193 was prepared from compound 199.4 and 61.4 following the procedure described in the synthesis of compound I-108. The product was purified by flash column chromatography on silica gel (CombiFlash®, 3.5% methanol in DCM). MS(ES): m/z: 522.7 [M+H]+, ¹H NMR (DMSO-$d_6$, 400 MHz): δ 10.93 (s, 1H), 8.65 (s, 1H), 8.33-8.32 (d, J=2.0 Hz, 1H), 8.24-8.23 (d, J=5.6 Hz, 1H), 8.19 (s, 1H), 7.68-7.67 (d, J=2.4 Hz, 1H), 7.54-7.28 (m, 1H), 7.27 (s, 1H), 6.73-6.71 (m, 1H), 3.84 (s, 3H), 3.57 (s, 3H), 2.00-1.96 (m, 1H), 1.86-1.82 (m, 1H), 0.91-0.85 (m, 2H), 0.78-0.76 (m, 4H), 0.63-0.59 (m, 2H).

Example 200: N-(4-((2-((1-(3,3-bis(hydroxymethyl) cyclobutyl)-5-(tert-butyl)-1H-pyrazol-3-yl)amino)-1-methyl-1H-imidazo[4,5-b]pyridin-6-yl)oxy)pyridin-2-yl)cyclopropanecarboxamide

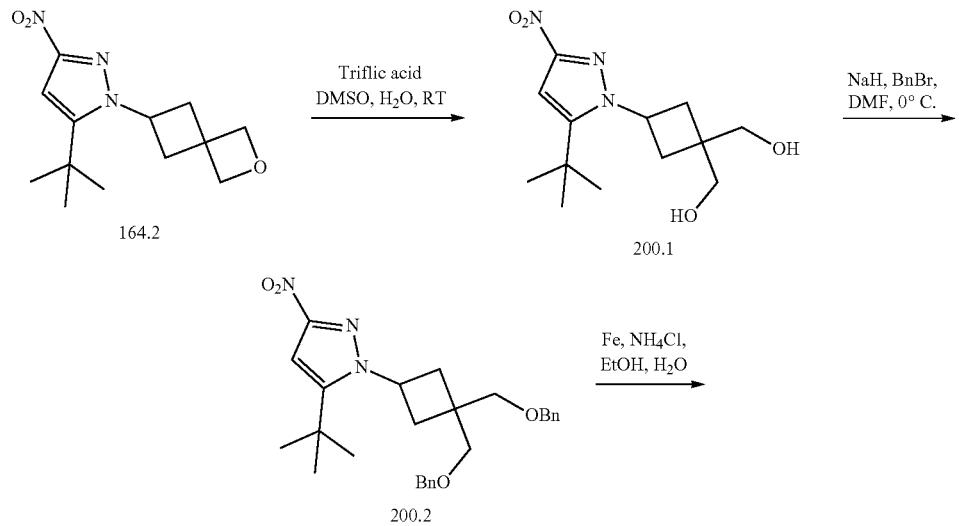

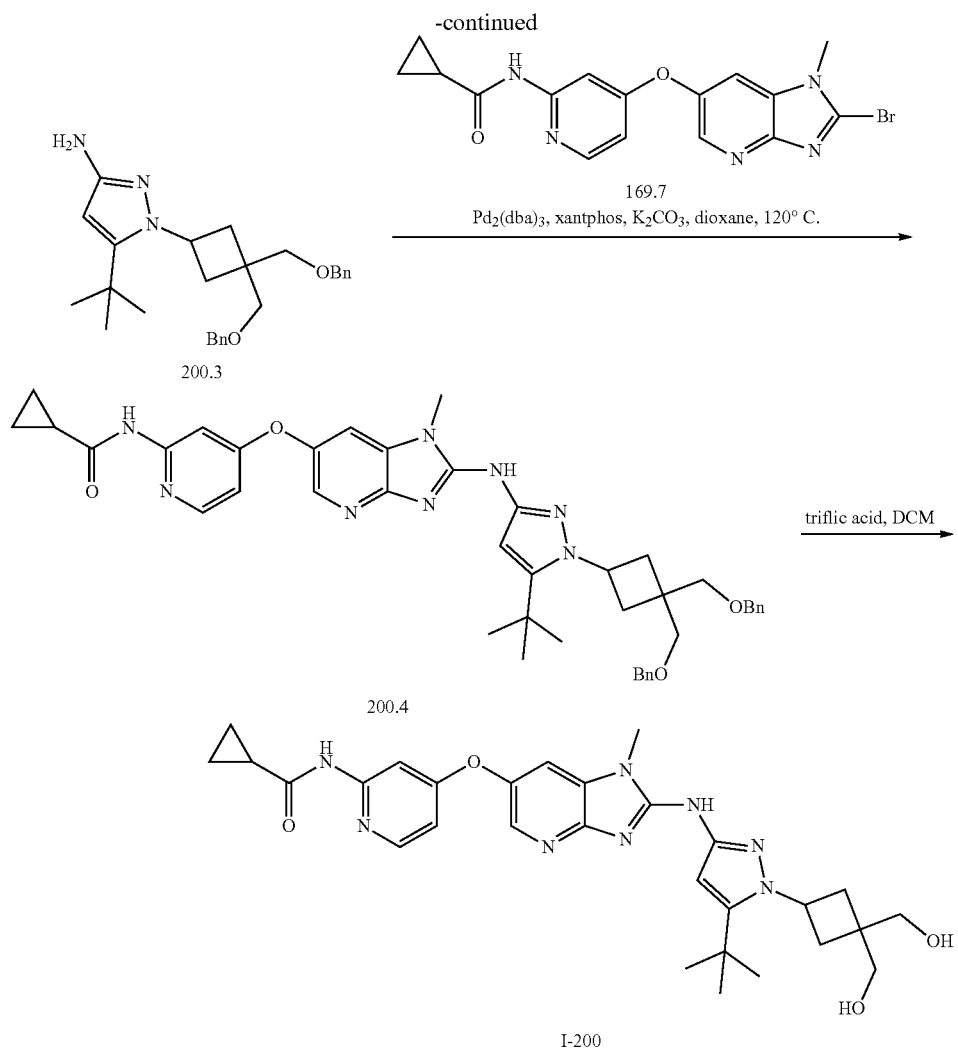

Synthesis of compound 200.1. To a solution of 164.2 (0.4 g, 1.51 mmol, 1.0 equiv) in DMSO (4 mL) and water (0.8 mL) was added trifluoromethanesulfonic acid (0.8 mL). The reaction mixture was stirred at room temperature for 3 h. It was poured over crushed ice-saturated sodium bicarbonate solution, stirred and extracted with ethyl acetate. The combined organic layers were washed with brine, dried over sodium sulfate, filtered and concentrated under reduced pressure. The residue was purified by flash column chromatography on silica gel (CombiFlash®, 70% ethyl acetate in hexane) to afford 200.1. MS (ES): m/z 284.3 [M+H]$^+$.

Synthesis of compound 200.2. To a solution of 200.2 (0.270 g, 0.952 mmol, 1.0 equiv) in DMF (5 mL) was added sodium hydride (0.190 g, 4.76 mmol, 5.0 equiv) in portions at 0° C. and stirred for 30 min followed by the addition of benzyl bromide (0.813 g, 4.76 mmol, 5.0 equiv). The reaction mixture was stirred at room temperature for 1 h. It was poured into a mixture of ice-water, stirred and extracted with ethyl acetate. The combined organic layers were washed with brine, dried over sodium sulfate, filtered and concentrated under reduced pressure. The residue was purified by flash column chromatography on silica gel (CombiFlash®, 20% ethyl acetate in hexane) to afford 200.2. MS (ES): m/z 464.5 [M+H]$^+$.

Synthesis of compound 200.3. To a solution of 200.2 (0.240 g, 0.517 mmol, 1.0 equiv) in ethanol:water (2:1, 8 mL) was added iron powder (0.144 g, 2.585 mmol, 5.0 equiv) followed by ammonium chloride (0.139 g, 2.585 mmol, 5.0 equiv). The reaction mixture was heated at 90° C. for 1 h. It was poured into a mixture of ice-water filtered and extracted with ethyl acetate. The combined organic layers were washed with brine, dried over sodium sulfate, filtered and concentrated under reduced pressure to obtain 200.3. MS(ES): m/z 434.5 [M+H]$^+$.

Synthesis of compound 200.4. Compound I-200 was prepared from compound 200.3 and 169.7 following the procedure described in the synthesis of compound I-108. The product was further purified by flash column chromatography on silica gel (CombiFlash®, 2.8% methanol in DCM) to afford 200.4. MS(ES): m/z: 741.9 [M+H]$^+$.

Synthesis of I-200. To a solution of 200.4 (0.075 g, 0.090 mmol, 1.0 equiv) in DCM (3 mL) was added trifluoromethanesulfonic acid (0.2 mL) at 0° C. and stirred for 5 min. The reaction mixture was poured over crushed ice-cold saturated sodium bicarbonate solution and extracted with DCM. The combined organic layers were washed with brine, dried over sodium sulfate, filtered and concentrated under reduced pressure. The residue was purified by flash column chromatography on silica gel (CombiFlash®, 4.5% methanol in DCM) to afford I-200. MS(ES): m/z 561.3 [M+H]⁺. ¹H NMR (DMSO-d₆, 400 MHz): δ 10.84 (s, 1H), 9.90 (s, 1H), 8.19-8.18 (d, J=6.0 Hz, 1H), 7.91 (s, 1H), 7.52 (s, 1H), 7.65-7.64 (d, J=2.0 Hz, 1H), 6.70-6.68 (m, 1H), 6.56 (s, 1H), 4.96 (bs, 1H), 4.77 (bs, 2H), 3.64 (s, 3H), 3.55 (s, 2H), 3.48 (s, 2H), 2.43-2.41 (m, 2H), 2.23-2.18 (m, 2H), 1.98-1.95 (m, 1H), 1.37 (s, 9H), 0.77-0.75 (m, 4H).

Example 201: N-(4-((7-methoxy-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)cyclopropanecarboxamide

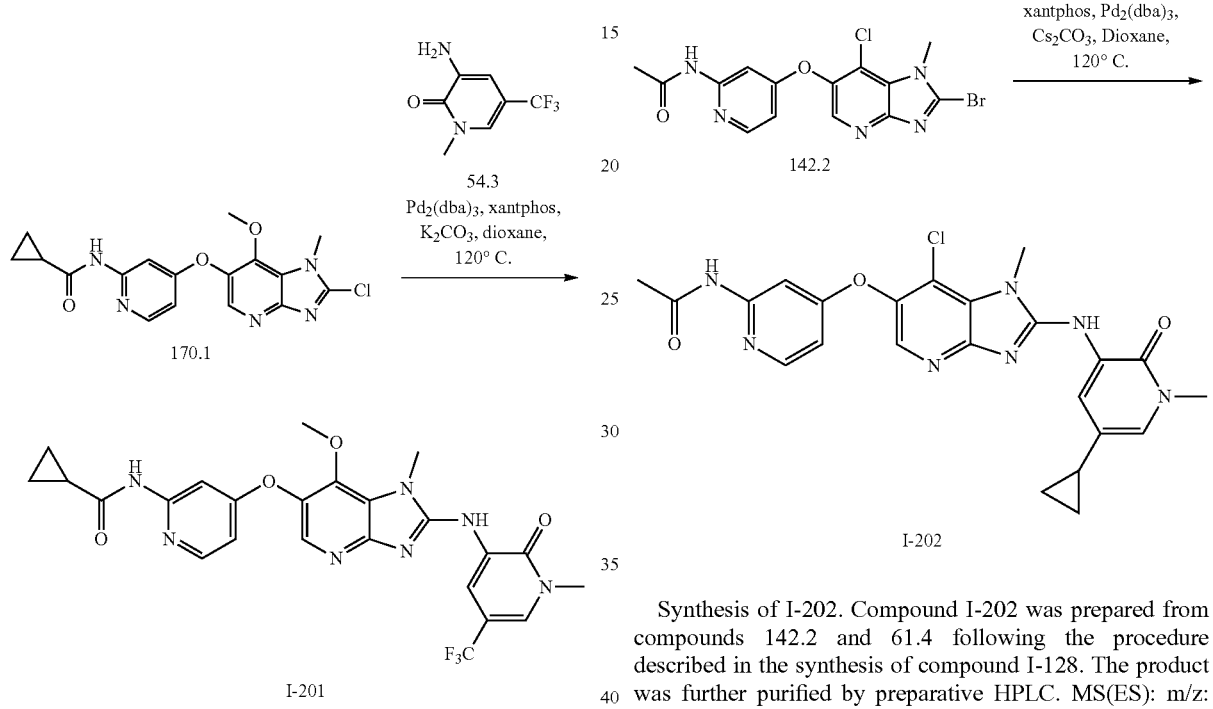

Synthesis of I-201. Compound I-201 was prepared from compounds 170.1 and 54.3 following the procedure described in the synthesis of compound I-108. The product was purified by flash column chromatography on silica gel (CombiFlash®, 2.6% methanol in DCM). MS(ES): m/z: 530.2 [M+H]⁺, ¹H NMR (DMSO-d₆, 400 MHz): δ 10.90 (s, 1H), 8.65 (s, 2H), 8.22-8.20 (d, J=5.6 Hz, 1H), 8.12 (s, 1H), 8.07 (s, 1H), 7.67 (s, 1H), 6.72-6.71 (m, 1H), 3.96 (s, 3H), 3.91 (s, 3H), 3.66 (s, 3H), 1.97 (bs, 1H), 0.75 (bs, 4H).

Example 202: N-(4-((7-chloro-2-((5-cyclopropyl-1-methyl-2-oxo-1,2-dihydropyridin-3-yl)amino)-1-methyl-1H-imidazo[4,5-b]pyridin-6-yl)oxy)pyridin-2-yl)acetamide

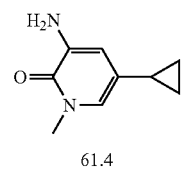

Synthesis of I-202. Compound I-202 was prepared from compounds 142.2 and 61.4 following the procedure described in the synthesis of compound I-128. The product was further purified by preparative HPLC. MS(ES): m/z: 480.4 [M]⁺, ¹H NMR (DMSO-d₆, 400 MHz): δ 10.60 (s, 1H), 8.56 (s, 1H), 8.31 (s, 1H), 8.20-8.19 (d, J=4.8 Hz, 2H), 7.66 (s, 1H), 7.26 (bs, 1H), 6.68-6.66 (m, 1H), 3.97 (s, 3H), 3.56 (s, 3H), 2.05 (s, 3H), 1.86-1.81 (m, 1H), 0.91-0.85 (m, 2H), 0.62-0.59 (m, 2H).

Example I-203: N-(4-((7-chloro-2-((4-((4-ethylpiperazin-1-yl)methyl)-3-(trifluoromethyl)phenyl)amino)-1-methyl-1H-imidazo[4,5-b]pyridin-6-yl)oxy)pyridin-2-yl)acetamide

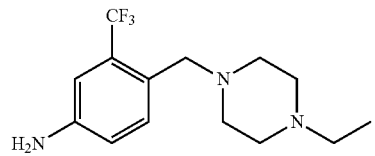

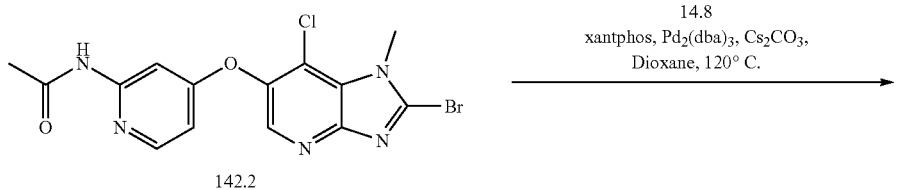

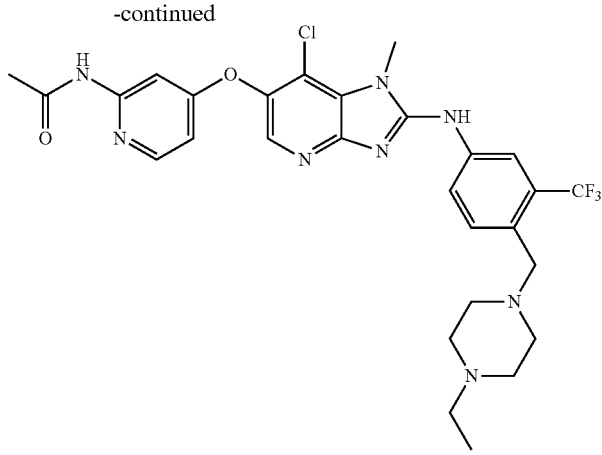

I-203

Synthesis of I-203. Compound I-203 was prepared from compound 142.2 and 14.8 following the procedure described in the synthesis of compound I-128. The product was further purified by preparative HPLC. MS(ES): m/z: 603.5 [M]$^+$, $^1$H NMR (DMSO-d$_6$, 400 MHz): δ 10.61 (s, 1H), 9.68 (s, 1H), 8.31 (s, 1H), 8.21-8.16 (m, 3H), 7.75-7.73 (d, J=8.4 Hz, 1H), 7.67 (s, 1H), 6.68-6.67 (m, 1H), 4.01 (bs, 4H), 3.59 (s, 3H), 3.35 (bs, 4H), 2.34 (s, 3H), 2.05 (s, 4H), 1.02-0.98 (t, 3H).

Example 204: N-(4-((7-chloro-1-methyl-2-((1-(3-morpholinopropyl)-2-oxo-5-(trifluoromethyl)-1,2-dihydropyridin-3-yl)amino)-1H-imidazo[4,5-b]pyridin-6-yl)oxy)pyridin-2-yl)acetamide

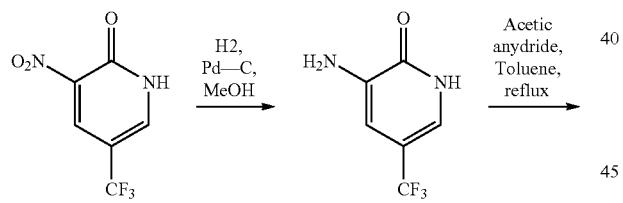

204.1

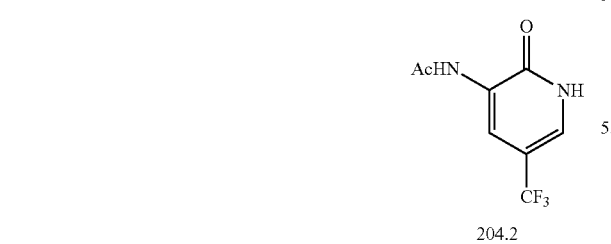

204.2

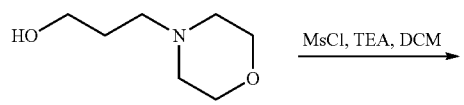

MsCl, TEA, DCM

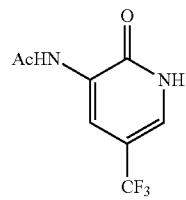

204.2

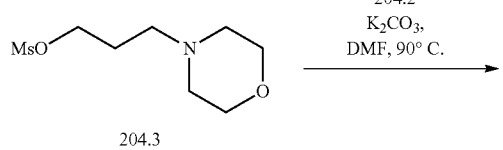

204.3

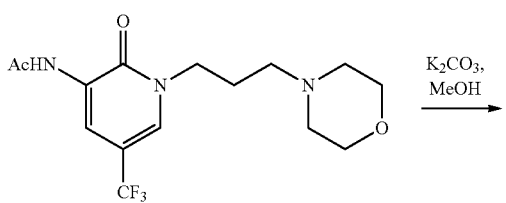

204.4

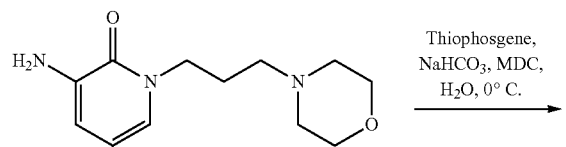

204.5

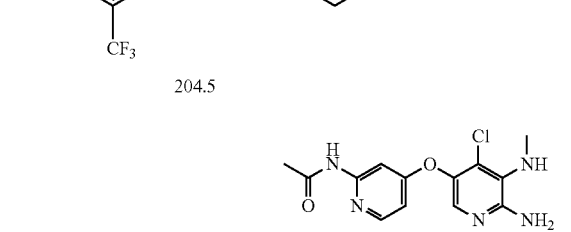

204.6

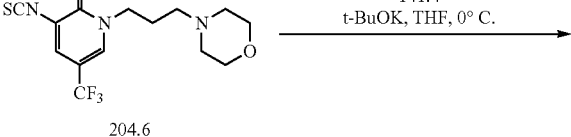

141.4
t-BuOK, THF, 0° C.

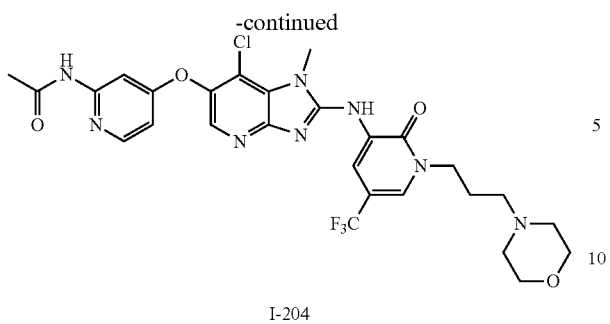

I-204

Synthesis of compound 204.1. A mixture of 54.2 (8.0 g, 38.44 mmol, 1.0 equiv) and 10% palladium on carbon (3.0 g) in methanol (30 mL) was stirred under hydrogen (1 atm) at rt for 2 h. The reaction mixture was filtered through a pad of Celite® and rinsed with methanol. The filtrate was concentrated under reduced pressure to afford 204.1. MS(ES): m/z 179.1 [M+H]$^+$.

Synthesis of compound 204.2. A solution of 204.1 (6.5 g, 36.49 mmol, 1.0 equiv) in toluene (25 mL) was added acetic anhydride (17 mL, 182.45 mmol, 5.0 equiv) and the reaction mixture was heated to reflux for 2 h. It was cooled to rt and concentrated under reduced pressure. The residue was purified by trituration with diethyl ether to afford 204.2. MS (ES): m/z 221.3 [M+H]$^+$.

Synthesis of compound 204.3. To a solution of 3-morpholinopropan-1-ol (2.0 g, 13.77 mmol, 1.0 equiv) and triethylamine (4.79 mL, 34.42 mmol, 2.5 equiv) in DCM (20 mL) at 0° C. was added methanesulfonyl chloride (1.4 mL, 17.90 mmol, 1.3 equiv). The reaction mixture was stirred at room temperature for 1 h. It was transferred into ice-water, stirred and extracted with dichloromethane. The combined organic layers were washed with brine, dried over sodium sulfate, filtered and concentrated under reduced pressure to afford 204.3. MS (ES): m/z 224.2 [M+H]$^+$.

Synthesis of compound 204.4 To a solution of 204.2 (2.0 g, 9.08 mmol, 1.0 equiv) in DMF (20 mL) was added potassium carbonate (3.75 g, 27.24 mmol, 3.0 equiv), followed by 204.3 (2.43 g, 10.90 mmol, 1.2 equiv). The reaction mixture stirred at 90° C. for 12 h. It was transferred into ice-water and extracted with ethyl acetate. The combined organic layers were washed with brine, dried over sodium sulfate, filtered and concentrated under reduced pressure. The residue was purified by flash column chromatography on silica gel (CombiFlash®, 1.4% methanol in DCM) to afford 204.4. MS(ES): m/z 348.2 [M+H]$^+$.

Synthesis of compound 204.5. A mixture of 204.4 (0.500 g, 1.44 mmol, 1.0 equiv) and potassium carbonate (3.97 g, 28.8 mmol, 20 equiv) in methanol (10 mL) was heated to reflux for 16 h. The reaction mixture was transferred into ice-water and extracted with ethyl acetate. The combined organic layers were washed with brine, dried over sodium sulfate, filtered and concentrated under reduced pressure. The residue was purified by flash column chromatography on silica gel (CombiFlash®, 2.6% methanol in DCM) to afford 204.5. MS(ES): m/z 306.3 [M+H]$^+$.

Synthesis of compound 204.6. Compound 204.6 was prepared from 204.5 following the procedure described in the synthesis of 11.8. The crude product was used in the next step without further purification. MS(ES): m/z:348.3 [M+H]$^+$.

Synthesis of I-204. To a solution of 141.4 (0.070 g, 0.227 mmol, 1.0 equiv) and 204.6 (0.095 g, 0.272 mmol, 1.2 equiv) in THF (3 mL) was added potassium tert-butoxide (1 M in THF) (0.68 mL, 0.681 mmol, 3.0 equiv) at 0° C. The reaction mixture was stirred at room temperature for 16 h. It was transferred into ice-water and extracted with ethyl acetate. The combined organic layers were washed with brine, dried over sodium sulfate, filtered and concentrated under reduced pressure. The residue was purified by flash column chromatography on silica gel (CombiFlash®, 2.8% methanol in DCM) to afford I-204. MS(ES): m/z: 621.3 [M]$^+$, $^1$H NMR (DMSO-d$_6$, 400 MHz): δ 10.61 (s, 1H), 8.87 (s, 1H), 8.64-8.63 (d, J=2.0 Hz, 1H), 8.24 (s, 1H), 8.19-8.18 (d, J=5.6 Hz, 1H), 8.14 (s, 1H), 7.65 (s, 1H), 6.67-6.65 (m, 1H), 4.17-4.14 (m, 2H), 3.98 (s, 3H), 3.55 (bs, 4H), 2.32 (bs, 6H), 2.03 (s, 3H), 1.94-1.90 (m, 2H).

Example I-205: N-(4-((7-chloro-1-methyl-2-((4-(morpholinomethyl)-3-(trifluoromethyl)phenyl)amino)-1H-imidazo[4,5-b]pyridin-6-yl)oxy)pyridin-2-yl)acetamide

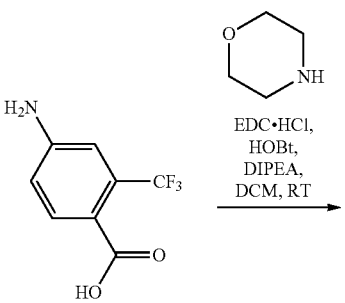

EDC·HCl, HOBt, DIPEA, DCM, RT

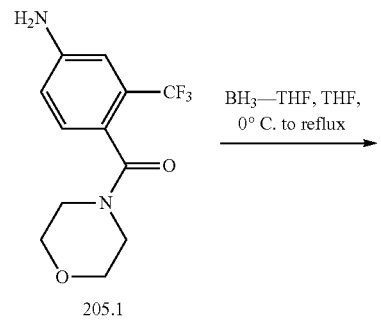

205.1

BH$_3$—THF, THF, 0° C. to reflux

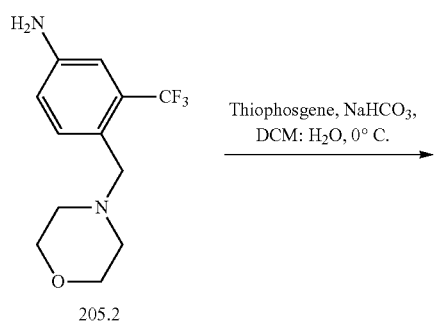

205.2

Thiophosgene, NaHCO$_3$, DCM: H$_2$O, 0° C.

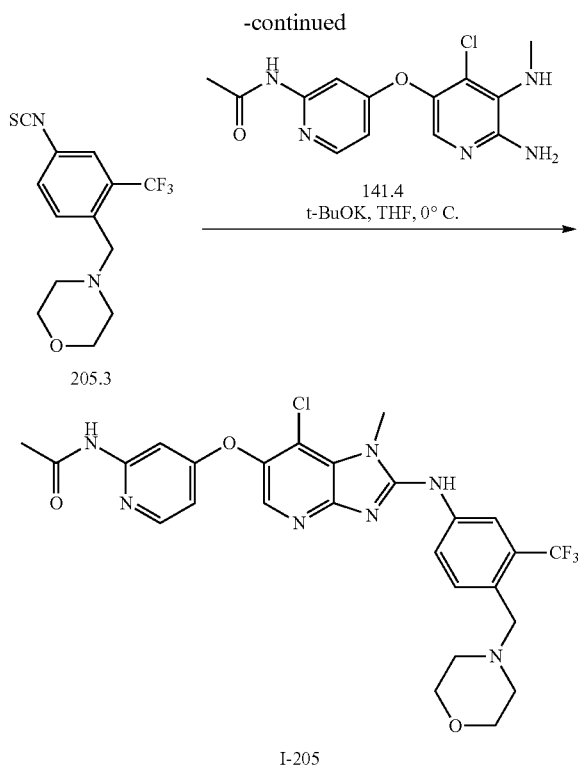

Synthesis of compound 205.1. To a solution of 4-amino-2-(trifluoromethyl)benzoic acid (3.0 g, 14.62 mmol, 1.0 equiv) and morpholine (1.91 g, 21.93 mmol, 1.5 equiv) in DCM (60 mL) was added 1-hydroxybenzotriazole (2.96 g, 21.93 mmol, 1.5 equiv), 1-ethyl-3-(3-dimethylaminopropyl) carbodiimide hydrochloride (4.18 g, 21.93 mmol, 1.5 equiv), N,N-diisopropylethylamine (5.65 g, 43.86 mmol, 3.0 equiv) and stirred at room temperature for 3 h. The reaction mixture was poured over ice-water, stirred and extracted with ethyl acetate. The combined organic layers were washed with brine, dried over sodium sulfate, filtered and concentrated under reduced pressure. The residue was purified by flash column chromatography on silica gel (CombiFlash®, 1.2% methanol in DCM) to afford 205.1. MS (ES): m/z 275.2 [M+H]$^+$.

Synthesis of compound 205.2. To a solution of 205.1 (1 g, 3.65 mmol, 1.0 equiv) in THF (10 mL) was added borane-THF (1.04 mL, 10.95 mmol, 3.0 equiv) at 0° C. The reaction mixture was heated to reflux for 3 h. It was cooled to room temperature, and a solution of 6 N hydrochloric acid (5 mL) was added. It was heated to reflux for another 2 h, cooled to room temperature, poured into ice-water and extracted with ethyl acetate. The combined organic layers were washed with brine, dried over sodium sulfate, filtered and concentrated under reduced pressure. The residue was purified by flash column chromatography on silica gel (CombiFlash®, 1.0% methanol in DCM) to afford 205.2. MS(ES): m/z 261.3 [M+H]$^+$.

Synthesis of compound 205.3. Compound 205.3 was prepared from 205.2 following the procedure described in the synthesis of 11.8. The crude product was purified by flash column chromatography on silica gel (CombiFlash®, 40% ethyl acetate in hexane). MS(ES): m/z 303.3 [M+H]$^+$.

Synthesis of I-205. Compound I-205 was prepared from 205.3 and 141.4 following the procedure described in the synthesis of 1-204. The product was purified by flash column chromatography on silica gel (CombiFlash®, 2.8% methanol in DCM). MS(ES): m/z: 575.8 [M]$^+$, $^1$H NMR (DMSO-d$_6$, 400 MHz): δ 10.62 (s, 1H), 9.71 (s, 1H), 8.31 (s, 1H), 8.21-8.16 (m, 3H), 7.77-7.74 (d, J=8.8 Hz, 1H), 7.67 (s, 1H), 6.68-6.66 (m, 1H), 4.00 (s, 3H), 3.62-3.60 (m, 6H), 2.41 (bs, 4H), 2.05 (s, 3H).

Example 206: N-(4-((7-methoxy-1-methyl-2-((1-(3-morpholinopropyl)-2-oxo-5-(trifluoromethyl)-1,2-dihydropyridin-3-yl)amino)-1H-imidazo[4,5-b]pyridin-6-yl)oxy)pyridin-2-yl)acetamide

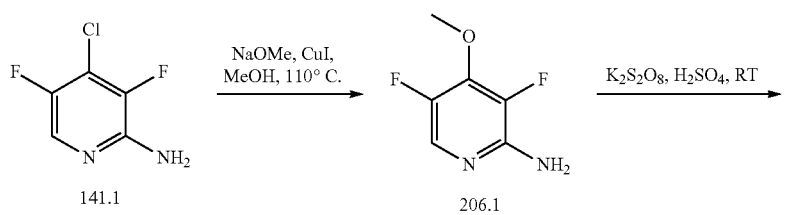

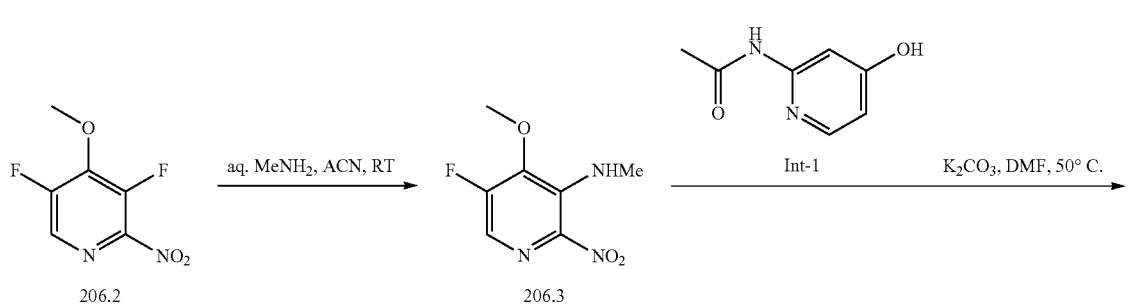

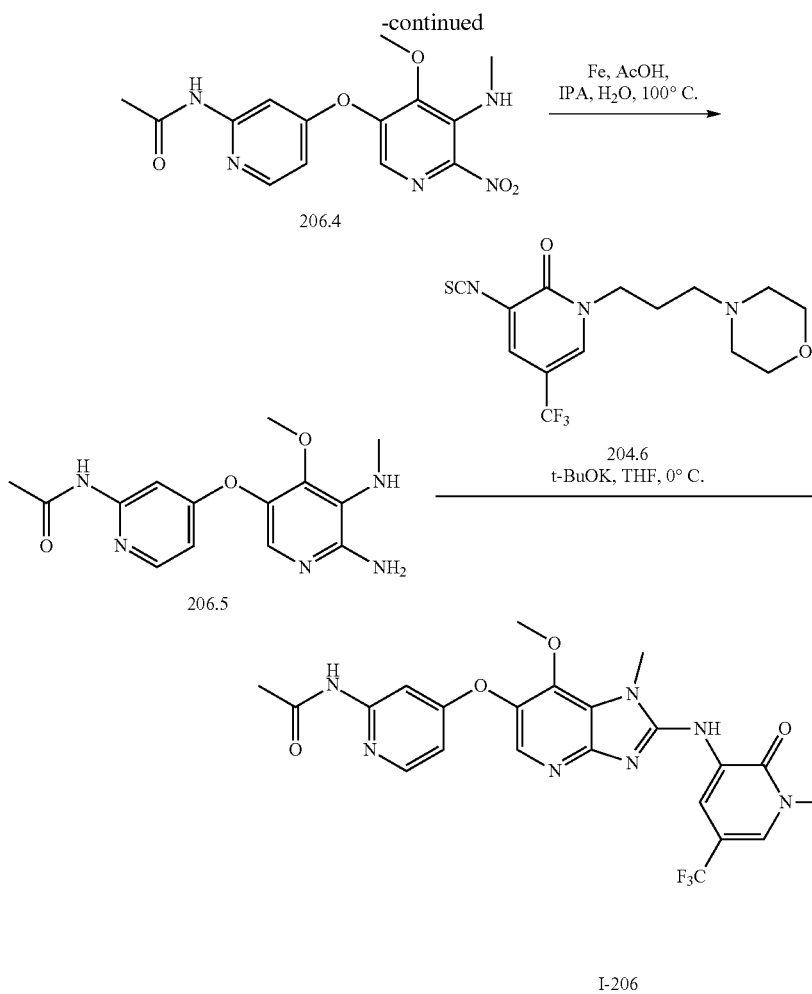

Synthesis of compound 206.1. To compound 141.1 (1.0 g, 6.08 mmol, 1.0 equiv) was added 0.5 M sodium methoxide solution in methanol (30 mL, 15.2 mmol, 2.5 equiv) and copper iodide (0.231 g, 1.216 mmol, 0.2 equiv). The reaction mixture was stirred at 110° C. for 24 h. It was cooled to room temperature, concentrated under reduced pressure. The residue was purified by flash column chromatography on silica gel (CombiFlash®, 18% ethyl acetate in hexane) to afford 206.1. MS(ES): m/z: 161 [M+H]$^+$.

Synthesis of compound 206.2. Concentrated sulfuric acid (6.6 mL, 6 vol.) was added dropwise to potassium persulfate (3.7 g, 13.74 mmol, 2.0 equiv) at room temperature and stirred for 15 min. To this solution was added 206.1 (1.1 g, 6.87 mmol, 1.0 equiv) in portions, while maintaining temperature between 30-40° C. The reaction mixture was stirred at room temperature for 24 h. It was transferred into crushed ice, stirred and basified with saturated sodium bicarbonate and extracted with ethyl acetate. The combined organic layers were washed with brine, dried over sodium sulfate, filtered and concentrated under reduced pressure. The residue was purified by flash column chromatography on silica gel (CombiFlash®, 6-8% ethyl acetate in hexane) to afford 206.2. $^1$H NMR (DMSO-$d_6$, 400 MHz): δ 8.52 (s, 1H), 4.26 (s, 3H).

Synthesis of compound 206.3. To a solution of 206.2 (0.165 g, 0.867 mmol, 1.0 equiv) in acetonitrile (1.5 mL) was added aqueous methylamine solution (40%, 0.1 mL, 1.30 mmol, 1.5 equiv) dropwise at 0° C. The reaction mixture was stirred at room temperature for 10-20 min. The reaction mixture was poured over crushed ice-water and extracted with ethyl acetate. The combined organic layers were washed with brine, dried over sodium sulfate, filtered and concentrated under reduced pressure to obtain 206.3. MS(ES): m/z: 201.9 [M+H]$^+$.

Synthesis of compound 206.4. A mixture of 206.3 (0.112 g, 0.556 mmol, 1.0 equiv), Int-1 (0.101 g, 0.668 mmol, 1.2 equiv) and potassium carbonate (0.230 g, 1.668 mmol, 3.0 equiv) in DMF (3 mL) was stirred at 50-60° C. for 5-6 h. The reaction mixture was cooled to room temperature and transferred into ice-water. The precipitated solids were collected by filtration, rinsed with water and dried to afford 206.4. MS(ES): m/z 334.2 [M+H]$^+$.

Synthesis of compound 206.5. To a solution of compound 206.5 (0.140 g, 0.420 mmol, 1.0 equiv) in isopropyl alcohol:water (8:2, 10 mL) was added iron powder (0.141 g, 2.52 mmol, 6.0 equiv) followed by acetic acid (0.151 g, 2.52 mmol, 6.0 equiv). The reaction mixture was heated at 100° C. for 3 h. It was filtered through a pad of Celite® and rinsed with isopropyl alcohol. The filtrate was concentrated under reduced pressure. The residue was purified by flash column chromatography on silica gel (CombiFlash®, 2.5% methanol in DCM) to afford 206.5. MS(ES): m/z 304.3 [M+H]$^+$.

Synthesis of I-206. Compound I-206 was prepared from 206.5 and 204.6 following the procedure described in the synthesis of I-204. The product was purified by flash column chromatography on silica gel (CombiFlash®, 2.5% methanol in DCM). MS(ES): m/z: 617.5 [M+H]⁺, ¹H NMR (DMSO-d₆, 400 MHz): δ 10.60 (s, 1H), 8.68 (s, 1H), 8.66-8.65 (d, J=1.6 Hz, 1H), 8.20-8.19 (d, J=5.6 Hz, 1H), 8.11 (s, 1H), 8.08 (s, 1H), 7.70 (s, 1H), 6.69-6.67 (m, 1H), 4.18-1.14 (m, 2H), 3.96 (s, 3H), 3.91 (s, 3H), 3.56 (bs, 4H), 2.34 (bs, 6H), 2.05 (s, 3H), 1.95-1.92 (m, 2H).

Example 207: N-(4-((7-cyano-2-((5-cyclopropyl-1-methyl-2-oxo-1,2-dihydropyridin-3-yl)amino)-1-methyl-1H-imidazo[4,5-b]pyridin-6-yl)oxy)pyridin-2-yl)acetamide Example 208: N-(4-((7-chloro-2-((4,4-dimethyl-4,5,6,7-tetrahydropyrazolo[1,5-a]pyridin-2-yl)amino)-1-methyl-1H-imidazo[4,5-b]pyridin-6-yl)oxy)pyridin-2-yl)acetamide

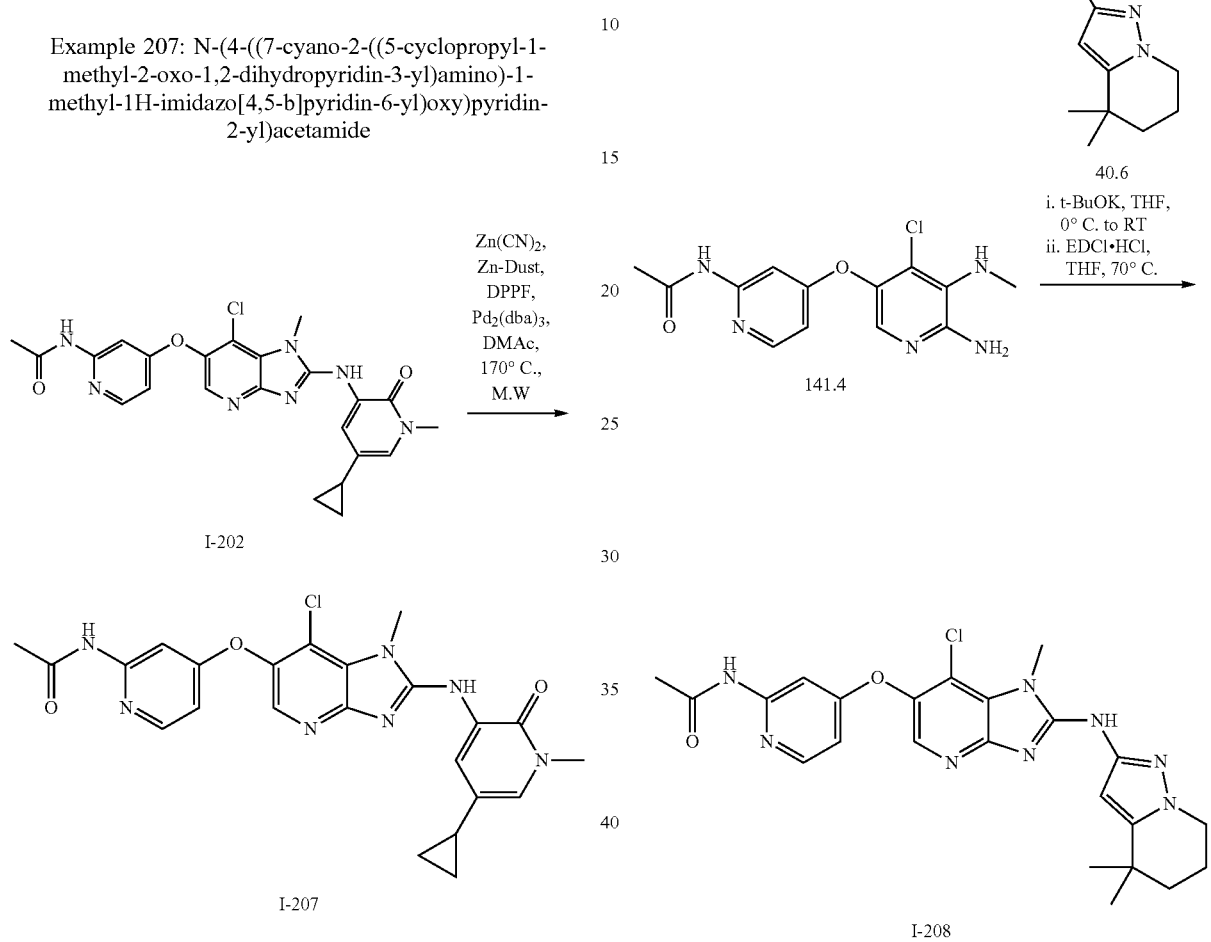

Synthesis of I-207. A mixture of I-202 (0.190 g, 0.395 mmol, 1.0 equiv), zinc dust (0.005 g, 0.079 mmol, 0.2 equiv) and zinc cyanide (0.231 g, 1.975 mmol, 5.0 equiv) in dimethylacetamide (6 mL) was degassed by bubbling through argon for 10 min. Under argon atmosphere, 1,1'-ferrocenediyl-bis(diphenylphosphine) (0.065 g, 0.118 mmol, 0.3 equiv) and tris(dibenzylideneacetone)dipalladium(0) (0.054 g, 0.059 mmol, 0.15 equiv) were added and degassed for another 5 min. The reaction mixture was stirred at 170° C. in a microwave reactor for 30 min. It was cooled to room temperature, transferred into water and extracted with ethyl acetate. The combined organic layers were washed with brine, dried over sodium sulfate, filtered and concentrated under reduced pressure. The residue was purified by flash column chromatography on silica gel (CombiFlash®, 2.7% methanol in DCM) to afford I-207. MS(ES): m/z:471.2 [M]⁺, ¹H NMR (DMSO-d₆, 400 MHz): δ 10.67 (s, 1H), 8.75 (s, 1H), 8.31 (s, 1H), 8.28 (s, 1H), 8.26-8.24 (d, J=6.0 Hz, 1H), 7.76 (s, 1H), 7.31 (s, 1H), 6.77-6.76 (d, J=3.2 Hz, 1H), 3.94 (s, 3H), 3.57 (s, 3H), 2.07 (s, 3H), 1.84 (bs, 1H), 0.90-0.87 (m, 2H), 0.61-0.60 (m, 2H).

Synthesis of compound I-208. To a solution of 141.4 (0.500 g, 1.62 mmol, 1.0 equiv) and 40.6 (0.370 g, 1.79 mmol, 1.1 equiv) in THF (5 mL) was added potassium tert-butoxide (1 M in THF, 3.24 mL, 3.24 mmol, 2.0 equiv) at 0° C. The reaction mixture was stirred at room temperature for 30 min. The reaction mixture was transferred into ice-water, and product was extracted with ethyl acetate. The combined organic layers were washed with brine, dried over sodium sulfate, filtered and concentrated under reduced pressure. The residue was dissolved in THF (5 mL) and added N-(3-dimethylaminopropyl)-N'-ethylcarbodiimide hydrochloride (0.928 g, 4.86 mmol, 3.0 equiv). The reaction mixture was heated at 70° C. for 4 h. The reaction mixture transferred into water, and product was extracted with ethyl acetate. The combined organic layers were washed with brine, dried over sodium sulfate, filtered and concentrated under reduced pressure. The residue was purified by flash column chromatography on silica gel (CombiFlash®, 3.0% methanol in DCM) to afford I-208. MS(ES): m/z: 481.6 [M+H]⁺.

Example 209: N-(4-((7-chloro-2-((4,4-dimethyl-4,5,6,7-tetrahydropyrazolo[1,5-c]pyridin-2-yl)amino)-1-methyl-1H-imidazo[4,5-b]pyridin-6-yl)oxy)pyridin-2-yl)acetamide

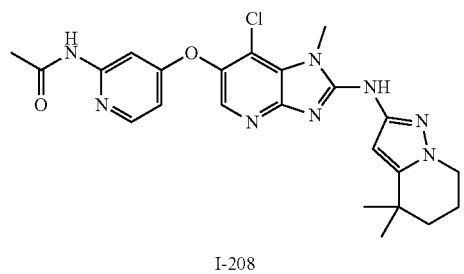
I-208

Zn(CN)₂, Zn-Dust, DPPF, Pd₂(dba)₃, DMAc, 170° C., M.W →

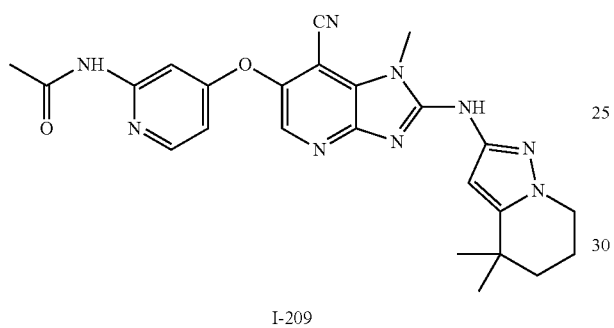
I-209

Synthesis of I-209. Compound I-209 was prepared from I-208 following the procedure described in the synthesis of 1-207. The product was purified by flash column chromatography on silica gel (CombiFlash®, 3.2% methanol in DCM). MS(ES): m/z:472.0 [M]⁺, ¹H NMR (DMSO-d₆, 400 MHz): δ 10.65 (s, 1H), 10.38 (s, 1H), 8.24-8.23 (d, J=5.2 Hz, 2H), 7.76 (s, 1H), 7.09-7.08 (d, J=6.0 Hz, 1H), 6.74 (bs, 1H), 3.98 (bs, 2H), 3.90 (s, 3H), 2.06 (s, 3H), 1.69 (bs, 2H), 1.56 (bs, 2H), 1.34 (s, 6H).

Example 210: N-(4-((7-chloro-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide

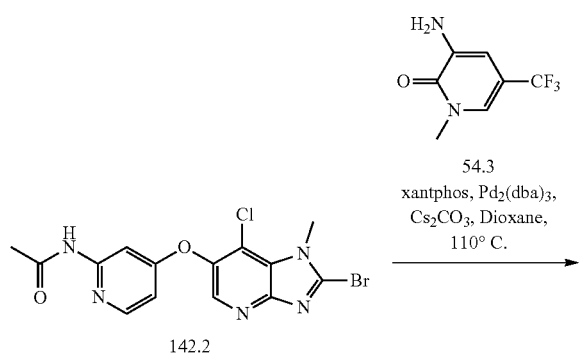
54.3
xantphos, Pd₂(dba)₃, Cs₂CO₃, Dioxane, 110° C. →

142.2

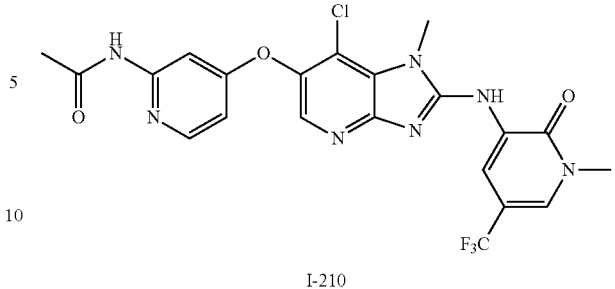
I-210

Synthesis of compound I-210. Compound I-210 was prepared from compound 142.2 and 54.3 following the procedure described in the synthesis of compound I-128. The product was purified by flash column chromatography on silica gel (CombiFlash®, 2.3% methanol in DCM). MS(ES): m/z:508.2 [M]⁺.

Example 211: N-(4-((7-chloro-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide

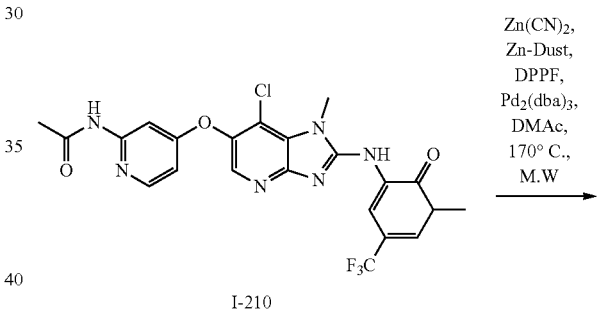
I-210

Zn(CN)₂, Zn-Dust, DPPF, Pd₂(dba)₃, DMAc, 170° C., M.W →

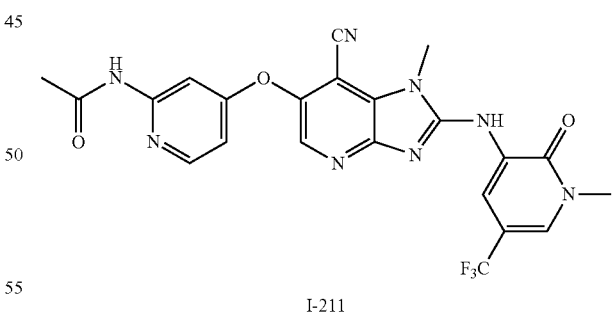
I-211

Synthesis of I-211. Compound I-211 was prepared from I-210 following the procedure described in the synthesis of 1-207. The product was further purified by flash column chromatography on silica gel (CombiFlash®, 2.5% methanol in DCM). MS(ES): m/z:499.0 [M]⁺, ¹H NMR (DMSO-d₆, 400 MHz): δ 10.67 (s, 1H), 9.06 (s, 1H), 8.65 (s, 1H), 8.32 (s, 1H), 8.25-8.23 (d, J=5.6 Hz, 1H), 8.19 (s, 1H), 7.75 (s, 1H), 6.76-6.75 (m, 1H), 3.96 (s, 3H), 3.66 (s, 3H), 2.06 (s, 3H).

Example 212: (S)—N-(4-((7-chloro-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)-2-(tetrahydro-2H-pyran-2-yl)acetamide and (R—N-(4-((7-chloro-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)-2-(tetrahydro-2H-pyran-2-yl)acetamide

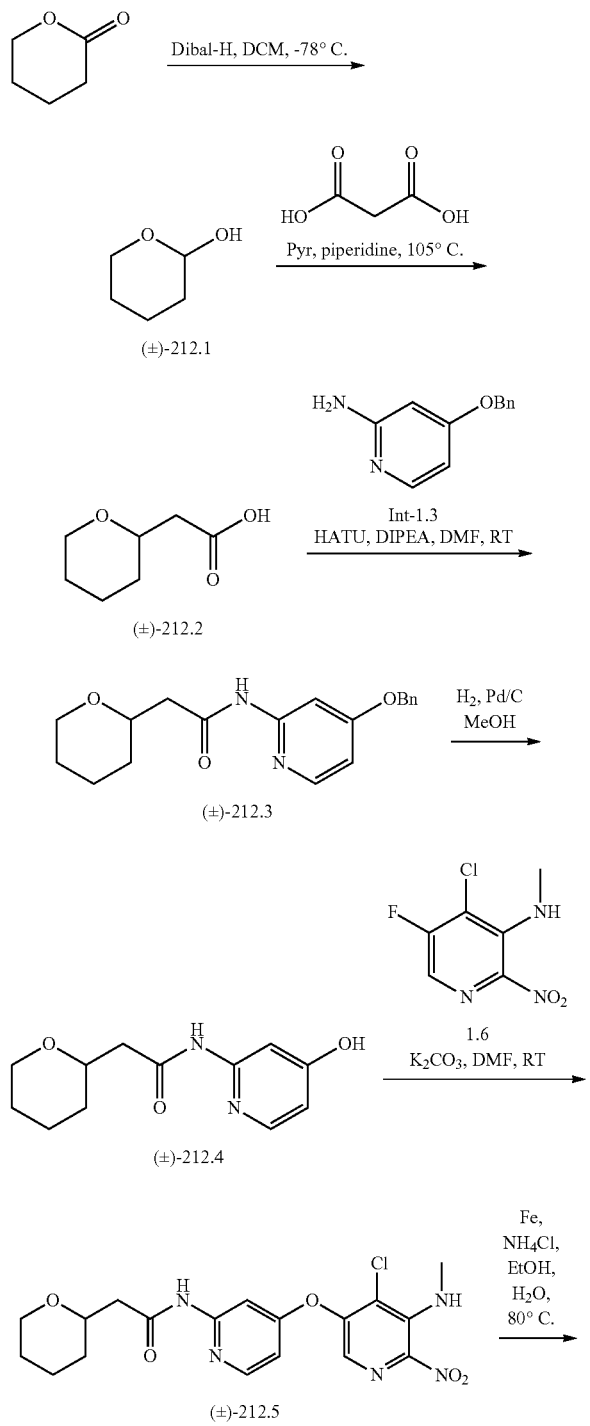

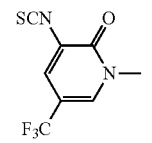

Synthesis of compound (±)-212.1. To a solution of δ-valerolactone (10.0 g, 99.88 mmol, 1.0 equiv) in DCM (300 mL) was added diisobutylaluminium hydride (1M in DCM, 120 mL, 119.85 mmol, 1.2 equiv) at −78° C. and stirred for 2 h. The reaction was quenched by the addition of methanol (30 mL) followed by saturated potassium sodium tartrate solution (100 mL). The precipitated solids were removed by filtration and the filtrate was extracted with ethyl acetate. The combined organic layers were washed with brine, dried over sodium sulfate, filtered and concentrated under reduced pressure to afford (±)-212.1. It was used in the next step without further purification. $^1$H NMR (DMSO-$d_6$, 400 MHz): δ 6.17-6.15 (m, 1H), 4.65 (bs, 1H), 3.84-3.81 (m, 1H), 3.38-3.34 (m, 1H), 1.73-1.57 (m, 2H), 1.45-1.32 (m, 4H).

Synthesis of compound (±)-212.2. A mixture of (±)-212.1 (8.0 g, 78.33 mmol, 1.0 equiv), malonic acid (9.78 g, 94 mmol, 1.2 equiv), pyridine (13 mL, 161 mmol, 2.06 equiv) and piperidine (0.77 mL, 7.833 mmol, 0.1 equiv) was stirred at room temperature for 16 h. It was stirred at 105° C. for another 4 h. The reaction mixture was cooled to rt, transferred into aqueous hydrochloric acid (2 N), and extracted with ethyl acetate. The combined organic layers were washed with brine, dried over sodium sulfate, filtered and concentrated under reduced pressure. The residue was purified by flash column chromatography on silica gel (CombiFlash®, 50% ethyl acetate in hexane) to afford (±)-212.2. $^1$H NMR (CDCl$_3$, 400 MHz): δ 4.24-4.11 (m, 1H), 3.71-3.68 (m, 1H), 3.40 (bs, 1H), 2.29-2.28 (m, 1H), 2.06 (bs, 1H), 1.72-1.67 (m, 1H), 1.61-1.57 (m, 4H), 1.29-1.26 (m, 1H).

Synthesis of compound (±)-212.3. To a solution of (±)-212.2 (1.6 g, 11.1 mmol, 1.0 equiv) and Int-1.3 (2.44 g, 12.21 mmol, 1.1 equiv) in DMF (20 mL) was added HATU (6.32 g, 16.65 mmol, 1.5 equiv) and reaction mixture stirred at room temperature for 30 min. To this was added N,N- diisopropylethylamine (4.8 mL, 27.75 mmol, 2.5 equiv). The reaction mixture was stirred at room temperature for 16 h. It was poured into ice-water and extracted with ethyl acetate. The combined organic layers were washed with brine solution, dried over sodium sulfate, filtered and concentrated under reduced pressure. The residue was purified by flash column chromatography on silica gel (CombiFlash®, 45% ethyl acetate in hexane) to afford (±)-212.3. MS(ES): m/z 327.2 [M+H]$^+$.

Synthesis of compound (±)-212.4. A mixture of compound (±)-212.3 (0.565 g, 1.73 mmol, 1.0 equiv) and 10% palladium on carbon (0.25 g) in methanol (15 mL) was stirred under hydrogen (1 atm) for 2 h. The reaction mixture was filtered through a pad of Celite® and washed with methanol. The filtrate was concentrated under reduced pressure to afford (±)-212.4. MS(ES): m/z 237.5 [M+H]$^+$.

Synthesis of compound (±)-212.5. A mixture of (±)-212.4 (0.340 g, 1.44 mmol, 1.0 equiv), 141.3 (0.295 g, 1.44 mmol, 1.0 equiv) and potassium carbonate (0.397 g, 2.88 mmol, 2.0 equiv) in DMF (5 mL) was stirred at room temperature for 1 h. It was transferred into water and extracted with ethyl acetate. The combined organic layers were washed with brine solution, dried over sodium sulfate, filtered and concentrated under reduced pressure. The residue was purified by flash column chromatography on silica gel (CombiFlash®, 3.5% methanol in DCM) to afford (±)-212.5. MS(ES): m/z 422.2 [M+H]$^+$.

Synthesis of compound (±)-212.6. To a solution of (±)-212.5 (0.260 g, 0.616 mmol, 1.0 equiv) in ethanol:water (2:1, 10 mL) was added iron powder (0.172 g, 3.08 mmol, 5.0 equiv) followed by ammonium chloride (0.166 g, 3.08 mmol, 5.0 equiv). The reaction mixture was stirred at 80° C. for 1 h. It was transferred into ice-water, filtered and extracted with ethyl acetate. The combined organic layers were washed with brine solution, dried over sodium sulfate, filtered and concentrated under reduced pressure. The residue was purified by flash column chromatography on silica gel (CombiFlash®, 4.2% methanol in DCM) to afford (±)-212.6. MS(ES): m/z 392.1 [M+H]$^+$.

Synthesis of compound (±)-I-212. Compound (±)-I-212 was prepared from (±)-212.6 and 54.4 following the procedure described in the synthesis of I-204. The product was purified by flash column chromatography on silica gel (CombiFlash®, 3.3% methanol in DCM). MS(ES): m/z: 592.5 [M+H]$^+$.

Synthesis of compounds I-212a and I-212b. The racemate (±)-I-212 was separated by HPLC (column CHIRALCEL OX-H (250 mm*21 mm, 5 μm); mobile phase: (A) 0.1% DEA in n-hexane (B) 0.1% DEA in isopropanol:acetonitrile (70:30); flow rate: 20 mL/min) to afford first eluting fraction (I-212-a) and second eluting fraction (I-212-b). (*Absolute stereochemistry not determined.)

I-212-a: MS(ES): m/z: 592.2 [M+H]$^+$; $^1$H NMR (DMSO-d$_6$, 400 MHz): δ 10.52 (s, 1H), 8.85 (s, 1H), 8.65 (s, 1H), 8.25 (s, 1H), 8.21-8.20 (d, J=5.2 Hz, 1H), 8.16 (s, 1H), 7.68 (s, 1H), 6.71-6.70 (d, J=4.8 Hz, 1H), 4.00 (s, 3H), 3.82-3.79 (m, 1H), 3.68 (s, 3H), 3.30 (bs, 2H), 2.42-2.34 (m, 2H), 1.74 (bs. 1H), 1.58-1.55 (m, 1H), 1.43 (bs, 2H), 1.25-1.18 (m, 2H).

I-212-b: MS(ES): m/z: 592.2 [M+H]$^+$, $^1$H NMR (DMSO-d$_6$, 400 MHz): δ 10.18 (s, 1H), 8.66-8.63 (m, 2H), 8.22-8.21 (d, J=2.0 Hz, 1H), 8.19 (s, 1H), 8.06 (s, 1H), 7.69 (s, 1H), 6.69-6.67 (m, 1H), 4.02 (s, 3H), 3.86-3.83 (m, 1H), 3.69 (s, 3H), 3.36 (bs, 2H), 2.44-2.40 (m, 2H), 1.76 (bs. 1H), 1.63-1.60 (m, 1H), 1.47 (bs, 2H), 1.26-1.18 (m, 2H).

Example 213: N-(4-((7-chloro-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)-3-morpholinopropanamide

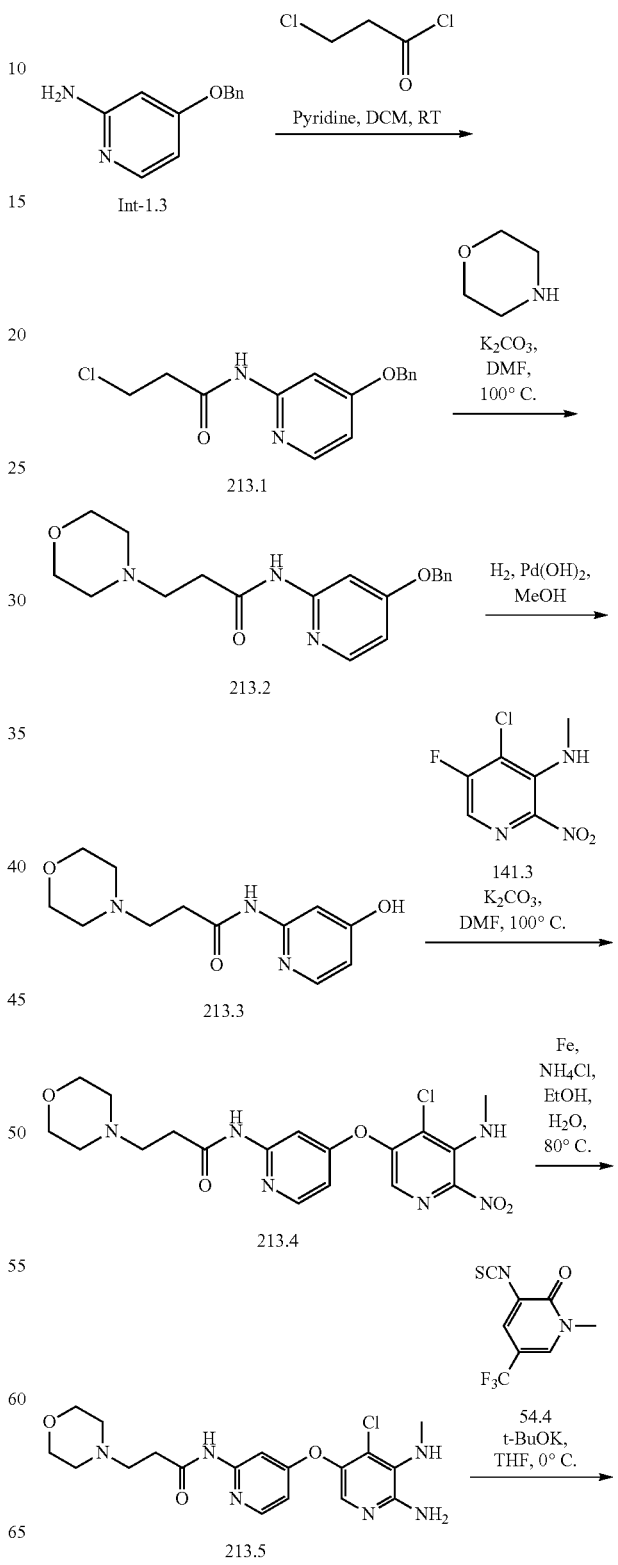

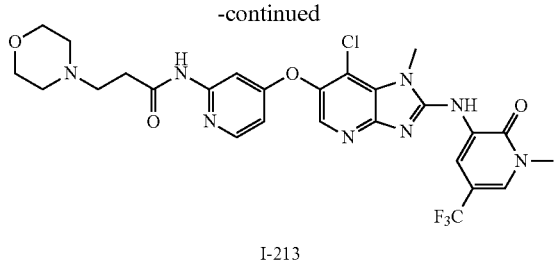

I-213

Synthesis of compound 213.1. To a solution of Int-1.3 (5.0 g, 24.97 mmol, 1.0 equiv) and pyridine (6.0 mL, 74.91 mmol, 3.0 equiv) in DCM (50 mL) at 0° C. was added 3-chloropropionyl chloride (9.5 mL, 99.88 mmol, 4.0 equiv) dropwise and the mixture was stirred at room temperature for 16 h. It was transferred into water and extracted with ethyl acetate. The combined organic layers were washed with brine, dried over sodium sulfate, filtered and concentrated under reduced pressure to afford 213.1. MS(ES): m/z 291.5 [M+H]$^+$.

Synthesis of compound 213.2. A mixture of 213.1 (6.0 g, 20.64 mmol, 1.0 equiv), morpholine (8.99 g, 103.18 mmol, 5.0 equiv) and potassium carbonate (8.54 g, 61.92 mmol, 3.0 equiv) in DMF (60 mL) was stirred at 100° C. for 1 h. It was cooled to room temperature, transferred into water and extracted with ethyl acetate. The combined organic layers were washed with brine solution, dried over sodium sulfate, filtered and concentrated under reduced pressure. The residue was purified by flash column chromatography on silica gel (CombiFlash®, 2.5% methanol in DCM) to afford 213.2. MS(ES): m/z 342.4 [M+H]$^+$.

Synthesis of compound 213.3. A mixture of 213.2 (1.2 g, 3.51 mmol, 1.0 equiv) and 20% palladium hydroxide (0.6 g) in methanol (15 mL) was stirred under hydrogen (1 atm) at rt for 1 h. The reaction mixture was filtered through a pad of Celite® and rinsed with methanol. The filtrate was concentrated under reduced pressure. The residue was purified by flash column chromatography on silica gel (CombiFlash®, 3.5% methanol in DCM) to afford 213.3. MS(ES): m/z 252.2 [M+H]$^+$.

Synthesis of compound 213.4. A mixture of 213.3 (0.650 g, 2.59 mmol, 1.0 equiv), 141.3 (0.531 g, 2.59 mmol, 1.0 equiv) and potassium carbonate (0.714 g, 5.18 mmol, 2.0 equiv) in DMF (7 mL) was stirred at 100° C. for 1 h. It was transferred into water and extracted with ethyl acetate. The combined organic layers were washed with brine solution, dried over sodium sulfate, filtered and concentrated under reduced pressure. The residue was purified by flash column chromatography on silica gel (CombiFlash®, 3.3% methanol in DCM) to afford 213.4. MS(ES): m/z 437.5 [M+H]$^+$.

Synthesis of compound 213.5. To a solution of 213.4 (0.300 g, 0.686 mmol, 1.0 equiv) in ethanol:water (2:1, 8 mL) was added iron powder (0.192 g, 3.43 mmol, 5.0 equiv) followed by ammonium chloride (0.185 g, 3.43 mmol, 5.0 equiv). The reaction mixture was stirred at 80° C. for 1 h. It was transferred into ice-water, filtered and extracted with ethyl acetate. The combined organic layers were washed with brine solution, dried over sodium sulfate, filtered and concentrated under reduced pressure. The residue was purified by flash column chromatography on silica gel (CombiFlash®, 4.5% methanol in DCM) to afford 213.5. MS(ES): m/z 407.5 [M+H]$^+$.

Synthesis of I-213. Compound I-213 was prepared from 213.5 and 54.4 following the procedure described in the synthesis of 1-204. The product was purified by flash column chromatography on silica gel (CombiFlash®, 6.5% methanol in DCM). MS(ES): m/z: 607.2 [M+H]$^+$, $^1$H NMR (DMSO-d$_6$, 400 MHz): δ 10.78 (s, 1H), 8.86 (s, 1H), 8.64 (s, 1H), 8.25 (s, 1H), 8.22-8.21 (d, J=5.6 Hz, 1H), 8.16 (s, 1H), 7.67 (s, 1H), 6.71-6.70 (m, 1H), 4.00 (s, 3H), 3.67 (s, 3H), 3.56 (s, 4H), 2.56 (bs, 4H), 2.38 (bs, 4H).

Example 215: N-(4-((7-methoxy-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide

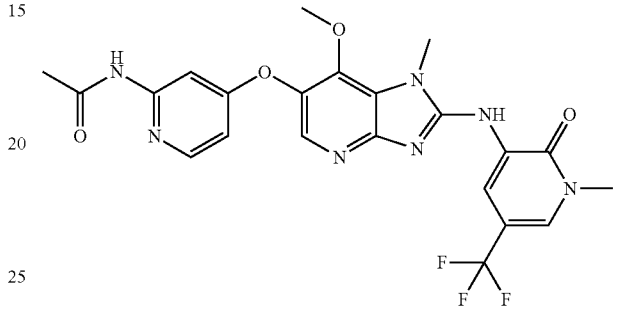

Compound I-215 is prepared from 206.5 and 54.4 following the procedure described in the synthesis of 1-204.

Example 216: N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)cyclopropanecarboxamide

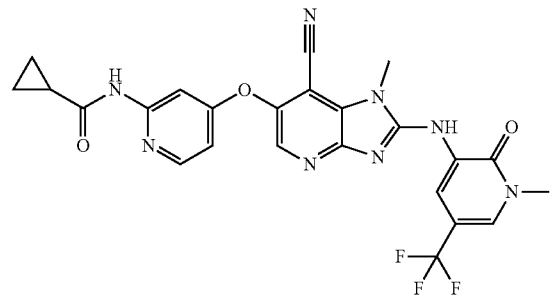 [SMILES: Cn1cc(C(F)(F)F)cc(Nc2nc3ncc(Oc4ccnc(NC(=O)C5CC5)c4)c(C#N)c3n2C)c1=O]

Compound I-216 is prepared from 181.4 and 54.3 according to the procedure described in the synthesis of 1-197, followed by cyanation according to the procedure described in the synthesis of 1-207.

JAK2 Binding Assay

JAK2 (JH1domain-catalytic, Y1007F,Y1008F) kinase was expressed as N-terminal fusion to the DNA binding domain of NFkB in transiently transfected HEK293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mmol/L DTT) to remove unbound ligand and to reduce nonspecific phage binding. Binding reactions were assembled by combining kinases, liganded affinity beads, and test compounds in 1× binding buffer (1×PBS, 0.05% Tween 20, 0.1% BSA, 1 mmol/L DTT). Test compound was prepared as 111× stocks in 100% DMSO and directly diluted into the assay wells. All reactions were performed in polypropylene 384-well plates in a final volume of 0.02 mL. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μmol/L non-biotinylated affinity ligand) and incubated at room temperature with shaking for 30 minutes. The kinase concentration in the eluate was measured by qPCR.

Results of the JAK2 JH1 Domain Binding Assay described above are presented in Table 2. Compounds denoted as "A" had a $K_d$<10 nM; compounds denoted as "B" had a $K_d$≥10 nM and <50 nM; compounds denoted as "C" had a $K_d$≥50 nM and <1 μM; compounds denoted as "D" had a $K_d$≥1 μM and <5 μM; and compounds denoted as "E" had a $K_d$≥5 μM.

TABLE 2

Results of JAK2 Binding Assay

| Compound | JAK2 $K_d$ |
| --- | --- |
| I-1 | A |
| I-2 | A |
| I-3 | A |
| I-4 | C |
| I-5 | B |
| I-6 | A |
| I-7 | C |
| I-8 | C |
| I-9 | D |
| I-10 | C |
| I-11 | B |
| I-12-a | B |
| I-12-b | B |
| I-13 | E |
| I-14 | A |
| I-15 | B |
| I-16 | C |
| I-17 | C |
| I-18 | B |
| I-19 | C |
| I-20 | A |
| I-21 | A |
| I-22 | A |
| I-23 | D |
| I-24 | A |
| I-25 | A |
| I-26 | A |
| I-27 | A |
| I-28 | A |
| I-29 | A |
| I-30 | A |
| I-31 | A |
| I-32 | A |
| I-33 | C |
| I-34 | A |
| I-35 | C |
| I-36-a | C |
| I-36-b | C |
| I-37 | A |
| I-38 | C |
| I-39 | A |
| I-40 | A |
| I-41 | A |
| I-42 | A |
| I-43 | D |
| I-44 | C |
| I-45-a | E |
| I-45-b | E |
| I-46 | B |
| I-47 | B |
| I-48 | B |
| I-49 | B |
| I-50-a | C |
| I-50-b | C |
| I-51 | D |
| I-52 | A |
| I-53 | A |
| I-54 | A |
| I-55 | A |
| I-56 | D |
| I-57 | C |
| I-58-a | B |
| I-58-b | C |
| I-59-a | B |
| I-59-b | B |
| I-60-a | B |
| I-60-b | A |
| I-61 | A |
| I-62 | A |
| I-63 | A |
| I-64 | B |
| I-65 | A |
| I-66-a | A |
| I-66-b | A |
| I-67-a | A |
| I-67-b | A |
| I-68-a | A |
| I-68-b | A |
| I-69 | A |
| I-70 | A |
| I-71 | A |
| I-72 | A |
| I-73 | A |
| I-74 | C |
| I-75-a | A |
| I-75-b | A |
| I-76-a | A |
| I-76-b | B |
| I-77-a | A |
| I-77-b | A |
| I-78-a | A |
| I-78-b | B |
| I-79-a | A |
| I-79-b | A |
| I-80 | A |
| I-81 | A |
| I-82 | D |
| I-83 | E |
| I-84 | A |
| I-85 | A |
| I-86 | C |
| I-87-a | C |
| I-87-b | C |
| I-88 | D |
| I-89 | B |
| I-90 | A |
| I-91 | D |
| I-92 | B |
| I-93 | B |
| I-94 | A |
| I-95 | C |
| I-96 | B |
| I-97 | B |
| I-98 | A |
| I-99 | A |
| I-100 | A |
| I-101 | C |
| I-103 | A |
| I-104 | A |
| I-105 | C |
| I-106 | C |
| I-108 | A |
| I-109 | A |
| I-110 | A |
| I-111 | A |
| I-112-a | A |
| I-112-b | A |

TABLE 2-continued

Results of JAK2 Binding Assay

| Compound | JAK2 $K_d$ |
| --- | --- |
| I-113 | B |
| I-114 | A |
| I-115 | A |
| I-116 | A |
| I-117-a | A |
| I-117-b | A |
| I-118 | A |
| I-119 | A |
| I-120 | B |
| I-121 | B |
| I-122 | A |
| I-123 | A |
| I-124 | A |
| I-125 | A |
| I-126 | A |
| I-127 | A |
| I-128-a | C |
| I-128-b | C |
| I-129-a | B |
| I-129-b | A |
| I-130 | A |
| I-131 | A |
| I-132 | A |
| I-133 | A |
| I-134 | A |
| I-135-a | A |
| I-135-b | B |
| I-136 | A |
| I-137 | A |
| I-138 | A |
| I-139 | A |
| I-140 | A |
| I-141 | A |
| I-142 | A |
| I-143 | B |
| I-144 | B |
| I-145 | A |
| I-146 | A |
| I-147 | A |
| I-148-a | D |
| I-148-b | D |
| I-149 | A |
| I-150 | A |
| I-151 | A |
| I-152 | A |
| I-153 | A |
| I-154 | A |
| I-155 | A |
| I-156 | A |
| I-157 | A |
| I-158 | A |
| I-159 | A |
| I-160 | A |
| I-161 | A |
| I-162-a | A |
| I-162-b | B |
| I-163-a | A |
| I-163-b | A |
| I-164 | A |
| I-165 | A |
| I-166 | A |
| I-167 | A |
| I-168 | A |
| I-169-b | B |
| I-170 | A |
| I-171 | A |
| I-172-a | A |
| I-172-b | B |
| I-173 | B |
| I-174 | C |
| I-175-a | A |
| I-175-b | C |
| I-176-a | A |
| I-176-b | A |
| I-177 | A |
| I-178 | A |
| I-179 | A |
| I-180 | B |
| I-181 | A |
| I-182 | A |
| I-183 | A |
| I-184 | A |
| I-185 | A |
| I-186 | A |
| I-187-a | A |
| I-187-b | A |
| I-188 | A |
| I-189-a | A |
| I-189-b | A |
| I-190-a | A |
| I-190-b | A |
| I-191 | A |
| I-192 | A |
| I-193 | A |
| I-194 | A |
| I-195-a | A |
| I-195-b | A |
| I-196 | A |
| I-197 | A |
| I-198-a | A |
| I-198-b | A |
| I-199 | A |
| I-200 | A |
| I-201 | A |
| I-202 | A |
| I-203 | A |
| I-204 | A |
| I-205 | B |
| I-206 | A |
| I-207 | B |
| I-208 | A |
| I-209 | A |
| I-210 | A |
| I-211 | A |

JAK Family Selectivity Assays

Provided compounds are evaluated for selectivity by comparing their JAK2 binding affinity ($K_d$) in the above JAK2 Binding Assay with their binding affinity ($K_d$) for one or more other kinases. Binding affinity for other kinases is determined as follows: Kinase-tagged T7 phage strains are prepared in an E. coli host derived from the BL21 strain. E. coli are grown to log-phase and infected with T7 phage and incubated with shaking at 32° C. until lysis. The lysates are centrifuged and filtered to remove cell debris. The remaining kinases are produced in HEK-293 cells and subsequently tagged with DNA for qPCR detection. Streptavidin-coated magnetic beads are treated with biotinylated small molecule ligands for 30 minutes at room temperature to generate affinity resins for kinase assays. The liganded beads are blocked with excess biotin and washed with blocking buffer (SeaBlock (Pierce), 1% BSA, 0.05% Tween 20, 1 mM DTT) to remove unbound ligand and to reduce non-specific binding. Binding reactions are assembled by combining kinases, liganded affinity beads, and test compounds in 1× binding buffer (20% SeaBlock, 0.17×PBS, 0.05% Tween 20, 6 mM DTT). Test compounds are prepared as 111× stocks in 100% DMSO. Kds are determined using an 11-point 3-fold compound dilution series with three DMSO control points. All compounds for $K_d$ measurements are distributed by acoustic transfer (non-contact dispensing) in 100% DMSO. The compounds are then diluted directly into the assays such that the final concentration of DMSO is 0.9%. All reactions are performed in polypropylene 384-well plate. Each has a final volume of 0.02 ml. The assay plates are incubated at room temperature with shaking for 1 hour and the affinity beads are washed with wash buffer (1×PBS, 0.05% Tween 20). The beads are then re-suspended in elution buffer (1x PBS, 0.05% Tween 20, 0.5 μM non-biotinylated affinity ligand) and incubated at room temperature with shaking for 30 minutes. The kinase concentration in the eluates is measured by qPCR. Compounds that exhibit a better binding affinity for JAK2 compared to one or more other kinases are considered to be JAK2-selective compounds. In some embodiments, provided compounds may be JAK2-selective over one or more of the following kinases: JAK1, JAK3, and Tyk2.

SET2-pSTAT5 Cellular Assay

This assay measures inhibition of JAK2-mediated pSTAT5 signaling in constitutively active essential thrombocytopenia cells carrying the V617F mutation. Cells are harvested from a flask into cell culture medium, and the number of cells is counted. The cells are diluted with culture medium and 100 μL of cell suspension (50000/well) is added into each well of a 96-well cell culture plate. A solution of test compound is added to the assay plate. The plates are covered with a lid and placed in a 37° C. 5% $CO_2$ incubator for 4 hours. After 4 hours, the cells are spun, and the cell pellets are re-suspended with 100 μL cold PBS. Then, the cells are spun again at 4° C. and 4000 rpm for 5 min. PBS is aspirated, and 25 μL lysis buffer (with protease and phosphatase inhibitor cocktail) is added to each cell pellet. The cell lysate is shaken at 4° C. for 20 min to fully lyse the cells. The cell lysate is spun at 4° C. and 4000 rpm for 15 min, and then the supernatant is transferred into a new plate and stored at −80° C. Meso-scale discovery (MSD) is used to analyze plates as follows: a standard MSD plate is coated with capture antibody in PBS (40 μL/well) and is incubated at 4° C. overnight with shaking. The MSD plate is washed three times with 150 μL/well of 1×MSD Wash Buffer (Tris-buffered saline with 0.1% Tween® 20 detergent, TBST). The MSD plates are then blocked with 150 μL of blocking buffer (5% BSA in TBST) and shaken for 1 h at room temperature and 600 rpm. The MSD plate is washed three times with 150 μL/well of 1×MSD Wash Buffer (TBST). Sample lysates are then added to MSD plates (25 μL/well) and shaken for 1 h at room temperature and 600 rpm. The MSD plate is washed three times with 150 μL/well of 1×MSD Wash Buffer (TBST). Detection antibody (prepared in Antibody Detection buffer, 1% BSA in 1×TBST) is then added to the MSD plates, and they are shaken for 1 h at room temperature and 600 rpm. The MSD plate is washed three times with 150 μL/well of 1×MSD Wash Buffer (TBST). A secondary detection antibody (prepared in Antibody Detection buffer, 1% BSA in 1×TBST) is then added to the MSD plates, and they are shaken for 1 h at room temperature and 600 rpm. The MSD plate is washed three times with 150 μL/well of 1×MSD Wash Buffer (TBST). MSD reading buffer (1x) is added to the plates (150 μL/well), and they are diluted from 4× with water. The plates are imaged using an MSD imaging instrument according to the manufacturer's instructions.

Caco2 Permeability Assay

Preparation of Caco-2 Cells: 50 μL and 25 mL of cell culture medium are added to each well of a Transwell® insert and reservoir, respectively. Then, the HTS Transwell® plates are incubated at 37° C., 5% $CO_2$ for 1 hour before cell seeding. Caco-2 cell cells are diluted to 6.86×105 cells/mL with culture medium, and 50 μL of cell suspension are dispensed into the filter well of the 96-well HTS Transwell® plate. Cells are cultivated for 14-18 days in a cell culture incubator at 37° C., 5% $CO_2$, 95% relative humidity. Cell culture medium is replaced every other day, beginning no later than 24 hours after initial plating.

Preparation of Stock Solutions: 10 mM stock solutions of test compounds are prepared in DMSO. The stock solutions of positive controls are prepared in DMSO at the concentration of 10 mM. Digoxin and propranolol are used as control compounds in this assay.

Assessment of Cell Monolayer Integrity: Medium is removed from the reservoir and each Transwell® insert and is replaced with prewarmed fresh cuture medium. Transepithelial electrical resistance (TEER) across the monolayer is measured using Millicell Epithelial Volt-Ohm measuring system (Millipore, USA). The Plate is returned to the incubator once the measurement is done. The TEER value isss calculated according to the following equation: TEER measurement (ohms)×Area of membrane $(cm^2)$=TEER value $(ohm·cm^2)$. A TEER value greater than 230 $ohm·cm^2$ indicates a well-qualified Caco-2 monolayer.

Assay Procedure: The Caco-2 plate is removed from the incubator and washed twice with pre-warmed HBSS (10 mM HEPES, pH 7.4), and then incubated at 37° C. for 30 minutes. The stock solutions of control compounds are diluted in DMSO to get 1 mM solutions and then diluted with HBSS (10 mM HEPES, pH 7.4) to get 5 μM working solutions. The stock solutions of the test compounds are diluted in DMSO to get 1 mM solutions and then diluted with HBSS (10 mM HEPES and 4% BSA, pH 7.4) to get 5 μM working solutions. The final concentration of DMSO in the incubation system is 0.5%. To determine the rate of drug transport in the apical to basolateral direction. 75 μL of 5 μM working solutions of test compounds are added to the Transwell® insert (apical compartment) and the wells in the receiver plate (basolateral compartment) are filled with 235 μL of HBSS (10 mM HEPES and 4% BSA, pH 7.4). To determine the rate of drug transport in the basolateral to apical direction, 235 μL of 5 μM working solutions of test compounds are added to the receiver plate wells (basolateral compartment) and then the Transwell® inserts (apical compartment) are filled with 75 μL of HBSS (10 mM HEPES and 4% BSA, pH 7.4). Time 0 samples are prepared by transferring 50 μL of 5 μM working solution to wells of the 96-deepwell plate, followed by the addition of 200 μL cold methanol containing appropriate internal standards (IS). The plates are incubated at 37° C. for 2 hours. At the end of the incubation, 50 μL samples from donor sides (apical compartment for Ap→Bl flux, and basolateral compartment for Bl→Ap) and receiver sides (basolateral compartment for Ap→Bl flux, and apical compartment for Bl→Ap) are transferred to wells of a new 96-well plate, followed by the addition of 4 volume of cold acetonitrile or methanol containing appropriate internal standards (IS). Samples are vortexed for 5 minutes and then centrifuged at 3,220 g for 40 minutes. An aliquot of 100 μL of the supernatant is mixed with an appropriate volume of ultra-pure water before LC-MS/MS analysis. To determine the Lucifer Yellow leakage after 2 hour transport period, stock solution of Lucifer yellow is prepared in ultra-pure water and diluted with HBSS (10 mM HEPES, pH 7.4) to reach the final concentration of 100 μM. 100 μL of the Lucifer yellow solution is added to each Transwell® insert (apical compartment), followed by filling the wells in the receiver plate (basolateral compartment) with 300 μL of HBSS (10 mM HEPES, pH 7.4). The plates are incubated at 37° C. for 30 minutes. 80 μL samples are removed directly from the apical and basolateral wells (using the basolateral access holes) and transferred to wells of new 96 wells plates. The Lucifer Yellow fluorescence (to monitor monolayer integrity) signal is measured in a fluorescence plate reader at 485 nM excitation and 530 nM emission.

Cytotoxicity Assay

HEK293T cells are harvested from flask into cell culture medium, and then the cells are counted. The cells are diluted with culture medium to the desired density, and 40 µL of cell suspension is added into each well of a 384-well cell culture plate. The plates are covered with a lid and spun at room temperature at 1,000 RPM for 1 minute and then transferred into 37° C. 5% $CO_2$ incubator overnight. Test compounds are dissolved at 10 mM DMSO stock solution. 45 µL of stock solution is then transferred to a 384 PP-plate. A 3-fold, 10-point dilution is performed via transferring 15 µL compound into 30 µL DMSO by using TECAN (EVO200) liquid handler. The plates are spun at room temperature at 1,000 RPM for 1 minute and shaken on a plate shaker for 2 minutes. 40 nL of diluted compound is transferred from compound source plate into the cell plate by using liquid handler Echo550. After compound treatment for 48 hours, CTG detection is performed for compound treatment plates: the plates are removed from incubators and equilibrated at room temperature for 15 minutes. 30 µL of CellTiter-Glo reagent is added into each well to be detected. The plates are then placed at room temperature for 30 min followed by reading on EnVision. Inhibition activity is calculated with the following formula: % Inhibition=100×(LumHC−LumSample)/(LumHC−LumLC), wherein HC is reading obtained from cells treated with 0.1% DMSO only and LC is reading from cells treated with 10 µL staurosporine. $IC_{50}$ values are calculated using XLFit (equation 201).

Hepatocyte Stability Assay 10 mM stock solutions of test compound and positive control are prepared in DMSO. Stock solutions are diluted to 100 µM by combining 198 µL of 50% acetonitrile/50% water and 2 µL of 10 mM stock solution. Verapamil is used as positive control in the assay. Vials of cryopreserved hepatocytes are thawed in a 37° C. water bath with gently shaking. The contents are poured into the 50 mL thawing medium conical tube. Vials are centrifuged at 100 g for 10 minutes at room temperature. Thawing medium is aspirated and hepatocytes are re-suspended with serum-free incubation medium to yield ~1.5×106 cells/mL. Cell viability and density are counted using a Trypan Blue exclusion, and then cells are diluted with serum-free incubation medium to a working cell density of 0.5×106 viable cells/mL. A portion of the hepatocytes at 0.5×106 viable cells/mL are boiled for 5 min prior to adding to the plate as negative control to eliminate the enzymatic activity so that little or no substrate turnover should be observed. Aliquots of 198 µL hepatocytes are dispensed into each well of a 96-well non-coated plate. The plate is placed in the incubator for approximately 10 minutes. Aliquots of 2 µL of the 100 µM test compound and 2 µL positive control are added into respective wells of a non-coated 96-well plate to start the reaction. The final concentration of test compound is 1 µM. This assay is performed in duplicate. The plate is incubated in the incubator for the designed time points. 25 µL of contents are transferred and mixed with 6 volumes (150 µL) of cold acetonitrile with internal standard (100 nM alprazolam, 200 nM labetalol, 200 nM caffeine and 200 nM diclofenac) to terminate the reaction at time points of 0, 15, 30, 60, 90 and 120 minutes. Samples are centrifuged for 25 minutes at 3,220 g and aliquots of 150 µL of the supernatants are used for LC-MS/MS analysis.

Kinetic Solubility Assay

Stock solutions of test compounds are prepared in DMSO at the concentration of 10 mM, and a stock solution of control compound is prepared in DMSO at the concentration of 30 mM. Diclofenac is used as positive control in the assay. 30 µL stock solution of each compound is placed into their a 96-well rack, followed by adding 970 µL of PBS at pH 4.0 and pH 7.4 into each vial of the cap-less solubility sample plate. This study is performed in duplicate. One stir stick is added to each vial and then vials are sealed using a molded PTDE/SIL 96-Well Plate Cover. The solubility sample plate is transferred to the Thermomixer comfort plate shaker and incubated at RT for 2 hours with shaking at 1100 rpm. After 2 hours incubation, stir sticks are removed using a big magnet and all samples from the solubility sample plate are transferred into the filter plate. All the samples are filtered by vacuum manifold. The filtered samples are diluted with methanol. Samples are analyzed by LC-MS/MS and quantified against a standard of known concentration in DMSO using LC coupled with Mass spectral peak identification and quantitation. The solubility values of the test compounds are calculated as follows, wherein INJ VOL is injection volume, DF is dilution factor, and STD is standard:

$$[Sample] = \frac{AREA_{Sample} \times INJ\ VOL_{Std} \times DF_{Sample} \times [STD]}{AREA_{Std} \times INJ\ VOL_{Sample}}$$

Plasma Protein Binding Assay

Working solutions of test compounds and control compound are prepared in DMSO at the concentration of 200 µM, and then the working solutions are spiked into plasma. The final concentration of compound is 1 µM. The final concentration of DMSO is 0.5%. Ketoconazole is used as positive control in the assay. Dialysis membranes are soaked in ultrapure water for 60 minutes to separate strips, then in 20% ethanol for 20 minutes, finally in dialysis buffer for 20 minutes. The dialysis set up is assembled according to the manufacturer's instruction. Each Cell is with 150 µL of plasma sample and dialyzed against equal volume of dialysis buffer (PBS). The assay is performed in duplicate. The dialysis plate is sealed and incubated in an incubator at 37° C. with 5% $CO_2$ at 100 rpm for 6 hours. At the end of incubation, 50 µL of samples from both buffer and plasma chambers are transferred to wells of a 96-well plate. 50 µL of plasma is added to each buffer samples and an equal volume of PBS is supplemented to the collected plasma sample. 400 µL of precipitation buffer acetonitrile containing internal standards (IS, 100 nM alprazolam, 200 nM labetalol, 200 nM imipramine and 2 µM ketoplofen) is added to precipitate protein and release compounds. Samples are vortexed for 2 minutes and centrifuged for 30 minutes at 3,220 g. Aliquot of 50 µL of the supernatant is diluted by 150 µL acetonitrile containing internal standards:ultra-pure H2O=1:1, and the mixture is used for LC-MS/MS analysis.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The invention claimed is:
1. A compound of Formula I-1:

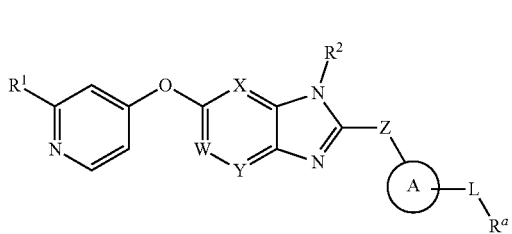

or a pharmaceutically acceptable salt thereof, wherein:
W is CR$^w$ or N;
X is CR$^x$ or N;
Y is CR$^y$ or N;
Z is —O— or —NR$^z$;
R$^w$, R$^x$, and R$^y$ are each independently hydrogen, halogen, —OR$^3$, —N(R$^3$)$_2$, —SR$^3$, optionally substituted C$_{1-6}$ aliphatic, or —CN;
R$^z$ is hydrogen or optionally substituted C$_{1-6}$ aliphatic;
R$^1$ is —N(R)$_2$, —N(R)C(O)R', —C(O)N(R)$_2$, or —N(R)C(O)N(R)$_2$;
R$^2$ is optionally substituted C$_{1-6}$ aliphatic;
R$^3$ is hydrogen or optionally substituted C$_{1-6}$ aliphatic;
Ring A is optionally substituted 5- to 6-membered monocyclic heteroaryl having 1-4 heteroatoms independently selected from nitrogen, oxygen, and sulfur, optionally substituted 8- to 10-membered bicyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur;
L is a covalent bond or a bivalent C$_{1-3}$ straight or branched hydrocarbon chain;
R$^a$ is hydrogen, halogen, optionally substituted C$_{1-6}$ aliphatic, optionally substituted phenyl, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur;
each R is independently hydrogen, optionally substituted C$_{1-6}$ aliphatic, optionally substituted 3- to 7-membered saturated or partially unsaturated carbocyclyl, or optionally substituted 3- to 7-membered saturated or partially unsaturated monocyclic heterocyclyl having 1-3 heteroatoms independently selected from nitrogen, oxygen, and sulfur, or two R when attached to the same nitrogen atom are taken together form an optionally substituted 3- to 7-membered saturated or partially unsaturated monocyclic heterocyclyl having 0-2 additional heteroatoms independently selected from nitrogen, oxygen, and sulfur; and
each R' is independently optionally substituted C$_{1-6}$ aliphatic or optionally substituted 3- to 7-membered saturated or partially unsaturated carbocyclyl.

2. The compound of claim 1, wherein Ring A is optionally substituted 5- to 6-membered monocyclic heteroaryl having 1-4 heteroatoms independently selected from nitrogen, oxygen, and sulfur.

3. The compound of claim 1, wherein R$^a$ is halogen, optionally substituted C$_{1-4}$ alkyl, optionally substituted 5-membered monocyclic heteroaryl having 1-4 heteroatoms independently selected from nitrogen, oxygen, and sulfur, optionally substituted 3- to 6-membered saturated monocyclic carbocyclyl, optionally substituted 3- to 6-membered saturated monocyclic heterocyclyl having 1-3 heteroatoms independently selected from nitrogen, oxygen, and sulfur, or optionally substituted 7-membered saturated, spirocyclic, bicyclic heterocyclyl having 1-4 heteroatoms independently selected from nitrogen, oxygen, and sulfur.

4. The compound of claim 3, wherein R$^a$ is C$_{1-4}$ alkyl, 3- to 6-membered saturated monocyclic heterocyclyl having 1-2 heteroatoms independently selected from nitrogen, oxygen, and sulfur, or 7- to 8-membered saturated, spirocyclic, bicyclic heterocyclyl having 1-2 heteroatoms independently selected from nitrogen, oxygen, and sulfur.

5. The compound of claim 1, wherein:

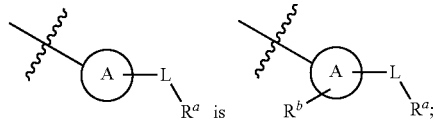

and
R$^b$ is hydrogen, halogen, —CN, —OR, —SR, —N(R)$_2$, —NO$_2$, —C(O)R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R', —SO$_2$N(R)$_2$, —SO$_3$R', optionally substituted C$_{1-6}$ aliphatic, optionally substituted 3- to 6-membered saturated or partially unsaturated carbocyclyl, optionally substituted 3- to 6-membered saturated or partially unsaturated monocyclic heterocyclyl having 1-3 heteroatoms independently selected from nitrogen, oxygen, and sulfur, or optionally substituted 5- to 6-membered monocyclic heteroaryl having 1-4 heteroatoms independently selected from nitrogen, oxygen, and sulfur.

6. The compound of claim 5, wherein

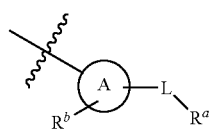

is:

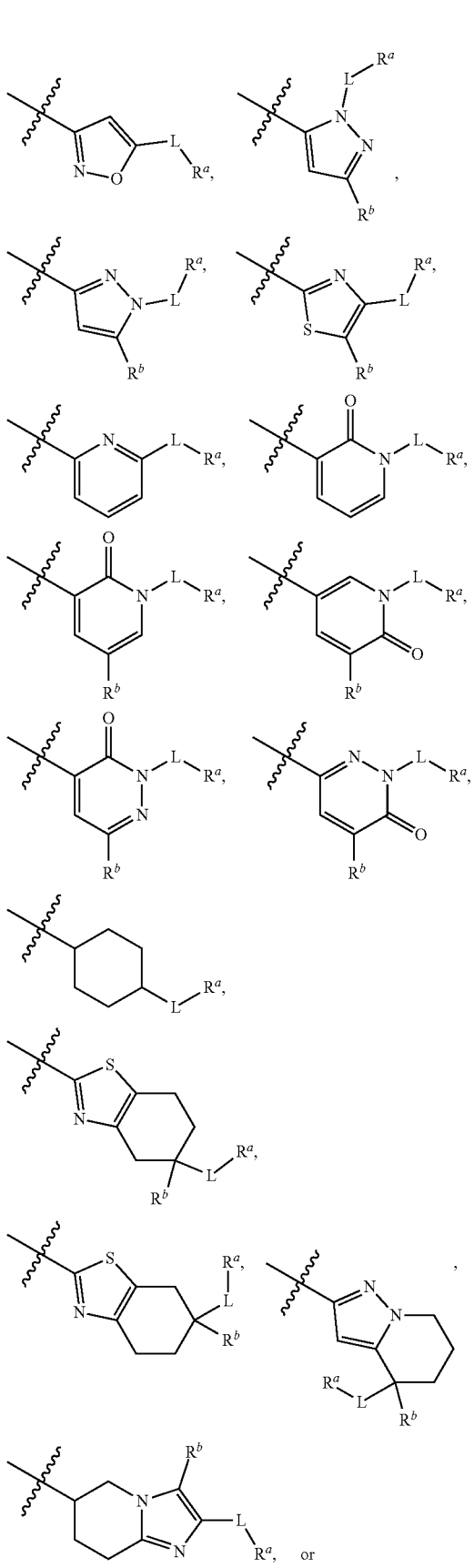

-continued

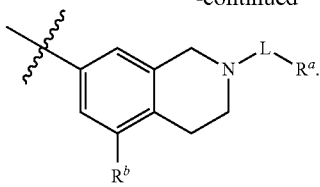

7. The compound of claim 6, wherein

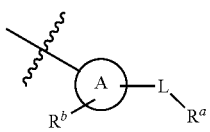

is:

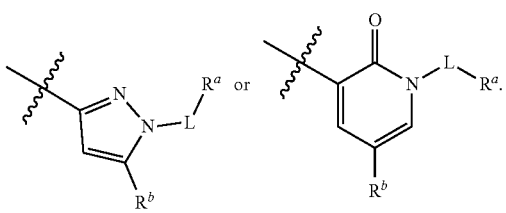

8. The compound of claim 5, wherein $R^b$ is hydrogen, halogen, optionally substituted $C_{1-4}$ alkyl, optionally substituted $C_{3-4}$ cycloalkyl, optionally substituted 3- to 5-membered saturated or partially unsaturated monocyclic heterocyclyl having 1-3 heteroatoms independently selected from nitrogen, oxygen, and sulfur, or optionally substituted 5-membered monocyclic heteroaryl having 1-4 heteroatoms independently selected from nitrogen, oxygen, and sulfur.

9. The compound of claim 8, wherein $R^b$ is $C_{3-4}$ cycloalkyl or $C_{1-4}$ alkyl optionally substituted with one or more fluoro.

10. The compound of claim 1, wherein L is a covalent bond or —$CH_2$—.

11. The compound of claim 1, wherein $R^1$ is —N(H)C(O)R'.

12. The compound of claim 11, wherein $R^1$ is —N(H)C(O)(optionally substituted $C_{1-4}$ alkyl).

13. The compound of claim 1, wherein $R^2$ is $C_{1-4}$ alkyl.

14. The compound of claim 1, wherein Z is —$NR^z$—.

15. The compound of claim 14, wherein $R^z$ is hydrogen.

16. The compound of claim 1, wherein Z is –O—.

17. The compound of claim 1, wherein each R is independently hydrogen or optionally substituted $C_{1-6}$ aliphatic.

18. The compound of claim 1, wherein:
W is CH;
$R^x$ and $R^y$ are each independently hydrogen, optionally substituted $C_{1-6}$ aliphatic, or —CN; and
each R is independently hydrogen, optionally substituted $C_{1-6}$ aliphatic, optionally substituted 3- to 7-membered saturated or partially unsaturated carbocyclyl, or optionally substituted 3- to 7-membered saturated or partially unsaturated monocyclic heterocyclyl having 1-3 heteroatoms independently selected from nitrogen, oxygen, and sulfur, or two R when attached to the same nitrogen atom are taken together form a 3- to 7-membered saturated or partially unsaturated monocyclic heterocyclyl having 0-2 additional heteroatoms independently selected from nitrogen, oxygen, and sulfur.

19. The compound of claim 1, wherein the compound is of Formula I-A:

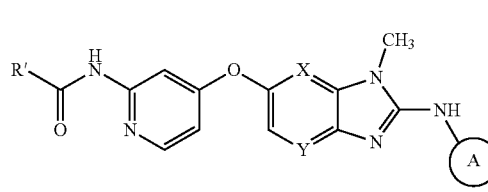

I-A or a pharmaceutically acceptable salt thereof.

20. The compound of claim 5, wherein the compound is of Formula I-B:

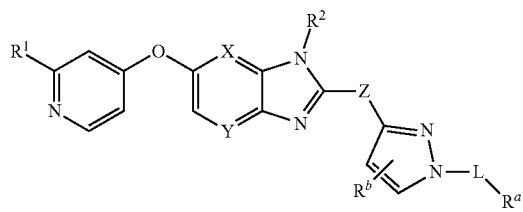

I-B or a pharmaceutically acceptable salt thereof.

21. The compound of claim 20, wherein the compound is of Formula I-C:

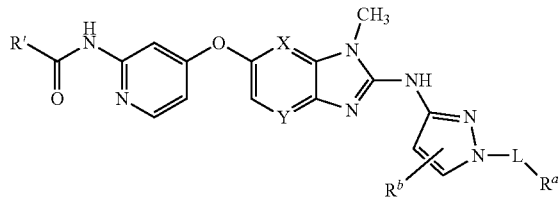

I-C or a pharmaceutically acceptable salt thereof.

22. The compound of claim 5, wherein the compound is of Formula I-D:

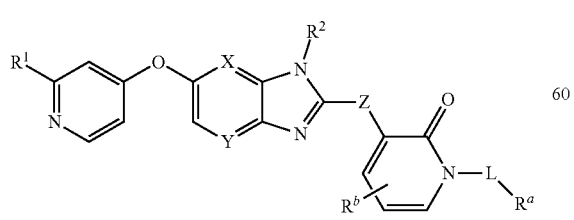

I-D or a pharmaceutically acceptable salt thereof.

23. The compound of claim 22, wherein the compound is of Formula I-E:

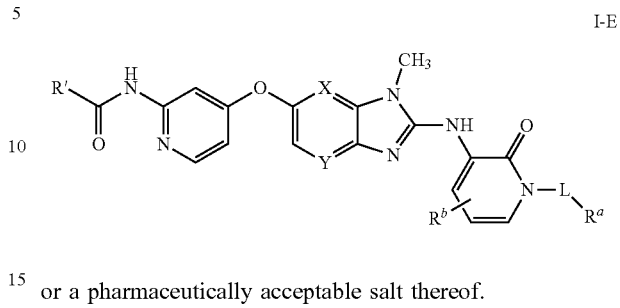

I-E or a pharmaceutically acceptable salt thereof.

24. A compound selected from:

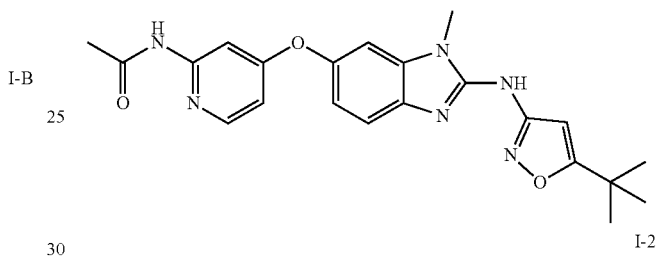

I-1

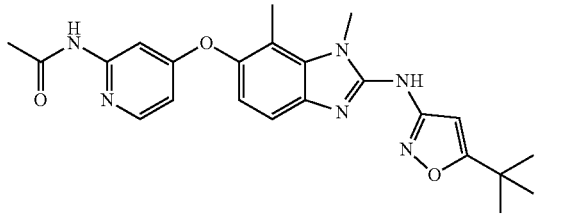

I-2

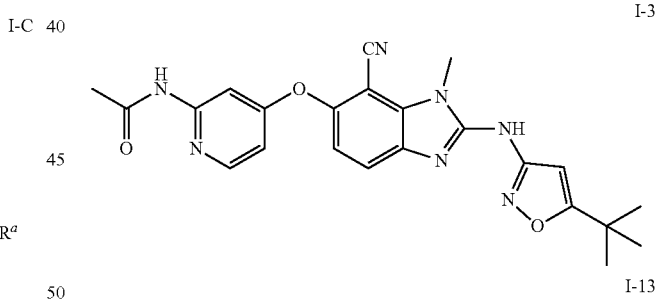

I-3

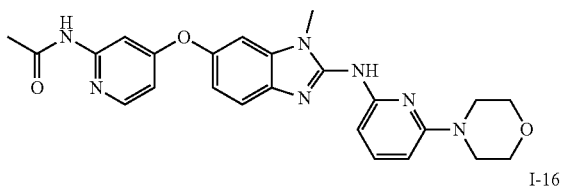

I-13

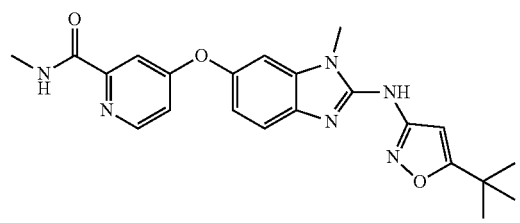

I-16

I-17
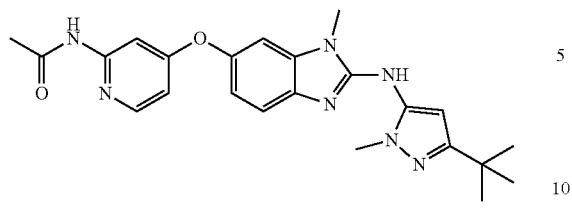
I-18
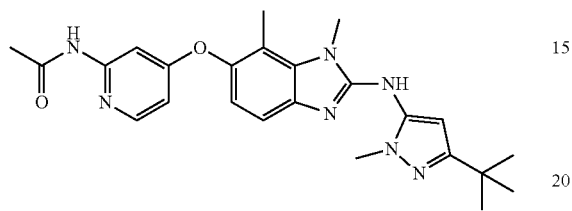
I-19'
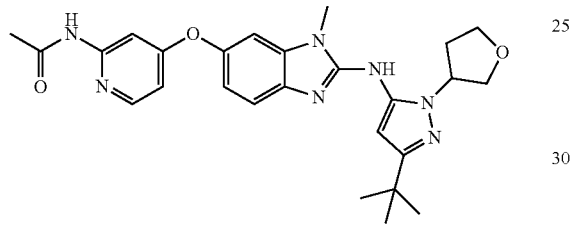
I-19
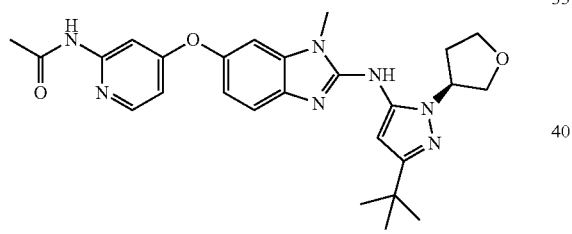
I-23
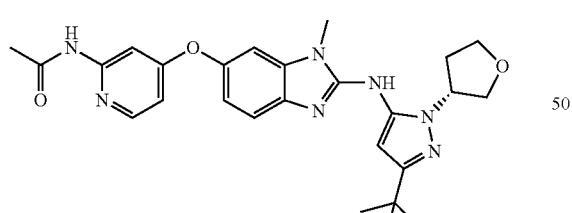
I-20'
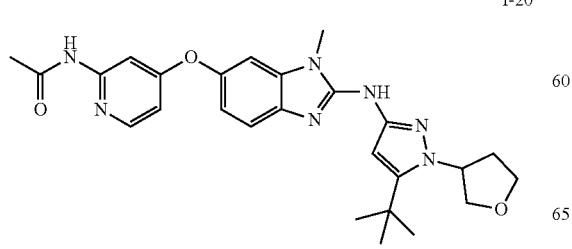
I-20
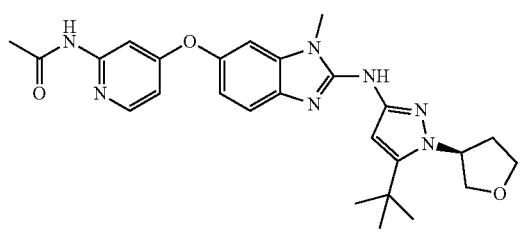
I-24
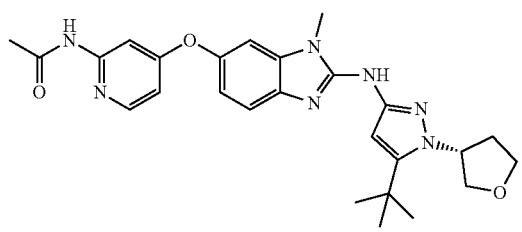
I-21'
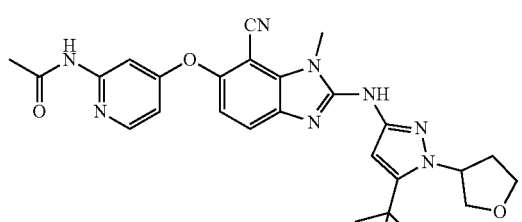
I-21
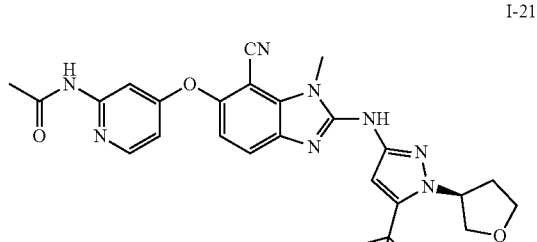
I-25
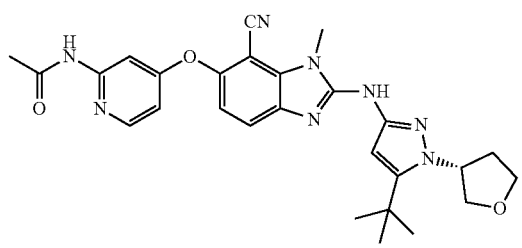
I-22'
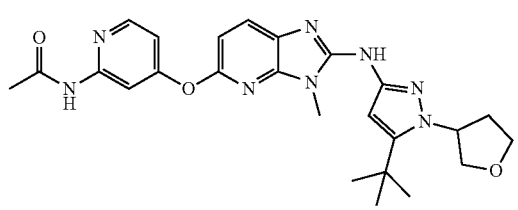

633
-continued
I-22
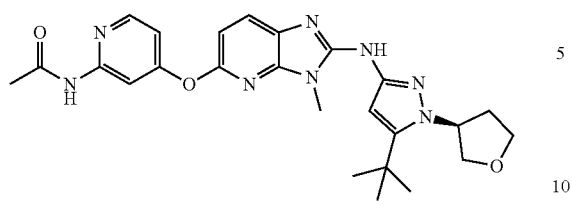
I-26
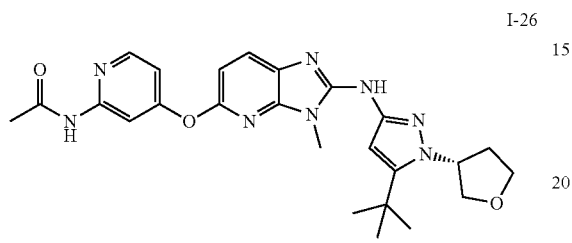
I-27
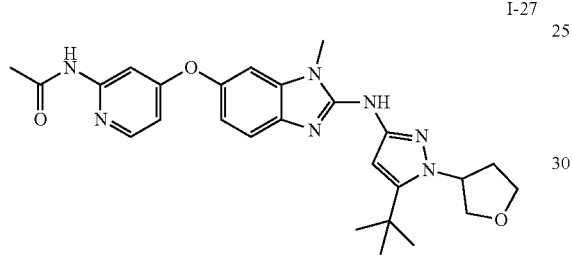
I-28
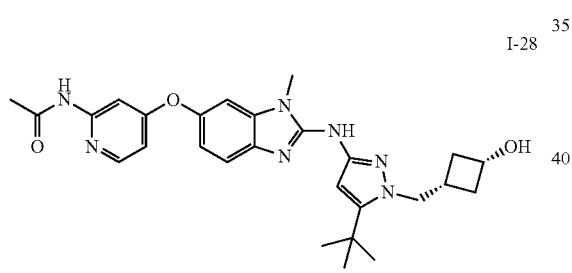
I-29
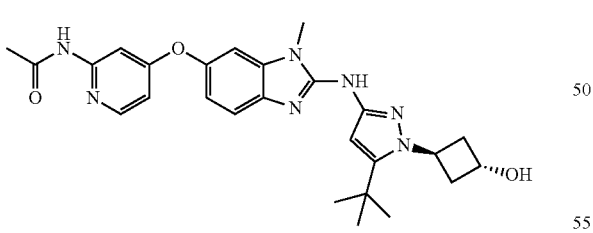
I-30
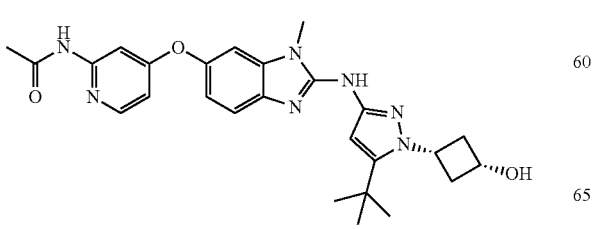
634
-continued
I-31
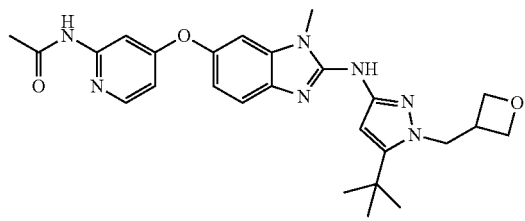
I-32
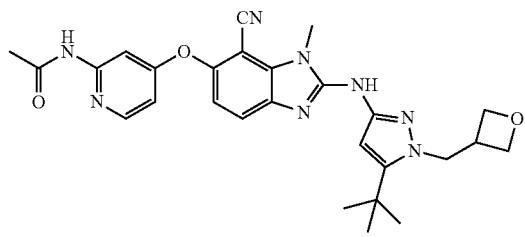
I-33
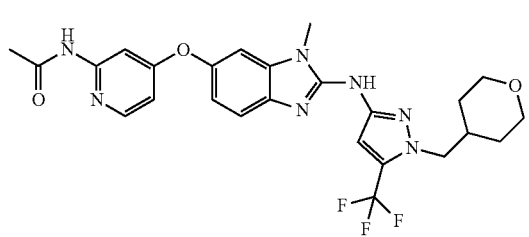
I-34
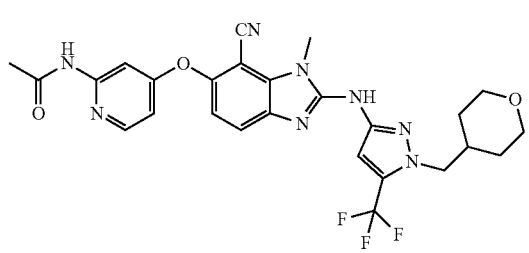
I-35
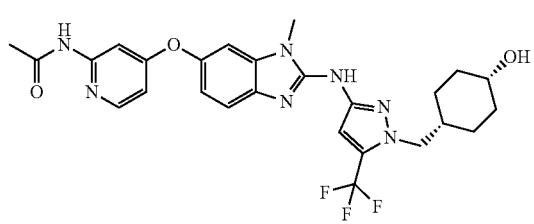
I-36

I-36-i
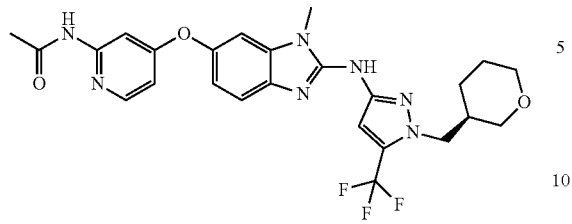
I-36-ii
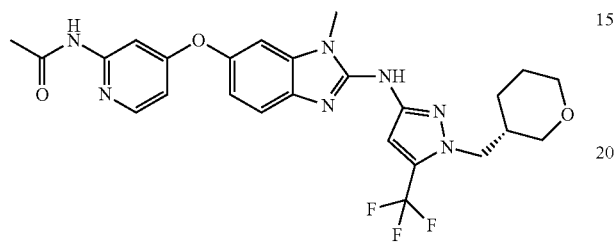
I-37
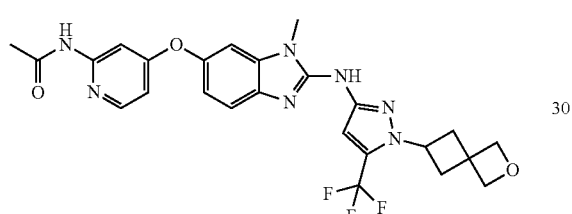
I-38
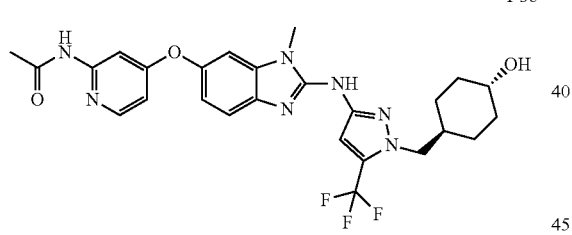
I-39
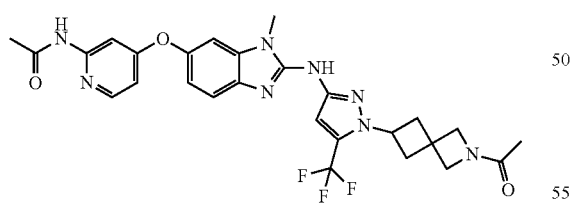
I-40
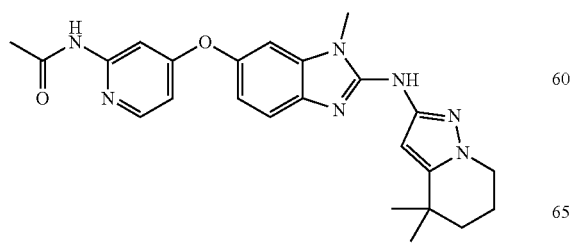
I-41
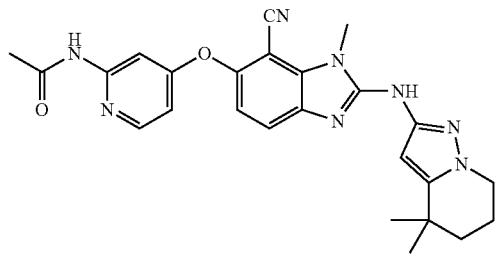
I-42
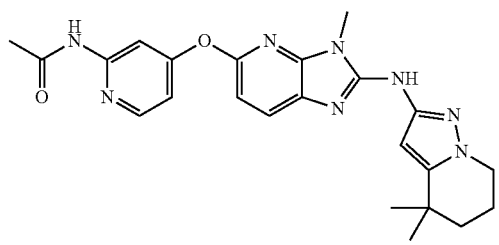
I-43
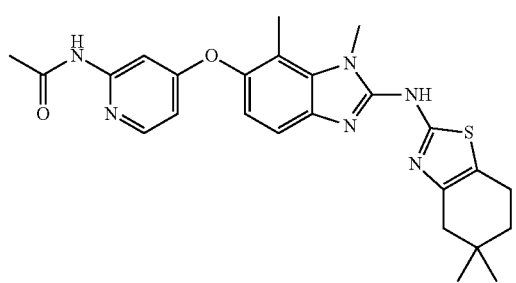
I-44
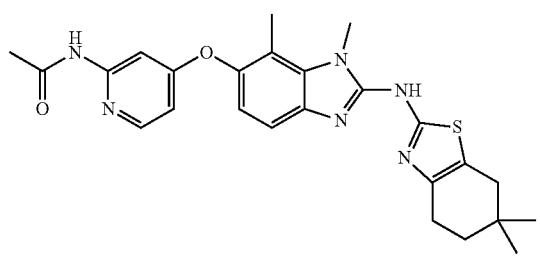
I-45
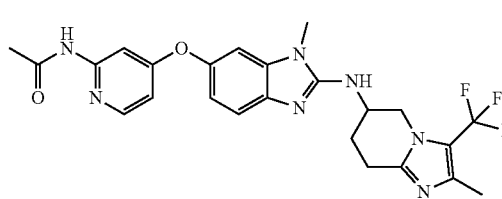
I-45-i
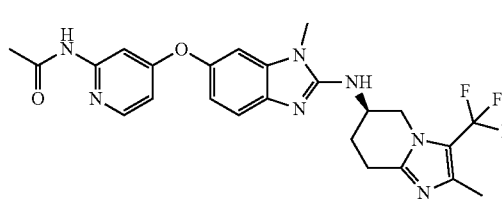

I-45-ii
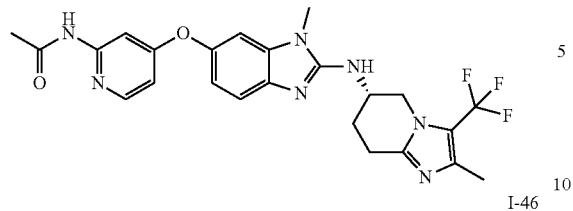
I-46
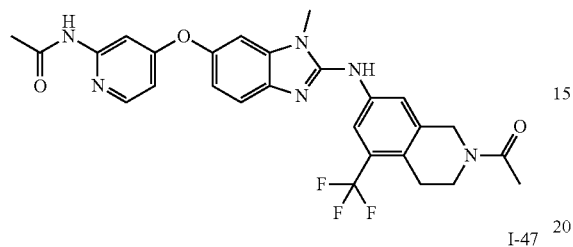
I-47
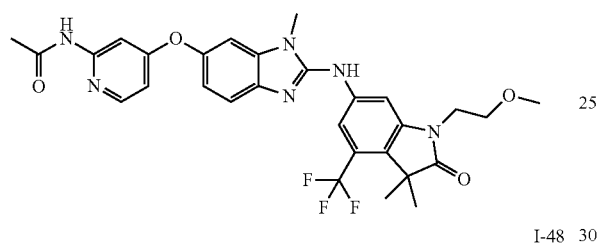
I-48
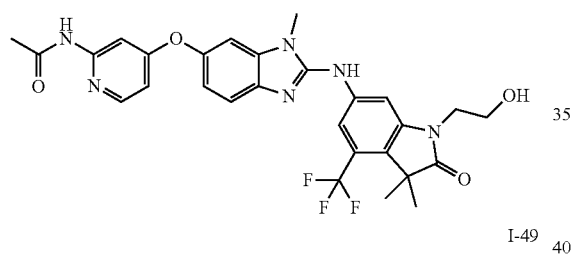
I-49
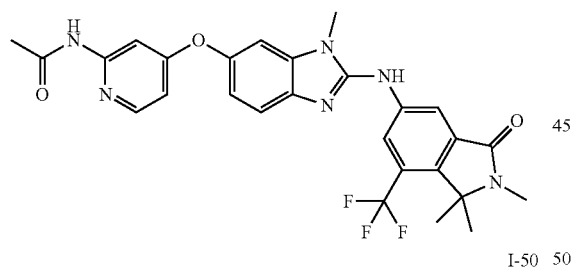
I-50
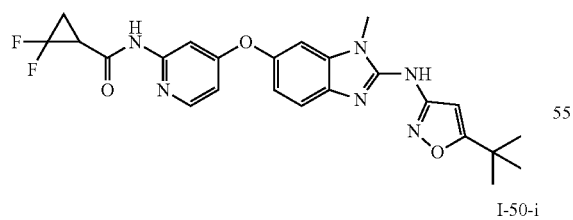
I-50-i
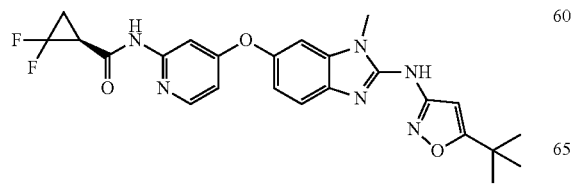
I-50-ii
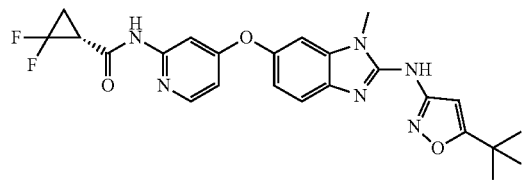
I-51
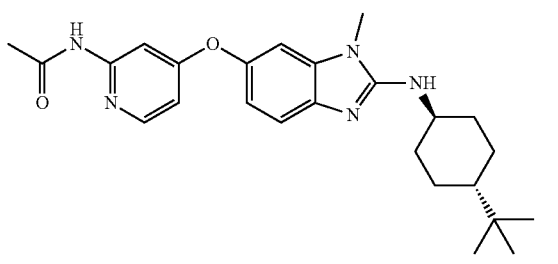
I-52
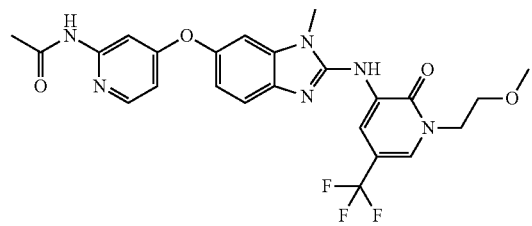
I-53
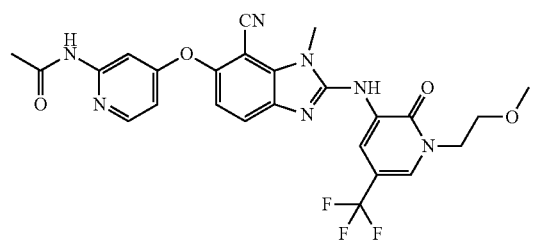
I-54
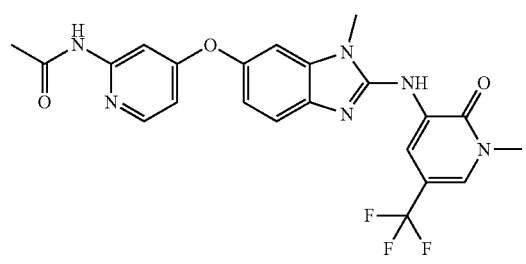
I-55
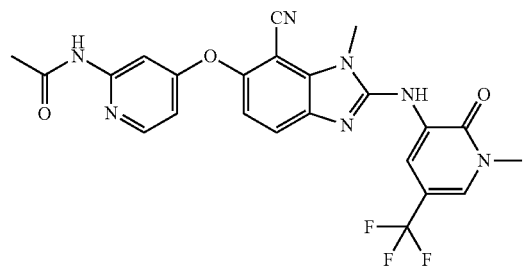

I-56
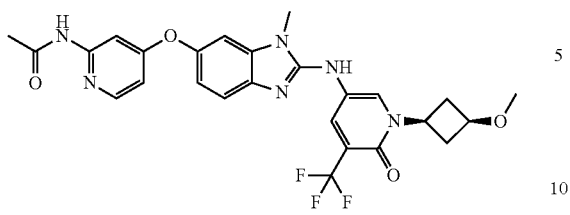
I-57
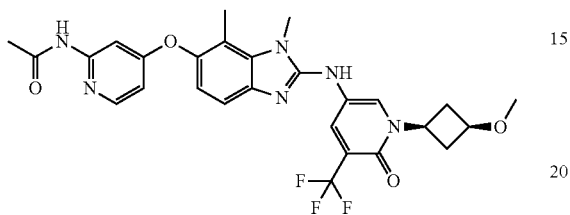
I-58
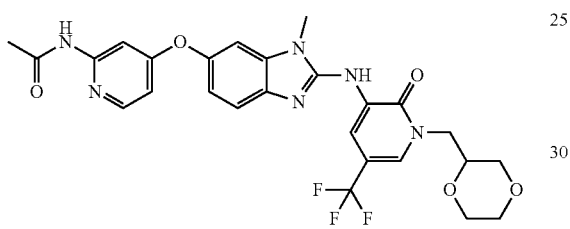
I-58-i
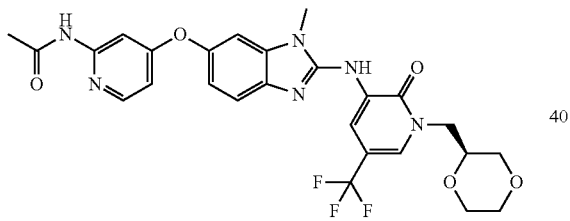
I-58-ii
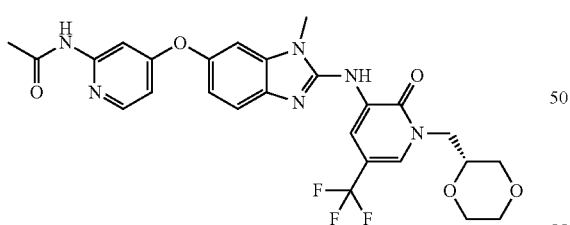
I-59'
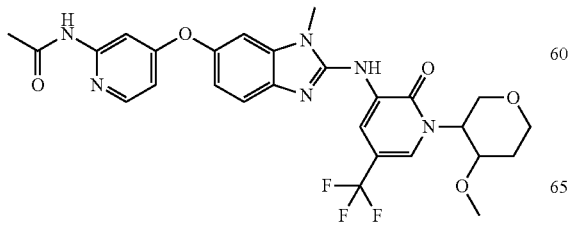
I-59-i
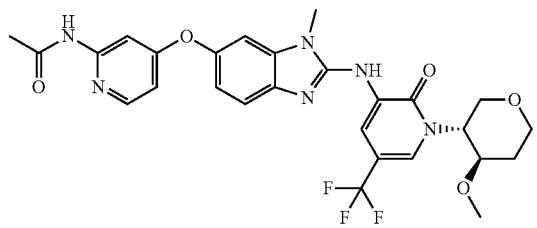
I-59-ii
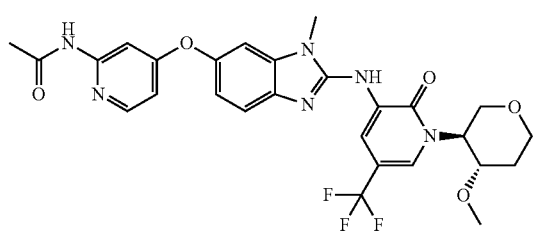
I-60-i
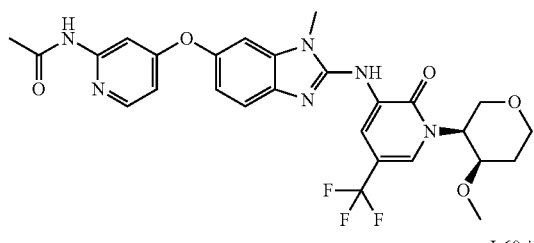
I-60-ii
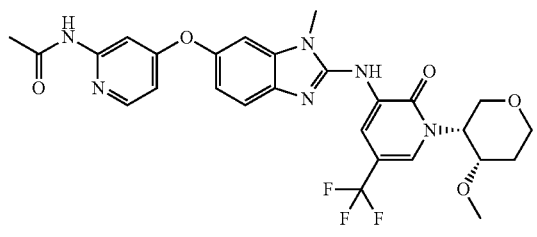
I-61
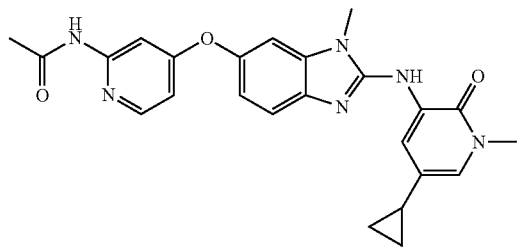
I-62
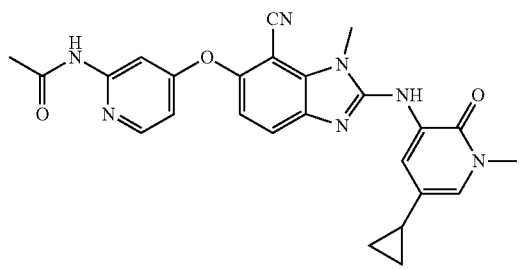

I-63
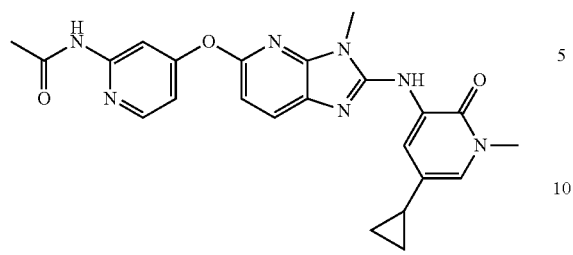
I-64
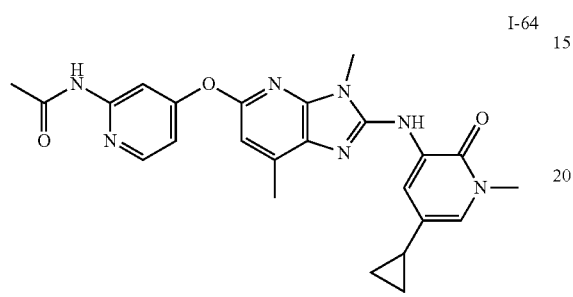
I-65
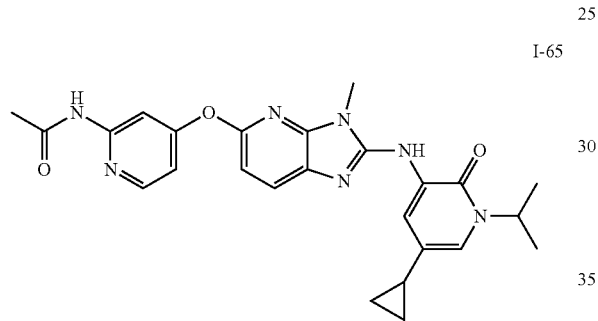
I-66
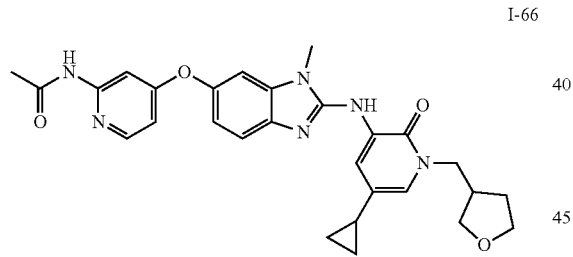
I-66-i
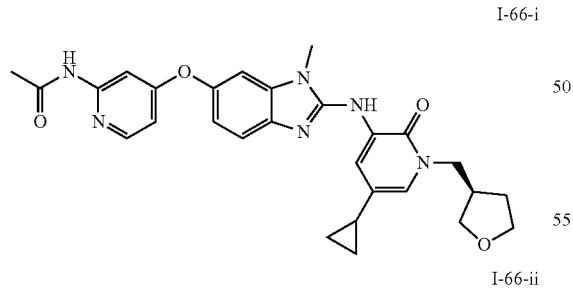
I-66-ii
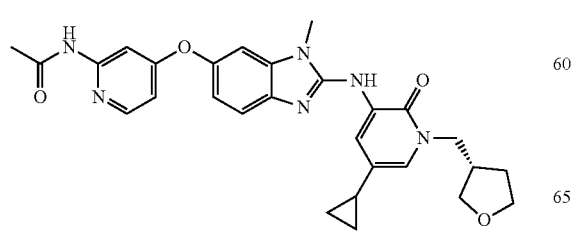
I-67
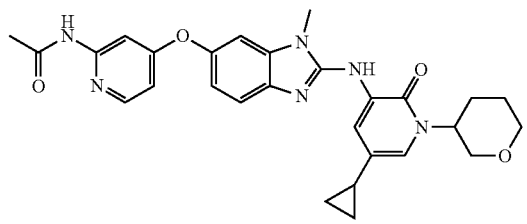
I-67-i
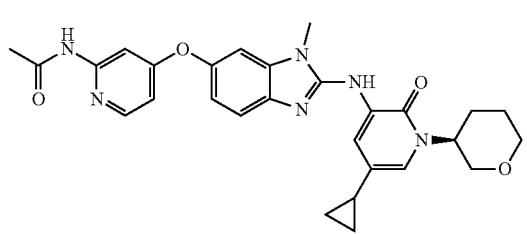
I-67-ii
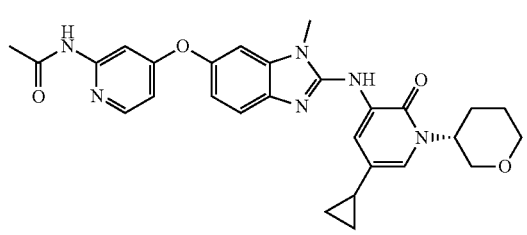
I-68
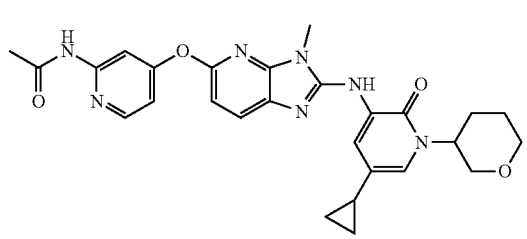
I-68-i
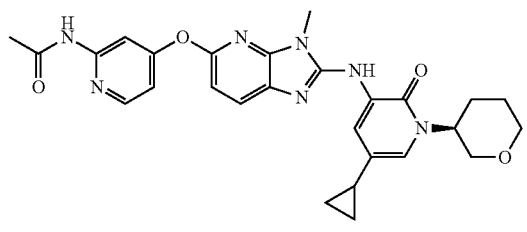
I-68-ii
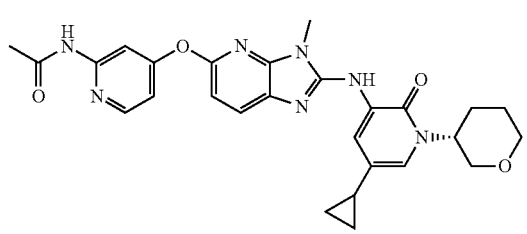

I-69
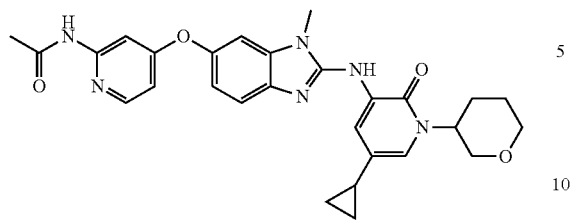
I-70
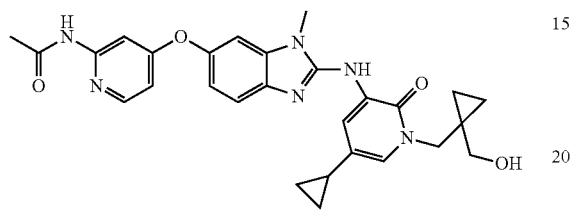
I-71
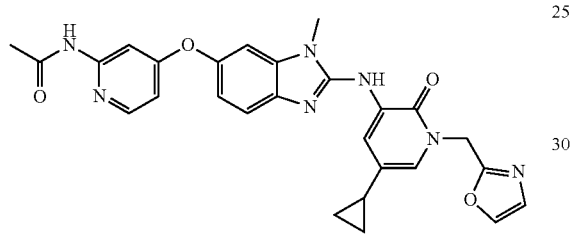
I-72
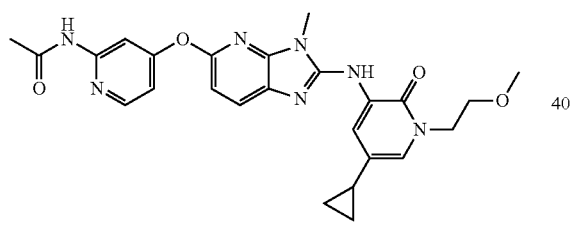
I-73
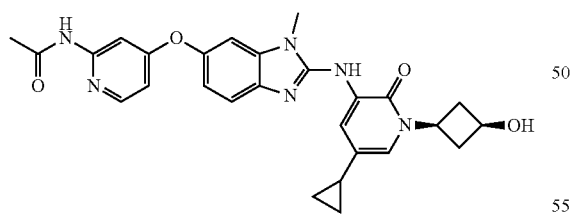
I-74
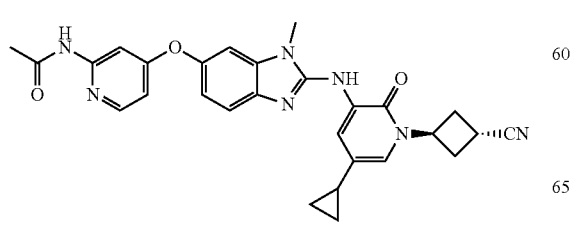
I-75
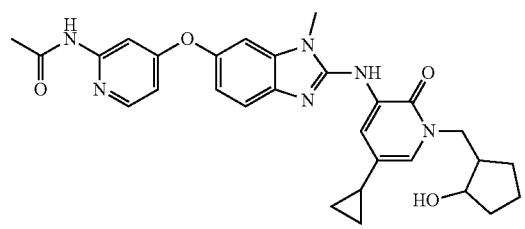
I-75-i
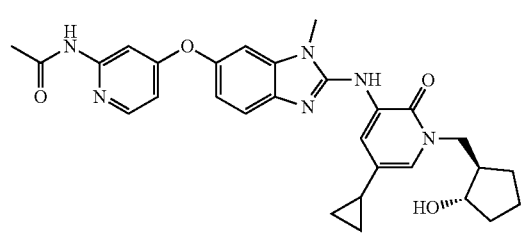
I-75-ii
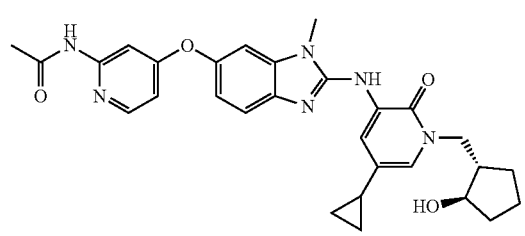
I-76
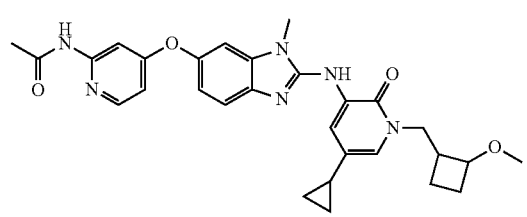
I-76-i
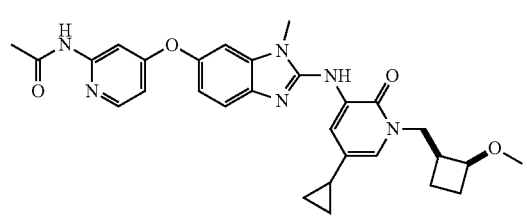
I-76-ii
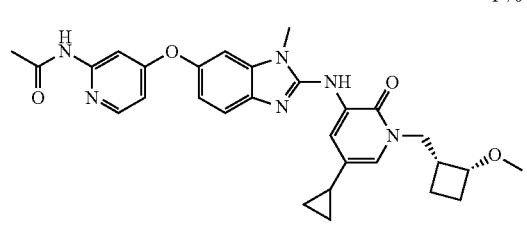

I-77
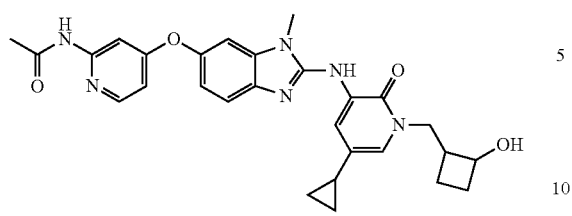
I-77-i
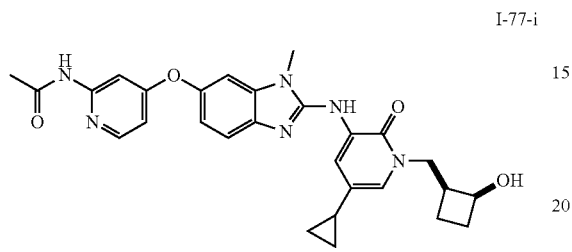
I-77-ii
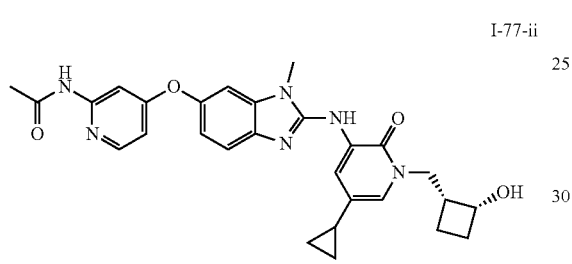
I-78
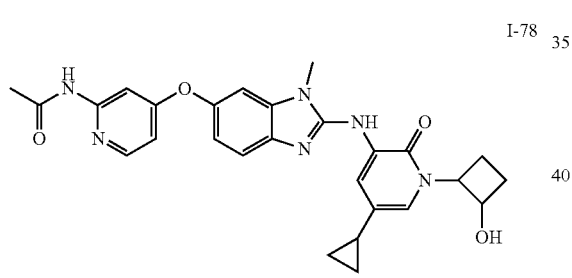
I-78-i
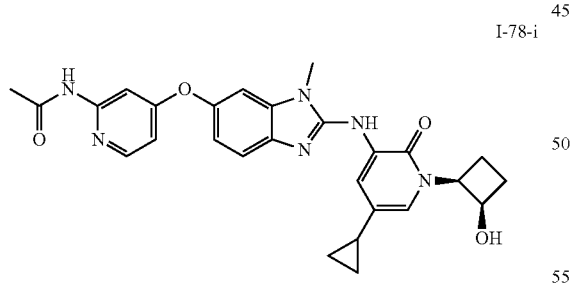
I-78-ii
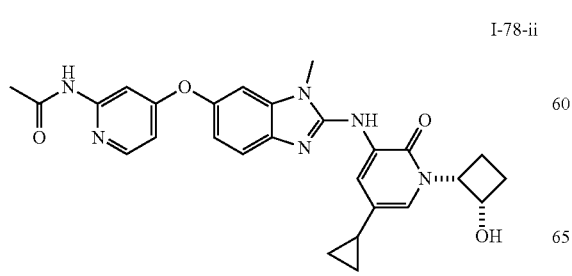
I-79-i
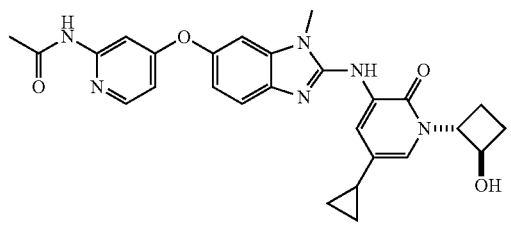
I-79-ii
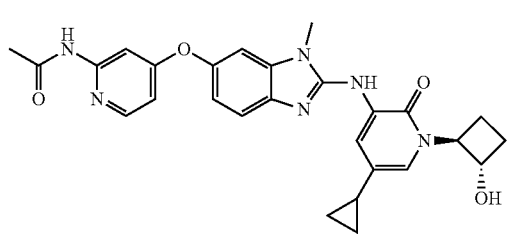
I-80
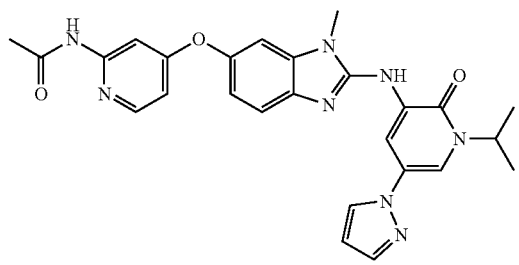
I-81
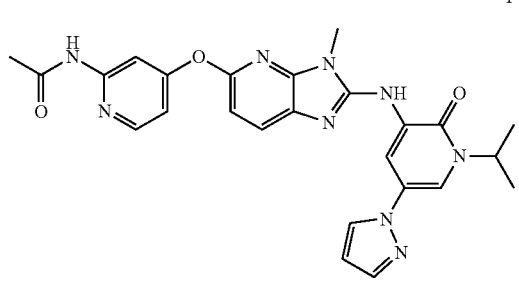
I-82
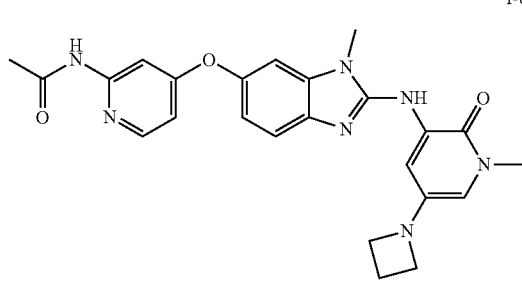
I-83
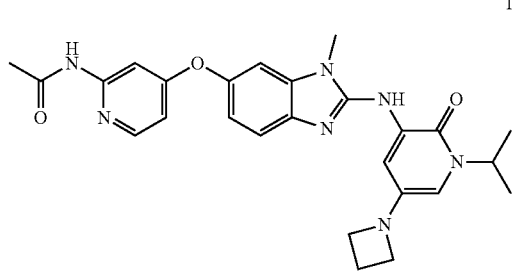

I-84
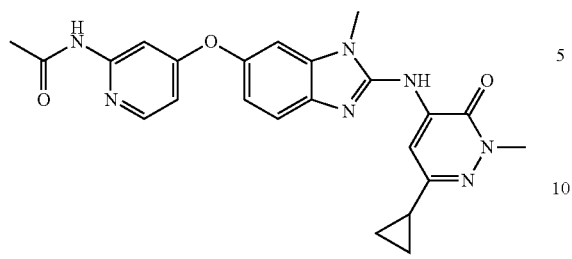
I-85
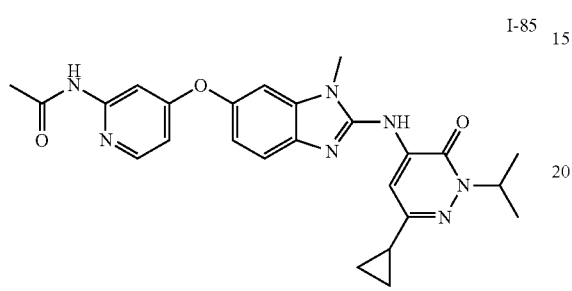
I-86
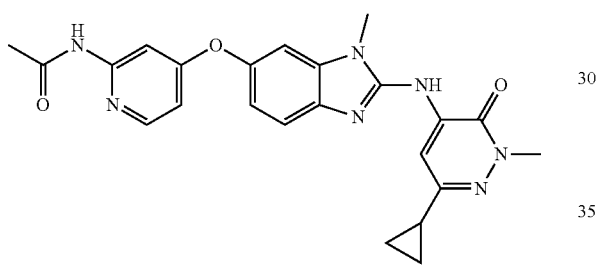
I-87
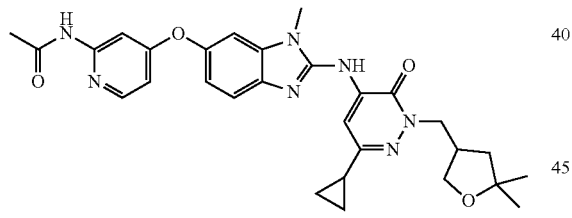
I-87-i
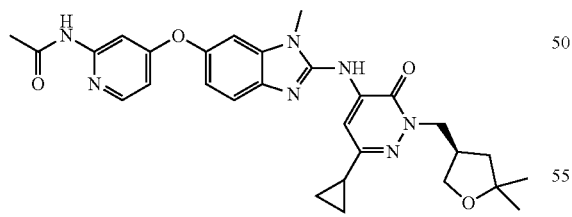
I-87-ii
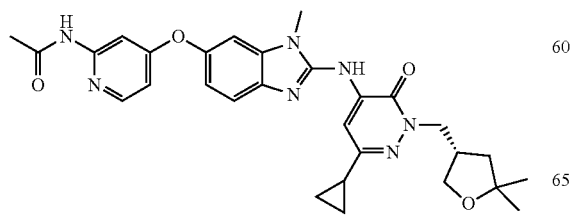
I-88
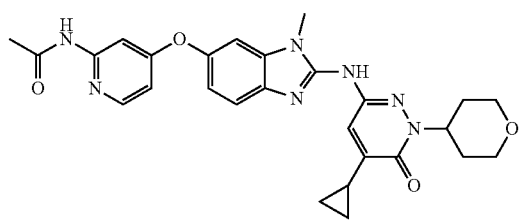
I-89
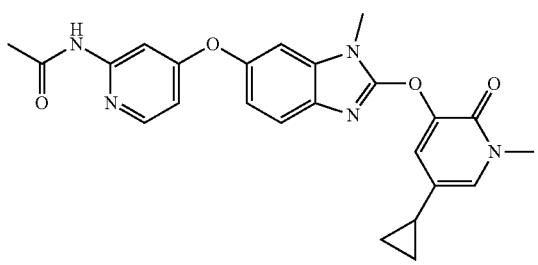
I-90
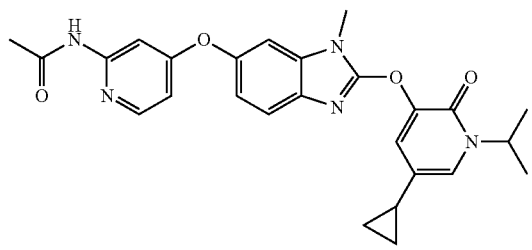
I-91
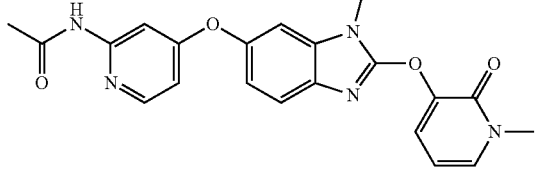
I-92
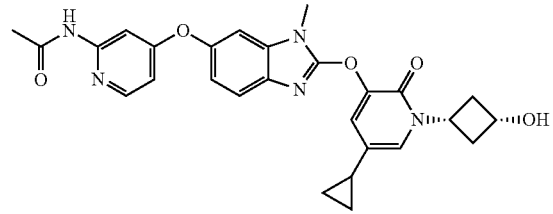
I-93
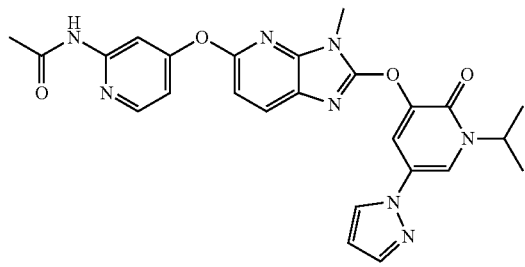

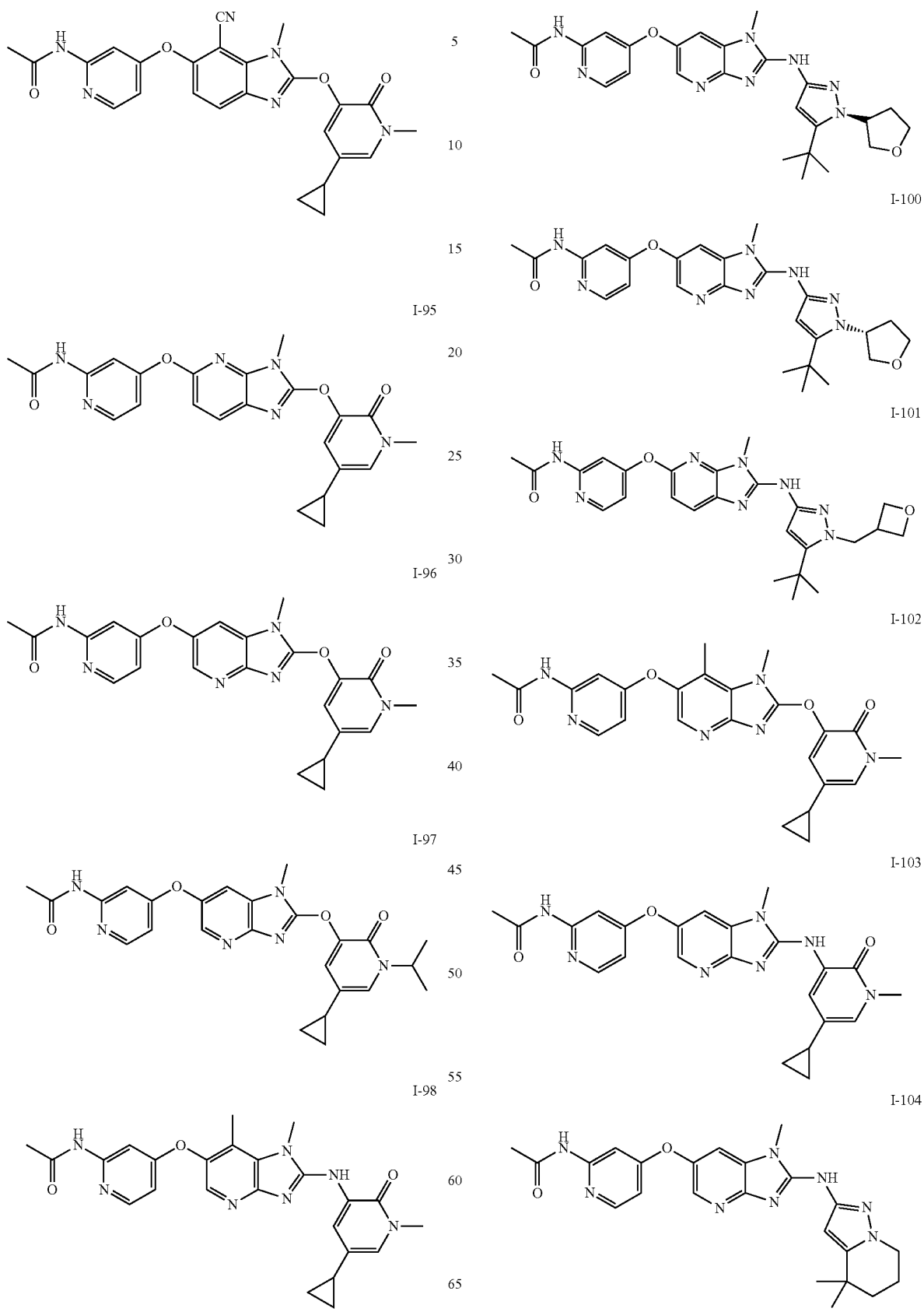

I-105'
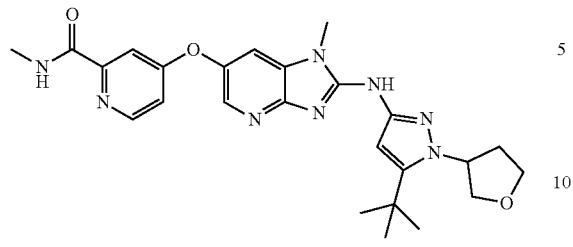
I-105
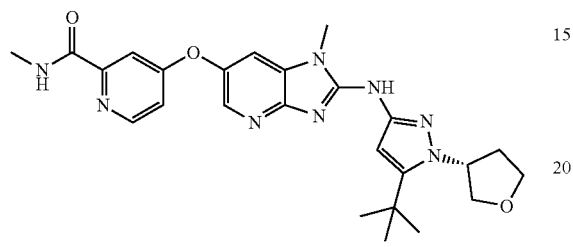
I-106
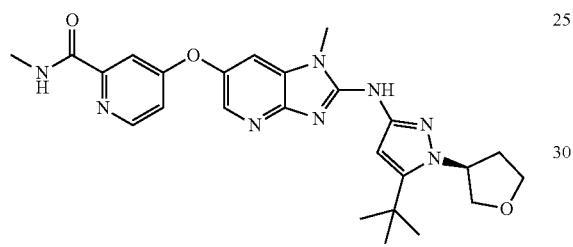
I-107
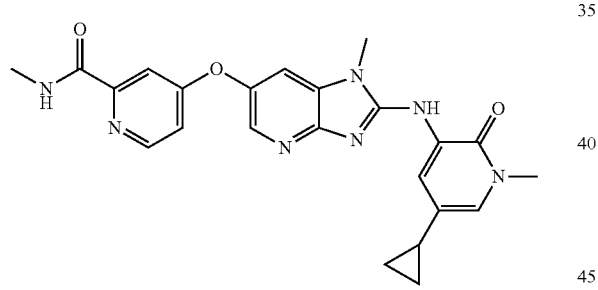
I-108'
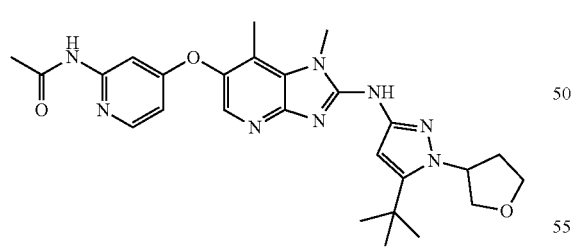
I-108
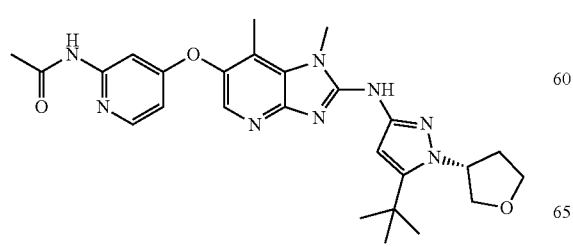
I-109'
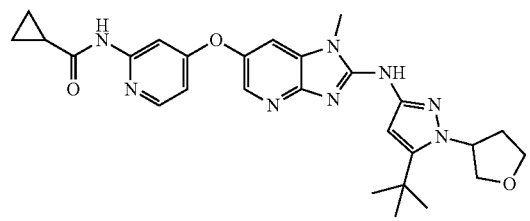
I-109
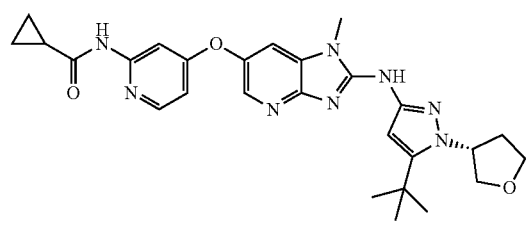
I-110
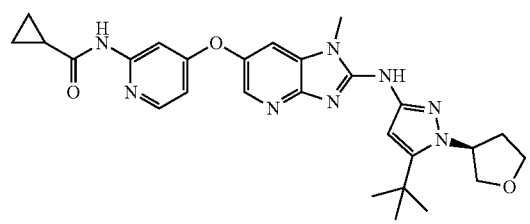
I-111
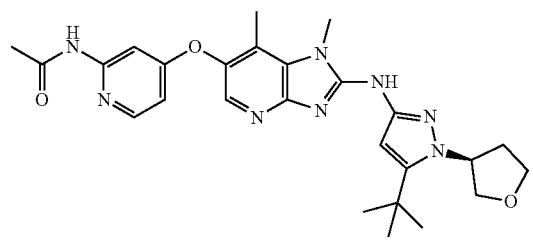
I-112
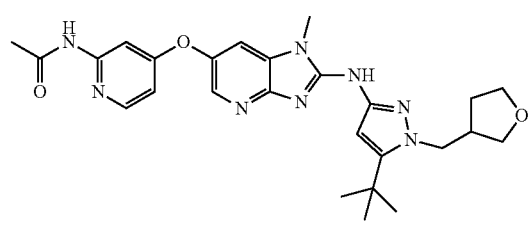
I-112-i
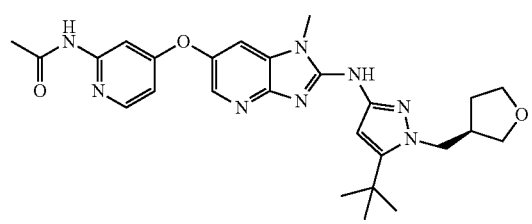

I-112-ii
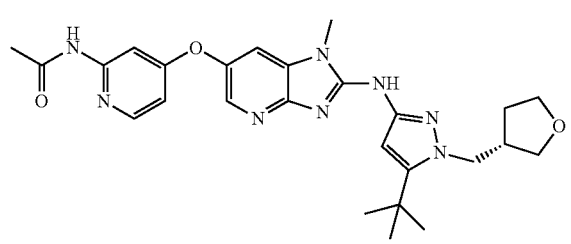
I-115
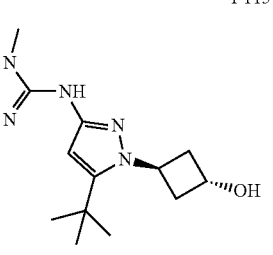
I-113
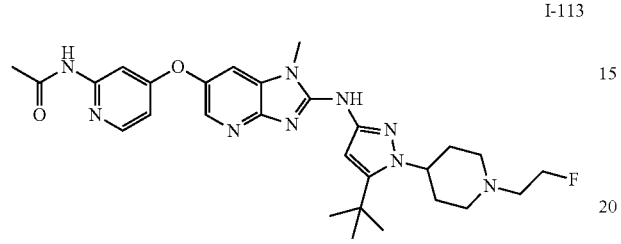
I-116
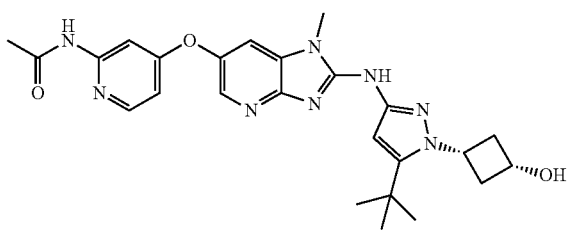
I-114
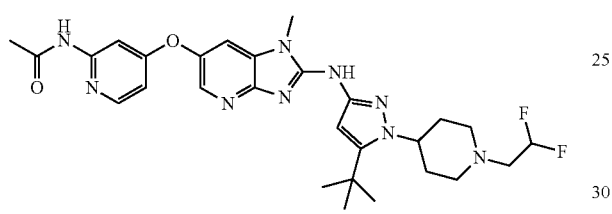
I-117
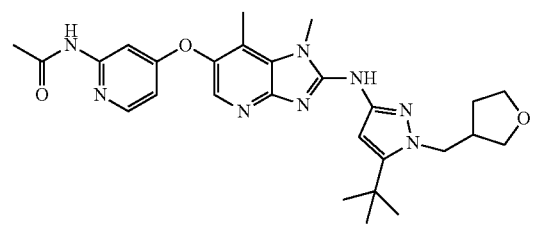
I-115'
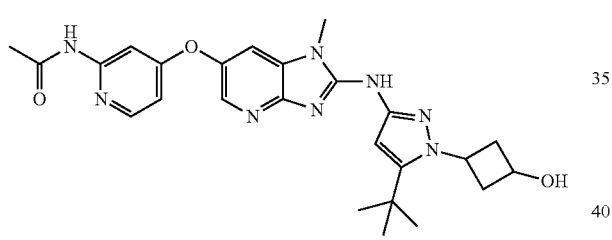
I-117-i
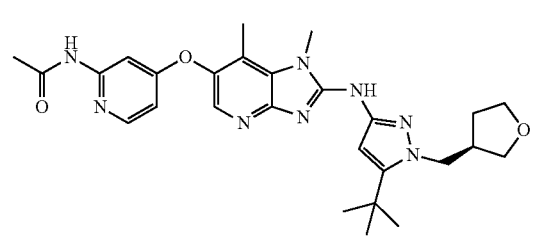
I-117-ii
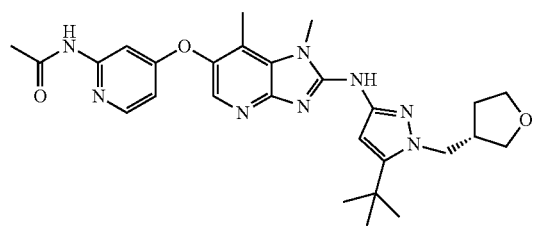
I-118'
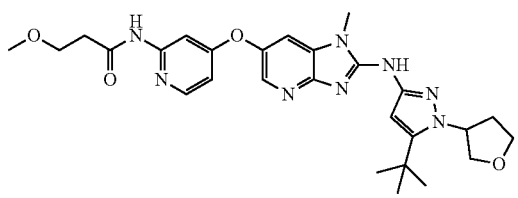
I-118
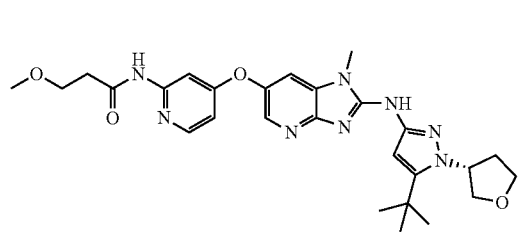
I-119
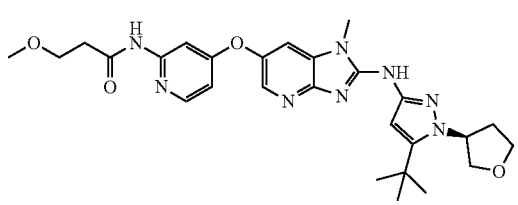

-continued
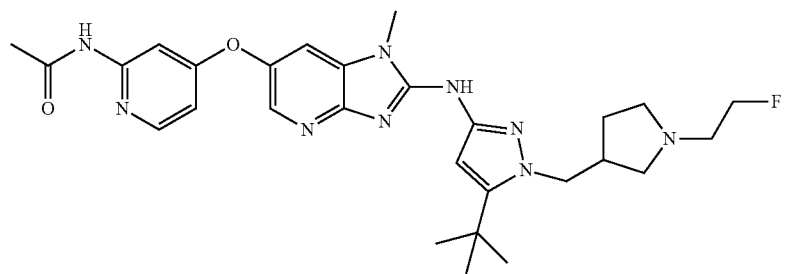
I-120'
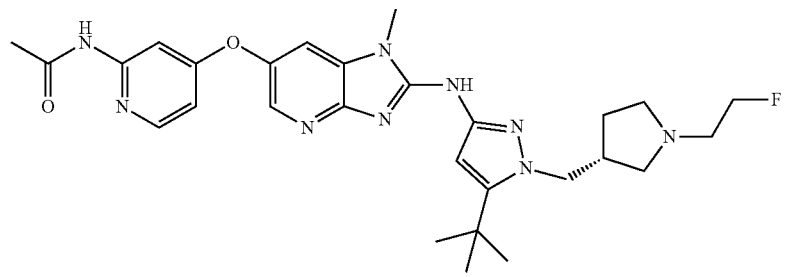
I-120
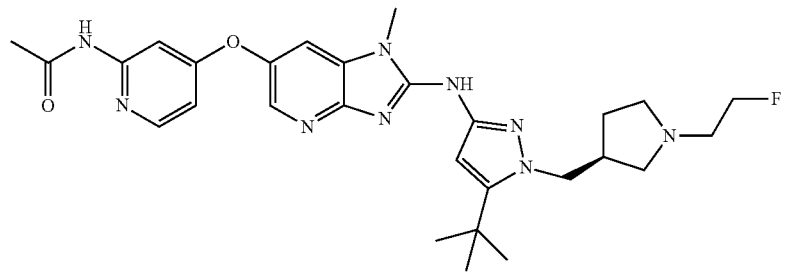
I-121
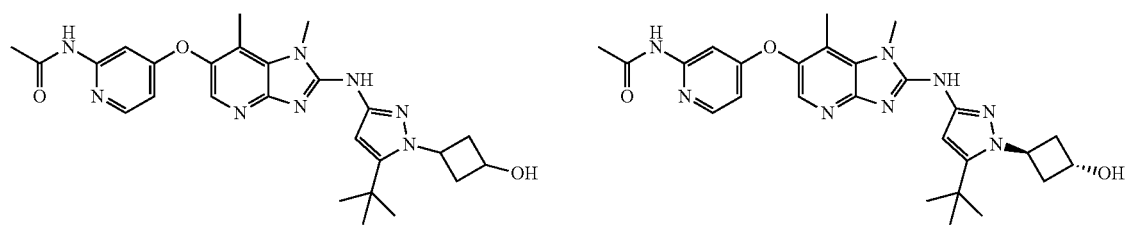
I-122'    I-122
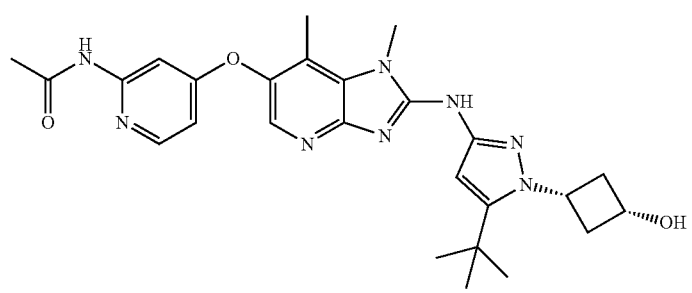
I-123

I-124'
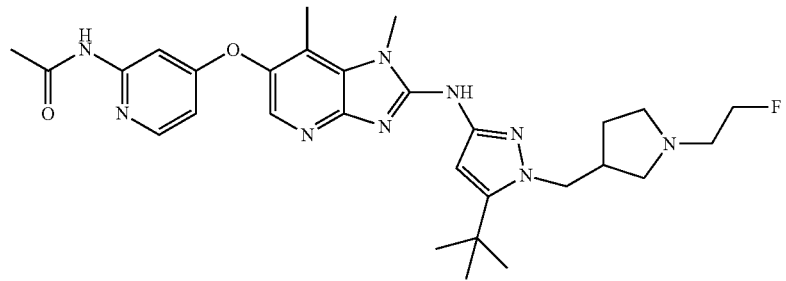
I-124
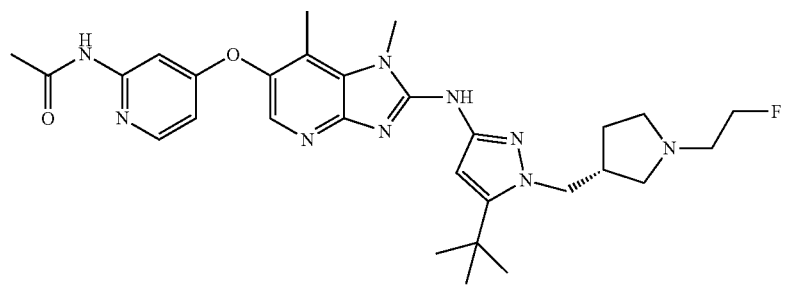
I-125
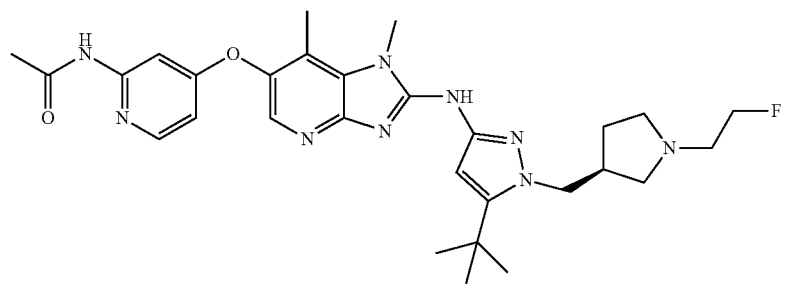
I-126' I-126
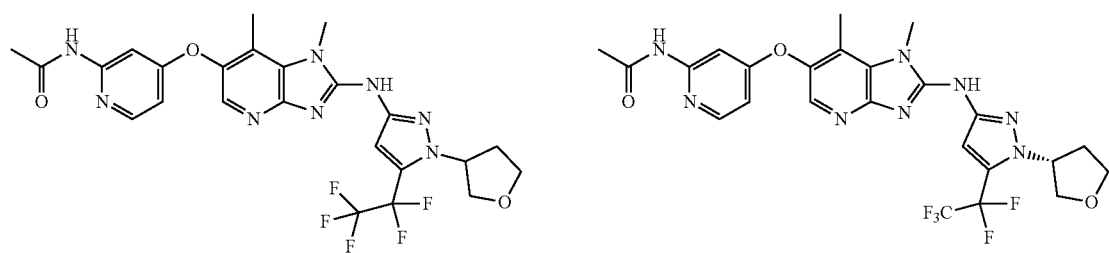
I-127
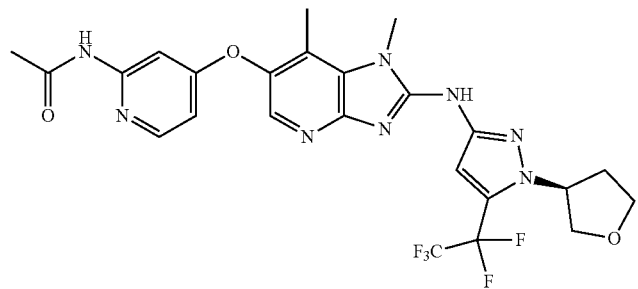

I-128
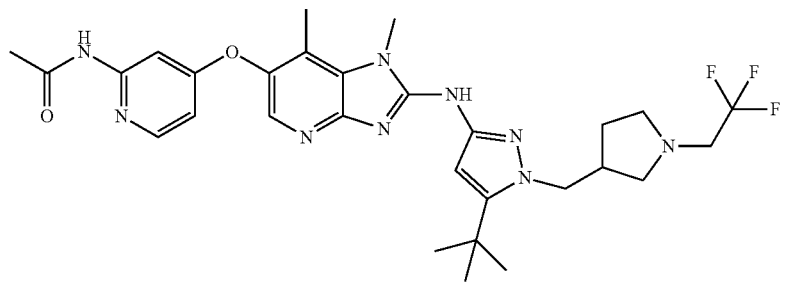
I-128-i
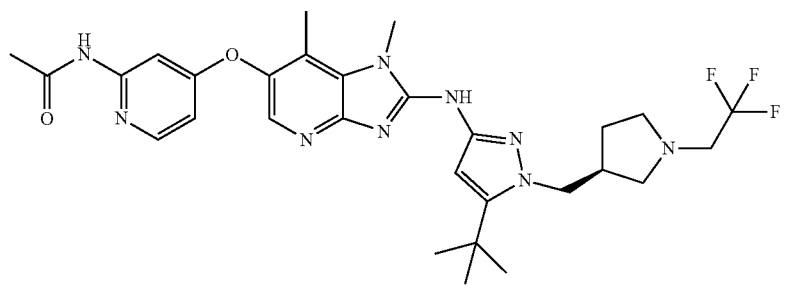
I-128-ii
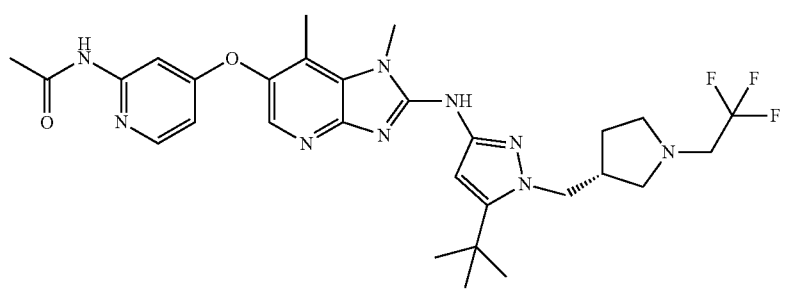
I-129
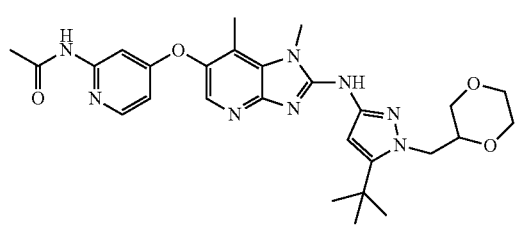
I-129-i
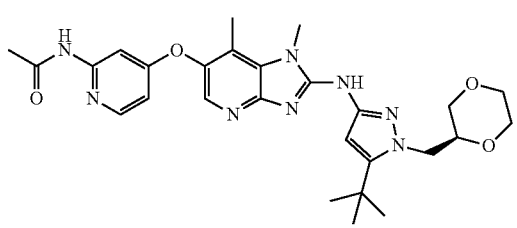
I-129-ii
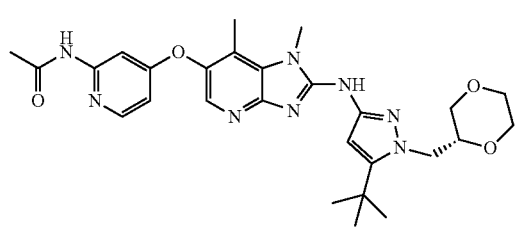
I-130
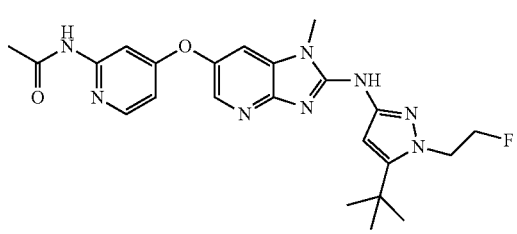
I-131
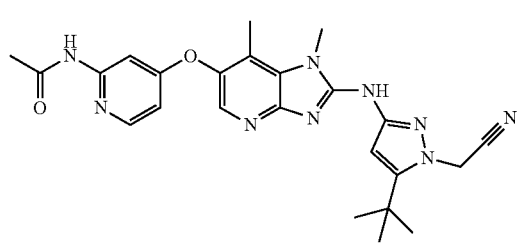
I-132
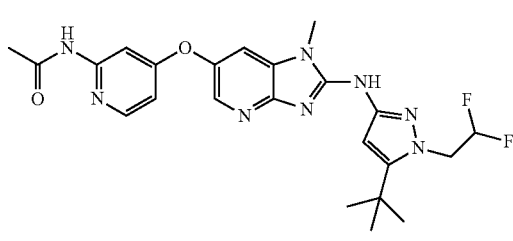

-continued
I-133'
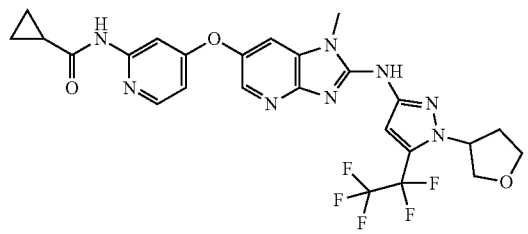
I-133
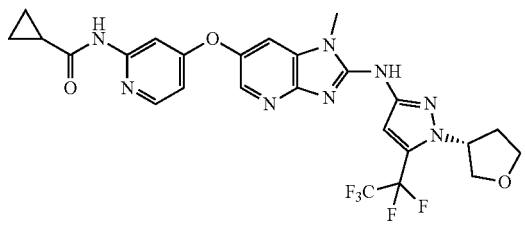
I-134
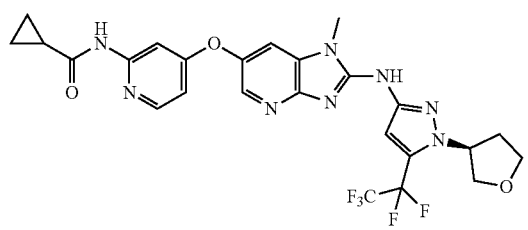
I-135
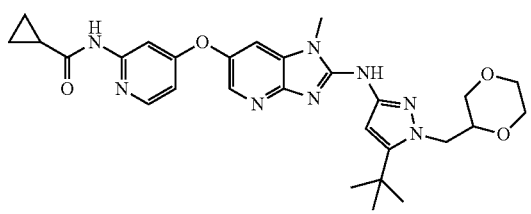
I-135-i
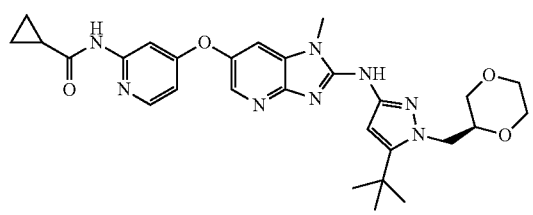
I-135-ii
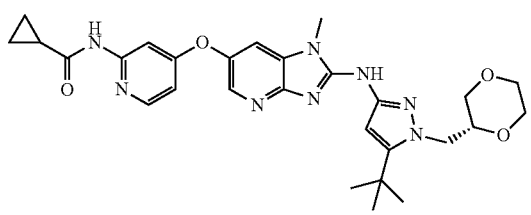
I-136
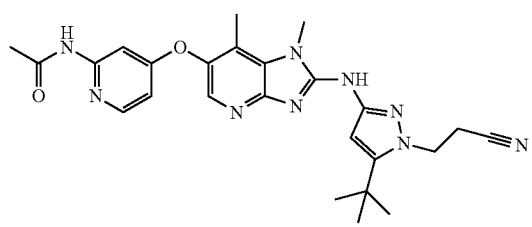
I-137
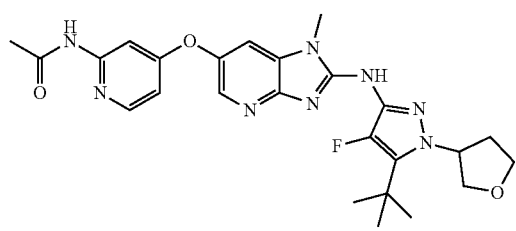
I-138'
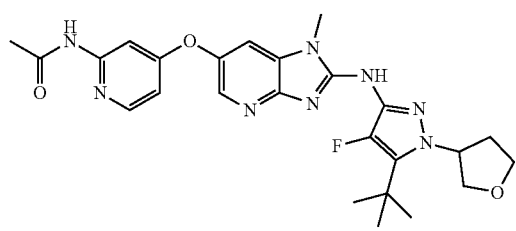
I-138
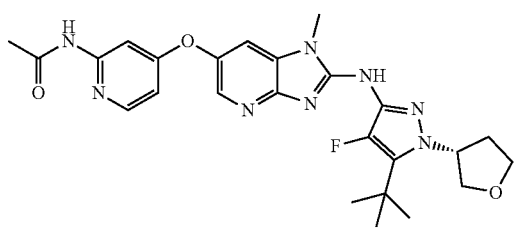
I-139
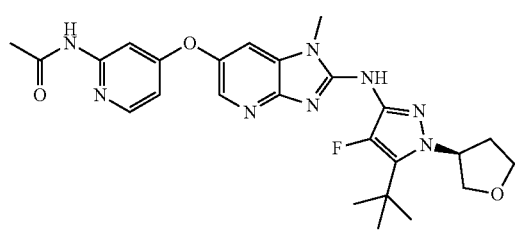
I-140

-continued
I-141'
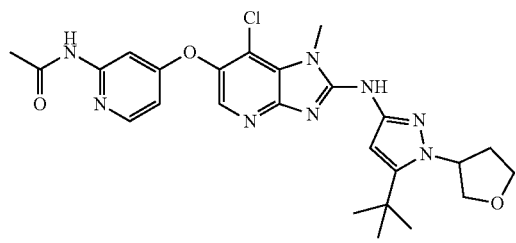
I-141
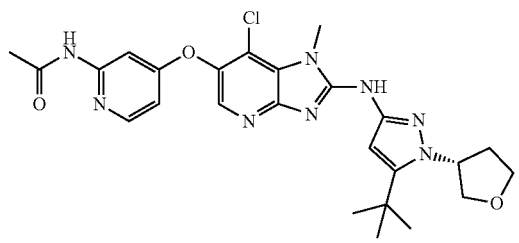
I-142
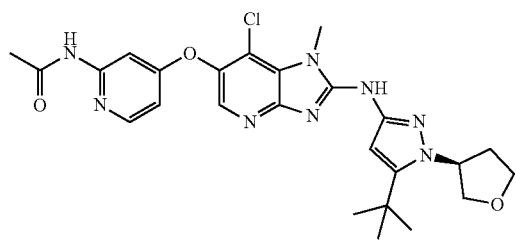
I-143'
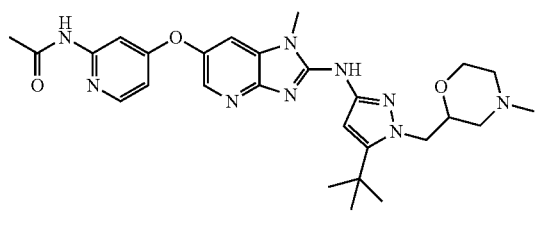
I-143
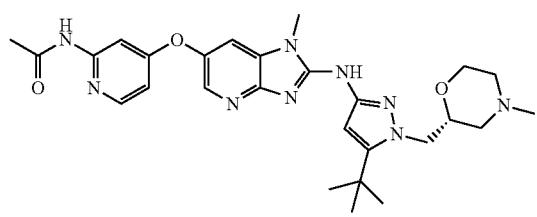
I-144
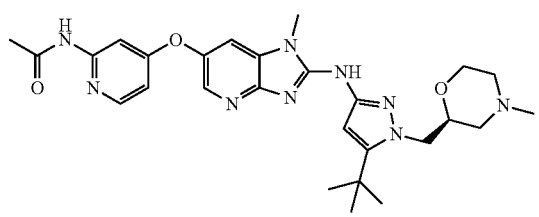
I-145'
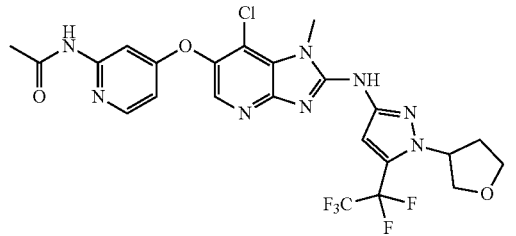
I-145
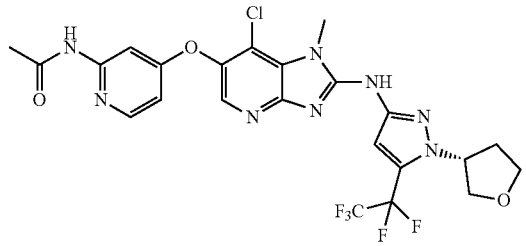
I-146
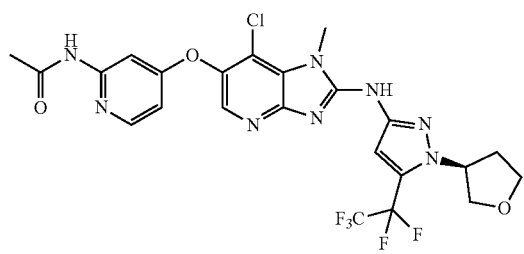
I-147'
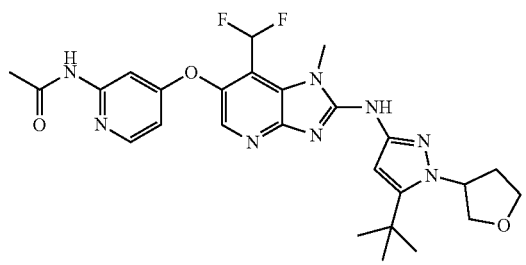
I-147
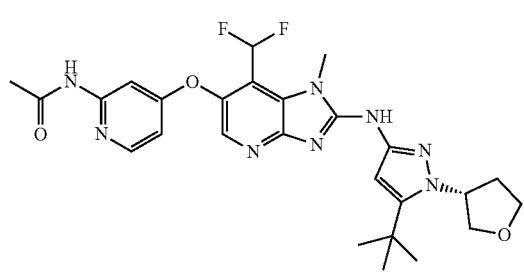
I-148
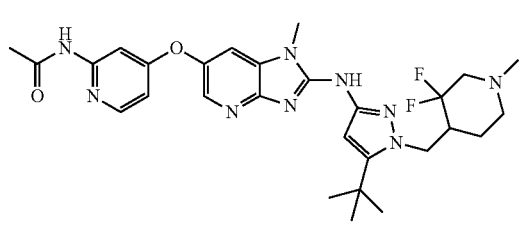

-continued
| I-148-i | I-148-ii |
|---|---|
| 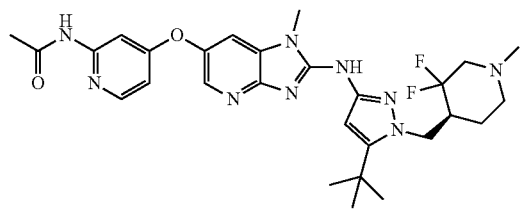 | 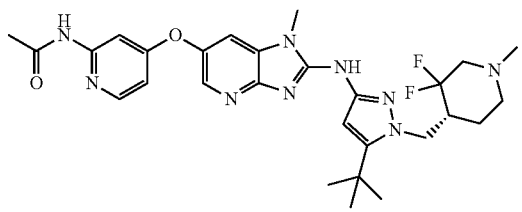 |
| I-149 | I-150' |
| 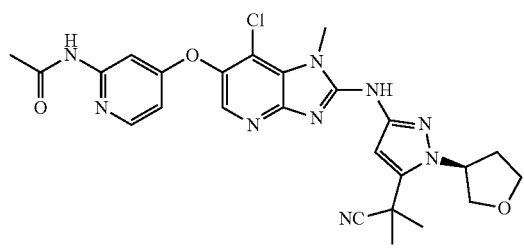 | 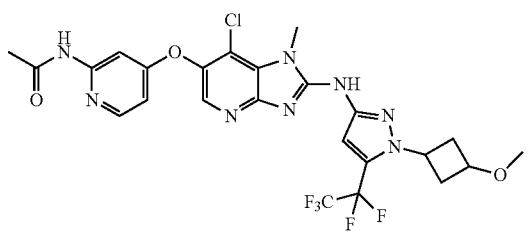 |
| I-150 | I-151' |
| 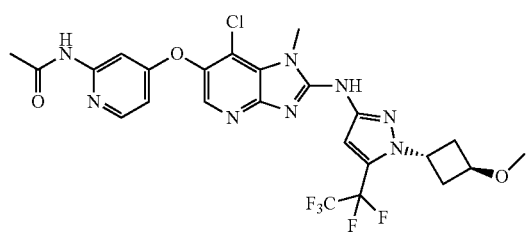 | 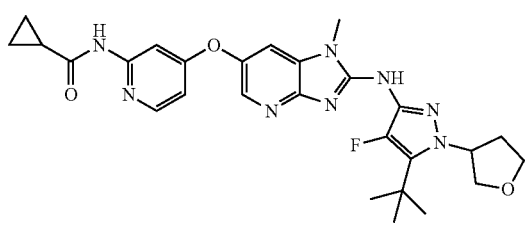 |
| I-151 | I-152 |
| 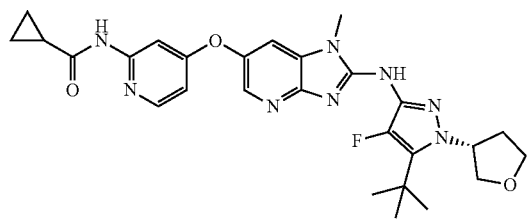 | 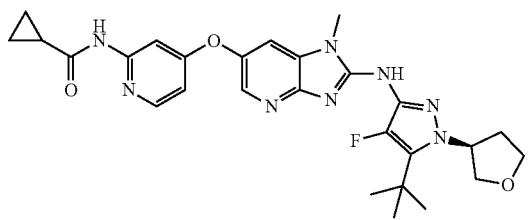 |
| I-153' | I-153 |
| 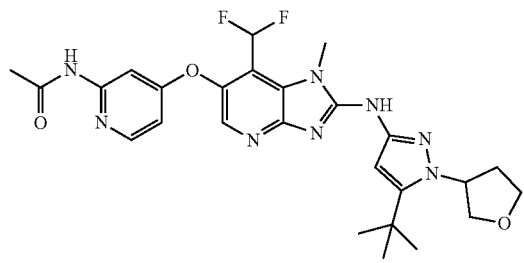 | 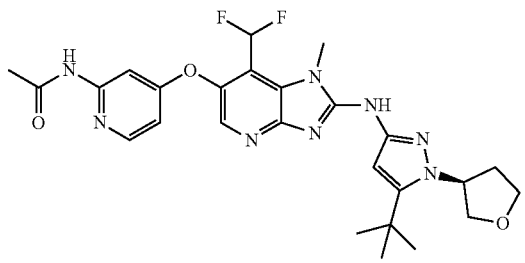 |
| I-154' | I-154 |
| 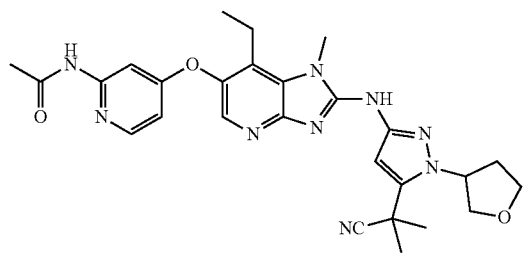 | 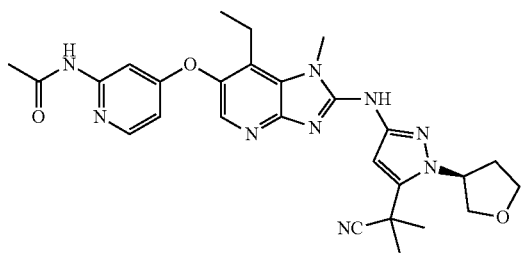 |

I-155' 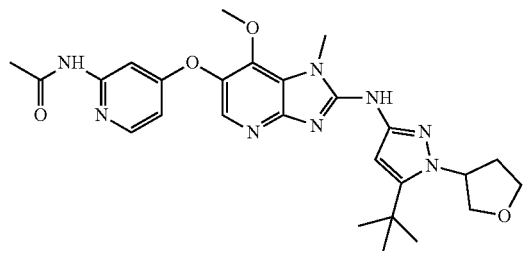
I-155 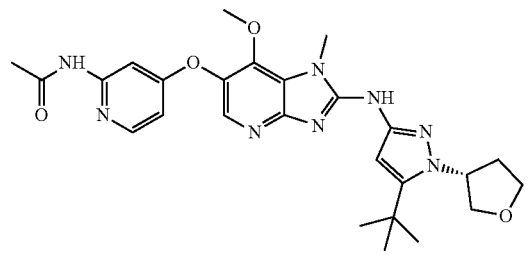
I-156 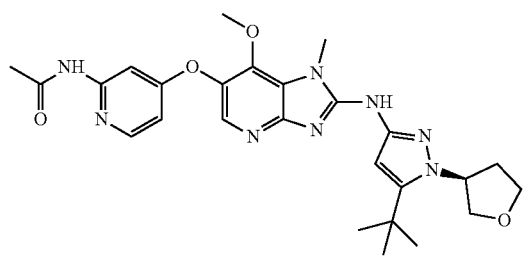
I-157' 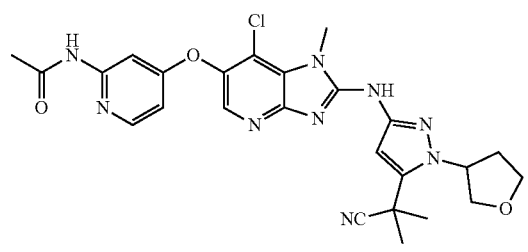
I-157 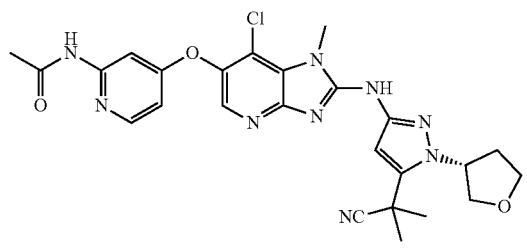
I-158 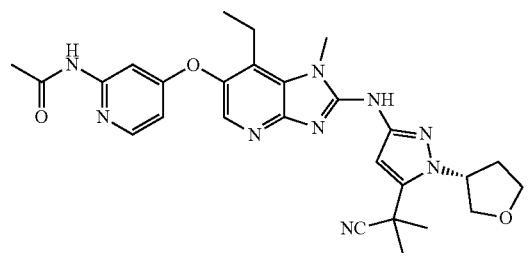
I-159 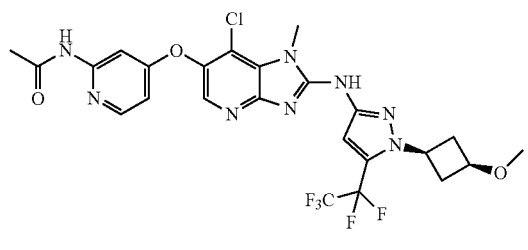
I-160' 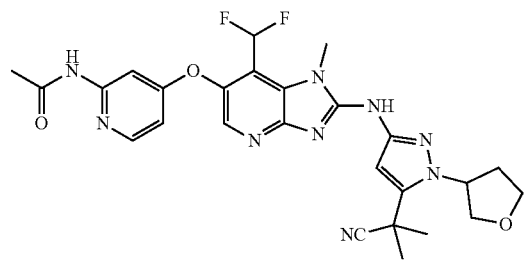
I-160 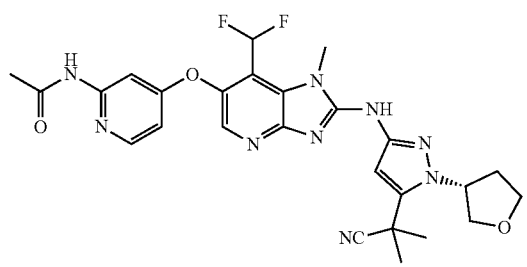
I-161 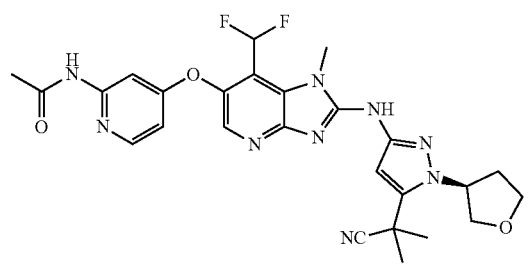

-continued
I-162
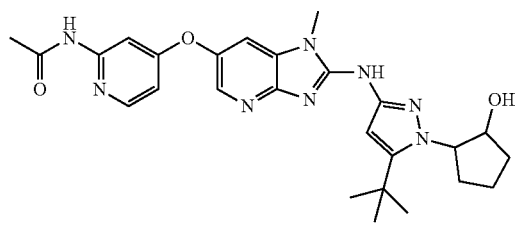
I-162-i
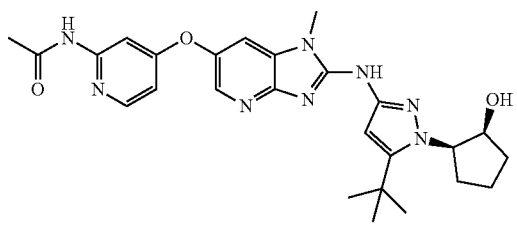
I-162-ii
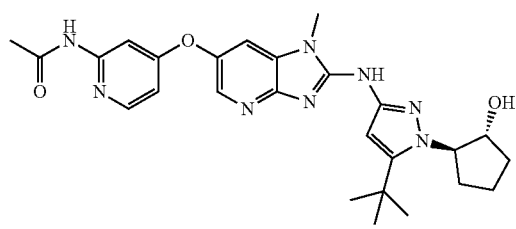
I-162-iii
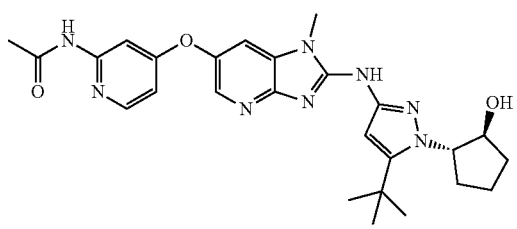
I-162-iv
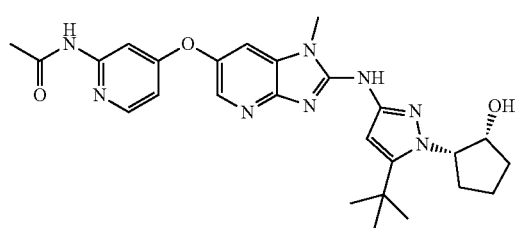
I-163
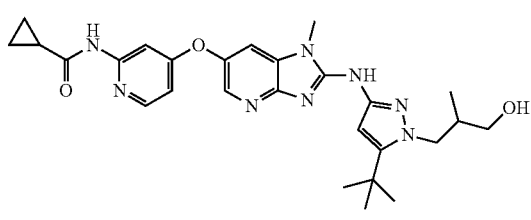
I-163-i
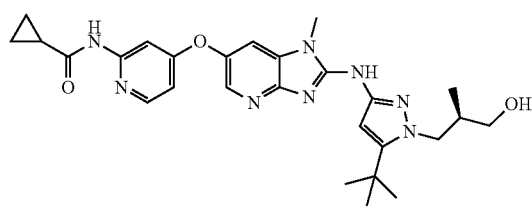
I-163-ii
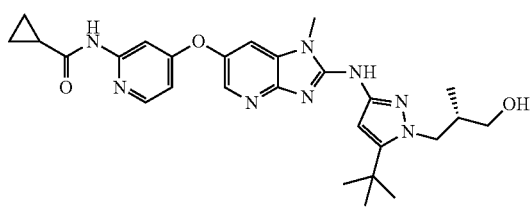
I-164
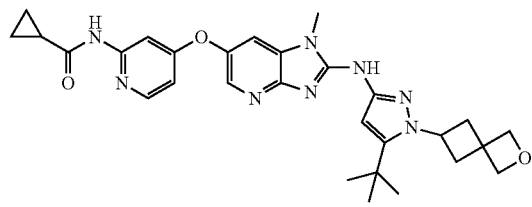
I-165'
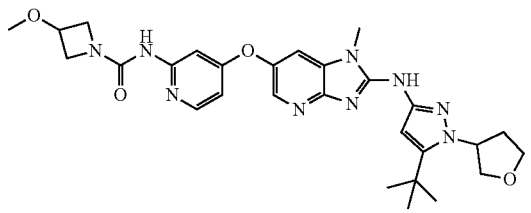
I-165
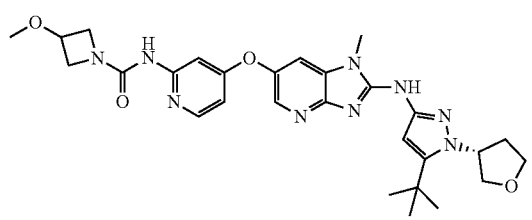
I-166
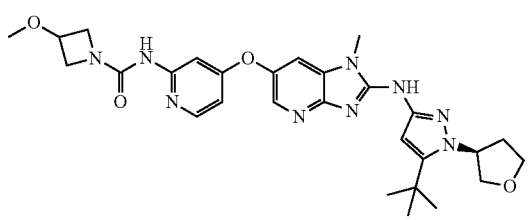

-continued
I-167'
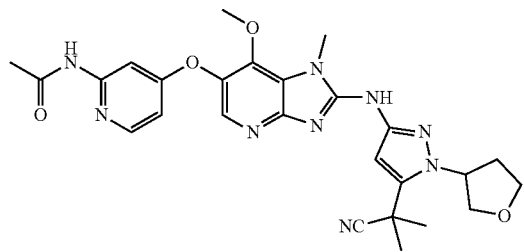
I-167
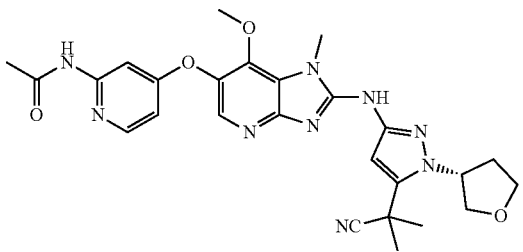
I-168
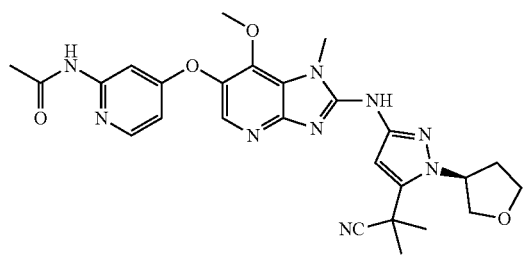
I-169
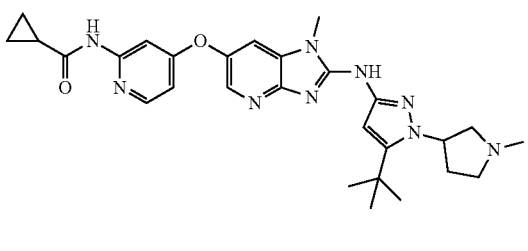
I-169-i
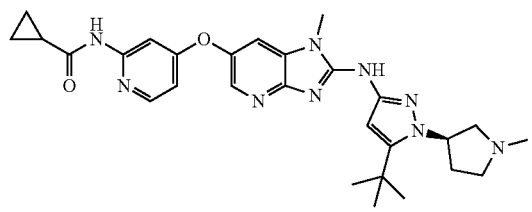
I-169-ii
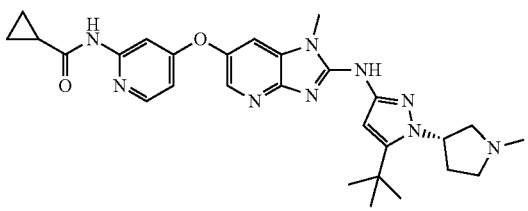
I-170
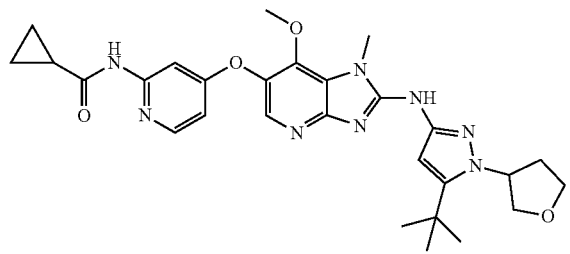
I-172
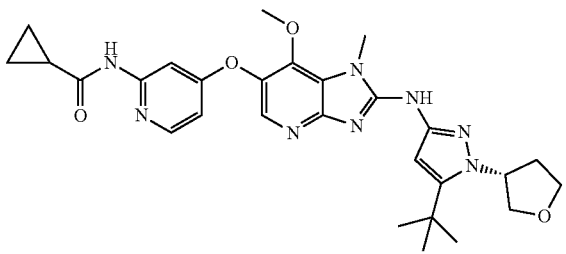
I-172-i
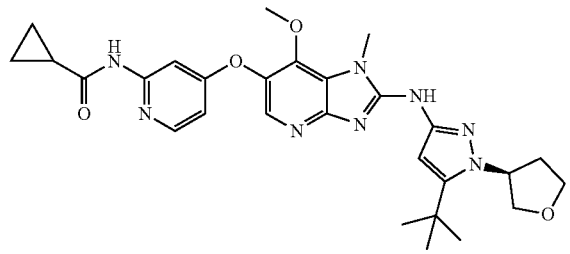
I-172-ii
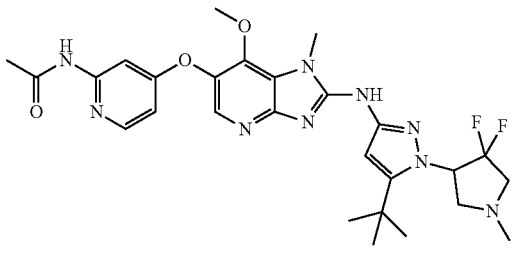
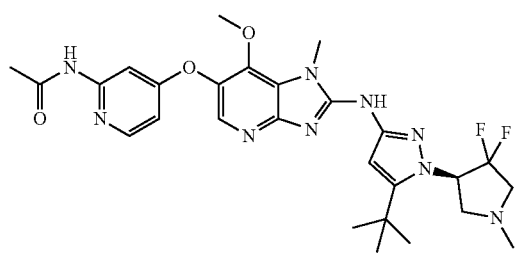
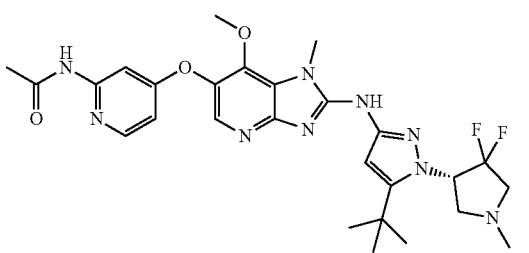

-continued
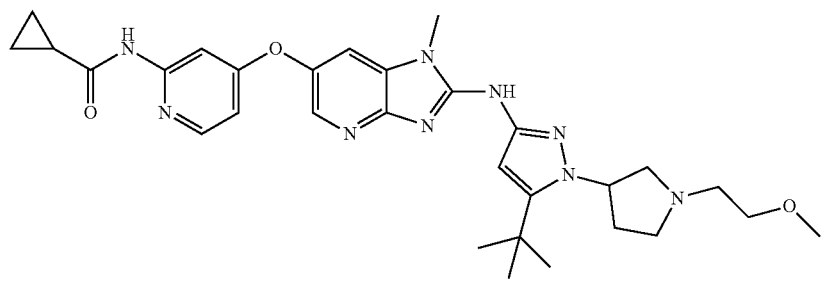
I-173'
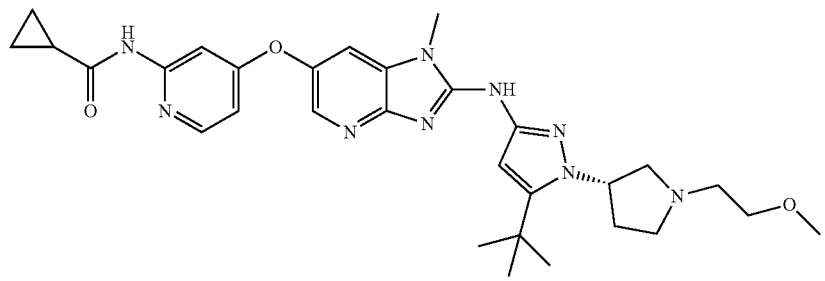
I-173
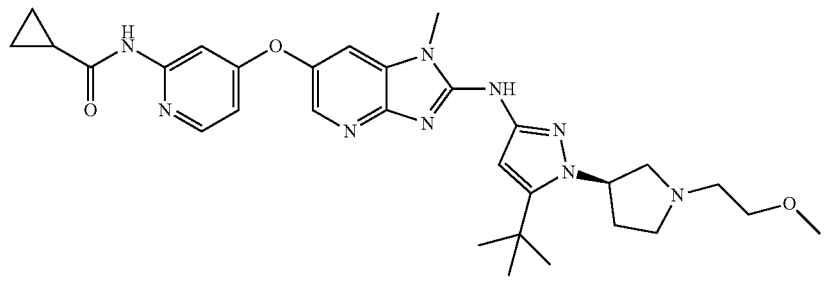
I-174
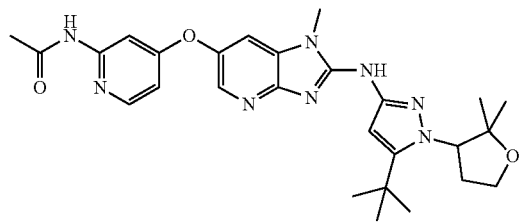
I-175
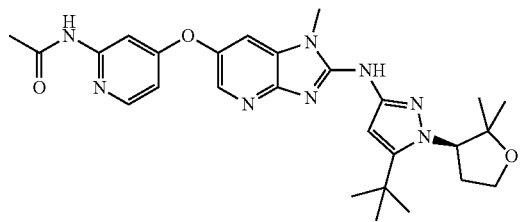
I-175-i
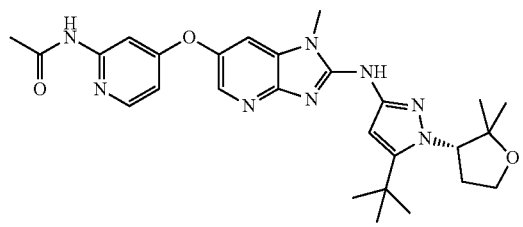
I-175-ii
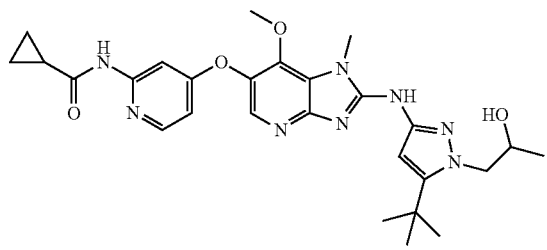
I-176
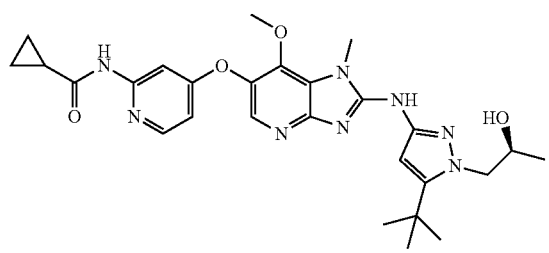
I-176-i
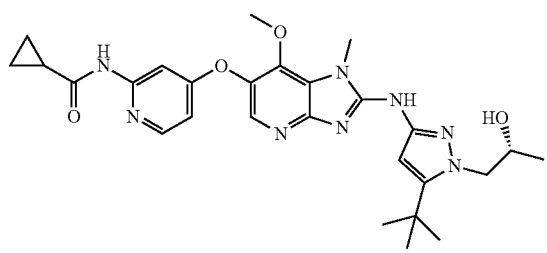
I-176-ii -continued
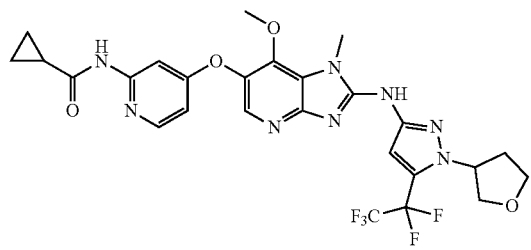
I-177'
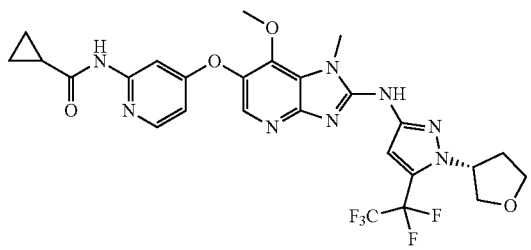
I-177
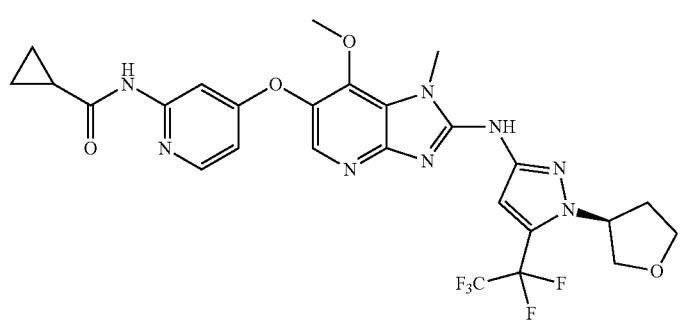
I-178
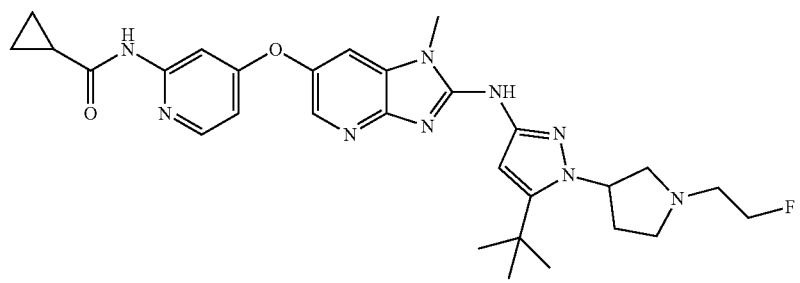
I-179'
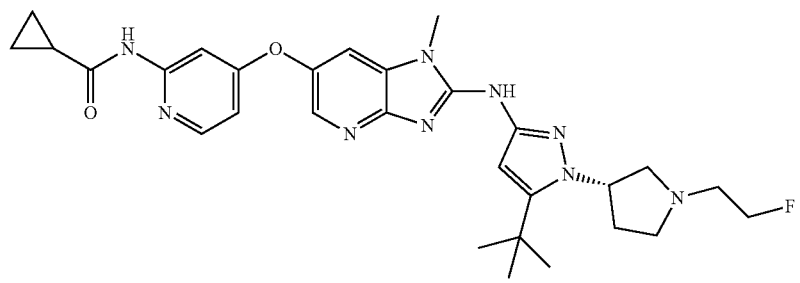
I-179
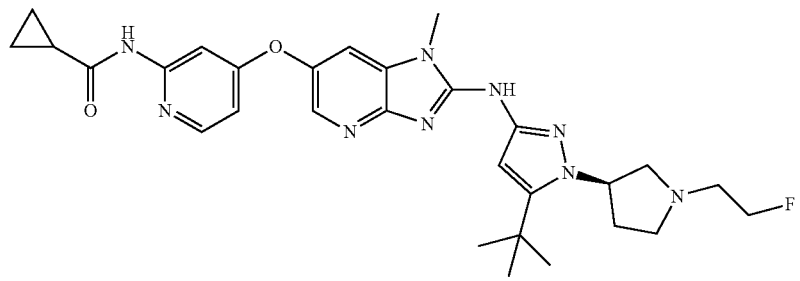
I-180

-continued
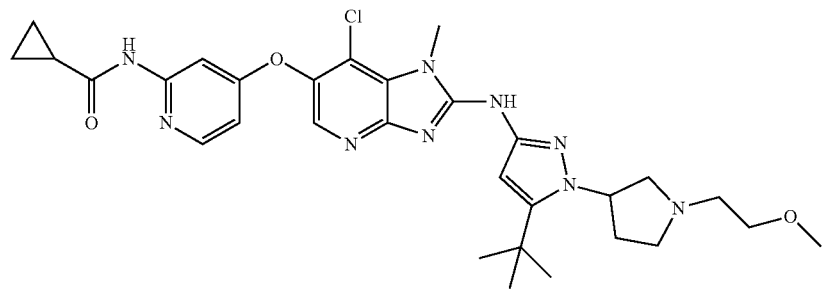
I-181'
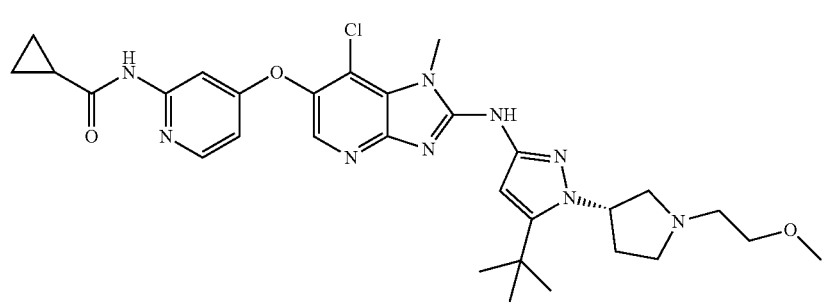
I-181
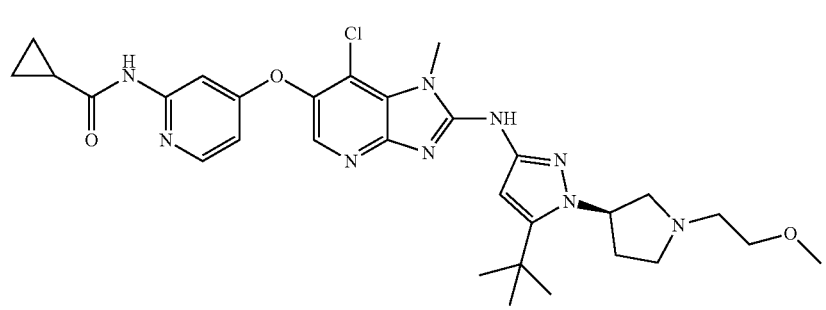
I-182
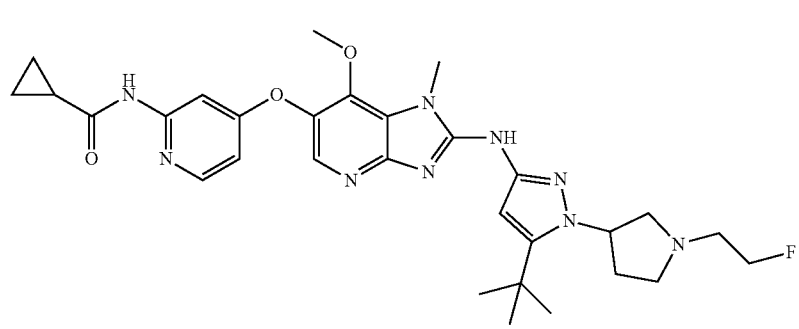
I-183'
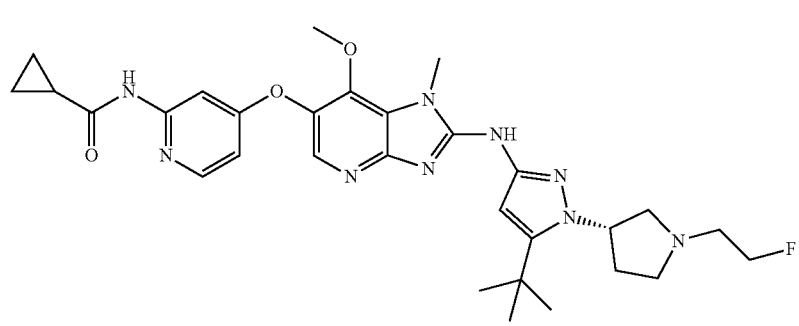
I-183

-continued
I-184
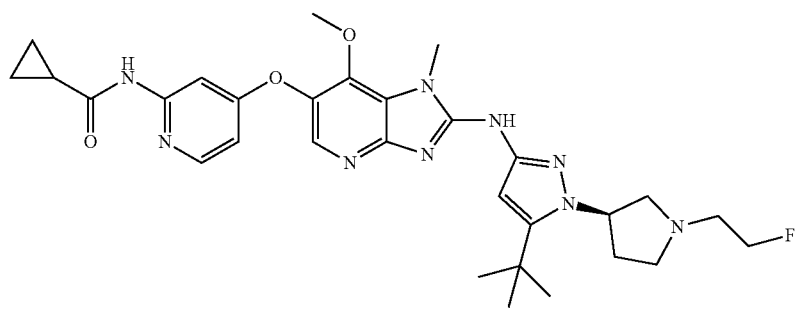
I-185' I-185
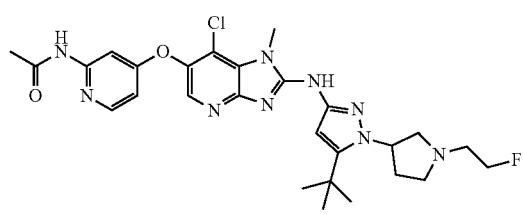
I-186 I-187
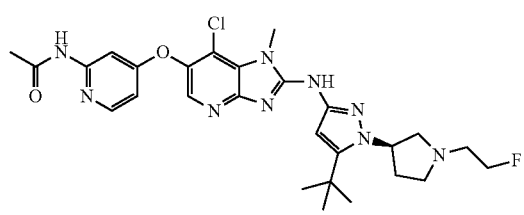
I-187-i I-187-ii
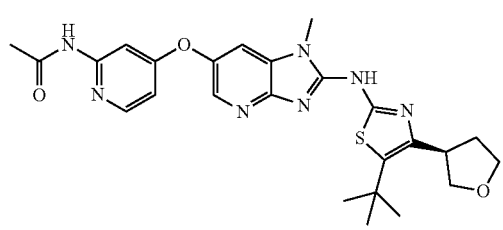
I-188 I-189
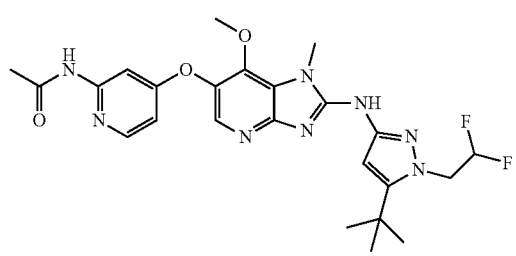
I-189-i I-189-ii
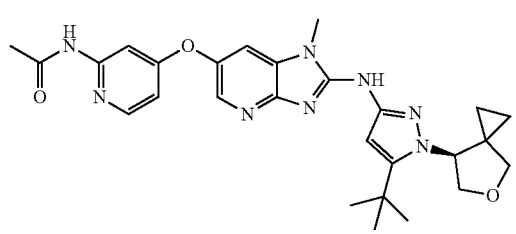

-continued
I-190
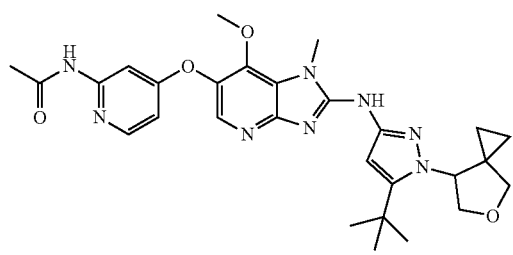
I-190-i
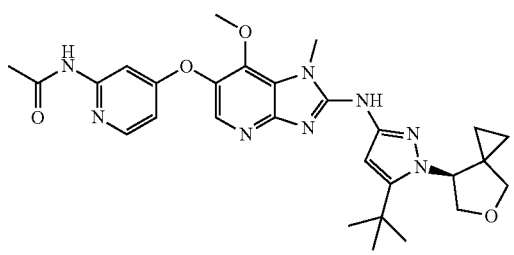
I-190-ii
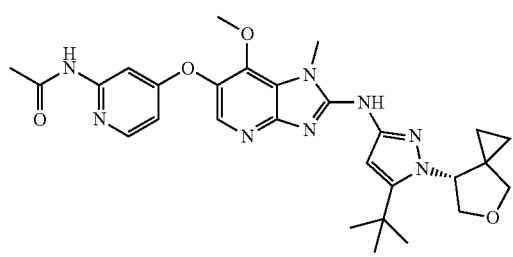
I-191
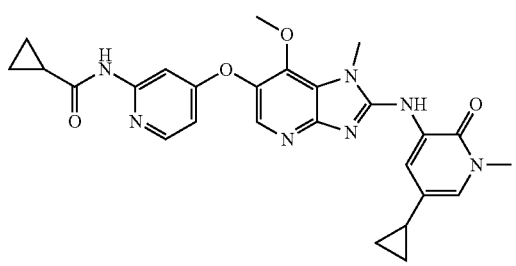
I-192
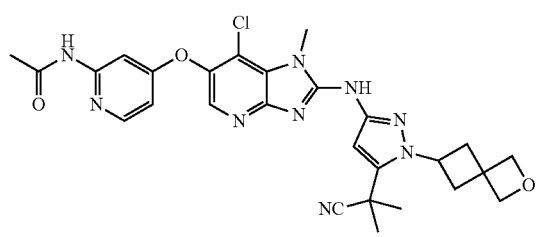
I-193
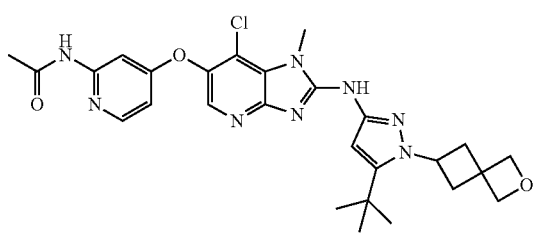
I-194
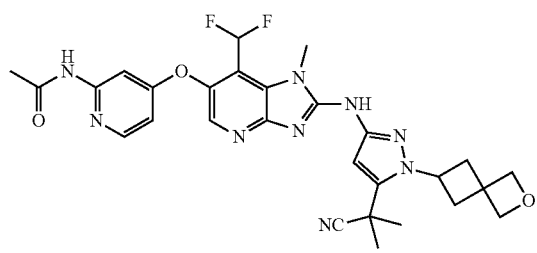
I-195
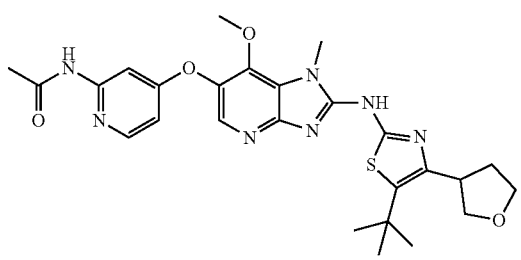
I-195-i
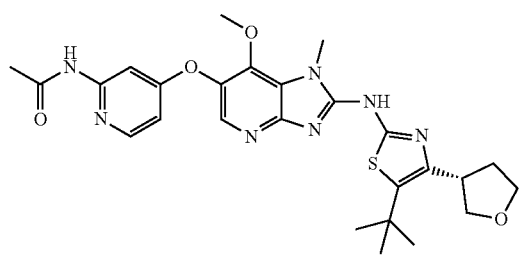
I-195-ii
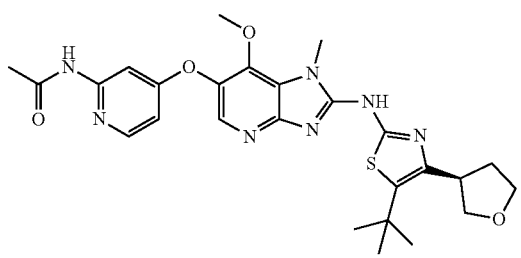
I-196
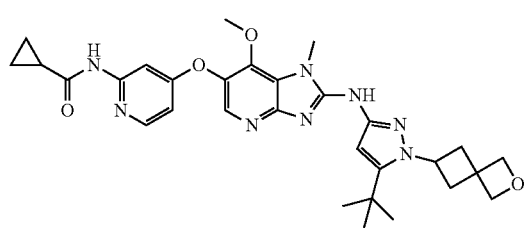
I-197
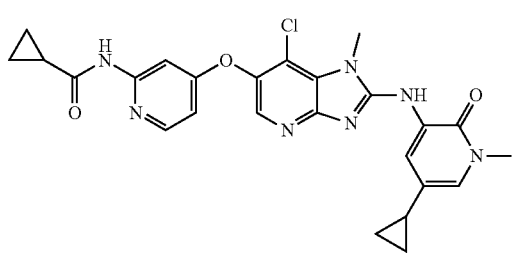

-continued
I-198
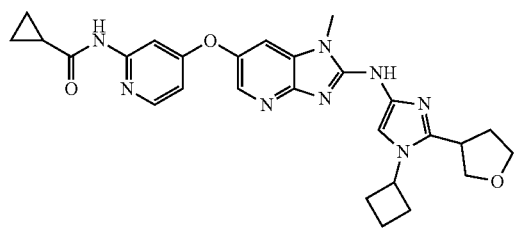
I-198-i
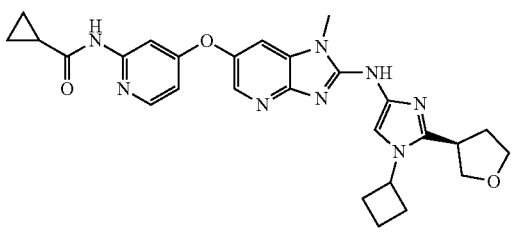
I-198-ii
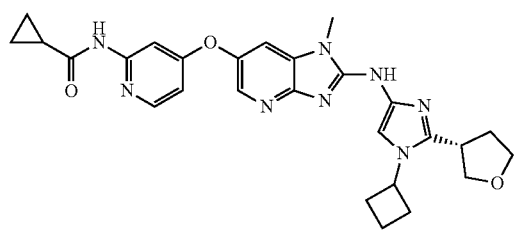
I-199
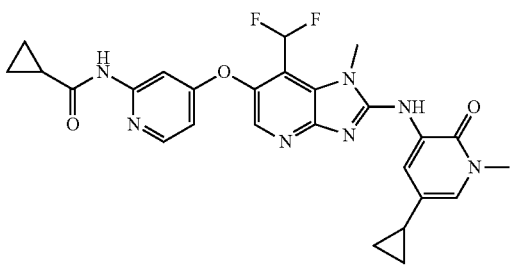
I-200
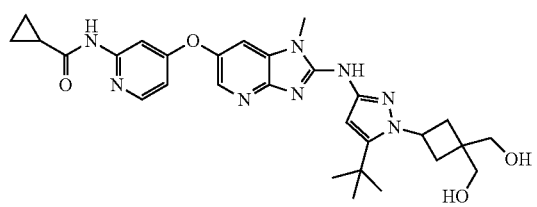
I-201
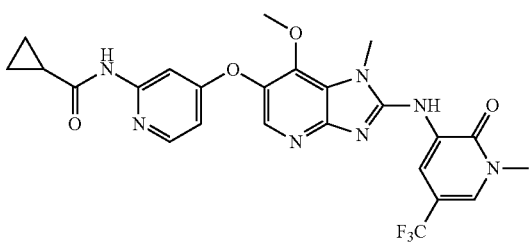
I-202
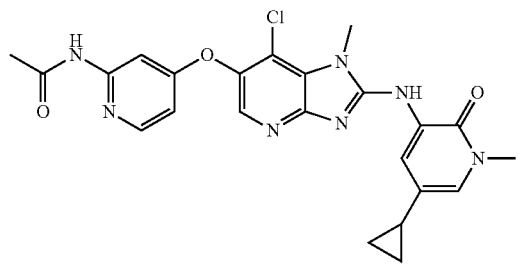
I-204
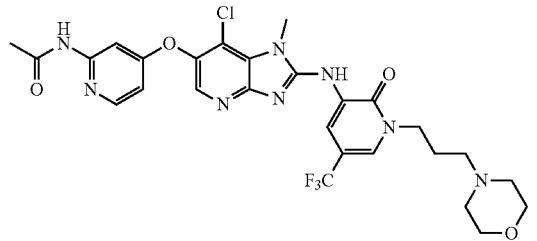
I-206
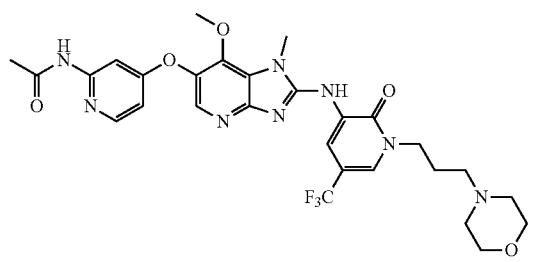
I-207
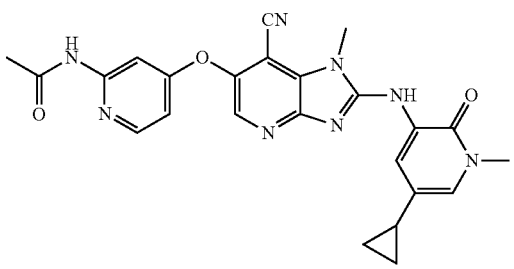

-continued
I-208
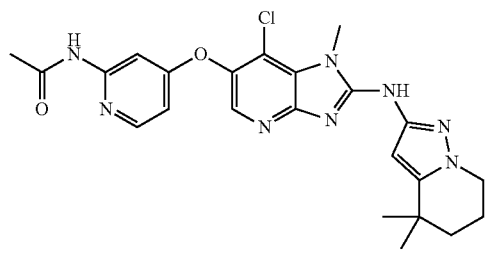
I-209
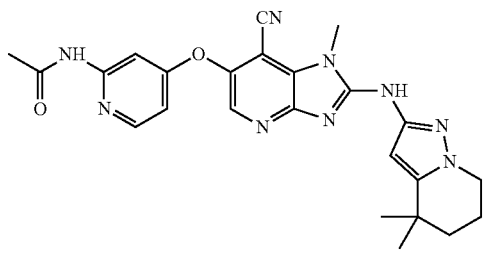
I-210
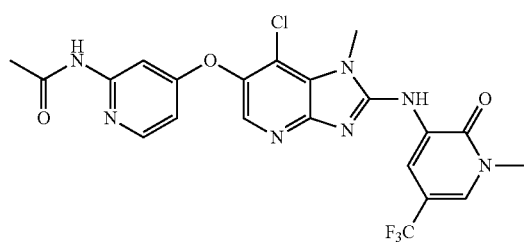
I-211
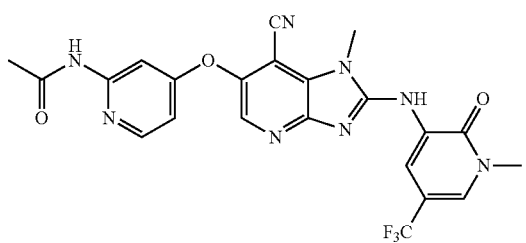
I-212
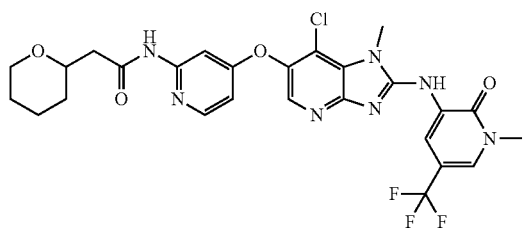
I-212-i
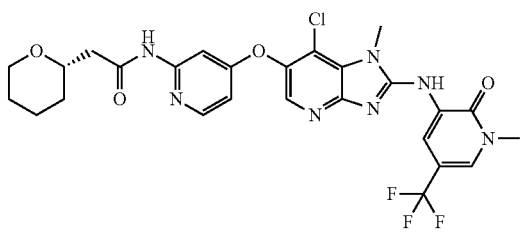
I-212-ii
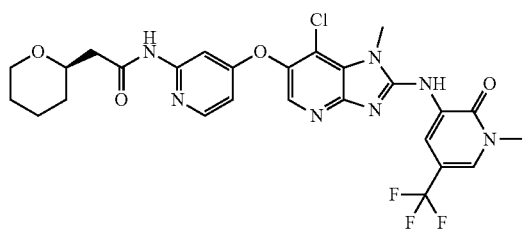
I-213
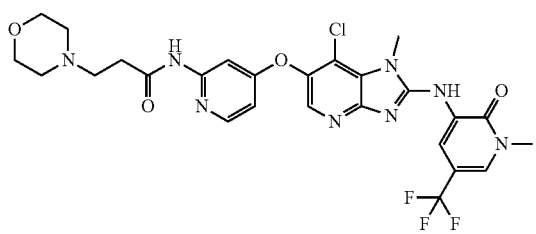
I-214
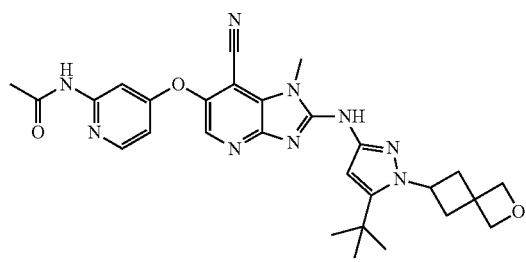
I-215
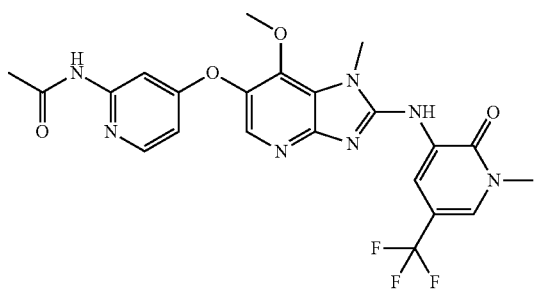

-continued

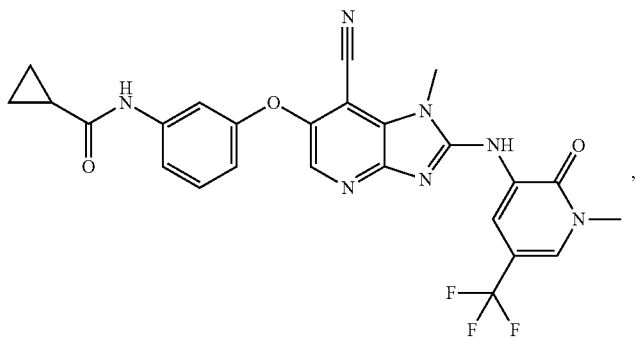

I-216 or a pharmaceutically acceptable salt thereof.

25. A pharmaceutical composition comprising a compound of claim 1, or a pharmaceutically acceptable salt thereof, and a pharmaceutically acceptable carrier.

26. A method of inhibiting JAK2 in a subject comprising administering the compound of claim 1.

27. A method of treating a disease, disorder, or condition associated with JAK2, comprising administering to a subject in need thereof the compound of claim 1, wherein the disease, disorder, or condition is cancer.

28. The compound of claim 21, wherein:
X is $CR^x$;
Y is N; and
$R^x$ is hydrogen, halogen, —$OR^3$, optionally substituted $C_{1-6}$ aliphatic, or —CN.

29. The compound of claim 5, wherein:
$R^a$ is $C_{1-4}$ alkyl, 3- to 6-membered saturated monocyclic heterocyclyl having 1-2 heteroatoms independently selected from nitrogen, oxygen, and sulfur, or 7- to 8-membered saturated, spirocyclic, bicyclic heterocyclyl having 1-2 heteroatoms independently selected from nitrogen, oxygen, and sulfur; and
$R^b$ is $C_{3-4}$ cycloalkyl or $C_{1-4}$ alkyl optionally substituted with one or more fluoro.

30. The compound of claim 23, wherein:
X is $CR^x$;
Y is N; and
$R^x$ is hydrogen, halogen, —$OR^3$, optionally substituted $C_{1-6}$ aliphatic, or —CN.

* * * * *

UNITED STATES PATENT AND TRADEMARK OFFICE
CERTIFICATE OF CORRECTION

PATENT NO. : 11,691,963 B2  
APPLICATION NO. : 17/308740  
DATED : July 4, 2023  
INVENTOR(S) : Craig E. Masse et al.

Page 1 of 5

It is certified that error appears in the above-identified patent and that said Letters Patent is hereby corrected as shown below:

In the Claims

In Claim 24, Column 633, beginning at Line 25 and ending at Line 35, please delete:

"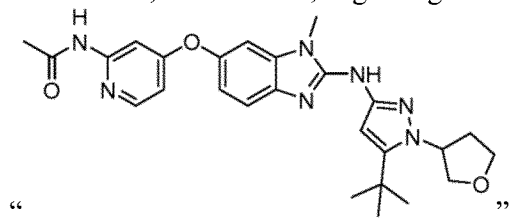"

Add insert:

--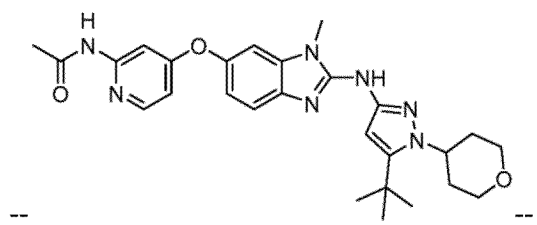--

In Claim 24, Column 643, beginning at Line 2 and ending at Line 12, please delete:

"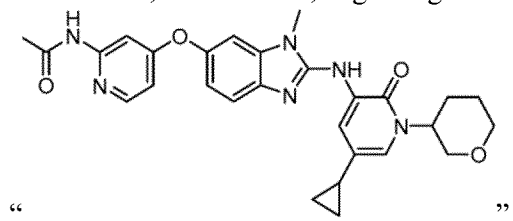"

And insert:

Signed and Sealed this  
Seventeenth Day of October, 2023

*Katherine Kelly Vidal*

Katherine Kelly Vidal  
*Director of the United States Patent and Trademark Office*

CERTIFICATE OF CORRECTION (continued)  Page 2 of 5
U.S. Pat. No. 11,691,963 B2

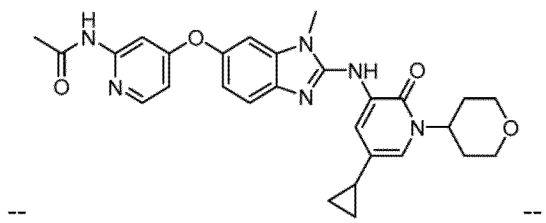
--  --

In Claim 24, Column 647, beginning at Line 28 and ending at Line 37, please delete:

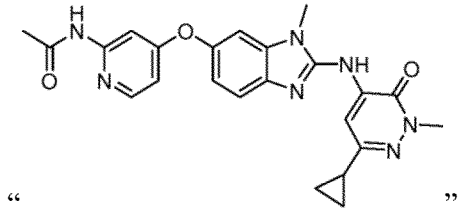
"  "

And insert:

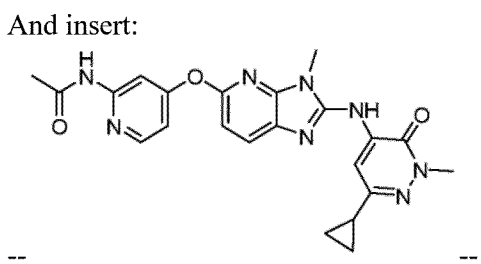
--  --

In Claim 24, Column 651, beginning at Line 35 and ending at Line 45, please delete:

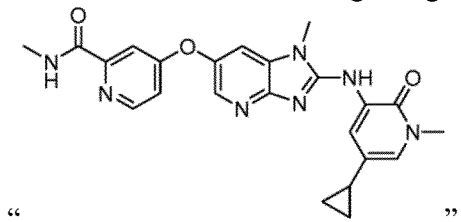
"  "

And insert:

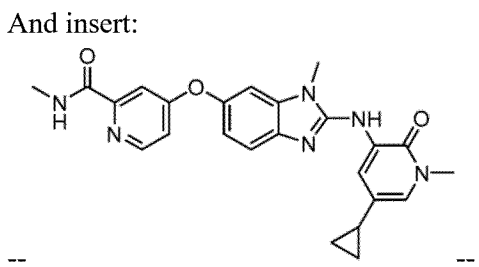
--  --

In Claim 24, Column 671, please delete the fourth entry:

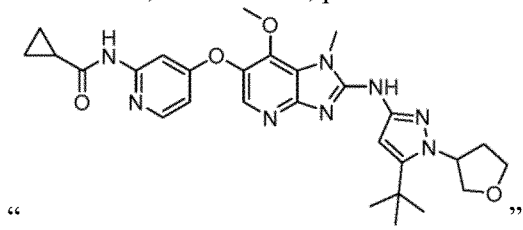
"  "

And insert:

I-170'
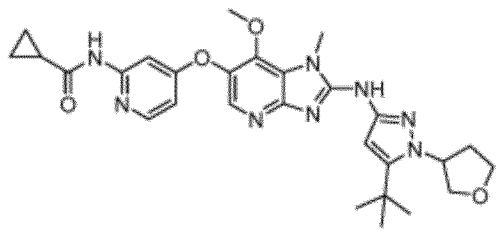
--  --
In Claim 24, Column 671, please delete the fifth entry:
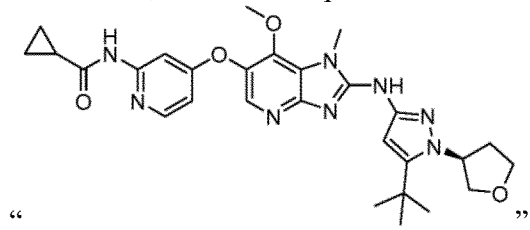
" "
And insert:
I-171
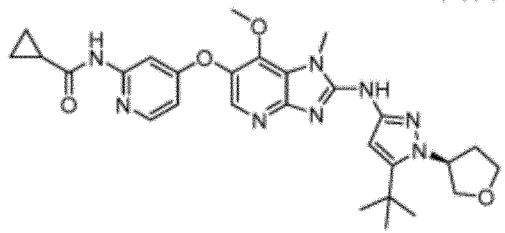
--  --
In Claim 24, Column 679, last entry (compound I-189-i), please delete:
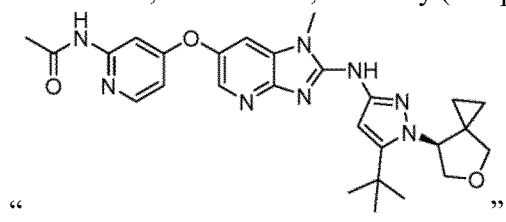
" "
And insert:
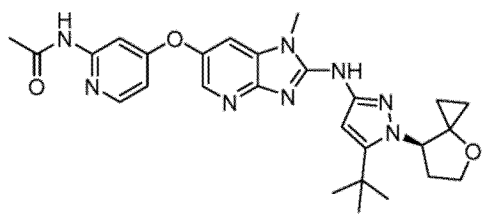
--  --
In Claim 24, Column 680, second-to-last entry (compound I-189), please delete:

CERTIFICATE OF CORRECTION (continued)
U.S. Pat. No. 11,691,963 B2

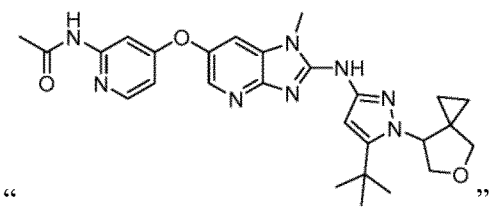

" "

And insert:

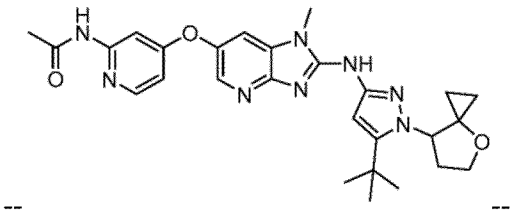

-- --

In Claim 24, Column 680, last entry (compound I-189-ii), please delete:

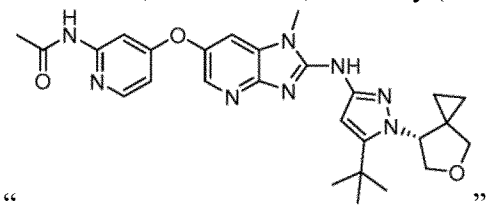

" "

And insert:

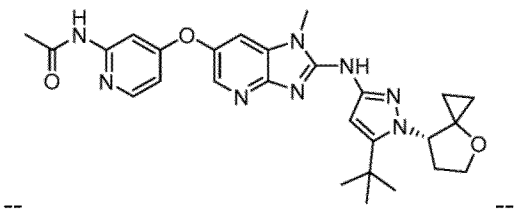

-- --

In Claim 24, Column 681, first entry (compound I-190), please delete:

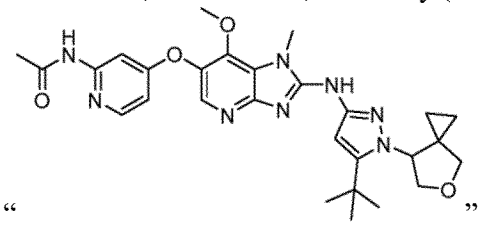

" "

And insert:

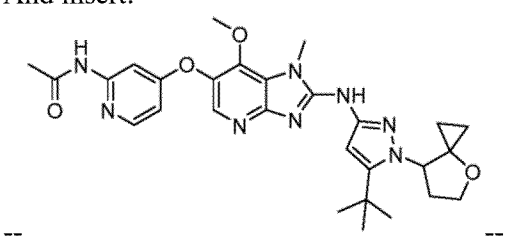

-- --

In Claim 24, Column 681, second entry (compound I-190-ii), please delete:

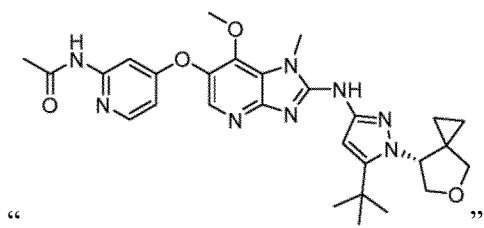
"
And insert:
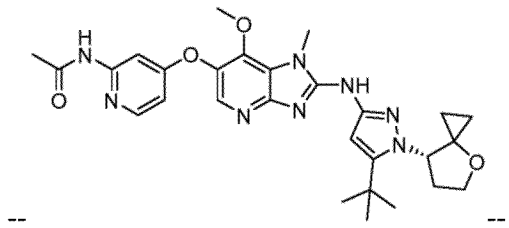
--
In Claim 24, Column 682, first entry (compound I-190-i), please delete:
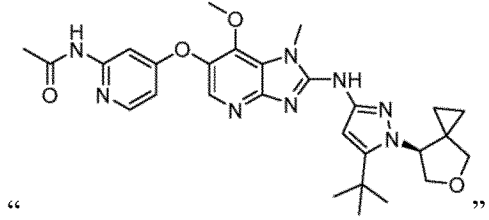
"
And insert:
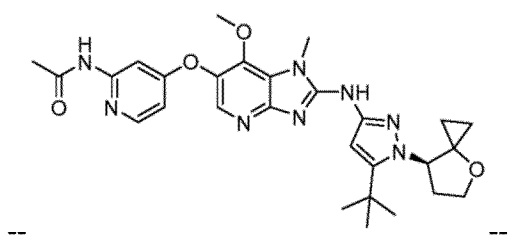
--
In Claim 24, Column 687, beginning at Line 1 and ending at Line 17, please delete:
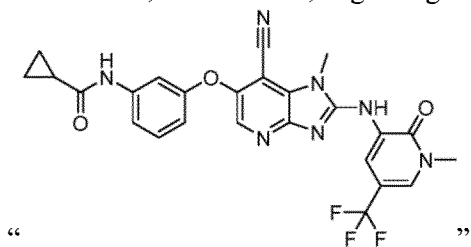
"
And insert:
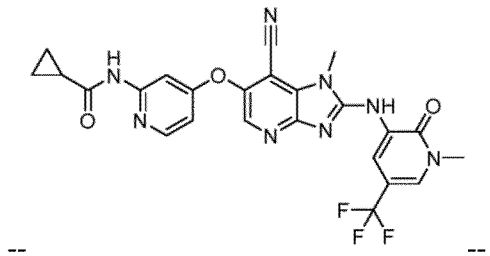
--